US012594264B2

(12) United States Patent
Crew et al.

(10) Patent No.: US 12,594,264 B2
(45) Date of Patent: Apr. 7, 2026

(54) MODULATORS OF ALPHA-SYNUCLEIN PROTEOLYSIS AND ASSOCIATED METHODS OF USE

(71) Applicant: Arvinas Operations, Inc., New Haven, CT (US)

(72) Inventors: Andrew P. Crew, Guilford, CT (US); Hanqing Dong, Madison, CT (US); Michael Berlin, Flemington, NJ (US); Steven M. Sparks, Guilford, CT (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 18/309,867

(22) Filed: Sep. 18, 2023

(65) Prior Publication Data

US 2024/0091204 A1 Mar. 21, 2024

Related U.S. Application Data

(62) Division of application No. 16/545,983, filed on Aug. 20, 2019, now Pat. No. 11,707,452.

(60) Provisional application No. 62/719,937, filed on Aug. 20, 2018.

(51) Int. Cl.

| | |
|---|---|
| *A61K 31/427* | (2006.01) |
| *A61K 31/4035* | (2006.01) |
| *A61K 31/4245* | (2006.01) |
| *A61K 31/437* | (2006.01) |
| *A61K 31/4439* | (2006.01) |
| *A61K 31/496* | (2006.01) |
| *A61K 31/541* | (2006.01) |
| *A61K 47/54* | (2017.01) |

(52) U.S. Cl.

CPC ........ *A61K 31/427* (2013.01); *A61K 31/4035* (2013.01); *A61K 31/4245* (2013.01); *A61K 31/437* (2013.01); *A61K 31/4439* (2013.01); *A61K 31/496* (2013.01); *A61K 31/541* (2013.01); *A61K 47/555* (2017.08)

(58) Field of Classification Search

CPC .................................................... A61K 31/427

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Deshaies et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh et al. |
| 9,447,070 | B2 | 9/2016 | Muller et al. |
| 9,500,653 | B2 | 11/2016 | Crews et al. |
| 9,632,089 | B2 | 4/2017 | Crews et al. |
| 2003/0096841 | A1 | 5/2003 | Robarge et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2011/0196150 | A1 | 8/2011 | Man et al. |
| 2011/0230457 | A1 | 9/2011 | Berghausen et al. |
| 2012/0270800 | A1 | 10/2012 | Verdine et al. |
| 2014/0235629 | A1 | 8/2014 | Bartberger et al. |
| 2014/0243372 | A1 | 8/2014 | Rew |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |

(Continued)

FOREIGN PATENT DOCUMENTS

| | | |
|---|---|---|
| CN | 1844118 | 10/2006 |
| CN | 103688176 A | 3/2014 |

(Continued)

OTHER PUBLICATIONS

Amako, "Development and Advances of PROTACs: Induced Protein Degradation by Hijacking Ubiquitin Ligase", *Journal of Synthetic Organic Chemistry Japan* 76(4):358-359 (2018).

Naito et al., "Chemical Protein Knockdown: Development of SNIPER compounds that induce degradation of target proteins", *MEDCHEM News* 28(1):29-35 (2018).

Ahn et al., "HIF-1alpha peptide derivatives with modifications at the hydroxyproline residue as activators of HIF-1alpha", *Bioorganic & Medicinal Chemistry Letters* 19(15):4403-4405 (2009).

Ardecky et al., "Design, synthesis and evaluation of inhibitor of apoptosis protein (IAP) antagonists that are highly selective for the BIR2 domain of XIAP", *Bioorganic & Medicinal Chemistry* 23(14):4253-4257 (2013).

(Continued)

*Primary Examiner* — Paul V Ward

(74) *Attorney, Agent, or Firm* — Hoxie & Associates LLC

(57) ABSTRACT

The present disclosure relates to bifunctional compounds, which find utility as modulators of α-synuclein (target protein). In particular, the present disclosure is directed to bifunctional compounds, which contain on one end a Von Hippel-Lindau, cereblon. Inhibitors of Apotosis Proteins or mouse double-minute homolog 2 ligand which binds to the respective E3 ubiquitin ligase and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

18 Claims, 7 Drawing Sheets

(56) References Cited

U.S. PATENT DOCUMENTS

| | | | |
|---|---|---|---|
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2018/0353501 | A1 | 12/2018 | Crew et al. |
| 2019/0151295 | A1 | 5/2019 | Crew et al. |
| 2020/0085793 | A1 | 3/2020 | Crew et al. |

FOREIGN PATENT DOCUMENTS

| | | | |
|---|---|---|---|
| EP | 2985285 | | 2/2016 |
| JP | A 2010-502627 | | 1/2010 |
| JP | 7297053 | B2 | 6/2023 |
| RU | 2008112221 | A | 10/2009 |
| RU | 2448101 | C2 | 4/2012 |
| RU | 2011121567 | A | 12/2012 |
| RU | 2012138709 | A | 3/2014 |
| WO | WO 1998/003502 | A1 | 1/1998 |
| WO | WO 2000/066119 | A1 | 11/2000 |
| WO | WO 2002/066512 | A1 | 8/2002 |
| WO | WO 2002/100845 | A1 | 12/2002 |
| WO | WO 2005/016326 | A2 | 2/2005 |
| WO | WO 2005/097791 | A1 | 10/2005 |
| WO | WO 2006/069063 | A1 | 6/2006 |
| WO | WO 2006/113942 | A2 | 10/2006 |
| WO | WO 2007/101347 | A1 | 9/2007 |
| WO | WO 2007/106670 | A2 | 9/2007 |
| WO | WO 2007/115289 | A2 | 10/2007 |
| WO | WO 2007/130626 | A2 | 11/2007 |
| WO | WO 2008/011392 | A2 | 1/2008 |
| WO | WO 2008/014236 | A1 | 1/2008 |
| WO | WO 2008/109057 | A1 | 9/2008 |
| WO | WO 2008/128121 | A1 | 10/2008 |
| WO | WO 2008/128171 | A2 | 10/2008 |
| WO | WO 2008/134679 | A1 | 11/2008 |
| WO | WO 2009/015254 | A1 | 1/2009 |
| WO | WO 2009/060292 | A2 | 5/2009 |
| WO | WO 2010/107485 | A1 | 9/2010 |
| WO | WO 2010/141805 | A1 | 12/2010 |
| WO | WO 2011/008260 | A2 | 1/2011 |
| WO | WO 2012/003281 | A2 | 1/2012 |
| WO | WO 2012/007409 | A1 | 1/2012 |
| WO | WO 2012/040527 | A2 | 3/2012 |
| WO | WO 2012/078559 | A2 | 6/2012 |
| WO | WO 2012/090104 | A1 | 7/2012 |
| WO | WO 2013/071035 | A1 | 5/2013 |
| WO | WO 2013/071039 | A1 | 5/2013 |
| WO | WO 2013/106535 | A1 | 7/2013 |
| WO | WO 2013/106643 | A2 | 7/2013 |
| WO | WO 2013/106646 | A2 | 7/2013 |
| WO | WO 2013/170147 | A1 | 11/2013 |
| WO | WO 2013/175417 | A1 | 11/2013 |
| WO | WO 2013/176698 | A1 | 11/2013 |
| WO | WO 2013/178570 | A1 | 12/2013 |
| WO | WO 2014/011712 | A1 | 1/2014 |
| WO | WO 2014/020502 | A2 | 2/2014 |
| WO | WO 2014/025759 | A1 | 2/2014 |
| WO | WO 2014/038606 | A1 | 3/2014 |
| WO | WO 2014/047024 | A1 | 3/2014 |
| WO | WO 2014/055461 | A1 | 4/2014 |
| WO | WO 2014/074658 | A1 | 5/2014 |
| WO | WO 2014/100065 | A1 | 6/2014 |
| WO | WO 2014/100071 | A2 | 6/2014 |
| WO | WO 2014/107713 | A1 | 7/2014 |
| WO | WO 2014/108452 | A1 | 7/2014 |
| WO | WO 2014/123418 | A1 | 8/2014 |
| WO | WO 2014/134201 | A1 | 9/2014 |
| WO | WO 2014/151863 | A1 | 9/2014 |
| WO | WO 2015/000868 | A1 | 1/2015 |
| WO | WO 2015/006524 | A1 | 1/2015 |
| WO | WO 2015/097621 | A2 | 7/2015 |
| WO | WO 2015/116663 | A1 | 8/2015 |
| WO | WO 2015/160845 | A2 | 10/2015 |
| WO | WO 2015/173225 | A1 | 11/2015 |
| WO | WO 2016/105518 | A1 | 6/2016 |
| WO | WO 2016/146985 | A1 | 9/2016 |
| WO | WO 2016/149668 | A1 | 9/2016 |
| WO | WO 2016/169989 | A1 | 10/2016 |
| WO | WO 2016/172134 | A2 | 10/2016 |
| WO | WO 2016/197032 | A1 | 12/2016 |
| WO | WO 2016/197114 | A1 | 12/2016 |
| WO | WO 2017/007612 | A1 | 1/2017 |
| WO | WO 2017/011590 | A1 | 1/2017 |
| WO | WO 2017/020010 | A1 | 2/2017 |
| WO | WO 2017/024317 | A2 | 2/2017 |
| WO | WO 2017/024318 | A1 | 2/2017 |
| WO | WO 2017/024319 | A1 | 2/2017 |
| WO | WO 2017/030814 | A1 | 2/2017 |
| WO | WO 2017/046036 | A1 | 3/2017 |
| WO | WO 2017/079267 | A1 | 5/2017 |
| WO | WO 2017/117473 | A1 | 7/2017 |
| WO | WO 2017/117474 | A1 | 7/2017 |
| WO | WO 2017/153601 | A1 | 9/2017 |
| WO | WO 2017/161119 | A1 | 9/2017 |
| WO | WO 2017/176957 | A1 | 10/2017 |
| WO | WO 2017/176958 | A1 | 10/2017 |
| WO | WO 2017/185023 | A1 | 10/2017 |
| WO | WO 2017/185031 | A1 | 10/2017 |
| WO | WO 2017/185034 | A1 | 10/2017 |
| WO | WO 2017/185036 | A1 | 10/2017 |
| WO | WO 2017/197051 | A1 | 11/2017 |
| WO | WO 2017/197055 | A1 | 11/2017 |
| WO | WO 2017/197056 | A1 | 11/2017 |
| WO | WO 2017/223415 | A1 | 12/2017 |
| WO | WO 2017/223452 | A1 | 12/2017 |
| WO | WO 2018/052945 | A1 | 3/2018 |
| WO | WO 2018/052949 | A1 | 3/2018 |
| WO | WO 2018/064589 | A1 | 4/2018 |
| WO | WO 2018/089736 | A1 | 5/2018 |
| WO | WO 2018/098275 | A1 | 5/2018 |
| WO | WO 2018/098280 | A1 | 5/2018 |
| WO | WO 2018/098288 | A1 | 5/2018 |
| WO | WO 2018/102067 | A2 | 6/2018 |
| WO | WO 2018/106870 | A1 | 6/2018 |
| WO | WO 2018/138086 | A1 | 8/2018 |
| WO | WO 2018/138088 | A1 | 8/2018 |
| WO | WO 2018/148440 | A1 | 8/2018 |
| WO | WO 2019/014429 | A1 | 1/2019 |
| WO | WO 2019/042444 | A1 | 3/2019 |
| WO | WO 2019/121661 | A1 | 6/2019 |
| WO | WO 2019/195201 | A1 | 10/2019 |

OTHER PUBLICATIONS

Asano et al., "Design, sterioselective synthesis, and biological evaluation of novel tri-cyclic compounds as inhibitor of apoptosis proteins (IAP) antagonists", *Bioorganic & Medicinal Chemistry* 21(18):5725-5737 (2013).

Banker et al., Modern Pharmaceutics, Third Edition, Revised and Expanded, Marcel Dekkar, Inc. (1997).

(56) References Cited

OTHER PUBLICATIONS

Bargagna-Mohan et al., "Use of PROTACS as molecular probes of angiogenesis", *Bioorganic & Medicinal Chemistry Letters* 15(11):2724-2727 (2005).
Bohnert et al., "Plasma Protein Binding: From Discovery to Development", *Journal of Pharmaceutical Sciences* 102(9):2953-2994 (2013).
Bondeson et al., "Catalytic in vivo protein knockdown by small-molecule PROTACS", *Nature Chemical Biology* 11(8):611-617 (2015).
Bondeson et al., "Targeted Protein Degradation by Small Molecules", *Annual Review of Pharmacology and Toxicology* 57:107-123 (2017).
Bondeson et al., "Lessons in PROTAC Design from Selective Degradation with a Promiscuous Warhead", *Cell Chemical Biology* 25(1):78-87, e75 (2018).
Buckley et al., "Targeting the von Hippel-Lindau E3 ubiquitin ligase using small molecules to disrupt the VHL/HIF-la interaction", *Journal of the American Chemical Society* 134(10):4465-4468 (Feb. 2012).
Buckley et al., "Small-molecule inhibitors of the interaction between the E3 ligase VHL and H1Fla", *Angew Chem Int Ed Engl* 51(46):11463-11467 (2012).
Buckley et al., "HaloPROTACS: use of small molecule PROTACS to induce degradation of HaloTag fusion proteins", *ACS Chemical Biology* 10(8):1831-1837 (2015).
Burslem et al., "Small-Molecule Modulation of Protein Homeostasis", *Chemical Review* 117(17):11269-11301 (2017).
Burslem et al., "The Advantages of Targeted Protein Degradation Over Inhibition: An RTK Case Study", *Cell Chemical Biology* 25(1):67-77, e63 (2018).
Capitosti et al., "Thalidomide analogues demonstrate dual inhibition of both angiogenesis and prostate cancer", *Bioorganic &Medicinal Chemistry* 12:327-336 (2004).
Carmony et al., "PROTAC-Induced Proteolytic Targeting", *Methods in Molecular Biology* 832:627-638 (2012).
CAS Registry No. 1004933-70-3, which entered STN on Feb. 21, 2008.
CAS Registry No. 1226974-40-8, indexed in the Registry file on STN CAS Online Jun. 4, 2010.
CAS Registry No. 871986-52-6 entered STN Jan. 16, 2006.
CAS RN 1542127-97-8 STN Entry, Feb. 11, 2014.
Chan et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds", *Journal of Medicinal Chemistry* 61(2):504-513 (2018).
Chene et al., "Inhibiting the p53-MDM2 interaction: an important target for cancer therapy", *Nature Reviews Cancer* 3:102-109 (2003).
Churcher, "Protac-Induced Protein Degradation in Drug Discovery: Breaking the Rules or Just Making New Ones?", *Journal of Medicinal Chemistry* 61(2):444-452 (2018).
Cohen et al., "Orally bioavailable antagonists of inhibitor of apoptosis proteins based on an azabicyclooctane scaffold", *Journal of Medicinal Chemistry* 52(6):1723-1730 (2009).
Cohen et al., "Antagonists of inhibitors of apoptosis proteins based on thiazole amide isosteres", *Bioorganic & Medicinal Chemistry Letters* 20(7):2229-2233 (2010).
Contino-Pepin et al., "Preliminary biological evaluations of new thalidomide analogues for multiple sclerosis application", *Bioorganic & Medicinal Chemistry Letters* 19:878-881 (2009).
Corson et al., "Design and applications of bifunctional small molecules: why two heads are better than one", *ACS Chemical Biology* 3(11):677-692 (2008).
Crew et al., "Identification and Characterization of Von Hippel-Lindau-Recruiting Proteolysis Targeting Chimeras (PROTACs) of TANK-Binding Kinase 1", *Journal of Medicinal Chemistry* 61(2):583-598 (2018).
Crews, "Targeting the undruggable proteome: the small molecules of my dreams", *Chemical Biology* 17:551-555 (2010).
Cromm et al., "Targeted Protein Degradation: from Chemical Biology to Drug Discovery", *Cell Chemical Biology* 24(9):1181-1190 (2017).
Cyrus et al., "Two-Headed PROTAC: An Effective New Tool for Targeted Protein Degradation", *ChemBioChem* 11:1531-1534 (2010).
Cyrus et al., "Jostling for position: optimizing linker location in the design of estrogen receptor-targeting PROTACs", *ChemMedChem* 5(7):979-985 (2010).
Cyrus et al., "Impact of Linker Length on the Activity of PROTACs", *Molecular Biosystems* 7(2):359-364 (2011).
Di et al., "Reactivation of p53 by inhibiting Mdm2 E3 Ligase: a novel antitumor approach", *Current Cancer Drug Targets* 11(8):987-994 (2011).
Ding et al., "Discovery of RG7388, a potent and selective p53-MDM2 inhibitor in clinical development", *Journal of Medicinal Chemistry* 56(14):5979-5983 (2013).
Dixon et al., "Identifying druggable disease-modifying gene products", *Current Opinion in Chemical Biology* 13:549-555 (2009).
Estrada et al., "Discovery of highly potent, selective, and brain-penetrable leucine-rich repeat kinase 2 (LRRK2) small molecule inhibitors", *Journal of Medicinal Chemistry* 55(22):9416-9433 (2012).
Fischer et al., "Structure of the DDB1-DRBN E3 Ubiquitin ligase in complex with thalidomide", *Nature* vol. 000, pp. 1-5 (2014).
Flygare et al., "Small-molecule pan-IAP antagonists: a patent review", *Expert Opinion on Therapeutic Patents* 20(2):251-267 (2010).
Gadd et al., "Structural basis of PROTAC cooperative recognition for selective protein degradation", *Nature Chemical Biology* 13:514-521 (2017).
Galdeano et al., "Structure-guided design and optimization of small molecules targeting the protein-protein interaction between the von hippel-lindau (Vhl) E3 ubiquitin ligase and the Hypoxia inducible factor (HIF) alpha subunit with in vitro nanomolar affinities", *Journal of Medicinal Chemistry* 57:8657-8663 (2014).
Golub et al., "Molecular classification of cancer: class discovery and class prediction by gene expression monitoring", *Science* 286:531-537 (1991).
Gosink et al., "Redirecting the specificity of ubiquitination by modifying ubiquitin-conjugating enzymes", *PNAS* 92:9117-9121 (1995).
Han et al., "Discovery of ARD-69 as a Highly Potent Proteolysis Targeting Chimera (PROTAC) Degrader of Androgen Receptor (AR) for the Treatment of Prostate Cancer", *Journal of Medicinal Chemistry* 62(2):941-964 (2019).
Harrington et al., "Cellular Models of Aggregation-dependent Template-directed Proteolysis to Characterize Tau Aggregation Inhibitors for Treatment of Alzheimer Disease", *The Journal of Biological Chemistry* 2909(17):10862-10875 (2015).
Haupt et al., "Mdm2 promotes the rapid degradation of p53", *Nature* 387:296-299 (1997).
Hennessy et al., "Discovery of aminopiperidine-based Smac mimetics as IAP antagonists", *Bioorganic & Medicinal Chemistry Letters* 22(4):1690-1694 (2012).
Hines et al., "Posttranslational protein knockdown coupled to receptor tyrosine kinase activation with phosphoPROTACs", *PNAS USA* 110:8942-8947 (2013).
Hird et al., "Structure-based design and synthesis of tricyclic IAP (Inhibitors of Apoptosis Proteins) inhibitors", *Bioorganic & Medicinal Chemistry Letters* 24(7):1820-1824 (2014).
Hon et al., "Structural basis for the recognition of hydroxyproline in HIf-1 alpha by pVHL", *Nature* 417:975-978 (2002).
Hu et al., "Discovery of ERD-308 as a Highly Potent Proteolysis Targeting Chimera (PROTAC) Degrader of Estrogen Receptor (ER)", *Journal of Medicinal Chemistry*, 62:1420-1442, 2019.
Huang et al., "Drugging the undruggables: exploring the ubiquitin system for drug development", *Cell Research* 26(4):484-498 (2016).
Huang et al., "A Chemoproteomic Approach to Query the Degradable Kinome Using a Multi-kinase Degrader", *Cell Chemical Biology* 25(1):88-99, e86 (2018).
Hughes et al., "Molecular recognition of ternary complexes: a new dimension in the structure-guided design of chemical degraders", *Essays in Biochemistry* 61(5):505-516 (2017).
International Preliminary Report on Patentability for PCT/US2019/047291 dated Feb. 23, 2021.

(56) References Cited

OTHER PUBLICATIONS

Itoh et al., "Protein knockdown using methyl bestatin-ligand hybrid molecules: design and synthesis of inducers of ubiquitination-mediated degradation of cellular retinoic acid-binding proteins", *Journal of the American Chemical Society* 132:5820-5826 (2010).
Itoh et al., "Development of target protein selective degradation inducer for protein knockdown", *Bioorganic & Medicinal Chemistry* 19:3229-3241 (2011).
Ivan et al., "HIFa Targeted for VHL-Mediated Destruction by Proline Hydroxylation: Implications for O2 Sensing", *Science* 292(5516):464-468 (2001).
Jang et al., "Targeted Degradation of Proteins by PROTACs", *Current Protocols in Chemical Biology* 2(2):71-87 (2010).
Kim, "Discovery of tetrahydroisoquinoline-based bivalent heterodimeric IAP antagonists", *Bioorganic & Medicinal Chemistry Letters* 24(21):5022-5029 (2014).
Knott, "Compounds containing sulphur chromophores. Part I. The action of bases on heterocyclic sulphide quarternary salts", *Journal of the Chemical Society* 949-954 (1955).
Kronke, et al., "Lenalidomide Causes Selective Degradation of IKZF1 and IKZF3 in Multiple Myeloma Cells", *Science* 343:301-305 (2014).
Lai et al., "Modular PROTAC Design for the Degradation of Oncogenic BCR-ABL", *Angew Chem Int Ed Engl* 55:807-810 (2016).
Lai et al., "Induced protein degradation: an emerging drug discovery paradigm." *Nature Reviews Drug Discovery* 16(2):101-114 (2017).
Lala et al., "Role of nitric oxide in tumor progression: Lessons from experimental tumors", *Cancer and Metastasis Reviews* 17:91-106 (1998).
Lebraud et al., "Protein Degradation by In-Cell Self-Assembly of Proteolysis Targeting Chimeras", *ACS Central Science* 2: 927-934 (2016).
Lee et al., "Targeted Degradation of the Aryl Hydrocarbon Receptor by the PROTAC Approach: A Useful Chemical Genetic Tool", *ChemBioChem* 8(17):2058-2062 (2007).
Levine et al., "Targeting the androgen receptor with steroid conjugates", *Journal of Medicinal Chemistry* 57(20):8224-8237 (2014).
Li et al., "Thiadiazole-a Promising Structure in Medicinal Chemistry", ChemMedChem 8:27-41 (2013).
Li et al., "Single Polymer-drug Conjugate Carrying Two Drugs for Fixed-dose Co-delivery", *Medicinal Chemistry* 4(10):676-683 (2014).
Liu et al., "Design and biological characterization of hybrid compounds of curcumin and thalidomide for multiple myeloma", *Organic and Biomolecular Chemistry* 11:4757-4763 (2013).
Lopez-Girona et al., "Cereblon is a direct protein target for immunomodulatory and antiproliferative activities of lenalidomide and pomalidomide", *Leukemia* 26:2326-2335 (2012).
Lu et al., "The myeloma drug lenalidomide promotes the cereblon-dependent destruction of ikaros proteins", *Science* 343:305-309 (2014).
Lu et al., "Hijacking the E3 ubiquitin ligase cereblon to efficiently target BRD4", *Chemical Biology* 22(6):755-763 (2015).
Maniaci et al., "Homo-PROTACs: bivalent small-molecule dimerizers of the VHL E3 ubiquitin ligase to induce self-degradation", *Nature Communications* 8:830 (2017).
Mannhold et al., "IAP antagonists: promising candidates for cancer therapy", *Drug Discovery Today* 15(5-6):210-219 (2010).
Medline Plus Trusted Health Information for You, www.nlm.nih.gov/medlineplus/cancer.html, pp. 1-10, (2007).
Min et al., "Structure of an HIV-1-alpha-pVHL complex: hydroxyproline recognition in signaling", *Science* 296(5574):1886-1889 (2002).
Miyazaki et al., "Discovery of DS-5272 as a promising candidate: a potent and orally active p53-MDM2 interaction inhibitor", *Bioorganic & Medicinal Chemistry Letters* 23:2360-2367 (2015).
Muller et al., "Amino-substituted thalodomide analogs: Potent inhibitors of TNF-α production", *Bioorganic & Medicinal Chemistry Letters* 9:1625-1630 (1999).
Ndubaku et al., "Antagonism of c-IAP and XIAP proteins is required for efficient induction of cell death by small-molecule IAP antagonists", *ACS Chemical Biology* 4(7):557-566 (2009).
Neklesa et al., "Chemical biology: Greasy tags for protein removal", *Nature* 487:308-309 (2012).
Neklesa, "Targeted protein degradation by PROTACs", *Pharmacology & Therapeutics* 174:138-144 (2017).
Nikolovska-Coleska et al., "Interaction of a cyclic, Bivalent Smac Mimetic with the X-linked inhibitor of apoptosis protein", *Biochemistry* 47(37):9811-9824 (2008).
Noguchi-Yachide et al., "BET Bromodomain as a Target of Epigenitic Therapy", *Chemical and Pharmaceutical Bulletin* 64(6):540-547 (2016).
Ohoka et al., "NIPER(TACC3) induces cytoplasmic vacuolization and sensitizes cancer cells to Bortezomib", *Cancer Science* 108:1032-1041 (2017).
Oost et al., "Discovery of potent antagonists of the antiapoptotic protein XIAP for the treatment of cancer", *Journal of Medicinal Chemistry* 47:4417-4426 (2004).
Ottis et al., "Proteolysis-Targeting Chimeras: Induced Protein Degradation as a Therapeutic Strategy", *ACS Chemical Biology* 12(4):892-898 (2017).
Ottis et al., "Assessing Different E3 Ligases for Small Molecule Induced Protein Ubiquitination and Degradation", *ACS Chemical Biology* 12(10):2570-2578 (2017).
Perez, "Discovery of potent heterodimeric antagonists of inhibitor of apoptosis proteins (IAPs) with sustained antitumor activity", *Journal of Medicinal Chemistry* 58(3):1556-1562 (2015).
Pickhardt et al., "Identification of small molecule inhibitors of Tau aggregation by targeting monomeric Tau as a potential therapeutic approach for Tauopathies", *Current Alzheimer Research* 12(9):814-828, (2015) (Author manuscript; available in PMC Aug. 8, 2016).
Powell et al., "Chemically Induced Degradation of Anaplastic Lymphoma Kinase (ALK)", *Journal of Medicinal Chemistry* 61:4249-4255 (2018).
Puppala et al., "Development of an Aryl Hydrocarbon Receptor Antagonist Using the Proteolysis-Targeting chimeric Molecules Approach: A Potential Tool for Chemoprevention", *Molecular Pharmacology* 73(4):1064-1071 (2008).
Raina et al., "Chemical Inducers of Targeted Protein Degradation", *The Journal of Biological Chemistry* 285(15):11057-11060 (2010).
Raina et al., "PROTAC-induced BET protein degradation as a therapy for castration-resistant prostate cancer", *PNAS USA* 113:7124-7129 (2016).
Raina et al., "Targeted protein knockdown using small molecule degraders", *Current Opinion in Chemical Biology* 39:46-53 (2017).
Rapoport et al., "Tau is essential to 0-amyloid-induced neurotoxicity", *PNAS* 99(9):6364-6369 (2002).
Rautio, "Inhibitors of LRRK2 Kinase Activity to Probe the Treatment Option in Parkinson's Disease", *Journal of Medicinal Chemistry* 55:9414-9415 (2012).
Remillard et al., "Degradation of the BAF Complex Factor BRD9 by Heterobifunctional Ligands", *Angew Chem Int Ed Engl* 56(21):5738-5743 (2017).
Rew et al., "Discovery of AM-7209, a Potent and Selective 4-Amidobenzoic Acid Inhibitor of the MDM2-p53 interaction", *Journal of Medicinal Chemistry* 57(24):10499-10511 (2014).
Rodriguez-Gonzalez et al., "Targeting steroid hormone receptors for ubiquitination and degradation in breast and prostate cancer", *Oncogene* 27(57):7201-7211 (2008).
Rotili et al., "Photoactivable peptides for identifying enzyme-substrate and protein-protein interactions", Chemical Communications (Carob) 47(5):1488-1490 (2011).
Rott et al., "a-Synuclein Ubiquitination and Novel Therapeutic Targets for Parkinson's Disease", *CNS & Neurological Disorders—Drug Targets* 13(4):630-637 (2014).
Ruchelman et al., "Isosteric analogs of lenalidominde and pomalidomide: Synthesis and biological activity", *Bioorganic & Medicinal Chemistry Letters* 23:360-365 (2013).
Sakamoto et al., "Protacs: chimeric molecules that target proteins to the Skp 1—Cullin-F box complex for ubiquitination and degradation", *PNAS USA* 98(15):8554-8559 (2001).

(56) References Cited

OTHER PUBLICATIONS

Sakamoto et al., "Development of Protacs to target cancer-promoting proteins for ubiquitination and degradation", *Molecular & Cellular Proteomics* 2(12):1350-1358 (2003).
Salami et al., "Waste disposal-An attractive strategy for cancer therapy", *Science* 355:1163-1167 (2017).
Schiedel et al., "Chemically Induced Degradation of Sirtuin 2 (Sirt2) by a Proteolysis Targeting Chimera (PROTAC) Based on Sirtuin Rearranging Ligands (SirReals)", *Journal of Medicinal Chemistry* 61:482-491 (2017).
Schneekloth et al., "Chemical Genetic Control of Protein Levels: Selective in Vivo Targeted Degradation", *Journal of the American Chemical Society* 126(12):3748-3754 (2004).
Schneekloth et al., "Targeted intracellular protein degradation induced by a small molecule: En route to chemical proteomics", *Bioorganic & Medicinal Chemistry Letters* 18:5904-5908 (2008).
Smith et al., "Targeted Intracellular Protein Degradation Induced by a Small Molecule: En Route to Chemical Proteomics", *Bioorganic & Medicinal Chemistry Letters* 18(22):5904-5908 (2008).
Stanton et al., "Chemically induced proximity in biology and medicine", *Science* 359(6380):3aa05902 (2018).
Stewart et al., "Efforts toward elucidating Thalidomide's molecular target: An Expedient Synthesis of the first Thalidomide Biotin Analogue", *Organic and Biomolecular Chemistry* 8:4059-4062 (2010).
STN transcript excerpt Nov. 24, 2017 "Compounds containing sulfur Chromophores v. Complex cyanines".
Stoppler, Melissa Conrad, Endometriosis [online], "Endometriosis Definition and Facts" URL http://www.medicinenet.com/endometriosis/article.htm, retrieved on Apr. 5, 2017.
Stoppler, Melissa Conrad, Endometriosis [online], "What about surgery for Endometriosis?" URL http://www.medicinenet.com/endometriosis/article.htm, retrieved on Apr. 5, 2017.
Sun et al., "Potent bivalent Smac mimetics: effect of the linker on binding to inhibitor apoptosis proteins (IAPs) and anticancer activity", *Journal of Medicinal Chemistry* 53:3306-3318 (2011).
Sun et al., "Discovery of AMG 232, a potent, selective, and orally bioavailable MDM2-p53 inhibitor in clinical development", *Journal of Medicinal Chemistry* 57(4):1454-1472 (2014).
Sun et al., "BET protein proteolysis targeting chimera (PROTAC) exerts potent lethal activity against mantle cell lymphoma cells", *Leukemia* 32:343-352 (2018).
Tomoshige et al., "Degradation of huntingtin mediated by a hybrid molecule composed of IAP antagonist linked to phenyldiazenyl benzothiazole derivative", *Bioorganic & Medicinal Chemistry Letters* 28(4):707-710 (2018).
Toure et al., "Small-Molecule PROTACS: New Approaches to Protein Degradation", *Angew Chem Int Ed Engl* 55(6):1966-1973 (2016).
Turk et al., "Binding of thalidomide to $\alpha_1$-acid glycoprotein may be involved in its inhibition of tumor necrosis factor $\alpha$ production", *PNAS USA* 93:7552-7556 (1996).
Vamos et al., "Expedient synthesis of highly potent antagonists of inhibitor of apoptosis proteins (IAPs) with unique selectivity for ML-IAP", *ACS Chemical Biology* 8(4):725-732 (2013).
Van Molle et al., "Dissecting fragment-based lead discovery at the von Hippel-Lindau protein: hypoxia inducible factor la protein-protein interface", *Chemical Biology* 19(10):1300-1312 (2012).
Vassilev et al., "In vivo activation of the p53 pathway by small-molecule antagonists of MDM2", *Science* 303:844-848 (2004).
Vippagunta et al., "Crystalline solids", *Advanced Drug Delivery Reviews* 48:3-26 (2001).
Vazquez et al., "The genetics of the p53 pathway, apoptosis and cancer therapy", *Nature Reviews Drug Discovery* 7:979-982 (2008).
Vu et al. "Discovery of RG7112: a small-molecule MDM2 inhibitor in clinical development", *ACS Medicinal Chemistry Letters* 4:466-469 (2013).
Wang et al., "Temporal activation of p53 by a specific MDM2 inhibitor is selectively toxic to tumors and leads to complete tumor growth inhabitation", *PNAS USA* 105:3933-3938 (2008).
Wang et al., "Discovery of novel second mitochondrial-derived activator of caspase mimetics as selective inhibitor or apoptosis protein inhibitors", *Journal of Pharmacology and Experimental Therapeutics* 349(2):319-329 (2014).
Wang et al., "Small-molecule inhibitors of the MDM2-p53 protein-protein interaction (MDM2 inhibitors) in clinical trials for cancer treatment", *Journal of Medicinal Chemistry* 58:1038-1052 (2015).
Winter et al., "Phthalimide Conjugation as a strategy for in vivo target protein degradation", *Science* 348(6241):1376-1381 (2015).
Wolff, Burger's Medicinal Chemistry and Drug Discovery, Fifth Edition, vol. I: Principles and Practice, John Wiley & Sons, Inc., 975-977 (1997).
Zengerle et al., "Selective Small Molecule Induced Degradation of the BET Bromodomain Protein BRD4", *ACS Chemical Biology* 10:1770-1777 (2015).
Zhang et al., "Targeted Degradation of Proteins by Small Molecules: A Novel Tool for Functional Proteomics," *Combinatorial Chemistry & High Throughput Screening* 7(7):689-697 (2004).
Zhang et al., "Small-molecule MDM2-p53 inhibitors: recent advances", *Future Medicinal Chemistry* 7:631-645 (2015).
Zhou et al., "Discovery of a Small-Molecule Degrader of Bromodomain and Extra-Terminal (BET) Proteins with Picomolar Cellular Potencies and Capable of Achieving Tumor Regression", *Journal of Medicinal Chemistry* 61(2):462-481 (2018).

VHL Ligand

Cereblon Ligand

MODULATORS OF ALPHA-SYNUCLEIN PROTEOLYSIS AND ASSOCIATED METHODS OF USE

CROSS-REFERENCE TO RELATED APPLICATIONS

The present application claims the benefit of and priority to U.S. Provisional Application No. 62/719,937, filed 20 Aug. 2018 and titled MODULATORS OF PROTEOLYSIS AND ASSOCIATED METHODS OF USE, which is incorporated herein in its entirety for all purposes.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/206,497 filed 11 Jul. 2016, published as U.S. Patent Application Publication No. 2017/0008904; and U.S. patent application Ser. No. 15/209,648 filed 13 Jul. 2016, published as U.S. Patent Application Publication No. 2017/0037004; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. patent application Serial No., filed Jan. 31, 2018; and U.S. patent application Ser. No. 15/885,671, filed Jan. 31, 2018, published as U.S. Patent Application Publication No. 2018/0215731 A1; and International Patent Application No. PCT/US2016/023258, filed Mar. 18, 2016, published as International Patent Application Publication No. WO2016/149668, are incorporated herein by reference in their entirety. Furthermore, all references cited herein are incorporated by reference herein in their entirety.

FIELD OF THE INVENTION

The description provides bifunctional compounds comprising a target protein binding moiety and an E3 ubiquitin ligase binding moiety, and associated methods of use. The bifunctional compounds are useful as modulators of targeted ubiquitination, especially with respect to α-synuclein, which is degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases.

Hetero-bifunctional small molecule compounds such as those that are described in U.S. Patent Application Publications 2015-0291562 and 2014-0356322 (incorporated herein by reference), function to recruit target proteins to an E3 ubiquiuin ligase, leading to poly-ubiquitylation of the target protein and its subsequent intracellular degradation via the proteasome. These compounds are comprised of a target protein ligand connected by a chemical linker to an E3 ligase binding moiety. Over the past decade, such compounds have been shown to degrade a variety of target proteins. These compounds provide the ability to turn weak ligands into highly potent degraders, convert promiscuous ligands into selective degraders, and use allosteric sites to degrade proteins.

An ongoing need exists in the art for effective treatments for disease associated with overexpression or aggregation of α-synuclein. However, non-specific effects, and the inability to target and modulate α-synuclein, remain as obstacles to the development of effective treatments. As such, small-molecule therapeutic agents that target α-synuclein and that leverage or potentiate E3 ubiquitin ligase substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as a disease or disorder associated with accumulation or aggregation of α-synuclein. These diseases or disorders include, but are not limited to, α-synucleinopathies or neurological or neurodegenerative diseases or disorders, such as, Parkinson Disease (PD), Alzheimer's Disease (AD), dementia (e.g., dementia with Lewy bodies), or multiple system atrophy.

As such, in one aspect the disclosure provides bifunctional or PROTAC compounds, which comprise an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

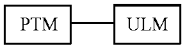

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

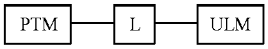

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

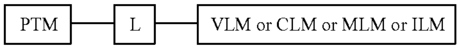

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety that binds MDM2; and ILM is a IAP binding moiety that binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation and/or inhibition in a patient or subject, for example, an animal such as a human, and can be used for treating or ameliorating disease states or conditions which are modulated through the degraded/inhibited protein. In certain embodiments, the therapeutic compositions as described herein may be used to effectuate the degradation of proteins of interest for the treatment or amelioration of a disease, e.g. α-synucleinopathies or a neurodegenerative disease or disorder. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiuitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 2A shows detection of total α-syn using MJFR1 antibody by WES™ analysis. Lanes 20 and 23 show control uninduced sarkosyl insoluble (SI) and soluble lysates, respectively. Total α-syn A53T expression was induced by doxycycline (Dox) and the resulting sarkosyl insoluble versus soluble fraction was characterized by examination of MJFR1 immunoreactivity and is shown in lane 22 compared to 25. Doxycycline (Dox) induced α-syn A53T cells were treated with pre-formed fibrils (PFFs) to produce higher order oligomeric α-syn A53T in the sarkosyl insoluble and soluble fractions, shown in lanes 21 and 24, respectively. In FIG. 2B, data are shown demonstrating that the presence of sarkosyl insoluble phospho-S129 containing α-syn species was only observed after treatment with PFF to induce the higher order oligomeric α-syn A53T (in lane 24 compared to lane 25).

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
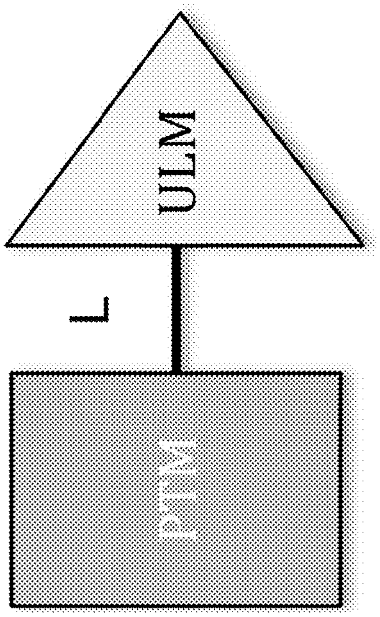
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
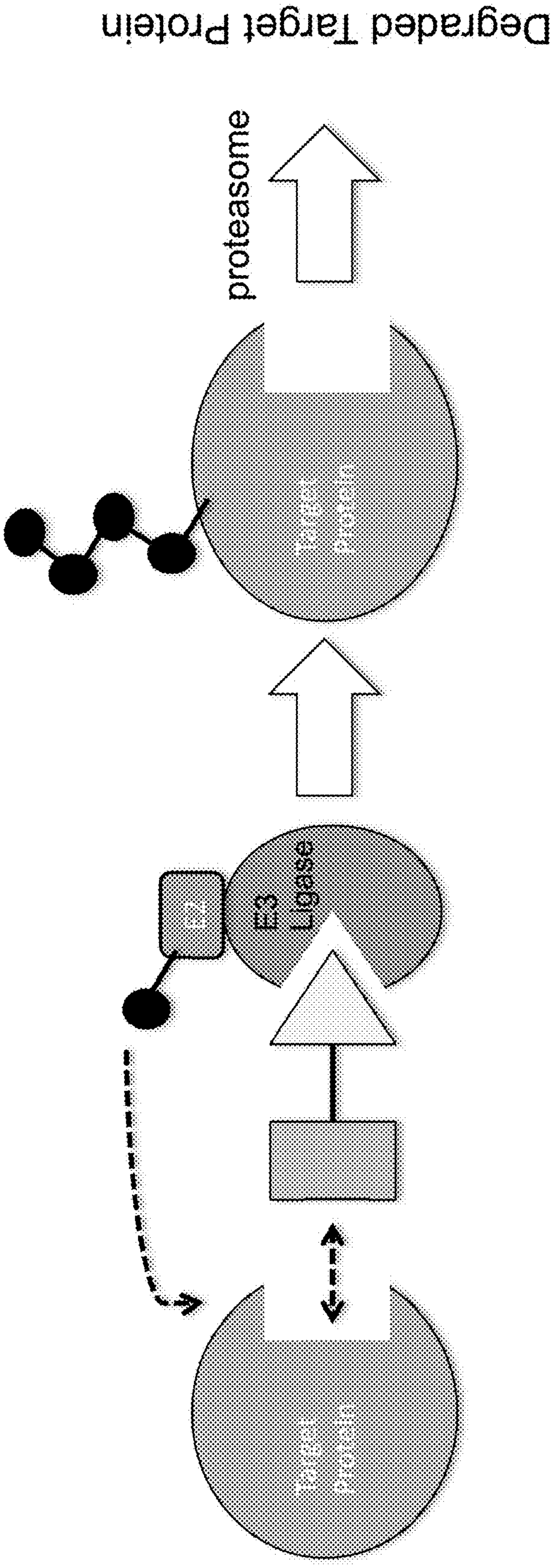

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A. and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anti-neurodegenerative agent. In particularly preferred aspects, the co-administration of compounds results in synergistic activity and/or therapy, including anti-neurodegenerative activity.

The term "anti-neurodegenerative agent" or "additional anti-neurodegenerative agent" is used to describe an anti-neurodegenerative agent, which may be combined with PROTAC compounds according to the present description to treat neurodenerative diseases.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-ILM (C) PTM-CLM (D) PTM-VLM (E) PTM-MLM

In certain embodiments, the bifunctional compound further comprises a chemical linker ("L"). For example, the bifunctional compound can be depicted as:

(F) PTM-L-ILM (G) PTM-L-CLM (H) PTM-L-VLM (I) PTM-L-MLM wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ULMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

(I)

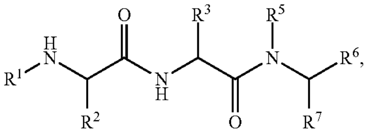

(II)

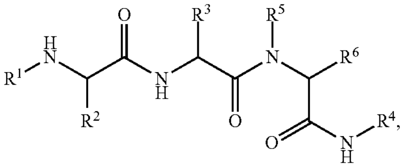

(III)

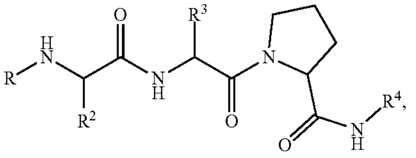

(IV)

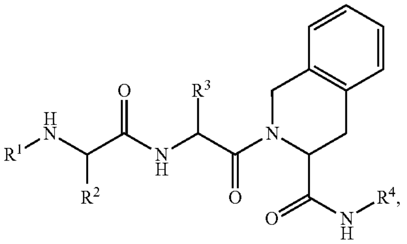

(V)

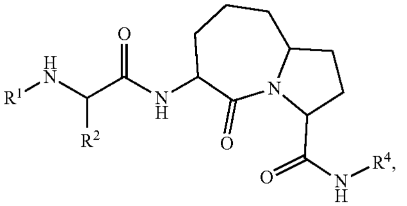

wherein:

$R^1$ for Formulas (I), (II), (III), (IV), and (V) is selected from H or alkyl;

$R^2$ for Formulas (I), (II), (III), (IV), and (V) is selected from H or alkyl;

$R^3$ for Formulas (I), (II), (III), (IV), and (V) is selected from H, alkyl, cycloalkyl and heterocycloalkyl;

$R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;

$R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;

$R^7$ for Formulas (I), (II), (III), (IV), and (V) is selected from cycloalkyl, cycloalkylalkyl, heterocycloalkyl, heterocycloalkylalkyl, aryl, aryl-C(O)—$R^4$, arylalkyl, heteroaryl, heteroaryl-C(O)—$R^4$, heteroaryl-$R^4$, heteroaryl-naphthalene, C(O)NH—$R^4$, or heteroarylalkyl, each one further optionally substituted with 1-3 substituents selected from halogen, alkyl, haloalkyl, hydroxyl, alkoxy, cyano, (hetero)cycloalkyl, (hetero) aryl, —C(O)NH—$R^4$, or —C(O)—$R^4$; and $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

(VI)

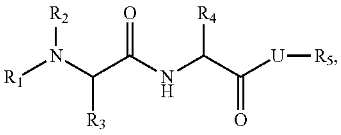

wherein:

$R_1$ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;

$R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;

$R_3$ of Formula (VI) is, independently selected from H, —$CF_3$, —$C_2H_5$, $C_1$-$C_4$-alkyl, $C_1$-$C_4$-alkenyl, $C_1$-$C_4$-alkynyl, —$CH_2$—Z or any $R_2$ and $R_3$ together form a heterocyclic ring; each Z of Formula (VI) is, independently selected from H, —OH, F, Cl, —$CH_3$, —$CF_3$, —$CH_2Cl$, —$CH_2F$ or —$CH_2OH$;

$R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}$—$Z_1$, —$(CH_2)_{0-6}$-aryl, and —$(CH_2)_{0-6}$-het, wherein alkyl, cycloalkyl, and phenyl are unsubstituted or substituted;

$R_5$ of Formula (VI) is, independently selected from H, $C_{1-10}$-alkyl, aryl, phenyl, $C_{3-7}$-cycloalkyl, —$(CH_2)_{1-6}$—$C_{3-7}$-cycloalkyl, —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—CH[$(CH_2)_{1-4}$-phenyl$]_2$, indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl, —$(CH_2)_{0-6}$—C(O)-phenyl, —$(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;

$Z_1$ of Formula (VI) is, independently selected from —$N(R_{10})$—C(O)—$C_{10}$-alkyl, —$N(R_{10})$—C(O)—$(CH_2)_{0-6}$—$C_{3-7}$-cycloalkyl, —$N(R_{10})$—C(O)—$(CH_2)_{0-6}$-phenyl, —$N(R_{10})$—C(O)$(CH_2)_{1-6}$-het, —C(O)—$N(R_{11})(R_{12})$, —C(O)—O—$C_{1-10}$-alkyl, —C(O)—O—$(CH_2)_{1-6}$—$C_{3-7}$-cycloalkyl, —C(O)—O—$(CH_2)_{1-6}$-phenyl, —C(O)—O—$(CH_2)_{1-6}$-het, —O—C(O)—$C_{1-10}$-alkyl, —O—C(O)—$(CH_2)_{1-6}$—$C_{3-7}$-cycloalkyl, —O—C(O)—$(CH_2)_{0-6}$-phenyl, —O—C(O)—$(CH_2)_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ of Formula (VI) is selected from H, —$CH_3$, —$CF_3$, —$CH_2OH$, or —$CH_2Cl$;

$R_{11}$ and $R_{12}$ of Formula (VI) are independently selected from H, $C_{1-4}$-alkyl, $C_{3-7}$-cycloalkyl, —$(CH_2)_{1-6}$—$C_{3-7}$— cycloakyl, $(CH_2)_{0-6}$-phenyl, wherein alkyl, cycloalkyl, and phenyl are unsubstituted or substituted; or $R_{11}$ and $R_{12}$ together with the nitrogen form bet, and U of Formula (VI) is, independently, as shown in Formula (VII):

(VII)

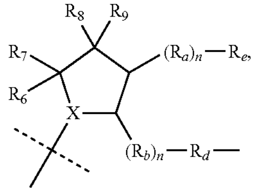

wherein:

each n of Formula (VII) is, independently selected from 0 to 5;

X of Formula (VII) is selected from the group —CH and N;

$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N, and where each alkyl is, independently, either unsubstituted or substituted;

$R_d$ of Formula (VII) is selected from the group Re-Q-$(R_f)_p$ $(R_g)_q$, and $Ar_1$-D-$Ar_2$;

$R_c$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;

p and q of Formula (VII) are independently selected from 0 or 1;

$R_e$ of Formula (VII) is selected from the group $C_{1-8}$-alkyl and alkylidene, and each Re is either unsubstituted or substituted;

Q is selected from the group N, O, S, S(O), and $S(O)_2$;

$Ar_1$ and $Ar_2$ of Formula (VII) are independently selected from the group of substituted or unsubstituted aryl and het;

$R_f$ and $R_g$ of Formula (VII) are independently selected from H, —C1-10-alkyl, $C_{1-10}$-alkylaryl, —OH, —O—$C_{1-10}$-alkyl, —$(CH_2)_{0-6}$—$C_{3-7}$-cycloalky, —O—$(CH_2)_{0-6}$-aryl, phenyl, aryl, phenyl-phenyl, —$(CH_2)_{1-6}$-het, —O—$(CH_2)_{1-6}$-het, —$OR_{13}$, —C(O)—$R_{13}$, —C(O)—$N(R_{13})(R_{14})$, —$N(R_{13})(R_{14})$, —S—$R_{13}$, —$S(O)_2$—$R_{13}$, —$S(O)_2$—$R_{13}$, —$S(O)_2$—$NR_{13}R_{14}$, —$NR_{13}$—$S(O)_2$—$R_{14}$, —S—$C_{t-10}$-alkyl, aryl-$C_{1-4}$-alkyl, or het-$C_{1-4}$-alkyl, wherein alkyl, cycloalkyl, het, and aryl are unsubstituted or substituted, —$SO_2$—$C_{1-2}$-alkyl, —$SO_2$—$C_{1-2}$-alkylphenyl, —O—$C_{1-4}$-alkyl, or any $R_g$ and $R_f$ together form a ring selected from het or aryl;

D of Formula (VII) is selected from the group —CO—, —C(O)—$C_{1-7}$-alkylene or arylene, —$CF_2$—, —O—, —$S(O)_r$ where r is 0-2, 1,3-dioxalane, or $C_{1-7}$-alkyl-OH; where alkyl, alkylene, or arylene are unsubstituted or substituted with one or more halogens, OH, —O—$C_{1-6}$-alkyl, —S—$C_{1-6}$-alkyl, or —$CF_3$; or each D is, independently selected from $N(R_h)$;

Rh is selected from the group H, unsubstituted or substituted $C_{1-7}$-alkyl, aryl, unsubstituted or substituted —O—($C_{1-7}$-cycloalkyl), —C(O)—$C_{1-10}$-alkyl, —C(O)—$C_{0-10}$-alkyl-aryl, —C—O—$C_{01-10}$-alkyl, —C—O—$C_{0-10}$-alkyl-aryl, —$SO_2$—$C_{1-10}$-alkyl, or —$SO_2$—($C_{0-10}$-alkylaryl);

$R_6$, $R_7$, $R_8$, and $R_9$ of Formula (VII) are, independently, selected from the group H, —$C_{1-10}$-alkyl, —$C_{1-10}$-alkoxy, aryl-$C_{1-10}$-alkoxy, —OH, —O—$C_{1-10}$-alkyl, —$(CH_2)_{0-6}$—$C_{3-7}$-cycloalkyl, —O—$(CH_2)_{0-6}$-aryl, phenyl, —$(CH_2)_{1-6}$-het, —O—$(CH_2)_{1-6}$-het, —$OR_{13}$, —C(O)—$R_{13}$, —C(O)—$N(R_{13})(R_{14})$, —$N(R_{13})(R_{14})$, —S—$R_{13}$, —S(O)—$R_{13}$, —$S(O)_2$—$R_{13}$, —$S(O)_2$—$NR_{13}R_{14}$, or —$NR_{13}$—$S(O)_2$—$R_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, $C_{1-10}$-alkyl, —$(CH_2)_{0-6}$—$C_{3-7}$-cycloalkyl, —$(CH_2)_{0-6}$—$(CH)_{0-1}$-$(aryl)_{1-2}$, —C(O)—$C_{1-10}$-alkyl, —C(O)—$(CH_2)_{1-6}$—$C_{3-7}$-cycloalkyl, —C(O)—O—$(CH_2)_{0-6}$-aryl, —C(O)—$(CH_2)_{0-6}$—O-fluorenyl, —C(O)—NH—$(CH_2)_{0-6}$-aryl, —C(O)—$(CH_2)_{0-6}$-aryl, —C(O)—$(CH_2)_{0-6}$-het, —C(S)—$C_{1-10}$-alkyl, —C(S)—$(CH_2)_{1-6}$—$C_{3-7}$-cycloalkyl, —C(S)—O—$(CH_2)_{0-6}$-aryl, —C(S)—$(CH_2)_{0-6}$—O-fluorenyl, —C(S)—NH—$(CH_2)_{0-6}$-aryl, —C(S)—$(CH_2)_{0-6}$-aryl, or —C(S)—$(CH_2)_{1-6}$-het, wherein each alkyl, cycloalkyl, and aryl is unsubstituted or substituted: or any $R_{13}$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —$CF_3$; and substituted phenyl or aryl of $R_{13}$ and $R_{14}$ are substituted by one or more substituents selected from halogen, hydroxyl. $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In any of the compounds described herein, the ILM can have the structure of Formula (VIII), which is based on the IAP ligands described in Ndubaku, C., et al. Antagonism of c-IAP and XIAP proteins is required for efficient induction of cell death by small-molecule IAP antagonists, *ACS Chem. Biol.,* 557-566, 4 (7) (2009), or an unnatural mimetic thereof:

(VIII)

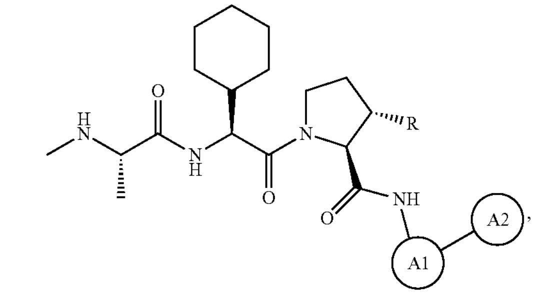

wherein each of A1 and A2 of Formula (VIII) is independently selected from optionally substituted monocyclic, fused rings, aryls and hetoroaryls; and R of Formula (VII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

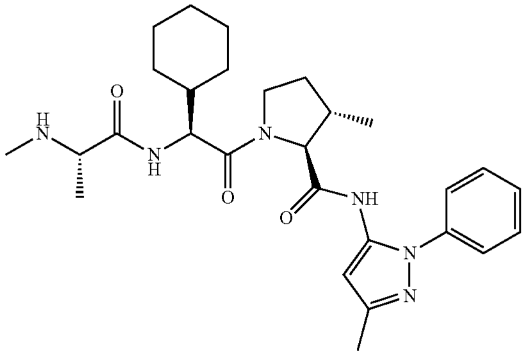

and (B)

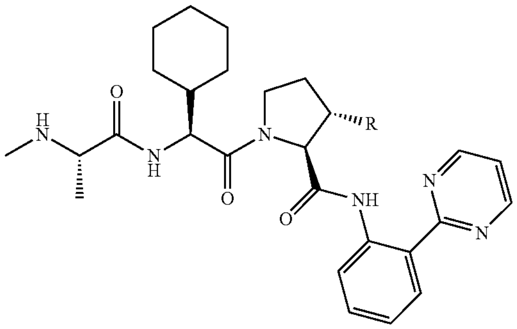

In any of the compounds described herein, the ILM can have the structure of Formula (IX), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(IX)

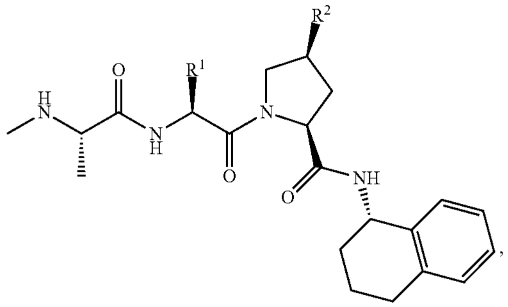

wherein $R^1$ is selected from alkyl, cycloalkyl and heterocycloalkyl and, most preferably, from isopropyl, tert-butyl, cyclohexyl and tetrabydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(X)

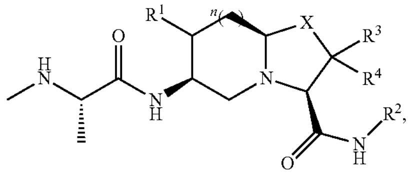

n = 1, 2, 3 wherein:

$R^1$ of Formula (X) is selected from H, —$CH_2OH$, —$CH_2CH_2OH$, —$CH_2NH_2$, —$CH_2CH_2NH_2$;

X of Formula (X) is selected from S or $CH_2$;

$R^2$ of Formula (X) is selected from:

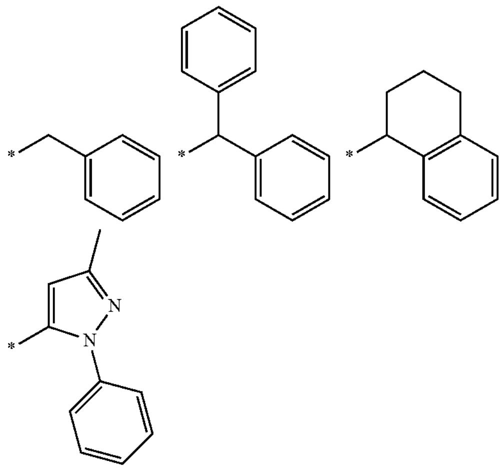

$R^3$ and $R^4$ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XI)

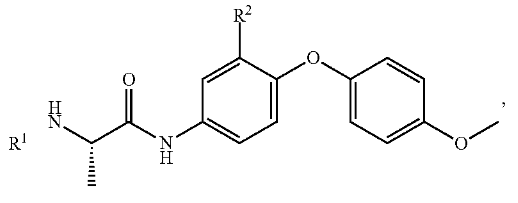

wherein $R^1$ of Formula (XI) is selected from H or Me, and $R^2$ of Formula (XI) is selected from H or

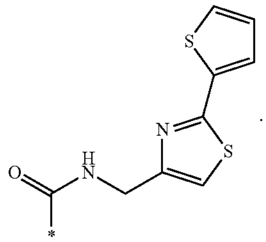 [SMILES: *C(=O)NCc1csc(-c2cccs2)n1]

In any of the compounds described herein, the ILM can have the structure of Formula (XII), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XII)

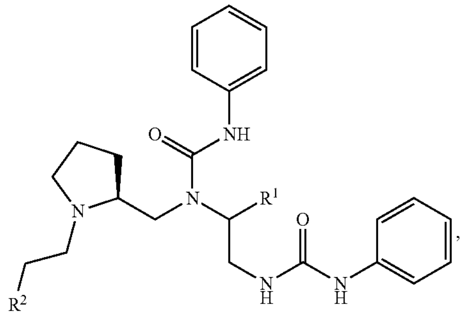

wherein:

$R^1$ of Formula (XII) is selected from:

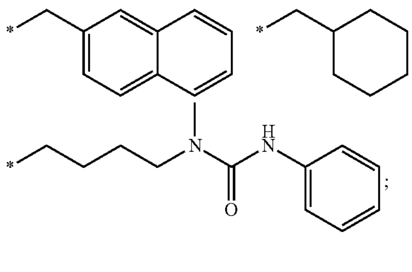

and $R^2$ of Formula (XII) is selected from:

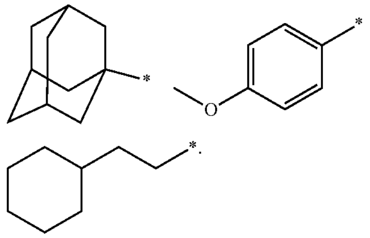

In any of the compounds described herein, the IAP E3 ubiquitin ligase binding moiety is selected from the group consisting of:

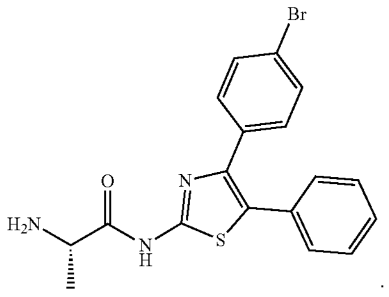 [SMILES: C[C@H](N)C(=O)Nc1nc(-c2ccc(Br)cc2)c(-c2ccccc2)s1]

In any of the compounds described herein, the ILM can have the structure of Formula (XIII), which is based on the IAP ligands summarized in Flygare. J. A., et al. Small-molecule pan-IAP antagonists: a patent review, *Expert Opin. Ther. Pat.,* 20 (2), 251-67 (2010), or an unnatural mimetic thereof:

(XIII)

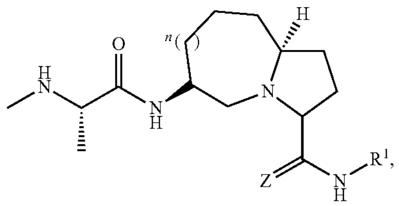

n = 0, 2 or, preferably, 1 wherein:

Z of Formula (XIII) is absent or O;

$R^1$ of Formula (XIII) is selected from:

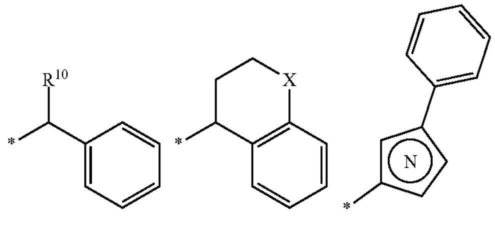

-continued

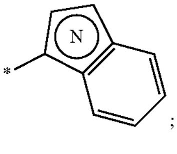

;

$R^{10}$ of

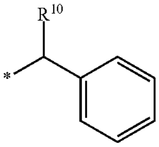

is selected from H, alkyl, or aryl;

X is selected from CH2 and O; and

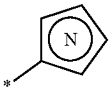

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.,* 20 (2), 251-67 (2010), or an unnatural mimetic thereof:

(XIV)

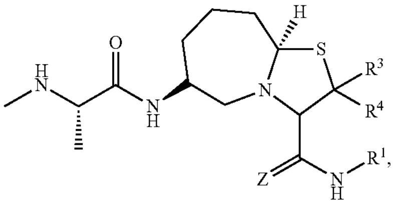

wherein:

Z of Formula (XIV) is absent or O;

$R^3$ and $R^4$ of Formula (XIV) are independently selected from H or Me;

$R^1$ of Formula (XIV) is selected from:

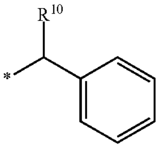

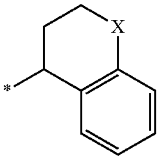

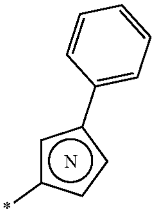

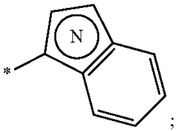

;

$R^{10}$ of

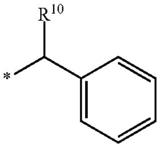

is selected from H, alkyl, or aryl;

X of

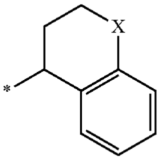

is selected from CH2 and O; and

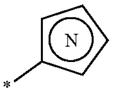

of

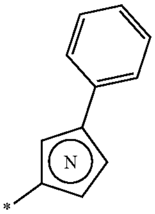

or

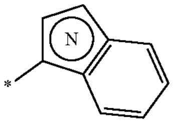

is a nitrogen-containing heteroaryl.

In any of the compounds described herein, the ILM is selected from the group consisting of:

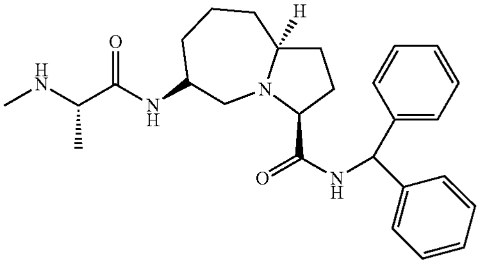

and

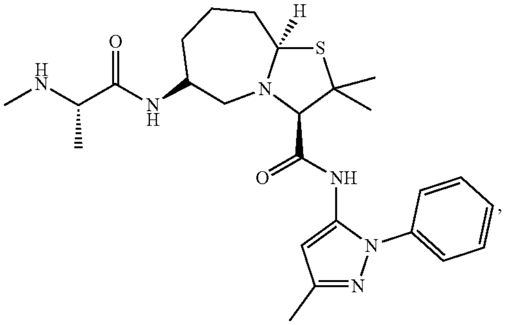

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

(XV)

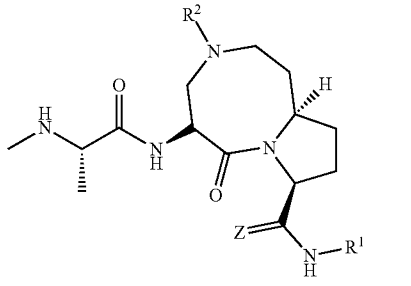

wherein:

Z of Formula (XV) is absent or O;

$R^1$ of Formula (XV) is selected from:

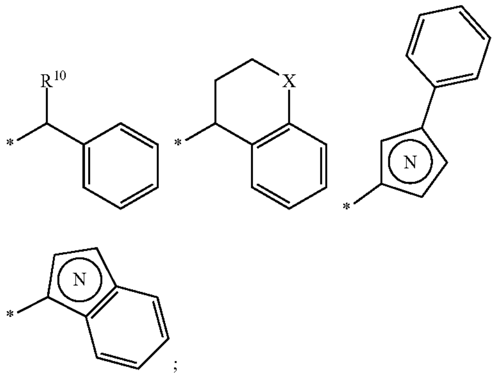

;

$R^{10}$ of

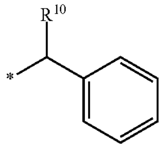

is selected from H, alkyl, or aryl;

X of

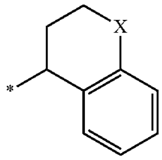

is selected from CH2 and O; and

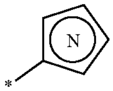

of

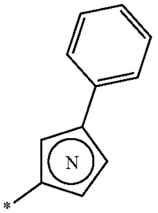

or

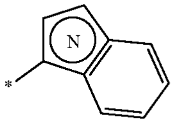

is a nitrogen-containing heteroaryl; and $R^2$ of Formula (XV) selected from H, alkyl, or acyl;

In a particular embodiment, the ILM has the following structure:

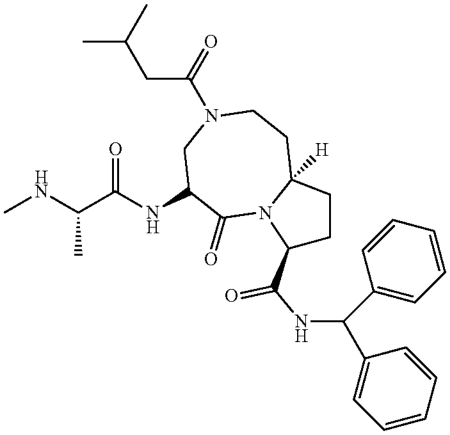

.

In any of the compounds described herein, the ILM can have the structure of Formula (XVI), which is based on the IAP ligand described in WO Pub. No. 2006/069063, or an unnatural mimetic thereof:

(XVI)

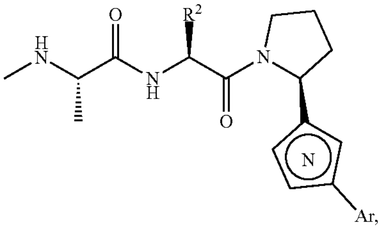

wherein:

$R^2$ of Formula (XVI) is selected from alkyl, cycloalkyl and heterocycloalkyl; more preferably, from isopropyl, tert-butyl, cyclohexyl and tetrahydropyranyl, most preferably from cyclohexyl;

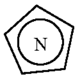

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, *Bioorg. Med. Chem. Lett.,* 20(7), 2229-33 (2010), or an unnatural mimetic thereof:

(XVII)

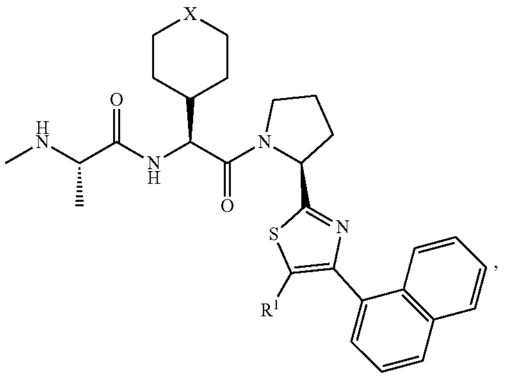

wherein:

$R^1$ of Formula (XVII) is selected from the group halogen (e.g. fluorine), cyano,

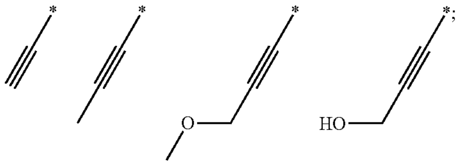

X of Formula (XVII) is selected from the group O or $CH_2$.

In any of the compounds described herein, the ILM can have the structure of Formula (XVIII), which is based on the IAP ligands described in Cohen, F. et al., Antogonists of inhibitors of apoptosis proteins based on thiazole amide isosteres, *Bioorg. Med. Chem. Lett.,* 20(7), 2229-33 (2010), or an unnatural mimetic thereof:

(XVIII)

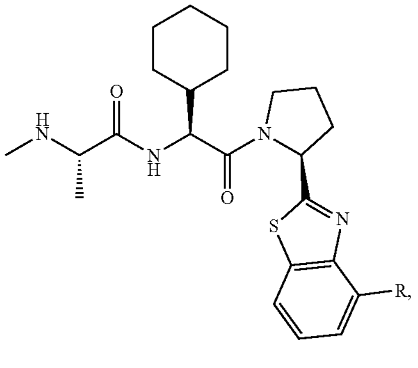

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., Antogonists of inhibitors of apoptosis proteins based on thiazole amide isosteres, *Bioorg. Med. Chem. Lett.,* 20(7), 2229-33 (2010), or an unnatural mimetic thereof:

(XIX)

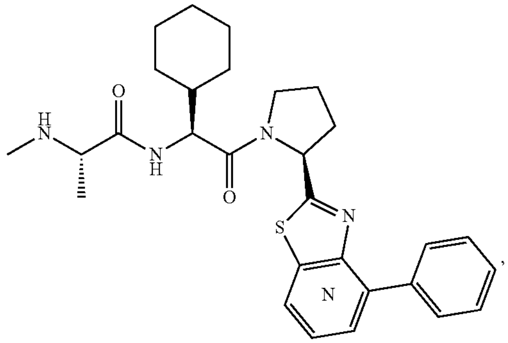

wherein

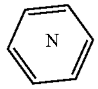

is a 6-member nitrogen heteroaryl.

In a certain embodiment, the ILM of the composition is selected from the group consisting of:

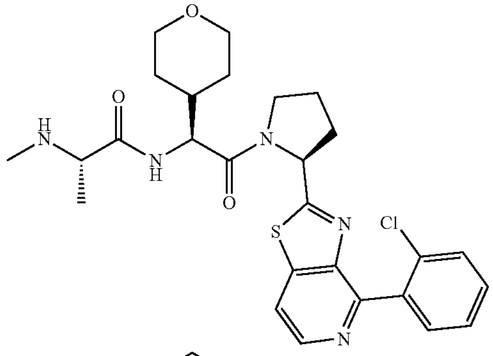

and

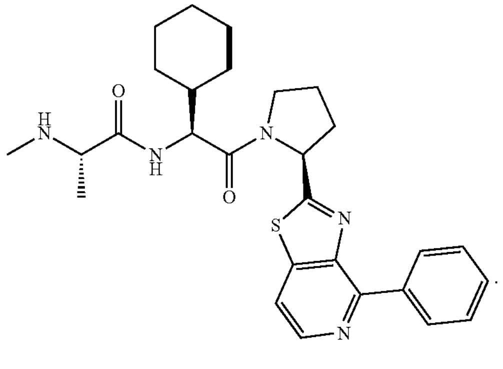

In certain embodiments, the ILM of the composition is selected from the group consisting of:

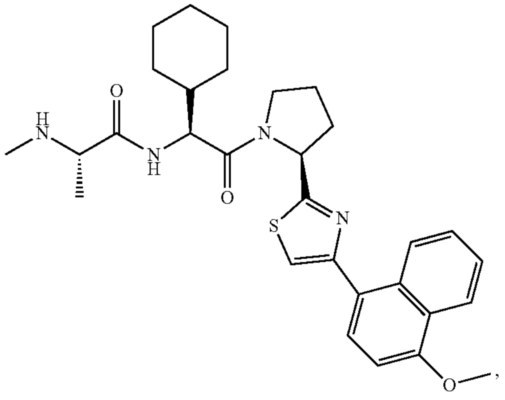

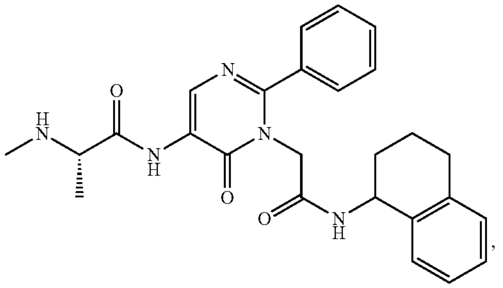

and

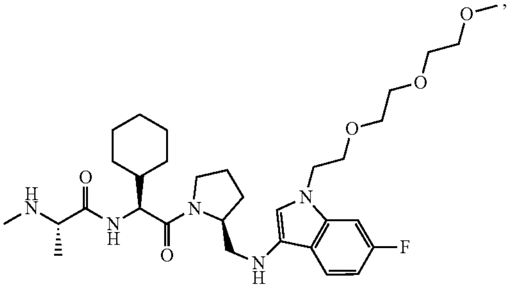

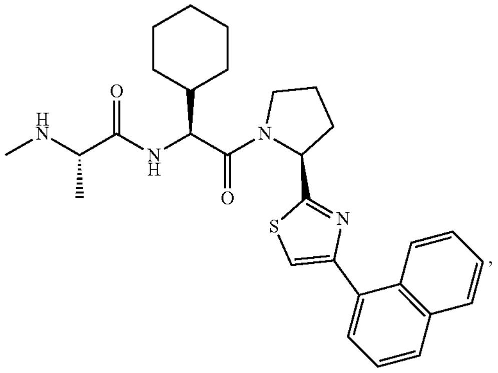 [SMILES: CN[C@H](C)C(=O)N[C@@H](C(=O)N1CCC[C@@H]1c1nc(-c2cccc3ccccc23)cs1)C1CCCCC1]

-continued

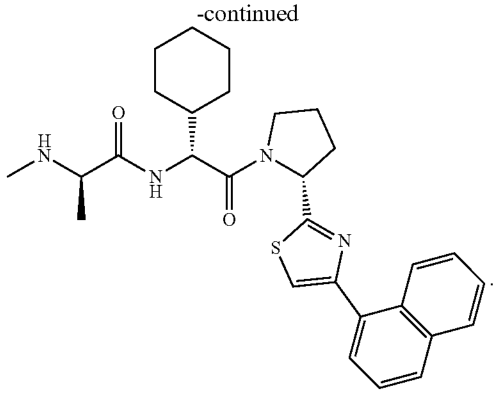

In any of the compounds described herein, the ILM can have the structure of Formula (XX), which is based on the IAP ligands described in WO Pub. No. 2007/101347, or an unnatural mimetic thereof:

(XX)

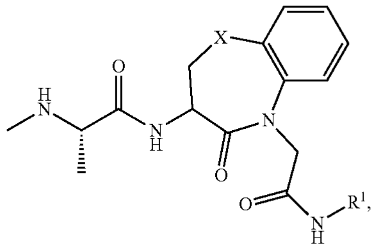

wherein X of Formula (XX) is selected from $CH_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

(XXI)

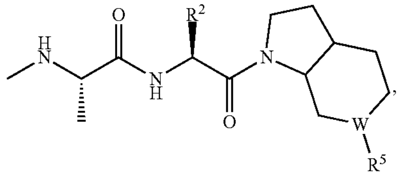

wherein:

$R^2$ of Formula (XXI) is selected from:

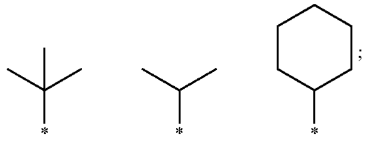

$R^5$ of Formula (XXI) is selected from:

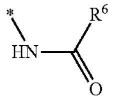
and
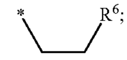

and

W of Formula (XXI) is selected from CH or N; and $R^6$ of

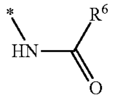
and
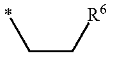

are independently a mono- or bicyclic fused aryl or heteroaryl.

In certain embodiments, the ILM of the compound is selected from the group consisting of:

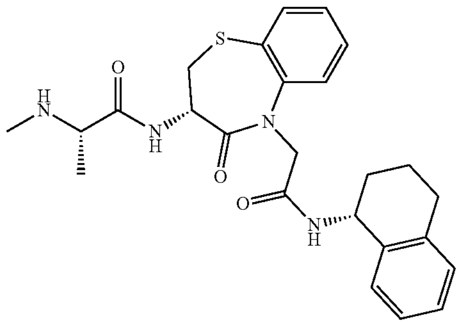
,

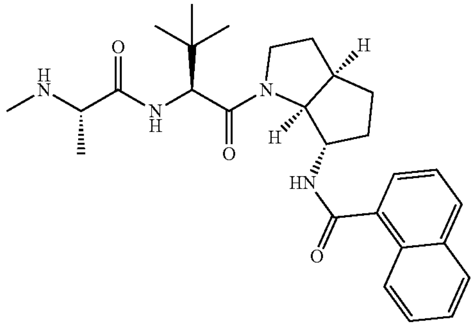
, and

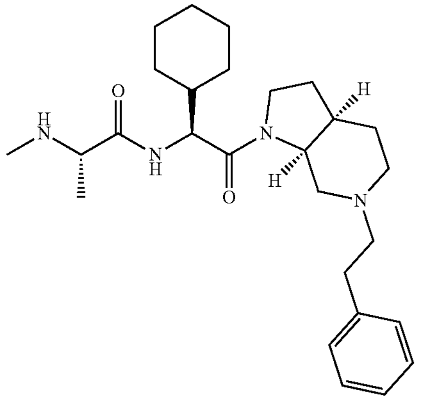

In any of the compounds described herein, the ILM can have the structure of Formula (XXII) or (XXIV), which are derived from the IAP ligands described in WO Pub. No. 2015/006524 and Perez H L, Discovery of potent heterodimeric antagonists of inhibitor of apoptosis proteins (IAPs) with sustained antitumor activity. *J. Med. Chem.* 58(3), 1556-62 (2015), or an unnatural mimetic thereof, and the chemical linker to linker group L as shown:

(XXII)

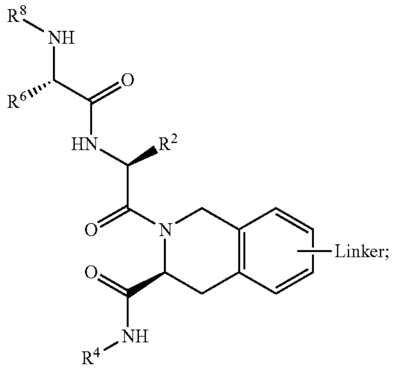

(XXIII)

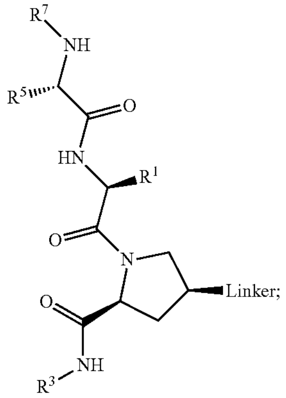
or (XXIV)

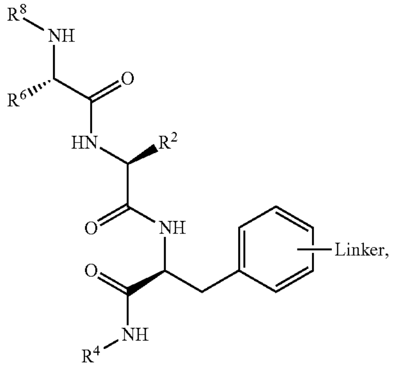

wherein:

$R^1$ of Formula (XXII), (XXIII) or (XXIV) is selected from optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXII), (XXIII) or (XXIV) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXII), (XXIII) or (XXIV) are independently selected from optionally substituted thioalkyl wherein the substituents attached to the S atom of the thioalkyl are optionally substituted alkyl, optionally substituted branched alkyl, optionally substituted heterocyclyl, $-(CH_2)_vCOR^{20}$, $-CH_2CHR^{21}COR^{22}$ or $-CH_2R^{23}$, wherein:

v is an integer from 1-3;

$R^{20}$ and $R^{22}$ of $-(CH_2)_vCOR^{20}$ and $-CH_2R^2$ are independently selected from OH, $NR^{24}R^{25}$ or $OR^{26}$;

$R^{21}$ of $-CH_2CHR^{21}COR^2$ is selected from $NR^{24}R^{25}$;

$R^{23}$ of $-CH_2R^{23}$ is selected from optionally substituted aryl or optionally substituted heterocyclyl, wherein the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $-CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXII), (XXIII) or (XXIV) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII), (XXIII) or (XXIV) are independently hydrogen, optionally substituted alkyl or optionally substituted cycloalkyl;

and/or a pharmaceutically acceptable salt, tautomer or stereoisomer thereof.

In a particular embodiment, the ILM according to Formulas (XXII) through (XXIV):

$R^7$ and $R^8$ are selected from the H or Me;

$R^5$ and $R^6$ are selected from the group comprising:

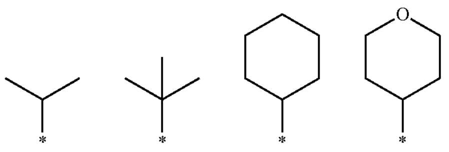

$R^3$ and $R^4$ are selected from the group comprising:

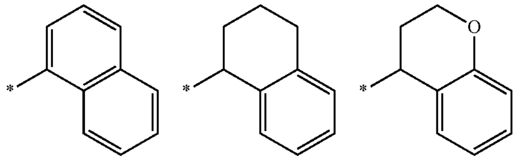

-continued

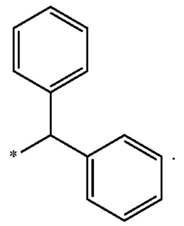

In any of the compounds described herein, the ILM can have the structure of Formula (XXV), (XXVI), (XXVII), or (XXVIII), which are derived from the IAP ligands described in WO Pub. No. 2014/055461 and Kim, K S, Discovery of tetrahydroisoquinoline-based bivalent heterodimeric IAP antagonists. *Bioorg. Med. Chem. Lett.* 24(21), 5022-9 (2014), or an unnatural mimetic thereof, and the chemical linker to linker group L as shown:

(XXV)

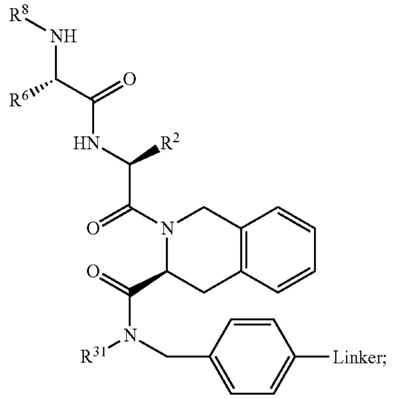

(XXVI)

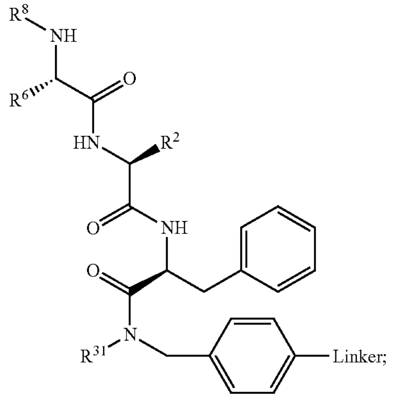

(XXVII)

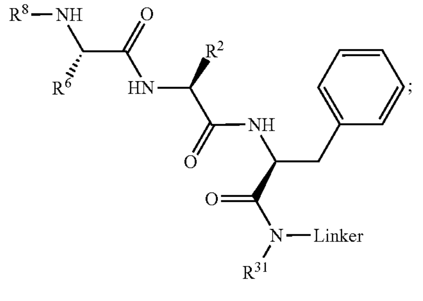

and

-continued (XXVIII)

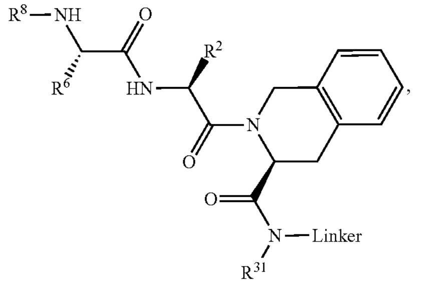

wherein:

$R^2$ of Formula (XXV) through (XXVIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;

$R^1$ and $R^2$ of Formula (XXV) through (XXVIII) are independently selected from H, an optionally substituted thioalkyl —$CR^{60}R^{61}SR^{70}$ wherein $R_{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]\psi CH_2CH_2(CH_2)\overline{\omega},NH_2$, such as spermine or spermidine, wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$;

m is an integer from 1-8;

$R^6$ and $R^8$ of Formula (XXV) through (XXVIII) are independently selected from hydrogen, optionally substituted alkyl or optionally substituted cycloalkyl; and $R^{31}$ of Formulas (XXV) through (XXVIII) is selected from alkyl, aryl, arylalkyl, heteroaryl or heteroarylalkyl optionally further substituted, preferably selected form the group consisting of:

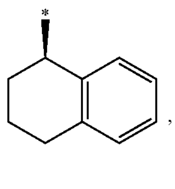
,
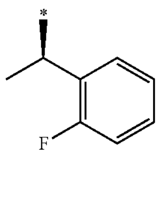
,

-continued

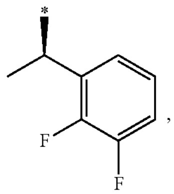
,
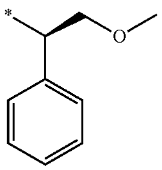
, and
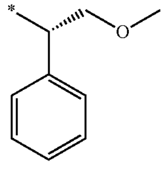
.

In any of the compounds described herein, the ILM can have the structure of Formula (XXIX) or (XXX), which are derived from the IAP ligands described in WO Pub. No. 2013/071039, or an unnatural mimetic thereof:

(XXIX)

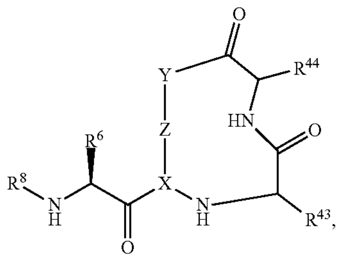

(XXX)

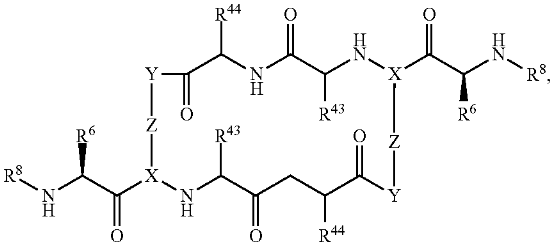

wherein:

$R^{43}$ and $R^{44}$ of Formulas (XXIX) and (XXX) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXIX) and (XXX) are independently selected from hydrogen, optionally substituted alkyl or optionally substituted cycloalkyl.

each X of Formulas (XXIX) and (XXX) is independently selected from:

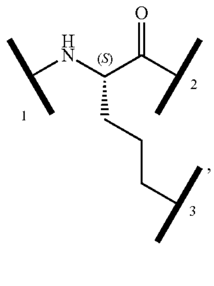
,

-continued
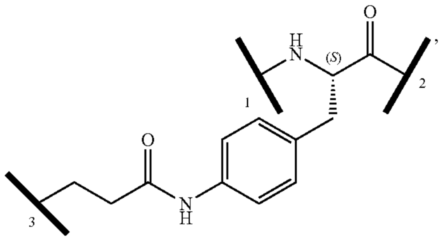
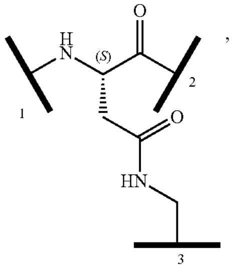
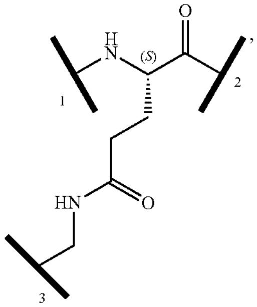
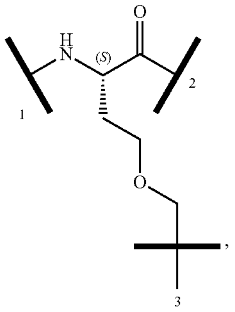
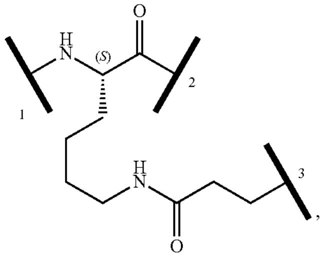
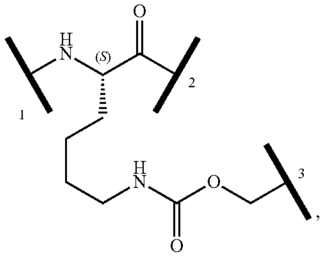
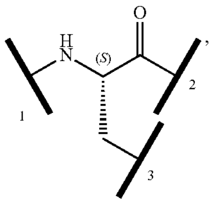
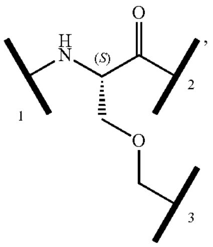
-continued
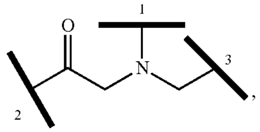
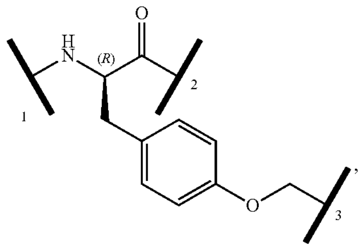
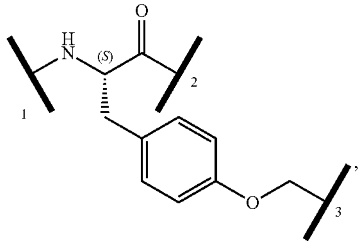
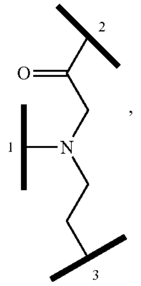
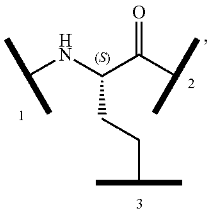
and
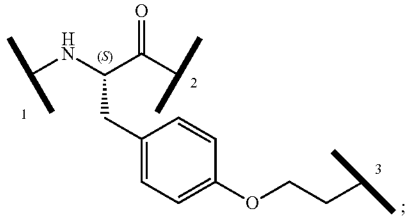
each Z of Formulas (XXIX) and (XXX) is selected from
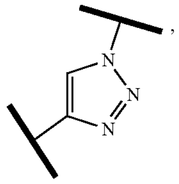
wherein each
represents a point of attachment to the compound; and each Y is selected from:
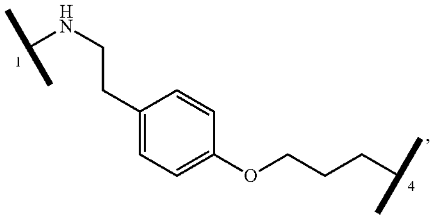
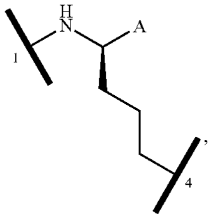
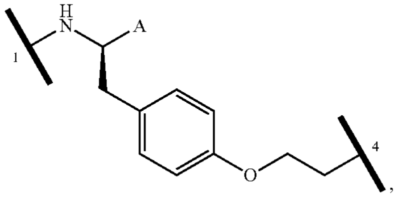
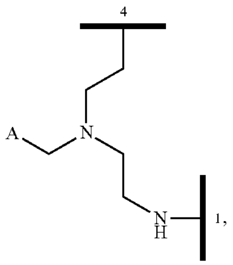
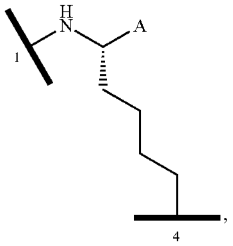
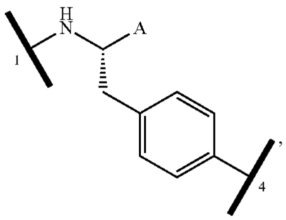
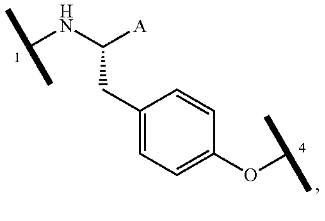
-continued
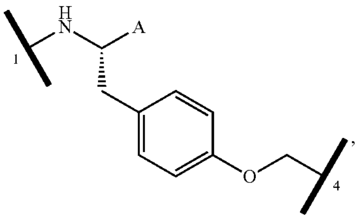
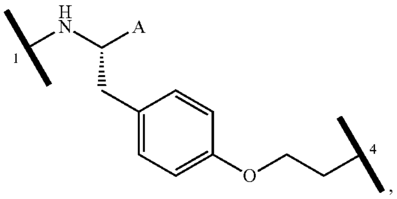
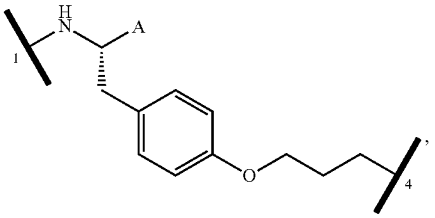
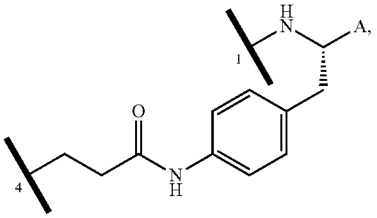
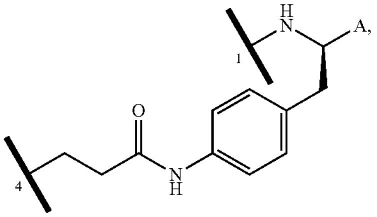
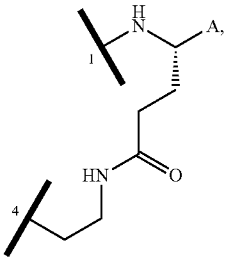
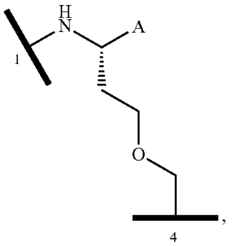

-continued
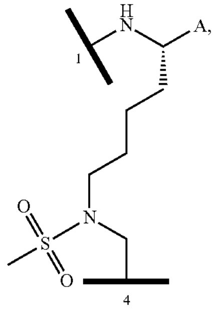
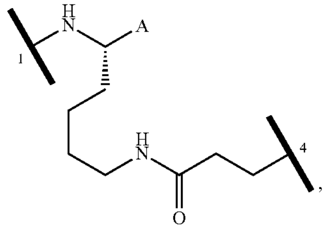
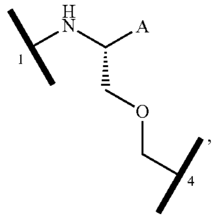
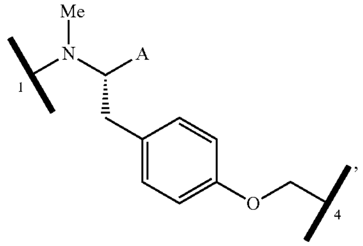
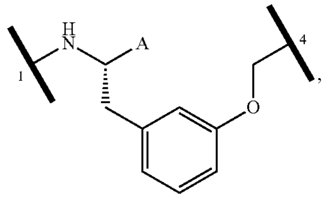
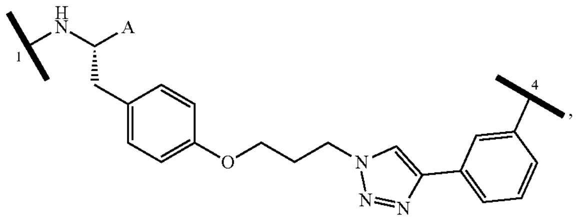
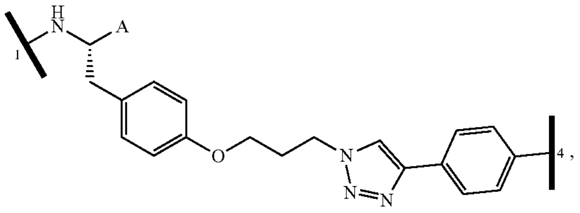
-continued
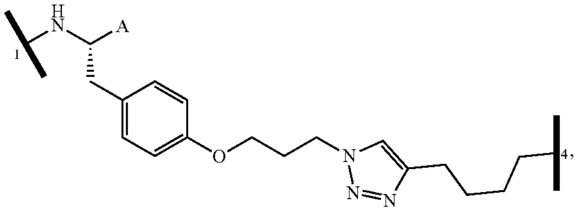
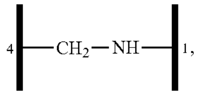
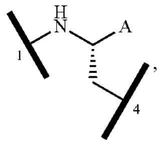
and
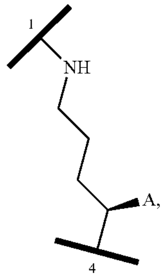
wherein:
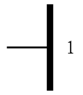
represents a point of attachment to a —C═O portion of the compound;
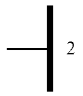
represents a point of attachment to an amino portion of the compound;
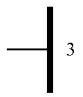
represents a first point of attachment to Z;
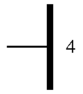
represents a second point of attachment to Z; and A is selected from $-C(O)R^3$ or

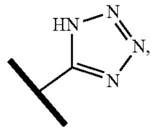, 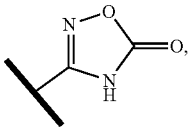,

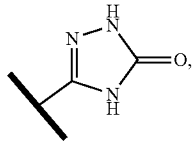, 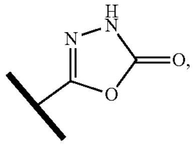,

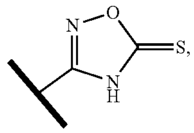, 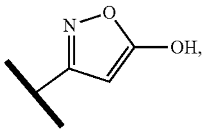,

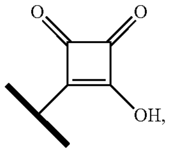, 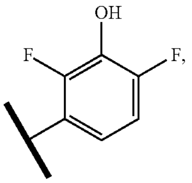, or a tautomeric form of any of the foregoing, wherein:

$R^3$ of $-C(O)R^3$ is selected from OH, NHCN, $NHSO_2R^{10}$, $NHOR^{11}$ or $N(R^{12})(R^{13})$;

$R^{10}$ and $R^{11}$ of $NHSO_2R^{10}$ and $NHOR^{11}$ are independently selected from $-C_1$-$C_4$ alkyl, cycloalkyl, aryl, heteroaryl, or heterocycloalkyl, any of which are optionally substituted, and hydrogen;

each of $R^{12}$ and $R^{13}$ of $N(R^{12})(R^{13})$ are independently selected from hydrogen, $-C_1$-$C_4$ alkyl, $-(C_1$-$C_4$ alkylene)-NH$-(C_1$-$C_4$ alkyl), benzyl, $-(C_1$-$C_4$ alkylene)-C(O)OH, $-(C_1$-$C_4$alkylene)-C(O)$CH_3$, —CH(benzyl)-COOH, $-C_1$-$C_4$ alkoxy, and $-(C_1$-$C_4$ alkylene)-O$-(C_1$-$C_4$ hydroxyalkyl); or $R^{12}$ and $R^{13}$ of $N(R^{12})(R^{13})$ are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXI), which are derived from the IAP ligands described in WO Pub. No. 2013/071039, or an unnatural mimetic thereof:

(XXXI)

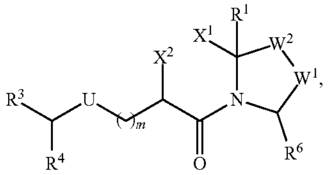

wherein:

$W^1$ of Formula (XXXI) is selected from O, S, N—$R^A$, or $C(R^{8a})(R^{8b})$ $W^2$ of Formula (XXXI) is selected from O, S, N—$R^A$, or $C(R^{8c})(R^{8d})$; provided that $W^1$ and $W^2$ are not both O, or both S;

$R^1$ of Formula (XXXI) is selected from H, $C_1$-$C_6$alkyl, $C_3$-$C_6$cycloalkyl, $-C_1$-$C_6$alkyl-(substituted or unsubstituted $C_3$-$C_6$cycloalkyl), substituted or unsubstituted aryl, substituted or unsubstituted heteroaryl, $-C_1$-$C_6$alkyl-(substituted or unsubstituted aryl), or $-C_1$-$C_6$alkyl-(substituted or unsubstituted heteroaryl);

when $X^1$ is selected from O, N—$R^A$, S, S(O), or $S(O)_2$, then $X^2$ is $C(R^{2a}R^{2b})$;

or:

$X^1$ of Formula (XXXI) is selected from $CR^{2c}R^{2d}$ and $X^2$ is $CR^{2a}R^{2b}$, and $R^{2c}$ and $R^{2a}$ together form a bond;

or:

$X^1$ and $X^2$ of Formula (XXXI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ of Formula (XXXI) is selected from $CH_2$ and $X^2$ is C=0, $C{\equiv}C(R^C)_2$, or $C{\equiv}NR^C$; where each $R^c$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, $-C_1$-$C_6$alkyl-(substituted or unsubstituted $C_3$-$C_6$cycloalkyl), $-C_1$-$C_6$alkyl-(substituted or unsubstituted $C_2$-$C_5$heterocycloalkyl), $-C_1$-$C_6$alkyl-(substituted or unsubstituted aryl), or $-C_1$-$C_6$alkyl-(substituted or unsubstituted heteroaryl);

$R^A$ of N—$R^A$ is selected from H, $C_1$-$C_6$alkyl, —C(=O)$C_1$-$C_2$alkyl, substituted or unsubstituted aryl, or substituted or unsubstituted heteroaryl;

$R^{2a}$, $R^{2b}$, $R^{2c}$, $R^{2d}$ of $CR^{2c}R^{2d}$ and $CR^{2a}R^{2b}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, $-C_1$-$C_6$alkyl-(substituted or unsubstituted $C_3$-$C_6$cycloalkyl), $-C_1$-$C_6$alkyl-(substituted or unsubstituted $C_2$-$C_5$heterocycloalkyl), $-C_1$-$C_6$alkyl- (substituted or unsubstituted aryl), $-C_1$-$C_6$alkyl-(substituted or unsubstituted heteroaryl) and $-C(=O)R^B$;

$R^B$ of $-C(=O)R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, $-C_1$-$C_6$alkyl-(substituted or unsubstituted $C_3$-$C_6$cycloalkyl), $-C_1$-$C_6$alkyl-(substituted or unsubstituted $C_2$-$C_5$heterocycloalkyl), $-C_1$-$C_6$alkyl- (substituted or unsubstituted aryl), $-C_1$-$C_6$alkyl-(substituted or unsubstituted heteroaryl), or $-NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, $-C_1$-$C_6$alkyl- (substituted or unsubstituted $C_3$-$C_6$cycloalkyl), $-C_1$-$C_6$alkyl-(substituted or unsubstituted $C_2$-$C_5$heterocycloalkyl), $-C_1$-$C_6$alkyl-(substituted or unsubstituted aryl), or —$C_1$-$C_6$alkyl- (substituted or unsubstituted heteroaryl);

m of Formula (XXXI) is selected from 0, 1 or 2;

—U— of Formula (XXXI) is selected from —NHC(═O)—, —C(═O)NH—, —NHS(═O)$_2$—, —S(═O)$_2$ NH—, —NHC(═O)NH—, —NH(C═O)O—, —O(C═O)NH—, or —NHS(═O)$_2$NH—;

$R^3$ of Formula (XXXI) is selected from $C_1$-$C_3$alkyl, or $C_1$-$C_3$fluoroalkyl;

$R^4$ of Formula (XXXI) is selected from —NHR$^5$, —N(R$^5$)2, —N+(R$^5$)3 or —OR$^5$;

each $R^5$ of —NHR$^5$, —N(R$^5$)2, —N+(R$^5$)3 and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXI) together with the atoms to which they are attached form a substituted or unsubstituted 5-7 membered ring;

or:

$R^3$ of Formula (XXXI) is bonded to a nitrogen atom of U to form a substituted or unsubstituted 5-7 membered ring;

$R^6$ of Formula (XXXI) is selected from —NHC(═O)R$^7$, —C(═O)NHR$^7$, —NHS(═O)2R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)$_2$R$^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)$_2$NHR$^7$, substituted or unsubstituted $C_2$-$C_{10}$heterocycloalkyl, or substituted or unsubstituted heteroaryl;

each $R^7$ of —NHC(═O)R$^7$, —C(═O)NHR$^7$, —NHS(═O)$_2$R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)$_2$R$^7$, —($C_1$-$C_3$alkyl)-S(═O)2NHR$^7$; —($C_1$-$C_3$alkyl)-NHC(═O)NHR$^7$, —($C_1$-$C_3$alkyl)-NHS(═O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)$_2$, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C(R$^{8a}$)(R$^{8b}$) and C(R$^{8c}$)(R$^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(═O)OH, —C(═O)NH$_2$, —C(═O)$C_1$-$C_3$alkyl, —S(═O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXII), which are derived from the IAP ligands described in WO Pub. No. 2013/071039, or an unnatural mimetic thereof:

(XXXII)

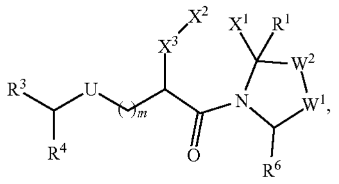

wherein:

$W^1$ of Formula (XXXII) is O, S, N—R$^A$, or C(R$^{8a}$)(R$^{8b}$);

$W^2$ of Formula (XXXII) is O, S, N—R$^A$, or C(R$^{8c}$)(R$^{8d}$); provided that $W^1$ and $W^2$ are not both O, or both S;

$R^1$ of Formula (XXXII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XXXII) is N—R$^A$, then $X^2$ is C═O, or CR$^{2c}$R$^{2d}$, and $X^3$ is CR$^{2a}$R$^{2b}$;

or:

when $X^1$ of Formula (XXXII) is selected from S, S(O), or S(O)$_2$, then $X^2$ is CR$^{2c}$R$^{2d}$, and $X^3$ is CR$^{2a}$R$^{2b}$;

or:

when $X^1$ of Formula (XXXII) is O, then $X^2$ is $CR^{2c}R^{2d}$ and N—$R^A$ and $X^3$ is $CR^{2a}R^{2b}$;

or:

when $X^1$ of Formula (XXXII) is $CH_3$, then $X^2$ is selected from O, N—$R^A$, 5, S(O), or $S(O)_2$, and $X^3$ is $CR^{2a}R^{2b}$;

when $X^1$ of Formula (XXXII) is $CR^{2e}R^{2f}$ and $X^2$ is $CR^{2c}R^{2d}$, and $R^{2e}$ and $R^{2c}$ together form a bond, and $X^3$ of Formula (XXXII) is $CR^{2a}R^{2b}$;

or:

$X^1$ and $X^3$ of Formula (XXXII) are both $CH_2$ and $X^2$ of Formula (XXXII) is C═O, C≡C($R^{2c}$)2, or C≡N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

or:

$X^1$ and $X^2$ of Formula (XXXII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XXXII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XXXII) is $CR^{2e}R^{2f}$;

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XXXII) is selected from 0, 1 or 2;

—U— of Formula (XXXII) is selected from —NHC(═O)—, —C(═O)NH—, —NHS(═O)$_2$—, —S(═O)$_2$ NH—, —NHC(═O)NH—, —NH(C═O)O—, —O(C═O)NH—, or —NHS(═O)$_2$NH—;

$R^3$ of Formula (XXXII) is selected from $C_1$-$C_3$alkyl, or $C_1$-$C_3$fluoroalkyl;

$R^4$ of Formula (XXXII) is selected from —NHR$^5$, —N($R^5$)$_2$, —N+($R^5$)$_3$ or —OR$^5$;

each $R^5$ of —NHR$^5$, —N($R^5$)$_2$, —N+($R^5$)$_3$ and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXII) together with the atoms to which they are attached form a substituted or unsubstituted 5-7 membered ring;

or:

$R^3$ of Formula (XXXII) is bonded to a nitrogen atom of U to form a substituted or unsubstituted 5-7 membered ring;

$R^6$ of Formula (XXXII) is selected from —NHC(═O)$R^7$, —C(═O)NHR$^7$, —NHS(═O)$_2R^7$, —S(═O)$_2$NHR$^7$; —NHC(═O)NHR$^7$, —NHS(═O)$_2$NHR$^7$, —($C_1$-$C_3$alkyl)-NHC(═O)$R^7$, —($C_1$-$C_3$alkyl)-C(═O)NHR$^7$, —($C_1$-$C_3$alkyl)-NHS(═O)$_2R^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)$_2$NHR$^7$, substituted or unsubstituted $C_2$-$C_{10}$heterocycloalkyl, or substituted or unsubstituted heteroaryl;

each $R^7$ of —NHC(═O)$R^7$, —C(═O)NHR$^7$, —NHS(═O)$_2R^7$, —S(═O)$_2$NHR$^7$; —NHC(═O)NHR$^7$, —NHS(═O)$_2$NHR$^7$, —($C_1$-$C_3$alkyl)-NHC(═O)$R^7$, —($C_1$-$C_3$alkyl)-C(═O)NHR$^7$, —($C_1$-$C_3$alkyl)-NHS(═O)2$R^7$, —($C_1$-$C_3$alkyl)-S(═O)2NHR$^7$; —($C_1$-$C_3$alkyl)-NHC(═O)NHR$^7$, —($C_1$-$C_3$alkyl)-NHS(═O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl- (substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —($CH_2$)$_p$—CH(substituted or unsubstituted heteroaryl)2, —($CH_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIII), which is derived from the IAP ligands described in WO Pub. No. 2013/071039, or an unnatural mimetic thereof:

(XXXIII)

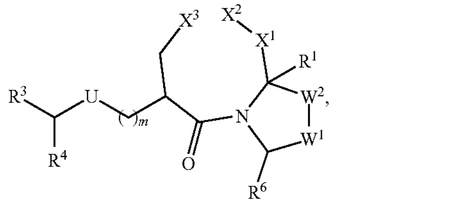

wherein:

$W^1$ of Formula (XXXIII) is selected from O, S, N—$R^A$, or $C(R^{8a})(R^{8b})$;

$W^2$ of Formula (XXXIII) is selected from O, S, N—$R^A$, or $C(R^{8c})(R^{8d})$; provided that $W^1$ and $W^2$ are not both O, or both S;

$R^1$ of Formula (XXXIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XXXII) is selected from N—$R^A$, S, S(O), or S(O)$_2$, then $X^2$ of Formula (XXXIII) is $CR^{2c}R^{2d}$, and $X^3$ of Formula (XXXIII) is $CR^{2a}R^{2b}$;

or:

when $X^1$ of Formula (XXXIII) is O, then $X^2$ of Formula (XXXIII) is selected from O, N—$R^A$, S, S(O), or S(O)$_2$, and $X^3$ of Formula (XXXIII) is $CR^{2a}R^{2b}$;

or:

when $X^1$ of Formula (XXXIII) is $CR^{2e}R^{2f}$ and $X^2$ of Formula (XXXIII) is $CR^{2c}R^{2d}$, and $R^{2e}$ and $R^{2c}$ together form a bond, and $X^3$ of Formula (XXXIII) is $CR^{2a}R^{2b}$;

or:

$X^1$ and $X^2$ of Formula (XXXIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XXXIII) is $CR^{2a}R^{2b}$;

or:

$X^2$ and $X^3$ of Formula (XXXIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XXXIII) is $CR^{2e}R^{2f}$;

$R^A$ of N—$R^A$ is H, $C_1$-$C_6$alkyl, —C(═O)$C_1$-$C_2$alkyl, substituted or unsubstituted aryl. or substituted or unsubstituted heteroaryl;

$R^{2a}$, $R^{2b}$, $R^{2c}$, $R^{2d}$, $R^{2e}$, and $R^{2f}$ of $CR^{2c}CR^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XXXIII) is 0, 1 or 2;

—U— of Formula (XXXIII) is —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XXXIII) is $C_1$-$C_3$alkyl, or $C_1$-$C_3$fluoroalkyl;

$R^4$ of Formula (XXXIII) is —NHR$^5$, —N(R$^5$)$_2$, —N+(R$^5$)$_3$ or —OR$^5$;

each $R^5$ of —NHR$^5$, —N(R$^5$)$_2$, —N+(R$^5$)$_3$ and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXXIII) together with the atoms to which they are attached form a substituted or unsubstituted 5-7 membered ring;

or:

$R^3$ of Formula (XXXIII) is bonded to a nitrogen atom of U to form a substituted or unsubstituted 5-7 membered ring;

$R^6$ of Formula (XXXIII) is selected from —NHC(═O)R$^7$, —C(═O)NHR$^7$, —NHS(═O)2R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)$_2$R$^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)$_2$NHR$^7$, substituted or unsubstituted $C_2$-$C_{10}$heterocycloalkyl, or substituted or unsubstituted heteroaryl;

each $R^7$ of —NHC(═O)R$^7$, —C(═O)NHR$^7$, —NHS(═O)$_2$R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)2R$^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH (substituted or unsubstituted aryl)2, —(CH$_2$)$_p$—CH (substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8a}$ and $R^{8b}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R_{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8a}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(═O)OH, —C(═O)NH$_2$, —C(═O)$C_1$-$C_3$alkyl, —S(═O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXIV), which is derived from the IAP ligands described in WO Pub. No. 2013/071039, or an unnatural mimetic thereof:

(XXIV)

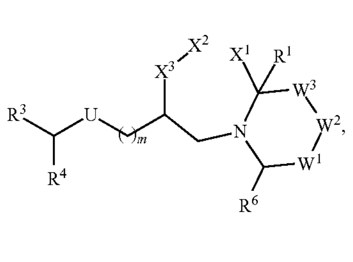

wherein:

$W^1$ of Formula (XXIV) is selected from O, S, N—$R^A$, or C($R^{8a}$)($R^{8b}$)

$W^2$ of Formula (XXIV) is selected from O, S, N—$R^A$, or C($R^{8c}$)($R^{8d}$); provided that $W^1$ and $W^2$ are not both O, or both S;

$W^3$ of Formula (XXIV) is selected from O, S, N—$R^A$, or C($R^{8e}$)($R^{8f}$), providing that the ring comprising $W^1$, $W^2$, and $W^3$ does not comprise two adjacent oxygen atoms or sulfur atoms;

$R^1$ of Formula (XXIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XXIV) is O, then $X^2$ of Formula (XXIV) is selected from $CR^{2c}R^{2d}$ and N—$R^A$, and $X^3$ of Formula (XXIV) is $CR^{2a}R^{2b}$;

or:

when $X^1$ of Formula (XXIV) is $CH_2$, then $X^2$ of Formula (XXIV) is selected from O, N—$R^A$, S, S(O), or $S(O)_2$, and $X^3$ of Formula (XXIV) is $CR^{2a}R^{2b}$;

or:

when $X^1$ of Formula (XXIV) is $CR^{2e}R^{2f}$ and $X^2$ of Formula (XXIV) is $CR^{2c}R^{2d}$, and $R^{2e}$ and $R^{2c}$ together form a bond, and $X^3$ of Formula (XXIV) is $CR^{2a}R^{2b}$;

or:

$X^1$ and $X^3$ of Formula (XXIV) are both $CH_2$ and $X^2$ of Formula (XXIV) is C═0, C≡C($R^C$)2, or C≡N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$ cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XXIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XXIV) is $CR^{2a}R^{2b}$;

or:

$X^2$ and $X^3$ of Formula (XXIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (XXIV) is $CR^{2e}R^{2f}$;

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^f$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl- (substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl- (substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl- (substituted or unsubstituted heteroaryl);

m of Formula (XXIV) is selected from 0, 1 or 2;

—U— of Formula (XXIV) is selected from —NHC(═O)—, —C(═O)NH—, —NHS(═O)$_2$—, —S(═O)$_2$ NH—, —NHC(═O)NH—, —NH(C═O)O—, —O(C═O)NH—, or —NHS(═O)$_2$NH—;

$R^3$ of Formula (XXIV) is selected from $C_1$-$C_3$alkyl, or $C_1$-$C_3$fluoroalkyl;

$R^4$ of Formula (XXIV) is selected from —$NHR^5$, —N$(R_5)_2$, —N+$(R^5)_3$ or —$OR^5$;

each $R^5$ of —$NHR^5$, —N$(R^5)_2$, —N+$(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XXIV) together with the atoms to which they are attached form a substituted or unsubstituted 5-7 membered ring;

or:

$R^3$ of Formula (XXIV) is bonded to a nitrogen atom of U to form a substituted or unsubstituted 5-7 membered ring;

$R^6$ of Formula (XXIV) is selected from —NHC(═O)$R^7$, —C(═O)$NHR^7$, —NHS(═O)2$R^7$, —S(═O)$_2NHR^7$; —NHC(═O)$NHR^7$, —NHS(═O)$_2NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)$_2R^7$, —($C_1$-$C_3$alkyl)-S(═O)$_2NHR^7$; —($C_1$-$C_3$alkyl)-NHC(═O)$NHR^7$, —($C_1$-$C_3$alkyl)-NHS(═O)$_2NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)2$R^7$, —S(═O)$_2NHR^7$; —NHC(═O)$NHR^7$, —NHS(═O)$_2NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)2$NHR^7$; —($C_1$-$C_3$alkyl)-NHC(═O)$NHR^7$, —($C_1$-$C_3$alkyl)-NHS(═O)2$NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —$(CH_2)_p$—CH (substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of $C(R^{8a})(R^{8b})$, $C(R^{8c})(R^{8d})$ and $C(R^{8e})(R^{8f})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of $C(R_{8a})(R^{8b})$, $C(R^{8c})(R^{8d})$ and $C(R^{8e})(R^{8f})$ are as defined above, and $R^{8b}$ and $R^{8c}$ together form a bond;

or:

$R^{8a}$, $R^{8b}$, $R^{8d}$, and $R^{8f}$ of $C(R^{8a})(R^{8b})$, $C(R^{8c})(R^{8d})$ and $C(R^{8c})(R^{8f})$ are as defined above, and $R^{8c}$ and $R^{8e}$ together form a bond;

or:

$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of $C(R^{8a})(R^{8b})$, $C(R^{8c})(R^{8d})$ and $C(R^{8e})(R^{8f})$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of $C(R^{8c})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of $C(R^{8a})(R^{8b})$ and $C(R^{8e})(R^{8f})$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of $C(R^{8a})(R^{8b})$ and $C(R^{8c})(R^{8d})$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C═O), CN, $C_1$-$C_4$alkyl, $C_1$-$C_4$fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XXXV), (XXXVI) or (XXXVII), which is derived from the IAP ligands described in Vamos, M., et al., Expedient synthesis of highly potent antagonists of inhibitor of apoptosis proteins (IAPs) with unique selectivity for ML-IAP, *ACS Chem. Biol.,* 8(4), 725-32 (2013), or an unnatural mimetic thereof:

(XXXV)

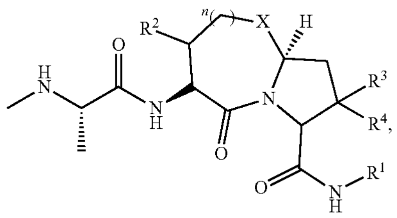

n = 0, 1

(XXXVI)

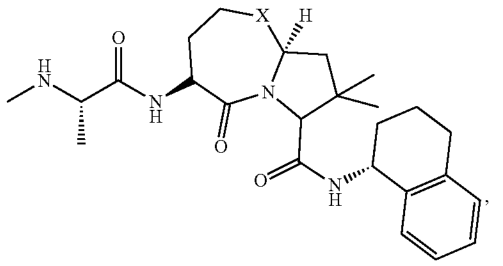

(XXXVII)

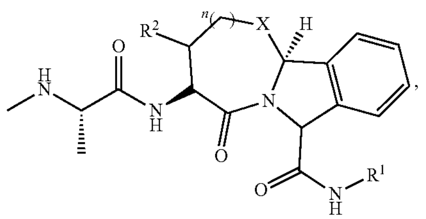

n = 0, 1 wherein:

$R^2$ of Formulas (XXXV) and (XXXVII) are independently selected from H or ME;

$R^3$ and $R^4$ of Formula (XXXV) are independently selected from H or ME;

X of Formulas (XXXV) and (XXXVII) is independently selected from O or S; and $R^1$ of Formulas (XXXV) and (XXXVII) is selected from:

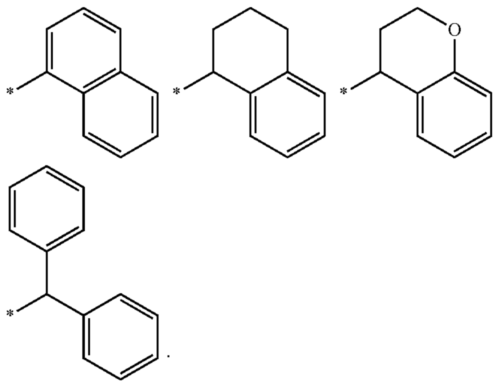

In a particular embodiment, the ILM has a structure according to Formula (XXXVIII):

(XXXVIII)

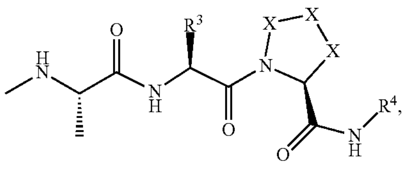

wherein $R^3$ and $R^4$ of Formula (XXXVIII) are independently selected from H or ME;

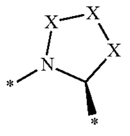

is a 5-member heterocycle selected from:

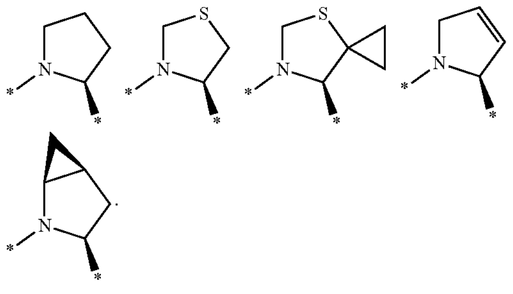

In a particular embodiment, the

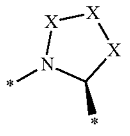

of Formula (XXXVIII) is

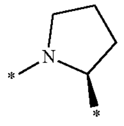 [SMILES: *[C@@H]1CCCN1*]

In a particular embodiment, the ILM has a structure and attached to a linker group L as shown below:

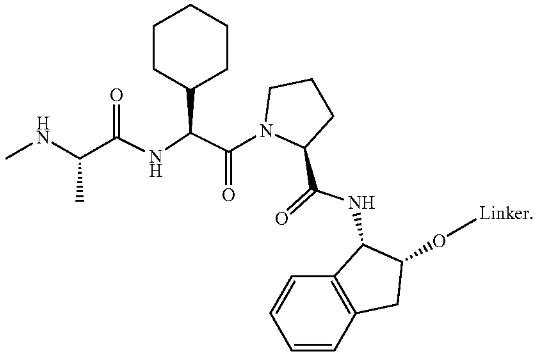

In any of the compounds described herein, the ILM can have the structure of Formula (XXXIX) or (XL), which is based on the IAP ligands described in Hennessy, E J, et al., Discovery of aminopiperidine-based Smac mimetics as IAP antagonists, *Bioorg. Med. Chem. Lett.,* 22(4), 1960-4 (2012), or an unnatural mimetic thereof:

(XXXIX)

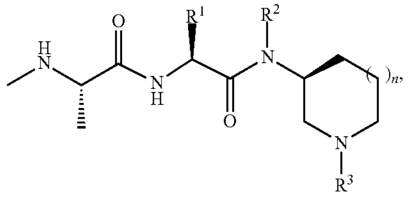

n = 0, 1, 2

(XL)

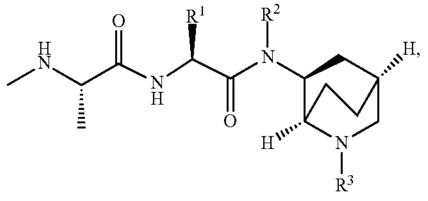

wherein:

$R^1$ of Formulas (XXXIX) and (XL) is selected from:

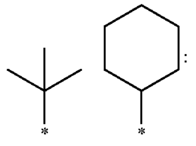

$R^2$ of Formulas (XXXIX) and (XL) is selected from H or Me;

$R^3$ of Formulas (XXXIX) and (XL) is selected from:

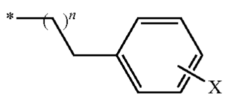

n = 0, 1, 2

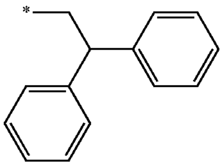

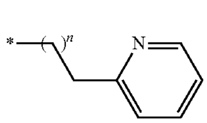

n = 0, 1, 2

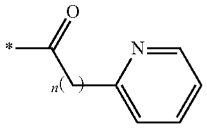

n = 0, 1

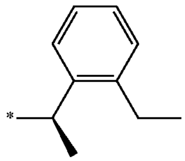

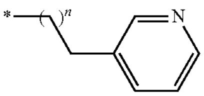

n = 0, 1, 2

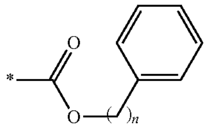

n = 0, 1

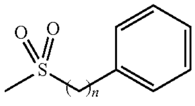

n = 0, 1

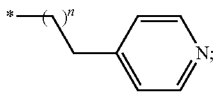

n = 0, 1, 2

X of is selected from H, halogen, methyl, methoxy, hydroxy, nitro or trifluoromethyl.

In any of the compounds described herein, the ILM can have the structure of and be chemically linked to the linker as shown in Formula (XLI) or (XLII), or an unnatural mimetic thereof:

(XLI)

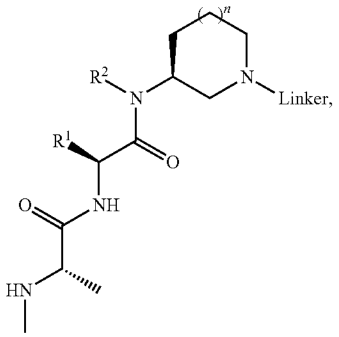

-continued (XLII)

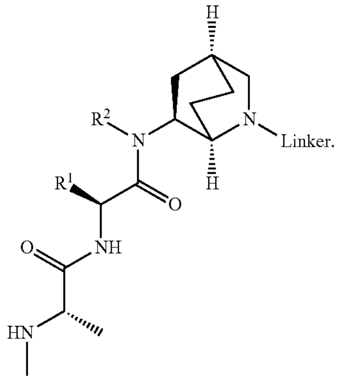

In any of the compounds described herein, the ILM can have the structure of Formula (XLIII), which is based on the IAP ligands described in Cohen. F. et al., Orally bioavailable antagonists of inhibitor of apoptosis proteins based on an azabicyclooctane scaffold, *J. Med. Chem.,* 52(6), 1723-30 (2009), or an unnatural mimetic thereof:

(XLIII)

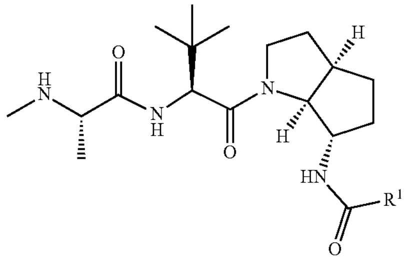

wherein:

R1 of Formulas (XLIII) is selected from:

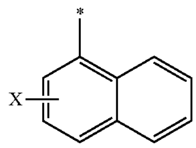

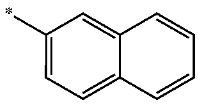

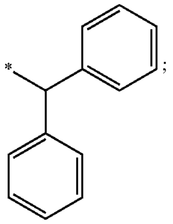

X of

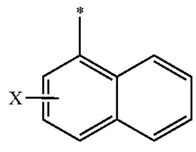

is selected from H, fluoro, methyl or methoxy.

In a particular embodiment, the ILM is represented by the following structure:

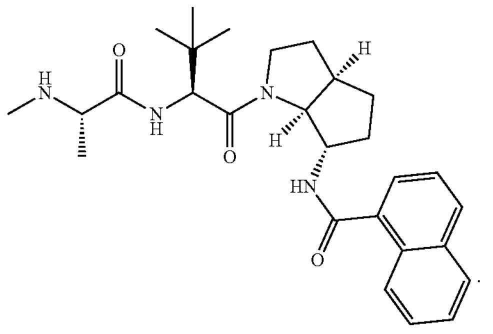 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

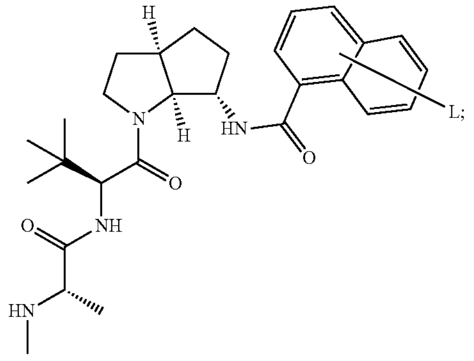

and

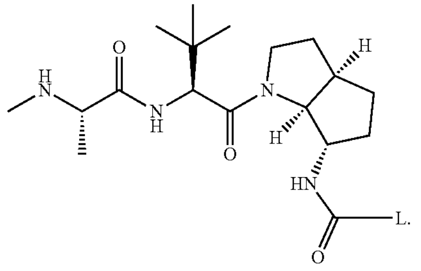

In any of the compounds described herein, the ILM is selected from the group consisting of the structures below, which are based on the IAP ligands described in Asano. M, et al., Design, stereoselective synthesis, and biological evaluation of novel tri-cyclic compounds as inhibitor of apoptosis proteins (IAP) antagonists, *Bioorg. Med. Chem.*, 21(18): 5725-37 (2013), or an unnatural mimetic thereof:

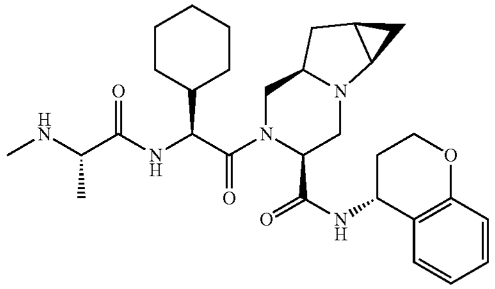

or

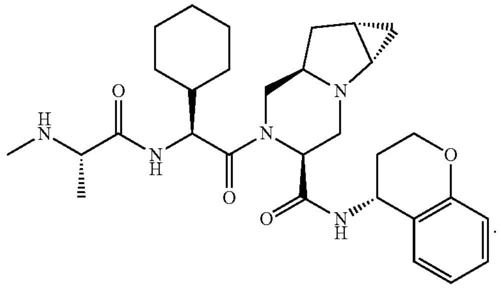

In a particular embodiment, the ILM is selected from the group consisting of, and which the chemical link between the ILM and linker group L is shown:

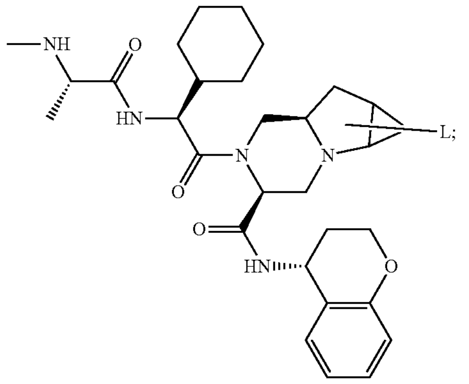

and

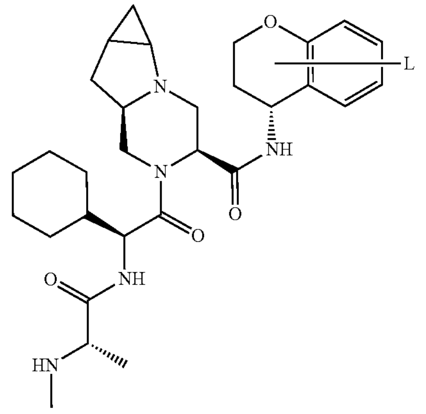

In any of the compounds described herein, the ILM can have the structure of Formula (LVIII), which is based on the IAP ligands described in Asano, M, et al., Design, stereo-selective synthesis, and biological evaluation of novel tri-cyclic compounds as inhibitor of apoptosis proteins (IAP) antagonists, *Bioorg. Med. Chem.*, 21(18): 5725-37 (2013), or an unnatural mimetic thereof:

(XLIV)

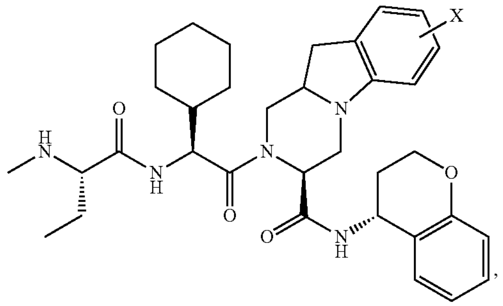

wherein X of Formula (XLIV) is one or two substituents independently selected from H, halogen or cyano.

In any of the compounds described herein, the ILM can have the structure of and be chemically linked to the linker group L as shown in Formula (XLV) or (XLVI), or an unnatural mimetic thereof:

(XLV)

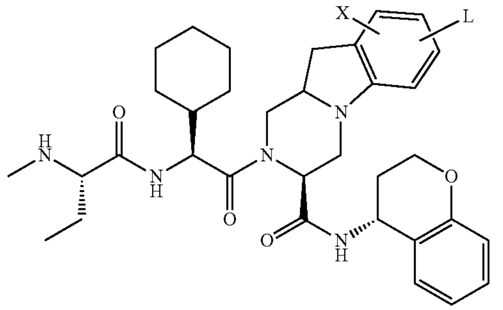

or (XLVI)

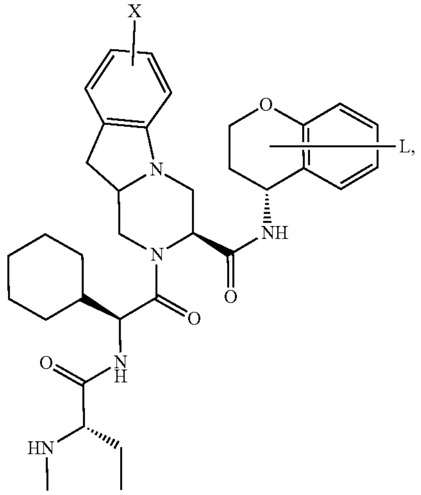

wherein X of Formula (XLV) and (XLVI) is one or two substituents independently selected from H, halogen or cyano, and; and L of Formulas (XLV) and (XLVI) is a linker group as described herein.

In any of the compounds described herein, the ILM can have the structure of Formula (XLVII), which is based on the IAP ligands described in Ardecky, R J, et al., Design, synthesis and evaluation of inhibitor of apoptosis (IAP) antagonists that are highly selective for the BIR2 domain of XIAP, *Bioorg. Med. Chem.*, 23(14): 4253-7 (2013), or an unnatural mimetic thereof:

(XLVII)

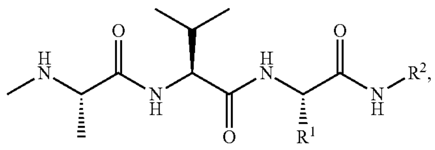

wherein:

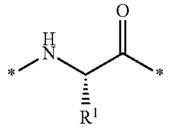

of Formula (LXI) is a natural or unnatural amino acid; and $R^2$ of Formula (LXI) is selected from:

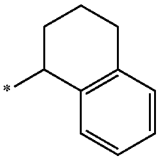

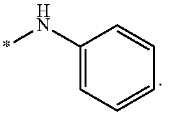

In any of the compounds described herein, the ILM can have the structure of and be chemically linked to the linker group L as shown in Formula (XLVIII) or (XLIX), or an unnatural mimetic thereof:

(LXII)

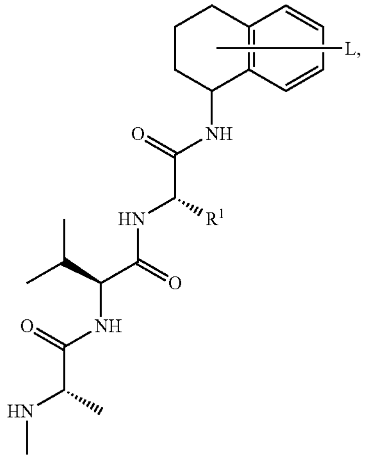

or (XLIX)

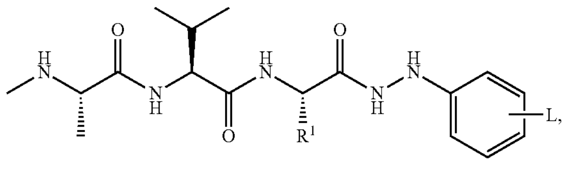

-continued

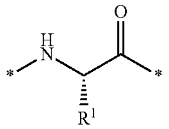

of Formulas (XLVIII) and (XLIX) is a natural or unnatural amino acid; and L of Formulas (XLVIII) and (XLIX) is a linker group as described herein.

In any of the compounds described herein, the ILM can have the structure selected from the group consisting of, which is based on the IAP ligands described in Wang, J, et al., Discovery of novel second mitochondrial-derived activator of caspase mimetics as selective inhibitor or apoptosis protein inhibitors, *J. Pharmacol. Exp. Ther.,* 349(2): 319-29 (2014), or an unnatural mimetic thereof:

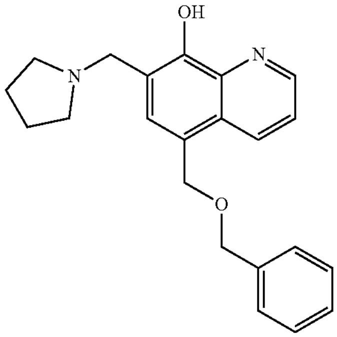

; and

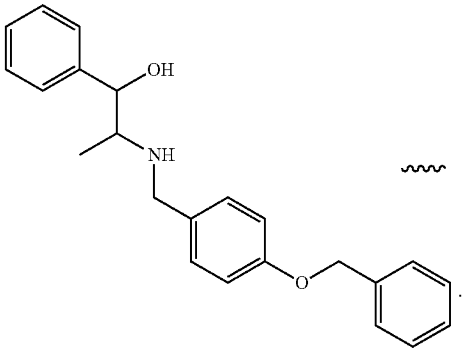

.

In any of the compounds described herein, the ILM has a structure according to Formula (L), which is based on the IAP ligands described in Hird, A W, et al., Structure-based design and synthesis of tricyclic IAP (Inhibitors of Apoptosis Proteins) inhibitors, *Bioorg. Med. Chem. Lett.,* 24(7): 1820-4 (2014), or an unnatural mimetic thereof:

(L)

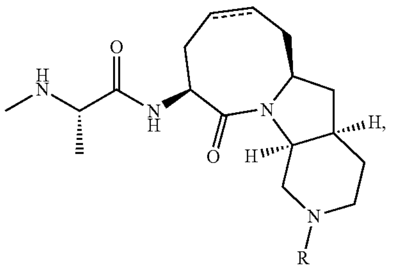

wherein R of Formula (L) is selected from the group consisting of:

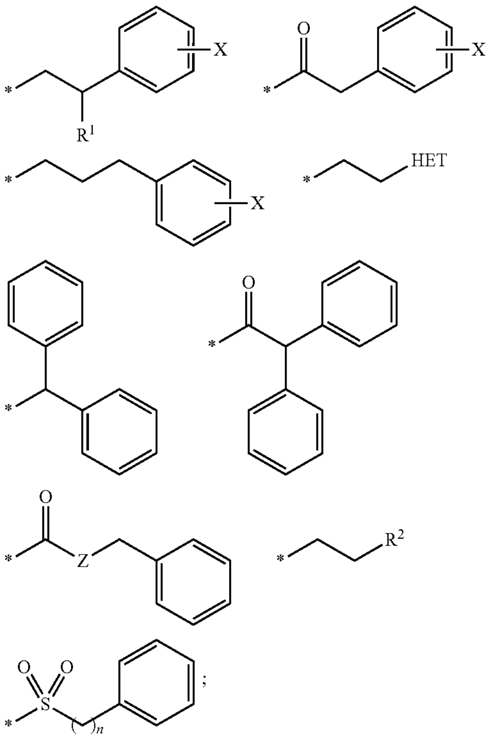

R1 of

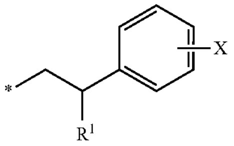

is selected from H or Me;

R2 of

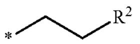

is selected from alkyl or cycloalkyl;

X of

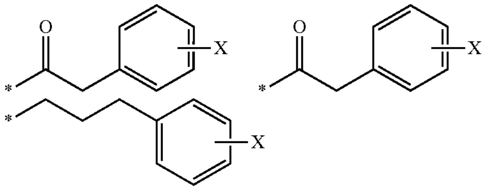

is 1-2 substitutents independently selected from halogen, hydroxy, methoxy, nitro and trifluoromethyl Z of
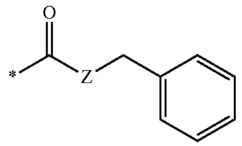
is O or NH;
HET of
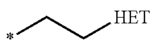
is mono- or fused bicyclic heteroaryl; and
--- of Formula (L) is an optional double bond.
In a particular embodiment, the ILM of the compound has a chemical structure selected from the group consisting of:
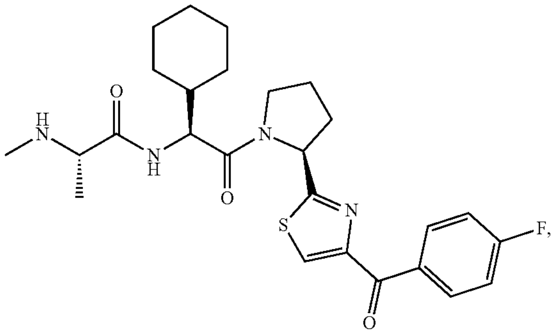
,
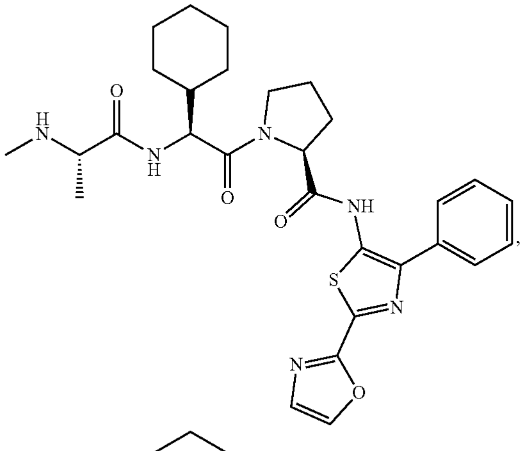
,
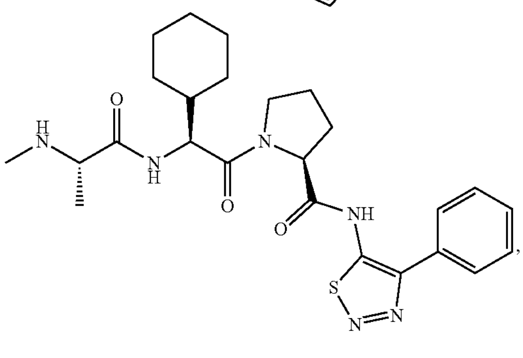
,
-continued
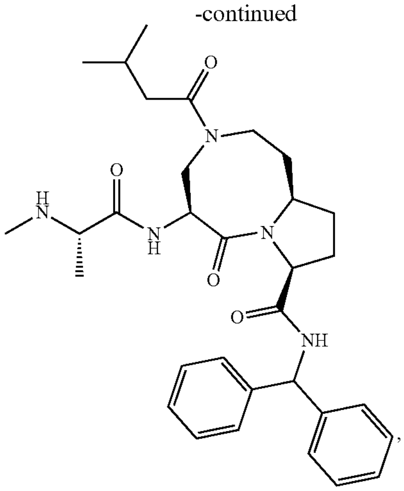
,
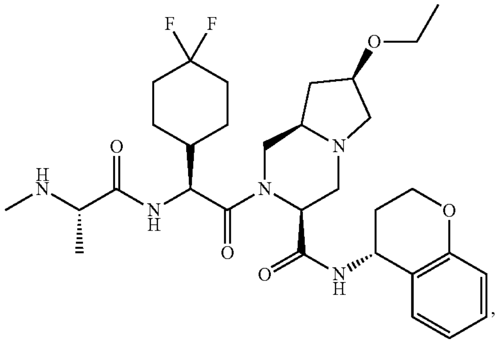
,
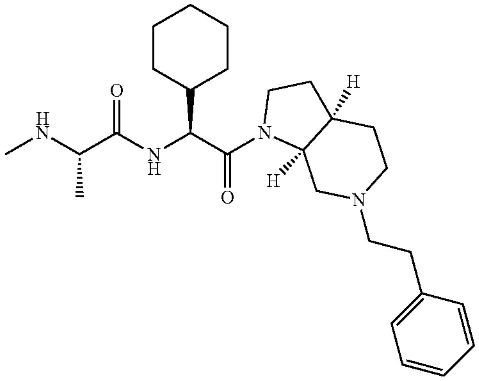
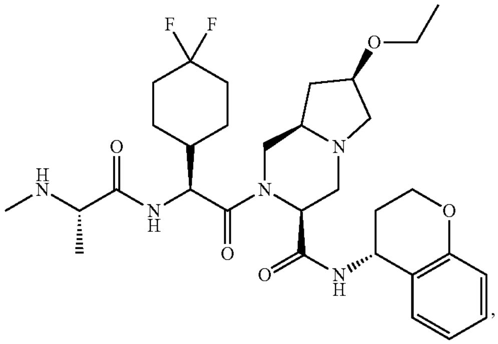
, -continued

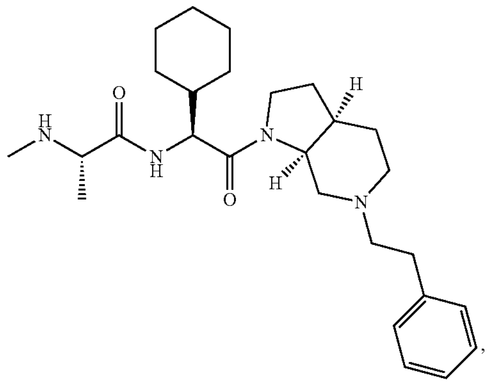

,

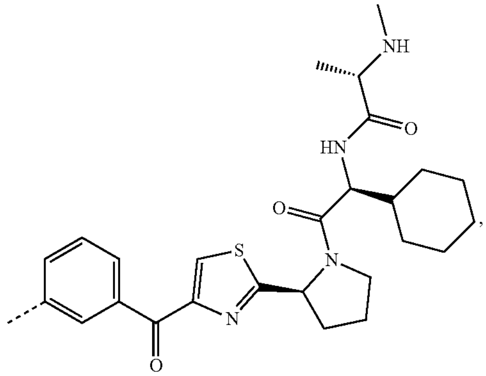

,

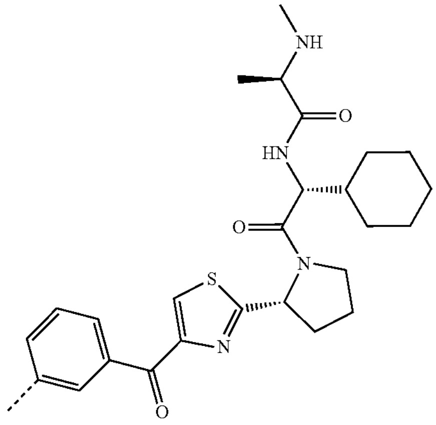

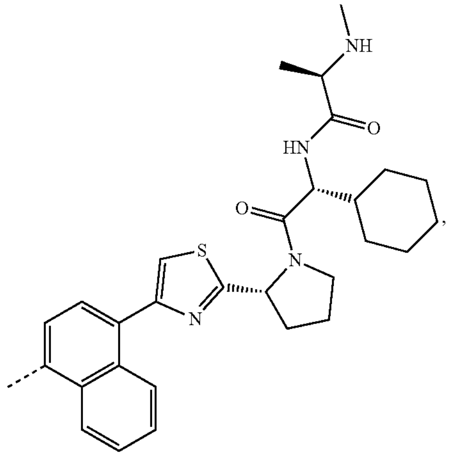

,

-continued

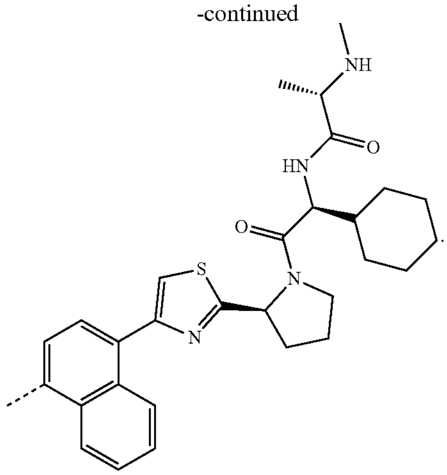

.

The term "independently" is used herein to indicate that the variable, which is independently applied, varies independently from application to application.

The term "alkyl" shall mean within its context a linear, branch-chained or cyclic fully saturated hydrocarbon radical or alkyl group. preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C≡C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a $-(CH_2)_n-$ group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heterary1 moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —($CH_2$O)~C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $-(CH_2)_nOH$, $-(CH_2)_n-O-(C_1\text{-}C_6)$alkyl, $-(CH_2)_n-O-(CH_2)_n-(C_1\text{-}C_6)$alkyl, $-(CH_2)_nO-C(O)(C_0\text{-}C_6)$ alkyl, $-(CH_2)_n-C(O)O(C_0\text{-}C_6)$alkyl, $-(CH_2)_n-OC(O)(C_0\text{-}C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term. "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1\text{-}C_6$ alkyl group or an optionally substituted $-(CH_2)_m-C(O)-O-C_1\text{-}C_6$ alkyl group), an optionally substituted pyridine (2-, 3, or 4-pyridine) or a group according to the chemical structure:

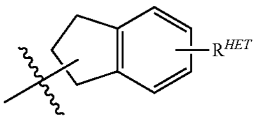
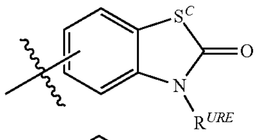
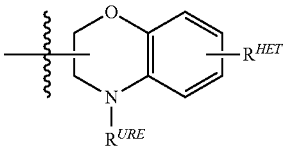
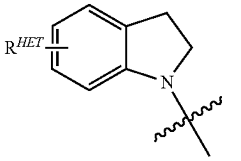
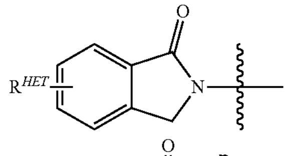
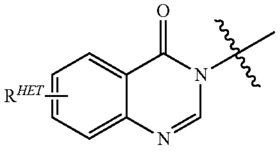
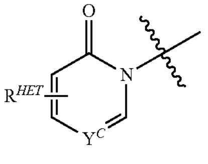

wherein:

$S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

Formula (A-1)

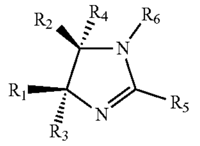

Formula (A-2)

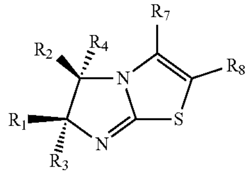

Formula (A-3)

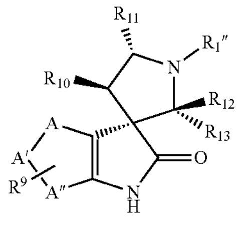

Formula (A-4)

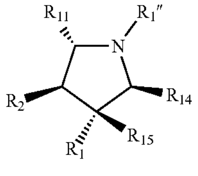

Formula (A-5)

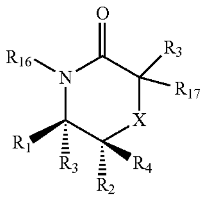

-continued

Formula (A-6)

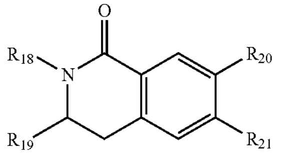

Formula (A-7)

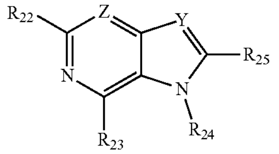

Formula (A-8)

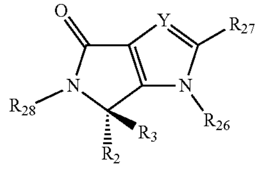

wherein above Formula (A-1) through Formula (A-8):

- X of Formula (A-1) through Formula (A-8) is selected from the group consisting of carbon, oxygen, sulfur, sulfoxide, sulfone, and N—$R^a$;
  - $R^a$ is independently H or an alkyl group with carbon number 1 to 6;
- Y and Z of Formula (A-1) through Formula (A-8) are independently carbon or nitrogen;
- A, A' and A" of Formula (A-1) through Formula (A-8) are independently selected from C, N, O or S, can also be one or two atoms forming a fused bicyclic ring, or a 6.5- and 5,5-fused aromatic bicyclic group;
- $R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  - halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;
- $R_3$, $R_4$ of Formula (A-1) through Formula (A-8) are independently selected from the group consisting of H, methyl and C1 to C6 alkyl;
- $R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  - halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(═O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H; optionally substituted linear or branched C1 to C6 alkyl; alkoxy substituted alkyl; mono- and di-hydroxy substituted alkyl (e.g., a C3 to C6), sulfone substituted alkyl; optionally substituted aryl; optionally substituted heteraryl; mono-, bis- or tri-substituted aryl or heteroaryl; phenyl-4-carboxylic acid; substituted phenyl-4-carboxylic acid, alkyl carboxylic acid; optionally substituted heteroaryl carboxylic acid; alkyl carboxylic acid; fluorine substituted alkyl carboxylic acid; optionally substituted cycloalky, 3-hydroxycyclobutane, 4-hydroxycyclohehexane, aryl substituted cycloalkyl; heteroaryl substituted cycloalkyl; or Rh and Ri taken together form a ring;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(═O), —S, or —S(═O)$_2$, alkyl or cycloalkyl with terminal $CH_3$ replaced by S(═O)$_2$N(alkyl)(alkyl), —C(═O)N(alkyl)(alkyl), —N(alkyl)S(═O)$_2$(alkyl), —C(═O)$_2$(alkyl), —O(alkyl), C1-6 alkyl or alkyl-cycloalkyl with hydron replaced by hydroxyl group, a 3 to 7 membered cycloalkyl or heterocycloalkyl, optionally containing a —(C═0)- group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of ($CH_2$)nC(O)N$R^k$$R^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted $C_{1-6}$ alkoxy, wherein $R^{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydoxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-($C_{1-6}$ alkyl), —CH2-cycloalkyl, —CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5, 6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—$S(O)_2$-alkyl, and —$S(O)_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1'''}$ of Formula (A-1) through Formula (A-8) is selected from the group consisting of H, alkyl, aryl substituted alkyl, alkoxy substituted alkyl, cycloalkyl, aryl- substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L" is a connector (i.e. a linker group), and "PTM" is a ligand binding to a target protein.

In certain embodiments, the description provides a bifunctional molecule comprising a structure selected from the group consisting of:

Formula (A-9)

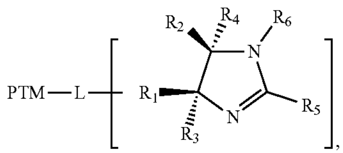

,

Formula (A-10)

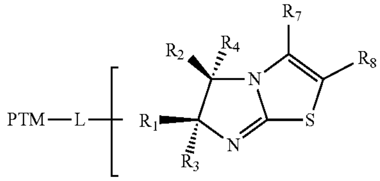

,

Formula (A-11)

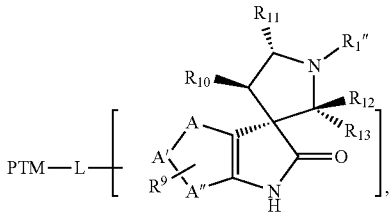

,

Formula (A-12)

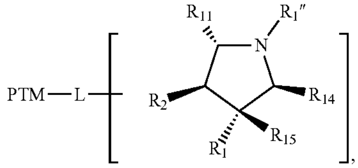

,

Formula (A-13)

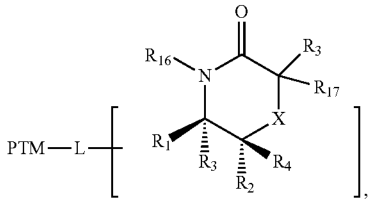

,

Formula (A-14)

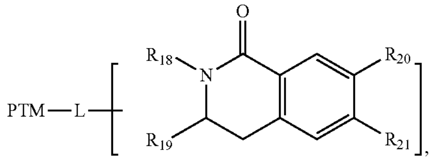

,

-continued

Formula (A-15)

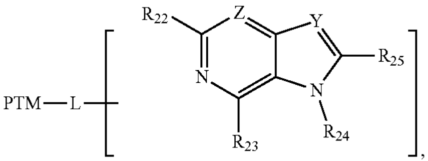

, and

Formula (A-16)

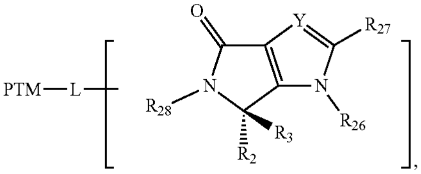

, wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

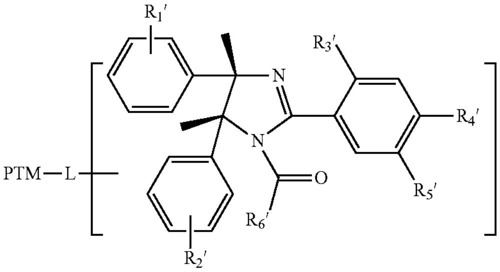

A-1-2

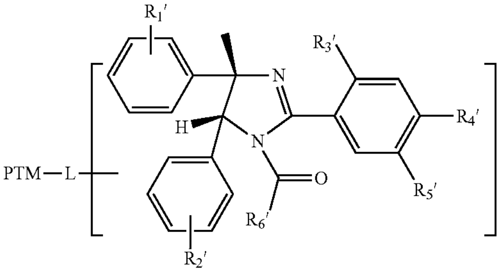

-continued

A-1-3

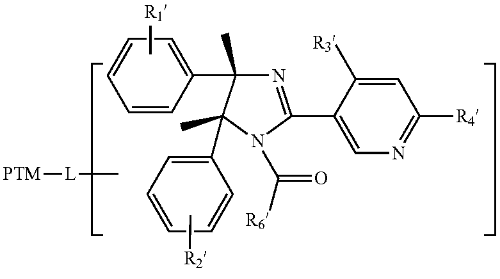

A-1-4

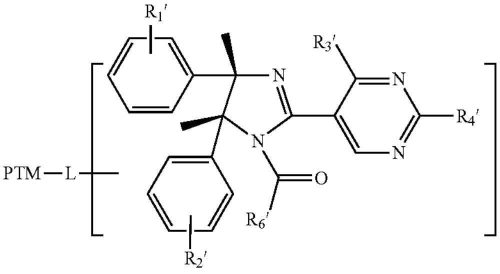

wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;

R3' is selected from the group consisting of $—OCH_3$, $—OCH_2CH_3$, $—OCH_2CH_2F$, $—OCH_2CH_2OCH_3$, and $—OCH(CH_3)_2$;

R4' of Formulas A-1-1 through A-1-4 is selected from the group consisting of H, halogen, $—CH_3$, $—CF_3$, $—OCH_3$, $—C(CH_3)_3$, $—CH(CH_3)_2$, -cyclopropyl, —CN, $—C(CH_3)_2OH$, $—C(CH_3)_2OCH_2CH_3$, $—C(CH_3)_2CH_2OH$, $—C(CH_3)_2CH_2OCH_2CH_3$, $—C(CH_3)_2CH_2OCH_2CH_2OH$, $—C(CH_3)_2CH_2OCH_2CH_3$, $—C(CH_3)_2CN$, $—C(CH_3)_2C(O)CH_3$, $—C(CH_3)_2C(O)NHCH_3$, $—C(CH_3)_2C(O)N(CH_3)_2$, $—SCH_3$, $—SCH_2CH_3$, $—S(O)_2CH_3$, $—S(O_2)CH_2CH_3$, $—NHC(CH_3)_3$, $—N(CH_3)_2$, pyrrolidinyl, and 4-morpholinyl;

R5' of Formulas A-1-1 through A-1-4 is selected from the group consisting of halogen, -cyclopropyl, $—S(O)_2CH_3$, $—S(O)_2CH_2CH_3$, 1-pyrrolidinyl, $—NH_2$, $—N(CH_3)_2$, and $—NHC(CH_3)_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

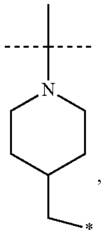,
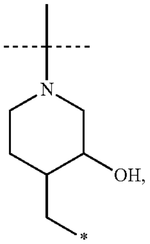
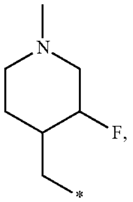
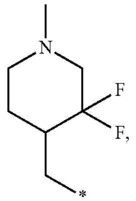
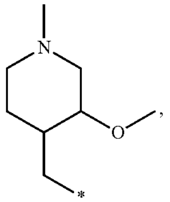
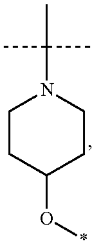
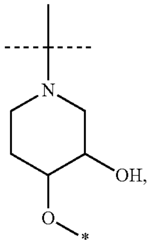
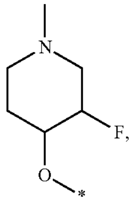
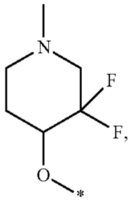
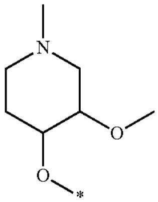,
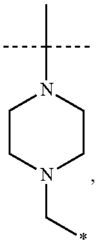,
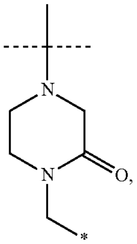
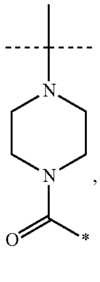,
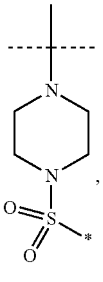,
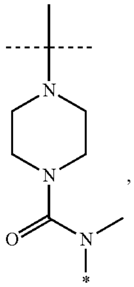,
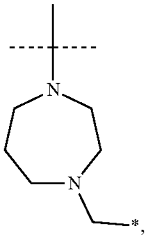
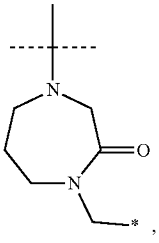,
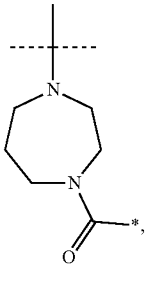

-continued

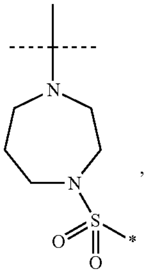,
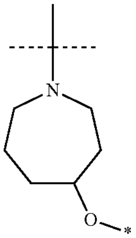,
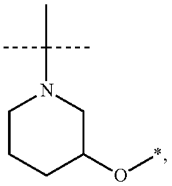
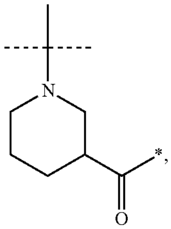
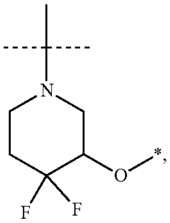
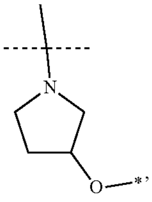
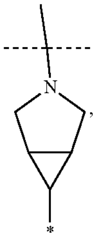
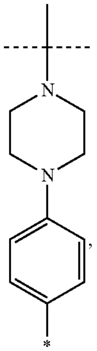
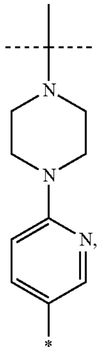
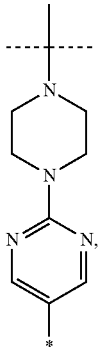
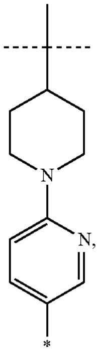
and
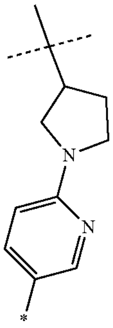

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-4, A-4-2, A-4-3, A-4-4, A-4-5, and A-4-6:

A-4-1

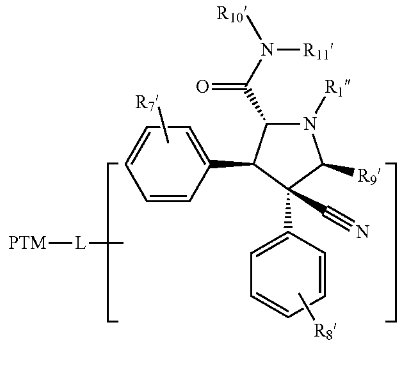

A-4-2

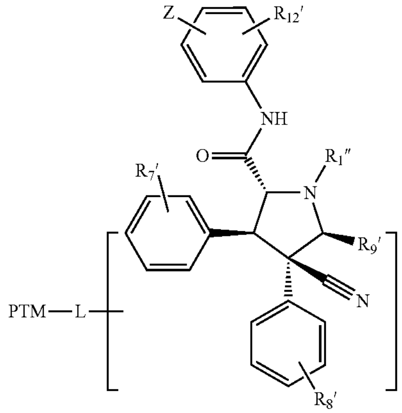

A-4-3

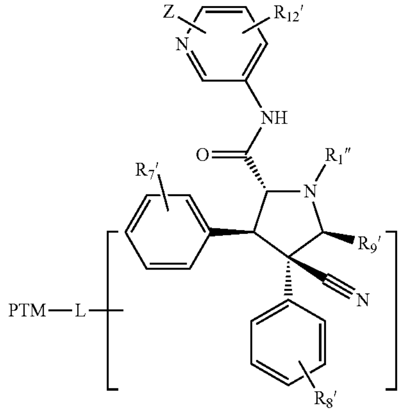

A-4-4

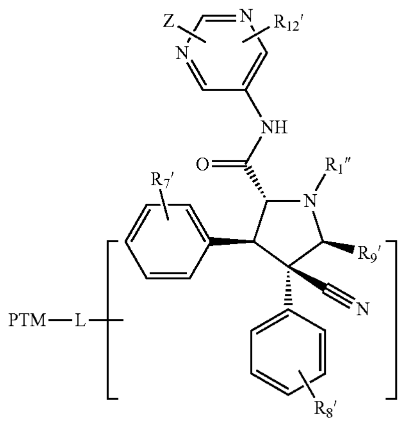

-continued

A-4-5

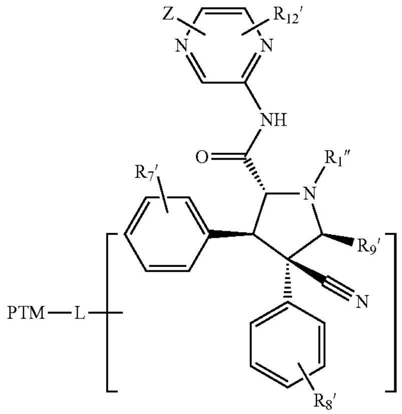

A-4-6

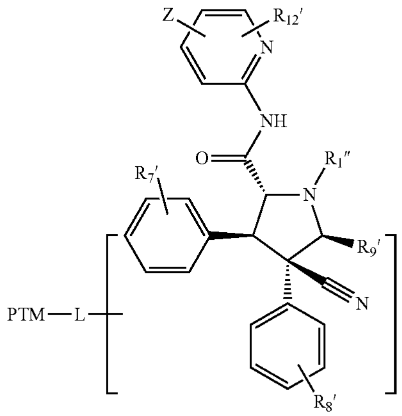

wherein:

R7' of Formula A-4-1 through A-4-6 (i.e., A-4-1, A-4-2, A-4-3, A-4-4, A-4-5, and A-4-6) is one or more (e.g., 1, 2, 3, or 4) halogens;

R8' of Formula A-4-1 through A-4-6 is one or more groups (e.g., 1, 2, 3, or 4 groups) selected from the group consisting of H, —F, —Cl, —Br, —I, —CN, —$NO_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;

R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z of Formula A-4-1 through A-4-6 is selected from the group consisting of H, —$OCH_3$, —$OCH_2CH_3$, and halogen;

R10' and R11' of Formula A-4-1 through A-4-6 are each independently selected from the group consisting of H, $(CH_2)_n$—R', $(CH_2)_n$—NR'R", $(CH_2)_n$—NR'COR", $(CH_2)_n$—NR'$SO_2$R", $(CH_2)_n$COOH, $(CH_2)_n$—COOR', $(CH)_n$—CONR'R", $(CH_2)_n$—OR', $(CH_2)_n$—SR', $(CH_2)_n$ —SOR', $(CH_2)_n$—CH(OH)—R', $(CH_2)_n$—COR', $(CH_2)_n$—$SO_2$R', $(CH_2)_n$—SONR'R", $(CH_2)_n$—$SO_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m(CH_2)_n$—NR'$SO_2$R", $(CH_2CH_2O)_m(CH_2)_n$—COOH, $(CH_2CH_2O)_m(CH_2)_n$—COOR', $(CH_2CH_2O)_m$—$(CH_2)_n$—CONR'R", $(CH_2CH_2O)_m$—$(CH_2)_n$—$SO_2$R', $(CH_2CH_2O)_m$—$(CH_2)_n$—COR', $(CH_2CH_2O)_m$—$(CH_2)_n$—SONR'R", $(CH_2CH_2O)_n$—$(CH_2)_n$—$SO_2NR'R''$, $(CH_2)_p$—$(CH_2CH_2O)_m$—$(CH_2)_nR'$, $(CH_2)_p$—$(CH_2CH_2O)_m$—$(CH_2)_n$—OH, $(CH_2)_p$—$(CH_2CH_2O)_m$—$(CH_2)_n$—OR', $(CH_2)_p$—$(CH_2CH_2O)_n$—$(CH_2)_n$—NR'R'', $(CH_2)_p$—$(CH_2CH_2O)_m$—$(CH_2)_n$—NR'COR'', $(CH_2)_p$—$(CH_2CH_2O)_m$—$(CH_2)_n$—$NR'SO_2R''$, $(CH_2)_p$—$(CH_2CH_2O)_m$ —$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R'', $(CH_2)_p$—$(CH_2CH_2O)_m$ —$(CH_2)_n$—$SO_2R$, $(CH_2)_p$—$(CH_2CH_2O)_m$ —$(CH_2)_n$—COR', $(CH_2)_p$—$(CH_2CH_2O)_m$ —$(CH_2)_n$—SONR'R'', $(CH_2)_p$—$(CH_2CH_2O)_n$—$(CH_2)_n$—$SO_2NR'R''$, Aryl-$(CH_2)_n$—COOH, and heteroaryl-alkyl-CO-alkyl-NR'R''m, wherein the alkyl may be substituted with OR', and heteroaryl-$(CH_2)_n$-heterocycle wherein the heterocycle may optionally be substituted with alkyl, hydroxyl, COOR' and COR'; wherein R' and R'' are selected from H, alkyl, alkyl substituted with halogen, hydroxyl, NH2, NH(alkyl), $N(alkyl)_2$, oxo, carboxy, cycloalkyl and heteroaryl;

m, n, and p are independently 0 to 6;

R12' of Formula A-4-1 through A-4-6 is selected from the group consisting of —O-(alkyl), —O-(alkyl)-alkoxy, —C(O)-(alkyl), —C(OH)-alkyl-alkoxy, —C(O)—NH-(alkyl), —C(O)—N-$(alkyl)_2$, —S(O)-(alkyl), $S(O)_2$-(alkyl), —C(O)-(cyclic amine), and —O-aryl-(alkyl), —O-aryl-(alkoxy);

R1'' of Formula A-4-1 through A-4-6 is selected from the group consisting of H, alkyl, aryl substituted alkyl, alkoxy substituted alkyl, cycloalkyl, ary- substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11'', R12'', or R1''.

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

1. The HDM2/MDM2 inhibitors identified in Vassilev, et al., In vivo activation of the p53 pathway by small-molecule antagonists of MDM2, *SCIENCE* vol: 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

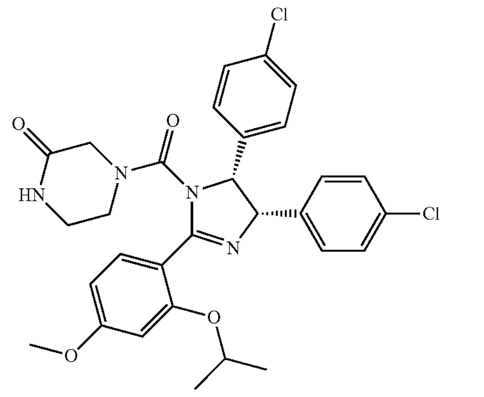 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

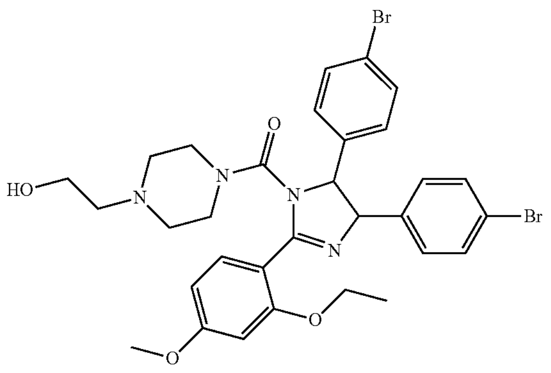 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group);

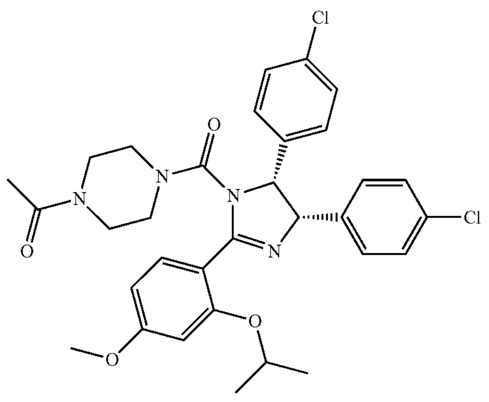 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group); and 2. Trans-4-Iodo-4'-Boranyl-Chalcone

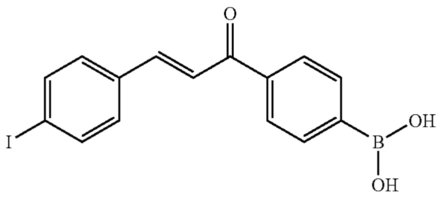 [SMILES: O=C(/C=C/c1ccc(I)cc1)c1ccc(B(O)O)cc1]

(derivatized where a linker group L or a linker group L or a-(L-MLM) group is attached, for example, via a hydroxy group).

Exemplary CLMs

Neo-Imide Compounds

In one aspect the description provides compounds useful for binding and/or inhibiting cereblon. In certain embodiments, the compound is selected from the group consisting of chemical structures:

(a1)

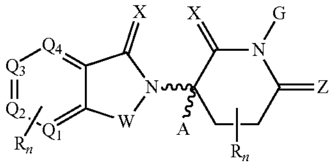

(b)

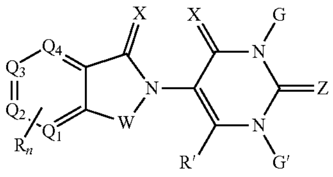

(c)

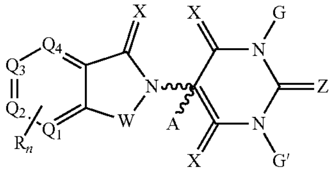

(d1)

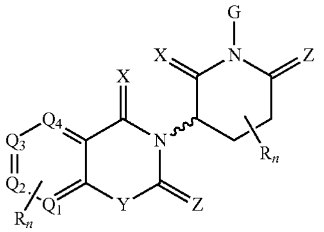

(e)

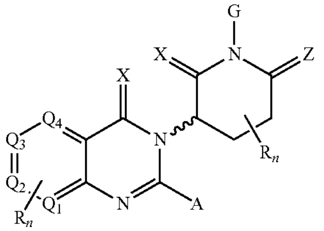

-continued (f)

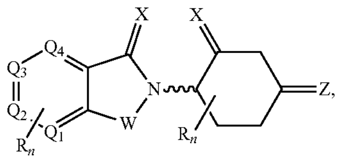

(a2)

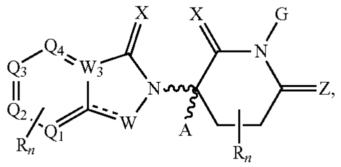

(d2)

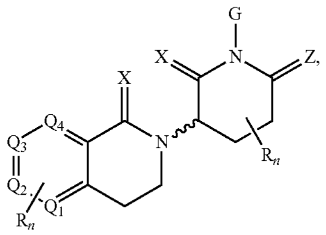

(a3)

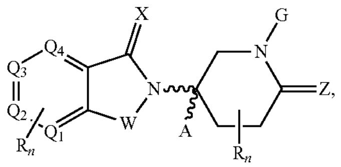

or (a4)

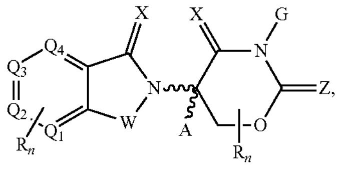

wherein:

W of Formulas (a) through (f) [e.g., (a1), (b), (c), (d1), (e), (f), (a2), (d2), (a3), and (a4)] is independently selected from the group $CH_2$, O, CHR, C═O, $SO_2$, NH, N, optionally substituted cyclopropyl group, optionally substituted cyclobutyl group, and N-alkyl;

$W_3$ is selected from C or N;

X of Formulas (a) through (f) is independently selected from the group absent, O, S and $CH_2$;

Y of Formulas (a) through (f) is independently selected from the group $CH_2$, —C≡CR', NH, N-alkyl, N-aryl, N-heteroaryl, N-cycloalkyl, N-heterocyclyl, O, and S;

Z of Formulas (a) through (f) is independently selected from the group absent, O, S or $CH_2$ except that both X and Z cannot be absent or $CH_2$;

G and G' of Formulas (a) through (f) are independently selected from the group H, optionally substituted linear or branched alkyl (e.g., optionally substituted with R'), OH, R'OCOOR, R'OCONRR", $CH_2$-heterocyclyl optionally substituted with R', and benzyl optionally substituted with R';

Q1-Q4 of Formulas (a) through (f) represent a carbon C substituted with a group independently selected from H, R, N or N-oxide;

A of Formulas (a) through (f) is independently selected from the group H, optionally substituted linear or branched alkyl, cycloalkyl, Cl and F;

R of Formulas (a) through (f) comprises, but is not limited to: —CONR'R", —OR', —NR'R", —SR', —$SO_2$R', —$SO_2$NR'R", —CR'R"—, —CR'NR'R"—, (—CR'O)$_{n'}$R", optionally substituted heterocyclyl (e.g., optionally substituted C3-$C_7$ heterocyclyl), optionally substituted-aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted-heteroaryl (e.g., an optionally substituted C5-C7 heteroaryl), unsubstituted or substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

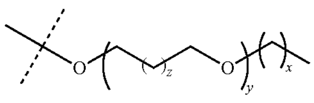

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

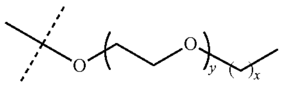

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted-cycloalkyl, optionally substituted-heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C≡$NO_2$)NR'R", —$SO_2$NR'COR", —$NO_2$, —$CO_2$R', —C(C≡N—OR') R", —CR'═CR'R", —CCR', —S(C═O)(C≡N—R') R", —$SF_5$ and —$OCF_3$, wherein at least one R is a functional group or atom independently selected from, for example, O, OH, N, NH, $NH_2$, C1-C6 alkyl, C1-C6 alkoxy, optionally substituted heterocyclyl (e.g., optionally substituted C3-C7 heterocyclyl), -alkyl-aryl (e.g., an -alkyl-aryl comprising at least one of C1-C6 alkyl, C4-C7 aryl, or a combination thereof), optionally substituted aryl (e.g., optionally substituted C5-C7 aryl), optionally substituted heteroaryl aryl (e.g., optionally substituted C5-C7 heteroaryl), amine, amide, or carboxy);

each of x, y, and z are independently 0, 1, 2, 3, 4, 5, or 6;

R' and R" of Formulas (a) through (f) are independently selected from a H, optionally substituted alkyl, optionally substituted cycloalkyl, optionally substituted aryl, optionally substituted heteroaryl, optionally substituted heterocyclic, —C(═O)R, optionally substituted heterocyclyl;

n' and n of Formulas (a) through (f) are each independently an integer from 1-10 (e.g. 1-4, 1, 2, 3, 4, 5, 6, 7, 8, 9, or 10);

 represents a single bond or a double bond; and of Formulas (a) through (f) represents a bond that may be stereospecific ((R) or (S)) or non-stereospecific.

Exemplary CLMs

In any of the compounds described herein, the CLM comprises a chemical structure selected from the group:

(a1)

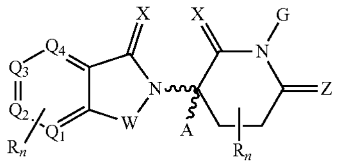

(b)

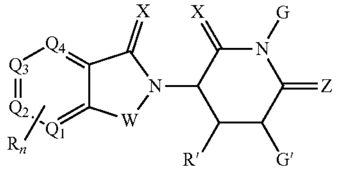

(c)

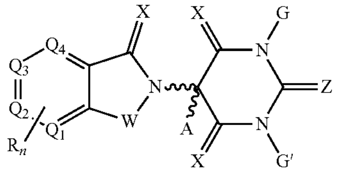

(d1)

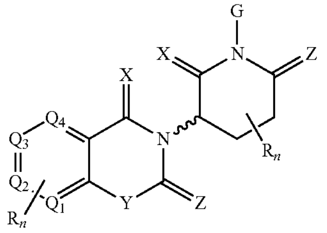

(e)

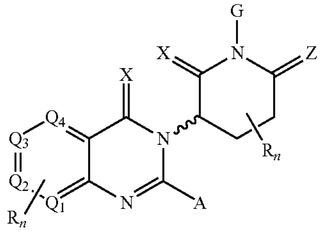

(f)

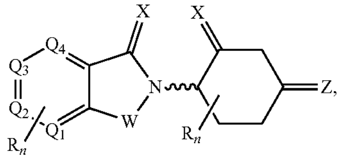

-continued (a2)

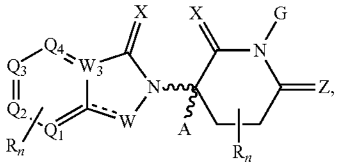

(d2)

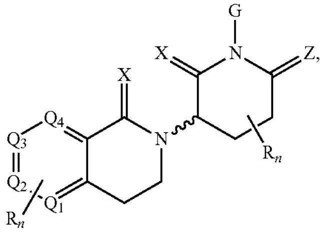

(a3)

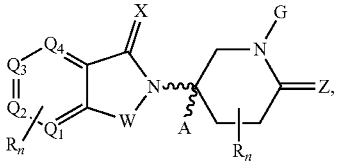

or (a4)

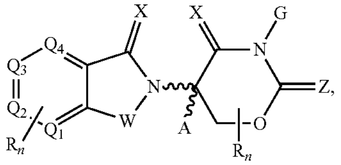

wherein:

W of Formulas (a) through (f) [e.g., (a1), (b), (c), (d1), (e), (f), (a2), (d2), (a3), and (a4)] is independently selected from the group $CH_2$, O, CHR, C═O, $SO_2$, NH, N, optionally substituted cyclopropyl group, optionally substituted cyclobutyl group, and N-alkyl;

X of Formulas (a) through (f) is independently selected from the group absent, O, S and CH2;

Y of Formulas (a) through (f) is independently selected from the group $CH_2$, —C≡CR', NH, N-alkyl, N-aryl, N-hetaryl, N-cycloalkyl, N-heterocyclyl, O, and S;

Z of Formulas (a) through (f) is independently selected from the group absent, O, S or $CH_2$ except that both X and Z cannot be absent or $CH_2$;

G and G' of Formulas (a) through (f) are independently selected from the group H, optionally substituted linear or branched alkyl (e.g., optionally substituted with R'), OH, R'OCOOR, R'OCONRR", $CH_2$-heterocyclyl optionally substituted with R', and benzyl optionally substituted with R';

Q1-Q4 of Formulas (a) through (f) represent a carbon C substituted with a group independently selected from H, R, N or N-oxide;

A of Formulas (a) through (f) is independently selected from the group H, optionally substituted linear or branched alkyl, cycloalkyl, Cl and F;

R of Formulas (a) through (f) comprises, but is not limited to: —CONR'R", —OR', —NR'R", —SR', —$SO_2$R', —$SO_2$NR'R", —CR'R"—, —CR'NR'R"—, $(—CR'O)_{n'}$R", optionally substituted-aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl (e.g., an optionally substituted C5-C7 aryl), -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

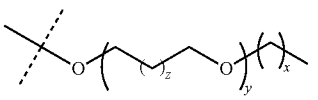

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

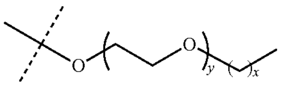

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted-cycloalkyl (e.g., optionally substituted C3-C7 cycloalkyl), optionally substituted-heterocyclyl (e.g., optionally substituted C3-C7 heterocyclyl), —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(═N—CN)NR'R", —C(═N—CN)NR'R", —NR'C(═N—CN)R", —NR'C(═C≡NO2)NR'R", —SO2NR'COR", —NO2, —CO2R', —C(C≡N—OR')R", —CR'═CR'R", —CCR', —S(C═O)(C≡N—R')R", —SF5 and —OCF3, wherein at least one R (e.g., at least one of O, OH, N, NH, $NH_2$, C1-C6 alkyl, C1-C6 alkoxy, optionally substituted-cycloalkyl (e.g., optionally substituted C3-C7 cycloalkyl), optionally substituted-heterocyclyl (e.g., optionally substituted C3-C7 heterocyclyl), -alkyl-aryl (e.g., an -alkyl-aryl comprising at least one of C1-C6 alkyl, C4-C7 aryl, or a combination thereof), optionally substituted aryl (e.g., optionally substituted C5-C7 aryl), optionally substituted heteroaryl aryl (e.g., optionally substituted C5-C7 heteroaryl), amine, amide, or carboxy) is modified to be covalently joined to a PTM, a chemical linker group (L), a ULM, a CLM' (e.g., CLM' is an additional CLM that has the same or different structure as a first CLM), or a combination thereof;

each of x, y, and z are independently 0, 1, 2, 3, 4, 5, or 6;

R' and R" of Formulas (a) through (f) are independently selected from a H, optionally substituted linear or branched alkyl, optionally substituted cycloalkyl, optionally substituted aryl, optionally substituted heteroaryl, optionally substituted heterocyclic, —C(═O)R, optionally substituted heterocyclyl;

n and n' of Formulas (a) through (f) are each independently an integer from 1-10;

 represents a single bond or a double bond; and of Formulas (a) through (f) represents a bond that may be stereospecific ((R) or (S)) or non-stereospecific.

In certain embodiments described herein, the CLM or ULM comprises a chemical structure selected from the group:

Formula (g)

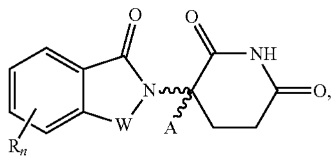

wherein:

W of Formula (g) is independently selected from the group $CH_2$, O, C═O, NH, and N-alkyl;

A of Formula (g) is selected from a H, methyl, or optionally substituted linear or branched alkyl;

R of Formula (g) is independently selected from a H, O, OH, N, NH, $NH_2$, methyl, optionally substituted linear or branched alkyl (e.g., optionally substituted linear or branched C1-C6 alkyl), optionally substituted C1-C6 alkoxy, optionally substituted heterocyclyl (e.g., optionally substituted C3-C7 heterocyclyl), optionally substituted -alkyl-aryl (e.g., an -alkyl-aryl comprising at least one of C1-C6 alkyl, C4-C7 aryl, or a combination thereof), optionally substituted aryl (e.g., optionally substituted C5-C7 aryl), optionally substituted heteroaryl aryl (e.g., optionally substituted C5-C7 heteroaryl), amine, amide, or carboxy);

n of Formulas (g) represent an integer from 1 to 4 (e.g., 1, 2, 3, or 4), wherein at least one R (e.g., at least one of O, OH, N, NH, $NH_2$, C1-C6 alkyl, C1-C6 alkoxy, optionally substituted heterocyclyl (e.g., C3-C7 heterocyclyl), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) is modified to be covalently joined to a PTM, a chemical linker group (L), a ULM, CLM (or CLM') or combination thereof; and ∿∿∿ of Formula (g) represents a bond that may be stereospecific ((R) or (S)) or non-stereospecific.

In any of the embodiments described herein, the W, X, Y, Z, G, G', R, R', R", Q1-Q4, A, and Rn of Formulas (a) through (g) [e.g., (a1), (b), (c), (d1), (e), (f), (a2), (d2), (a3), (a4), and (g)] can independently be covalently coupled to a linker and/or a linker to which is attached one or more PTM, ULM, CLM or CLM' groups.

In any of the aspects or embodiments described herein, the CLM comprises from 1 to 4 R groups independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In some embodiments, the CLM is represented by the following structures with the dashed lines indicating linker attachment points:

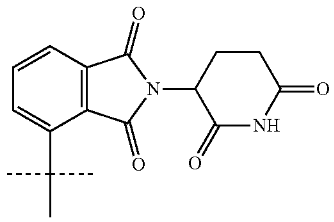

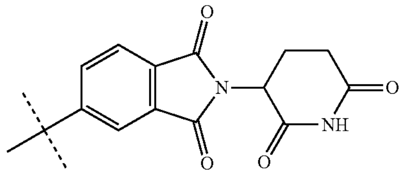

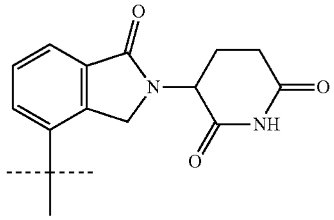

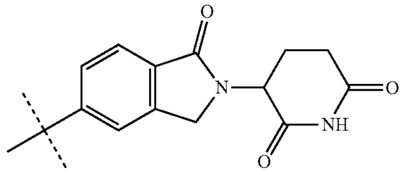

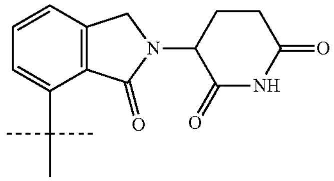

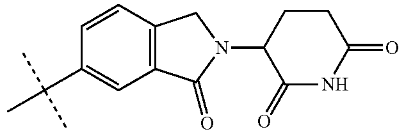

More specifically, non-limiting examples of CLMs include those shown below as well as those "hybrid" molecules that arise from the combination of 1 or more of the different features shown in the molecules below.

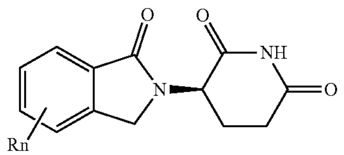

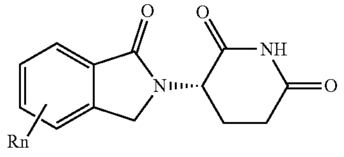

-continued
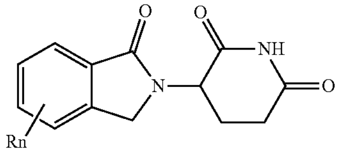
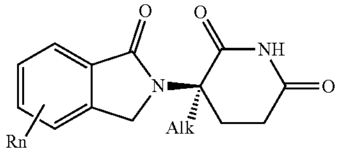
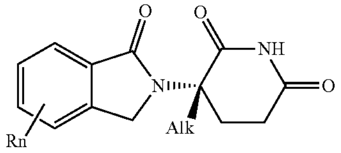
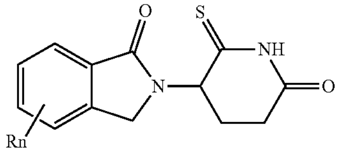
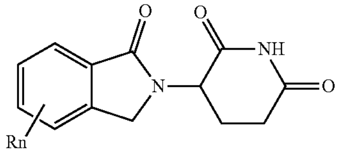
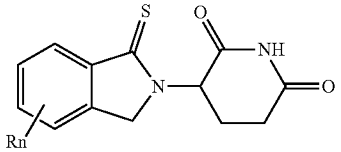
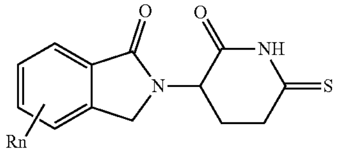
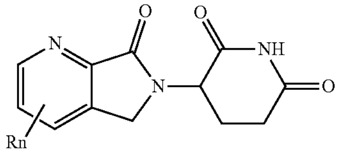
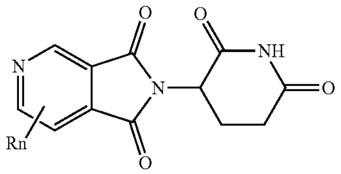
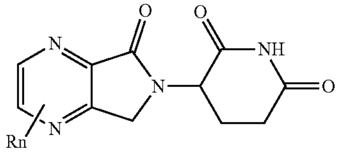
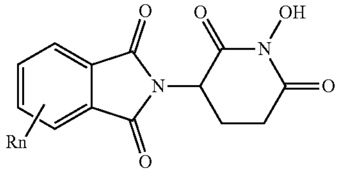
-continued
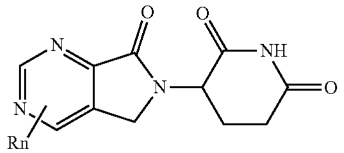
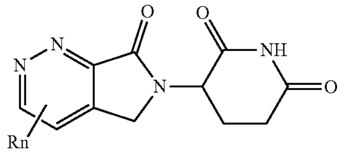
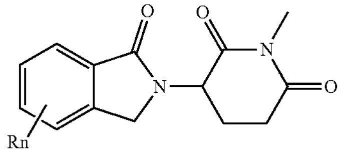
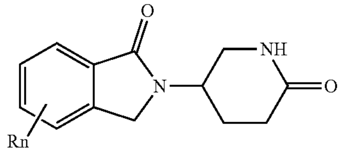
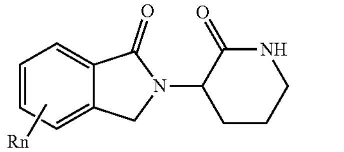
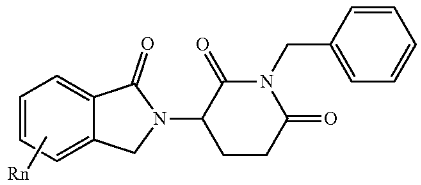
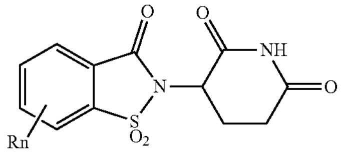
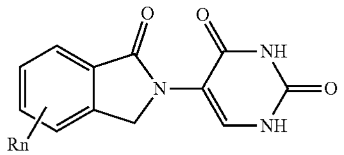
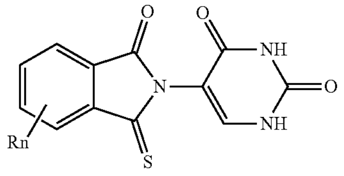
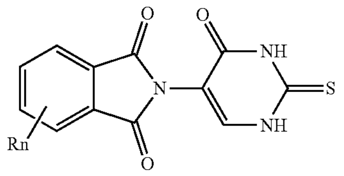

-continued
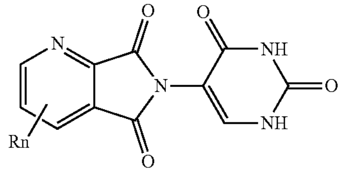
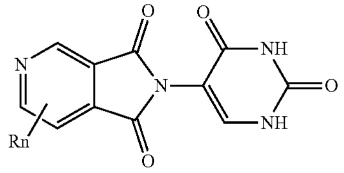
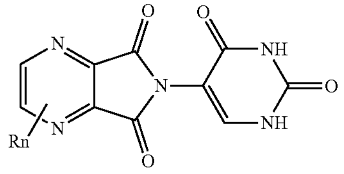
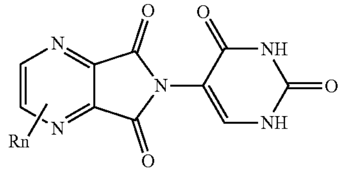
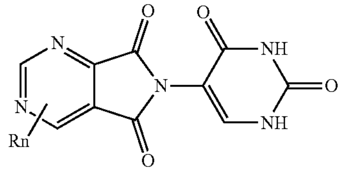
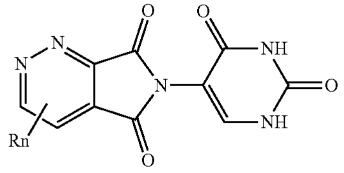
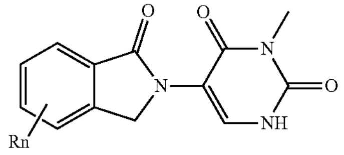
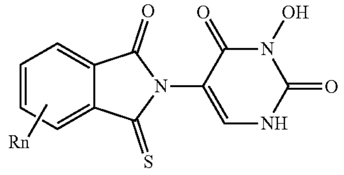
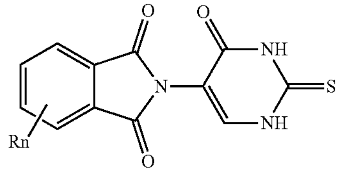
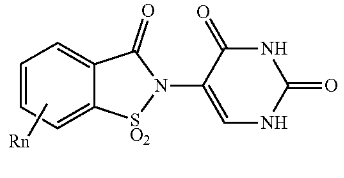
-continued
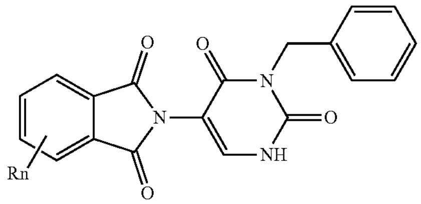
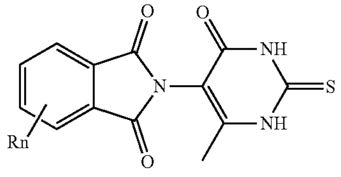
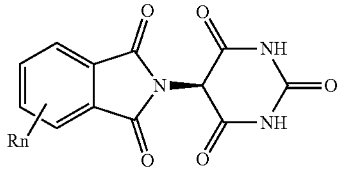
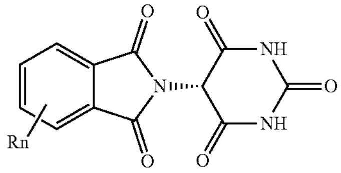
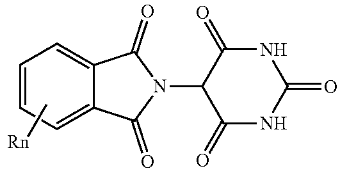
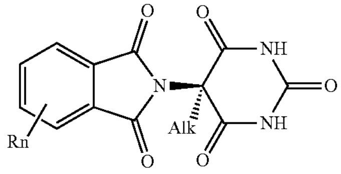
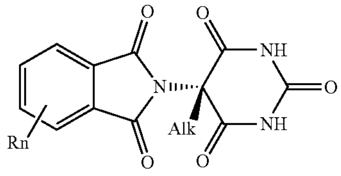
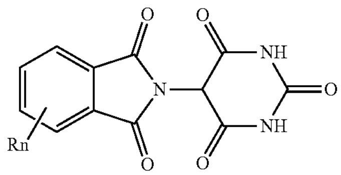
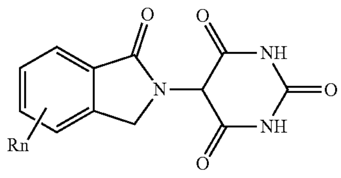

-continued
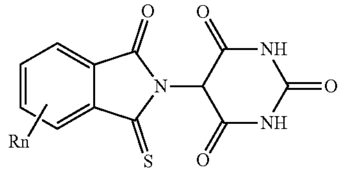
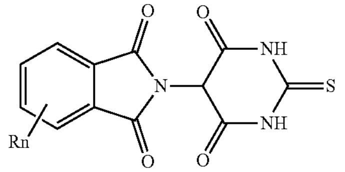
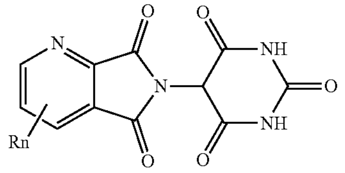
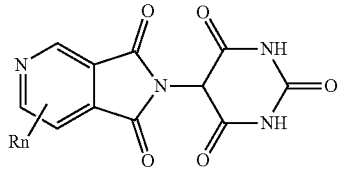
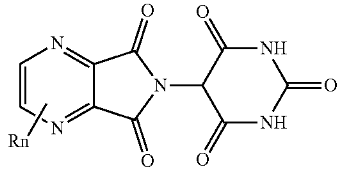
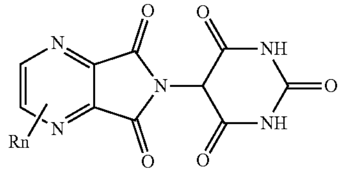
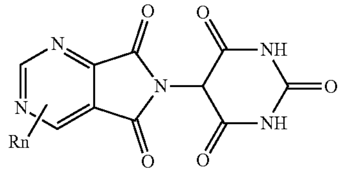
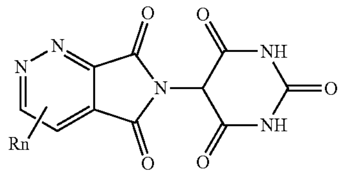
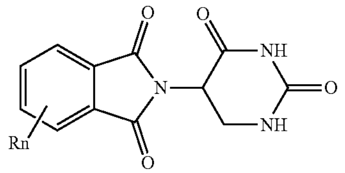
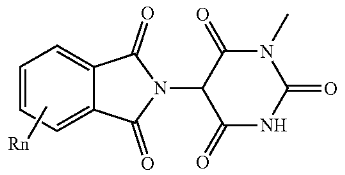
-continued
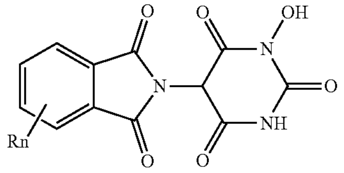
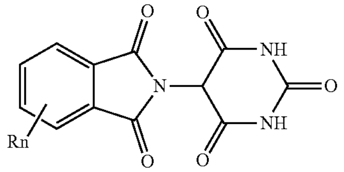
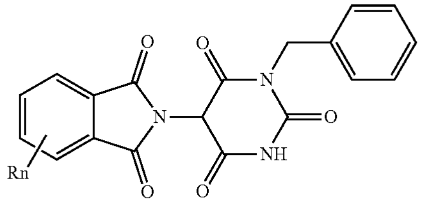
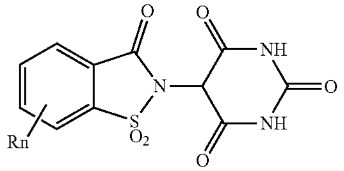
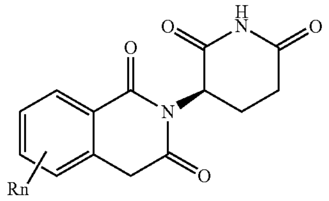
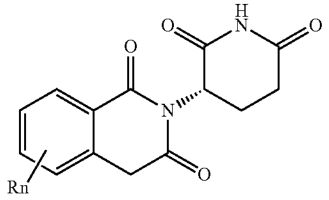
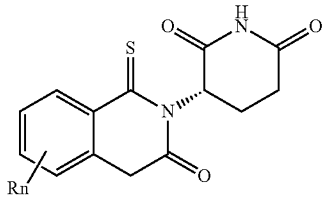
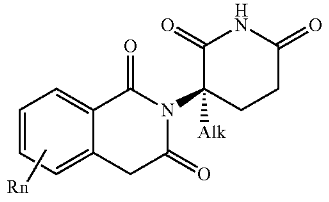
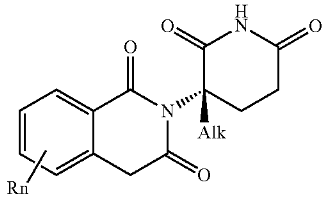

-continued
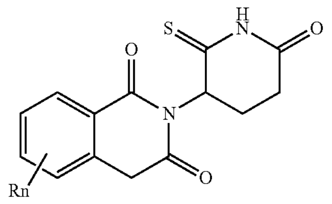
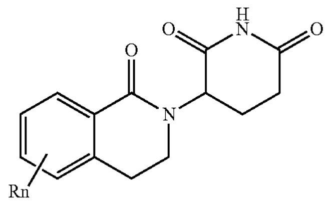
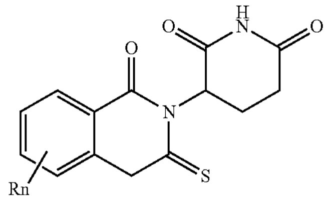
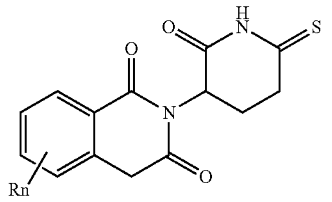
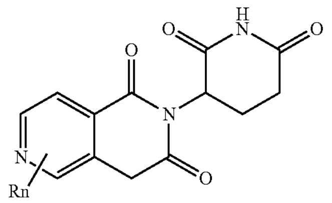
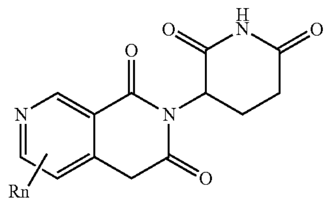
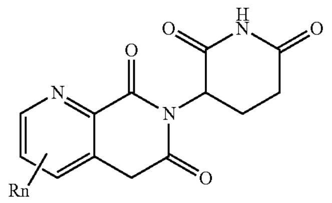
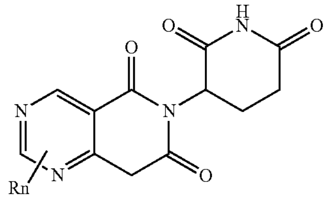
-continued
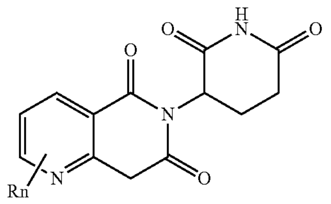
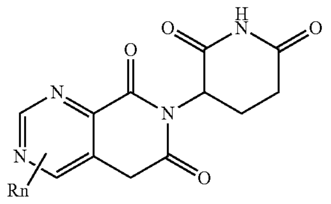
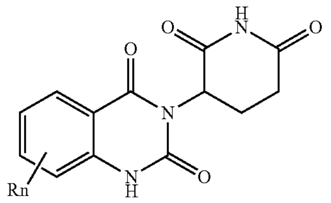
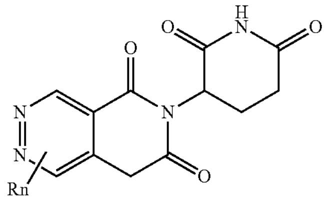
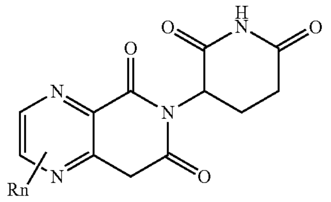
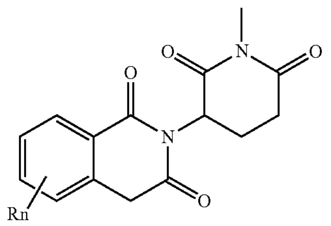
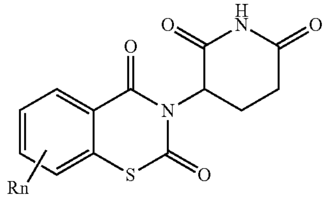
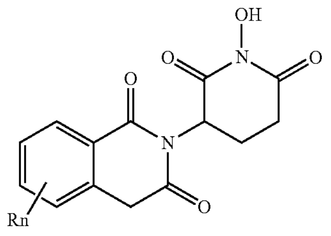

-continued
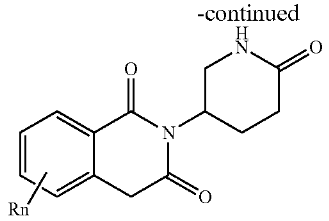
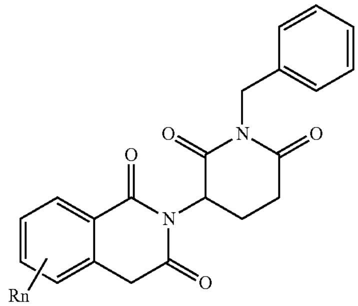
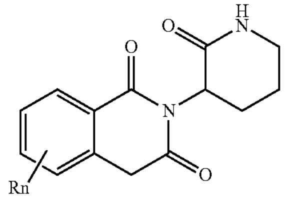
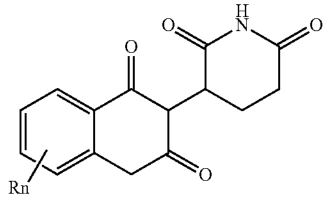
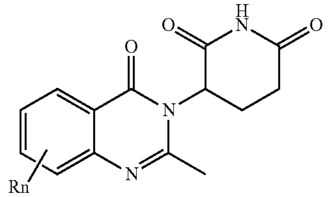
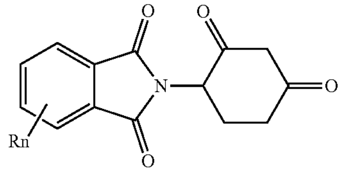
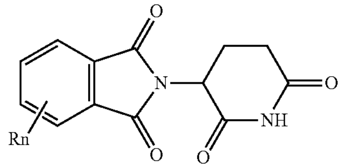
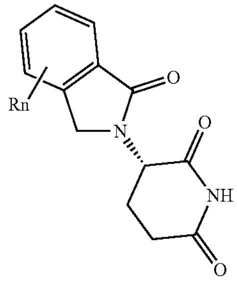
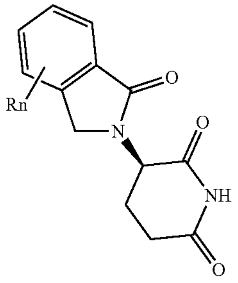
-continued
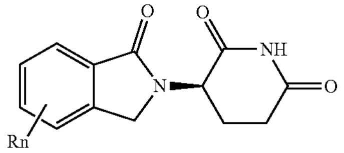
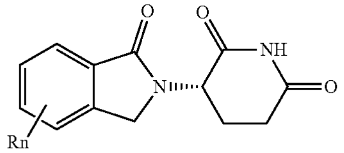
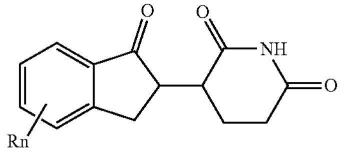
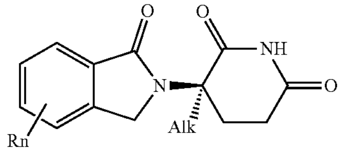
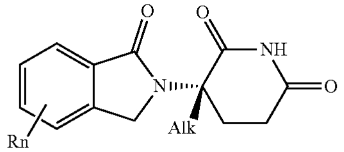
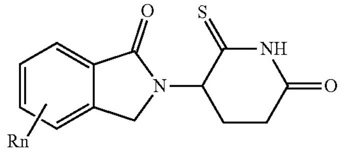
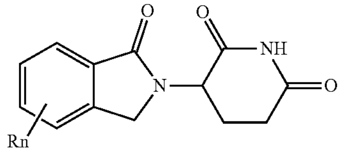
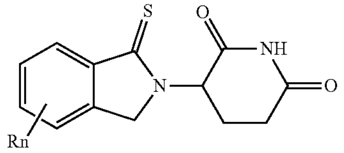
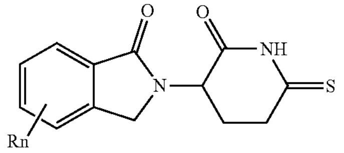
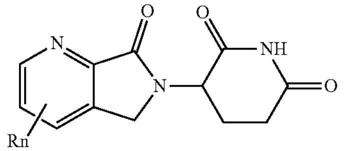
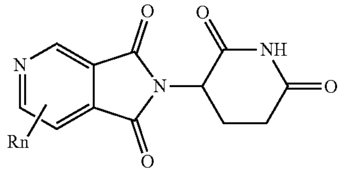

-continued
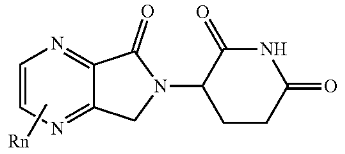
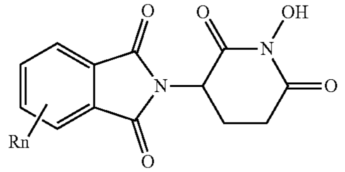
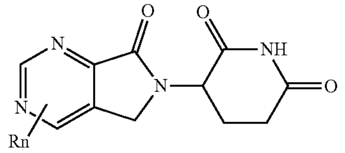
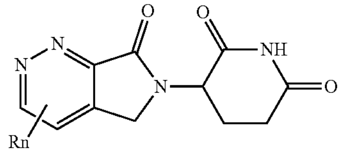
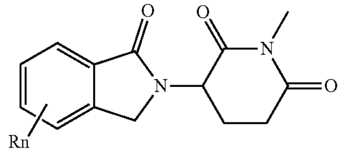
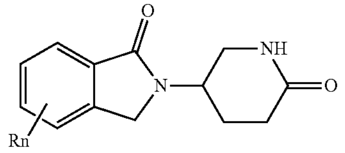
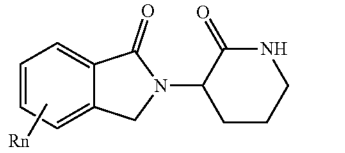
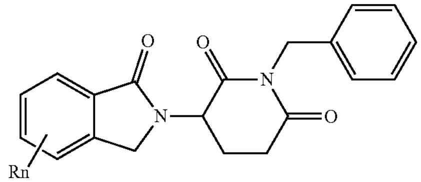
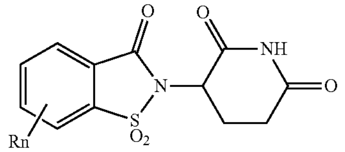
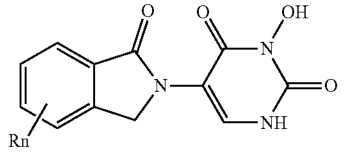
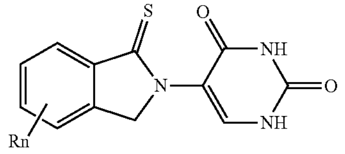
-continued
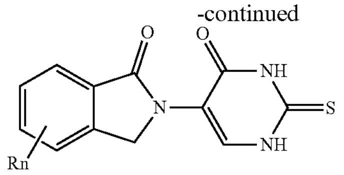
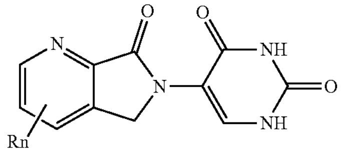
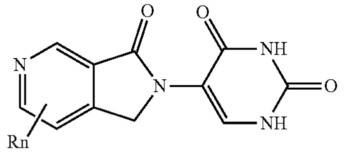
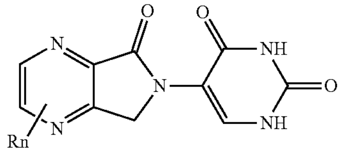
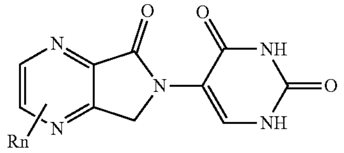
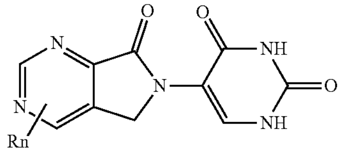
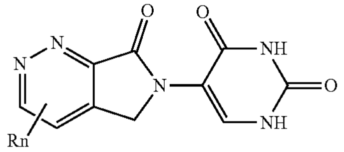
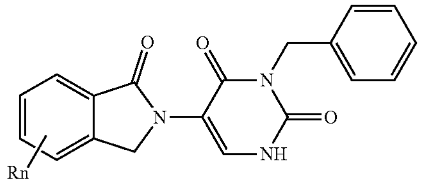
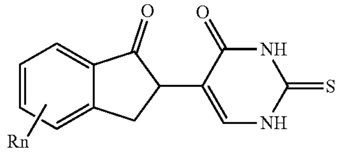
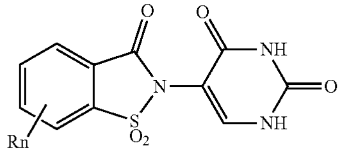
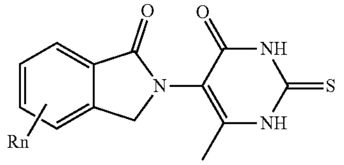

-continued
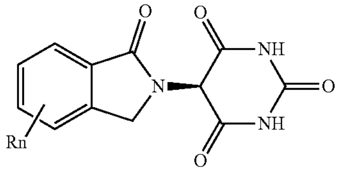
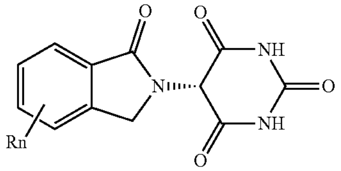
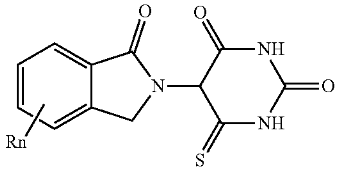
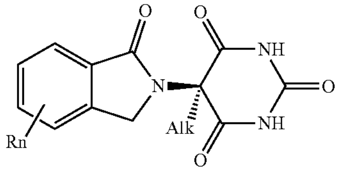
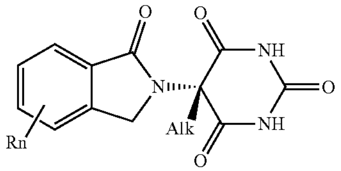
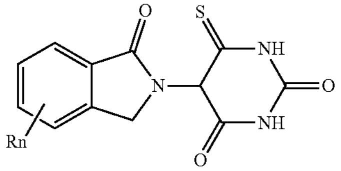
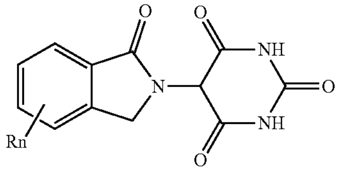
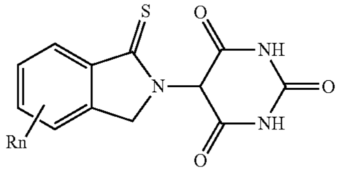
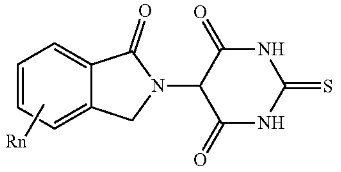
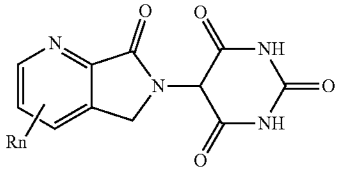
-continued
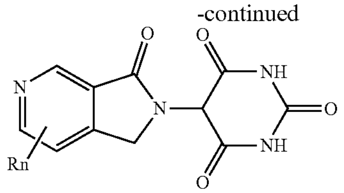
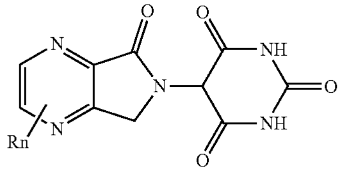
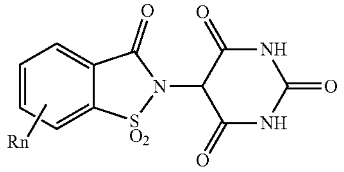
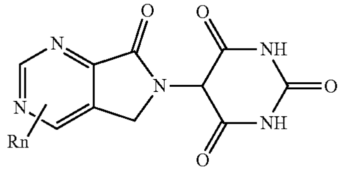
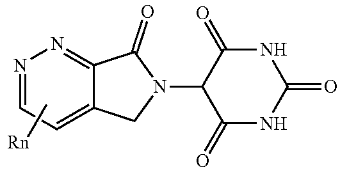
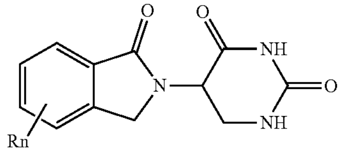
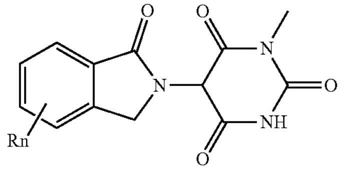
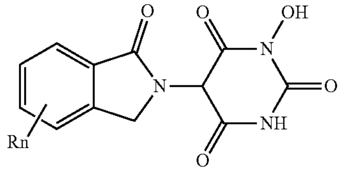
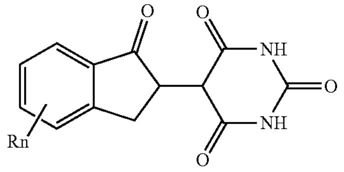
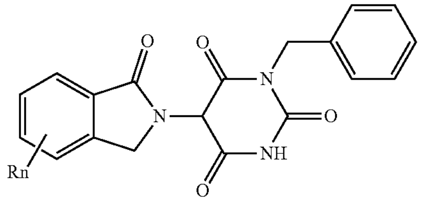

-continued
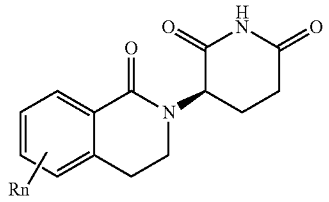
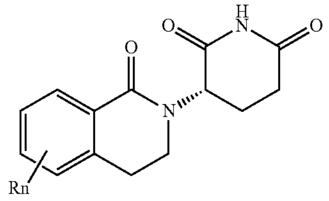
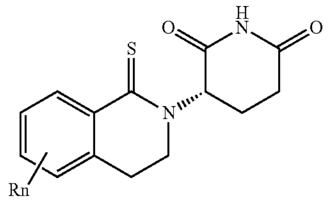
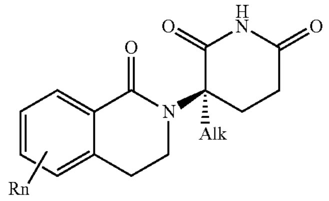
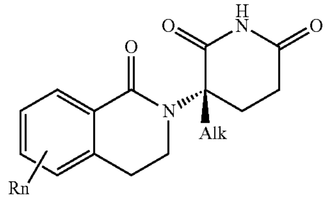
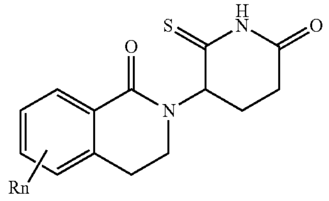
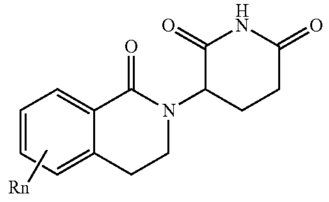
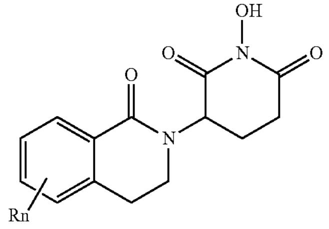
-continued
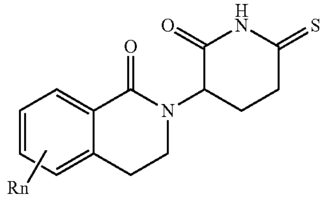
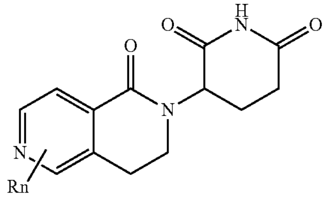
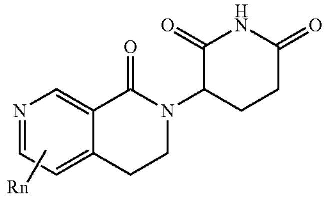
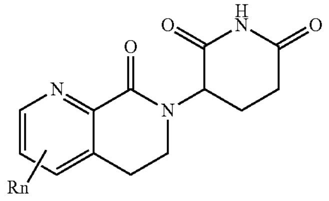
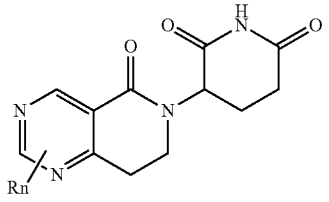
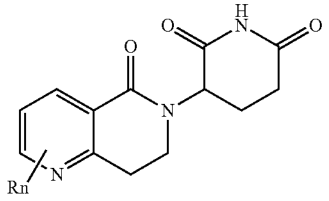
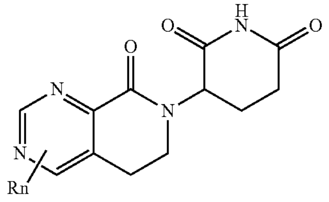
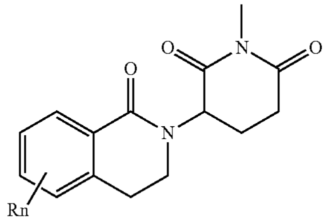

-continued
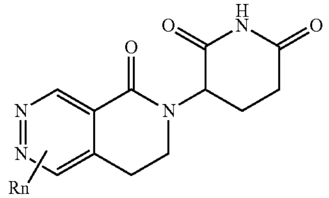
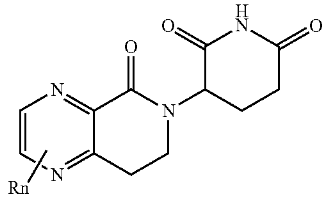
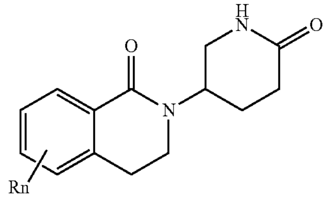
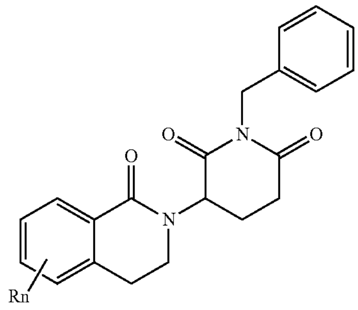
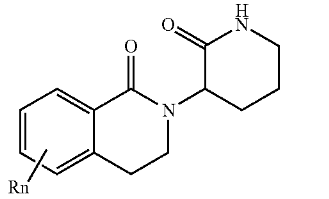
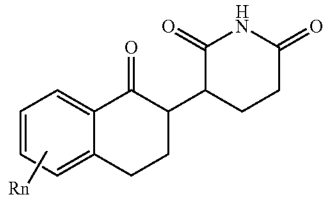
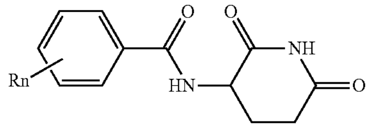
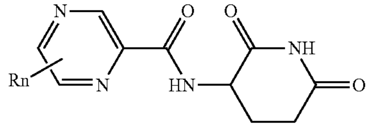
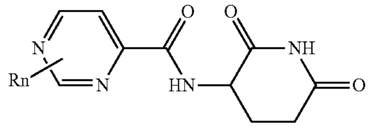
-continued
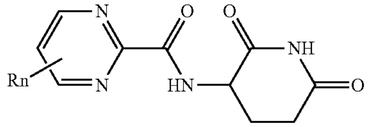
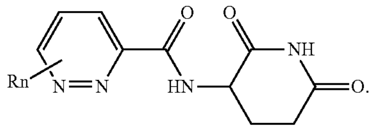
In any of the compounds described herein, the CLM comprises a chemical structure selected from the group:
(h)
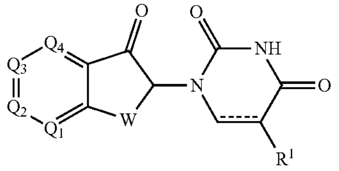
(i)
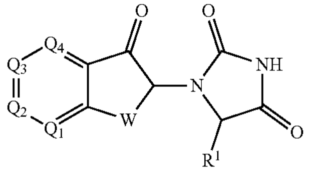
(j)
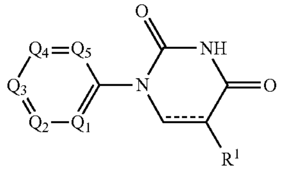
(k)
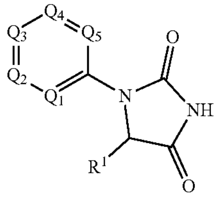
(l)
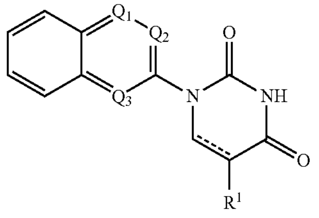
(m)
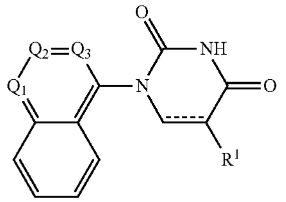

-continued
(n)
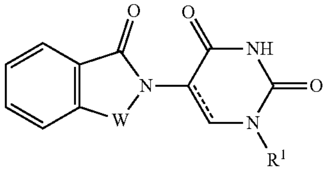
(o)
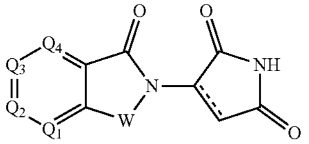
(p)
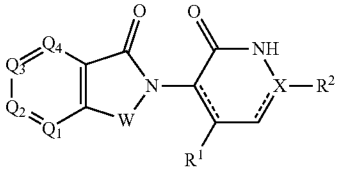
(q)
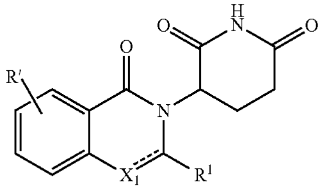
(r)
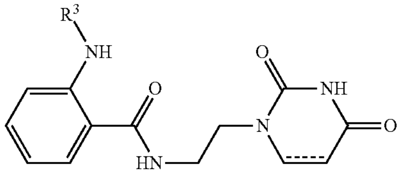
(s)
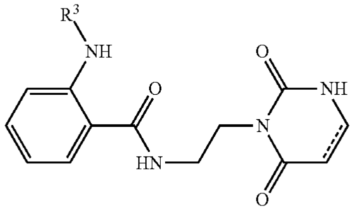
(t)
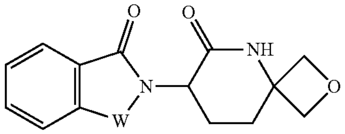
(u)
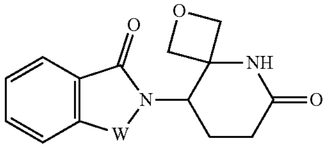
(v)
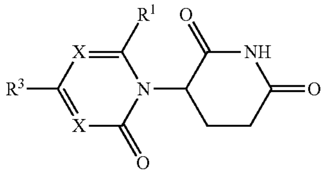
-continued
(w)
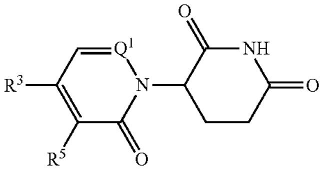
(x)
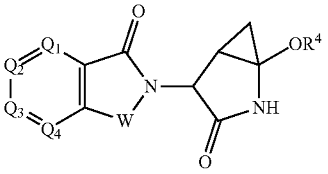
(y)
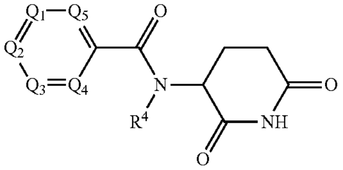
(z)
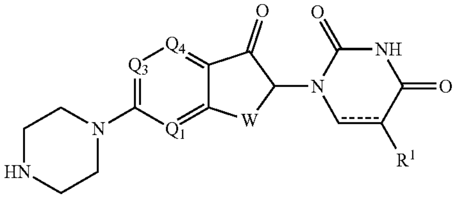
(aa)
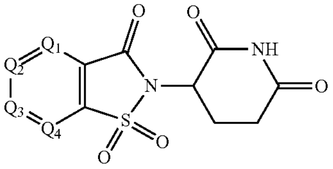
(ab)
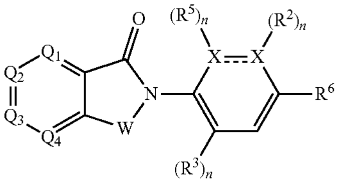
(ac)
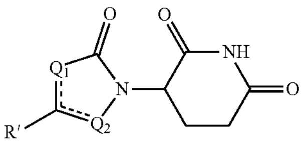
(ad)
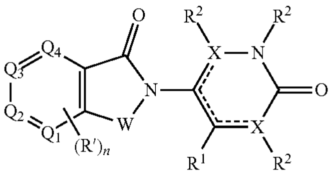
(ae)
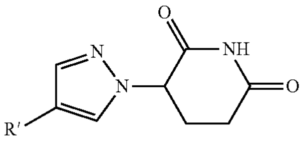

-continued (af)

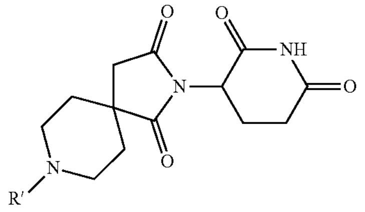

(ag)

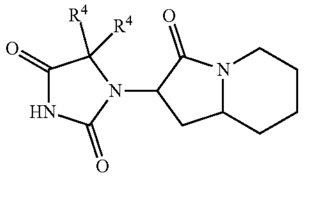

(ah)

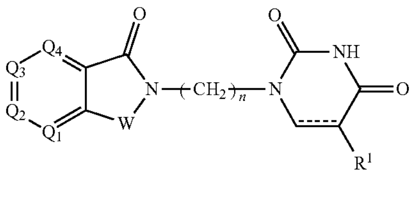

(ai)

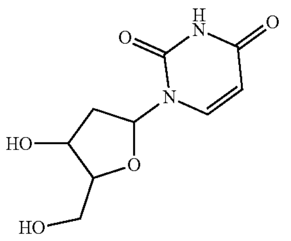

(aj)

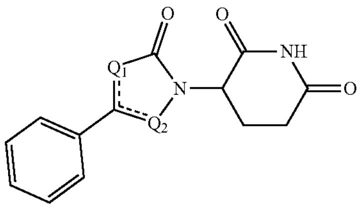

(ak)

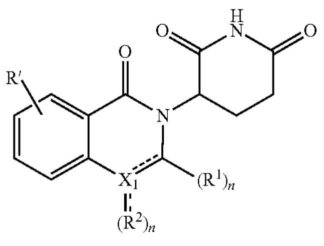

(al)

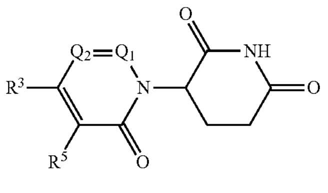

-continued (am)

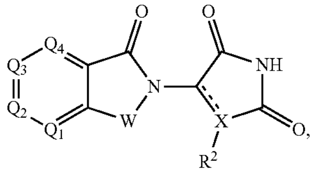

wherein:

W is independently selected from $CH_2$, CHR, C═O, $SO_2$, NH, and N-alkyl;

$Q_1$, $Q_2$, $Q_3$, $Q_4$, $Q_5$ are each independently represent a carbon C or N substituted with a group independently selected from R', N or N-oxide;

$R^1$ is selected from absent, H, OH, CN, C1-C3 alkyl, C═O;

$R^2$ is selected from the group absent, H, OH, CN, C1-C3 alkyl, $CHF_2$, $CF_3$, CHO, C(═O)$NH_2$;

$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(═O)R', CN, OH, $CF_3$;

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4;

⋰ is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$.

In any of the embodiments described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

(an)

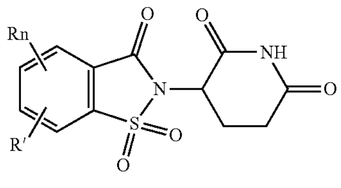

-continued
(ao)
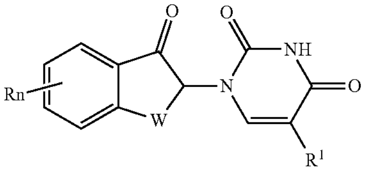
(ap)
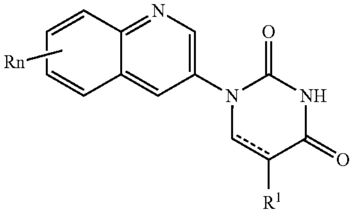
(aq)
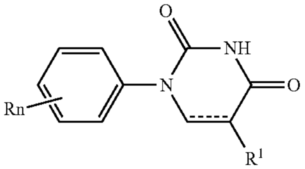
(ar)
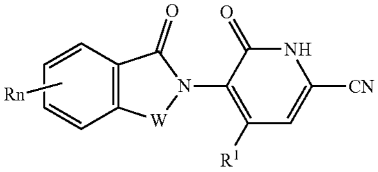
(as)
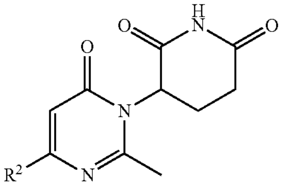
(at)
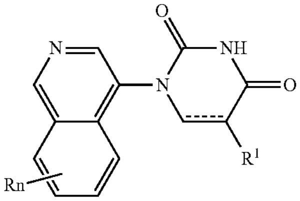
(au)
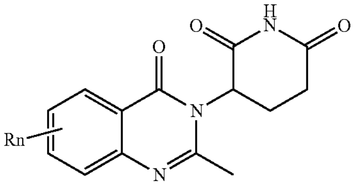
(av)
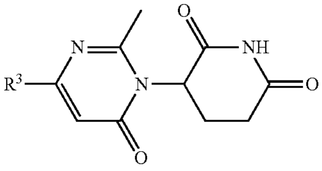
-continued
(aw)
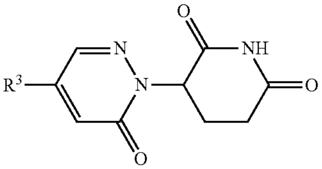
(ax)
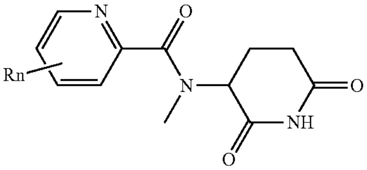
(ay)
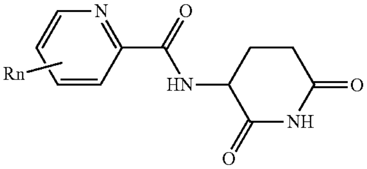
(az)
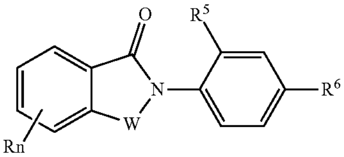
(ba)
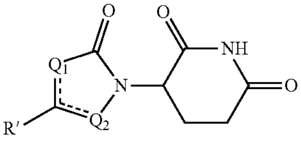
(bb)
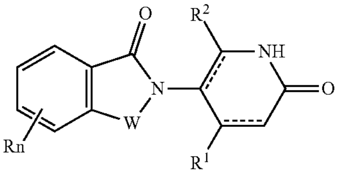
(bc)
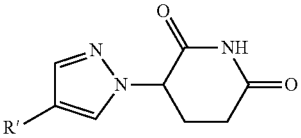
(bd)
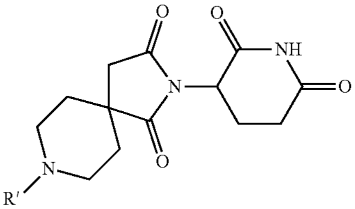
(be)
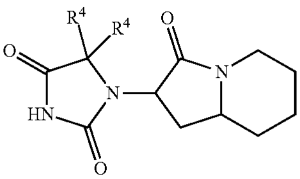

-continued (bf)

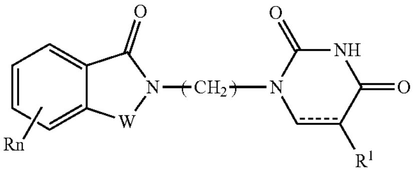

(bg)

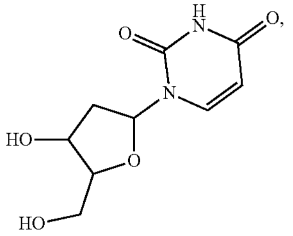

wherein:

W is independently selected from the group $CH_2$, CHR, C═O, $SO_2$, NH, and N-alkyl;

$R^1$ is selected from the group absent, H, CH, CN, C1-C3 alkyl;

$R^2$ is H or a C1-C3 alkyl;

$R^3$ is selected from H, alkyl, substituted alkyl, alkoxy, substituted alkoxy;

$R^4$ is methyl or ethyl;

$R^5$ is H or halo;

$R^6$ is H or halo;

R' is H: or an attachment point for a PTM, a PTM', a chemical linker group (L), a ULM, a CLM, a CLM', $Q_1$ and $Q_2$ are each independently C or N substituted with a group independently selected from H or C1-C3 alkyl;

 is a single or double bond;

R comprises a functional group or an atom, e.g., a functional group or atom selected from: CONR'R", —OR', —NR'R", —SR', —$SO_2$R', —$SO_2$NR'R", —CR'R"—, —CR'NR'R"—, (—CR'O)$_n$R", optionally substituted heterocyclyl, optionally substituted -aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl (e.g., an optionally substituted C5-C7 aryl), -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted

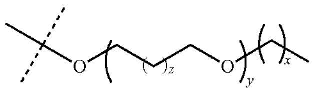

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted

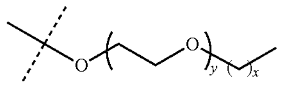

(e.g., optionally substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(═N—CN)NR'R", —C(═N—CN)NR'R", —NR'C(═N—CN)R", —NR'C(═C≡NO2)NR'R", —SO2NR'COR", —NO2, —CO2R', —C(C≡N—OR')R", —CR'═CR'R", —CCR', —S(C═O)(C≡N—R')R", —SF5 and —OCF3.

In any aspect or embodiment described herein, at least one R (e.g., at least one of OH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) is modified to be covalently joined to a PTM, a chemical linker group (L), a ULM, a CLM' (e.g., CLM' is an additional CLM that has the same or different structure as a first CLM), or a combination thereof.

In any of the embodiments described herein, the W, $R^1$, $R^2$, $Q_1$, $Q_2$, $Q_3$, $Q_4$, and R can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and R can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and R can independently be covalently coupled to a linker and/or a linker to which is attached one or more PTM, ULM, ULM', CLM or CLM' groups.

In any aspect or embodiment described herein, R is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

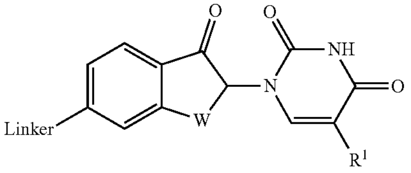

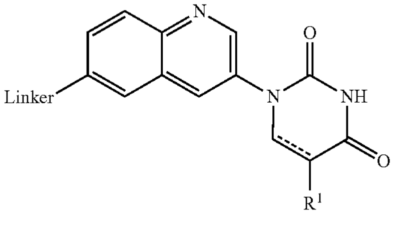

-continued
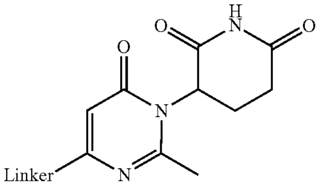
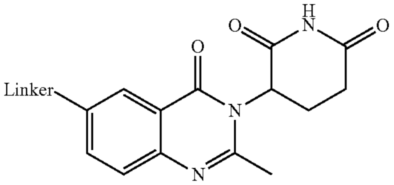
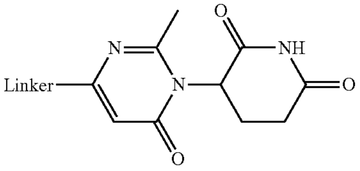
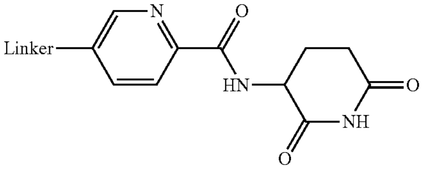
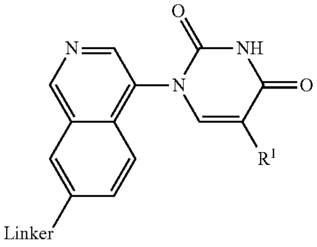
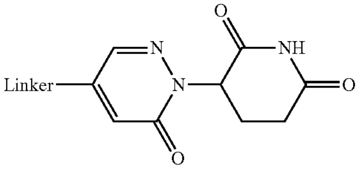
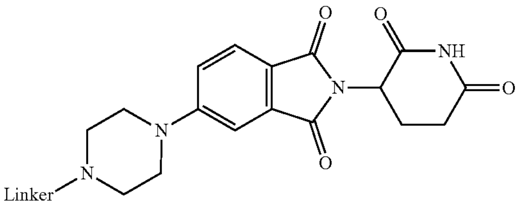
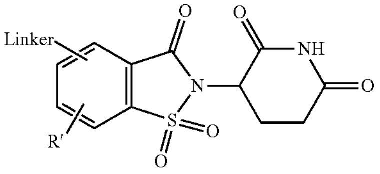
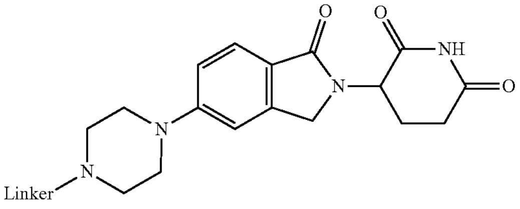
-continued
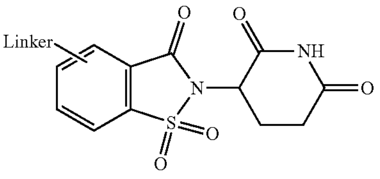
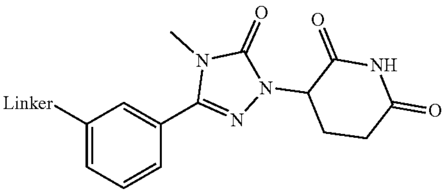
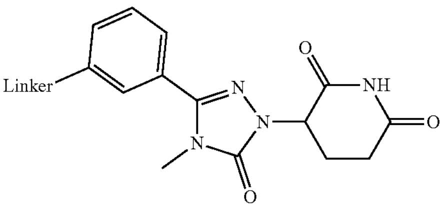
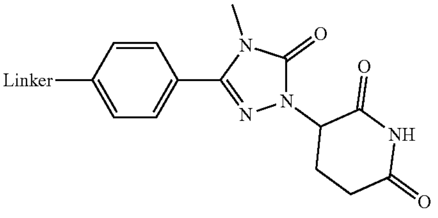
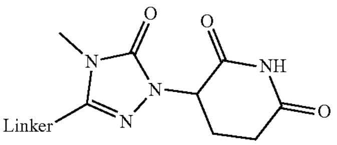
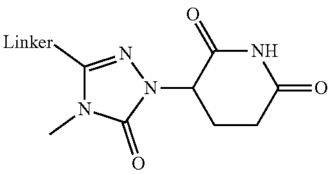
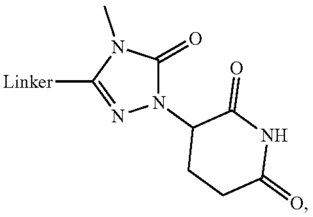
wherein R' is a halogen and $R^1$ is as described in any aspect or embodiment described herein.
In certain cases, "CLM" can be imides that bind to cereblon E3 ligase. These imides and linker attachment point can be but not limited to the following structures:

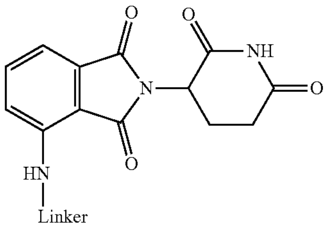

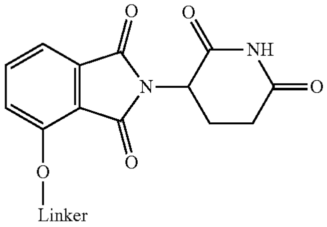

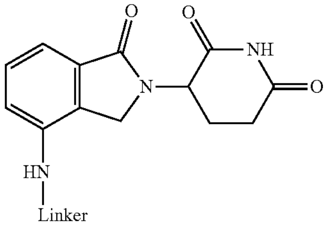

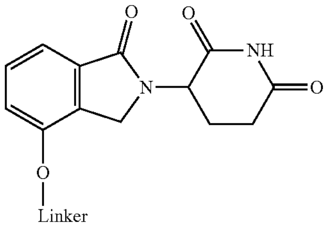

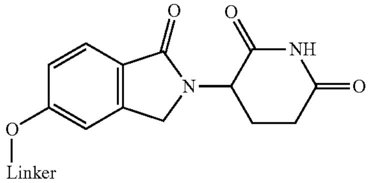

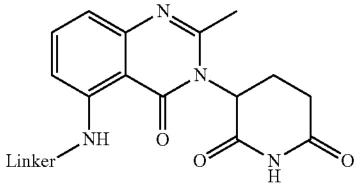

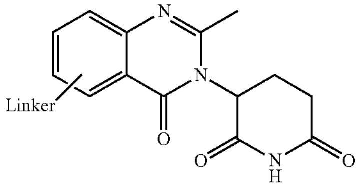

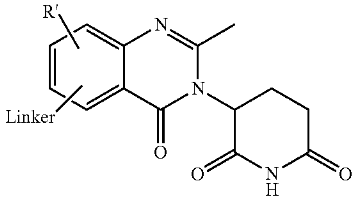

-continued

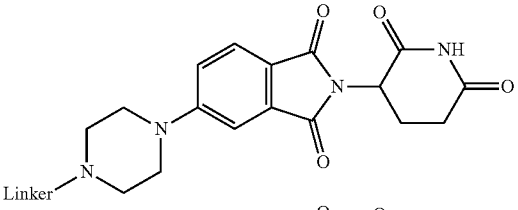

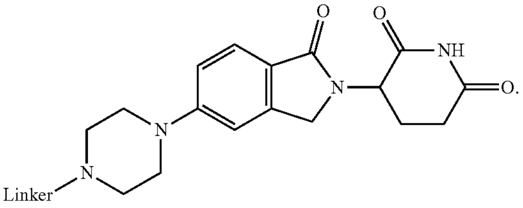

Exemplary VLMs

In certain embodiments of the compounds as described herein, ULM is VLM and comprises a chemical structure selected from the group ULM-a:

ULM-a

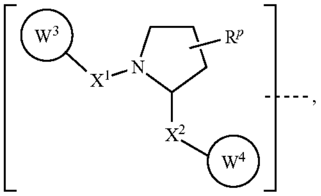

wherein:

a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;

$X^1$, $X^2$ of Formula ULM-a are each independently selected from the group of a bond, O, $NR^{Y3}$, $CR^{Y3}R^{Y4}$, C═O, C═S, SO, and $SO_2$;

$R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3 $R^P$ groups);

$R^P$ of Formula ULM-a is 0, 1, 2, or 3 groups, each independently selected from the group H, halo, —OH, $C_{1-3}$ alkyl, C═O;

$W^3$ of Formula ULM-a is selected from the group of an optionally substituted T, an optionally substituted -T-N($R^{1a}R^{1b}$)$X^3$, optionally substituted -T-N($R_{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR_1$-T-Aryl, an optionally substituted —$NR^1$-T-Heteroaryl or an optionally substituted —$NR^1$-T-Heterocycle;

$X^3$ of Formula ULM-a is C═O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}C{=}O$, $R^{Y3}C{=}S$, $R^{Y3}SO$, $R^{Y3}SO_2$, $N(R^{Y3}R^{Y4})C{=}O$, $N(R^{Y3}R^{Y4})C{=}S$, $N(R^{Y3}R^{Y4})SO$, and $N(R^{Y3}R^{Y4})SO_2$;

T of Formula ULM-a is selected from the group of an optionally substituted alkyl, $—(CH_2)_n—$ group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, $C(O)NR^1R^{1a}$, or $NR^1R^{1a}$ or $R^1$ and $R^{1a}$ are joined to form an optionally substituted heterocycle, or —OH groups or an amino acid side chain optionally substituted;

n is 0 to 6, often 0, 1, 2, or 3, preferably 0 or 1;

$W^4$ of Formula ULM-a is an optionally substituted —NR1-T-Aryl wherein the aryl group may be optionally substituted with an optionally substituted 5-6 membered heteroaryl or aryl, an optionally substituted —NR1-T-Heteroaryl group or an optionally substituted —NR1-T-Heterocycle, where —NR1 is covalently bonded to $X^2$ and $R^1$ is H or $CH_3$, preferably H.

In any of the embodiments described herein, T is selected from the group of an optionally substituted alkyl, $—(CH_2)_n—$ group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, $C(O)\ NR^1R^{1a}$, or $NR^1R^{1a}$ or $R^1$ and $R^{1a}$ are joined to form an optionally substituted heterocycle, or —OH groups or an amino acid side chain optionally substituted; and n is 0 to 6, often 0, 1, 2, or 3, preferably 0 or 1.

In certain embodiments, $W^4$ of Formula ULM-a is

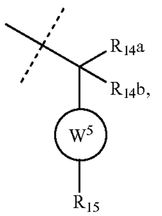

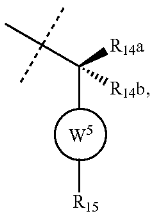

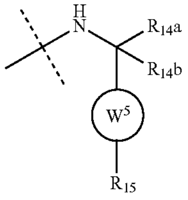

or

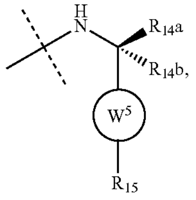

wherein: $W^5$ is optionally substituted (e.g., $W^5$ is an optionally substituted phenyl, an optionally substituted napthyl, or an optionally substituted 5-10 membered heteroaryl); and $R_{14a}$, $R_{14b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R^{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl.

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C═O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

ULM-b

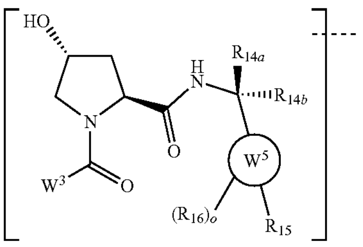

wherein:

$W^3$ of Formula ULM-b is selected from the group of an optionally substituted aryl, optionally substituted heteroaryl, or

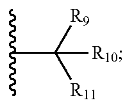

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

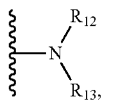

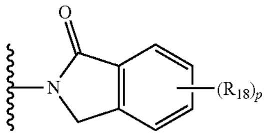

or

-continued

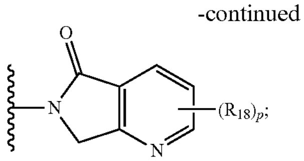

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, or optionally substituted alkyl;

$W^5$ of Formula ULM-b is selected from the group of an optionally substituted phenyl or an optionally substituted 5-10 membered heteroaryl, $R_{15}$ of Formula ULM-b is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

each $R_{16}$ of Formula ULM-b is independently selected from the group of H, CN, halo, optionally substituted alkyl, optionally substituted haloalkyl, hydroxy, or optionally substituted haloalkoxy;

o of Formula ULM-b is 0, 1, 2, 3, or 4;

$R_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

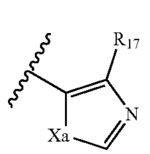

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

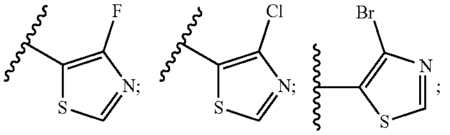
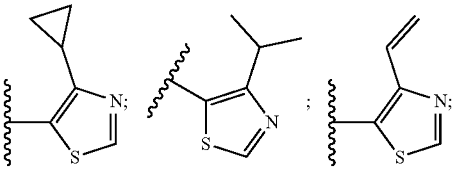
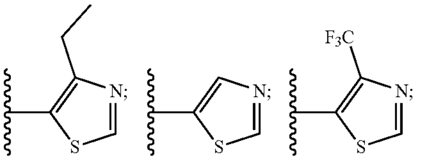
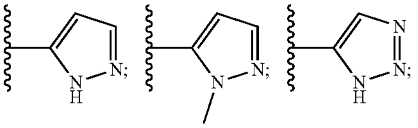
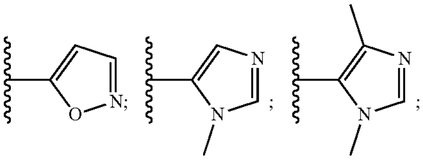
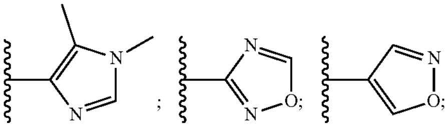
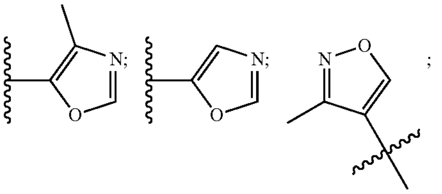
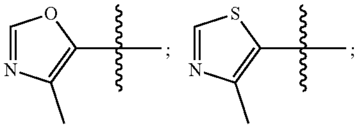
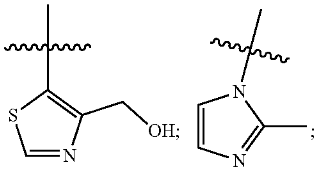

and

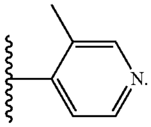

In certain embodiments, $R_{11}$ of Formula ULM-b is selected from the group consisting of:

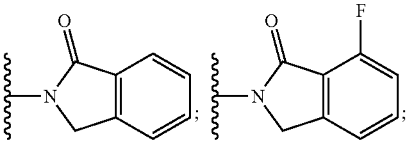

-continued

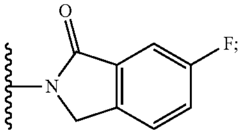

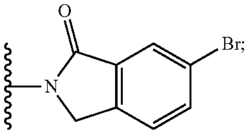

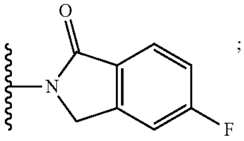

;

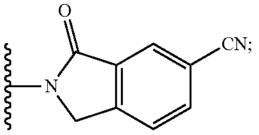

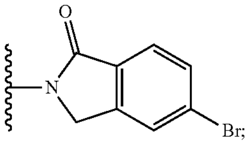

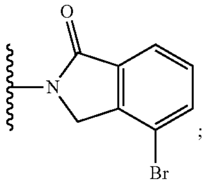

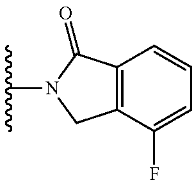

;

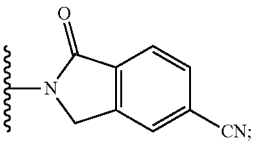

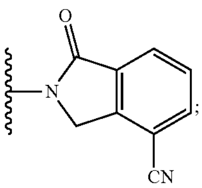

;

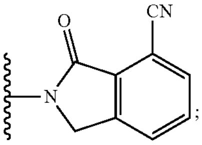

;

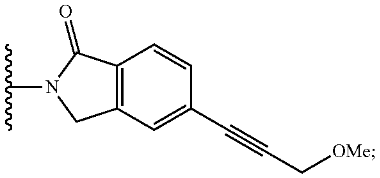

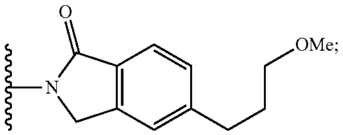

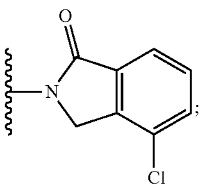

;

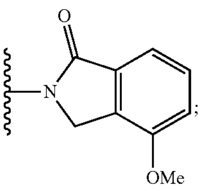

;

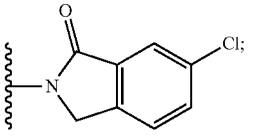

and

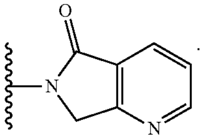

.

In certain embodiments, ULM has a chemical structure selected from the group of:

ULM-c

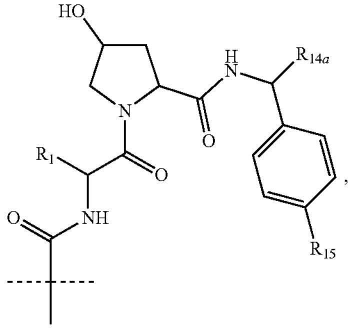

ULM-d

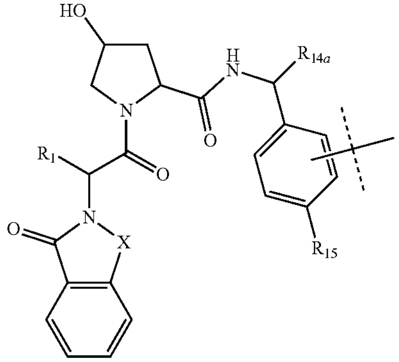

ULM-e

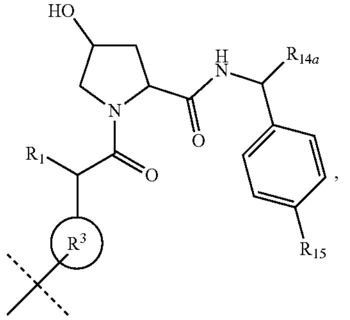

wherein:

$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl, optionally substituted alkyl, optionally substituted haloalkyl, optionally substituted haloalkoxy, optionally substituted cycloalkyl, or optionally substituted cycloheteroalkyl (each optionally substituted);

X of Formulas ULM-c, ULM-d, and ULM-e is C, $CH_2$, or C=O $R_3$ of Formulas ULM-c, ULM-d, and ULM-e is absent or an optionally substituted 5 or 6 membered heteroaryl; and the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

ULM-f

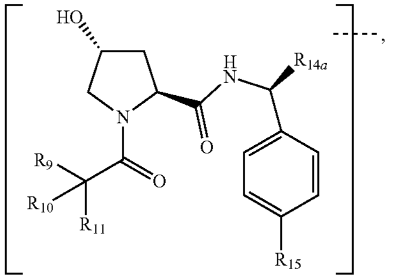

wherein:

$R_{14a}$ of Formula ULM-f is H, haloalkyl, optionally substituted alkyl, methyl, fluoromethyl, hydroxymethyl, ethyl, isopropyl, or cyclopropyl;

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

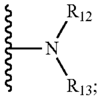

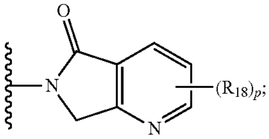

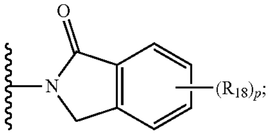

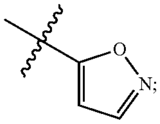

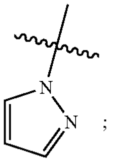

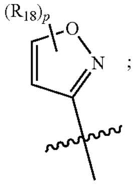

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C═O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, OH, $NO_2$, optionally substituted heteroaryl, optionally substituted aryl;

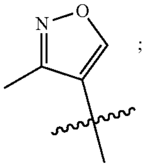
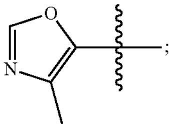
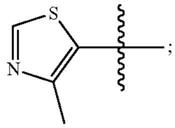

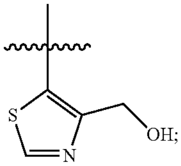
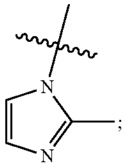
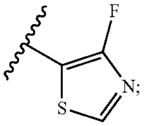

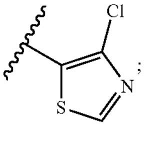
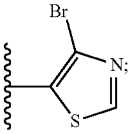
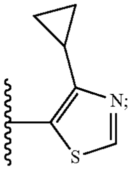

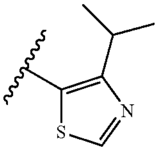
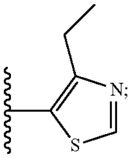
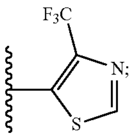

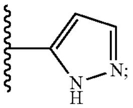
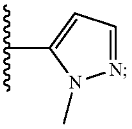
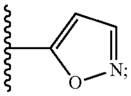

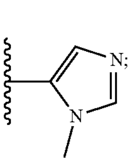
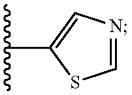
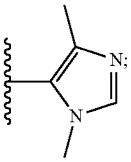

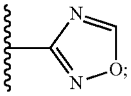

and wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

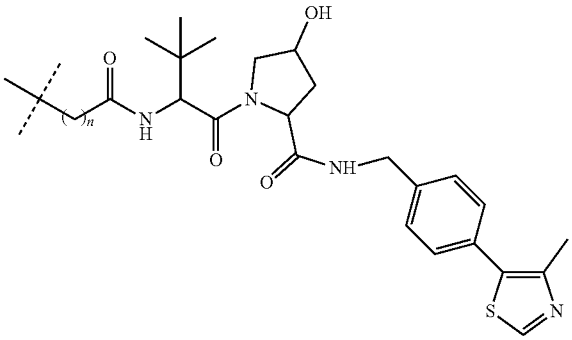
ULM-a2
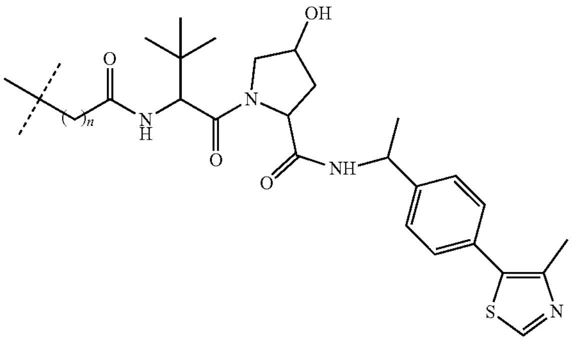
ULM-a3
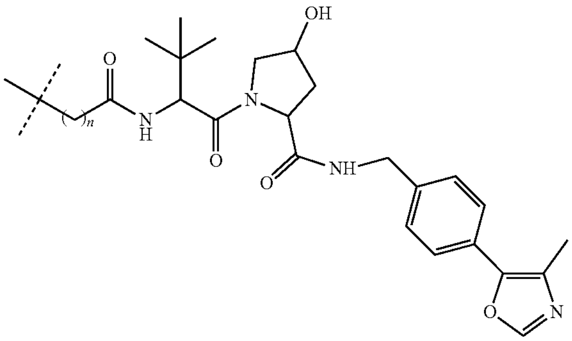
ULM-a4
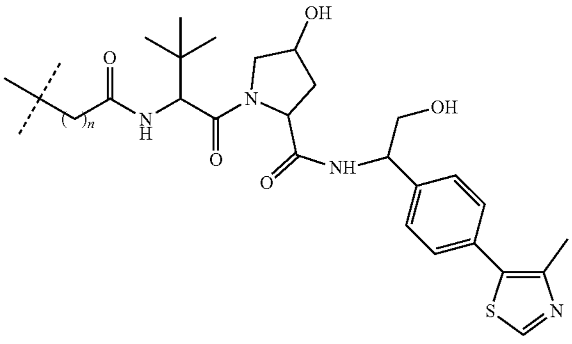
-continued
ULM-a5
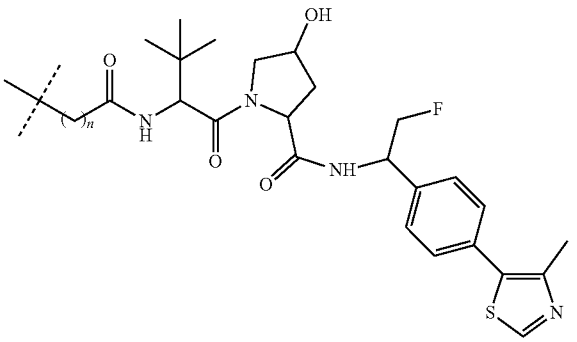
ULM-a6
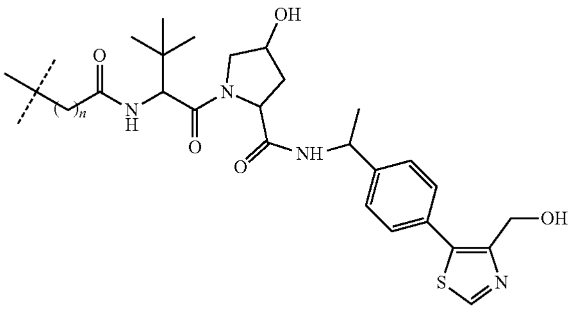
ULM-a7
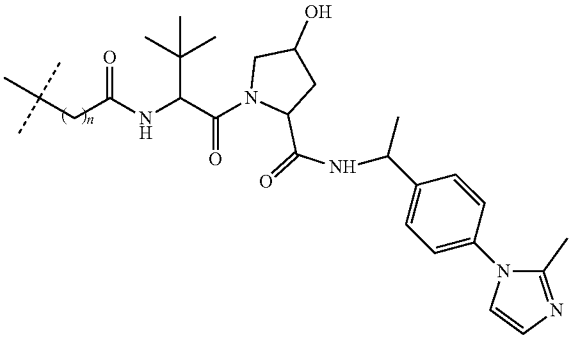
ULM-a8
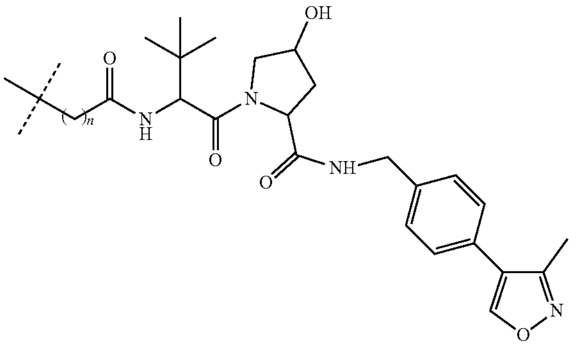

-continued
ULM-a9
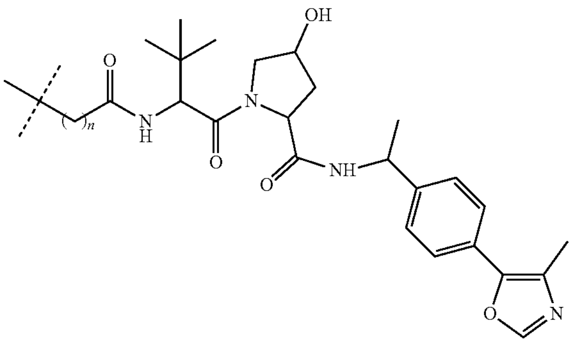
ULM-a10
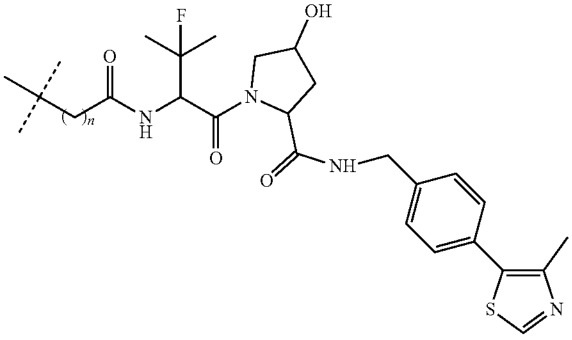
ULM-a11
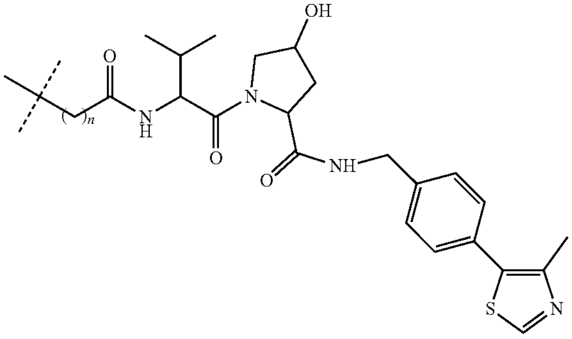
ULM-a12
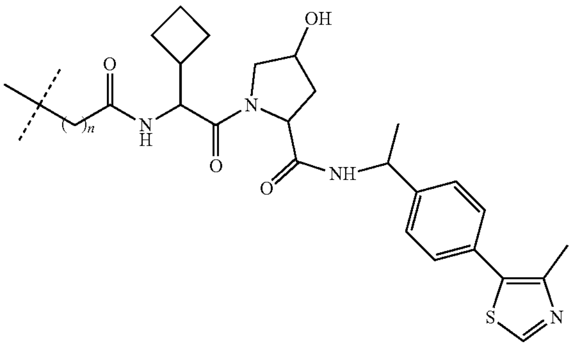
-continued
ULM-a13
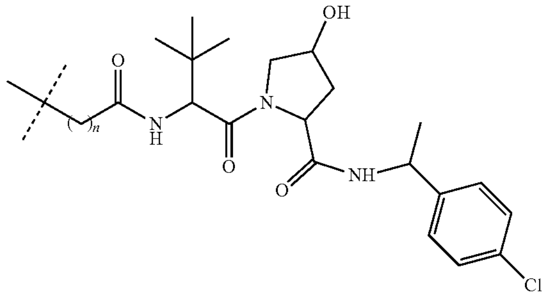
ULM-a14
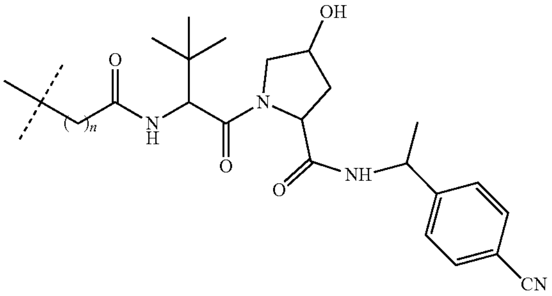
ULM-a15
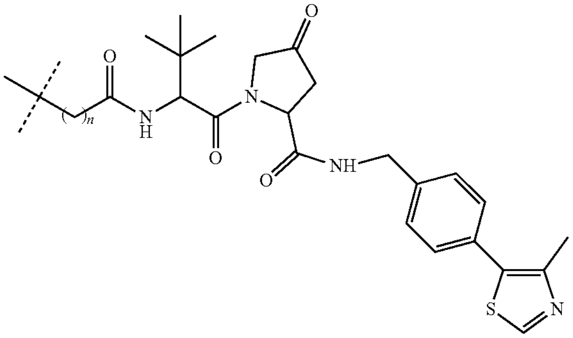
wherein n is 0 or 1.
In certain embodiments, the ULM is selected from the following structures:
ULM-b1
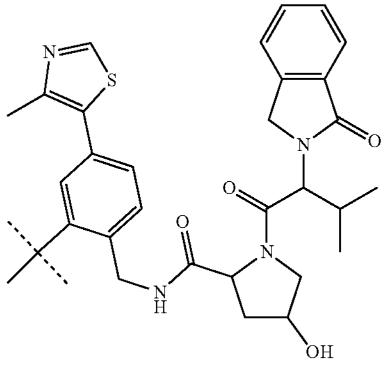

-continued
ULM-b2
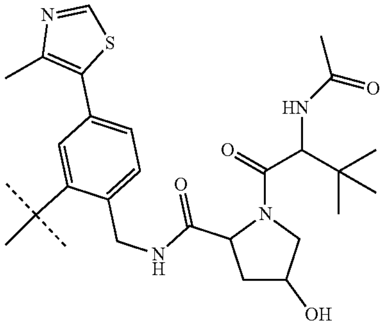
ULM-b3
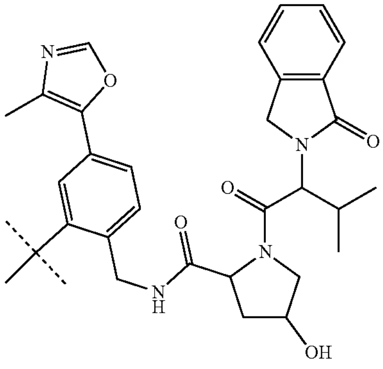
ULM-b4
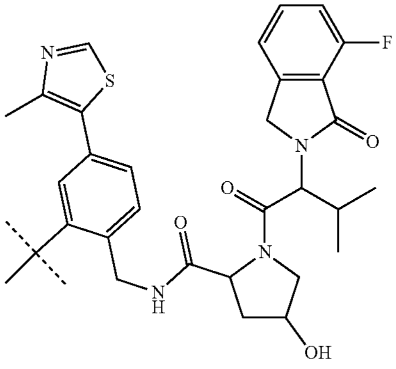
ULM-b5
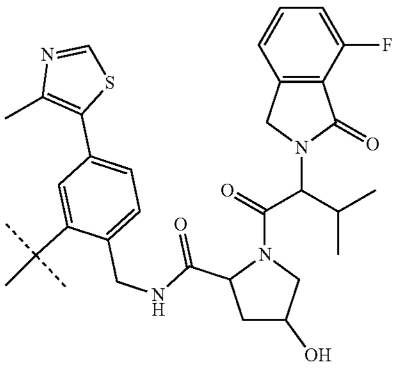
-continued
ULM-b6
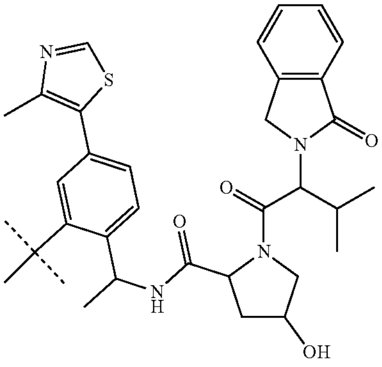
ULM-b7
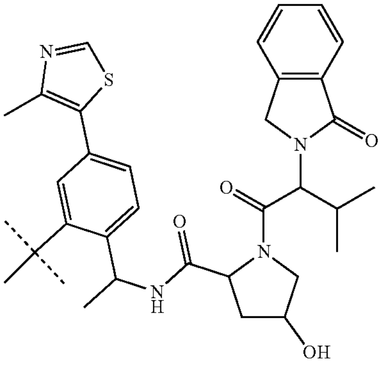
ULM-b8
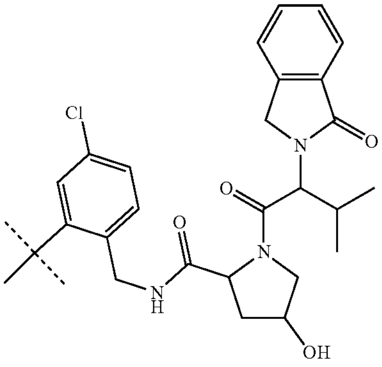
ULM-b9
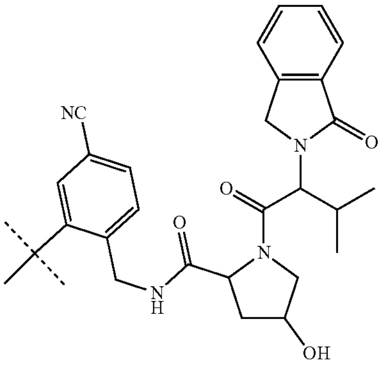

ULM-b10
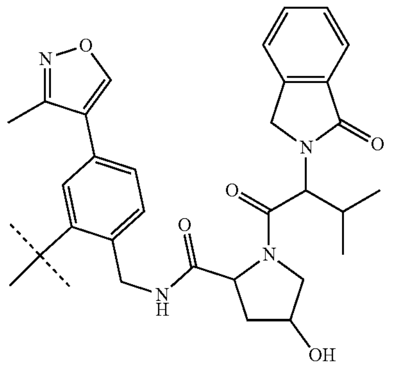
ULM-b11
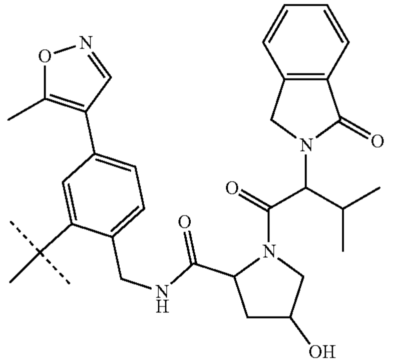
ULM-b12
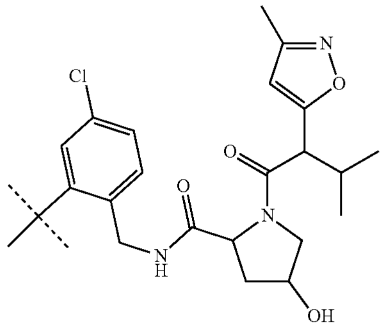
ULM-c1
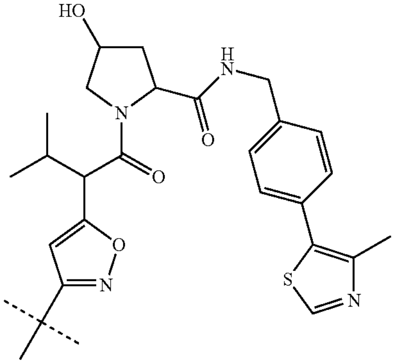
ULM-c2
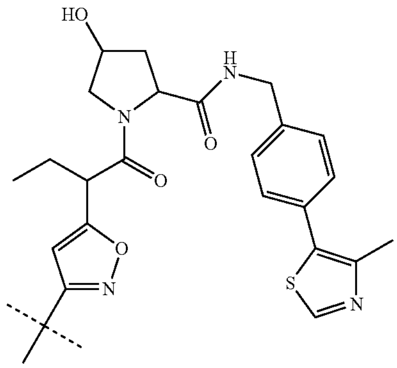
ULM-c3
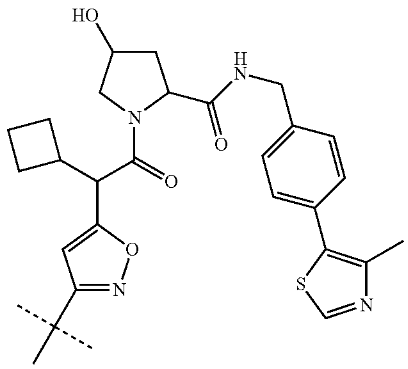
ULM-c4
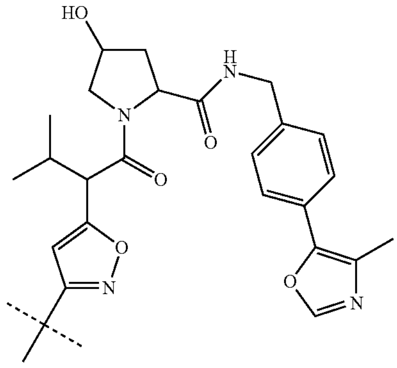
ULM-c5
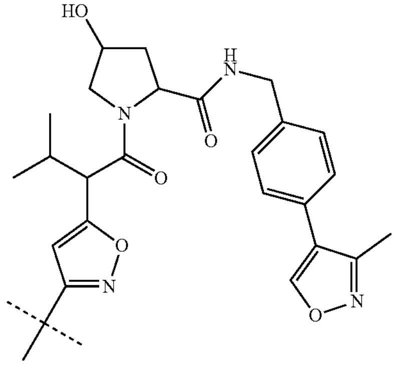

-continued
ULM-c6
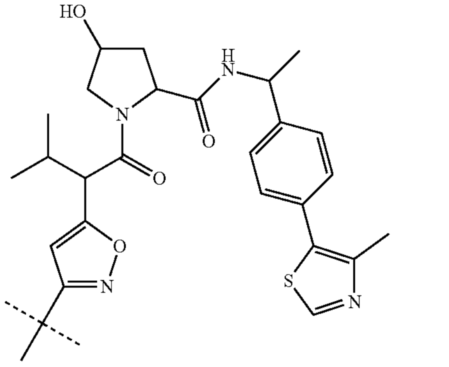
ULM-c7
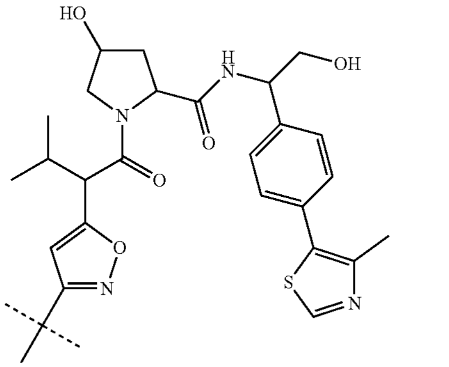
ULM-c8
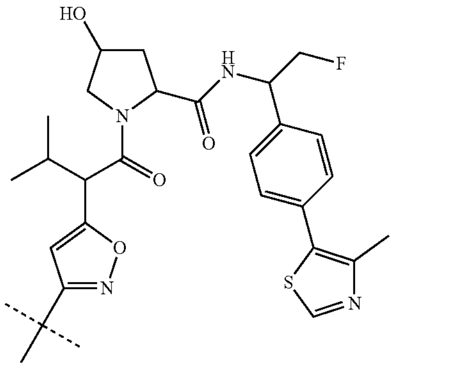
ULM-c9
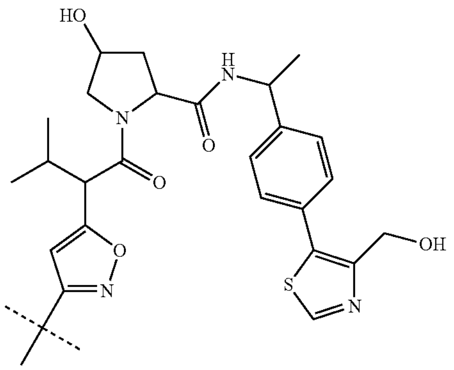
-continued
ULM-c10
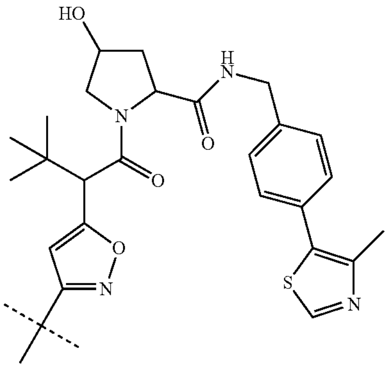
ULM-c11
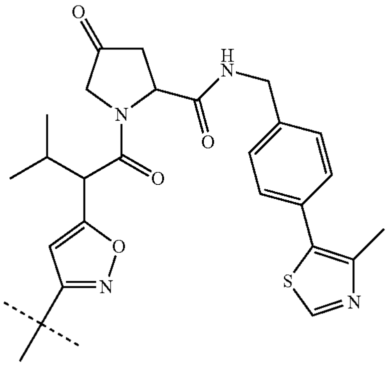
ULM-c12
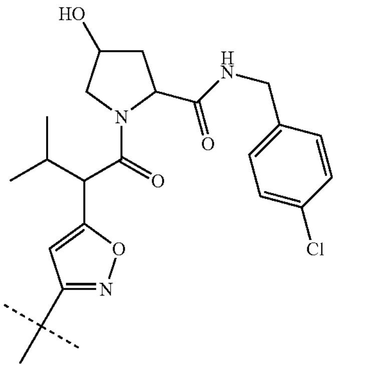
ULM-c13
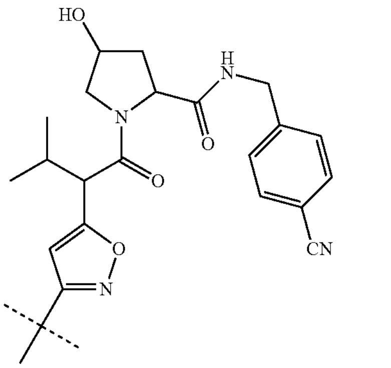

-continued
ULM-c14
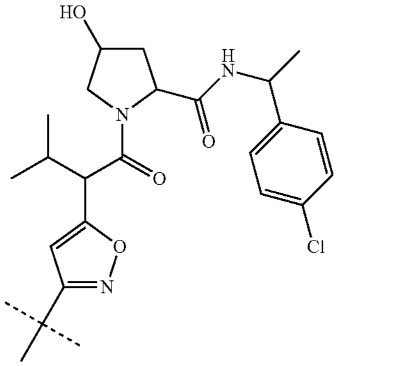
ULM-c15
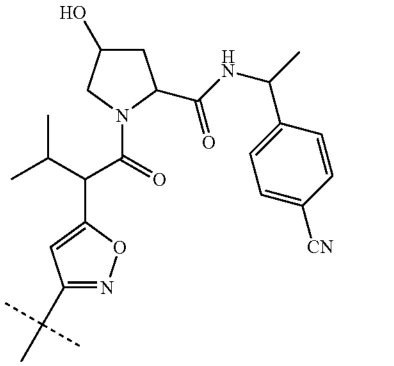
ULM-d1
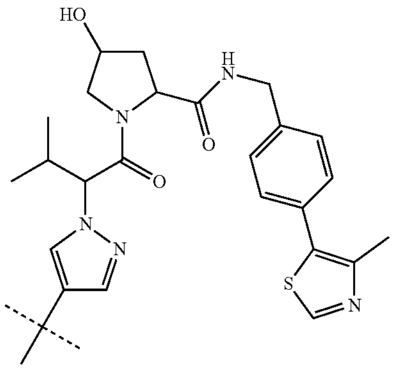
ULM-d2
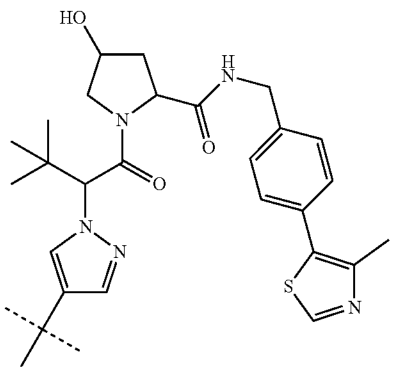
-continued
ULM-d3
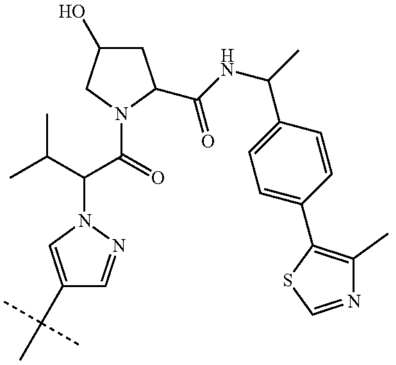
ULM-d4
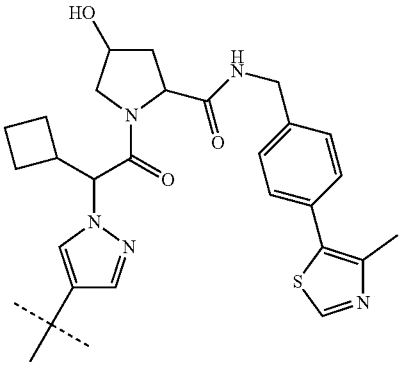
ULM-d5
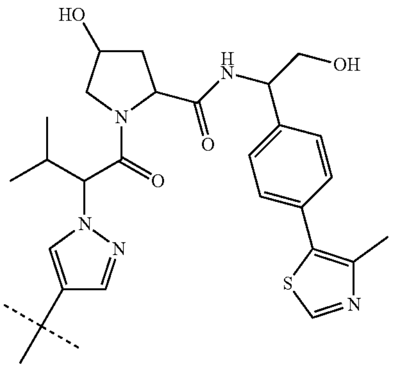
ULM-d6
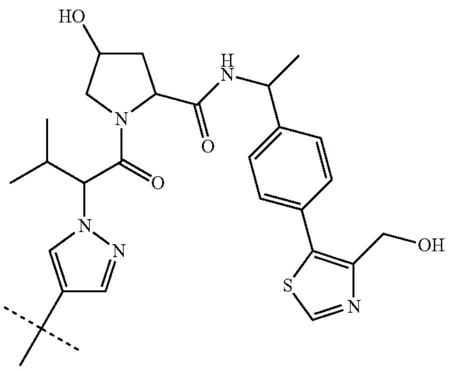

-continued

ULM-d7

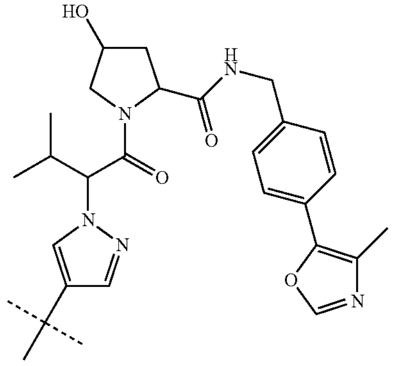

ULM-d8

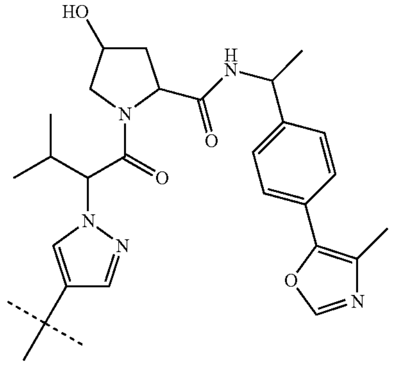

ULM-d9

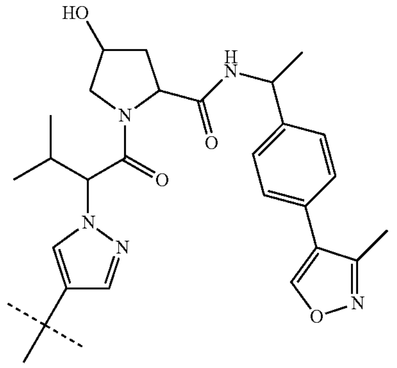

wherein, the phenyl ring in ULM-a1 through ULM-a15, ULM-b1 through ULM-b12. ULM-c1 through UJLM-c15 and UJLM-d1 through UJLM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g

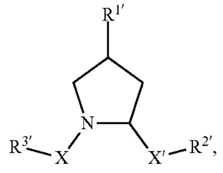

wherein:

$R^{1'}$ of ULM-g is an optionally substituted $C_1$-$C_6$ alkyl group, an optionally substituted $—(CH_2)_nOH$, an optionally substituted $—(CH_2)_nSH$, an optionally substituted $(CH_2)_n—O—(C_1\text{-}C_6)$alkyl group, an optionally substituted $(CH_2)_n—WCOCW—(C_0\text{-}C_6)$alkyl group containing an epoxide moiety WCOCW where each W is independently H or a $C_1$-$C_3$ alkyl group, an optionally substituted $—(CH_2)_nCOOH$, an optionally substituted $—(CH_2)_nC(O)—(C_1\text{-}C_6$ alkyl), an optionally substituted $—(CH_2)_nNHC(O)—R_1$, an optionally substituted $—(CH_2)_nC(O)—NR_1R_2$, an optionally substituted $—(CH_2)_nOC(O)—NR_1R_2$, $—(CH_2O)_nH$, an optionally substituted $—(CH_2)_nOC(O)—(C_1\text{-}C_6$ alkyl), an optionally substituted $—(CH_2)_nC(O)—O—(C_1\text{-}C_6$ alkyl), an optionally substituted $—(CH_2O)_nCOOH$, an optionally substituted $—(OCH_2)_nO—(C_1\text{-}C_6$ alkyl), an optionally substituted $—(CH_2O)_nC(O)—(C_1\text{-}C_6$ alkyl), an optionally substituted $—(OCH_2)_nNHC(O)—R_1$, an optionally substituted $—(CH_2O)_nC(O)—NR_1R_2$, $—(CH_2CH_2O)_nH$, an optionally substituted $—(CH_2CH_2O)_nCOOH$, an optionally substituted $—(OCH_2CH_2)_nO—(C_1\text{-}C_6$ alkyl), an optionally substituted $—(CH_2CH_2O)_nC(O)—(C_1\text{-}C_6$ alkyl), an optionally substituted $—(OCH_2CH_2)_nNHC(O)—R_1$, an optionally substituted $—(CH_2CH_2O)_nC(O)—NR_1R_2$, an optionally substituted $—SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a $—(CH_2)_mNR_1R_2$ group;

X and X' of ULM-g are each independently C═O, C═S, —S(O), $S(O)_2$, (preferably X and X' are both C═));

$R^{2'}$ of ULM-g is an optionally substituted $—(CH_2)_n—(C{=}O)_u(NR_1)_v(SO_2)_w$-alkyl group, an optionally substituted $—(CH_2)_n—(C{=}O)_u(NR_1)_v(SO_2)_wNR_{1N}R_{2N}$ group, an optionally substituted $—(CH_2)_n—(C{=}O)_u(NR_1)_v(SO_2)_w$-Aryl, an optionally substituted $—(CH_2)_n$ $—(C{=}O)_u(NR_1)_v(SO_2)_w$-Heteroaryl, an optionally substituted $—(CH_2)_n—(C{=}O)_vNR_1(SO_2)_w$-Heterocycle, an optionally substituted $—NR_1—(CH_2)_n—C(O)_u(NR_1)_v(SO_2)_w$-alkyl, an optionally substituted $—NR^1—(CH_2)_n—C(O)_u(NR_1)_v(SO_2)_w—NR_{1N}R_{2N}$, an optionally substituted $—NR^1—(CH_2)_n—C(O)_u(NR_1)_v(SO_2)_w—NR_1C(O)R_{1N}$, an optionally substituted $—NR^1—(CH_2)_n—(C{=}O)_u(NR_1)_v(SO_2)_w$-Aryl, an optionally substituted $—NR^1—(CH_2)_n—(C{=}O)_u(NR_1)_v(SO_2)_w$-Heteroaryl or an optionally substituted $—NR^1—(CH_2)_n—(C{=}O)_vNR_1(SO_2)_w$-Heterocycle, an optionally substituted $—X^{R2'}$-alkyl group; an optionally substituted $—X^{R2'}$-Aryl group; an optionally substituted —$X^{R2'}$-Heteroaryl group; an optionally substituted —$X^{R2'}$-Heterocycle group; an optionally substituted;

$R^{3'}$ of ULM-g is an optionally substituted alkyl, an optionally substituted —$(CH_2)_n$—$(O)_u(NR_1)_v(SO_2)_w$-alkyl, an optionally substituted —$(CH_2)_n$—$C(O)_u(NR_1)_v(SO_2)_w$—$NR_{1N}R_{2N}$, an optionally substituted —$(CH_2)_n$—$C(O)_u(NR_1)_v(SO_2)_w$—$NR_1C(O)R_{1N}$, an optionally substituted —$(CH_2)_n$—$C(O)_u(NR_1)_v(SO_2)_w$—$C(O)NR_1R_2$, an optionally substituted —$(CH_2)_n$—$C(O)_u(NR_1)_v(SO_2)_w$-Aryl, an optionally substituted —$(CH_2)_n$ —$C(O)_u(NR_1)_v(SO_2)_w$-Heteroaryl, an optionally substituted —$(CH_2)_n$—$C(O)_u(NR_1)_v(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_{1N}R_{2N}$, an optionally substituted —$NR^1$—$(CH_2)_n$—$C(O)_u(NR_1)_v(SO_2)_w$—$NR_1C(O)R_{1N}$, an optionally substituted —$NR^1$—$(CH_2)_n$—$C(O)_u(NR_1)_v(SO_2)_w$-Aryl, an optionally substituted —$NR^1$—$(CH_2)_n$ —$C(O)_u(NR_1)_v(SO_2)_w$-Heteroaryl, an optionally substituted —$NR^1$—$(CH_2)_n$—$C(O)_u(NR_1)_v(SO_2)_w$-Heterocycle, an optionally substituted —O—$(CH_2)$n-$(C{=}O)_u(NR_1)_v(SO_2)_w$-alkyl, an optionally substituted —O—$(CH_2)$n-$(C{=}O)_u(NR_1)_v(SO_2)_w$—$NR_{1N}R_{2N}$, an optionally substituted —O—$(CH_2)$n-$(C{=}O)_u(NR_1)_v(SO_2)_w$—$NR_1C(O)R_{1N}$, an optionally substituted —O—$(CH_2)$n-$(C{=}O)_u(NR_1)_v(SO_2)_w$-Aryl, an optionally substituted —O—$(CH_2)_n$—$(C{=}O)_u$ $(NR_1)_v(SO_2)_w$-Heteroaryl or an optionally substituted —O—$(CH_2)_n$—$(C{=}O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C{=}O)_{m'}$—$(V)_{n'}$-alkyl group, an optionally substituted —$(CH_2)_n$—$N(R_{1'})(C{=}O)_{m'}$—$(V)_{n'}$-Aryl group, an optionally substituted —$(CH_2)_n$—$N(R_{1'})(C{=}O)_{m'}$—$(V)_{n'}$-Heteroaryl group, an optionally substituted —$(CH_2)_n$—$N(R_{1'})(C{=}O)_{m'}$—$(V)_{n'}$-Heterocycle group, an optionally substituted —$X^{R3'}$-alkyl group; an optionally substituted —$X^{R3'}$-Aryl group; an optionally substituted —$X^{R3'}$-Heteroaryl group; an optionally substituted —$X^{R3'}$-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$CH_2)_n$—, —$CH_2)_n$—$CH(X_v)$=$CH(X_v)$— (cis or trans), —$CH_2)_n$—CH≡CH—, —$(CH_2CH_2O)_n$— or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

ULM-h

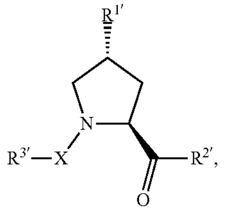

wherein:

each of $R^{1'}$, $R^{2'}$ and $R^{3'}$ of ULM-h are the same as above and X is C═O, C═S, —S(O) group or a $S(O)_2$ group, more preferably a C═O group, and any one or more of $R_{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

ULM-i

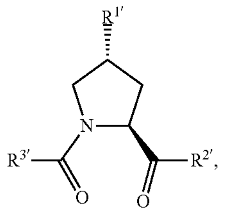

wherein:

any one or more of $R_{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In further preferred aspects of the disclosure, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, $-(CH_2)_nOH$, $(CH_2)_n-O-(C_1-C_6)$alkyl group, $-(CH_2)C_nOH$, $-(CH_2O)_nH$, an optionally substituted $-(CH_2)_n\ OC(O)-(C_1-C_6$ alkyl), or an optionally substituted $-(CH_2)_nC(O)-O-(C_1-C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a $S(O)_2$ group, more preferably a C=O group;

$R^{2'}$ of ULM-g through ULM-i is preferably an optionally substituted $-NR^1$-T-Aryl, an optionally substituted $-NR^1$-T-Heteroaryl group or an optionally substituted $-NR^1$-T-Heterocycle, where $R^1$ is H or $CH_3$, preferably H and T is an optionally substituted $-(CH_2)_n-$ group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1. Alternatively, T may also be a $-(CH_2O)_n-$ group, a $-(OCH_2)_n-$ group, a $-(CH_2CH_2O)_n-$ group, a $-(OCH_2CH_2)_n-$ group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

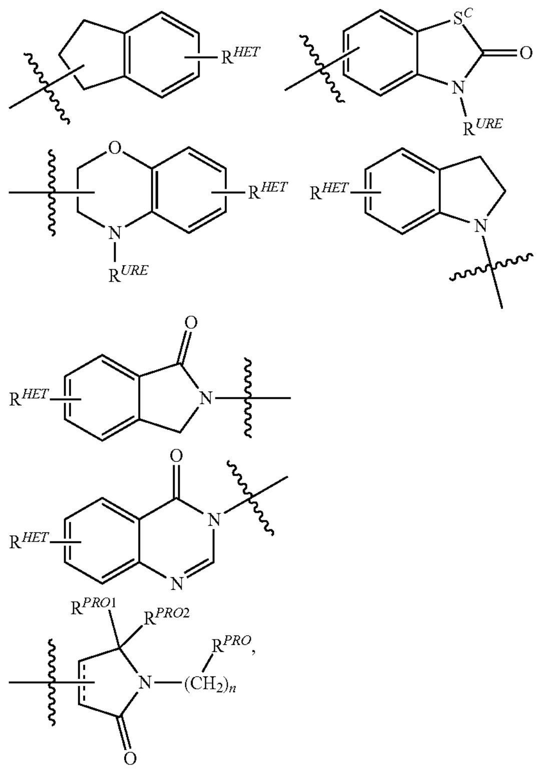

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $-C(O)(C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrabydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

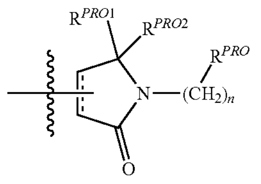

of ULM-g through ULM-i is

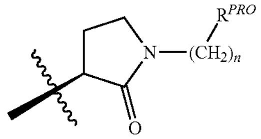

or

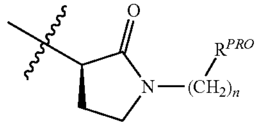

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

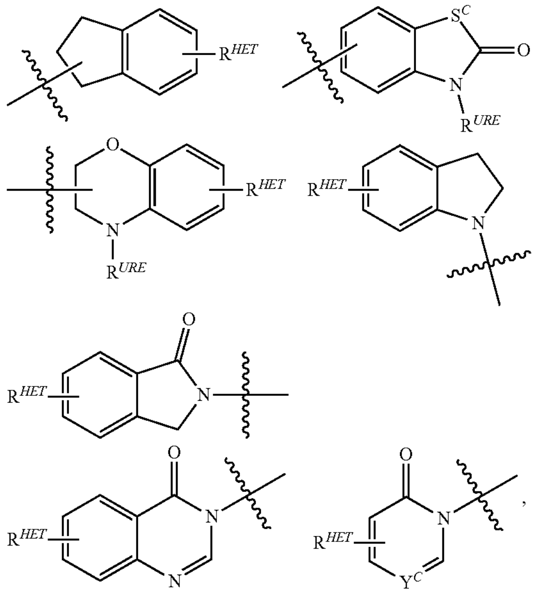

, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where Rye is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

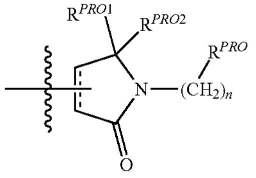

or

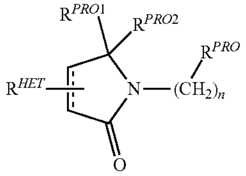

preferably, a

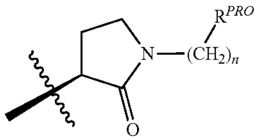

or

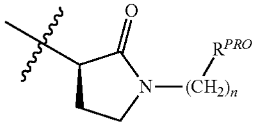

group, wherein:

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted -T-Heteroaryl, an optionally substituted -T-Heterocycle, an optionally substituted $-NR^1$-T-Aryl, an optionally substituted $-NR^1$-T-Heteroaryl or an optionally substituted $-NR^1$-T-Heterocycle, where $R^1$ is H or a $C_1$-$C_3$ alkyl group, preferably H or $CH_3$, T is an optionally substituted $-(CH_2)_n-$ group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a $-(CH_2O)_n-$ group, a $-(OCH_2)_n-$ group, a $-(CH_2CH_2O)_n-$ group, a $-(OCH_2CH_2)_n-$ group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a $-(CH_2)_m-NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_5$ group ($R_S$ is a $C_1$-$C_6$ alkyl group, an optionally substituted aryl, heteroaryl or heterocycle group or a $-(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrabydrofuran, tetrabydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

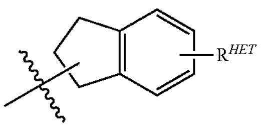

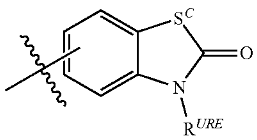

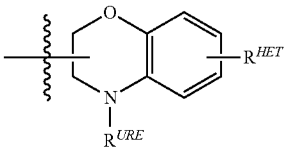

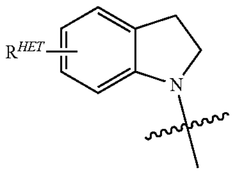

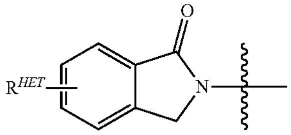

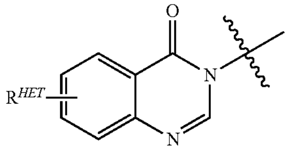

or

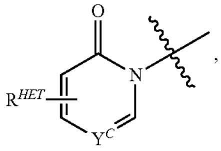

, wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

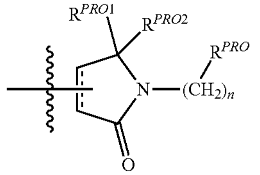

or

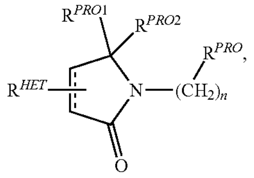

preferably, a

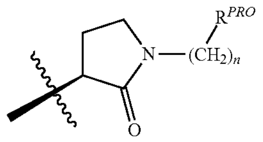

or

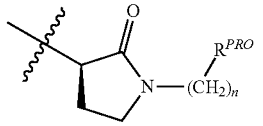

group, wherein:

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^3$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted $—NR_1—X^{R2'}$-alkyl group, $—NR_1—X^{R2'}$-Aryl group; an optionally substituted $—NR_1—X^{R2'}$-HET, an optionally substituted $—NR_1—X^{R2'}$-Aryl-HET or an optionally substituted $—NR_1—X^{R2'}$-HET-Aryl, wherein:

$R_1$ of ULM-g through ULM-i is H or a $C_1$-$C_3$ alkyl group (preferably H);

$X^{R2'}$ of ULM-g through ULM-i is an optionally substituted $—CH_2)_n—$, $—CH_2)_n—CH(X_v)═CH(X_v)—$ (cis or trans), $—(CH_2)_n—CH≡CH—$, $—(CH_2CH_2O)_n—$ or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

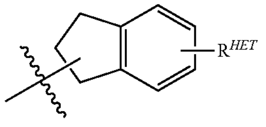

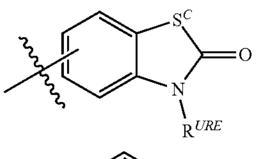

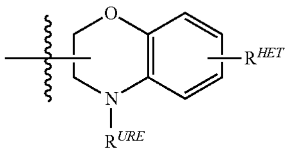

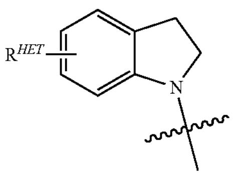

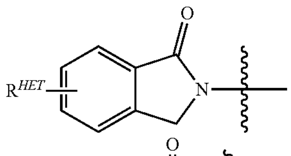

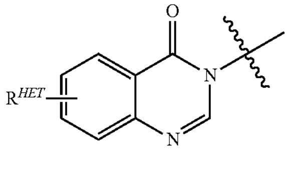

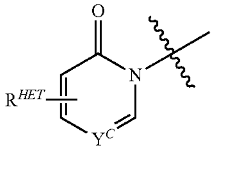

-continued

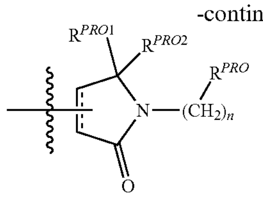

or

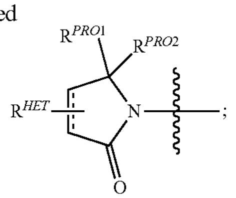

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C≡C—R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted $O—(C_1$-$C_6$ alkyl) (preferably substituted with one or two hydroxyl groups or up to three halo groups) or an optionally substituted $—C(O)(C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $—C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or $C—R^{YC}$, where $R^{YC}$ is H, OH, CN, $N_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C≡C—R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present disclosure, $R^{3'}$ of ULM-g through ULM-i is an optionally substituted $-(CH_2)_n-(V)_{n'}-(CH_2)_n-(V)_{n'}-R^{S3'}$ group, an optionally substituted $-(CH_2)_n-N(R_{1'})(C{=}O)_{m'}-(V)_{n'}-R^{S3'}$ group, an optionally substituted $-X^{R3'}$-alkyl group, an optionally substituted $-X^{R3'}$-Aryl group; an optionally substituted $-X^{R3'}$-HET group, an optionally substituted $-X^{R2'}$-Aryl-HET group or an optionally substituted $-X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is $-(CH_2)_n-$, $-(CH_2CH_2O)_n-$, $-CH_2)_n-CH(X_v){=}CH(X_v)-$ (cis or trans), $-CH_2)_n-CH{\equiv}CH-$, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

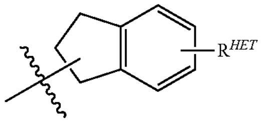

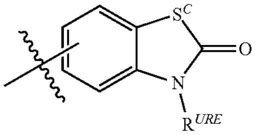

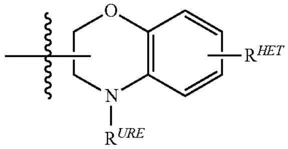

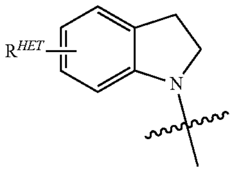

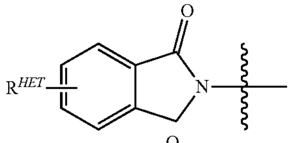

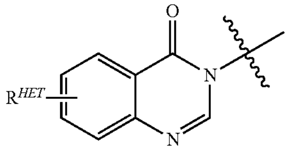

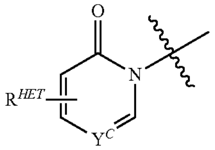

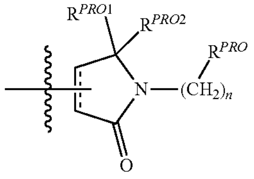

or

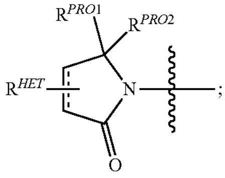

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O-($C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $-C(O)(C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or $C-R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is $-(CH_2)_n$-Aryl, $-(CH_2CH_2O)_n$-Aryl, $-(CH_2)_n$-HET or $-(CH_2CH_2O)_n$-HET, wherein:

said Aryl of ULM-g through ULM-i is phenyl which is optionally substituted with one or two substitutents, wherein said substituent(s) is preferably selected from $-(CH_2)_nOH$, $C_1$-$C_6$ alkyl which itself is further optionally substituted with CN, halo (up to three halo groups), OH, —$(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)(CO—$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_{n'}$—$R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

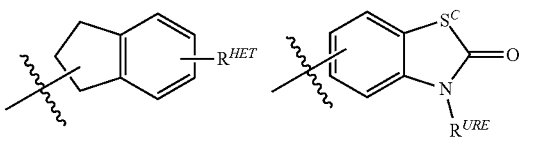

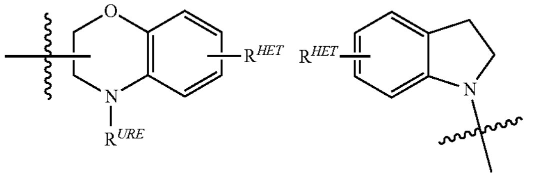

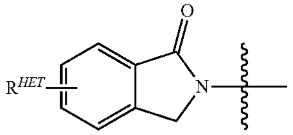

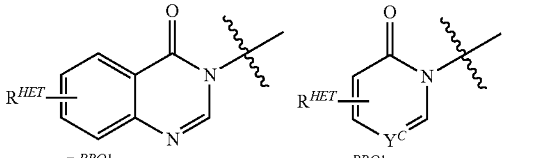

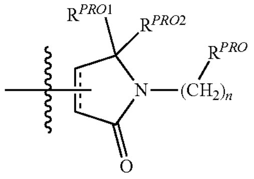

or

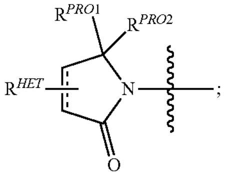

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where Rye is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

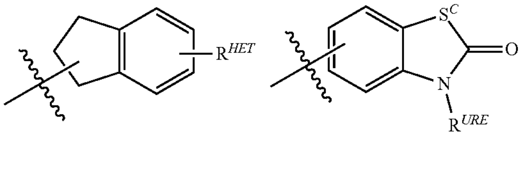

-continued

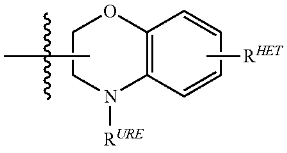

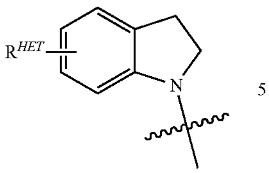

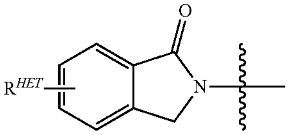

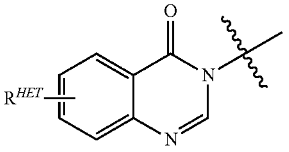

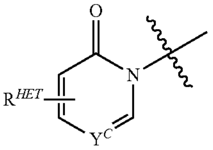

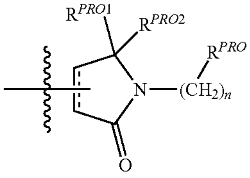

or

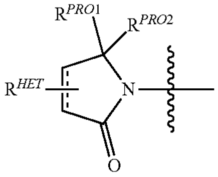

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

ULM-i

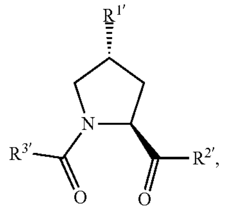

wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_n OCH_3$ group where n is 1 or 2 (preferably 2), or a

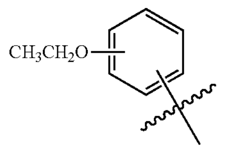

group (the ethyl ether group is preferably meta-substituted on the phenyl moiety), a morpholino group (linked to the carbonyl at the 2- or 3-position;

$R^{3P2}$ of ULM-i is a

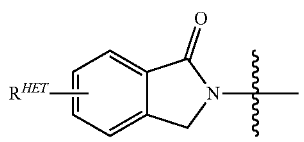

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

ULM-j1

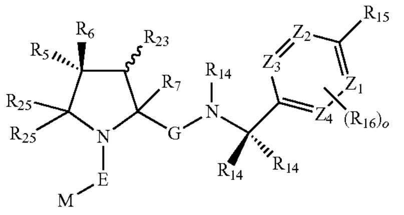

ULM-j2

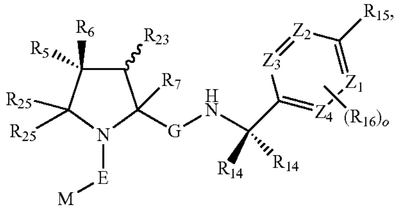

wherein:

each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C═O, or C═S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy;

M of ULM-j is optionally substituted aryl, optionally substituted heteroaryl, optionally substituted heterocyclic or

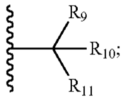

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R^9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

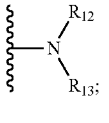

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C═O and M is

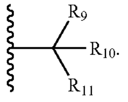

In certain embodiments, wherein E of ULM-j is C═O, $R_{11}$ is optionally substituted heterocyclic or

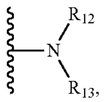

and M is

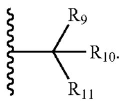

In certain embodiments, wherein E of ULM-j is C═O, M is

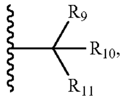

and $R_{11}$ is

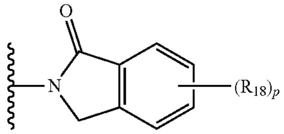 or

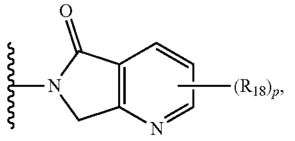

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

ULM-k

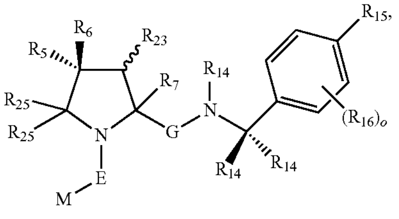

wherein:

G of ULM-k is C=J, J is O;

$R_7$ of ULM-k is H;

each $R_{14}$ of ULM-k is H;

o of ULM-k is 0;

$R^{15}$ of ULM-k is

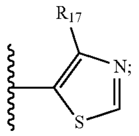

and $R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

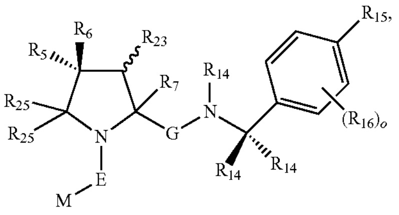

wherein:

G of ULM-k is C=J, J is O;

$R_7$ of ULM-k is H;

each $R_{14}$ of ULM-k is H;

o of ULM-k is 0; and $R_{15}$ of ULM-k is selected from the group consisting of:

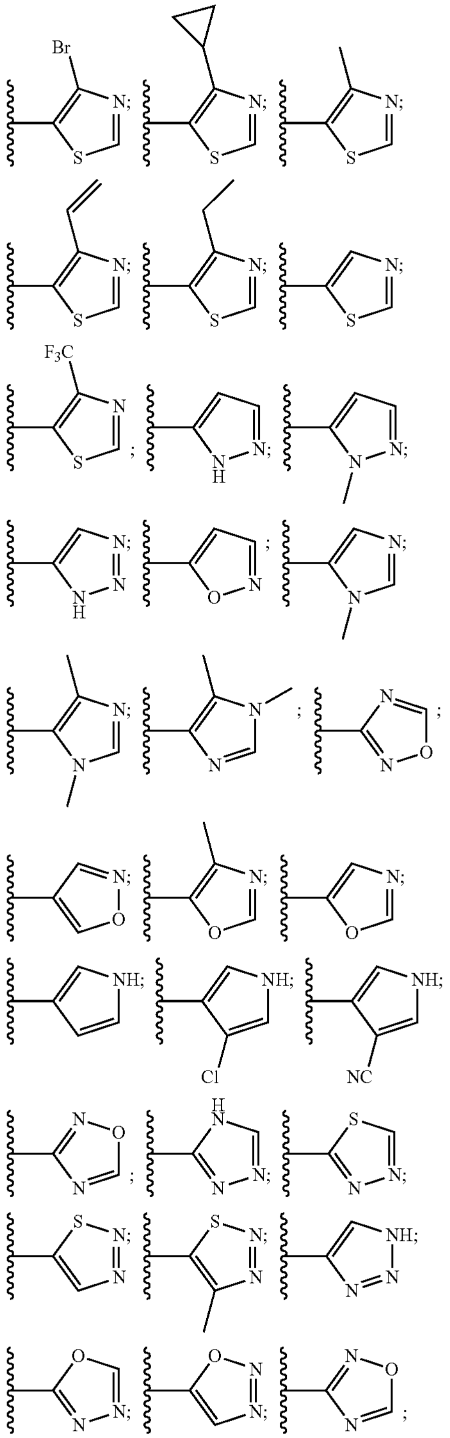

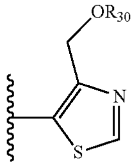 and 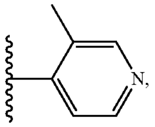

wherein $R_{30}$ of ULM-k is H or an optionally substituted alkyl.

In other embodiments, ULM and where present. ULM', are each independently a group according to the chemical structure:
ULM-k1
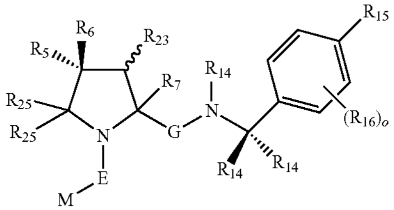
ULM-k2
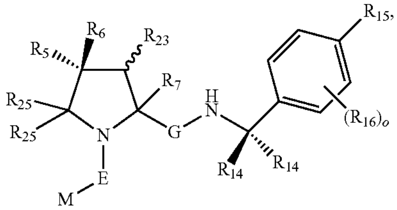
wherein:
E of ULM-k is C═O;
M of ULM-k is
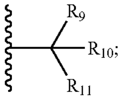
and
$R_{11}$ of ULM-k is selected from the group consisting of:
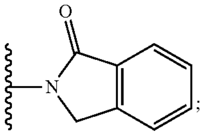
;
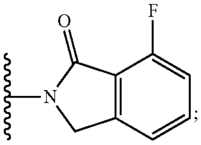
;
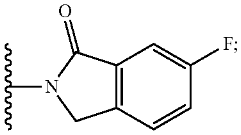
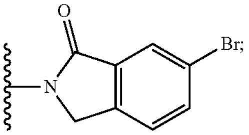
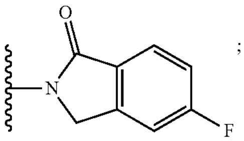
;
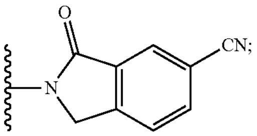
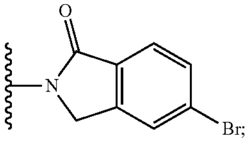
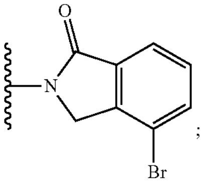
;
-continued
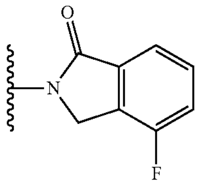
;
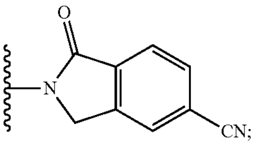
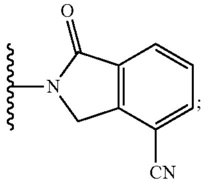
;
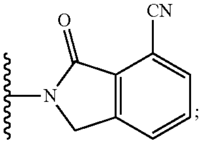
;
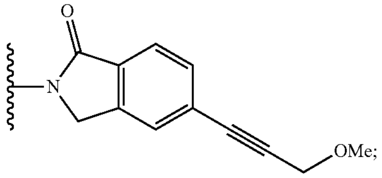
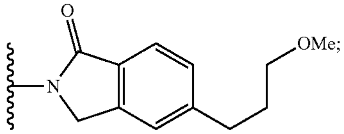
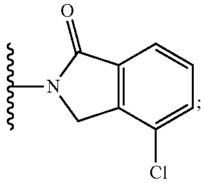
;
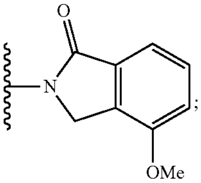
;
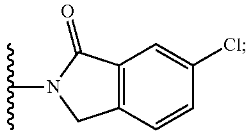
and
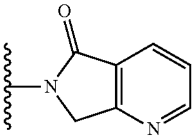
.
In still other embodiments, a compound of the chemical structure,
ULM-k1
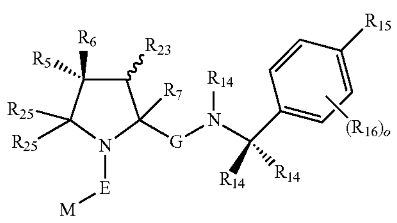
ULM-k2
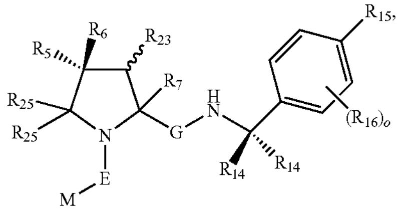
wherein E of ULM-k is C═O;

$R_{11}$ of ULM-k is

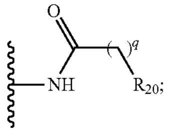

and

M of ULM-k is

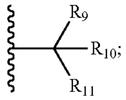

q of ULM-k is 1 or 2;

$R_{20}$ of ULM-k is H, optionally substituted alkyl, optionally substituted cycloalkyl, optionally substituted aryl, or

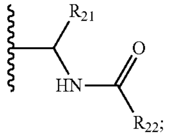

$R^{21}$ of ULM-k is H or optionally substituted alkyl; and $R^{22}$ of ULM-k is H, optionally substituted alkyl, optionally substituted alkoxy, or haloalkyl.

In any embodiment described herein, $R_{11}$ of ULM-j or ULM-k is selected from the group consisting of:

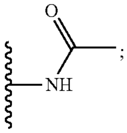 ; 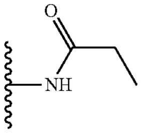 ; 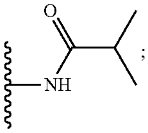 ;

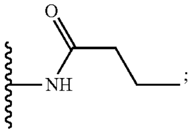 ; 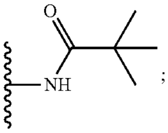 ;

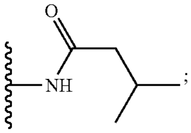 ; 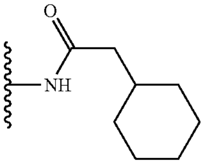 ;

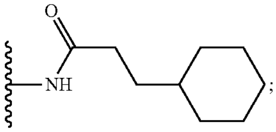 ; 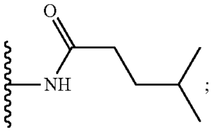 ;

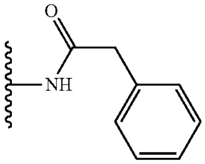 ; 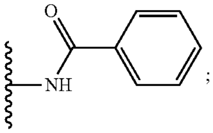 ;

-continued

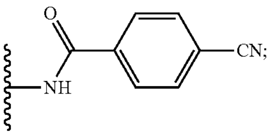 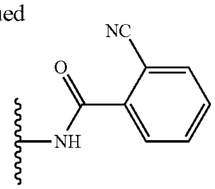 ;

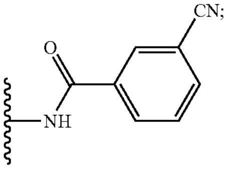 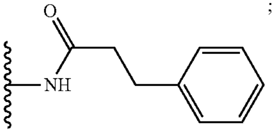 ;

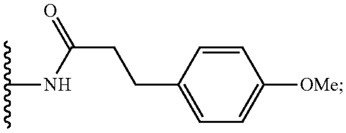

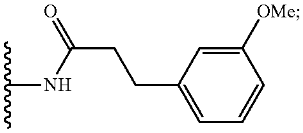

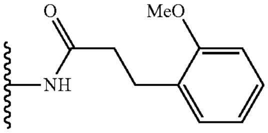 ;

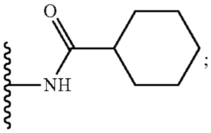 ; 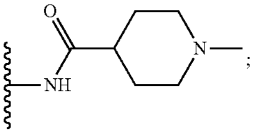 ;

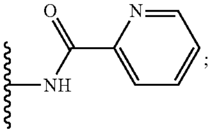 ; 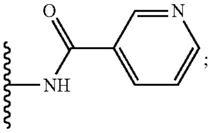 ;

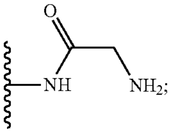 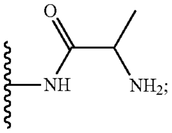 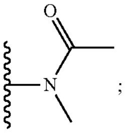 ;

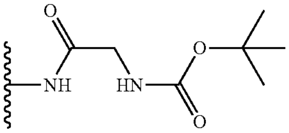 ;

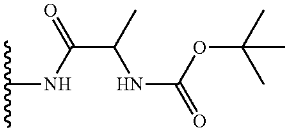 ; 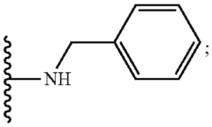 ;

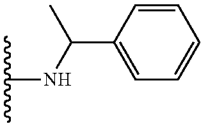 ; 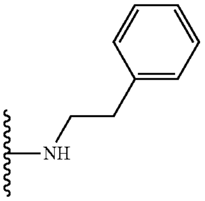 ;

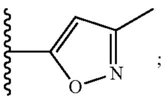 ; 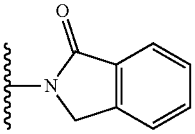 ;

-continued
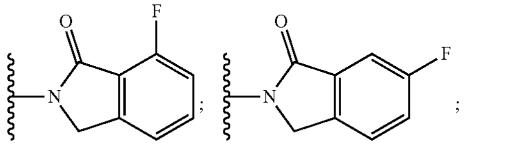
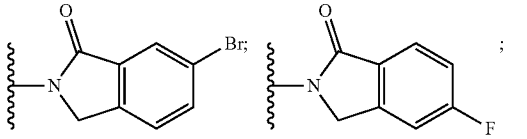
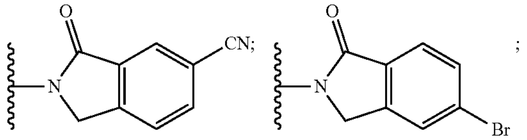
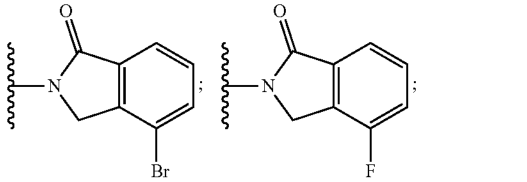
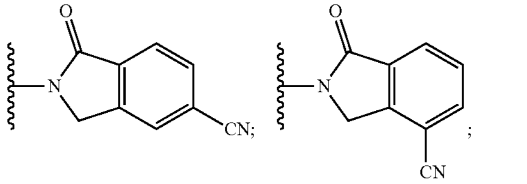
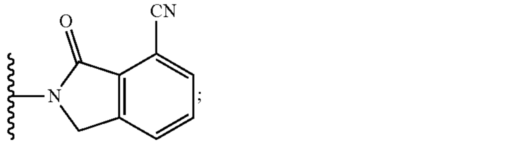
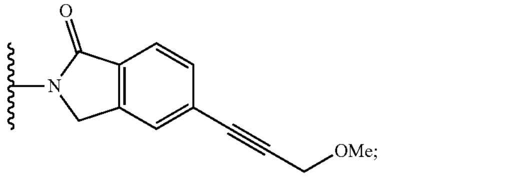
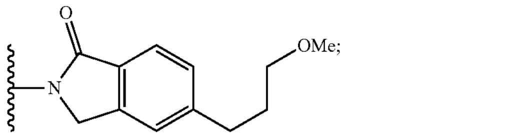
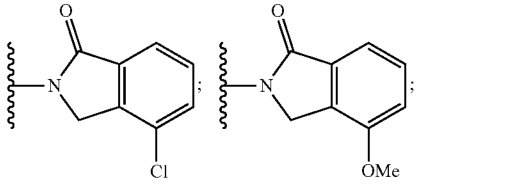
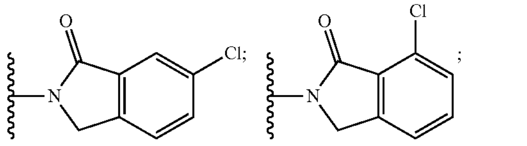
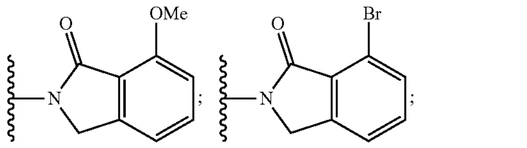
-continued
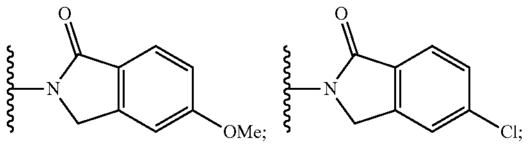
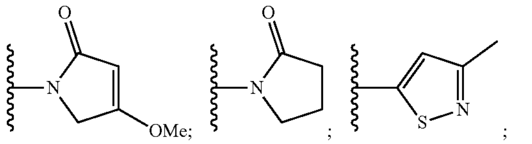
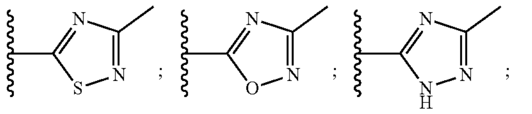
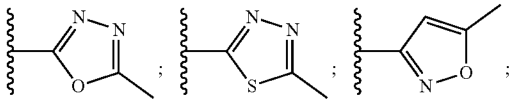
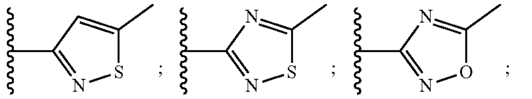
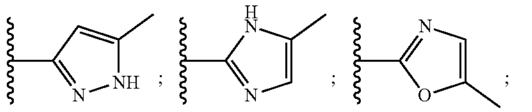
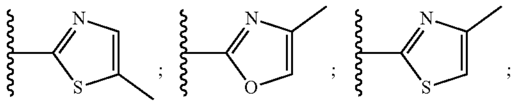
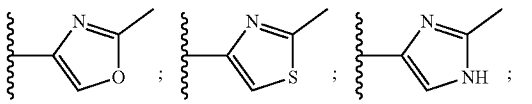
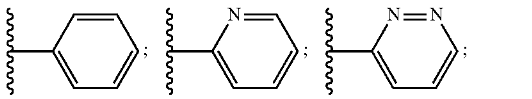
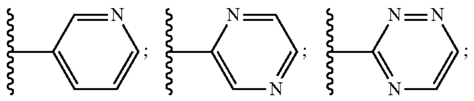
and
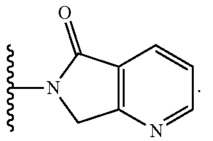
In certain embodiments, $R_{11}$ of ULM-j or ULM-k is selected from the group consisting of:
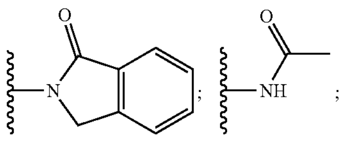
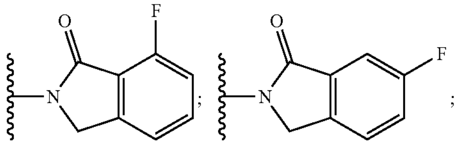

-continued
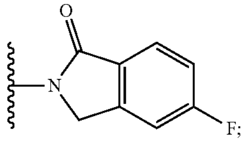 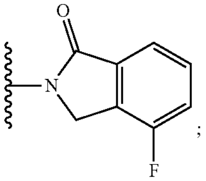
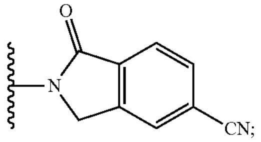 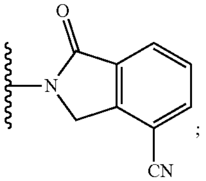
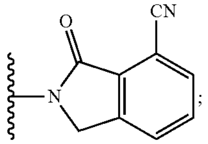 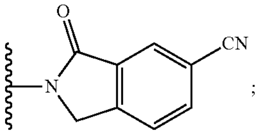
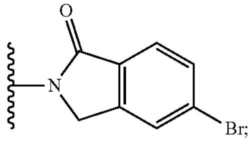 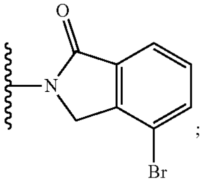
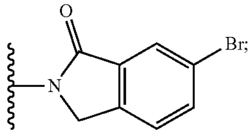 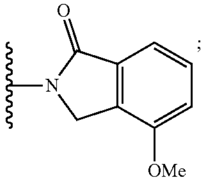
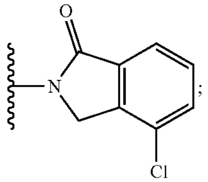 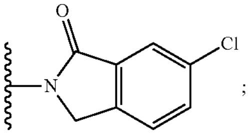
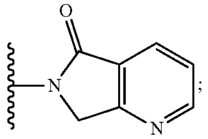
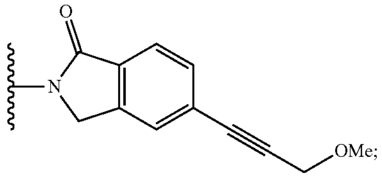
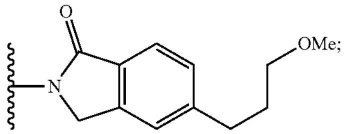
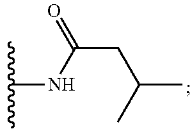 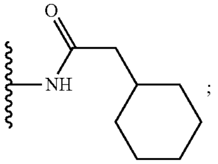
-continued
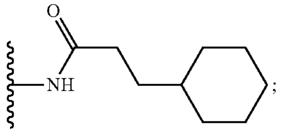 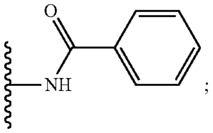
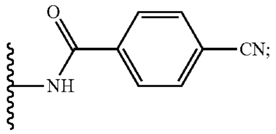
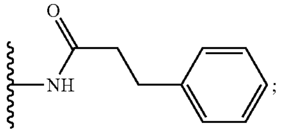
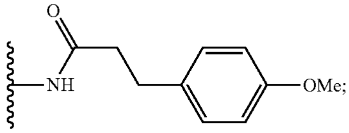
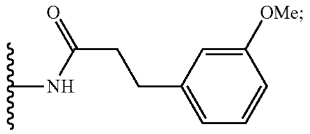
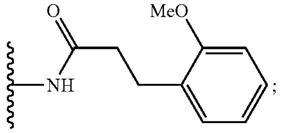 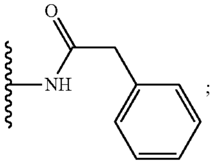
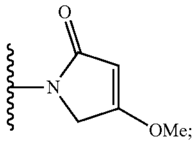 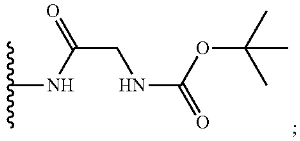
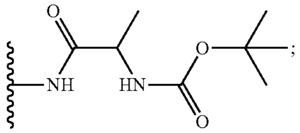 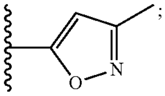
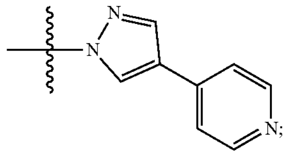
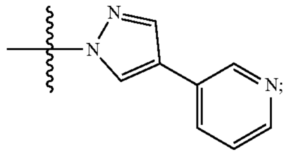
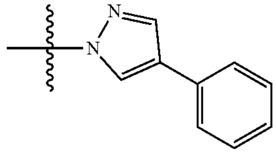 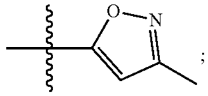
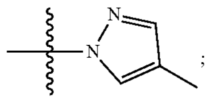 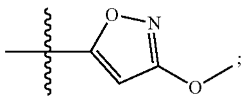

-continued

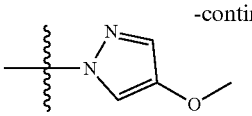

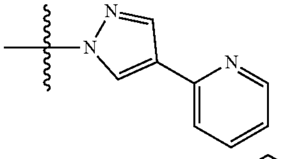

and

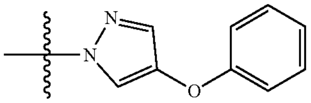

In certain embodiments, ULM (or when present ULM') is a group according to the chemical structure:

ULM-1

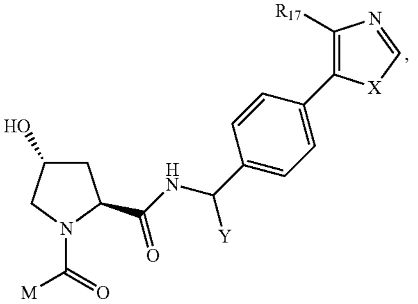

wherein:

X of ULM-1 is O or S;

Y of ULM-1 is H, methyl or ethyl;

$R_{17}$ of ULM-1 is H, methyl, ethyl, hydroxymethyl or cyclopropyl;

M of ULM-1 is optionally substituted aryl, optionally substituted heteroaryl, or

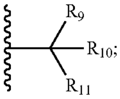

$R^9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

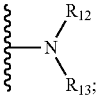

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

ULM-m

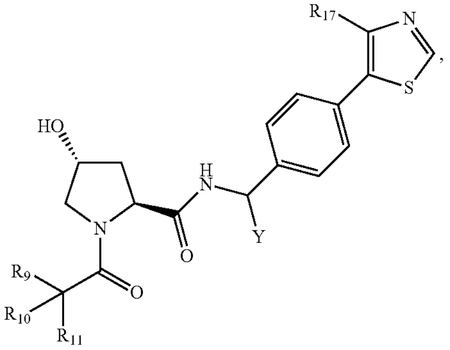

wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other preferred embodiments of the disclosure, ULM and where present, ULM', are each independently a group according to the chemical structure:

ULM-n

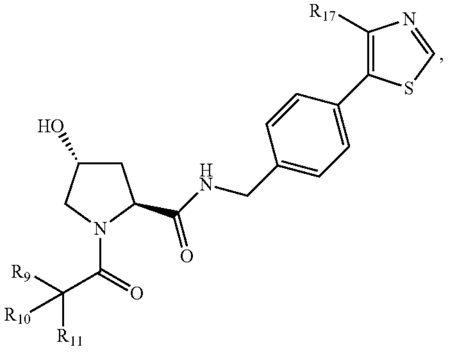

wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.
In certain aspects of the disclosure, the ULM moiety is selected from the group consisting of:
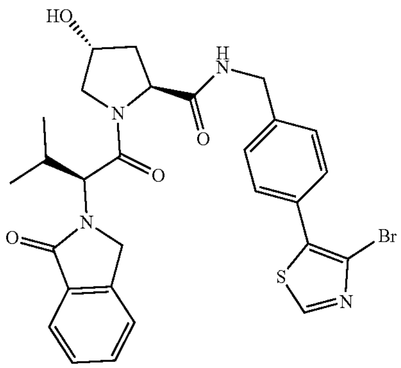
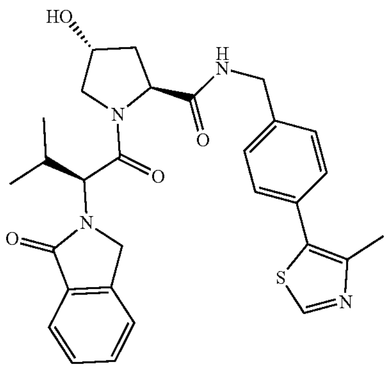
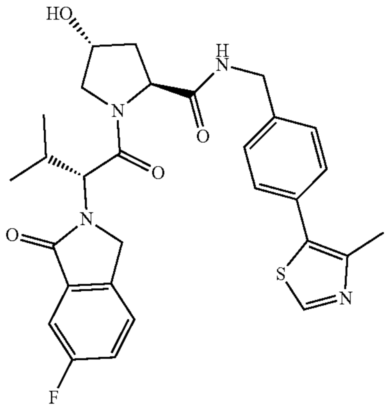
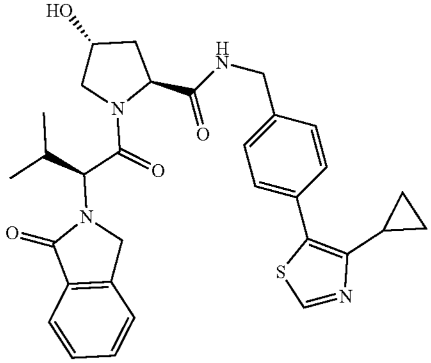
-continued
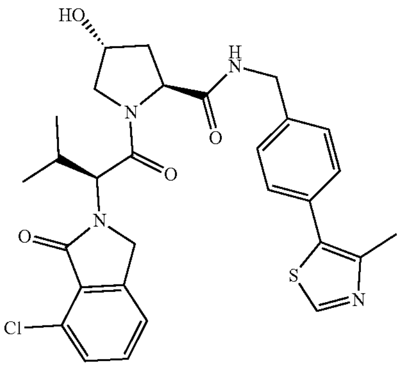
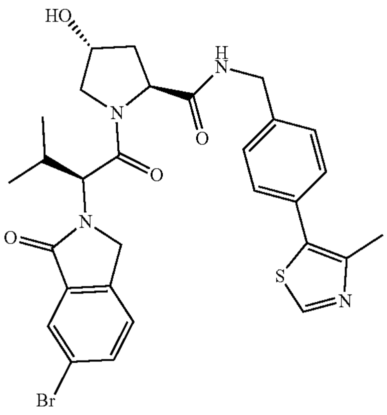
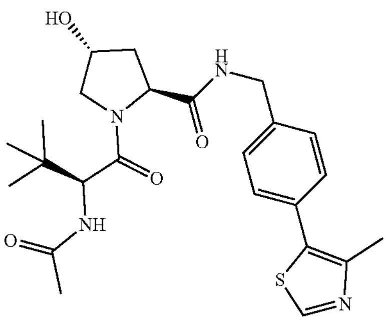
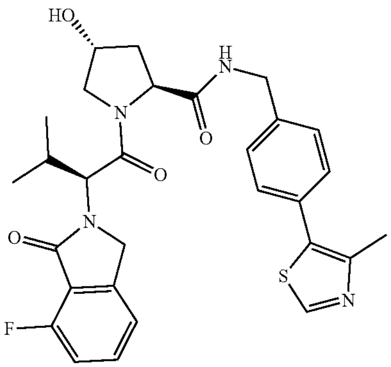

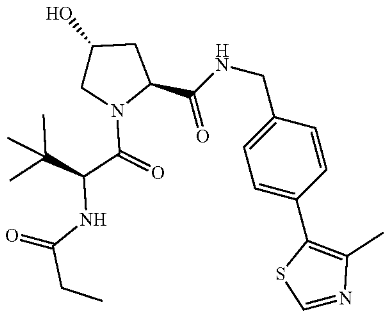
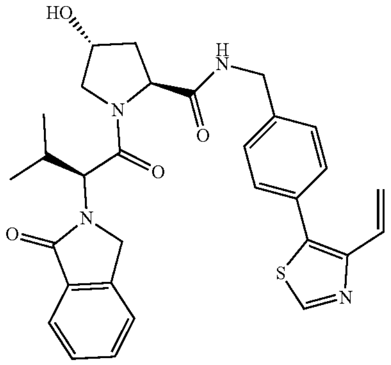
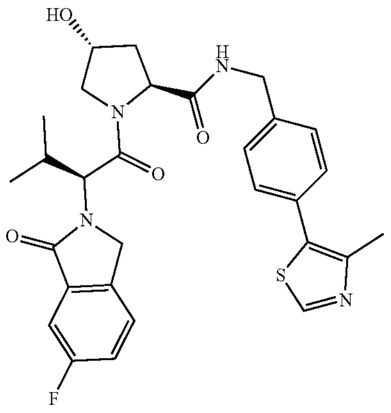
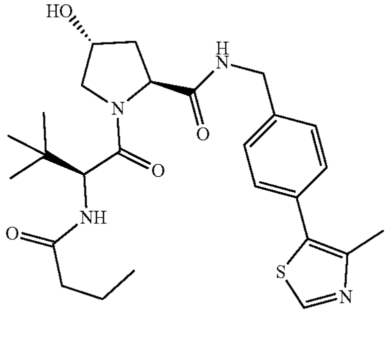
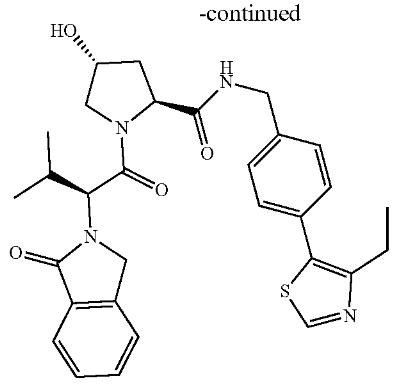
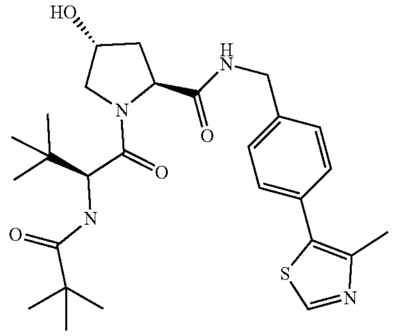
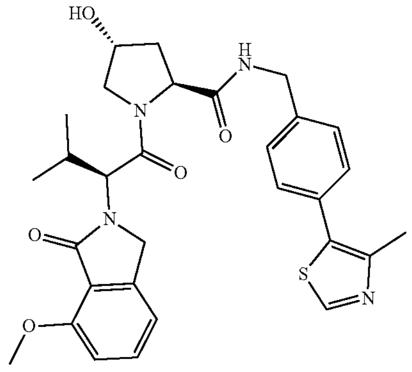
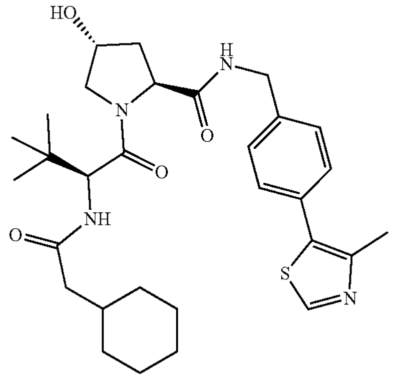

-continued
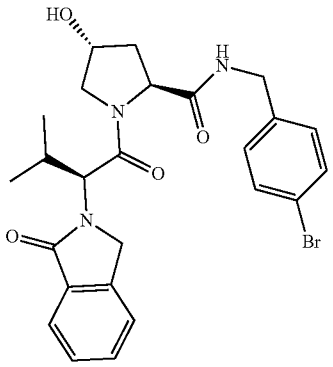
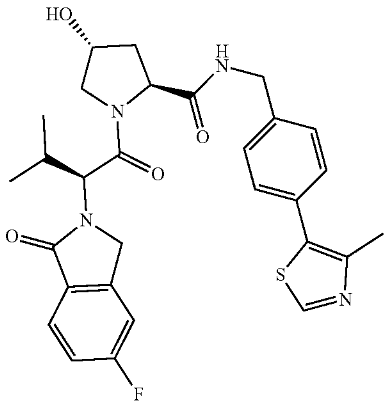
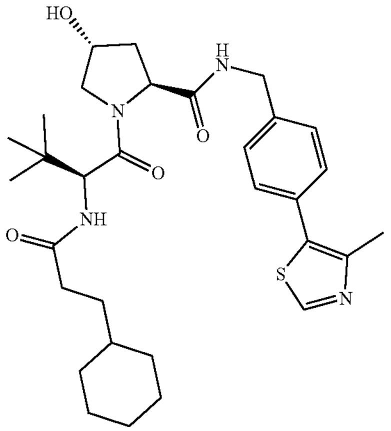
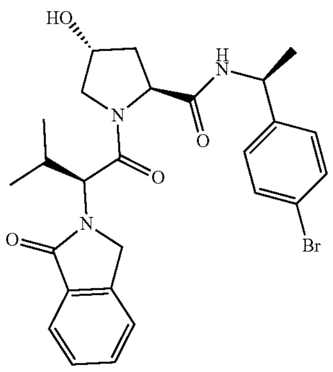
-continued
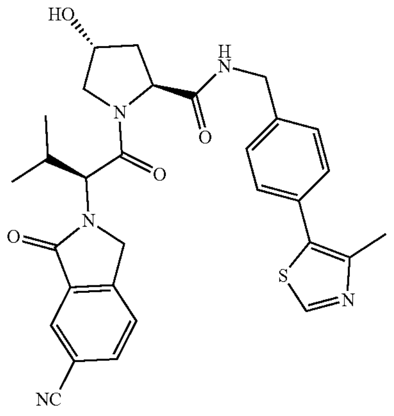
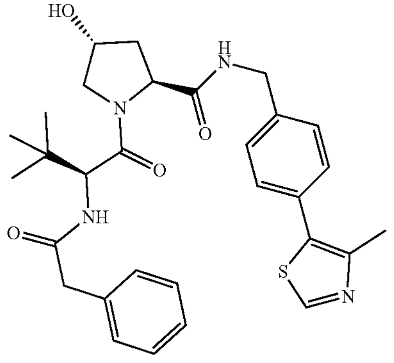
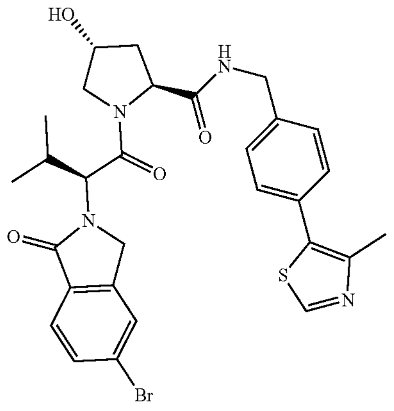
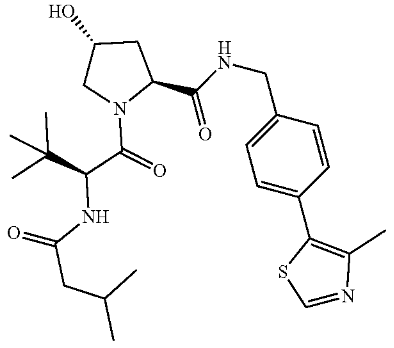

-continued
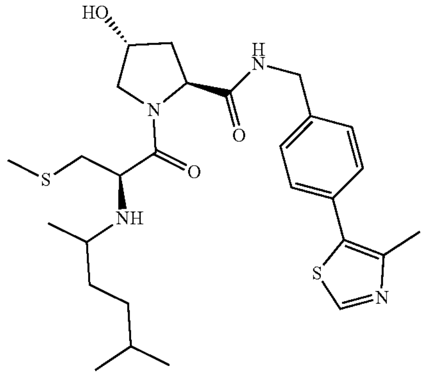
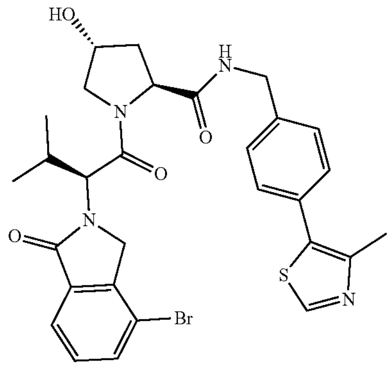
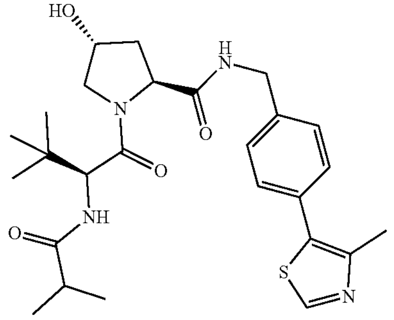
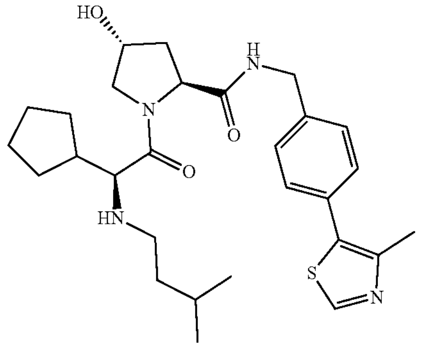
-continued
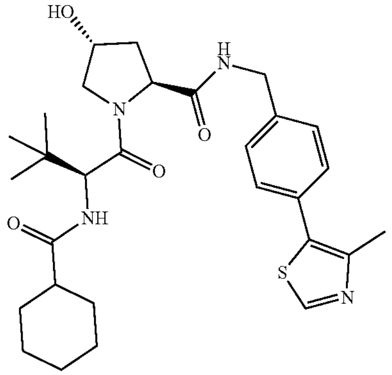
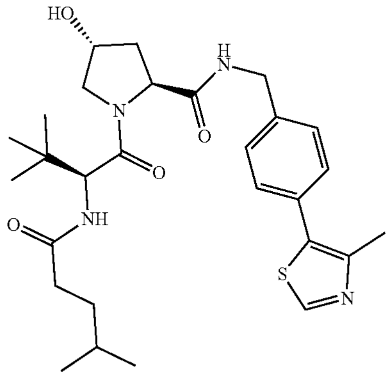
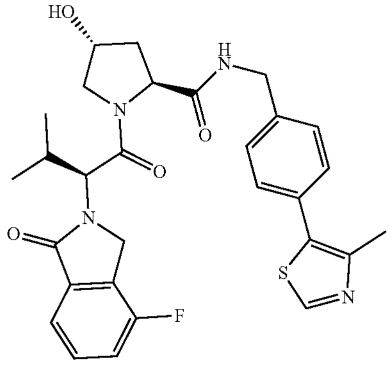
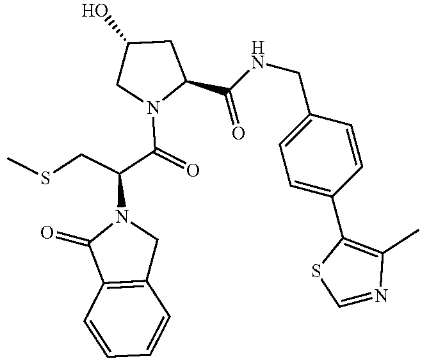

-continued
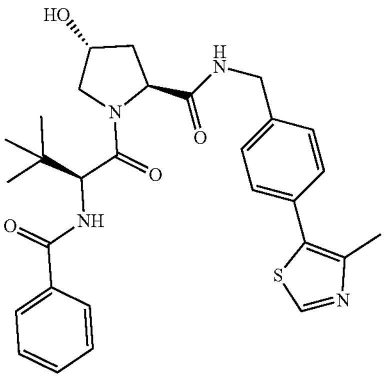
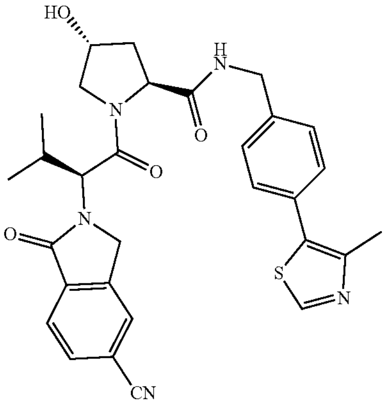
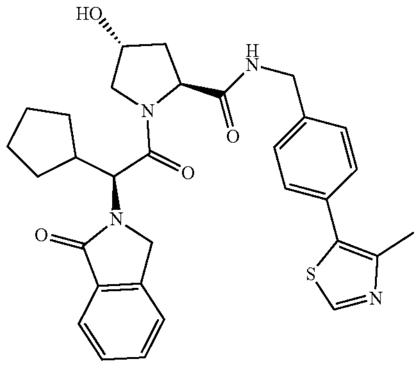
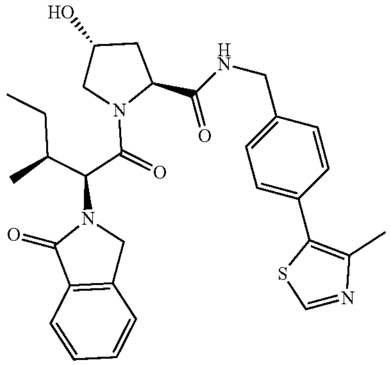
-continued
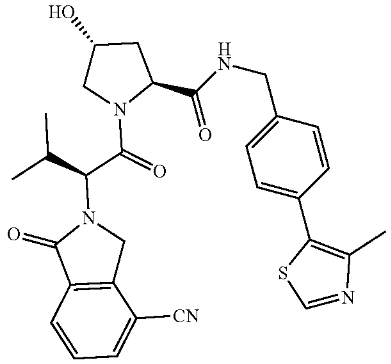
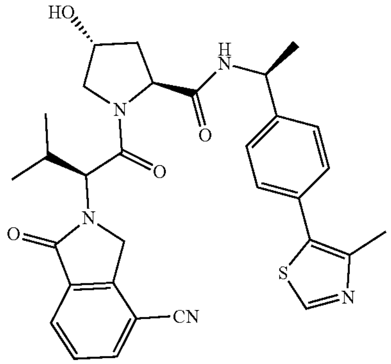
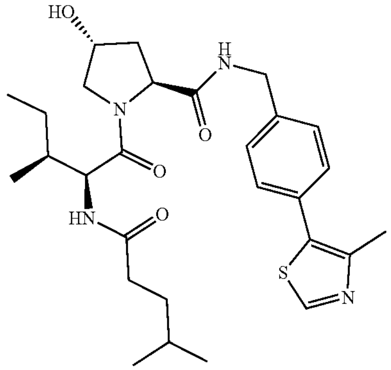
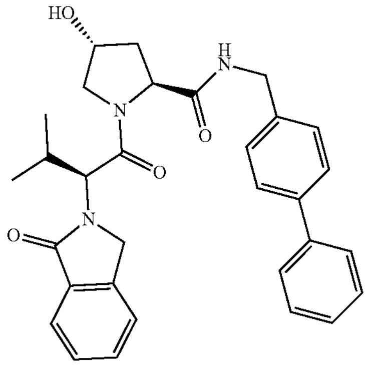

-continued
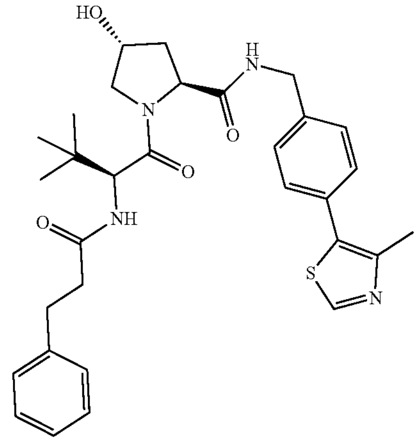
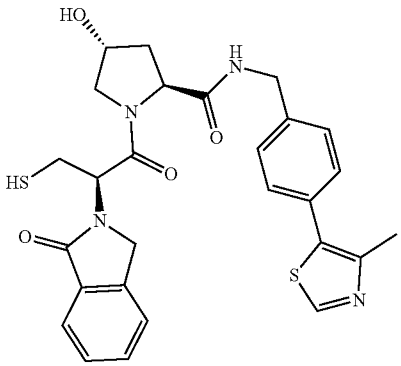
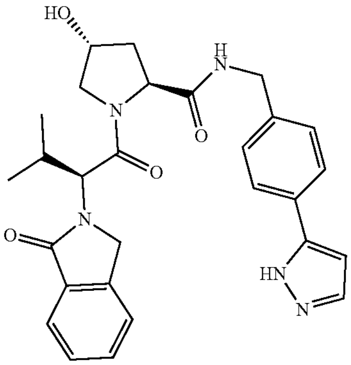
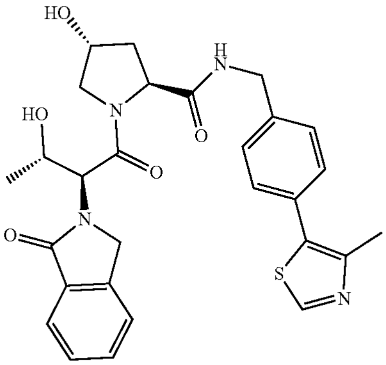
-continued
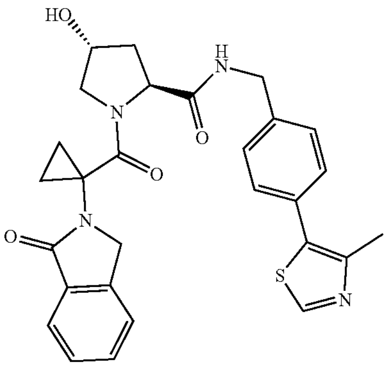
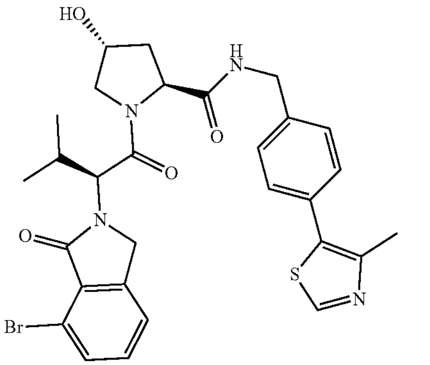
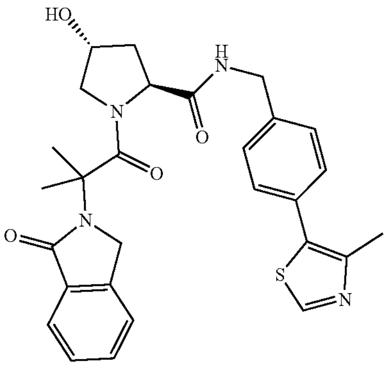
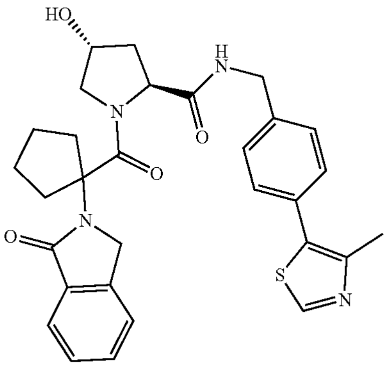

-continued
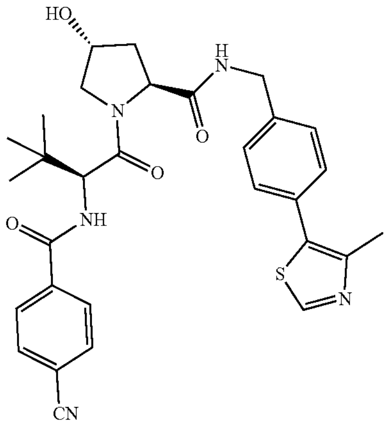
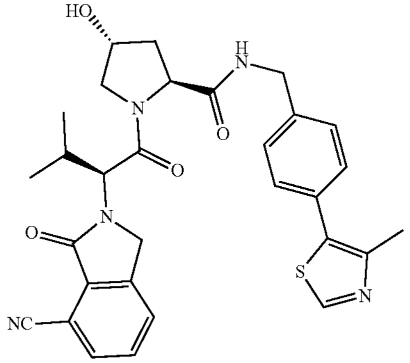
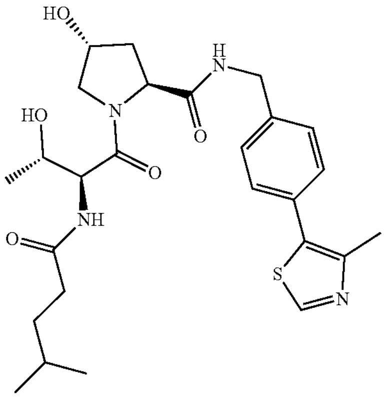
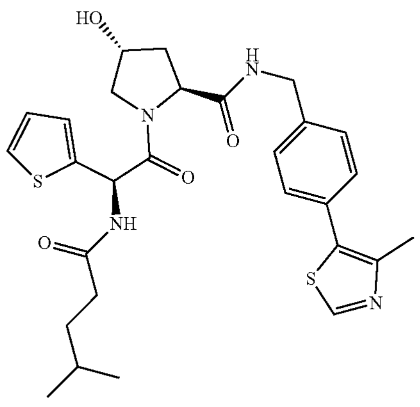
-continued
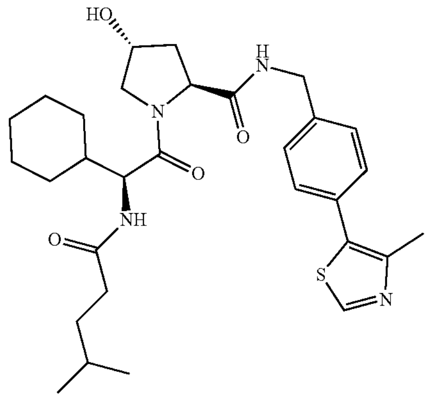
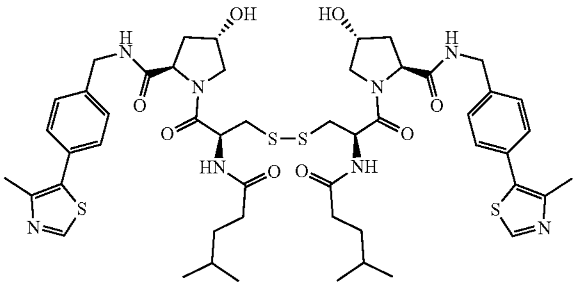
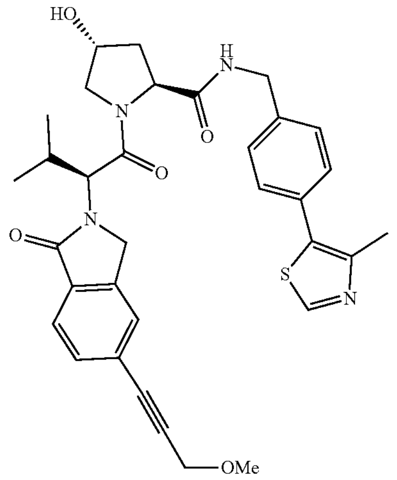
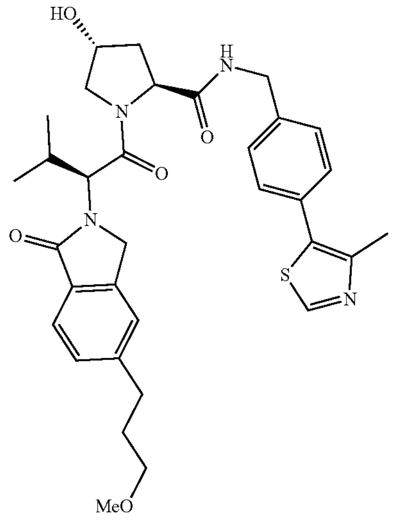

-continued
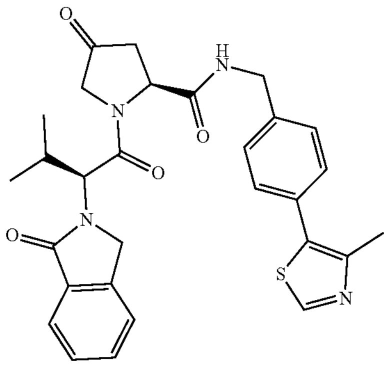
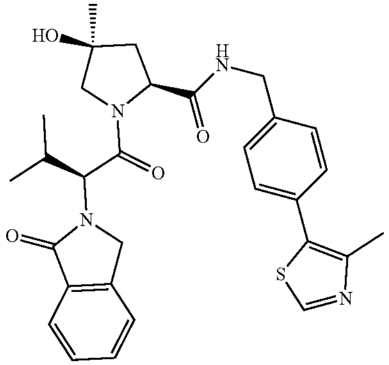
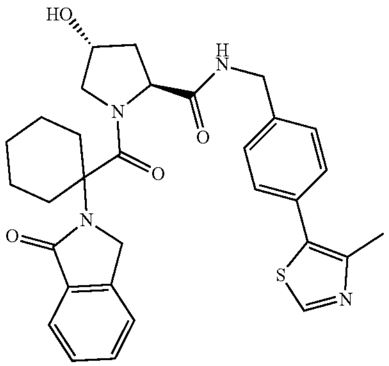
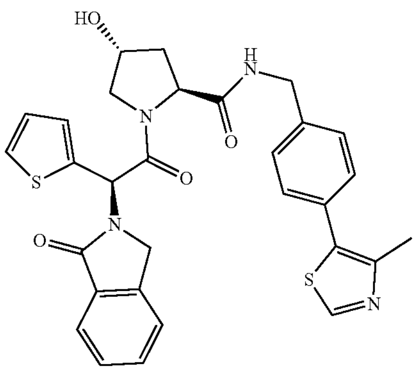
-continued
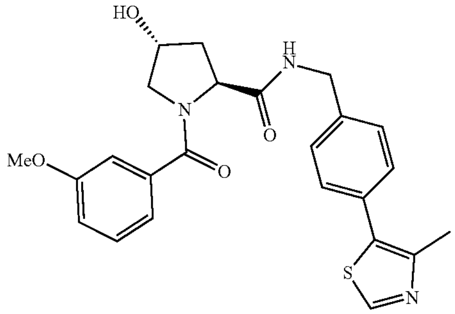
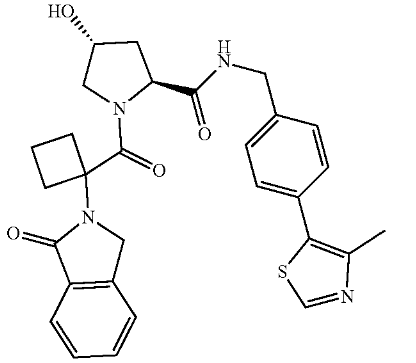
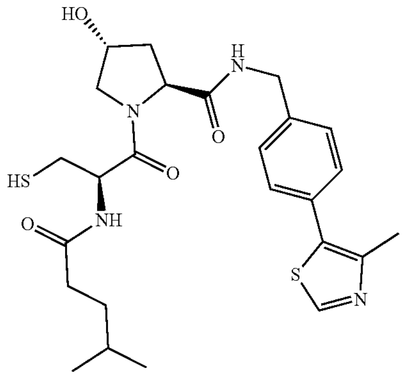
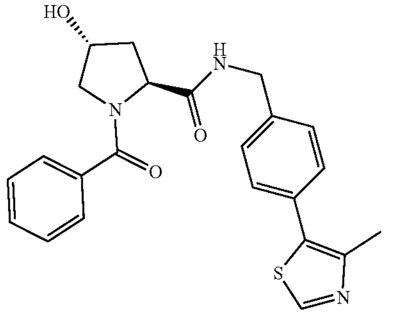
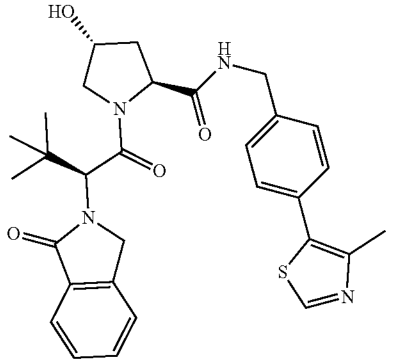

-continued
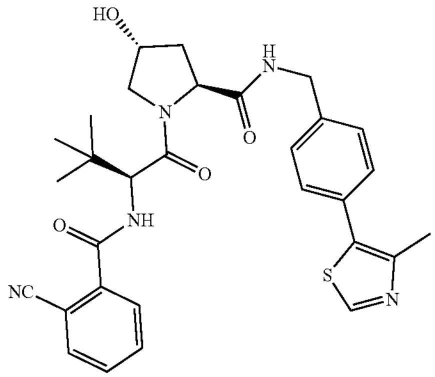
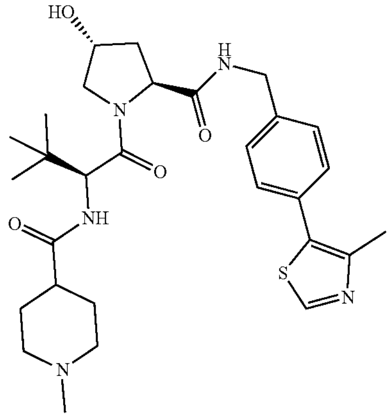
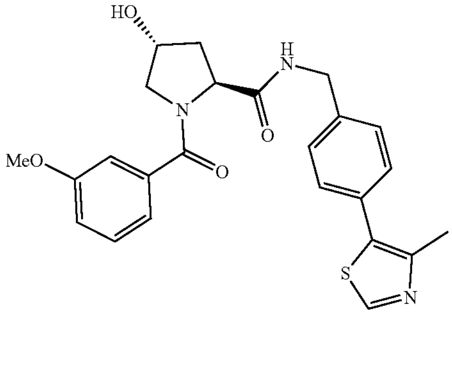
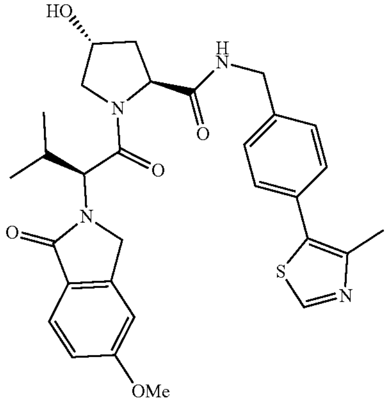
-continued
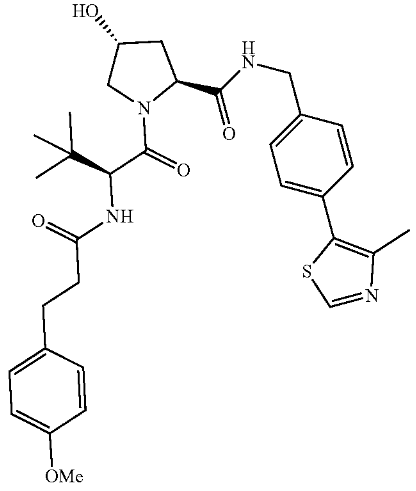
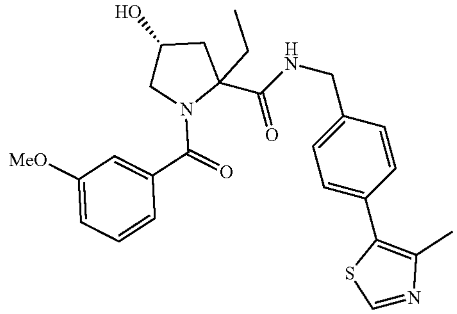
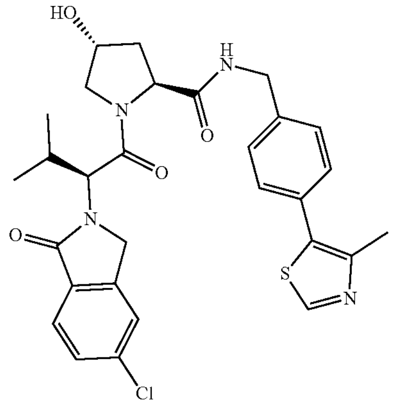
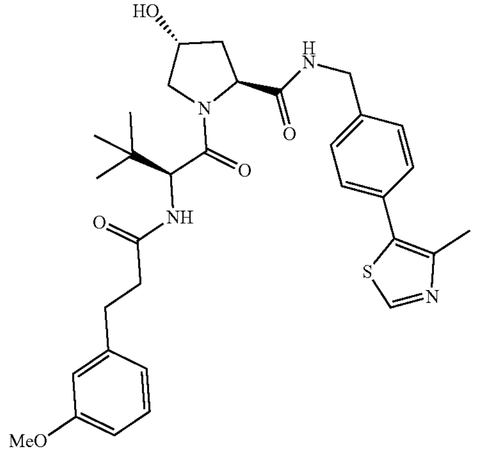

-continued
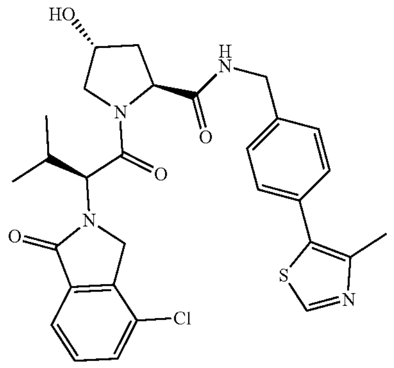
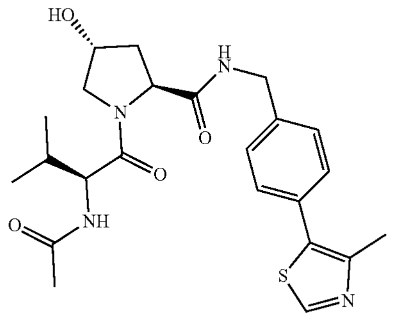
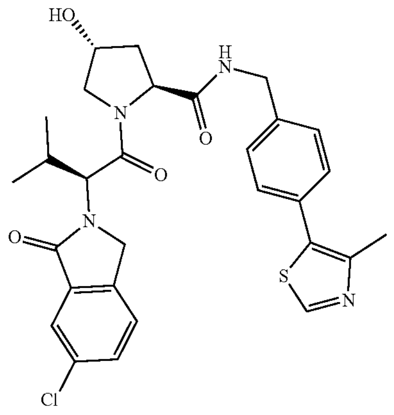
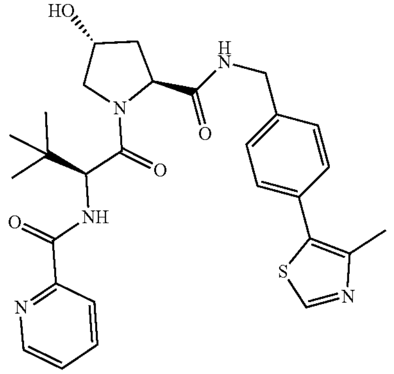
-continued
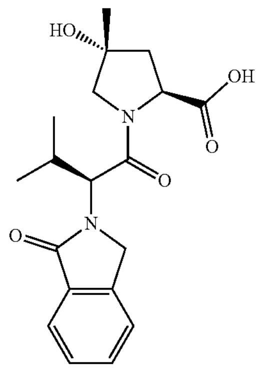
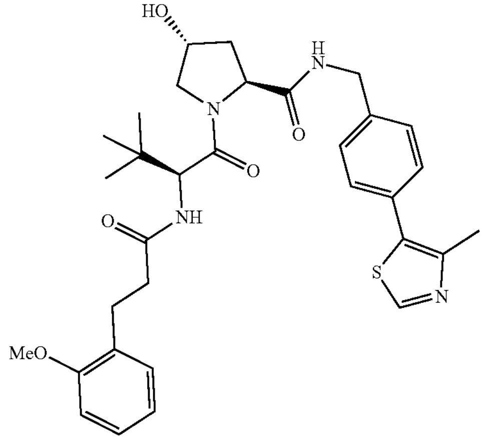
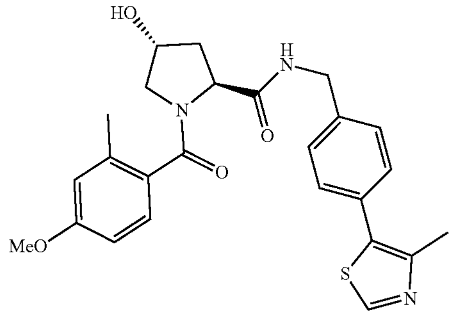
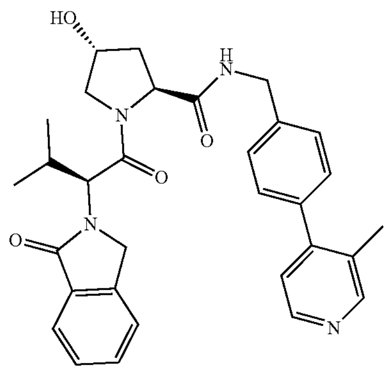

-continued
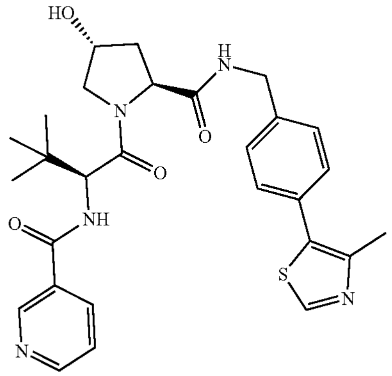
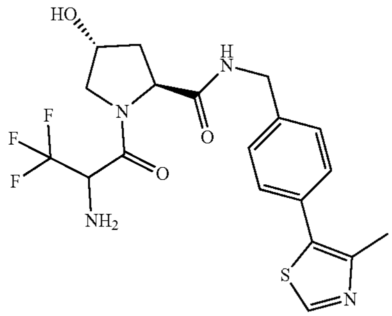
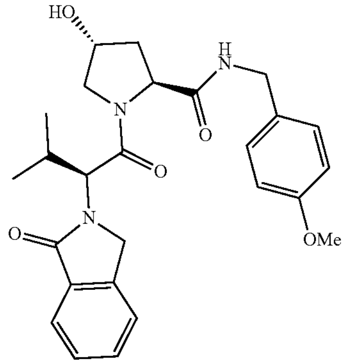
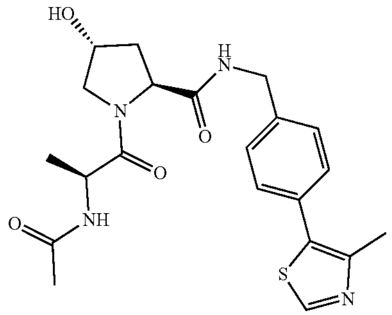
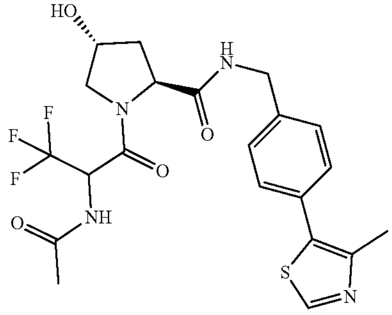
-continued
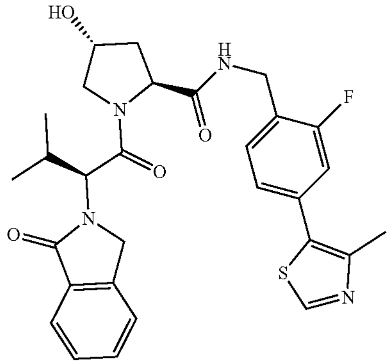
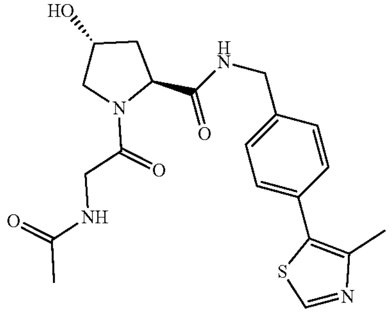
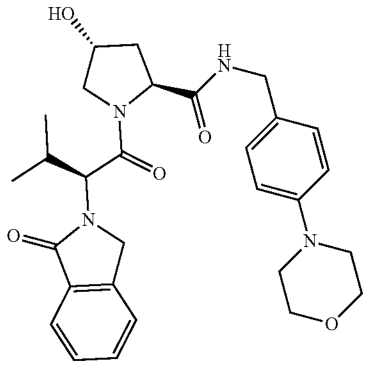
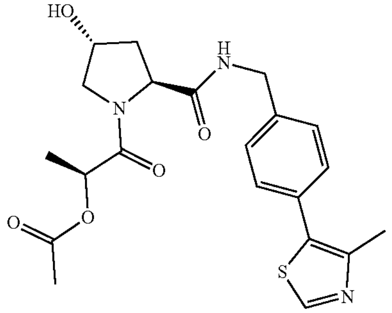
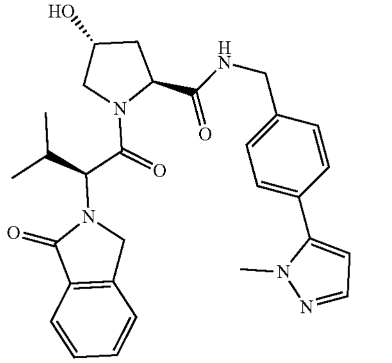

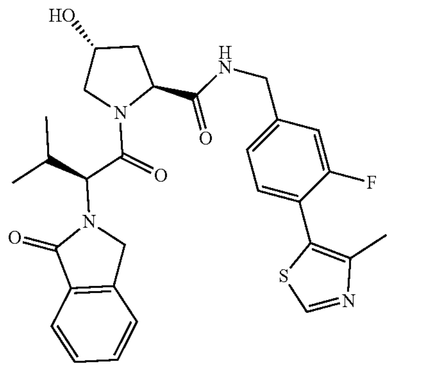
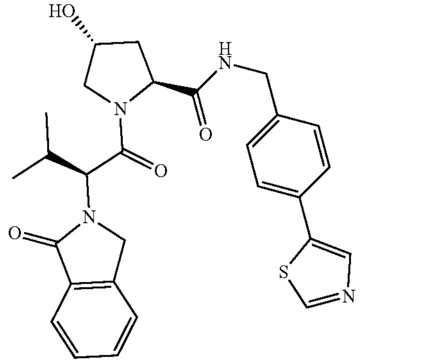
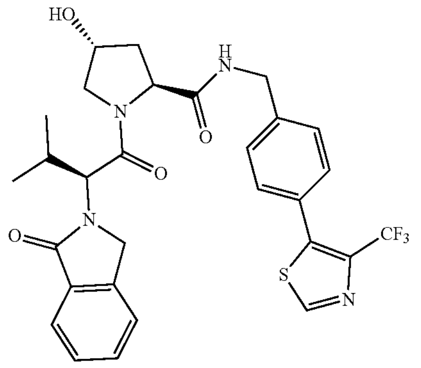
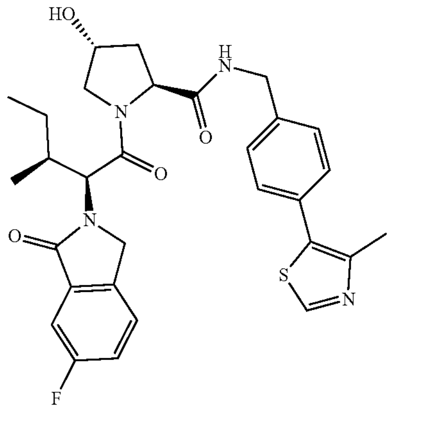
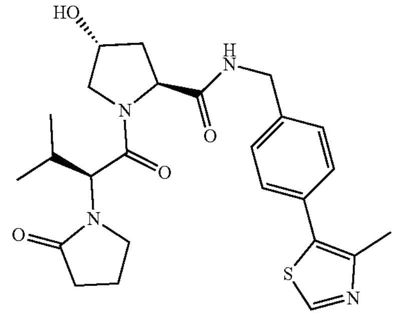
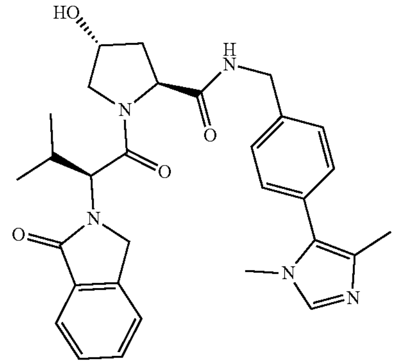
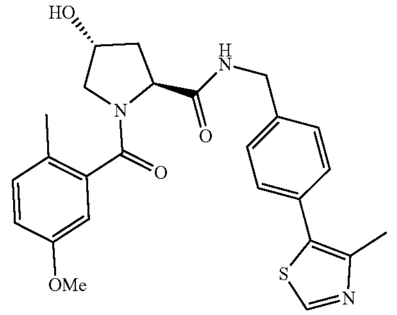
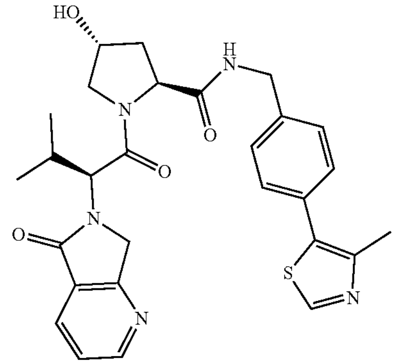
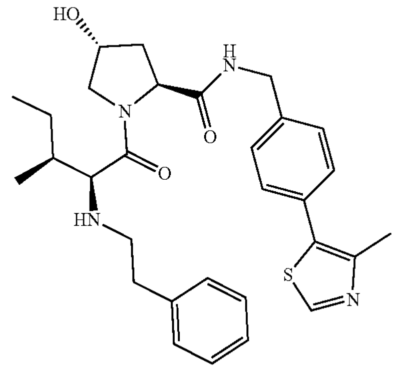

-continued
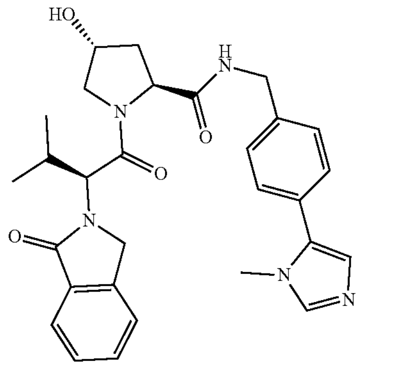
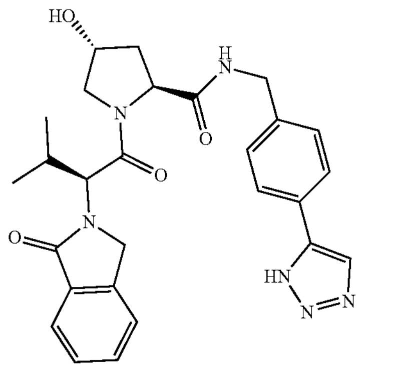
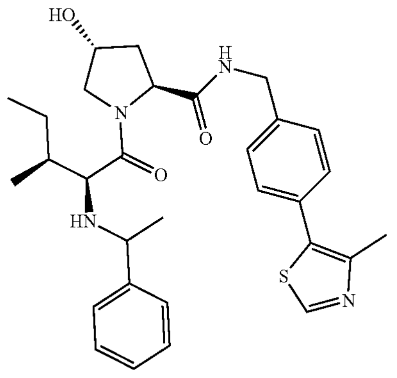
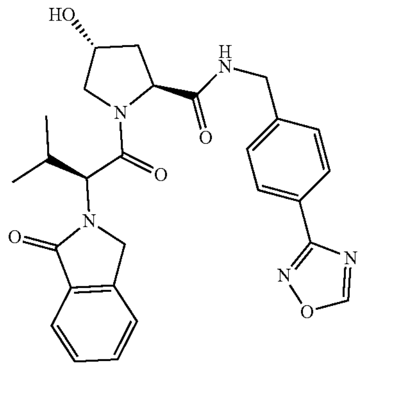
-continued
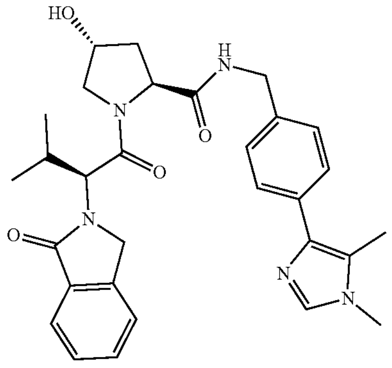
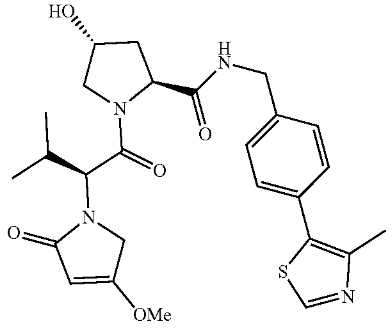
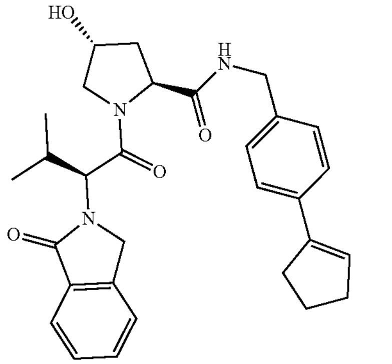
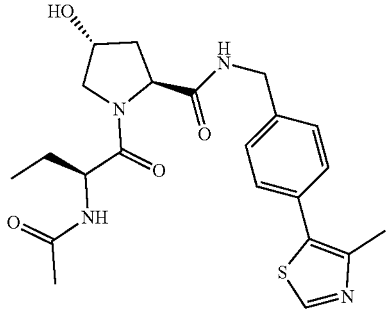
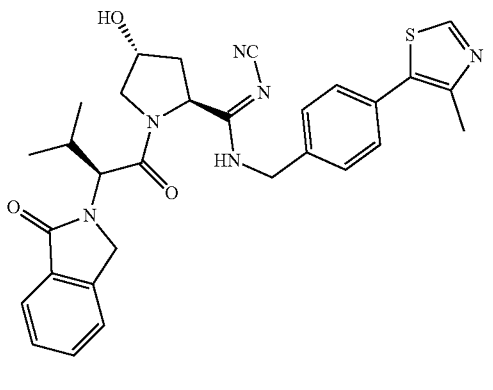

-continued
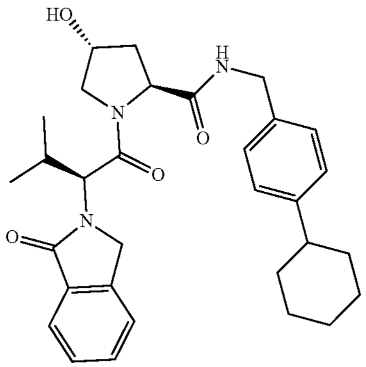
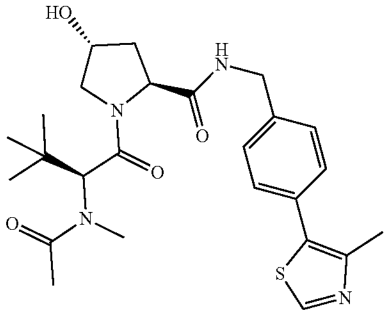
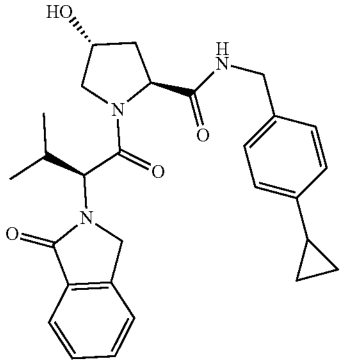
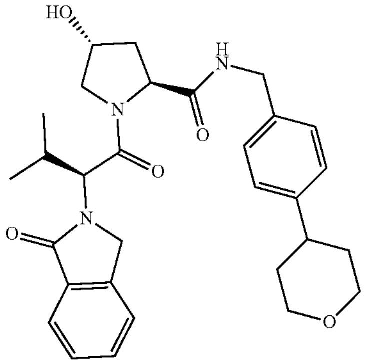
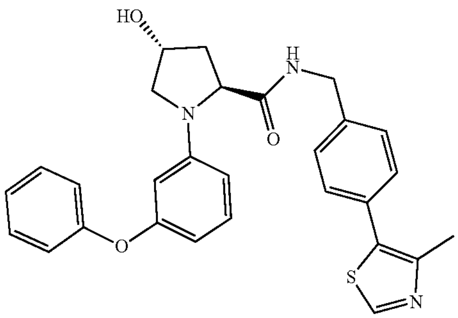
-continued
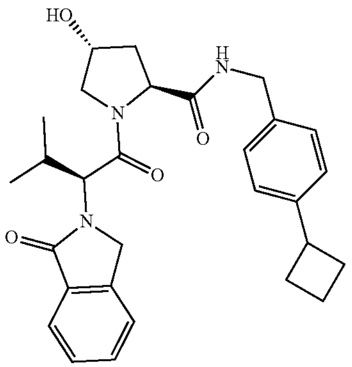
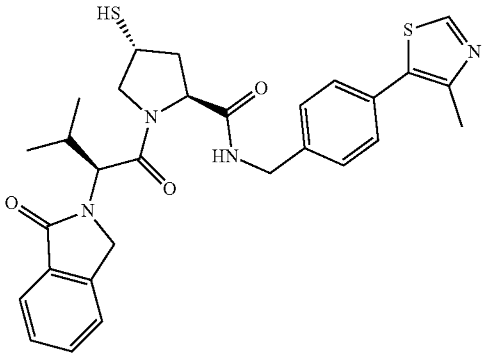
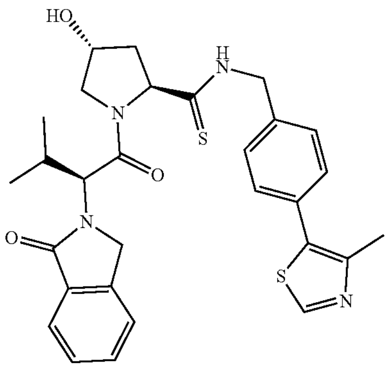
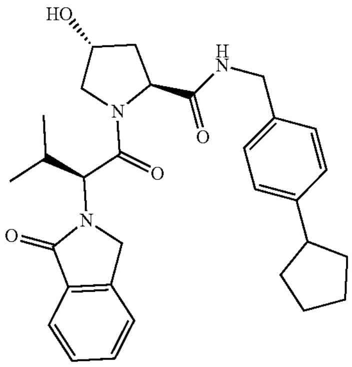

-continued
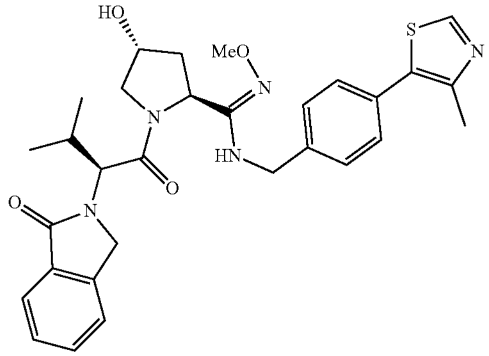
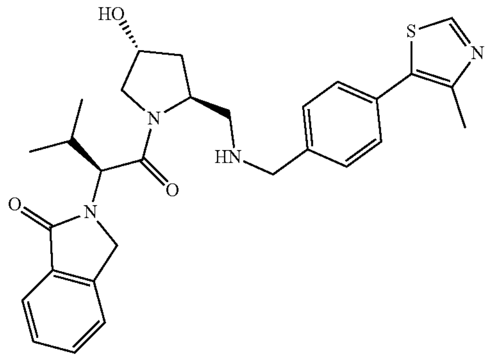
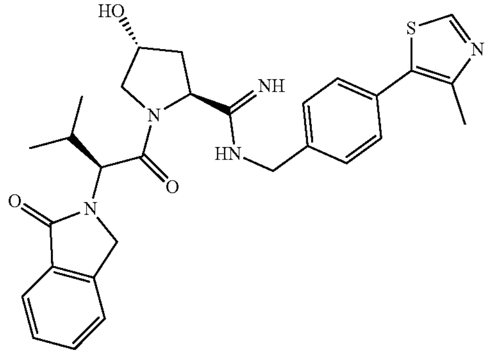
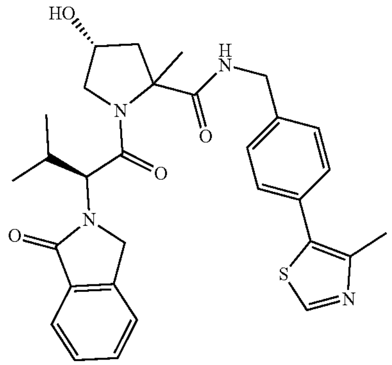
-continued
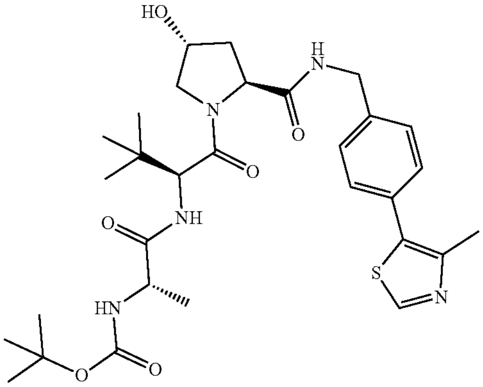
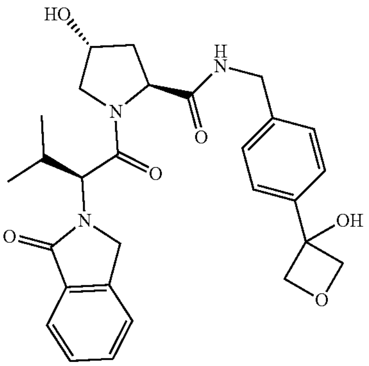
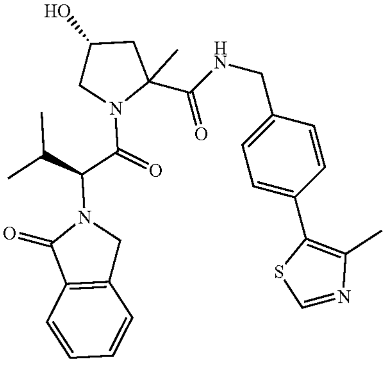
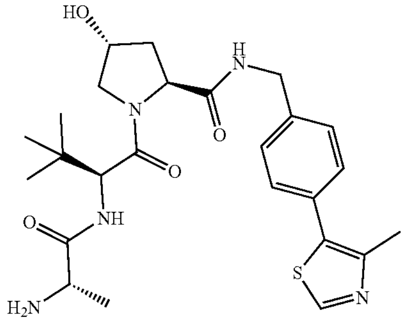

-continued
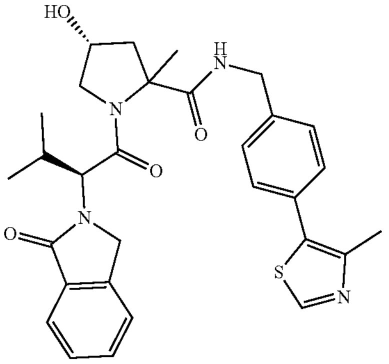
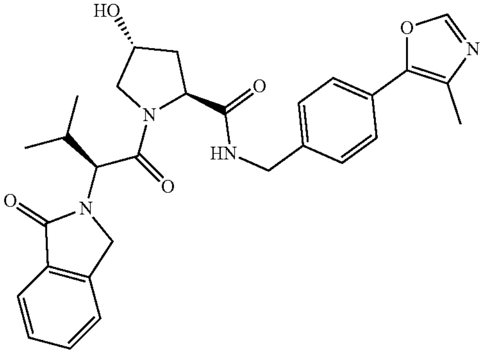
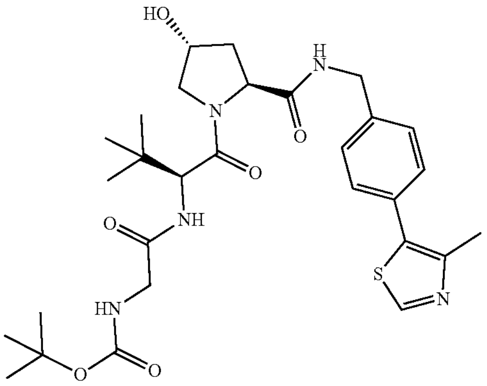
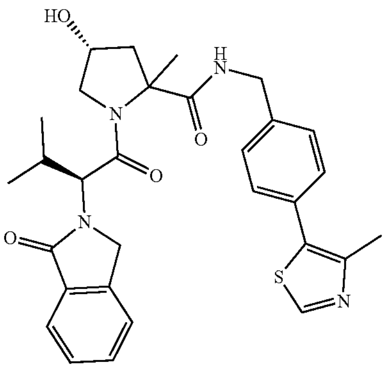
-continued
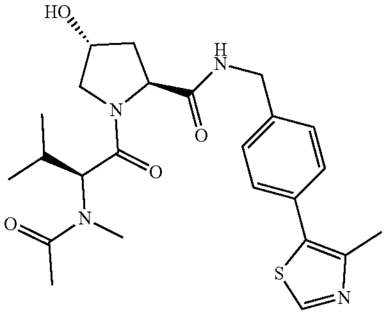
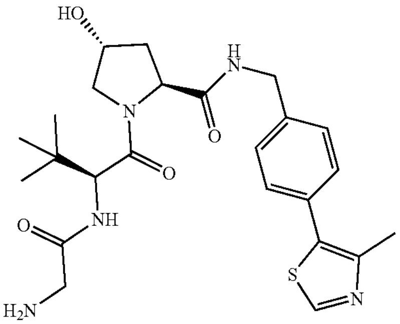
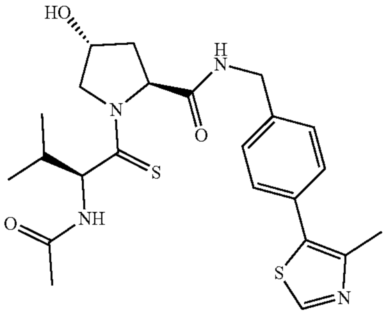
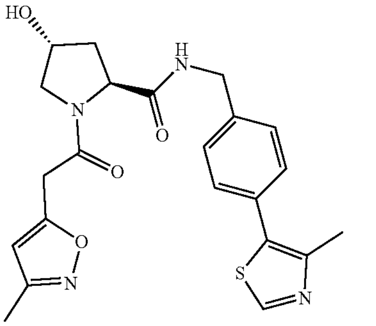
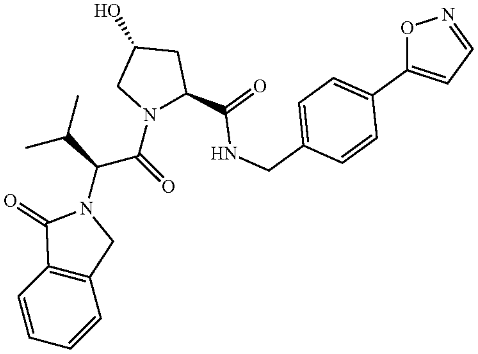

-continued
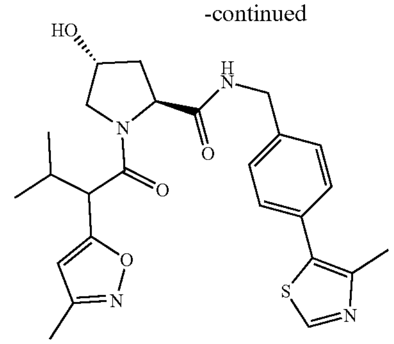
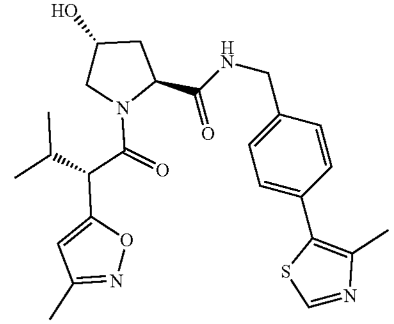
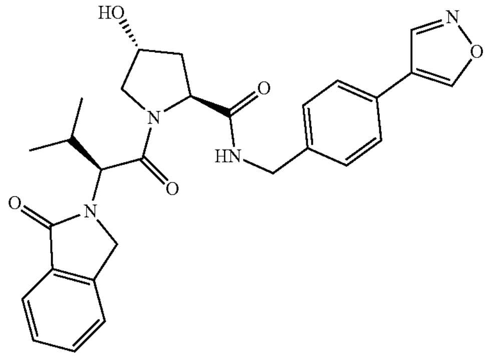
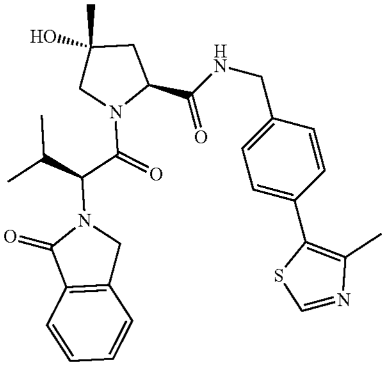
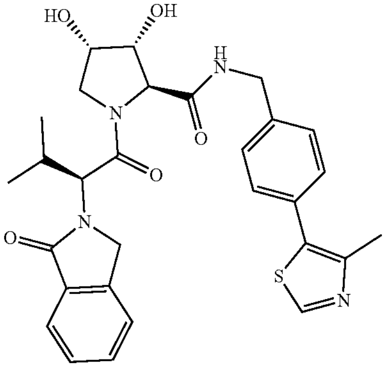
-continued
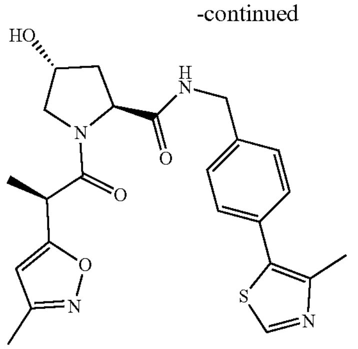
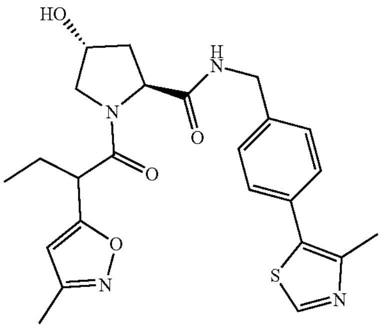
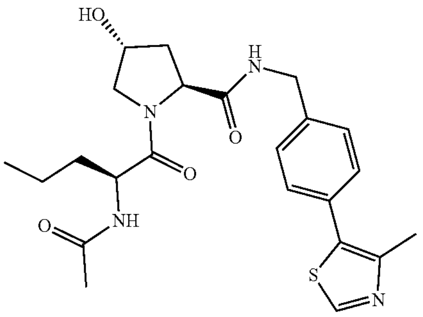
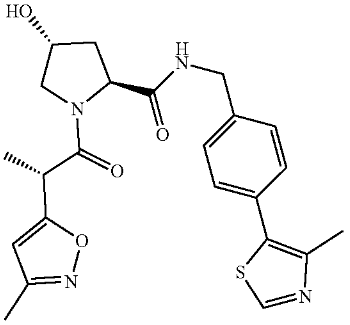
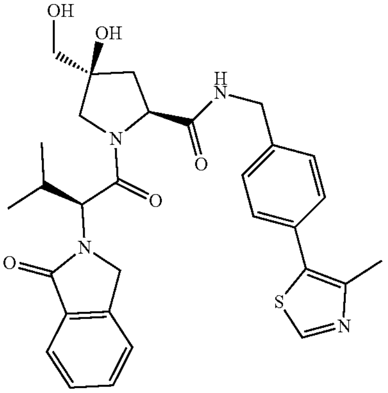

-continued
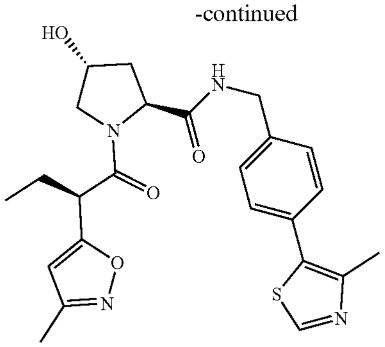
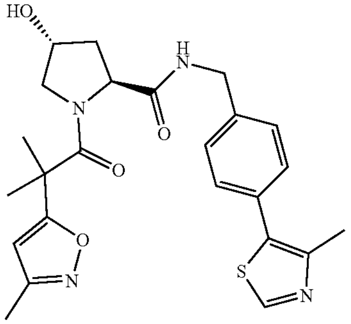
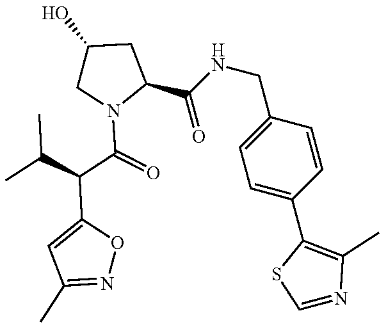
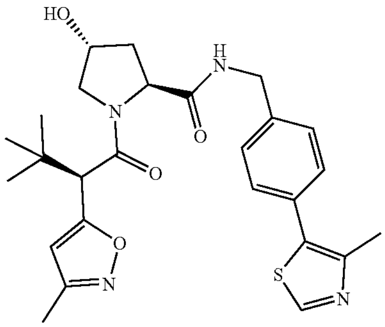
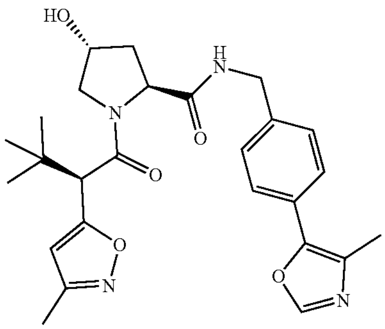
-continued
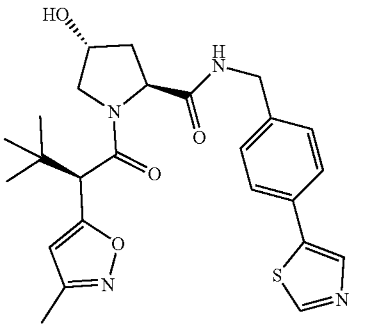
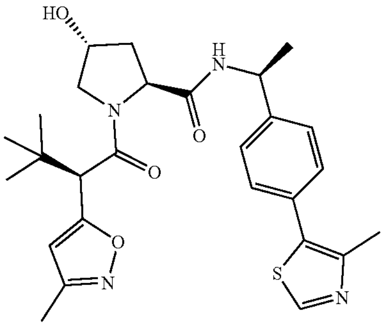
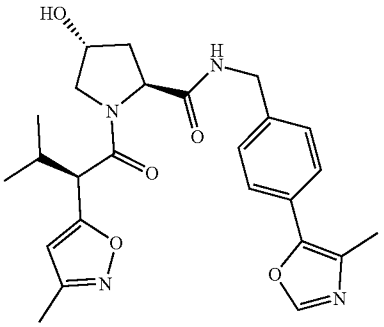
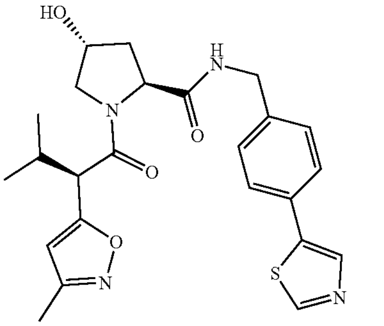
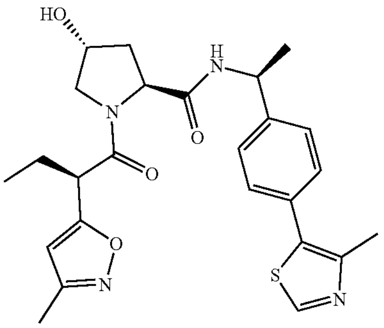

-continued
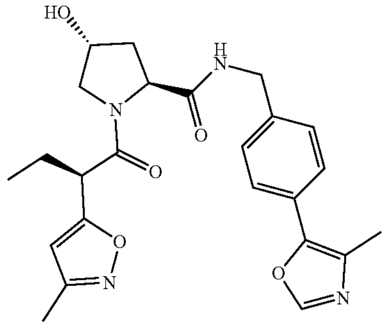
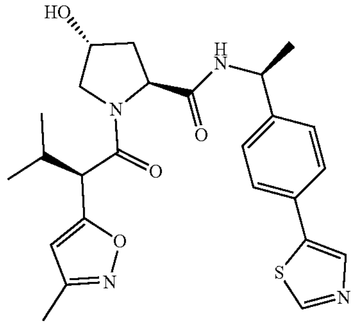
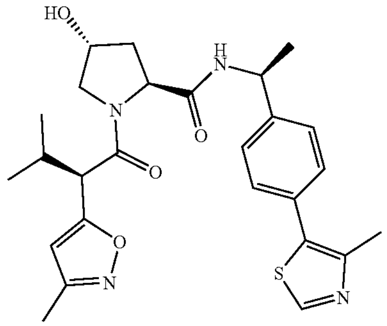
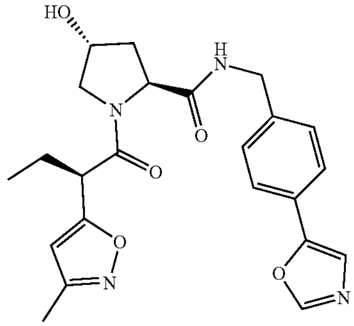
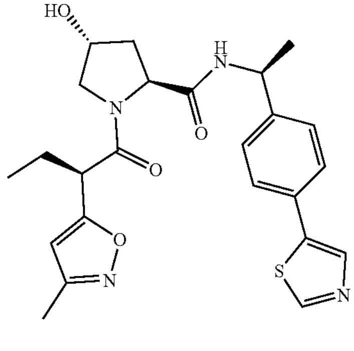
-continued
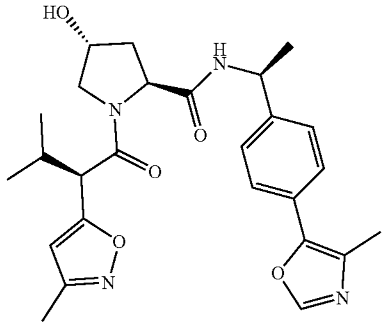
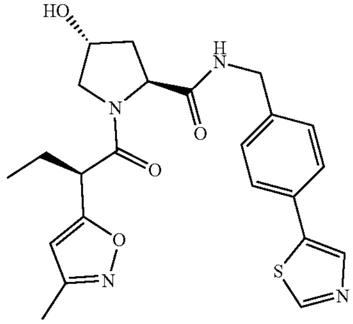
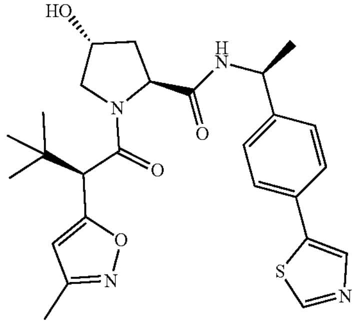
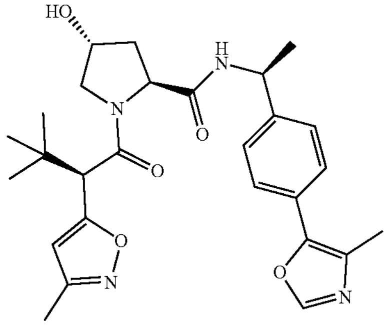
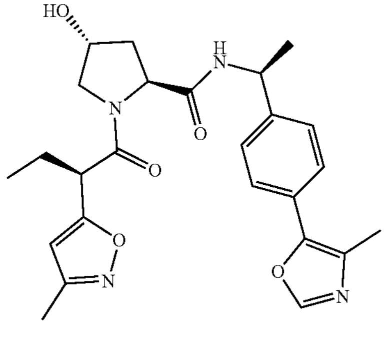

-continued
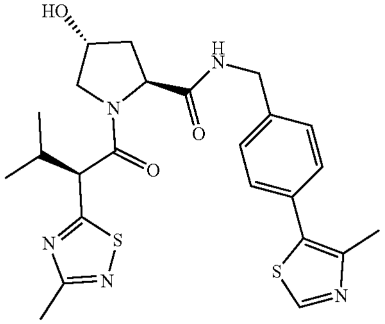
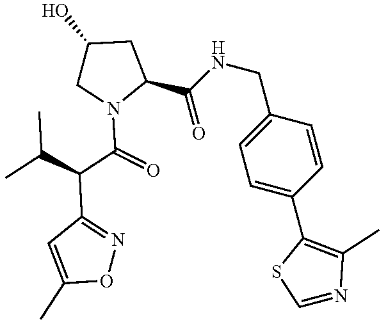
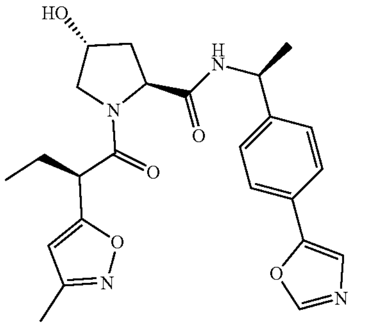
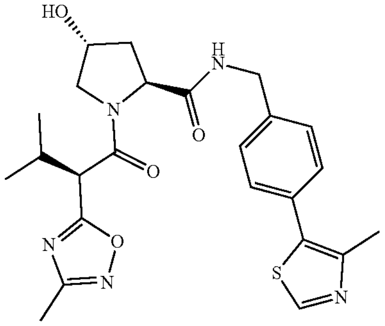
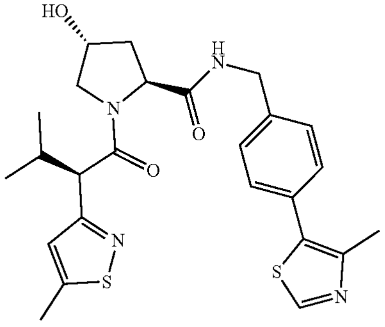
-continued
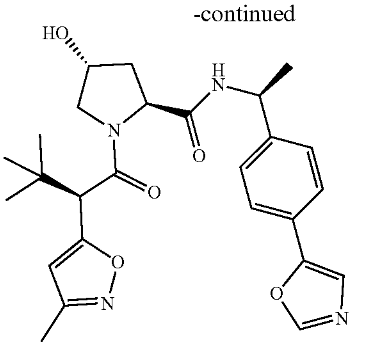
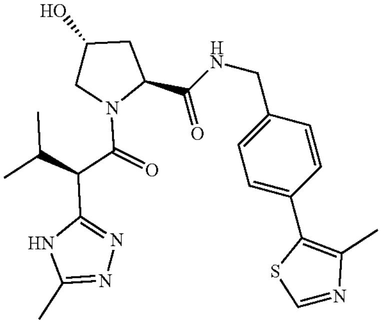
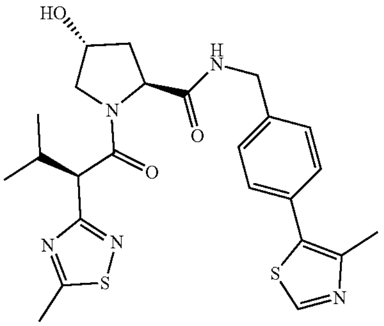
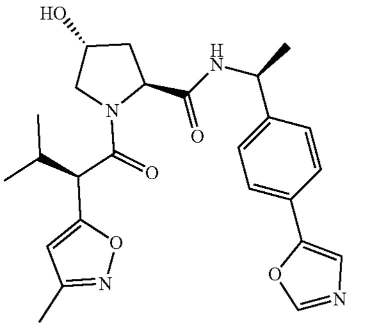
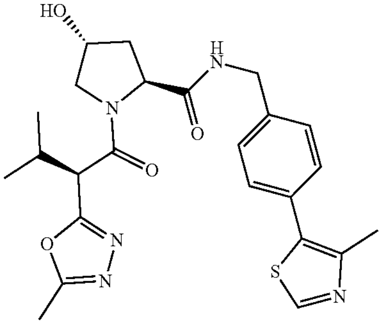

-continued
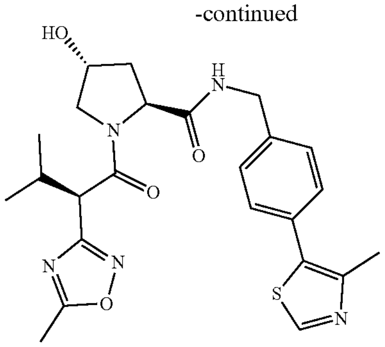
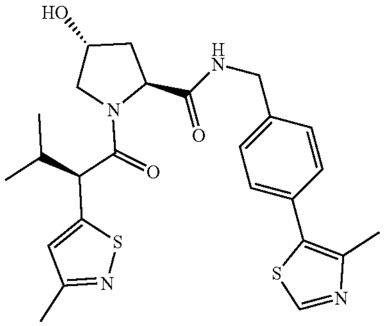
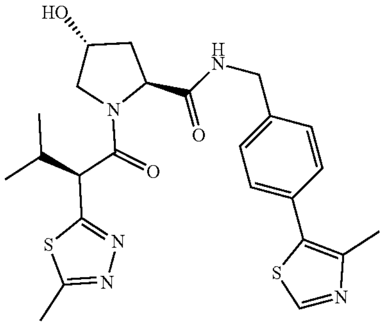
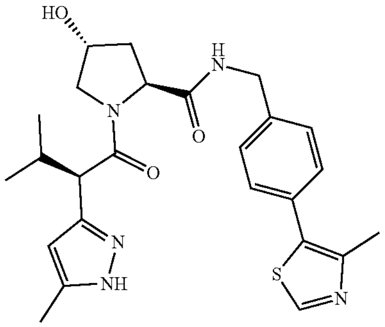
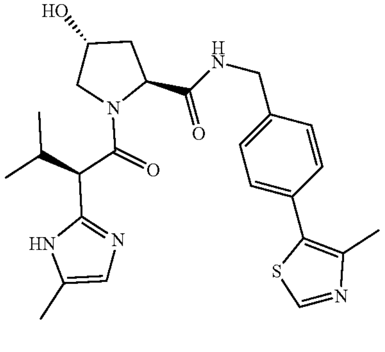
-continued
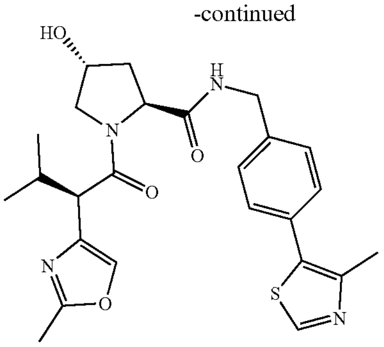
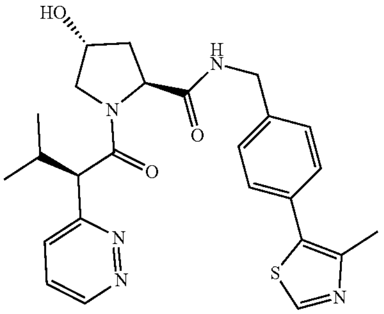
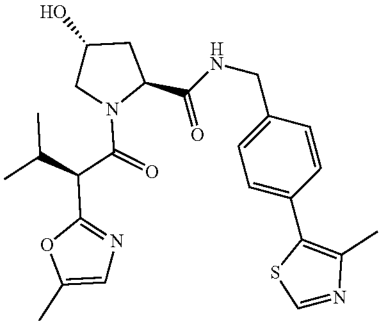
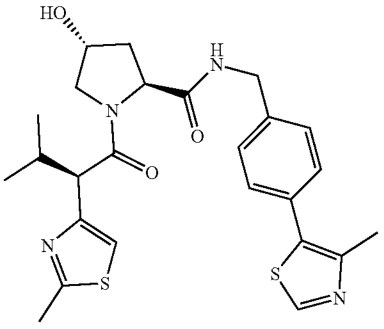
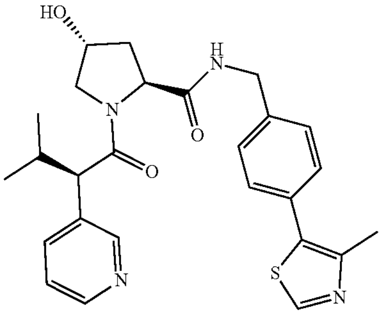

-continued
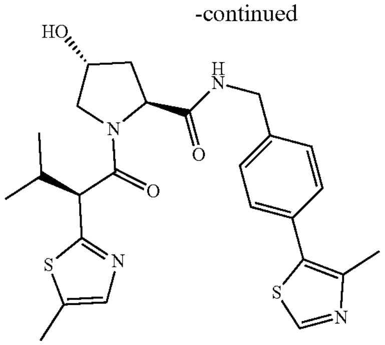
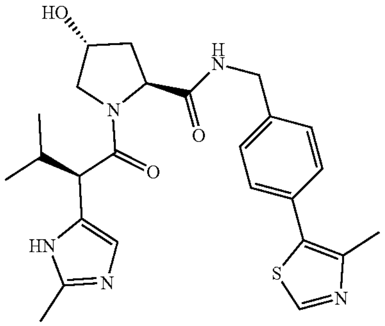
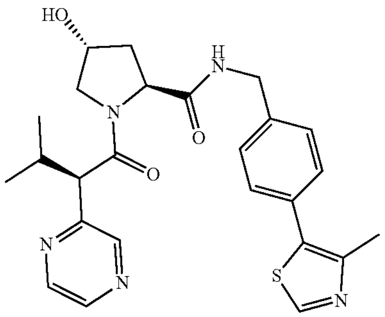
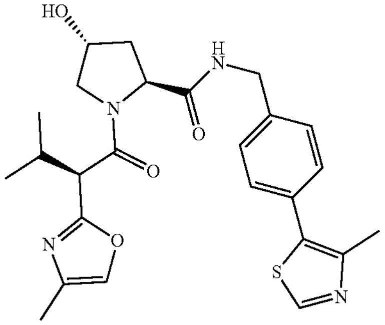
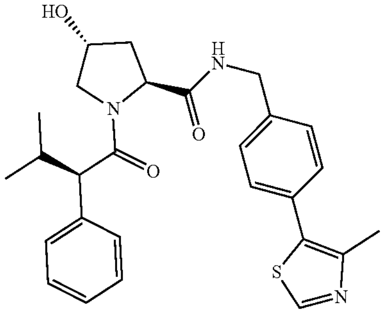
-continued
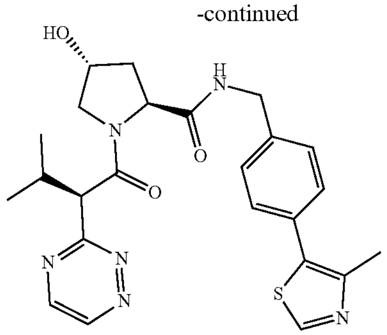
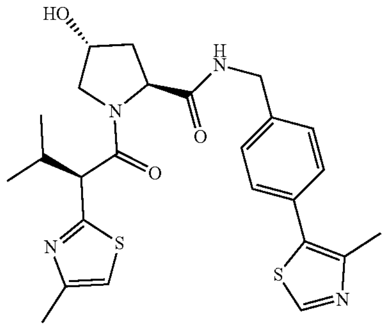
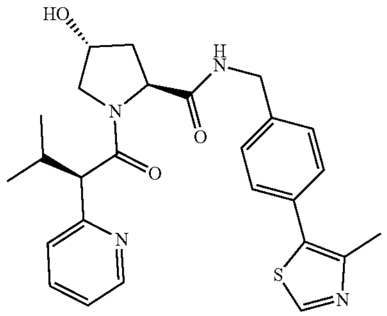
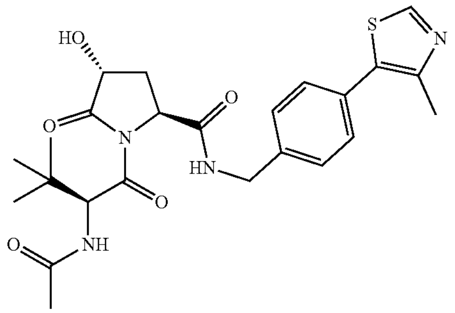
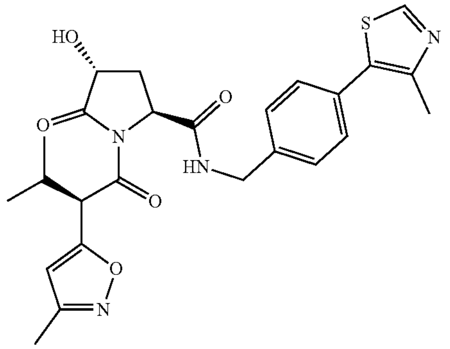

-continued
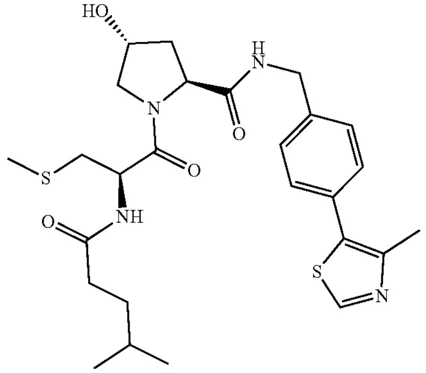
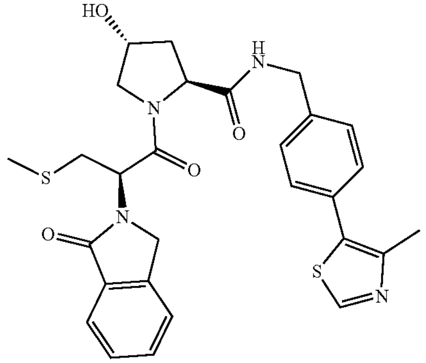
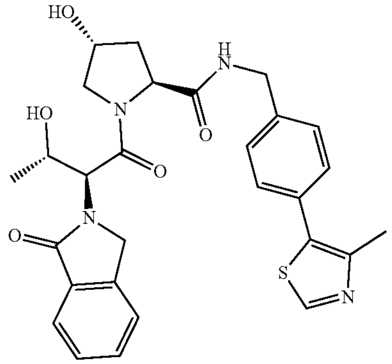
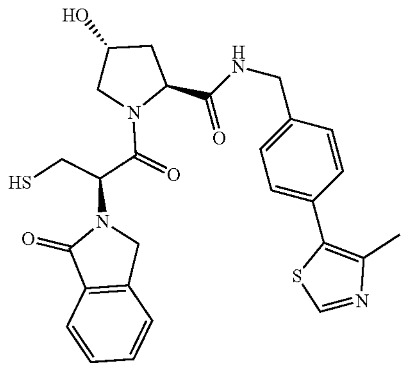
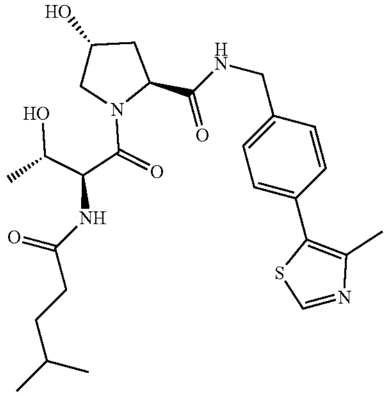
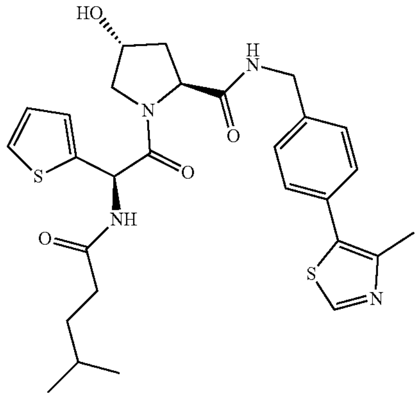
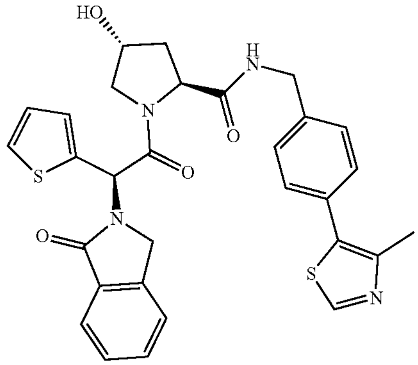
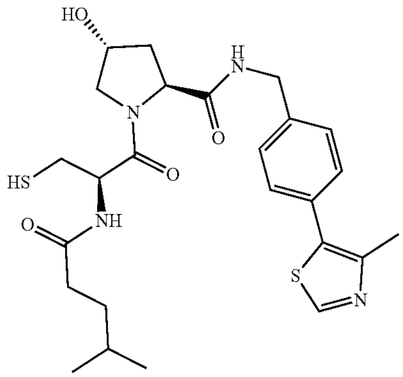
-continued -continued
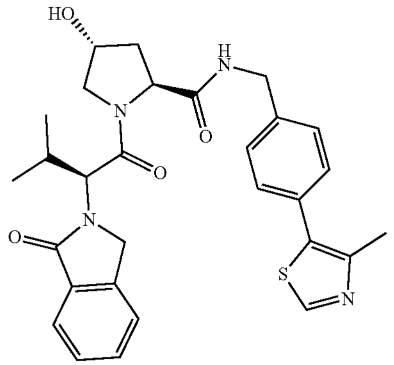
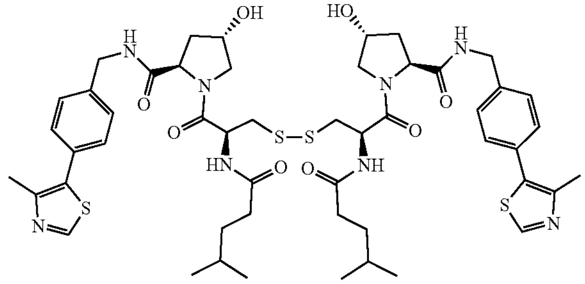
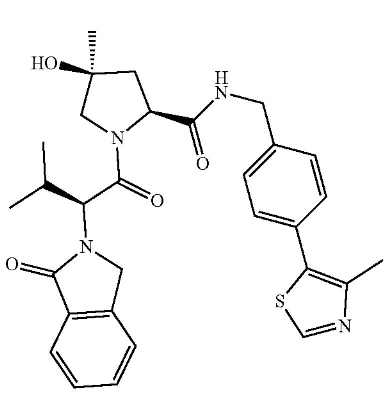
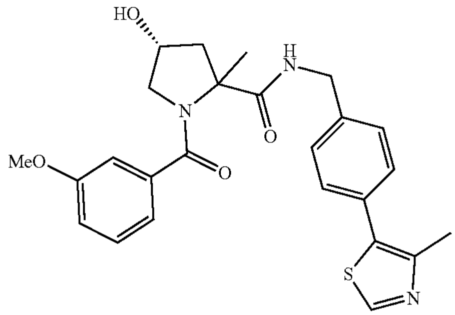
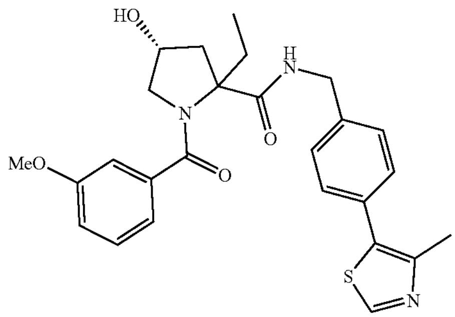
-continued
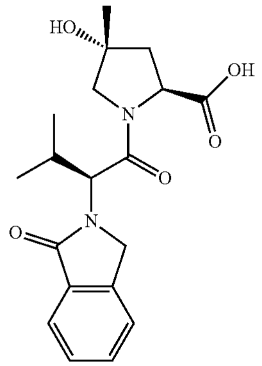
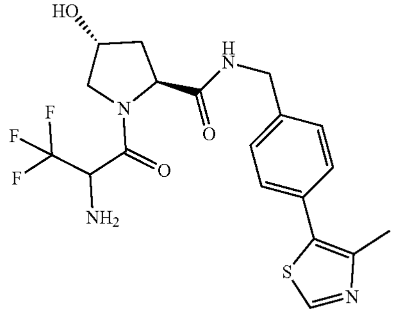
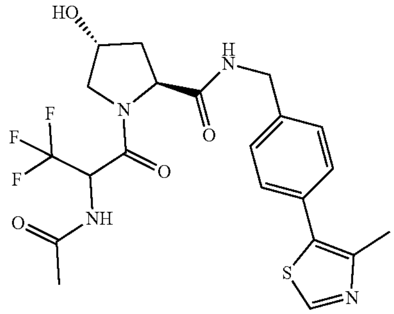
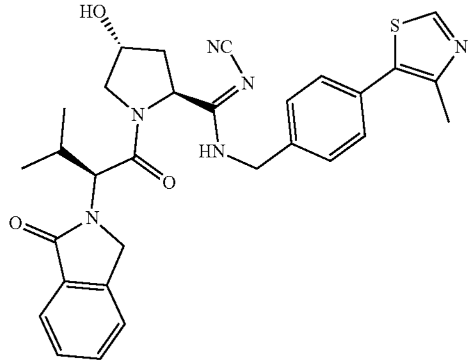
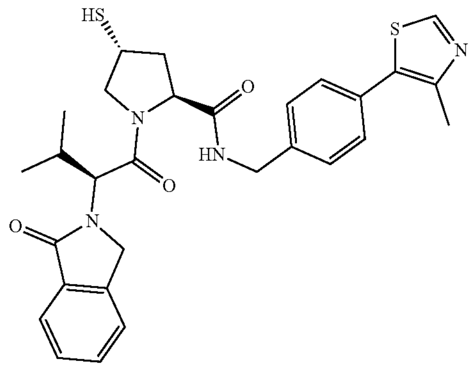

-continued
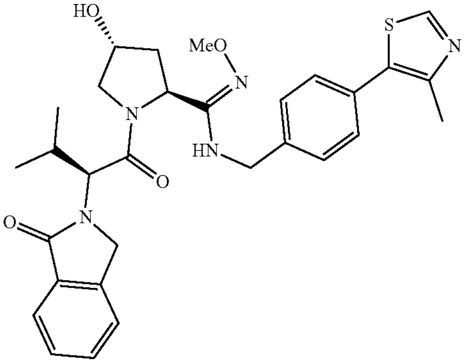
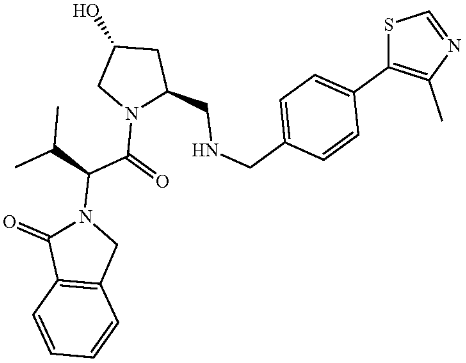
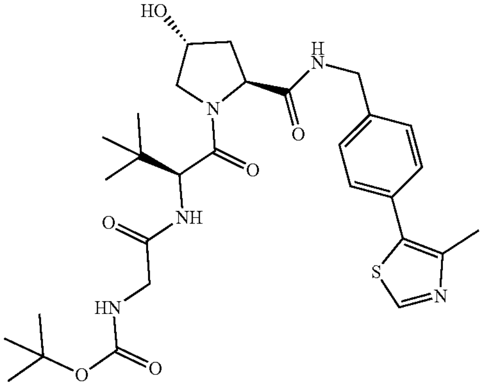
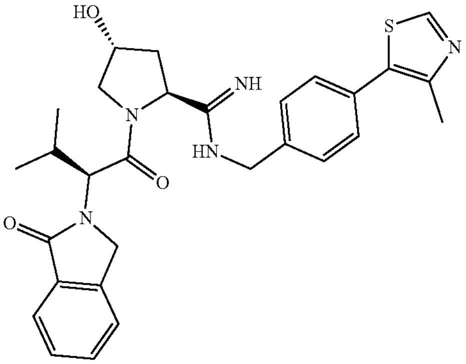
-continued
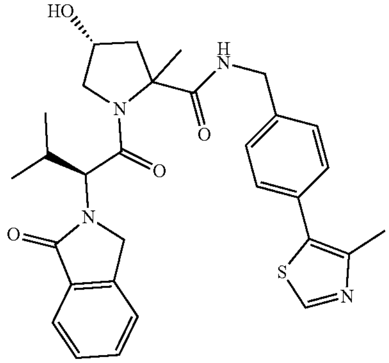
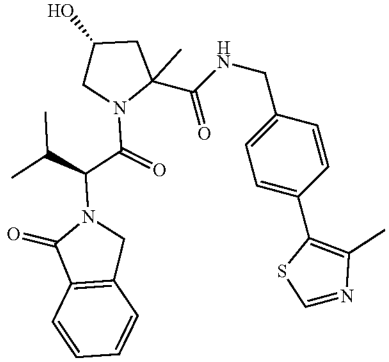
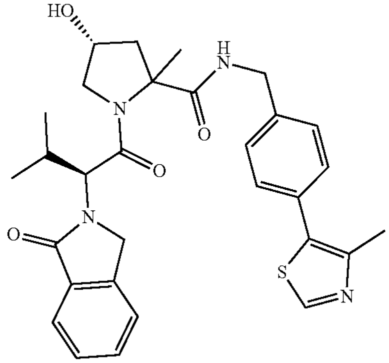
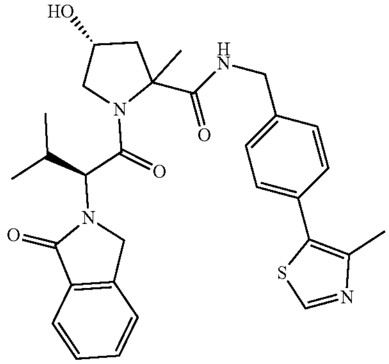

-continued
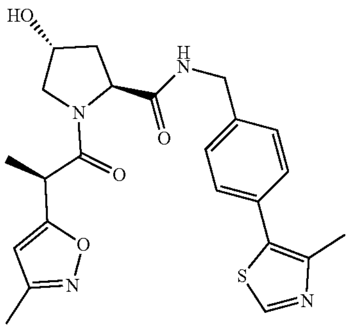
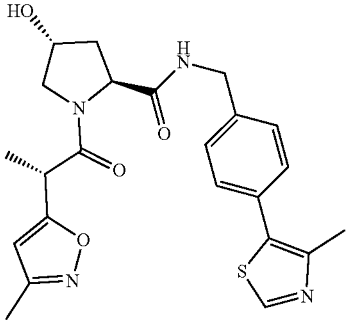
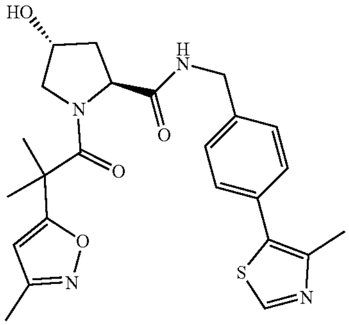
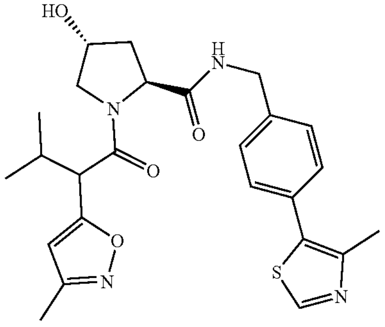
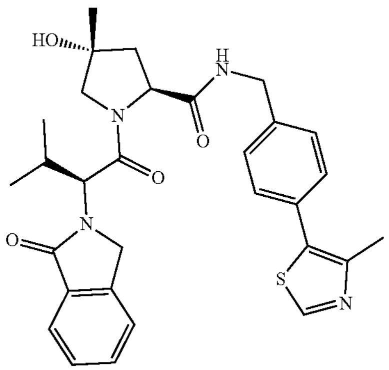
-continued
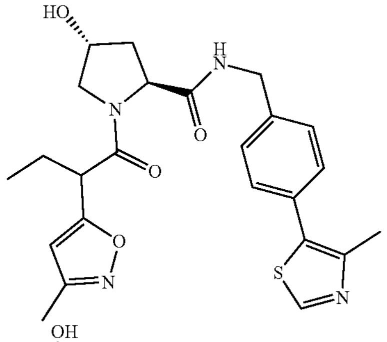
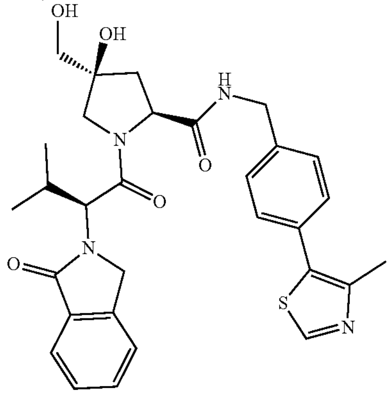
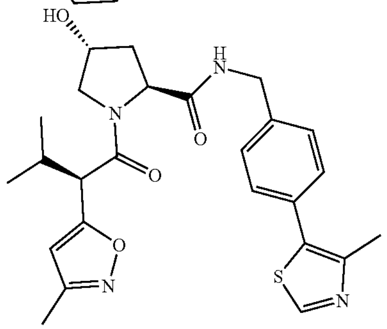
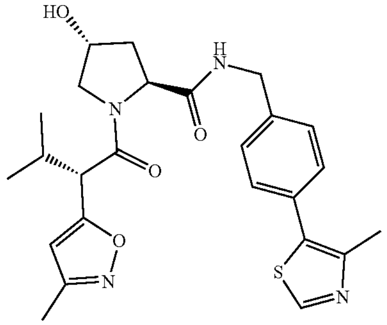
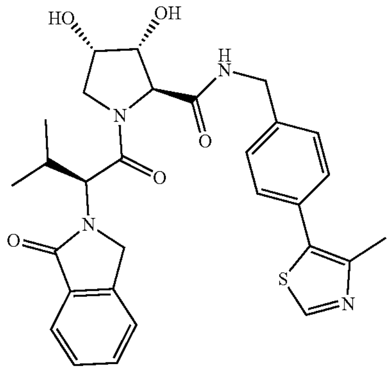

-continued
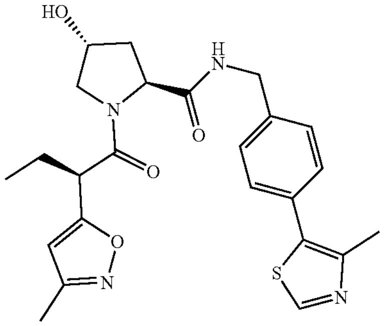
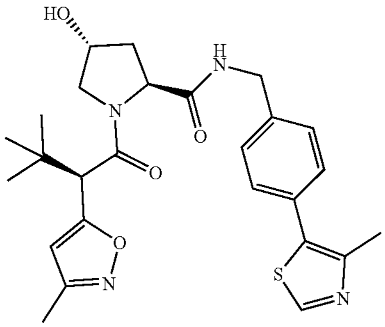
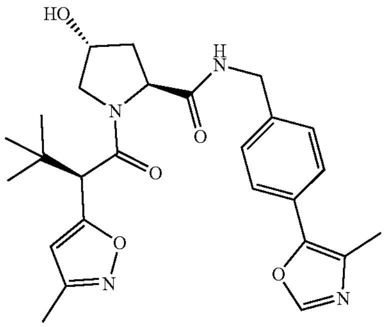
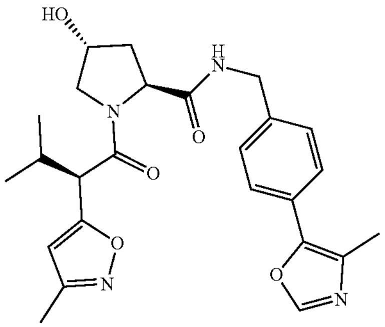
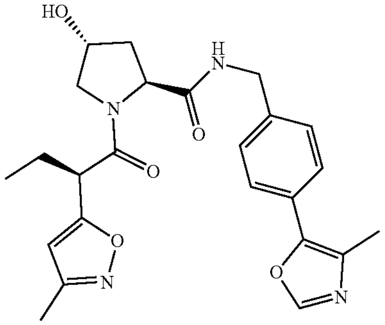
-continued
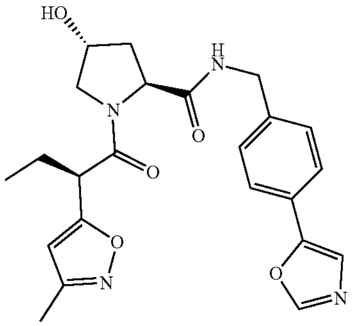
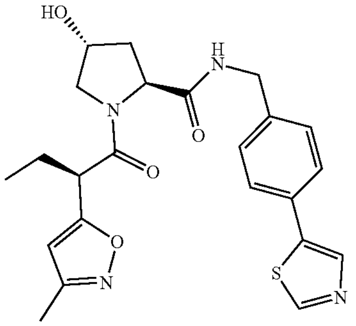
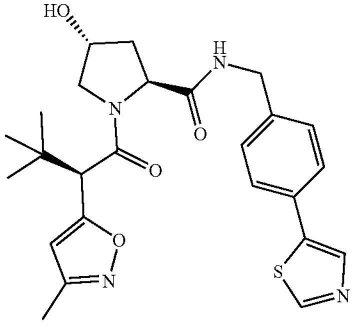
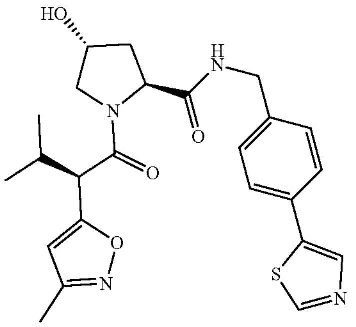
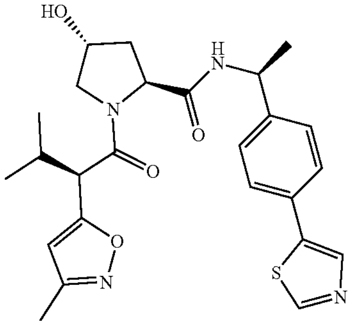

-continued
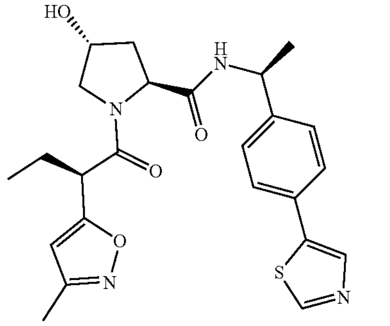
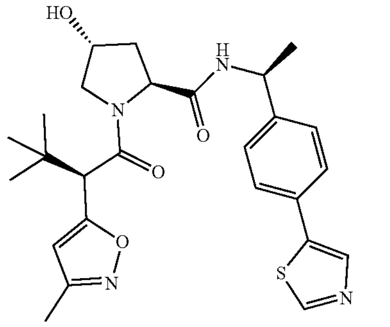
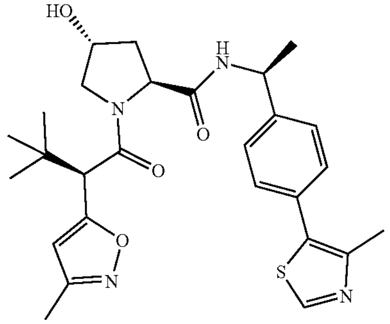
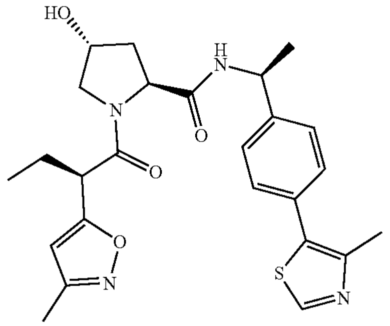
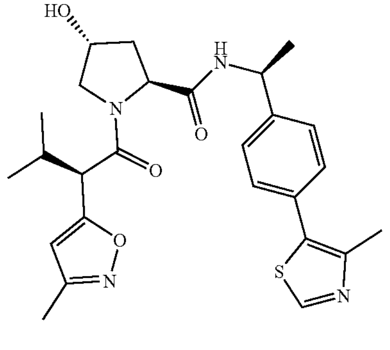
-continued
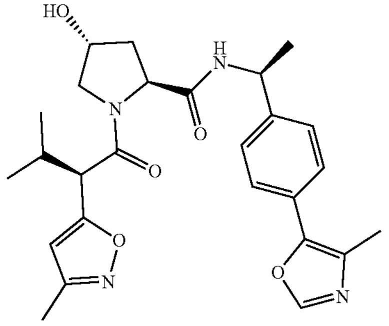
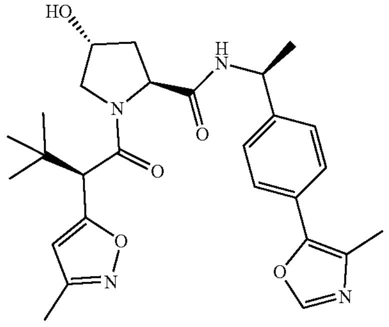
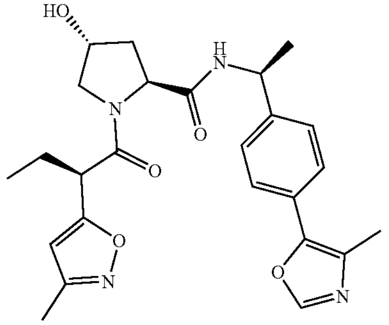
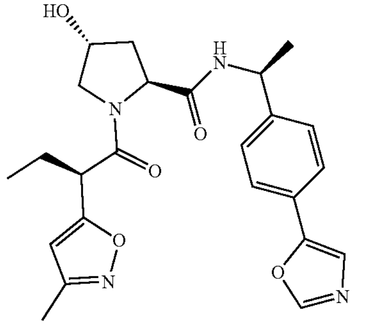
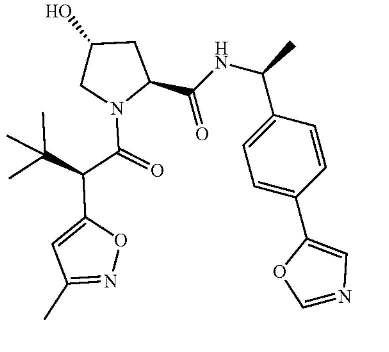

-continued
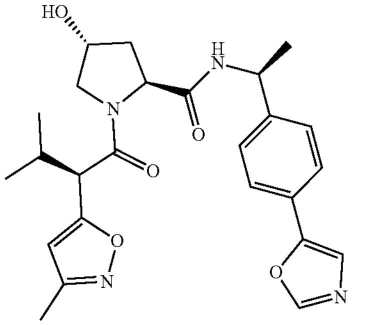
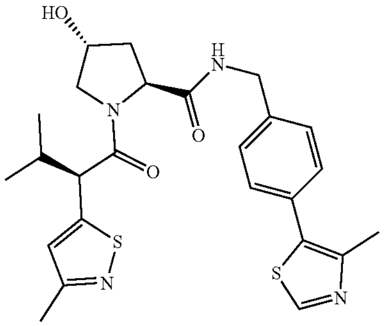
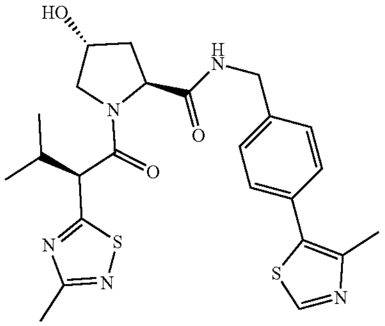
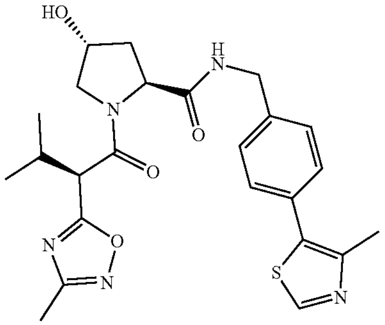
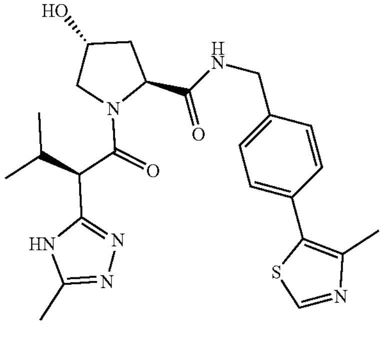
-continued
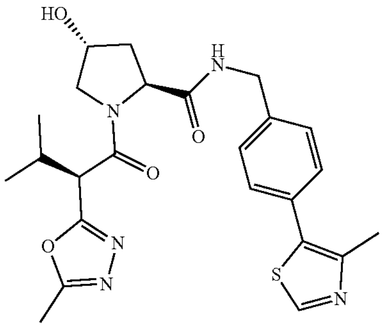
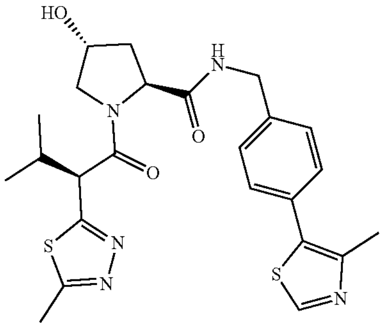
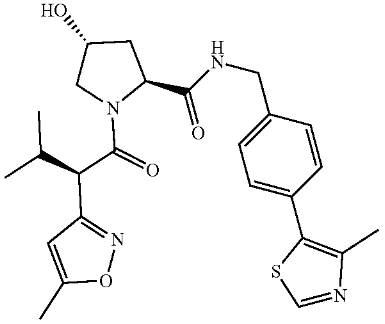
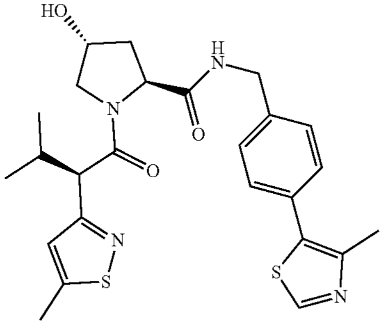
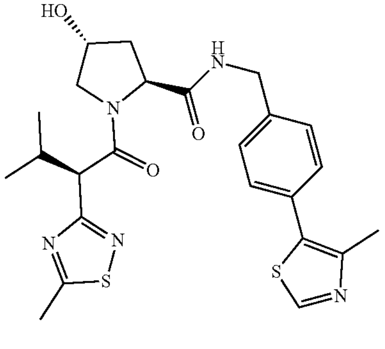

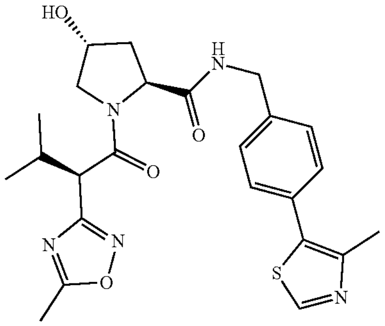
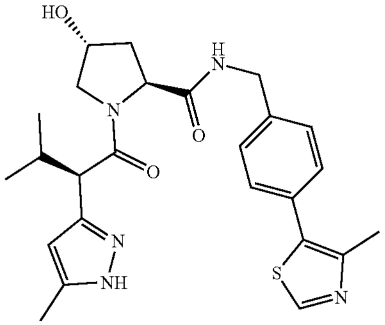
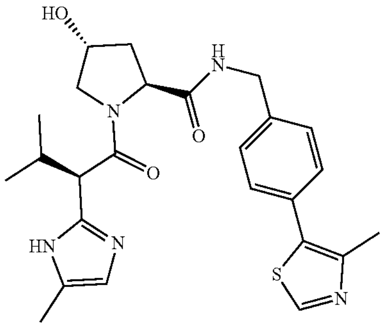
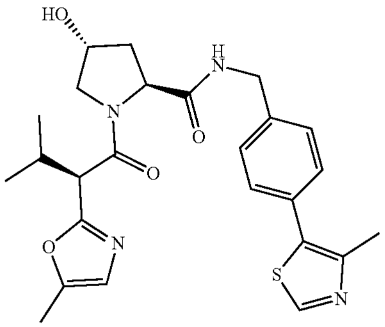
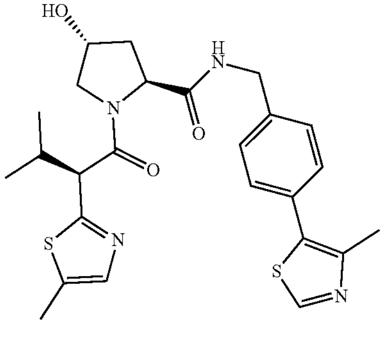
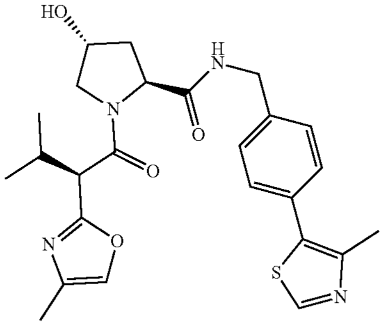
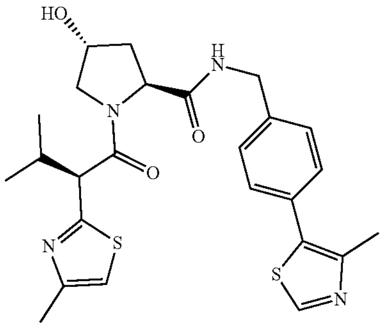
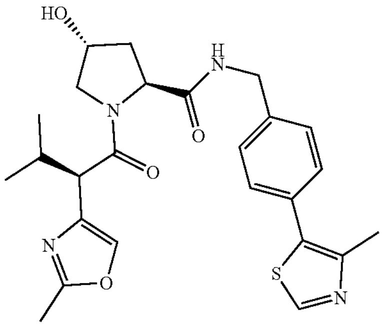
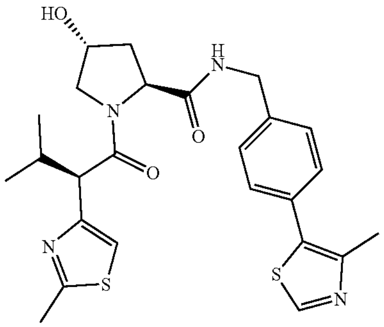
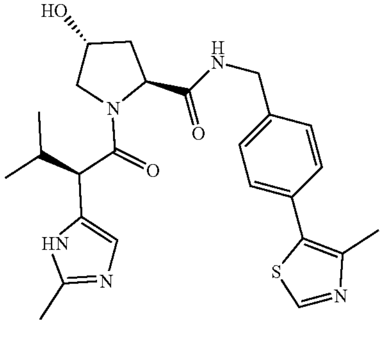

-continued
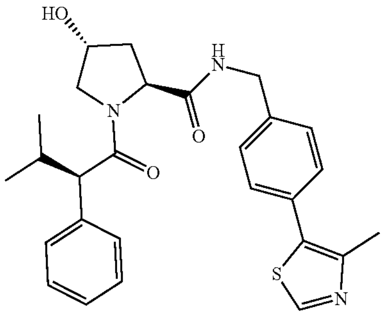
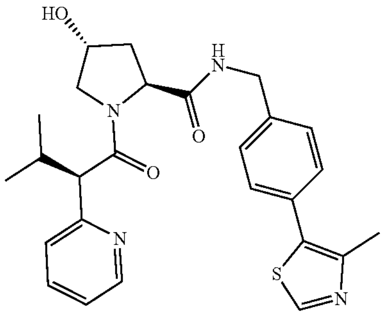
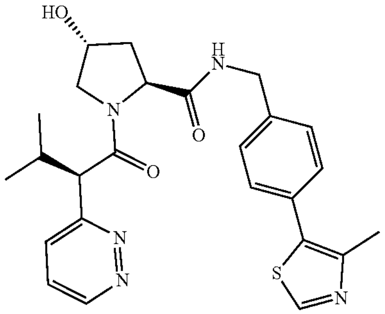
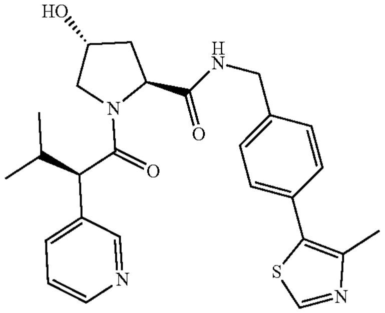
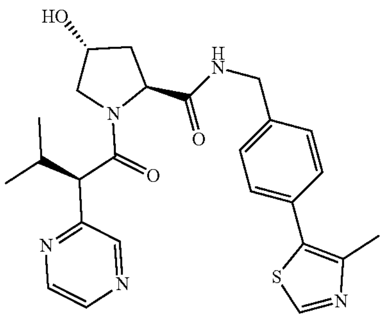
-continued
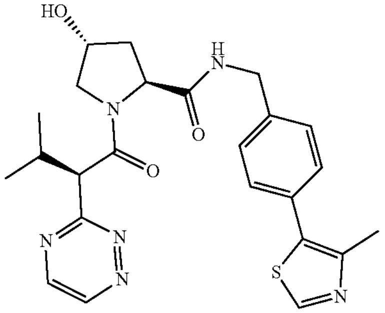
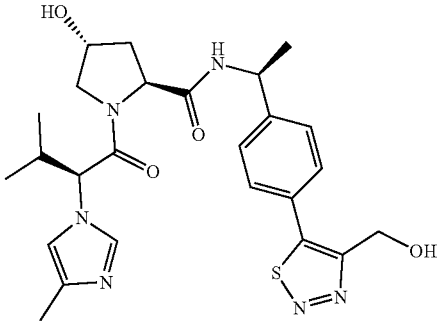
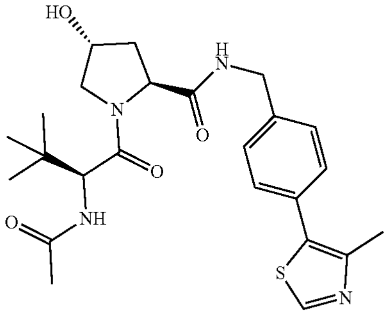
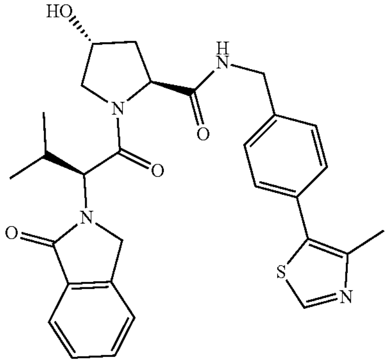
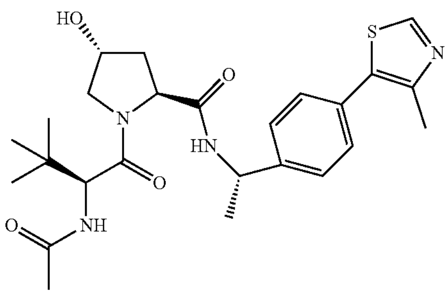

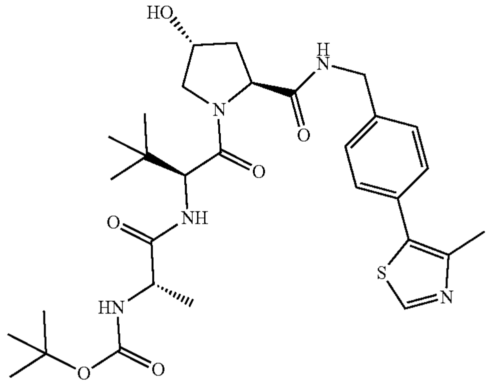
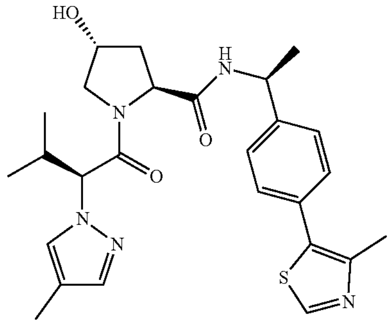
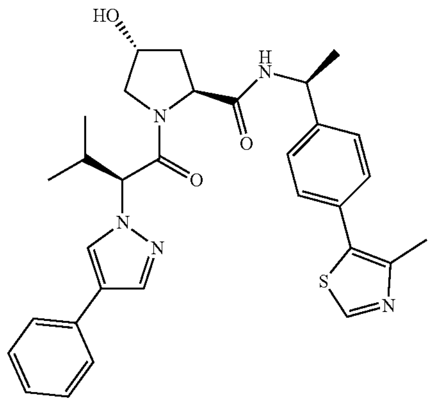
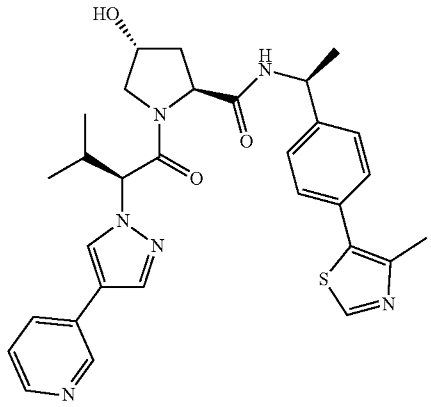
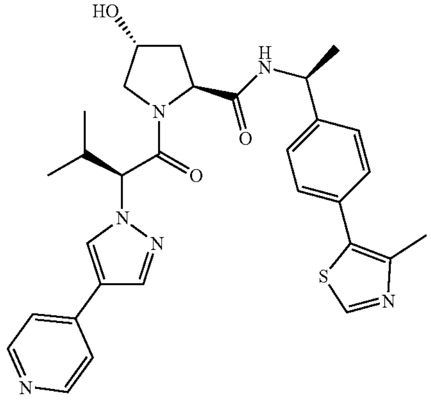
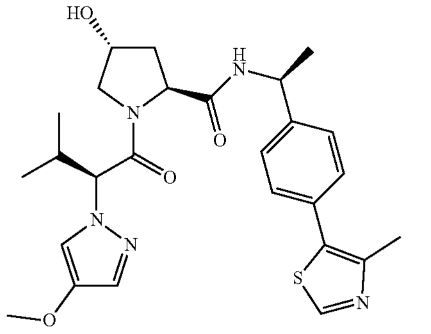
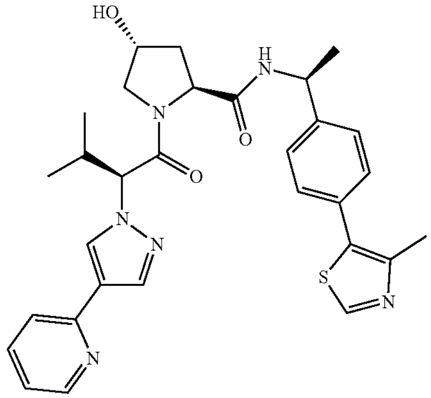
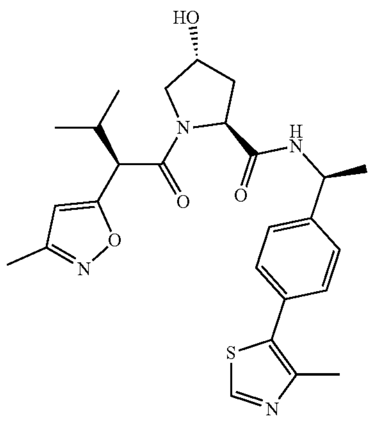

-continued
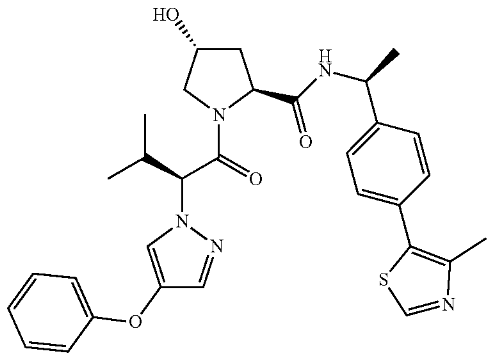
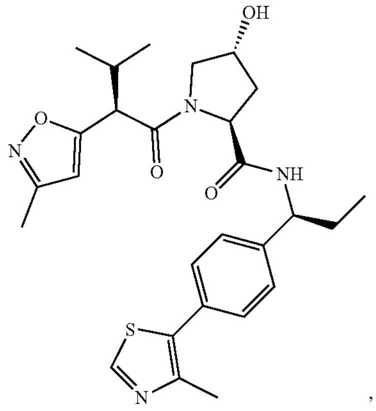
,
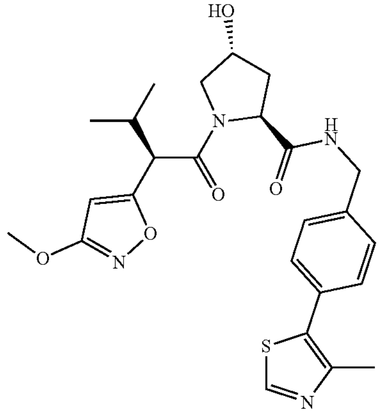
,
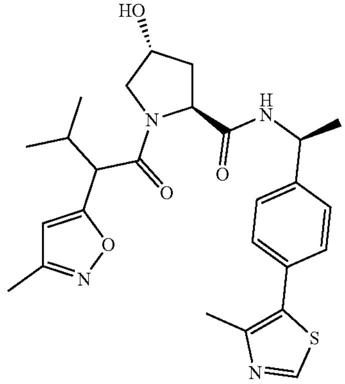
, and
-continued
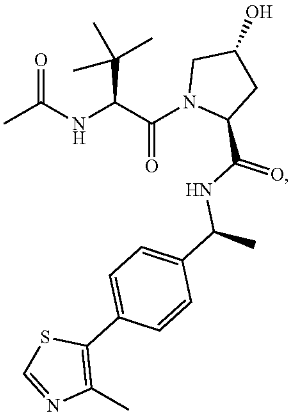
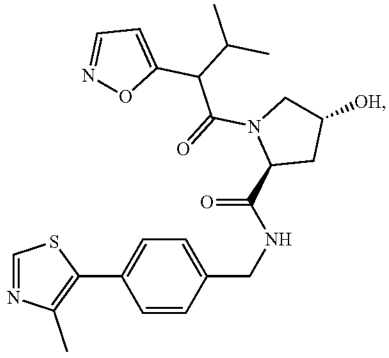
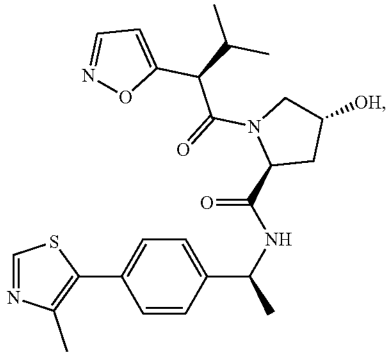
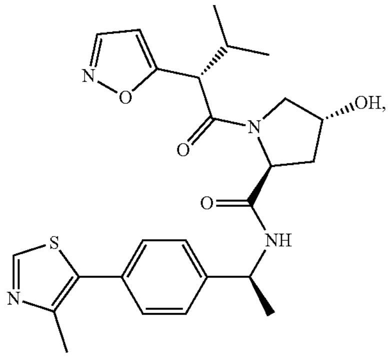
and -continued

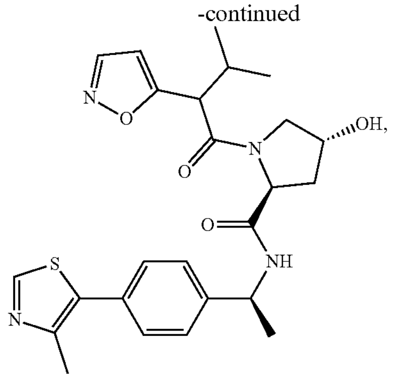

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A_1 \ldots (A^L)_q-$ or $-(A^L)_q-$), wherein $A^L{}_1$ is a group coupled to PTM, and $(A^L)_q$ is a group coupled to ULM.

In any aspect or embodiment described herein, the linker (L) to ULM (e.g., VLM, ILM, CLM, or MLM) connection or coupling is a stable L-ULM connection. For example, in any aspect or embodiment described herein, when a linker (L) and a ULM is connected via a heteroatom, any subsequent heteroatom, if present, is separated by at least one single carbon atom (e.g., —$CH_2$—), such as with an acetal or aminal group.

In any aspect or embodiment described herein, the linker group L is a bond or a chemical linker group represented by the formula $-(A^L)_q-$, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100), and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is a bond or a chemical linker group represented by the formula $-(A^L)_q-$, wherein A is a chemical moiety and q is an integer from 1-100, and wherein L is covalently bound to the PTM and the ULM, and provides for sufficient binding of the PTM to the protein target and the ULM to an E3 ubiquitin ligase to result in target protein ubiquitination.

In any aspect or embodiment described herein, the linker group L is $-(A^L)_q-$, wherein:

$(A^L)_q$ is a group which is connected to at least one of a ULM (such as a CLM or a VLM), PTM moiety, or a combination thereof;

q of the linker is an integer greater than or equal to 1 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100);

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}$ C(=NCN)$NR^{L4}$, $NR^{L3}$C(=NCN), $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^L$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC^{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)_2$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC{\equiv}C_{1-8}$ alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)\ SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is $A^L{}_1$ and $(A^L)_q$ wherein the units $A^L$ are couple a PTM to a ULM.

In certain embodiments, e.g., where q of the linker is 2, $(A^L)_q$ is a group which is connected to $A^L{}_1$ and to a ULM.

In certain embodiments, e.g., where q of the linker is 1, the structure of the linker group L is $-A^L{}_1-$, and $A^L{}_1$ is a group which is connected to a ULM moiety and a PTM moiety.

In any aspect or embodiment described herein, the unit $A^L$ of linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(hetero cycloalkyl)-, —$NR(CH_2CH_2O)_n$-(lower alkyl)-O—$CH_2$—, —$NR(CH_2CH_2O)_n$-(hetero cycloalkyl)-O—$CH_2$—, —$NR(CH_2CH_2O)_n$-Aryl-O—$CH_2$—, —$NR(CH_2CH_2O)_n$-(hetero aryl)-O—$CH_2$—, —$NR(CH_2CH_2O)_n$-(cyclo alkyl)-O-(hetero aryl)-O—

$CH_2$—, —NR$(CH_2CH_2O)_n$-(cyclo alkyl)-O-Aryl-O—$CH_2$—, —NR$(CH_2CH_2O)_n$-(lower alkyl)-NH-Aryl-O—$CH_2$—, —NR$(CH_2CH_2O)_n$-(lower alkyl)-O-Aryl-$CH_2$, —NR$(CH_2CH_2O)_n$-cycloalkyl-O-Aryl-, —NR$(CH_2CH_2O)_n$-cycloalkyl-O-(heteroaryl)1-, —NR$(CH_2CH_2)_n$-(cycloalkyl)-O-(heterocycle)-$CH_2$, —NR$(CH_2CH_2)_n$-(heterocycle)-(heterocycle)-$CH_2$, —N(R1R2)-(heterocycle)-$CH_2$; where n of the linker can be 0 to 10;

R of the linker can be H, lower alkyl;

R1 and R2 of the linker can form a ring with the connecting N.

In any aspect or embodiment described herein, the unit $A^L$ of linker (L) comprises a group represented by a general structure selected from the group consisting of:

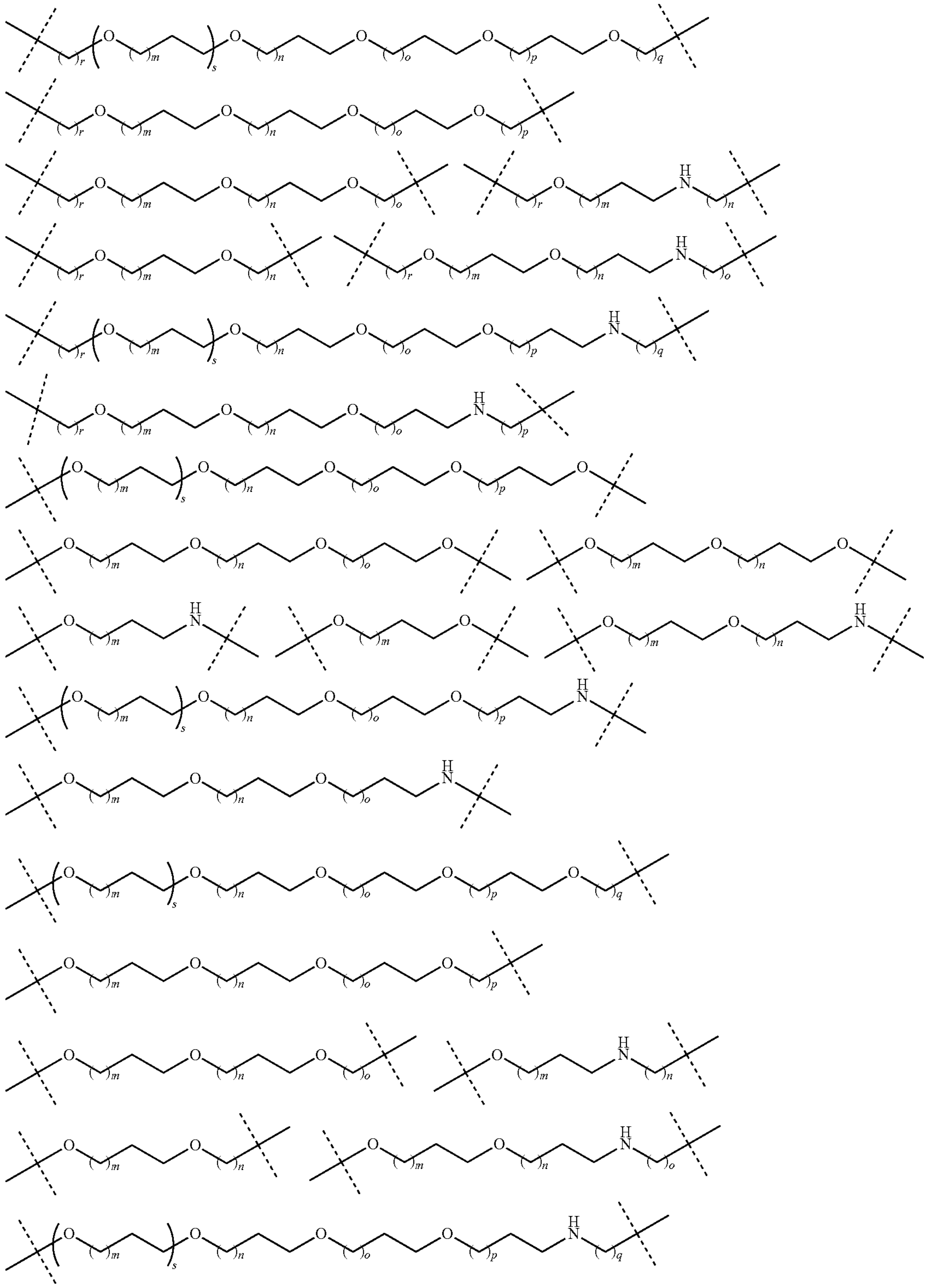

-continued

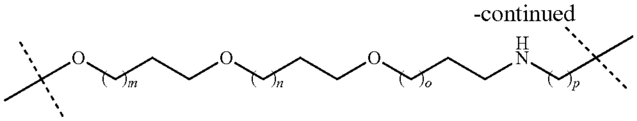

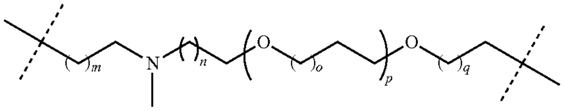

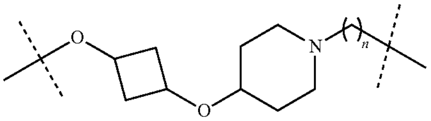

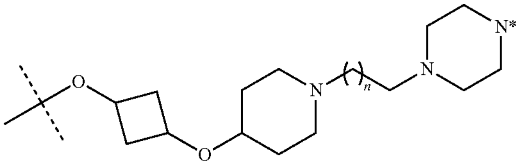

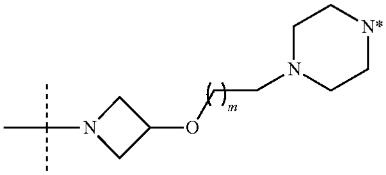

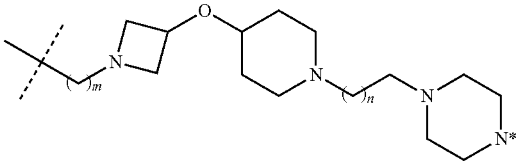

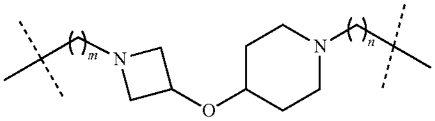

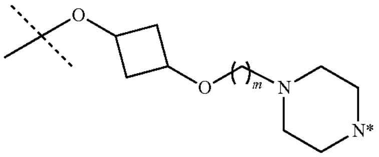

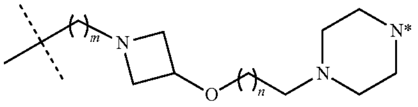

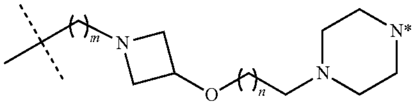

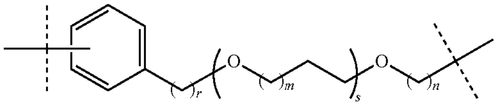

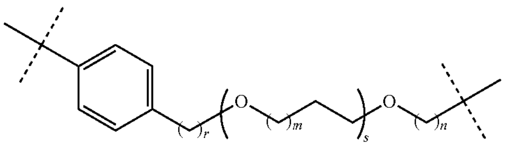

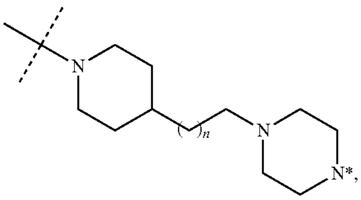

, wherein:

each m, n, o, p, q, r, and s are independently selected from 0, 1, 2, 3, 4, 5, 6, 7, 8, 9, 10, 11, 12, 13, 14, 15, 16, 17, 18, 19, and 20; and N* of the heterocycloalkyl is shared with the PTM or the ULM or is linked to the PTM or the ULM via a bond.

In any aspect or embodiment described herein, the unit $A^L$ of linker (L) comprises a group represented by a general structure selected from the group consisting of:

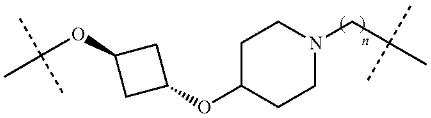

-continued

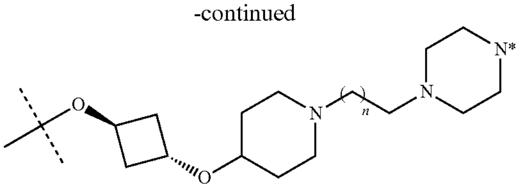

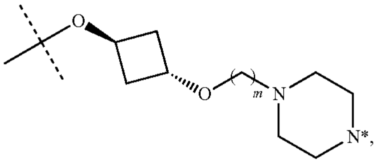

, wherein:

each m, n, o, p, q, r, and s are independently selected from 0, 1, 2, 3, 4, 5, 6, 7, 8, 9, 10, 11, 12, 13, 14, 15, 16, 17, 18, 19, and 20; and N* of the heterocycloalkyl is shared with the PTM or the ULM or is linked to the PTM or the ULM via a bond In any aspect or embodiment described herein, the unit $A^L$ of linker (L) is selected from:
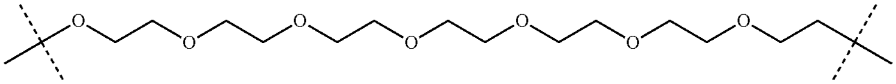
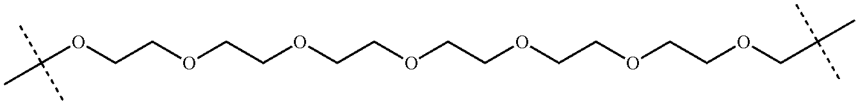
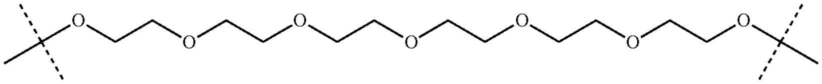
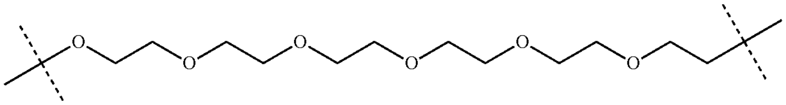
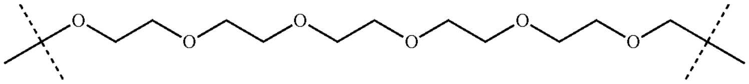
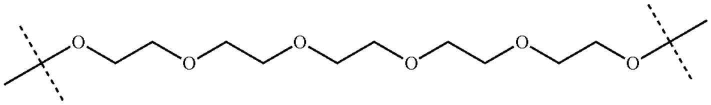
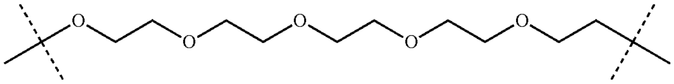
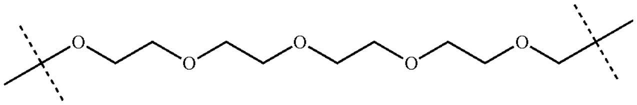
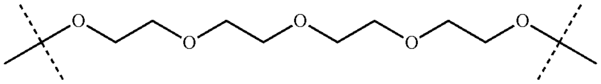
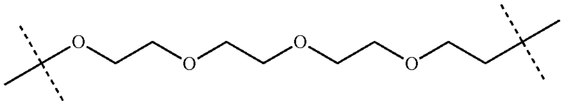
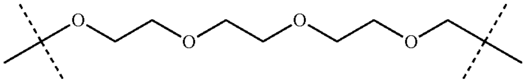
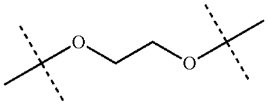
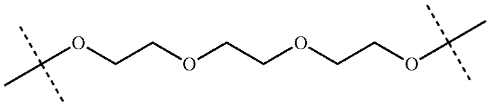
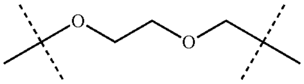
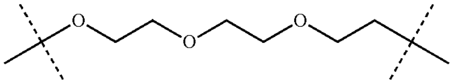
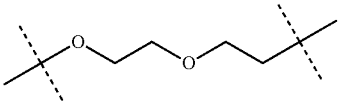
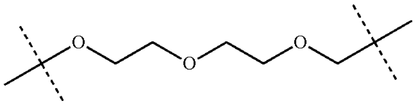
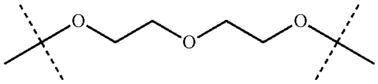
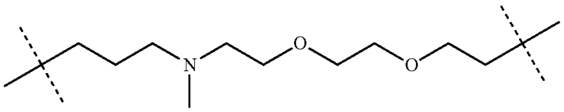
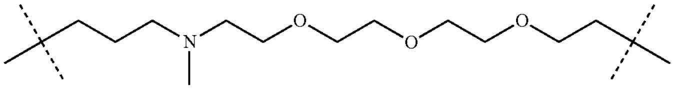
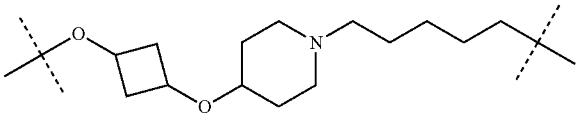

-continued
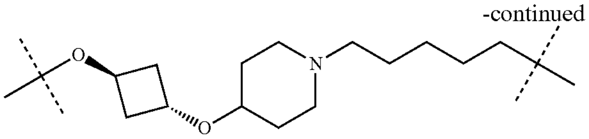
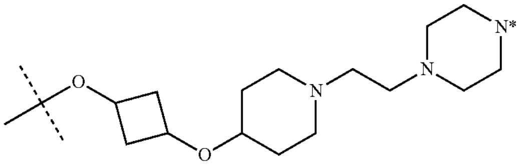
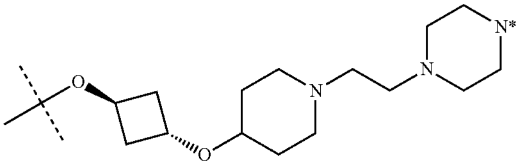
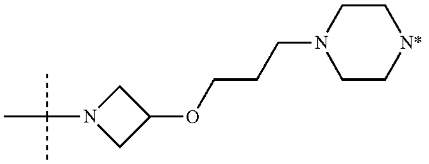
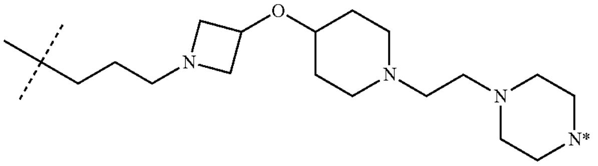
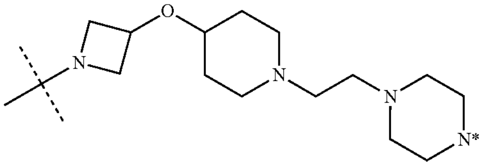
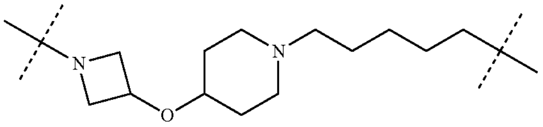
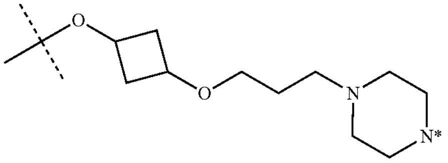
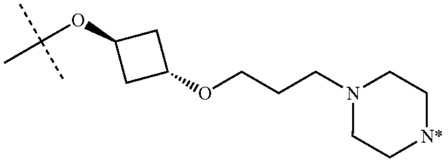
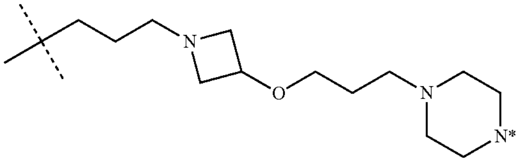
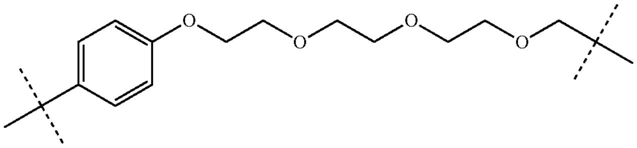
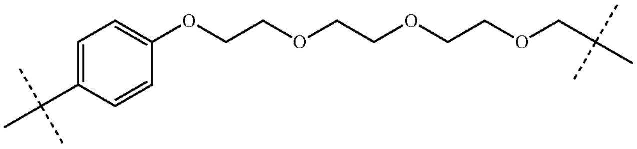
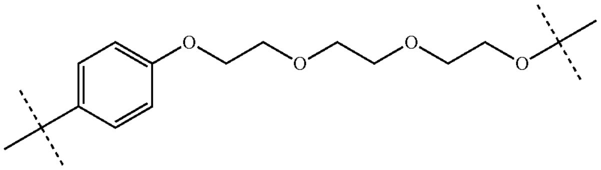
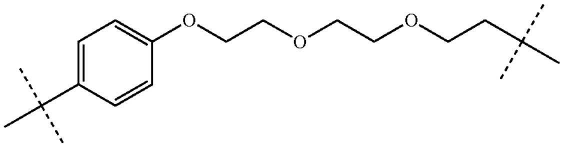
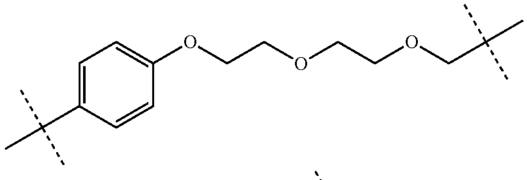
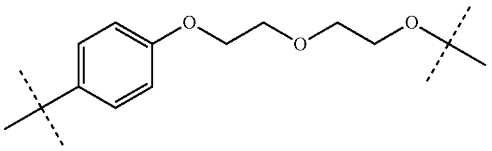
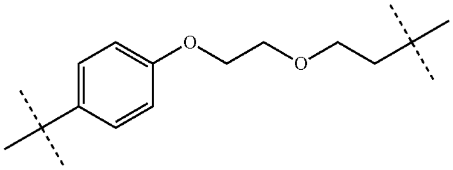

-continued
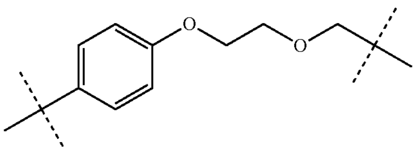 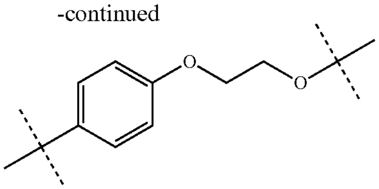
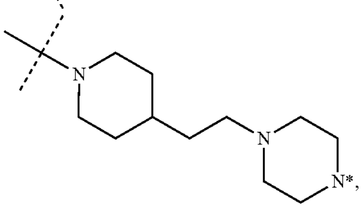,
wherein N* of the heterocycloalkyl is shared with the PTM or the ULM or is linked to the PTM or the ULM via a bond.
In any aspect or embodiment described herein, the unit $A^L$ of the linker (L) includes a group selected from:
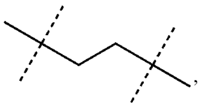, 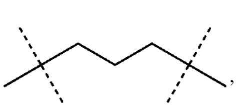, 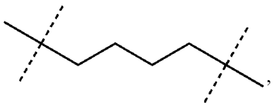, 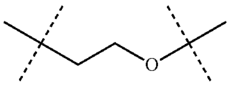,
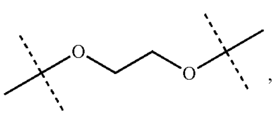, 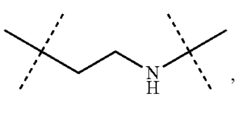, 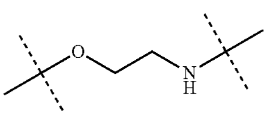, 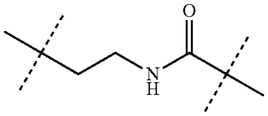,
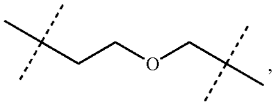, 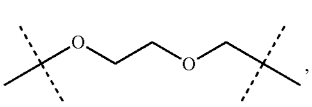, 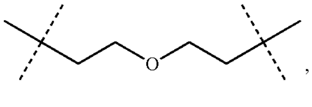,
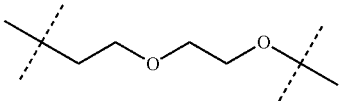, 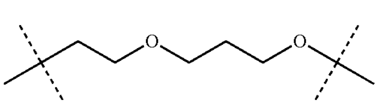,
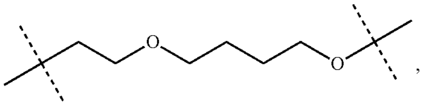, 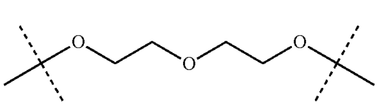,
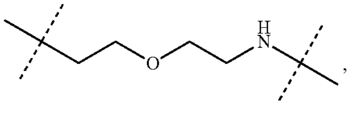, 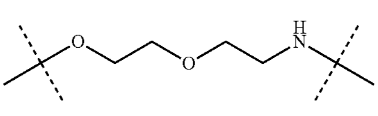, 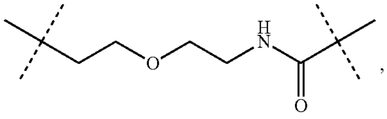,
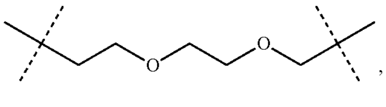, 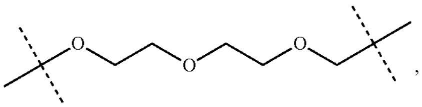,
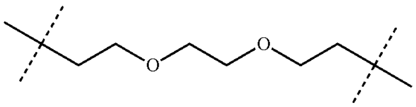, 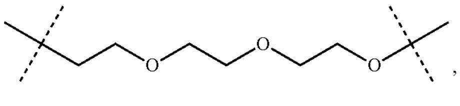,
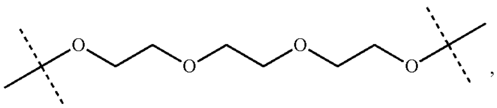, 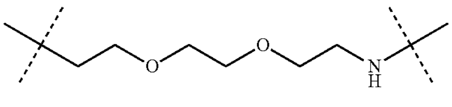,
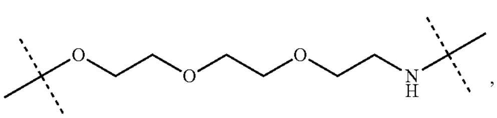, 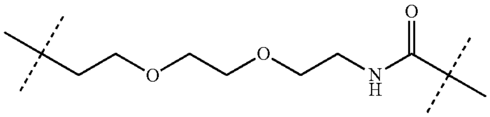, -continued
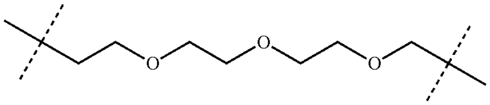, 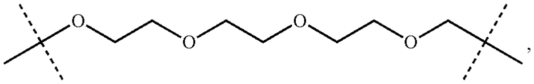,
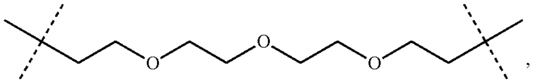, 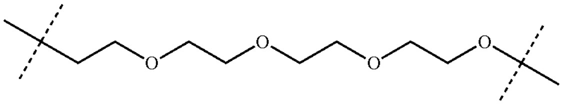,
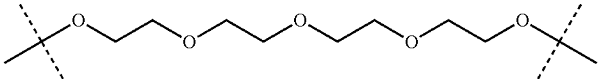,
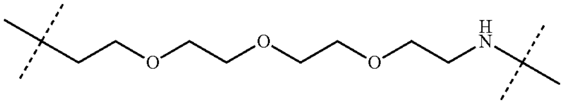,
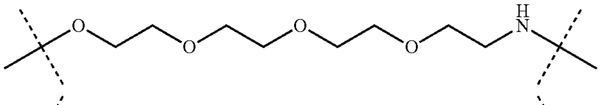,
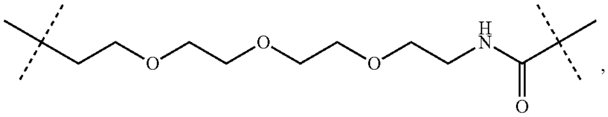,
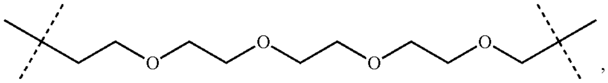,
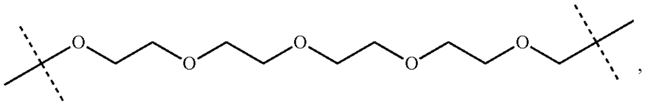,
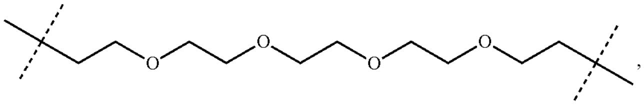,
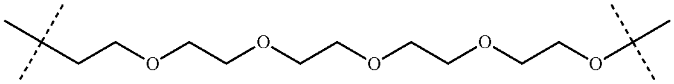,
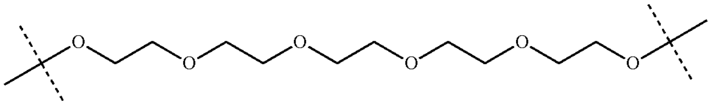,
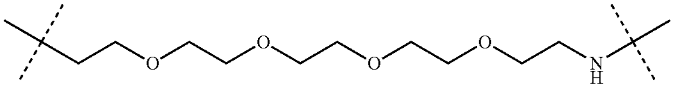,
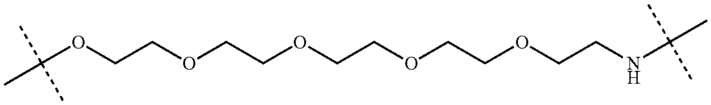,
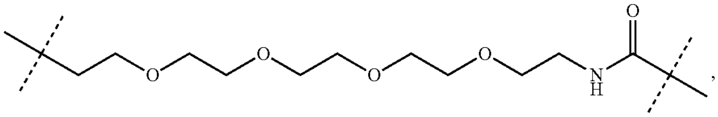,
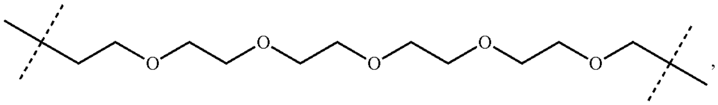,
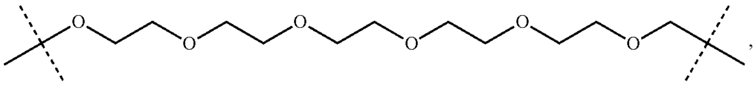,
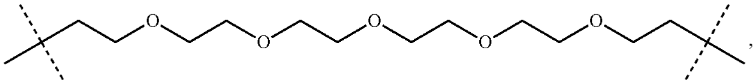, -continued
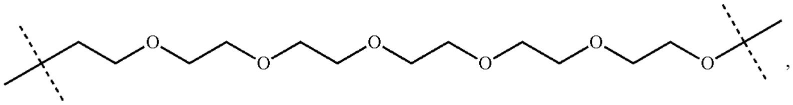,
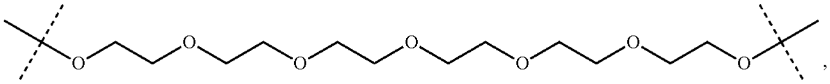,
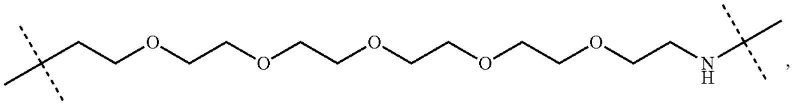,
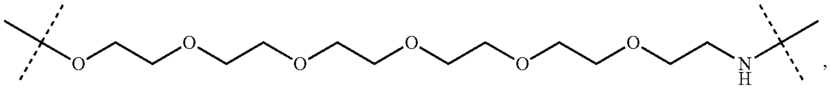,
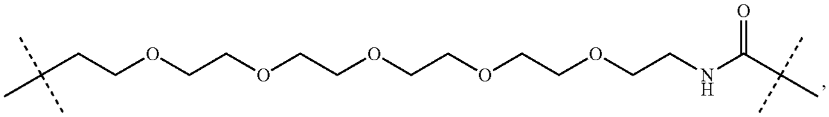,
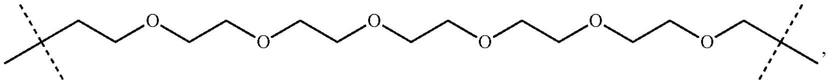,
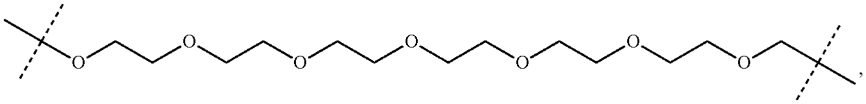,
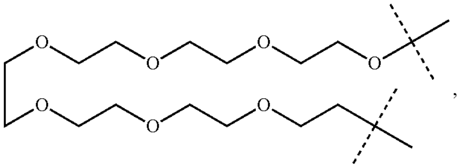, 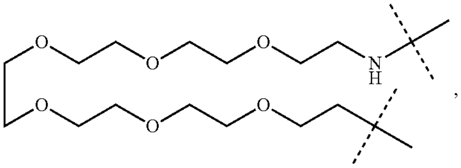,
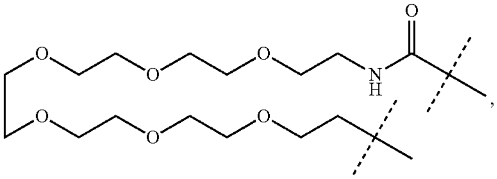, 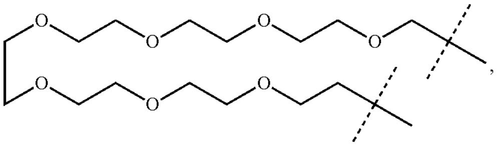,
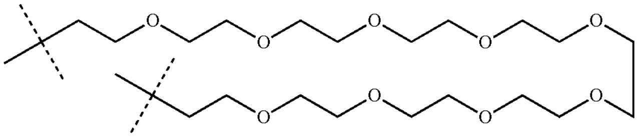,
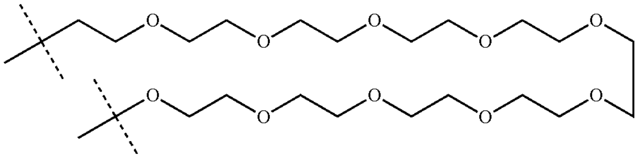,
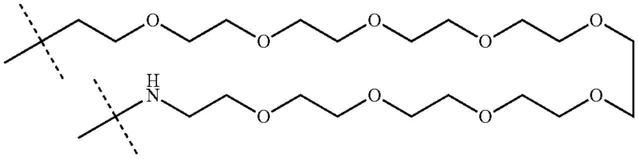,
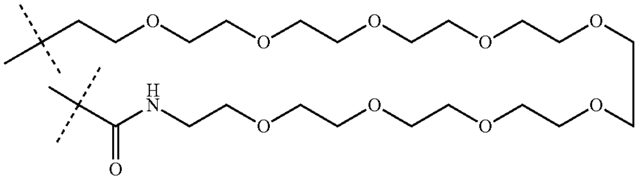, -continued

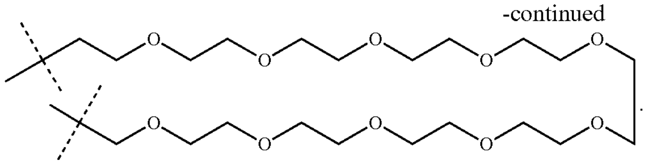

In any aspect or embodiment described herein, the unit $A^L$ of linker (L) comprises a group represented by a general structure selected from the group consisting of:

—N(R)—$(CH2)_m$—$O(CH2)_n$—$O(CH2)_o$—$O(CH2)_p$—O $(CH2)_q$—$O(CH2)_r$OCH2-, —O—$(CH2)_m$—$O(CH2)_n$—$O(CH2)_o$—$O(CH2)_p$—$O(CH2)_q$—$O(CH2)_r$OCH2-, —O—$(CH2)_m$—$O(CH2)_n$—$O(CH2)_o$—$O(CH2)_p$—O (CH2)-$O(CH2)_r$O—; —N(R)—$(CH2)_m$—$O(CH2)_n$—$O(CH2)_o$—$O(CH2)_p$—O(CH2)-$O(CH2)_r$O—; —$(CH2)_m$—$O(CH2)_n$—$O(CH2)_o$—$O(CH2)_p$—O $(CH2)_q$—$O(CH2)_r$O—; —$(CH2)_m$—$O(CH2)_n$—O $(CH2)_o$—$O(CH2)_p$—O(CH2)-$O(CH2)_r$OCH2-;

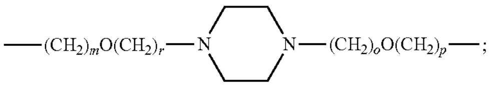

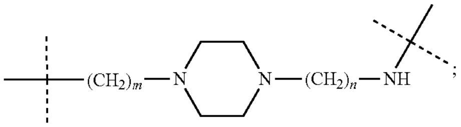

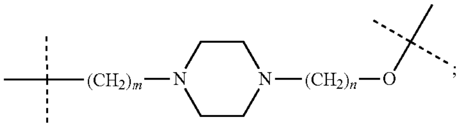

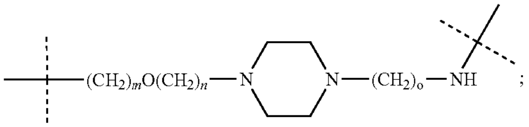

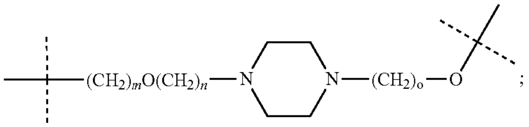

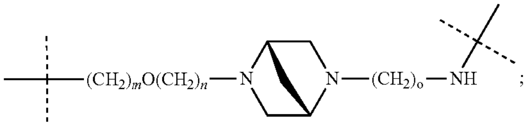

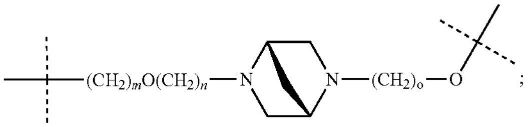

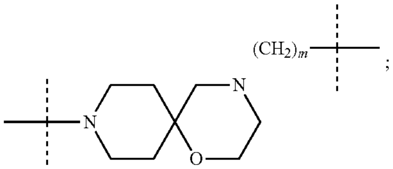

-continued

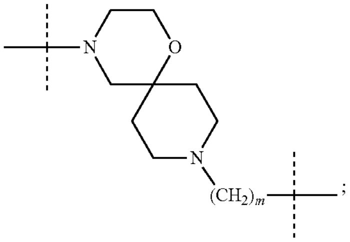

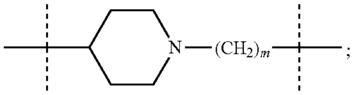

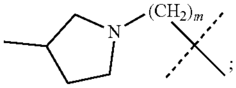

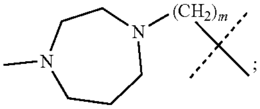

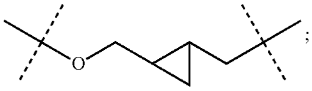

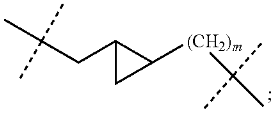

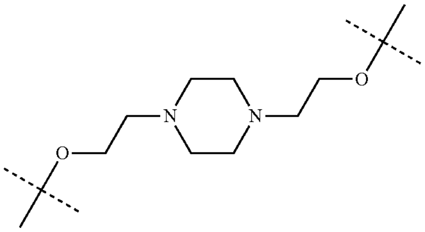

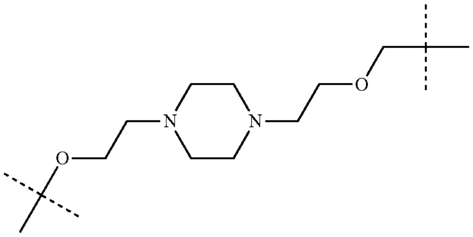

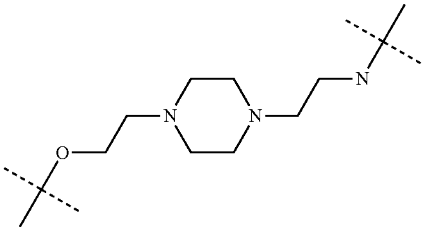

-continued
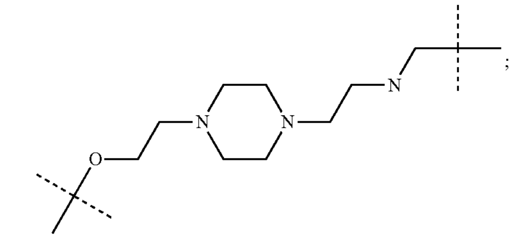
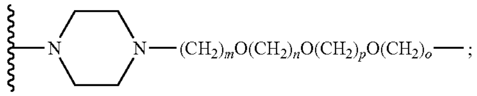
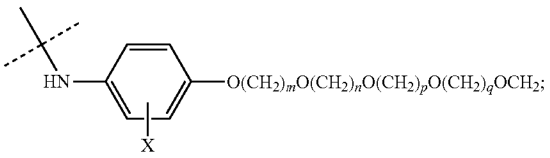
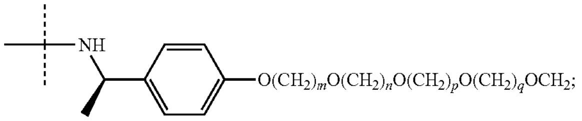
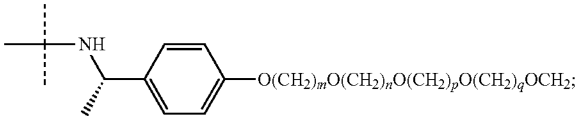
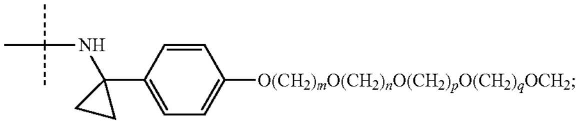
-continued
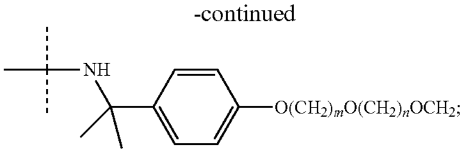
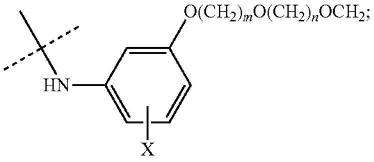
and
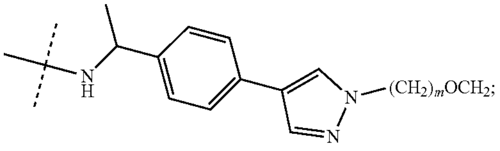
wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F
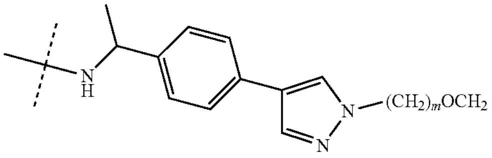
where m of the linker can be 2, 3, 4, 5
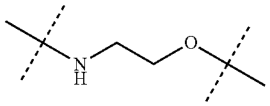
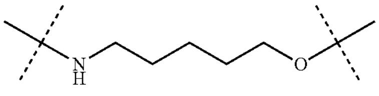
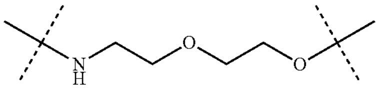
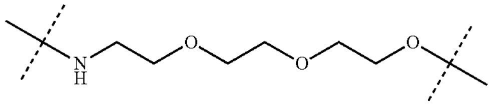
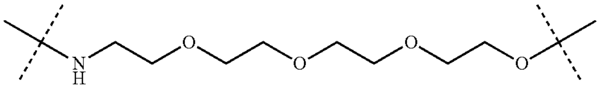
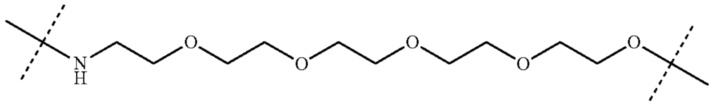
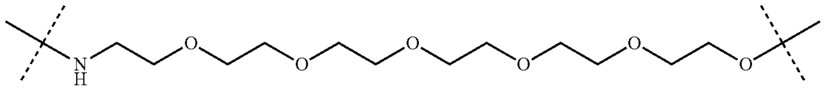
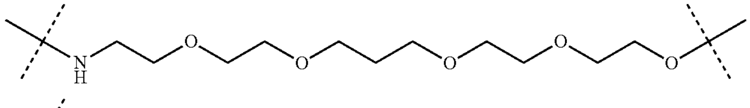
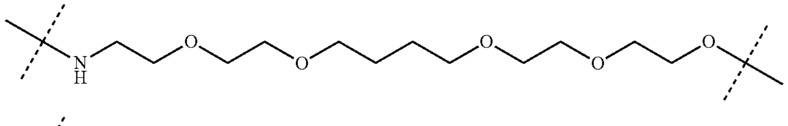
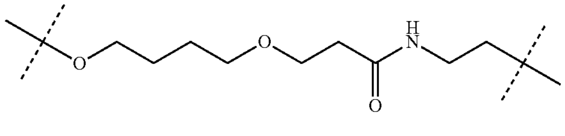

-continued
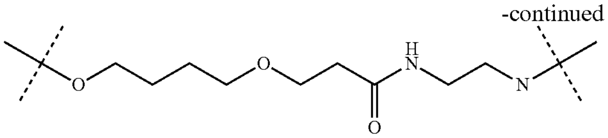
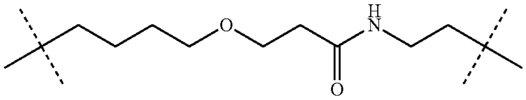
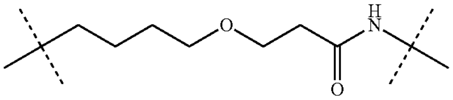
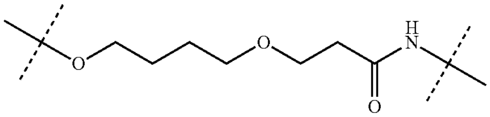
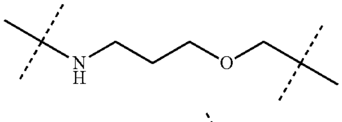
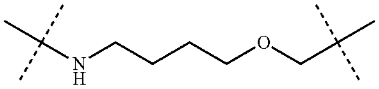
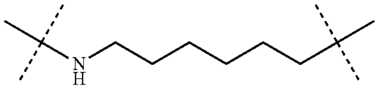
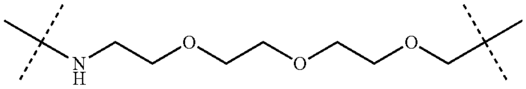
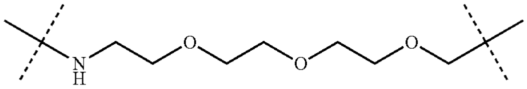
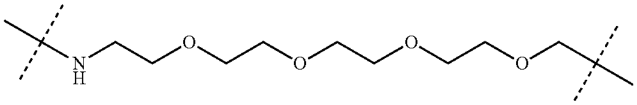
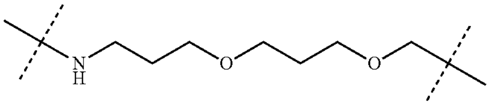
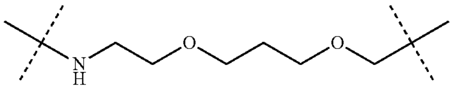
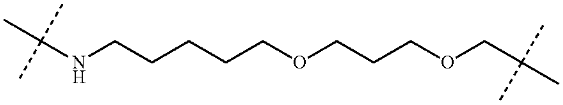
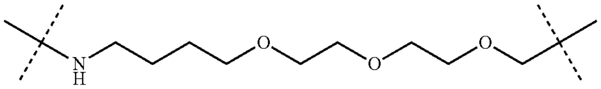
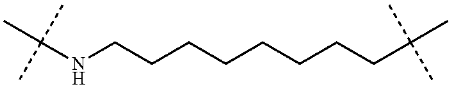
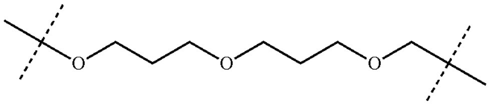
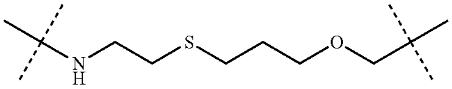
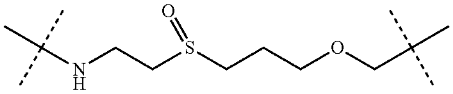
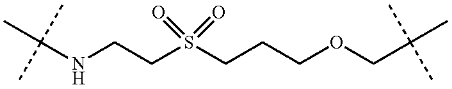
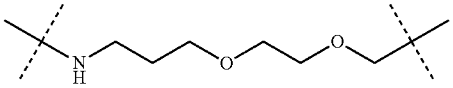
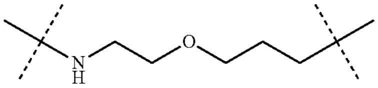
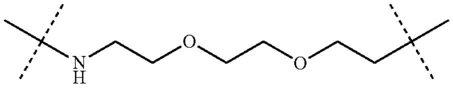
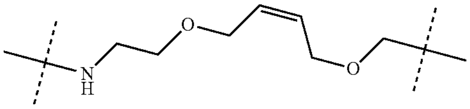
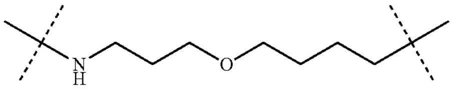
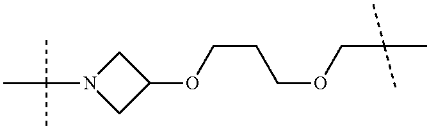
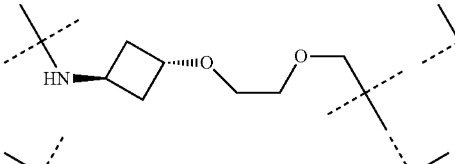
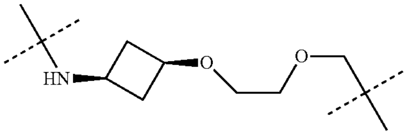
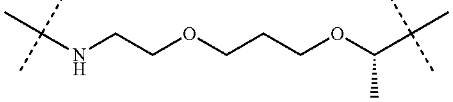
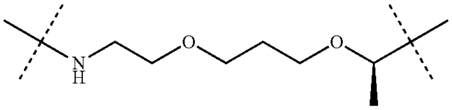
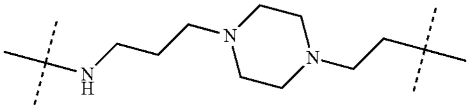
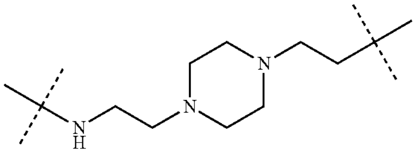

-continued
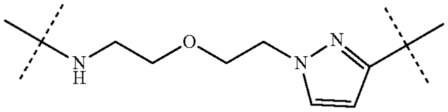
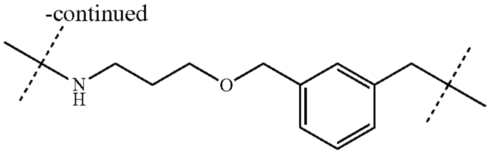
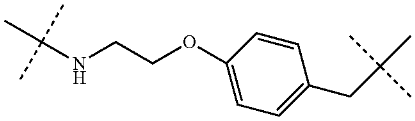
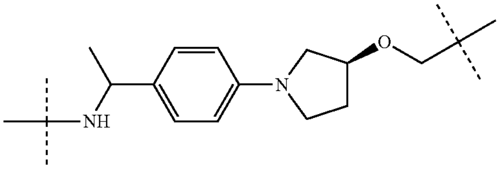
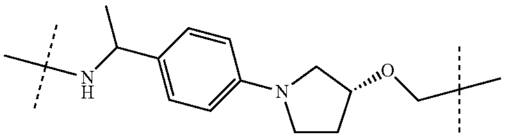
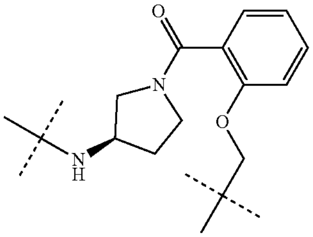
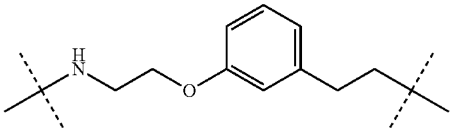
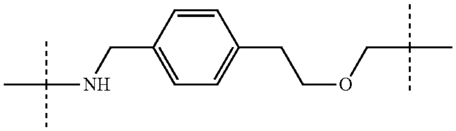
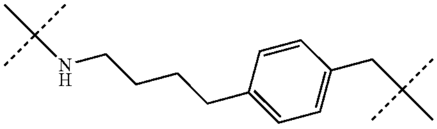
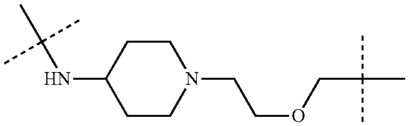
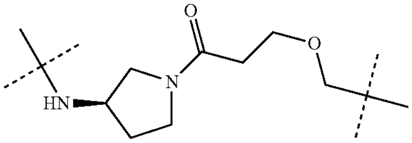
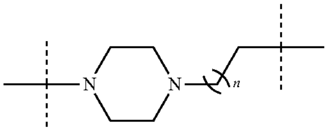
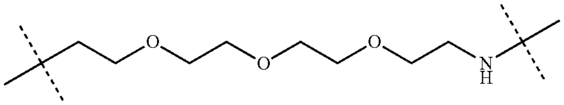
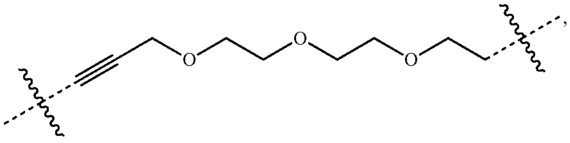,
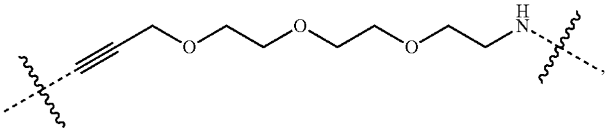,
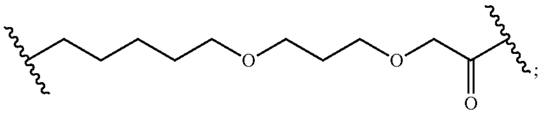;
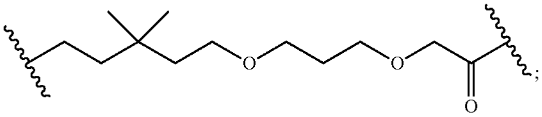;
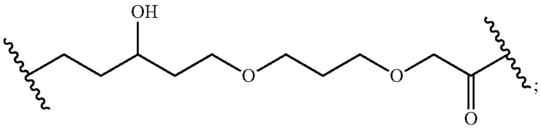;
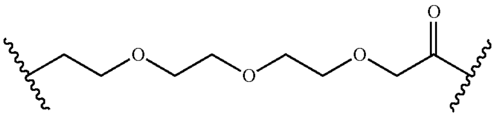;
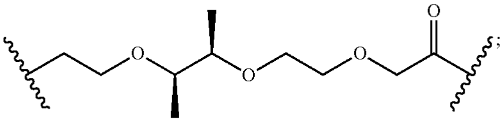;
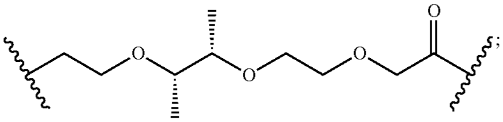;
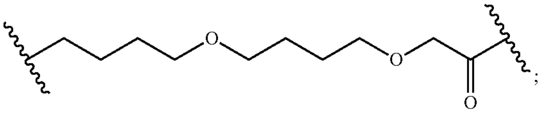;
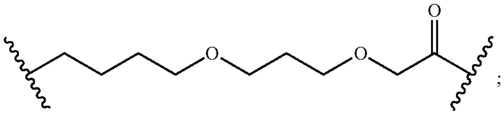;

-continued
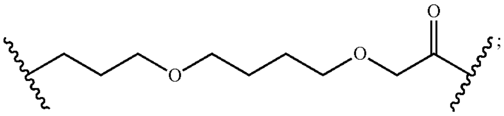;
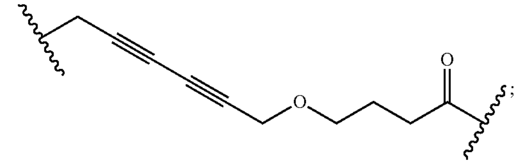;
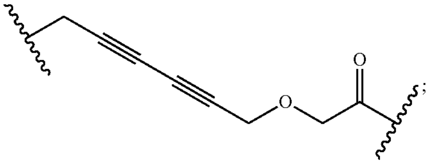;
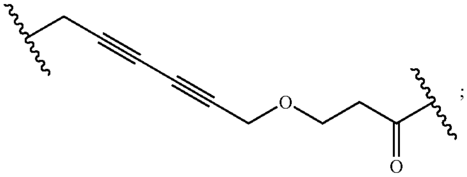;
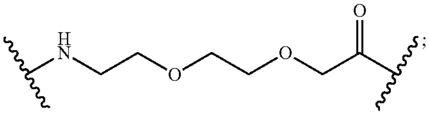;
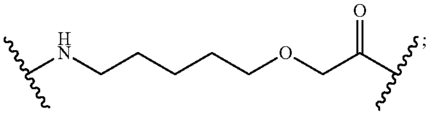;
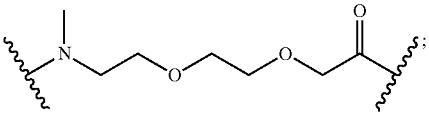;
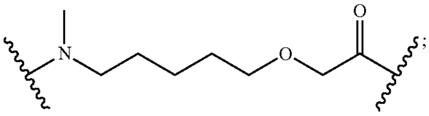;
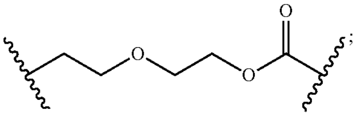;
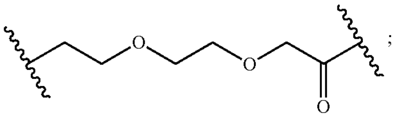;
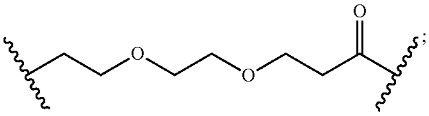;
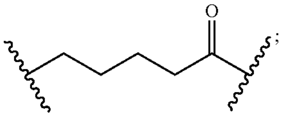;
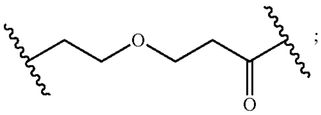;
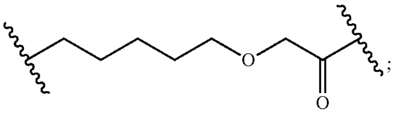;
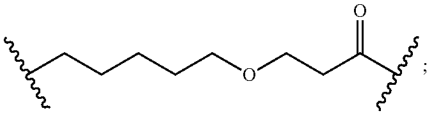;
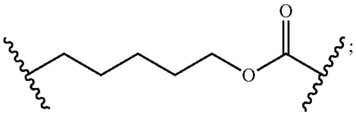;
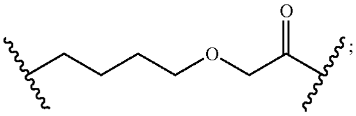;
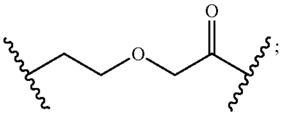;
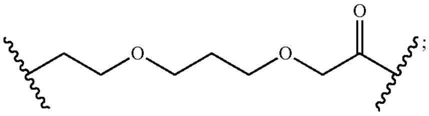;
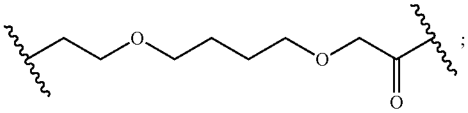;
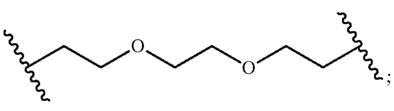;
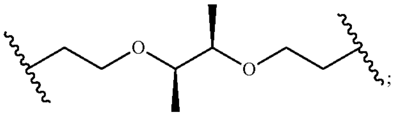;
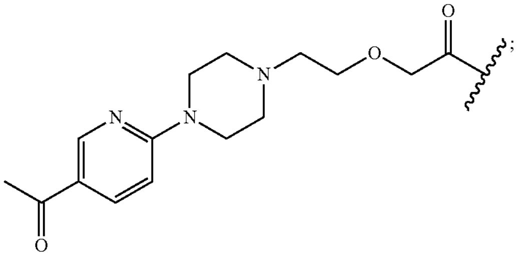;
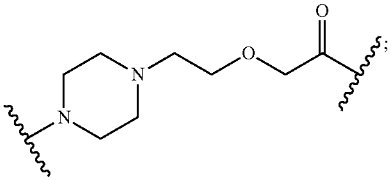;
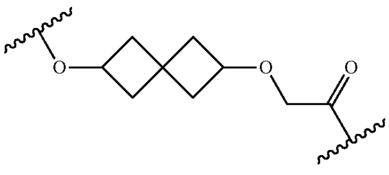;
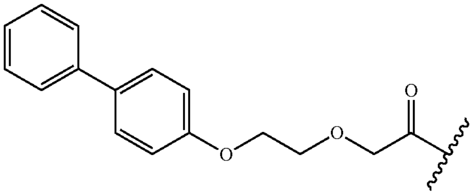;

-continued
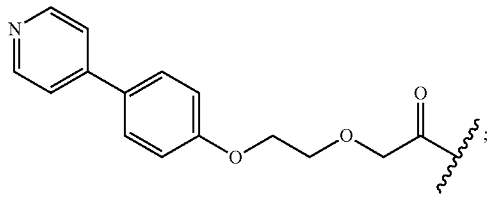
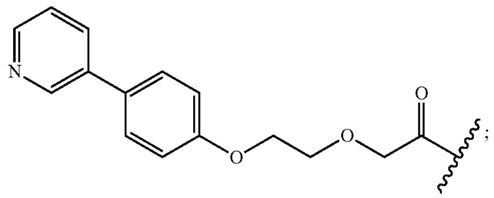
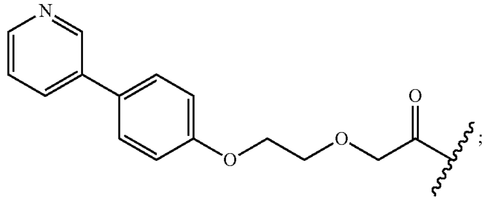
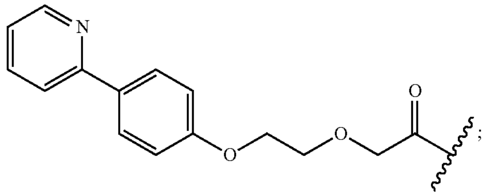
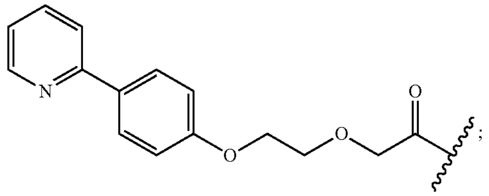
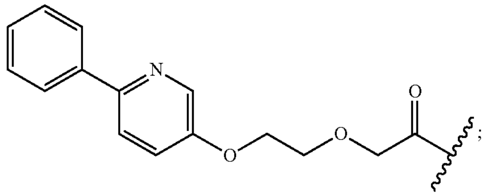
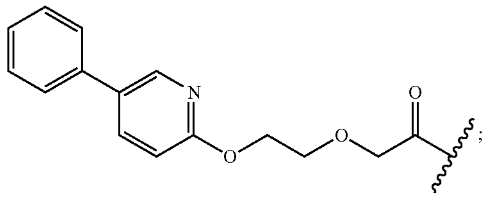
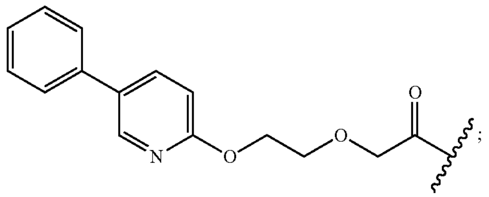
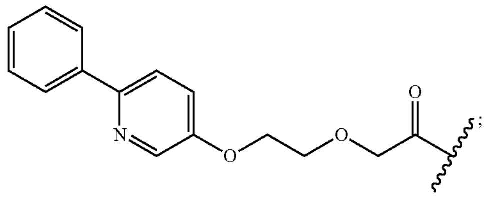
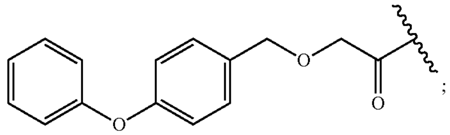
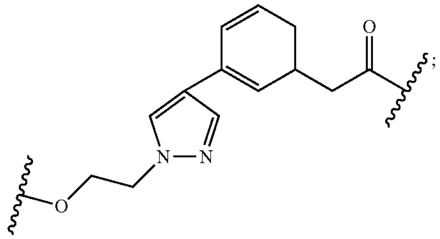
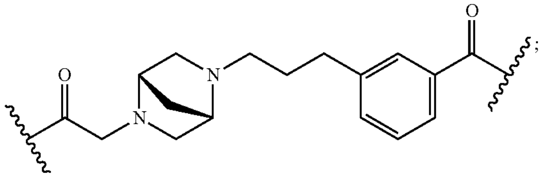
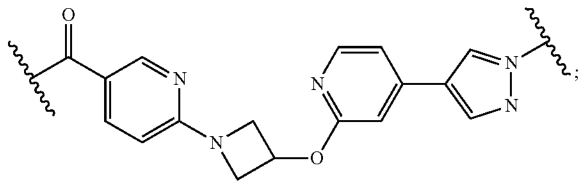
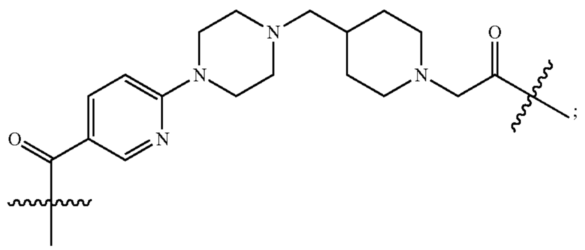

-continued
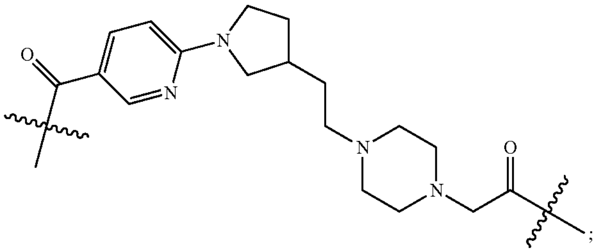
;
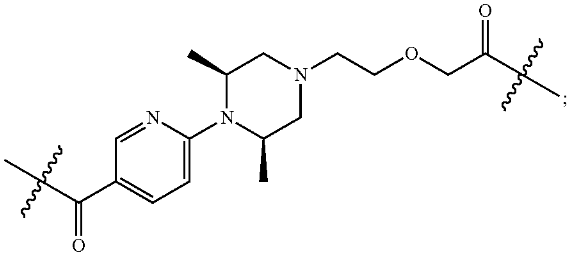
;
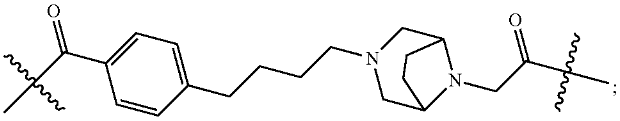
;
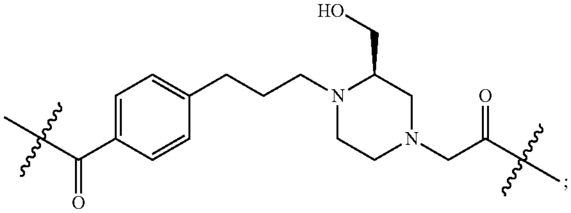
;
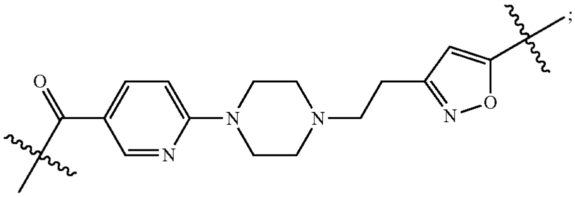
;
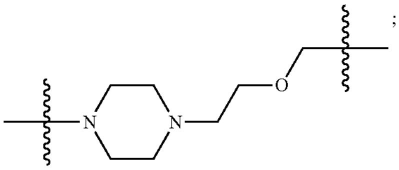
;
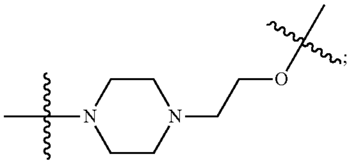
;
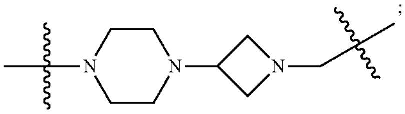
;
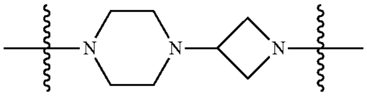
;
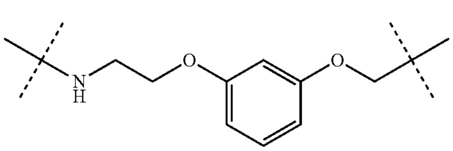
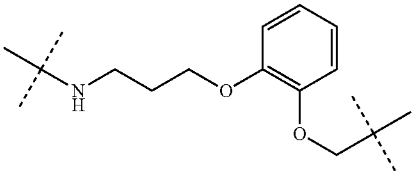
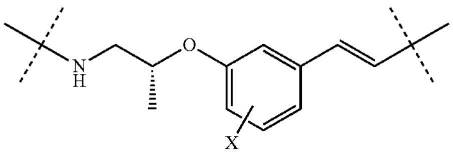
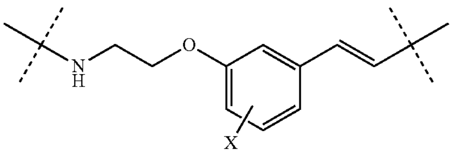
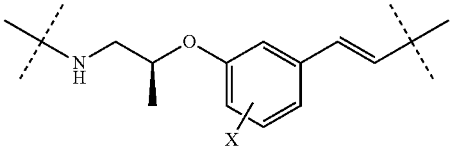
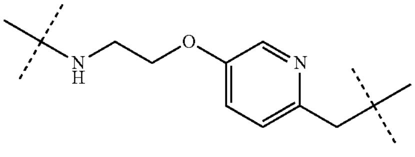

-continued
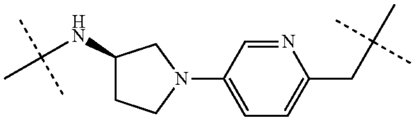
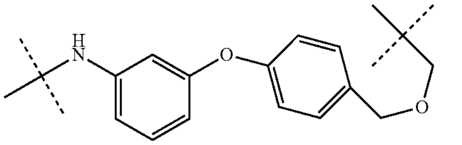
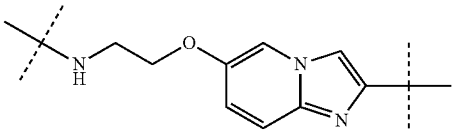
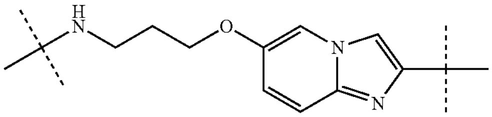
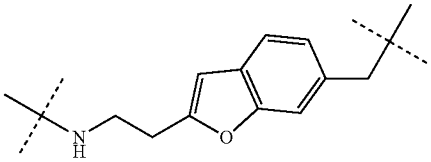
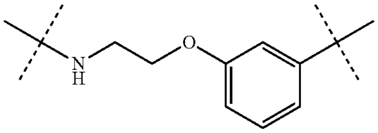
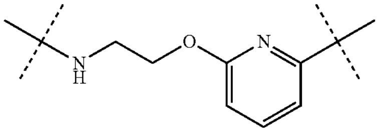
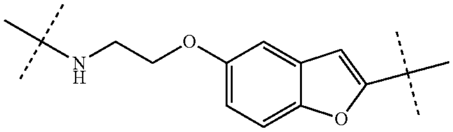
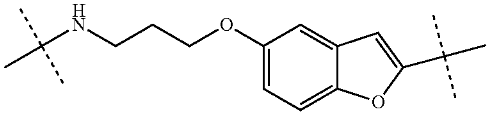
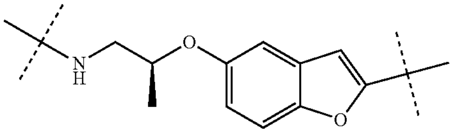
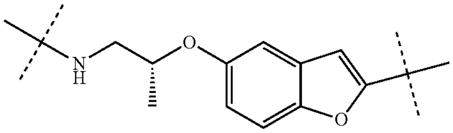
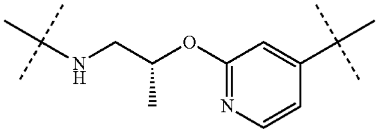
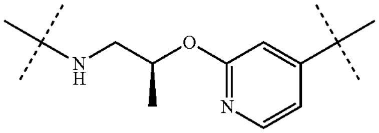
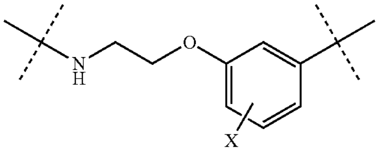
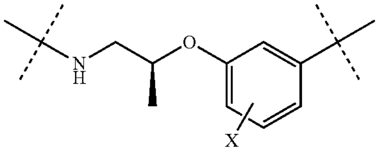
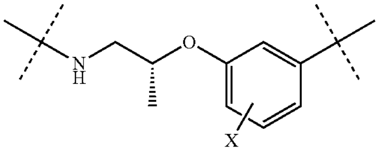
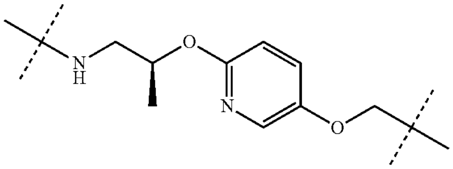
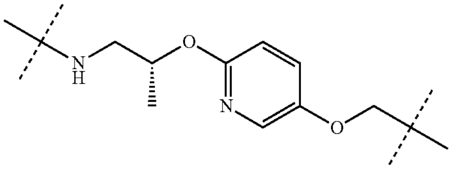
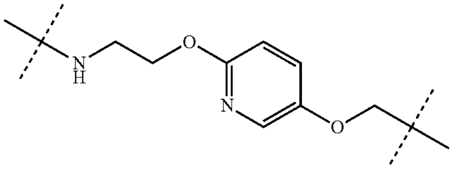
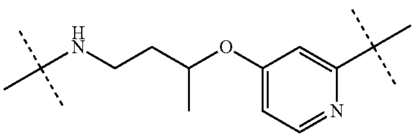
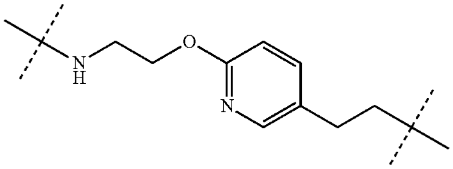
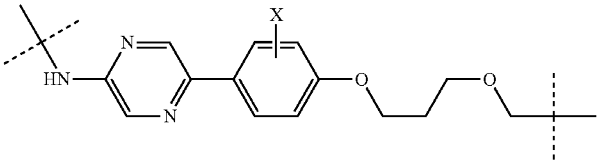

-continued
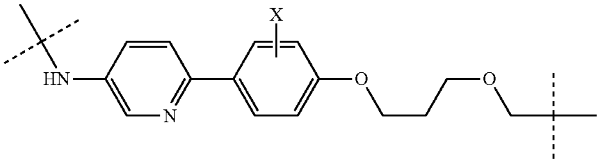
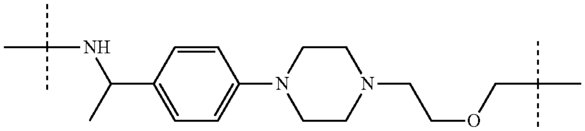
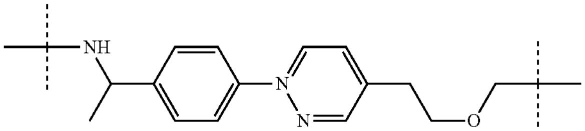
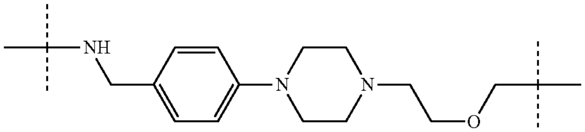
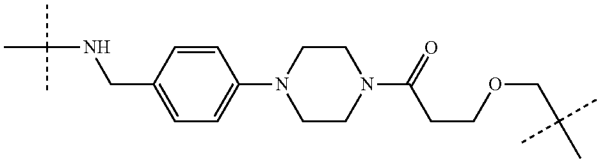
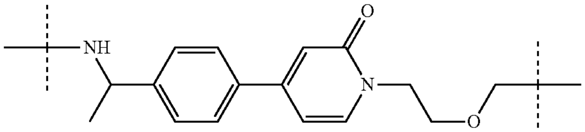
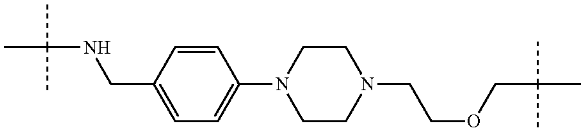
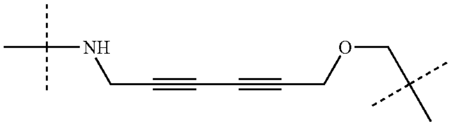
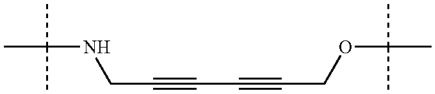
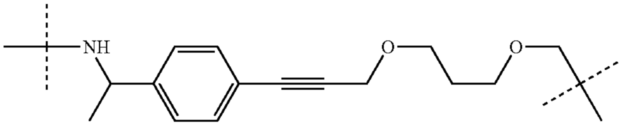
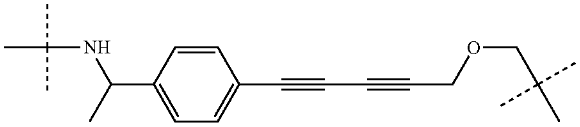
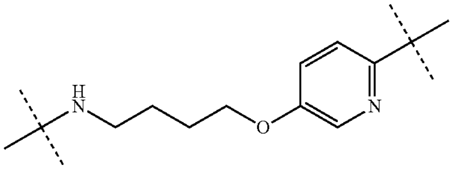
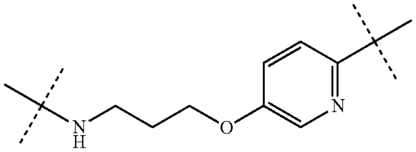
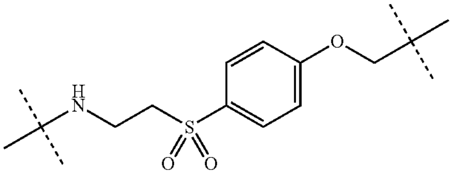
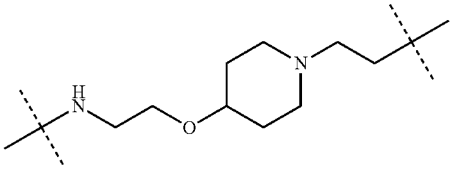
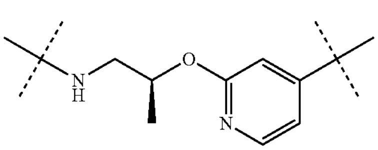

-continued
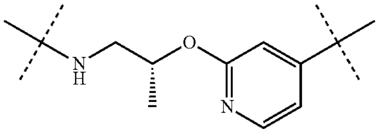
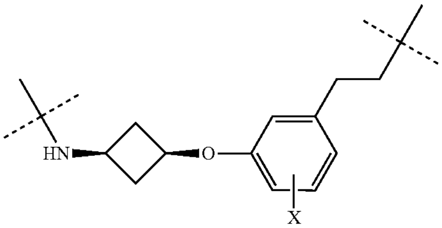
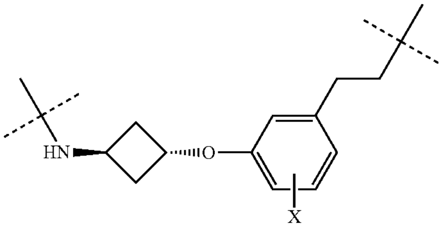
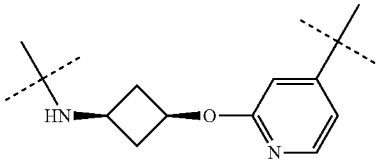
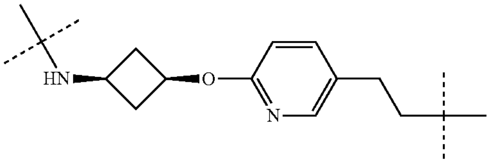
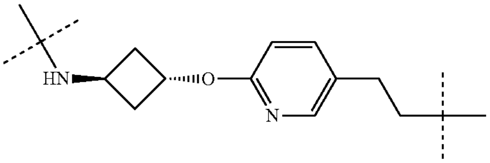
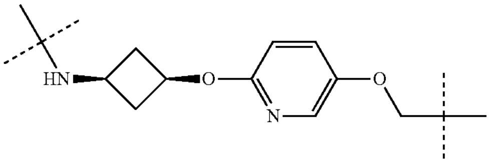
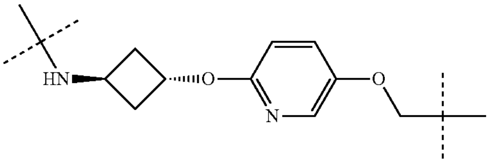
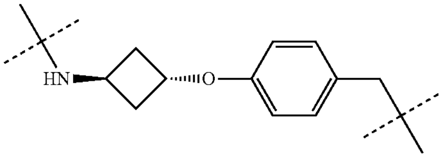
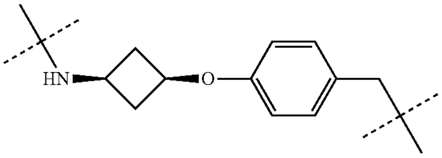
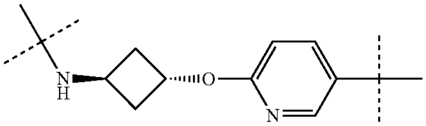
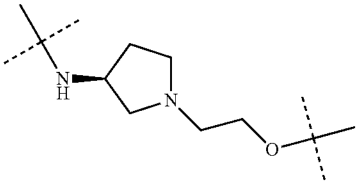
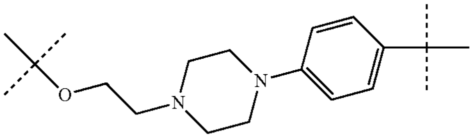
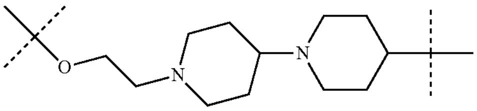
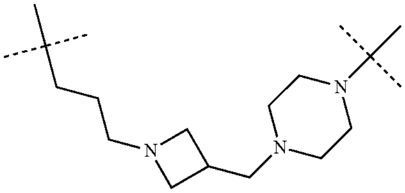
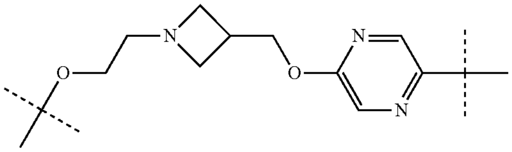
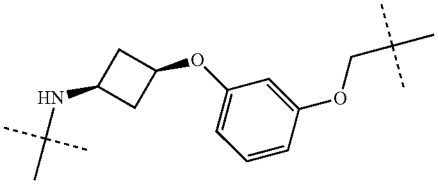
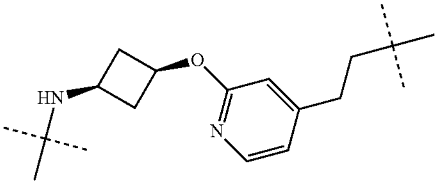

-continued
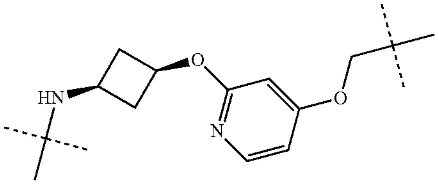
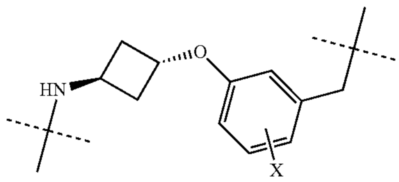
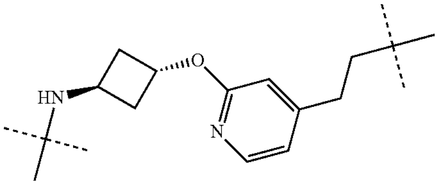
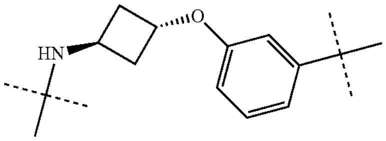
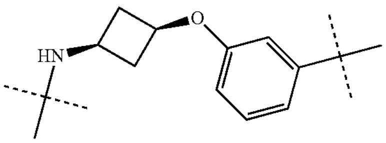
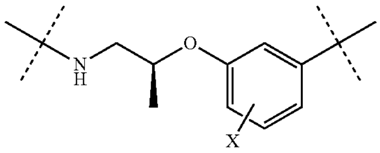
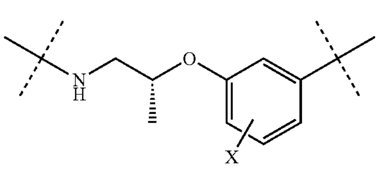
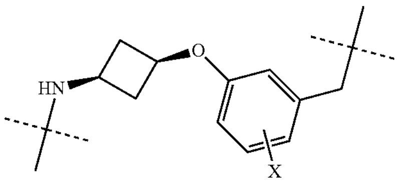
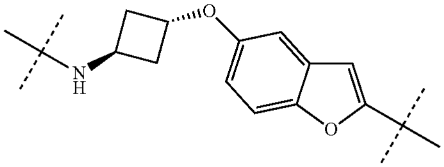
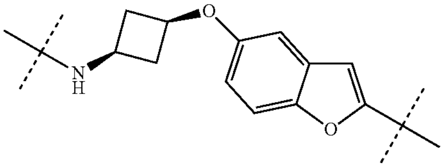
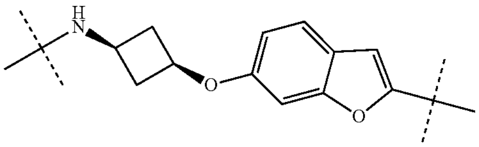
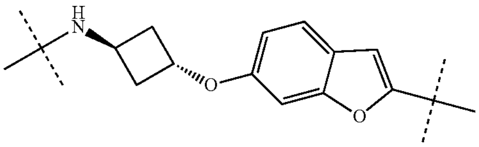
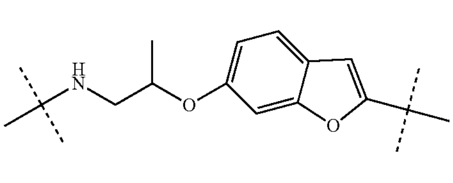
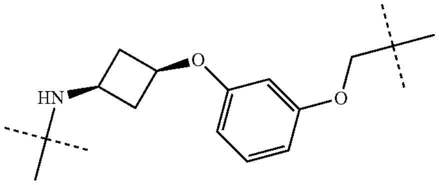
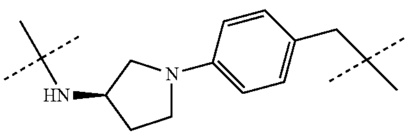
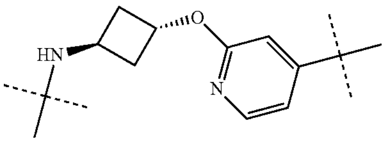
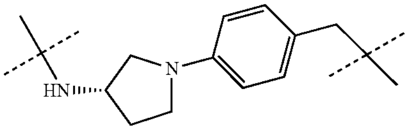
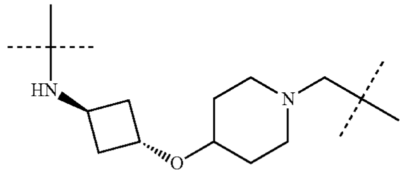
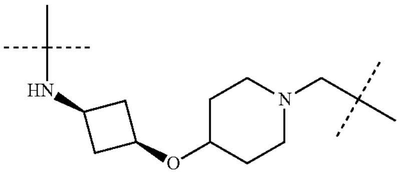
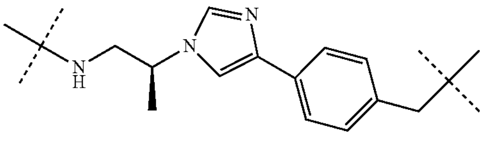

-continued
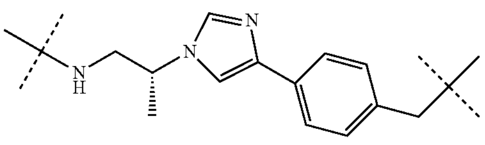
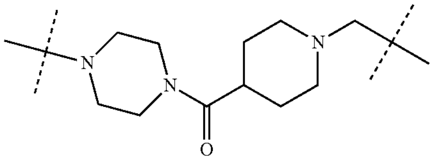
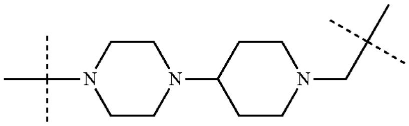
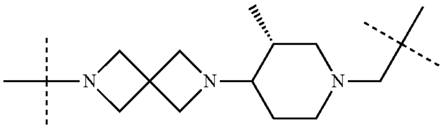
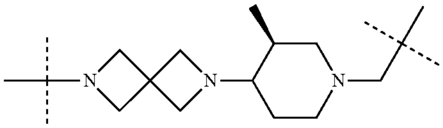
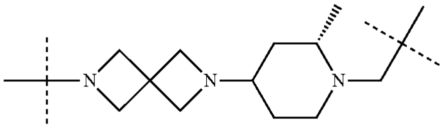
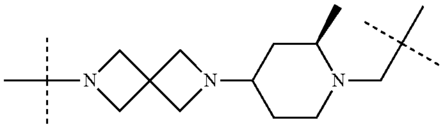
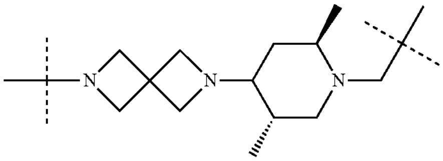
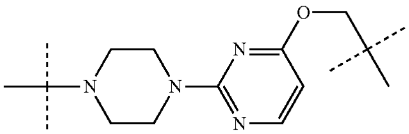
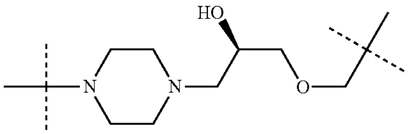
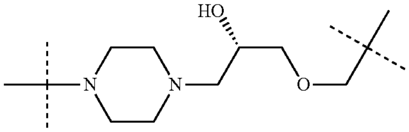
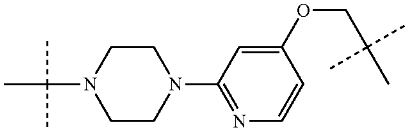
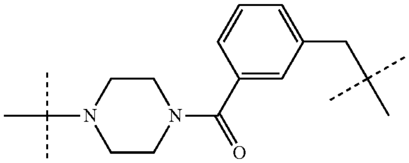
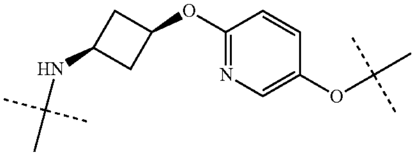
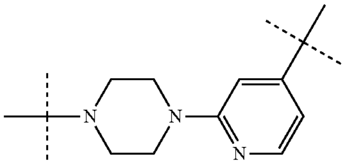
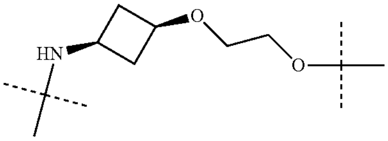
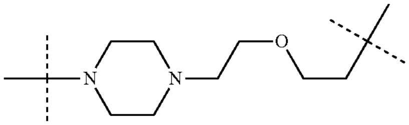
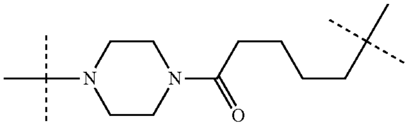
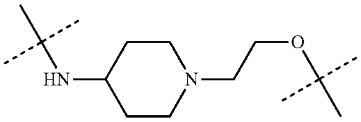
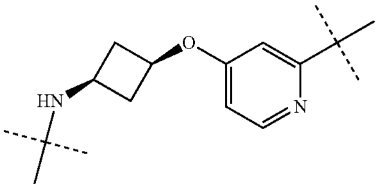
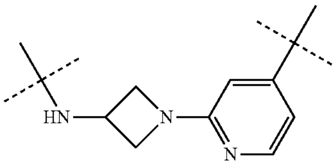
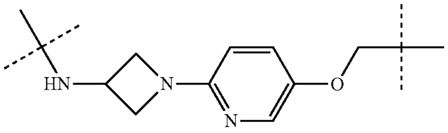

-continued
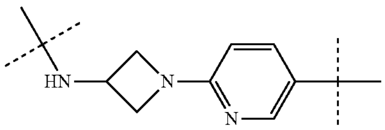
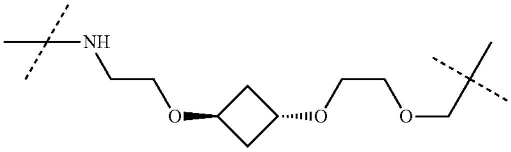
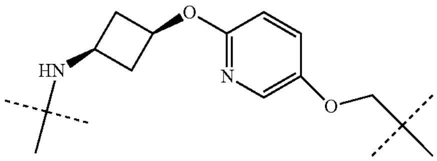
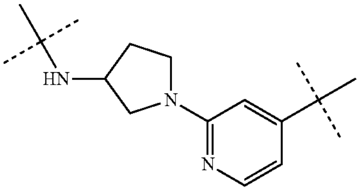
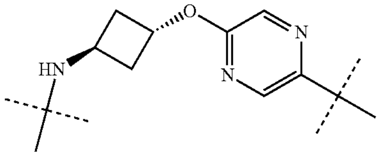
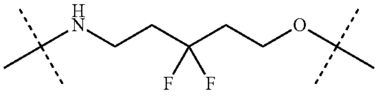
X = H, F
where each n and m of the linker can independently be 0, 1, 2, 3, 4, 5, 6, 7, 8, 9, 10, 11, 12, 13, 14, 15, 16, 17, 18, 19, or 20 (e.g., 0, 1, 2, 3, 4, 5, or 6).
In any aspect or embodiment described herein, the unit $A^L$ of linker (L) is selected from the group consisting of:
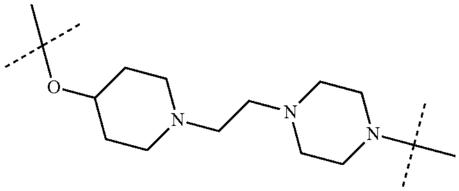
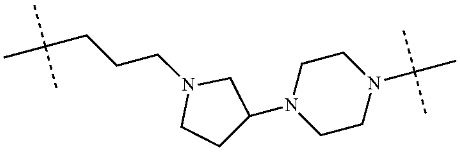
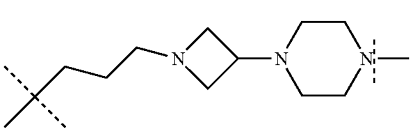
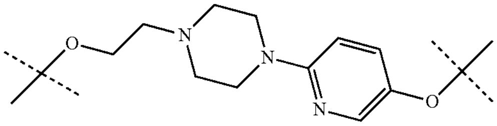
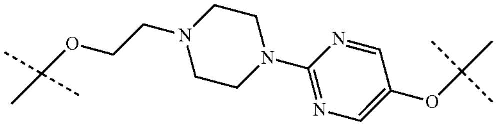
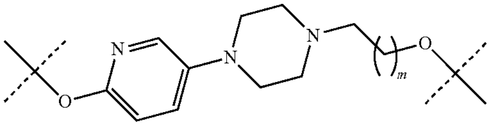
-continued
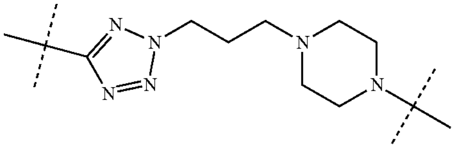
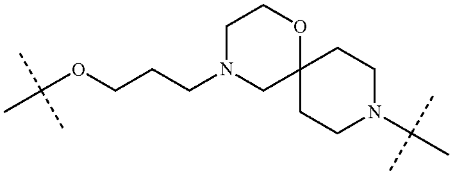
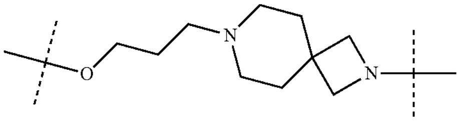
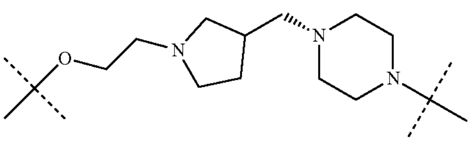
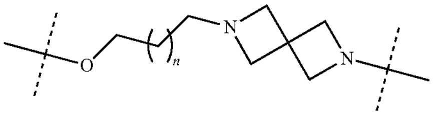
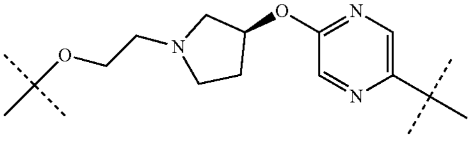
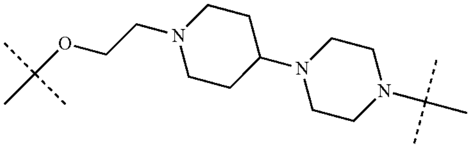

-continued
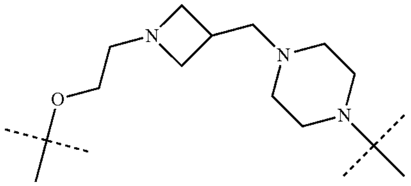
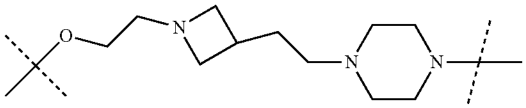
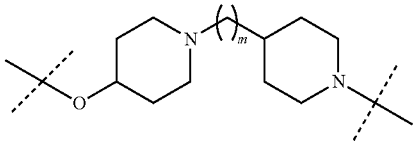
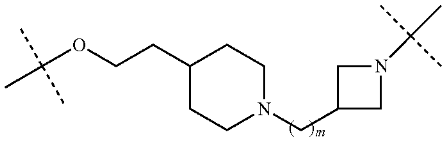
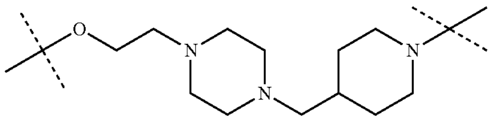
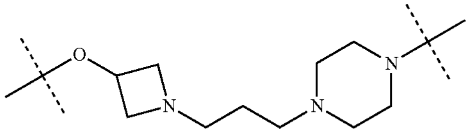
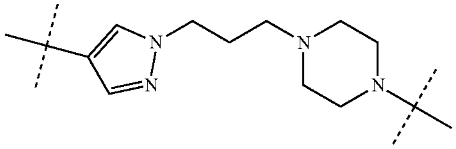
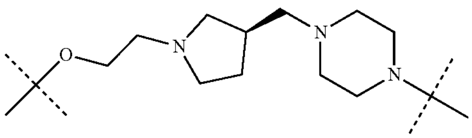
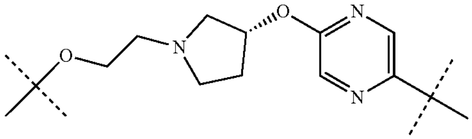
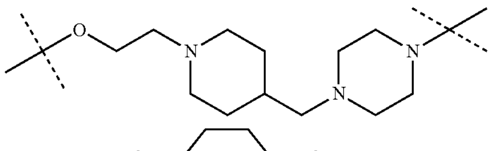
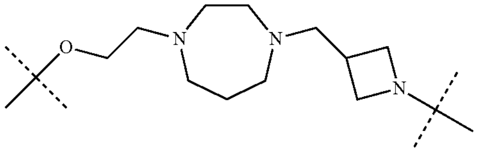
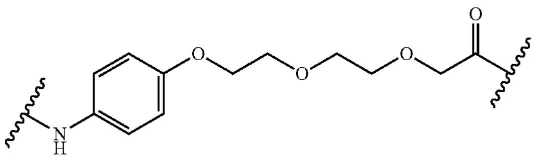
;
-continued
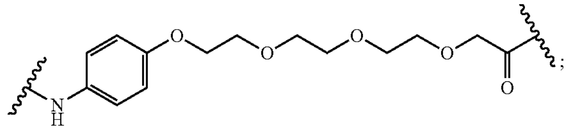
;
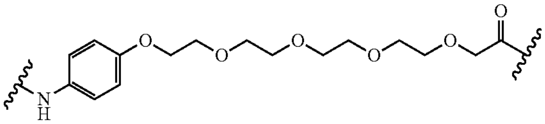
;
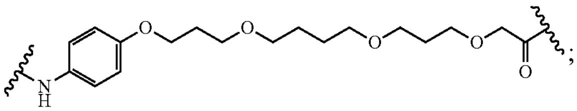
;
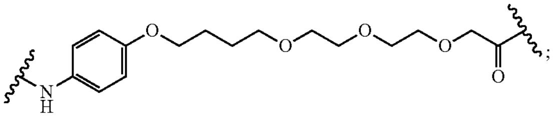
;
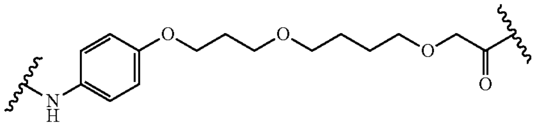
;
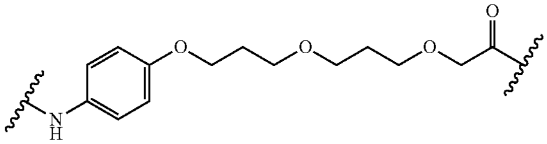
;
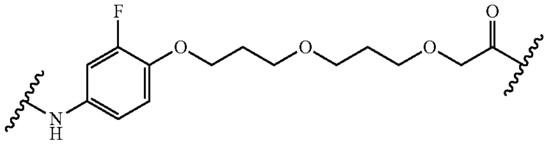
;
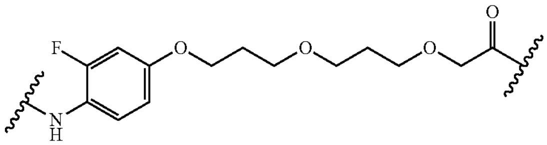
;
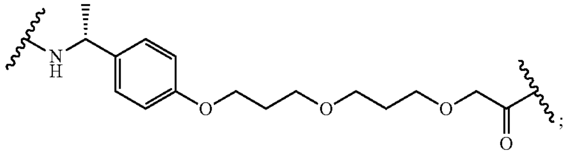
;
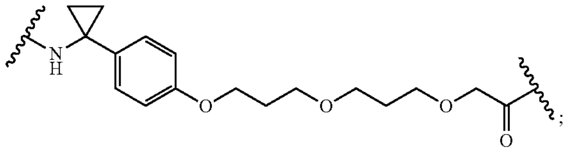
;
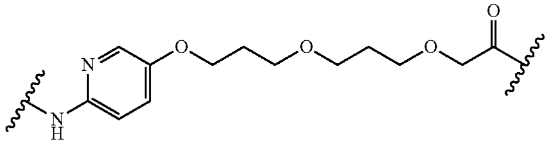
;
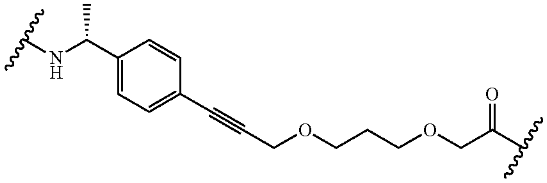
;

-continued
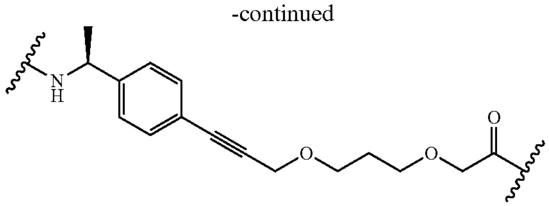
;
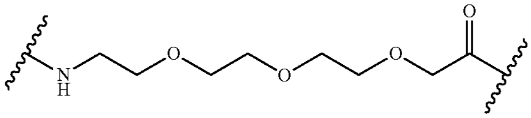
;
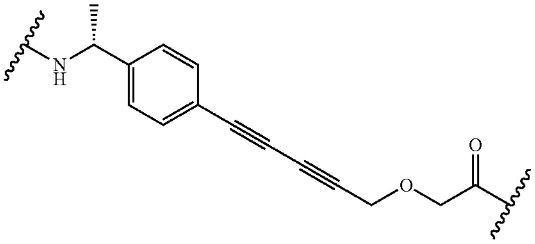
;
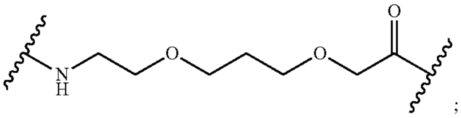
;
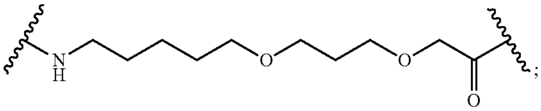
;
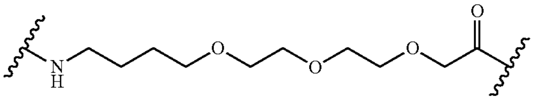
;
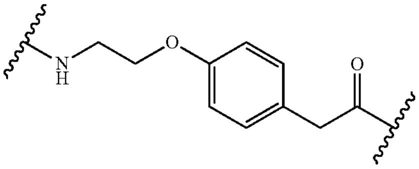
;
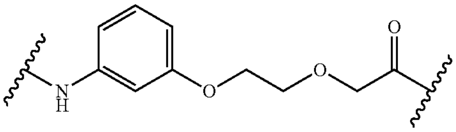
;
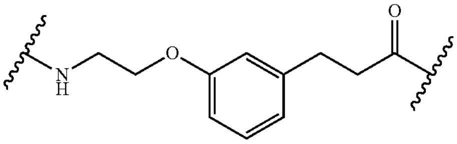
;
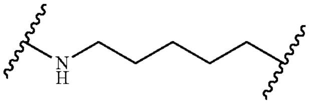
;
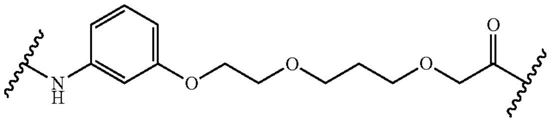
;
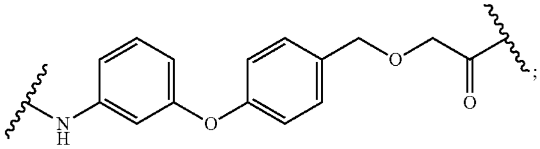
;
-continued
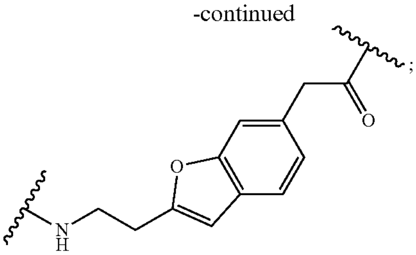
;
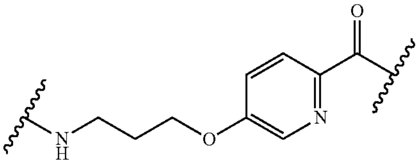
;
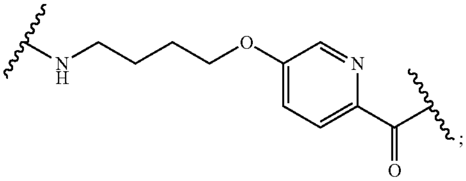
;
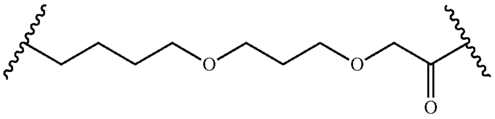
;
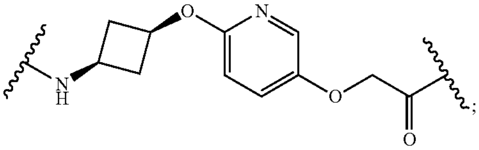
;
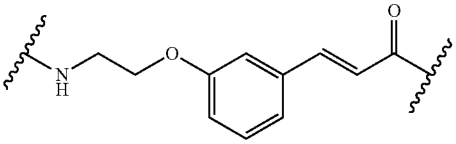
;
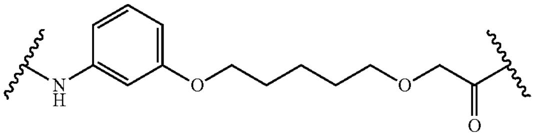
;
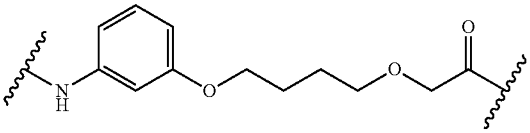
;
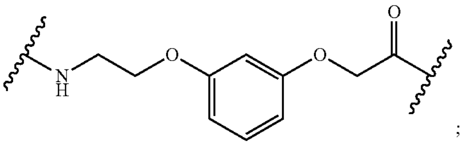
;
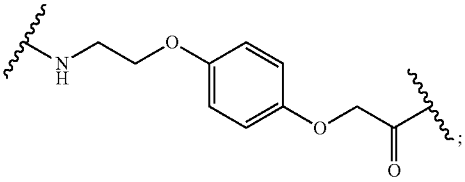
;
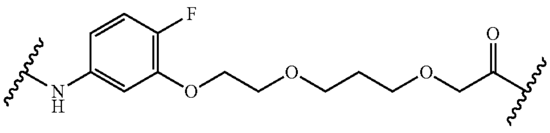
;

-continued
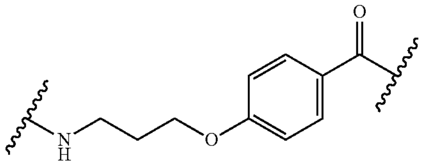
;
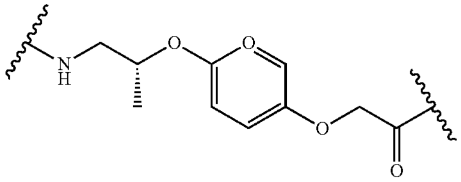
;
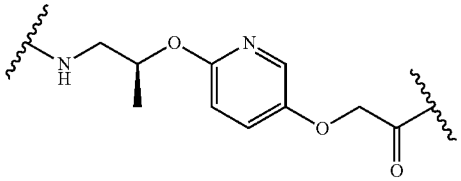
;
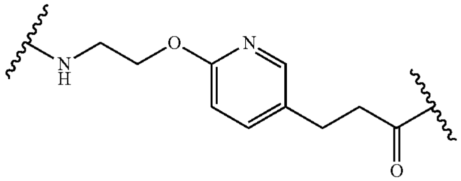
;
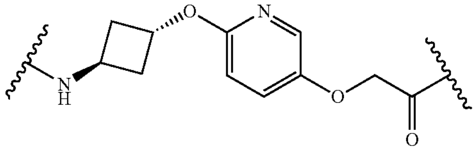
;
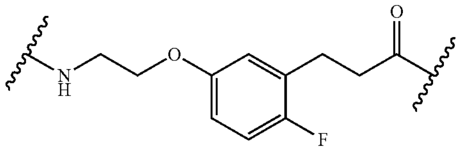
;
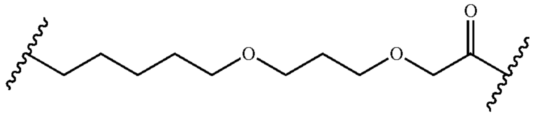
;
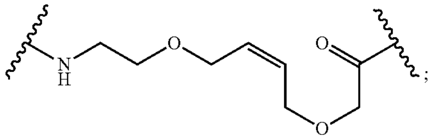
;
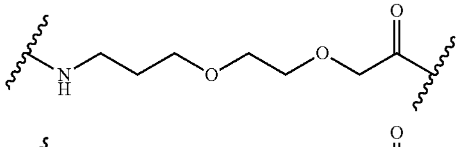
;
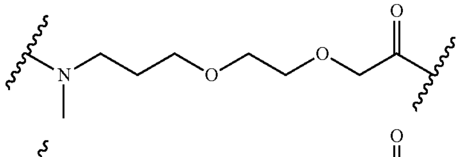
;
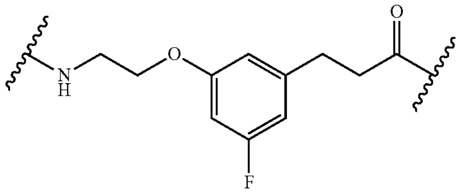
;
-continued
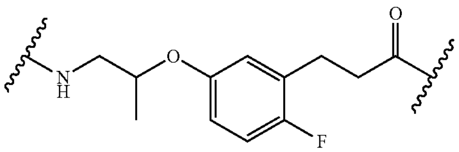
;
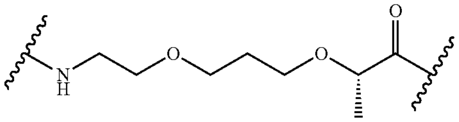
;
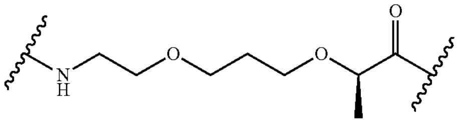
;
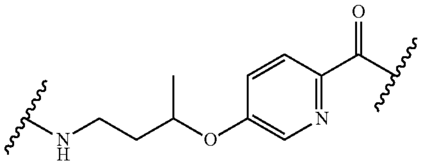
;
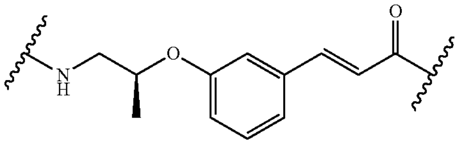
;
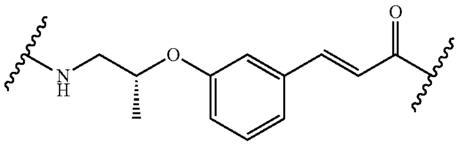
;
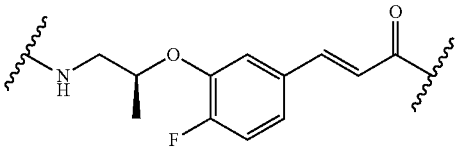
;
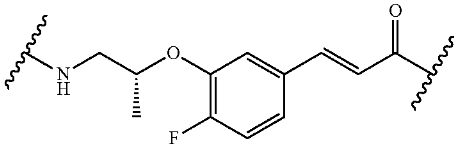
;
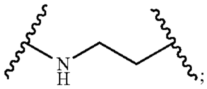
;
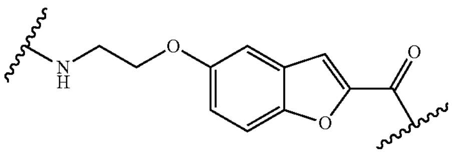
;
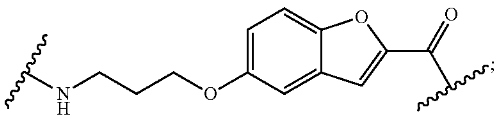
;
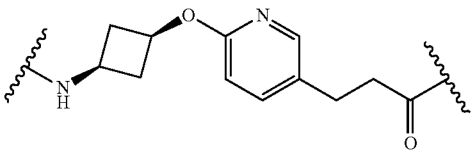
;

-continued
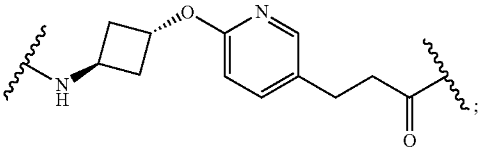
;
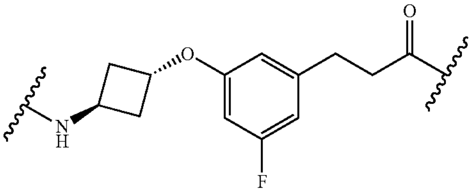
;
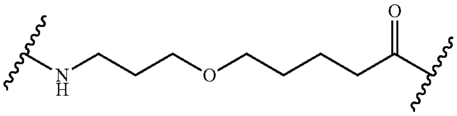
;
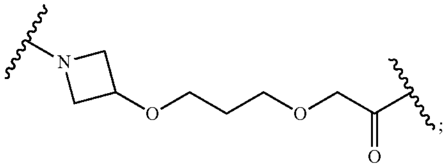
;
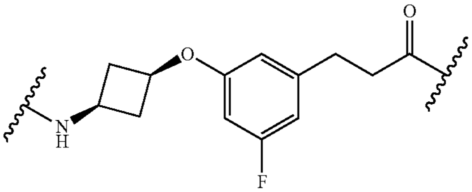
;
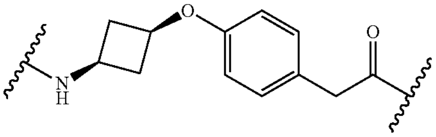
;
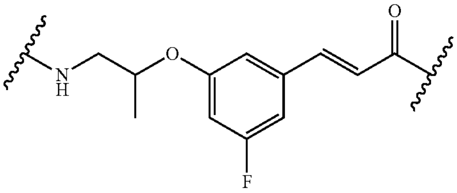
;
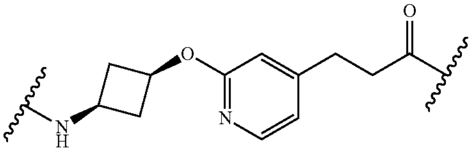
;
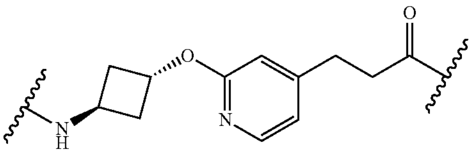
;
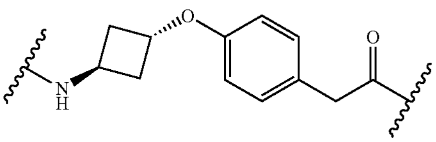
;
-continued
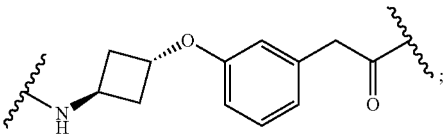
;
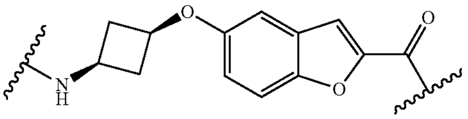
;
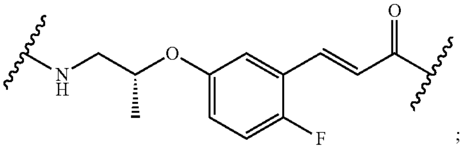
;
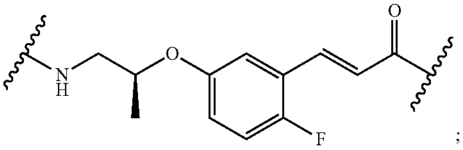
;
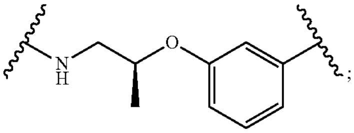
;
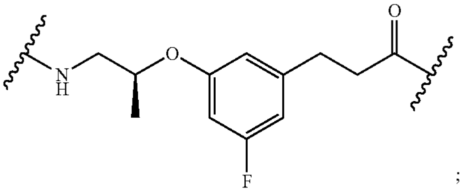
;
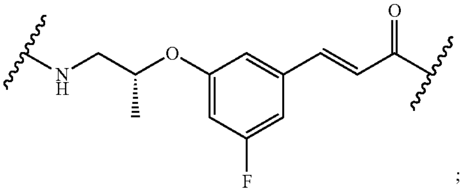
;
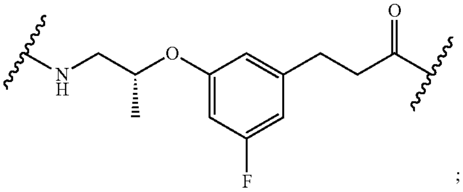
;
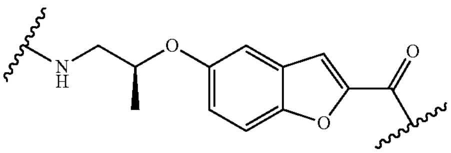
;
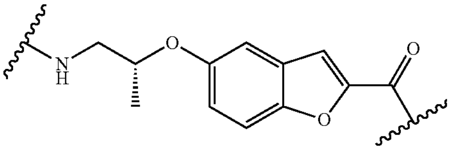
;
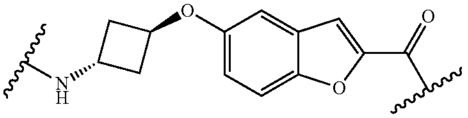
;

-continued
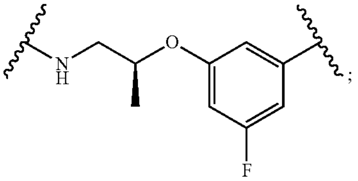
;
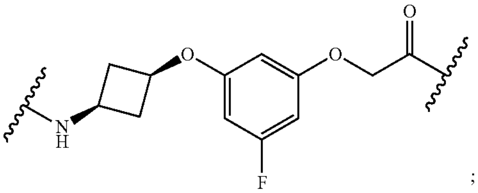
;
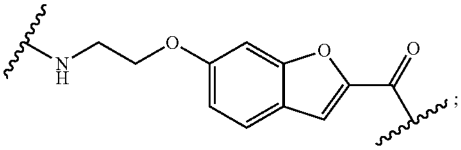
;
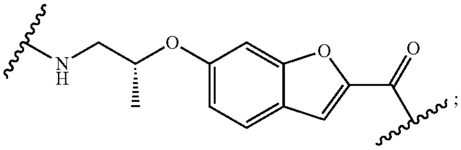
;
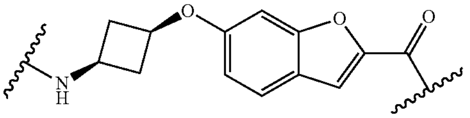
;
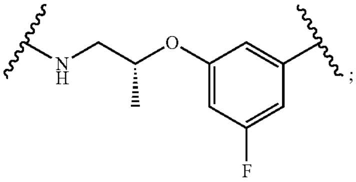
;
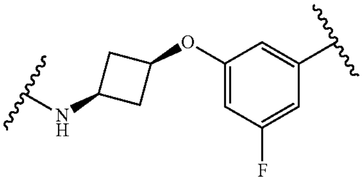
;
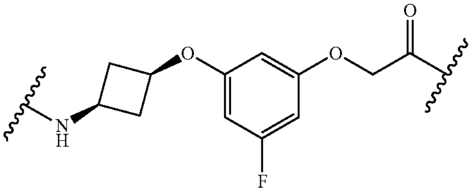
;
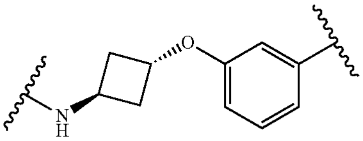
;
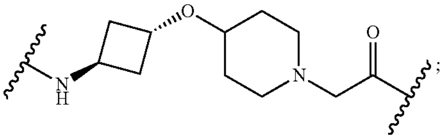
;
-continued
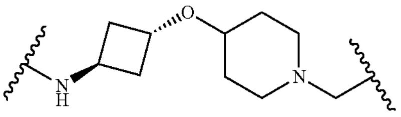
and
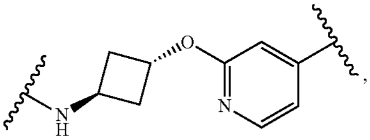
,
wherein each m and n is independently selected from 0-20 (e.g., 0-6, 0, 1, 2, 3, 4, 5, 6, 7, 8, 9, 10, 11, 12, 13, 14, 15, 16, 17, 18, 19, or 20).
In any aspect or embodiment described herein, the unit $A^L$ of linker (L) is selected from the group consisting of:
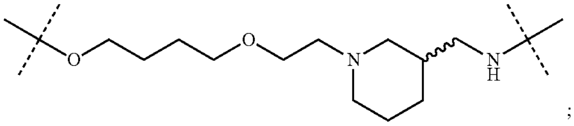
;
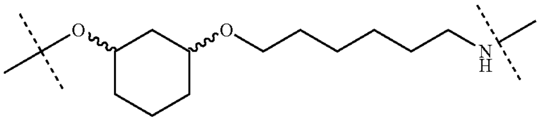
;
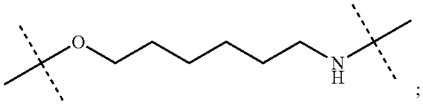
;
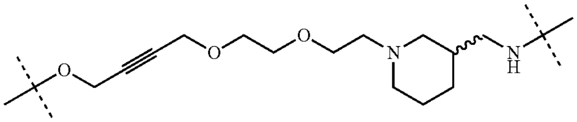
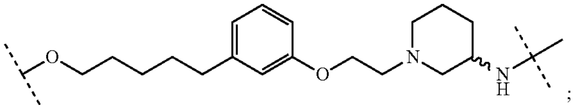
;
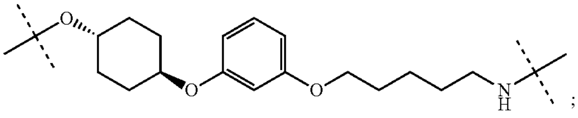
;
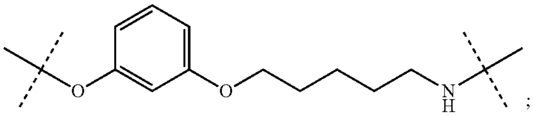
;
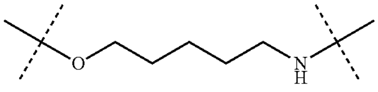
;
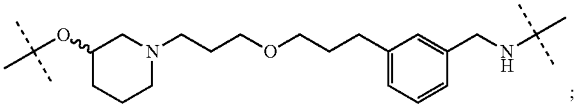
;
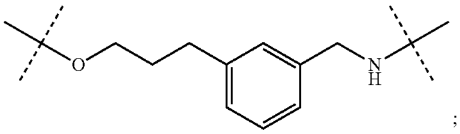
;

-continued
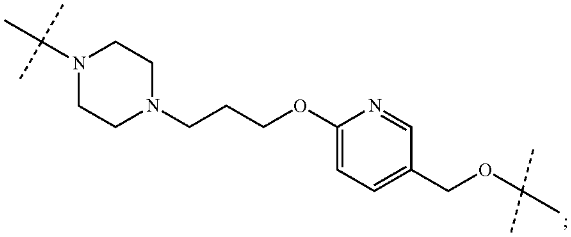
;
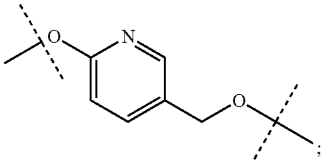
;
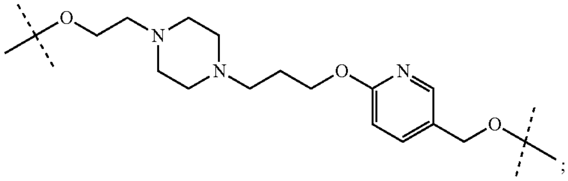
;
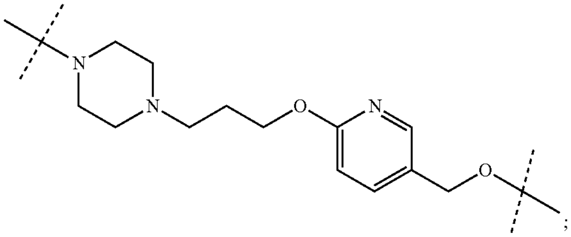
;
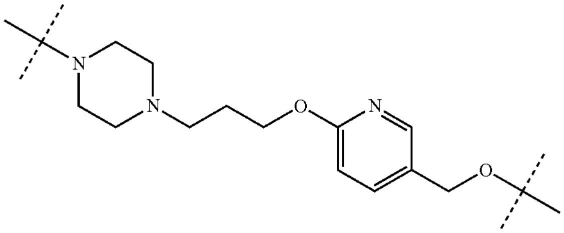
;
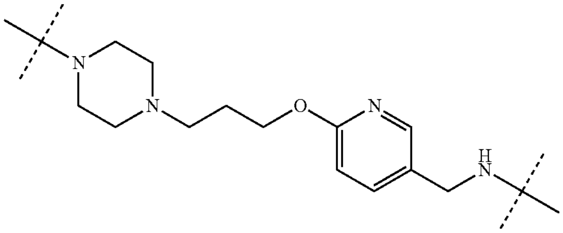
;
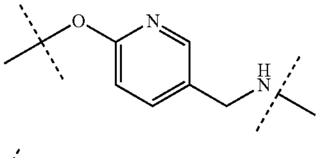
;
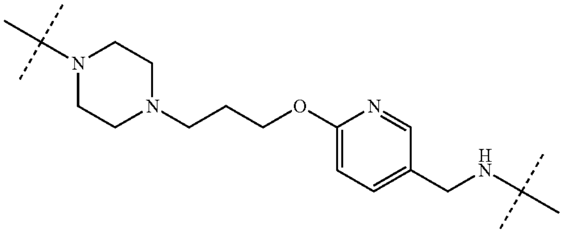
;
-continued
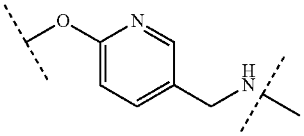
;
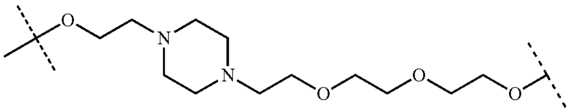
;
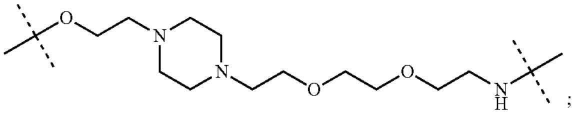
;
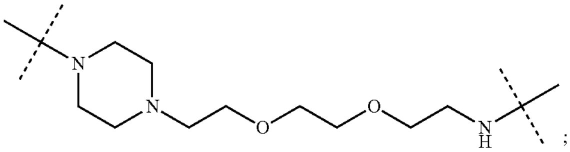
;
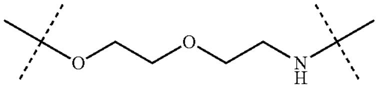
;
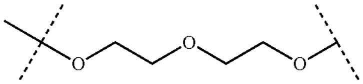
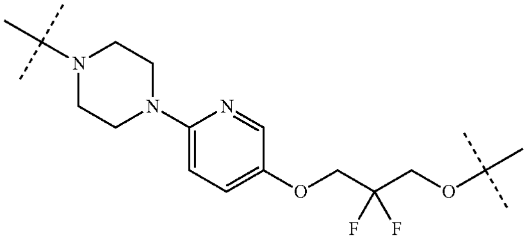
;
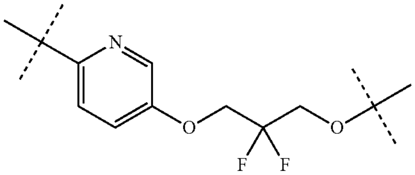
;
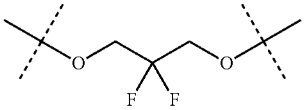
;
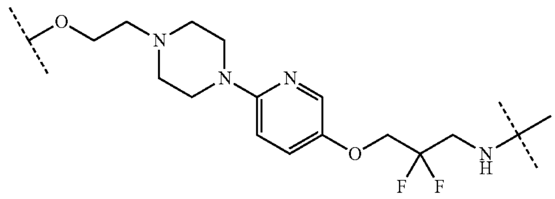
;
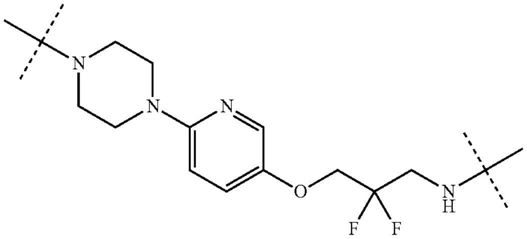
;

-continued
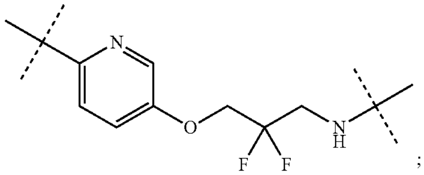
;
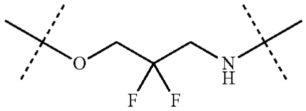
;
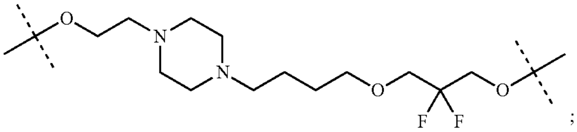
;
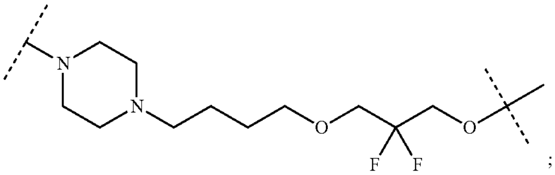
;
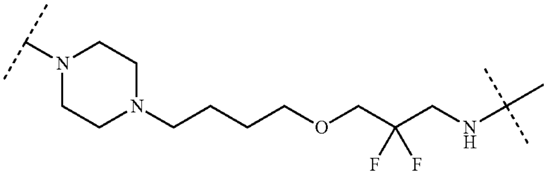
;
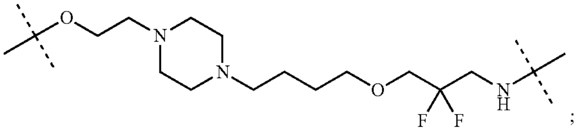
;
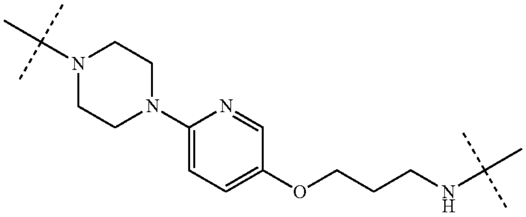
;
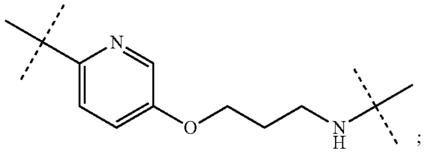
;
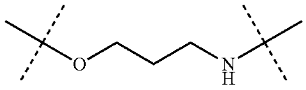
;
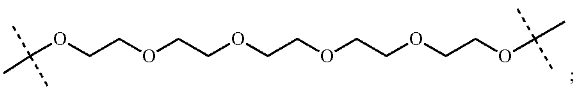
;
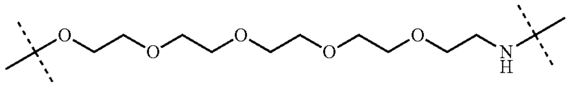
;
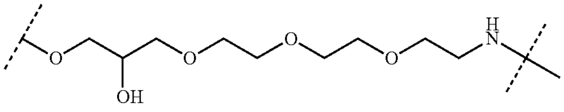
;
-continued
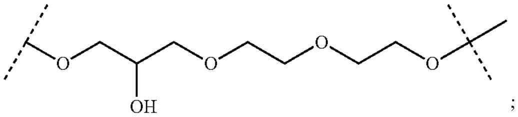
;
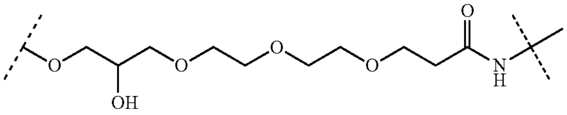
;
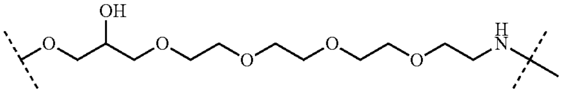
;
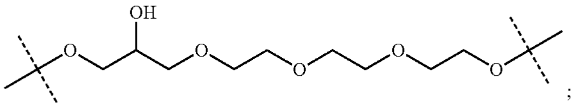
;
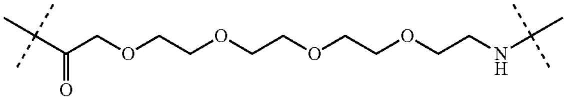
;
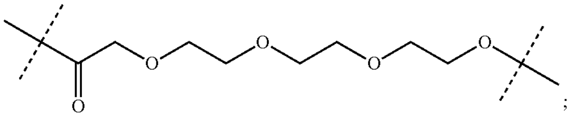
;
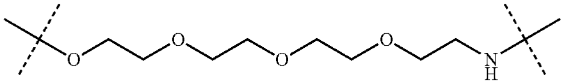
;
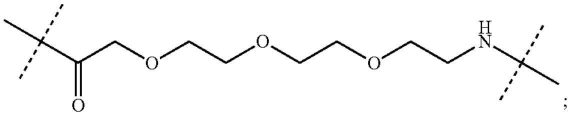
;
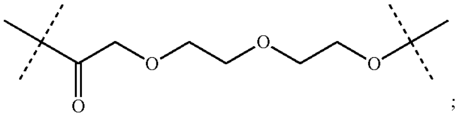
;
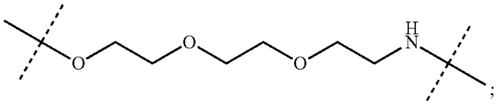
;
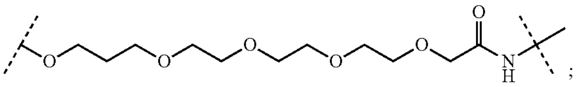
;
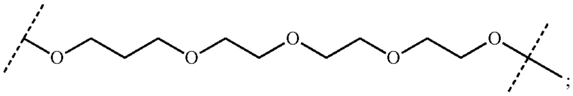
;
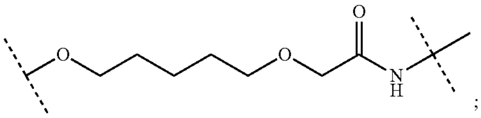
;
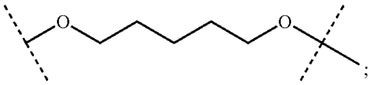
;
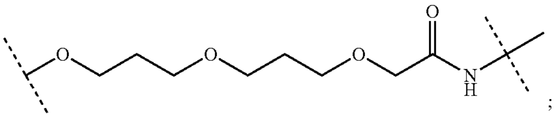
;
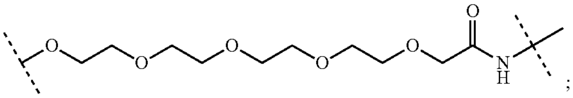
;

-continued
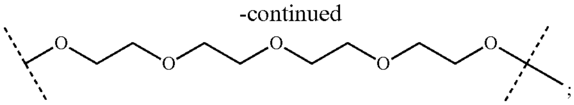
;
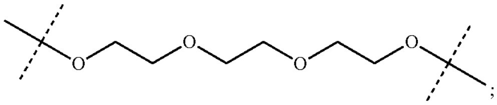
;
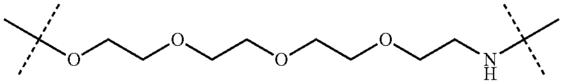
;
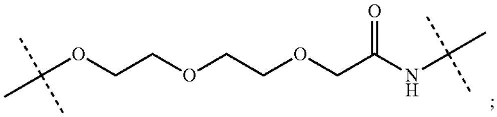
;
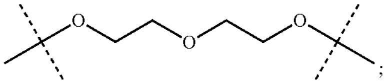
;
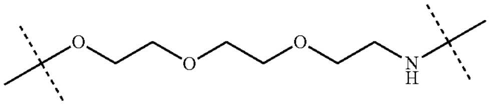
;
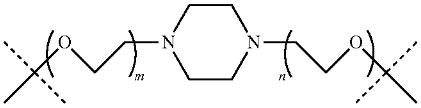
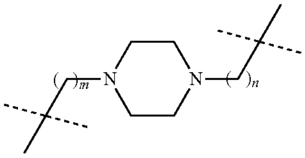
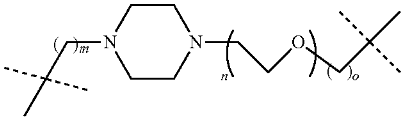
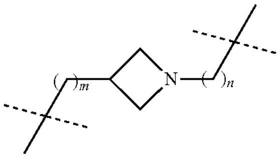
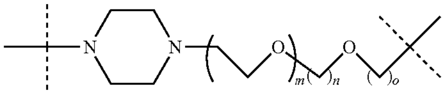
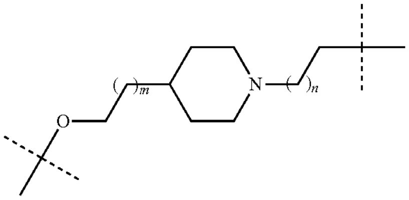
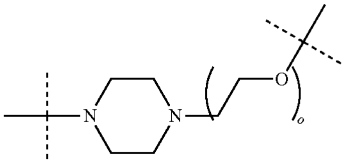
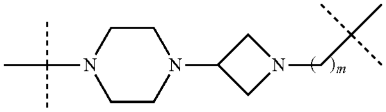
-continued
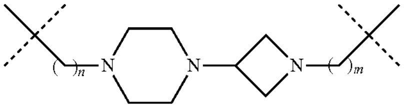
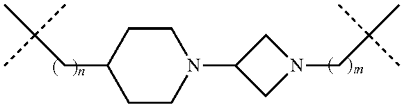
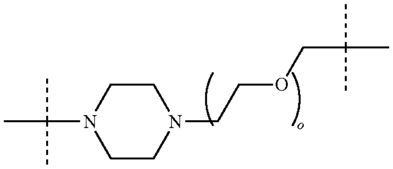
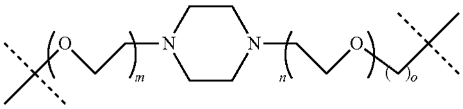
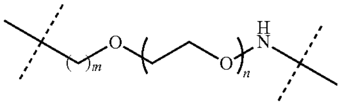
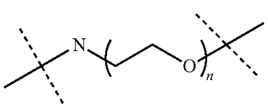
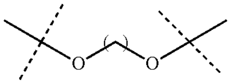
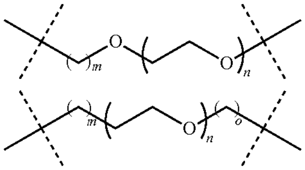
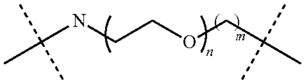
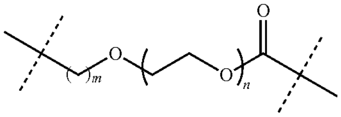
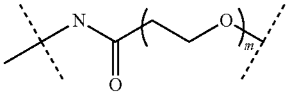
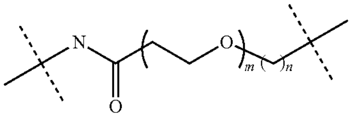
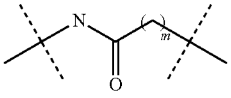
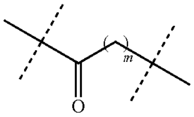
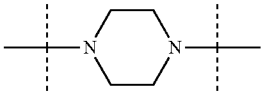
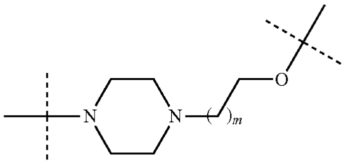

-continued
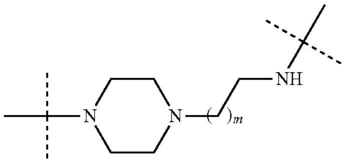
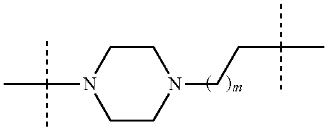
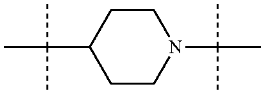
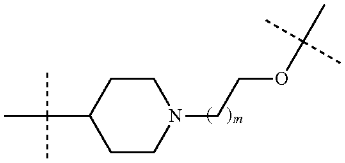
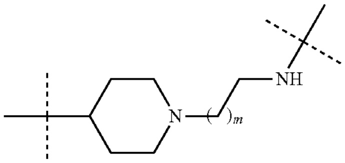
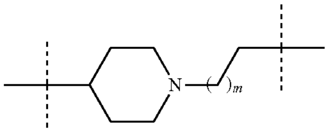
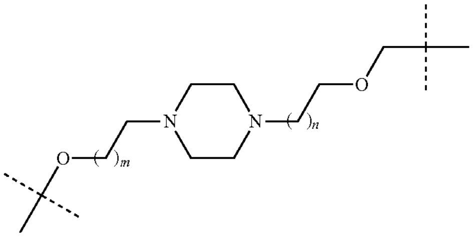
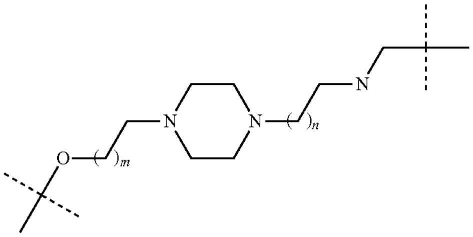
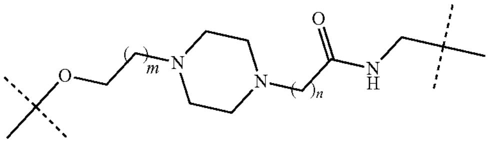
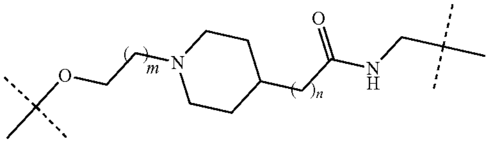
-continued
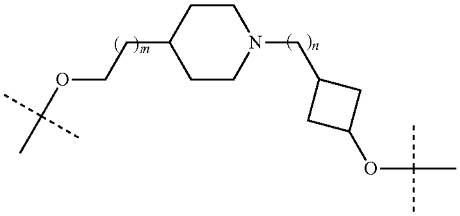
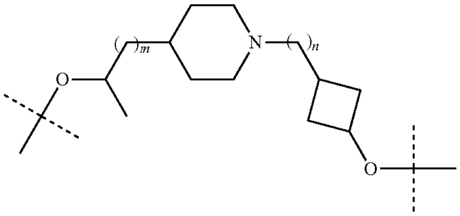
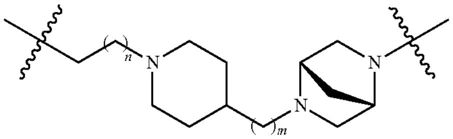
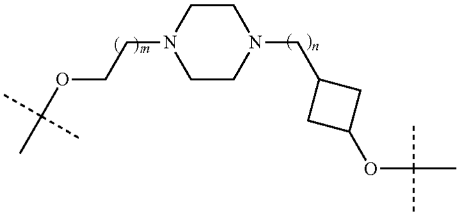
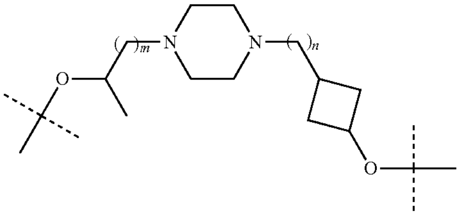
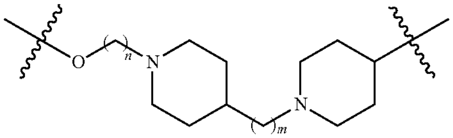
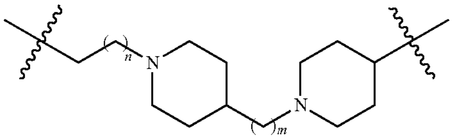
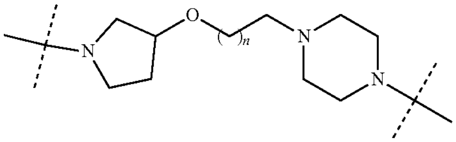
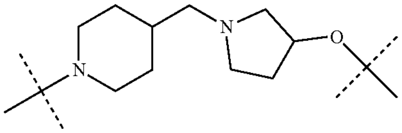
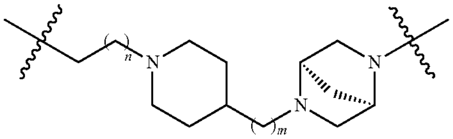

-continued
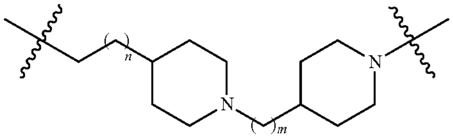
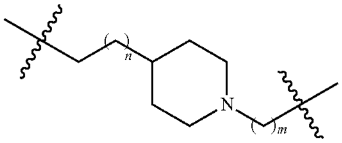
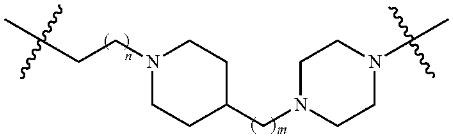
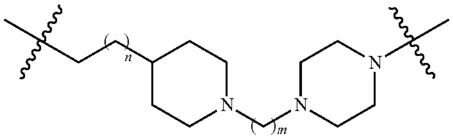
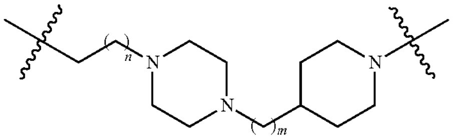
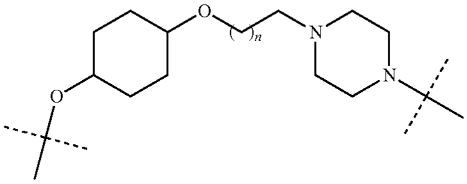
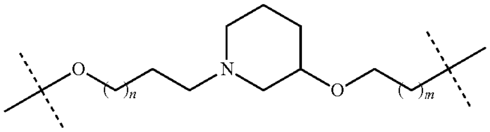
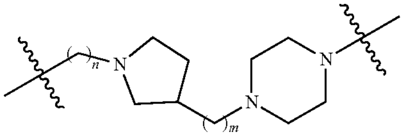
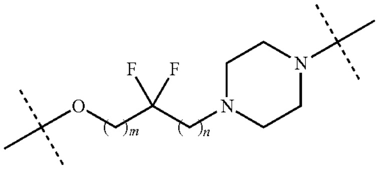
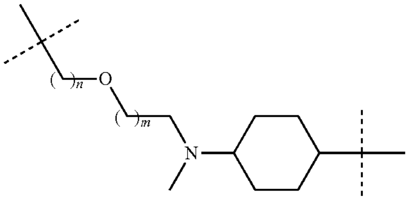
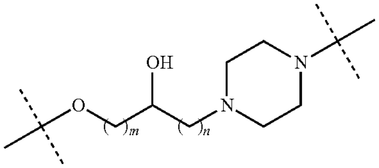
-continued
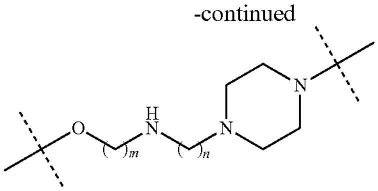
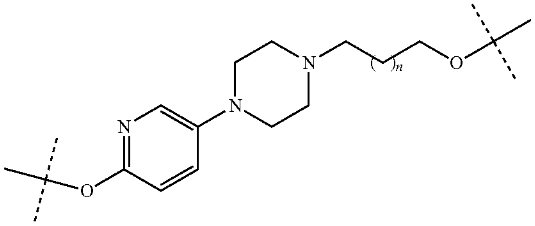
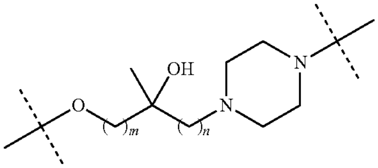
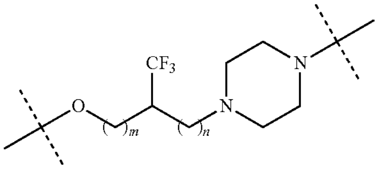
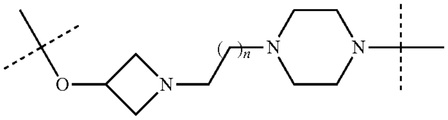
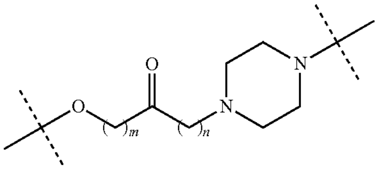
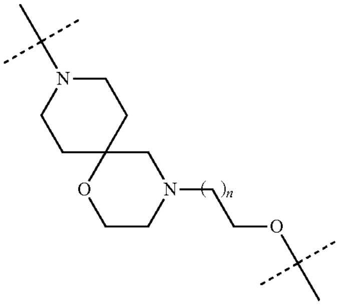
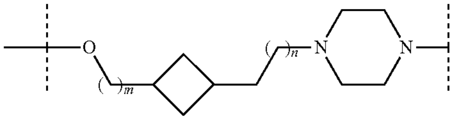
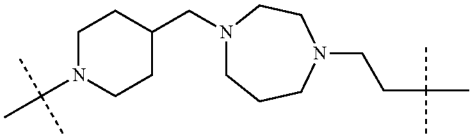
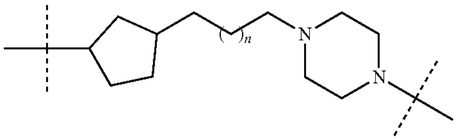

-continued
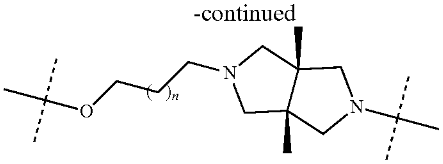
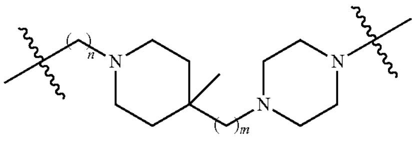
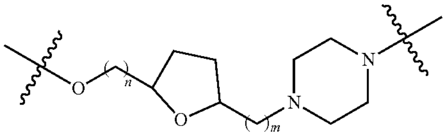
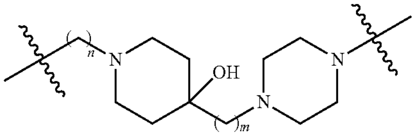
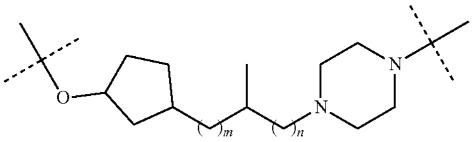
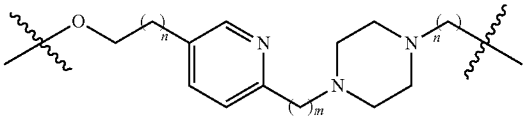
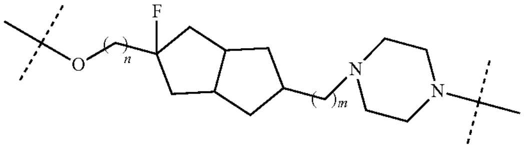
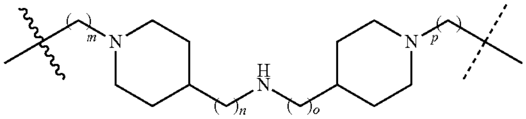
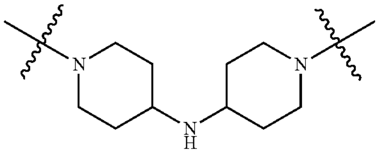
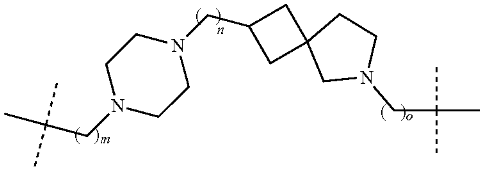
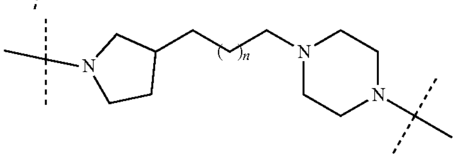
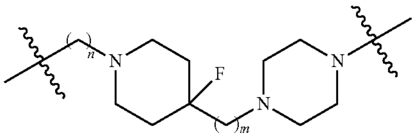
-continued
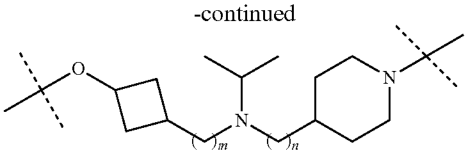
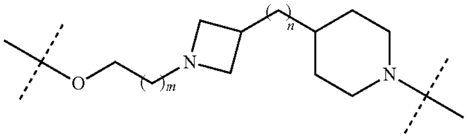
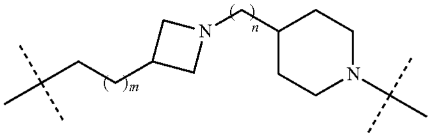
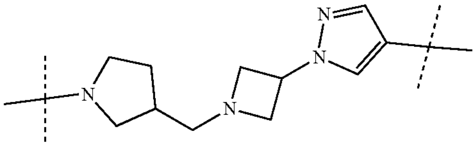
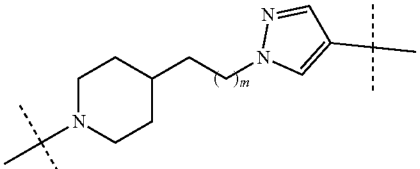
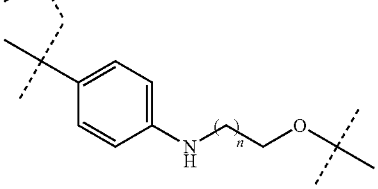
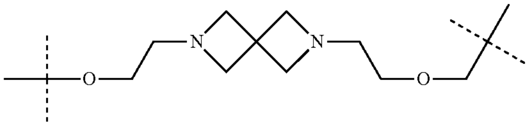
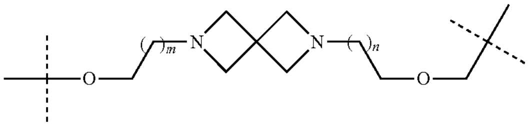
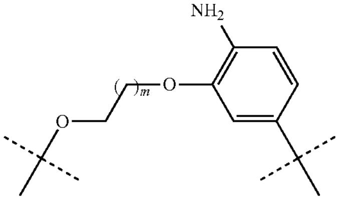
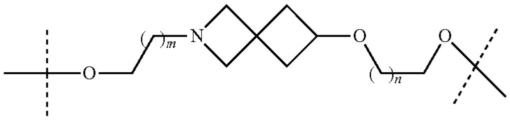
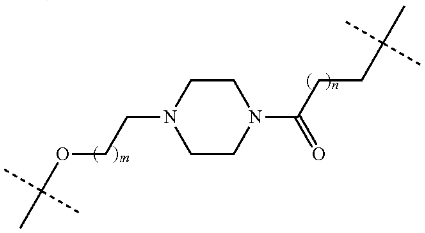

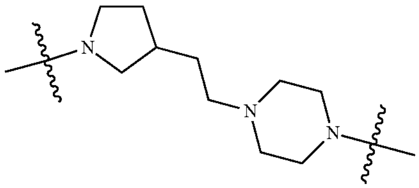
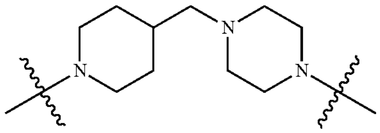
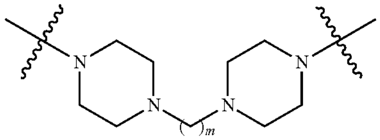
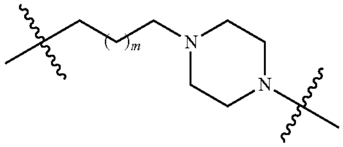
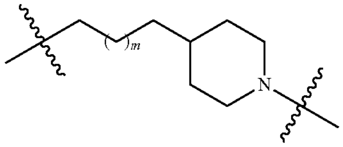
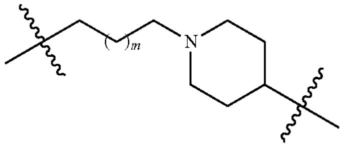
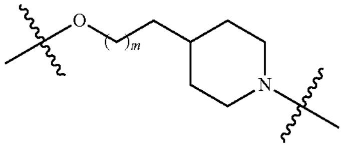
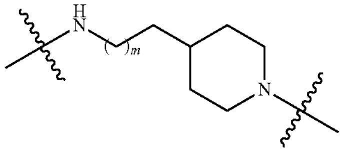
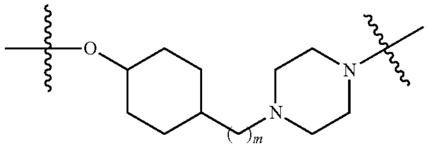
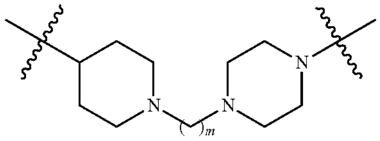
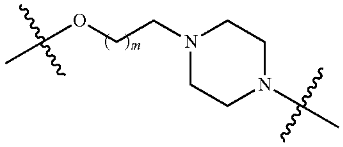
-continued
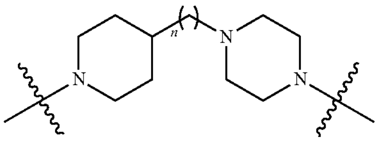
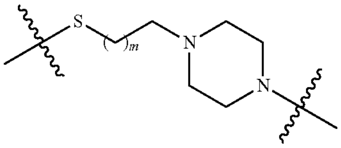
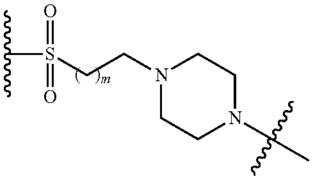
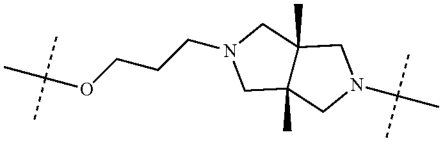
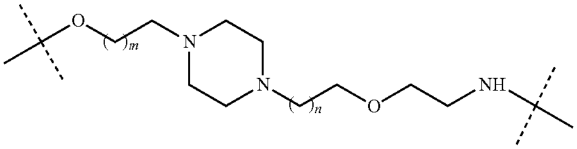
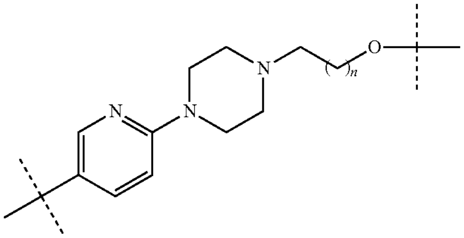
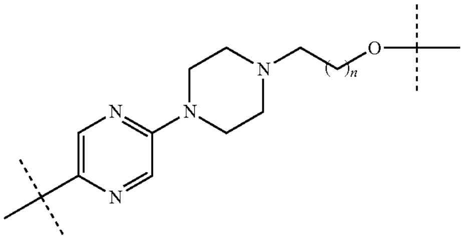
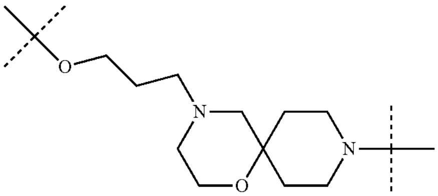
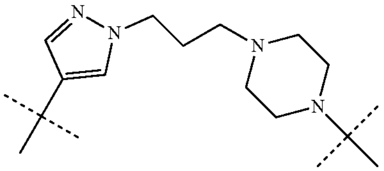

-continued
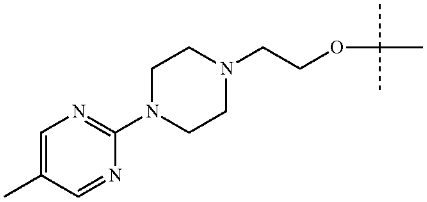
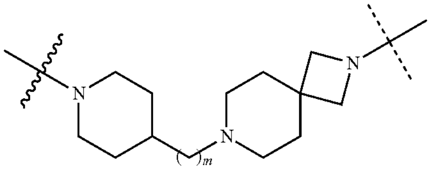
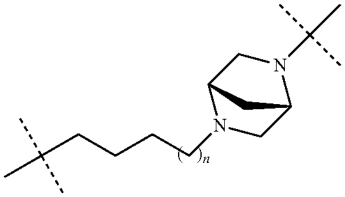
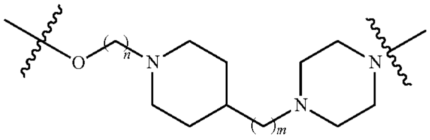
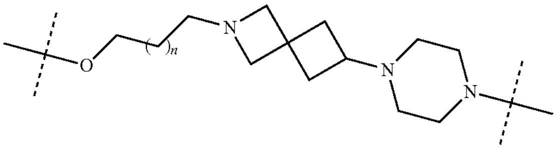
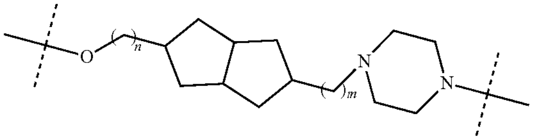
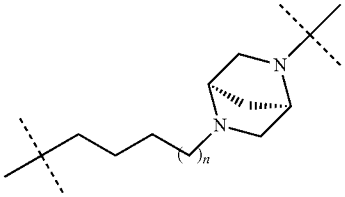
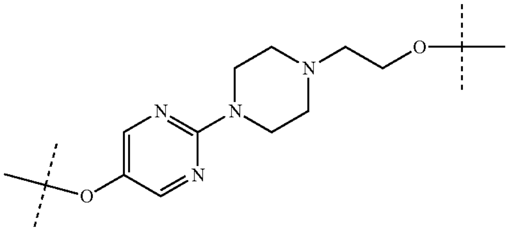
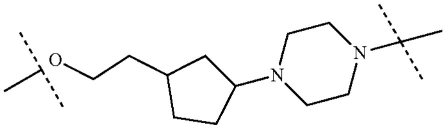
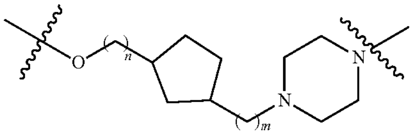
-continued
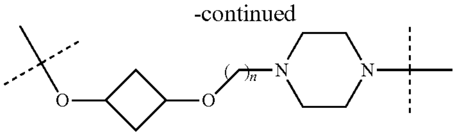
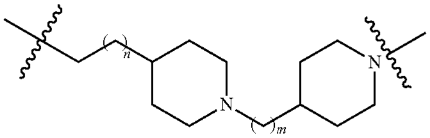
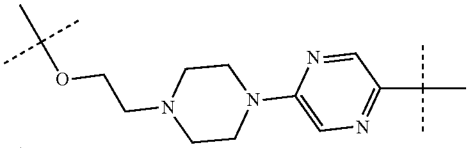
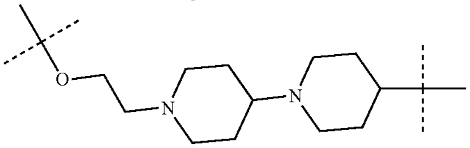
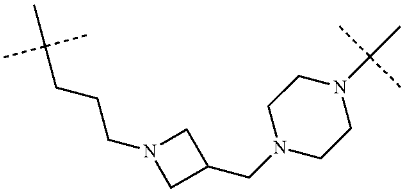
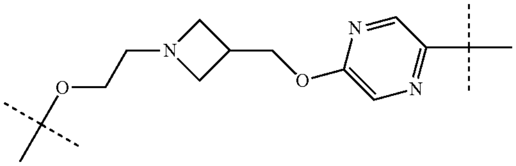
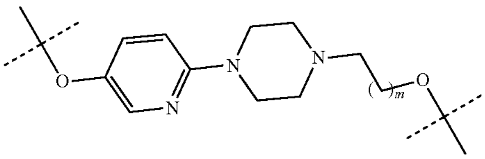
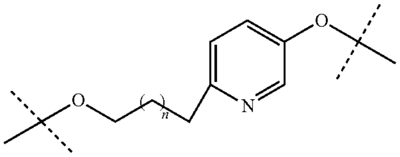
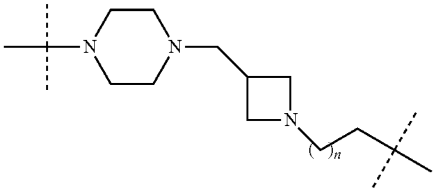
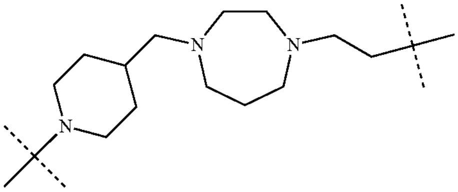
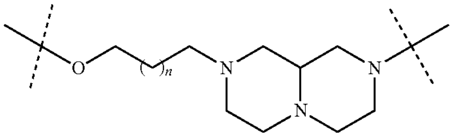

-continued
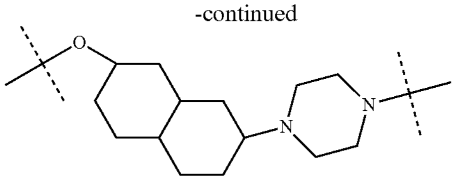
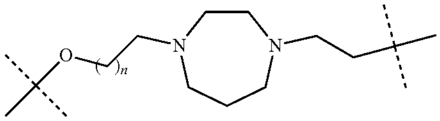
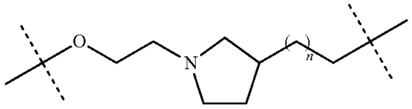
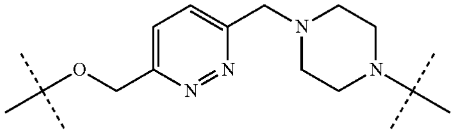
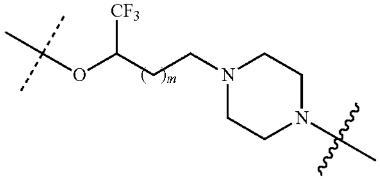
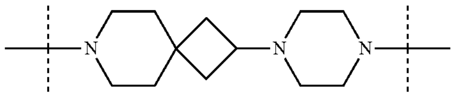
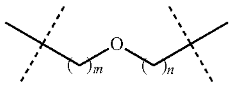
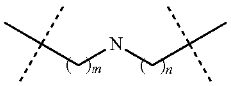
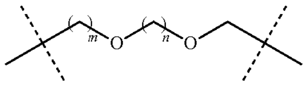
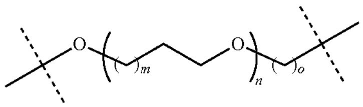
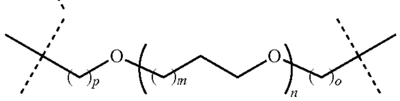
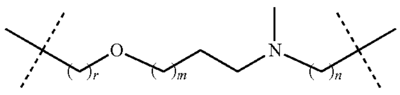
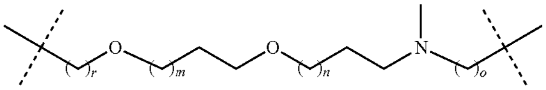
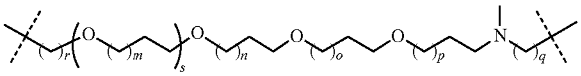
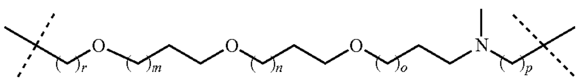
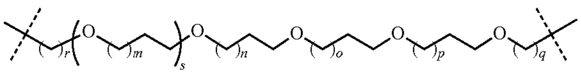
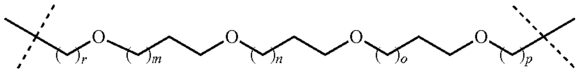
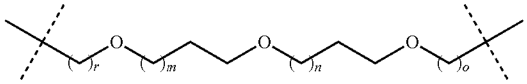
-continued
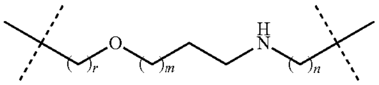
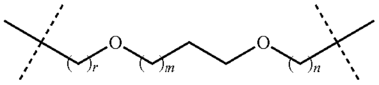
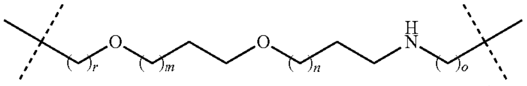
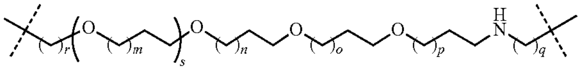
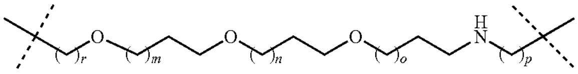
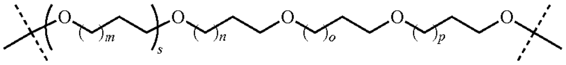
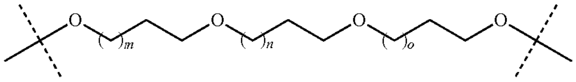
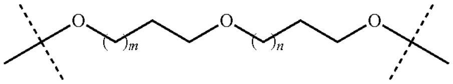
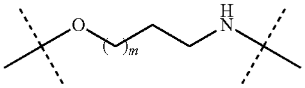
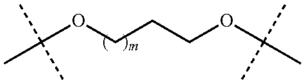
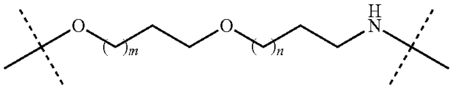
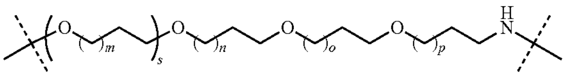
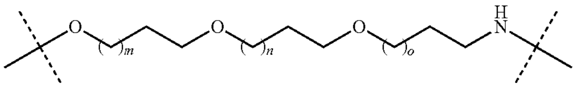
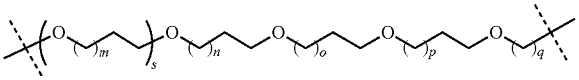
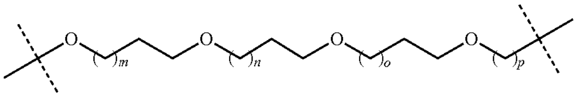
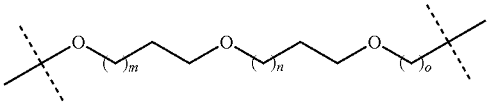
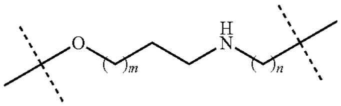
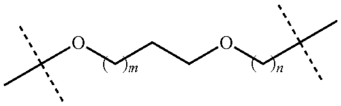
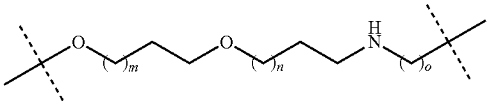
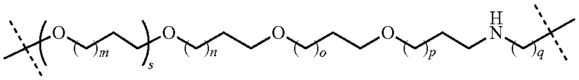

-continued
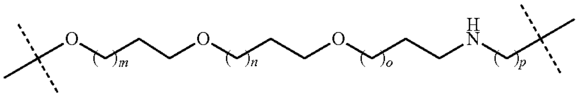
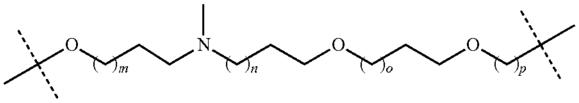
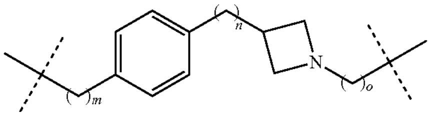
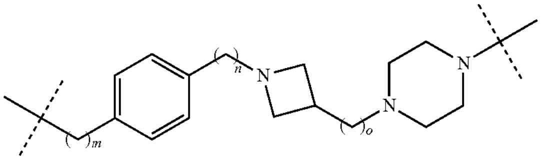
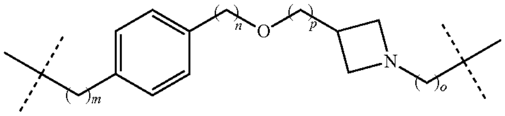
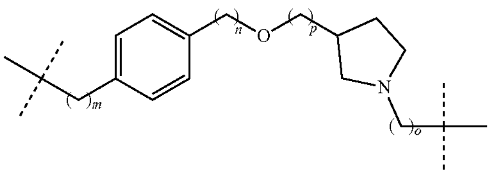
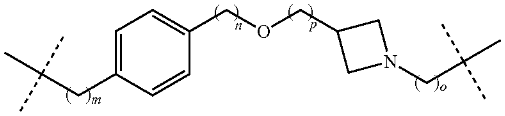
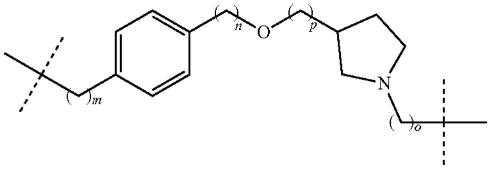
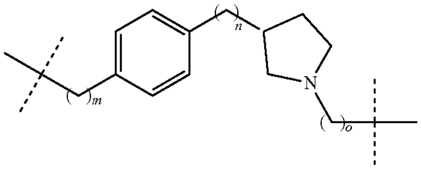
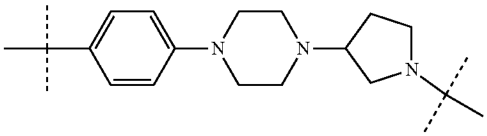
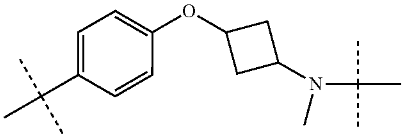
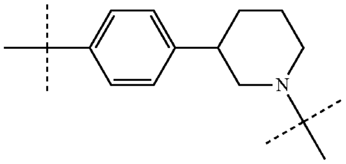
-continued
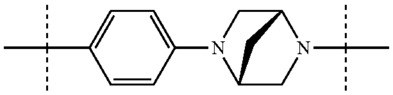
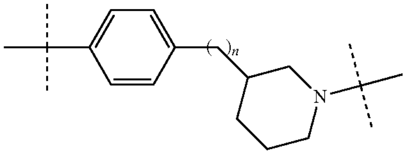
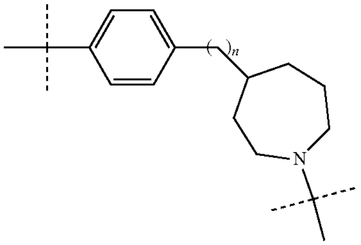
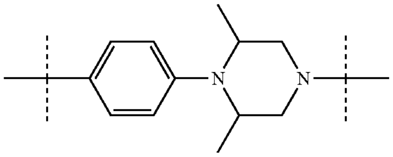
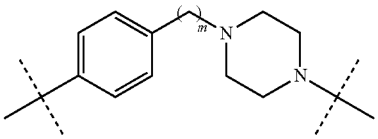
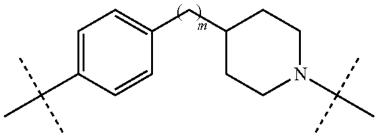
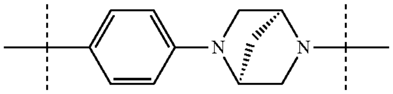
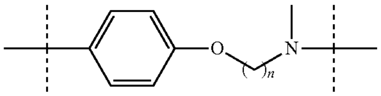
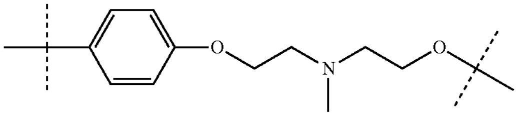
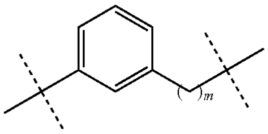
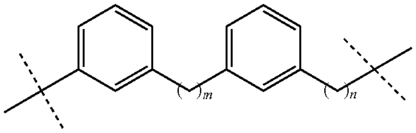

-continued
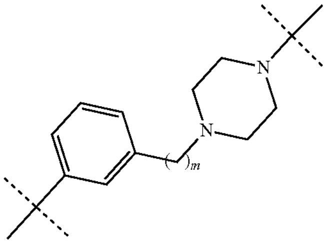
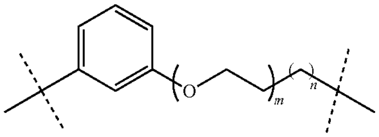
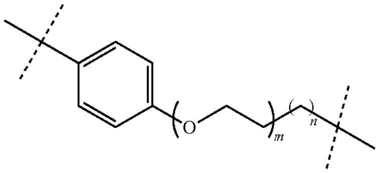
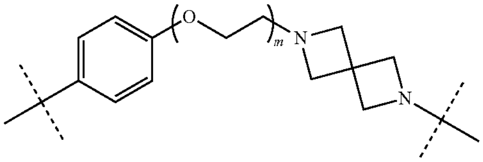
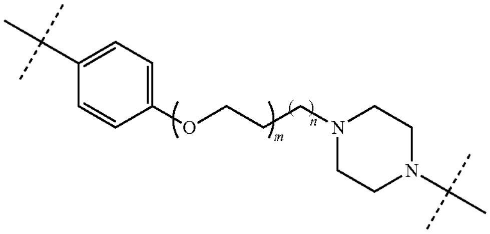
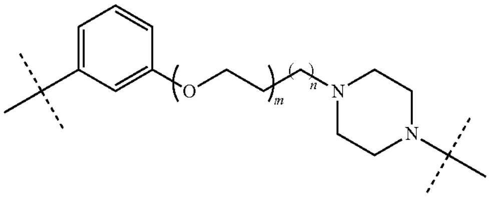
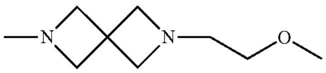
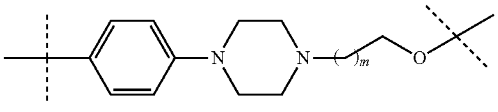
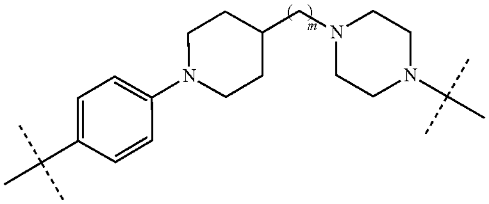
-continued
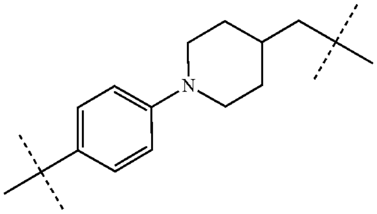
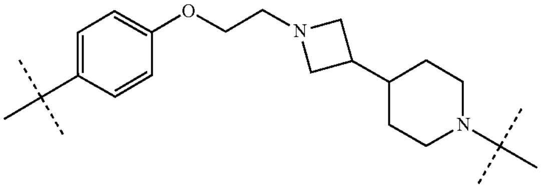
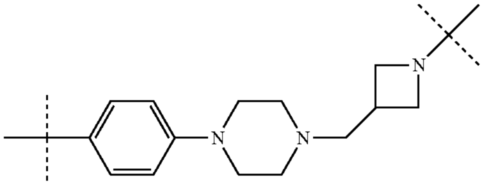
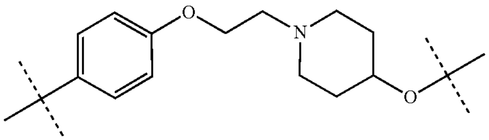
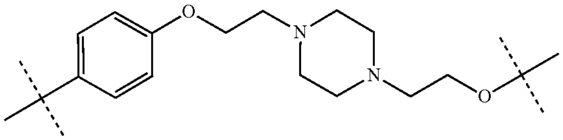
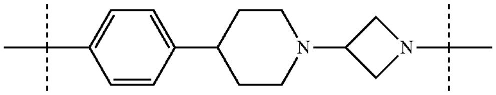
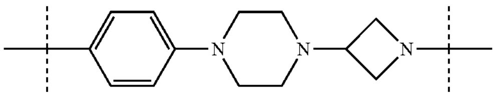
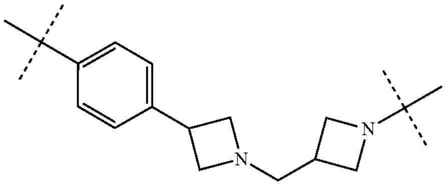
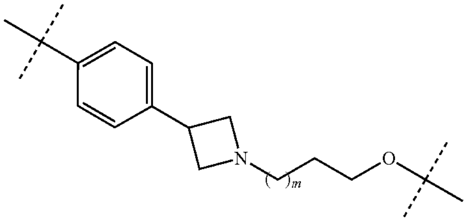
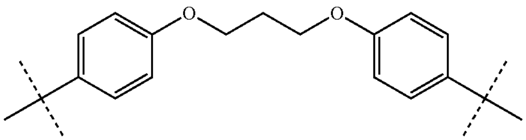
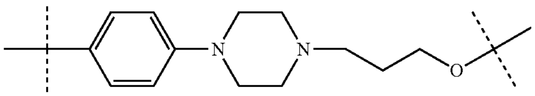

-continued
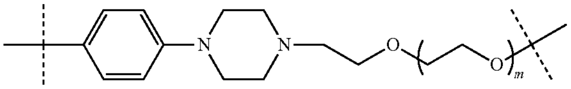
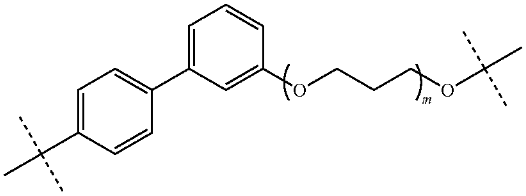
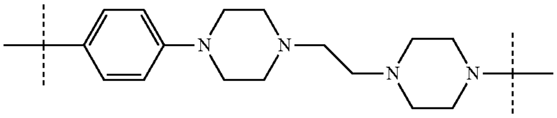
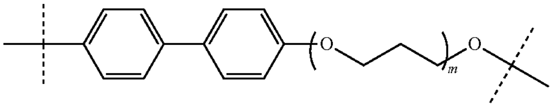
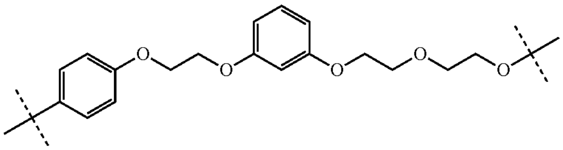
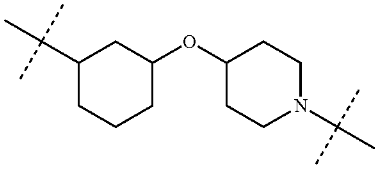
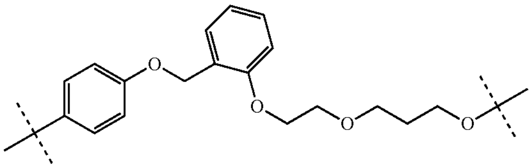
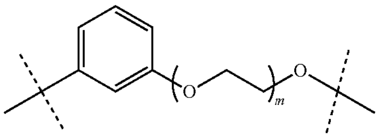
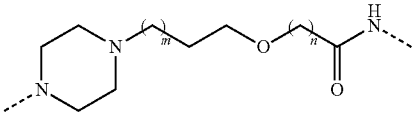
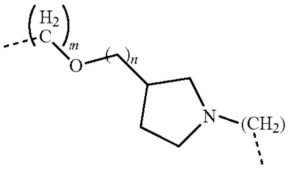
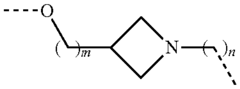
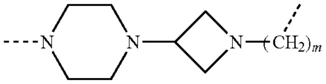
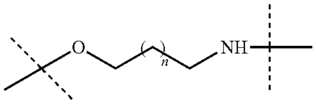
-continued
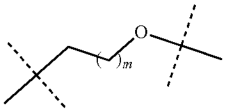
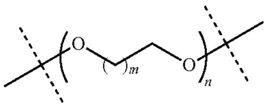
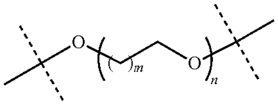
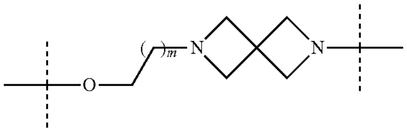
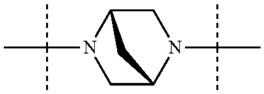
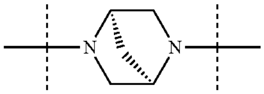
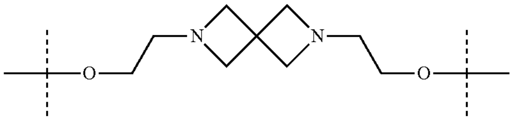
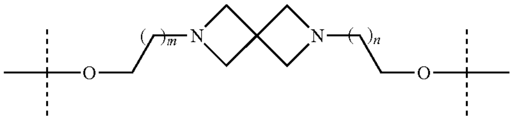
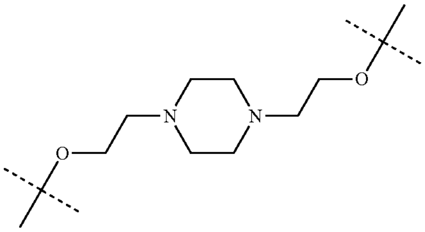
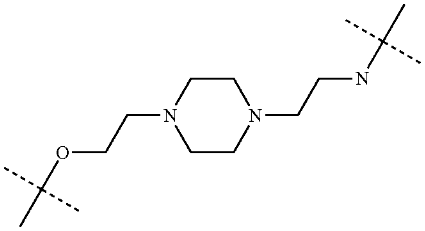
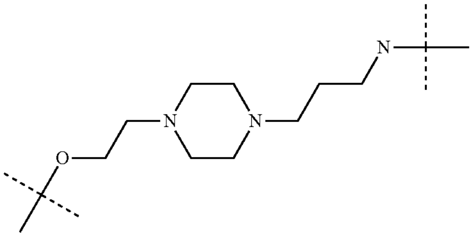

-continued
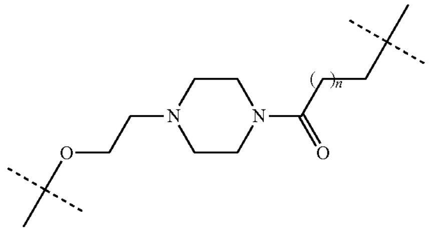
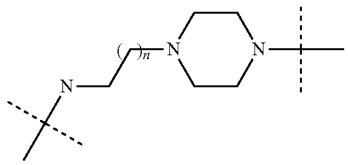
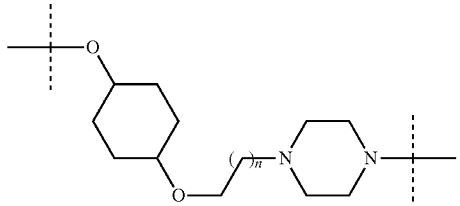
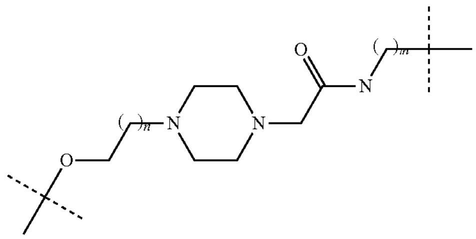
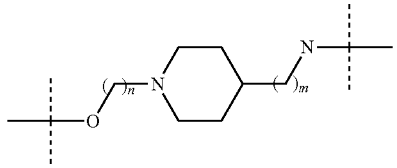
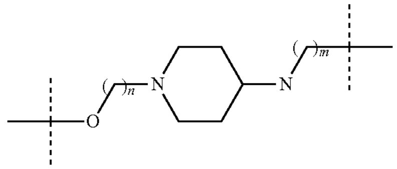
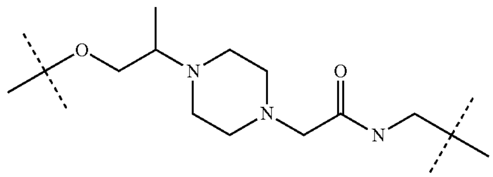
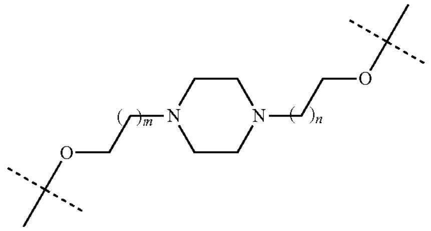
-continued
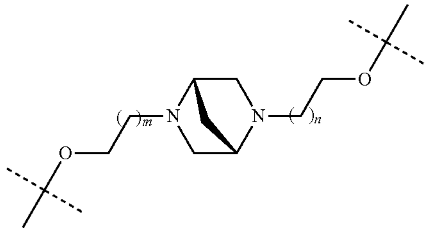
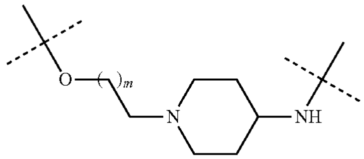
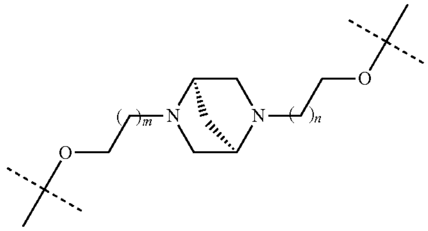
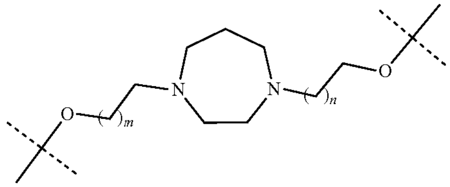
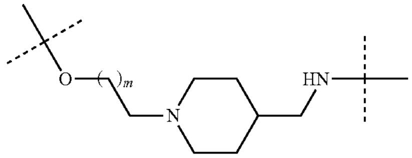
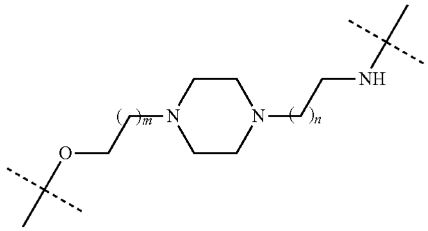
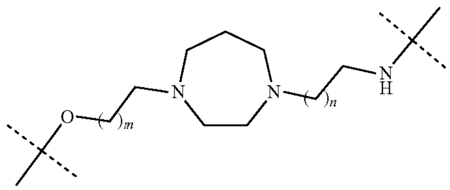
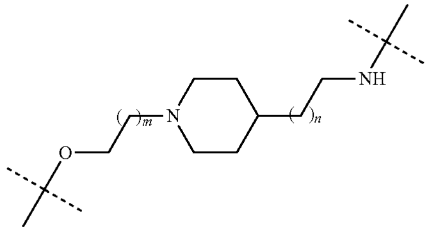

-continued
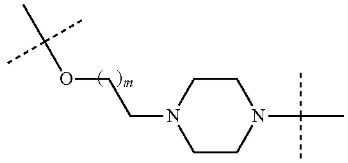
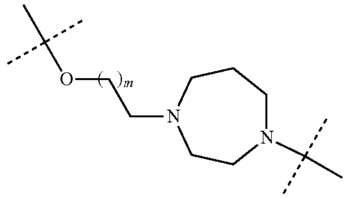
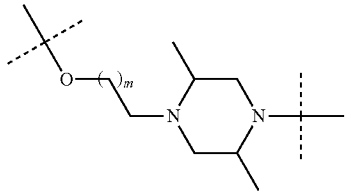
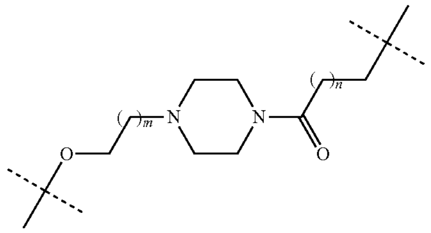
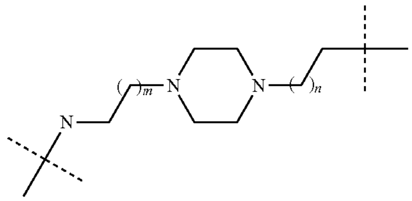
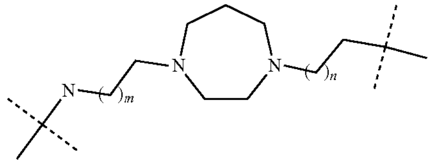
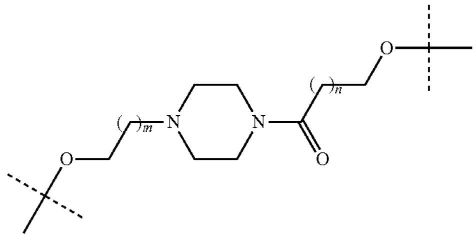
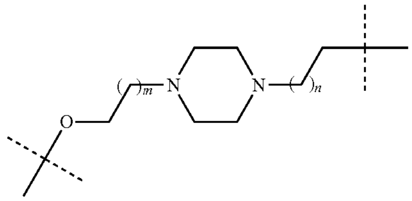
-continued
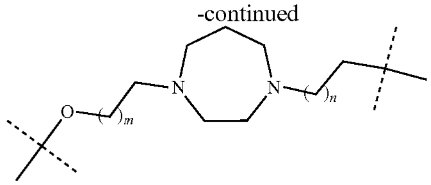
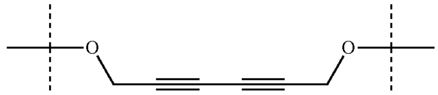
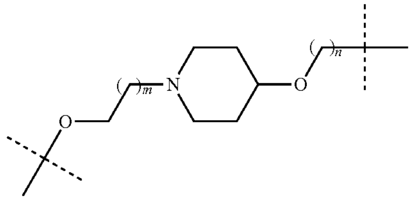
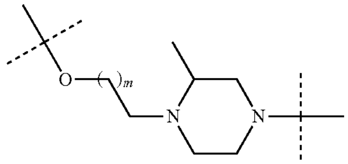
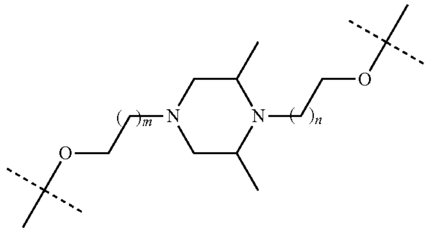
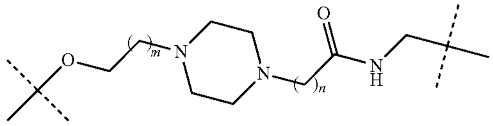
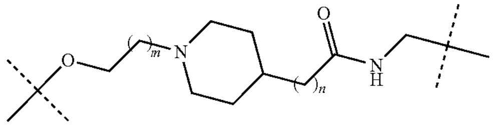
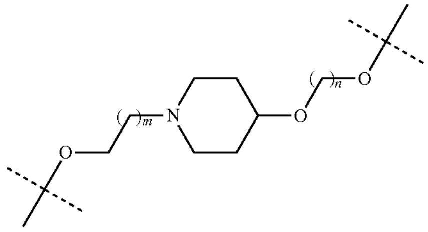
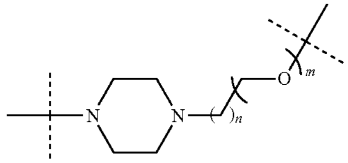
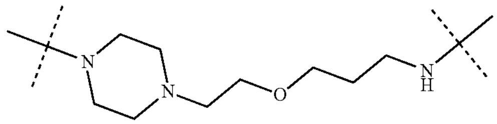
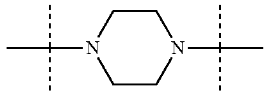

-continued
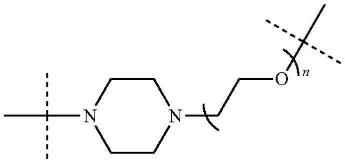
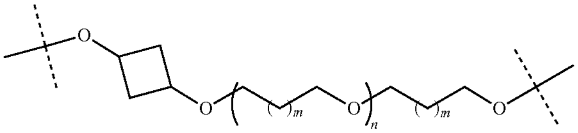
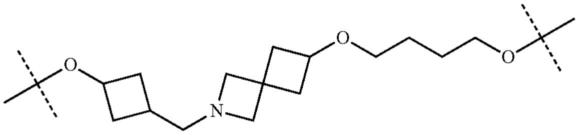
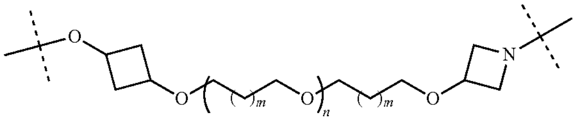
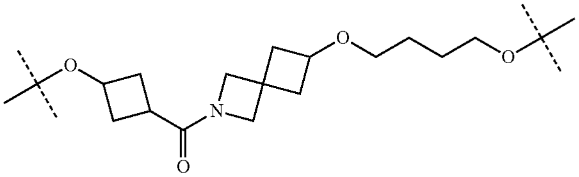
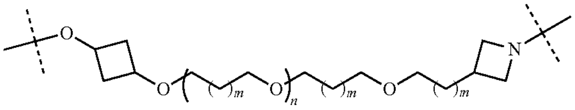
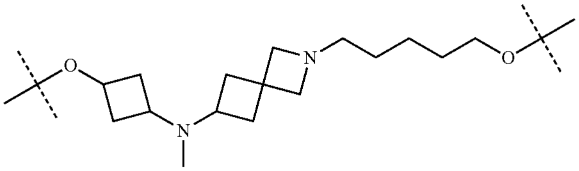
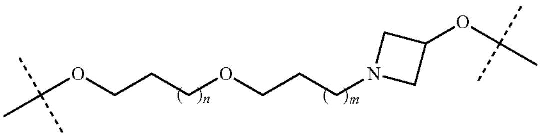
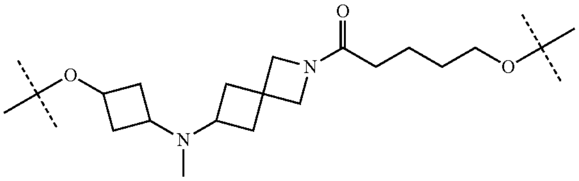
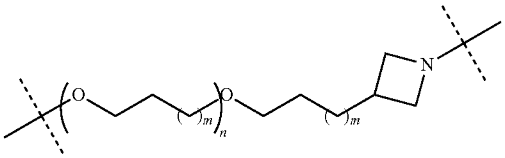
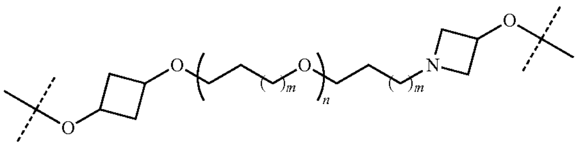
-continued
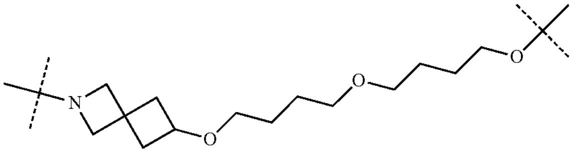
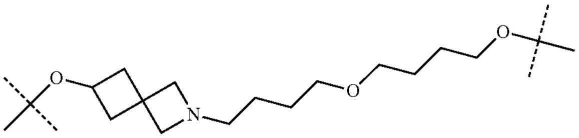
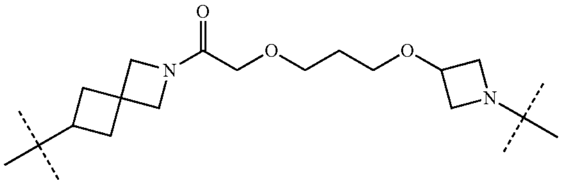
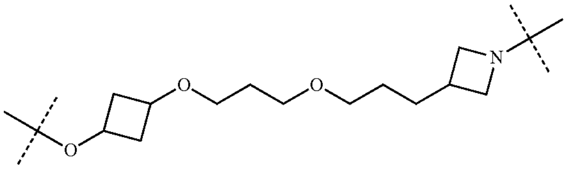
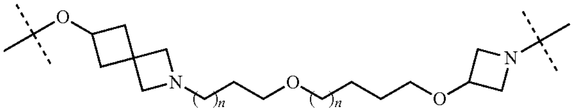
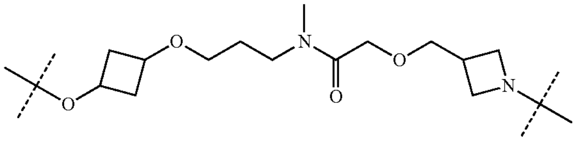
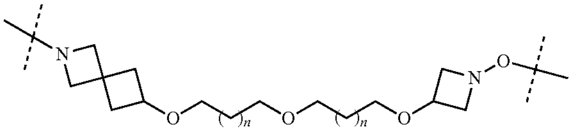
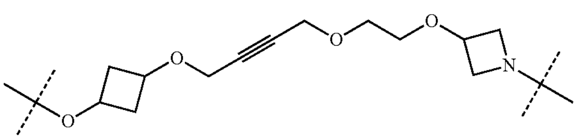
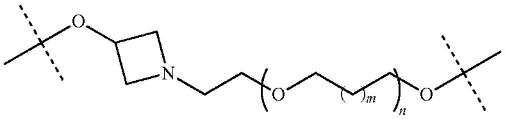
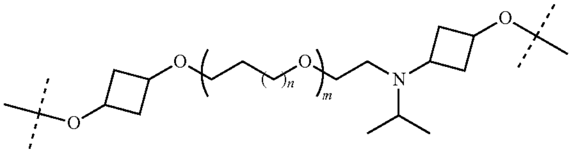
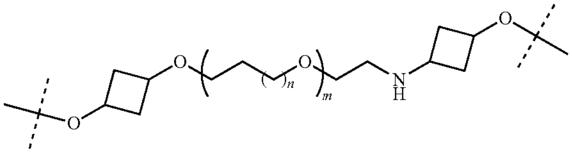

-continued
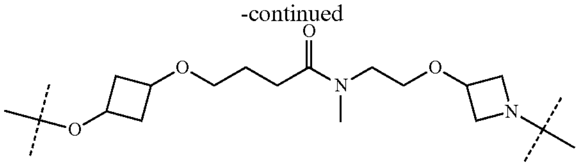
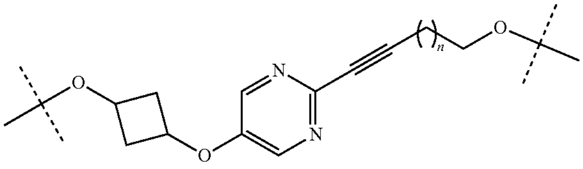
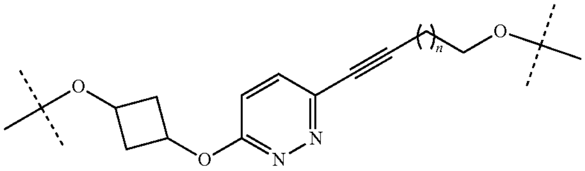
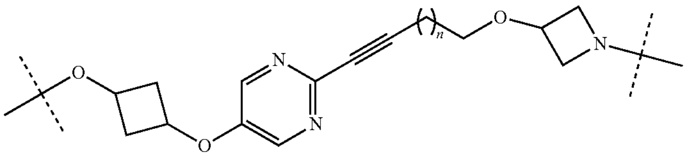
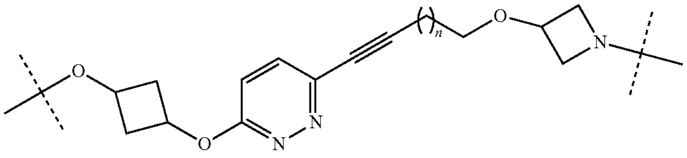
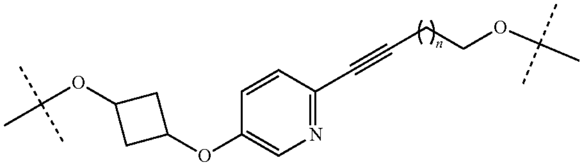
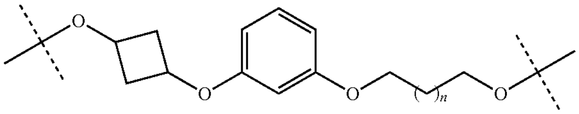
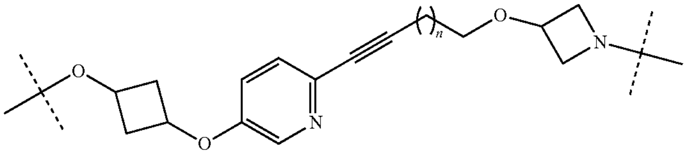
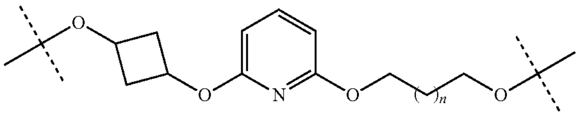
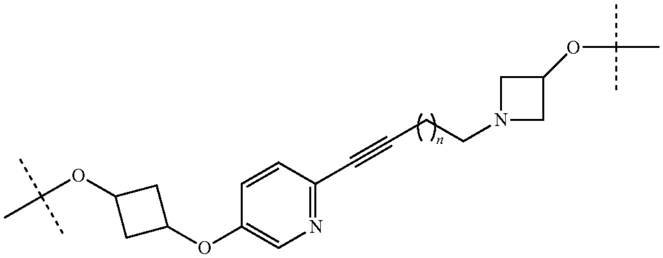

-continued
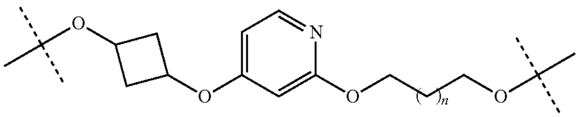
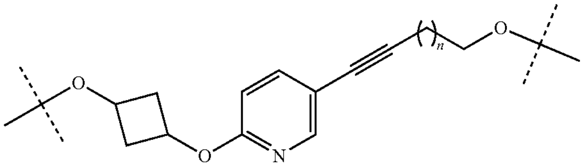
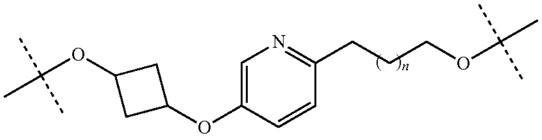
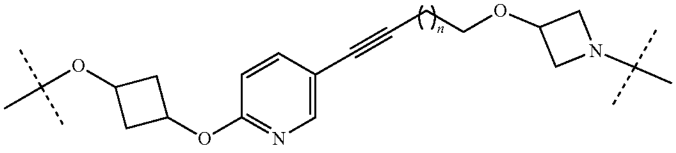
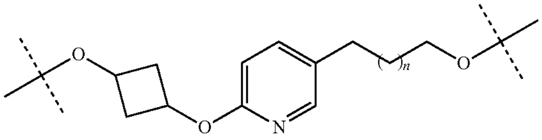
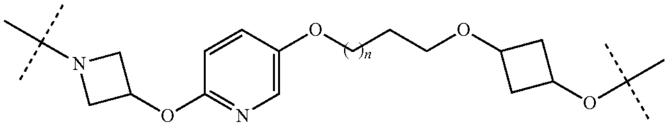
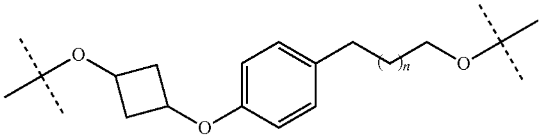
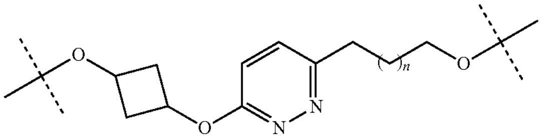
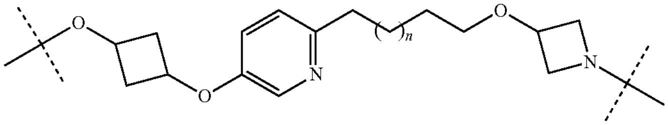
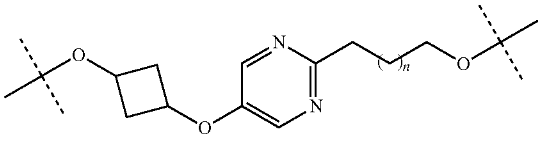
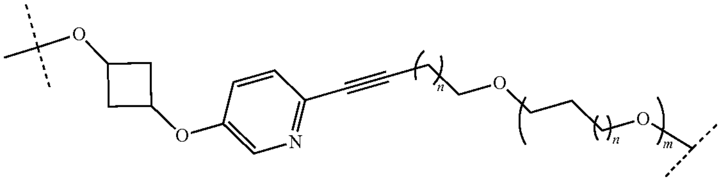
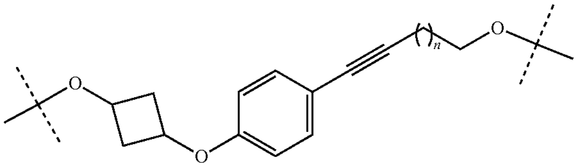
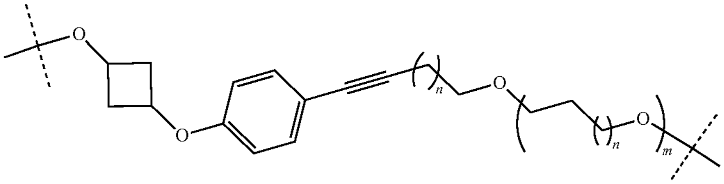

-continued
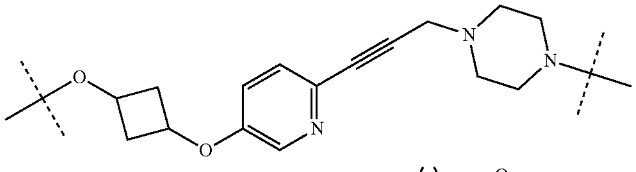
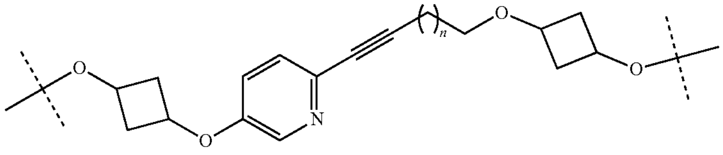
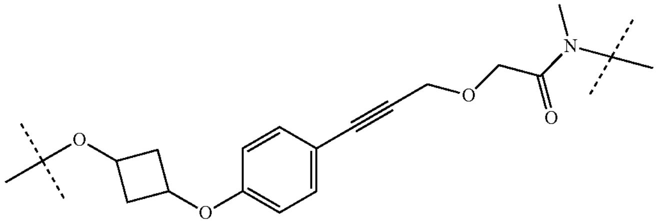
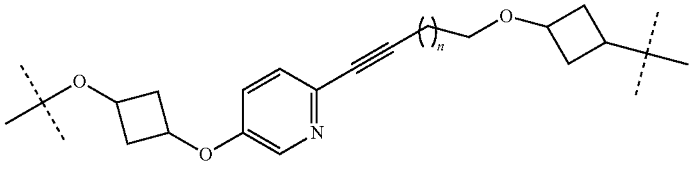
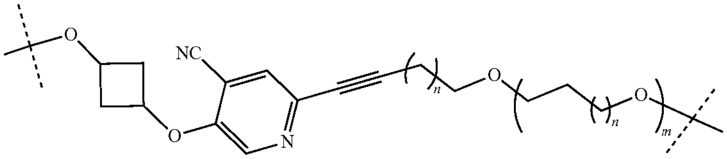
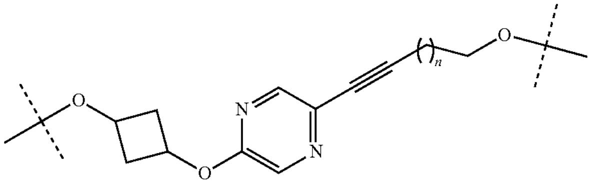
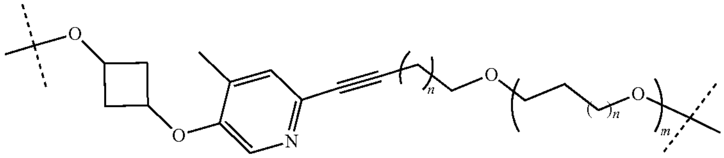
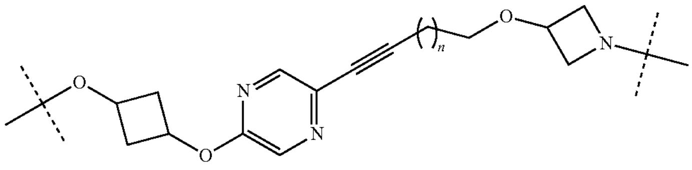
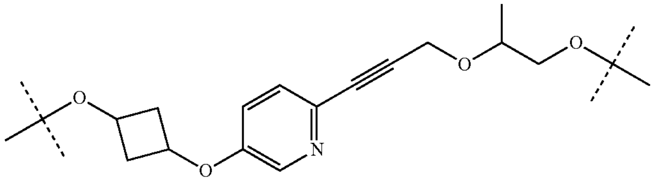
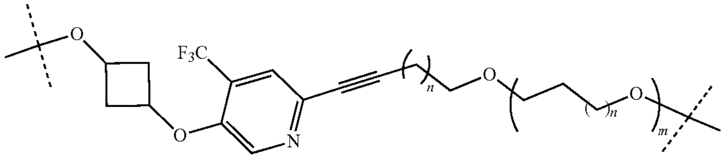

-continued
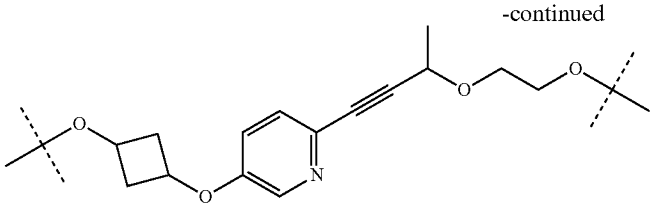
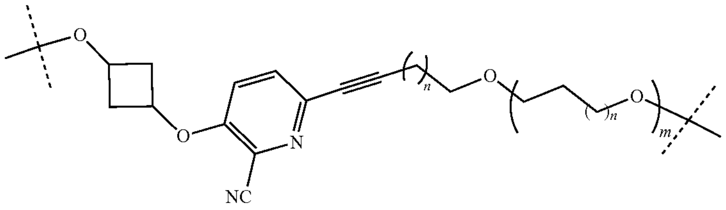
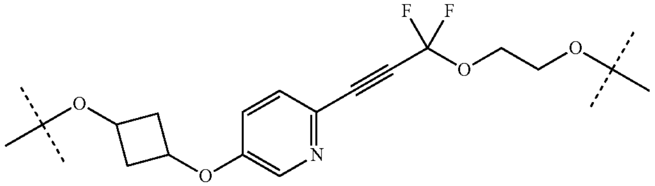
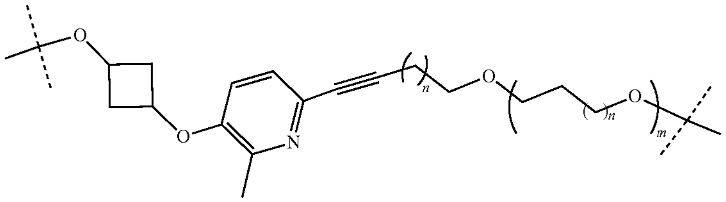
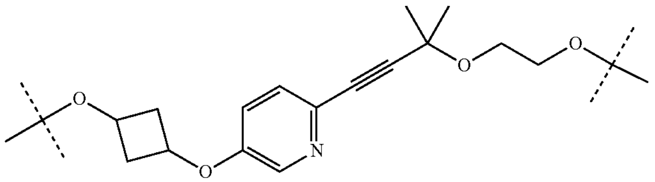
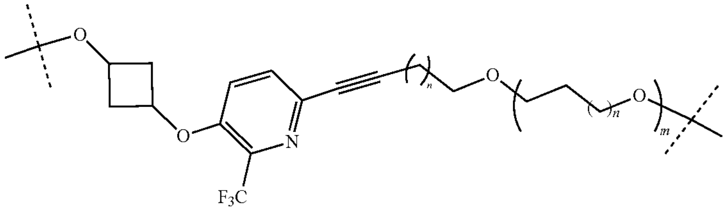
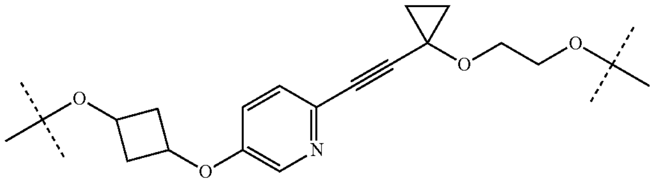
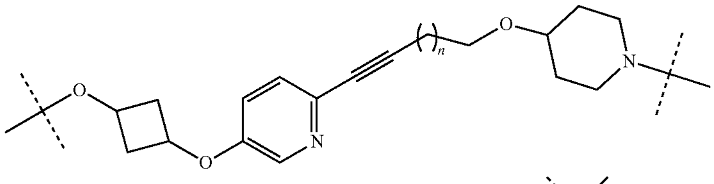
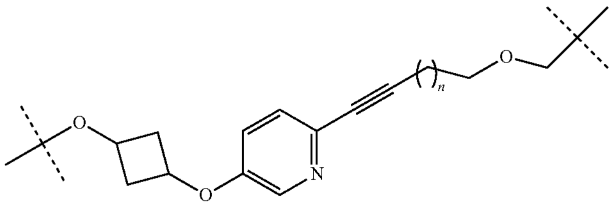

-continued
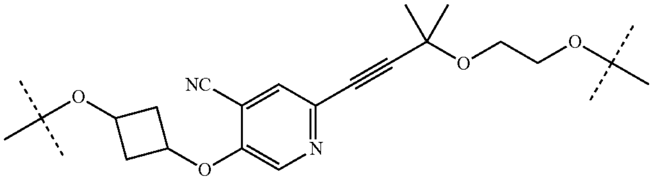
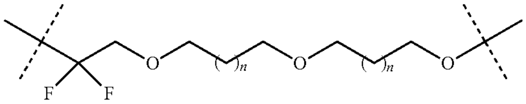
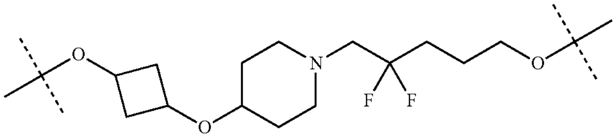
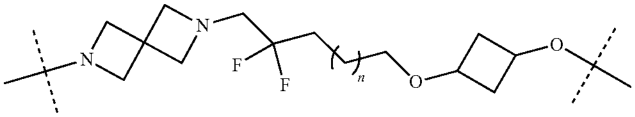
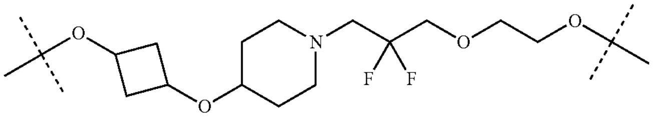
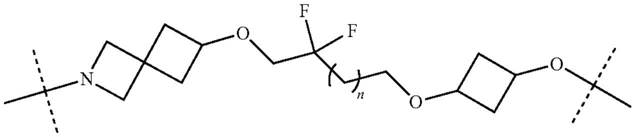
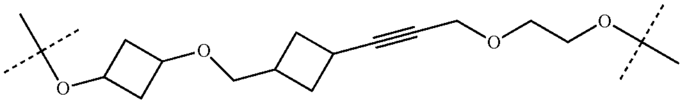
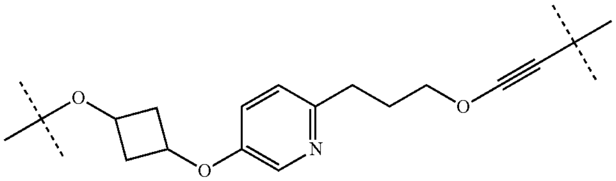
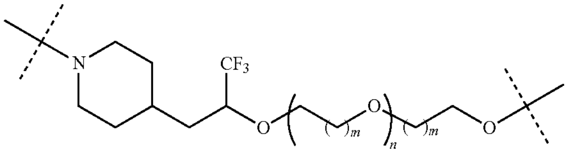
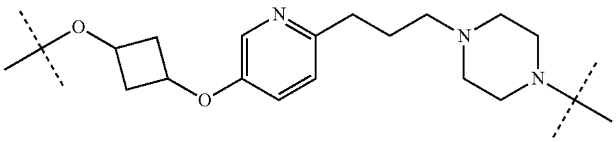
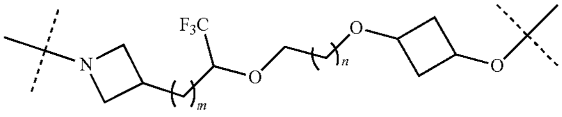
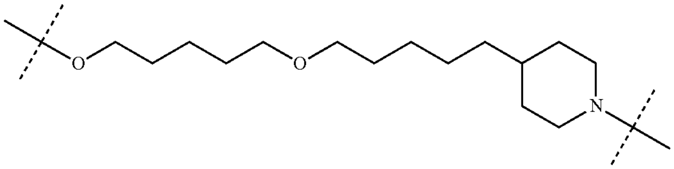

-continued
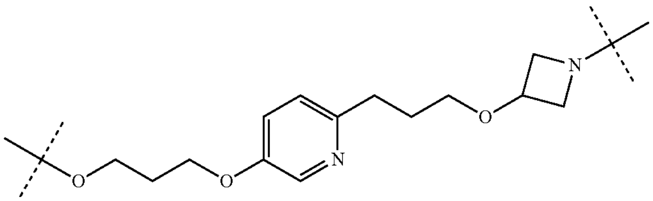
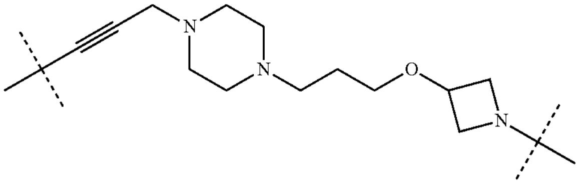
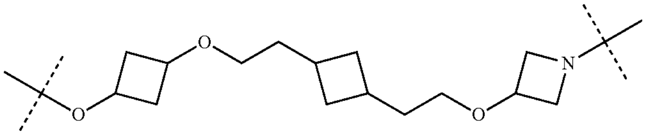
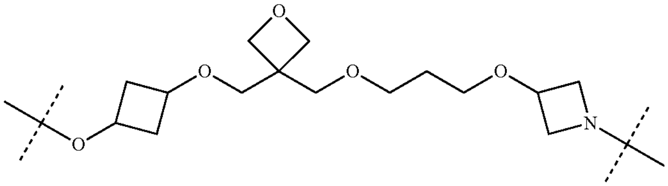
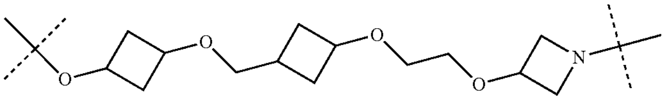
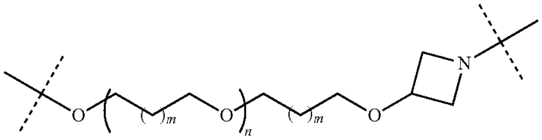
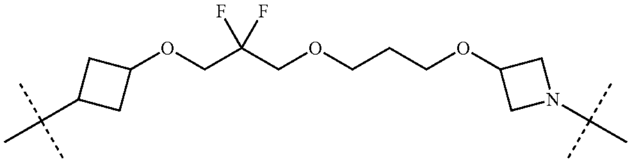
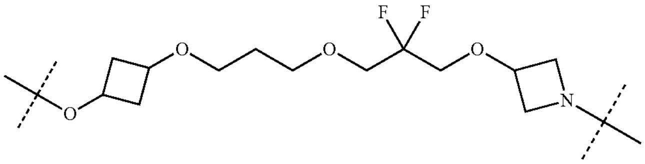
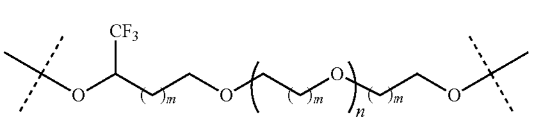
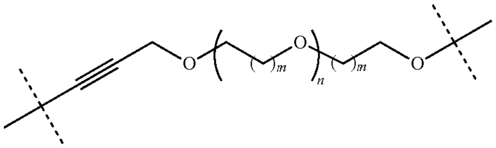
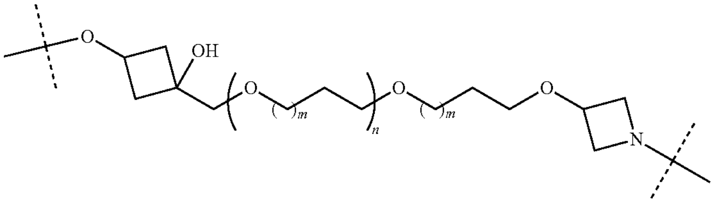

-continued
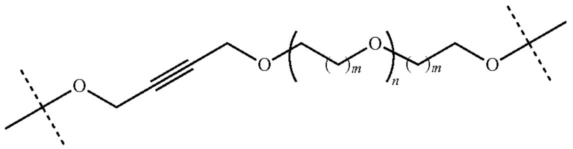
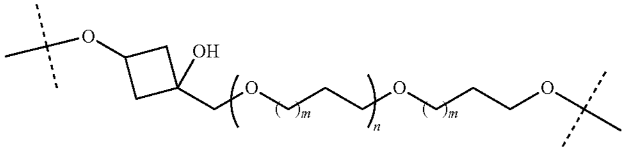
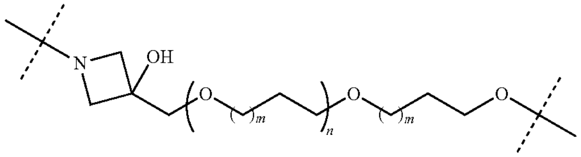
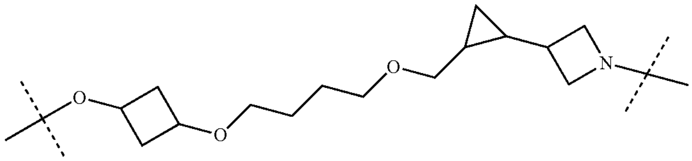
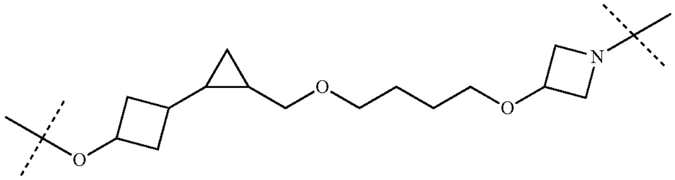
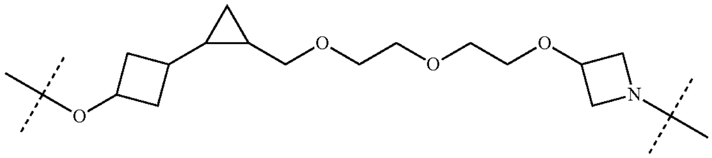
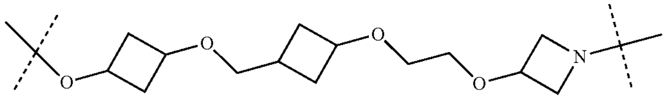
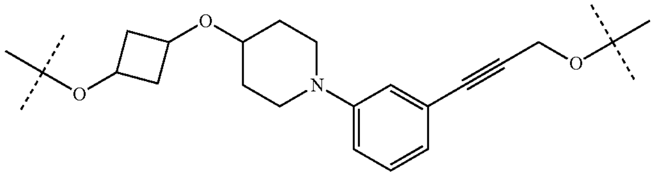
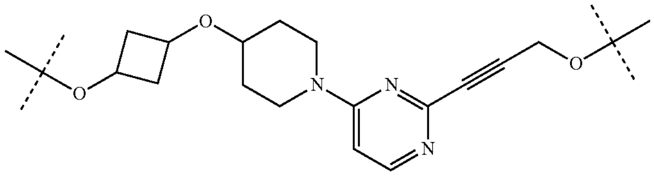
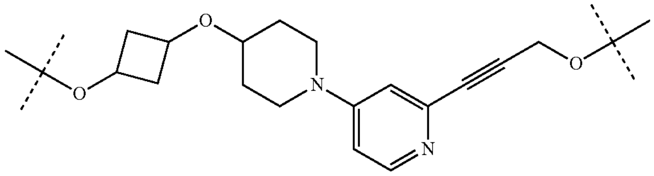

-continued
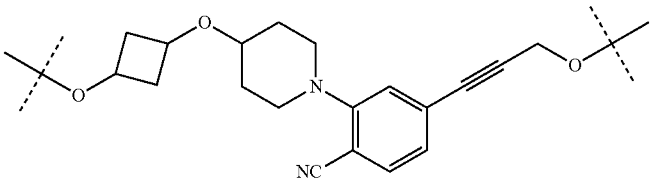
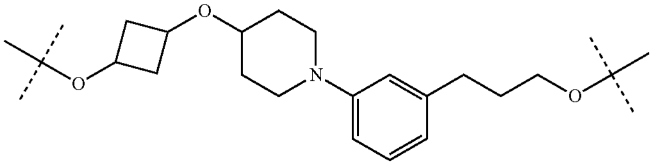
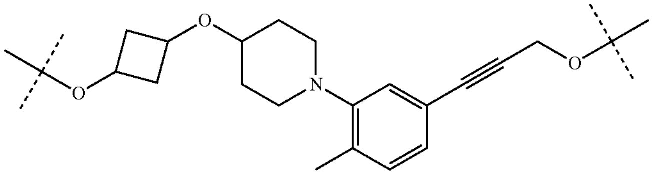
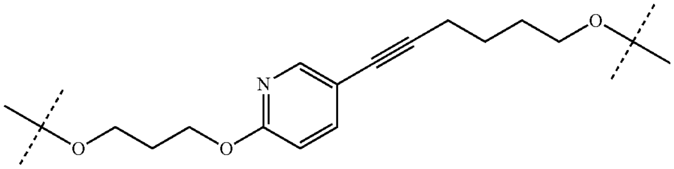
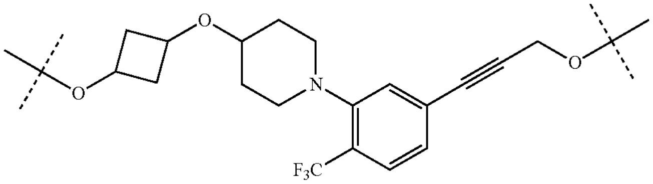
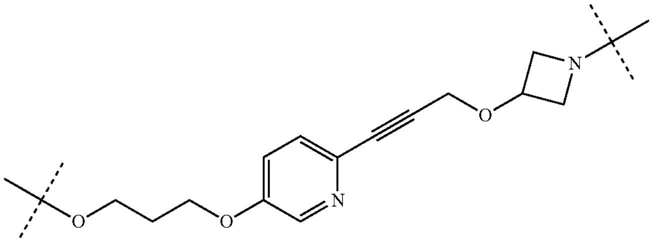
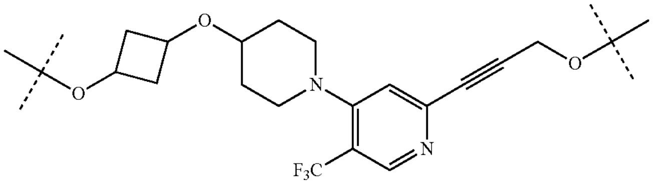
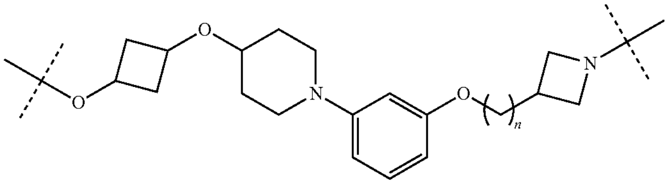
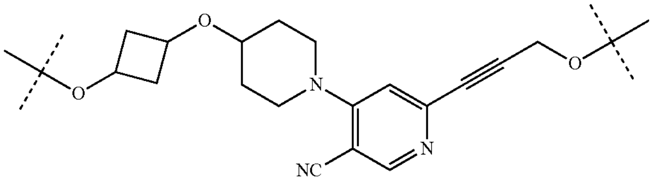

-continued
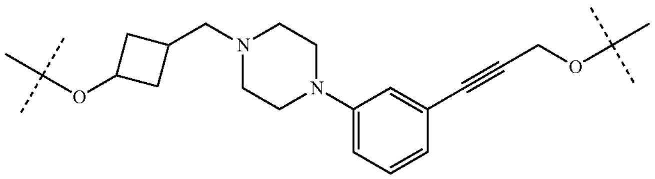
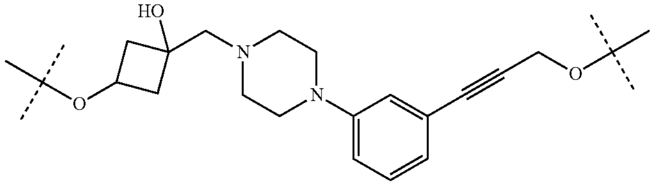
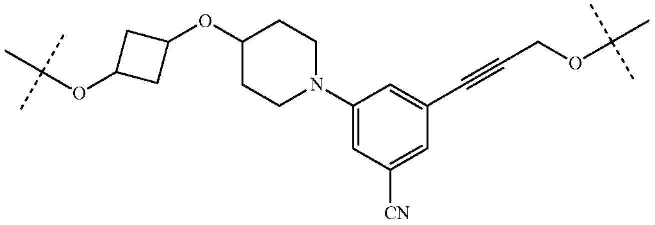
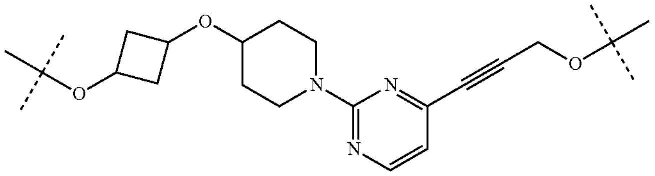
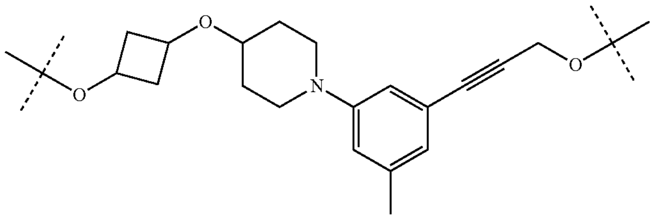
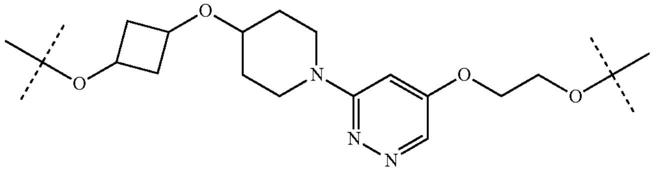
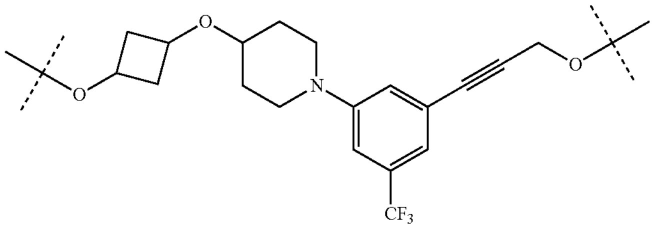
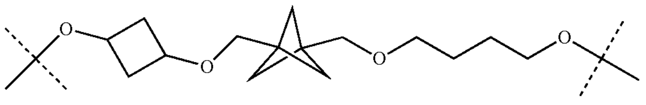
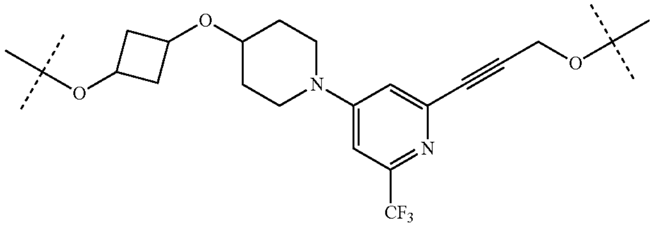

-continued
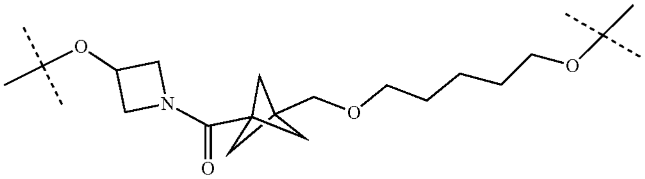
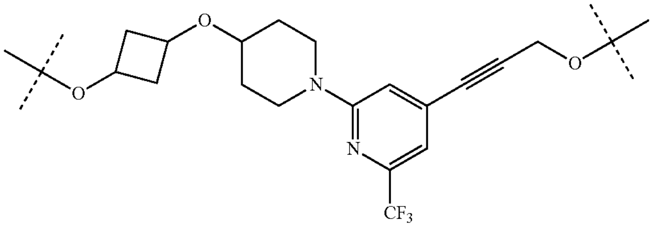
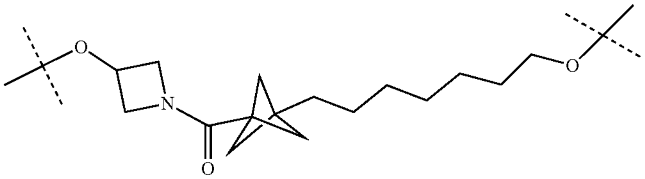
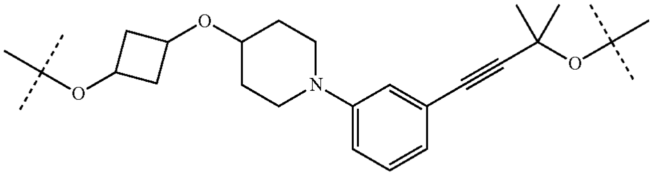
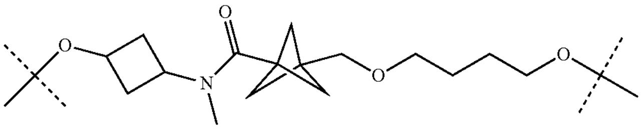
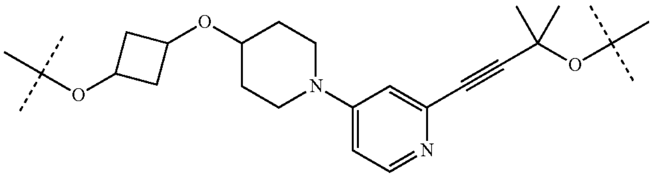
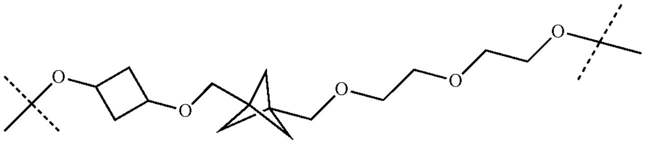
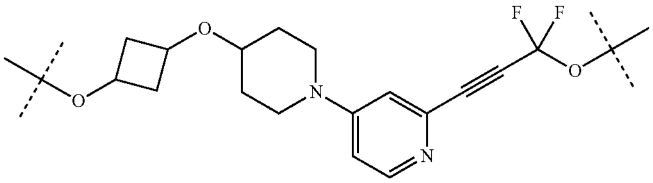
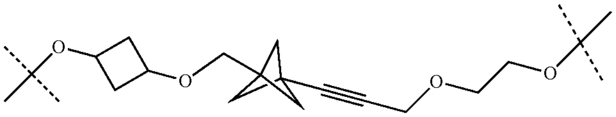
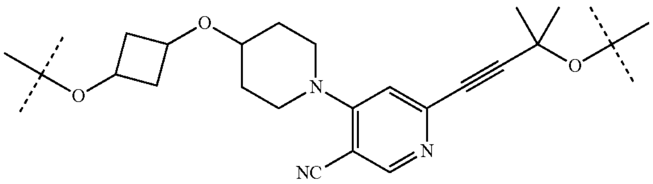

-continued
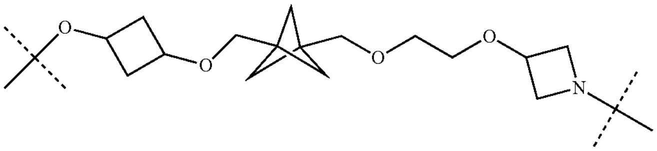
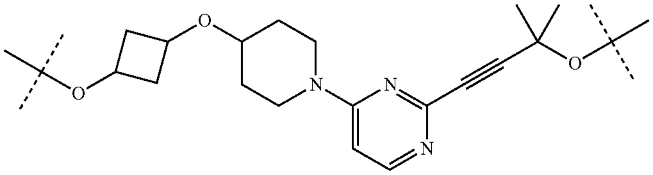
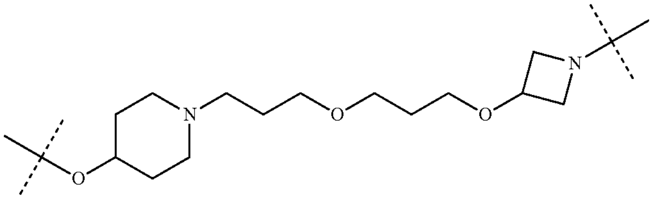
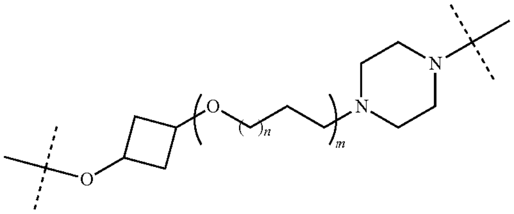
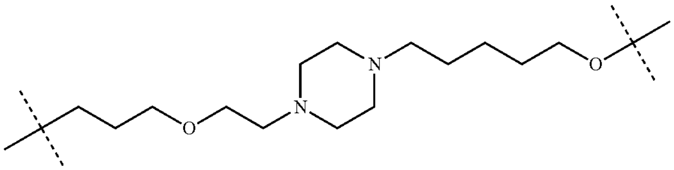
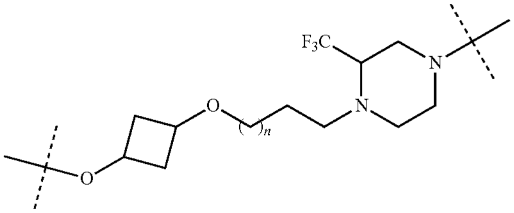
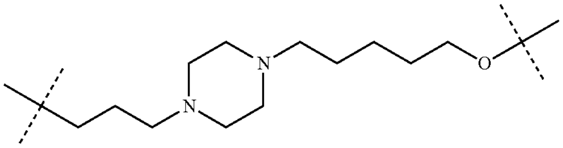
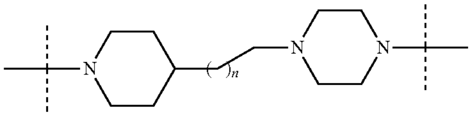
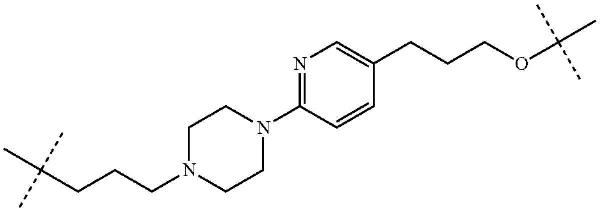
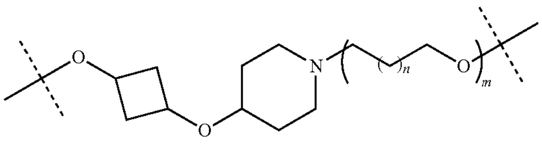
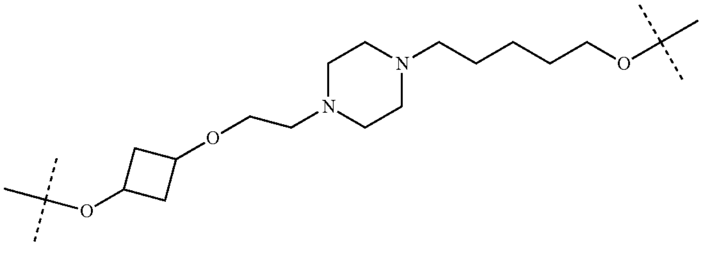

-continued
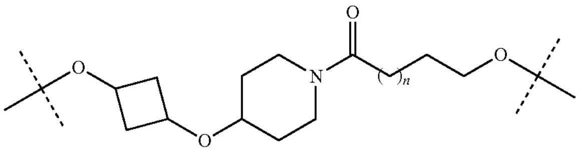
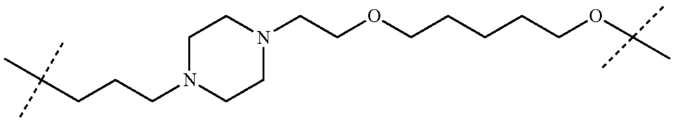
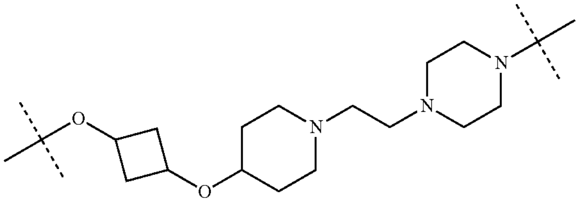
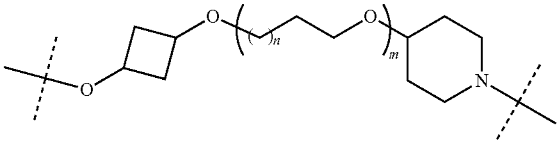
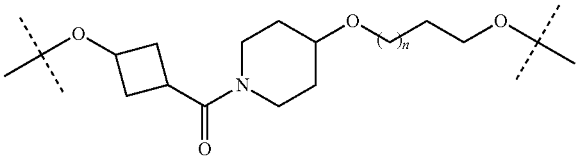
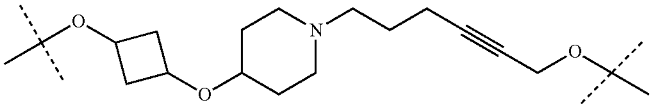
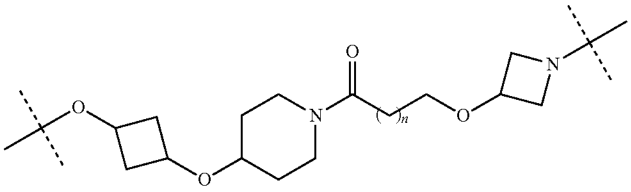
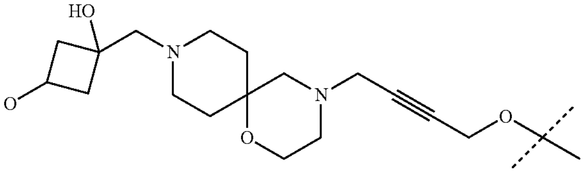
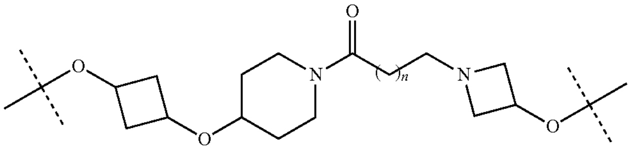
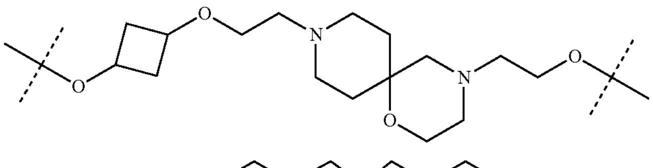
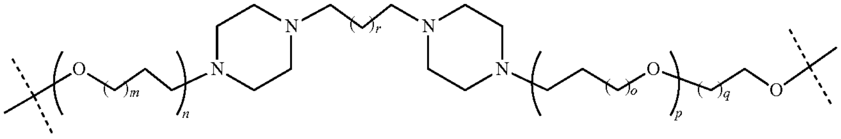
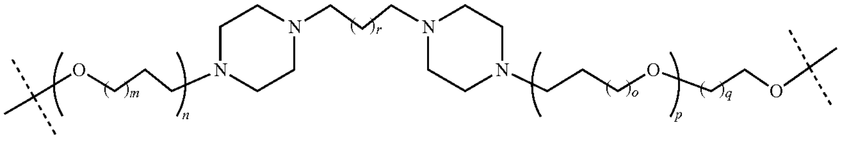

-continued
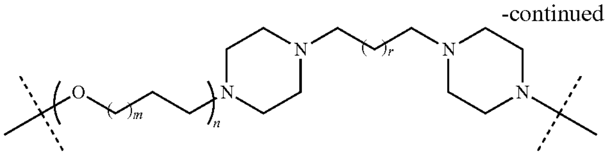
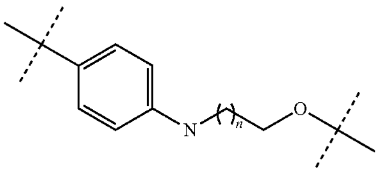
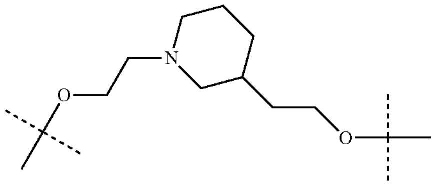
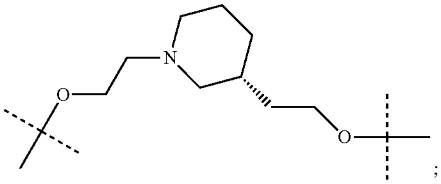
;
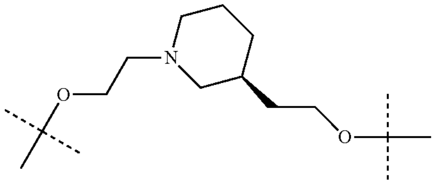
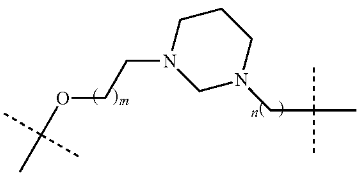
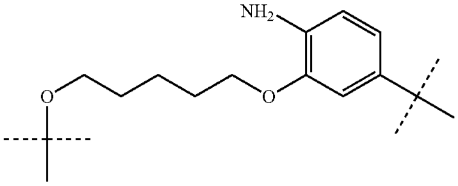
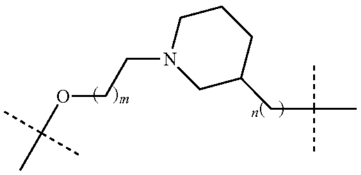
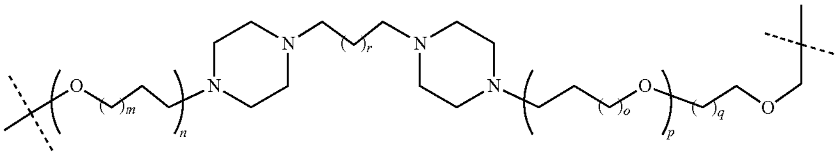
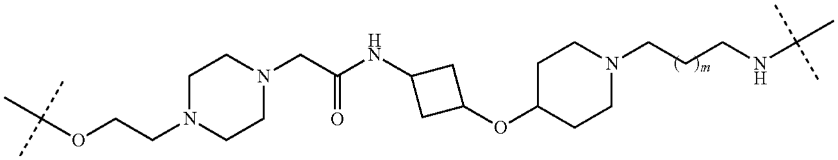
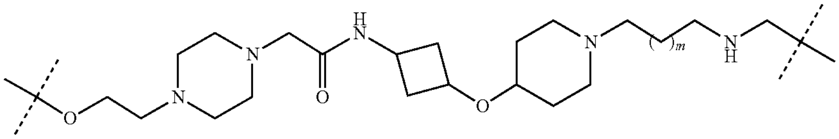
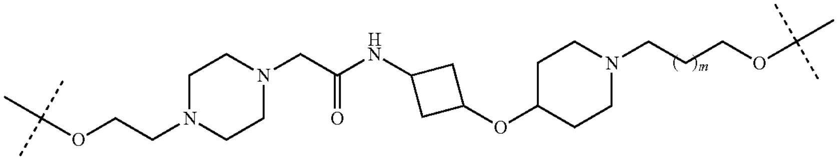
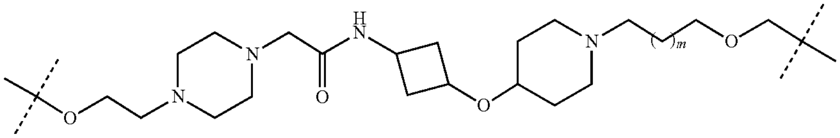
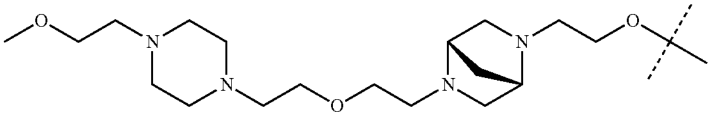

-continued
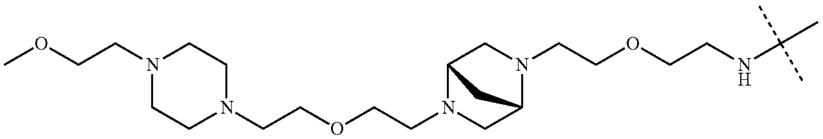
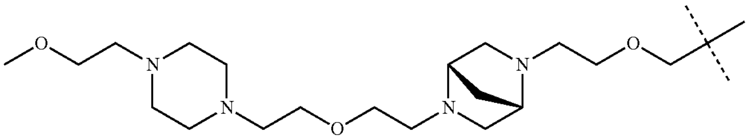
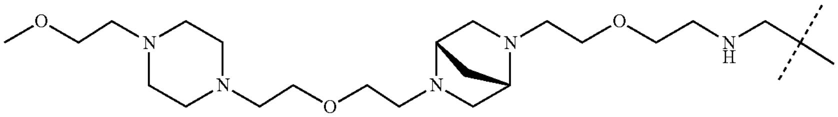
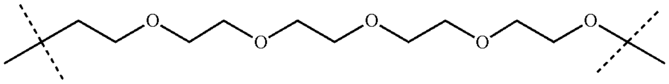
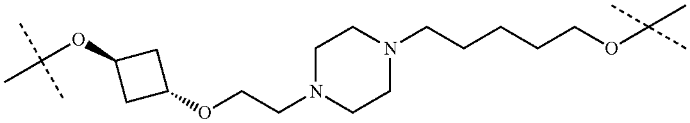
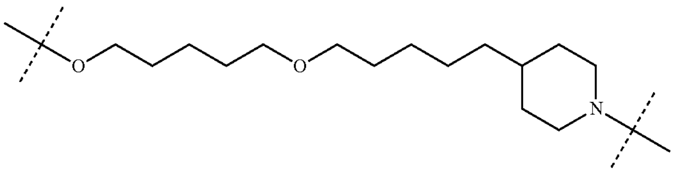
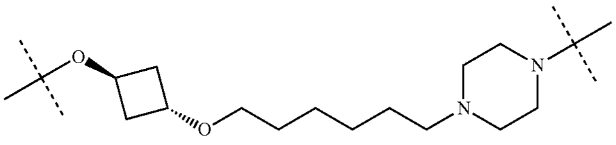
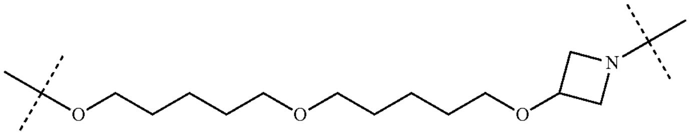
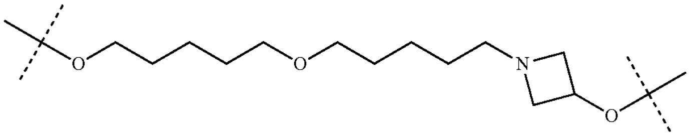
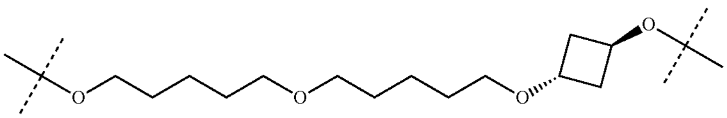
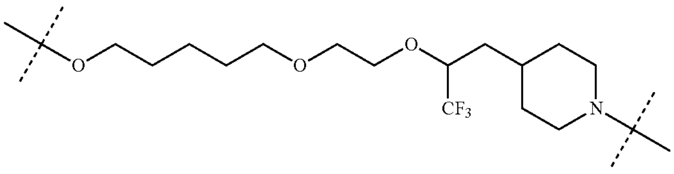
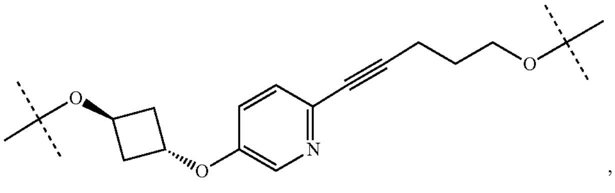
, wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
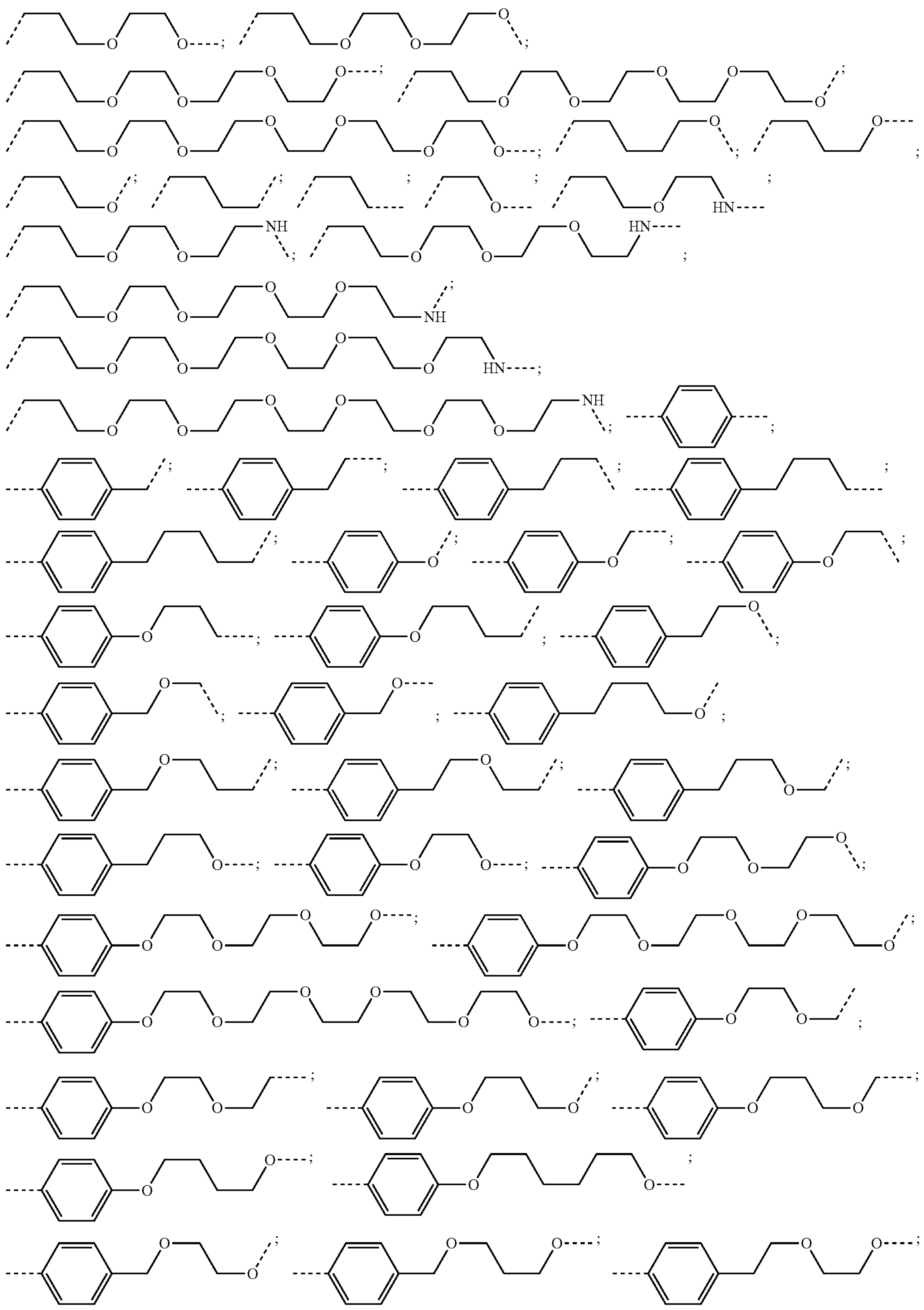

-continued
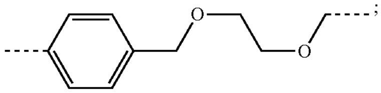;
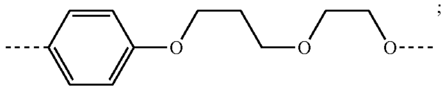;
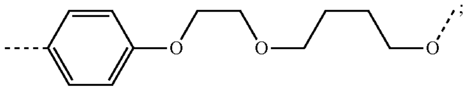;
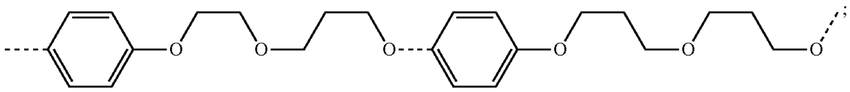;
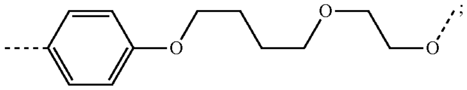;
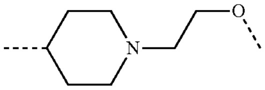;
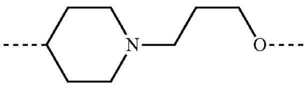;
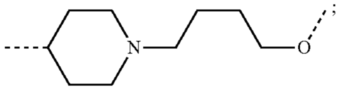;
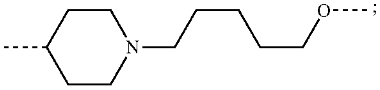;
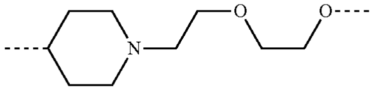;
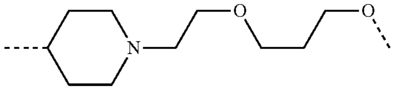;
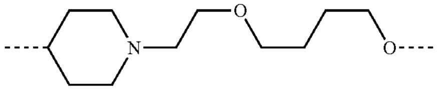;
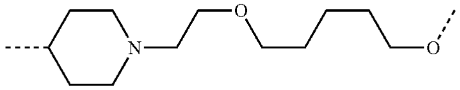;
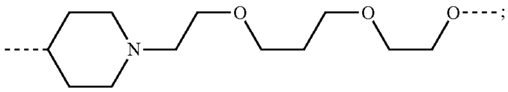;
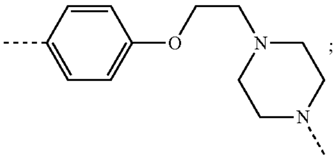;
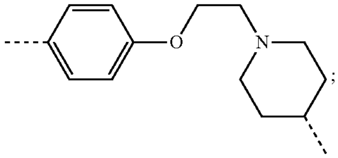;
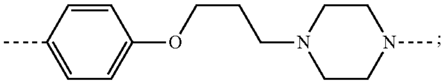;
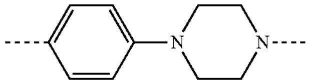;
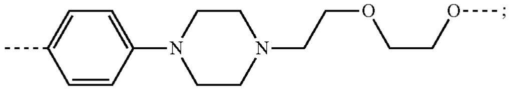;
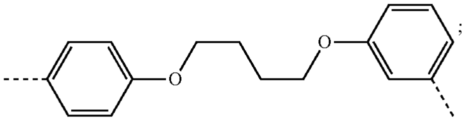;
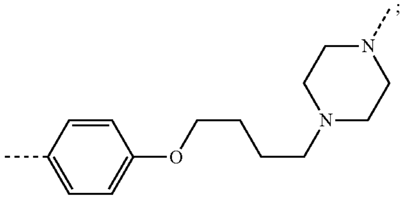;
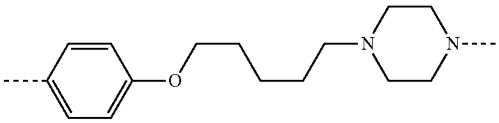;
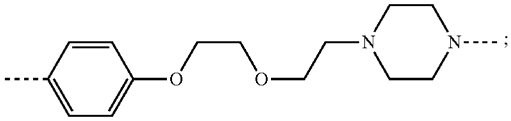;
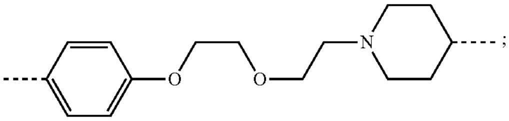;
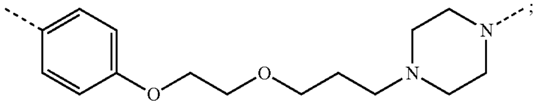;
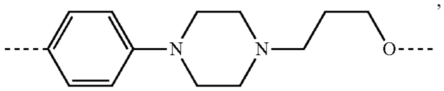;
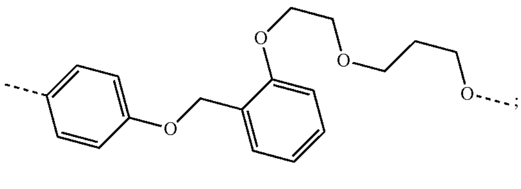;

-continued
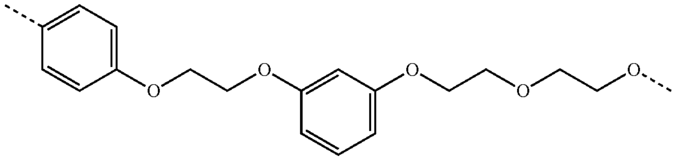
;
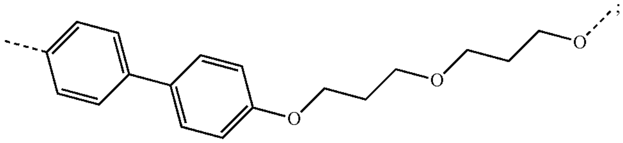
;
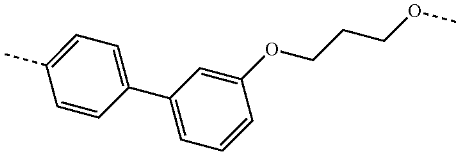
;
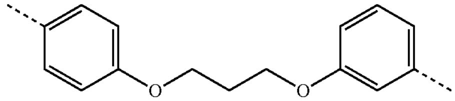
;
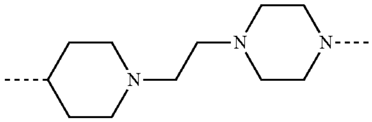
;
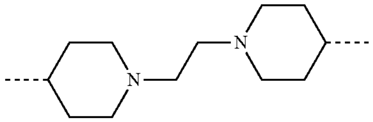
;
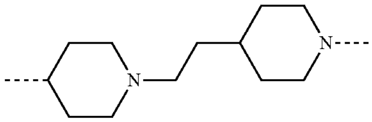
;
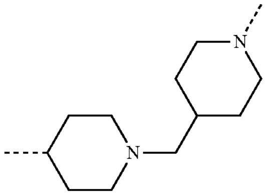
;
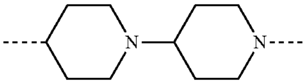
;
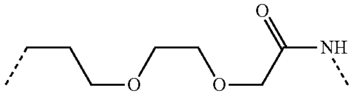
;
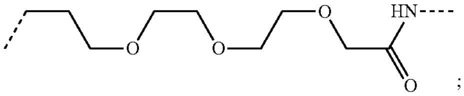
;
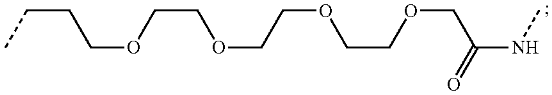
;
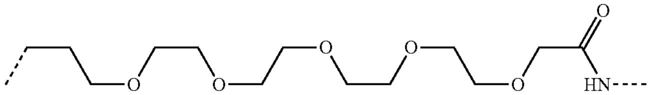
;
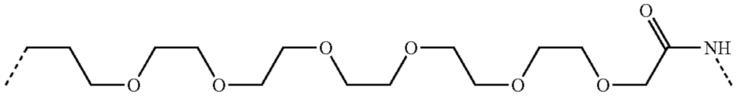
;
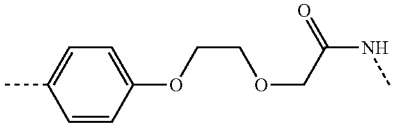
;
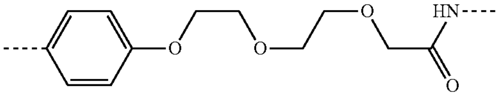
;
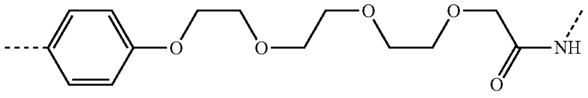
;
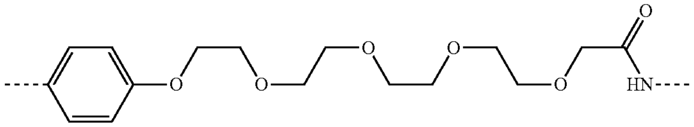
;
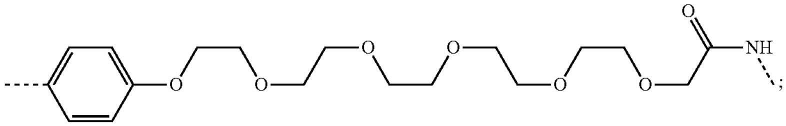
;

-continued
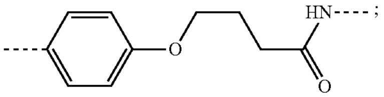
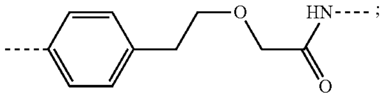
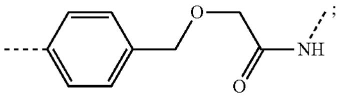
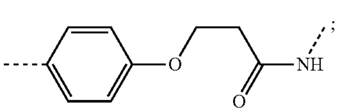
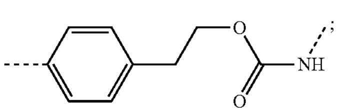
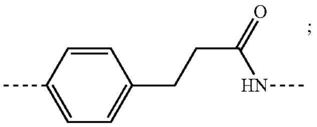
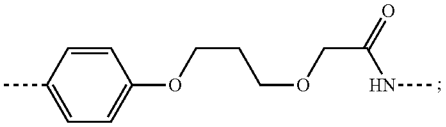
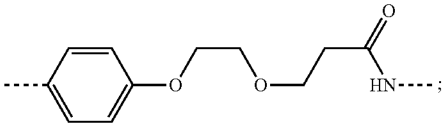
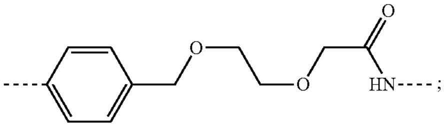
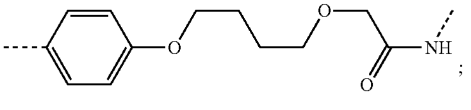
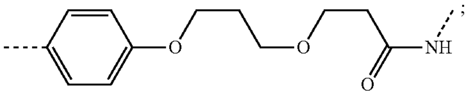
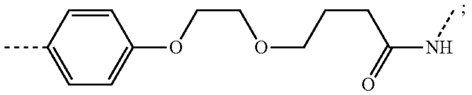
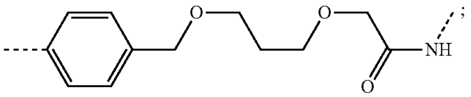
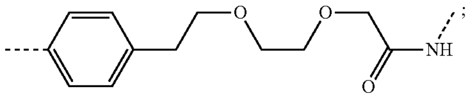
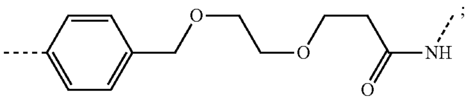
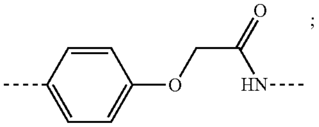
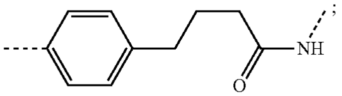
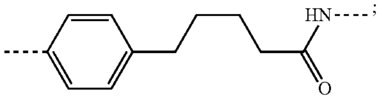
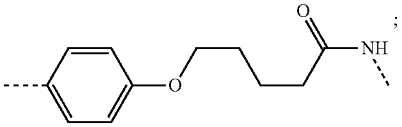
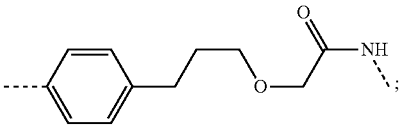
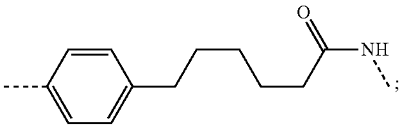
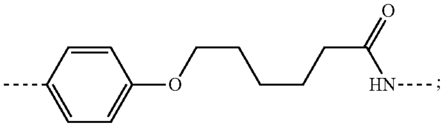
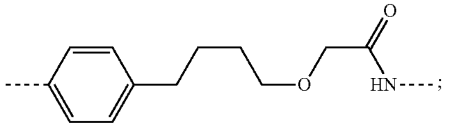
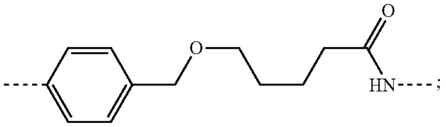
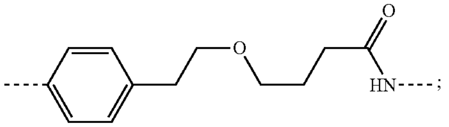
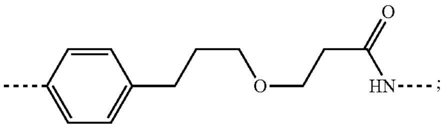
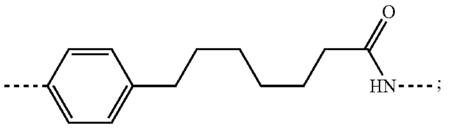
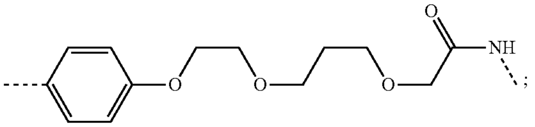
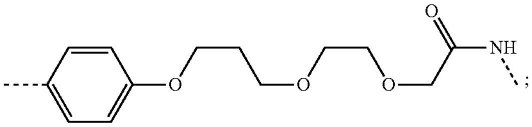
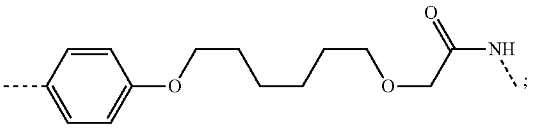
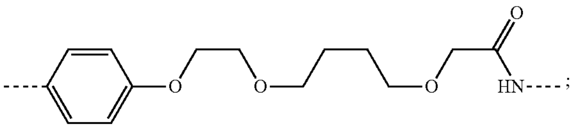

-continued
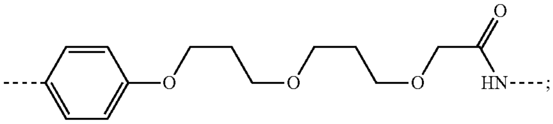
;
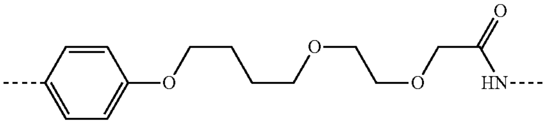
;
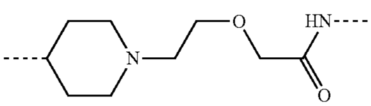
;
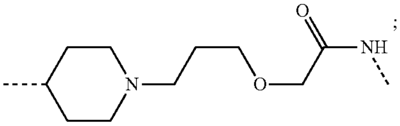
;
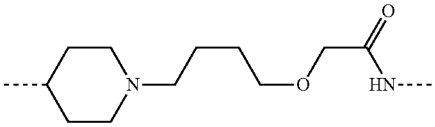
;
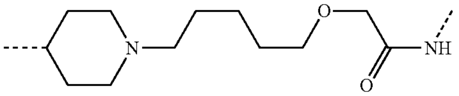
;
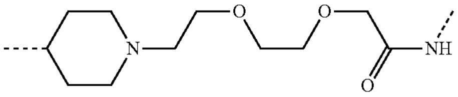
;
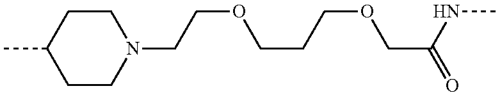
;
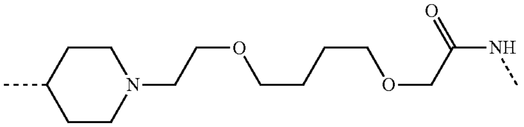
;
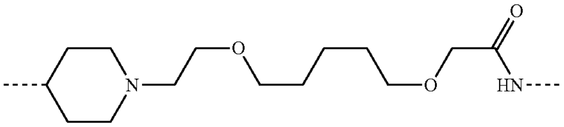
;
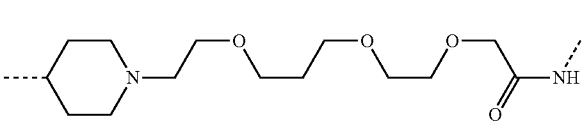
;
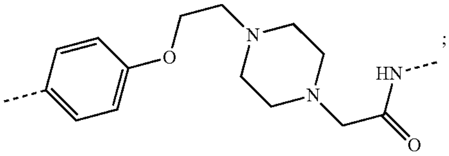
;
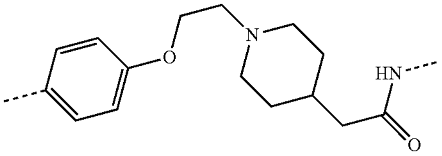
;
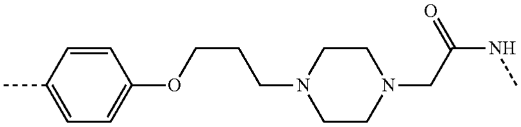
;
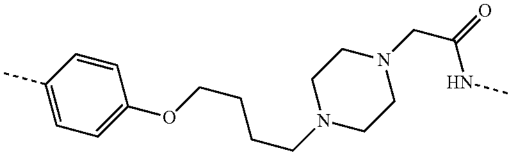
;
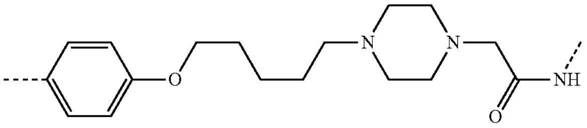
;
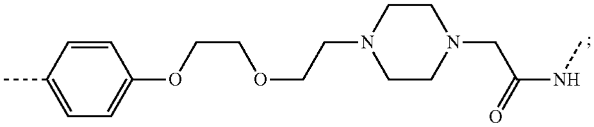
;
;
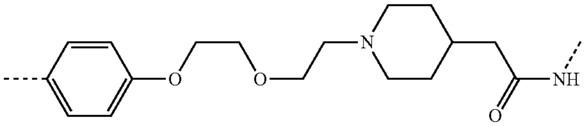
;
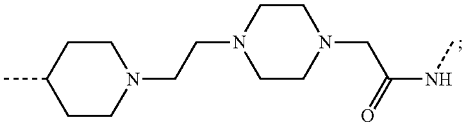
;
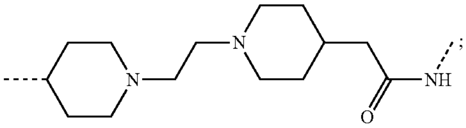
;
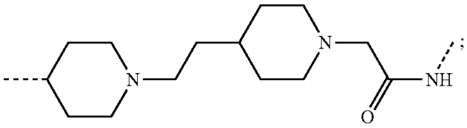
;
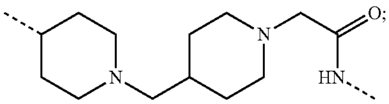
;
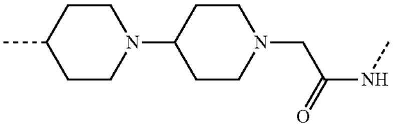
;
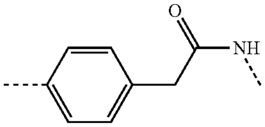
;
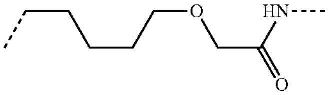
;
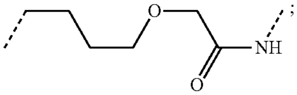
;
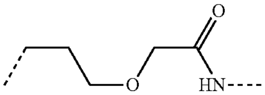

-continued
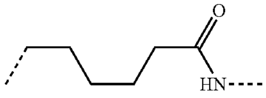 ; 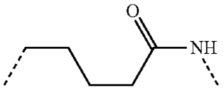 ; 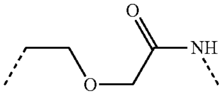 ; 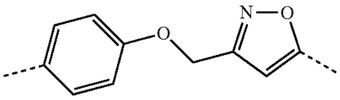 ;
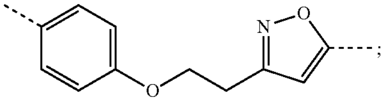 ; 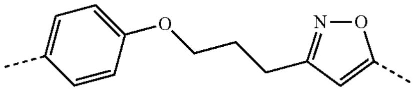 ;
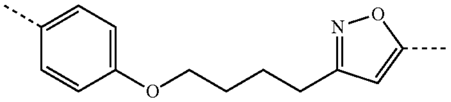 ; 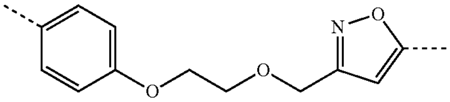 ;
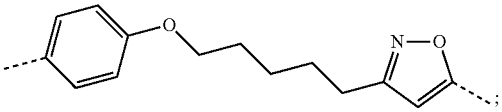 ; 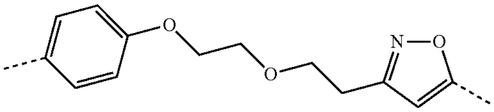 ;
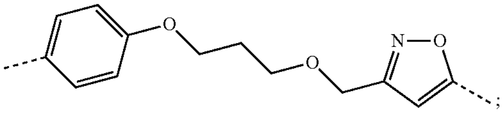 ; 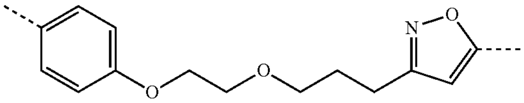 ;
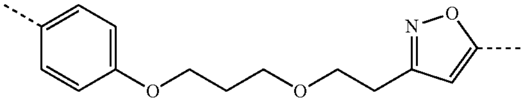 ; 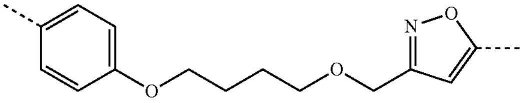 ;
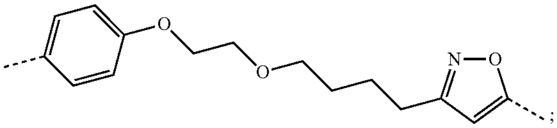 ; 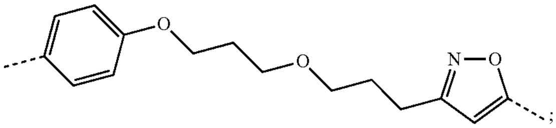 ;
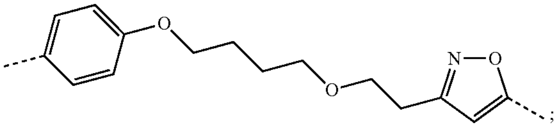 ; 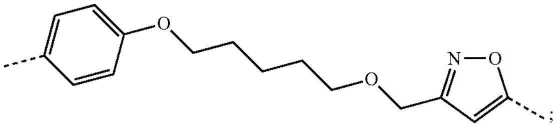 ;
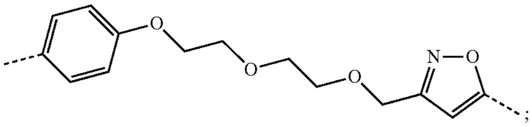 ; 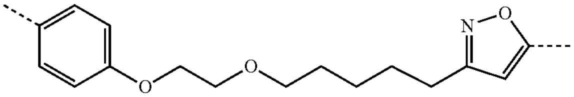 ;
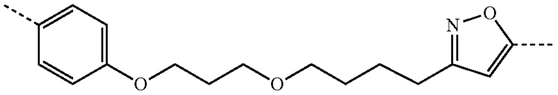 ; 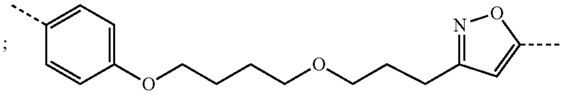 ;
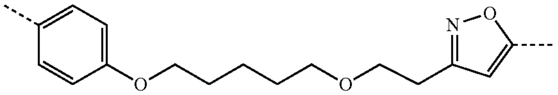 ; 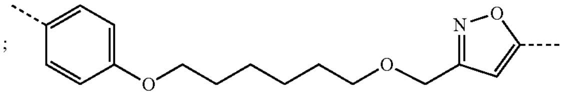 ;
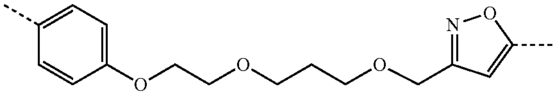 ; 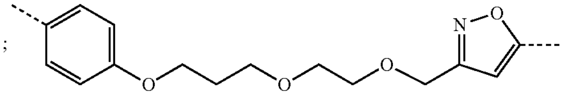 ;
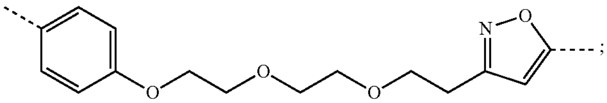 ; 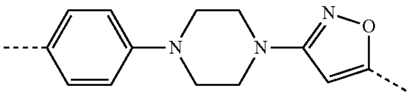 ;
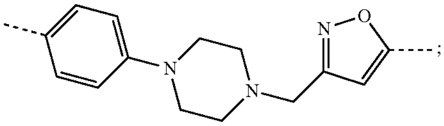 ; 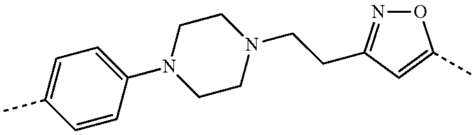 ;

-continued
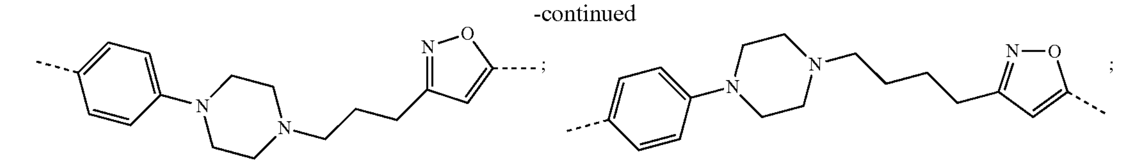
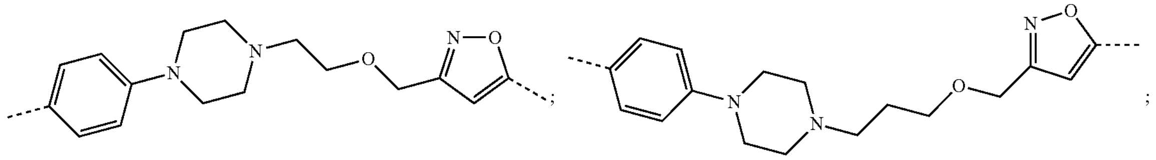
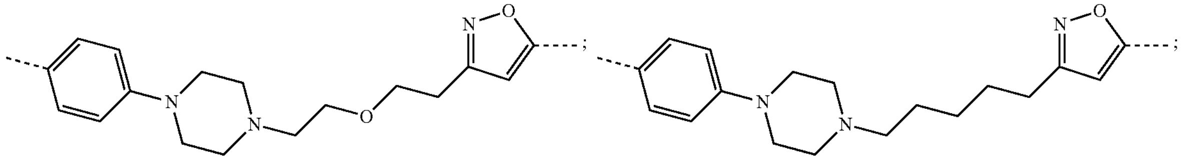
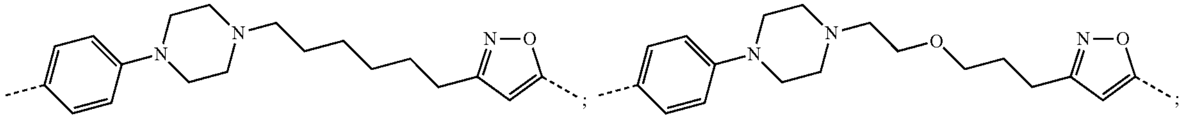
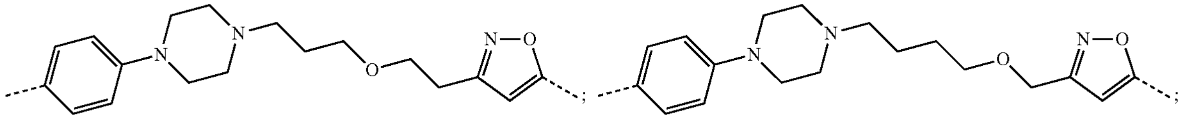
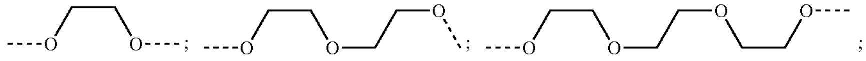
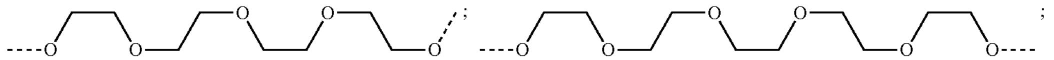
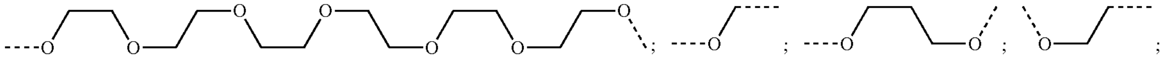
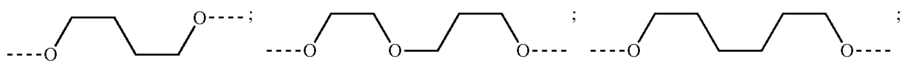
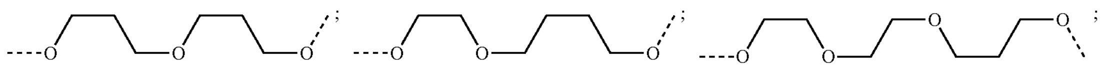
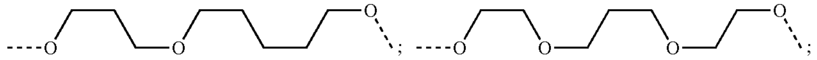
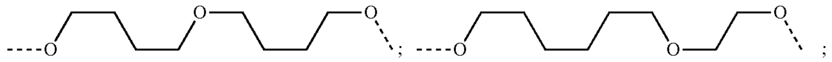
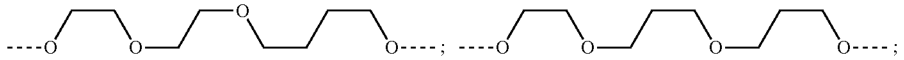
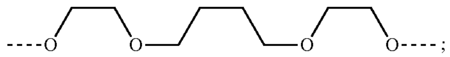
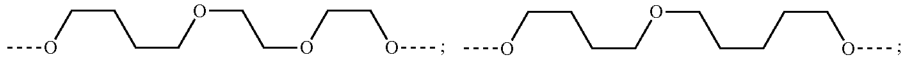
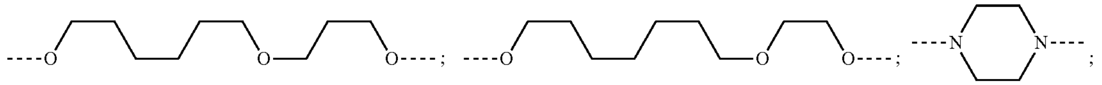
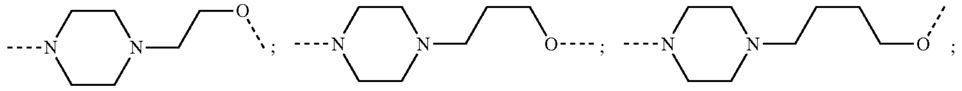
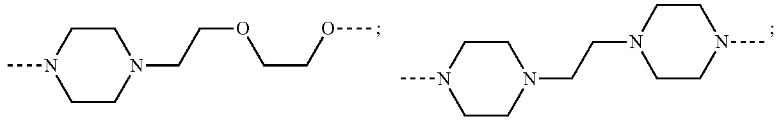
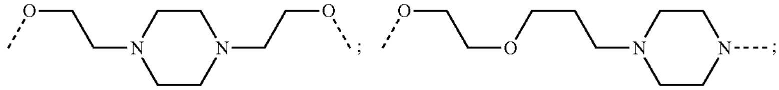

-continued
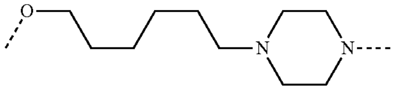;
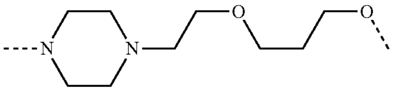;
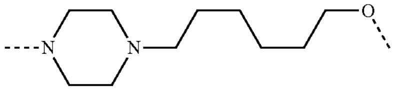;
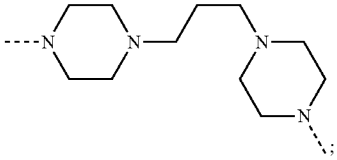;
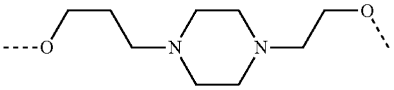;
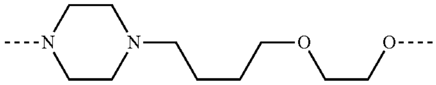;
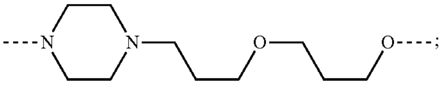;
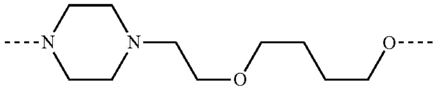;
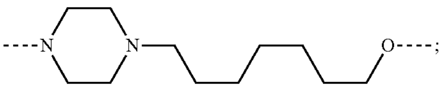;
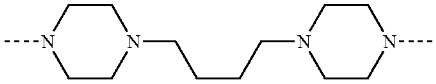;
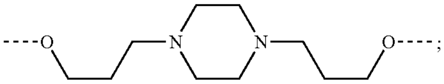;
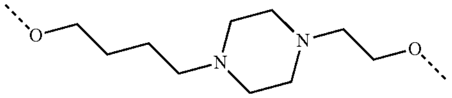;
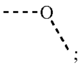;
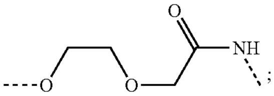;
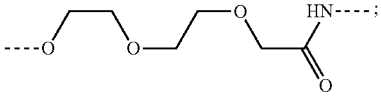;
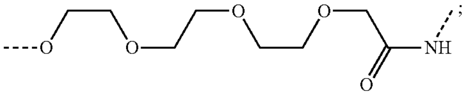;
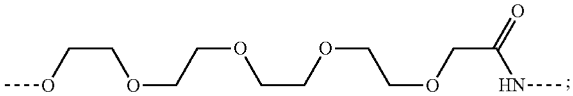;
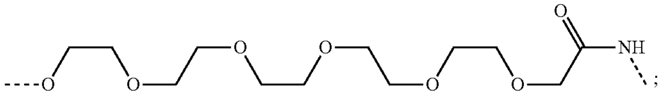;
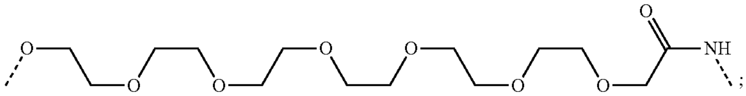;
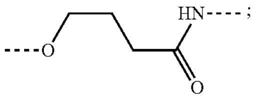;
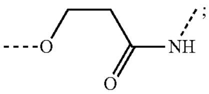;
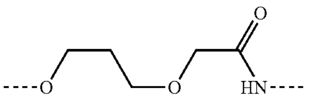;
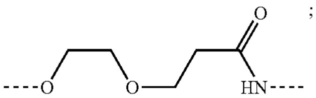;
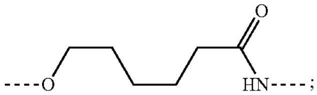;
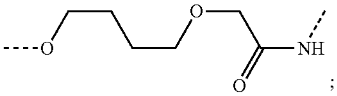;
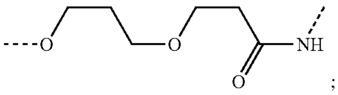;
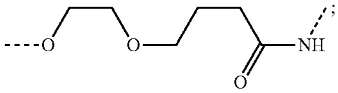;
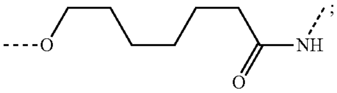;
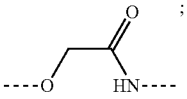;
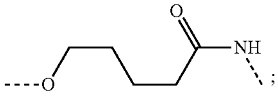;
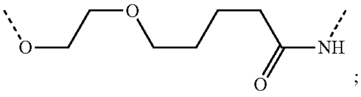;
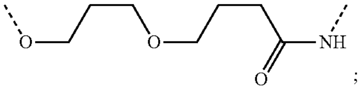;
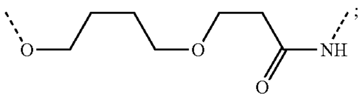;
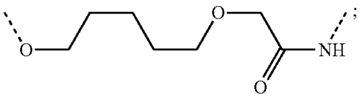;
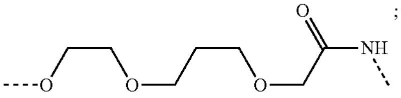;
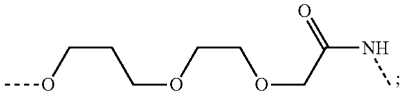;
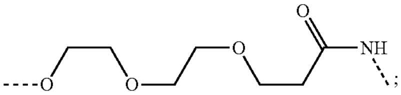;

-continued
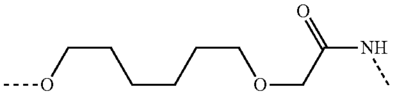; 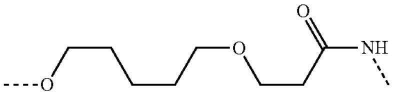;
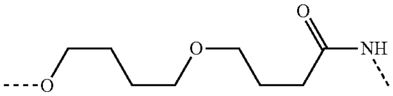; 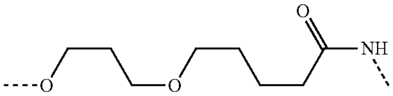;
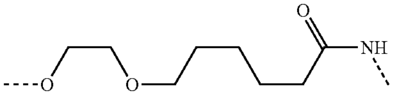; 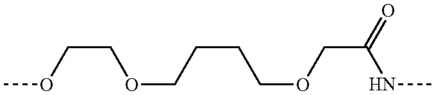;
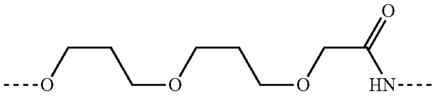; 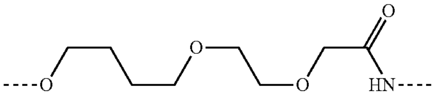;
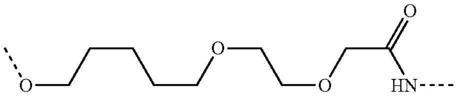; 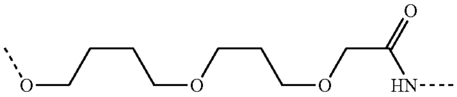;
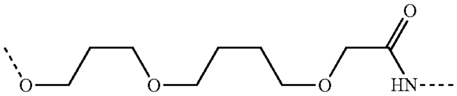; 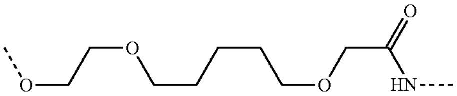;
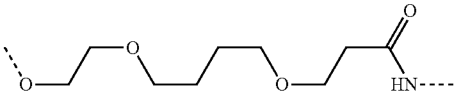; 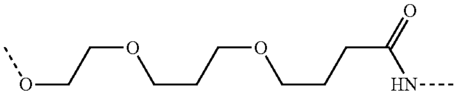;
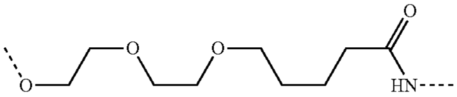; 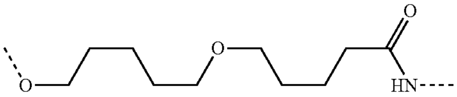;
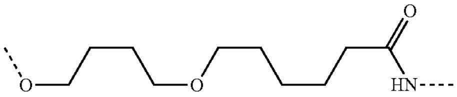; 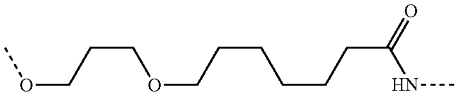;
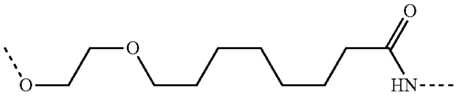; 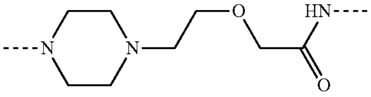;
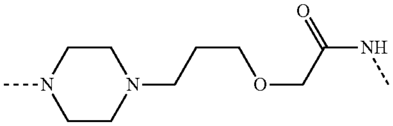; 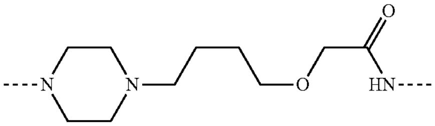;
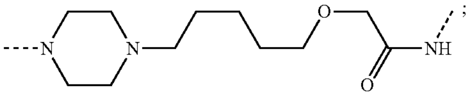; 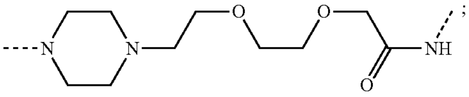;
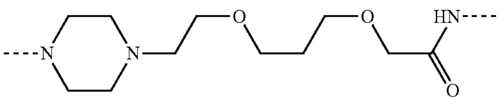; 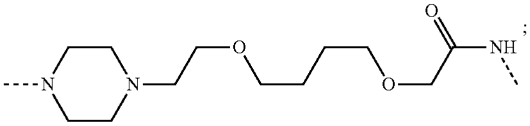;
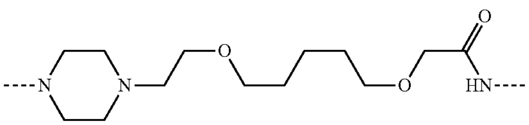; 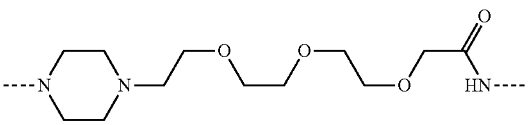;
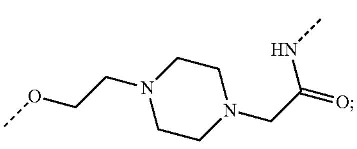; 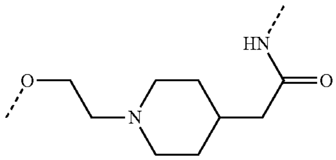; 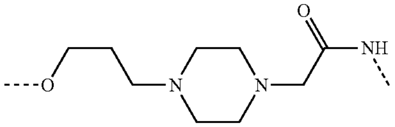;

-continued
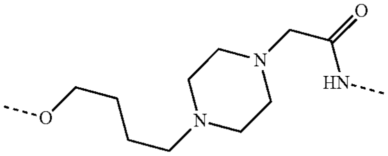 ; 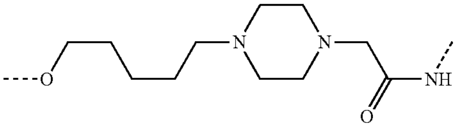 ;
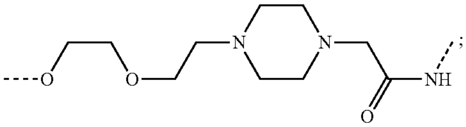 ; 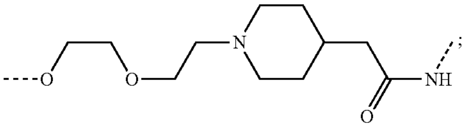 ;
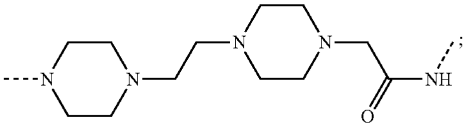 ; 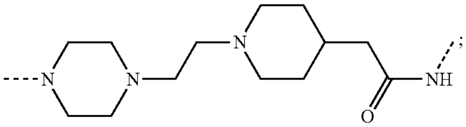 ;
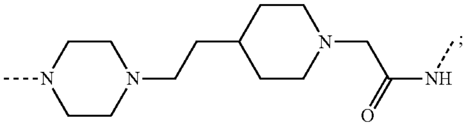 ; 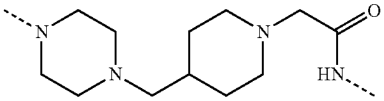 ;
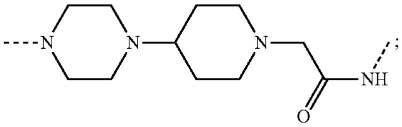 ; 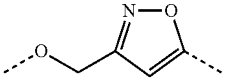 ; 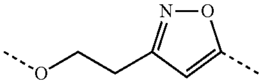 ;
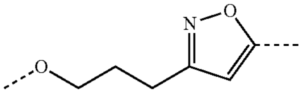 ; 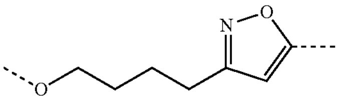 ; 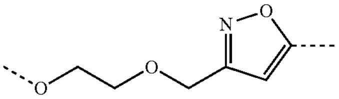 ;
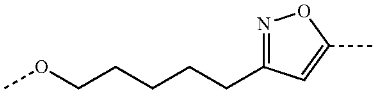 ; 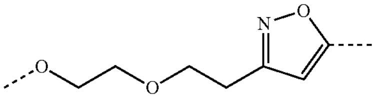 ;
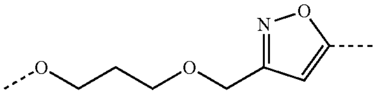 ; 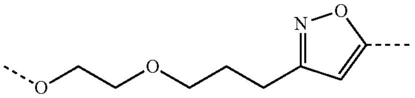 ;
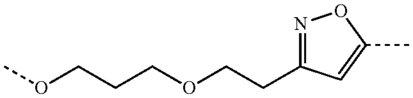 ; 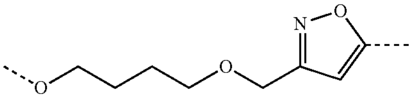 ;
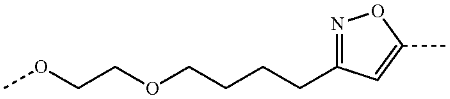 ; 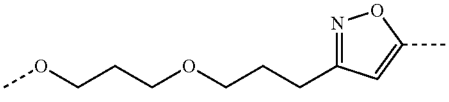 ;
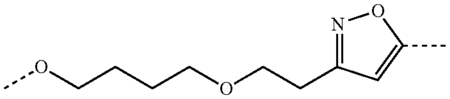 ; 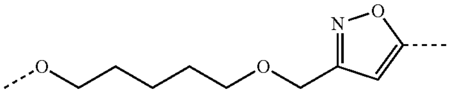 ;
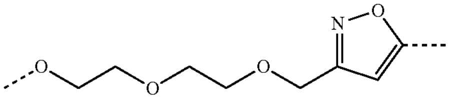 ; 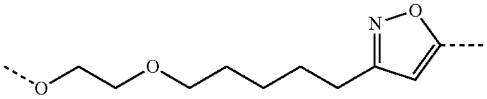 ;
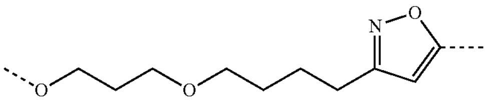 ; 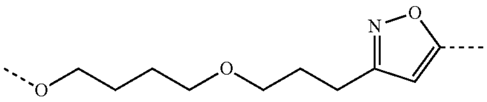 ;
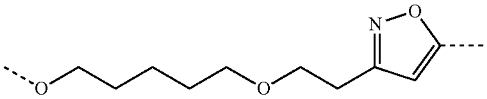 ; 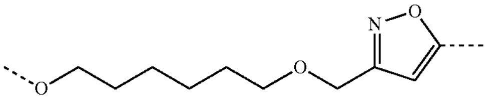 ;
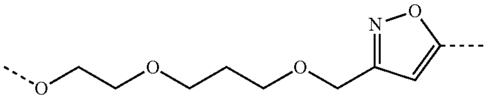 ; 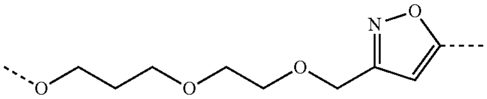 ;

-continued

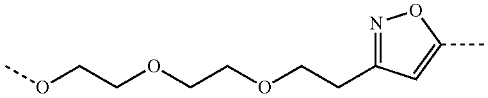 ; 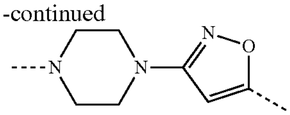 ; 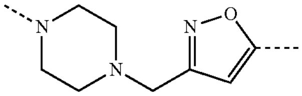 ;

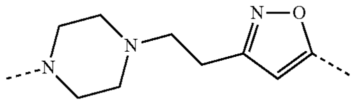 ; 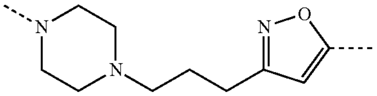 ;

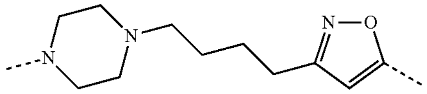 ; 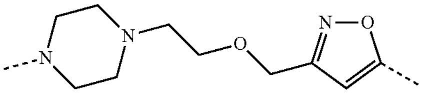 ;

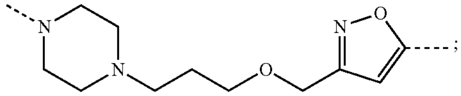 ; 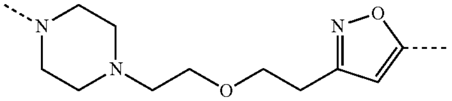 ;

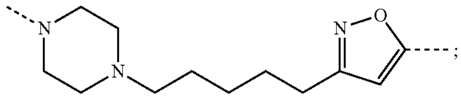 ; 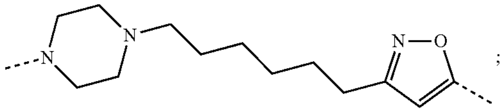 ;

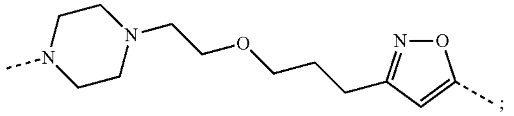 ; 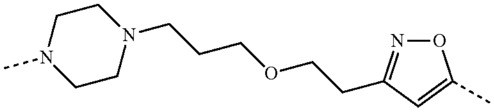 ;

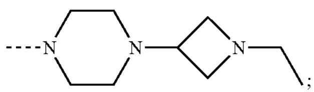 ; and 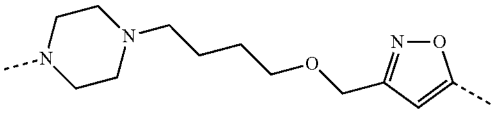 .

In any aspect or embodiment described herein, the linker (L) comprises a structure selected from, but not limited to the structure shown below, where a dashed line indicates the attachment point to the PTM or ULM moieties:

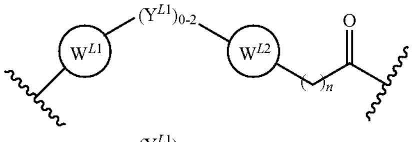 or

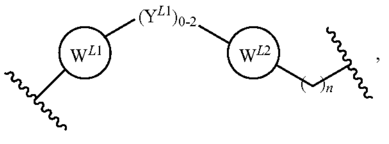 , wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;

$Y^{L1}$ is each independently a bond, optionally substituted linear or branched $C_1$-$C_6$ alkyl and optionally one or more C atoms are replaced with O; or optionally substituted linear or branched $C_1$-$C_6$ alkoxy;

n is 0-10; and

 indicates the attachment point to the PTM or ULM moieties.

In any aspect or embodiment described herein, the linker (L) comprises a structure selected from, but not limited to the structure shown below, where a dashed line indicates the attachment point to the PTM or ULM moieties:

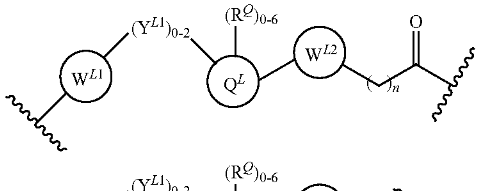

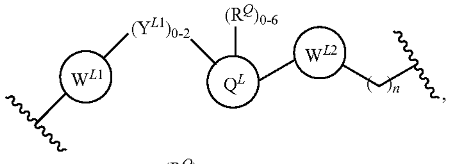 ,

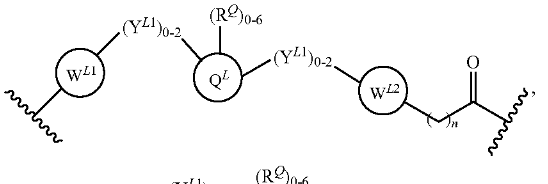 , or

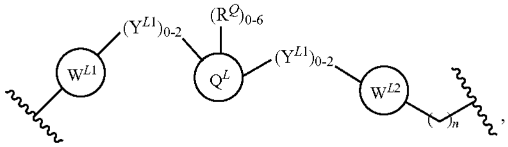 , wherein:

$W^1$ and $W^{L2}$ are each independently absent, aryl, heteroaryl, alicyclic, heterocyclic, $C_{1-6}$ alkyl and optionally one or more C atoms are replaced with O, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C ≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, optionally substituted linear or branched $C_{1-6}$ alkyl (e.g., optionally substituted by 1 or more halo or $C_{1-6}$ alkoxyl), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$alkyl (e.g., optionally substituted by 1 or more halo or $C_{1-6}$ alkoxyl), or $R^1$, $R^2$ together with the atom they are attached to, form a 3-8 membered ring system containing 0-2 heteroatoms;

n is 0-10; and

 indicates the attachment point to the PTM or ULM moieties.

In any aspect or embodiment described herein, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any aspect or embodiment described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein each carbon is optionally substituted with (1) a heteroatom selected from N, S, P, or Si atoms that has an appropriate number of hydrogens, substitutions, or both to complete valency, (2) an optionally substituted cycloalkyl or bicyclic cycloalkly, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linker or adjacently located).

In any aspect or embodiment describe herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally substituted with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$═$CR^{L2}$, C≡C, $SiR^{L1}R^{L2}$, $P(O)R^{L1}$, $P(O)OR^{L1}$, $NR^{L3}C$(═NCN)$NR^{L4}$, $NR^{L3}C$(═NCN), $NR^{L3}C(═CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heteocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{12}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^L$ and RV are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC≡C_{1-8}$ alkyl, CCH, CH═CH($C_{1-8}$alkyl), C($C_{1-8}$alkyl)═CH($C_{1-8}$alkyl), $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$. In any aspect or embodiment described herein, the linker (L) does not have heteroatom-heteroatom bonding (e.g., no heteroatoms are covalently linker or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

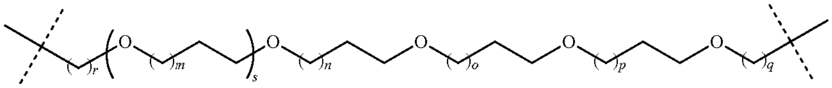
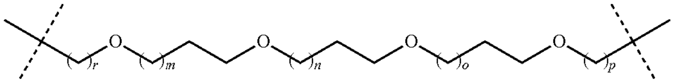
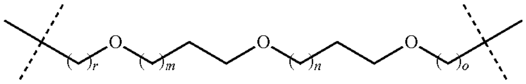
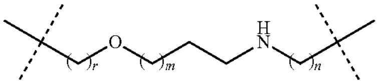
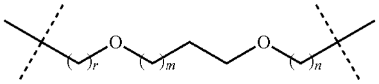
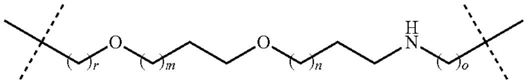
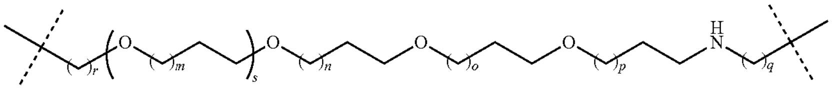
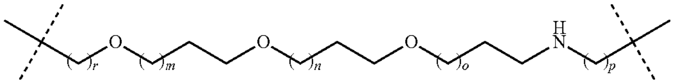
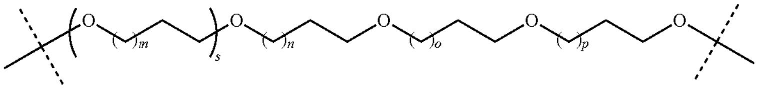
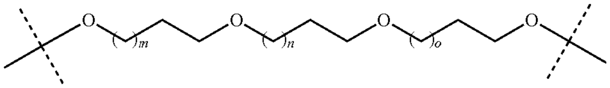
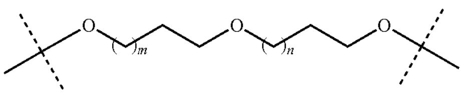
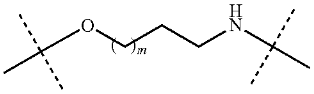
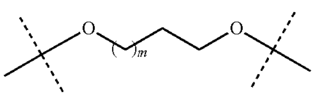
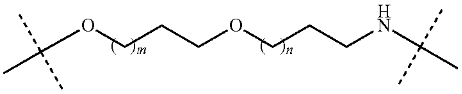
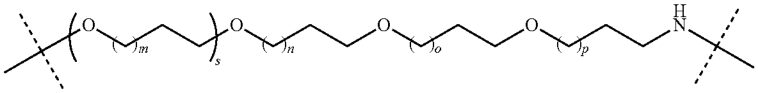
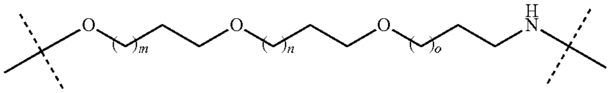
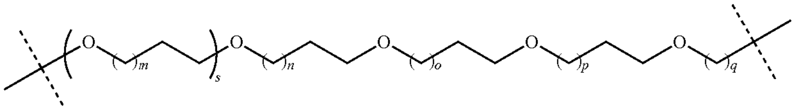
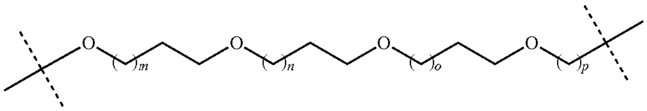
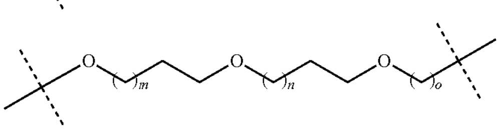
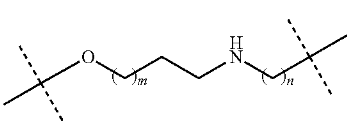
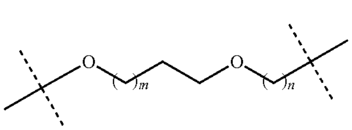
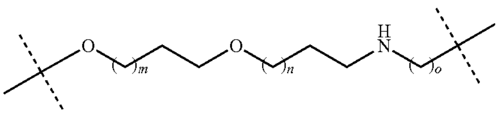
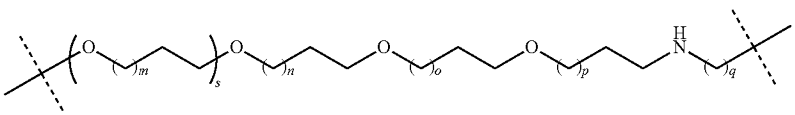

-continued

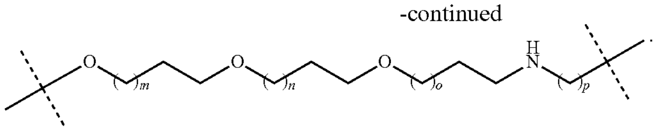

wherein carbon or oxygen may be substituted with a heteroatom selected from N, S, P, or Si atoms with an appropriate number of hydrogens to complete valency, and m, n, o, p, q, r, and s are independently selected from 0, 1, 2, 3, 4, 5, 6, 7, 8, 9, 10, 11, 12, 13, 14, 15, 16, 17, 18, 19, and 20.

In any aspect or embodiment described herein, the present disclosure is directed to a compound which comprises a PTM group as described above, which binds to a target protein or polypeptide (e.g., α-synuclein), which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In any aspect or embodiment described herein, the linker group L is a group comprising one or more covalently connected structural units independently selected from the group consisting of:

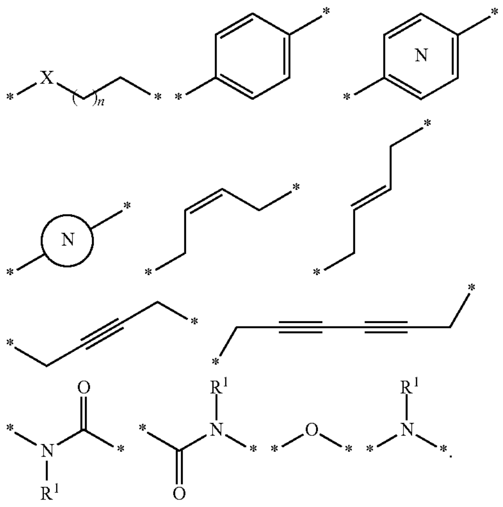

The X is selected from the group consisting of O, N, S, S(O) and $SO_2$; n is integer from 1 to 5; $R^{L1}$ is hydrogen or alkyl,

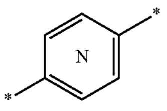

is a mono- or bicyclic aryl or heteroaryl optionally substituted with 1-3 substituents selected from alkyl, halogen, haloalkyl, hydroxy, alkoxy or cyano;

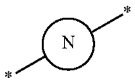

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term “protein” includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to a protein specifically (binds to a target protein) and includes the following non-limiting examples of small molecule target protein moieties: Hsp90 inhibitors, α-synuclein inhibitor or ligand, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation and/or inhibition of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., α-synucleinopathies or neurological neurodegenerative disease or disorder. In certain additional embodiments, the disease is Parkinson's Disease, Alzheimer's Disease, dementia (e.g., dementia with Lewy bodies), or multiple system atrophy.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including neurological or neurodegenerative diseases or disorders, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE 1, PDEII, PDEIII, squalene cyclase inhibitor. CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, α-synuclein, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras/Raf/MEK/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include haloalkane halogenase inhibitors, Hsp90 inhibitors, α-synuclein inhibitor or ligand, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

The compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM is represented by Formulas $I_{PTM}$ through $VIII_{PTM}$ (e.g., $I_{PTM}$, $IA_{PTM}$, $IB_{PTM}$, $II_{PTM}$, $IIA_{PTM}$, $IIB_{PTM}$, $IIIA_{PTM}$, $IIIB_{PTM}$, $IIIC_{PTM}$, $IIID_{PTM}$, $IV_{PTM}$, $IVA_{PTM}$, $IVB_{PTM}$, $IVC_{PTM}$, $IVD_{PTM}$, $V_{PTM}$, $VA_{PTM}$, $VB_{PTM}$, $VC_{PTM}$, $VI_{PTM}$, $VIA_{PTM}$, $VIB_{PTM}$, $VIC_{PTM}$, $VID_{PTM}$, $VIE_{PTM}$, $VII_{PTM}$, $VIIA_{PTM}$, $VIIB_{PTM}$, $VIIC_{PTM}$, $VIID_{PTM}$, $VIII_{PTM}$, $VIIIA_{PTM}$, $VIIIB_{PTM}$, $VIIIC_{PTM}$, $VIIID_{PTM}$, $VIIIE_{PTM}$, $IX_{PTM}$, $IXA_{PTM}$, $IXB_{PTM}$, $IXC_{PTM}$, $IXD_{PTM}$, and $IXE_{PTM}$):

Formula $I_{PTM}$

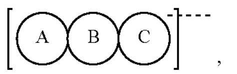

-continued

Formula $IA_{PTM}$

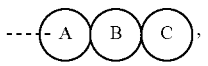

Formula $IB_{PTM}$

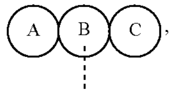

Formula $II_{PTM}$

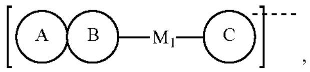

Formula $IIA_{PTM}$

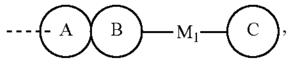

Formula $IIB_{PTM}$

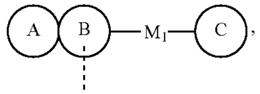

Formula $IIC_{PTM}$

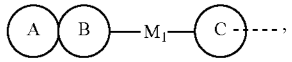

Formula $IIIA_{PTM}$

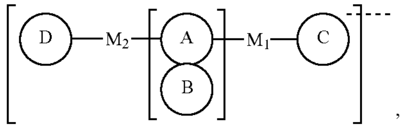

Formula $IIIB_{PTM}$

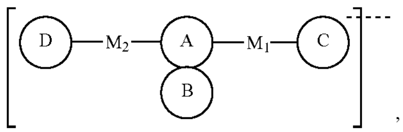

Formula $IIIC_{PTM}$

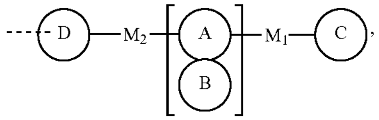

Formula $IIID_{PTM}$

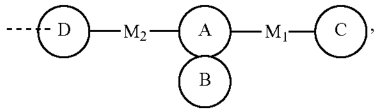

Formula $IV_{PTM}$

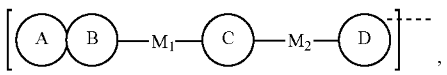

Formula $IVA_{PTM}$

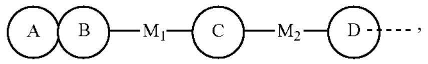

Formula $IVB_{PTM}$

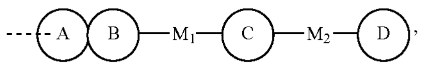

Formula $IVC_{PTM}$

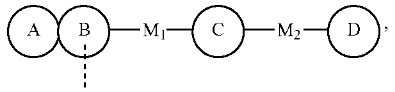

-continued

Formula IVD$_{PTM}$

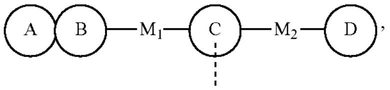

Formula V$_{PTM}$

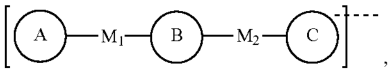

Formula VA$_{PTM}$

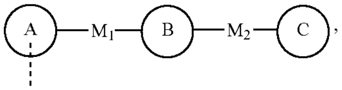

Formula VB$_{PTM}$

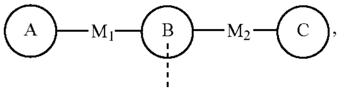

Formula VI$_{PTM}$

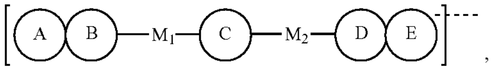

Formula VIA$_{PTM}$

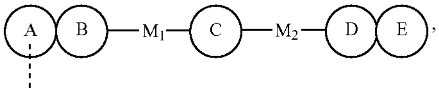

Formula VIB$_{PTM}$

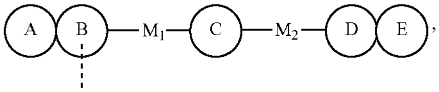

Formula VIC$_{PTM}$

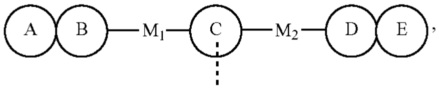

Formula VID$_{PTM}$

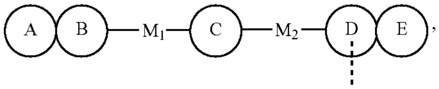

Formula VIE$_{PTM}$

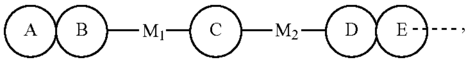

Formula VII$_{PTM}$

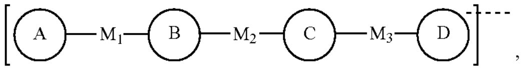

Formula VIIA$_{PTM}$

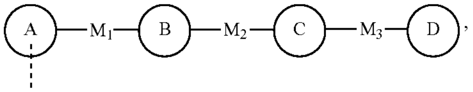

Formula VIIB$_{PTM}$

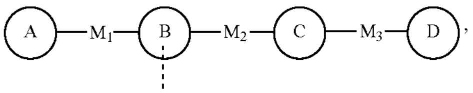

-continued

Formula VIIC$_{PTM}$

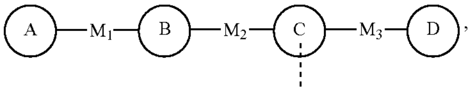

Formula VIID$_{PTM}$

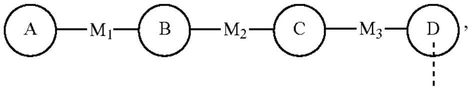

Formula VIII$_{PTM}$

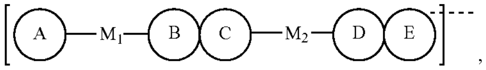

Formula VIIIA$_{PTM}$

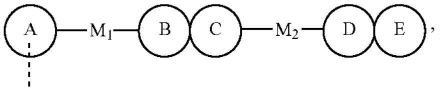

Formula VIIIB$_{PTM}$

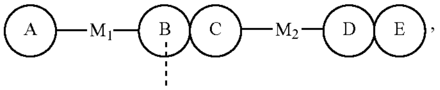

Formula VIIIC$_{PTM}$

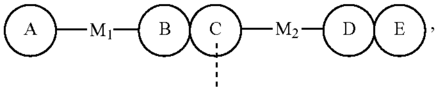

Formula VIIID$_{PTM}$

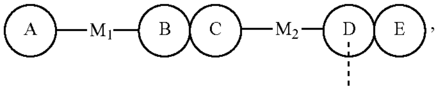

Formula VIIIE$_{PTM}$

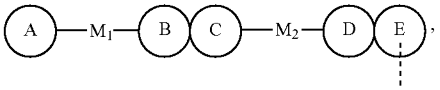

Formula IX$_{PTM}$

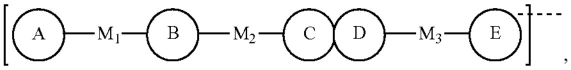

Formula IXA$_{PTM}$

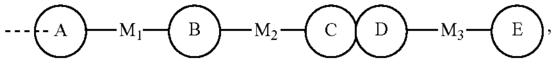

Formula IXB$_{PTM}$

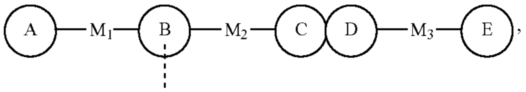

Formula IXC$_{PTM}$

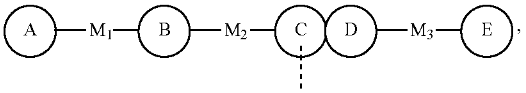

Formula IXD$_{PTM}$

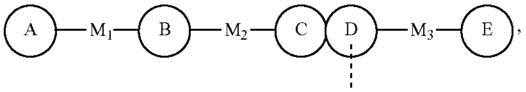

-continued

Formula $IXE_{PTM}$

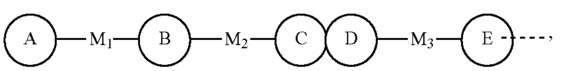

wherein:

A, B, C, D, and E are independently an optionally substituted 5- or 6-membered aryl or heteroaryl rings (e.g., a 5- or 6-membered aryl or heteroaryl, each optionally substituted with 1, 2, 3, or 4 substituents selected from H, alkyl, O, N, halogen, haloalkyl, alkoxy, hydroxy, carbonyl, amino, alkylamino, dialkylamino, cyano, nitro, —$SO_2$—) or an optionally substituted 4- to 7-membered cycloalkyl or heterocycloalkyl (e.g., an 4- to 7-membered cycloalkyl or heterocycloalkyl, optionally substituted with 1, 2, 3, or 4 substituted selected from H, alkyl such as a C1-C6 alkyl, O, N, halogen, haloalkyl, such as a C1-C6 haloalkyl, alkoxy, hydroxy, carbonyl, amino, alkylamino, dialkylamino, cyano, nitro, —$SO_2$—), wherein contact between circles indicates ring fusion and each of $M_3$ and $M_4$ may be attached to $A_1$ or $B_1$ (i.e., $M_3$ may be attached to $A_1$ or attached to $B_1$) or $D_1$ and E (i.e., $M_4$ may be attached to $D_1$ or attached to E);

$M_1$, $M_2$ and $M_3$ are independently selected from: a single bond; O—; —S—; —$NR^{100}$—; —$SO_2$—; —S(O)—; —$SO_2$NH—; —C(O)—; —C(O)NH—; an optionally substituted alkyl wherein a carbon of the alkyl group may be replaced with a group independently selected from —O—, —S—, —$NR^{100}$—, —$SO_2$—, —S(O)—, —$SO_2$NH—, —C(O)— or —C(O)NH— (e.g., the alkyl group is optionally substituted by a halogen, amino, alkyl or a haloalkyl, such as a C1-C6 alkyl or haloalkyl), an alkenyl fragment (e.g., —CH═CH—), an alkynyl fragment (e.g., —C≡C—), a two to four carbon conjugated alkenyl or alkynyl fragments (e.g., —CH═CH—CH═CH—, —C≡C—C≡C—, or —CH═CH—C≡C—), or an alkyl group (e.g., —$CH_2$—), wherein at least one of the carbon of the alkenyl or alkynyl group may be part of A, B, C, or D;

each $R^{100}$ is independently selected from H, an optionally substituted alkyl (e.g., optionally substituted C1-C6 alkyl), an optionally substituted halolakyl (e.g., optionally substituted C1-C6 haloalkyl); and --- indicates the attachment of a chemical linker moiety or a ULM (e.g., VLM or CLM).

In any aspect or embodiment described herein, the PTM is selected according to formulas $I_{PTM}$ through $VIII_{PTM}$ (e.g., $I_{PTM}$, $IA_{PTM}$, $IB_{PTM}$, $II_{PTM}$, $IIA_{PTM}$, $IIB_{PTM}$, $IIIA_{PTM}$, $IIIB_{PTM}$, $IIIC_{PTM}$, $IIID_{PTM}$, $IV_{PTM}$, $IVA_{PTM}$, $IVB_{PTM}$, $IVC_{PTM}$, $IVD_{PTM}$, $V_{PTM}$, $VA_{PTM}$, $VB_{PTM}$, $VC_{PTM}$, $VI_{PTM}$, $VIA_{PTM}$, $VIB_{PTM}$, $VIC_{PTM}$, $VID_{PTM}$, $VIE_{PTM}$, $VII_{PTM}$, $VIIA_{PTM}$, $VIIB_{PTM}$, $VIIC_{PTM}$, $VIID_{PTM}$, $VIII_{PTM}$, $VIIIA_{PTM}$, $VIIIB_{PTM}$, $VIIIC_{PTM}$, $VIIID_{PTM}$, $VIIIE_{PTM}$, $IX_{PTM}$, $IXA_{PTM}$, $IXB_{PTM}$, $IXC_{PTM}$, $IXD_{PTM}$, and $IXE_{PTM}$), wherein $M_1$ and $M_2$ are selected from a single bond, or a C2-C4 conjugated alkenyl fragment (e.g., —CH═CH—CH═CH—).

Preferred compounds of the current invention can be synthesized via typical transition metal-mediated aryl-aryl or aryl-alkenyl coupling approaches known to those skilled in the art and exemplified in the scheme below.

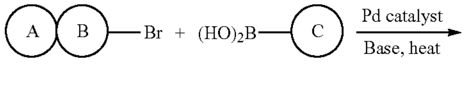

-continued

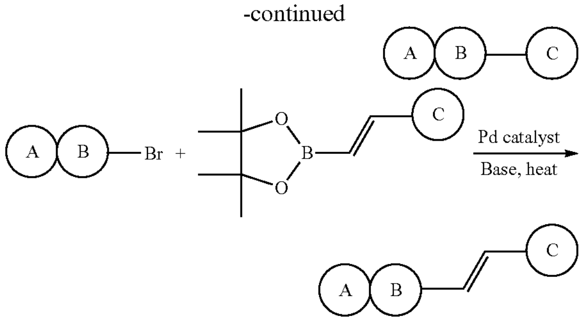

Additional ways of linking together heterocyclic ring systems (e.g., AB to C) exist and are provided below for the specific examples of the compounds of the present disclosure.

Functional group elaborations preceding and following the linking of the heterocyclic ring systems depends on the particular compound and are exemplified below for the compounds of the current invention.

The fused heterocyclic ring systems (i.e., AB, ABC) may be obtained commercially or synthesized from the individual heteroaryls using methods known to those skilled in the art and also exemplified in the synthesis of exemplary compounds of the present disclosure.

In any aspect or embodiment described herein, B of Formula $I_{PTM}$, $IA_{PTM}$, or $IB_{PTM}$ includes or is optionally substituted

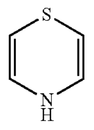

or optionally substituted

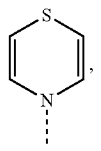

wherein --- indicates a point of attachment with a chemical linker moiety or a ULM.

In any aspect or embodiment described herein, C of Formula $IA_{PTM}$ includes or is optionally substituted

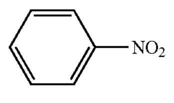

or optionally substituted

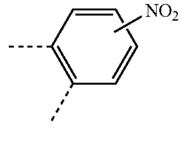

(e.g., as optionally substituted

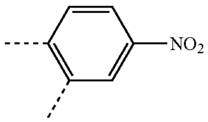

or optionally substituted

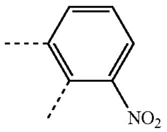

), wherein --- indicate the attachment points of the fusion with B.

In any aspect or embodiment describe herein, at least one (e.g., A, C, or A and C) of A and C of Formula $I_{PTM}$, $IB_{PTM}$, $V_{PTM}$, $VA_{PTM}$, and $VB_{PTM}$ includes or is optionally substituted

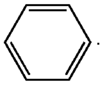

.

In any aspect or embodiment described herein,

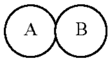

of Formula $II_{PTM}$, $IIA_{PTM}$, or $IIB_{PTM}$ includes or is optionally substituted

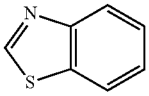

, optionally substituted

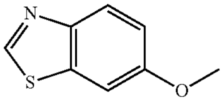

, optionally substituted

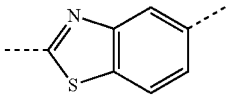

, optionally substituted

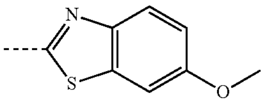

, optionally substituted

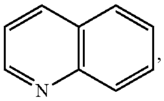

, optionally substituted

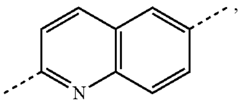

, optionally substituted

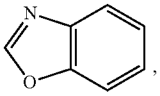

, optionally substituted

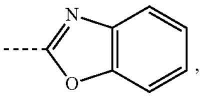

, optionally substituted

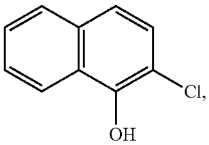 [SMILES: Oc1c(Cl)ccc2ccccc12]

optionally substituted

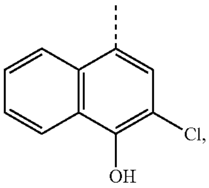

optionally substituted

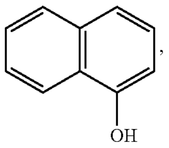 [SMILES: Oc1cccc2ccccc12]

optionally substituted

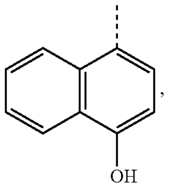

optionally substituted

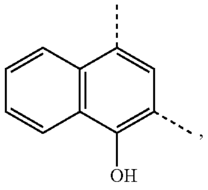

optionally substituted

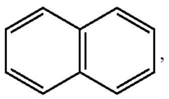

optionally substituted

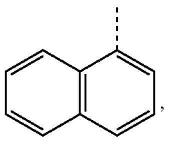

optionally substituted

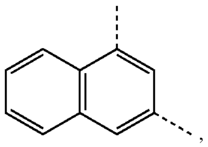

optionally substituted

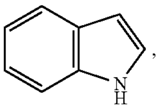

or optionally substituted

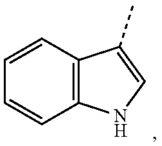

wherein --- indicates a point of attachment with C, the chemical linker moiety, or a ULM.

In any aspect or embodiment described herein, C of Formula $II_{PTM}$, $IIA_{PTM}$, $IIB_{PTM}$ includes or is optionally substituted

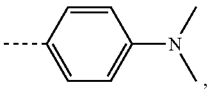

optionally substituted

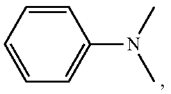

optionally substituted

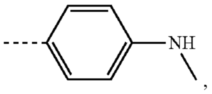

optionally substituted

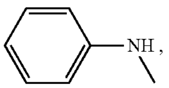

optionally substituted

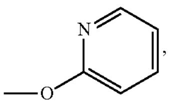

optionally substituted

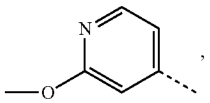

optionally substituted

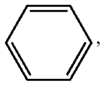

optionally substituted

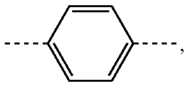

optionally substituted

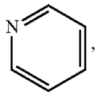

optionally substituted

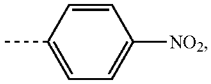

optionally substituted

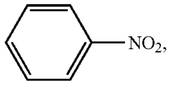

optionally substituted

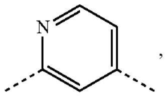

optionally substituted

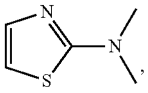

optionally substituted

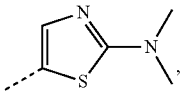

optionally substituted

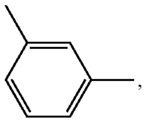

optionally substituted

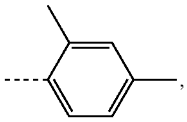

optionally substituted

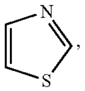

optionally substituted

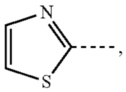

optionally substituted

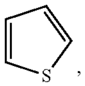

optionally substituted

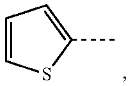

wherein - - - indicates a point of attachment with A, B, the chemical linker moiety, or a ULM.

In any aspect or embodiment described herein, C of Formula $IIC_{PTM}$ includes or is optionally substituted

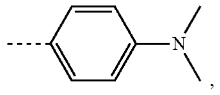

optionally substituted

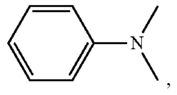

optionally substituted

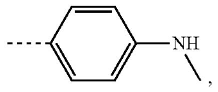

optionally substituted

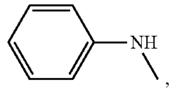

optionally substituted

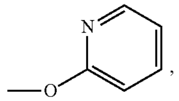

optionally substituted

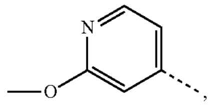

optionally substituted

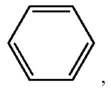

optionally substituted

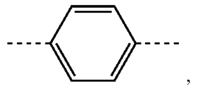

optionally substituted

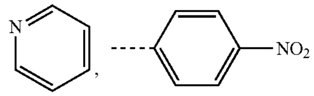

optionally substituted

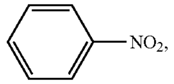

optionally substituted

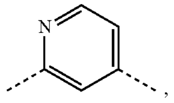

optionally substituted

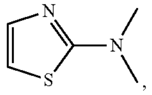

optionally substituted

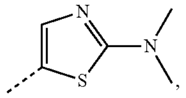

optionally substituted

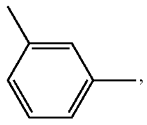

optionally substituted

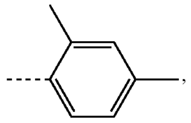

optionally substituted

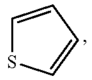

optionally substituted

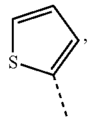

optionally substituted

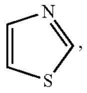

or optionally substituted

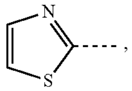

wherein --- indicates a point of attachment with C, the chemical linker moiety, or the ULM.

In any aspect or embodiment described herein,

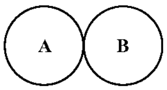

of Formula $III_{PTM}$, $IIIA_{PTM}$, or $IIIB_{PTM}$ includes or is optionally substituted

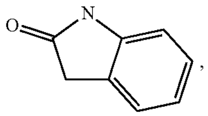

optionally substituted

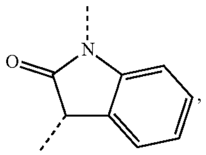

optionally substituted

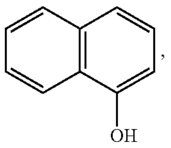

or optionally substituted

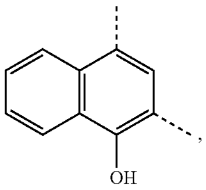

wherein --- indicates a point of attachment with C or D.

In any aspect or embodiment described herein, C of Formula $IIIA_{PTM}$, $IIIB_{PTM}$, $IIIC_{PTM}$, and $IIID_{PTM}$ includes optionally substituted

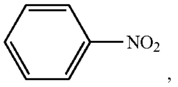

optionally substituted

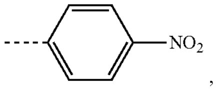

optionally substituted

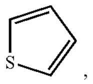

optionally substituted

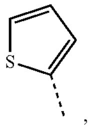

optionally substituted

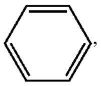

optionally substituted

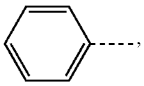

optionally substituted

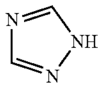

or optionally substituted

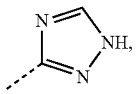

wherein --- indicates a point of attachment with A or B.

In any aspect or embodiment described herein, D of Formula IIIA$_{PTM}$, IIIB$_{PTM}$, IIIC$_{PTM}$, and IIID$_{PTM}$ includes optionally substituted

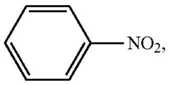

optionally substituted

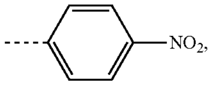

optionally substituted

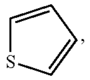

optionally substituted

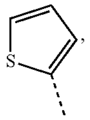

optionally substituted

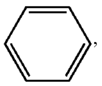

optionally substituted

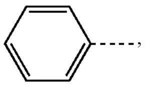

optionally substituted

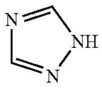

or optionally substituted

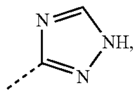

wherein --- indicates a point of attachment with A or B.

In any aspect or embodiment described herein, C of Formula IIIA$_{PTM}$, IIIB$_{PTM}$, IIIC$_{PTM}$, or IIID$_{PTM}$ includes or is optionally substituted

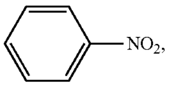

optionally substituted

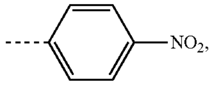

optionally substituted

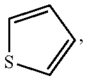

optionally substituted

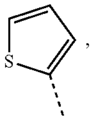

optionally substituted

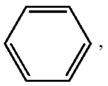

optionally substituted

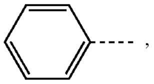

wherein --- indicates a point of attachment to A or B.

In any aspect or embodiment described herein, D of Formula $IIIC_{PTM}$ or $IIID_{PTM}$ includes or is optionally substituted

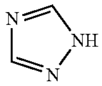

or optionally substituted

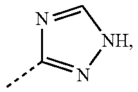

wherein --- indicates a point of attachment to A or B.

In any aspect or embodiment described herein, each of D of Formula $IIIC_{PTM}$ or $IIID_{PTM}$ includes or is optionally substituted

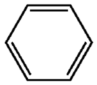

or optionally substituted

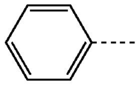 , wherein --- indicates a point of attachment to A or B.

In any aspect or embodiment described herein, C of Formula $IIIC_{PTM}$ or $IIID_{PTM}$ includes or is optionally substituted

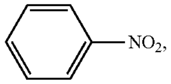

optionally substituted

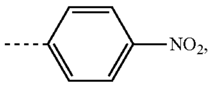

optionally substituted

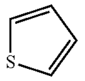 , or optionally substituted

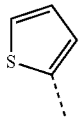 , wherein --- indicates a point of attachment to A or B.

In any aspect or embodiment described herein,

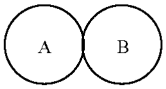

of Formula $IV_{PTM}$, $IVA_{PTM}$, $IVB_{PTM}$, $IVC_{PTM}$, or $IVD_{PTM}$ includes or is optionally substituted

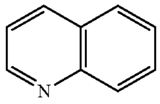 , optionally substituted

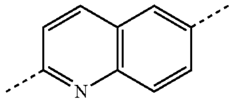 , optionally substituted

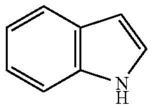 , or optionally substituted

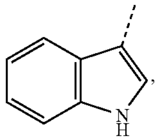

wherein --- indicates a point of attachment with C, the chemical linker moiety, or ULM.

In any aspect or embodiment described herein, C of Formula $IV_{PTM}$, $IVA_{PTM}$, $IVB_{PTM}$, or $IVC_{PTM}$, includes or is optionally substituted

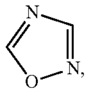

optionally substituted

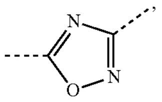

optionally substituted

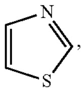, or optionally substituted

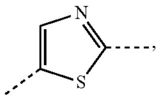, wherein --- indicates a point of attachment with C.

In any aspect or embodiment described herein, D of Formula $IV_{PTM}$, $IVB_{PTM}$, $IVC_{PTM}$, or $IVD_{PTM}$ includes or is optionally substituted

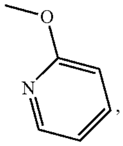, optionally substituted

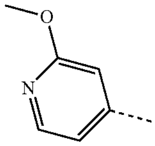, optionally substituted

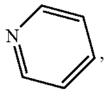, or optionally substituted

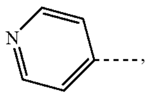, wherein --- indicates a point of attachment with C.

In any aspect or embodiment described herein, D of Formula $IV_{PTM}$, $IVB_{PTM}$, $IVC_{PTM}$, or $IVD_{PTM}$ includes or is optionally substituted

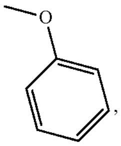, optionally substituted

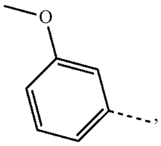, optionally substituted

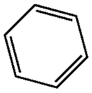, or optionally substituted

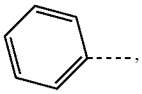, wherein --- indicates a point of attachment with C.

In any aspect or embodiment described herein, A of Formulas $V_{PTM}$, $VA_{PTM}$, or $VB_{PTM}$ includes or is optionally substituted

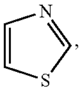, optionally substituted

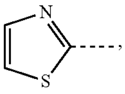, optionally substituted

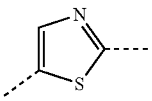, optionally substituted

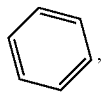

or optionally substituted

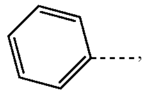

wherein --- indicates a point of attachment with B.

In any aspect or embodiment described herein, C of Formulas $V_{PTM}$, $VA_{PTM}$, or $VB_{PTM}$ includes or is optionally substituted

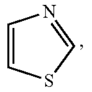

optionally substituted

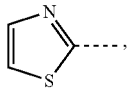

optionally substituted

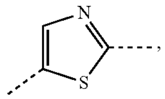

optionally substituted

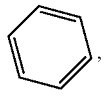

or optionally substituted

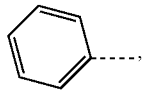

wherein --- indicates a point of attachment with B.

In any aspect or embodiment described herein, A of Formulas $VA_{PTM}$ includes or is optionally substituted

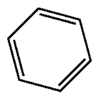

or optionally substituted

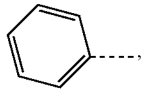

wherein --- indicates a point of attachment with B.

In any aspect or embodiment described herein, C of Formulas $VA_{PTM}$ includes or is optionally substituted

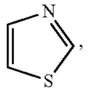

optionally substituted

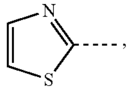

or optionally substituted

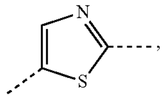

wherein --- indicates a point of attachment with B, the chemical linker moiety, or ULM.

In any aspect or embodiment described herein, B of Formulas $V_{PTM}$, $VA_{PTM}$, or $VB_{PTM}$ includes or is optionally substituted

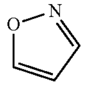

or optionally substituted

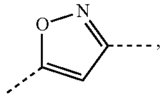

wherein --- indicates a point of attachment with A or C.

In any aspect or embodiment described herein.

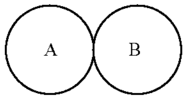

of Formula $VI_{PTM}$, $VIA_{PTM}$, $VIB_{PTM}$, $VIC_{PTM}$, $VID_{PTM}$, or $VIE_{PTM}$ includes or is optionally substituted

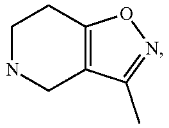

optionally substituted

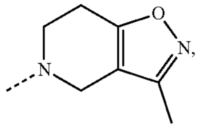

optionally substituted

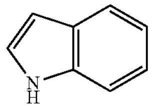
, or optionally substituted

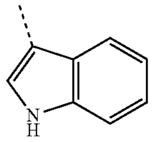
, wherein --- indicates a point of attachment with C.

In any aspect or embodiment described herein

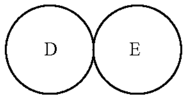

of Formula $VI_{PTM}$, $VIA_{PTM}$, $VIB_{PTM}$, $VIC_{PTM}$, $VID_{PTM}$, $VIE_{PTM}$, $VIII_{PTM}$, $VIIIA_{PTM}$, $VIIIB_{PTM}$, $VIIIC_{PTM}$, $VIIID_{PTM}$, or $VIIIE_{PTM}$ is optionally substituted

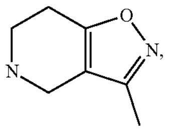

optionally substituted

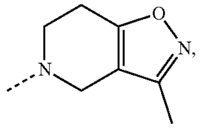

optionally substituted

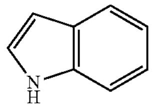
, or optionally substituted

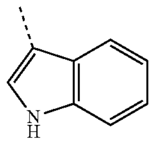
, wherein --- indicates a point of attachment with C.

In any aspect or embodiment described herein,

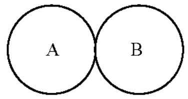

of Formula $VI_{PTM}$, $VIA_{PTM}$, $VIB_{PTM}$, $VIC_{PTM}$, $VID_{PTM}$, or $VIE_{PTM}$ includes or is optionally substituted

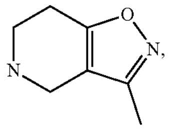

optionally substituted

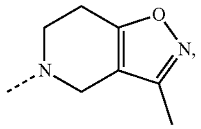

optionally substituted

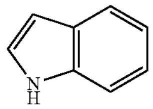
, or optionally substituted

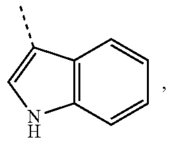

wherein --- indicates a point of attachment with C; and

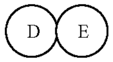

of Formula $VI_{PTM}$, $VIA_{PTM}$, $VIB_{PTM}$, $VICP_{PTM}$, $VID_{PTM}$, $VIE_{PTM}$, $VIII_{PTM}$, $VIIIA_{PTM}$, $VIIIB_{PTM}$, $VIIIC_{PTM}$, $VIID_{PTM}$, or $VIIIE_{PTM}$ is optionally substituted

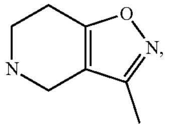

optionally substituted

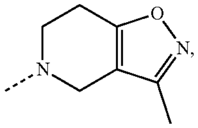

optionally substituted

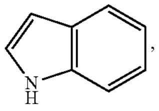

or optionally substituted

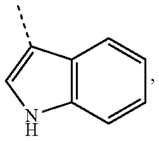

wherein --- indicates a point of attachment with C.

In any aspect or embodiment described herein, A of Formula $VII_{PTM}$, $VIIA_{PTM}$, $VIIB_{PTM}$, $VIIC_{PTM}$, or $VIID_{PTM}$ includes or is optionally substituted

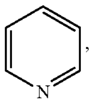

optionally substituted

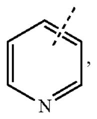

optionally substituted

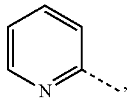

optionally substituted

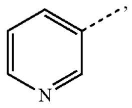

optionally substituted

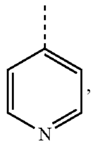

optionally substituted

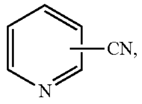

optionally substituted

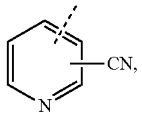

optionally substituted

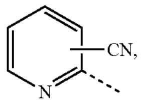

optionally substituted

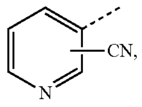

optionally substituted

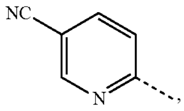, optionally substituted

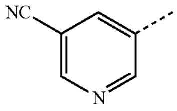, optionally substituted

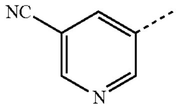, optionally substituted

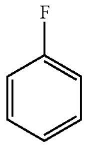, optionally substituted

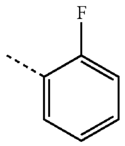, optionally substituted

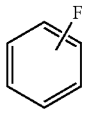, optionally substituted

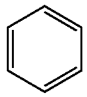, optionally substituted

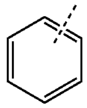, wherein --- indicates a point of attachment B.

In any aspect or embodiment described herein, D of Formula $VII_{PTM}$, $VIIA_{PTM}$, $VIIB_{PTM}$, $VIIC_{PTM}$, or $VIID_{PTM}$ includes or is optionally substituted

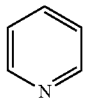, optionally substituted

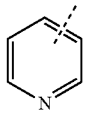, optionally substituted

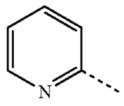, optionally substituted

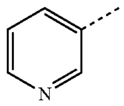, optionally substituted

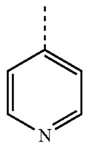, optionally substituted

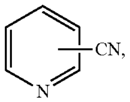

optionally substituted

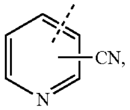

optionally substituted

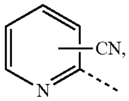

optionally substituted

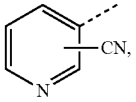

optionally substituted

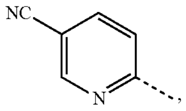

optionally substituted

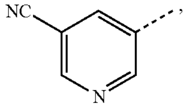

optionally substituted

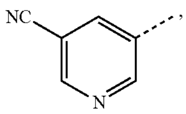

optionally substituted

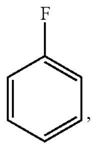

optionally substituted

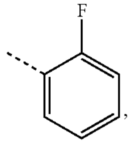

optionally substituted

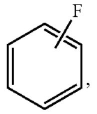

or optionally substituted

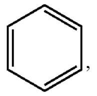

optionally substituted

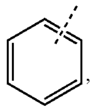

wherein --- indicates a point of attachment C.

In any aspect or embodiment described herein, A of Formula $VII_{PTM}$, $VIIA_{PTM}$, $VIIB_{PTM}$, $VIIC_{PTM}$, or $VIID_{PTM}$ includes or is optionally substituted

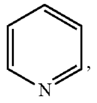

optionally substituted

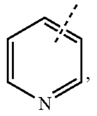

optionally substituted

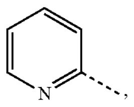

optionally substituted

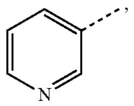

optionally substituted

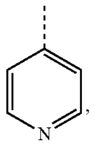

optionally substituted

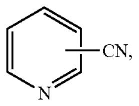

optionally substituted

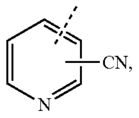

optionally substituted

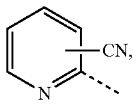

optionally substituted

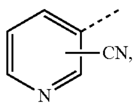

optionally substituted

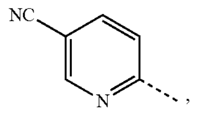

optionally substituted

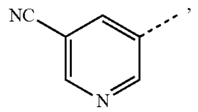

optionally substituted or optionally substituted

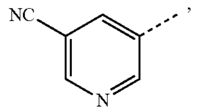

wherein --- indicates a point of attachment B; and D of Formula $VII_{PTM}$, $VIIA_{PTM}$, $VIIB_{PTM}$, $VIIC_{PTM}$, or $VIID_{PTM}$ includes or is optionally substituted

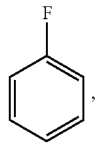

optionally substituted

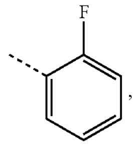

optionally substituted

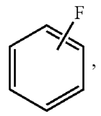

optionally substituted

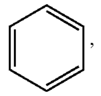

optionally substituted

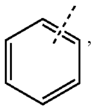

wherein --- indicates a point of attachment C.

In any aspect or embodiment described herein, B of Formula $VII_{PTM}$, $VIIA_{PTM}$, $VIIB_{PTM}$, $VIIC_{PTM}$, or $VIID_{PTM}$ includes or is optionally substituted

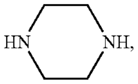

optionally substituted

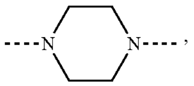

optionally substituted

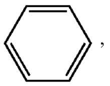

or optionally substituted

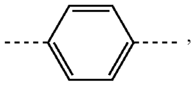

wherein --- indicates a point of attachment A or C.

In any aspect or embodiment described herein, C of Formula $VII_{PTM}$, $VIIA_{PTM}$, $VIIB_{PTM}$, $VIIC_{PTM}$, or $VIID_{PTM}$ includes or is optionally substituted

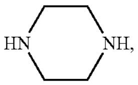

optionally substituted

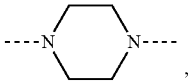

optionally substituted

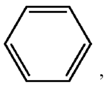

or optionally substituted

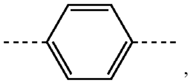

wherein --- indicates a point of attachment B or D.

In any aspect or embodiment described herein,

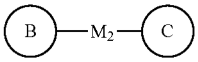

of Formula $VII_{PTM}$, $VIIA_{PTM}$, $VIIB_{PTM}$, $VII_{PTM}$, or $VID_{PTM}$ includes or is optionally substituted

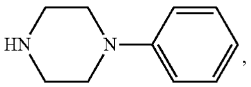

optionally substituted

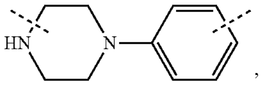

or optionally substituted

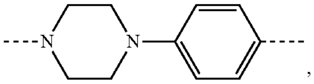

wherein --- indicates a point of attachment A or D.

In any aspect or embodiment described herein,

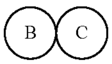

of Formula $VIII_{PTM}$, $VIIIA_{PTM}$, $VIIIB_{PTM}$, $VIIIC_{PTM}$, $VIIID_{PTM}$, or $VIIIE_{PTM}$ is optionally substituted

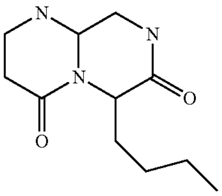

or optionally substituted

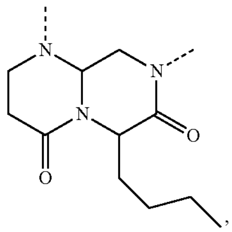

wherein --- indicates a point of attachment with A or D.

In any aspect or embodiment described herein, A of Formula $IX_{PTM}$, $IXA_{PTM}$, $IXB_{PTM}$, $IXC_{PTM}$, $IXD_{PTM}$, or $IXE_{PTM}$ includes or is optionally substituted

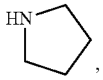

optionally substituted

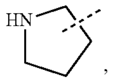

or optionally substituted

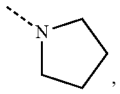

wherein --- indicates a point of attachment with B.

In any aspect or embodiment described herein, B of Formula $IX_{PTM}$, $IXA_{PTM}$, $IXB_{PTM}$, $IXC_{PTM}$, $IXD_{PTM}$, or $IXE_{PTM}$ includes or is optionally substituted

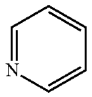

or optionally substituted

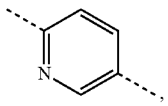

wherein --- indicates a point of attachment with A or C.

In any aspect or embodiment described herein, E of Formula $IX_{PTM}$, $IXA_{PTM}$, $IXB_{PTM}$, $IXC_{PTM}$, $IXD_{PTM}$, or $IXE_{PTM}$ includes or is optionally substituted

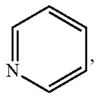

optionally substituted

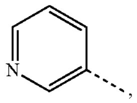

optionally substituted

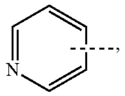

optionally substituted

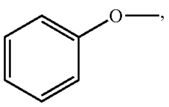

optionally substituted

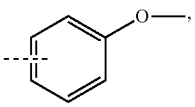

optionally substituted

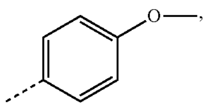

optionally substituted

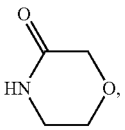

optionally substituted

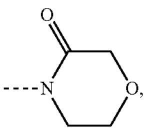

optionally substituted

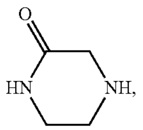

optionally substituted

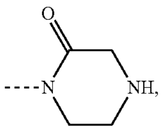

optionally substituted

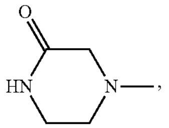

or optionally substituted

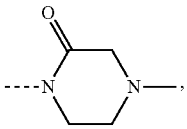

wherein --- indicates a point of attachment with D.

In any aspect or embodiment described herein,

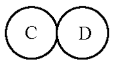

of Formula $IX_{PTM}$ $IXA_{PTM}$, $IXB_{PTM}$, $IXC_{PTM}$, $IXD_{PTM}$, or $IXE_{PTM}$ includes or is optionally substituted

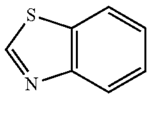
, optionally substituted

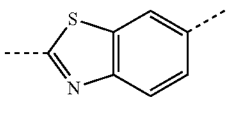
, optionally substituted

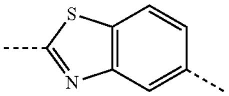
, optionally substituted

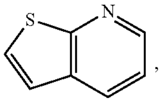
, optionally substituted

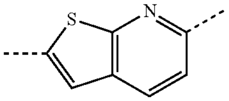
, optionally substituted

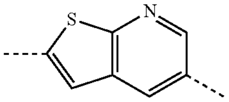
, optionally substituted

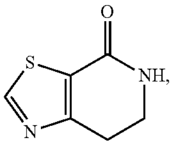

or optionally substituted

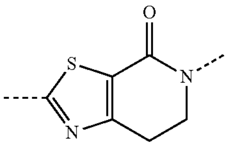
, wherein --- indicates a point of attachment with B or E.

In any aspect or embodiment described herein, the PTM is selected from an optionally substituted:

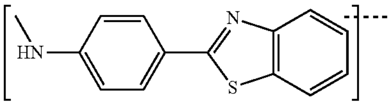
,

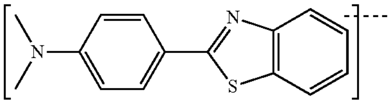
,

-continued
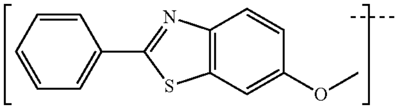
,
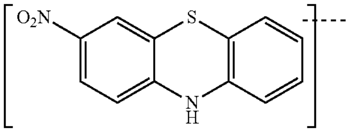
,
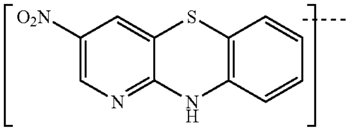
,
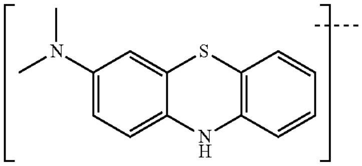
,
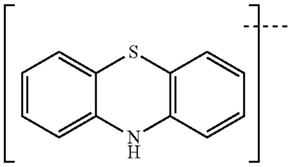
,
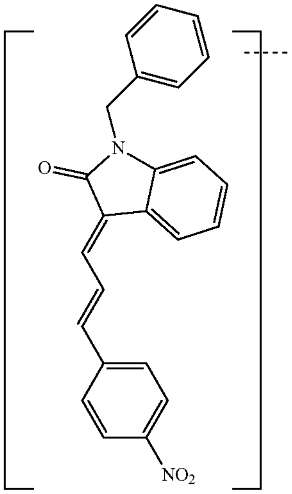
,
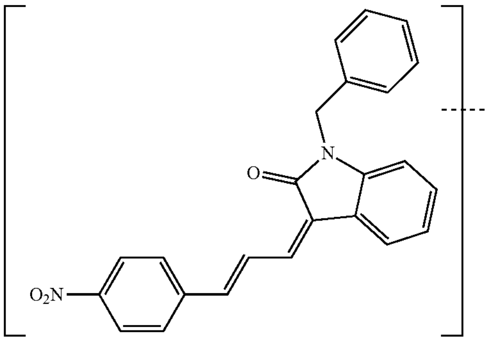
,
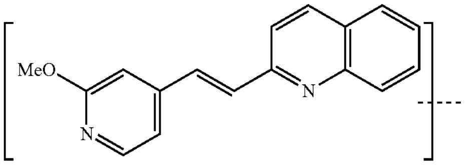
,
-continued
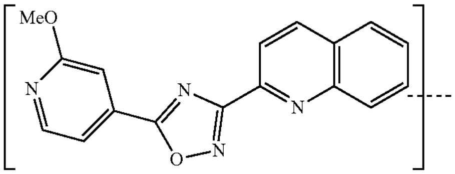
,
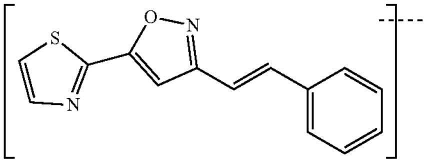
,
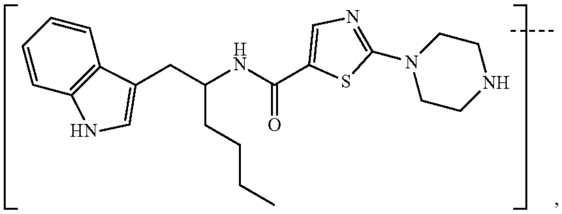
,
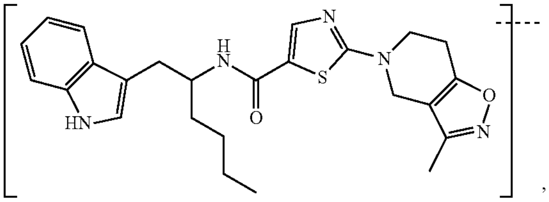
,
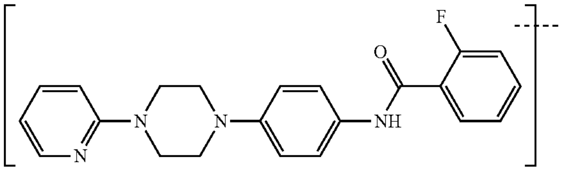
,
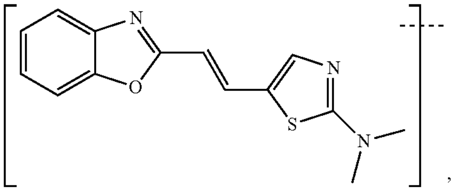
,
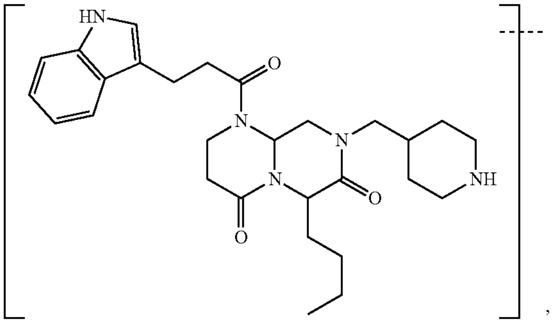
, -continued
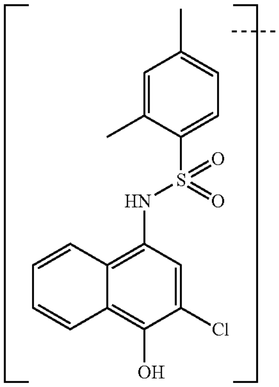
,
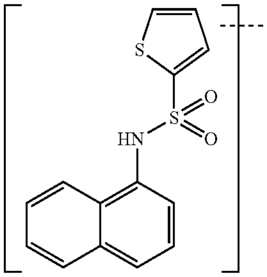
,
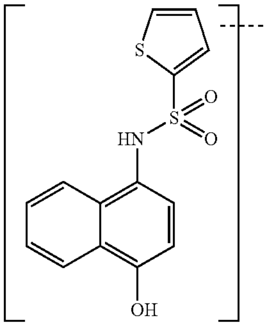
,
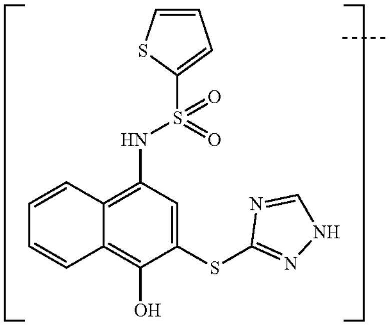
,
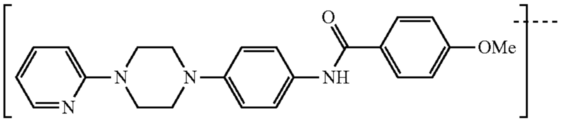
,
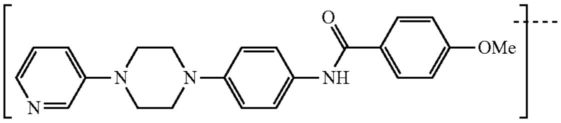
,
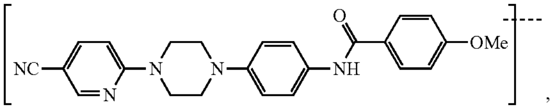
,
-continued
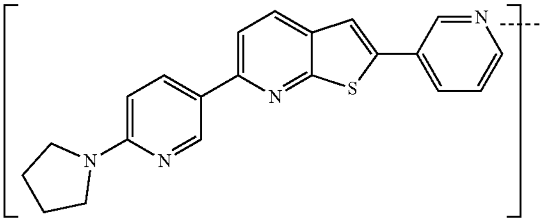
,
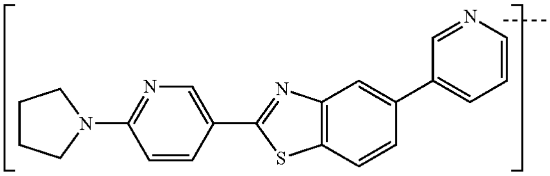
,
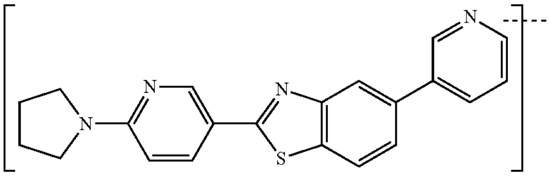
,
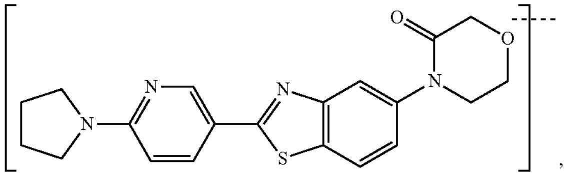
,
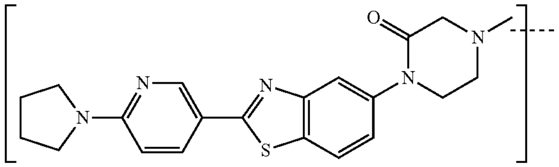
,
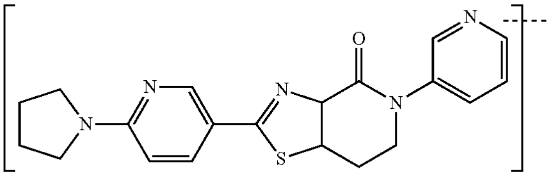
,
wherein - - - indicates the point of attachment of a chemical linker moiety or a ULM (e.g., VLM or CLM) (e.g., the - - - indicates the point of attachment of a chemical linker moiety or a ULM (e.g., VLM or CLM) via any cyclic group (e.g., A, B, C, or D) directly or via a functional group or atom).
In any aspect or embodiment described herein, the PTM is selected from:
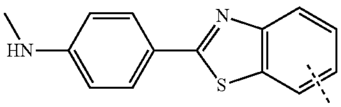
,
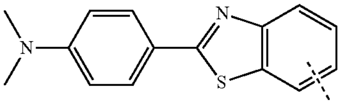
, -continued
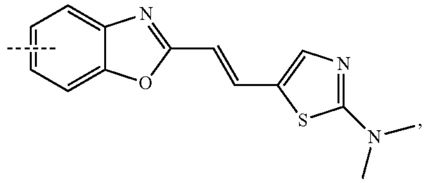
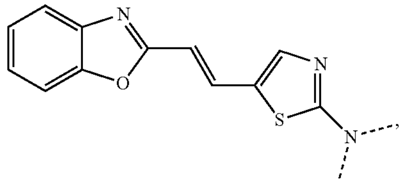
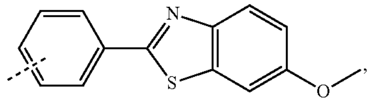
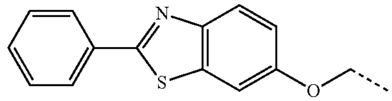
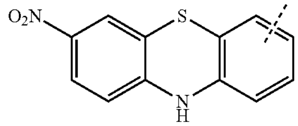
,
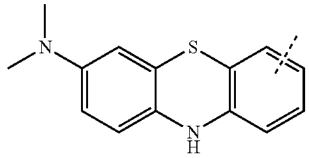
,
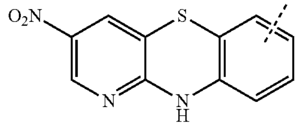
,
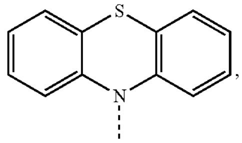
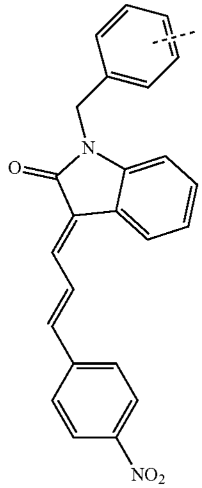
,
-continued
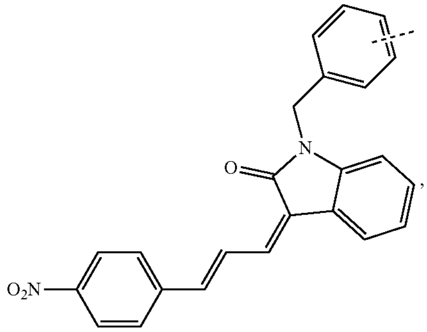
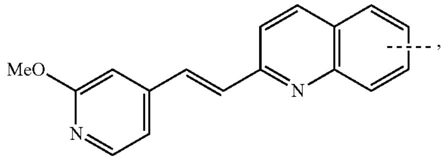
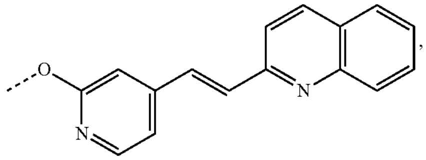
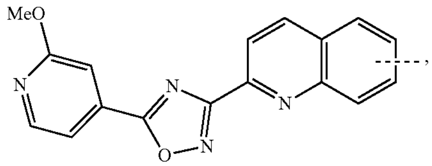
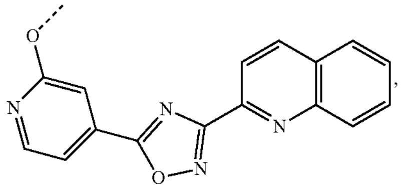
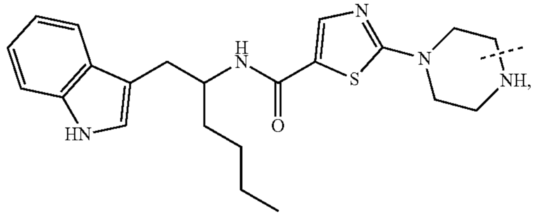
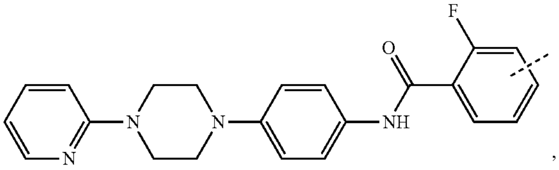
,
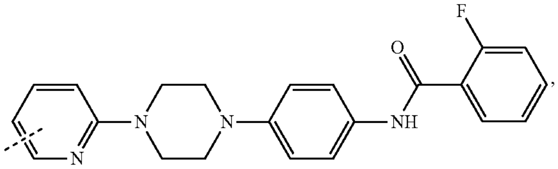
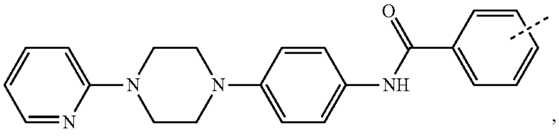
, -continued
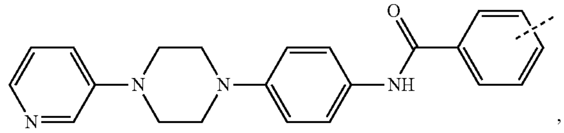
,
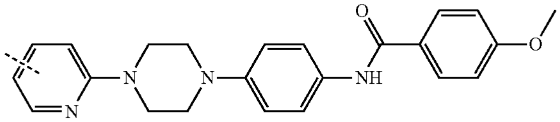
,
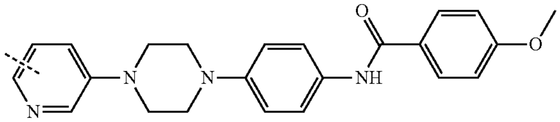
,
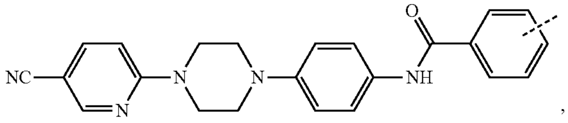
,
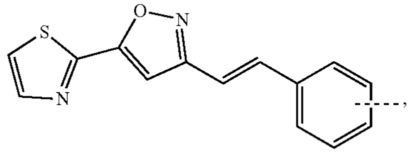
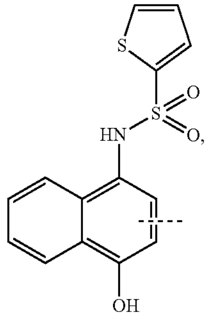
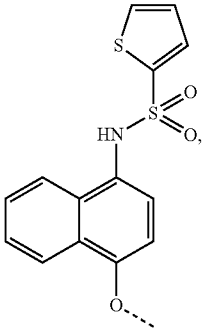
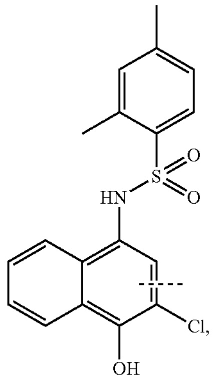
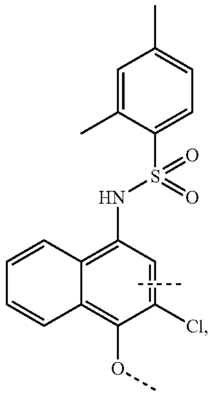
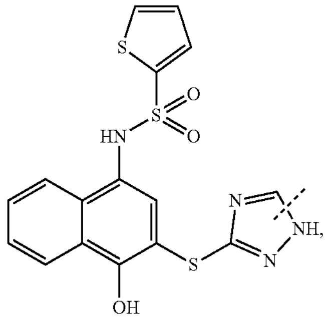
-continued
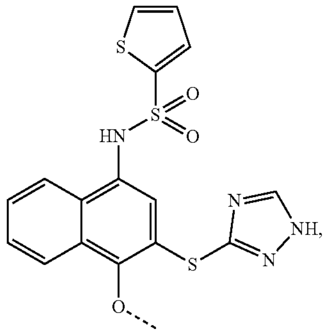
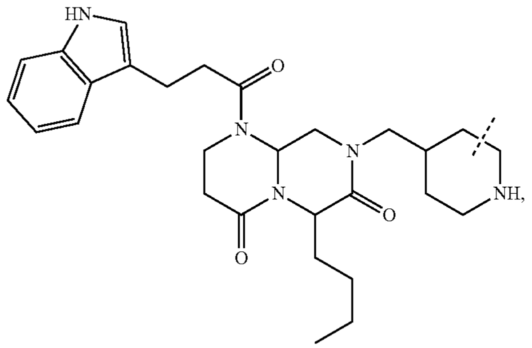
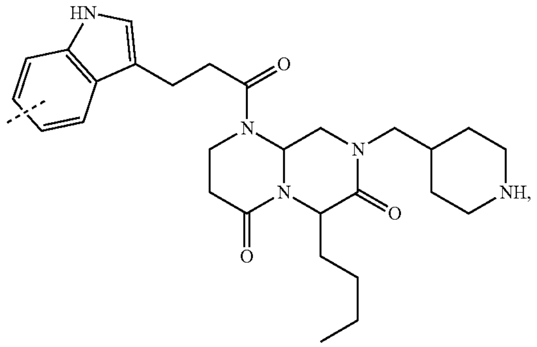
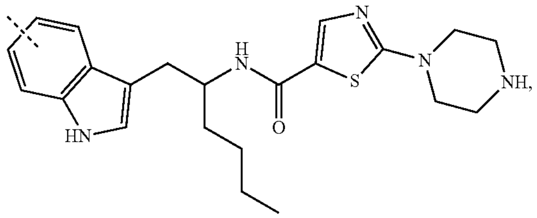
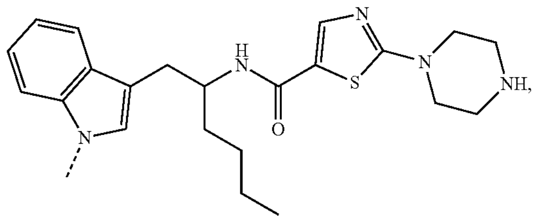
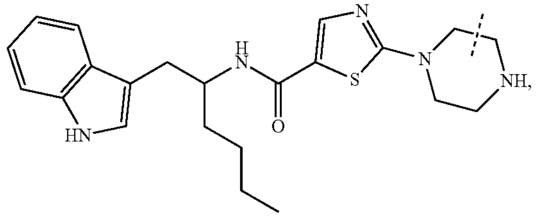

-continued
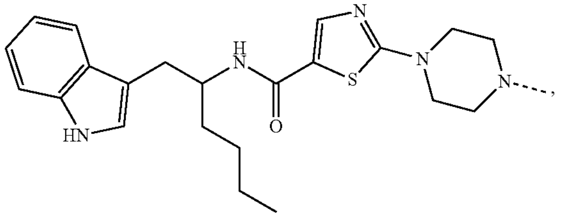
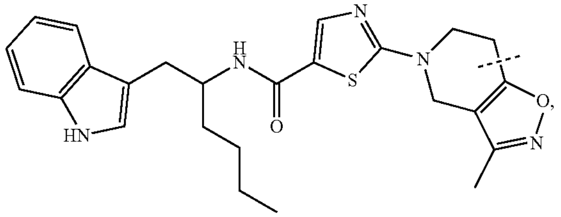
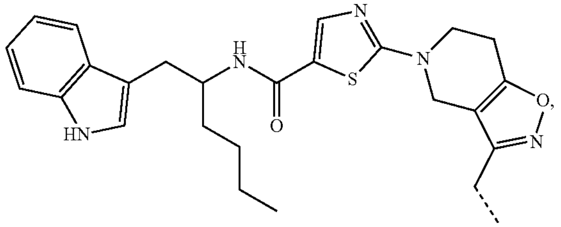
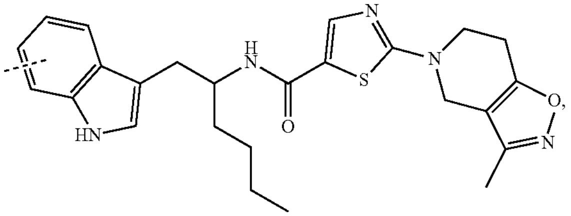
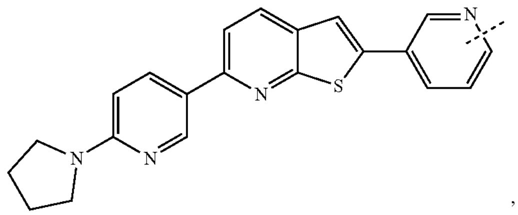
,
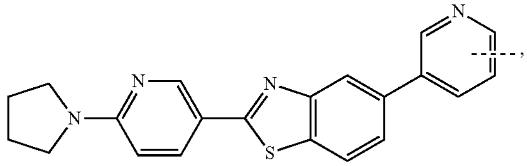
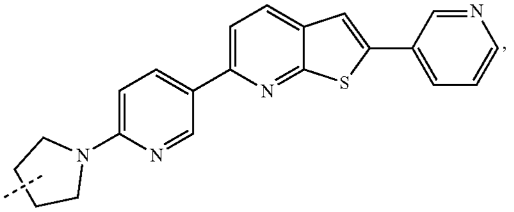
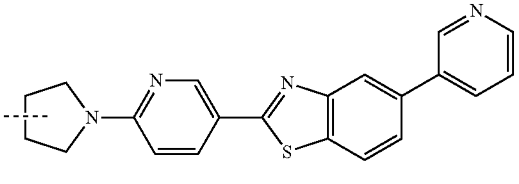
,
-continued
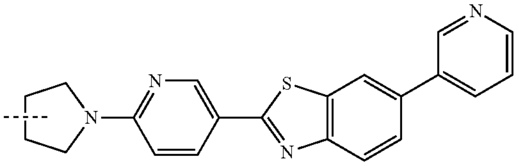
,
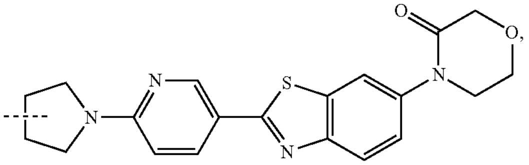
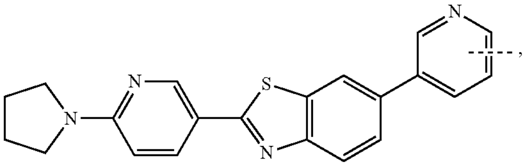
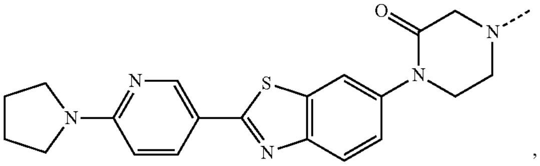
,
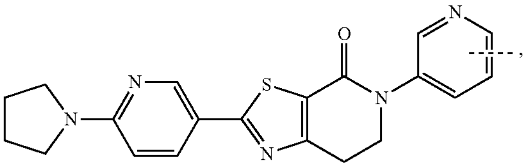
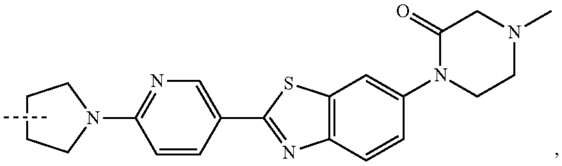
,
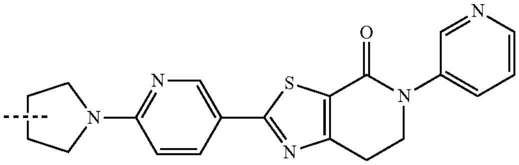
,
wherein --- indicates the point of attachment of a chemical linker moiety or a ULM (e.g., VLM or CLM).
In any aspect or embodiment described herein, the PTM is selected from:
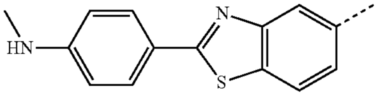
,
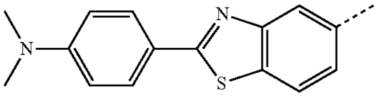
,
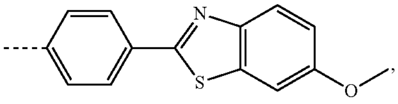

-continued
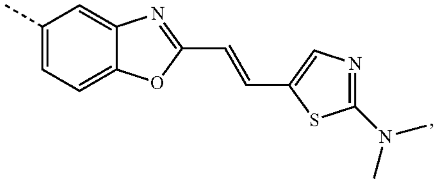
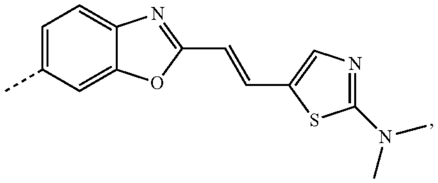
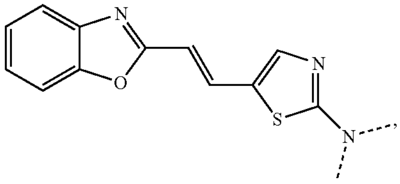
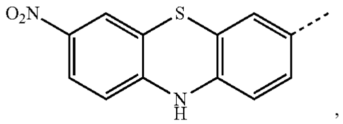
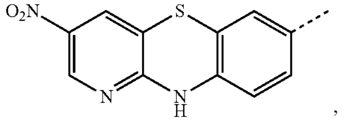
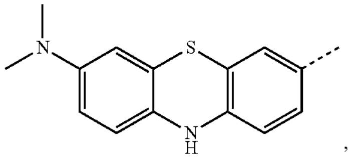
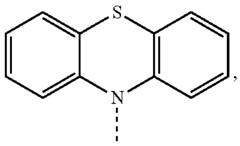
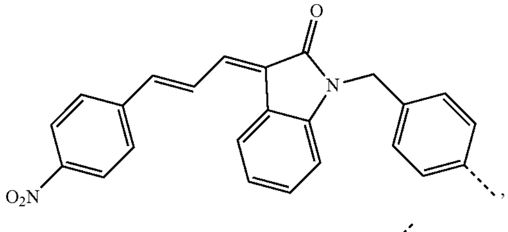
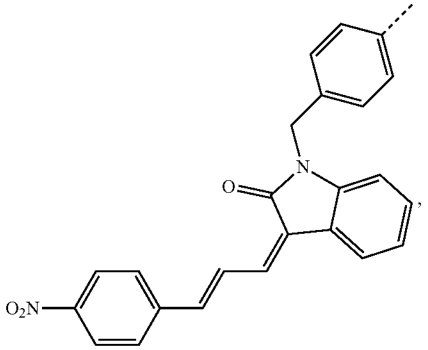
-continued
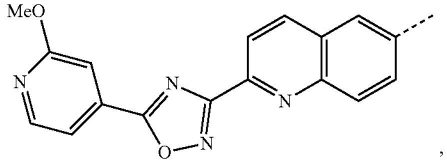
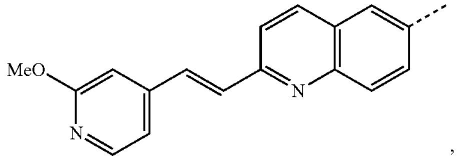
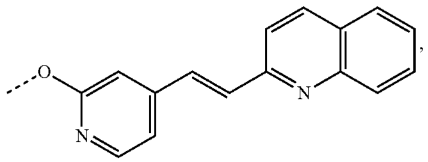
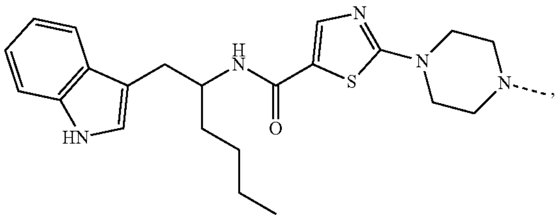
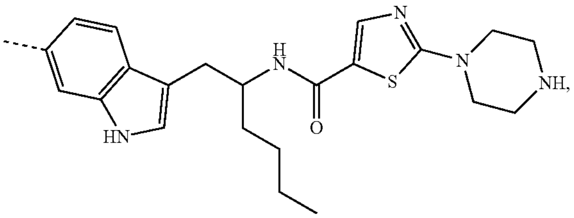
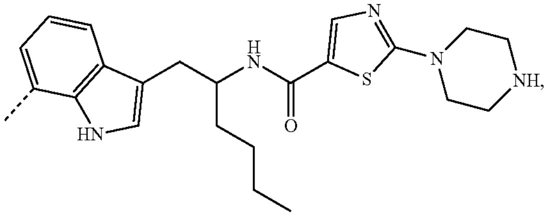
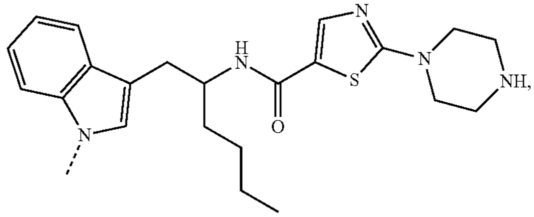
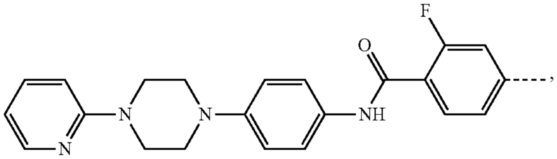
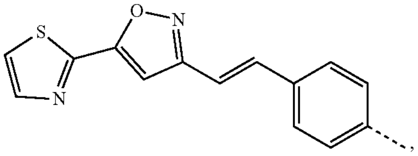

-continued
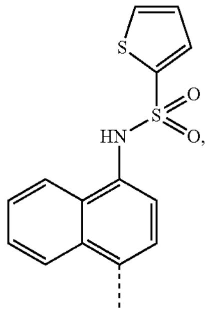
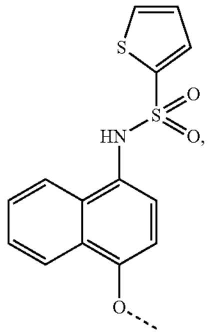
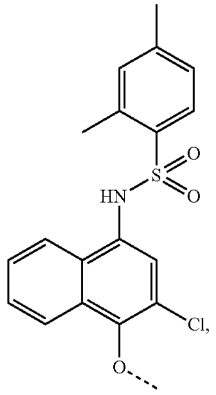
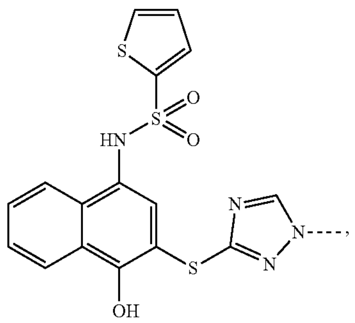
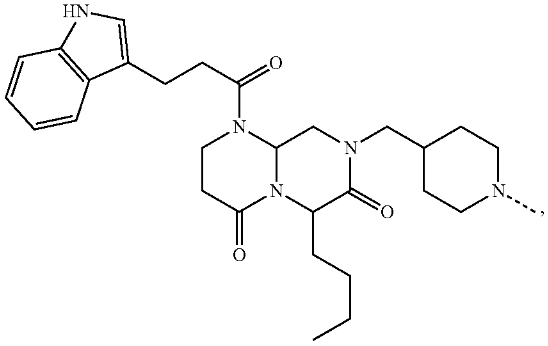
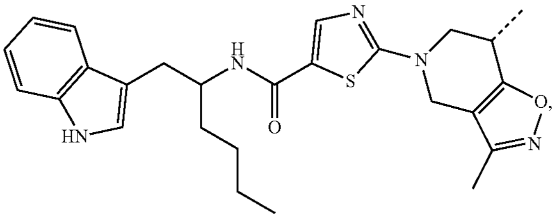
-continued
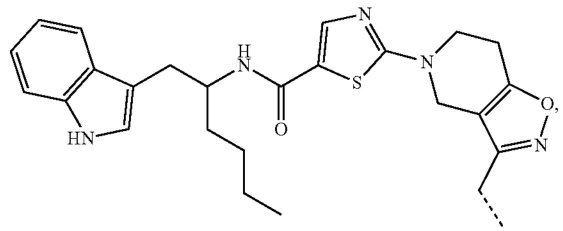
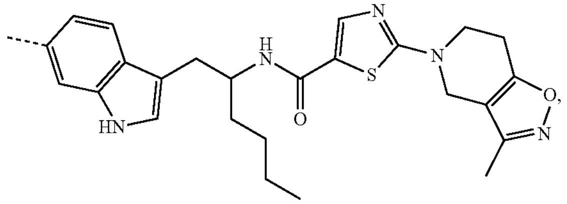
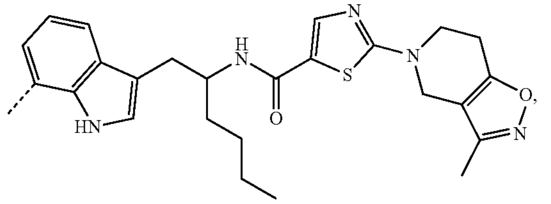
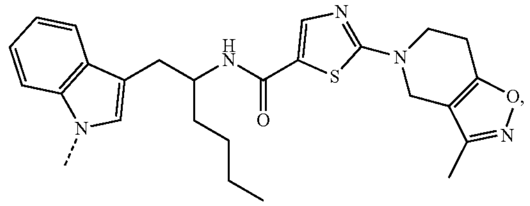
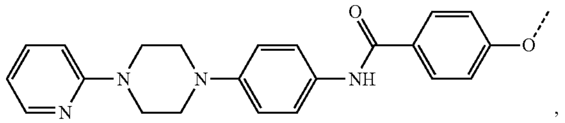
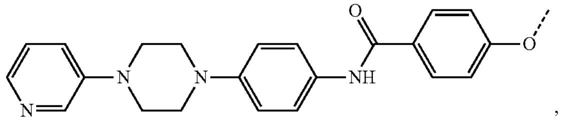
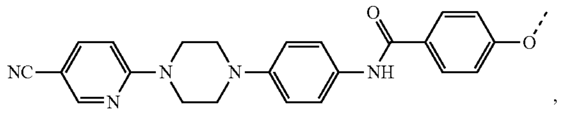
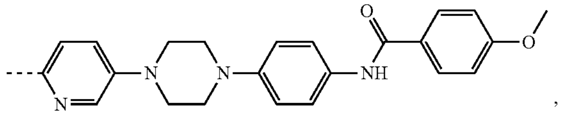
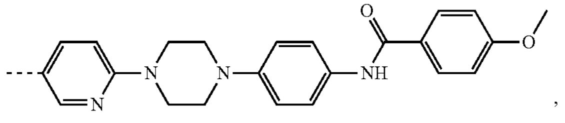
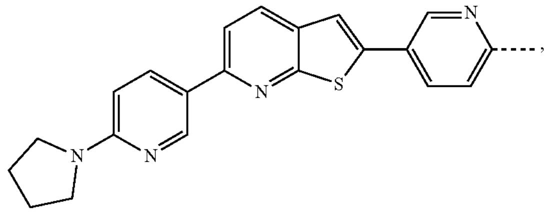

-continued

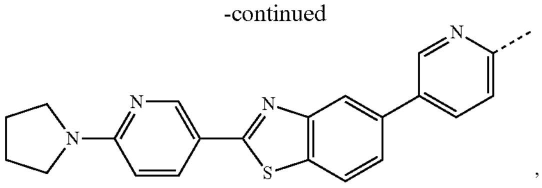

,

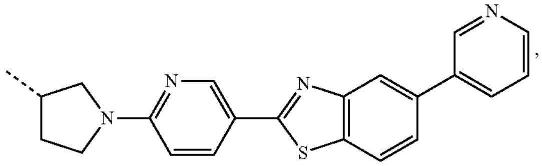

,

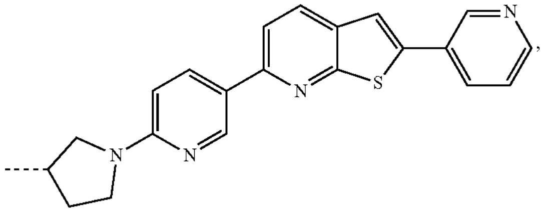

,

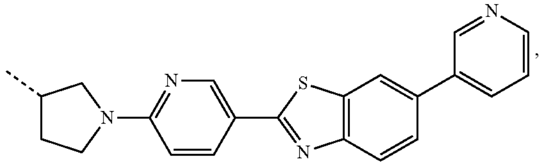

,

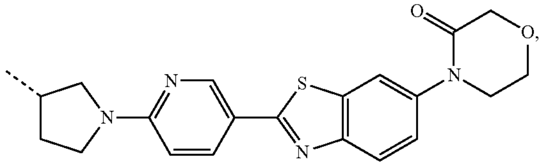

,

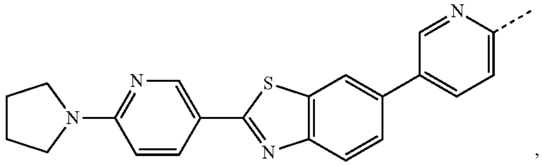

,

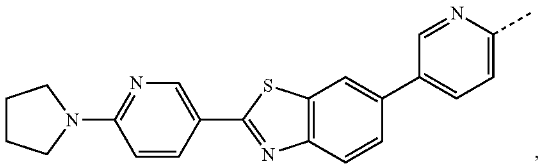

,

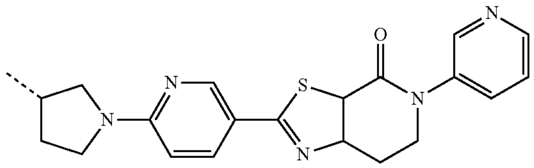

,

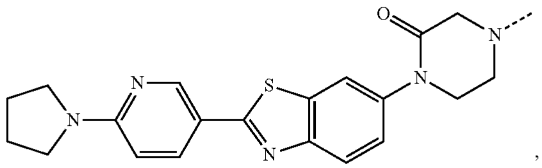

,

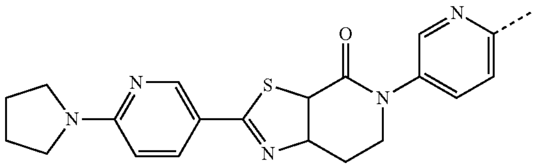

, wherein --- indicates the point of attachment of a chemical linker moiety or a ULM (e.g., VLM or CLM).

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

These compounds can be administered by any appropriate route, for example, orally, parenterally, intravenously, intradermally, subcutaneously, or topically, including transdermally, in liquid, cream, gel, or solid for, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-neurodegenerative agents, among others. In certain preferred aspects of the disclosure, one or more compounds according to the present disclosure are coadministered with another bioactive agent, such as an anti-neurogenerative agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including α-synucleinopathies, neurological or neurodegenerative disease or disorder, which may be treated using compounds according to the present disclosure are set forth hereinabove.

The description provides therapeutic compositions as described herein for effectuating the degradation of proteins of interest for the treatment or amelioration of a disease, e.g. α-synucleinopathies or neurological or neurodegenerative diseases or disorders, such as Parkinson Disease, Alzheimer's Disease, dementia (e.g., dementia with Lewy bodies), or multiple system atrophy. In certain additional embodiments, the disease is Parkinson's Disease, dementia, or multiple system atrophy. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative (e.g., an eighth embodiment may include the features recited in a first embodiment, as recited, and/or the features of any of the second through seventh embodiments).

In certain embodiments, the description provides the following exemplary compounds 1-135 of Tables 1 and 2, including salts, prodrugs, polymorphs, analogs, derivatives, and deuterated forms thereof:

EXAMPLES

Exemplary Synthesis of Exemplary Compounds of the Present Disclosure

Exemplary Synthesis of Exemplary Compound 1

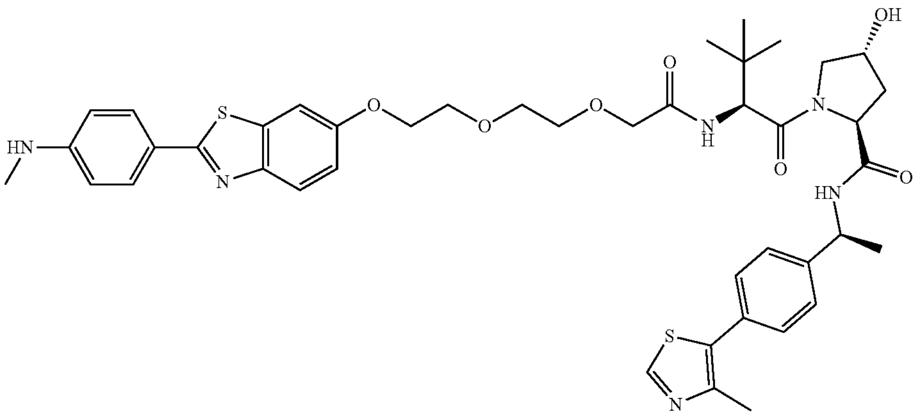 [SMILES: CNc1ccc(-c2nc3ccc(OCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1]

Step 1

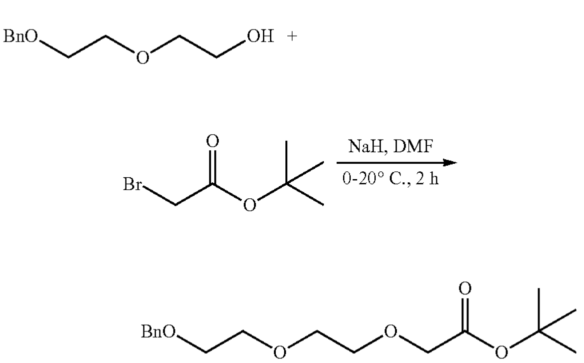

To a solution of 2-(2-benzyloxyethoxy)ethanol (30 g, 152.87 mmol, 1.00 eq) in N,N-dimethylformamide (250 mL) was added sodium hydride (9.17 g, 229.31 mmol, 60% in mineral oil, 1.50 eq) at 0° C. The mixture was stirred at 20° C. for 1 hour. Then the mixture was cooled back to 0° C., and tert-butyl 2-bromoacetate (44.73 g, 229.31 mmol, 33.89 mL, 1.50 eq) was added. The reaction mixture was stirred at 20° C. for 2 hours. The reaction was quenched by saturated ammonium chloride (600 mL), and the resulting mixture was extracted with ethyl acetate (300 mL×3). The combined organic phase was washed with brine (300 mL×2), dried over sodium sulfate, filtered and concentrated in vacuum. The residue was purified by silica gel chromatography (petroleum ether:ethyl acetate=30:1 to 5:1) to give tert-butyl 2-[2-(2-benzyloxyethoxy)ethoxy]acetate (11 g, 35.44 mmol, 23% yield) as a colorless oil.

Step 2

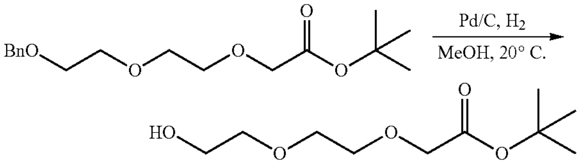

To a solution of tert-butyl 2-[2-(2-benzyloxyethoxy)ethoxy]acetate (11 g, 35.44 mmol, 1.00 eq) in methanol (150 mL) was added 10% Pd/C (800 mg) under nitrogen. The suspension was degassed under vacuum and purged with hydrogen several times. The reaction mixture was stirred at 20° C. for 18 hours under hydrogen (50 psi). The mixture was filtered and the filtrate was concentrated in vacuum to give tert-butyl 2-[2-(2-hydroxyethoxy)ethoxy] acetate (7.5 g, 96% yield) as a colorless oil.

Step 3

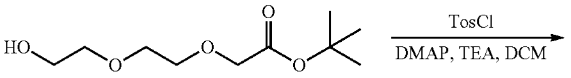

-continued

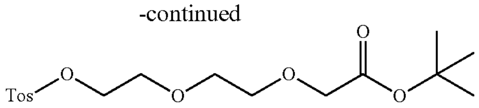

To a mixture of tert-butyl 2-[2-(2-hydroxyethoxy)ethoxy] acetate (1.00 g, 4.54 mmol, 1.00 eq) triethylamine (1.38 g, 13.62 mmol, 3.00 eq) and dimethylaminopyridine (166 mg, 1.36 mmol, 0.30 eq) in dichloromethane (10 mL) was added p-toluenesulfonyl chloride (1.73 g, 9.08 mmol, 2.00 eq). The mixture was stirred at 14° C. for 1 hour. The reaction mixture was quenched by the addition of water (200 mL), and then diluted with ethyl acetate (30 mL), and extracted with ethyl acetate (40 mL×3). The combined organic layers were washed with brine (30 mL), dried over anhydrous sodium sulfate, filtered and concentrated under reduced pressure. The residue was purified by silica gel column chromatography (Petroleum ether/Ethyl acetate=15/1 to 10/1). Tert-butyl 2-[2-[2-(p-tolylsulfonyloxy)ethoxy]ethoxy]acetate (800 mg, 2.14 mmol, 47% yield) was obtained as a colorless oil.

Step 4

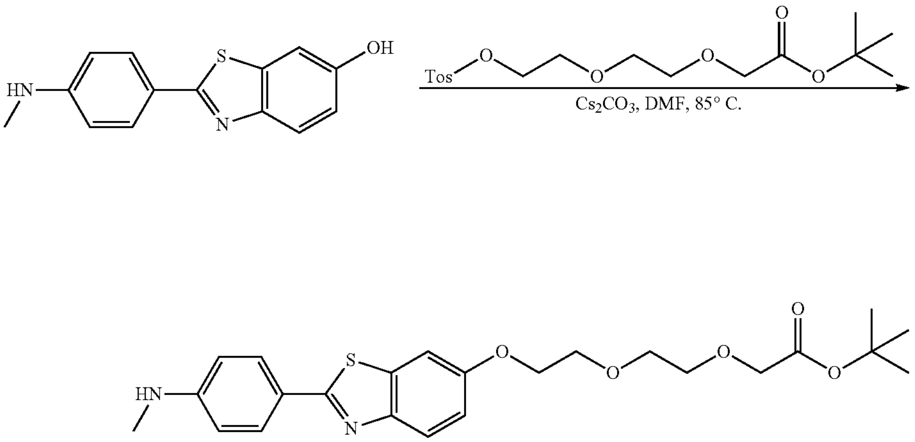

To a mixture of 2-[4-(methylamino)phenyl]-1,3-benzothiazol-6-ol (100 mg, 0.39 mmol, 1.00 eq) and tert-butyl 2-[2-[2-(p-tolylsulfonyloxy)ethoxy]ethoxy]acetate (146 mg, 0.39 mmol, 1.00 eq) in dimethylformamide (5 mL) was added cesium carbonate (381 mg, 1.17 mmol, 3.00 eq). The mixture stirred at 85° C. for 1 hour. The reaction mixture was quenched by the addition of water (50 mL), and then diluted with ethyl acetate (10 mL) and extracted with ethyl acetate (20 mL×3). The combined organic layers were washed with brine (20 mL×3), dried over anhydrous sodium sulfate, filtered and concentrated under reduced pressure to give a residue which was purified by prep-TLC (petroleum ether:ethyl acetate=1:1). Tert-butyl 2-[2-[2-[[2-[4-(methylamino)phenyl]-1,3-benzothiazol-6-yl]oxy]ethoxy]ethoxy] acetate (100 mg, 0.22 mmol, 56% yield) was obtained as a yellow oil.

Step 5

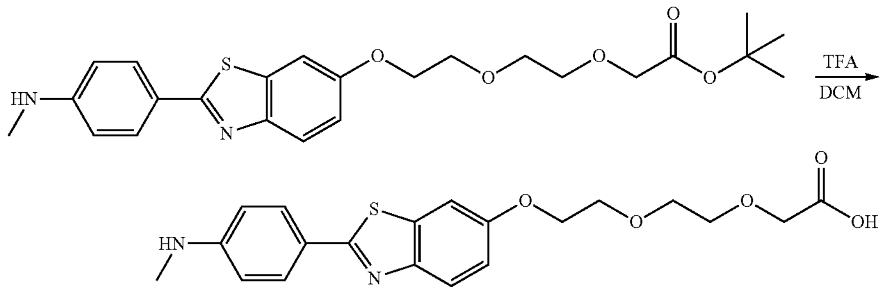

To a mixture of tert-butyl 2-[2-[2-[[2-[4-(methylamino) phenyl]-1,3-benzothiazol-6-yl] oxy]ethoxy]ethoxy]acetate (100 mg, 0.22 mmol, 1.00 eq) in dichloromethane (2 mL) was added trifluoroacetic acid (249 mg, 2.18 mmol, 10.00 eq). The mixture stirred at 12° C. for 12 hours. The reaction solution was concentrated under reduced pressure. The residue was used for the next step without further purification. 2-[2-[2-[[2-[4-(Methylamino) phenyl]-1,3-benzothiazol-6-yl]oxy]ethoxy]ethoxy]acetic acid (100 mg, crude) was obtained as a yellow oil.

Step 6

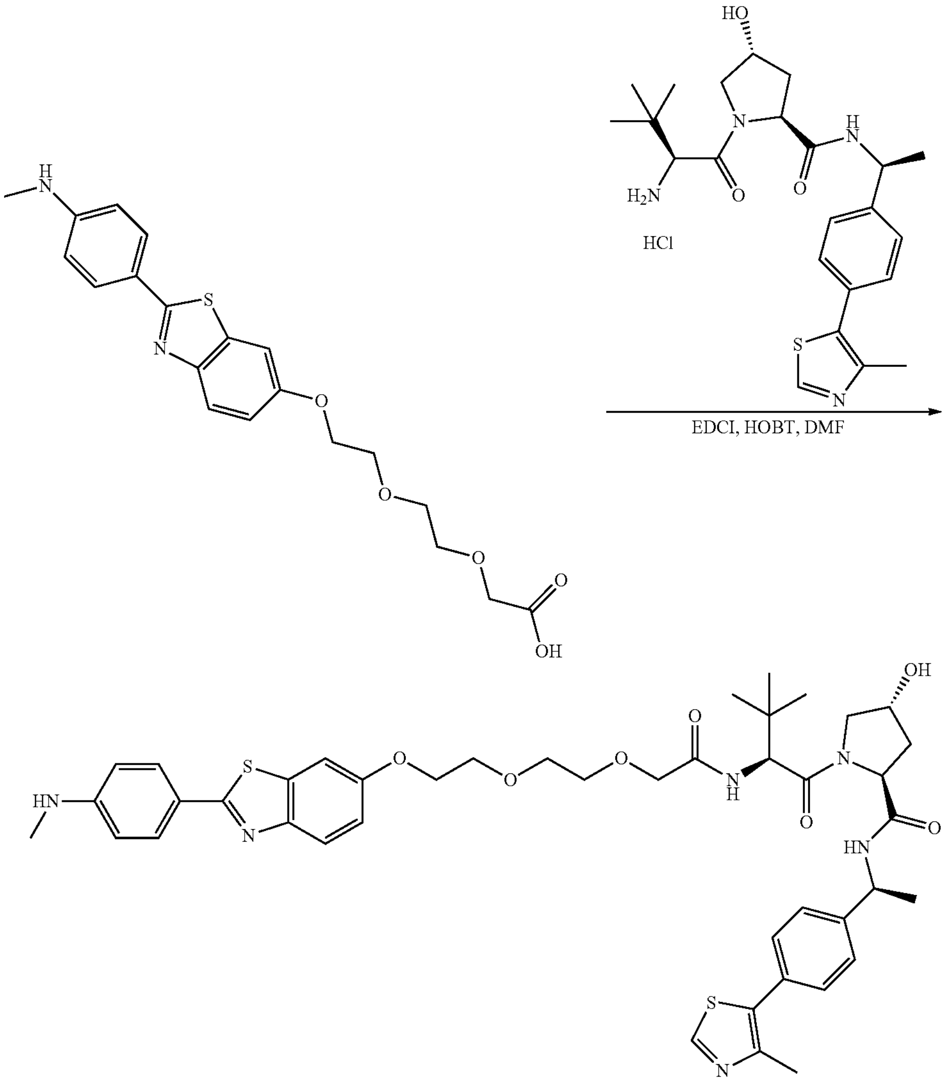

Exemplary Compound 1

A mixture of (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide hydrochloride (72 mg, 0.15 mmol, 1.00 eq), hydroxybenzotriazole (20 mg, 0.15 mmol, 1.00 eq) carbodiimide hydrochloride (34 mg, 0.18 mmol, 1.20 eq) and diisopropylethylamine (58 mg, 0.45 mmol, 3.00 eq) in dimethylformamide (5 mL) was stirred at 12° C. for 30 minutes. To the reaction was added 2-[2-[2-[[2-[4-(methylamino)phenyl]-1,3-benzothiazol-6-yl]oxy]ethoxy]ethoxy]acetic acid (60 mg, 0.15 mmol, 1.00 eq). The mixture stirred at 30° C. for 12 hours. The reaction mixture was quenched by the addition of water (100 mL), and then diluted with ethyl acetate (20 mL) and extracted with ethyl acetate (40 mL×3). The combined organic layers were washed with saturated brine (20 mL×3), dried over anhydrous sodium sulfate, filtered and concentrated under reduced pressure. The residue purified by prep-HPLC (column: Boston Green ODS 150*30 5 u; mobile phase: [water (0.225% FA)-ACN]; B %: 45%-75%, 10 min). (2S,4R)-1-[(2S)-3,3-dimethyl-2-[[2-[2-[2-[[2-[4-(methylamino) phenyl]-1,3-benzothiazol-6-yl]oxy]ethoxy]ethoxy]acetyl]amino] butanoyl]-4-hydroxy-N-[(1S)-1-[4-(4-methylthiazol-5-yl)phenyl]ethyl]pyrrolidine-2-carboxamide (32 mg, 0.04 mmol, 25% yield) was obtained as a yellow solid.

Exemplary Synthesis of Exemplary Compound 2

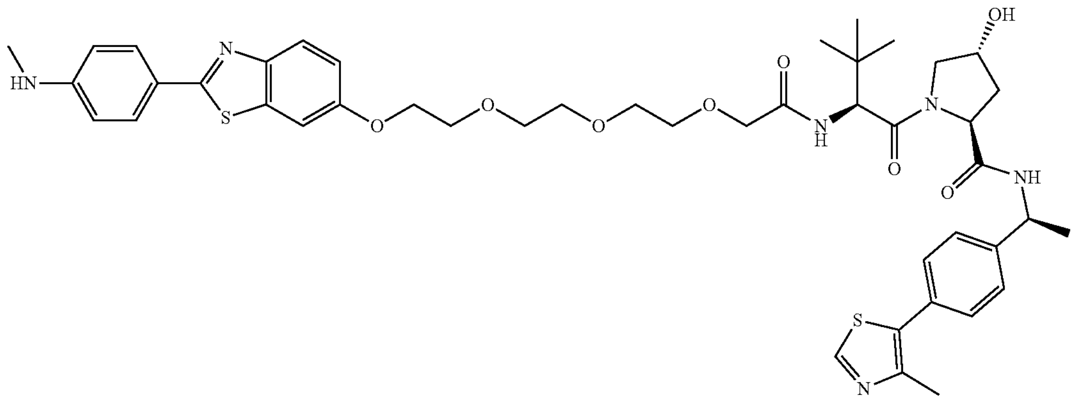 [SMILES: CNc1ccc(-c2nc3ccc(OCCOCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1]

Step 1

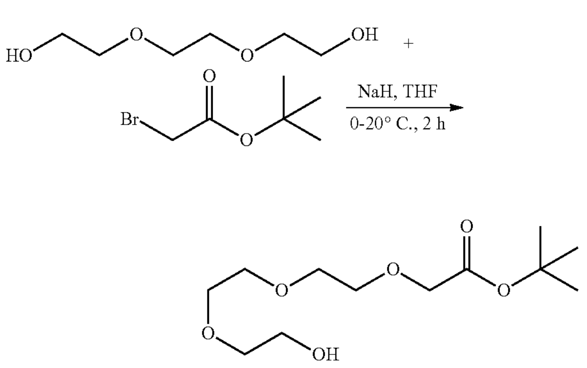

To a mixture of sodium hydride (2.26 g, 56.4 mmol, 60% in mineral oil, 1.10 eq) in tetrahydrofuran (300 mL) was added a solution of 2-[2-(2-hydroxyethoxy)ethoxy]ethanol (38.5 g, 256 mmol, 34.38 mL, 5.00 eq) in tetrahydrofuran (100 mL) at 0° C. The mixture was then stirred at 20° C. for 1 hour. A solution of tert-butyl 2-bromoacetate (10 g, 51.3 mmol, 7.58 mL, 1.00 eq) in tetrahydrofuran (100 mL) was added to the mixture at 0° C. The mixture was stirred at 20° C. for 2 hours. The reaction mixture was quenched with saturated ammonium chloride solution (100 mL) and water (50 mL). The organic layer was separated, and aqueous layer was extracted with dichloromethane (100 mL×3). The organic layers were combined and dried over sodium sulfate. The crude material was purified by column chromatography (dichloromethane:methanol=200:1-60:1). Tert-butyl 2-[2-[2-(2-hydroxyethoxy)ethoxy]ethoxy]acetate (10 g, 37.8 mmol, 37% yield) was obtained as a yellow oil.

Tert-butyl 2-[2-[2-(2-hydroxyethoxy)ethoxy]ethoxy]acetate was converted to the title compound, (2S,4R)-1-((S)-2-(tert-butyl)-14-((2-(4-(methylamino)phenyl)benzo[d]thiazol-6-yl)oxy)-4-oxo-6,9,12-trioxa-3-azatetradecanoyl)-4-hydroxy-N—((S)-1-(4-(4-methylthiazol-5-yl)phenyl)ethyl) pyrrolidine-2-carboxamide, using procedures analogous to those described above for Exemplary Compound 1.

Using procedures described above the following examples were prepared: Exemplary Compound 3, Exemplary Compound 4, and Exemplary Compound 5.

Exemplary Synthesis of Exemplary Compound 6 and Exemplary Compound
Exemplary Compound 6
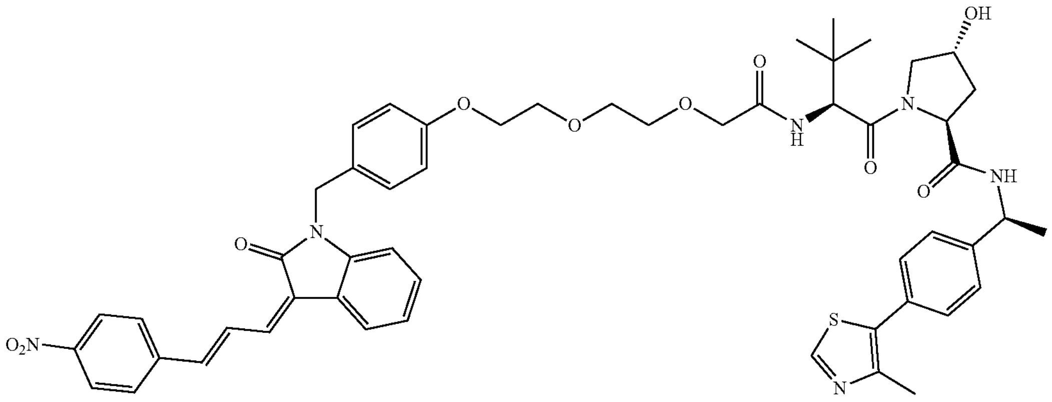
E/Z individual isomer 1-tentative assignment
Exemplary Compound 7
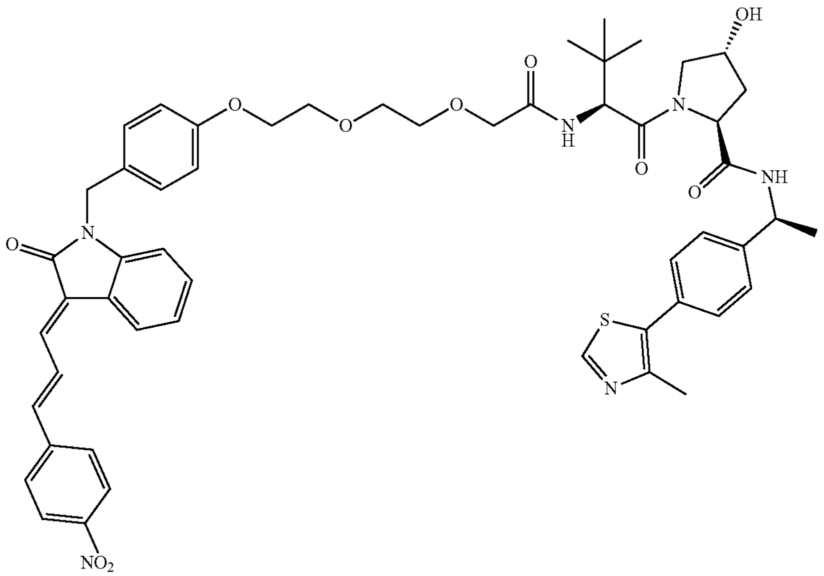
E/Z individual isomer 2-tentative assignment Step 1

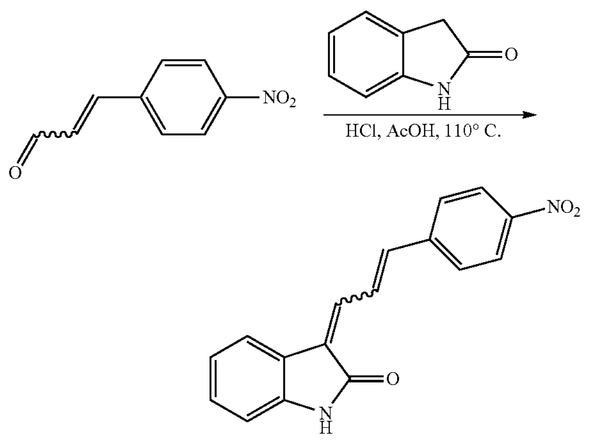

To a solution of indolin-2-one (13 g, 99.89 mmol. 1.00 eq) and 3-(4-nitrophenyl) acrylaldehyde (17 g, 99.89 mmol, 1.00) eq) in acetic acid (300 mL) was added hydrochloric acid (conc. 6 mL). The reaction mixture was heated to 100° C. and stirred at 100° C. for 3 hours. The mixture was poured into 1000 mL of water. The solid formed was filtered and dried in a vacuum. 3-(3-(4-Nitrophenyl)allylidene) indolin-2-one (20 g, 34.21 mmol, 68% yield) was obtained as a red solid.

Step 2

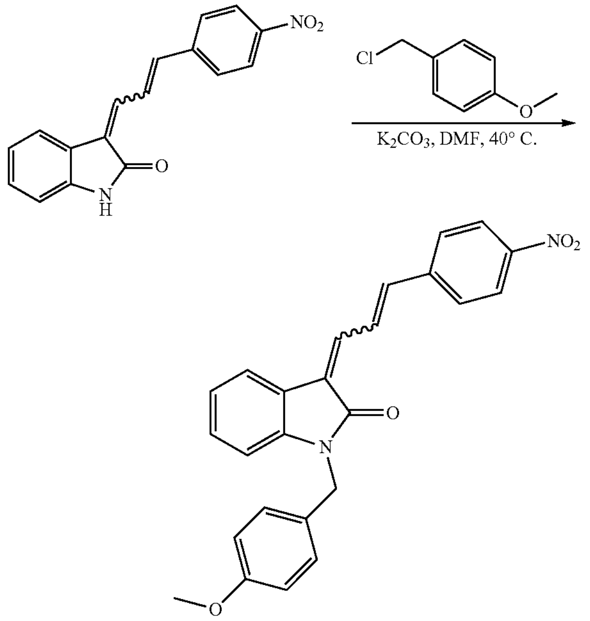

To a solution of 3-(3-(4-nitrophenyl)allylidene)indolin-2-one (20 g, 68 mmol, 1.00 eq) in N,N-dimethylformamide (500 mL) was added potassium carbonate (19 g, 137 mmol, 2.00 eq) and 1-(chloromethyl)-4-methoxy-benzene (16 g, 102 mmol, 14 mL, 1.50 eq). The mixture was stirred at 40° C. for 3 hours. The mixture was poured into brine (1500 mL), and the extracted with ethyl acetate (500 mL×2). The combined organic layers were washed with brine (500 mL×4), dried over anhydrous sodium sulfate, filtered and concentrated in vacuum. The residue was triturated with petroleum ether:ethyl acetate (v/v=3:1, 200 mL). 1-(4-methoxybenzyl)-3-(3-(4-Nitrophenyl)allylidene)indolin-2-one (20 g, 48 mmol, 71% yield) was obtained as a red solid.

Step 3

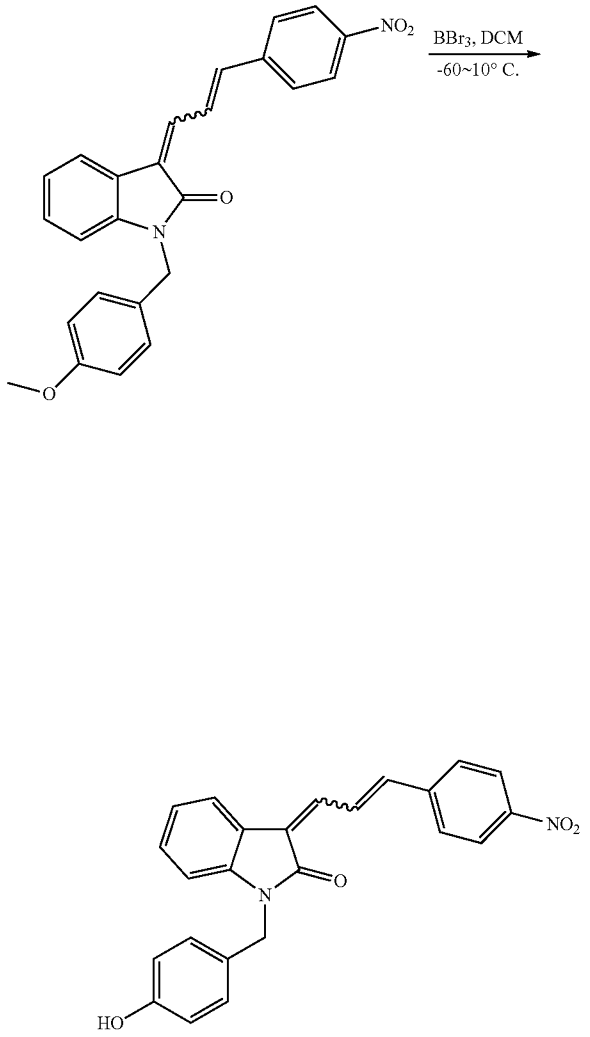

To a solution of 3-1-[(4-methoxyphenyl)methyl]-3-[3-(4-nitrophenyl)prop-2-enylidene] indolin-2-one (1.24 g, 3.01 mmol, 1.00 eq) in dichloromethane (40 mL) was added boron tribromide (3 g, 12.03 mmol, 4.00 eq) at −60° C. When addition was completed, the mixture was stirred at −60° C.~0° C. for 2 hours. The mixture was poured into 500 mL saturated sodium bicarbonate solution, and stirred at 0° C. for 15 minutes. The solid formed was filtered and dried in vacuum. The residue was triturated with ethyl acetate: petroleum ether (v/v=3:1, 50 mL). 3-1-[(4-Hydroxyphenyl) methyl]-3-[3-(4-nitrophenyl)prop-2-enylidene]indolin-2-one (820 mg, 2.06 mmol, 68% yield) was obtained as a red solid.

Step 4

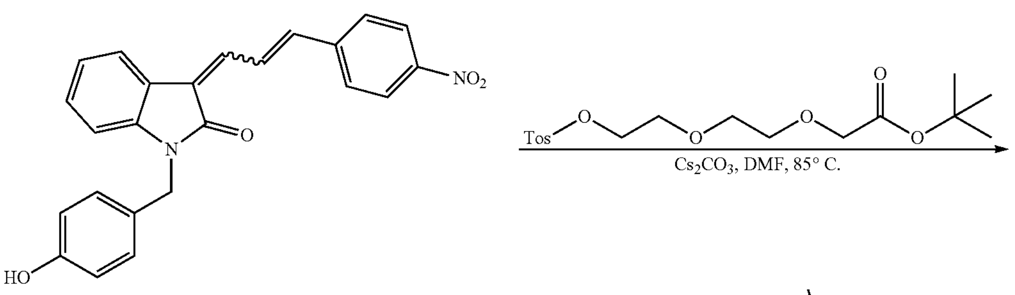

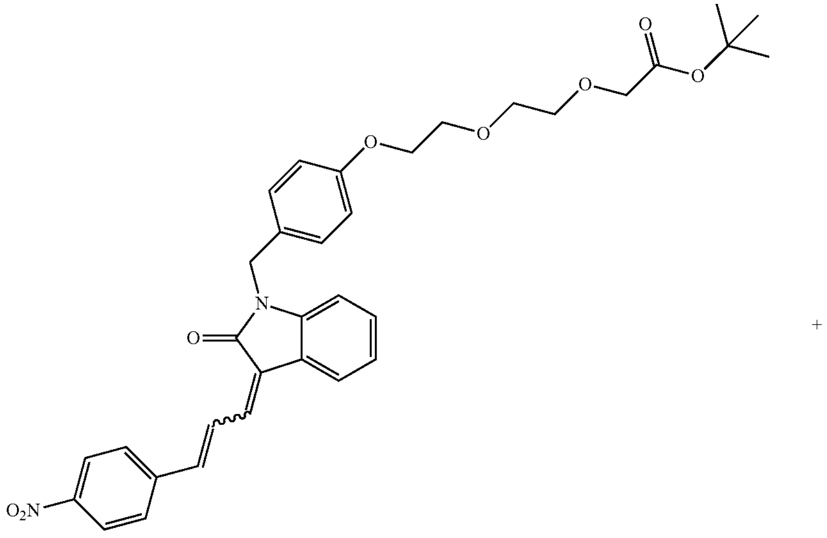

isomer 1

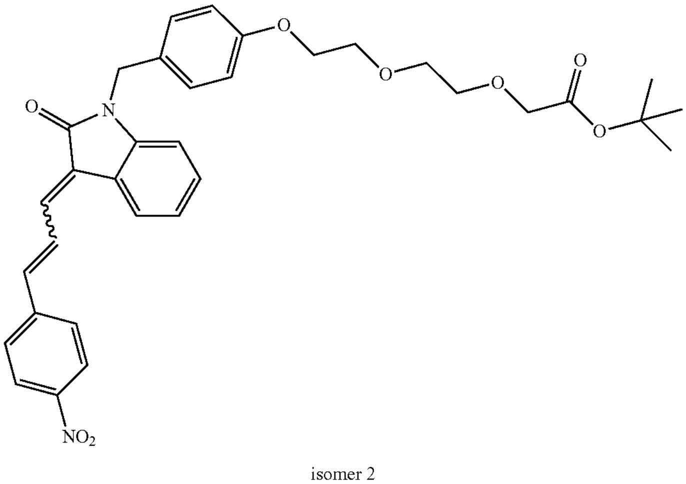

isomer 2

To a solution of 3-1-[(4-hydroxyphenyl)methyl]-3-[3-(4-nitrophenyl)prop-2-enylidene] indolin-2-one (200 mg, 0.5 mmol, 1.00 eq) and tert-butyl 2-[2-[2-(p-tolylsulfonyloxy) ethoxy]ethoxy]acetate (188 mg, 0.5 mmol, 1.0) eq) in dimethylformamide (5 mL) was added cesium carbonate (490 mg, 1.51 mmol, 3.00 eq). The reaction mixture was stirred at 85° C. for 1 hour. The reaction mixture was diluted with ethyl acetate (50 mL), washed with brine (30 mL×3), dried over anhydrous sodium sulfate, filtered and concentrated under reduced pressure. The residue was purified by silica gel column chromatography (petroleum ether:ethyl acetate=80:1 to 20:1) to produce, in order of elution, two individual configurational isomers: isomer 1 (50 mg, 0.08 mmol, 33% yield) as a red solid tentatively assigned as tert-butyl 2-(2-(2-(4-(((Z)-3-((E)-3-(4-nitrophenyl)allylidene)-2-oxoindolin-1-yl)methyl)phenoxy)ethoxy)ethoxy) acetate (50 mg, 0.08 mmol, 33% yield), and isomer 2 (120 mg, 0.2 mmol, 79% yield) as a red solid tentatively assigned as tert-butyl 2-(2-(2-(4-(((E)-3-((E)-3-(4-nitrophenyl)allylidene)-2-oxoindolin-1-yl)methyl)phenoxy)ethoxy)ethoxy) acetate.

Step 5

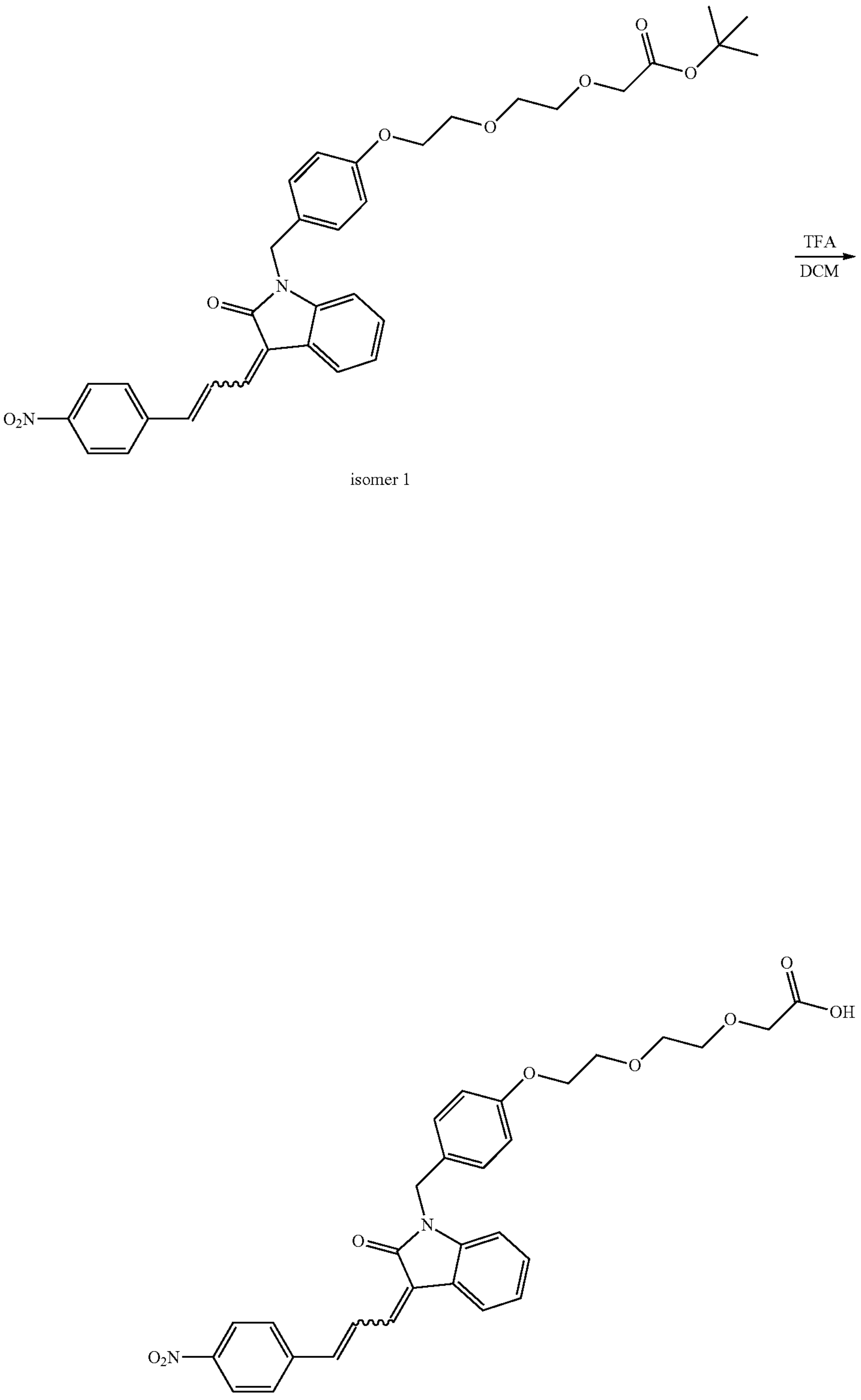

isomer 1

To a solution of isomer 1 tentatively assigned as tert-butyl 2-(2-(2-(4-(((Z)-3-((E)-3-(4-nitrophenyl)allylidene)-2-oxoindolin-1-yl)methyl)phenoxy)ethoxy)ethoxy)acetate (50 mg. 0.08 mmol, 1.00 eq) in dichloromethane (2 mL) was added trifluoroacetic acid (2 mL). The reaction mixture was stirred at 25° C. for 12 hours. The reaction mixture was concentrated under reduced pressure. Tentatively assigned configurational isomer 2-(2-(2-(4-(((Z)-3-((E)-3-(4-nitrophenyl)allylidene)-2-oxoindolin-1-yl)methyl)phenoxy)ethoxy)ethoxy)acetic acid (50 mg, crude) was obtained as a red solid.

Step 6

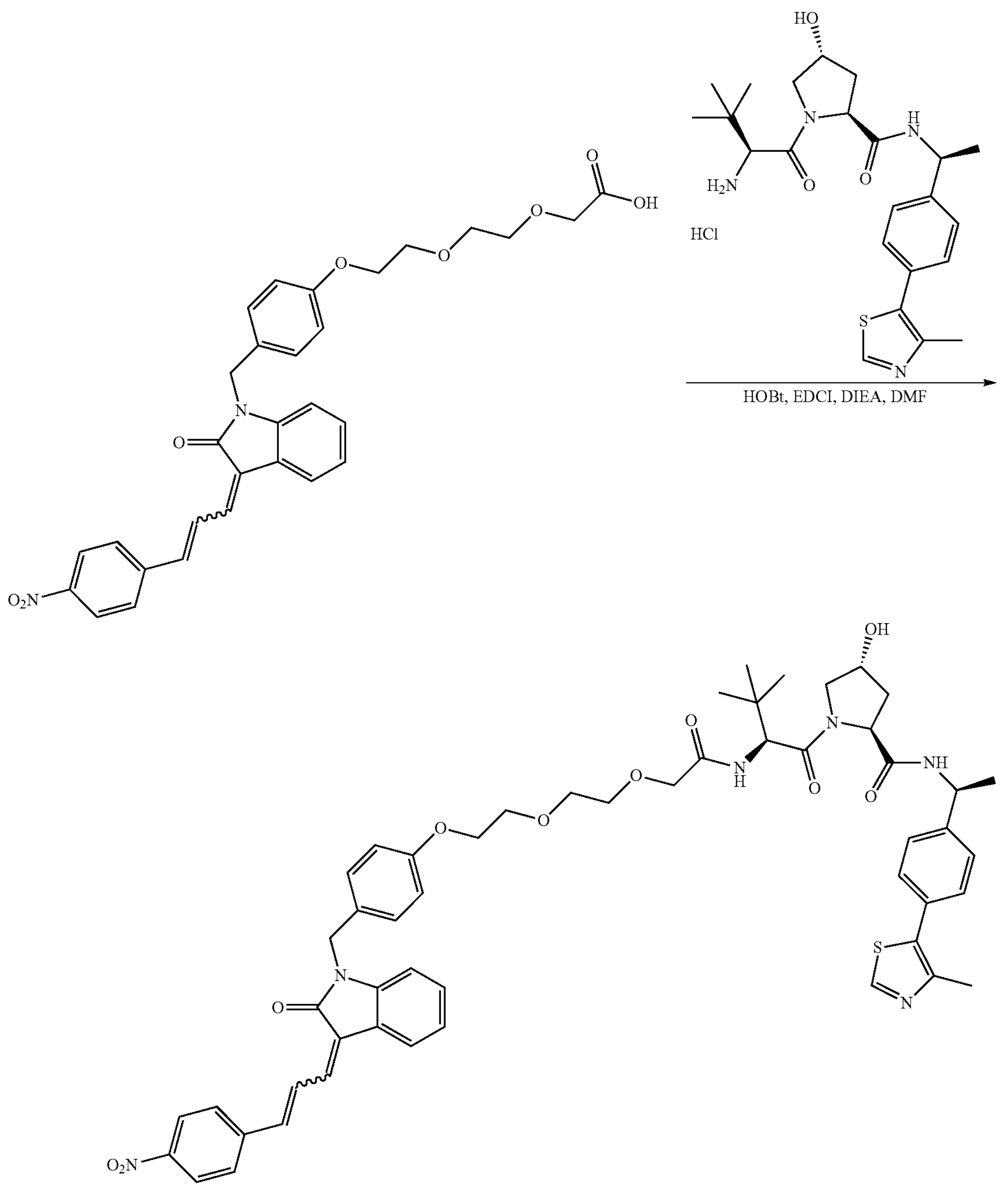

Exempary Copund 6

To a solution 2-(2-(2-(4-(((Z)-3-((E)-3-(4-nitrophenyl)allylidene)-2-oxoindolin-1-yl)methyl)phenoxy)ethoxy) ethoxy)acetic acid (50 mg, 0.09 mmol, 1.00 eq), 1-hydroxybenzotriazole (12 mg, 0.09 mmol, 1.00 eq), 1-ethyl-3-[3-(dimethylamino) propyl]carbodiimide hydrochloride (21 mg, 0.11 mmol, 1.20 eq) in dimethylformamide (5 mL) was added (2S,4R)-1-[(2S)-2-amino-3,3-dimethyl-butanoyl]-4-hydroxy-N-[(1S)-1-[4-(4-methylthiazol-5-yl)phenyl]ethyl] pyrrolidine-2-carboxamide (44 mg. 0.09 mmol, 1.00 eq, hydrochloric acid) and diisopropylethylamine (71 mg, 0.55 mmol, 6.00 eq). The reaction mixture was stirred at 25° C. for 12 hours. The reaction mixture was diluted with water (50 mL) and extracted with ethyl acetate (30 mL×3). The combined organic layers were washed with brine (50 mL×3), dried over anhydrous sodium sulfate, filtered and concentrated under reduced pressure. The residue was purified by Semi-preparative reverse phase HPLC (column: Boston Green ODS 150*30 5 um; mobile phase: [water (0.225% formic acid)-acetonitrile]; B %: 62%-89%, 10 min). Tentatively assigned configurational isomer Exemplary Compound 6 (2S,4R)-1-((S)-3,3-dimethyl-2-(2-(2-(2-(4-(((Z)-3-((E)-3-(4-Nitrophenyl)allylidene)-2-oxoindolin-1-yl)methyl)phenoxy)ethoxy)ethoxy)acetamido)butanoyl)-4-hydroxy-N—((S)-1-(4-(4-methylthiazol-5-yl)phenyl)

ethyl)pyrrolidine-2-carboxamide (11.3 mg, 0.01 mmol, 5% yield, 74% purity) was obtained as a red solid.

Step 7

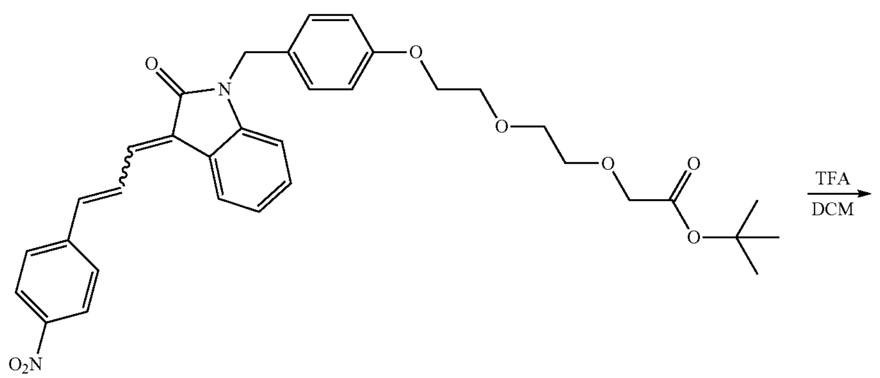

isomer 2

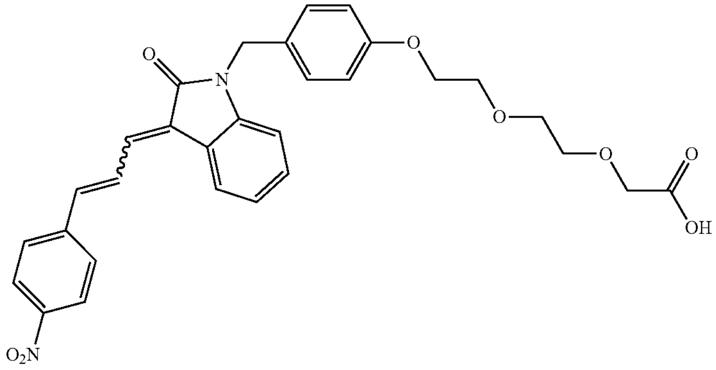

To a solution of tentatively assigned isomer 2 tert-butyl 2-(2-(2-(4-(((E)-3-((E)-3-(4-nitrophenyl)allylidene)-2-oxoindolin-1-yl)methyl)phenoxy)ethoxy)ethoxy)acetate (120 mg, 0.2 mmol, 1.00 eq) in dichloromethane (2 mL) was added trifluoroacetic acid (2 mL). The reaction mixture was stirred at 25° C. for 12 hours. The reaction mixture was concentrated under reduced pressure. Tentatively assigned configurational isomer 2-(2-(2-(4-(((E)-3-((E)-3-(4-Nitrophenyl)allylidene)-2-oxoindolin-1-yl)methyl)phenoxy)ethoxy)ethoxy)acetic acid (120 mg, crude) was obtained as a red solid.

Step 8

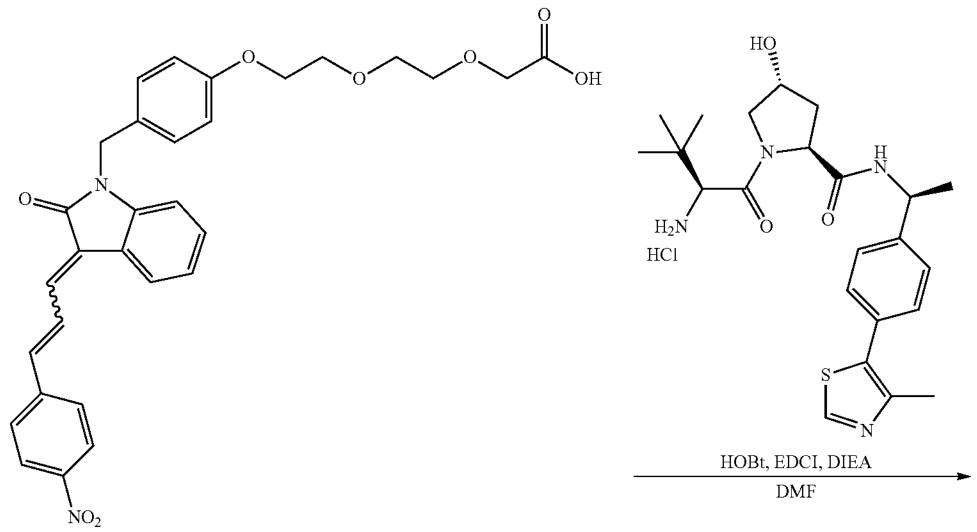

-continued

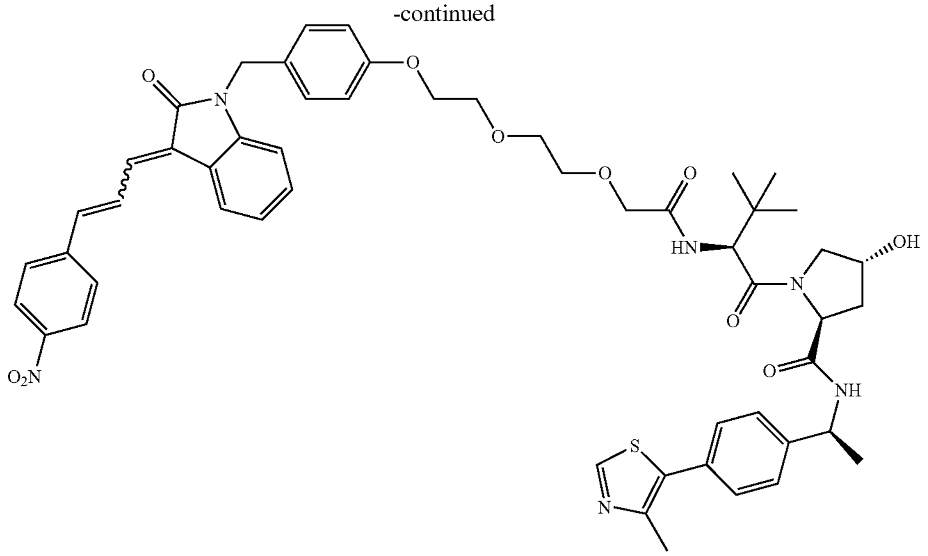

Exemplary Compoun 7

To a solution of 2-(2-(2-(4-(((E)-3-((E)-3-(4-nitrophenyl) allylidene)-2-oxoindolin-1-yl)methyl)phenoxy)ethoxy) ethoxy)acetic acid (100 mg, 0.2 mmol, 1.00 eq), 1-hydroxy-benzotriazole (27 mg, 0.2 mmol, 1.00 eq), 1-ethyl-3-[3-(dimethylamino) propyl]carbodiimide hydrochloride (42 mg, 0.22 mmol, 1.10 eq) in dimethylformamide (5 mL) was added (2S,4R)-1-[(2S)-2-amino-3,3-dimethyl-butanoyl]-4-hydroxy-N-[(1S)-1-[4-(4-methylthiazol-5-yl)phenyl]ethyl] pyrrolidine-2-carboxamide (120 mg, 0.2 mmol, 1.00 eq, hydrochloride) and diisopropylethylamine (142 mg, 0.11 mmol, 5.5 eq). The reaction mixture was stirred at 25° C. for 12 hours. The reaction mixture was diluted with water (50 mL) and extracted with ethyl acetate (30 mL×3). The combined organic layers were washed with brine (50 mL×3), dried over anhydrous sodium sulfate, filtered and concentrated under reduced pressure. The residue was purified by Semi-preparative reverse phase HPLC (column: Boston Green ODS 150*30 5um; mobile phase: [water (0.225% formic acid)-acetonitrile]; B %: 65%-92%, 10 min). Tentatively assigned configurational isomer Exemplary Compound 7 (2S,4R)-1-((S)-3,3-dimethyl-2-(2-(2-(2-(4-(((E)-3-((E)-3-(4-nitrophenyl)allylidene)-2-oxoindolin-1-yl)methyl)phenoxy)ethoxy)ethoxy)acetamido)butanoyl)-4-hydroxy-N—((S)-1-(4-(4-methylthiazol-5-yl)phenyl) ethyl)pyrrolidine-2-carboxamide (16 mg, 0.08 mmol, 12% yield, 96% purity) was obtained as a red solid.

Exemplary Synthesis of Exemplary Compound 8

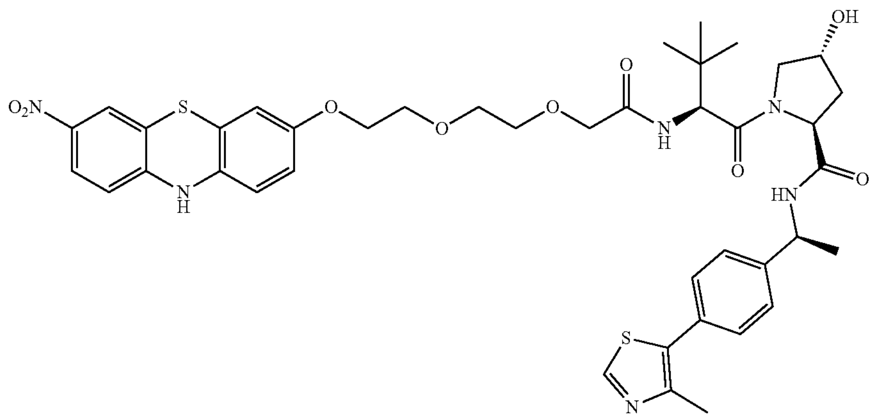 [SMILES: Cc1ncsc1-c1ccc([C@H](C)NC(=O)[C@@H]2C[C@@H](O)CN2C(=O)[C@@H](NC(=O)COCCOCCOc2ccc3c(c2)Sc2cc([N+](=O)[O-])ccc2N3)C(C)(C)C)cc1]

Step 1

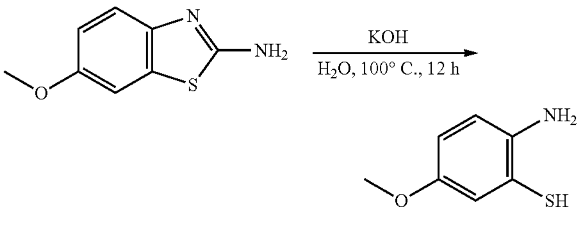

6-Methoxy-1,3-benzothiazol-2-amine (30.00 g, 166.5 mmol, 1.00 eq) was suspended in 100 mL of aqueous potassium hydroxide (9.34 g, 166.5 mmol, 1.00 eq) solution, and the mixture was stirred at 100° C. for 12 hours. 2-amino-5-methoxy-benzenethiol (25.80 g, crude) was obtained in the solution of water and was used in the next step without further purification.

Step 2

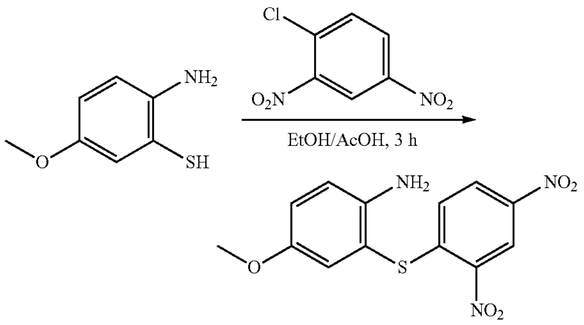

2-Amino-5-methoxy-benzenethiol (24.0 g, 154.6 mmol, 1.00 eq) was added dropwise to the solution of 1-chloro-2, 4-dinitro-benzene (40.1 g, 197.9 mmol, 1.28 eq) in ethyl alcohol (1200 mL) and acetic acid (3000 mL). The mixture was stirred at 25° C. for 3 hours. The reaction mixture was then filtered, and the solid was washed with water/ethanol (v/v=1/1, 200 mL) to give 2-(2,4-dinitrophenyl)sulfanyl-4-methoxy-aniline (22.0 g, crude) as a brown solid.

Step 3

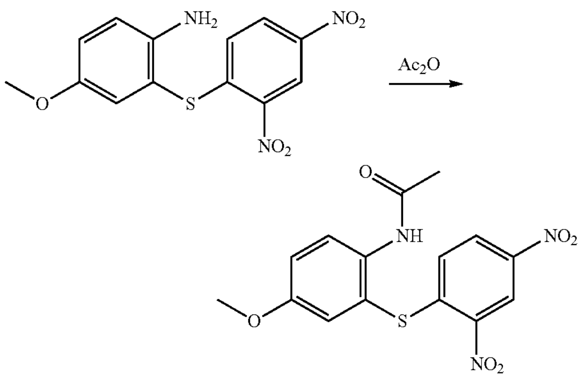

To a solution of 2-(2,4-dinitrophenyl)sulfanyl-4-methoxy-aniline (22.0 g, 68.5 mmol, 1.00 eq) in acetic anhydride (450 mL) was added pyridine (86.2 g, 1.1 mol, 15.93 eq). Then the mixture was stirred at 18° C. for 1.5 hours. The reaction mixture was then quenched by the addition of water (5000 mL) at 0° C., and pH was then adjusted to 7-8 with sodium bicarbonate solution. The solution was extracted with ethyl acetate (500 mL×3). The combined organic layers were washed with brine (300 mL×2), dried over sodium sulfate, filtered and concentrated under reduced pressure. The residue was washed with petroleum ether (500 mL) and ethyl acetate (20 mL). N-[2-(2,4-Dinitrophenyl)sulfanyl-4-methoxy-phenyl]acetamide (21.0 g, 57.8 mmol, 84% yield) was isolated as a yellow solid.

Step 4

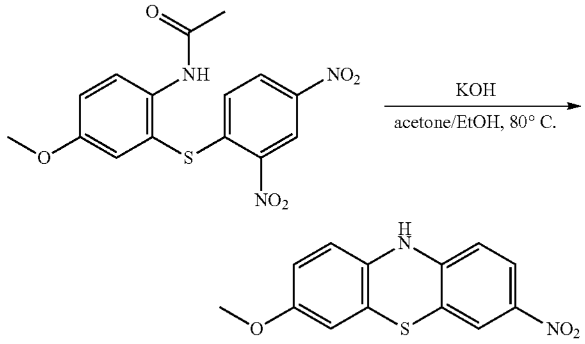

To a solution of N-[2-(2,4-dinitrophenyl)sulfanyl-4-methoxy-phenyl]acetamide (21.0 g, 57.8 mmol, 1.00 eq) in acetone (1200 mL) and ethyl alcohol (400 mL) at 80° C. was added potassium hydroxide (6.88 g, 122.5 mmol, 2.12 eq), and the mixture was stirred at 80° C. for 2 hours. The reaction mixture was then quenched by the addition of water (1500 mL) at 0° C. and concentrated under reduced pressure to remove acetone. The residue was filtered to get the filter cake. The filter cake was washed with ethyl acetate/petroleum ether (v/v=1:10, 2000 mL) to give 3-methoxy-7-nitro-10H-phenothiazine (19.0 g, crude) as a black solid.

Step 5

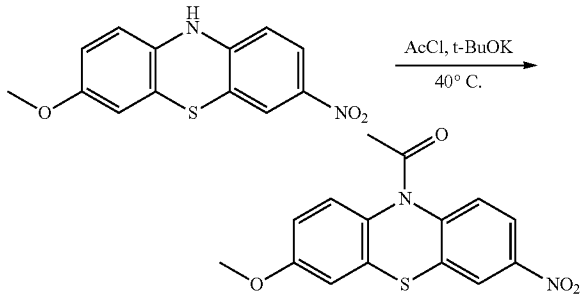

To a solution of 3-methoxy-7-nitro-10H-phenothiazine (8.10 g, 29.5 mmol, 1.00 eq) in dimethylformamide (250 mL) was added potassium tert-butoxide (9.94 g, 88.6 mmol, 3.00 eq) at 0° C. The mixture was stirred at 0° C. for 30 minutes. Then acetyl chloride (23.18 g, 295.3 mmol, 10.00 eq) was added. The reaction mixture was stirred at 40° C. for 48 hours. The mixture was poured into 400 mL saturated sodium bicarbonate solution, and then extracted with ethyl acetate (300 mL×2). The combined organic layers were washed with brine (400 mL×4), dried over anhydrous sodium carbonate, filtered and concentrated in vacuum. The residue was further purified by column chromatography (petroleum ether/ethyl acetate=10/1 to 5/1). 1-(3-methoxy-7-nitro-phenothiazin-10-yl)ethanone (3.60 g, 11.4 mmol, 38% yield) was obtained as a red solid and used directly in the next step without further purification.

Step 6

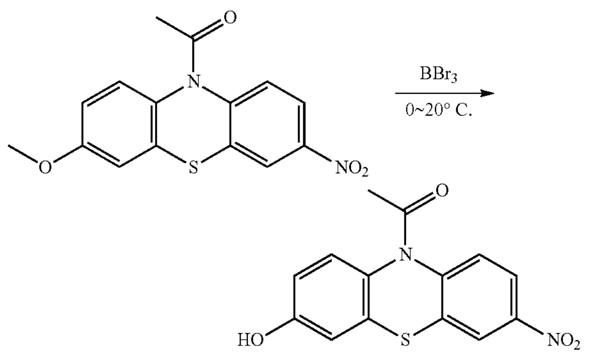

To a mixture of 1-(3-methoxy-7-nitro-phenothiazin-10-yl)ethanone (3.60 g, 11.4 mmol, 1.00 eq) in dichloromethane (50 mL) was added a solution of boron tribromide (8.55 g, 34.1 mmol, 3.00 eq) in dichloromethane (50 mL) at −20° C. The mixture was stirred at −20° C. for 30 minutes and then at 14° C. for 2 hours. The reaction mixture was quenched by the addition of saturated sodium bicarbonate solution (200 mL), diluted with dichloromethane (100 mL), and then extracted with dichloromethane (200 mL×3). The combined organic phase washed with brine, filtered and concentrated under reduce pressure. The residue was purified by column chromatography (petroleum ether/ethyl acetate=10/1 to 5/1). Compound 1-(3-hydroxy-7-nitro-phenothiazin-10-yl)ethanone (2.30 g, 7.61 mmol, 67% yield) was obtained as a brown solid.

Step 7

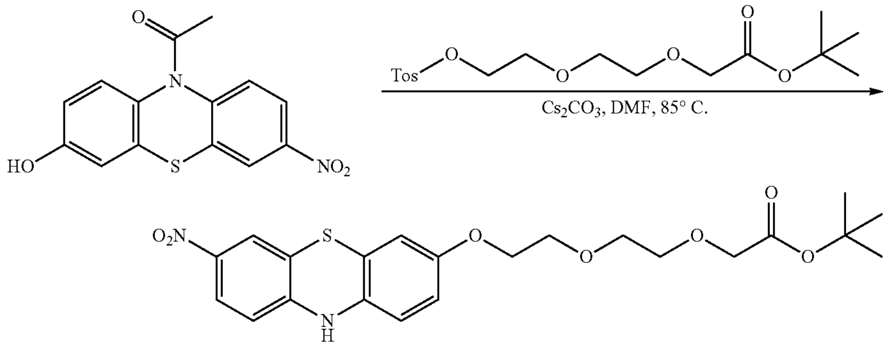

To a mixture of 1-(3-hydroxy-7-nitro-phenothiazin-10-yl) ethanone (150 mg, 0.50 mmol, 1.00 eq) and tert-butyl 2-[2-[2-(p-tolylsulfonyloxy)ethoxy]ethoxy]acetate (186 mg, 0.50 mmol, 1.00 eq) in dimethylformamide (5 mL) was added cesium carbonate (485 mg, 1.49 mmol, 3.00 eq). The mixture was stirred at 85° C. for 1 hour. The mixture was quenched by the addition of water (100 mL), diluted with ethyl acetate (20 mL) and further extracted with ethyl acetate (30 mL×3). The combined organic phase was washed with brine (20 mL×3), dried over anhydrous sodium sulfate, filtered and concentrated under reduce pressure. The residue was purified by preparative thin layer chromatography (petroleum ether/ethyl acetate=10/1). Compound tert-butyl 2-[2-[2-[(7-Nitro-10H-phenothiazin-3-yl)oxy]ethoxy] ethoxy] acetate (220 mg, crude) was obtained as a brown oil.

Step 8

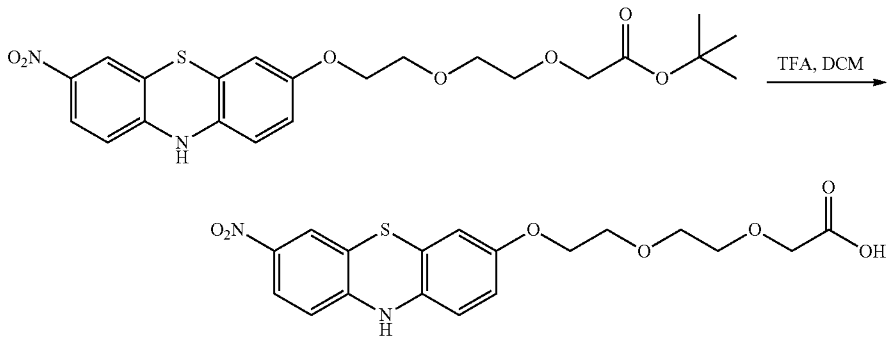

To a mixture of tert-butyl 2-[2-[2-[(7-nitro-10H-phenothiazin-3-yl)oxy]ethoxy]ethoxy]acetate (220 mg, 0.48 mmol, 1.00 eq) in dichloromethane (5 mL) was added trifluoroacetic acid (1.08 g, 9.51 mmol, 20.00 eq). The mixture was stirred at 14° C. for 12 hours. The reaction mixture was concentrated under reduced pressure. The residue was purified by Semi-preparative reverse phase HPLC (column: Boston Green ODS 150*30 5 u; mobile phase: [water (0.225% formic acid)-acetonitrile]; B %: 38%-68%, 10 min). Compound 2-[2-[2-[(7-nitro-10H-phenothiazin-3-yl)oxy]ethoxy]ethoxy]acetic acid (40 mg, 0.10 mmol, 21% yield) was obtained as a brown solid.

Step 9

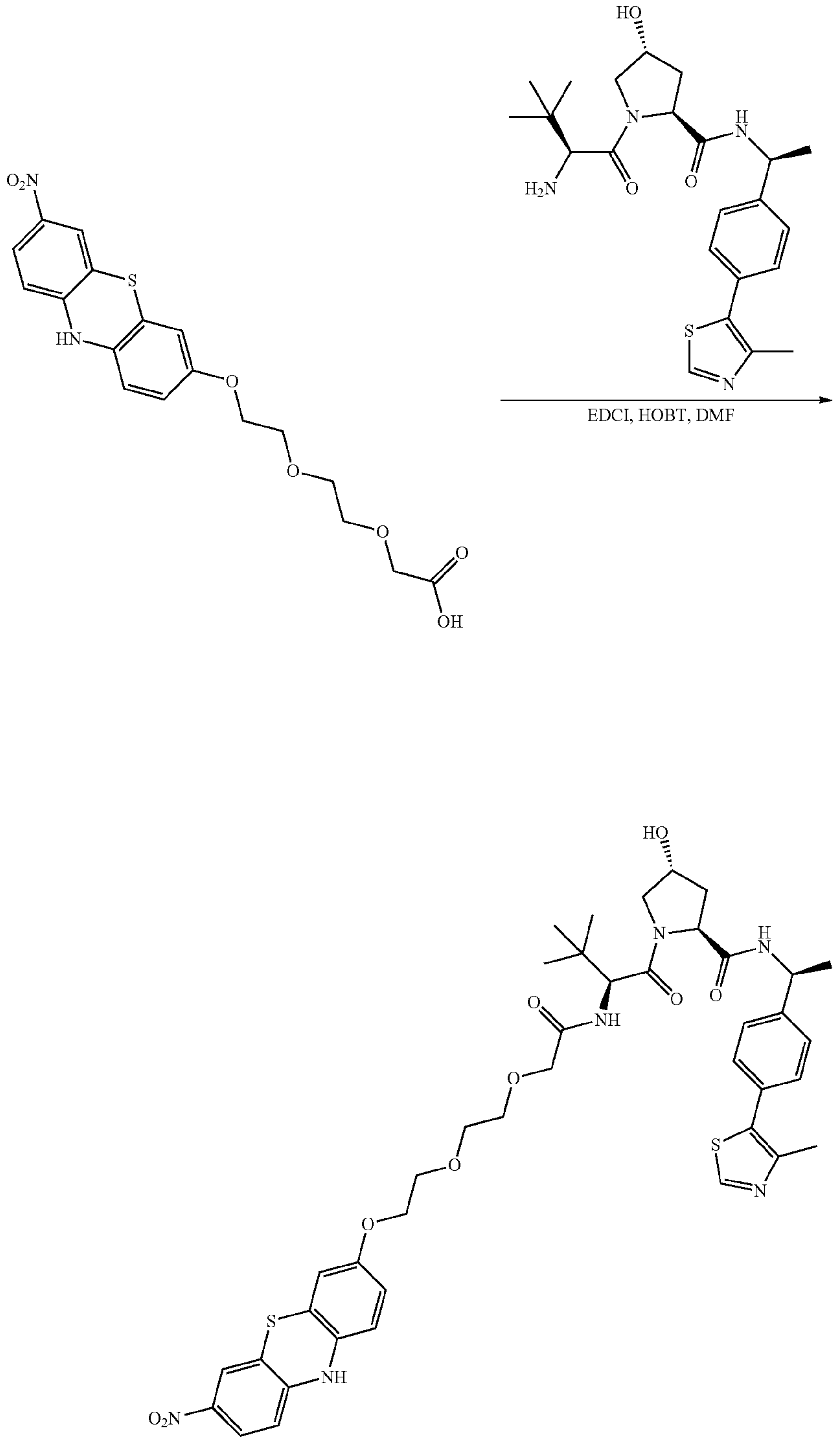

To a mixture of 2-[2-[2-[(7-nitro-10H-phenothiazin-3-yl)oxy]ethoxy]ethoxy]acetic acid (40 mg, 0.10 mmol, 1.00 eq) and (2S,4R)-1-[(2S)-2-amino-3,3-dimethyl-butanoyl]-4-hydroxy —N-[(1S)-1-[4-(4-methylthiazol-5-yl)phenyl]ethyl]pyrrolidine-2-carboxamide hydrochloride (47 mg, 0.10 mmol, 1.00 eq) in dimethylformamide (4 mL) was added hydroxybenzotriazole (13 mg, 0.10 mmol, 1.00 eq), carbodiimide hydrochloride (23 mg, 0.12 mmol, 1.20 eq) and diisopropylethylamine (13 mg, 0.10 mmol, 1.00 eq). The mixture was stirred at 40° C. for 12 hours and then quenched by the addition of water (100 mL), diluted with ethyl acetate (20 mL) and further extracted with ethyl acetate (30 mL×3). The combined organic layers were washed with brine (30 mL×3), dried over anhydrous sodium sulfate, filtered and concentrated under reduced pressure. The residue was purified by Semi-preparative reverse phase HPLC (column: Phenomenex Synergi C18 150*30 mm*4 um; mobile phase: [water (0.225% formic acid)-acetonitrile]; B %: 45%-75%, 10.5 min). Compound (2S,4R)-1-[(2S)-3,3-dimethyl-2-[[2-[2-[2-[(7-nitro-10H-phenothiazin-3-yl)oxy]ethoxy]ethoxy]acetyl]amino]butanoyl]-4-hydroxy-N-[(1S)-1-[4-(4-methylthiazol-5-yl)phenyl]ethyl]pyrrolidine-2-carboxamide (15 mg, 0.02 mmol, 19% yield) was obtained as a brown solid.

Exemplary Compounds 9, 10, 11, and 13 were prepared following the procedures described above for Exemplary Compound 8.

Exemplary Synthesis of Exemplary Compound 13

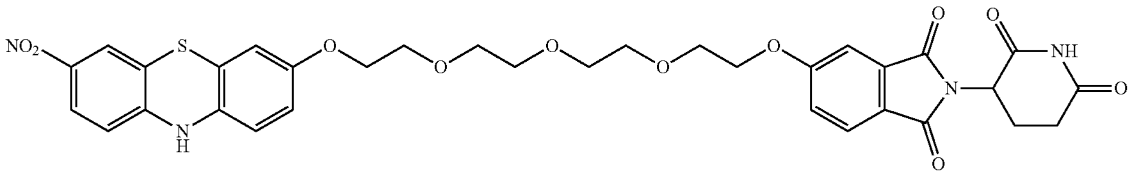 [SMILES: O=C1CCC(N2C(=O)c3ccc(OCCOCCOCCOCCOc4ccc5c(c4)Sc4cc([N+](=O)[O-])ccc4N5)cc3C2=O)C(=O)N1]

Step 1

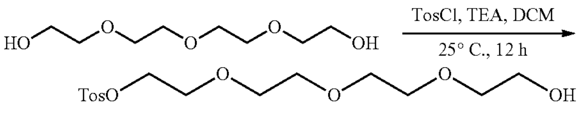

To a mixture of 2-[2-[2-(2-hydroxyethoxy)ethoxy]ethoxy]ethanol (5 g, 25.7 mmol, 4.4 mL, 1 eq) and 4-methylbenzenesulfonyl chloride (1.23 g, 6.4 mmol, 0.25 eq) in dichloromethane (50 mL) was added triethylamine (1.30 g, 12.9 mmol, 1.8 mL, 0.5 eq) in one portion at 25° C. under nitrogen. The mixture was stirred at 25° C. for 12 hours. The mixture was washed with brine (30 mL×2), dried with anhydrous sodium sulfate, filtered and concentrated in vacuum. The residue was purified by silica gel chromatography (petroleum ether/ethyl acetate=1/1 to 0/1) to afford 2-[2-[2-(2-hydroxyethoxy)ethoxy]ethoxy]ethyl 4-methylbenzenesulfonate (1.98 g, 5.68 mmol, 22% yield) as a colorless oil.

Step 2

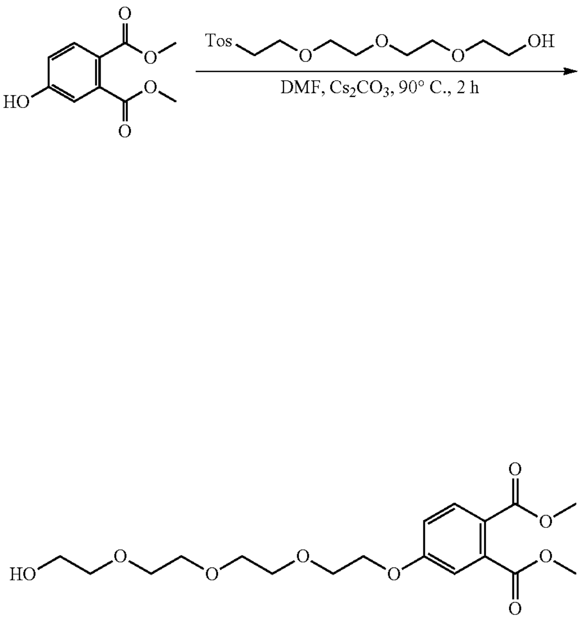

To a mixture of dimethyl 4-hydroxybenzene-1,2-dicarboxylate (500 mg, 2.38 mmol, 1.00 eq) and 2-[2-[2-(2-hydroxyethoxy)ethoxy]ethoxy]ethyl 4-methylbenzenesulfonate (828 mg, 2.38 mmol, 1.00 eq) in N,N-dimethylformamide (10 mL) was added cesium carbonate (1.55 g, 4.76 mmol, 2.00 eq) in one portion at 15° C. under nitrogen. The mixture was heated to 90° C. and stirred for 2 hours. The mixture was cooled to 25° C. and poured into ice-water (w/w=1/1) (20 mL) and stirred for 10 minutes. The aqueous phase was extracted with ethyl acetate (30 mL×3). The combined organic phase was washed with brine (30 mL×3), dried with anhydrous sodium sulfate, filtered and concentrated under vacuum. The residue was purified by prep-HPLC (Waters Xbridge 150*50 10 um; mobile phase: [water (0.05% ammonia hydroxide v/v)-ACN]; B %: 15%-45%, 11.5 min) to afford dimethyl 4-[2-[2-[2-(2-hydroxyethoxy)ethoxy]ethoxy]ethoxy]benzene-1,2-dicarboxylate (262 mg, 0.67 mmol, 29% yield) as a yellow oil.

Step 3

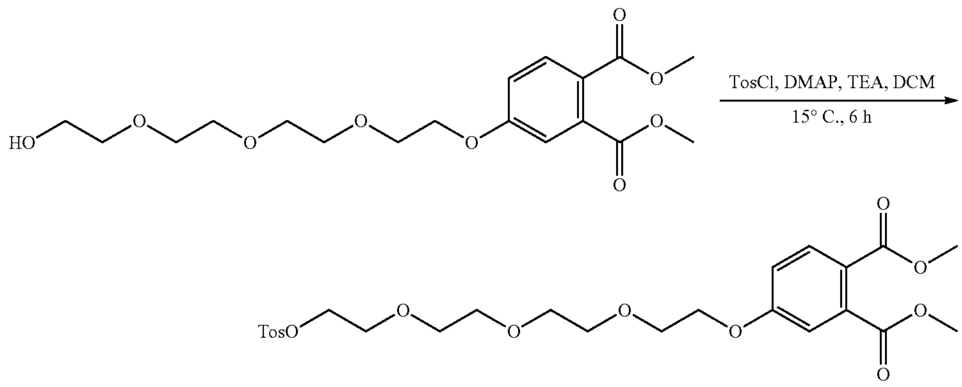

To a mixture of dimethyl 4-[2-[2-[2-(2-hydroxyethoxy)ethoxy]ethoxy]ethoxy]benzene-1,2-dicarboxylate (261 mg, 0.67 mmol, 1.00 eq), p-toluenesulfonyl chloride (193 mg, 1.01 mmol, 1.50 eq) and triethylamine (205 mg, 2.03 mmol, 3.00 eq) in dichloromethane (6 mL) was added N,N-dimethylaminopyridine (8.25 mg, 0.06 mmol, 0.1 eq) in one portion at 15° C. under nitrogen. The mixture was stirred at 15° C. for 6 hours. The mixture was cooled to 25° C. and concentrated under reduced pressure at 45° C. The residue was purified by silica gel chromatography (petroleum ether/ethyl acetate=1/1) to afford dimethyl 4-[2-[2-[2-[2-(p-tolylsulfonyloxy)ethoxy]ethoxy]ethoxy]ethoxy]benzene-1,2-dicarboxylate (216 mg, 0.39 mmol, 59% yield) as a yellow oil.

Step 4

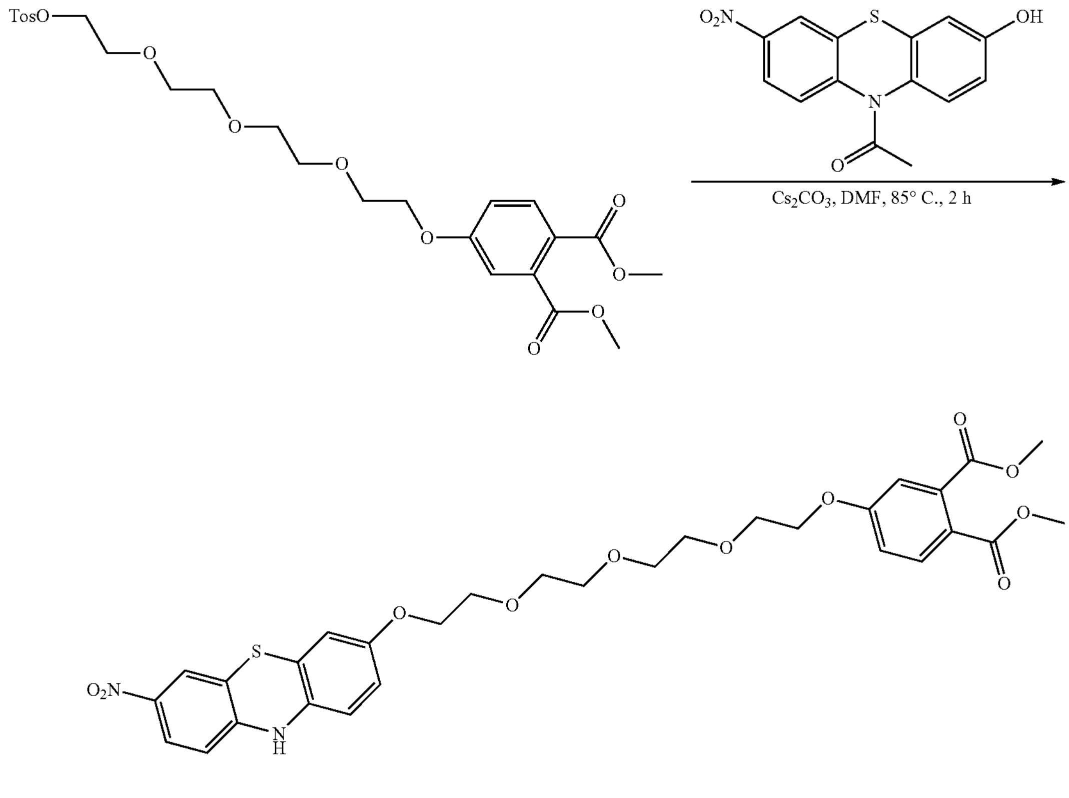

To a mixture of dimethyl 4-[2-[2-[2-[2-(p-tolylsulfonyloxy)ethoxy]ethoxy]ethoxy]ethoxy]benzene-1,2-dicarboxylate (115 mg, 0.21 mmol, 1.00 eq) and 1-(3-hydroxy-7-nitro-phenothiazin-10-yl)ethanone (64 mg, 0.21 mmol, 1.00 eq) in N,N-dimethylformamide (2 mL) was added cesium carbonate (138 mg, 0.42 mmol, 2.00 eq) in one portion at 15° C. under nitrogen. The mixture was stirred at 85° C. for 2 hours. The mixture was cooled to 25° C. and poured into ice-water (w/w=1/1) (30 mL) and stirred for 15 minutes. The aqueous phase was extracted with ethyl acetate (30 mL×3). The combined organic phase was washed with brine (30 mL×3), dried with anhydrous sodium sulfate, filtered and concentrated under vacuum. The residue was purified by prep-TLC (petroleum ether/ethyl acetate=1/1) to afford dimethyl 4-[2-[2-[2-[2-[(7-nitro-10H-phenothiazin-3-yl)oxy]ethoxy]ethoxy]ethoxy]ethoxy]benzene-1,2-dicarboxylate (43 mg, 0.06 mmol, 30% yield) as a brown solid.

Step 5

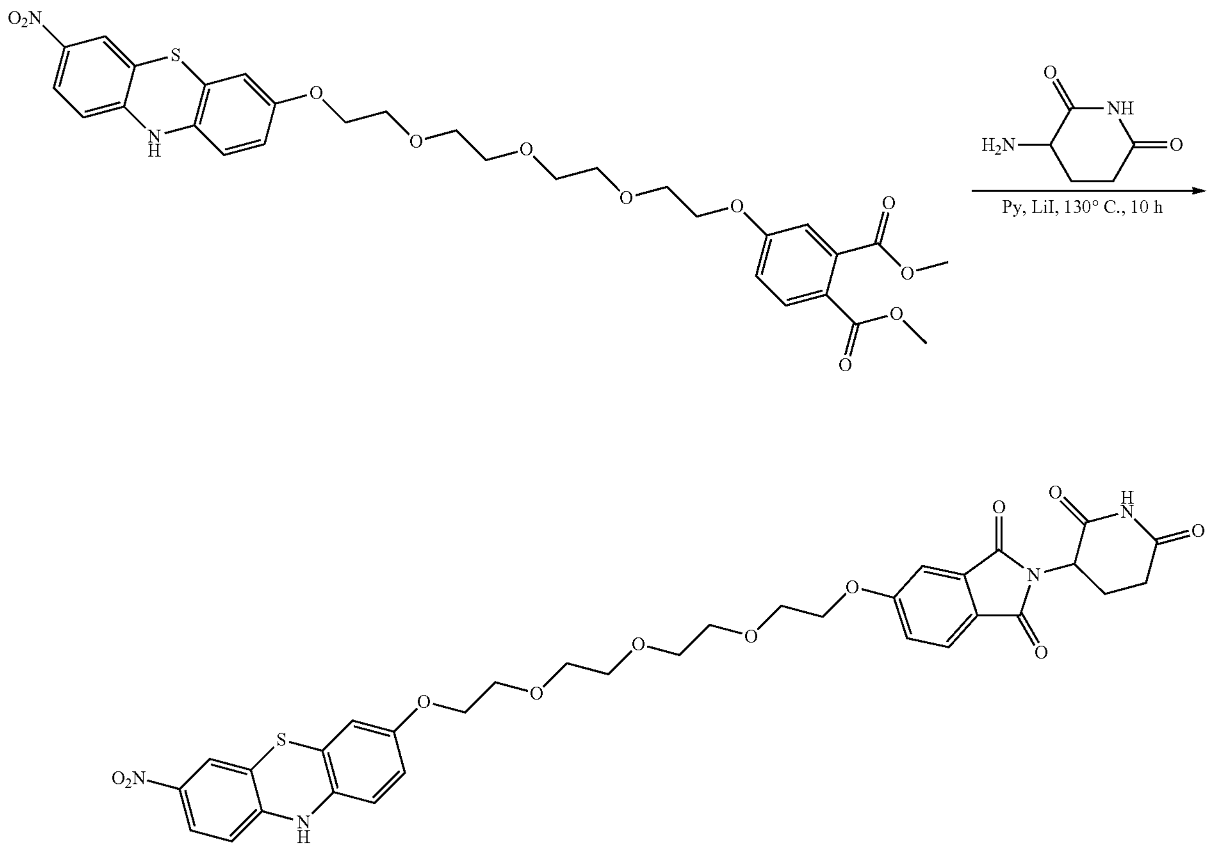

To a mixture of dimethyl 4-[2-[2-[2-[2-[(7-nitro-10H-phenothiazin-3-yl)oxy]ethoxy]ethoxy]ethoxy]ethoxy]benzene-1,2-dicarboxylate (43 mg, 0.06 mmol, 1.00 eq) and 3-aminopiperidine-2,6-dione (22 mg, 0.13 mmol, 2.00 eq, hydrochloride) in pyridine (5 mL) was added lithium iodide (137 mg, 1.03 mmol, 15 eq) in one portion at 15° C. under nitrogen. The mixture was stirred at 130° C. for 10 h. The mixture was cooled to 25° C. and concentrated under reduced pressure at 45° C. The residue was purified by prep-TLC (dichloromethane:methanol=10/1) to afford 2-(2,6-dioxo-3-piperidyl)-5-[2-[2-[2-[2-[(7-nitro-10H-phenothiazin-3-yl)oxy]ethoxy]ethoxy]ethoxy]ethoxy]isoindoline-1,3-dione (27 mg, 0.03 mmol, 57% yield) as a red solid.

Exemplary Compounds 14 was prepared following the procedures described above for Exemplary Compound 13.

Exemplary Synthesis of Exemplary Compound 16

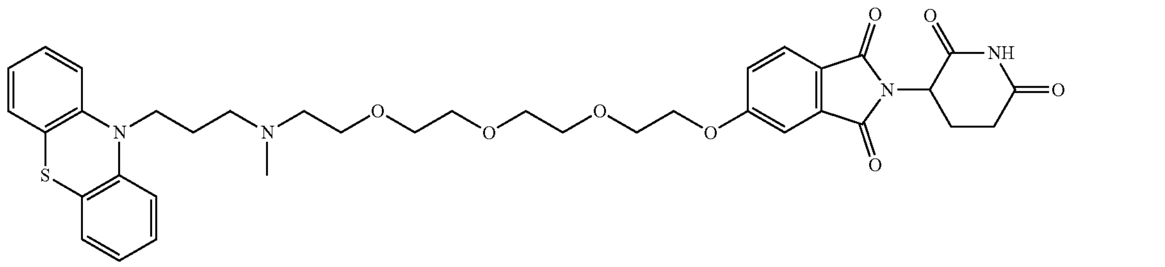 [SMILES: CN(CCCN1c2ccccc2Sc2ccccc21)CCOCCOCCOCCOc1ccc2c(c1)C(=O)N(C1CCC(=O)NC1=O)C2=O]

Step 1

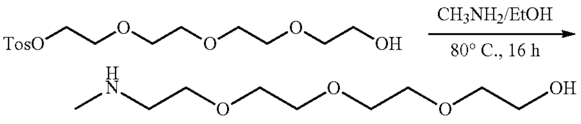

To 2-[2-[2-(2-hydroxyethoxy)ethoxy]ethoxy]ethyl 4-methylbenzenesulfonate (6 g, 17.22 mmol, 1 eq) was added 33 wt. % methylamine solution in EtOH (16.21 g, 172.2 mmol, 10 eq). The mixture was stirred at 80° C. for 16 hours. The reaction mixture was concentrated in vacuum to provide 2-[2-[2-[2-(methylamino)ethoxy]ethoxy]ethoxy]ethanol (4.6 g, crude) as a light yellow oil.

Step 2

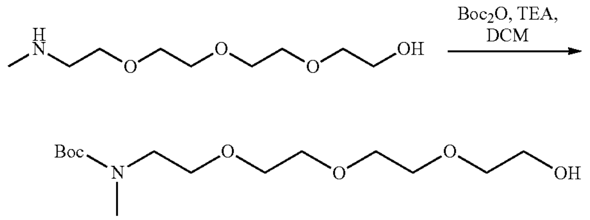

To a solution of 2-[2-[2-[2-(methylamino)ethoxy]ethoxy] ethoxy]ethanol (3.86 g, 18.6 mmol, 1 eq) in dichloromethane (30 mL) was added di-tert-butyl dicarbonate (4.88 g, 22.4 mmol, 5.13 mL, 1.2 eq) at 0° C., and the mixture was stirred at 15° C. for 16 hours. TLC showed some starting material remaining, so triethylamine (3.77 g, 37.25 mmol, 5.18 mL, 2 eq) was added, and the mixture stirred at 15° C. for an additional 12 hours. The reaction mixture was concentrated in vacuum, and the residue was purified by silica gel column chromatography (petroleum ether/ethyl acetate=5/1 to 1/3) to give tert-butyl N-[2-[2-[2-(2-hydroxyethoxy)ethoxy]ethoxy]ethyl]-N-methyl-carbamate (5.74 g, crude) as a light yellow oil.

Step 3

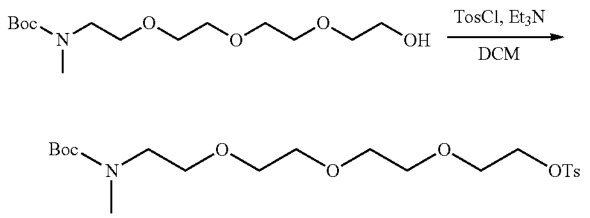

To a solution of tert-butyl N-[2-[2-[2-(2-hydroxyethoxy) ethoxy]ethoxy]ethyl]-N-methyl-carbamate (1 g, 3.25 mmol, 1 eq) in dichloromethane (10 mL) was added triethylamine (987 mg, 9.76 mmol, 1.36 mL, 3 eq) and p-toluenesulfonyl chloride (1.24 g, 6.51 mmol, 2 eq) sequentially at 15° C., after which the mixture was stirred at this temperature for 16 hours. The reaction mixture was concentrated to give a residue which was purified by silica gel column chromatography (petroleum ether/ethyl acetate=20/1 to 1/1). 2-[2-[2-[2-[tert-butoxycarbonyl(methyl)amino]ethoxy]ethoxy] ethoxy]ethyl 4-methylbenzene sulfonate (1.09 g, 2.36 mmol, 72% yield) was obtained as a light yellow oil.

Step 4

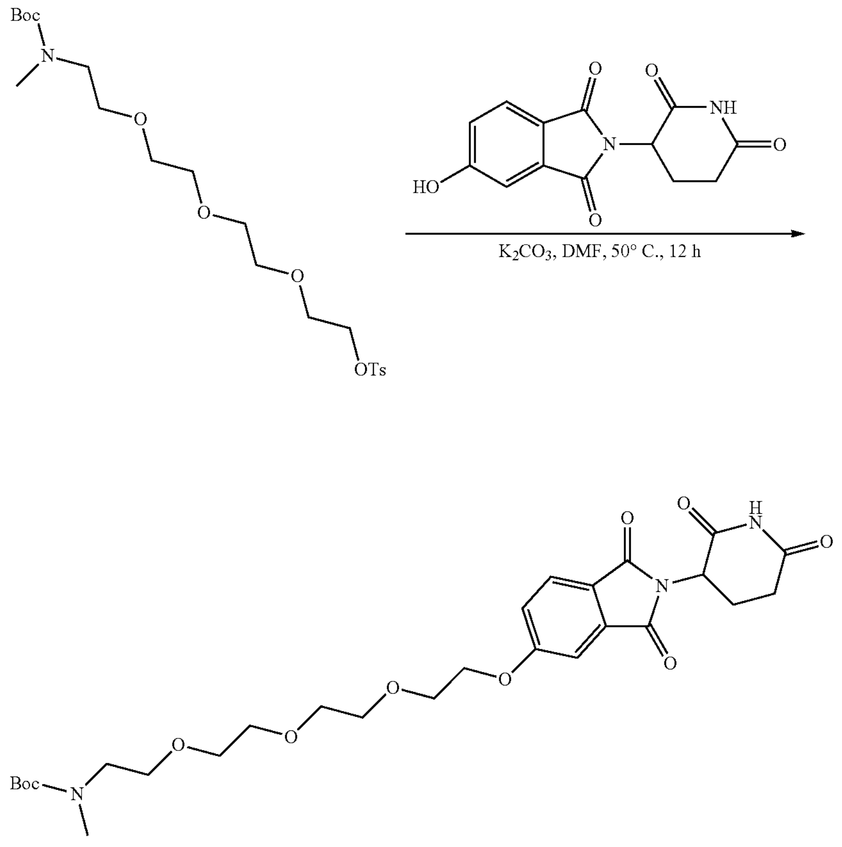

To a solution of 2-[2-[2-[2-[tert-butoxycarbonyl(methyl) amino]ethoxy]ethoxy]ethoxy]ethyl 4-methylbenzenesulfonate (351 mg, 0.76 mmol, 1.1 eq) and 2-(2,6-dioxo-3-piperidyl)-5-hydroxy-isoindoline-1,3-dione (190 mg, 0.69 mmol, 1 eq) in N,N-dimethylformamide (5 mL) was added potassium carbonate (191 mg. 1.39 mmol, 2 eq). The reaction mixture was then stirred at 50° C. for 12 hours. The reaction mixture was diluted with water (30 mL) and extracted with ethyl acetate (20 mL×3). The combined organic layer was washed with brine (10 mL), dried with anhydrous sodium sulfate, filtered and concentrated under vacuum to give a residue. The residue was purified by semi-preparative reverse phase HPLC (column: Phenomenex Synergi Max-RP 250*50 mm*10 um; mobile phase: [water (0.225% FA)-ACN]; B %: 30ACN %-60ACN %, 20 min; 50% min) to give tert-butyl N-[2-[2-[2-[2-[2-(2,6-dioxo-3-piperidyl)-1,3-dioxo-isoindolin-5-yl]oxyethoxy] ethoxy]ethoxy]ethyl]-N-methyl-carbamate (205 mg, 0.35 mmol, 50% yield) as a colorless oil.

Step 5

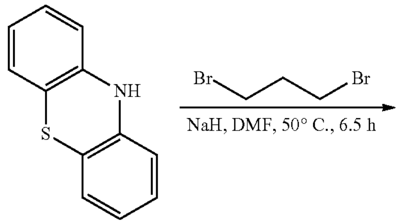

-continued

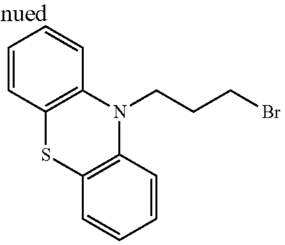

To a solution of 10H-phenothiazine (5 g, 25.09 mmol, 1 eq) in N,N-dimethylformamide (70 mL) was added sodium hydride (722 mg, 60% suspension in mineral oil, 18.07 mmol, 0.72 eq) at 0° C., and the mixture was stirred for 0.5 h under nitrogen. To the mixture was then added 1,3-dibromopropane (25.33 g, 125.46 mmol, 12.79 mL, 5 eq), the mixture was heated to 50° C. and stirred for 6 hours. The mixture was cooled to 25° C. and poured into saturated ammonium chloride solution (30 mL) and stirred for 15 minutes. The aqueous phase was extracted with ethyl acetate (50 mL×3). The combined organic phase was washed with brine (50 mL×3), dried with anhydrous sodium sulfate, filtered and concentrated in vacuum. The residue was purified by silica gel chromatography (petroleum ether/ethyl acetate=20/1, 10/1) to afford 10-(3-bromopropyl)phenothiazine (1.6 g, 5.0) mmol, 19% yield) as a yellow oil.

Step 6

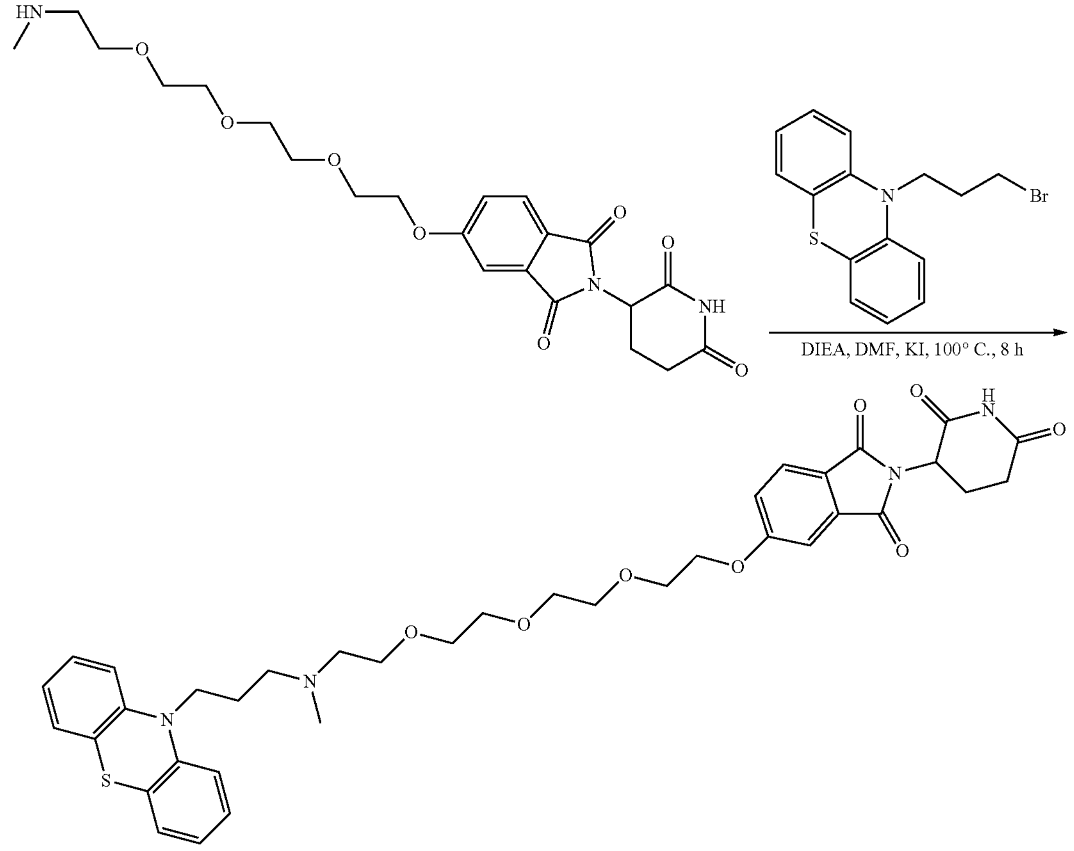

To a solution of 2-(2,6-dioxo-3-piperidyl)-5-[2-[2-[2-[2-(methylamino)ethoxy]ethoxy]ethoxy]ethoxy]isoindoline-1,3-dione hydrochloride (150 mg, 0.30 mmol, 1 eq) and 10-(3-bromopropyl)phenothiazine (192 mg, 0.60 mmol, 2 eq) in N,N-dimethylformamide (2 mL) was added potassium iodide (5 mg, 0.03 mmol, 0.1 eq) and N,N-diisopropylethylamine (116 mg, 0.9 mmol, 0.16 mL, 3 eq). The mixture was stirred at 100° C. for 8 hours. The reaction mixture was diluted with water (10 mL) and then was extracted with ethyl acetate (10 mL×3). Then the combined organic layer was washed with brine (10 mL), dried with anhydrous sodium sulfate, filtered and concentrated under vacuum to give a residue. The residue was purified by prep-TLC (dichloromethane:methanol=10:1) to give 2-(2,6-dioxo-3-piperidyl)-5-[2-[2-[2-[2-[methyl(3-phenothiazin-10-ylpropyl)amino]ethoxy]ethoxy]ethoxy]ethoxy]isoindoline-1,3-dione (38 mg, 0.05 mmol, 17% yield) as a yellow solid.

Exemplary Compound 15 was prepared following the procedures described for Exemplary Compound 16.

Exemplary Synthesis of Exemplary Compound 17

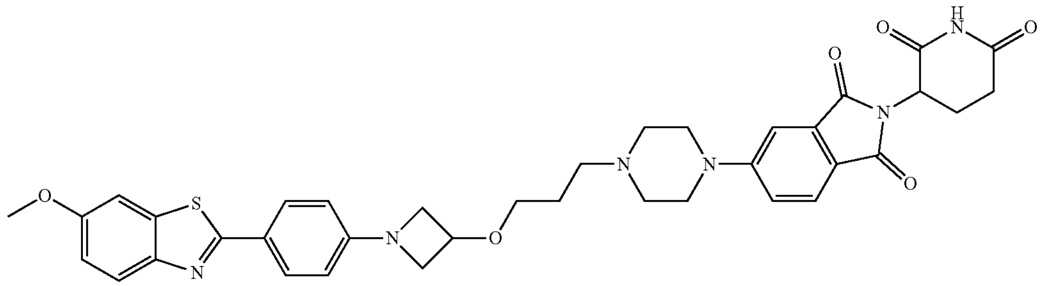 [SMILES: COc1ccc2nc(-c3ccc(N4CC(OCCCN5CCN(c6ccc7c(c6)C(=O)N(C6CCC(=O)NC6=O)C7=O)CC5)C4)cc3)sc2c1]

Step 1

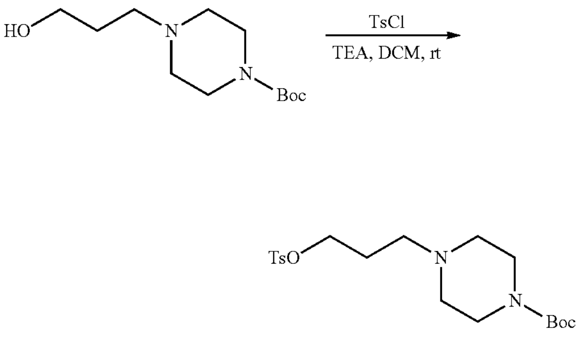 [SMILES: CC(C)(C)OC(=O)N1CCN(CCCO)CC1 ; "TsCl" ; Cc1ccc(S(=O)(=O)OCCCN2CCN(C(=O)OC(C)(C)C)CC2)cc1]

Into a 250-mL round-bottom flask were added tert-butyl 4-(3-hydroxypropyl)piperazine-1-carboxylate (10 g, 40.93 mmol, 1 equiv) and TEA (12.4 g, 122.78 mmol, 3 equiv) in dichloromethane (150 mL), to which was added 4-methylbenzene-1-sulfonyl chloride (11.8 g, 61.80 mmol, 1.51 equiv) in multiple batches at room temperature. Then DMAP (0.5 g, 4.09 mmol, 0.1 equiv) was added, and the resulting mixture was stirred overnight, and then was concentrated under vacuum. The residue was purified by flash chromatography eluting with ethyl acetate to afford tert-butyl 4-[3-[(4-methylbenzenesulfonyl) oxy]propyl]piperazine-1-carboxylate (8.8 g, 49%) as a brown oil.

Step 2

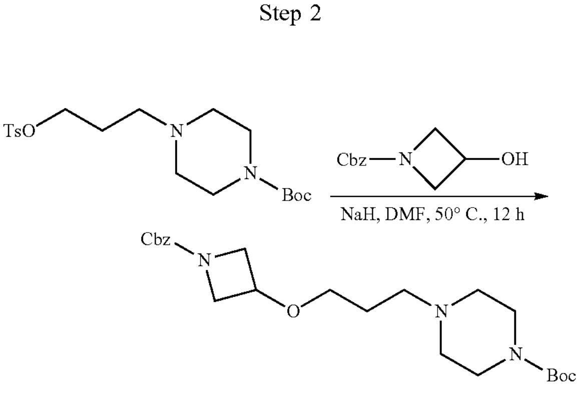

Into a 100-mL round-bottom flask was placed a solution of benzyl 3-hydroxyazetidine-1-carboxylate (1.4 g, 6.76 mmol, 1.35 equiv) in DMF (20 mL), to which was added NaH (400 mg, 10.04 mmol, 2.00 equiv, 60%) slowly at 0° C. The resulting mixture was stirred at 0° C. for 30 minutes, to which was then added a solution of tert-butyl 4-[3-[(4-methylbenzenesulfonyl)oxy]propyl]piperazine-1-carboxylate (2 g, 5.02 mmol, 1 equiv) in DMF (10 mL) dropwise at 0° C. The reaction mixture was stirred for 12 hours at 50° C. The reaction was then quenched with water/ice (10 mL) at 0° C., and the mixture was extracted with ethyl acetate (50 mL×3). The combined organic layer was washed with brine, dried over sodium sulfate and concentrated under vacuum. The residue was purified by flash chromatography eluting with ethyl acetate/petroleum ether (1:1) to afford tert-butyl 4-[3-([1-[(benzyloxy)carbonyl]azetidin-3-yl]oxy)propyl]piperazine-1-carboxylate (800 mg, 29%) as a yellow oil.

Step 3

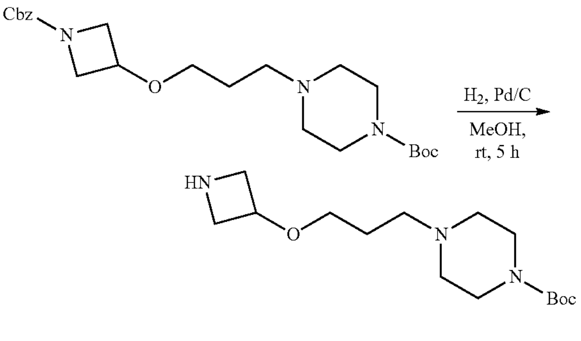

Into a 50-mL round-bottom flask were added tert-butyl 4-[3-([1-[(benzyloxy)carbonyl]azetidin-3-yl]oxy)propyl]

piperazine-1-carboxylate (500 mg, 1.15 mmol, 1 equiv) and Pd/C (10%, 245.5 mg, 2.31 mmol, 2.00 equiv) in MeOH (20 mL) under nitrogen atmosphere. The flask was then vacuumed and flushed with hydrogen. The reaction mixture was hydrogenated at room temperature for 5 hours under hydrogen atmosphere using a hydrogen balloon. Then the reaction mixture was filtered through a celite pad and the filtrate was concentrated under reduced pressure. This resulted in tert-butyl 4-[3-(azetidin-3-yloxy)propyl]piperazine-1-carboxylate (200 mg, 46%) as a yellow oil.

Step 4

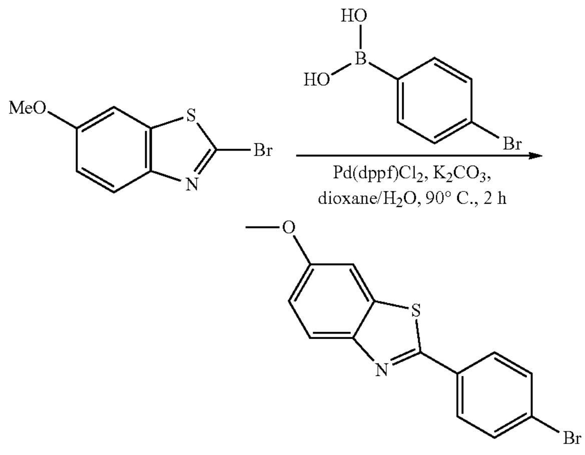

Into a 250-mL round-bottom flask purged and maintained with an inert atmosphere of nitrogen, was placed 2-bromo-6-methoxy-1,3-benzothiazole (7.3 g, 29.90 mmol, 1 equiv), (4-bromophenyl)boronic acid (8.4 g, 0.04 mmol, 1.40 equiv), $K_2CO_3$ (8.3 g, 60.06 mmol, 2.01 equiv), $Pd(dppf)Cl_2$ $CH_2Cl_2$ (500 mg, 0.68 mmol, 0.02 equiv) in dioxane (100 mL) and $H_2O$ (20 mL). The resulting mixture was stirred for 3 hours at 90° C. in an oil bath. The reaction mixture was cooled to room temperature and quenched by the addition of water (200 mL). The insoluble solids were removed by filtration and the filtrate was extracted with ethyl acetate (150 mL×3). The resulting mixture was washed with brine (100 mL×2), dried over $Na_2SO_4$ and concentrated under reduced pressure. The residue was purified by flash chromatography eluting with ethyl acetate/petroleum ether 1:1 (100 mL). This resulted in 4 g of 2-(4-bromophenyl)$_{1-6}$-methoxy-1,3-benzothiazole as a brown solid.

Step 5

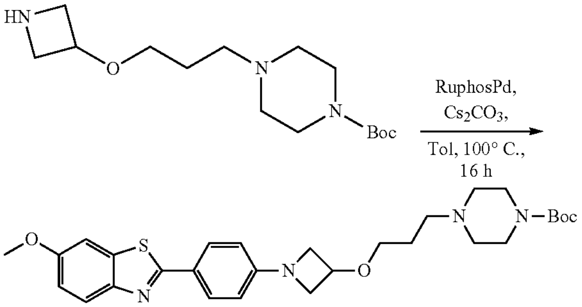

Into a 10-mL vial were added tert-butyl 4-(3-(azetidin-3-yloxy)propyl)piperazine-1-carboxylate (200 mg, 0.70 mmol, 1 equiv), 2-(4-bromophenyl)$_{1-6}$-methoxy-1,3-benzothiazole (222.8 mg, 0.70 mmol, 1.00 equiv), $Cs_2CO_3$ (113.4 mg, 0.35 mmol, 2 equiv), RuPhos precatalyst (58.2 mg, 0.07 mmol, 0.1 equiv) in toluene (5 mL). The resulting mixture was stirred 16 hours at 100° C. under nitrogen atmosphere, and then was concentrated under vacuum. The residue was purified on a silica gel column eluting with dichloromethane/MeOH (10:1) to afford tert-butyl 4-[3-([1-[4-(6-methoxy-1,3-benzothiazol-2-yl)phenyl]azetidin-3-yl]oxy)propyl]piperazine-1-carboxylate (200 mg, 43%) as a yellow solid.

Step 6

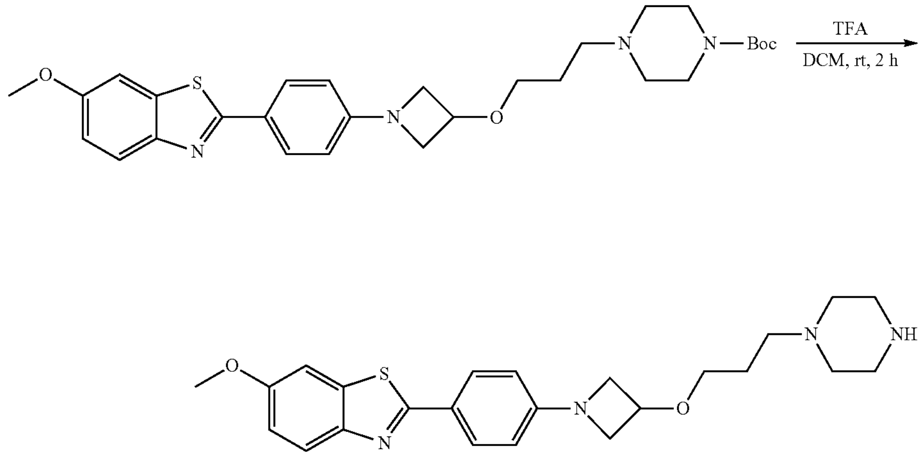 [SMILES: COc1ccc2nc(-c3ccc(N4CC(OCCCN5CCN(C(=O)OC(C)(C)C)CC5)C4)cc3)sc2c1 ; COc1ccc2nc(-c3ccc(N4CC(OCCCN5CCNCC5)C4)cc3)sc2c1 ; "TFA"]

Into a 50 mL round-bottom flask was added tert-butyl 4-[3-([1-[4-(6-methoxy-1,3-benzothiazol-2-yl)phenyl]azetidin-3-yl]oxy)propyl]piperazine-1-carboxylate (200 mg, 0.37 mmol, 1 equiv) in dichloromethane (10 mL), to which was added TFA (3 mL) at room temperature. The resulting mixture was stirred for 2 hours at 25° C., and then was concentrated under vacuum. This resulted in 6-methoxy-2-(4-[3-[3-(piperazin-1-yl)propoxy]azetidin-1-yl]phenyl)-1,3-benzothiazole trifluoroacetate (crude, 200 mg) as a yellow solid.

Step 7

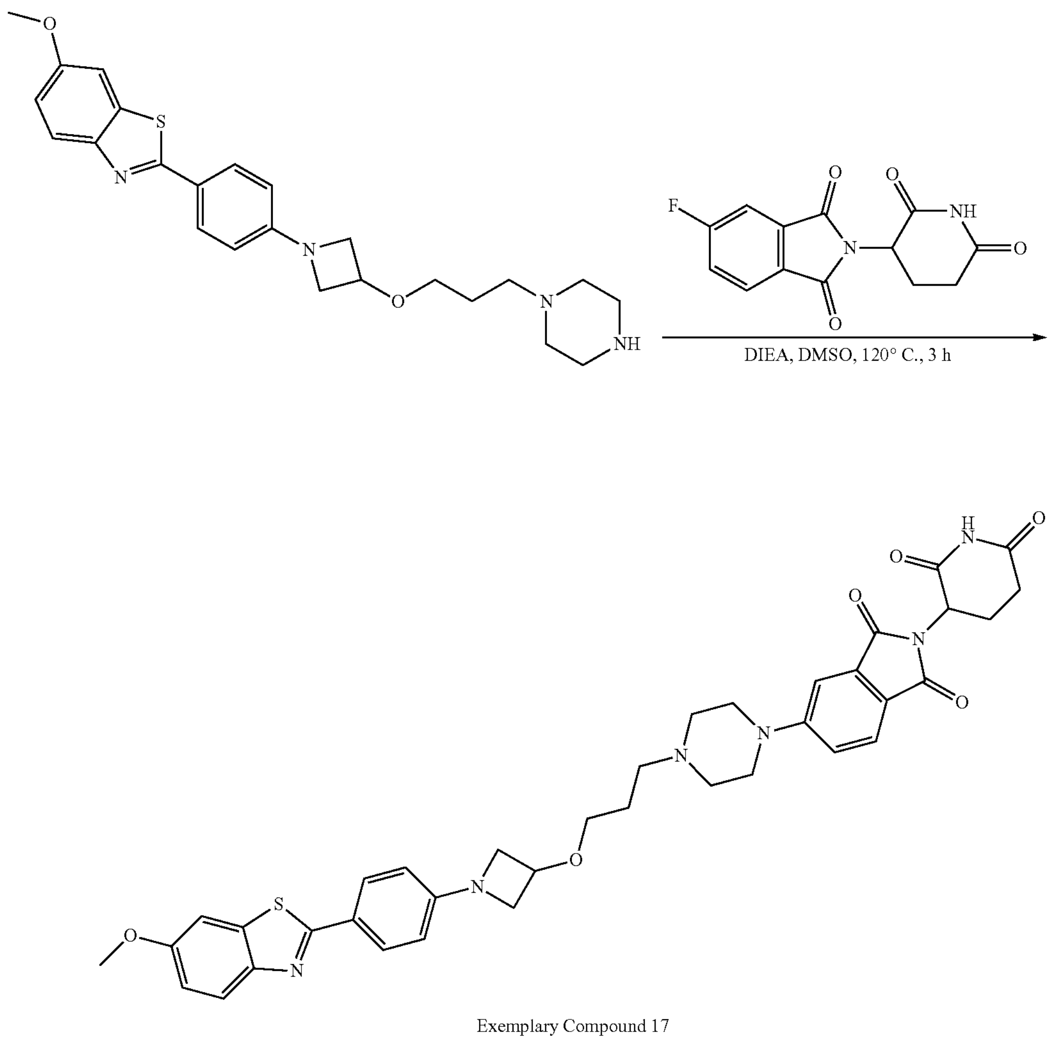 [SMILES: COc1ccc2nc(-c3ccc(N4CC(OCCCN5CCNCC5)C4)cc3)sc2c1 ; O=C1CCC(N2C(=O)c3ccc(F)cc3C2=O)C(=O)N1 ; COc1ccc2nc(-c3ccc(N4CC(OCCCN5CCN(c6ccc7c(c6)C(=O)N(C6CCC(=O)NC6=O)C7=O)CC5)C4)cc3)sc2c1]

Exemplary Compound 17

Into a 10 mL vial were added 6-methoxy-2-(4-[3-[3-(piperazin-1-yl)propoxy]azetidin-1-yl]phenyl)-1,3-benzothiazole (100 mg, 0.23 mmol, 1 equiv), 2-(2,6-dioxopiperidin-3-yl)-5-fluoro-2,3-dihydro-1H-isoindole-1,3-dione (75.6 mg, 0.27 mmol, 1.20 equiv), DIEA (0.3 mL) in DMSO (3 mL) under nitrogen atmosphere. The resulting mixture was stirred for 3 hours at 130° C. under nitrogen atmosphere. The reaction mixture was diluted with water (25 mL) and extracted with ethyl acetate (50 mL×4). The organic layers were combined, dried over sodium sulfate and concentrated. The crude product was purified by prep-HPLC under the following conditions: XBridge Prep OBD C18 Column 30*50 mm 5 um; Mobile Phase A: water (10 mmol/L $NH_4HCO_3$), Mobile Phase B: acetonitrile; Flow rate: 60 mL/min; Gradient: 49% B to 69% B in 8 min; 254 nm; Rt: 7.93 min. After lyophilization, this resulted in 24.7 mg (40%) of 2-(2,6-dioxopiperidin-3-yl)-5-[4-[3-([1-[4-(6-methoxy-1,3-benzothiazol-2-yl)phenyl]azetidin-3-yl]oxy)propyl]piperazin-1-yl]-2,3-dihydro-1H-isoindole-1,3-dione as a yellow solid.

Exemplary Synthesis of Exemplary Compound 19

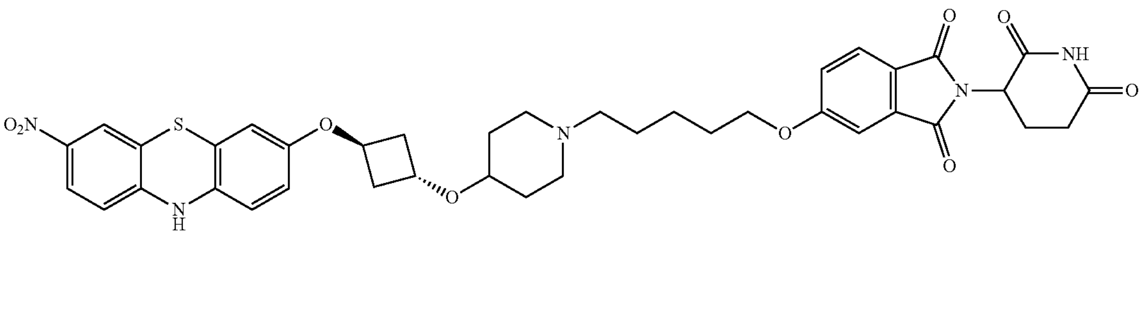 [SMILES: O=C1CCC(N2C(=O)c3ccc(OCCCCCN4CCC(O[C@H]5C[C@H](Oc6ccc7c(c6)Sc6cc([N+](=O)[O-])ccc6N7)C5)CC4)cc3C2=O)C(=O)N1]

Step 1

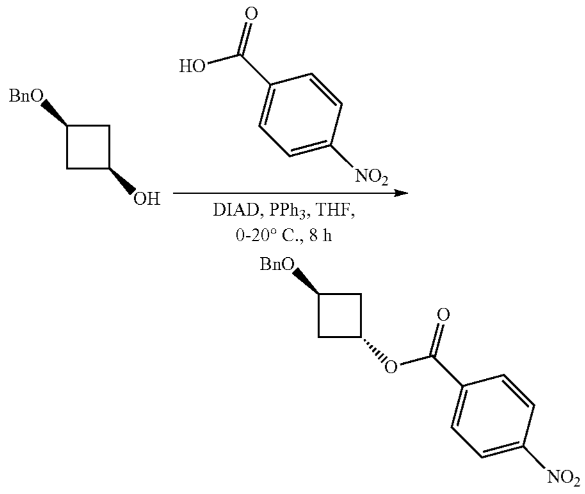

To a solution of 3-benzyloxycyclobutanol (7.5 g, 42.08 mmol, 1 eq) and 4-nitrobenzoic acid (8.44 g, 50.50 mmol, 1.2 eq) in tetrahydrofuran (70 mL) was added triphenylphosphine (13.24 g, 50.50 mmol, 1.2 eq) and diisopropyl azodicarboxylate (10.21 g, 50.50 mmol, 9.82 mL, 1.2 eq) at 0° C. The mixture was stirred at 20° C. for 8 hours. The reaction mixture was diluted with water (100 mL) and extracted with ethyl acetate (80 mL×2). The combined organic phase was washed with brine (20 mL), dried with anhydrous sodium sulfate, filtered and concentrated in vacuum. The residue was purified by silica gel column chromatography (petroleum ether/ethyl acetate=30/1 to 6:1). (3-benzyloxycyclobutyl) 4-nitrobenzoate (7.7 g, 23.5 mmol, 55% yield) was obtained as a light yellow solid.

Step 2

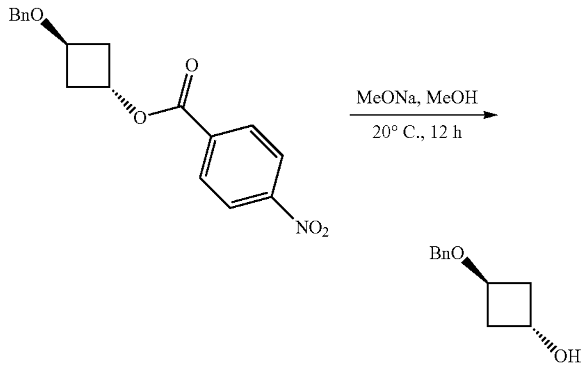

To a solution of (3-benzyloxycyclobutyl) 4-nitrobenzoate (7.7 g, 23.52 mmol, 1 eq) in methanol (100 mL) was added sodium methoxide (12.71 g, 235 mmol, 10 eq). The mixture was stirred at 20° C. for 12 hours. The reaction mixture was concentrated to remove methanol, then diluted with water (100 mL) and then extracted with ethyl acetate (80 mL×3). The combined organic phase was washed with brine (10 mL), dried with anhydrous sodium sulfate, filtered and concentrated in vacuum to give a residue. The residue was purified by silica gel column chromatography (petroleum ether/ethyl acetate=20/1 to 1:1) to afford 3-benzyloxycyclobutanol (7.1 g) as a light yellow oil.

Step 3

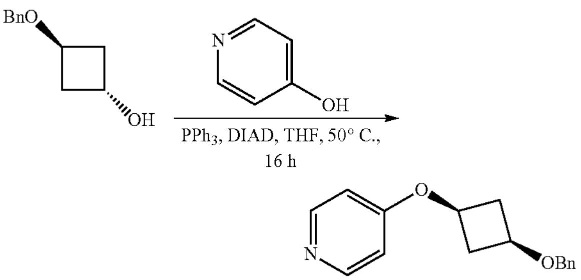

To a solution of 3-benzyloxycyclobutanol (7.1 g, 39.84 mmol, 1 eq) and pyridin-4-ol (5.68 g, 59.76 mmol, 1.5 eq) in tetrahydrofuran (100 mL) was added triphenylphosphine (12.54 g, 47.80 mmol, 1.2 eq) and diisopropyl azodicarboxylate (9.67 g, 47.80 mmol, 9.29 mL, 1.2 eq) in one portion at 15° C., and the mixture was stirred at 50° C. for 16 hours. The reaction mixture was concentrated under reduced pressure to remove tetrahydrofuran. Water (50 mL) was poured into the mixture and stirred for 1 minute. The aqueous phase was extracted with ethyl acetate (60 mL×3). The combined organic phase was washed with brine (20 mL×2), dried with anhydrous sodium sulfate, filtered and concentrated in vacuum to give a residue. The residue was purified by flash silica gel chromatography, then triturated by petroleum ether/ethyl acetate=5/1 to give crude product, which was purified by semi-preparative reverse phase HPLC (column: Phenomenex Synergi Max-RP 250*80 mm*10 um; mobile phase: [water (0.225% FA)-ACN]; B %: 15%-45%, 35 min, 40% min). 4-(3-benzyloxycyclobutoxy)pyridine (4.63 g, 18.13 mmol, 45% yield) was obtained as a light yellow oil.

Step 4

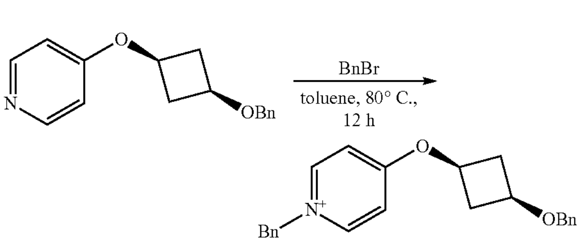

To a solution of 4-(3-benzyloxycyclobutoxy)pyridine (4.63 g, 18.13 mmol, 1 eq) in toluene (70 mL) was added benzyl bromide (3.10 g, 18.13 mmol, 2.15 mL, 1 eq). The mixture was stirred at 80° C. for 12 hours. The reaction mixture was concentrated under reduced pressure to remove toluene. The crude product was triturated with petroleum ether (80 mL). 1-benzyl-4-(3-benzyloxycyclobutoxy)pyridin-1-ium (6.3 g, crude) was obtained as a white solid and used without purification.

Step 5

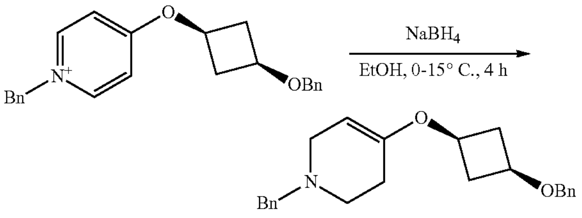

To a solution of 1-benzyl-4-(3-benzyloxycyclobutoxy) pyridin-1-ium (6.28 g, 18.13 mmol, 1 eq) in ethanol (120 mL) was added sodium borohydride (4.11 g, 108.8 mmol, 6 eq) at 0° C. The mixture was stirred at 15° C. for 4 hours. The reaction mixture was quenched by water (50 mL), then concentrated to remove ethanol, then was extracted with ethyl acetate (50 mL×3). The combined organic phase was washed with saturated brine (20 mL), dried with anhydrous sodium sulfate, filtered and concentrated in vacuum. The residue was purified by silica gel column chromatography (petroleum ether/ethyl acetate=20/1 to 1/1). 1-benzyl-4-(3-benzyloxycyclobutoxy)-3,6-dihydro-2H-pyridine (4.33 g, 12.4 mmol, 68% yield) was obtained as a light yellow solid.

Step 6

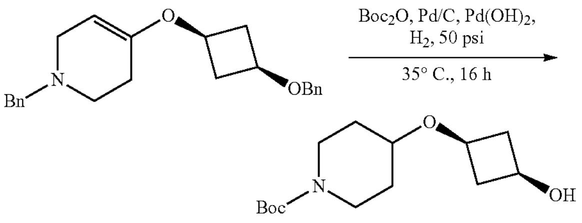

To a solution of 1-benzyl-4-(3-benzyloxycyclobutoxy)-3,6-dihydro-2H-pyridine (4.13 g, 11.82 mmol, 1 eq) in ethanol (30 mL) and tetrahydrofuran (30 mL) was added 20% palladium hydroxide/carbon (1 g), 10% palladium/carbon (1 g) and di-tert-butyl dicarbonate (5.16 g, 23.64 mmol, 5.43 mL, 2 eq) under nitrogen atmosphere. The suspension was degassed and purged with hydrogen three times. The mixture was stirred under hydrogen (50 psi) at 35° C. for 16 hours. The reaction mixture was filtered, and the filtrate was concentrated. The crude product was purified by silica gel chromatography eluted with petroleum ether/ethyl acetate=20/1 to 1/1. tert-Butyl 4-(3-hydroxycyclobutoxy) piperidine-1-carboxylate (1.7 g, 6.26 mmol, 53% yield) was obtained as a white solid.

Step 7

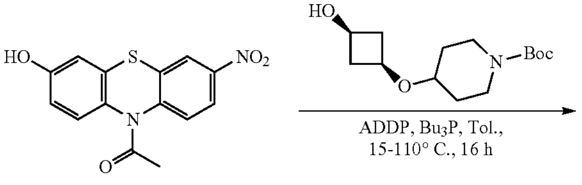

-continued

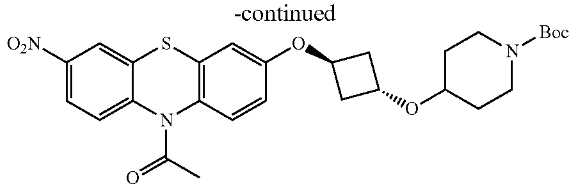

To a mixture of tert-butyl 4-(3-hydroxycyclobutoxy)piperidine-1-carboxylate (3M) mg, 1.1.1 mmol, 1 eq) and 1-(3-hydroxy-7-nitro-phenothiazin-10-yl)ethanone (367 mg, 1.22 mmol, 1.1 eq) in toluene (5 mL) was added 1,1'-(azodicarbonyl)dipiperidine (418 mg, 1.66 mmol, 1.5 eq) and tributylphosphine (335 mg, 1.66 mmol, 0.41 mL, 1.5 eq) in one portion at 15° C. under nitrogen. The mixture was stirred at 110° C. for 16 hours. The reaction mixture was concentrated to give a residue. The residue was purified by silica gel column chromatography (petroleum ether/ethyl acetate=10/1 to 1/2) to give 700 mg crude product, which was then purified by prep-TLC (petroleum ether/ethyl acetate=1/2). tert-Butyl 4-[3-(10-acetyl-7-nitro-phenothiazin-3-yl)oxycyclobutoxy]piperidine-1-carboxylate (227 mg, 0.36 mmol, 32% yield) was obtained as a red solid.

Step 8

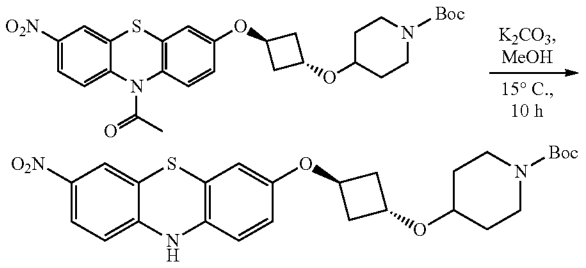

To a mixture of tert-butyl 4-[3-(10-acetyl-7-nitro-phenothiazin-3-yl)oxycyclobutoxy]piperidine-1-carboxylate (225 mg, 0.40 mmol, 1 eq) in methanol (15 mL) was added potassium carbonate (167 mg, 1.21 mmol, 3 eq) in one portion, then stirred at 15° C. for 10 hours. The reaction mixture was diluted with water 20 mL and then extracted with ethyl acetate (20 mL×3). Then the combined organic layer was washed with brine (10 mL), dried with anhydrous sodium sulfate, filtered and concentrated under vacuum to give a residue. The residue was purified by prep-TLC (petroleum ether/ethyl acetate=1/1). tert-butyl 4-[3-[(7-nitro-10H-phenothiazin-3-yl)oxy]cyclobutoxy]piperidine-1-carboxylate (177 mg, 0.34 mmol, 85% yield) was obtained as a red gum.

Step 9

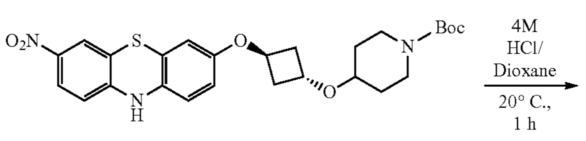

-continued

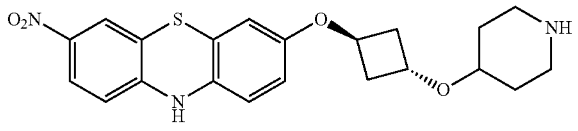

To a solution of tert-butyl 4-[3-[(7-nitro-10H-phenothiazin-3-yl)oxy]cyclobutoxy]piperidine-1-carboxylate (127 mg, 0.25 mmol, 1 eq) in dichloromethane (5 mL) was added hydrochloric acid (4 M in dioxane, 12.7 mL, 205 eq) in one portion. The mixture was stirred at 20° C. for 1 hour. The reaction mixture was concentrated to give a residue. 3-nitro-7-[3-(4-piperidyloxy)cyclobutoxy]-10H-phenothiazine (120 mg, crude, hydrochloride) was obtained as a red solid and used without purification.

Step 10

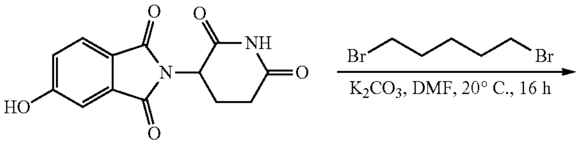

-continued

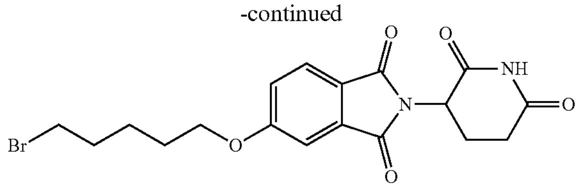

To a mixture of 1,5-dibromopentane (377 mg, 1.64 mmol, 0.22 mL, 0.9 eq) and 2-(2,6-dioxo-3-piperidyl)-5-hydroxy-isoindoline-1,3-dione (500 mg, 1.82 mmol, 1 eq) in N,N-dimethylformamide (40 mL) was added potassium carbonate (252 mg, 1.82 mmol, 1 eq) in one portion. The mixture was stirred at 20° C. for 16 hours. The reaction mixture was poured into 1 M hydrochloric acid (40 mL), then diluted with water 20 mL and extracted with ethyl acetate (30 mL×3). The combined organic layers were washed with brine 20 mL, dried over anhydrous sodium sulfate, filtered and concentrated under reduced pressure to give a residue. The residue was purified by silica gel column chromatography (petroleum ether/ethyl acetate=20/1 to 5/1) and then purified by prep-TLC (dichloromethane/methanol=10/1) to give crude product, then the crude product was purified by semi-preparative reverse phase HPLC (33-63% acetonitrile+0.225% formic acid in water, over 25 min). 5-(5-bromopentoxy)-2-(2,6-dioxo-3-piperidyl)isoindoline-1,3-dione (220 mg, 0.52 mmol, 28% yield) was obtained as a light yellow solid.

Step 11

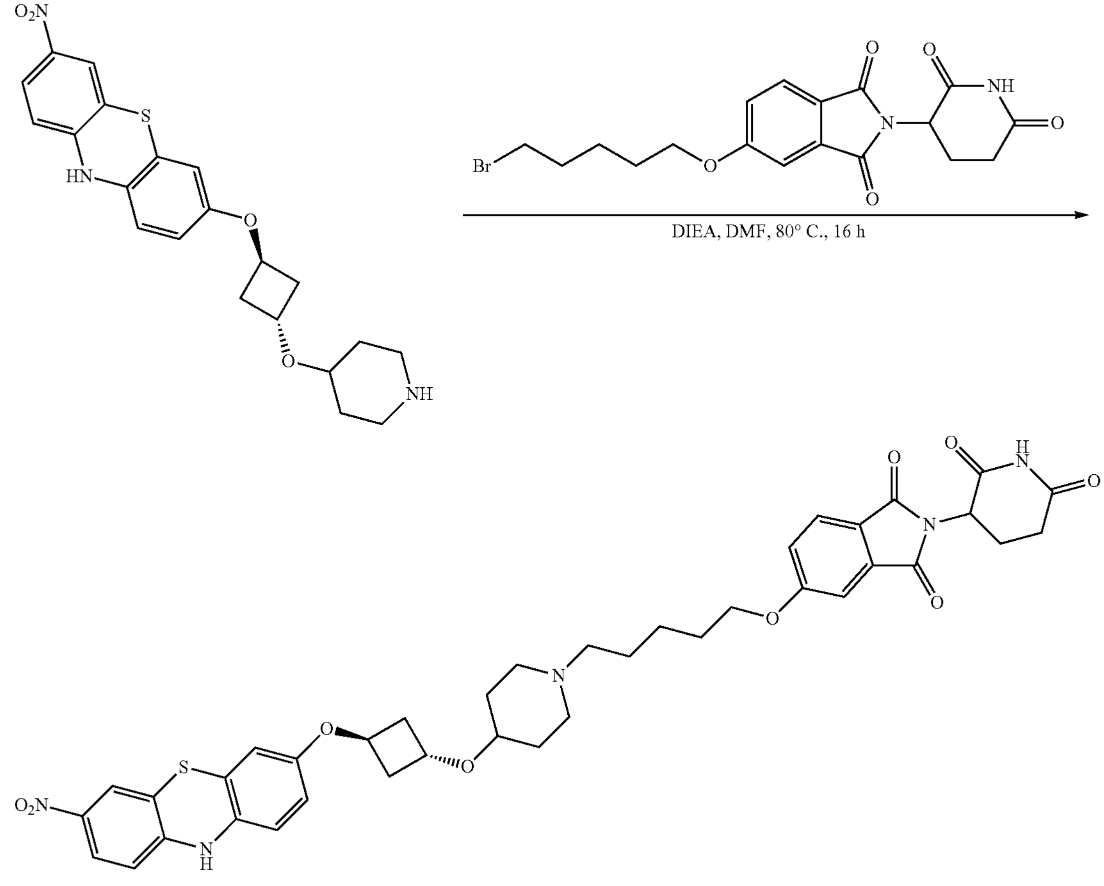

Exemplary Compound 19

To a solution of 3-nitro-7-[3-(4-piperidyloxy)cyclobutoxy]-10H-phenothiazine (100 mg, 0.22 mmol, 1 eq, hydrochloride) and 5-(5-bromopentoxy)-2-(2,6-dioxo-3-piperidyl)isoindoline-1,3-dione (98 mg, 0.23 mmol, 1.05 eq) in N,N-dimethylformamide (5 mL) was added N,N-diisopropylethylamine (86 mg, 0.66 mmol, 0.12 mL, 3 eq), then stirred at 80° C. for 16 hours. The reaction mixture was diluted with water 10 mL and then was extracted with ethyl acetate (10 mL×3). Then the combined organic layer was washed with brine (10 mL), dried with anhydrous sodium sulfate, filtered and concentrated under vacuum to give a residue. The residue was purified by prep-TLC (dichloromethane/methanol=10/1) to give crude product. The crude product was purified by semi-preparative reverse phase HPLC (35-65% acetonitrile+0.225% formic acid in water, over 9 min). 2-(2,6-dioxo-3-piperidyl)-5-[5-[4-[3-[(7-nitro-10H-phenothiazin-3-yl)oxy]cyclobutoxy]-1-piperidyl]pentoxy]isoindoline-1,3-dione (24 mg, 0.03 mmol, 13% yield, formate) was obtained as a dark red solid.

Exemplary Synthesis of Exemplary Compound 18

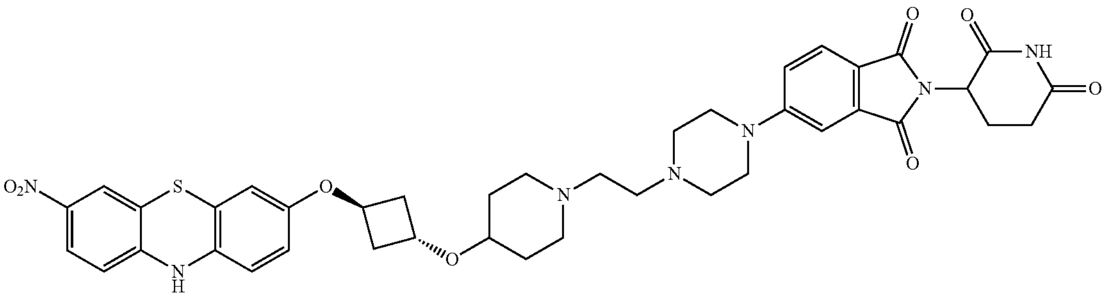 [SMILES: O=C1CCC(N2C(=O)c3ccc(N4CCN(CCN5CCC(O[C@H]6C[C@H](Oc7ccc8c(c7)Sc7cc([N+](=O)[O-])ccc7N8)C6)CC5)CC4)cc3C2=O)C(=O)N1]

Step 1

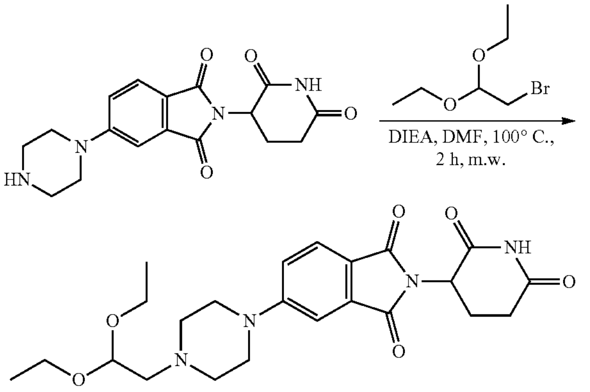

2-(2,6-dioxo-3-piperidyl)-5-piperazin-1-yl-isoindoline-1,3-dione (1 g, 2.64 mmol, 1 eq, hydrochloride), 2-bromo-1,1-diethoxy-ethane (1.56 g, 7.92 mmol, 1.2 mL, 3 eq) and N,N-diisopropylethylamine (1.71 g, 13.20 mmol, 2.30 mL, 5 eq) were taken up into a microwave tube in N,N-dimethylformamide (12 mL). The sealed tube was heated at 100° C. for 2 hours under microwave irradiation. The reaction solution was diluted with water (50 mL), and the organic layer was extracted with ethyl acetate (40 mL×3). The combined organic layer was washed with brine (20 mL), dried over anhydrous sodium sulfate, filtered and concentrated under vacuum to get the residue. The residue was purified by semi-preparative reverse phase HPLC (column: Kromasil 250*50 mm*10 um; mobile phase: [water (0.1% TFA)-ACN]; B %: 6ACN %-36ACN %, 27 min) to give 5-[4-(2,2-diethoxyethyl)piperazin-1-yl]-2-(2,6-dioxo-3-piperidyl)isoindoline-1,3-dione (890 mg, 1.94 mmol, 74% yield) as a yellow solid.

Step 2

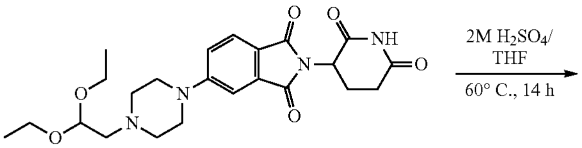

-continued

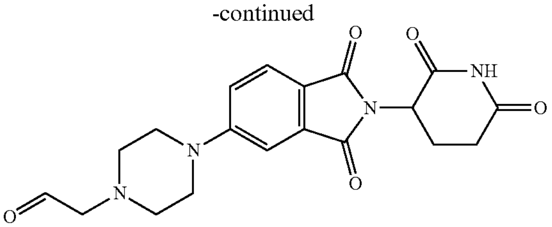

To a solution of 5-[4-(2,2-diethoxyethyl)piperazin-1-yl]-2-(2,6-dioxo-3-piperidyl)isoindoline-1,3-dione (400 mg, 0.87 mmol, 1 eq) in tetrahydrofuran (13 mL) was added sulfuric acid solution (2 M. 13 mL, 29.80 eq). The reaction mixture was stirred at 60° C. for 14 hours. The pH of reaction solution was adjusted to 7 by the addition of saturated sodium bicarbonate solution. The organic layer was extracted with ethyl acetate (50 mL×3). The combined organic layers were dried over anhydrous sodium sulfate and concentrated under vacuum to get the residue. The residue was purified by prep-TLC (10% methanol in dichloromethane) to get 2-[4-[2-(2,6-dioxo-3-piperidyl)-1,3-dioxo-isoindolin-5-yl]piperazin-1-yl]acetaldehyde (140 mg, 0.36 mmol, 42% yield) as a yellow solid.

Step 3

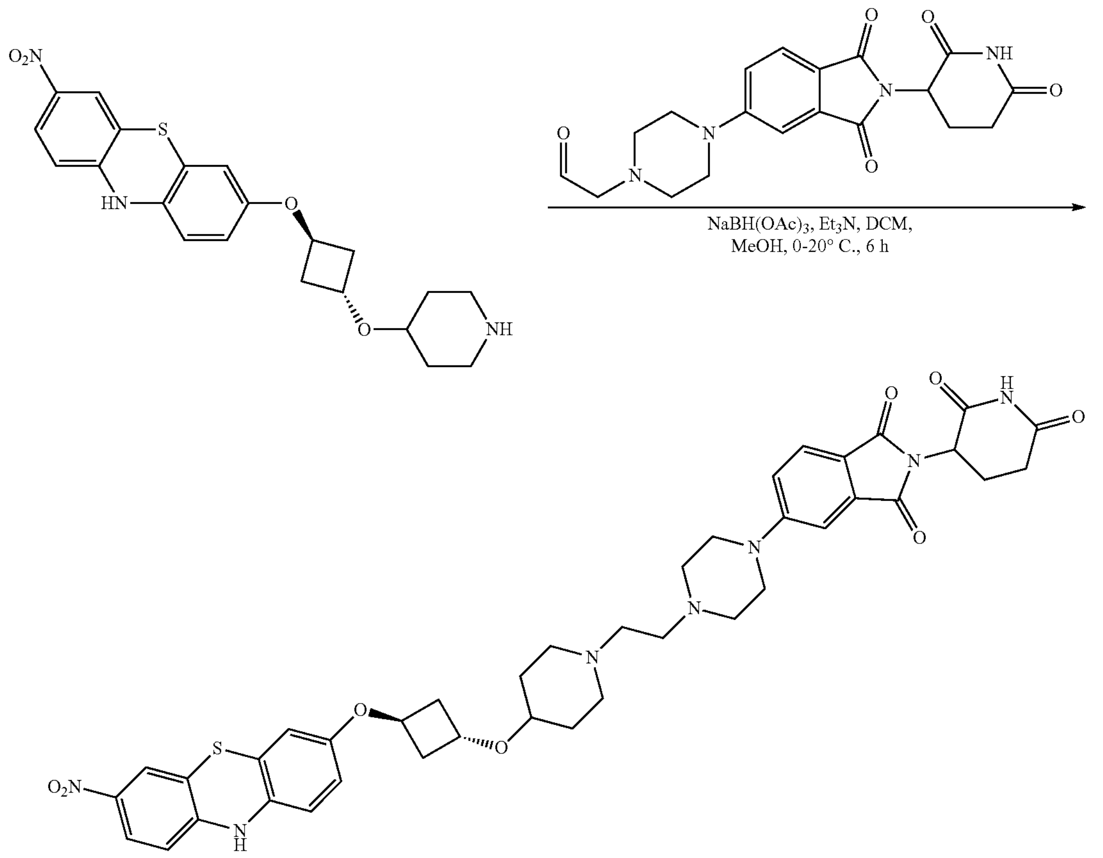

Exemplary Compound 18

To a solution of 3-nitro-7-[3-(4-piperidyloxy)cyclobutoxy]-10H-phenothiazine hydrochloride (43 mg, 0.09 mmol, 1 eq) in dichloromethane (5 mL) and methanol (2 mL) was added triethylamine (19 mg, 0.19 mmol, 0.03 mL, 2 eq) and stirred at 20° C. for 0.5 hour. Then 2-[4-[2-(2,6-dioxo-3-piperidyl)-1,3-dioxo-isoindolin-5-yl]piperazin-1-yl]acetaldehyde (36 mg, 0.09 mmol, 1 eq) was added and stirred at 20° C. for another 0.5 hour. After that, sodium triacetoxyborohydride (60 mg, 0.28 mmol, 3 eq) was added at 0° C. and stirred at 20° C. for 5 hours. The reaction mixture was diluted with water 20 mL and then was extracted with ethyl acetate (20 mL×3). The combined organic layer was washed with brine (10 mL), dried with anhydrous sodium sulfate, filtered and concentrated under vacuum to give a residue. The residue was purified by semi-preparative reverse phase HPLC (25-55% acetonitrile+0.225% formic acid in water, over 9 min). 2-(2,6-dioxo-3-piperidyl)-5-[4-[2-[4-[3-[(7-nitro-10H-phenothiazin-3-yl)oxy]cyclobutoxy]-1-piperidyl]ethyl]piperazin-1-yl]isoindoline-1,3-dione (16 mg, 0.02 mmol, 19% yield, formate) was obtained as a red solid.

Exemplary Synthesis of Exemplary Compound 20

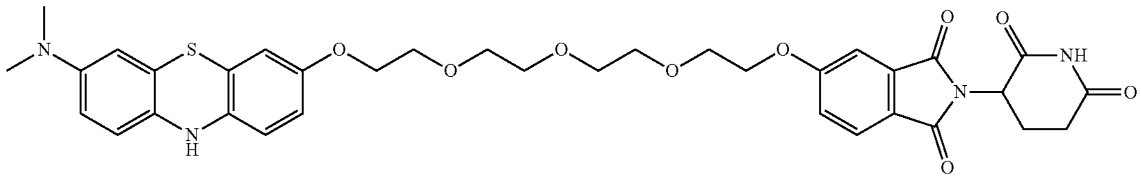 [SMILES: CN(C)c1ccc2c(c1)Sc1cc(OCCOCCOCCOCCOc3ccc4c(c3)C(=O)N(C3CCC(=O)NC3=O)C4=O)ccc1N2]

Step 1

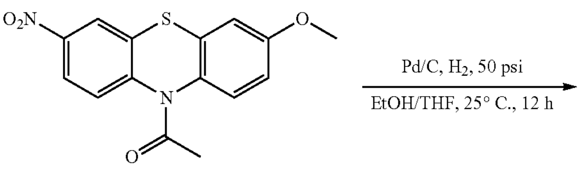

-continued

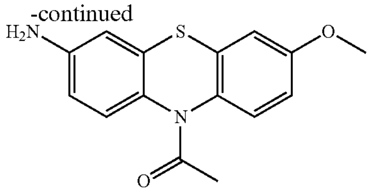

To a solution of 1-(3-methoxy-7-nitro-phenothiazin-10-yl)ethanone (1.6 g, 5.06 mmol, 1 eq) in ethyl alcohol (100 mL) and tetrahydrofuran (100 mL) was added 10% palladium on activated carbon catalyst (100 mg) under nitrogen. The suspension was degassed under vacuum and purged with hydrogen 3 times. The mixture was stirred under hydrogen (50 psi) at 25° C. for 12 hours. The reaction mixture was filtered and concentrated under reduced pressure to give 1-(3-amino-7-methoxy-phenothiazin-10-yl) ethanone (1.2 g, 3.56 mmol) as a brown solid.

Step 2

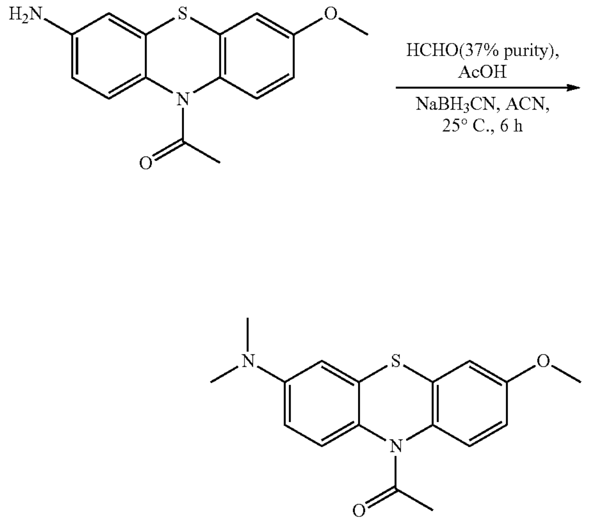

To a solution of 1-(3-amino-7-methoxy-phenothiazin-10-yl)ethanone (1.2 g, 4.19 mmol, 1 eq) in acetonitrile (10 mL) was added sodium cyanoborohydride (790 mg, 12.57 mmol, 3 eq) and acetic acid (251 mg, 4.19 mmol, 239 μL, 1 eq). The mixture was stirred at 25° C. for 1 hour. Then formaldehyde (5.10 g, 62.86 mmol, 4.68 mL, 37% in water, 15 eq) was added, and the mixture was stirred at 25° C. for 5 hours. The reaction mixture was quenched by the addition of water (100 mL) and extracted with ethyl acetate (200 mL×3). The combined organic layers were washed with brine (100 mL×3), dried over anhydrous sodium sulfate, filtered and concentrated under reduced pressure to give a residue which was purified by column chromatography (petroleum ether/ethyl acetate=30/1 to 3:1). Compound 1-[3-(dimethylamino)-7-methoxy-phenothiazin-10-yl]ethanone (270 mg, 0.85 mmol, 20% yield) was obtained as a bluish oil.

Step 3

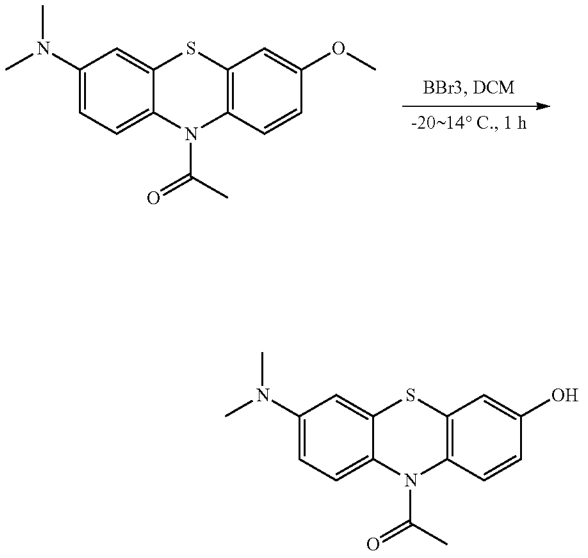

To a mixture of 1-[3-(dimethylamino)-7-methoxy-phenothiazin-10-yl]ethanone (280 mg, 0.89 mmol, 1 eq) in dichloromethane (8 mL) was added boron tribromide (1.12 g, 4.45 mmol, 0.43 mL, 5 eq) at −20° C. Then the mixture was stirred at 14° C. for 0.5 hour. The reaction mixture was quenched with saturated sodium bicarbonate solution (50 mL) at 0° C., and then extracted with ethyl acetate (50 mL×2). The combined organic layers were washed with brine (30 mL×2), dried over anhydrous sodium sulfate, filtered and concentrated under reduced pressure to give a residue which was purified by prep-TLC (10% ethyl acetate in petroleum ether). Compound 1-[3-(dimethylamino)-7-hydroxy-phenothiazin-10-yl]ethanone (170 mg, 0.56 mmol, 63% yield) was obtained as a bluish oil.

Step 4

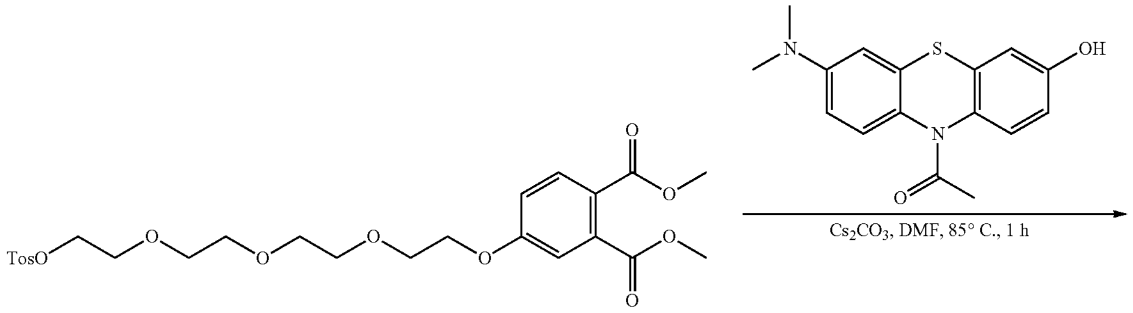

-continued

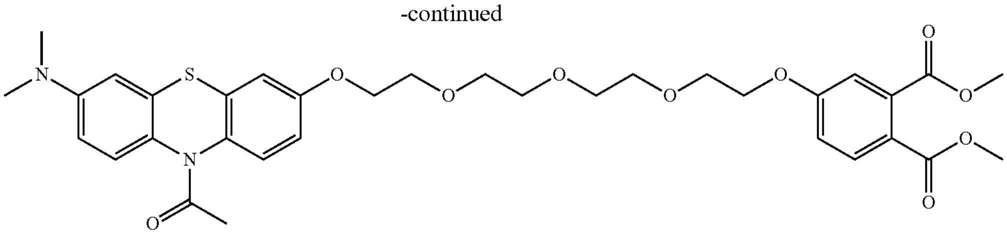

A mixture of dimethyl 4-[2-[2-[2-[2-(p-tolylsulfonyloxy) ethoxy]ethoxy]ethoxy]ethoxy]benzene-1,2-dicarboxylate (150 mg, 0.27 mmol, 1 eq), 1-[3-(dimethylamino)-7-hydroxy-phenothiazin-10-yl]ethanone (85.85 mg, 0.28 mmol, 1.03 eq) and cesium carbonate (180 mg, 0.55 mmol, 2 eq) in N,N-dimethylformamide (3 mL) was degassed and purged with nitrogen for 3 times, and then the mixture was stirred at 85° C. for 1 hour under nitrogen. The residue was diluted with water (50 mL) and extracted with ethyl acetate (50 mL×3). The combined organic layers were washed with brine (30 mL×2), dried over anhydrous sodium sulfate, filtered and concentrated under reduced pressure to give a residue which was purified by prep-TLC (9% methanol in dichloromethane). Compound dimethyl 4-[2-[2-[2-[2-[10-acetyl-7-(dimethylamino)phenothiazin-3-yl]oxyethoxy] ethoxy]ethoxy]ethoxy]benzene-1,2-dicarboxylate (130 mg, 0.19 mmol, 70% yield) was obtained as a bluish oil.

Step 5

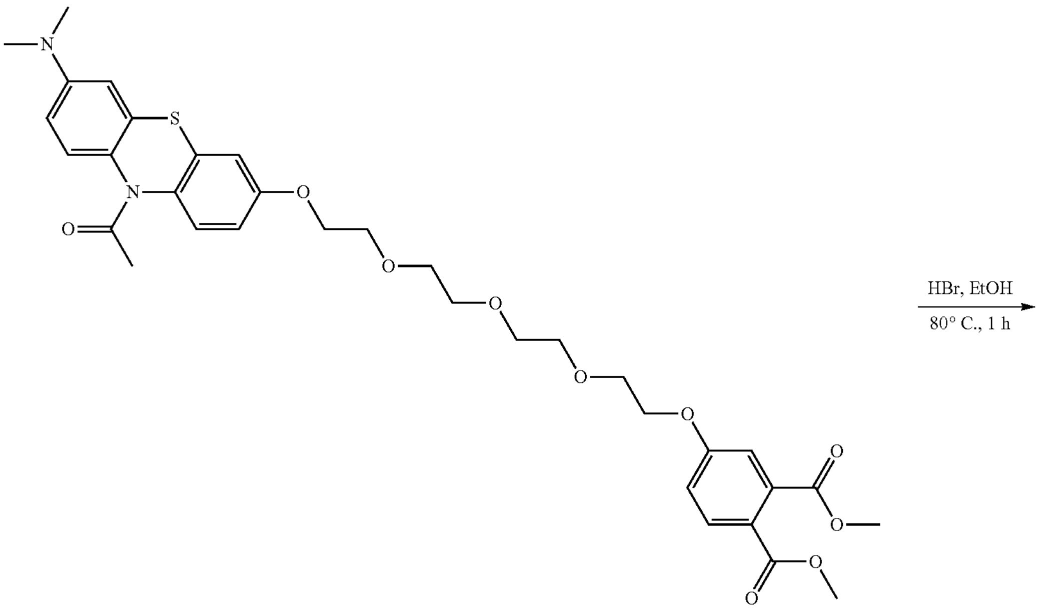

-continued

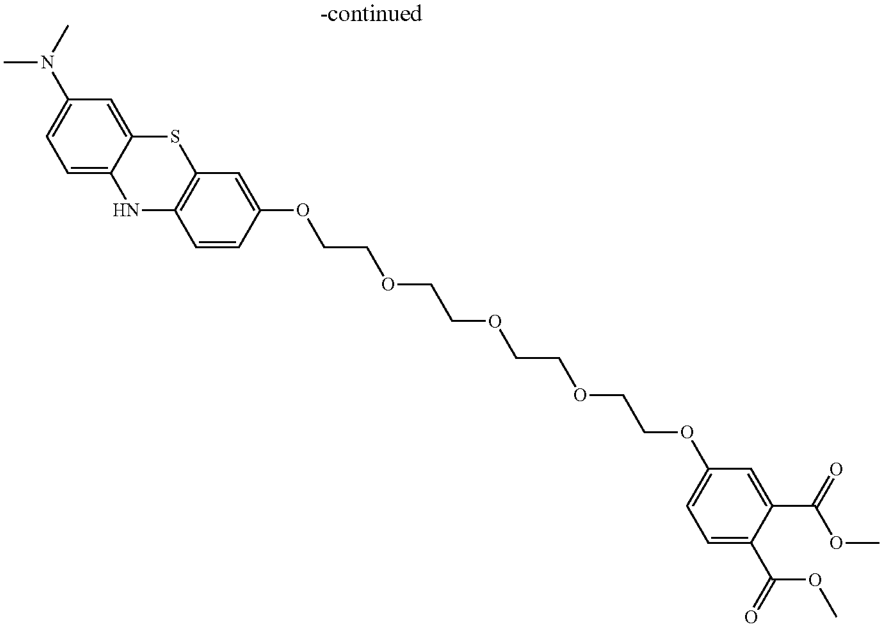

A mixture of dimethyl 4-[2-[2-[2-[2-[10-acetyl-7-(dimethylamino)phenothiazin-3-yl]oxyethoxy]ethoxy]ethoxy]ethoxy]benzene-1,2-dicarboxylate (60 mg, 0.09 mmol, 1 eq) and hydrobromic acid (357 mg, 2.12 mmol, 0.24 mL, 48% in water, 23.65 eq) in ethanol (1 mL) was degassed and purged with nitrogen 3 times, and then the mixture was stirred at 80° C. for 1 hour. The reaction mixture was quenched by the addition of aqueous sodium bicarbonate (40 mL) at 0° C., and extracted with ethyl acetate (50 mL×2). The combined organic layers were washed with brine (50 mL×2), dried over anhydrous sodium sulfate, filtered and concentrated under reduced pressure to give a residue. The residue was purified by prep-TLC (5% methanol in dichloromethane). Compound dimethyl 4-[2-[2-[2-[2-[[7-(dimethylamino)-10H-phenothiazin-3-yl]oxy]ethoxy]ethoxy]ethoxy]ethoxy]benzene-1,2-dicarboxylate (36 mg. 0.05 mmol, 64% yield) was obtained as a bluish oil.

Step 6

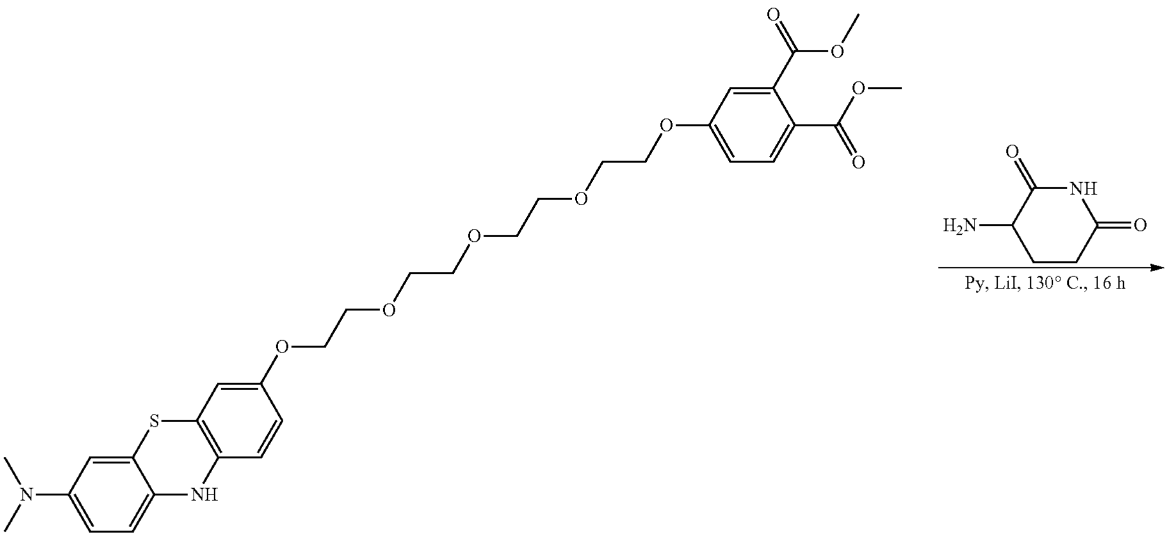

-continued

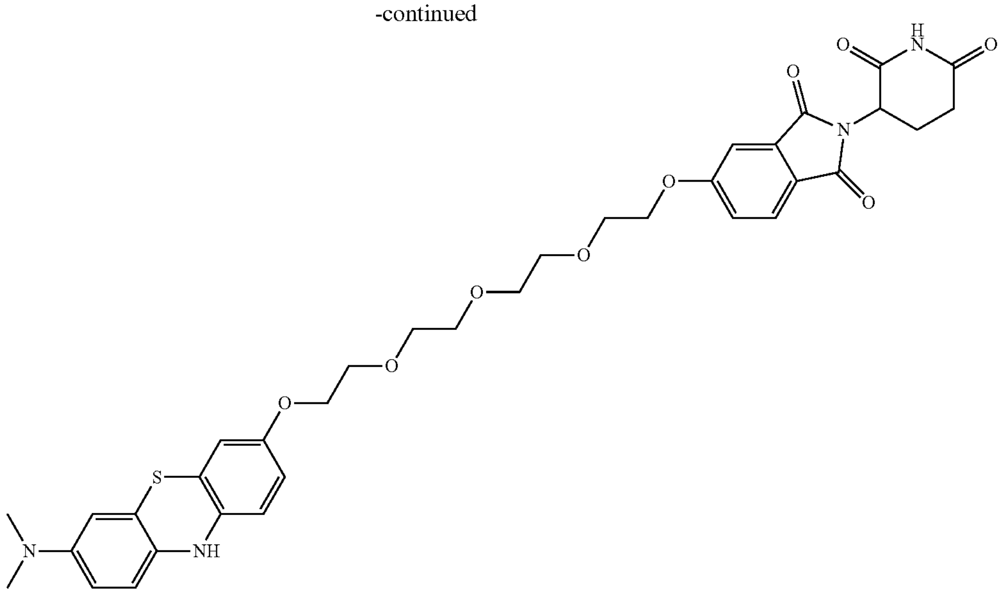

Exemplary Compound 20

A mixture of dimethyl 4-[2-[2-[2-[2-[[7-(dimethylamino)-10H-phenothiazin-3-yl]oxy]ethoxy]ethoxy]ethoxy]ethoxy]benzene-1,2-dicarboxylate (80 mg, 0.12 mmol, 1 eq), 3-aminopiperidine-2,6-dione hydrochloride (42 mg, 0.25 mmol, 2 eq) and lithium iodide (205 mg, 1.53 mmol, 12 eq) in pyridine (8 mL) was degassed and purged with nitrogen for 3 times, and then the mixture was stirred at 130° C. for 16 hours. The reaction mixture was concentrated under reduced pressure to give a residue which was purified by semi-preparative reverse phase HPLC (column: Phenomenex Synergi C18 150*25*10 um; mobile phase: [water (0.225% FA)-ACN]; B %: 20%-50%, 9 min). 5-[2-[2-[2-[2-[[7-(dimethylamino)-10H-phenothiazin-3-yl]oxy]ethoxy]ethoxy]ethoxy]ethoxy]-2-(2,6-dioxo-3-piperidyl)isoindoline-1,3-dione (10.6 mg, 0.01 mmol, 11% yield, formate) was obtained as a dark blue solid.

Exemplary Compound 21 was prepared following the procedures described above for Exemplary Compound 20.

Exemplary Synthesis of Exemplary Compound 22

Step 1

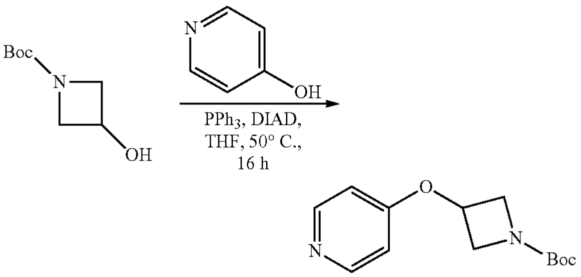

A mixture of pyridin-4-ol (4.12 g, 43.30 mmol, 1.5 eq), tert-butyl 3-hydroxyazetidine-1-carboxylate (5 g, 28.87 mmol, 1 eq), triphenylphosphine (9.09 g, 34.64 mmol, 1.2 eq) and diisopropyl azodicarboxylate (7.00 g, 34.64 mmol, 6.7 mL, 1.2 eq) in tetrahydrofuran (80 mL) was degassed and purged with nitrogen 3 times, and then the mixture was stirred at 50° C. for 16 hours under nitrogen atmosphere. The reaction mixture was quenched by the addition of water (200 mL) and extracted with ethyl acetate (200 mL×3). The combined organic layers were washed with brine (50 mL×3), dried over anhydrous sodium sulfate, filtered and

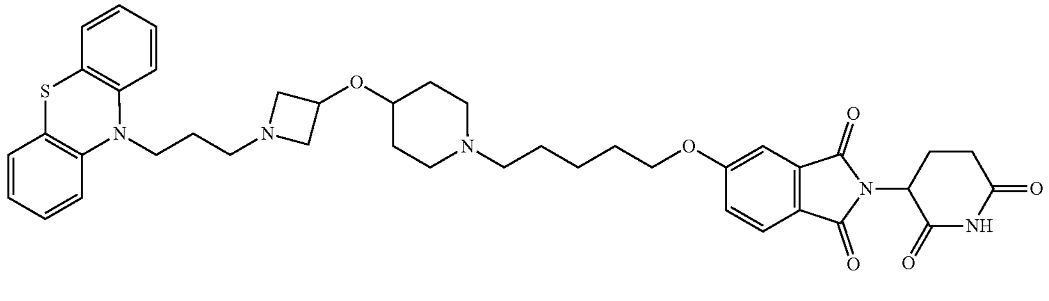 [SMILES: O=C1CCC(N2C(=O)c3ccc(OCCCCCN4CCC(OC5CN(CCCN6c7ccccc7Sc7ccccc76)C5)CC4)cc3C2=O)C(=O)N1]

concentrated under reduced pressure to give a residue, which was purified by silica gel column chromatography (petroleum ether/ethyl acetate=20/1 to 5/1) to get the crude product. The crude product was purified deeply by prep-HPLC (column: Phenomenex Synergi Max-RP 250*50 mm*10 um; mobile phase: [water (0.225% formic acid)-acetonitrile]; B %: 10%-40%, 25 min, 55% min) to produce tert-butyl 3-(4-pyridyloxy)azetidine-1-carboxylate (4.71 g, 15.90 mmol, 78% yield, formate) as a light yellow gum.

Step 2

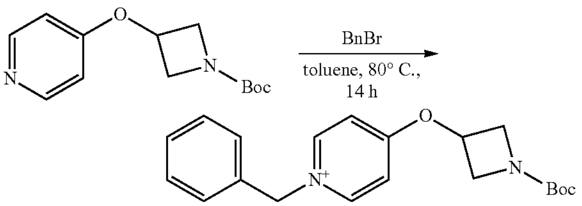

To a solution of tert-butyl 3-(4-pyridyloxy)azetidine-1-carboxylate formate (4.71 g, 15.90 mmol, 1 eq) in toluene (47 mL) was added benzyl bromide (2.72 g, 15.90 mmol, 1.9 mL, 1 eq). The reaction was stirred at 80° C. for 14 hours. The reaction solution was concentrated under vacuum to afford the residue which was triturated with ethyl acetate (80 mL) and filtered to produce crude tert-butyl 3-(1-benzylpyridin-1-ium-4-yl)oxyazetidine-1-carboxylate (6.55 g) as a white solid.

Step 3

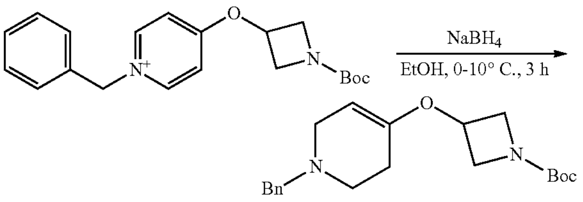

To a solution of tert-butyl 3-(1-benzylpyridin-1-ium-4-yl)oxyazetidine-1-carboxylate (6.05 g, 17.72 mmol, 1 eq) in ethanol (120 mL) was added sodium borohydride (4.02 g, 106.3 mmol, 6 eq) at 0° C. The reaction was stirred at 10° C. for 3 hours. The reaction solution was quenched with saturated aqueous ammonium chloride (50 mL). The reaction mixture was concentrated to remove solvent and then diluted with water (30 mL) and extracted with ethyl acetate (50 mL×3). The combined organic layers were dried over anhydrous sodium sulfate and concentrated under vacuum to afford the residue which was purified by silica gel column chromatography (petroleum ether/ethyl acetate=30/1 to 1:1) to get the crude product which was purified by prep-HPLC (column: Phenomenex Synergi Max-RP 250*80 mm*10 um; mobile phase: [water (0.225% formic acid)-acetonitrile]; B %: 30ACN %-60ACN %, 20 min; 50% min) to afford tert-butyl 3-[(1-benzyl-3,6-dihydro-2H-pyridin-4-yl)oxy]azetidine-1-carboxylate (1.34 g, 3.89 mmol, 21% yield) as a light yellow gum.

Step 4

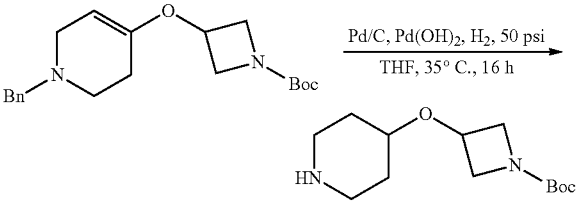

To a solution of tert-butyl 3-[(1-benzyl-3,6-dihydro-2H-pyridin-4-yl)oxy]azetidine-1-carboxylate (1.34 g, 3.89 mmol, 1 eq) in tetrahydrofuran (20 mL) were added 20% palladium hydroxide on activated carbon catalyst (200 mg) and 10% palladium on activated carbon catalyst (200 mg) under nitrogen. The suspension was degassed under vacuum and purged with hydrogen three times. The reaction mixture was stirred under hydrogen (50 psi) at 35° C. for 16 hours. The reaction mixture was filtered through a pad of celite, and the filtrate was concentrated under vacuum to produce crude tert-butyl 3-(4-piperidyloxy)azetidine-1-carboxylate (830 mg, 3.24 mmol) as a light yellow gum.

Step 5

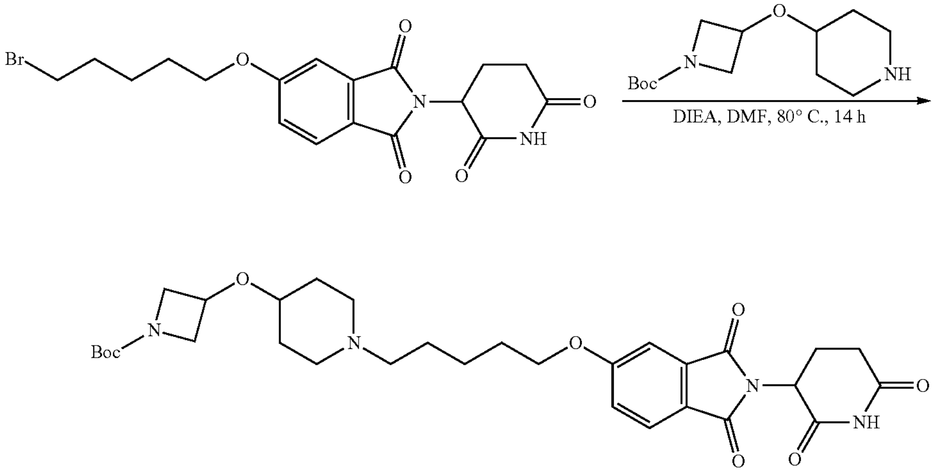

To a solution of tert-butyl 3-(4-piperidyloxy)azetidine-1-carboxylate (242 mg, 0.95 mmol, 1 eq) and 5-(5-bromopentoxy)-2-(2,6-dioxo-3-piperidyl)isoindoline-1,3-dione (400 mg, 0.95 mmol, 1 eq) in N,N-dimethylformamide (15 mL) was added diisopropylethylamine (366 mg, 2.84 mmol, 0.5 mL, 3 eq). The reaction solution was stirred at 80° C. for 14 hours. The reaction solution was diluted with ethyl acetate (20 mL) and washed with water (50 mL). The water layer was extracted with ethyl acetate (40 mL×2). The combined organic layers were washed with brine (20 mL), dried over anhydrous sodium sulfate and concentrated under vacuum to produce the residue which was purified by prep-TLC (dichloromethane/methanol=10/1) to get tert-butyl 3-[[1-[5-[2-(2,6-dioxo-3-piperidyl)-1,3-dioxo-isoindolin-5-yl]oxypentyl]-4-piperidyl]oxy]azetidine-1-carboxylate (260 mg, 0.42 mmol, 45% yield) as a yellow solid.

Step 6

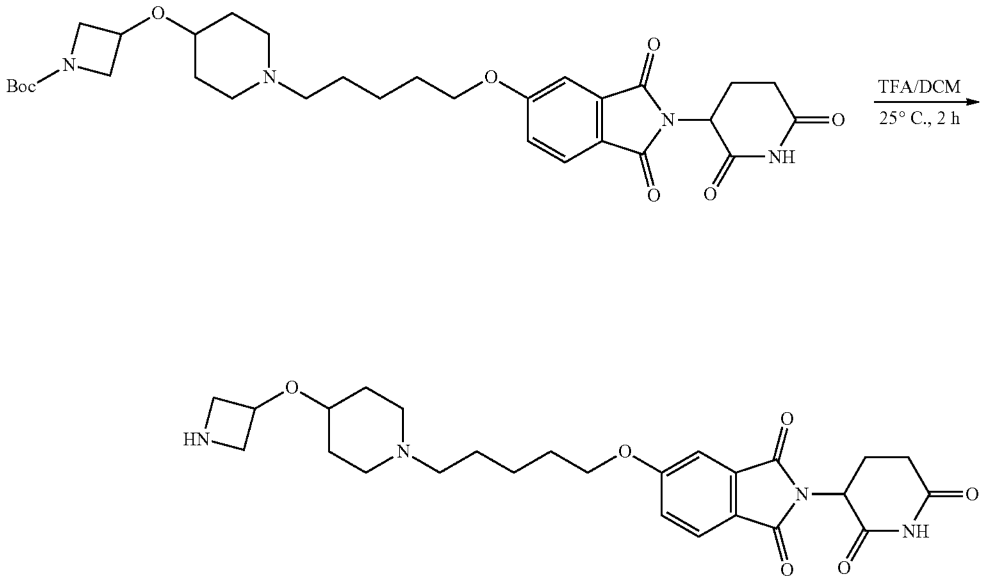

To a solution of tert-butyl 3-[[1-[5-[2-(2,6-dioxo-3-piperidyl)-1,3-dioxo-isoindolin-5-yl]oxypentyl]-4-piperidyl]oxy]azetidine-1-carboxylate (260 mg, 0.43 mmol, 1 eq) in dichloromethane (6 mL) was added trifluoroacetic acid (924 mg, 8.10 mmol, 0.6 mL, 18.7 eq). The reaction solution was stirred at 20° C. for 1 hour. To the reaction was added more trifluoroacetic acid (924 mg, 8.10 mmol, 0.6 mL, 18.6 eq), and the reaction was stirred at 20° C. for another 1 hour. The reaction solution was concentrated under vacuum to afford the residue which was diluted with pure water (30 mL) and lyophilized to produce crude 5-[5-[4-(azetidin-3-yloxy)-1-piperidyl]pentoxy]-2-(2,6-dioxo-3-piperidyl)isoindoline-1,3-dione as a brown solid.

Step 7

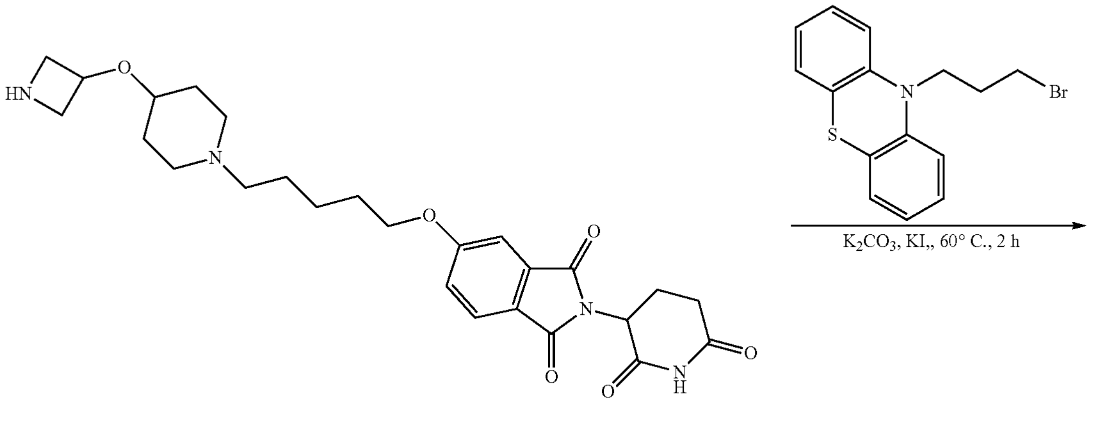

-continued

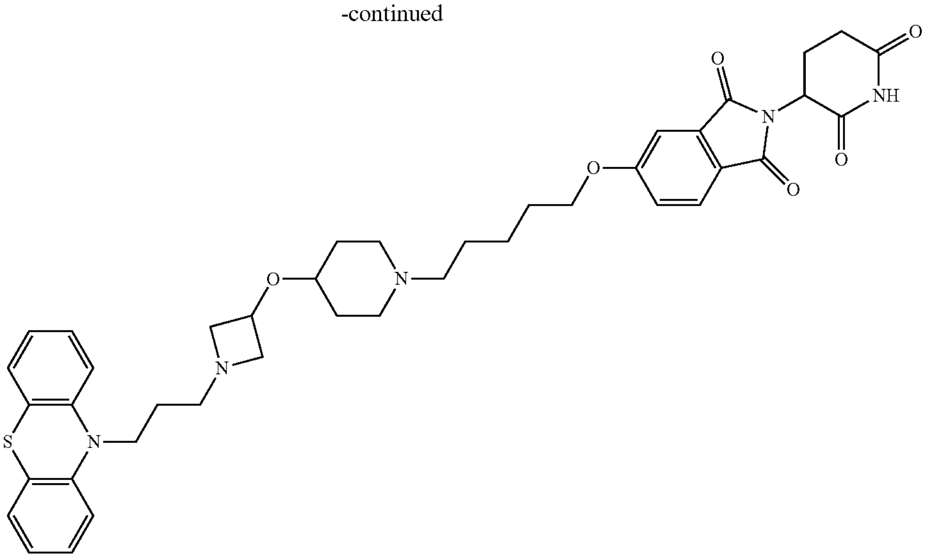

Exemplary Compound 22

To a mixture of 5-[5-[4-(azetidin-3-yloxy)-1-piperidyl] pentoxy]-2-(2,6-dioxo-3-piperidyl)isoindoline-1,3-dione (110 mg, 0.22 mmol, 1 eq) and 10-(3-bromopropyl)phenothiazine (85 mg, 0.26 mmol, 1.2 eq) in N,N-dimethylformamide (3 mL) were added potassium carbonate (61 mg, 0.44 mmol, 2 eq) and potassium iodide (4 mg, 0.022 mmol, 0.1 eq). The reaction was stirred at 60° C. for 2 hours. The reaction mixture was filtered, the pH of filtrate was adjusted to 4-5 with trifluoroacetic acid, and the solution was concentrated under vacuum to afford the residue. The residue was purified by prep-HPLC (column: Phenomenex Synergi C18 150*25*10 um; mobile phase: [water (0.1% trifluoroacetic acid)-acetonitrile]; B %: 17%-47%, 10 min) to produce 2-(2,6-dioxo-3-piperidyl)-5-[5-[4-[1-(3-phenothiazin-10-ylpropyl)azetidin-3-yl]oxy-1-piperidyl]pentoxy] isoindoline-1,3-dione (94 mg, trifluoroacetate) as a yellow solid.

Exemplary Synthesis of Exemplary Compound 23

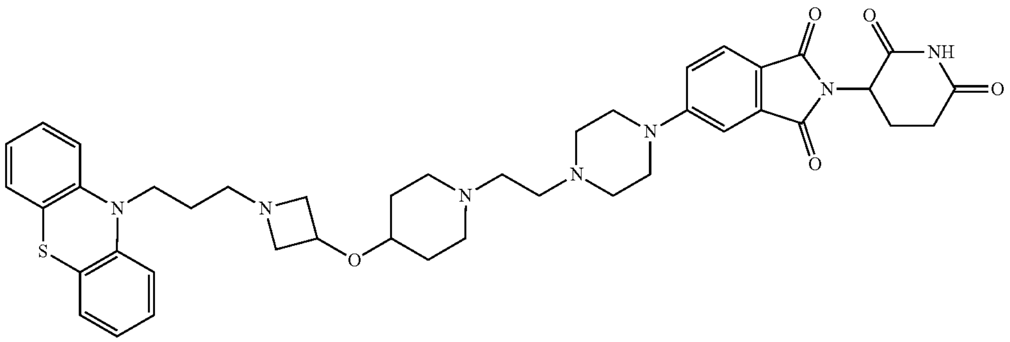 [SMILES: O=C1CCC(N2C(=O)c3ccc(N4CCN(CCN5CCC(OC6CN(CCCN7c8ccccc8Sc8ccccc87)C6)CC5)CC4)cc3C2=O)C(=O)N1]

Step 1

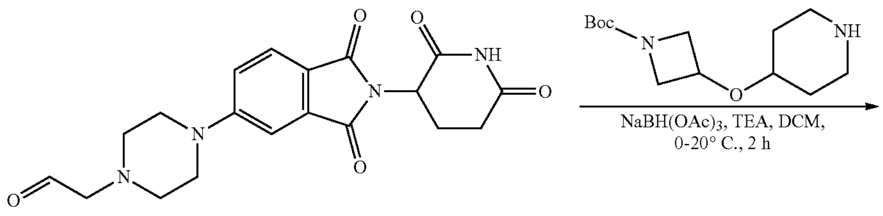

-continued

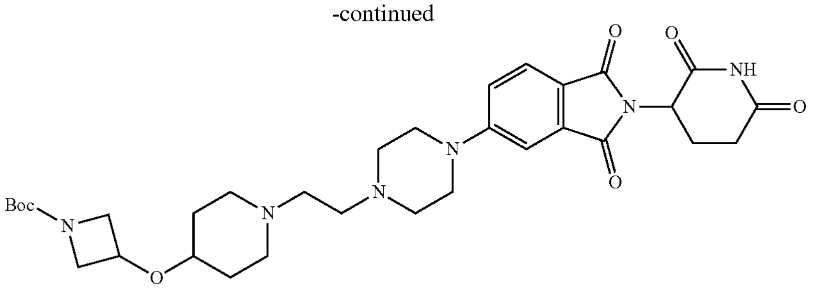

To a solution of tert-butyl 3-(4-piperidyloxy)azetidine-1-carboxylate (93 mg, 0.36 mmol, 1 eq) in dichloromethane (4 mL) was added triethylamine (74 mg, 0.73 mmol, 0.1 mL, 2 eq), and the mixture was stirred at 20° C. for 0.5 hour. Then 2-[4-[2-(2,6-dioxo-3-piperidyl)-1,3-dioxo-isoindolin-5-yl]piperazin-1-yl]acetaldehyde (140 mg, 0.36 mmol, 1 eq) in dichloromethane (6 mL) was added, and the mixture was stirred at 20° C. for another 0.5 hour. After that, sodium triacetoxyborohydride (232 mg, 1.09 mmol, 3 eq) was added at 0° C., and the mixture was stirred at 20° C. for 1 hour. The reaction solution was diluted with water (30 mL). The organic layer was extracted with dichloromethane (20 mL×3). The combined organic layers were dried over anhydrous sodium sulfate and concentrated under vacuum to afford the residue which was purified by prep-TLC (10% methanol in dichloromethane) and then by prep-HPLC (column: Phenomenex Synergi C18 150*25*10 um; mobile phase: [water (0.225% FA)-ACN]; B %: 20%-50%, 9 min) to produce tert-butyl 3-[[1-[2-[4-[2-(2,6-dioxo-3-piperidyl)-1,3-dioxo-isoindolin-5-yl]piperazin-1-yl]ethyl]-4-piperidyl]oxy]azetidine-1-carboxylate (140 mg, 0.22 mmol, 62% yield) as a yellow solid.

tert-Butyl 3-[[1-[2-[4-[2-(2,6-dioxo-3-piperidyl)-1,3-dioxo-isoindolin-5-yl]piperazin-1-yl]ethyl]-4-piperidyl]oxy]azetidine-1-carboxylate was converted into the final compound, 5-(4-(2-(4-((1-(3-(10H-phenothiazin-10-yl)propyl)azetidin-3-yl)oxy)piperidin-1-yl)ethyl)piperazin-1-yl)-2-(2,6-dioxopiperidin-3-yl)isoindoline-1,3-dione (Exemplary Compound 23) was prepared following the procedures described above for Exemplary Compound 22.

Exemplary Synthesis of Exemplary Compound 24

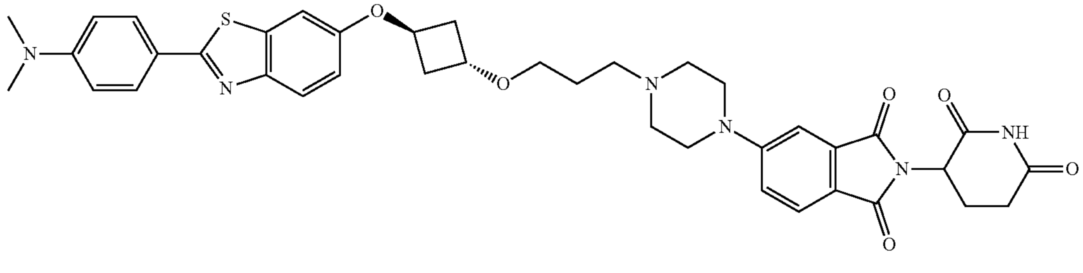 [SMILES: CN(C)c1ccc(-c2nc3ccc(O[C@H]4C[C@H](OCCCN5CCN(c6ccc7c(c6)C(=O)N(C6CCC(=O)NC6=O)C7=O)CC5)C4)cc3s2)cc1]

Step 1

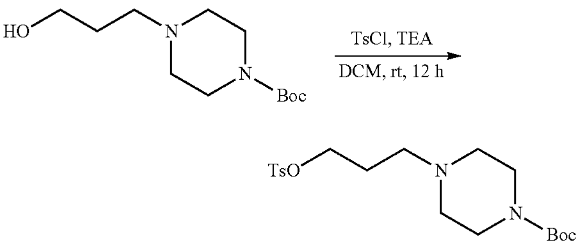

Into a 250-mL round-bottom flask were added a solution of tert-butyl 4-(3-hydroxypropyl)piperazine-1-carboxylate (10 g, 40.93 mmol, 1 equiv) and TEA (12.4 g, 122.78 mmol, 3 equiv) in dichloromethane (150 mL), to which was added 4-methylbenzene-1-sulfonyl chloride (11.8 g, 61.80 mmol, 1.51 equiv) in multiple batches. Then DMAP (0.5 g, 4.09 mmol, 0.1 equiv) was added, and the resulting mixture was stirred at room temperature overnight. The reaction mixture was concentrated under vacuum. The residue was purified by flash chromatography eluting with ethyl acetate/petroleum ether (1:2) to afford tert-butyl 4-[3-[(4-methylbenzenesulfonyl) oxy]propyl]piperazine-1-carboxylate (8.8 g, 49%) as a brown oil.

Step 2

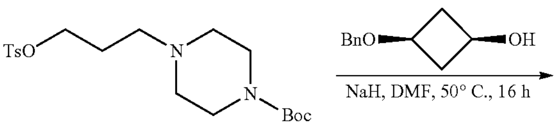

-continued

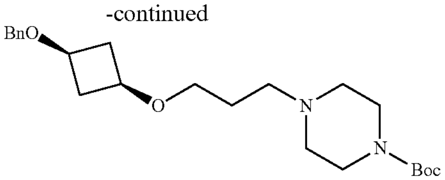

Into a 100-mL round-bottom flask were added (1s,3s)-3-(benzyloxy)cyclobutan-1-ol (1.2 g, 6.73 mmol, 1.34 equiv) in DMF (40 mL), to which was added NaH (401 mg, 10.04 mmol, 2.00 equiv, 60%) at 0° C. The resulting mixture was stirred for 30 minutes, to which was then added tert-butyl 4-[3-[(4-methylbenzenesulfonyl)oxy]propyl]piperazine-1-carboxylate (2 g, 5.02 mmol, 1 equiv) at 0° C. The reaction mixture was stirred for an additional 6 h at 50° C. The reaction was then quenched with water/ice, and the mixture was extracted with ethyl acetate (100 mL×3). The combined organic layer was washed with brine, dried over sodium sulfate and concentrated under vacuum. The residue was purified by flash chromatography eluting with ethyl acetate/petroleum ether (3:1) to afford tert-butyl 4-[3-[(1s,3s)-3-(benzyloxy)cyclobutoxy]propyl]piperazine-1-carboxylate (600 mg, 23%) as a yellow oil.

Step 3

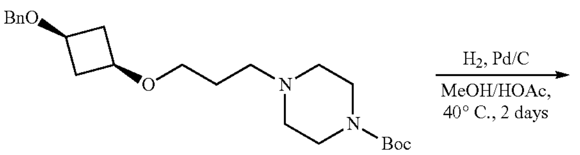

-continued

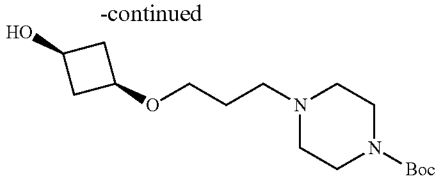

Into a 50-mL container was added tert-butyl 4-[3-[(1s,3s)-3-(benzyloxy)cyclobutoxy]propyl]piperazine-1-carboxylate (800 mg, 1.98 mmol, 1 equiv) in MeOH (20 mL), to which was added 10% Pd/C (421 mg) at room temperature under nitrogen atmosphere. The container was vacuumed and flushed with hydrogen, the sequence repeated 3 times. Then the resulting mixture was hydrogenated under 50 atm hydrogen atmosphere for 2 days at 55° C. The solids were removed by filtration and rinsed with MeOH (100 mL×3). The filtrate was concentrated under vacuum, and the crude product was purified by prep-HPLC with following conditions: XBridge Prep OBD C18 Column 30*50 mm 5 um; Mobile Phase A: Water (with 10 mmol/L $NH_4HCO_3$), Mobile Phase B: ACN; Flow rate: 60 mL/min; Gradient: 60% B to 85% B in 8 min; 254 nm; Rt: 254 min. This afforded tert-butyl 4-[3-[(1s,3s)-3-hydroxycyclobutoxy]propyl]piperazine-1-carboxylate (380 mg, 49%) as an off-white oil.

Step 4

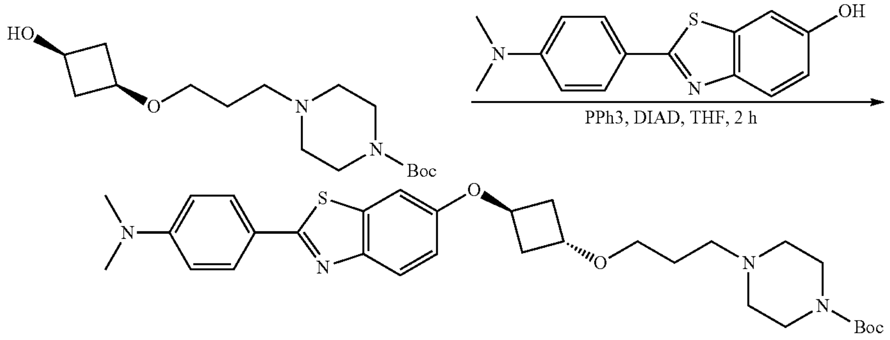

Into a 20-mL vial purged and maintained under an atmosphere of nitrogen, were added a solution of tert-butyl 4-[3-[(1s,3s)-3-hydroxycyclobutoxy]propyl]piperazine-1-carboxylate (300 mg, 0.95 mmol, 1 equiv), 2-[4-(dimethylamino)phenyl]-1,3-benzothiazol-6-ol (258 mg, 0.95 mmol, 1.00 equiv), and $PPh_3$ (375 mg, 1.43 mmol, 1.5 equiv) in toluene (10 mL). Then DIAD (289 mg, 1.43 mmol, 1.5 equiv) was added, and the resulting mixture was stirred for 2 hours at room temperature. The reaction mixture was diluted with water (20 mL), and the mixture was extracted with ethyl acetate (50 mL×3). The combined organic layer was washed with brine, dried over sodium sulfate and concentrated under vacuum. The residue was purified by prep-TLC eluting with ethyl acetate/petroleum ether (1:1) to afford tert-butyl 4-[3-[(1r,3r)-3-([2-[4-(dimethylamino)phenyl]-1,3-benzothiazol-6-yl]oxy)cyclobutoxy]propyl]piperazine-1-carboxylate (280 mg, 47%) as a yellow oil.

Step 5

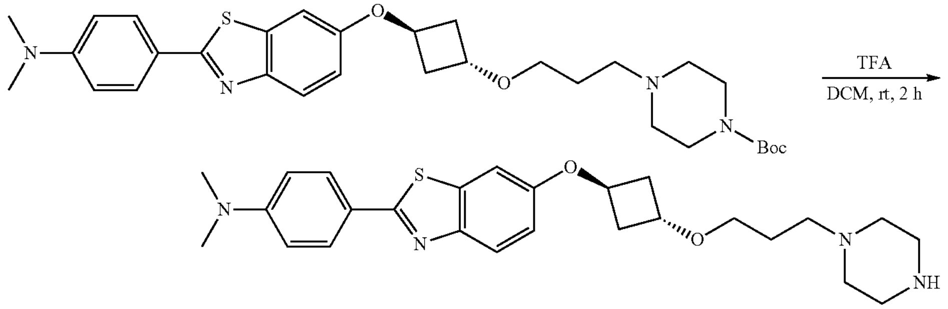

Into a 25-mL round-bottom flask was added tert-butyl 4-[3-[(1r,3r)-3-([2-[4-(dimethylamino)phenyl]-1,3-benzothiazol-6-yl]oxy)cyclobutoxy]propyl]piperazine-1-carboxylate (30 mg, 0.05 mmol, 1 equiv) in dichloromethane (10 mL), to which was added TFA (4 mL) at room temperature. The resulting mixture was stirred for 2 h, and then was concentrated under vacuum. This resulted in N,N-dimethyl-4-[6-[(1r,3r)-3-[3-(piperazin-1-yl)propoxy]cyclobutoxy]-1,3-benzothiazol-2-yl]aniline (300 mg, crude) as a yellow solid.

Step 6

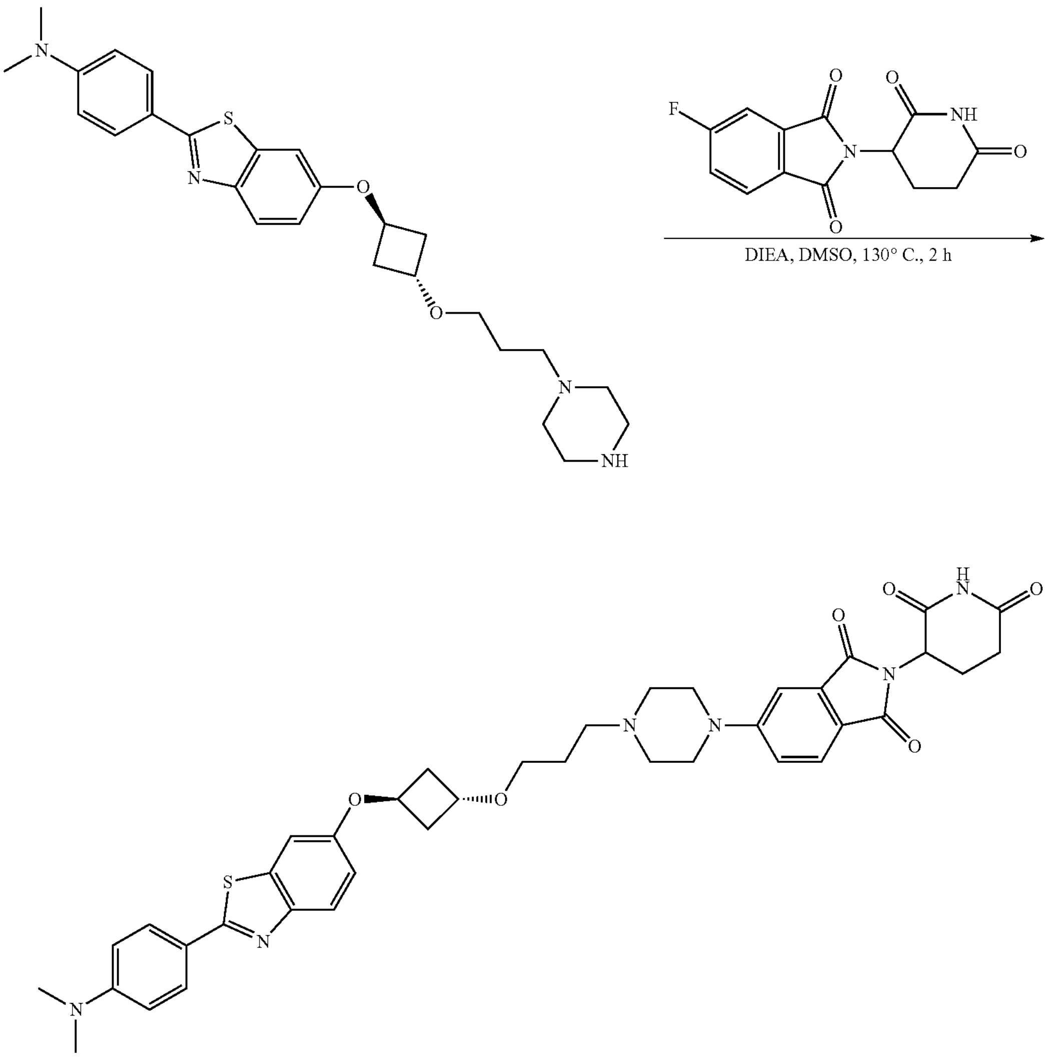

Exemplaary Compound 24

Into a 10-mL vial were added a solution of N,N-dimethyl-4-[6-[(1r,3r)-3-[3-(piperazin-1-yl)propoxy]cyclobutoxy]-1,3-benzothiazol-2-yl]aniline (270 mg, 0.58 mmol, 1 equiv), 2-(2,6-dioxopiperidin-3-yl)-5-fluoro-2,3-dihydro-1H-isoindole-1,3-dione (191.8 mg, 0.69 mmol, 1.20 equiv), and DIEA (0.9 mL, 6.96 mmol, 9.41 equiv) in DMSO (5 mL) at room temperature. The resulting mixture was stirred at 130° C. for 3 hours, and then cooled to room temperature and diluted with water (10 mL). The mixture was extracted with ethyl acetate (100 mL×3). The combined organic phase was washed with brine, dried over sodium sulfate and concentrated under vacuum. The crude product was purified by prep-HPLC: XBridge Prep OBD C18 Column 30*150 mm 5 um; Mobile Phase A: Water (with 10 mmol/L $NH_4HCO_3$), Mobile Phase B: ACN; Flow rate: 60 mL/min; Gradient: 54% B to 74% B in 8 min; Detector: UV 254 nm; Rt: 254 min. This resulted in 42.7 mg (10%) of 2-(2,6-dioxopiperidin-3-yl)-5-(4-[3-[(1r,3r)-3-([2-[4-(dimethylamino)phenyl]-1,3-benzothiazol-6-yl]oxy)cyclobutoxy]propyl]piperazin-1-yl)-2,3-dihydro-1H-isoindole-1,3-dione as a yellow solid.

Exemplary Synthesis of Exemplary Compound 25

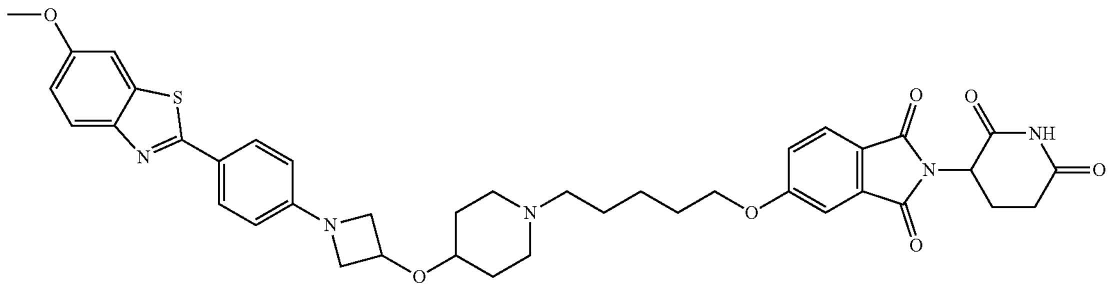 [SMILES: COc1ccc2nc(-c3ccc(N4CC(OC5CCN(CCCCCOc6ccc7c(c6)C(=O)N(C6CCC(=O)NC6=O)C7=O)CC5)C4)cc3)sc2c1]

Step 1

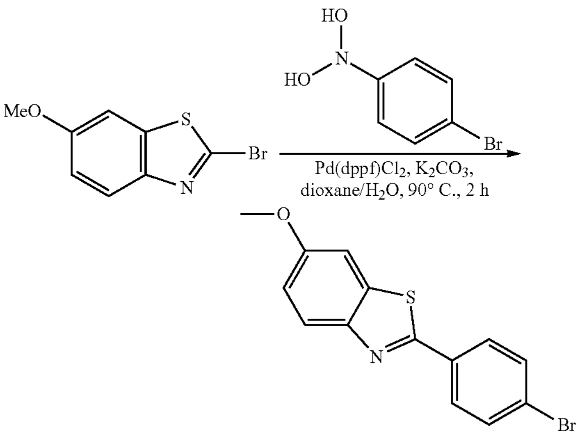

Into a 250-mL round-bottom flask purged and maintained under an inert atmosphere of nitrogen, was placed a solution of 2-bromo-6-methoxy-1,3-benzothiazole (7.3 g, 29.9 mmol, 1.0 equiv), (4-bromophenyl)boronic acid (8.4 g, 41.8 mmol, 1.40 equiv), $K_2CO_3$ (8.3 g, 60.1 mmol, 2.0 equiv), $Pd(dppf)Cl_2$ $CH_2Cl_2$ (500 mg, 0.68 mmol, 0.02 equiv) in dioxane (100 mL) and $H_2O$ (20 mL). The resulting mixture was stirred for 3 hours at 90° C. in an oil bath. The reaction mixture was cooled to room temperature and quenched with water (200 mL). The insoluble solids were removed by filtration, and the filtrate was extracted with ethyl acetate (150 mL×3). The combined organic layer was washed with brine (100 mL×2), dried over $Na_2SO_4$ and concentrated under reduced pressure. The residue was purified by flash chromatography eluting with ethyl acetate/petroleum ether (1:1). This resulted in 4 g (crude) of 2-(4-bromophenyl)$_{1-6}$-methoxy-1,3-benzothiazole as a brown solid.

Step 2

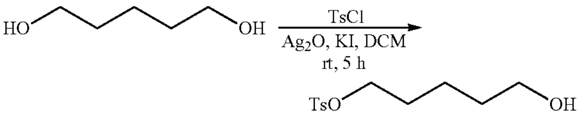

Into a 250-mL round-bottom flask, was placed pentane-1,5-diol (6 g, 57.61 mmol, 1.00 equiv) silver oxide (20 g) and potassium iodide (2.9 g) in dichloromethane (100 mL), to which was added 4-toluene sulfonyl chloride (10.96 g, 57.49 mmol, 1.00 equiv) at room temperature. The resulting mixture was stirred for 4 h at 25° C. The solids were filtered off, and the filtrate was concentrated. The residue was diluted with water (50 mL), and the mixture was extracted with dichloromethane (30 mL×3). The organic layers were combined, washed with brine (50 mL×2), dried over anhydrous sodium sulfate and concentrated under vacuum. The residue was applied onto a silica gel column eluting with ethyl acetate/petroleum ether (1:4). This resulted in 6.1 g (41%) of 5-[[(4-methylbenzene)sulfonyl]oxy]pentan-1-ol as a colorless oil.

Step 3

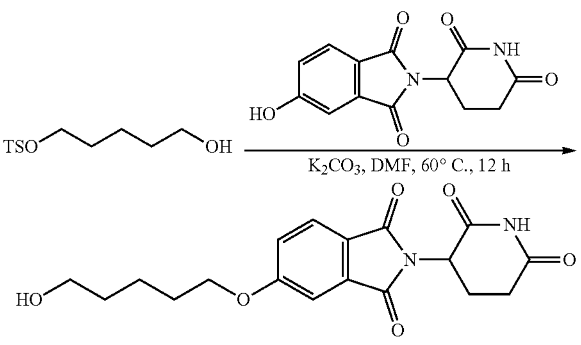

Into a 100-mL round-bottom flask were added a solution of 2-(2,6-dioxopiperidin-3-yl)-5-hydroxy-2,3-dihydro-1H-isoindole-1,3-dione (3 g, 10.9 mmol, 1 equiv) in DMF (50 mL), $K_2CO_3$ (3.0 g, 21.9 mmol, 2.0 equiv) and 5-[(4-methylbenzenesulfonyl)oxy]pentan-1-ol (8.5 g, 32.9 mmol, 3.0 equiv). The resulting mixture was stirred for 16 hours at 60° C. The reaction was then quenched by the addition of water (50 mL) at room temperature, and the mixture was extracted with ethyl acetate (100 mL), washed with brine, dried over sodium sulfate and concentrated under reduced pressure. The residue was purified by flash chromatography eluting with ethyl acetate to afford 2-(2,6-dioxopiperidin-3-yl)-5-[(5-hydroxypentyl)oxy]-2,3-dihydro-1H-isoindole-1,3-dione (1.5 g, 38%) as a yellow solid.

Step 4

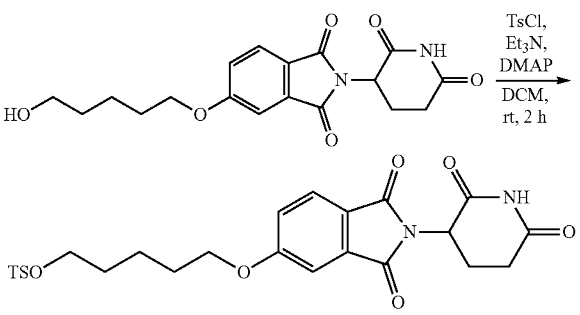

Into a 250-mL round-bottom flask were added a solution of 2-(2,6-dioxopiperidin-3-yl)-5-[(5-hydroxypentyl)oxy]-2,3-dihydro-1H-isoindole-1,3-dione (2 g, 5.55 mmol, 1 equiv), $Et_3N$ (1.7 g, 16.65 mmol, 3.0 equiv) and DMAP (67.8 mg, 0.55 mmol, 0.1 equiv) in dichloromethane (40 mL), to which was added TsCl (1.3 g, 6.82 mmol, 1.23 equiv) at room temperature. The resulting mixture was stirred for 16 hours at room temperature, and then was concentrated under vacuum. The residue was purified by flash chromatography, eluting with ethyl acetate/petroleum ether (1:1) to afford 5-[[2-(2,6-dioxopiperidin-3-yl)-1,3-dioxo-2,3-dihydro-1H-isoindol-5-yl]oxy]pentyl 4-methylbenzene-1-sulfonate (1.8 g, 63%) as a yellow solid.

Step 5

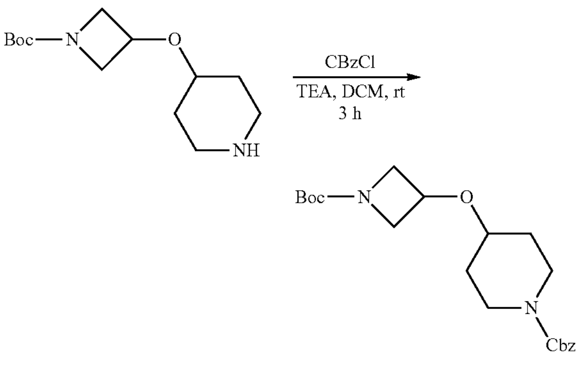

Into a 500-mL round-bottom flask purged and maintained under an inert atmosphere of nitrogen, was placed a solution of tert-butyl 3-(piperidin-4-yloxy)azetidine-1-carboxylate (5 g, 19.5 mmol, 1 equiv) and TEA (6 mL) in dichloromethane (100 mL), to which was added slowly CbzCl (4.0 g, 23.4 mmol, 1.2 equiv). The resulting solution was stirred for 3 hours at room temperature. The reaction was then quenched by the addition of water (100 mL), and the mixture was extracted with dichloromethane (200 mL×3). The combined organic layer was washed with brine (100 mL), dried over anhydrous sodium sulfate and concentrated. The residue was applied onto a silica gel column eluting with ethyl acetate/petroleum ether (1:1). This resulted in 2.3 g (30%) of benzyl-4-([1-[(tert-butoxy)carbonyl]azetidin-3-yl]oxy)piperidine-1-carboxylate as a yellow oil.

Step 6

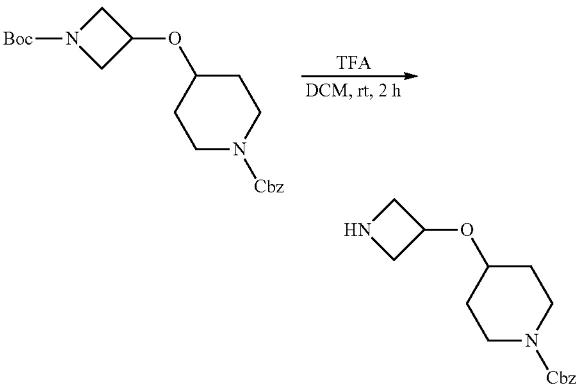

Into a 100-mL round-bottom flask, was placed benzyl-4-([1-[(tert-butoxy)carbonyl]azetidin-3-yl]oxy)piperidine-1-carboxylate (500 mg, 1.28 mmol, 1 equiv) in dichloromethane (40 mL), to which was added TFA (10 mL). The resulting solution was stirred for 2 hours at room temperature. The reaction mixture was concentrated under vacuum and diluted with water (10 mL). The pH value of the mixture was adjusted to 7 with TEA, and then concentrated under vacuum. The residue was applied onto a silica gel column eluting with ethyl acetate. This resulted in 400 mg (crude) of benzyl 4-(azetidin-3-yloxy)piperidine-1-carboxylate as a yellow oil.

Step 7

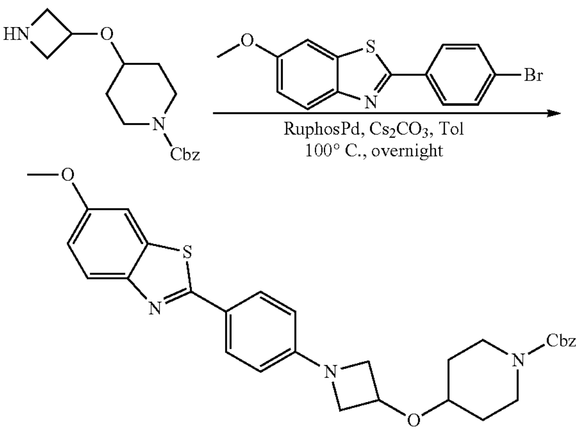

Into a 25-mL microwave tube purged and maintained with an inert atmosphere of nitrogen. was placed a solution of benzyl-4-(azetidin-3-yloxy)piperidine-1-carboxylate (1 g, 3.44 mmol, 1 equiv), $Cs_2CO_3$ (4.5 g, 13.78 mmol, 4.00 equiv), 2-(4-bromophenyl)$_{1-6}$-methoxy-1,3-benzothiazole (1.1 g, 3.44 mmol, 1.00 equiv), RuPhos Palladium precatalyst (0.3 g, 0.34 mmol, 0.1 equiv) in toluene (8 mL). The resulting mixture was stirred overnight at 100° C., and then was concentrated under vacuum. The residue was applied onto a silica gel column eluting with ethyl acetate/petroleum ether (100:1). This resulted in 500 mg (27% for 2 steps) of benzyl-4-([1-[4-(6-methoxy-1,3-benzothiazol-2-yl)phenyl]azetidin-3-yl]oxy)piperidine-1-carboxylate as a yellow solid.

Step 8

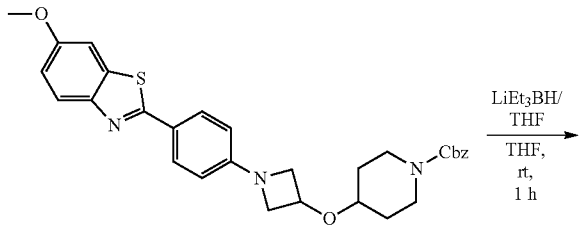

-continued

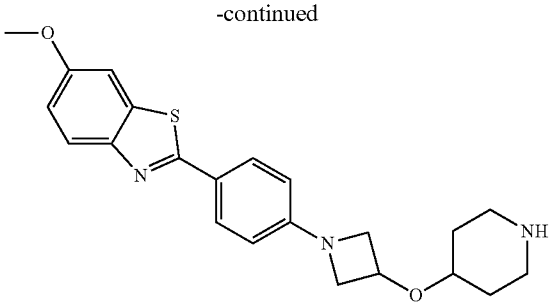

Into a 100-mL round-bottom flask, was placed benzyl-4-([1-[4-(6-methoxy-1,3-benzothiazol-2-yl)phenyl]azetidin-3-yl]oxy)piperidine-1-carboxylate (600 mg, 1.13 mmol, 1 equiv) in THF (10 mL), to which was added $LiEt_3BH/THF$ dropwise (1 M, 7 mL) at 0° C. The resulting solution was stirred for 1 hour at room temperature. The solids in the reaction mixture were filtered out and rinsed with DMF. The filtrate was concentrated and the residue was applied onto a silica gel column eluting with dichloromethane/methanol (5:1). This resulted in 380 mg (85%) of 6-methoxy-2-[4-[3-(piperidin-4-yloxy)azetidin-1-yl]phenyl]-1,3-benzothiazole as a yellow green solid.

Step 9

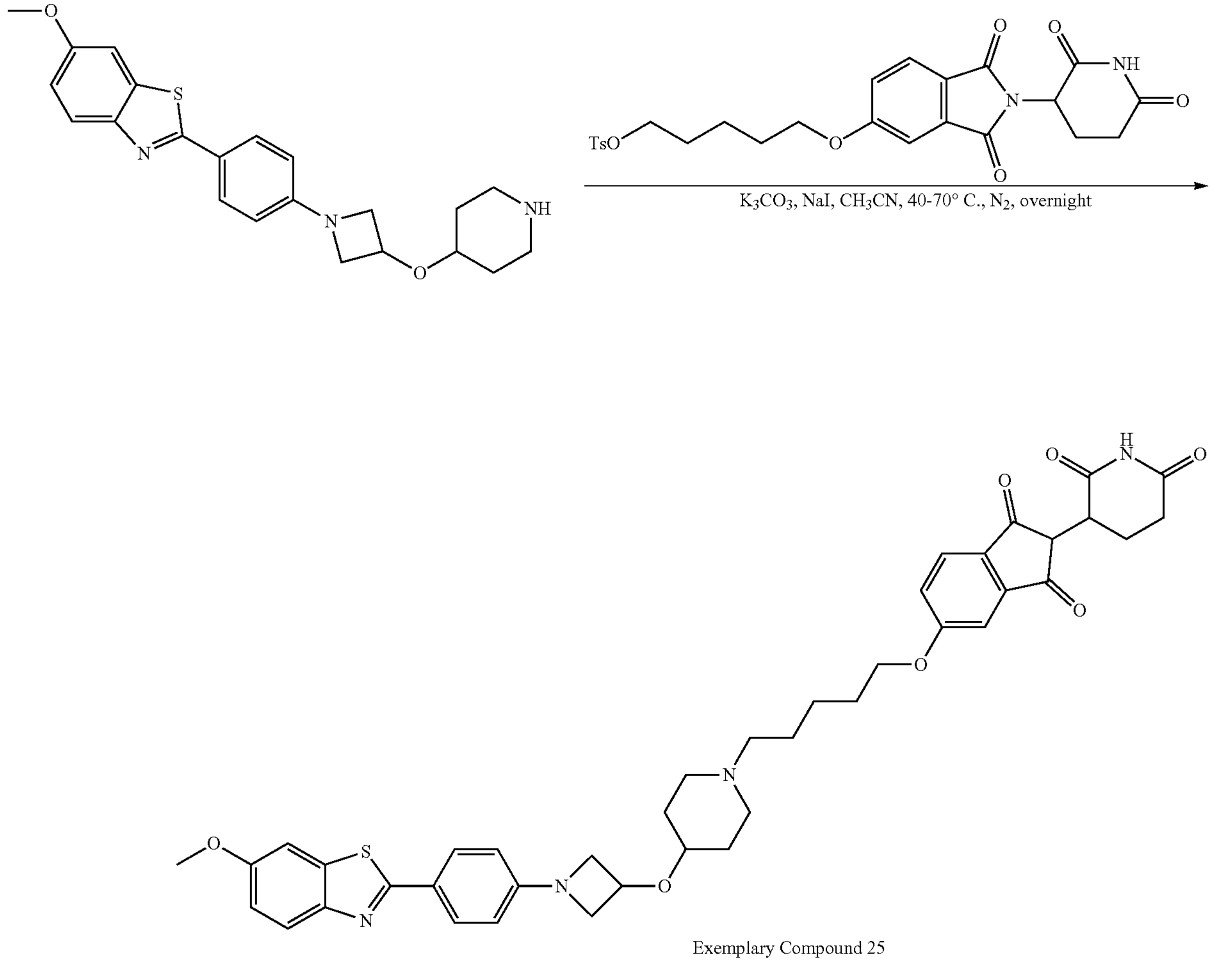

Exemplary Compound 25

Into a 25-mL microwave tube purged and maintained under an inert atmosphere of nitrogen, was placed a mixture of 6-methoxy-2-[4-[3-(piperidin-4-yloxy)azetidin-1-yl]phenyl]-1,3-benzothiazole (70 mg, 0.18 mmol, 1.0 equiv), $K_2CO_3$ (73 mg, 0.53 mmol, 3.0 equiv), 5-[[2-(2,6-dioxopiperidin-3-yl)-1,3-dioxo-2,3-dihydro-1H-isoindol-5-yl]oxy]pentyl 4-methylbenzene-1-sulfonate (91.1 mg, 0.18 mmol, 1.0 equiv), and NaI (26.5 mg, 0.18 mmol, 1 equiv) in $CH_3CN$ (5 mL). The resulting mixture was stirred overnight at 40° C., and then heated up to 70° C. and stirred for an additional 5 hours at 70° C. The solids were filtered off, and the filtrate was concentrated under vacuum. The crude product was purified by prep-HPLC with the following conditions: Column, XBridge Prep OBD C18 Column, 30*150 mm 5 um; mobile phase, acetonitrile in water (with 10 mmol/L $NH_4HCO_3$), 49% to 69% gradient in 8 min; Detector, UV. This resulted in 49 mg (33%) of 2-(2,6-dioxopiperidin-3-yl)-5-([5-[4-([1-[4-(6-methoxy-1,3-benzothiazol-2-yl)phenyl]azetidin-3-yl]oxy)piperidin-1-yl]pentyl]oxy)-2,3-dihydro-1H-isoindole-1,3-dione as a light yellow solid.

Exemplary Synthesis of Exemplary Compound 26

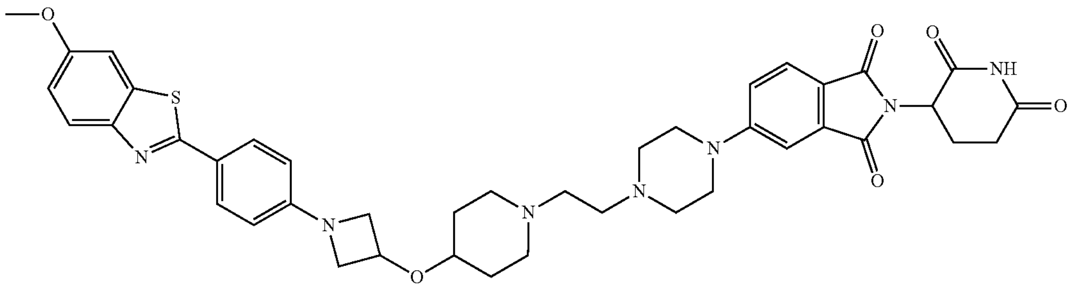 [SMILES: COc1ccc2nc(-c3ccc(N4CC(OC5CCN(CCN6CCN(c7ccc8c(c7)C(=O)N(C7CCC(=O)NC7=O)C8=O)CC6)CC5)C4)cc3)sc2c1]

Step 1

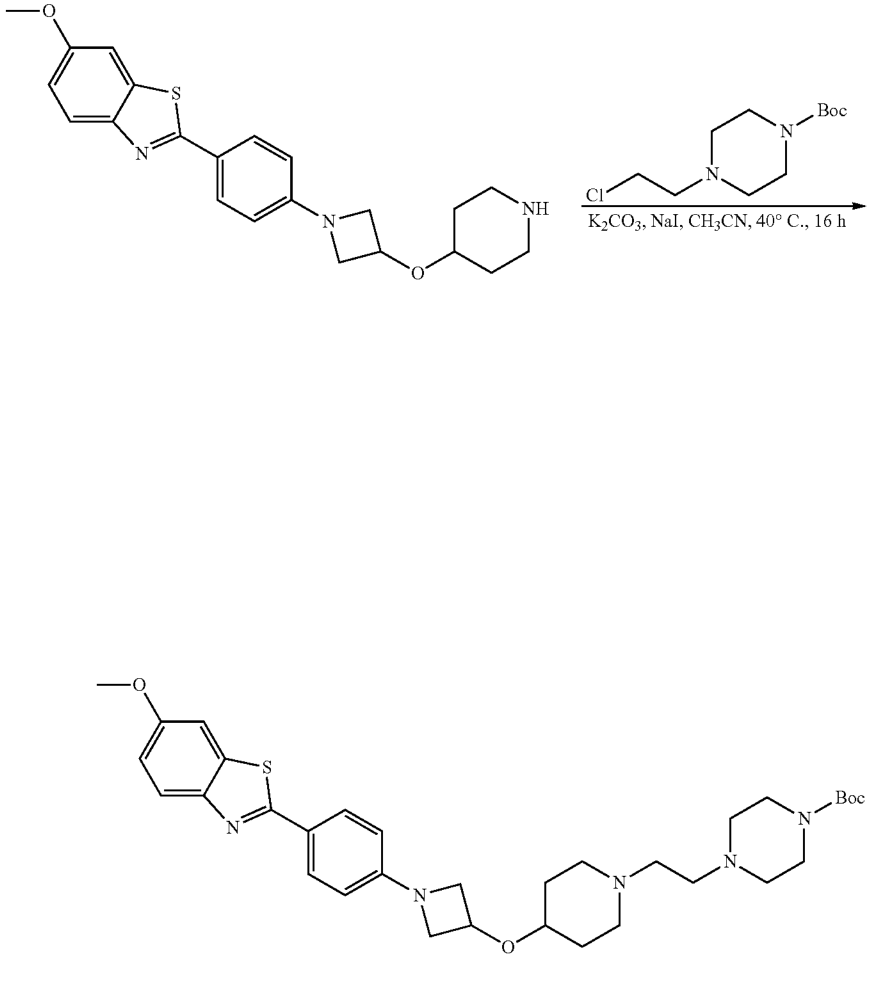

Into a 25-mL sealed tube purged and maintained under an inert atmosphere of nitrogen, was placed a solution of 6-methoxy-2-[4-[3-(piperidin-4-yloxy)azetidin-1-yl]phenyl]-1,3-benzothiazole (110 mg, 0.28 mmol, 1 equiv), $K_2CO_3$ (115 mg, 0.83 mmol, 3 equiv), tert-butyl-4-(2-chloroethyl)piperazine-1-carboxylate (69 mg, 0.28 mmol, 1 equiv), and NaI (4.2 mg, 0.03 mmol, 0.1 equiv) in $CH_3CN$ (5 mL). The resulting mixture was stirred for 16 hours at 40° C. The solids were filtered off, and the filtrate was concentrated. The residue was applied onto a silica gel column eluting with dichloromethane/methanol (10:1). This resulted in 178 mg of tert-butyl-4-[2-[4-([1-[4-(6-methoxy-1,3-benzothiazol-2-yl)phenyl]azetidin-3-yl]oxy)piperidin-1-yl]ethyl]piperazine-1-carboxylate as a yellow-green solid.

Step 2

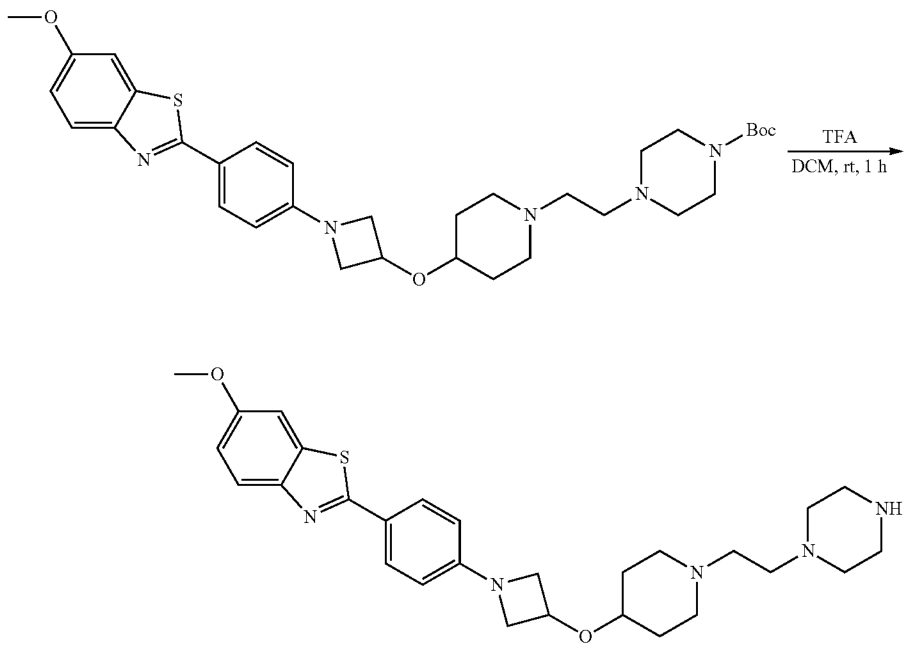

Into a 50-mL round-bottom flask, was placed tert-butyl-4-[2-[4-([1-[4-(6-methoxy-1,3-benzothiazol-2-yl)phenyl]azetidin-3-yl]oxy)piperidin-1-yl]ethyl]piperazine-1-carboxylate (178 mg, 0.29 mmol, 1 equiv) in DCM (25 mL), to which was added TFA (5 mL). The resulting solution was stirred for 1 hour at room temperature, and then was concentrated under vacuum. This resulted in 130 mg (crude) of 6-methoxy-2-[4-[3-([1-[2-(piperazin-1-yl)ethyl]piperidin-4-yl]oxy)azetidin-1-yl]phenyl]-1,3-benzothiazole as a red solid.

Step 3

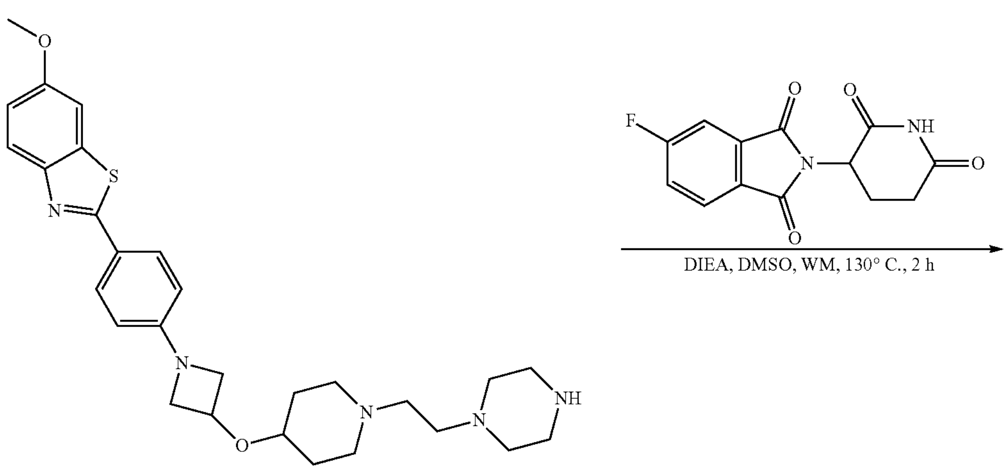

-continued

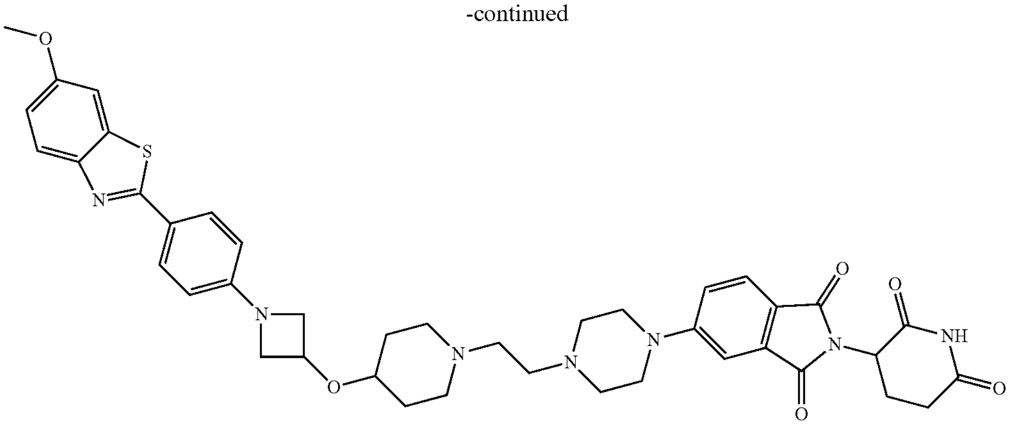

Exemplary Compound 26

Into a 25-mL tube purged and maintained with an inert atmosphere of nitrogen, was placed a solution of 6-methoxy-2-[4-[3-([I-[2-(piperazin-1-yl)ethyl]piperidin-4-yl]oxy)azetidin-1-yl]phenyl]-1,3-benzothiazole (130 mg, crude), DIEA (1 mL), and 2-(2,6-dioxopiperidin-3-yl)-5-fluoro-2,3-dihydro-1H-isoindole-1,3-dione (94.7 mg, 0.34 mmol, 1.16 equiv) in DMSO (5 mL). The reaction mixture was irradiated with microwave for 2 hours at 130° C., and was then concentrated. The crude product was purified by Prep-HPLC with the following conditions: Column, XBridge Prep OBD C18 Column, 30*150 mm 5 um; mobile phase, water (with 10 mmol/L $NH_4HCO_3$) and CAN, 44% up to 64% CAN in 8 min; Detector, UV. This resulted in 45.7 mg (10%) of 2-(2,6-dioxopiperidin-3-yl)-5-(4-[2-[4-([1-[4-(6-methoxy-1,3-benzothiazol-2-yl)phenyl]azetidin-3-yl]oxy)piperidin-1-yl]ethyl]piperazin-1-yl)-2,3-dihydro-1H-isoindole-1,3-dione as a yellow solid.

Exemplary Synthesis of Exemplary Compound 27

Into a 250-mL round-bottom flask, was placed (1r,3r)-3-(benzyloxy)cyclobutan-1-ol (8 g, 44.9 mmol, 1 equiv), pyridin-4-ol (4.27 g, 44.9 mmol, 1 equiv), $PPh_3$ (17.66 g, 67.3 mmol, 1.5 equiv), DIAD (10.89 g, 53.9 mmol, 1.2 equiv) in toluene (20 mL). The resulting solution was stirred overnight at 110° C. in an oil bath. The mixture was quenched by the addition of water (20 mL). The resulting mixture was extracted with ethyl acetate (3×30 mL). The combined organic layer was washed with brine (2×10 mL), dried over anhydrous sodium sulfate and concentrated. The residue was applied onto a silica gel column, eluted with ethyl acetate/petroleum ether (1/1). This resulted in 11.4 g (99%) of 4-[(1s,3s)-3-(benzyloxy)cyclobutoxy]pyridine as a yellow oil.

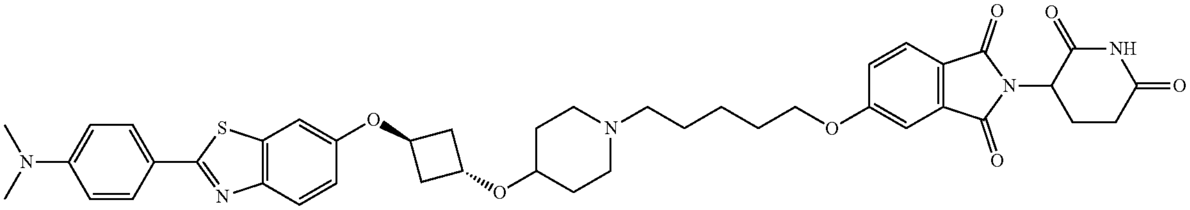 [SMILES: CN(C)c1ccc(-c2nc3ccc(O[C@H]4C[C@H](OC5CCN(CCCCCOc6ccc7c(c6)C(=O)N(C6CCC(=O)NC6=O)C7=O)CC5)C4)cc3s2)cc1]

Step 1

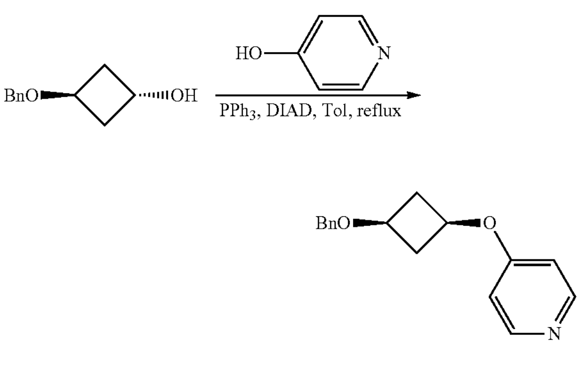

Step 2

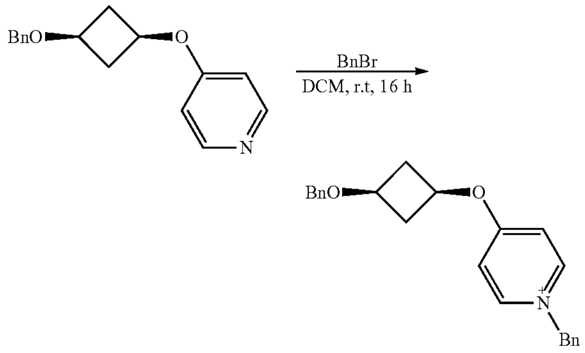

Into a 250-mL round-bottom flask, was placed 4-[(1s,3s)-3-(benzyloxy)cyclobutoxy]pyridine (11.4 g, 44.7 mmol, 1 equiv), (bromomethyl)benzene (8.40 g, 49.1 mmol, 1.1 equiv) in dichloromethane (20 mL). The resulting solution was stirred overnight at room temperature. The mixture was concentrated and the residue was applied onto a silica gel column, eluted with ethyl acetate/petroleum ether (1/2). This resulted in 15 g (97%) of 1-benzyl-4-[(1s,3s)-3-(benzyloxy) cyclobutoxy]pyridin-1-ium as a white solid.

Step 3

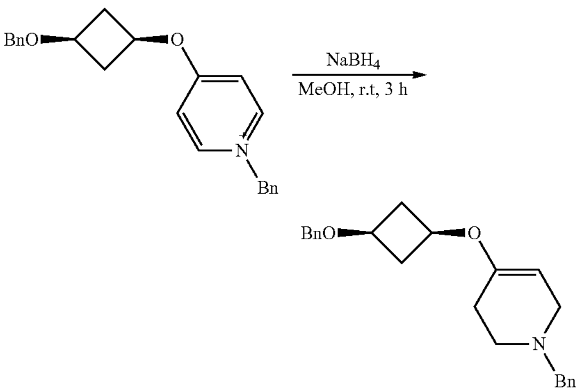

Into a 250-mL round-bottom flask, was placed 1-benzyl-4-[(1s,3s)-3-(benzyloxy)cyclobutoxy]pyridin-1-ium (15 g, 43.3 mmol, 1 equiv) in methanol (20 mL), to which was added sodium borohydride (3.29 g, 86.6 mmol, 2.00 equiv) slowly. The resulting solution was stirred overnight at room temperature. The resulting mixture was concentrated and then quenched by the addition of water (20 mL). The resulting mixture was extracted with ethyl acetate (3×40 mL). The combined organic layer was washed with brine (2×20 mL), dried over anhydrous sodium sulfate and concentrated. The residue was applied onto a silica gel column eluting with ethyl acetate/petroleum ether (1/1). This resulted in 9.2 g (61%) of 1-benzyl-4-[(1s,3s)-3-(benzyloxy) cyclobutoxy]-1,2,3,6-tetrahydropyridine as a yellow oil.

Step 4

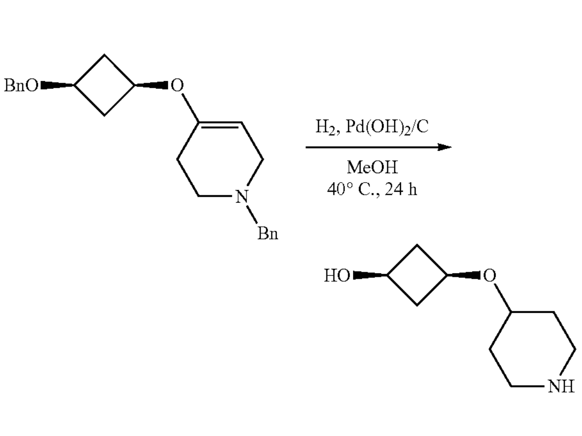

Into a 250-mL round-bottom flask, was placed 1-benzyl-4-[(1s,3s)-3-(benzyloxy)cyclobutoxy]-1,2,3,6-tetrahydropyridine (9.2 g, 26.3 mmol, 1 equiv) in methanol (30 mL), to which was added AcOH (0.5 mL) and 20% Pd(OH)/C (3 g) under nitrogen atmosphere. The flask was then vacuumed and flushed with hydrogen. The reaction mixture was hydrogenated overnight at 40° C. under hydrogen atmosphere using a hydrogen balloon, then filtered through a Celite pad and concentrated under reduced pressure. This resulted in 5.2 g of crude (1s,3s)-3-(piperidin-4-yloxy)cyclobutan-1-ol as a yellow oil.

Step 5

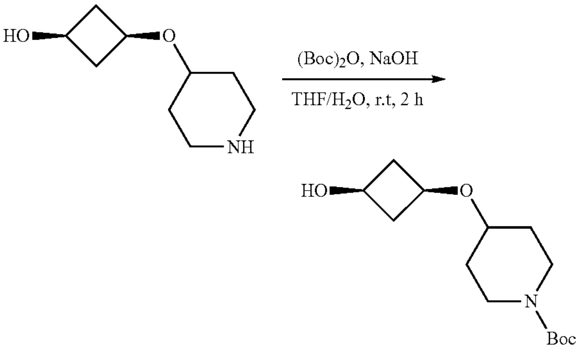

Into a 250-mL round-bottom flask, was placed (1s,3s)-3-(piperidin-4-yloxy)cyclobutan-1-ol (5 g, 29.2 mmol, 1 equiv) in tetrahydrofuran (40 mL), to which was added a solution of NaOH (3.50 g, 87.6 mmol, 3 equiv) in $H_2O$ (10 mL) and $(Boc)_2O$ (6.37 g, 29.2 mmol, 1.00 equiv). The resulting mixture was stirred for 2 hours at room temperature. The mixture was concentrated and the residue was applied onto a silica gel column eluting with ethyl acetate/petroleum ether (1/1). This resulted in 5.06 g (64%) of tert-butyl 4-[(1s,3s)-3-hydroxycyclobutoxy]piperidine-1-carboxylate as a yellow oil.

Step 6

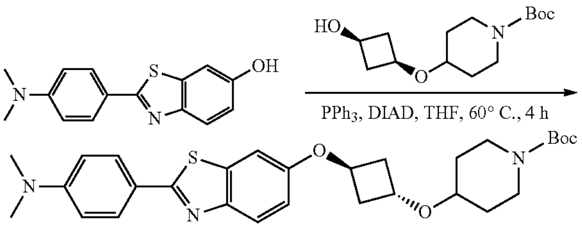

Into a 50-mL round-bottom flask, was placed $PPh_3$ (291 mg, 1.11 mmol, 1.5 equiv), DIEA (114 mg, 0.89 mmol, 1.2 equiv), tert-butyl 4-[(1s,3s)-3-hydroxycyclobutoxy]piperidine-1-carboxylate (201 mg, 0.74 mmol, 1 equiv), and 2-[4-(dimethylamino)phenyl]-1,3-benzothiazol-6-ol (200 mg, 0.74 mmol, 1 equiv) in tetrahydrofuran (15 mL). The resulting solution was stirred for 4 hours at 60° C. in an oil bath. The reaction was then quenched by the addition of water (10 mL). The resulting mixture was extracted with ethyl acetate (50 mL). The organic phase was washed with brine (10 mL), dried over anhydrous sodium sulfate and concentrated. The residue was applied onto a silica gel column, eluting with ethyl acetate/petroleum ether (1/1).

The collected fractions were combined and concentrated. This resulted in 250 mg (65%) of tert-butyl 4-[(1r,3r)-3-([2-[4-(dimethylamino)phenyl]-1,3-benzothiazol-6-yl]oxy)cyclobutoxy]piperidine-1-carboxylate as a yellow solid.

Step 7

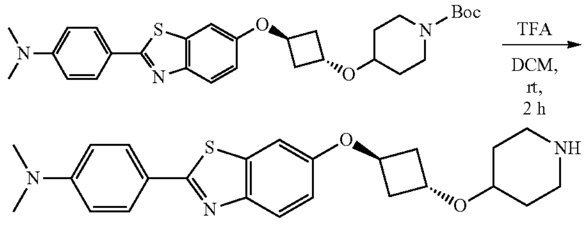

Into a 50-mL round-bottom flask, was placed tert-butyl 4-[(1r,3r)-3-([2-[4-(dimethylamino)phenyl]-1,3-benzothiazol-6-yl]oxy)cyclobutoxy]piperidine-1-carboxylate (250 mg, 0.48 mmol, 1 equiv) in dichloromethane (10 mL), to which was added trifluoroacetic acid (3 mL). The resulting solution was stirred for 2 hours at room temperature. The mixture was concentrated. This resulted in 240 mg of crude N, N-dimethyl-4-[6-[(1r,3r)-3-(piperidin-4-yloxy)cyclobutoxy]-1,3-benzothiazol-2-yl]aniline trifluoroacetic acid salt as a yellow solid.

Step 8

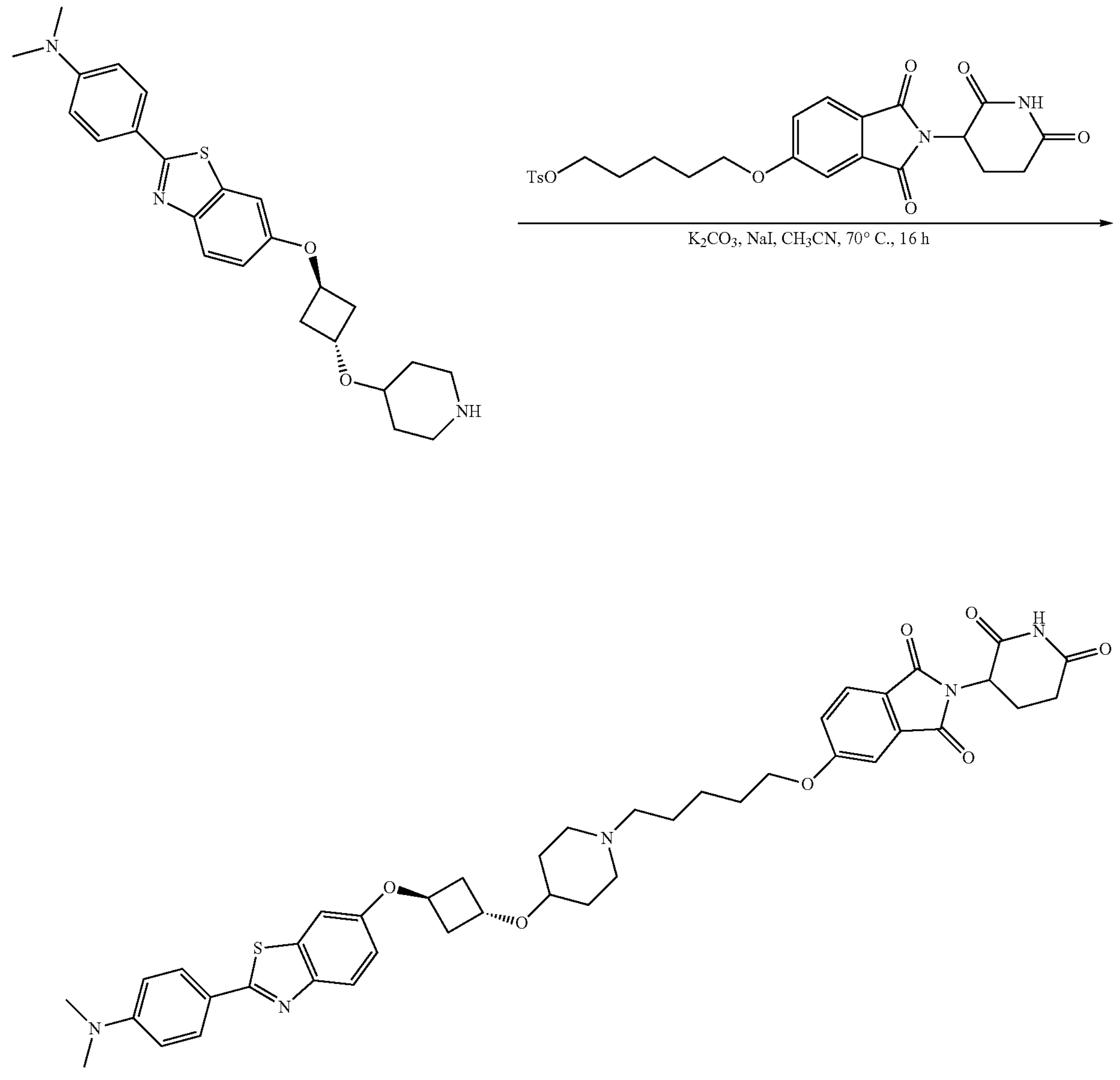

Exemplary Compound 27

Into a 50-mL round-bottom flask, was placed 5-[[2-(2,6-dioxopiperidin-3-yl)-1,3-dioxo-2,3-dihydro-1H-isoindol-5-yl]oxy]pentyl 4-methylbenzene-1-sulfonate (220 mg, 0.43 mmol, 1 equiv), $K_2CO_3$ (177 mg, 1.28 mmol, 3 equiv), N,N-dimethyl-4-[6-[(1r,3r)-3-(piperidin-4-yloxy)cyclobutoxy]-1,3-benzothiazol-2-yl]aniline trifluoroacetic acid (223 mg, 0.428 mmol, 1 equiv), NaI (64 mg, 0.43 mmol, 1 equiv) in acetonitrile (15 mL). The resulting mixture was stirred for 16 hours at 70° C. in an oil bath. The reaction mixture was filtered, and the filtrate was concentrated. The crude product was purified by Prep-HPLC with the following conditions: Column, XBridge Prep OBD C18 Column 30*150 mm 5 um; Mobile Phase A: Water (with 10 mmol/L $NH_4HCO_3$), Mobile Phase B: $CH_3CN$; Flow rate: 60 mL/min; Gradient: 62% B to 76% B in 8 min; 254 nm; Rt: 6.65 min. After lyophilization this resulted in 42.9 mg (13%) of 2-(2,6-dioxopiperidin-3-yl)-5-[(5-[4-[(1r,3r)-3-([2-[4-(dimethylamino)phenyl]-1,3-benzothiazol-6-yl]oxy)cyclobutoxy]piperidin-1-yl]pentyl)oxy]-2,3-dihydro-1H-isoindole-1,3-dione as a yellow solid.

Exemplary Synthesis of Exemplary Compound 28

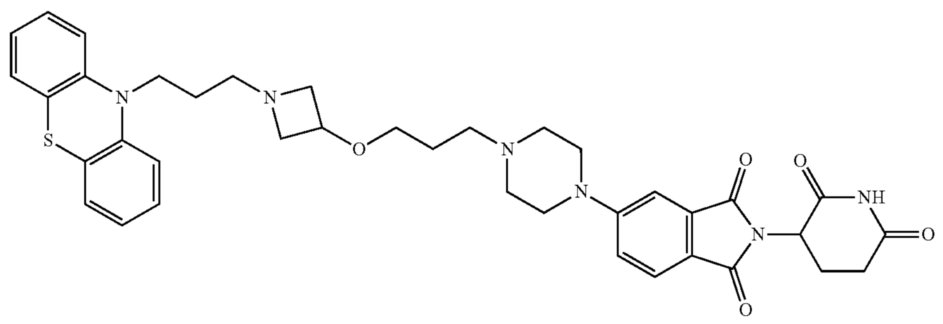

Exemplary Synthesis of Exemplary Compound 29

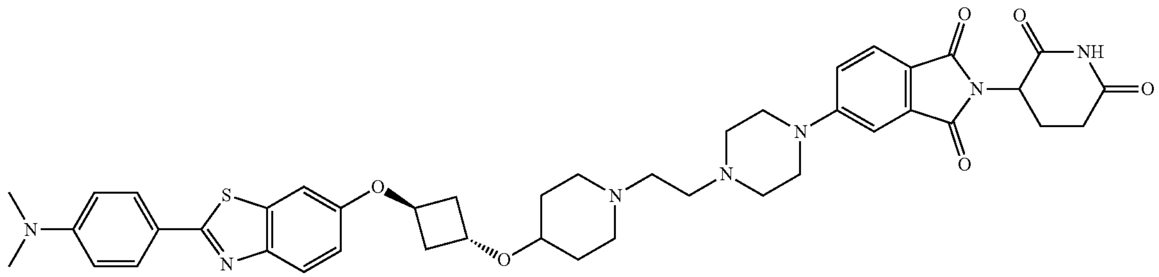 [SMILES: CN(C)c1ccc(-c2nc3ccc(O[C@H]4C[C@H](OC5CCN(CCN6CCN(c7ccc8c(c7)C(=O)N(C7CCC(=O)NC7=O)C8=O)CC6)CC5)C4)cc3s2)cc1]

Compound 5-(4-(2-(4-((1r,3r)-3-((2-(4-(dimethylamino)phenyl)benzo[d]thiazol-6-yl)oxy)cyclobutoxy)piperidin-1-yl)ethyl)piperazin-1-yl)-2-(2,6-dioxopiperidin-3-yl)isoindoline-1,3-dione was prepared according to the scheme below using procedures analogous to those described for the examples above.

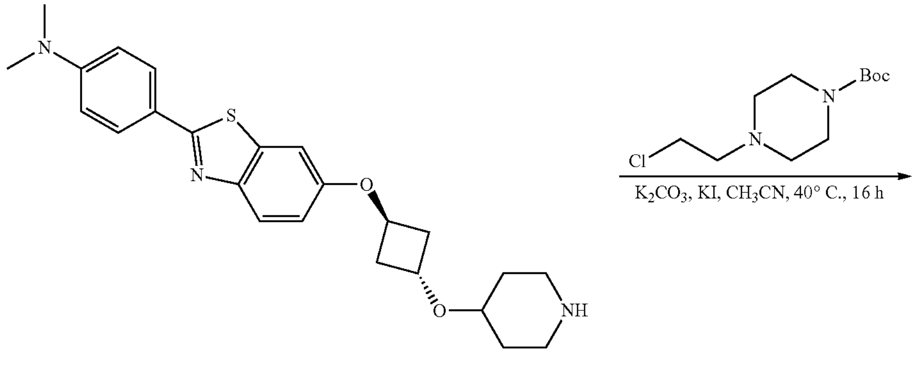

-continued
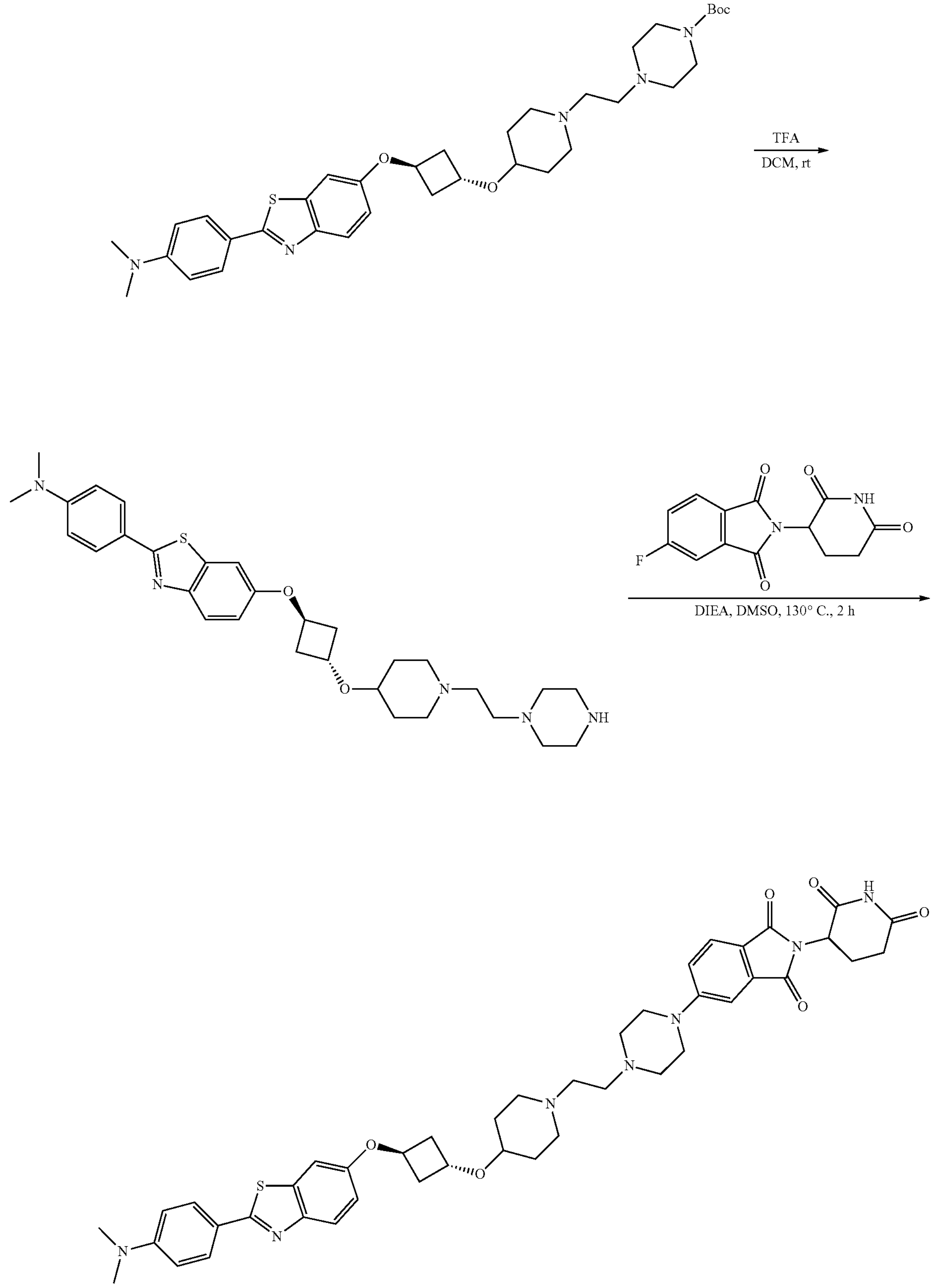
Exemlary Compound 29

Exemplary Synthesis of Exemplary Compound 30

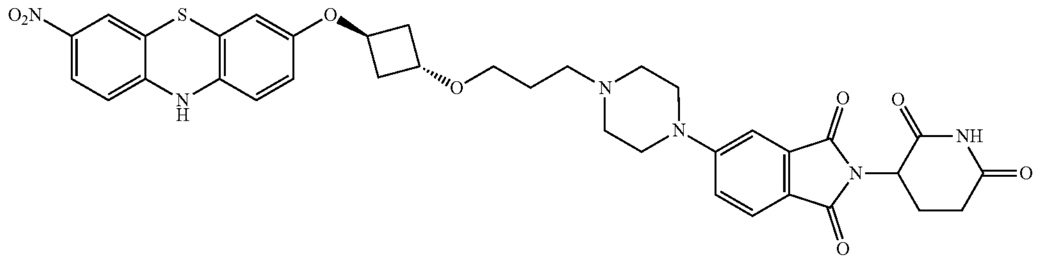 [SMILES: O=C1CCC(N2C(=O)c3ccc(N4CCN(CCCO[C@H]5C[C@H](Oc6ccc7c(c6)Sc6cc([N+](=O)[O-])ccc6N7)C5)CC4)cc3C2=O)C(=O)N1]

Step 1

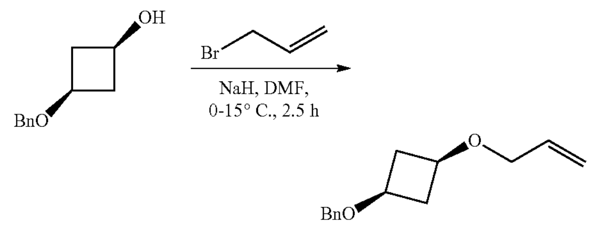

To a solution of 3-benzyloxycyclobutanol (5 g, 28.05 mmol, 1 eq) in N,N-dimethylformamide (75 mL) was added sodium hydride (1.68 g, 42.08 mmol, 60% in mineral oil, 1.5 eq) at 0° C., and the mixture was stirred at 0° C. for 0.5 h. To the mixture was added 3-bromoprop-1-ene (3.39 g, 28.05 mmol, 1 eq), and the reaction was stirred at 15° C. for 2 h. The reaction mixture was quenched by the addition of ammonium chloride (200 mL) at 15° C. and extracted with ethyl acetate (100 mL×3). The combined organic layers were washed with brine (50 mL×2), dried over anhydrous sodium sulfate, filtered and concentrated under reduced pressure to give a residue which was purified by silica gel column chromatography (petroleum ether/ethyl acetate=1:0 to 10:1) to produce 3-allyloxycyclobutoxymethylbenzene (5.8 g, 26.57 mmol, 94% yield) as a colorless oil.

Step 2

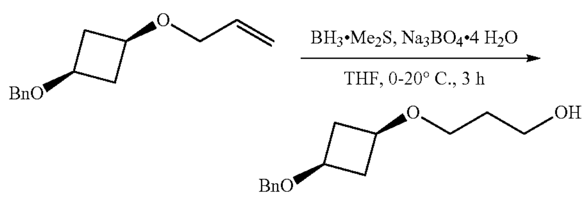

To a solution of (3-allyloxycyclobutoxy)methylbenzene (5.8 g, 26.57 mmol, 1 eq) in tetrahydrofuran (125 mL) was added borane dimethyl sulfide complex (10 M, 5.3 mL, 2 eq) at 0° C., and the mixture was stirred at 20° C. for 1 h. To the solution was added a solution of sodium perborate tetrahydrate (12.26 g, 79.71 mmol, 15.3 mL, 3 eq) in water (98 mL) at 0° C., and the reaction was stirred at 20° C. for 2 h. The suspension was filtered, and to the filtrate was added saturated ammonium chloride (100 mL). The organic layer was extracted with ethyl acetate (800 mL×3). The combined organic phase was washed with brine (50 mL), dried with anhydrous sodium sulfate, filtered and concentrated in vacuum. The residue was purified by silica gel column chromatography (petroleum ether/ethyl acetate=30:1 to 1:1) to provide 3-(3-benzyloxycyclobutoxy)propan-1-ol (3.92 g, 16.59 mmol, 62% yield) as a colorless oil.

Step 3

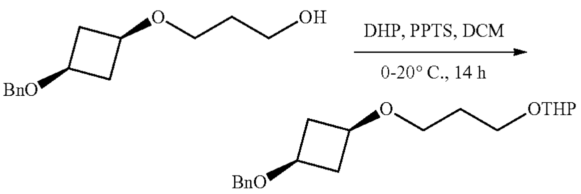

To a solution of 3-(3-benzyloxycyclobutoxy)propan-1-ol (3.92 g, 16.59 mmol, 1 eq) in dichloromethane (50 mL) was added pyridinium p-toluenesulfonate (334 mg, 1.33 mmol, 0.08 eq) at 0° C. Then to the solution was added a solution of 3,4-dihydro-2H-pyran (2.09 g, 24.88 mmol, 2.3 mL, 1.5 eq) in dichloromethane (8 mL) dropwise at 0° C., and the reaction was stirred at 20° C. for 14 h. The reaction mixture was washed with saturated sodium bicarbonate (30 mL×2). The organic phase was extracted with dichloromethane (30 mL×2). The combined organic phase was dried over anhydrous sodium sulfate, filtered and concentrated under reduced pressure to give a residue which was purified by silica gel column chromatography (petroleum ether/ethyl acetate=20:1 to 10:1) to provide 2-[3-(3-benzyloxycyclobutoxy)propoxy]tetrahydropyran (4.54 g, 14.17 mmol, 85% yield) as a colorless oil.

Step 4

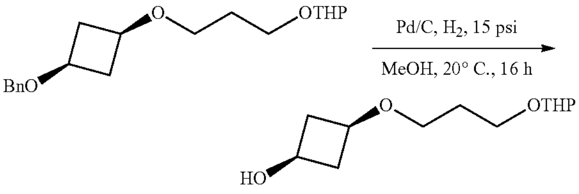

To a solution of 2-[3-(3-benzyloxycyclobutoxy)propoxy] tetrahydropyran (2.27 g, 7.08 mmol, 1 eq) in methanol (20 mL) was added palladium on activated carbon catalyst (300 mg, 10% purity) under nitrogen. The suspension was degassed under vacuum and purged with hydrogen three times. The reaction mixture was stirred under 15 psi at 20° C. for 16 h. The reaction mixture was filtered, and the filtrate was concentrated. The residue was purified by silica gel column chromatography (petroleum ether/ethyl acetate=20:1 to 8:1) to provide 3 g of 3-(3-tetrahydropyran-2-yloxypropoxy)cyclobutanol as a colorless gum.

Step 5

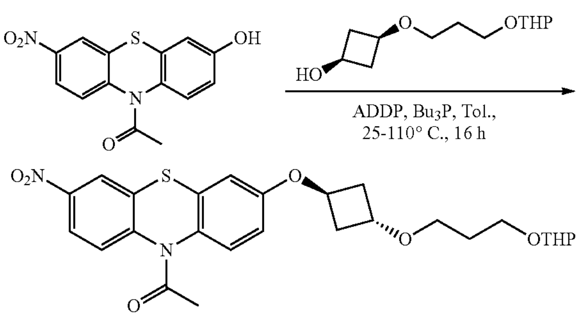

To a solution of 1-(3-hydroxy-7-nitro-phenothiazin-10-yl) ethanone (680 mg, 2.25 mmol, 1 eq) and 3-(3-tetrahydro-pyran-2-yloxypropoxy)cyclobutanol (621 mg, 2.70 mmol, 1.2 eq) in toluene (10 mL) was added 1,1'-(azodicarbonyl) dipiperidine (681 mg, 2.70 mmol, 1.2 eq) and tributylphosphine (546 mg, 2.70 mmol, 0.66 mL, 1.2 eq) sequentially under nitrogen at 25° C. The mixture was stirred at 25° C. for 10 min, then was heated to 110° C. and stirred for 16 h. The reaction mixture was concentrated to give a residue. The residue was purified by silica gel column chromatography (petroleum ether/ethyl acetate=20:1 to 1:1) to give crude product which was purified by semi-preparative reverse phase HPLC (column: Phenomenex Synergi Max-RP 250*50 mm*10 um; mobile phase: [water (0.225% FA)-ACN]; B %: 50%-80%, 25 min, 45% min) to provide 1-[3-nitro-7-[3-(3-tetrahydropyran-2-yloxypropoxy)cyclobutoxy]phenothiazin-10-yl]ethanone (548 mg, 1.06 mmol, 47% yield) as a brown oil.

Step 6

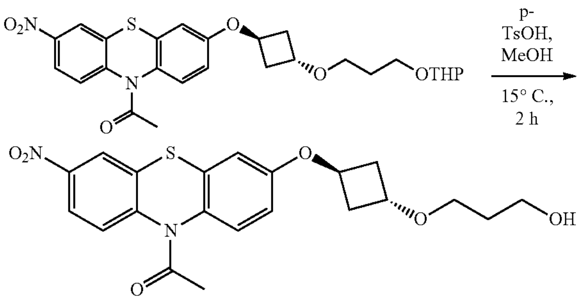

To a solution of 1-[3-nitro-7-[3-(3-tetrahydropyran-2-yloxypropoxy)cyclobutoxy]phenothiazin-10-yl]ethanone (548 mg, 1.06 mmol, 1 eq) in methanol (10 mL) was added 4-toluenesulfonic acid (37 mg, 0.21 mmol, 0.2 eq) at 15° C., and the mixture was stirred at 15° C. for 2 h. The reaction mixture was basified with saturated sodium bicarbonate aqueous solution until pH 8-9, and was then extracted with ethyl acetate (10 mL×3). The combined organic layers were washed with brine (10 mL), dried over anhydrous sodium sulfate, filtered and concentrated under reduced pressure to give a residue. The residue was purified by prep-TLC (petroleum ether/ethyl acetate=1:2) to afford 1-[3-[3-(3-hydroxypropoxy)cyclobutoxy]-7-nitro-phenothiazin-10-yl] ethanone (387 mg, 0.90 mmol, 84% yield) as a red oil.

Step 7

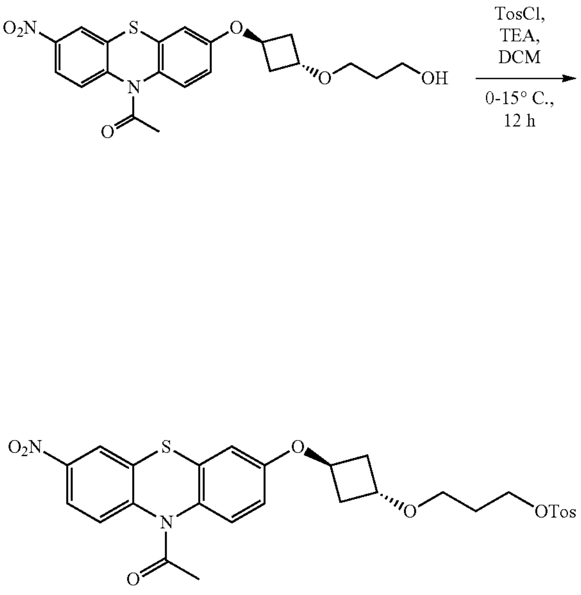

To a solution of 1-[3-[3-(3-hydroxypropoxy)cyclobutoxy]-7-nitro-phenothiazin-10-yl]ethanone (387 mg, 0.90 mmol, 1 eq) in dichloromethane (10 mL) was added triethylamine (182 mg, 1.80 mmol, 0.25 mL, 2 eq) and p-toluenesulfonyl chloride (257 mg, 1.35 mmol, 1.5 eq) sequentially at 0° C., and the mixture was then stirred at 15° C. for 12 h. The reaction mixture was concentrated to give a residue which was purified by prep-TLC (petroleum ether/ethyl acetate=1:1). 3-[3-(10-acetyl-7-nitro-phenothiazin-3-yl)oxycyclobutoxy]propyl 4-methylbenzenesulfonate (305 mg, 0.52 mmol, 58% yield) was obtained as a red oil. In addition, 100 mg of starting material was recovered.

Step 8

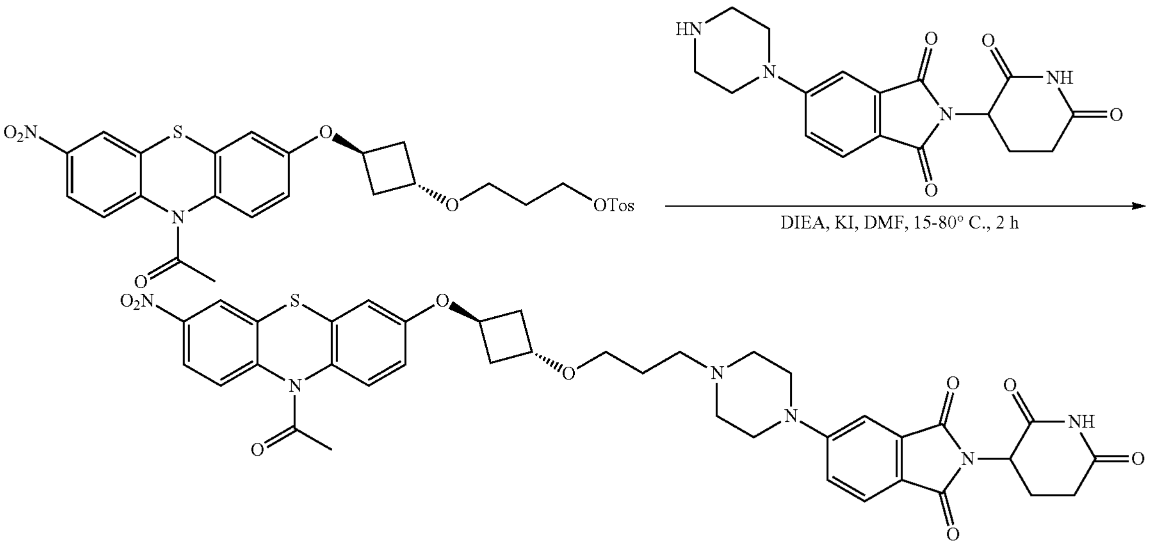

To a solution of 3-[3-(10-acetyl-7-nitro-phenothiazin-3-yl)oxycyclobutoxy]propyl 4-methylbenzenesulfonate (305 mg, 0.52 mmol, 1 eq) and 2-(2,6-dioxo-3-piperidyl)-5-piperazin-1-yl-isoindoline-1,3-dione (217 mg, 0.57 mmol, 1.1 eq, hydrochloride) at N,N-dimethylformamide (8 mL) was added N,N-diisopropylethylamine (202 mg, 1.57 mmol, 0.27 mL, 3 eq) and potassium iodide (9 mg, 0.05 mmol, 0.1 eq) at 15° C., and then stirred at 80° C. for 2 h. The reaction mixture was diluted with 20 mL water, then extracted with ethyl acetate (15 mL×3). The combined organic layers were washed with brine 10 mL, dried over anhydrous sodium sulfate, filtered and concentrated under reduced pressure to give a residue. The residue was purified by prep-TLC (dichloromethane/methanol=10/1) to give 5-[4-[3-[3-(10-acetyl-7-nitro-phenothiazin-3-yl)oxycyclobutoxy]propyl]piperazin-1-yl]-2-(2,6-dioxo-3-piperidyl)isoindoline-1,3-dione (115 mg, 0.15 mmol, 28% yield) as a yellow solid.

Step 9

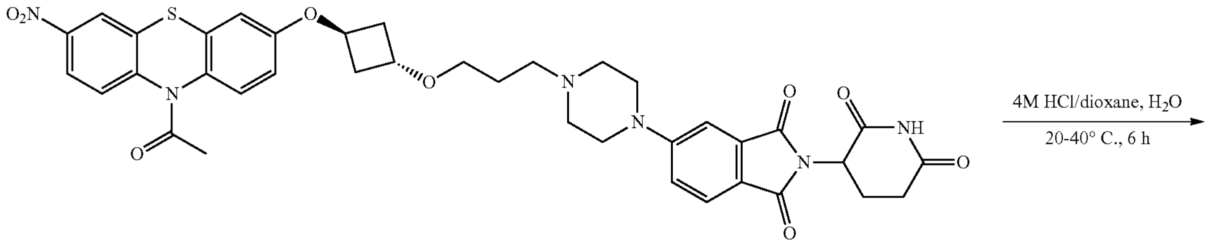

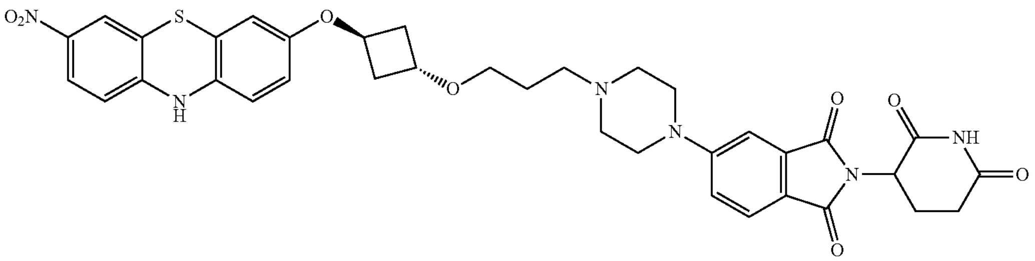

To a solution of 5-[4-[3-[3-(10-acetyl-7-nitro-phenothiazin-3-yl)oxycyclobutoxy]propyl]piperazin-1-yl]-2-(2,6-dioxo-3-piperidyl)isoindoline-1,3-dione (115 mg, 0.15 mmol, 1 eq) in water (1 mL) was added hydrogen chloride/dioxane (4 M, 5 mL, 131.27 eq) at 20° C., and the mixture was stirred at 40° C. for 6 h. The reaction mixture was concentrated to give a residue. The residue was purified by semi-preparative reverse phase HPLC (25-52% acetonitrile+0.225% formic acid in water, over 10 min). 2-(2,6-dioxo-3-piperidyl)-5-[4-[3-[3-[(7-nitro-10H-phenothiazin-3-yl)oxy]cyclobutoxy]propyl]piperazin-1-yl]isoindoline-1,3-dione formate (36 mg, 0.04 mmol, 29% yield) was obtained as a red solid.

Exemplary Synthesis of Exemplary Compound 31 and Exemplary Compound 32

31

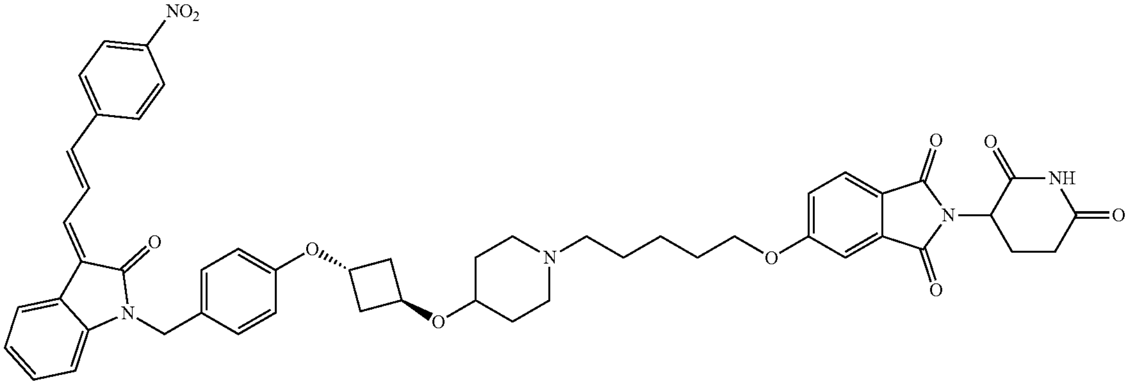

32

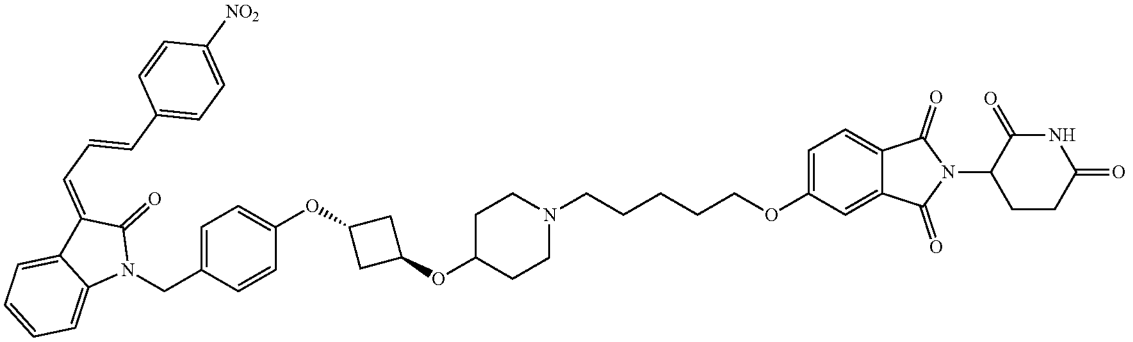

Step 1

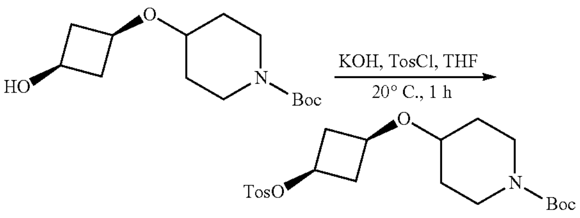

A mixture of tert-butyl 4-(3-hydroxycyclobutoxy)piperidine-1-carboxylate (1.2 g, 4.42 mmol, 1 eq), potassium hydroxide (744 mg, 13.27 mmol, 3 eq) and p-toluenesulfonyl chloride (2.53 g, 13.27 mmol, 3 eq) in tetrahydrofuran (5 mL) was degassed and purged with nitrogen 3 times, and then the mixture was stirred at 20° C. for 1 h under nitrogen. The reaction mixture was quenched by the addition of water (100 mL) and extracted with ethyl acetate (100 mL×3). The combined organic layers were washed with brine (50 mL×3), dried over anhydrous sodium sulfate, filtered and concentrated under reduced pressure to give a residue which was purified by column chromatography (petroleum ether/ethyl acetate=10/1 to 1/1). tert-Butyl 4-[3-(p-tolylsulfonyloxy)cyclobutoxy]piperidine-1-carboxylate (1.6 g, 3.71 mmol, 84% yield) was obtained as a white solid.

tert-Butyl 4-[3-(p-tolylsulfonyloxy)cyclobutoxy]piperidine-1-carboxylate was converted to the final compounds, 2-(2,6-dioxopiperidin-3-yl)-5-((5-(4-((1r,3r)-3-(4-(((Z)-3-((E)-3-(4-nitrophenyl)allylidene)-2-oxoindolin-1-yl)methyl)phenoxy)cyclobutoxy)piperidin-1-yl)pentyl)oxy)isoindoline-1,3-dione and 2-(2,6-dioxopiperidin-3-yl)-5-((5-(4-((1r,3r)-3-(4-(((Z)-3-((E)-3-(4-nitrophenyl)allylidene)-2-oxoindolin-1-yl)methyl)phenoxy)cyclobutoxy)piperidin-1-yl)pentyl)oxy)isoindoline-1,3-dione, according to the scheme below and using procedures described above for the exemplary compounds 6, 7, and 19.

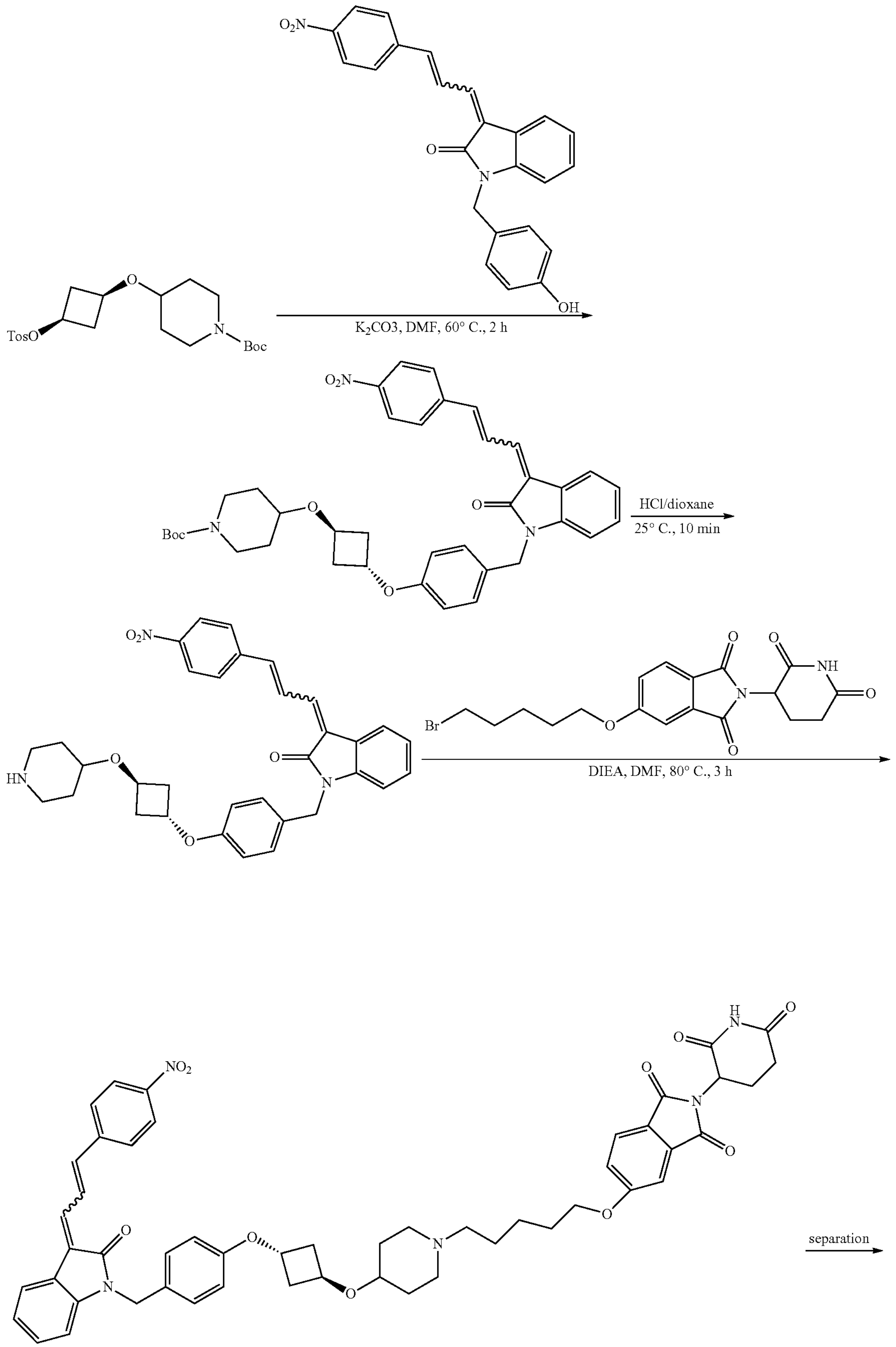
K2CO3, DMF, 60° C., 2 h
HCl/dioxane
25° C., 10 min
DIEA, DMF, 80° C., 3 h
separation -continued
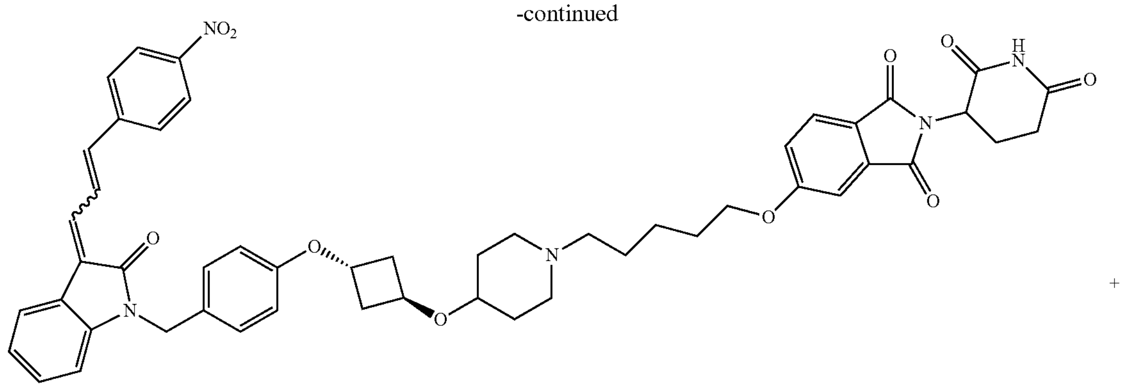
31
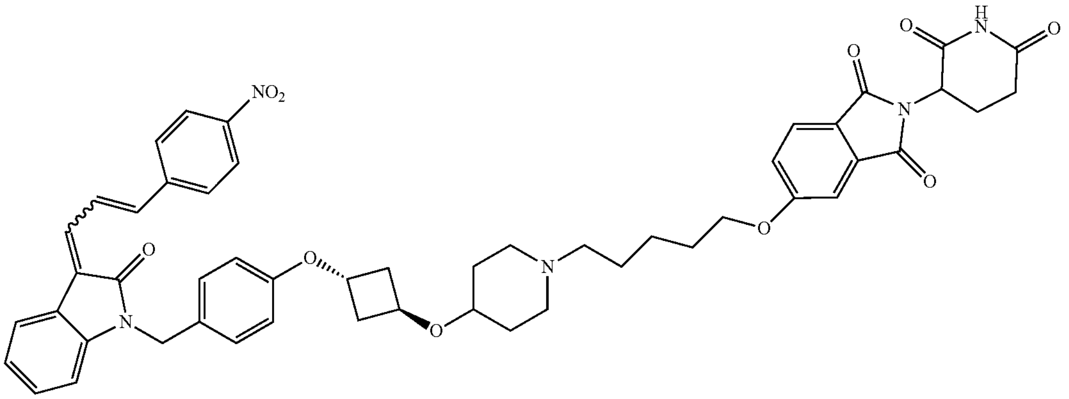
32
Exemplary Synthesis of Exemplary Compound 33
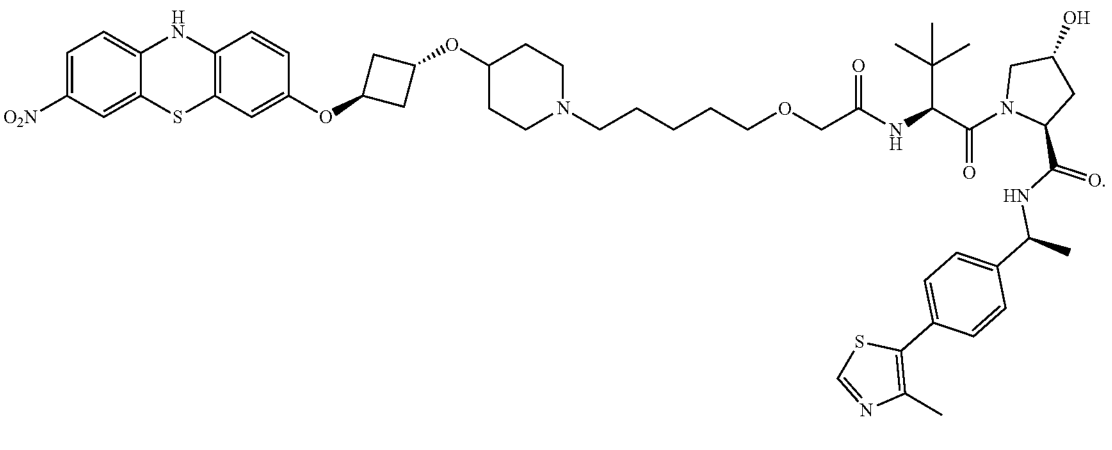 [SMILES: Cc1ncsc1-c1ccc([C@H](C)NC(=O)[C@@H]2C[C@@H](O)CN2C(=O)[C@@H](NC(=O)COCCCCCN2CCC(O[C@H]3C[C@H](Oc4ccc5c(c4)Sc4cc([N+](=O)[O-])ccc4N5)C3)CC2)C(C)(C)C)cc1]

Exemplary Synthesis of Exemplary Compound 35

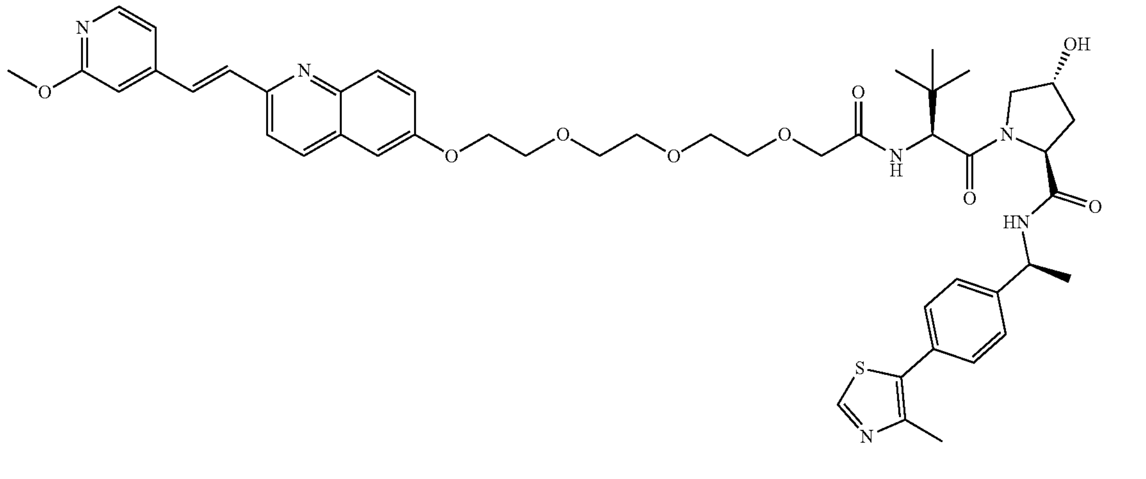 [SMILES: COc1cc(/C=C/c2ccc3cc(OCCOCCOCCOCC(=O)N[C@H](C(=O)N4C[C@H](O)C[C@H]4C(=O)N[C@@H](C)c4ccc(-c5scnc5C)cc4)C(C)(C)C)ccc3n2)ccn1]

Step 1

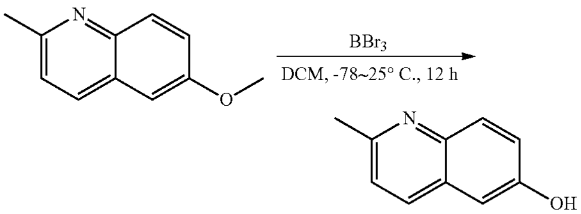

To a solution of 6-methoxy-2-methyl-quinoline (10 g, 57.73 mmol, 1 eq) in dichloromethane (100 mL) was added dropwise a solution of boron tribromide (43.39 g, 173.20 mmol, 16.69 mL, 3 eq) in dichloromethane (100 mL) at −78° C. The mixture was allowed to warm to 25° C. and stirred at 25° C. for 12 h. The reaction mixture was quenched by addition methanol (100 mL), and then diluted with water (200 mL) and extracted with dichloromethane (200 mL×3). The combined organic layers were washed with brine (200 mL×3), dried over anhydrous sodium sulfate, filtered and concentrated under reduced pressure. 2-methylquinolin-6-ol (9 g, 56.54 mmol) was obtained as a white solid and used directly in the next step.

Step 2

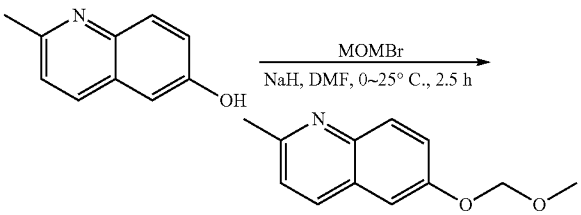

To a solution of 2-methylquinolin-6-ol (10 g, 62.82 mmol, 1 eq) in dimethyl formamide (60 mL) was added sodium hydride (2.76 g, 69.10 mmol, 60% suspension, 1.1 eq) at 0° C. The reaction mixture was stirred at 25° C. for 0.5 hour. Then bromo(methoxy)methane (7.85 g, 62.82 mmol, 5.13 mL, 1 eq) was added. The reaction mixture was stirred at 25° C. for 2 h. The reaction mixture was quenched by addition water (200 mL) and extracted with ethyl acetate (200 mL×3). The combined organic layers were washed with brine (200 mL×3), dried over anhydrous sodium sulfate, filtered and concentrated under reduced pressure. The residue was purified by silica gel column chromatography (petroleum ether/ethyl acetate=100/1 to 1/1). 6-(methoxymethoxy)-2-methyl-quinoline (11 g, 54.12 mmol) was obtained as a yellow oil.

Step 3

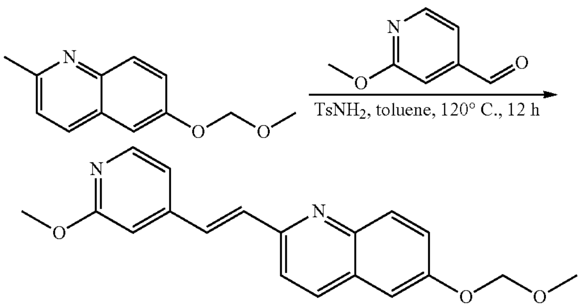

A solution of 2-methoxypyridine-4-carbaldehyde (2 g, 14.58 mmol, 1 eq), 6-(methoxymethoxy)-2-methyl-quinoline (2.96 g, 14.58 mmol, 1 eq) and 4-methylbenzenesulfonamide (2.50 g, 14.58 mmol, 1 eq) in toluene (50 mL) was stirred at 120° C. for 12 h. The reaction mixture was concentrated under reduced pressure. The residue was purified by silica gel column chromatography (petroleum ether/ethyl acetate=100/1 to 1/1). 6-(methoxymethoxy)-2-[(E)-2-(2-methoxy-4-pyridyl)vinyl]quinoline (4.1 g, 12.72 mmol) was obtained as a white solid.

Step 4

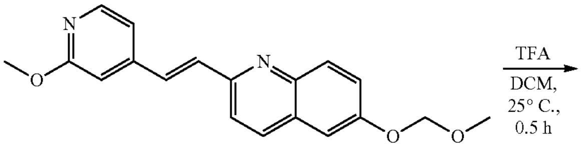

-continued

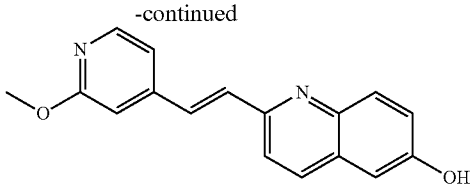

To a solution of 6-(methoxymethoxy)-2-[(E)-2-(2-methoxy-4-pyridyl)vinyl]quinoline (2 g, 6.20 mmol, 1 eq) in dichloromethane (20 mL) was added trifluoroacetic acid (6.16 g, 54.02 mmol, 4 mL, 8.71 eq). The reaction mixture was stirred at 25° C. for 0.5 h. The pH was adjusted to 8 with sodium bicarbonate. The reaction mixture was extracted with ethyl acetate (100 mL×3). The combined organic layers were washed with brine (150 mL×3), dried over anhydrous sodium sulfate, filtered and concentrated under reduced pressure. 2-[(E)-2-(2-methoxy-4-pyridyl)vinyl]quinolin-6-ol (1.4 g, 5.03 mmol) was obtained as a yellow solid and used directly in the next step.

2-[(E)-2-(2-methoxy-4-pyridyl)vinyl]quinolin-6-ol was converted to the final compound, (2S,4R)-1-((S)-2-(tert-butyl)-14-((2-((E)-2-(2-methoxypyridin-4-yl)vinyl)quinolin-6-yl)oxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide, using procedures described for Exemplary Compound 1.

Using analogous procedures the following examples were prepared: Exemplary Compound 48.

Exemplary Synthesis of Exemplary Compound 36

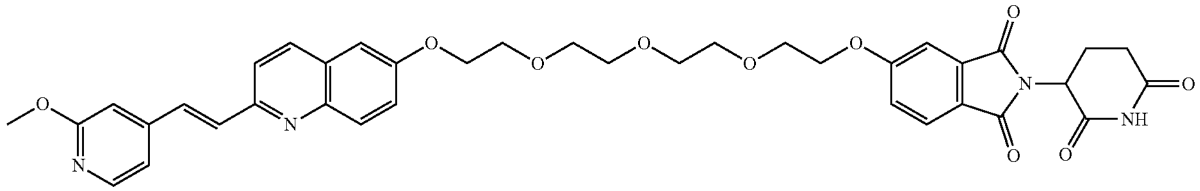 [SMILES: COc1cc(/C=C/c2ccc3cc(OCCOCCOCCOCCOc4ccc5c(c4)C(=O)N(C4CCC(=O)NC4=O)C5=O)ccc3n2)ccn1]

Step 1

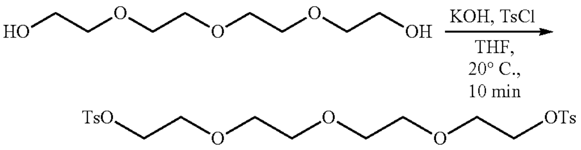

To a solution of 2-[2-[2-(2-hydroxyethoxy)ethoxy]ethoxy]ethanol (500 mg, 2.57 mmol, 1 eq), potassium hydroxide (1.16 g, 20.59 mmol, 8 eq) in tetrahydrofuran (5 mL) was added p-toluensulfonyl chloride (1.47 g, 7.72 mmol, 3 eq). The mixture was stirred at 20° C. for 10 min. The mixture was quenched by addition water (10 mL), extracted with ethyl acetate (10 mL×3), and the combined organic phase washed with brine (20 mL), dried over anhydrous sodium sulfate, filtered and concentrated under reduced pressure. The residue was purified by column chromatography (petroleum ether/ethyl acetate=100/1 to 3/1) to give 2-[2-[2-[2-(p-tolylsulfonyloxy)ethoxy]ethoxy]ethoxy]ethyl4-methylbenzenesulfonate (0.9 g, 1.79 mmol) as a colorless oil.

Step 2

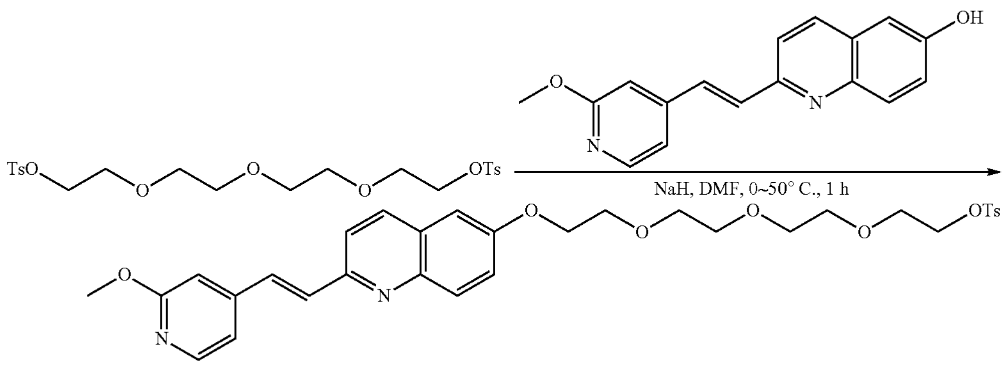

To a solution of 2-[(E)-2-(2-methoxy-4-pyridyl)vinyl]quinolin-6-ol (100 mg, 0.35 mmol, 1 eq) in dimethyl formamide (3 mL) was added NaH (17 mg, 0.44 mmol, 60% suspension, 1.25 eq) at 0° C., and the mixture was stirred at 25° C. for 0.5 h. Then 2-[2-[2-[2-(p-tolylsulfonyloxy)ethoxy] ethoxy] ethoxy]ethyl 4-methylbenzenesulfonate (180 mg, 0.35 mmol, 1 eq) was added. The reaction mixture was stirred at 50° C. for 0.5 h. The reaction mixture was diluted with water (50 mL) and extracted with ethyl acetate (50 mL×3). The combined organic layers were washed with brine (50 mL×3), dried over anhydrous sodium sulfate, filtered and concentrated under reduced pressure. The residue was purified by silica gel column chromatography (Petroleum ether/Ethyl acetate=100/1 to 1/1). 2-[2-[2-[2-[[2-[(E)-2-(2-methoxy-4-pyridyl)vinyl]-6-quinolyl]oxy]ethoxy] ethoxy]ethoxy]ethyl 4-methylbenzenesulfonate (100 mg, 0.16 mmol, 45% yield) was obtained as a yellow solid.

Step 3

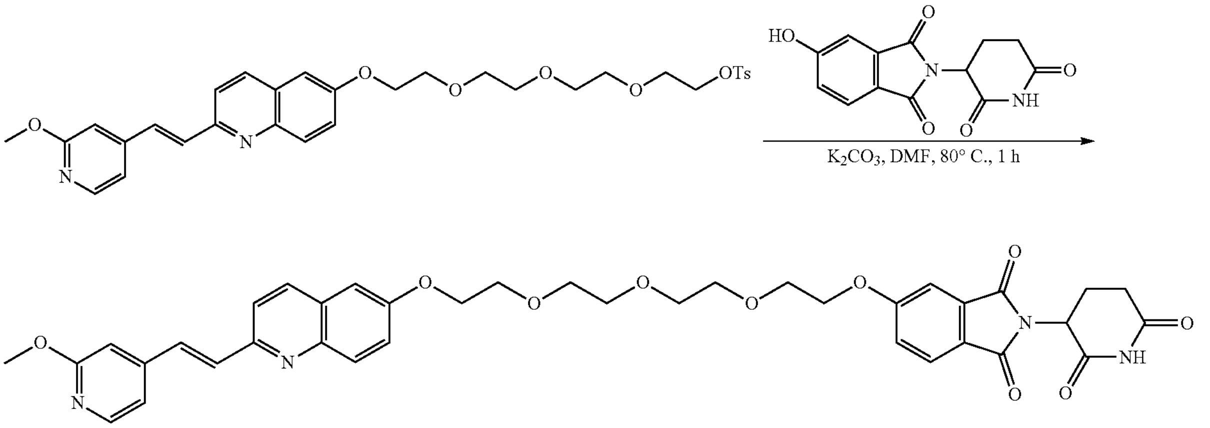

Exemplary Compound 36

To a solution of 2-[2-[2-[2-[[2-[(E)-2-(2-methoxy-4-pyridyl)vinyl]-6-quinolyl]oxy]ethoxy]ethoxy]ethoxy]ethyl 4-methylbenzenesulfonate (70 mg, 0.11 mmol, 1 eq), 2-(2,6-dioxo-3-piperidyl)-5-hydroxy-isoindoline-1,3-dione (37 mg, 0.13 mmol, 1.2 eq) in dimethyl formamide (3 mL) was added potassium carbonate (31 mg, 0.23 mmol, 2 eq). The reaction mixture was stirred at 80° C. for 1 h. The reaction mixture was filtered and concentrated under reduced pressure. The residue was purified by prep-HPLC (column: Phenomenex Luna C18 150*25 mm*10 um; mobile phase: [water (0.1% TFA)-ACN]; B %: 23%-53%, 10 min). 2-(2,6-dioxo-3-piperidyl)-5-[2-[2-[2-[2-[[2-[(E)-2-(2-methoxy-4-pyridyl)vinyl]-6-quinolyl]oxy]ethoxy]ethoxy]ethoxy] ethoxy]isoindoline-1,3-dione (22 mg, 0.02 mmol) was obtained as an orange solid.

Using analogous procedures the following examples were prepared: Exemplary Compound 47.

Exemplary Synthesis of Exemplary Compound 49

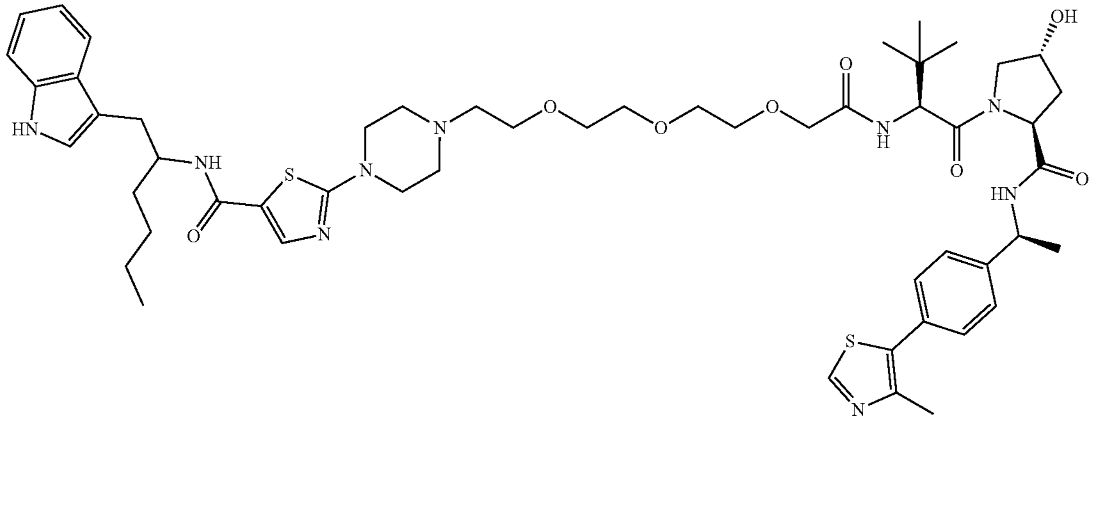 [SMILES: CCCCC(Cc1c[nH]c2ccccc12)NC(=O)c1cnc(N2CCN(CCOCCOCCOCC(=O)N[C@H](C(=O)N3C[C@H](O)C[C@H]3C(=O)N[C@@H](C)c3ccc(-c4scnc4C)cc3)C(C)(C)C)CC2)s1]

Step 1

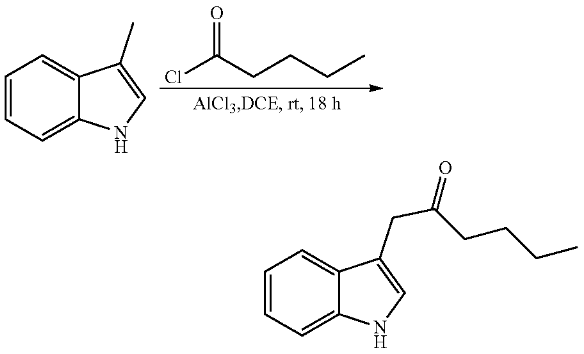

To a stirred mixture of 3-methyl-1H-indole (20 g, 152.46 mmol, 1.0 equiv) and $AlCl_3$ (61.0 g, 457 mmol, 3.0 equiv) in DCE (300 mL) was added pentanoyl chloride (22.0 g, 182.45 mmol, 1.2 equiv) in portions at 0° C. The resulting mixture was stirred for 18 hr at room temperature. The reaction was quenched with water/ice at 0° C. The mixture was extracted with $CH_2Cl_2$ (3×200 mL). The combined organic phase was washed with 3×100 ml of brine, dried with $Na_2SO_4$, and concentrated under vacuum. The residue was purified by silica gel column chromatography eluting with petroleum ether. The crude product was further purified by reverse flash chromatography under the following conditions: column, C18; mobile phase, MeOH/water=10% to 50% gradient in 3 h; detector, UV 254 nm. This resulted in 9.0 g of 1-(1H-indol-3-yl) hexan-2-one as a brown oil.

Step 2

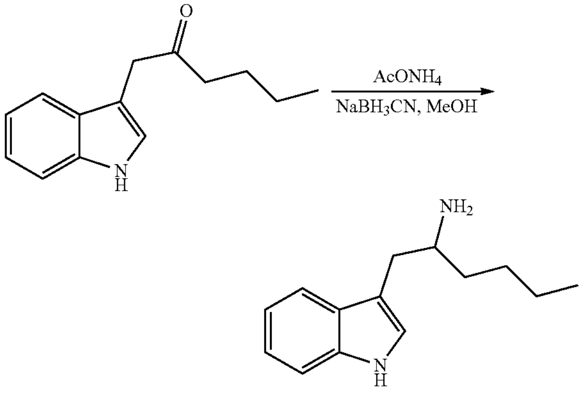

Into a 100-mL round-bottom flask purged and maintained with an inert atmosphere of nitrogen, was placed 1-(1H-indol-3-yl)hexan-2-one (8.0 g, 37.16 mmol, 1.0 equiv), $AcONH_4$ (5.7 g, 74.31 mmol, 2.0 equiv), and MeOH (100 mL). The resulting solution was stirred for 30 min at 0° C. Then $NaBH_3CN$ (4.6 g, 73.84 mmol, 2.0 equiv) was added to the flask. The resulting mixture was allowed to react, with stirring, for an additional 3 hr at 70° C. in an oil bath. The resulting mixture was concentrated under reduced pressure. The residue was poured into 100 mL of water. The resulting mixture was extracted with 2×50 mL of ethyl acetate. The organic layers were combined, washed with 2×100 mL of brine, dried over anhydrous sodium sulfate, and concentrated under vacuum. The residue was purified by silica gel column chromatography eluting with ethyl acetate/petroleum ether=0 to 50% within 40 min. This resulted in 1-(1H-indol-3-yl)hexan-2-amine (5.4 g) as a light yellow oil.

Step 3

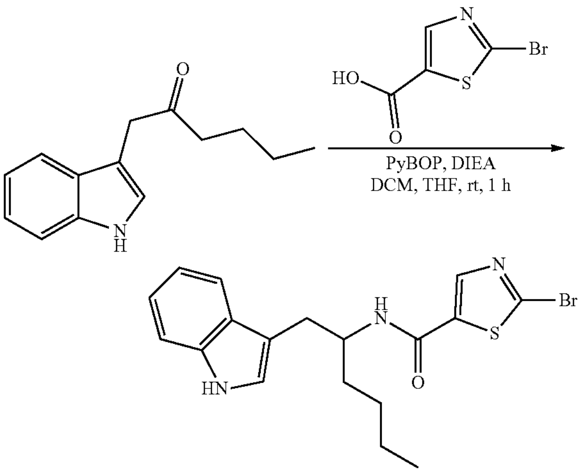

To the solution of 2-bromo-1,3-thiazole-5-carboxylic acid (580 mg, 2.79 mmol, 1.0 equiv) and 1-(1H-indol-3-yl) hexan-2-amine (786 mg, 3.63 mmol, 1.3 equiv), DIEA (1.80 g, 13.93 mmol, 5.0 equiv) in DCM (10 mL) and THF (10 mL), was added PyBOP (1.75 g, 3.36 mmol, 1.2 equiv). The reaction mixture was stirred for 1 hr at room temperature. The reaction was quenched with 50 mL of water at room temperature. The resulting mixture was extracted with EtOAc (3×100 mL). The combined organic phase was concentrated under vacuum. The residue was purified by silica gel column chromatography eluting with petroleum ether/EtOAc (80:20) to afford 2-bromo-N-[1-(1H-indol-3-yl)hexan-2-yl]-1,3-thiazole-5-carboxamide (703 mg) as a light yellow solid.

Step 4

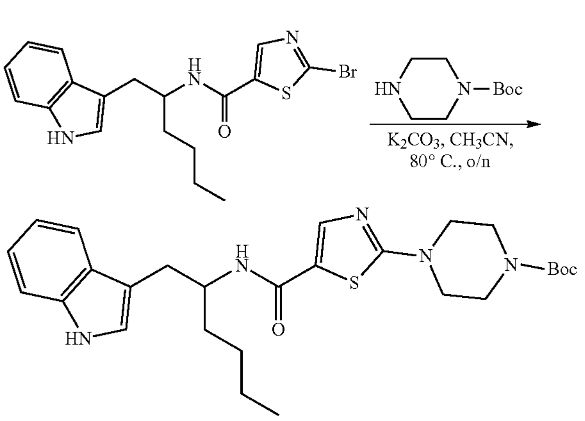

Into a 30-mL sealed tube was placed N-(1-(1H-indol-3-yl)hexan-2-yl)-2-bromothiazole-5-carboxamide (325 mg, 0.80 mmol, 1.0 equiv), tert-butyl piperazine-1-carboxylate (224 mg, 1.2 mmol, 1.5 equiv), $K_2CO_3$ (332 mg, 2.4 mmol, 3.0 equiv) and $CH_3CN$ (15 mL). The reaction mixture was stirred overnight at 80° C. in an oil bath. The reaction was concentrated under vacuum. The residue was purified by silica gel column chromatography eluting with EtOAc/petroleum ether (0 to 100%) to afford 225 mg of tert-butyl 4-(5-((1-(1H-indol-3-yl)hexan-2-yl)carbamoyl)thiazol-2-yl)-piperazine-1-carboxylate as a light yellow solid.

Step 5

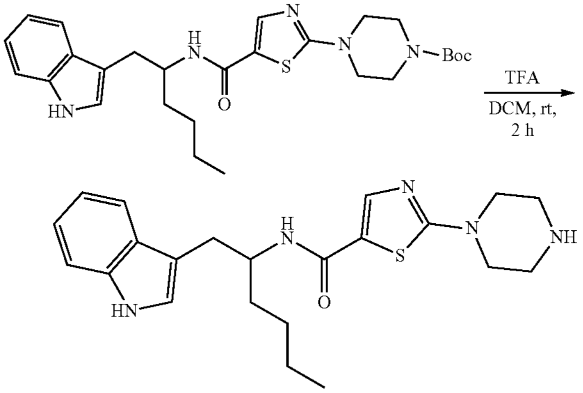

A solution of tert-butyl 4-(5-((1-(1H-indol-3-yl)hexan-2-yl)-carbamoyl)-thiazol-2-yl)-piperazine-1-carboxylate (225 mg, 0.44 mmol, 1.0 equiv), DCM (30 mL), and TFA (10 mL) was stirred for 1 hr at room temperature. The reaction mixture was concentrated under vacuum. This resulted in 181 mg (crude) of N-(1-(1H-indol-3-yl)hexan-2-yl)-2-(piperazin-1-yl)thiazole-5-carboxamide as a light yellow semi-solid.

Step 6 equiv), $CH_3CN$ (3 mL), and DIEA (1 mL). The reaction mixture was stirred overnight at 80° C. in an oil bath. The reaction mixture was concentrated under vacuum. The residue was purified by silica gel column chromatography eluting with ethyl acetate/petroleum ether=0 to 100% within 40 min. This resulted in tert-butyl 2-(2-(2-(2-(4-(5-((1-(1H-indol-3-yl)hexan-2-yl)carbamoyl)thiazol-2-yl)-piperazin-1-yl)ethoxy)ethoxy)ethoxy)acetate (69 mg) as a light yellow solid.

tert-Butyl 2-(2-(2-(2-(4-(5-((1-(1H-indol-3-yl)hexan-2-yl)carbamoyl)thiazol-2-yl)-piperazin-1-yl)ethoxy)ethoxy)ethoxy)acetate was converted to the title compound using procedures described for Exemplary Compound 1.

Using analogous procedures the following examples were prepared: Exemplary Compound 50.

Exemplary Synthesis of Exemplary Compound 52

Step 1

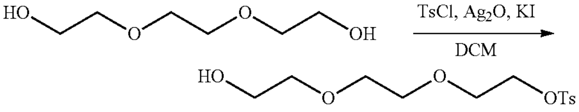

Into a 500-mL 3-neck round-bottom flask purged and maintained with an inert atmosphere of nitrogen, was placed triethylene glycol (2.50 g, 16.65 mmol, 1.00 equiv), $Ag_2O$ (7.72 g, 33.29 mmol, 2.00 equiv) and KI (2.76 g, 16.65 mmol, 1.00 equiv) in DCM (100 mL). This was followed by the addition of a solution of TsCl (1.59 g, 8.32 mmol, 0.50 equiv) in DCM (50 mL) dropwise with stirring at 0° C. in 5 min. The resulting solution was stirred for 1 hr at 0° C. in a water/ice bath. The solids were filtered out. The resulting

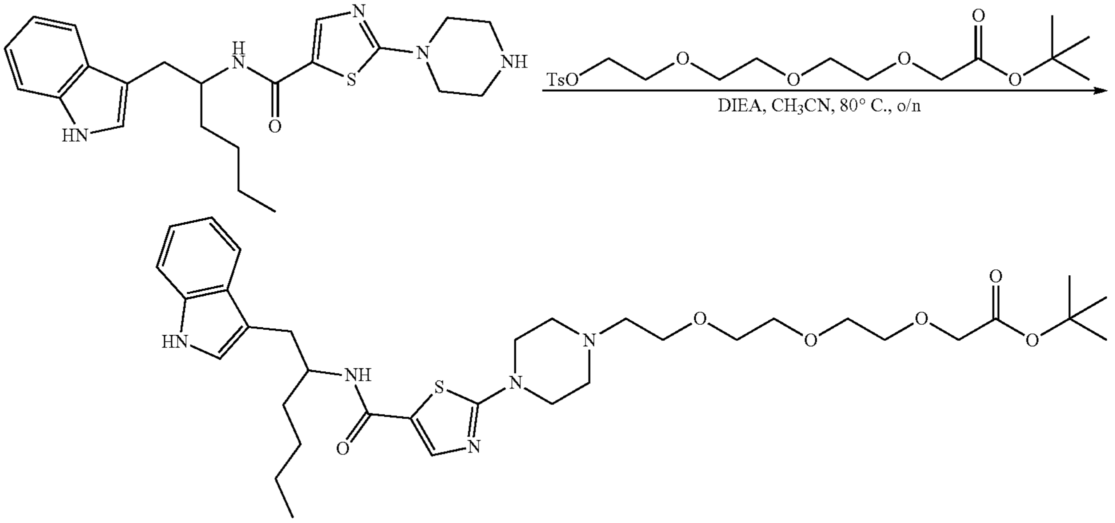

Into a 8-mL sealed tube, was placed N-(1-(1H-indol-3-yl)hexan-2-yl)-2-(piperazin-1-yl)thiazole-5-carboxamide (103 mg, 0.25 mmol, 1.0 equiv), tert-butyl 2-(2-(2-(2-(tosyloxy)ethoxy)ethoxy)ethoxy)acetate (157 mg, 0.38 mmol, 1.5 filtrate was concentrated. The residue was applied onto a silica gel column eluting with dichloromethane/methanol (100:1 to 10:1) to give 2-(2-[2-[(4-methylbenzenesulfonyl)oxy]ethoxy]ethoxy)ethanol (1.2 g) as a colorless oil.

Step 2

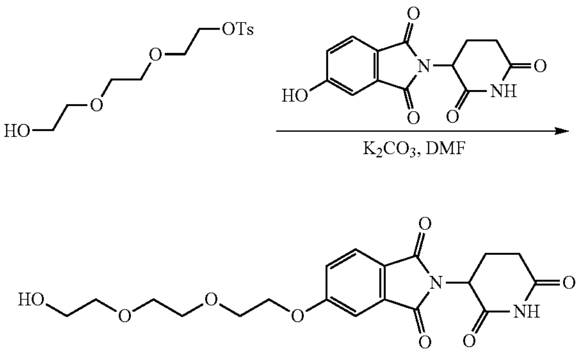

Into a 100-mL round-bottom flask purged and maintained with an inert atmosphere of nitrogen, was placed 2-(2-[2-[(4-methylbenzenesulfonyl)oxy]ethoxy]ethoxy)ethanol (1.10 g, 3.61 mmol, 1.0 equiv) and 2-(2,6-dioxopiperidin-3-yl)-5-hydroxyisoindole-1,3-dione (1.09 g, 3.98 mmol, 1.1 equiv) in DMF (20 mL), to which mixture $K_2CO_3$ (1.50 g, 10.84 mmol, 3.0 equiv) was added. The resulting solution was stirred for 16 hrs at 70° C. in an oil bath. The reaction mixture was cooled to RT. The resulting mixture was concentrated. The residue was applied onto a silica gel column eluting with dichloromethane/methanol (50:1 to 15:1) to give 2-(2,6-dioxopiperidin-3-yl)-5-[2-[2-(2-hydroxyethoxy)ethoxy]ethoxy]isoindole-1,3-dione (550 mg) as a yellow oil.

Step 3

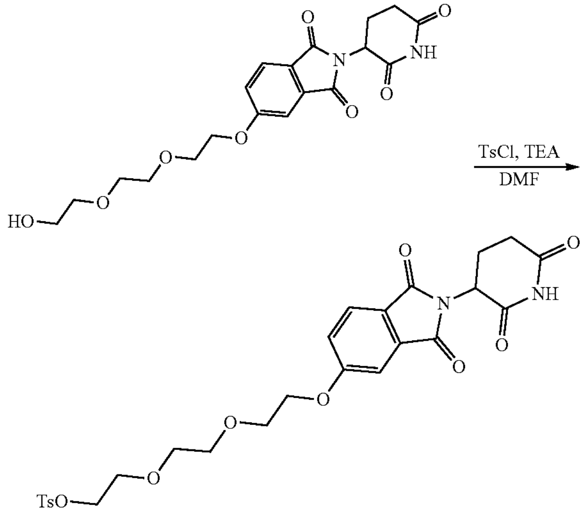

Into a 100-mL round-bottom flask purged and maintained with an inert atmosphere of nitrogen, was placed 2-(2,6-dioxopiperidin-3-yl)-5-[2-[2-(2-hydroxyethoxy)ethoxy]ethoxy]isoindole-1,3-dione (300 mg, 0.74 mmol, 1.0 equiv) in DCM (15 mL), to which was added TEA (298 mg, 2.95 mmol, 4.0 equiv) and TsCl (211 mg. 1.11 mmol, 1.5 equiv). The resulting solution was stirred for 12 hr at room temperature. The resulting mixture was concentrated under vacuum. The residue was applied onto prep-TLC (DCM: MeOH=10:1). This resulted in 219 mg of 2-[2-(2-[[2-(2,6-dioxopiperidin-3-yl)-1,3-dioxoisoindol-5-yl]oxy]ethoxy)ethoxy]ethyl 4-methylbenzenesulfonate as a yellow oil.

Step 4

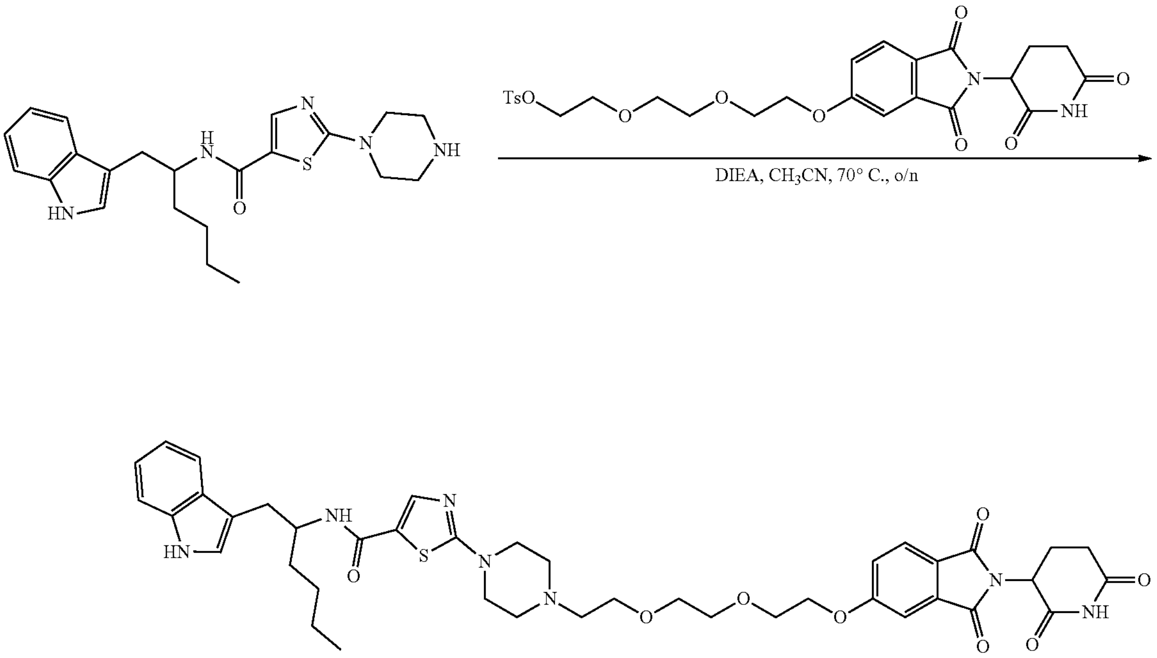

Exemplary Compound 52

To a stirred mixture of N-[1-(1H-indol-3-yl)hexan-2-yl]-2-(piperazin-1-yl)-1,3-thiazole-5-carboxamide (100 mg, 0.24 mmol, 1.0 equiv) and 2-[2-(2-[[2-(2,6-dioxopiperidin-3-yl)-1,3-dioxoisoindol-5-yl]oxy]-ethoxy)ethoxy]ethyl 4-methylbenzenesulfonate (204 mg, 0.36 mmol, 1.5 equiv) in DMF (3 ml) was added DIEA (94 mg, 0.73 mmol, 3.0 equiv). The resulting mixture was stirred overnight at 70° C. in an oil bath under nitrogen atmosphere. The reaction was quenched with 100 mL of water. The resulting mixture was extracted with EtOAc (100x3 mL). The combined organic layers were washed with brine (3x50 mL), dried over anhydrous $Na_2SO_4$, and concentrated under vacuum. The residue was purified by prep-HPLC under the following conditions: Column, Xselect CSH OBD Column 30*150 mm 5 um; mobile phase, water (0.1% FA) and ACN (16% Phase B up to 47% in 9 min); Detector, UV. This resulted in 2-(4-[2-[2-(2-[[2-(2,6-dioxopiperidin-3-yl)-1,3-dioxoisoindol-5-yl]oxy]ethoxy)ethoxy]ethyl]piperazin-1-yl)-N-[1-(1H-indol-3-yl)hexan-2-yl]-1,3-thiazole-5-carboxamide (15.6 mg) as a white solid.

Using analogous procedures the following examples were prepared: Exemplary Compound 53 and Exemplary Compound 54.

Exemplary Synthesis of Exemplary Compound 57

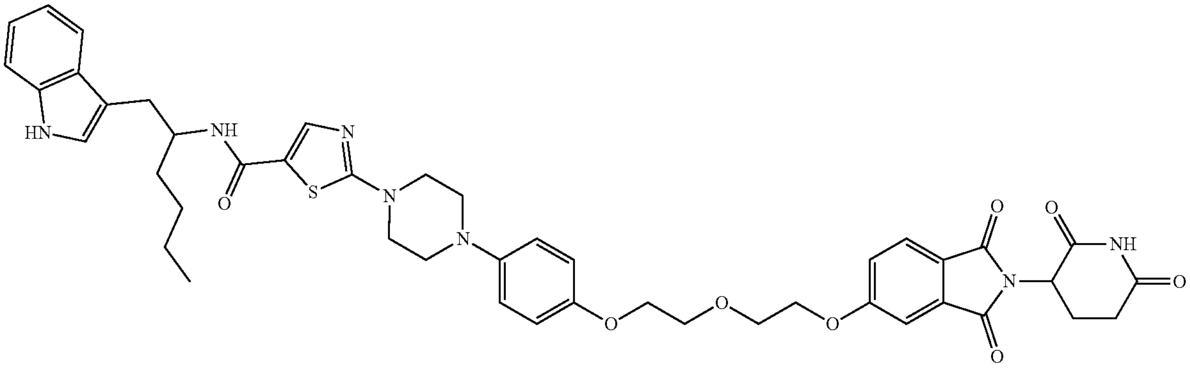 [SMILES: CCCCC(Cc1c[nH]c2ccccc12)NC(=O)c1cnc(N2CCN(c3ccc(OCCOCCOc4ccc5c(c4)C(=O)N(C4CCC(=O)NC4=O)C5=O)cc3)CC2)s1]

Step 1

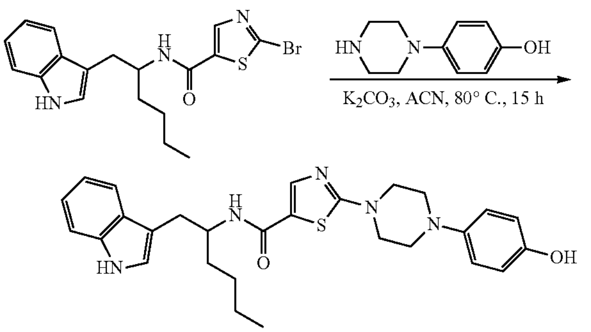

Into a 30-mL sealed tube, was placed 2-bromo-N-[1-(1H-indol-3-yl)hexan-2-yl]-1,3-thiazole-5-carboxamide (700 mg, 1.72 mmol, 1.0 equiv), 4-(piperazin-1-yl) phenol (335 mg, 1.89 mmol, 1.1 equiv), $K_2CO_3$ (477 mg, 3.45 mmol, 2.0 equiv) and $CH_3CN$ (15 mL). The tube was purged and maintained with an inert atmosphere of nitrogen. The mixture was stirred for 15 hr at 80° C. in an oil bath. The reaction mixture was cooled to room temperature, and then quenched by the addition of water (100 mL). The resulting mixture was extracted with EtOAc (3x100 mL). The combined organic layers were washed with brine (3x50 mL), dried over anhydrous $Na_2SO_4$, and concentrated under reduced pressure. The residue was purified by silica gel column chromatography, eluting with EtOAc/petroleum ether (0:1 to 7:3) to afford 2-[4-(4-hydroxyphenyl)piperazin-1-yl]-N-[1-(1H-indol-3-yl)hexan-2-yl]-1,3-thiazole-5-carboxamide (300 mg) as a light yellow solid.

Step 2

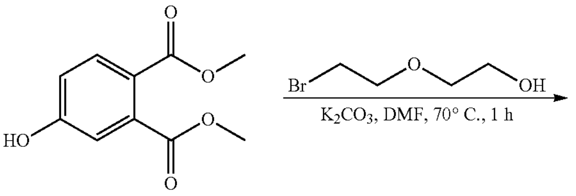

-continued

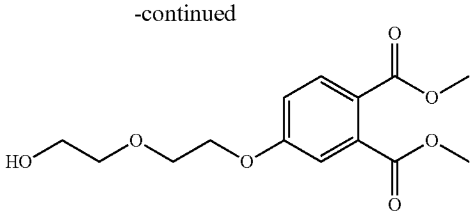

To a stirred mixture of 1,2-dimethyl 4-hydroxyphthalate (2 g, 9.52 mmol, 1.0 equiv) and $K_2CO_3$ (2.64 g, 19.1 mmol, 2.0 equiv) in DMF (30 ml), was added 2-(2-bromoethoxy) ethanol (5 g, 29.6 mmol, 3.1 equiv) under nitrogen atmosphere. The reaction mixture was stirred for 1 hr at 70° C. in an oil bath, and then cooled to room temperature. The reaction was quenched by the addition of water (100 mL). The resulting mixture was extracted with EtOAc (3x150 mL). The combined organic layers were washed with brine (4x100 ml), dried over anhydrous $Na_2SO_4$. After filtration, the filtrate was concentrated under reduced pressure. The residue was purified by silica gel column chromatography, eluting with EtOAc/petroleum ether (0:1 to 3:2) to afford 1,2-dimethyl 4-[2-(2-hydroxyethoxy)ethoxy]phthalate (2.22 g) as a light yellow oil.

Step 3

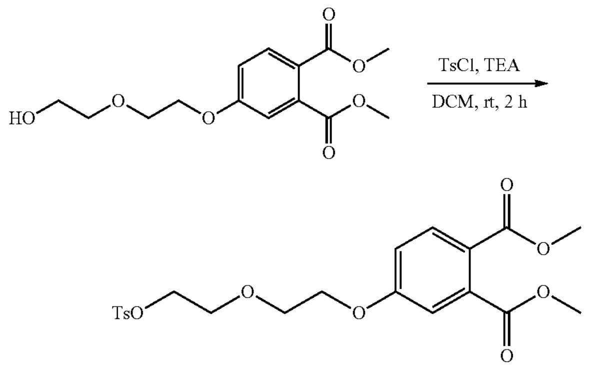

Into a 0° C. 50 mL round-bottom flask cooled in an ice/water bath were placed 1,2-dimethyl 4-[2-(2-hydroxyethoxy)ethoxy]phthalate (1.65 g, 5.53 mmol, 1.0 equiv), DCM (15 mL), TsCl (1.90 g, 9.97 mmol, 1.8 equiv) and TEA (1.35 g, 13.3 mmol, 2.4 equiv). The resulting mixture was stirred for 2 hr at room temperature, and then concentrated under vacuum. The residue was purified by prep-TLC (petroleum ether: EtOAc=58:42) to afford 1,2-dimethyl 4-(2-[2-[(4-me-thylbenzenesulfonyl)oxy]ethoxy]ethoxy)phthalate (1.5 g) as a light yellow oil.

Step 4

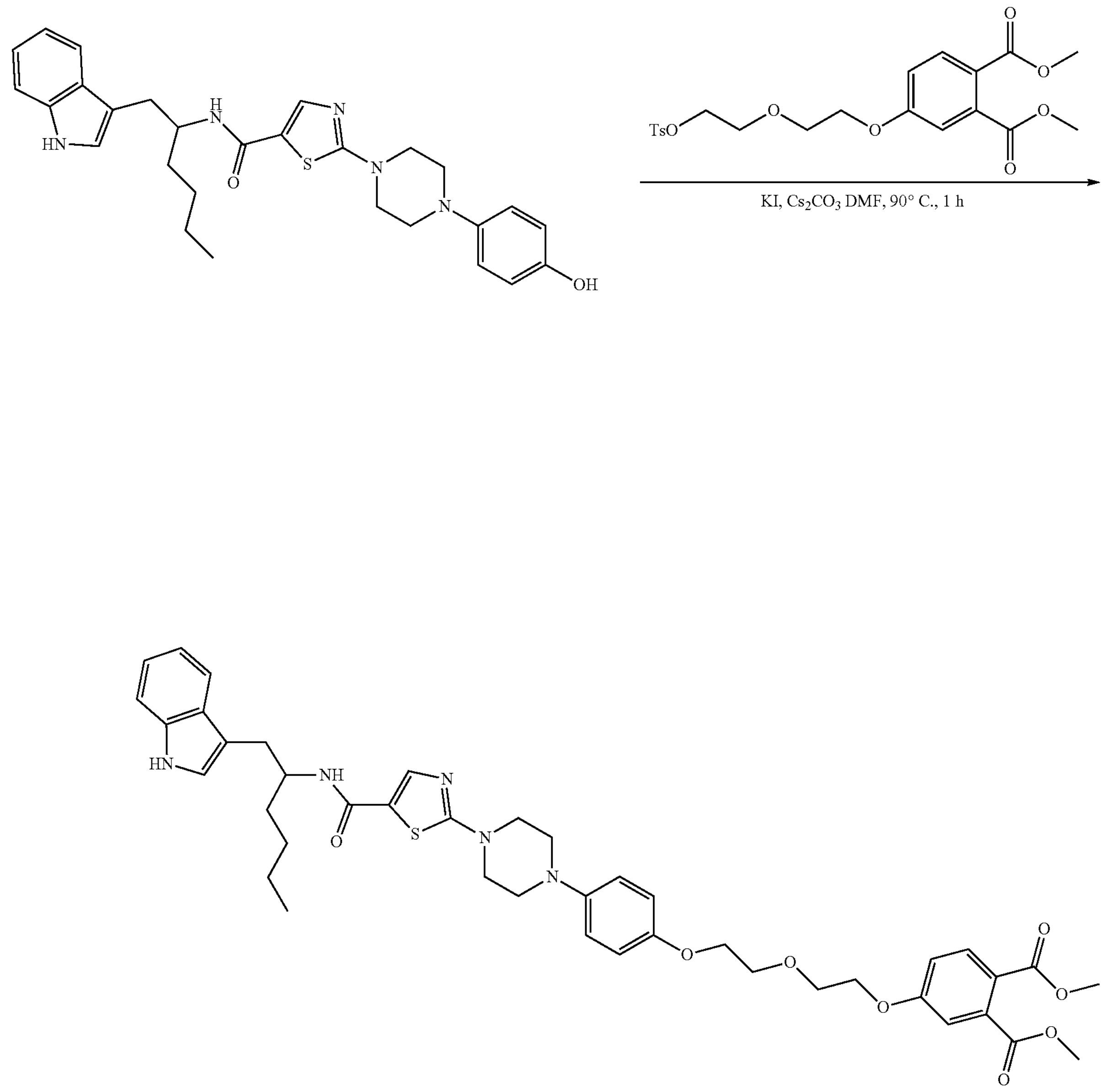

Into a 30-mL sealed tube, was placed 2-[4-(4-hydroxyphenyl)piperazin-1-yl]-N—[1-(1H-indol-3-yl) hexan-2-yl]-1,3-thiazole-5-carbox-amide (300 mg, 0.60 mmol, 1.0 equiv), 1,2-dimethyl 4-(2-[2-[(4-methylbenzenesulfonyl) oxy]ethoxy]-ethoxy)phthalate (810 mg, 1.79 mmol, 3.0 equiv), $Cs_2CO_3$ (585 mg, 1.80 mmol, 3.0 equiv), KI (300 mg, 1.81 mmol, 3.0 equiv) and DMF (15 mL). The tube was purged and maintained with an inert atmosphere of nitrogen. The resulting mixture was stirred for 1 hr at 90° C. in an oil bath. The reaction mixture was cooled to room temperature, and then quenched by the addition of water (100 mL). The resulting mixture was extracted with EtOAc (3×100 mL). The combined organic layers were washed with brine (3×100 mL), dried over anhydrous $Na_2SO_4$, and concentrated under reduced pressure. The residue was purified by Prep-TLC (EA) to afford 1,2-dimethyl 4-[2-(2-[4-[4-(5-[[1-(1H-indol-3-yl)hexan-2-yl]carbamoyl]-1,3-thiazol-2-yl) piperazin-1-yl]phenoxy]ethoxy)ethoxy]phthalate (260 mg, 55.7%) as a light yellow solid.

Step 5

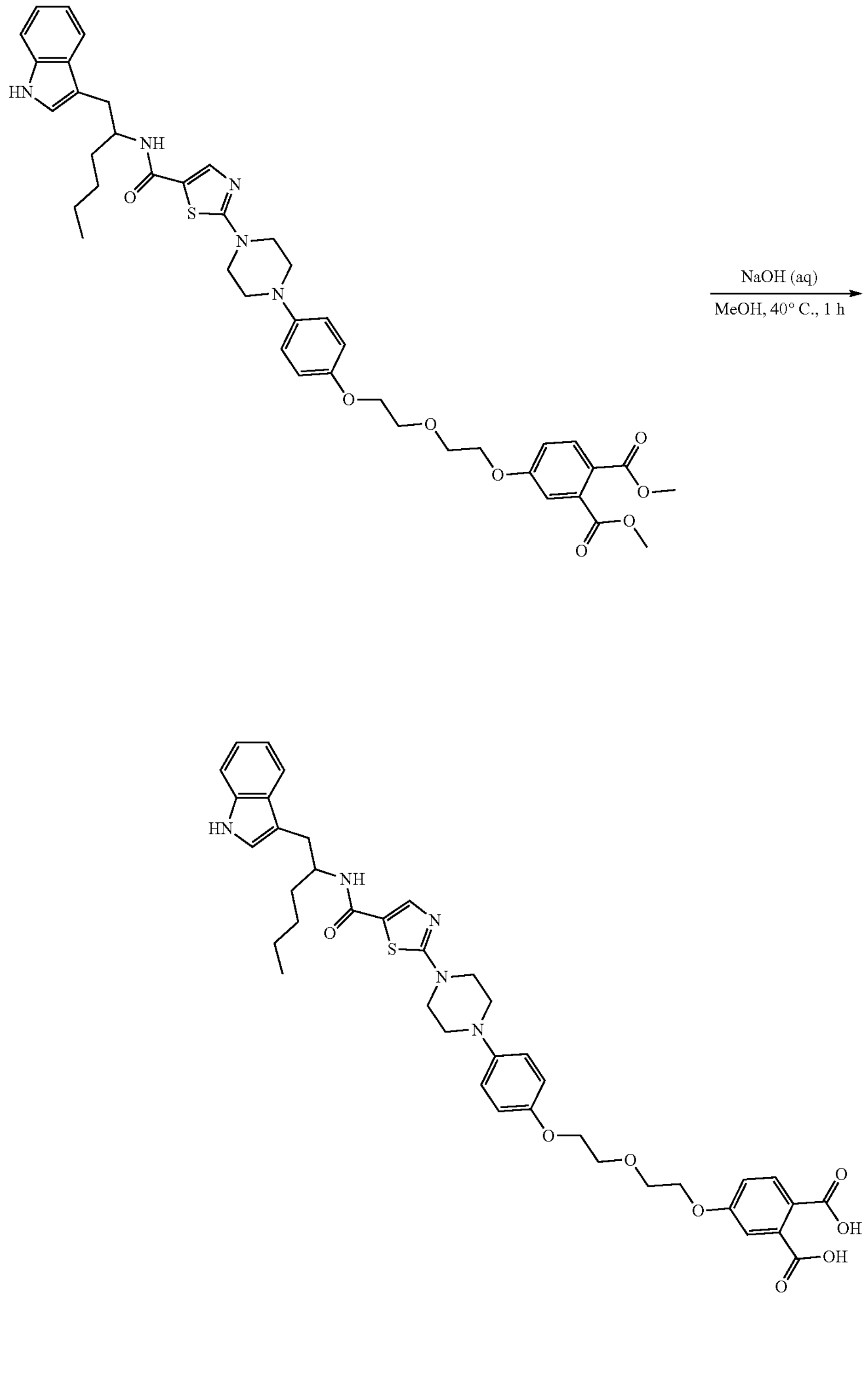

Into a 50-mL round-bottom flask, was placed 1,2-dimethyl 4-[2-(2-[4-[4-(5-[[1-(1H-indol-3-yl)hexan-2-yl]carbamoyl]-1,3-thiazol-2-yl)piperazin-1-yl]phenoxy]ethoxy)ethoxy]phthalate (260 mg, 0.33 mmol, 1.0 equiv), MeOH (12 mL), and NaOH (4M, 3.0 mL). The resulting mixture was stirred for 1 hr at 40° C. in an oil bath. The reaction mixture was cooled to 0° C. with a water/ice bath, and its pH value was adjusted to 5 with 1M HCl. The resulting mixture was extracted with 3×50 mL of DCM:MeOH (10:1). The organic layers were combined, dried over anhydrous sodium sulfate, and concentrated under vacuum. This resulted in 216 mg of 4-[2-(2-[4-[4-(5-[[1-(1H-indol-3-yl)-hexan-2-yl]carbamoyl]-1,3-thiazol-2-yl)piperazin-1-yl]phenoxy]ethoxy)ethoxy]benzene-1,2-dicarboxylic acid as a light yellow solid.

Step 6

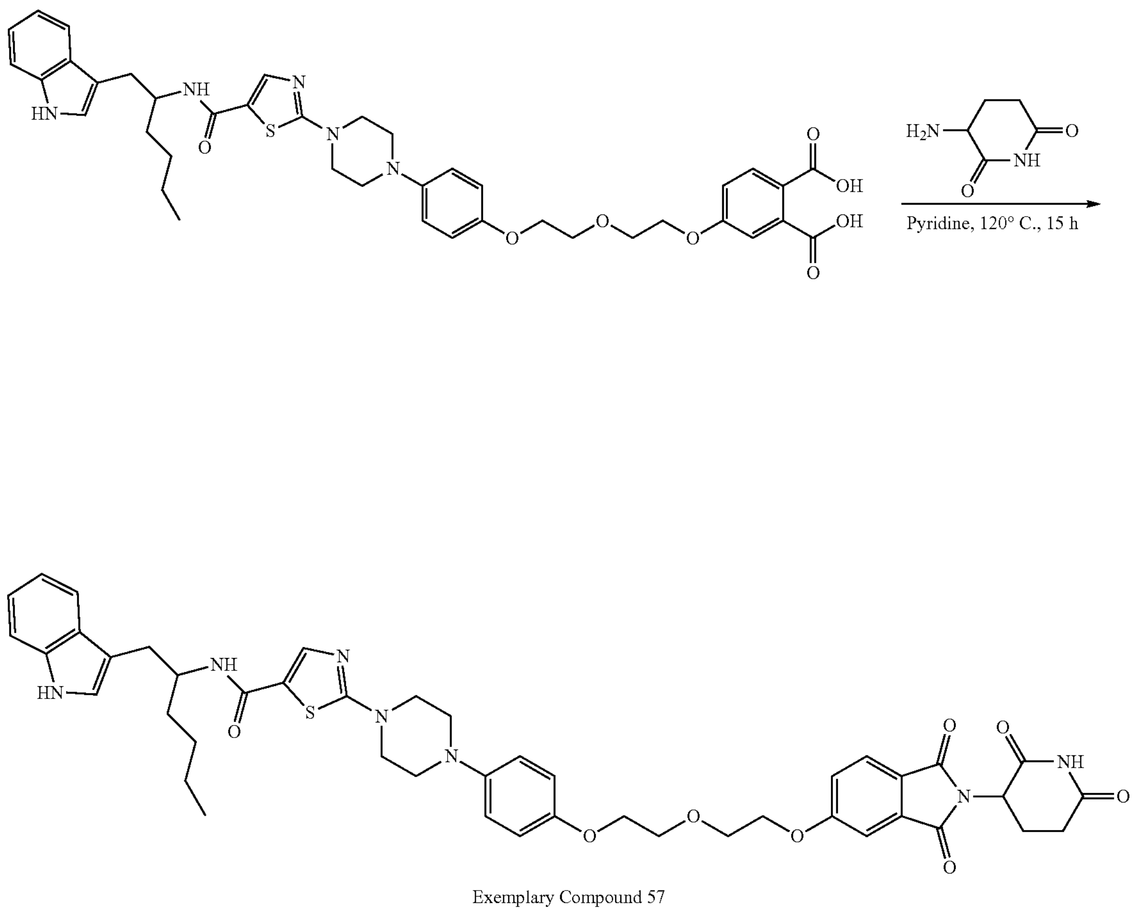

Exemplary Compound 57

Into a 50-mL round-bottom flask were added 4-[2-(2-[4-[4-(5-[[1-(1H-indol-3-yl)hexan-2-yl]carbam-oyl]-1,3-thiazol-2-yl)piperazin-1-yl]phenoxy]ethoxy)ethoxy]benzene-1,2-dicarboxylic acid (50 mg, 0.07 mmol, 1.0 equiv), pyridine (5.0 mL) and 3-aminopiperidine-2,6-dione (20 mg, 0.16 mmol, 2.4 equiv) under nitrogen atmosphere. The resulting mixture was stirred for 15 hr at 120° C. in an oil bath. The reaction mixture was cooled to room temperature, and then quenched with 50 mL of water. The resulting mixture was extracted with EtOAc (3×50 mL). The combined organic layers were washed with brine (2×30 mL), dried over anhydrous $Na_2SO_4$. After filtration, the filtrate was concentrated under reduced pressure. The crude product was purified by prep-HPLC under the following conditions (Column: YMC-Actus Triart C18, 30*250, 5 um; Mobile Phase A: water (10 mmol/L $NH_4HCO_3$), Mobile Phase B: $CH_3CN$; Flow rate: 50 mL/min; Gradient: 65 B to 88 B in 7 min; UV: 254 nm) to afford 2-(4-[4-[2-(2-[[2-(2,6-dioxopiperidin-3-yl)-1,3-dioxoisoindol-5-yl]oxy]ethoxy)ethoxy]phenyl]-piperazin-1-yl)-N-[1-(1H-indol-3-yl) hexan-2-yl]-1,3-thiazole-5-carboxamide (26 mg) as an off-white solid.

Using analogous procedures, as well as procedures described for example A4295, the following examples were prepared: Exemplary Compound 55, Exemplary Compound 56, Exemplary Compound 58

Exemplary Synthesis of Examples Exemplary Compound 65, Exemplary Compound 66, Exemplary Compound 67 and Exemplary Compound 68
Exemplary compound 65
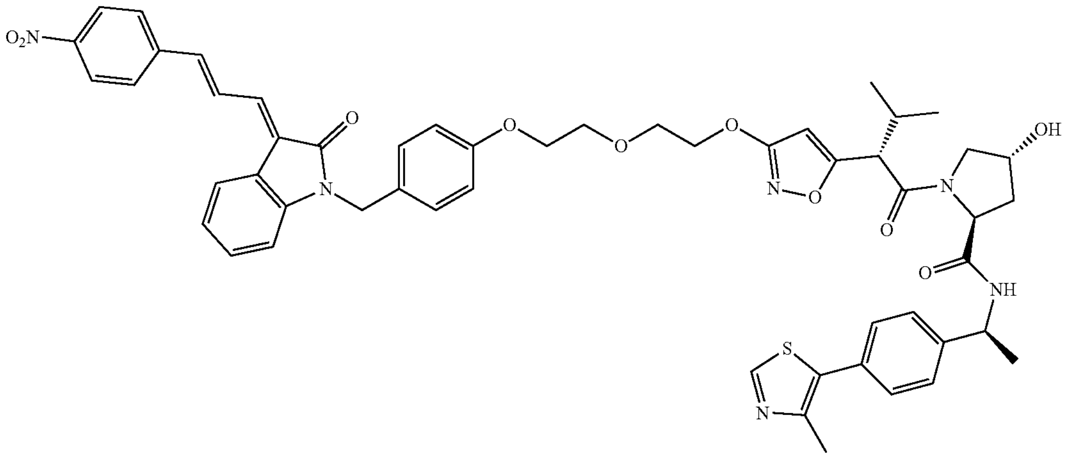
Exemplary compound 66
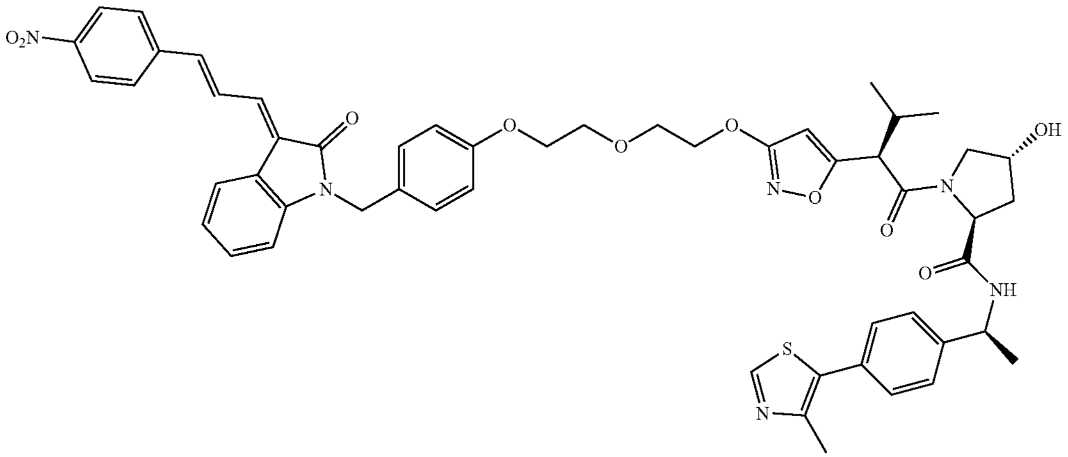

-continued
Exemplary compound 67
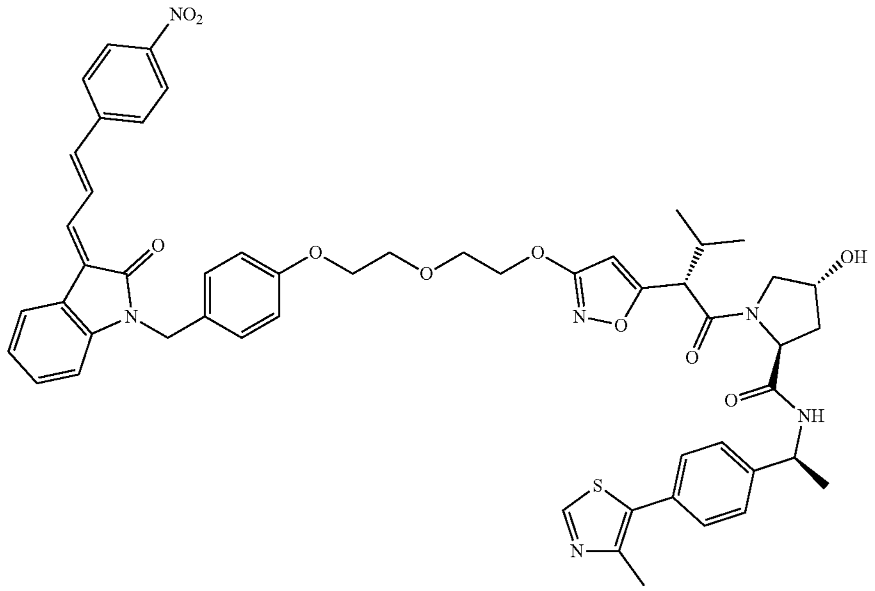
Exemplary compound 68
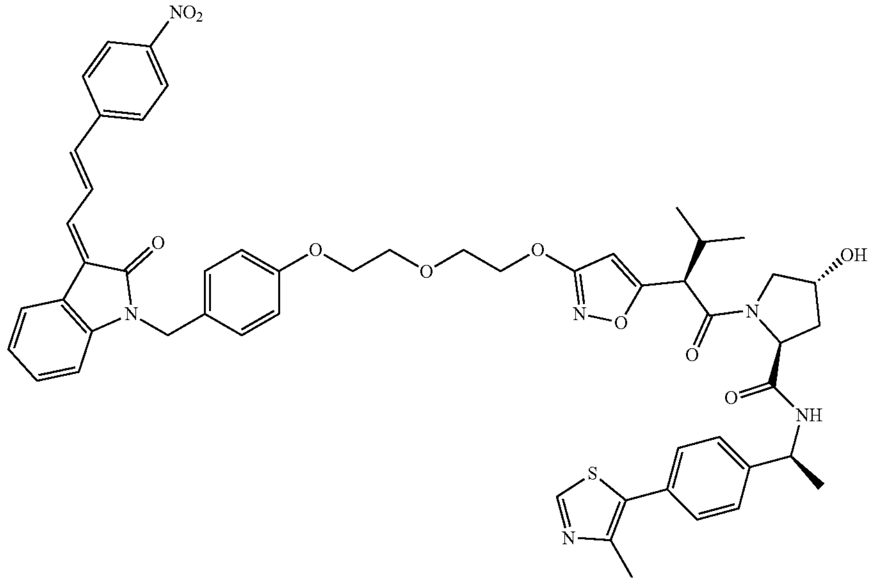

Step 1

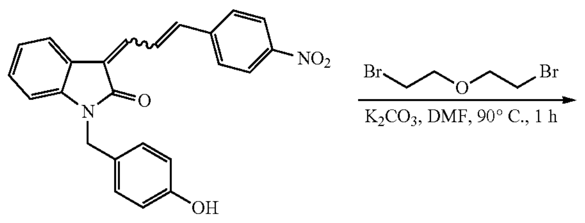

[prepared as described for Exemplary Compound 6 and Exemplary Compound 7]

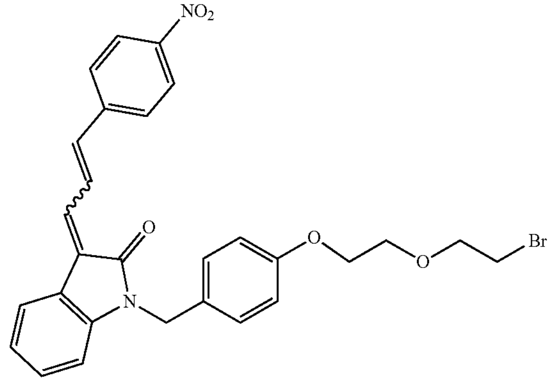

To a stirred mixture of (3Z)-1-[(4-hydroxyphenyl)methyl]-3-[(2E)-3-(4-nitrophenyl)prop-2-en-1-ylidene]indol-2-one (400 mg, 1.00 mmol, 1.0 equiv) and 1-bromo-2-(2-bromoethoxy)ethane (699 mg, 3.01 mmol, 3.0 equiv) in DMF (20 mL) was added $Cs_2CO_3$ (981 mg, 3.01 mmol, 3.0 equiv). The resulting mixture was stirred for 1 h at 90° C. in an oil bath, and then cooled to room temperature. The reaction was quenched with 50 mL of water. The resulting mixture was extracted with DCM (50 mL×3). The combined organic layers were washed with brine (30 mL×2), dried over anhydrous sodium sulfate and concentrated under reduced pressure. The residue was purified by silica gel column chromatography, eluting with DCM to afford 1-([4-[2-(2-bromoethoxy)ethoxy]phenyl]methyl)-3-[(2E)-3-(4-nitrophenyl)prop-2-en-1-ylidene]indol-2-one (300 mg) as a red solid.

Step 2

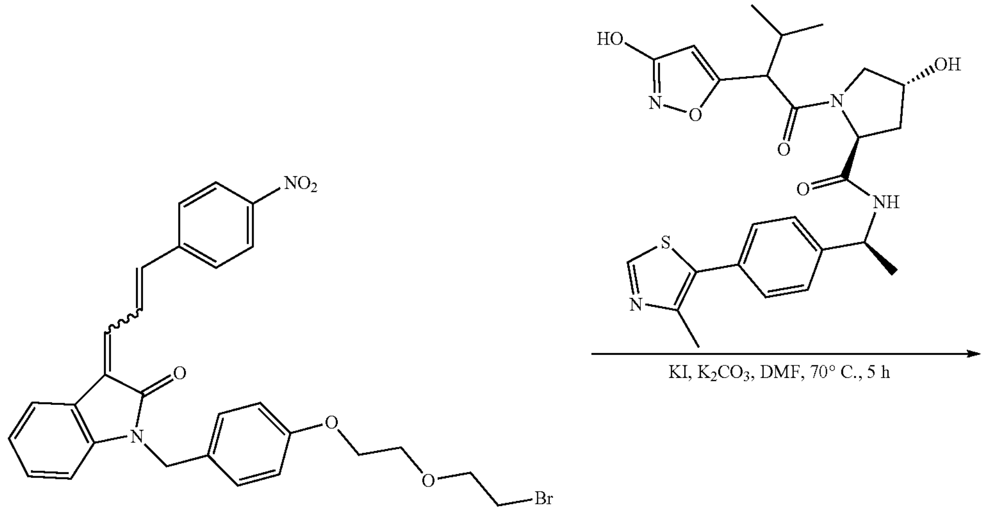

-continued

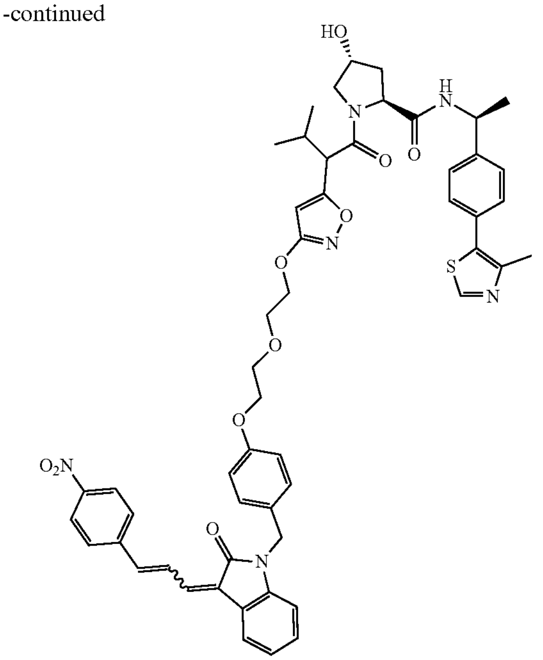

To a stirred solution of 1-([4-[2-(2-bromoethoxy)ethoxy]phenyl]methyl)-3-[3-(4-nitrophenyl)prop-2-en-1-ylidene]indol-2-one (3M) mg, 0.55 mmol, 1.0 equiv), (2S,4R)-4-hydroxy-1-[2-(3-hydroxy-1,2-oxazol-5-yl)-3-methylbutanoyl]-N-[(1S)-1-[4-(4-methyl-1,3-thiazol-5-yl)phenyl]ethyl]pyrrolidine-2-carboxamide (226 mg, 0.45 mmol, 0.8 equiv), and KI (188 mg, 1.09 mmol, 2.0 equiv) in DMF (5 mL) was added $K_2CO_3$ (226 mg, 1.64 mmol, 3.0 equiv). The resulting mixture was stirred for 5 h at 70° C. in an oil bath. The reaction mixture was diluted with water (50 mL) and extracted with DCM (50 mL×3). The combined organic layers were washed with brine (20 mL×3), dried over anhydrous sodium sulfate, filtered and concentrated under reduced pressure. The residue was purified by silica gel column chromatography, eluting with $MeOH/CH_2Cl_2$ (1:20) to afford (2S,4R)-4-hydroxy-N-[(1S)-1-[4-(4-methyl-1,3-thiazol-5-yl)phenyl]ethyl]-1-[3-methyl-2-(3-[2-[2-(4-[[(3Z)-3-[3-(4-nitrophenyl)prop-2-en-1-ylidene]-2-oxoindol-1-yl]methyl]phenoxy)ethoxy]ethoxy]-1,2-oxazol-5-yl)butanoyl]pyrrolidine-2-carboxamide (270 mg) as a red solid.

Step 3

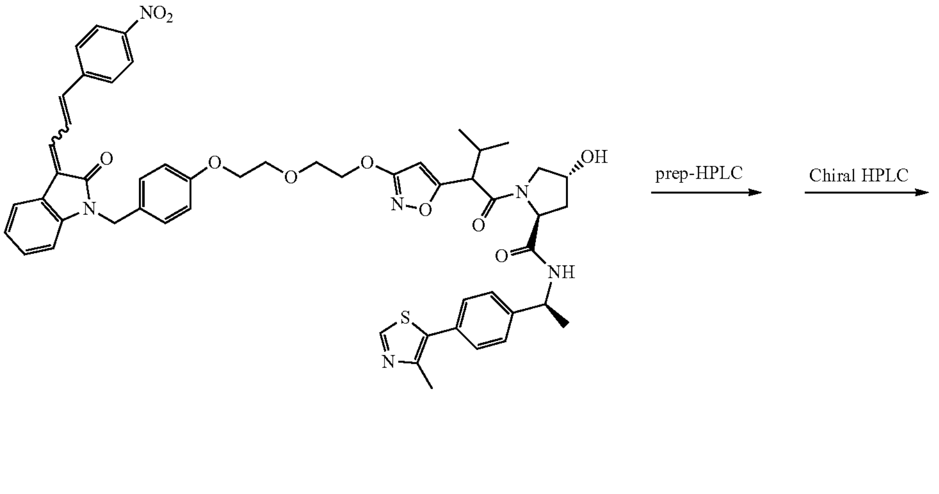

Exemplary Compound 65
Exemplary Compound 66
Exemplary Compound 67
Exemplary Compound 68

(2S,4R)-4-hydroxy-N-[(1S)-1-[4-(4-methyl-1,3-thiazol-5-yl)phenyl]ethyl]-1-[3-methyl-2-(3-[2-[2-(4-[[(3Z)-3-[3-(4-nitrophenyl)prop-2-en-1-ylidene]-2-oxoindol-1-yl]methyl]phenoxy)-ethoxy]ethoxy]-1,2-oxazol-5-yl)butanoyl]pyrrolidine-2-carboxamide (400 mg) was separated by prep-HPLC with following conditions: Column: XBridge prep OBD C18 Column, 30*150 mm (5 um); Mobile Phase A: Water (10 mmol/L $NH_4HCO_3$), Mobile Phase B: ACN; Flow rate: 60 mL/min; Gradient: 56 B to 66 B in 12 min; 254 nm. This resulted in (2S,4R)-4-hydroxy-1-(3-methyl-2-(3-(2-(2-(4-(((E)-3-((E)-3-(4-nitrophenyl)allylidene)-2-oxoindolin-1-yl)methyl)phenoxy)ethoxy)ethoxy)isoxazol-5-yl)butanoyl)-N—((S)-1-(4-(4-methylthiazol-5-yl)phenyl)ethyl)pyrrolidine-2-carboxamide (140 mg, 35%) as a red solid, and (2S,4R)-4-hydroxy-1-(3-methyl-2-(3-(2-(2-(4-(((Z)-3-((E)-3-(4-nitrophenyl)allylidene)-2-oxoindolin-1-yl)methyl)phenoxy)ethoxy)ethoxy)isoxazol-5-yl)butanoyl)-N—((S)-1-(4-(4-methylthiazol-5-yl)phenyl)ethyl)pyrrolidine-2-carboxamide (190 mg, 47%) as a red solid. The diene geometrical isomer configurations were assigned on the basis of reference NMR data described by Chu, W. et al. in Journal of Medicinal Chemistry 2015, 58, 6002-6017. Then, the two diastereomers of (2S,4R)-4-hydroxy-1-(3-methyl-2-(3-(2-(2-(4-(((E)-3-((E)-3-(4-nitrophenyl)allylidene)-2-oxoindolin-1-yl)methyl)phenoxy)ethoxy)ethoxy)isoxazol-5-yl)butanoyl)-N—((S)-1-(4-(4-methylthiazol-5-yl)phenyl)ethyl)pyrrolidine-2-carboxamide (140 mg) were separated by Chiral-HPLC with the following conditions: Column: CHIRALPAK IA-3, 4.6*50 mm (5 um); Mobile Phase A: MTBE (0.1% DEA), Mobile Phase B: EtOH; Flow rate: 20 mL/min; Gradient: 50 B to 50 B in 17 min; 254 nm; This resulted in 33.7 mg (8.4%) of (2S,4R)-4-hydroxy-N-[(1S)-1-[4-(4-methyl-1,3-thiazol-5-yl)phenyl]ethyl]-1-[(2S)-3-methyl-2-(3-[2-[2-(4-[[(3E)-3-[(2E)-3-(4-nitrophenyl)prop-2-en-1-ylidene]-2-oxoindol-1-yl]methyl]phenoxy)ethoxy]ethoxy]-1,2-oxazol-5-yl)butanoyl]pyrrolidine-2-carboxamide as a red solid (i-Pr stereocenter configuration tentatively assigned), and 71.4 mg (18%) of (2S,4R)-4-hydroxy-N-[(1S)-1-[4-(4-methyl-1,3-thiazol-5-yl)phenyl]ethyl]-1-[(2S)-3-methyl-2-(3-[2-[2-(4-[[(3Z)-3-[(2E)-3-(4-nitrophenyl)prop-2-en-1-ylidene]-2-oxoindol-1-yl]methyl]phenoxy)ethoxy]ethoxy]-1,2-oxazol-5-yl)butanoyl]pyrrolidine-2-carboxamide as a red solid (i-Pr stereocenter configuration tentatively assigned).

The (2S,4R)-4-hydroxy-1-(3-methyl-2-(3-(2-(2-(4-(((Z)-3-((E)-3-(4-nitrophenyl)allylidene)-2-oxoindolin-1-yl)methyl)phenoxy)ethoxy)ethoxy)isoxazol-5-yl)butanoyl)-N—((S)-1-(4-(4-methylthiazol-5-yl)phenyl)ethyl)pyrrolidine-2-carboxamide (190 mg) was separated by Chiral-HPLC with the following conditions: Column: CHIRALPAK IA-3, 4.6*50 mm (5 um); Mobile Phase A: MTBE (0.1% DEA), Mobile Phase B: EtOH; Flow rate: 20 mL/min; Gradient: 50 B to 50 B in 17 min; 254 nm; This resulted in (2S,4R)-4-hydroxy-N-[(1S)-1-[4-(4-methyl-1,3-thiazol-5-yl)phenyl]ethyl]-1-[(2S)-3-methyl-2-(3-[2-[2-(4-[[(3Z)-3-[(2E)-3-(4-nitrophenyl)prop-2-en-1-ylidene]-2-oxoindol-1-yl]methyl]phenoxy)ethoxy]ethoxy]-1,2-oxazol-5-yl)butanoyl]pyrrolidine-2-carboxamide (44 mg, 11%) as a red solid (i-Pr stereocenter configuration tentatively assigned), and (2S,4R)-4-hydroxy-N-[(1S)-1-[4-(4-methyl-1,3-thiazol-5-yl)phenyl]ethyl]-1-[(2R)-3-methyl-2-(3-[2-[2-(4-[[(3Z)-3-[(2E)-3-(4-nitrophenyl)prop-2-en-1-ylidene]-2-oxoindol-1-yl]methyl]phenoxy)ethoxy]ethoxy]-1,2-oxazol-5-yl)butanoyl]pyrrolidine-2-carboxamide (84 mg, 21%) as a red solid (i-Pr stereocenter configuration tentatively assigned).

Exemplary Synthesis of Exemplary Compound 73, Exemplary Compound 74, Exemplary Compound 75, and Exemplary Compound 76

Exemplary Compound 73

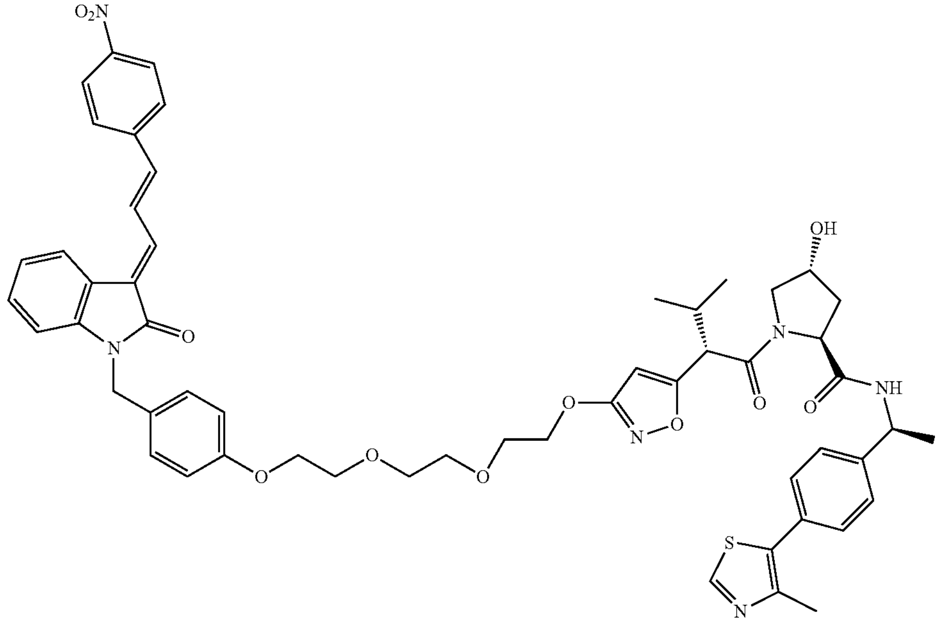

-continued
Exemplary Compound 74
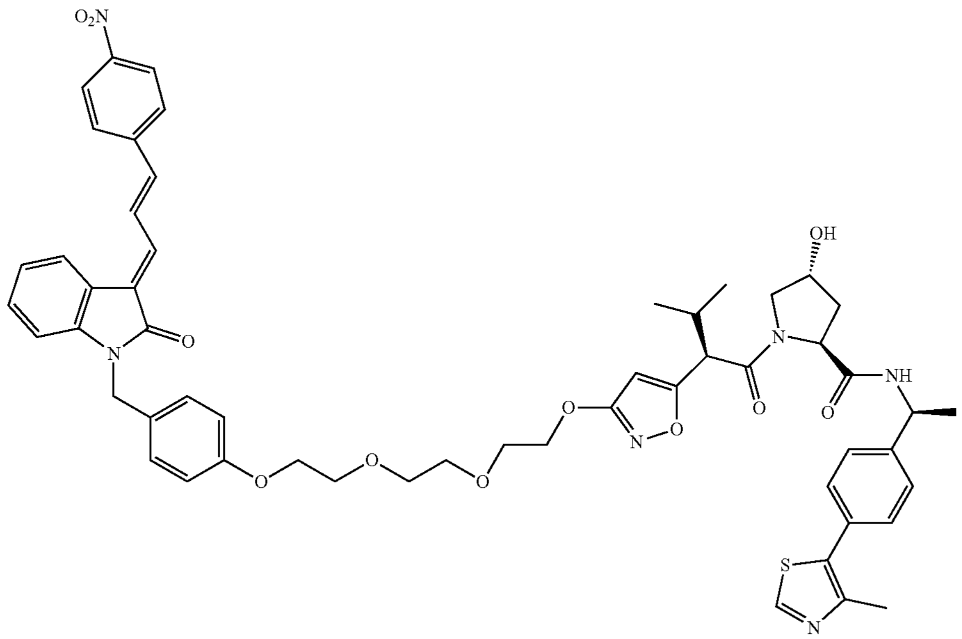
Exemplary Compound 75
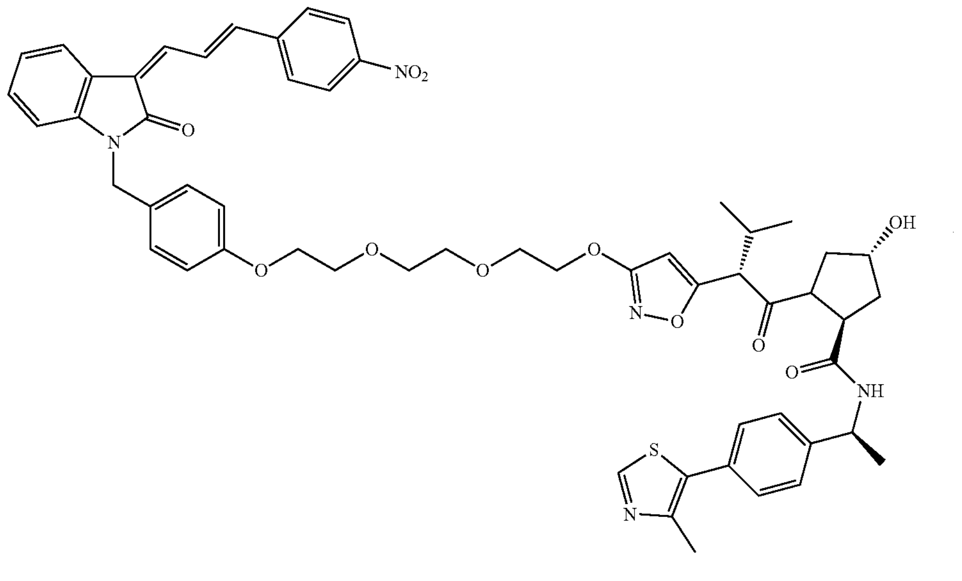

-continued

Exemplary Compound 76

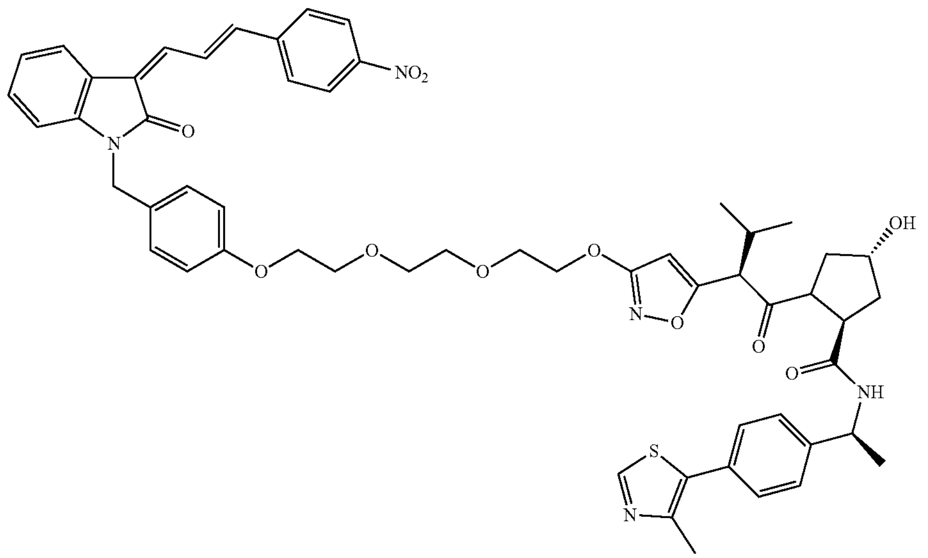

Step 1

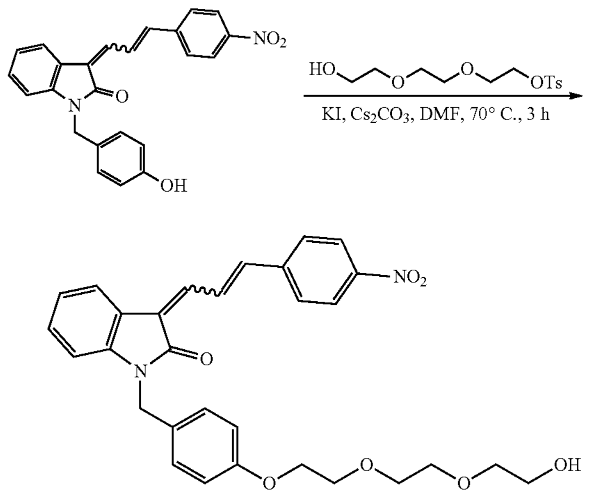

To a stirred mixture of 1-[(4-hydroxyphenyl)methyl]-3-[(2E)-3-(4-nitrophenyl)prop-2-en-1-ylidene]indol-2-one (400 mg, 1.00 mmol, 1.0 equiv), 2-(2-[2-[(4-nitrobenzene-sulfonyl)oxy]ethoxy]ethoxy)ethanol (404 mg, 1.21 mmol, 1.2 equiv), and KI (333 mg, 2.01 mmol, 2.0 equiv) in DMF (5 mL) was added $Cs_2CO_3$ (981 mg, 3.01 mmol, 3.0 equiv). The resulting mixture was stirred for 3 h at 70° C. in an oil bath. The reaction was quenched with water (50 mL) at room temperature, and the resulting mixture was extracted with DCM (50 mL×3). The combined organic layers were washed with brine (30 mL×2), dried over anhydrous sodium sulfate and concentrated under reduced pressure. The residue was purified by silica gel column chromatography, eluting with MeOH/$CH_2Cl_2$ (0 to 3%) to afford 1-[(4-[2-[2-(2-hydroxyethoxy)ethoxy]ethoxy]phenyl)methyl]-3-[(2E)-3-(4-nitrophenyl)prop-2-en-1-ylidene]indol-2-one as (449 mg) as a red solid.

Step 2

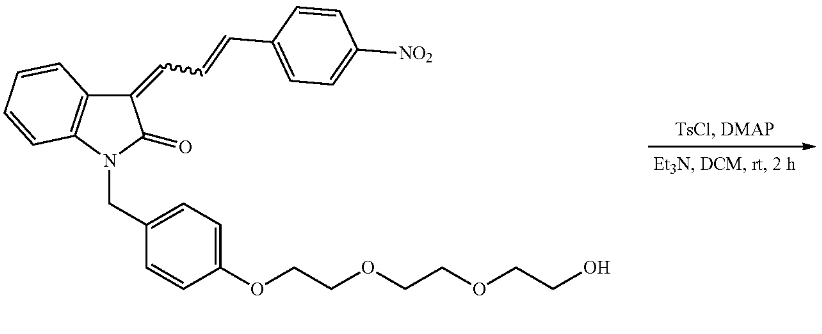

-continued

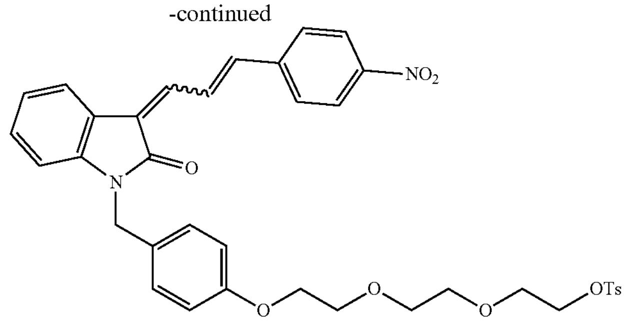

To a stirred solution of 1-[(4-[2-[2-(2-hydroxyethoxy) ethoxy]ethoxy]phenyl)methyl]-3-[(2E)-3-(4-nitrophenyl) prop-2-en-1-ylidene]indol-2-one (449 mg, 0.85 mmol, 1.0 equiv), DMAP (10 mg, 0.09 mmol, 0.1 equiv), $Et_3N$ (257 mg, 2.54 mmol, 3.0 equiv) in DCM (50 mL) was added p-toluenesulfonyl chloride (242 mg, 1.27 mmol, 1.5 equiv). The resulting mixture was stirred for 2 hr at room temperature. The reaction was quenched with water (100 mL) at room temperature, and the resulting mixture was extracted with DCM (50 mL×3). The combined organic layers were washed with brine (50 mL×2), dried over anhydrous sodium sulfate and concentrated under reduced pressure. The product was isolated by flash chromatography on silica gel eluting with DCM to give 2-(2-[2-[4-([3-[(2E)-3-(4-nitrophenyl)prop-2-en-1-ylidene]-2-oxoindol-1-yl]methyl)phenoxy]ethoxy]ethoxy)ethyl 4-nitrobenzenesulfonate (400 mg) as a red solid.

2-(2-[2-[4-([3-[(2E)-3-(4-nitrophenyl)prop-2-en-1-ylidene]-2-oxoindol-1-yl]methyl)phenoxy]ethoxy]ethoxy) ethyl 4-nitrobenzenesulfonate was converted to the title compounds as described for the Exemplary Compounds 65-68 above.

Using analogous procedures the following examples were prepared: Exemplary Compound 69, Exemplary Compound 70, Exemplary Compound 71, and Exemplary Compound 72.

Using analogous procedures combined with the procedure of step 3 of Exemplary Compound 36 the following examples were prepared: Exemplary Compound 59, Exemplary Compound 60, Exemplary Compound 61, Exemplary Compound 62, Exemplary Compound 63, Exemplary Compound 64.

The following examples of the application were prepared from 3-1-[(4-hydroxyphenyl)methyl]-3-[3-(4-nitrophenyl) prop-2-enylidene]indolin-2-one (see Exemplary Compound 6) using the corresponding procedures described earlier for other examples above. Exemplary Compounds 77 and 78 were prepared following the exemplary procedures described for Exemplary Compound 30. Exemplary compounds 79 and 80 were prepared following the exemplary procedures described for Exemplary Compounds 29 and 30.

Assays and Degradation Data

All reagents were purchased from Thermo Fisher Scientific unless indicated otherwise.

Table 2 Degradation Data.

Figure 5:
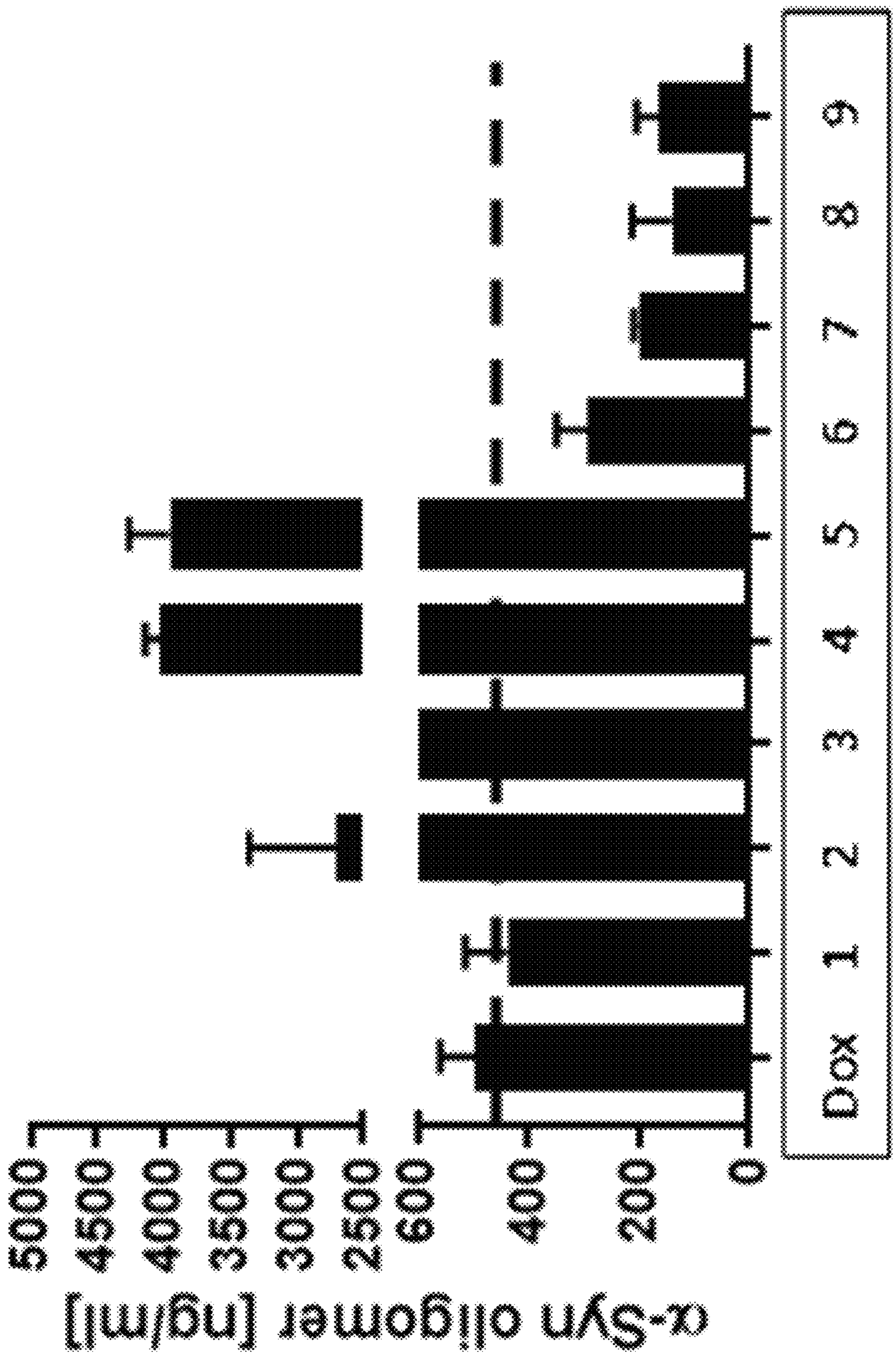
FIG. 5. Exemplary α-synuclein targeting bifunctional degrader compounds induce degradation of oligomeric α-synuclein. Targeted degradation of sarkosyl insoluble (SI) α-synuclein via exemplary bifunctional compounds was assessed by MJFF-14-6-4-2 conformation specific ELISA following treatment of PFF induced A53T α-synuclein overexpressing HEK293 cells with 1 μM bifunctional compounds compared to DMSO vehicle control lanes. Exemplary bifunctional degrading compounds 25, 12, and 9 used to generate the data shown in bars 2, 4 and 5, were cytotoxic at the concentration tested and did not sarkosyl insoluble fraction. Exemplary bifunctional degrading compounds 6, 7, 2, and 5 used to generate the data shown in bars 6-9, greatly reduced sarkosyl insoluble α-synuclein conformational species. These data demonstrate that bifunctional compounds of the present disclosure are effective at degrading α-synuclein aggregates.

Targeted degradation of sarkosyl insoluble (SI) α-synuclein via exemplary bifunctional compounds was assessed by MJFF-14-6-4-2 conformation specific ELISA following treatment of PFF induced A53T α-synuclein overexpressing HEK293 cells with 1 μM exemplary compound compared to DMSO vehicle control. Degradation activity of the exemplary compounds of Table 2 is expressed as % DMSO control. Some exemplary bifunctional compounds were shown to have toxic effects at the concentration tested (1 μM), which manifested as either not effectively degrading α-synuclein or the cells were no longer present. In addition, some of the alpha synuclein binding moiety have been shown to block formation of α-synuclein aggregates in this assay. However, the effect of bifunctional targeting degraders, shown in FIG. 5, required the intact E3 ligase binding domain.

Methods

Cell Culture.

Trex293 (doxycycline inducible) cells stably expressing human α-SYN A53T (monoclonal) were plated in poly-d-lysine coated T-75 tissue culture flasks (4.5×10e6 cells/flask) in DMEM with 10% tet-free FBS, 10 μg/ml blasticidin, and 400 μg/ml zeocin. After an overnight incubation, the cells were induced to express α-SYN by treatment with 1 μg/ml doxycycline (Dox) and exemplary bifunctional compound. After a 24 hour dox induction, the medium on the cells was changed to Opti-MEM followed by treatment with α-SYN pre-formed fibrils** (PFFs)(5 μg/flask) pre-complexed with Lipofectamine 2000 transfection reagent for 4 hours. After PFF treatment, the medium was changed back to DMEM with the supplements described above and exemplary bifunctional compound for 48 hours.

Sarkosyl Insoluble α-SYN Isolation.

Cell pellets were harvested from each flask using 0.25% trypsin followed by spinning at 500×g for 5 minutes. Each pellet was resuspended in 1 ml cold buffer H [Buffer H-10 mM Tris, 1 mM EGTA, 0.8M NaCl, 10% sucrose, pH7.4 containing 1× protease and phosphatase inhibitors] containing protease and phosphatase inhibitors. The resuspended pellets were incubated on ice for 20 minutes followed by centrifugation at 27,200×g for 20 minutes at 4° C. The supernatants were adjusted to 1% sarkosyl (Sigma) and 1% 2-mercaptoethanol followed by incubation for 1 hour at 37° C. on an orbital shaker set to 400 rpm. The samples were then spun at 150,000×g for 35 minutes at room temperature. The supernatant was removed and saved as the soluble fraction and the insoluble pellet was resuspended in 25 μl tris-buffered saline (TBS). Protein concentrations were determined by NanoDrop, and normalized protein concentrations were analyzed by WES capillary electrophoresis as well as an α-SYN oligomer ELISA.

Pre-Formed Fibril (PFF) Preparation.

Recombinant human α-SYN was purchased from Proteos. 1 mg aliquots were supplied at 10 mg/ml in 10 mM Tris, 50 mM NaCl, pH7.6. The aliquot was thawed on ice followed by centrifugation at 4° C. for 10 minutes at 12,000×g to pellet any insoluble material. The supernatant was removed and quantitated on a NanoDrop (A280) using Beer's Law (ε=5960 M-1 cm-1). The concentration was adjusted to 5 mg/ml in PBS followed by vortexing for 3 seconds to mix contents. The mixture was incubated in an orbital shaker set to 37° C. at 1,000 rpm for 7 days followed by aliquoting into individual use vials. Prior to addition to cells, an aliquot was thawed at room temperature, then diluted to 1 mg/ml with phosphate-buffered saline (PBS) followed by sonication for 1 minute with a probe sonicator (output 1; 90% duty cycle) in a chem hood.

α-SYN Oligomer ELISA.

Coming Costar high bind black well plates were coated with MJFR 14-6-4-2 (Abcam) at 1 μg/ml for 1 hour at 37° C. followed by washing with 1×TBS+0.1% tween-20 (TBS-T) then blocking with 3% bovine serum albumin (BSA) in TBS. After re-washing, samples were added after dilution in diluent (1% BSA/TBS-T). Non-sonicated PFF was used to generate a standard curve. The plates were incubated with sample overnight at 4° C. with shaking. The following day alkaline phosphatase (AP) conjugated MJFR 14-6-4-2 was added to the plate without washing followed by incubation at room temperature for 1 hour with shaking or rocking. The plates were then re-washed and substrate (CDP star alkaline phosphatase detection reagent) was added followed by a 30 minute incubation at room temperature. The plate was read on a luminescence plate reader. The counts were log transformed and read off the standard curve. Bifunctional compound treated samples were compared to DMSO control.

Analysis of Sarkosyl Insoluble α-Synuclein.

Figure 2B:
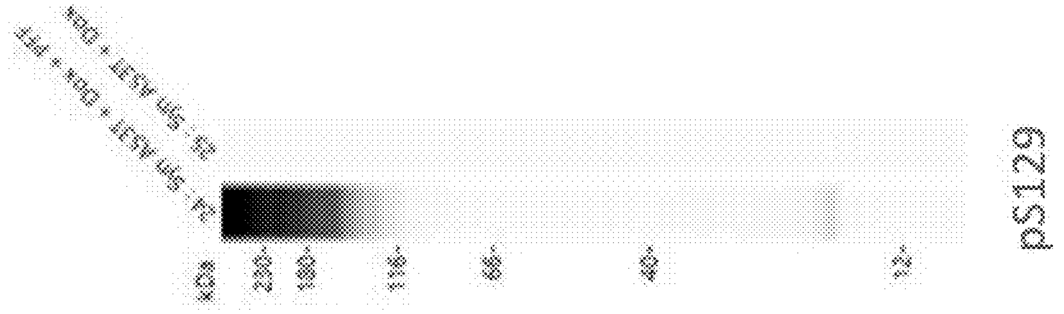
FIGS. 2A and 2B. Pre-formed alpha-synuclein fibrils (α-syn PFFs) were added to TREX tetracycline inducible HEK293 cells that overexpress A53T mutant α-syn to induce detergent-insoluble aggregates as measured by WES™ (capillary protein separation and immunoblot analysis).
Figure 2A:
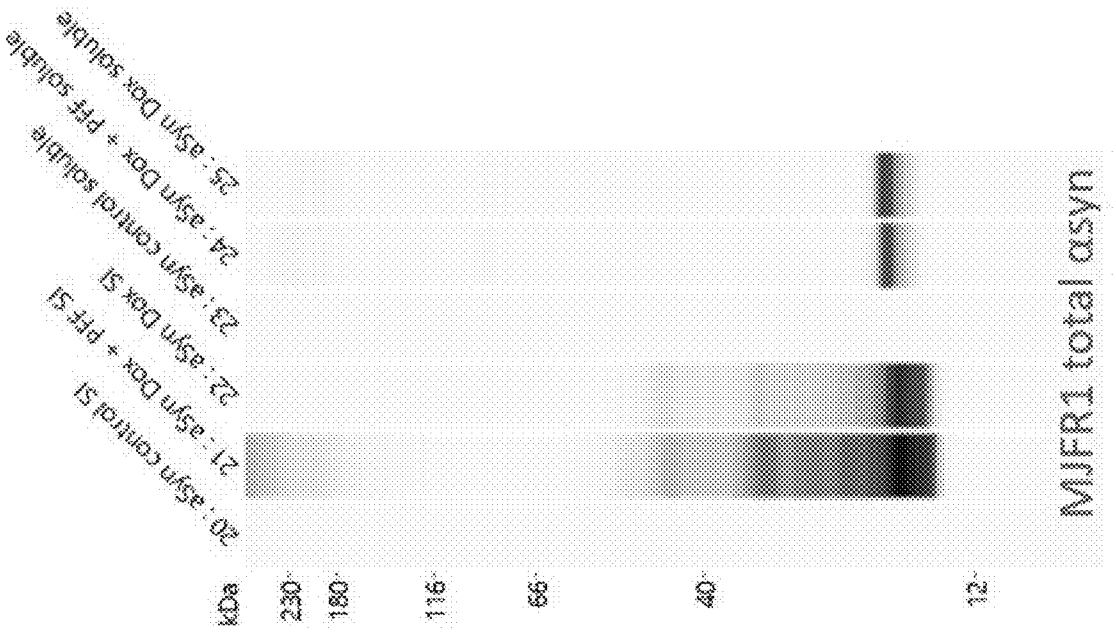

Detergent (sarkosyl) insoluble α-synuclein (α-syn) has been implicated in pathologic progression and transmission in Lewy body dementias including Parkinson's Disease. In an effort to investigate the ability of bifunctional compounds targeting α-syn to clear both insoluble and soluble α-syn oligomeric species, a sarkosyl insoluble α-syn assay was developed. To this end, tetracycline-inducible HEK293 cell clones stably expressing mutant A53T α-synuclein have been generated and characterized. Pre-formed fibrils (PFFs) synthesized from recombinant α-syn were added to seed recruitment of α-syn into aggregates characterized by sarkosyl insoluble (SI) and α-syn soluble fractions (FIG. 2A) as well as detergent insoluble α-syn phosphorylated on serine 129 (FIG. 2B).

Degradation of Sarkosyl-Insoluble α-Synuclein Via Exemplary Bifunctional Compounds.

Figure 3:
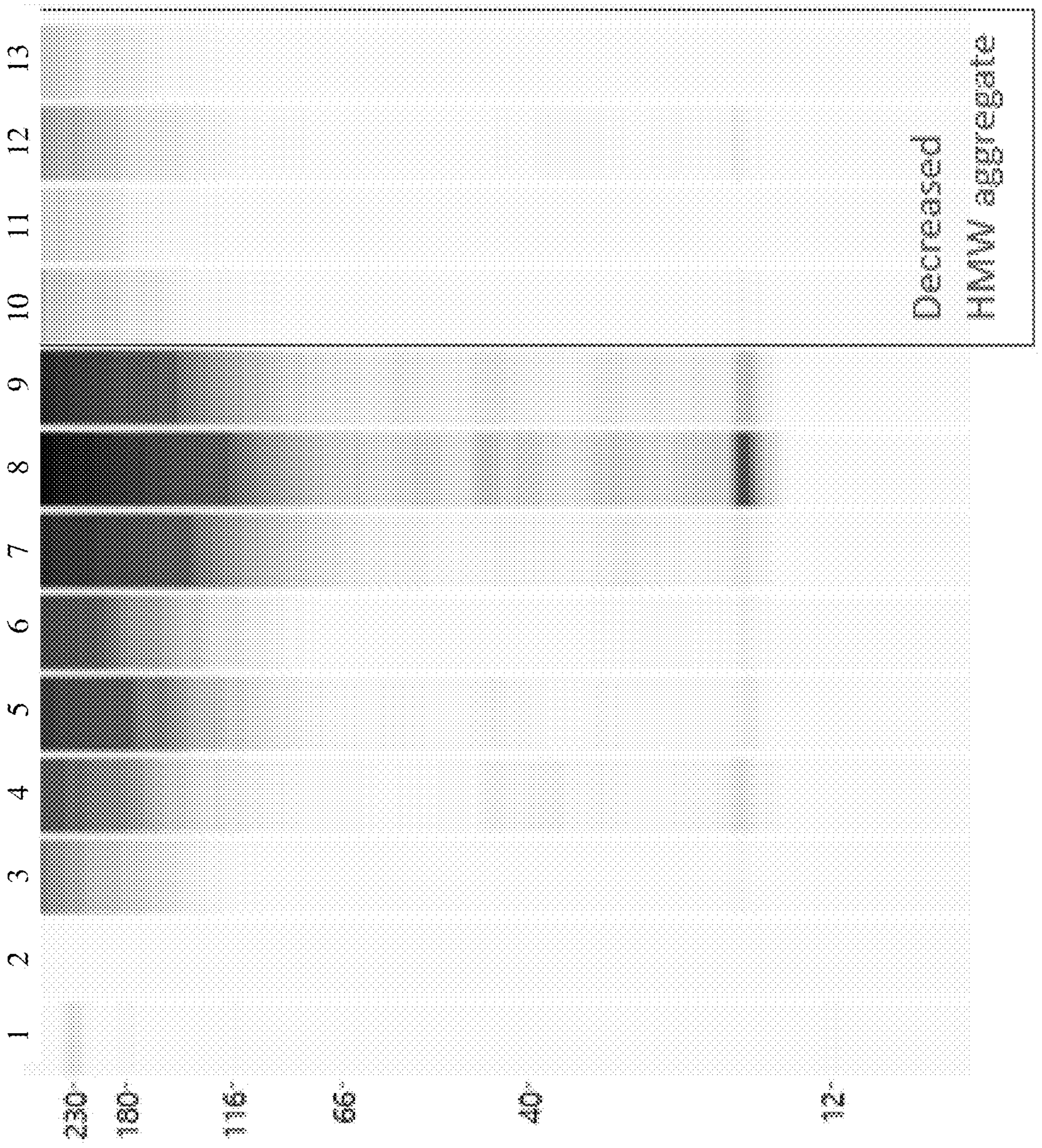
FIG. 3. Targeted degradation of sarkosyl-insoluble α-synuclein via exemplary bifunctional degradation compounds. Targeted degradation of sarkosyl insoluble (SI) α-synuclein via bifunctional degradation compounds was assessed by MJFR1 immunoreactivity by WES™ following treatment of PFF induced A53T α-synuclein overexpressing HEK293 cells with 1 μM bifunctional compound to DMSO vehicle control lane (lane 3). The molecular weight ladder lane 1 and uninduced A53T α-synuclein lane 2 is shown. Bifunctional degrading compounds in lanes 5 (Exemplary Compound 25), 7 (Exemplary Compound 13), 8 (Exemplary Compound 12), and 9 (Exemplary Compound 9) resulted in cytotoxicity (data not shown) at the concentration tested and did not see a decrease in sarkosyl insoluble α-synuclein. Bifunctional degrading compounds in lanes 10 (Exemplary Compound 6), 11 (Exemplary Compound 7), 12 (Exemplary Compound 2), and 13 (Exemplary Compound 5) greatly reduced sarkosyl insoluble α-synuclein. These data indicate that exemplary bifunctional compounds that effectively degrade α-synuclein aggregates have been identified.

To assess targeted degradation of sarkosyl insoluble α-synuclein, exemplary bifunctional compounds designed to bind to oligomeric α-synuclein were tested at 1 μM in PFF induced HEK293 TREX α-syn A53T cells. As shown in FIG. 3, it was observed that some exemplary bifunctional compounds (e.g., exemplary compounds 25, 13, 12, and 9 in lanes 5, 7, 8 and 9) were cytotoxic at the concentration tested (1 μM), determined via visual inspection, and did not effectively degrade α-synuclein. Importantly, exemplary compounds 6, 7, 2, and 5 (lanes 10-13) greatly reduced sarkosyl insoluble α-synuclein, as measured using MJFR1 antibody by WES™, when compared to the DMSO control lane (lane 3), without any visual impact to cell health.

Development of a Conformational Specific ELISA for α-Synuclein Aggregates.

Figure 4:
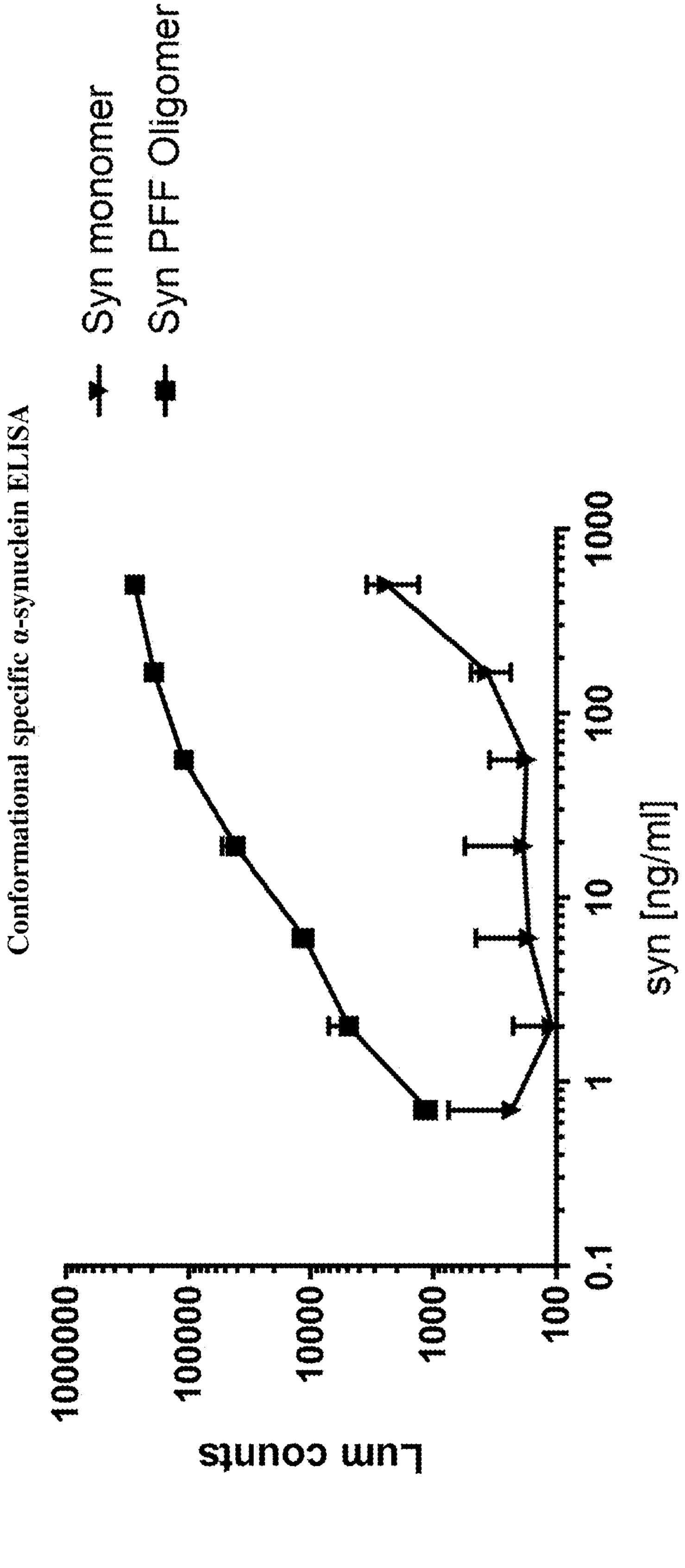
FIG. 4. Development of a conformational specific ELISA for α-Synuclein aggregates. Conformational specific α-synuclein ELISA was developed by coating High Binding 96-well ELISA plates with MJFF-14-6-4-2 antibody (Corning; Abcam). PFF oligomeric synuclein or monomeric synuclein were made as described in Graef et al., 2019 (full citation included below) and dilution curves were generated with the highest standard concentration of 600 ng/ml. Following incubation, MJFF-14-6-4-2 secondary antibody previously conjugated to alkaline phosphatase (AP; Novus Biologicals) was added to the ELISA plates for detection. Specificity for oligomeric α-synuclein is shown in squares compared to monomer in triangles. The linear range for detection of oligomeric α-synuclein is about 2 to about 150 ng/ml.

To quantify degradation of α-synuclein aggregating species for in vitro and in vivo pharmacology studies, we developed an enzyme-linked immunosorbent assay (ELISA) using an antibody that recognizes pathologic, conformational specific α-synuclein protein species. The MJFR 14-6-4-2 antibody that recognizes fibrillar forms of α-synuclein was used for both capture of fibrillar forms of α-synuclein and for detection. To assess specificity of this ELISA for α-synuclein oligomers compared to monomers, α-synuclein oligomers were made as described (Graef et al., 2019; Lassen et al., 2018). As shown in FIG. 4, the MJFR 14-6-4-2 antibody capture and detection ELISA specifically recognizes oligomeric (squares), not monomeric (triangle) forms of α-synuclein. The linear range of this conformational specific α-synuclein ELISA is approximately 2 ng/ml to about 150 ng/ml and is used to study α-synuclein degradation in vitro and in vivo. α-synuclein biophysical assays using microthermophoresis and quantitative ELISA specific for monomeric α-synuclein enable the qualification of bifunctional degradation compounds that distinguish between monomer versus oligomer binding and degradation (Wolff et al., 2016).

Exemplary α-Synuclein Targeting Compounds Induce Degradation of Oligomeric α-Synuclein.

The conformational specific ELISA described above was used to assess degradation of α-synuclein in HEK293 TREX α-syn A53T cells treated with PFF to induce sarkosyl insoluble α-synuclein aggregates. As show in FIG. 5, it was observed that after treatment certain exemplary bifunctional compounds (e.g., exemplary compounds 25, 12, and 9 of bars 2, 4 and 5) were cytotoxic at the concentration tested (1 μM) and did not effectively degrade oligomeric α-synuclein in the sarkosyl insoluble fraction, thereby confirming the cytotoxicity described in FIG. 3. More importantly, exemplary compounds 6, 7, 2, and 5 (bars 6-9) significantly reduced sarkosyl insoluble oligomeric α-synuclein, as measured using the MJFF-14-6-4-2 conformation specific ELISA. These α-synuclein targeting bifunctional compounds were further assessed in vitro and in vivo in synucleinopathy models for pharmacologic efficacy. Additional experiments shown in FIG. 6A, as discussed below, examine E3 ligase competition for confirmation of mechanism.

Alpha Synuclein Targeted Degradation Via Exemplary Bifunctional Compounds Requires the E3 Ligase Activity for Effective Degradation.

Figure 6A:
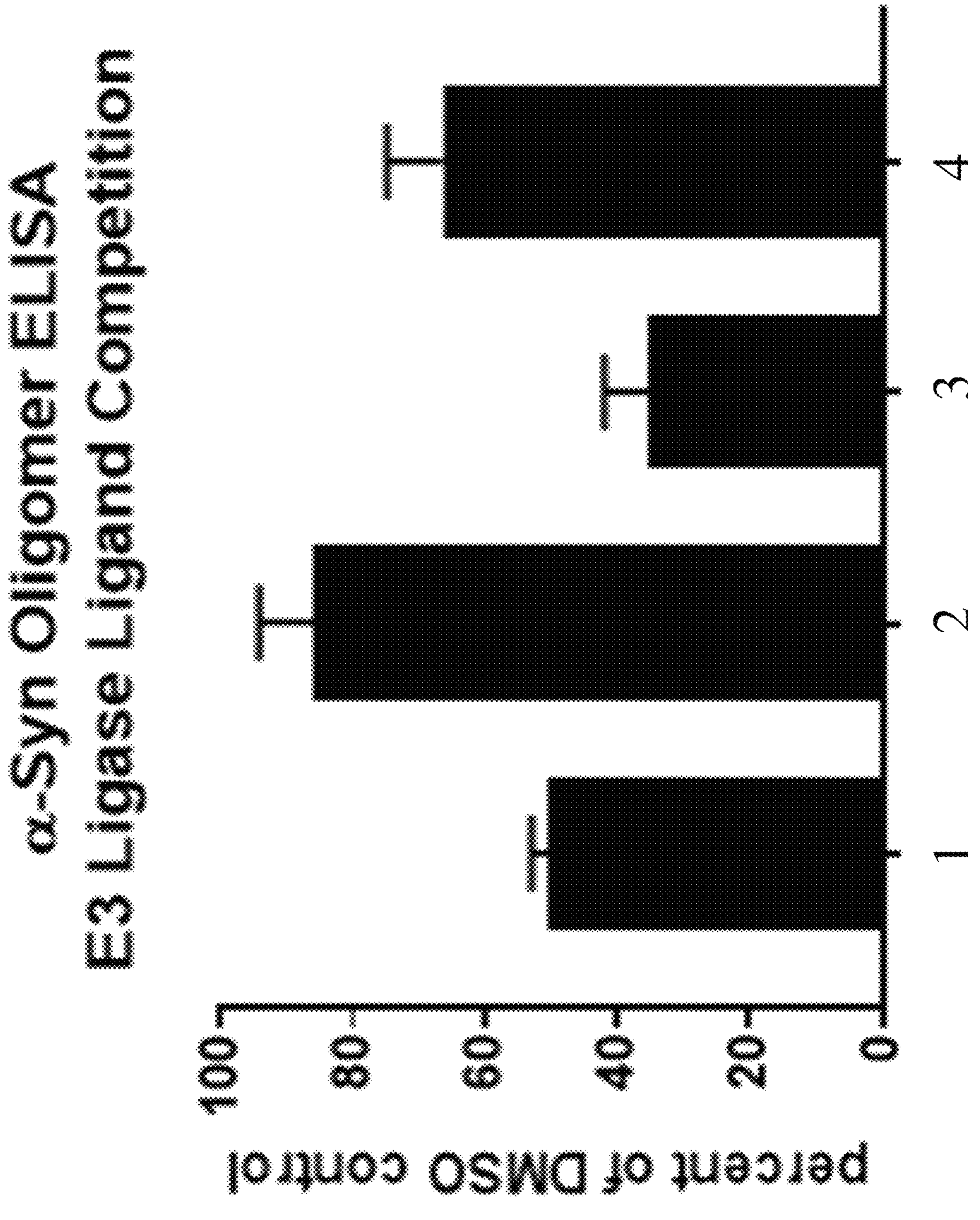
FIGS. 6A and 6B. α-Synuclein bifunctional degradation compound activity requires the E3 ligase activity for effective degradation. Pre-formed alpha-synuclein fibrils (α-syn PFFs) were added to TREX tetracycline inducible HEK293 cells that overexpress A53T mutant α-syn to induce detergent-insoluble oligomers as measured by Oligomer ELISA. Doxycycline induced α-syn A53T cells were treated with PFFs to produce higher order oligomeric α-syn A53T in the sarkosyl insoluble fraction and SI α-syn oligomers were detected by ELISA, as described in below. Exemplary bifunctional degradation compounds 7 and 23 at 1 uM concentration, used to generate the data shown in bars 1 and 3, reduced sarkosyl insoluble α-syn. Fifteen-fold excess E3 ligase ligands, VHL Ligand and Cereblon Ligand, shown in FIG. 6B, used to generate the data shown in bars 2 and 4, when co-incubated with the exemplary bifunctional compound treatment effectively competed the activity of the exemplary bifunctional compound to induce targeted degradation of α-syn. These data indicate that the exemplary bifunctional compound requires E3 ligase recruitment to α-syn to effectively induce degradation, thereby confirming the bifunctional compound mechanism of action.
Figure 6B:
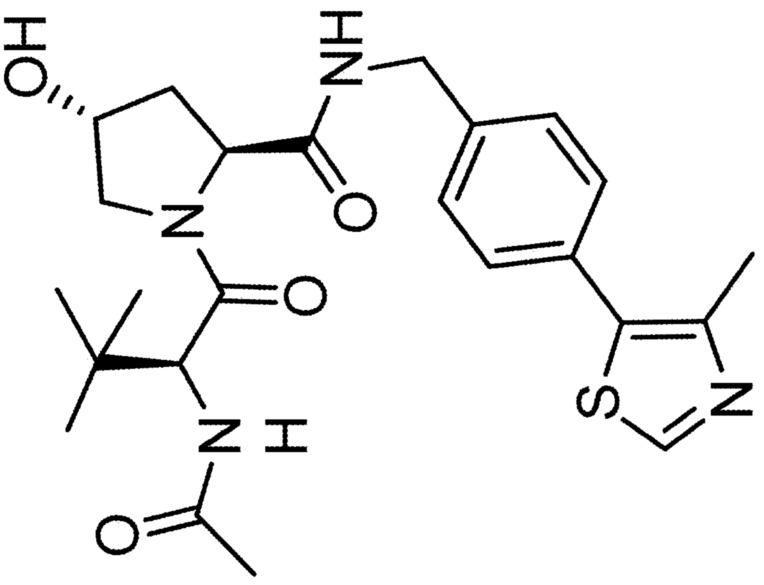
Figure 6B:
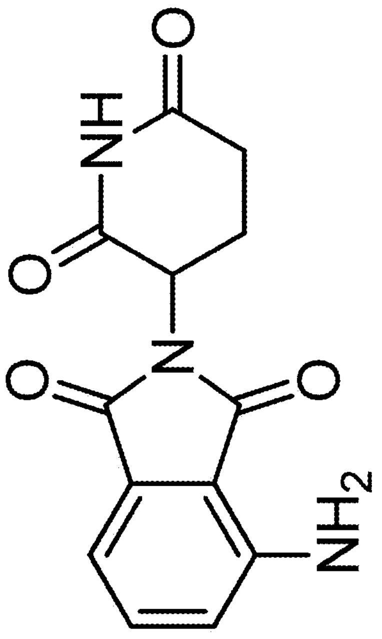

To determine if the degradation required activity of the E3 ligase, an E3 ligase ligand competition experiment was performed. To this end, tetracycline-inducible HEK293 cell clones stably expressing mutant A53T α-syn have been generated and characterized. Pre-formed fibrils (PFFs) synthesized from recombinant α-syn was added to seed recruitment of α-syn into oligomeric species characterized by being sarkosyl insoluble (SI), as described above. Exemplary compounds 7 and 23 (bars 1 and 3) effectively reduced SI A53T α-synuclein protein oligomers, as measured using the Oligomer ELISA, when compared to the DMSO control lane (Data not shown). To assess if this reduction in α-syn was in fact dependent upon ubiquitination induced by the exemplary bifunctional compounds, E3 ligase ligands, VHL Ligand and Cereblon Ligand (each shown in FIG. 6B) were co-incubated, in 15-fold molar excess, with exemplary compound 7 and exemplary compound 23, respectively, during treatment (bars 2 and 4). As shown in FIG. 6A, the activity of each exemplary bifunctional compound was effectively competed with the addition of excess E3 ligase ligand, indicating that E3 ligase recruitment is required for the degradation activity of the exemplary compounds.

Exemplary compounds are shown in Table 1 with the associated experimental data shown in Table 2.

TABLE 1

| Exemplary Compounds of the Present Disclosure | | |
|---|---|---|
| Ex. No. | Structure | Compound Name |
| 1 | 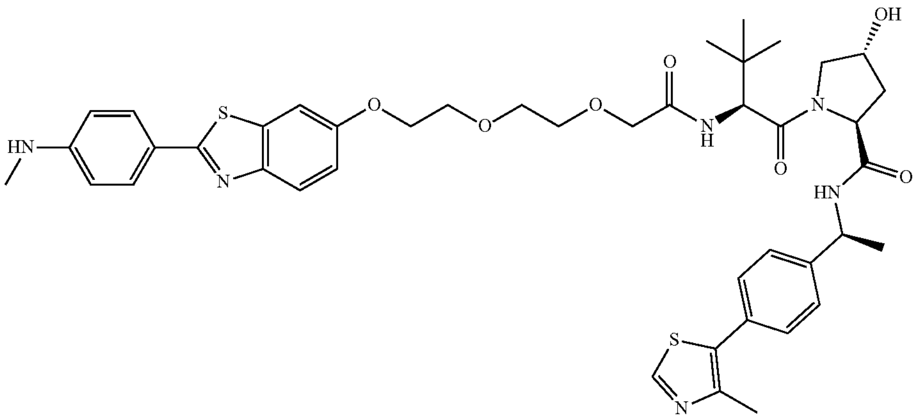 [SMILES: CNc1ccc(-c2nc3ccc(OCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1] | (2S,4R)-1-((S)-3,3-dimethyl-2-(2-(2-(2-((2-(4-(methylamino)phenyl)benzo[d]thiazol-6-yl)oxy)ethoxy)ethoxy)acetamido)butanoyl)-4-hydroxy-N-((S)-1-(4-(4-methylthiazol-5-yl)phenyl)ethyl)pyrrolidine-2-carboxamide |
| 2 | 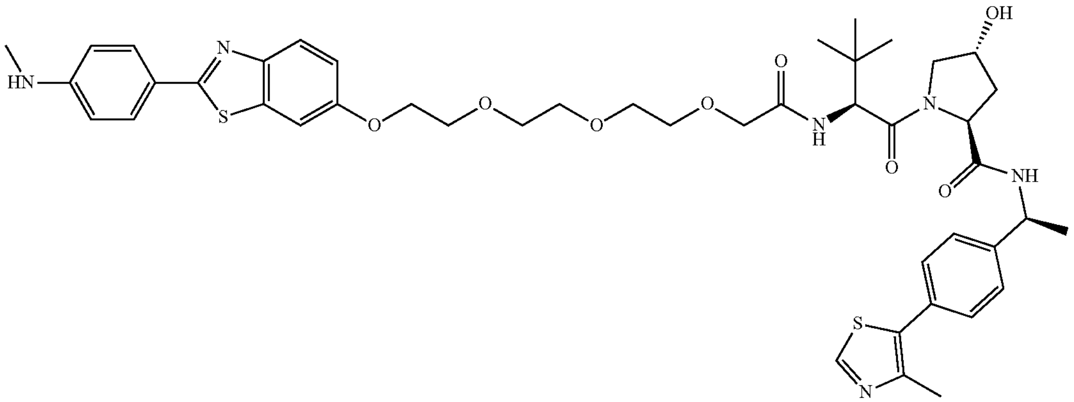 [SMILES: CNc1ccc(-c2nc3ccc(OCCOCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1] | (2S,4R)-1-((S)-2-(tert-butyl)-14-((2-(4-(methylamino)phenyl)benzo[d]thiazol-6-yl)oxy)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |

TABLE 1-continued

| Ex. No. | Structure | Compound Name |
|---|---|---|
| | Exemplary Compounds of the Present Disclosure | |
| 3 | 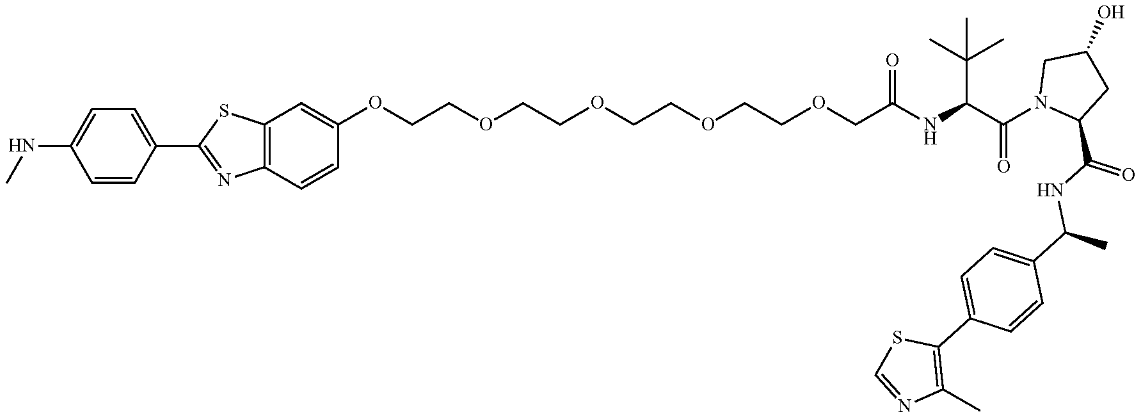 [SMILES: CNc1ccc(-c2nc3ccc(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1] | (2S,4R)-1-((S)-2-(tert-butyl)-17-((2-(4-(methylamino)phenyl) benzo[d]thiazol-6-yl)oxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide |
| 4 | 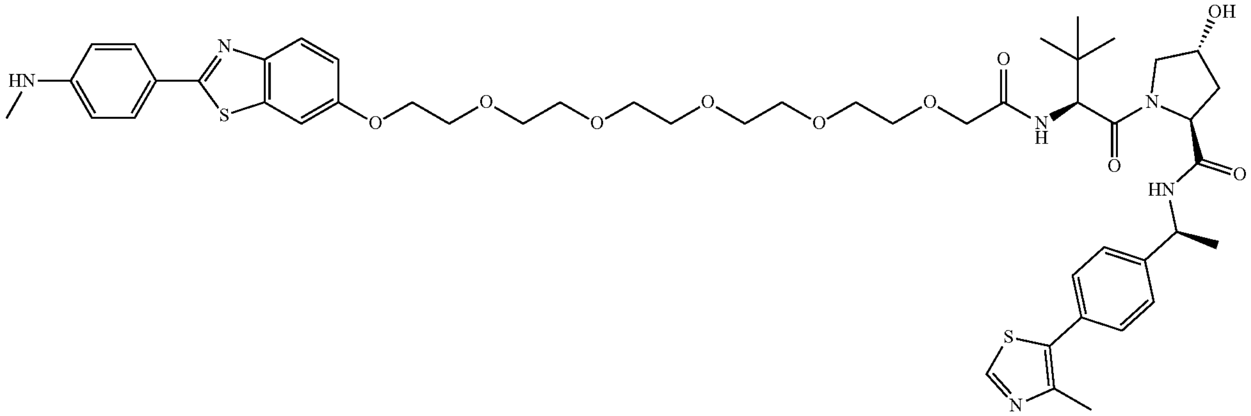 [SMILES: CNc1ccc(-c2nc3ccc(OCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1] | (2S,4R)-1-((S)-2-(tert-butyl)-20-((2-(4-(methylamino)phenyl) benzo[d]thiazol-6-yl)oxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 5 | 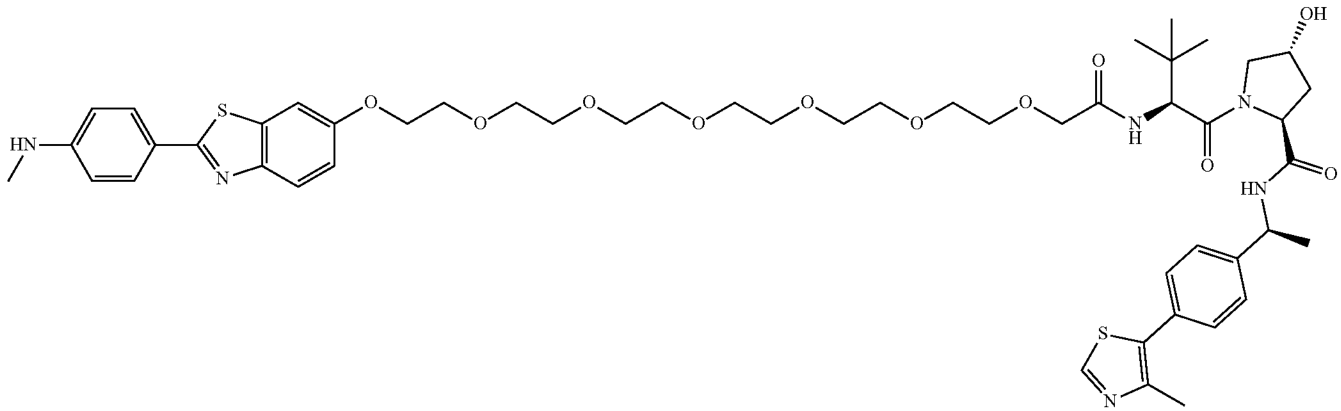 [SMILES: CNc1ccc(-c2nc3ccc(OCCOCCOCCOCCOCCOCCOCC(=O)N[C@H](C(=O)N4C[C@H](O)C[C@H]4C(=O)N[C@@H](C)c4ccc(-c5scnc5C)cc4)C(C)(C)C)cc3s2)cc1] | (2S,4R)-1-((S)-2-(tert-butyl)-23-((2-(4-(methylamino)phenyl) benzo[d]thiazol-6-yl)oxy)-4-oxo-6,9,12,15,18,21-hexaoxa-3-azatricosanoyl)-4-hydroxy-N-((S)-1-(4-(4-methylthiazol-5-yl)phenyl)ethyl)pyrrolidine-2-carboxamide |
| 6 | 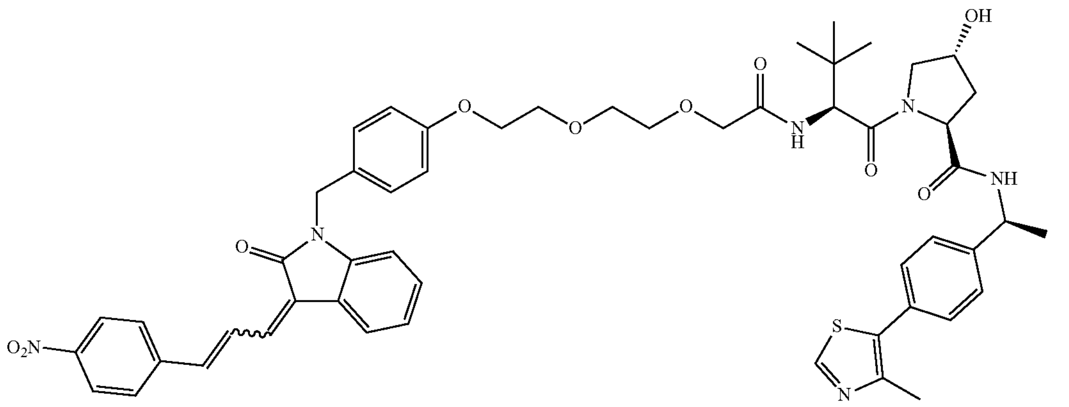 [SMILES: Cc1ncsc1-c1ccc([C@H](C)NC(=O)[C@@H]2C[C@@H](O)CN2C(=O)[C@@H](NC(=O)COCCOCCOc2ccc(CN3C(=O)C(=CC=Cc4ccc([N+](=O)[O-])cc4)c4ccccc43)cc2)C(C)(C)C)cc1] | (2S,4R)-1-((S)-3,3-dimethyl-2-(2-(2-(2-(4-(((Z)-3-((E)-3-(4-nitrophenyl)allylidene)-2-oxoindolin-1-yl)methyl)phenoxy)ethoxy) ethoxy)acetamido)butanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 7 | 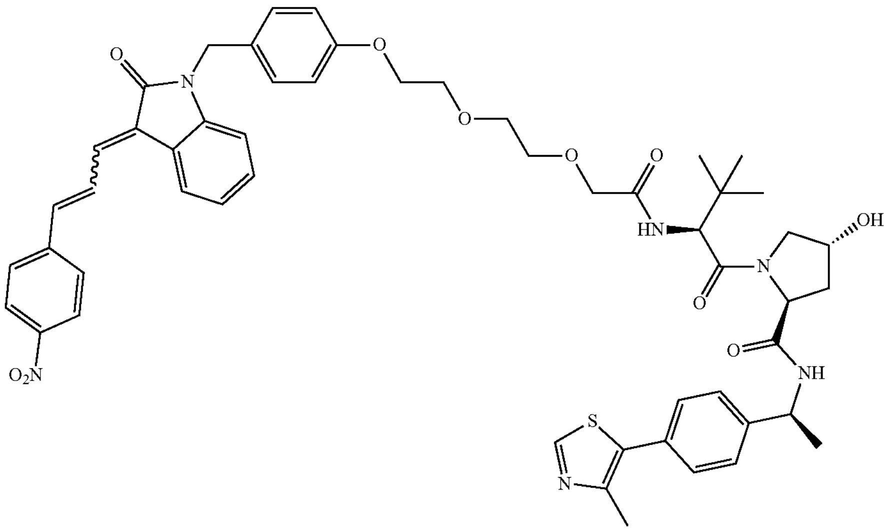 [SMILES: Cc1ncsc1-c1ccc([C@H](C)NC(=O)[C@@H]2C[C@@H](O)CN2C(=O)[C@@H](NC(=O)COCCOCCOc2ccc(CN3C(=O)C(=CC=Cc4ccc([N+](=O)[O-])cc4)c4ccccc43)cc2)C(C)(C)C)cc1] | (2S,4R)-1-((S)-3,3-dimethyl-2-(2-(2-(2-(4-(((E)-3-((E)-3-(4-nitrophenyl)allylidene)-2-oxoindolin-1-yl)methyl)phenoxy)ethoxy)ethoxy)acetamido)butanoyl)-4-hydroxy-N-((S)-1-(4-(4-methylthiazol-5-yl)phenyl)ethyl)pyrrolidine-2-carboxamide |
| 8 | 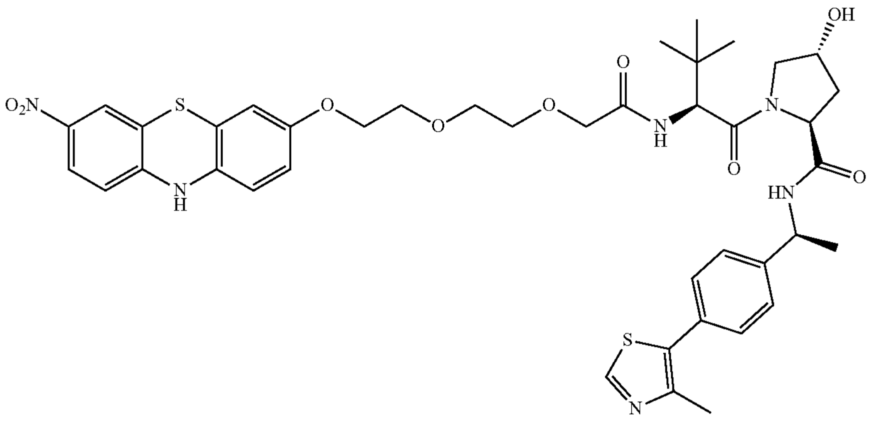 [SMILES: Cc1ncsc1-c1ccc([C@H](C)NC(=O)[C@@H]2C[C@@H](O)CN2C(=O)[C@@H](NC(=O)COCCOCCOc2ccc3c(c2)Sc2cc([N+](=O)[O-])ccc2N3)C(C)(C)C)cc1] | (2S,4R)-1-((S)-3,3-dimethyl-2-(2-(2-(2-((7-nitro-10H-phenothiazin-3-yl)oxy)ethoxy)ethoxy)acetamido)butanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 9 | 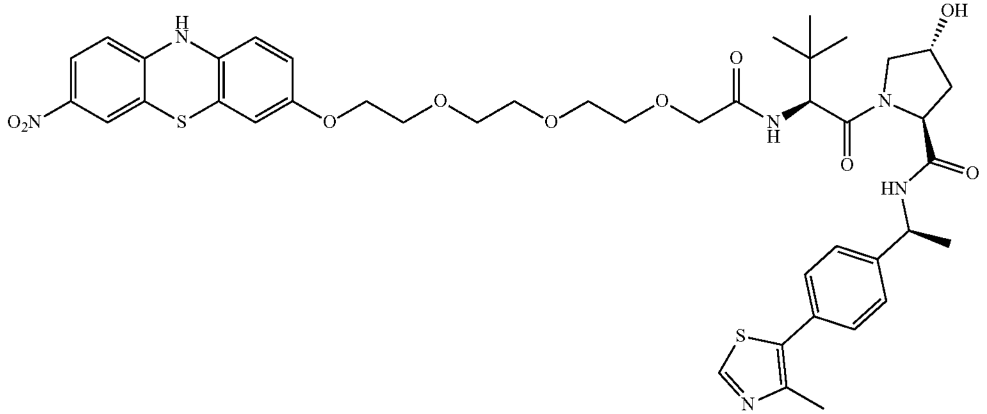 [SMILES: Cc1ncsc1-c1ccc([C@H](C)NC(=O)[C@@H]2C[C@@H](O)CN2C(=O)[C@@H](NC(=O)COCCOCCOCCOc2ccc3c(c2)Sc2cc([N+](=O)[O-])ccc2N3)C(C)(C)C)cc1] | (2S,4R)-1-((S)-2-(tert-butyl)-14-((7-nitro-10H-phenothiazin-3-yl)oxy)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |
| 10 | 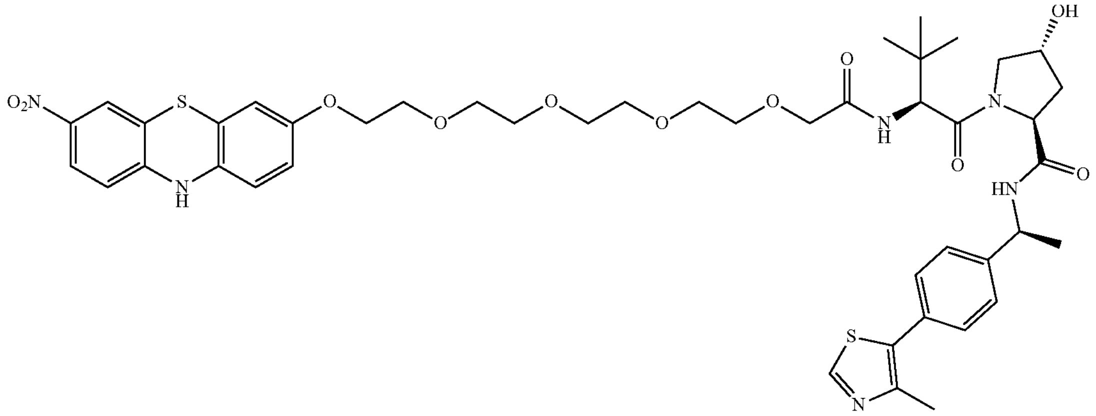 [SMILES: Cc1ncsc1-c1ccc([C@H](C)NC(=O)[C@@H]2C[C@@H](O)CN2C(=O)[C@@H](NC(=O)COCCOCCOCCOCCOc2ccc3c(c2)Sc2cc([N+](=O)[O-])ccc2N3)C(C)(C)C)cc1] | (2S,4R)-1-((S)-2-(tert-butyl)-17-((7-nitro-10H-phenothiazin-3-yl)oxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 11 | 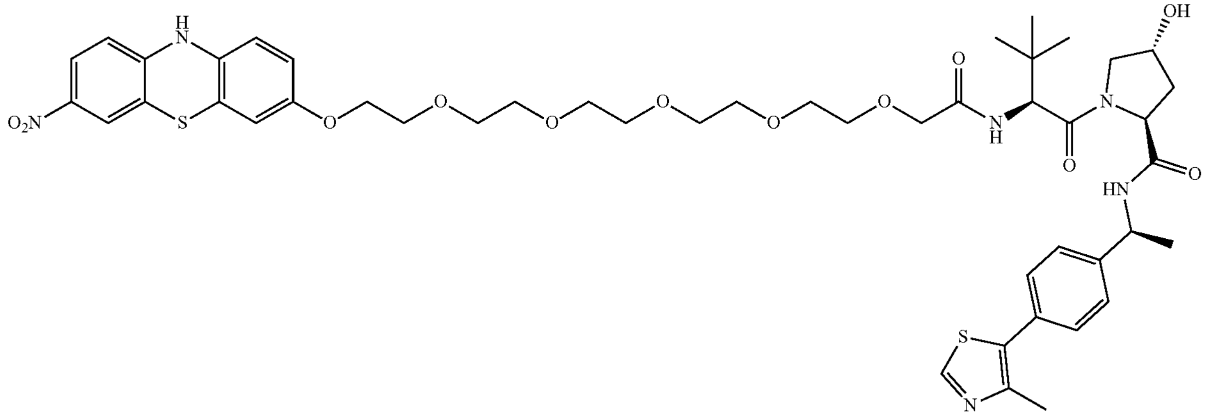 [SMILES: Cc1ncsc1-c1ccc([C@H](C)NC(=O)[C@@H]2C[C@@H](O)CN2C(=O)[C@@H](NC(=O)COCCOCCOCCOCCOCCOc2ccc3c(c2)Sc2cc([N+](=O)[O-])ccc2N3)C(C)(C)C)cc1] | (2S,4R)-1-((S)-2-(tert-butyl)-20-((7-nitro-10H-phenothiazin-3-yl)oxy)-4-oxo-6,9,12,15,18-pentaoxa-3-azaicosanoyl)-4-hydroxy-N-((S)-1-(4-(4-methylthiazol-5-yl)phenyl)ethyl)pyrrolidine-2-carboxamide |
| 12 | 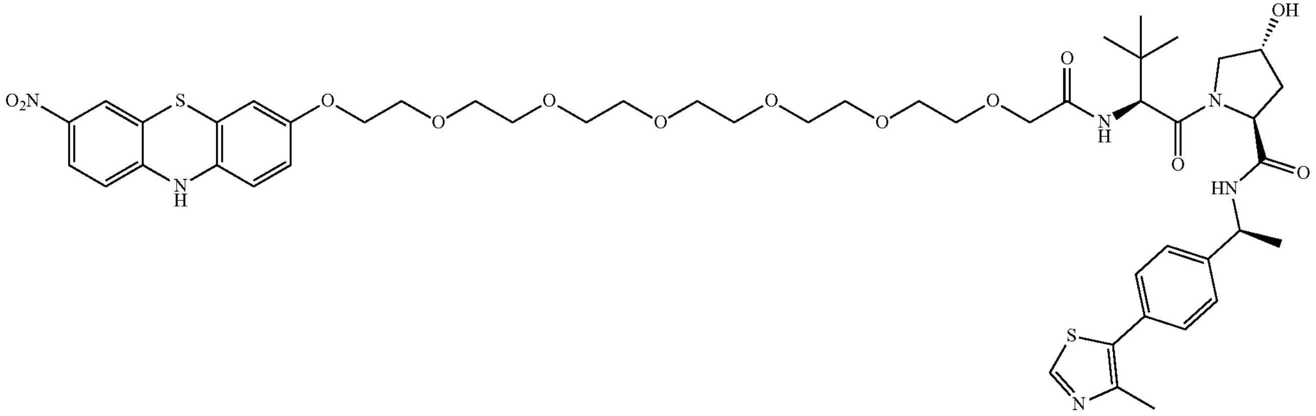 [SMILES: Cc1ncsc1-c1ccc([C@H](C)NC(=O)[C@@H]2C[C@@H](O)CN2C(=O)[C@@H](NC(=O)COCCOCCOCCOCCOCCOCCOc2ccc3c(c2)Sc2cc([N+](=O)[O-])ccc2N3)C(C)(C)C)cc1] | (2S,4R)-1-((S)-2-(tert-butyl)-23-((7-nitro-10H-phenothiazin-3-yl)oxy)-4-oxo-6,9,12,15,18,21-hexaoxa-3-azatricosanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 13 | 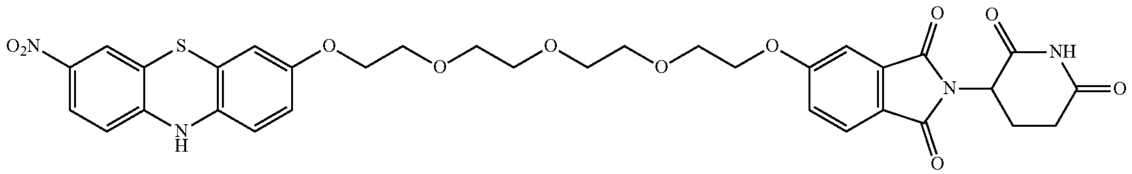 [SMILES: O=C1CCC(N2C(=O)c3ccc(OCCOCCOCCOCCOc4ccc5c(c4)Sc4cc([N+](=O)[O-])ccc4N5)cc3C2=O)C(=O)N1] | 2-(2,6-dioxopiperidin-3-yl)-5-(2-(2-(2-(2-((7-nitro-10H-phenothiazin-3-yl)oxy)ethoxy)ethoxy)ethoxy)ethoxy)isoindoline-1,3-dione |
| 14 | 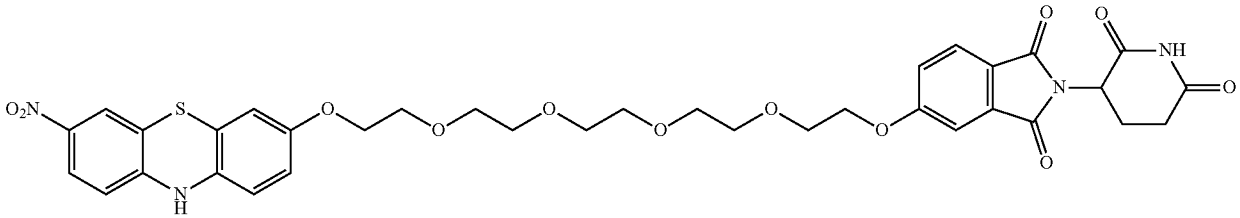 [SMILES: O=C1CCC(N2C(=O)c3ccc(OCCOCCOCCOCCOCCOc4ccc5c(c4)Sc4cc([N+](=O)[O-])ccc4N5)cc3C2=O)C(=O)N1] | 2-(2,6-dioxopiperidin-3-yl)-5-((14-((7-nitro-10H-phenothiazin-3-yl)oxy)-3,6,9,12-tetraoxatetradecyl)oxy)isoindoline-1,3-dione |
| 15 | 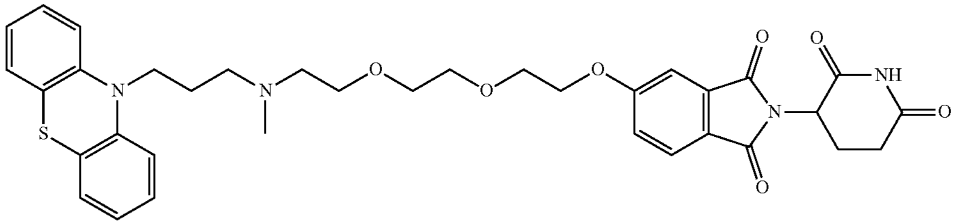 [SMILES: CN(CCCN1c2ccccc2Sc2ccccc21)CCOCCOCCOc1ccc2c(c1)C(=O)N(C1CCC(=O)NC1=O)C2=O] | 5-(2-(2-(2-((3-(10H-phenothiazin-10-yl)propyl)(methyl)amino)ethoxy)ethoxy)ethoxy)-2-(2,6-dioxopiperidin-3-yl)isoindoline-1,3-dione |
| 16 | 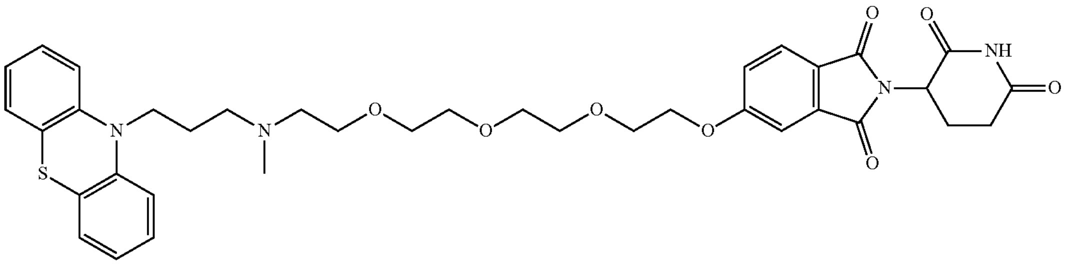 [SMILES: CN(CCCN1c2ccccc2Sc2ccccc21)CCOCCOCCOCCOc1ccc2c(c1)C(=O)N(C1CCC(=O)NC1=O)C2=O] | 2-(2,6-dioxopiperidin-3-yl)-5-((12-methyl-15-(10H-phenothiazin-10-yl)-3,6,9-trioxa-12-azapentadecyl)oxy)isoindoline-1,3-dione |

TABLE 1-continued

| Exemplary Compounds of the Present Disclosure | | |
|---|---|---|
| Ex. No. | Structure | Compound Name |
| 17 | 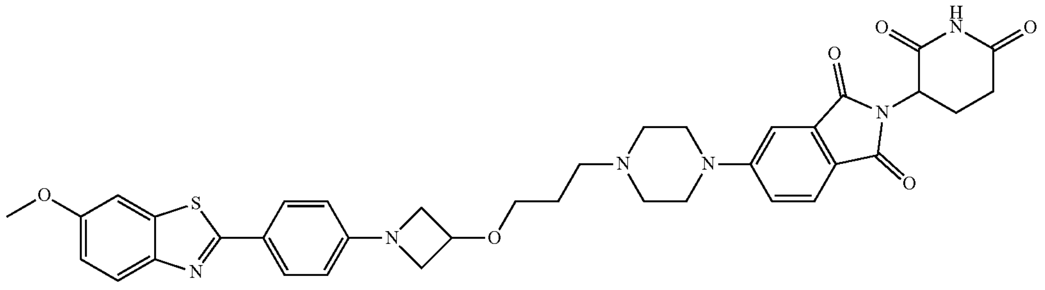 [SMILES: COc1ccc2nc(-c3ccc(N4CC(OCCCN5CCN(c6ccc7c(c6)C(=O)N(C6CCC(=O)NC6=O)C7=O)CC5)C4)cc3)sc2c1] | 2-(2,6-dioxopiperidin-3-yl)-5-(4-(3-((1-(4-(6-methoxybenzo[d]thiazol-2-yl)phenyl)azetidin-3-yl)oxy)propyl)piperazin-1-yl)isoindoline-1,3-dione |
| 18 | 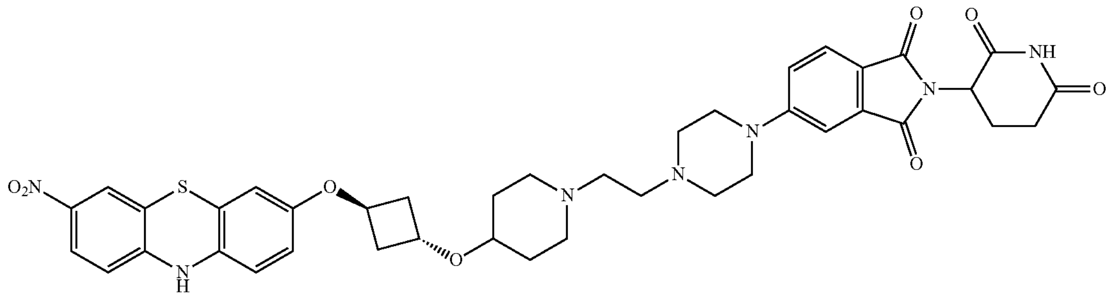 [SMILES: O=C1CCC(N2C(=O)c3ccc(N4CCN(CCN5CCC(O[C@H]6C[C@H](Oc7ccc8c(c7)Sc7cc([N+](=O)[O-])ccc7N8)C6)CC5)CC4)cc3C2=O)C(=O)N1] | 2-(2,6-dioxopiperidin-3-yl)-5-(4-(2-(4-((1r,3r)-3-((7-nitro-10H-phenothiazin-3-yl)oxy)cyclobutoxy)piperidin-1-yl)ethyl)piperazin-1-yl)isoindoline-1,3-dione |
| 19 | 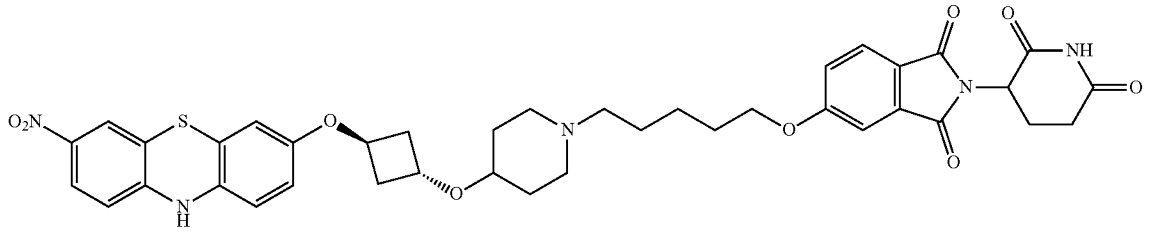 [SMILES: O=C1CCC(N2C(=O)c3ccc(OCCCCCN4CCC(O[C@H]5C[C@H](Oc6ccc7c(c6)Sc6cc([N+](=O)[O-])ccc6N7)C5)CC4)cc3C2=O)C(=O)N1] | 2-(2,6-dioxopiperidin-3-yl)-5-((5-(4-((1r,3r)-3-((7-nitro-10H-phenothiazin-3-yl)oxy)cyclobutoxy)piperidin-1-yl)pentyl)oxy)isoindoline-1,3-dione |

TABLE 1-continued

Exemplary Compounds of the Present Disclosure

| Ex. No. | Structure | Compound Name |
|---|---|---|
| 20 | 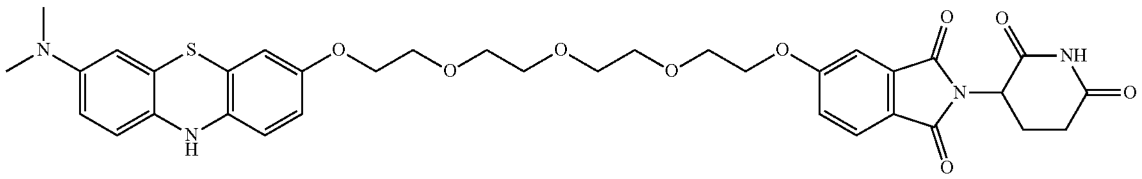 [SMILES: CN(C)c1ccc2c(c1)Sc1cc(OCCOCCOCCOCCOc3ccc4c(c3)C(=O)N(C3CCC(=O)NC3=O)C4=O)ccc1N2] | 5-(2-(2-(2-(2-((7-(dimethylamino)-10H-phenothiazin-3-yl)oxy)ethoxy)ethoxy)ethoxy)ethoxy)-2-(2,6-dioxopiperidin-3-yl)isoindoline-1,3-dione |
| 21 | 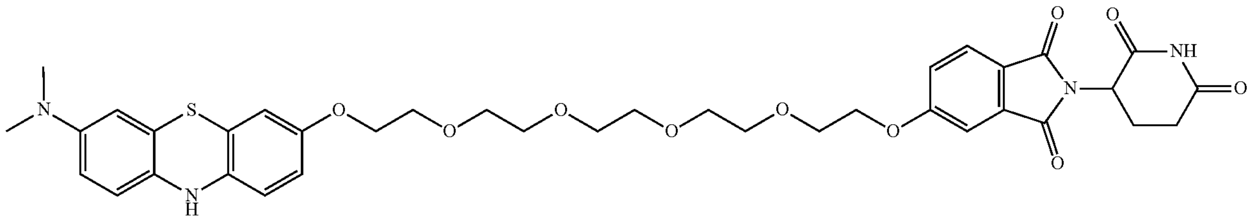 [SMILES: CN(C)c1ccc2c(c1)Sc1cc(OCCOCCOCCOCCOCCOc3ccc4c(c3)C(=O)N(C3CCC(=O)NC3=O)C4=O)ccc1N2] | 5-((14-((7-(dimethylamino)-10H-phenothiazin-3-yl)oxy)-3,6,9,12-tetraoxatetradecyl)oxy)-2-(2,6-dioxopiperidin-3-yl)isoindoline-1,3-dione |
| 22 | 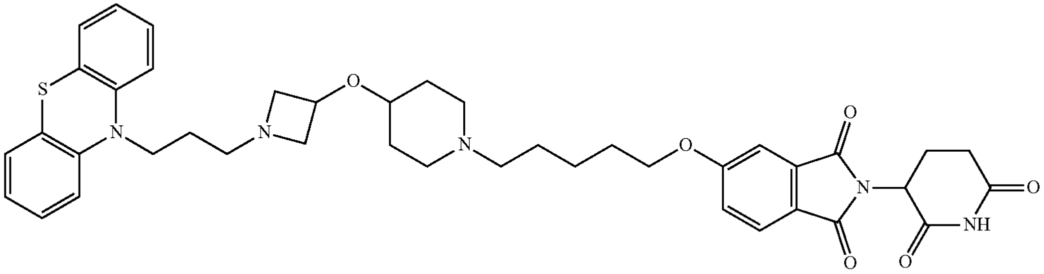 [SMILES: O=C1CCC(N2C(=O)c3ccc(OCCCCCN4CCC(OC5CN(CCCN6c7ccccc7Sc7ccccc76)C5)CC4)cc3C2=O)C(=O)N1] | 5-((5-(4-((1-(3-(10H-phenothiazin-10-yl)propyl)azetidin-3-yl)oxy)piperidin-1-yl)pentyl)oxy)-2-(2,6-dioxopiperidin-3-yl)isoindoline-1,3-dione |

TABLE 1-continued

Exemplary Compounds of the Present Disclosure

| Ex. No. | Structure | Compound Name |
| --- | --- | --- |
| 23 | 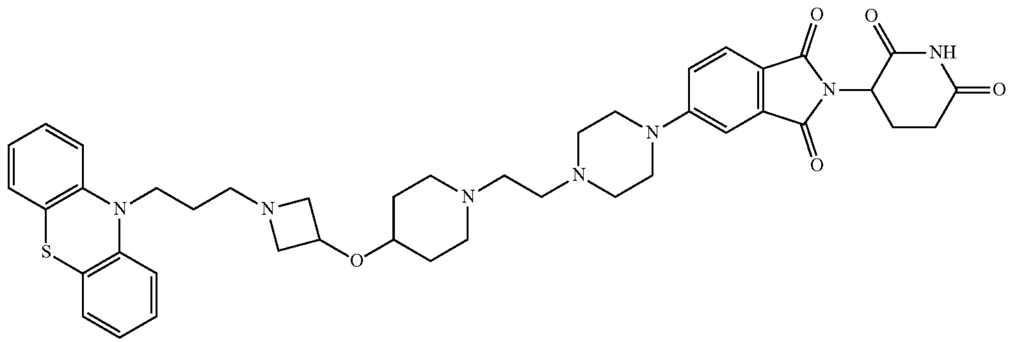 [SMILES: O=C1CCC(N2C(=O)c3ccc(N4CCN(CCN5CCC(OC6CN(CCCN7c8ccccc8Sc8ccccc87)C6)CC5)CC4)cc3C2=O)C(=O)N1] | 5-(4-(2-(4-((1-(3-(10H-phenothiazin-10-yl)propyl)azetidin-3-yl)oxy)piperidin-1-yl)ethyl)piperazin-1-yl)-2-(2,6-dioxopiperidin-3-yl)isoindoline-1,3-dione |
| 24 | 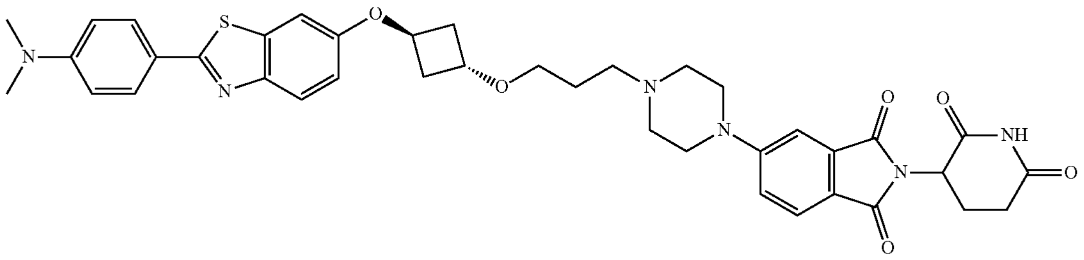 [SMILES: CN(C)c1ccc(-c2nc3ccc(O[C@H]4C[C@H](OCCCN5CCN(c6ccc7c(c6)C(=O)N(C6CCC(=O)NC6=O)C7=O)CC5)C4)cc3s2)cc1] | 5-(4-(3-((1r,3r)-3-((2-(4-(dimethylamino)phenyl)benzo[d]thiazol-6-yl)oxy)cyclobutoxy)propyl)piperazin-1-yl)-2-(2,6-dioxopiperidin-3-yl)isoindoline-1,3-dione |
| 25 | 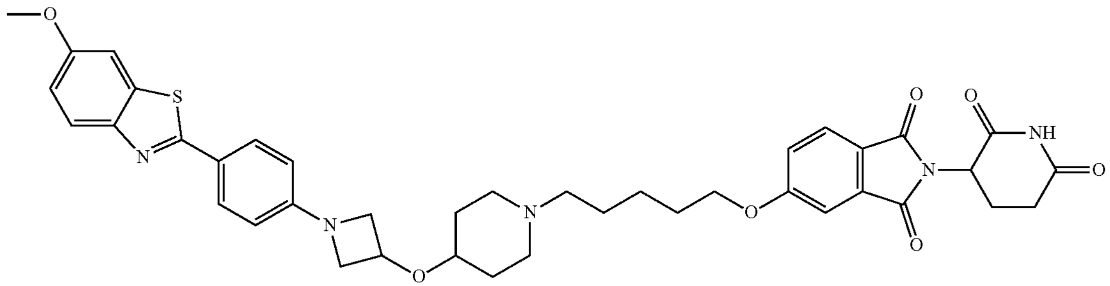 [SMILES: COc1ccc2nc(-c3ccc(N4CC(OC5CCN(CCCCCOc6ccc7c(c6)C(=O)N(C6CCC(=O)NC6=O)C7=O)CC5)C4)cc3)sc2c1] | 2-(2,6-dioxopiperidin-3-yl)-5-((5-(4-((1-(4-(6-methoxybenzo[d]thiazol-2-yl)phenyl)azetidin-3-yl)oxy)piperidin-1-yl)pentyl)oxy)isoindoline-1,3-dione |

TABLE 1-continued

| Exemplary Compounds of the Present Disclosure | | |
|---|---|---|
| Ex. No. | Structure | Compound Name |
| 26 | 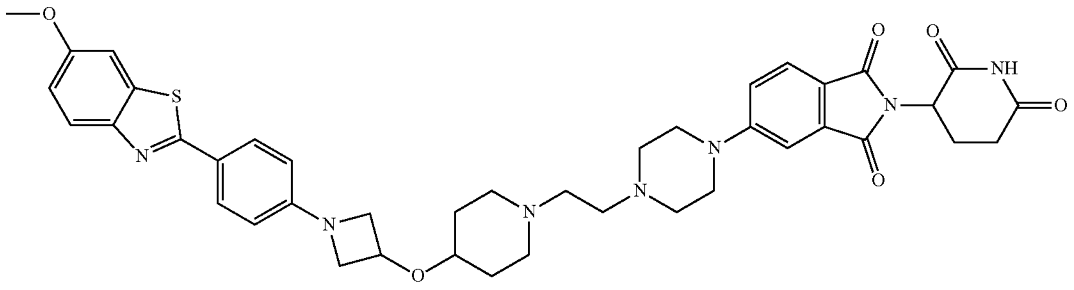 [SMILES: COc1ccc2nc(-c3ccc(N4CC(OC5CCN(CCN6CCN(c7ccc8c(c7)C(=O)N(C7CCC(=O)NC7=O)C8=O)CC6)CC5)C4)cc3)sc2c1] | 2-(2,6-dioxopiperidin-3-yl)-5-(4-(2-(4-((1-(4-(6-methoxybenzo[d]thiazol-2-yl)phenyl)azetidin-3-yl)oxy)piperidin-1-yl)ethyl)piperazin-1-yl)isoindoline-1,3-dione |
| 27 | 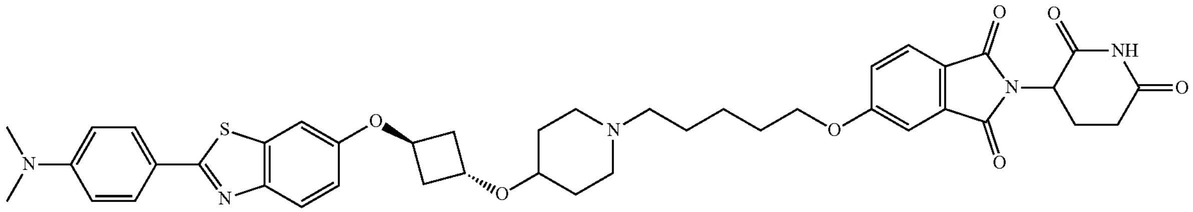 [SMILES: CN(C)c1ccc(-c2nc3ccc(O[C@H]4C[C@H](OC5CCN(CCCCCOc6ccc7c(c6)C(=O)N(C6CCC(=O)NC6=O)C7=O)CC5)C4)cc3s2)cc1] | 5-((5-(4-((1r,3r)-3-((2-(4-(dimethylamino)phenyl)benzo[d]thiazol-6-yl)oxy)cyclobutoxy)piperidin-1-yl)pentyl)oxy)-2-(2,6-dioxopiperidin-3-yl)isoindoline-1,3-dione |
| 28 | 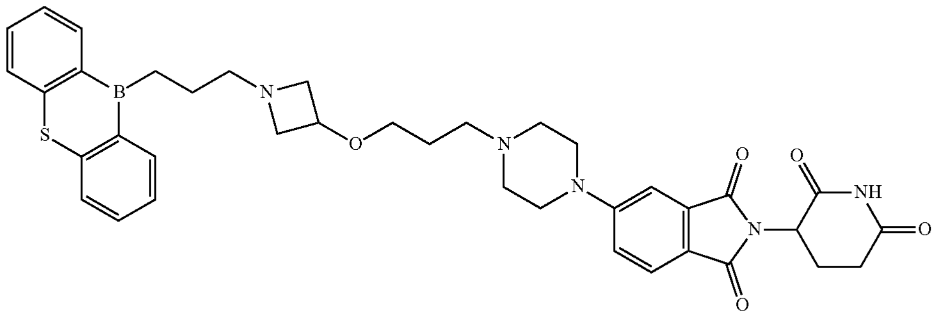 | 5-(4-(3-((1-(3-(10H-phenothiazin-10-yl)propyl)azetidin-3-yl)oxy)propyl)piperazin-1-yl)-2-(2,6-dioxopiperidin-3-yl)isoindoline-1,3-dione |

TABLE 1-continued

| Exemplary Compounds of the Present Disclosure | | |
|---|---|---|
| Ex. No. | Structure | Compound Name |
| 29 | 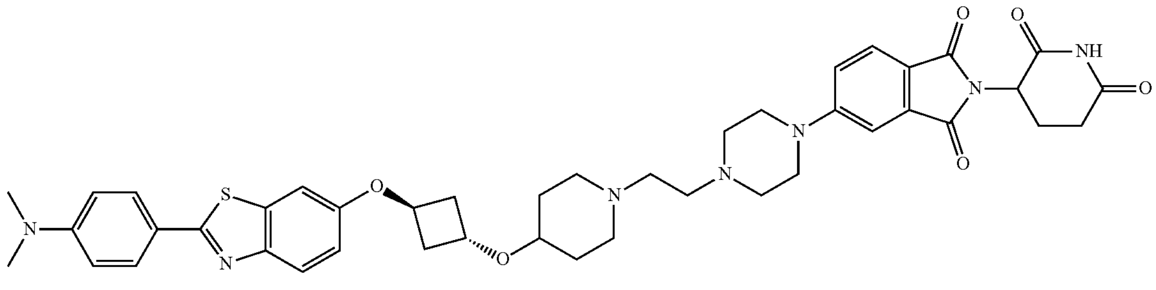 [SMILES: CN(C)c1ccc(-c2nc3ccc(O[C@H]4C[C@H](OC5CCN(CCN6CCN(c7ccc8c(c7)C(=O)N(C7CCC(=O)NC7=O)C8=O)CC6)CC5)C4)cc3s2)cc1] | 5-(4-(2-(4-((1r,3r)-3-((2-(4-(dimethylamino)phenyl)benzo[d]thiazol-6-yl)oxy)cyclobutoxy)piperidin-1-yl)ethyl)piperazin-1-yl)-2-(2,6-dioxopiperidin-3-yl)isoindoline-1,3-dione |
| 30 | 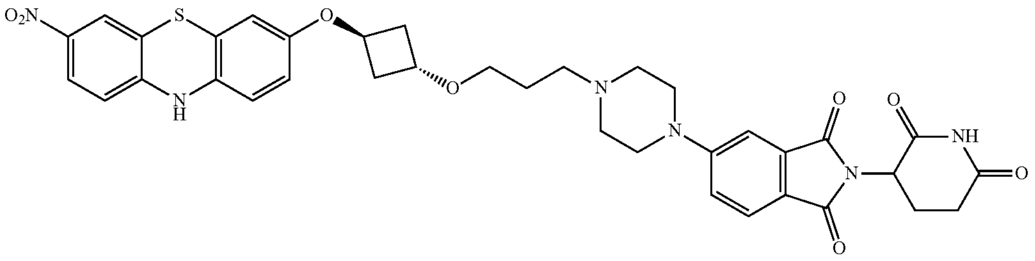 [SMILES: O=C1CCC(N2C(=O)c3ccc(N4CCN(CCCO[C@H]5C[C@H](Oc6ccc7c(c6)Sc6cc([N+](=O)[O-])ccc6N7)C5)CC4)cc3C2=O)C(=O)N1] | 2-(2,6-dioxopiperidin-3-yl)-5-(4-(3-((1r,3r)-3-((7-nitro-10H-phenothiazin-3-yl)oxy)cyclobutoxy)propyl)piperazin-1-yl)isoindoline-1,3-dione |
| 31 | 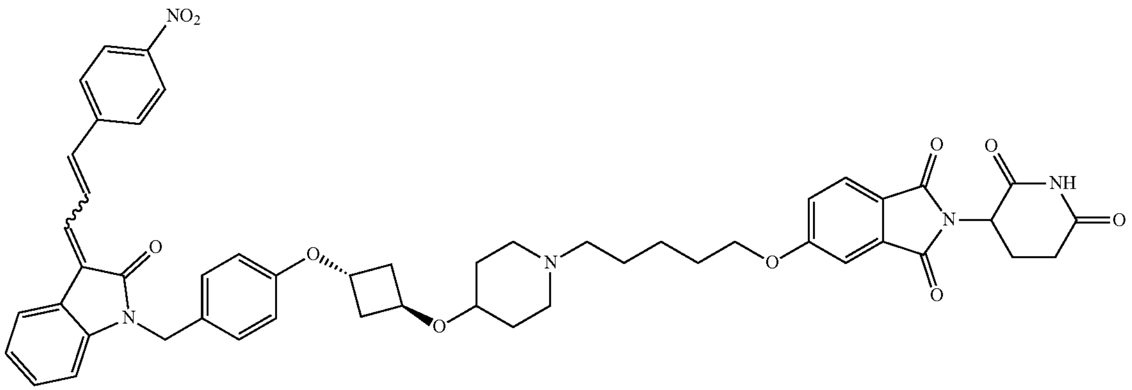 [SMILES: O=C1CCC(N2C(=O)c3ccc(OCCCCCN4CCC(O[C@H]5C[C@H](Oc6ccc(CN7C(=O)C(=CC=Cc8ccc([N+](=O)[O-])cc8)c8ccccc87)cc6)C5)CC4)cc3C2=O)C(=O)N1] | 2-(2,6-dioxopiperidin-3-yl)-5-((5-(4-((1r,3r)-3-(4-(((Z)-3-((E)-3-(4-nitrophenyl)allylidene)-2-oxoindolin-1-yl)methyl)phenoxy)cyclobutoxy)piperidin-1-yl)pentyl)oxy)isoindoline-1,3-dione |

TABLE 1-continued

Exemplary Compounds of the Present Disclosure

| Ex. No. | Structure | Compound Name |
| --- | --- | --- |
| 32 | 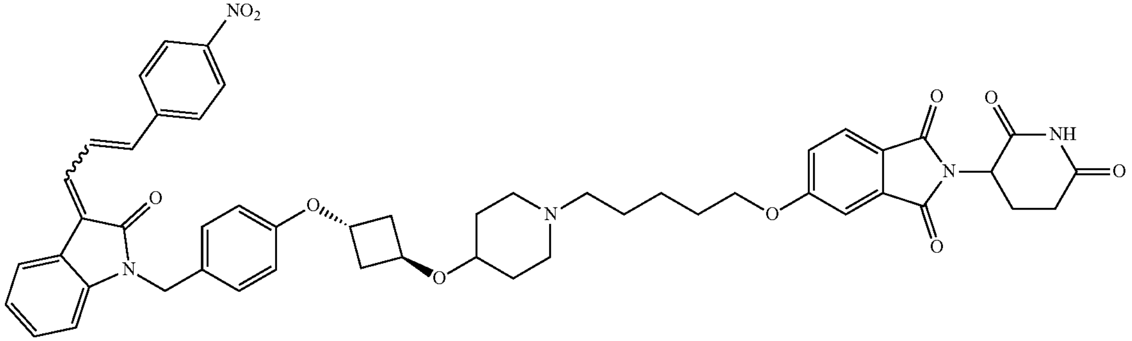 [SMILES: O=C1CCC(N2C(=O)c3ccc(OCCCCCN4CCC(O[C@H]5C[C@H](Oc6ccc(CN7C(=O)C(=CC=Cc8ccc([N+](=O)[O-])cc8)c8ccccc87)cc6)C5)CC4)cc3C2=O)C(=O)N1] | 2-(2,6-dioxopiperidin-3-yl)-5-((5-(4-((1r,3r)-3-(4-(((Z)-3-((E)-3-(4-nitrophenyl)allylidene)-2-oxoindolin-1-yl)methyl)phenoxy)cyclobutoxy)piperidin-1-yl)pentyl)oxy)isoindoline-1,3-dione |
| 33 | 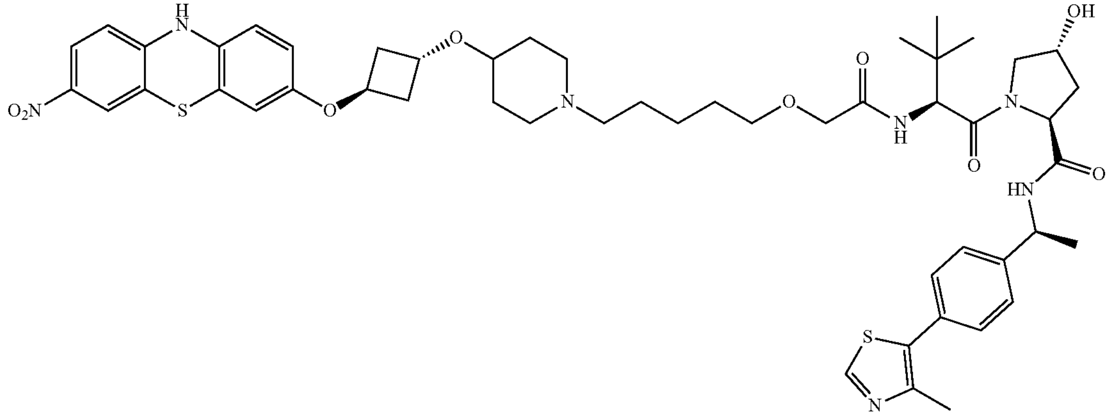 [SMILES: Cc1ncsc1-c1ccc([C@H](C)NC(=O)[C@@H]2C[C@@H](O)CN2C(=O)[C@@H](NC(=O)COCCCCCN2CCC(O[C@H]3C[C@H](Oc4ccc5c(c4)Sc4cc([N+](=O)[O-])ccc4N5)C3)CC2)C(C)(C)C)cc1] | (2S,4R)-1-((S)-3,3-dimethyl-2-(2-((5-(4-((1r,3r)-3-((7-nitro-10H-phenothiazin-3-yl)oxy)cyclobutoxy)piperidin-1-yl)pentyl)oxy)acetamido)butanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 34 | 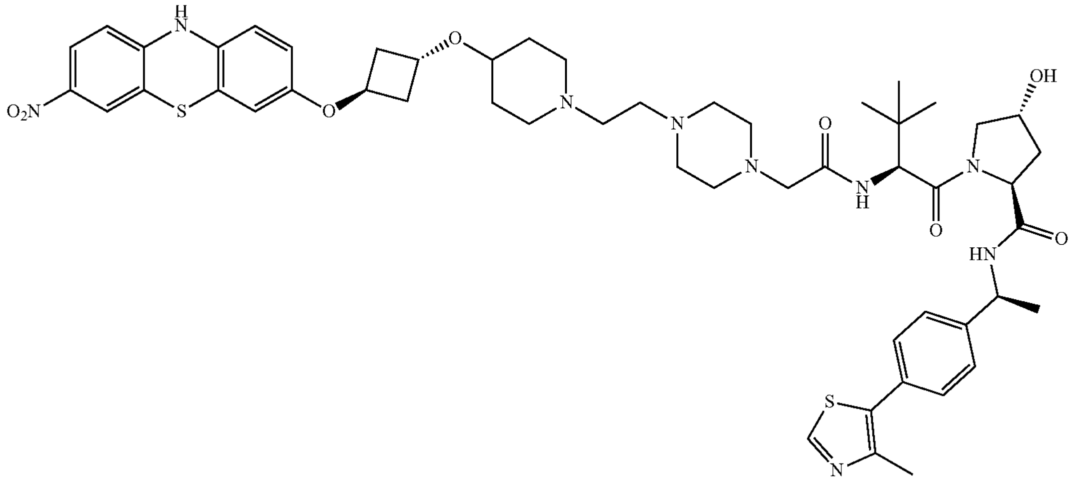 [SMILES: Cc1ncsc1-c1ccc([C@H](C)NC(=O)[C@@H]2C[C@@H](O)CN2C(=O)[C@@H](NC(=O)CN2CCN(CCN3CCC(O[C@H]4C[C@H](Oc5ccc6c(c5)Sc5cc([N+](=O)[O-])ccc5N6)C4)CC3)CC2)C(C)(C)C)cc1] | (2S,4R)-1-((S)-3,3-dimethyl-2-(2-(4-(2-(4-((1r,3r)-3-((7-nitro-10H-phenothiazin-3-yl)oxy)cyclobutoxy)piperidin-1-yl)ethyl)piperazin-1-yl)acetamido)butanoyl)-4-hydroxy-N-((S)-1-(4-(4-methylthiazol-5-yl)phenyl)ethyl)pyrrolidine-2-carboxamide |
| 35 | 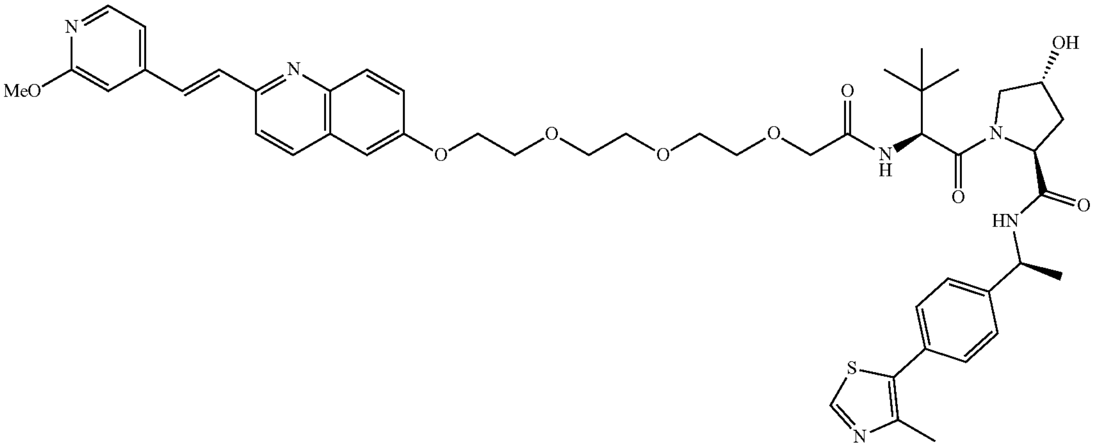 [SMILES: COc1cc(/C=C/c2ccc3cc(OCCOCCOCCOCC(=O)N[C@H](C(=O)N4C[C@H](O)C[C@H]4C(=O)N[C@@H](C)c4ccc(-c5scnc5C)cc4)C(C)(C)C)ccc3n2)ccn1] | (2S,4R)-1-((S)-2-(tert-butyl)-14-((2-((E)-2-(2-methoxypyridin-4-yl)vinyl)quinolin-6-yl)oxy)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |

TABLE 1-continued
Exemplary Compounds of the Present Disclosure
| Ex. No. | Structure | Compound Name |
| --- | --- | --- |
| 36 | 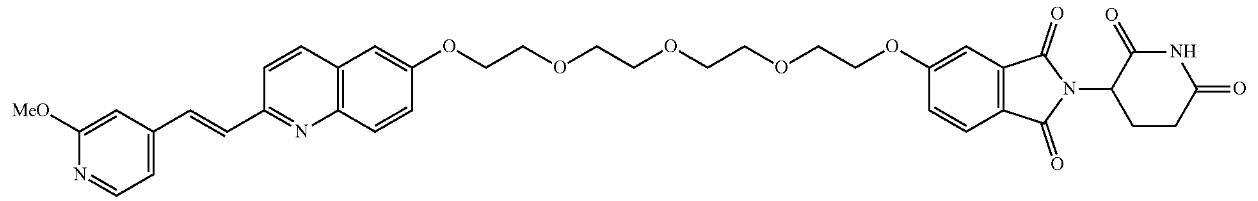 [SMILES: COc1cc(/C=C/c2ccc3cc(OCCOCCOCCOCCOc4ccc5c(c4)C(=O)N(C4CCC(=O)NC4=O)C5=O)ccc3n2)ccn1] | (E)-2-(2,6-dioxopiperidin-3-yl)-5-(2-(2-(2-(2-((2-(2-(2-methoxypyridin-4-yl)vinyl)quinolin-6-yl)oxy)ethoxy)ethoxy)ethoxy)ethoxy)isoindoline-1,3-dione |
| 37 | 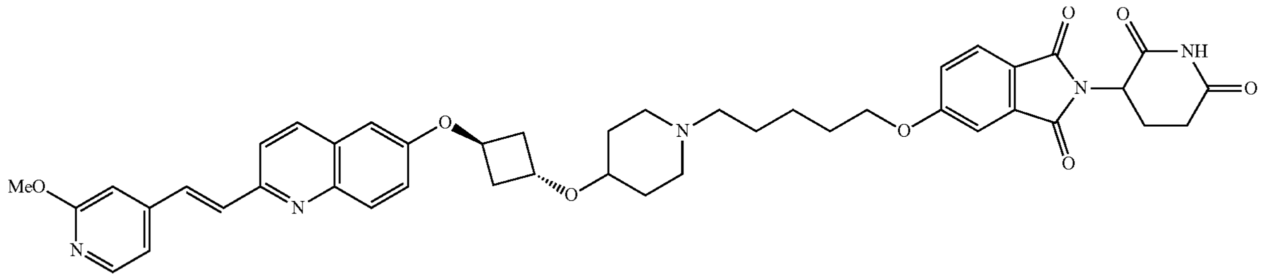 [SMILES: COc1cc(/C=C/c2ccc3cc(O[C@H]4C[C@H](OC5CCN(CCCCCOc6ccc7c(c6)C(=O)N(C6CCC(=O)NC6=O)C7=O)CC5)C4)ccc3n2)ccn1] | |
| 38 | 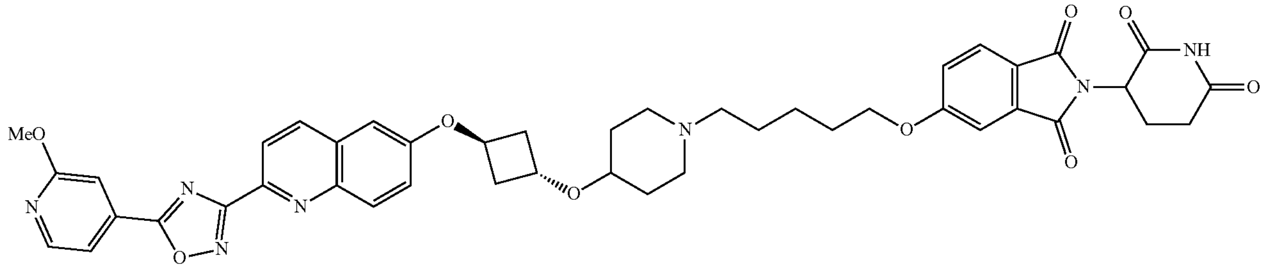 [SMILES: COc1cc(-c2nc(-c3ccc4cc(O[C@H]5C[C@H](OC6CCN(CCCCCOc7ccc8c(c7)C(=O)N(C7CCC(=O)NC7=O)C8=O)CC6)C5)ccc4n3)no2)ccn1] | |

TABLE 1-continued
| Exemplary Compounds of the Present Disclosure | | |
| --- | --- | --- |
| Ex. No. | Structure | Compound Name |
| 39 | 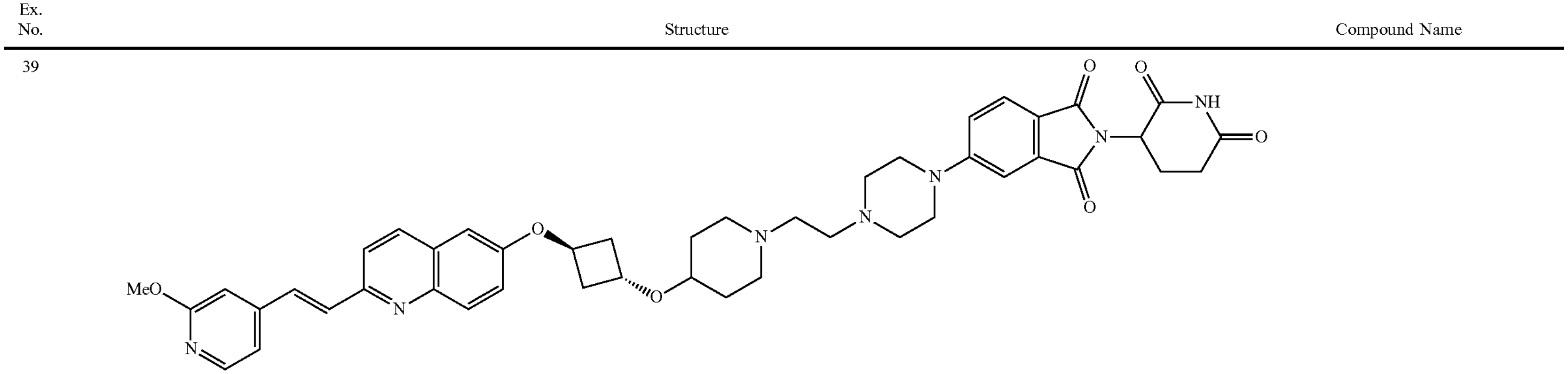 | |
| 40 | 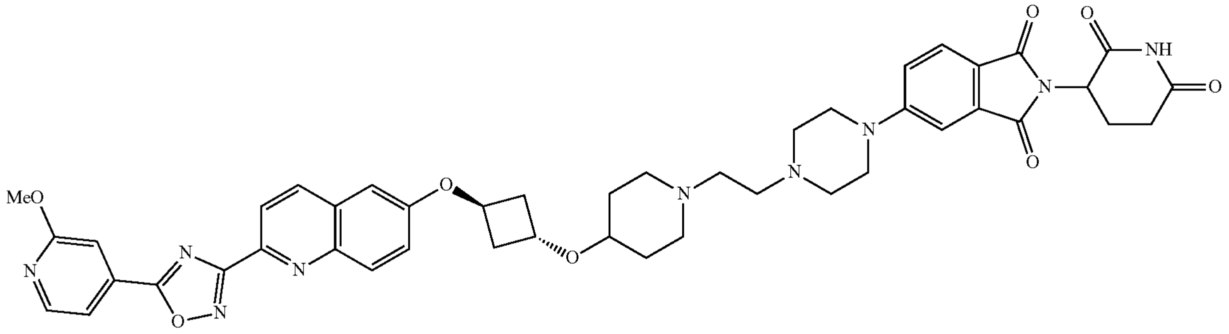 [SMILES: COc1cc(-c2nc(-c3ccc4cc(O[C@H]5C[C@H](OC6CCN(CCN7CCN(c8ccc9c(c8)C(=O)N(C8CCC(=O)NC8=O)C9=O)CC7)CC6)C5)ccc4n3)no2)ccn1] | |

TABLE 1-continued
Exemplary Compounds of the Present Disclosure
| Ex. No. | Structure | Compound Name |
|---|---|---|
| 41 | 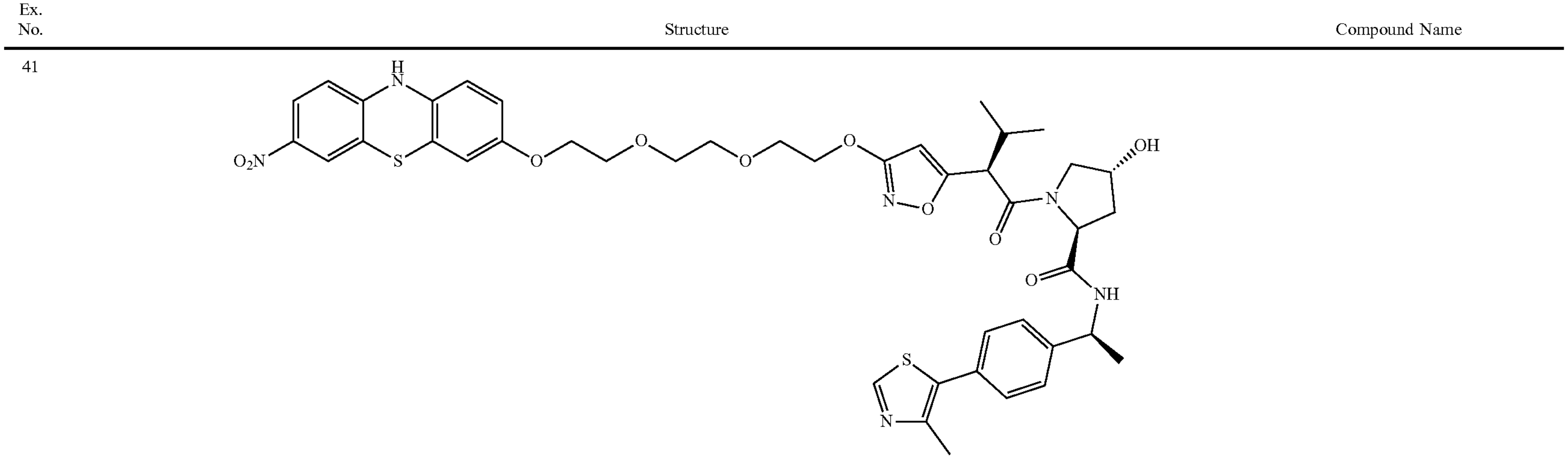 | |
| 42 | 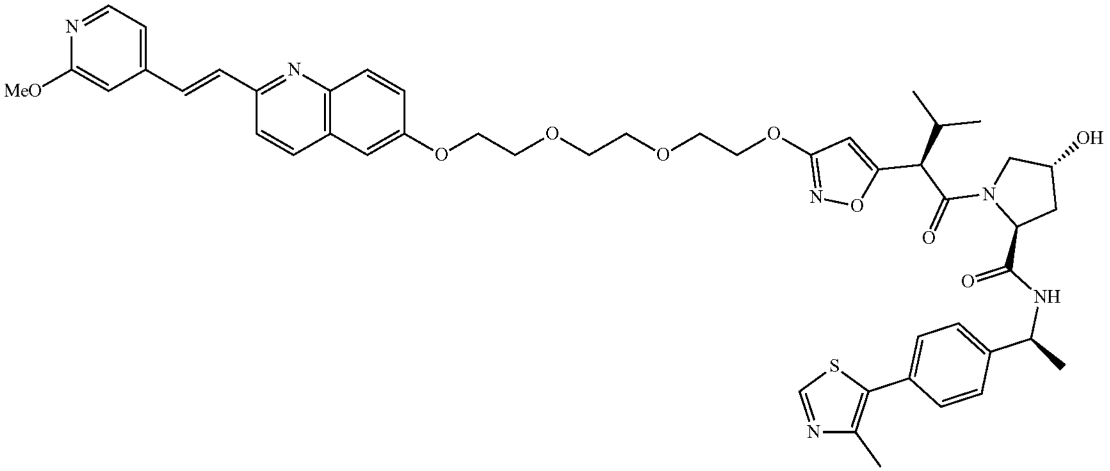 [SMILES: COc1cc(/C=C/c2ccc3cc(OCCOCCOCCOc4cc([C@H](C(=O)N5C[C@H](O)C[C@H]5C(=O)N[C@@H](C)c5ccc(-c6scnc6C)cc5)C(C)C)on4)ccc3n2)ccn1] | |

TABLE 1-continued
| Exemplary Compounds of the Present Disclosure | | |
|---|---|---|
| Ex. No. | Structure | Compound Name |
| 43 | 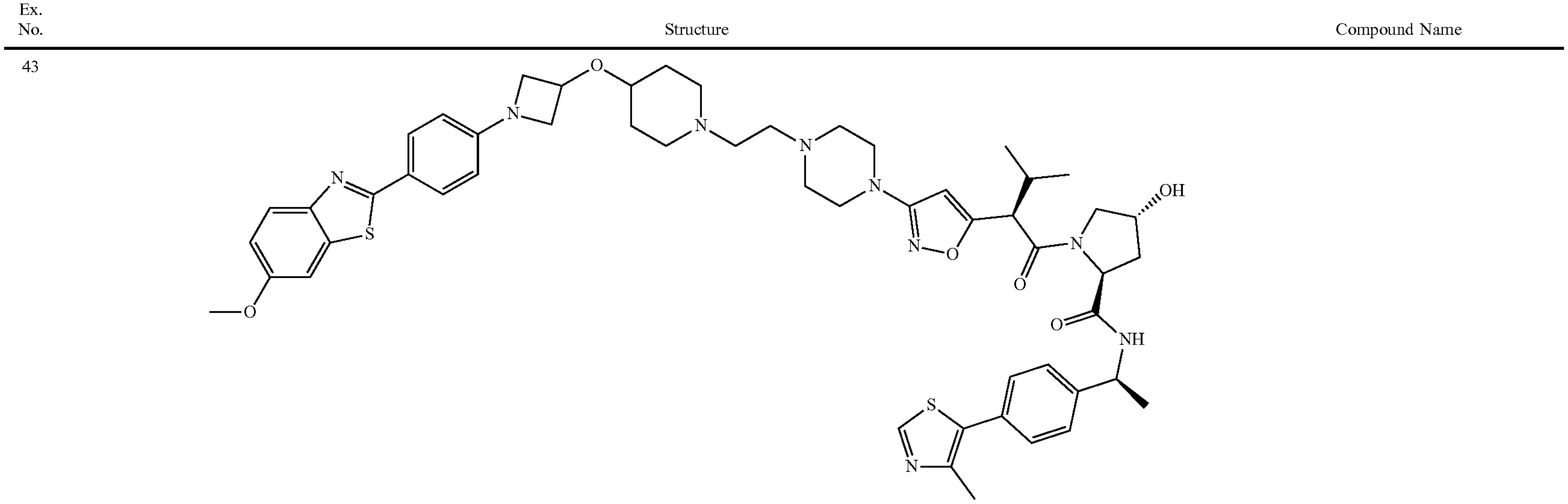 | |
| 44 | 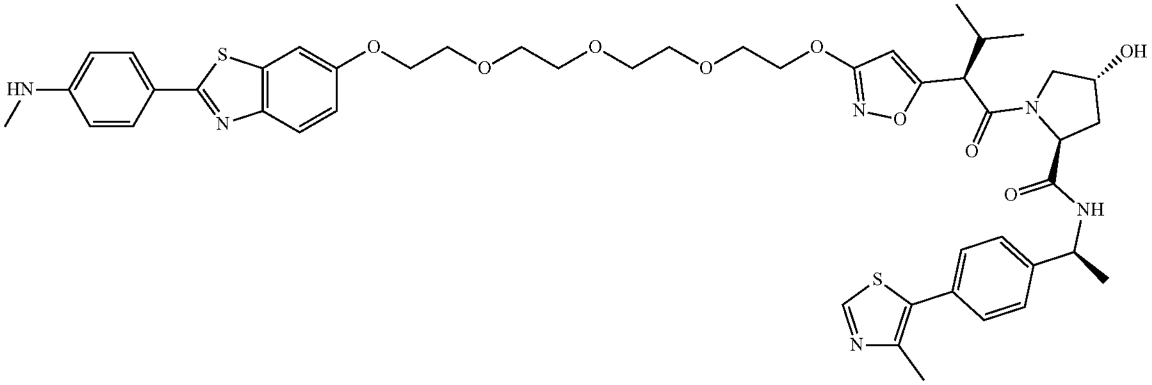 [SMILES: CNc1ccc(-c2nc3ccc(OCCOCCOCCOCCOc4cc([C@H](C(=O)N5C[C@H](O)C[C@H]5C(=O)N[C@@H](C)c5ccc(-c6scnc6C)cc5)C(C)C)on4)cc3s2)cc1] | |

TABLE 1-continued
| Exemplary Compounds of the Present Disclosure | | |
|---|---|---|
| Ex. No. | Structure | Compound Name |
| 45 | 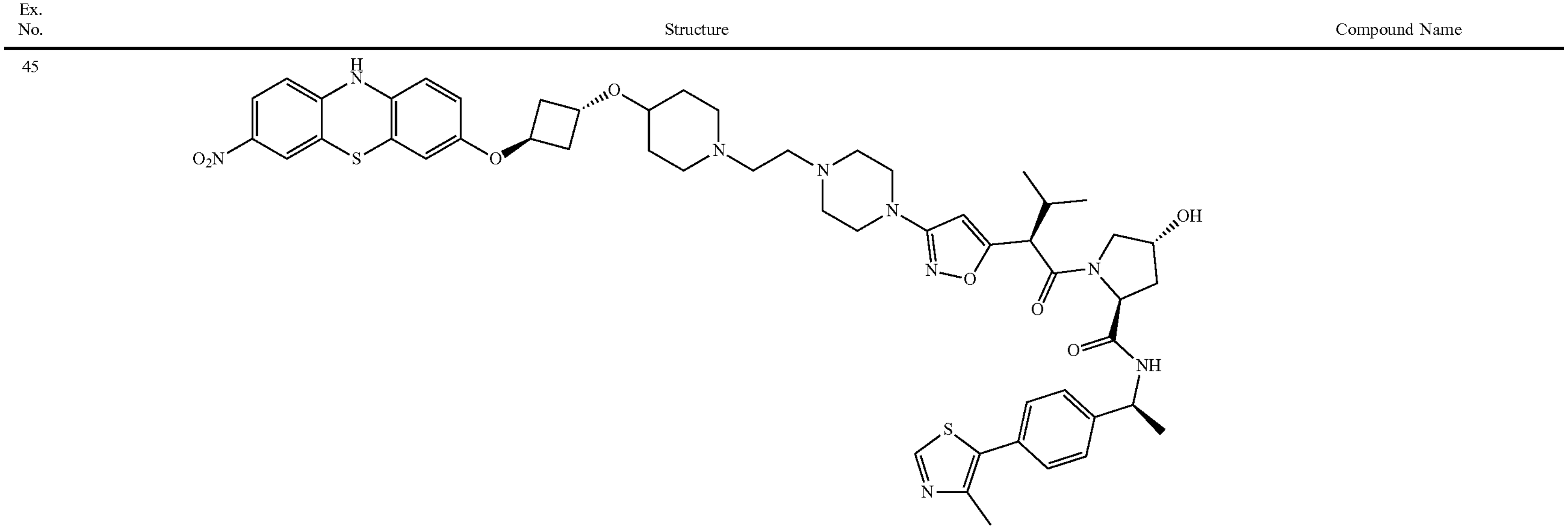 | |
| 46 | 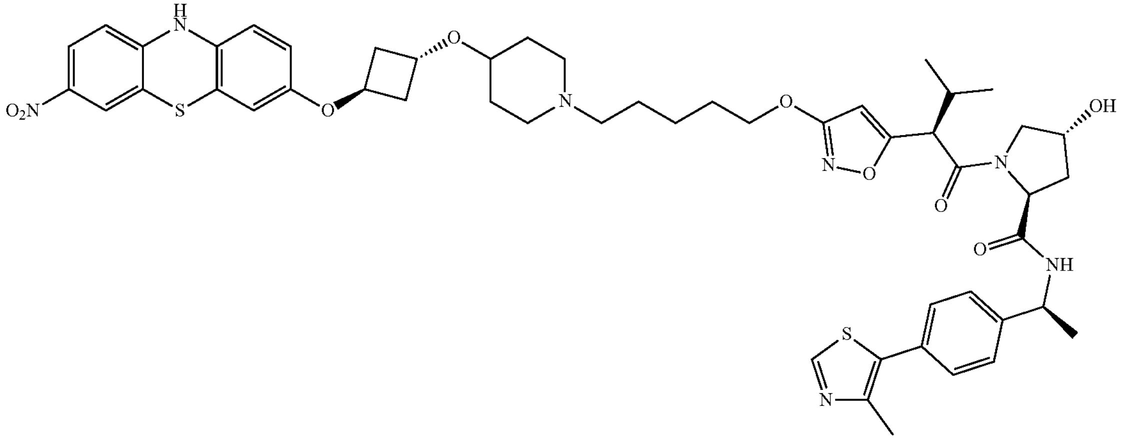 [SMILES: Cc1ncsc1-c1ccc([C@H](C)NC(=O)[C@@H]2C[C@@H](O)CN2C(=O)[C@@H](c2cc(OCCCCCN3CCC(O[C@H]4C[C@H](Oc5ccc6c(c5)Sc5cc([N+](=O)[O-])ccc5N6)C4)CC3)no2)C(C)C)cc1] | |

TABLE 1-continued
| Exemplary Compounds of the Present Disclosure | | |
|---|---|---|
| Ex. No. | Structure | Compound Name |
| 47 | 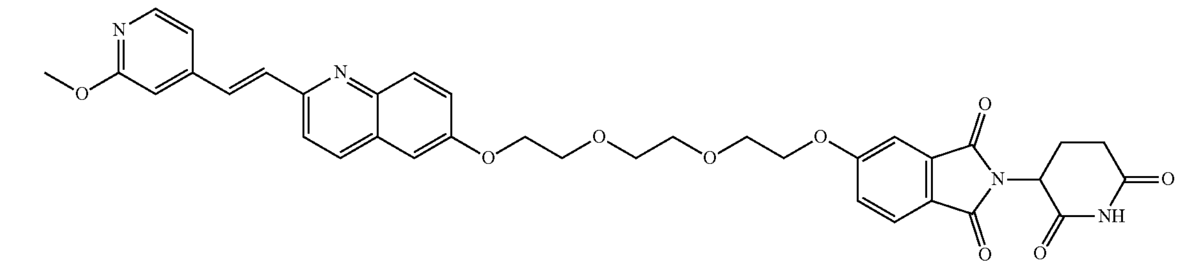 [SMILES: COc1cc(/C=C/c2ccc3cc(OCCOCCOCCOc4ccc5c(c4)C(=O)N(C4CCC(=O)NC4=O)C5=O)ccc3n2)ccn1] | (E)-2-(2,6-dioxopiperidin-3-yl)-5-(2-(2-(2-((2-(2-(2-methoxypyridin-4-yl)vinyl)quinolin-6-yl)oxy)ethoxy)ethoxy)ethoxy)isoindoline-1,3-dione |
| 48 | 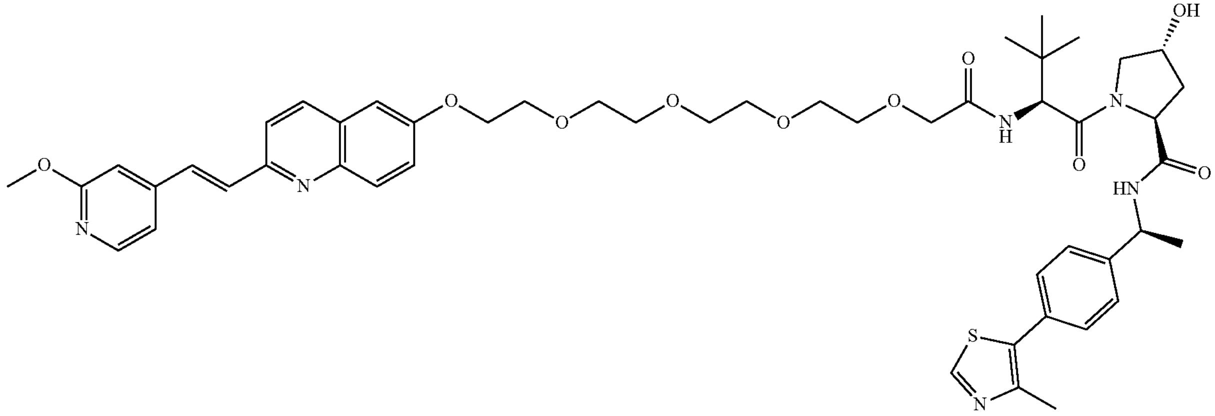 [SMILES: COc1cc(/C=C/c2ccc3cc(OCCOCCOCCOCCOCC(=O)N[C@H](C(=O)N4C[C@H](O)C[C@H]4C(=O)N[C@@H](C)c4ccc(-c5scnc5C)cc4)C(C)(C)C)ccc3n2)ccn1] | (2S,4R)-1-((S)-2-(tert-butyl)-17-((2-((E)-2-(2-methoxypyridin-4-yl)vinyl)quinolin-6-yl)oxy)-4-oxo-6,9,12,15-tetraoxa-3-azaheptadecanoyl)-4-hydroxy-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 49 | 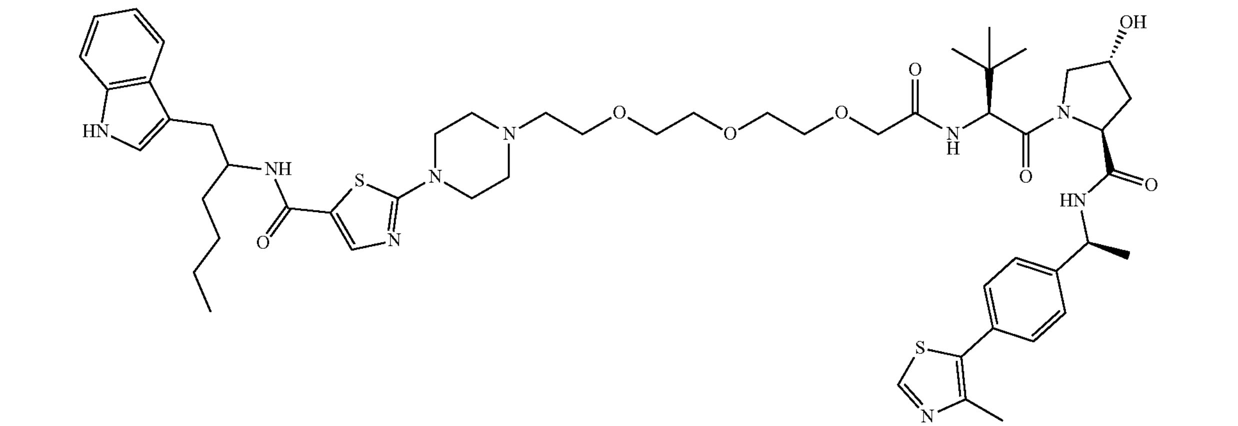 [SMILES: CCCCC(Cc1c[nH]c2ccccc12)NC(=O)c1cnc(N2CCN(CCOCCOCCOCC(=O)N[C@H](C(=O)N3C[C@H](O)C[C@H]3C(=O)N[C@@H](C)c3ccc(-c4scnc4C)cc3)C(C)(C)C)CC2)s1] | N-(1-(1H-indol-3-yl)hexan-2-yl)-2-(4-((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)piperazin-1-yl)thiazole-5-carboxamide |
| 50 | 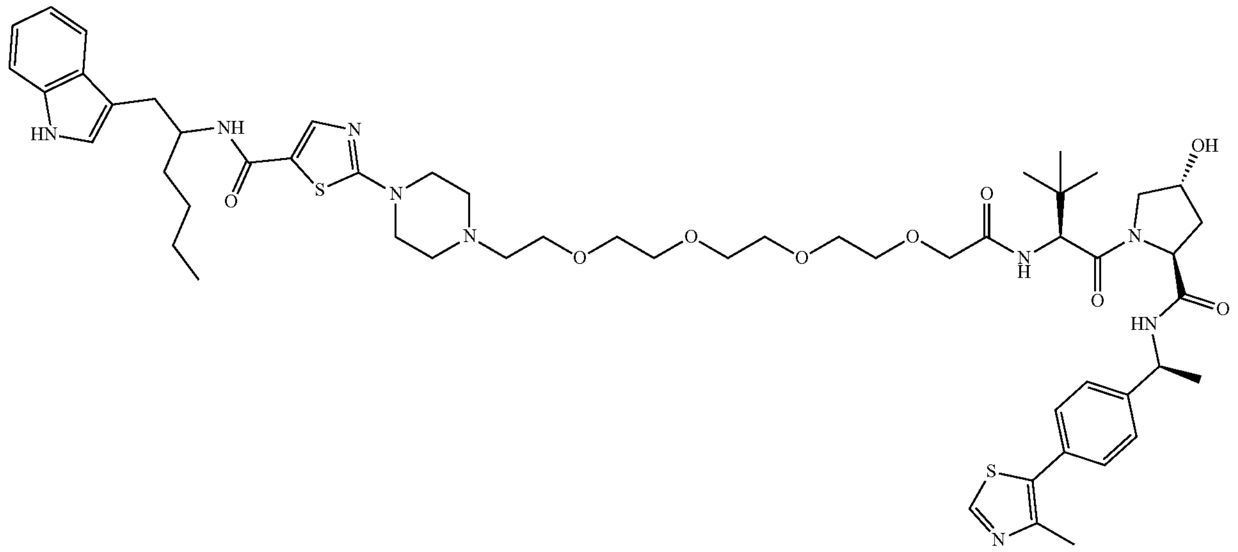 [SMILES: CCCCC(Cc1c[nH]c2ccccc12)NC(=O)c1cnc(N2CCN(CCOCCOCCOCCOCC(=O)N[C@H](C(=O)N3C[C@H](O)C[C@H]3C(=O)N[C@@H](C)c3ccc(-c4scnc4C)cc3)C(C)(C)C)CC2)s1] | N-(1-(1H-indol-3-yl)hexan-2-yl)-2-(4-((S)-16-((2S,4R)-4-hydroxy-2-(((S)-1-(4-(4-methylthiazol-5-yl)phenyl)ethyl)carbamoyl)pyrrolidine-1-carbonyl)-17,17-dimethyl-14-oxo-3,6,9,12-tetraoxa-15-azaoctadecyl)piperazin-1-yl)thiazole-5-carboxamide |

TABLE 1-continued

| Exemplary Compounds of the Present Disclosure | | |
|---|---|---|
| Ex. No. | Structure | Compound Name |
| 51 | 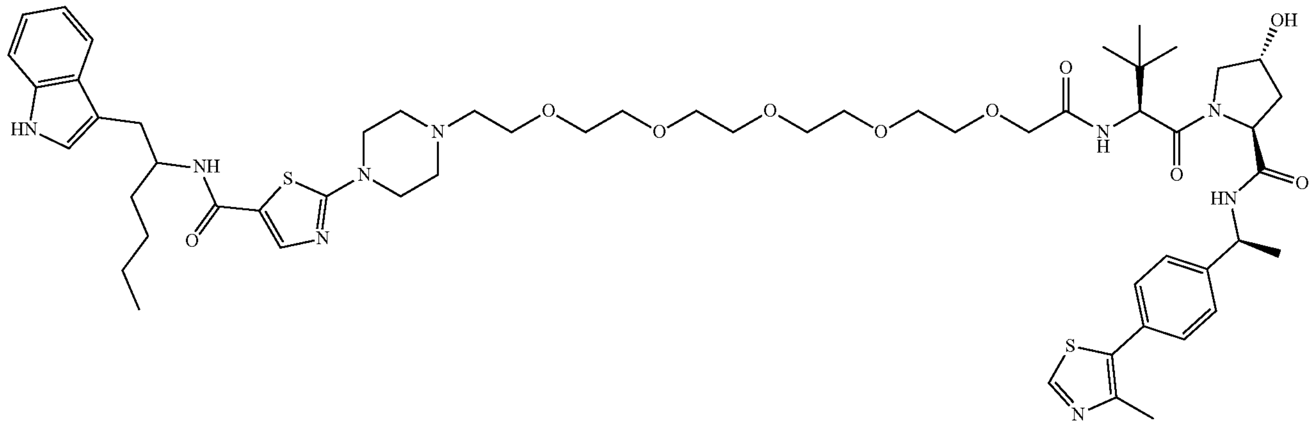 [SMILES: CCCCC(Cc1c[nH]c2ccccc12)NC(=O)c1cnc(N2CCN(CCOCCOCCOCCOCCOCC(=O)N[C@H](C(=O)N3C[C@H](O)C[C@H]3C(=O)N[C@@H](C)c3ccc(-c4scnc4C)cc3)C(C)(C)C)CC2)s1] | N-(1-(1H-indol-3-yl)hexan-2-yl)-2-(4-((S)-19-((2S,4R)-4-hydroxy-2-(((S)-1-(4-(4-methylthiazol-5-yl)phenyl)ethyl)carbamoyl)pyrrolidine-1-carbonyl)-20,20-dimethyl-17-oxo-3,6,9,12,15-pentaoxa-18-azahenicosyl)piperazin-1-yl)thiazole-5-carboxamide |
| 52 | 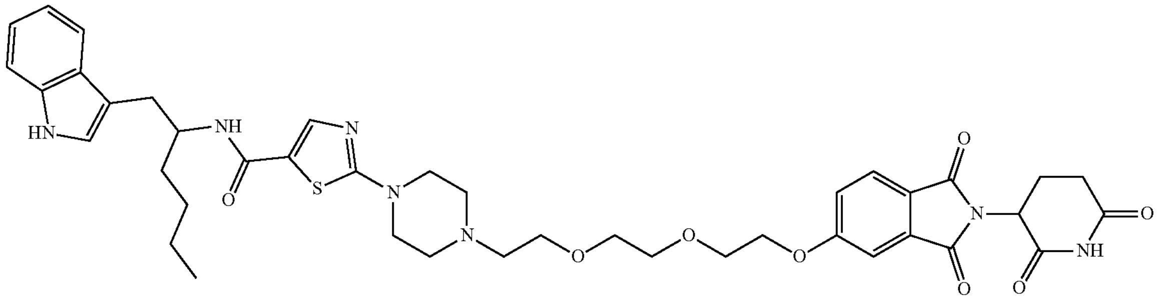 [SMILES: CCCCC(Cc1c[nH]c2ccccc12)NC(=O)c1cnc(N2CCN(CCOCCOCCOc3ccc4c(c3)C(=O)N(C3CCC(=O)NC3=O)C4=O)CC2)s1] | N-(1-(1H-indol-3-yl)hexan-2-yl)-2-(4-(2-(2-(2-((2-(2,6-dioxopiperidin-3-yl)-1,3-dioxoisoindolin-5-yl)oxy)ethoxy)ethoxy)ethyl)piperazin-1-yl)thiazole-5-carboxamide |

TABLE 1-continued
| Exemplary Compounds of the Present Disclosure | | |
|---|---|---|
| Ex. No. | Structure | Compound Name |
| 53 | 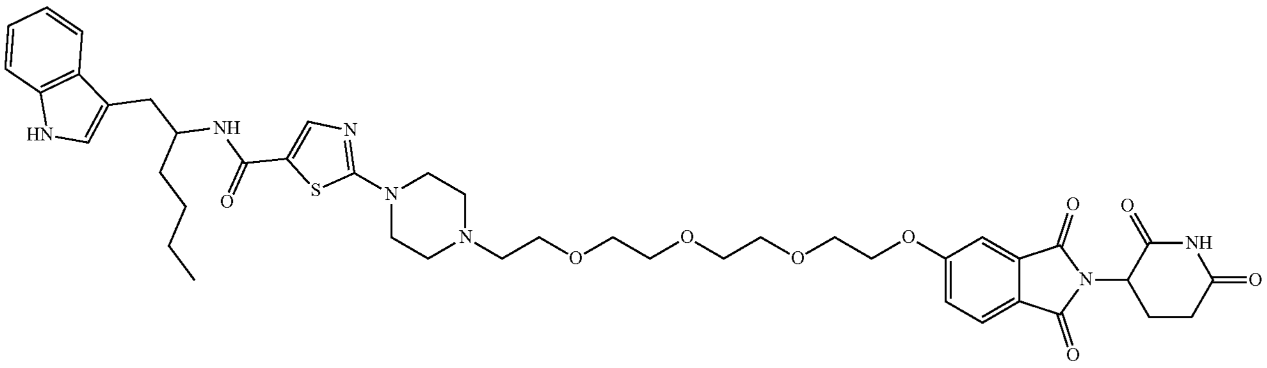 [SMILES: CCCCC(Cc1c[nH]c2ccccc12)NC(=O)c1cnc(N2CCN(CCOCCOCCOCCOc3ccc4c(c3)C(=O)N(C3CCC(=O)NC3=O)C4=O)CC2)s1] | N-(1-(1H-indol-3-yl)hexan-2-yl)-2-(4-(2-(2-(2-(2-((2-(2,6-dioxopiperidin-3-yl)-1,3-dioxoisoindolin-5-yl)oxy)ethoxy)ethoxy)ethoxy)ethyl)piperazin-1-yl)thiazole-5-carboxamide |
| 54 | 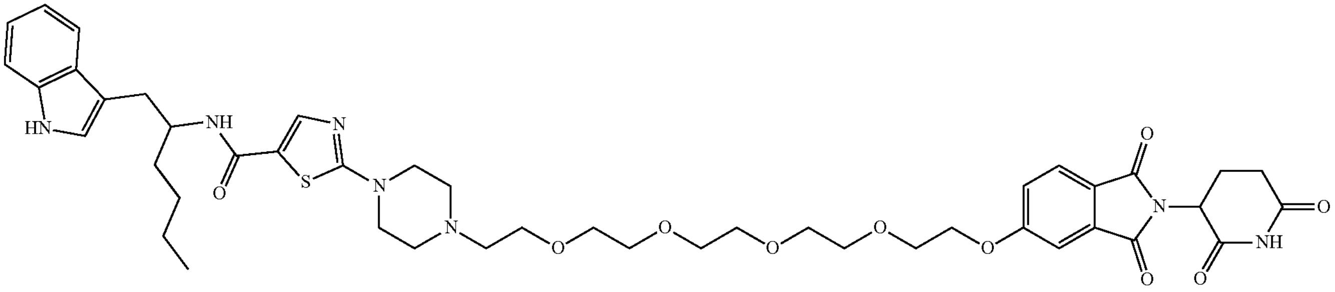 [SMILES: CCCCC(Cc1c[nH]c2ccccc12)NC(=O)c1cnc(N2CCN(CCOCCOCCOCCOCCOc3ccc4c(c3)C(=O)N(C3CCC(=O)NC3=O)C4=O)CC2)s1] | N-(1-(1H-indol-3-yl)hexan-2-yl)-2-(4-(14-((2-(2,6-dioxopiperidin-3-yl)-1,3-dioxoisoindolin-5-yl)oxy)-3,6,9,12-tetraoxatetradecyl)piperazin-1-yl)thiazole-5-carboxamide |

TABLE 1-continued
| Exemplary Compounds of the Present Disclosure | | |
|---|---|---|
| Ex. No. | Structure | Compound Name |
| 55 | 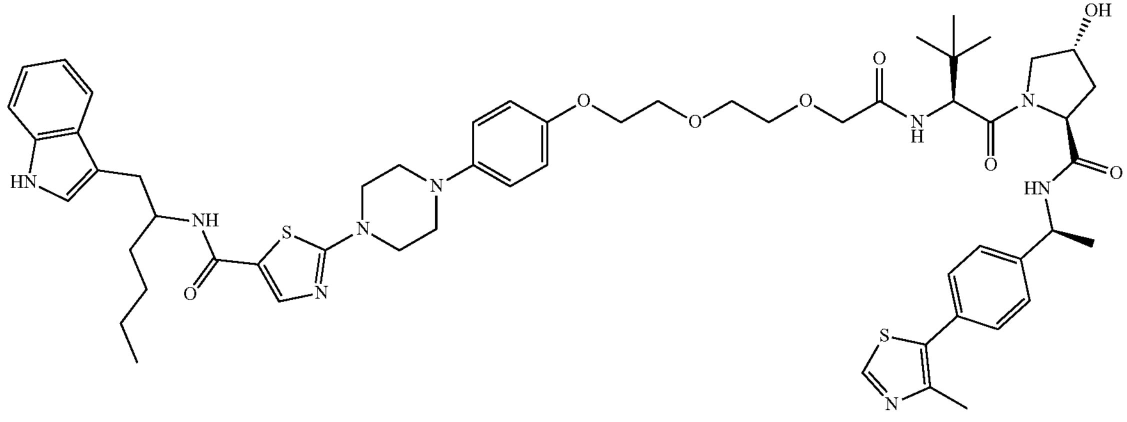 [SMILES: CCCCC(Cc1c[nH]c2ccccc12)NC(=O)c1cnc(N2CCN(c3ccc(OCCOCCOCC(=O)N[C@H](C(=O)N4C[C@H](O)C[C@H]4C(=O)N[C@@H](C)c4ccc(-c5scnc5C)cc4)C(C)(C)C)cc3)CC2)s1] | N-(1-(1H-indol-3-yl)hexan-2-yl)-2-(4-(4-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethoxy)phenyl)piperazin-1-yl)thiazole-5-carboxamide |

TABLE 1-continued

| Exemplary Compounds of the Present Disclosure | | |
|---|---|---|
| Ex. No. | Structure | Compound Name |
| 56 | 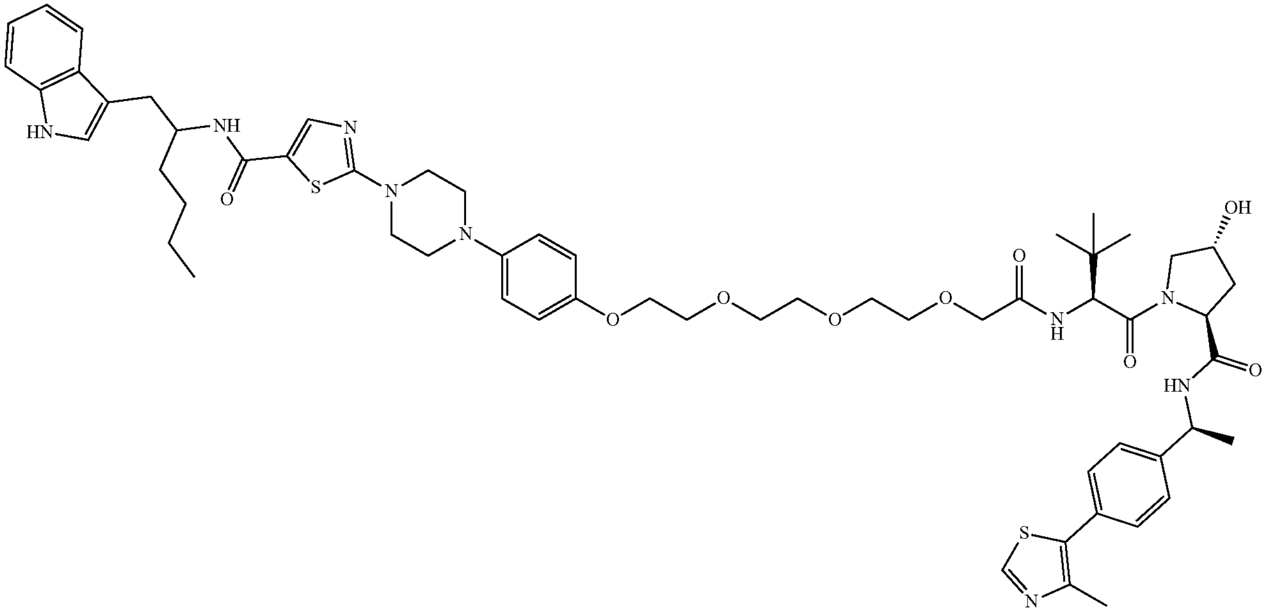 [SMILES: CCCCC(Cc1c[nH]c2ccccc12)NC(=O)c1cnc(N2CCN(c3ccc(OCCOCCOCCOCC(=O)N[C@H](C(=O)N4C[C@H](O)C[C@H]4C(=O)N[C@@H](C)c4ccc(-c5scnc5C)cc4)C(C)(C)C)cc3)CC2)s1] | N-(1-(1H-indol-3-yl)hexan-2-yl)-2-(4-(4-(((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)oxy)phenyl)piperazin-1-yl)thiazole-5-carboxamide |
| 57 | 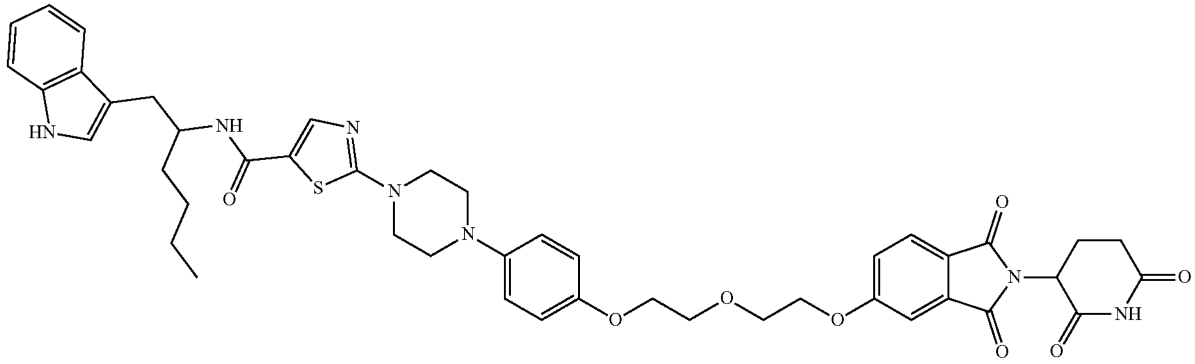 [SMILES: CCCCC(Cc1c[nH]c2ccccc12)NC(=O)c1cnc(N2CCN(c3ccc(OCCOCCOc4ccc5c(c4)C(=O)N(C4CCC(=O)NC4=O)C5=O)cc3)CC2)s1] | N-(1-(1H-indol-3-yl)hexan-2-yl)-2-(4-(4-(2-(2-((2-(2,6-dioxopiperidin-3-yl)-1,3-dioxoisoindolin-5-yl)oxy)ethoxy)ethoxy)phenyl)piperazin-1-yl)thiazole-5-carboxamide |

TABLE 1-continued
Exemplary Compounds of the Present Disclosure
| Ex. No. | Structure | Compound Name |
| --- | --- | --- |
| 58 | 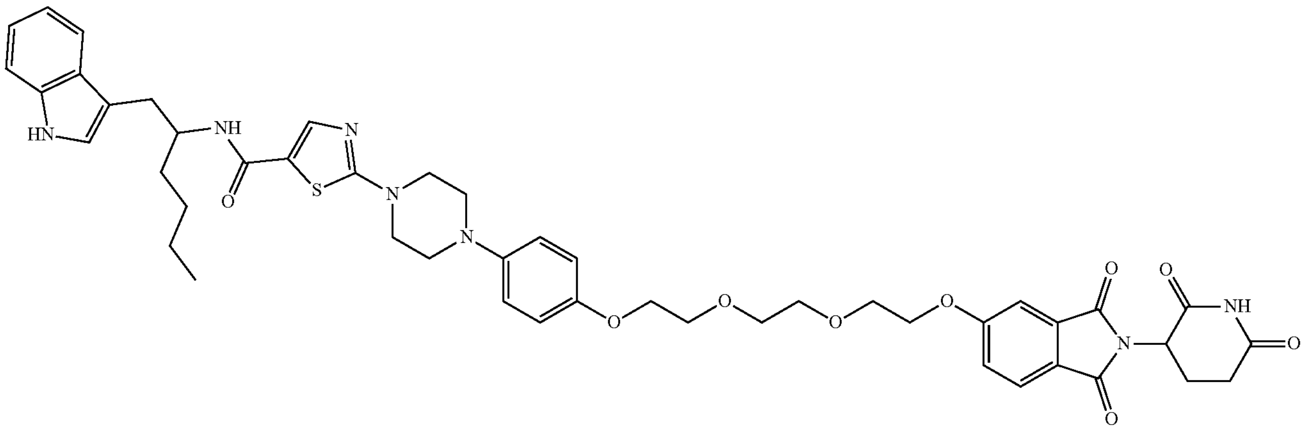 [SMILES: CCCCC(Cc1c[nH]c2ccccc12)NC(=O)c1cnc(N2CCN(c3ccc(OCCOCCOCCOc4ccc5c(c4)C(=O)N(C4CCC(=O)NC4=O)C5=O)cc3)CC2)s1] | N-(1-(1H-indol-3-yl)hexan-2-yl)-2-(4-(4-(2-(2-(2-((2-(2,6-dioxopiperidin-3-yl)-1,3-dioxoisoindolin-5-yl)oxy)ethoxy)ethoxy)ethoxy)phenyl)piperazin-1-yl)thiazole-5-carboxamide |
| 59 | 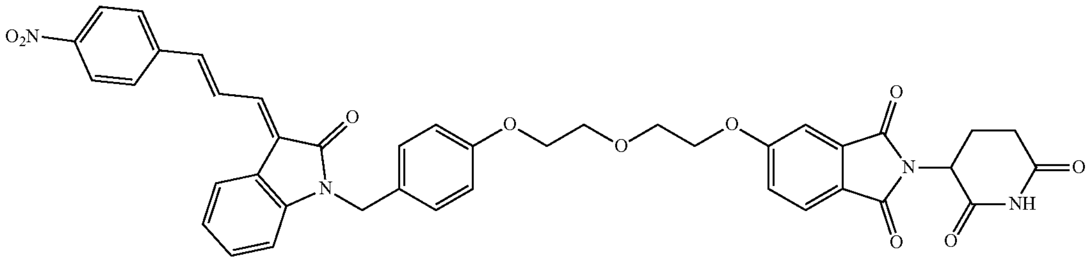 [SMILES: O=C1CCC(N2C(=O)c3ccc(OCCOCCOc4ccc(CN5C(=O)/C(=C/C=C/c6ccc([N+](=O)[O-])cc6)c6ccccc65)cc4)cc3C2=O)C(=O)N1] | 2-(2,6-dioxopiperidin-3-yl)-5-(2-(2-(4-(((E)-3-((E)-3-(4-nitrophenyl)allylidene)-2-oxoindolin-1-yl)methyl)phenoxy)ethoxy)ethoxy)isoindoline-1,3-dione |

TABLE 1-continued
Exemplary Compounds of the Present Disclosure
| Ex. No. | Structure | Compound Name |
| --- | --- | --- |
| 60 | 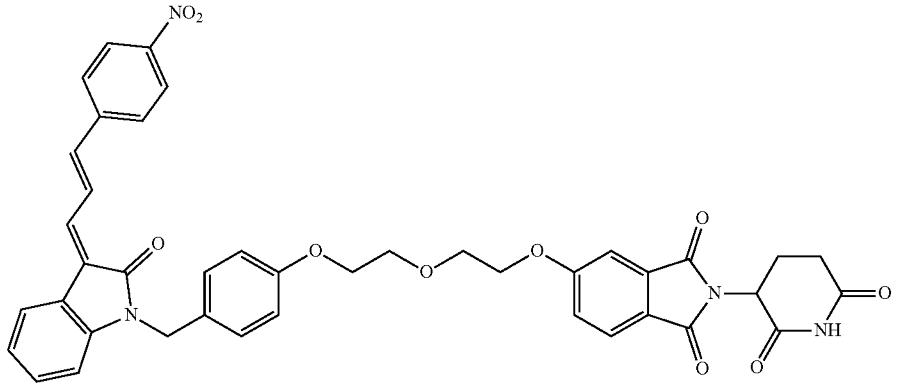 [SMILES: O=C1CCC(N2C(=O)c3ccc(OCCOCCOc4ccc(CN5C(=O)/C(=C\C=C\c6ccc([N+](=O)[O-])cc6)c6ccccc65)cc4)cc3C2=O)C(=O)N1] | 2-(2,6-dioxopiperidin-3-yl)-5-(2-(2-(4-(((Z)-3-((E)-3-(4-nitrophenyl)allylidene)-2-oxoindolin-1-yl)methyl)phenoxy)ethoxy)ethoxy)isoindoline-1,3-dione |
| 61 | 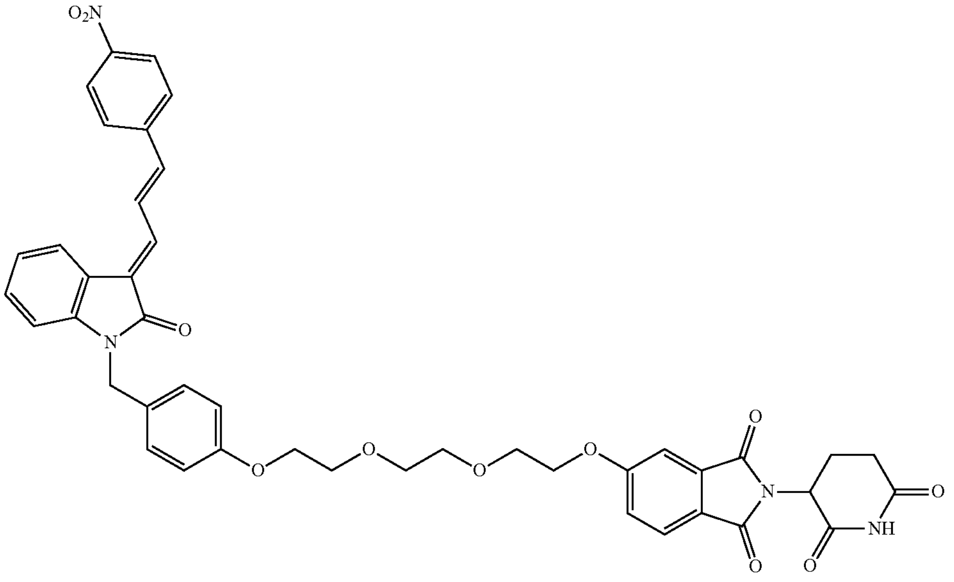 [SMILES: O=C1CCC(N2C(=O)c3ccc(OCCOCCOCCOc4ccc(CN5C(=O)/C(=C/C=C/c6ccc([N+](=O)[O-])cc6)c6ccccc65)cc4)cc3C2=O)C(=O)N1] | 2-(2,6-dioxopiperidin-3-yl)-5-(2-(2-(2-(4-(((E)-3-((E)-3-(4-nitrophenyl)allylidene)-2-oxoindolin-1-yl)methyl)phenoxy)ethoxy)ethoxy)ethoxy)isoindoline-1,3-dione |

TABLE 1-continued
| Exemplary Compounds of the Present Disclosure | | |
|---|---|---|
| Ex. No. | Structure | Compound Name |
| 62 | 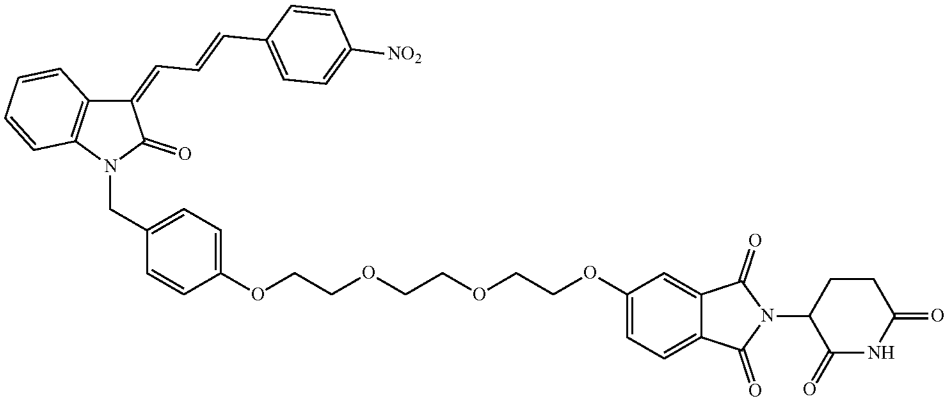 [SMILES: O=C1CCC(N2C(=O)c3ccc(OCCOCCOCCOc4ccc(CN5C(=O)/C(=C\C=C\c6ccc([N+](=O)[O-])cc6)c6ccccc65)cc4)cc3C2=O)C(=O)N1] | 2-(2,6-dioxopiperidin-3-yl)-5-(2-(2-(2-(4-(((Z)-3-((E)-3-(4-nitrophenyl)allylidene)-2-oxoindolin-1-yl)methyl)phenoxy)ethoxy)ethoxy)ethoxy)isoindoline-1,3-dione |
| 63 | 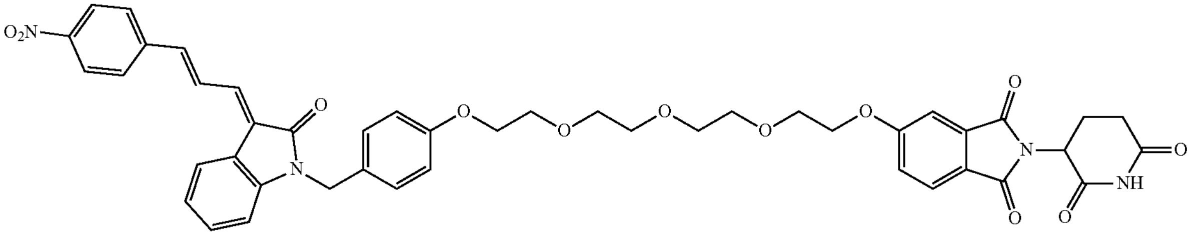 [SMILES: O=C1CCC(N2C(=O)c3ccc(OCCOCCOCCOCCOc4ccc(CN5C(=O)/C(=C/C=C/c6ccc([N+](=O)[O-])cc6)c6ccccc65)cc4)cc3C2=O)C(=O)N1] | 2-(2,6-dioxopiperidin-3-yl)-5-(2-(2-(2-(2-(4-(((E)-3-((E)-3-(4-nitrophenyl)allylidene)-2-oxoindolin-1-yl)methyl)phenoxy)ethoxy)ethoxy)ethoxy)ethoxy)isoindoline-1,3-dione |

TABLE 1-continued

| Exemplary Compounds of the Present Disclosure | | |
|---|---|---|
| Ex. No. | Structure | Compound Name |
| 64 | 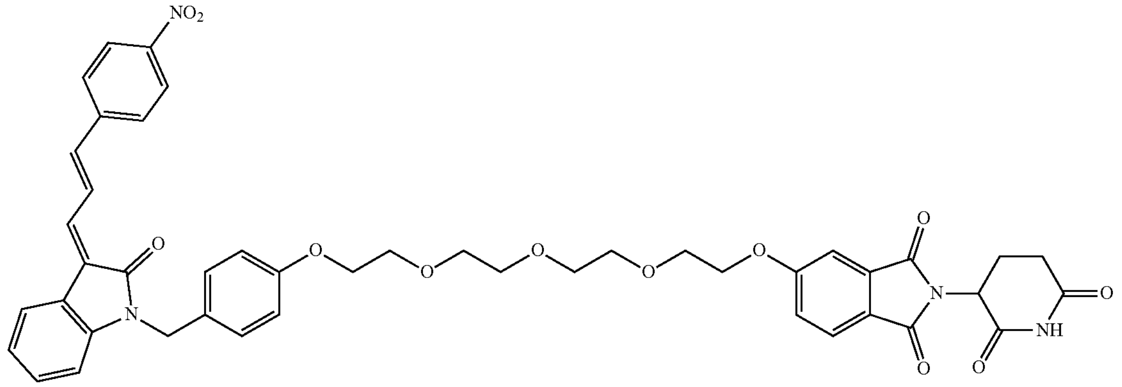 [SMILES: O=C1CCC(N2C(=O)c3ccc(OCCOCCOCCOCCOc4ccc(CN5C(=O)/C(=C\C=C\c6ccc([N+](=O)[O-])cc6)c6ccccc65)cc4)cc3C2=O)C(=O)N1] | 2-(2,6-dioxopiperidin-3-yl)-5-(2-(2-(2-(2-(4-(((Z)-3-((E)-3-(4-nitrophenyl)allylidene)-2-oxoindolin-1-yl)methyl)phenoxy)ethoxy)ethoxy)ethoxy)ethoxy)isoindoline-1,3-dione |
| 65 | 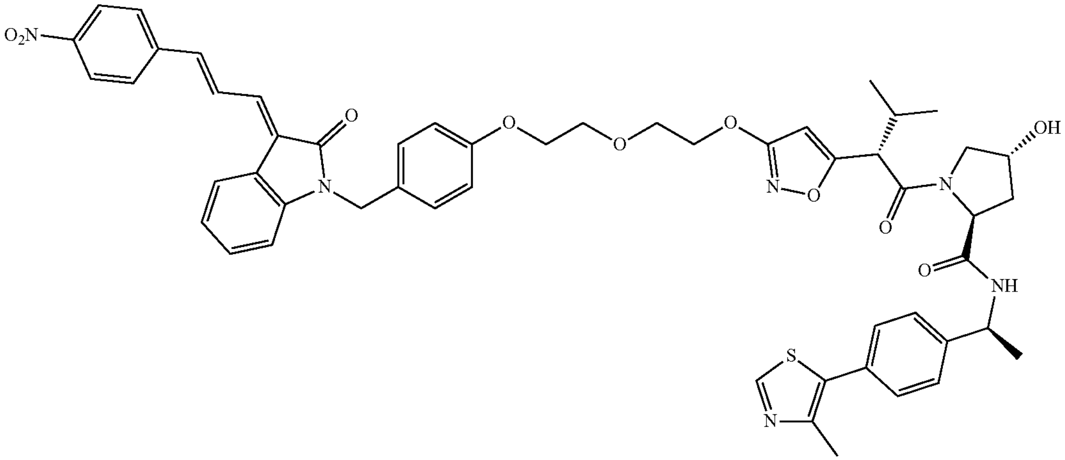 [SMILES: Cc1ncsc1-c1ccc([C@H](C)NC(=O)[C@@H]2C[C@@H](O)CN2C(=O)[C@H](c2cc(OCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-((S)-3-methyl-2-(3-(2-(2-(4-(((E)-3-((E)-3-(4-nitrophenyl)allylidene)-2-oxoindolin-1-yl)methyl)phenoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 66 | 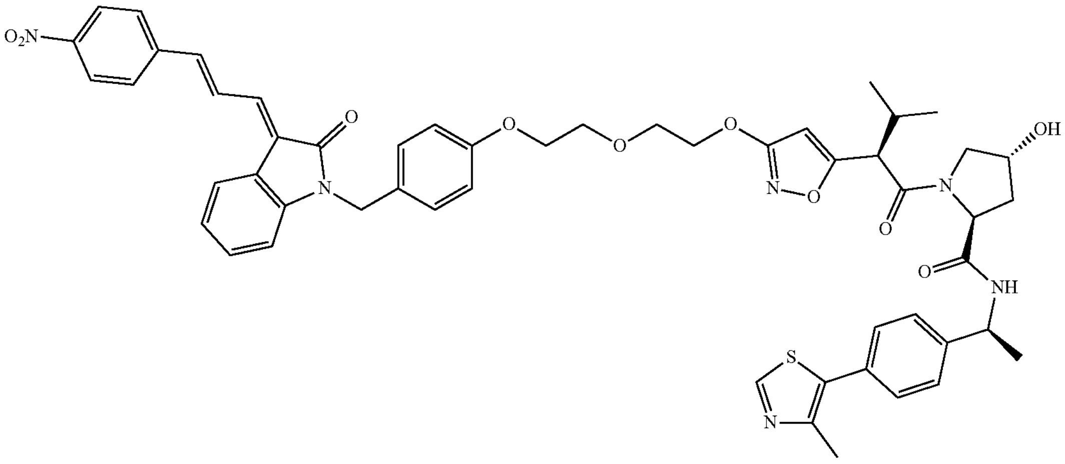 [SMILES: Cc1ncsc1-c1ccc([C@H](C)NC(=O)[C@@H]2C[C@@H](O)CN2C(=O)[C@@H](c2cc(OCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-((R)-3-methyl-2-(3-(2-(2-(4-(((E)-3-((E)-3-(4-nitrophenyl)allylidene)-2-oxoindolin-1-yl)methyl)phenoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 67 | 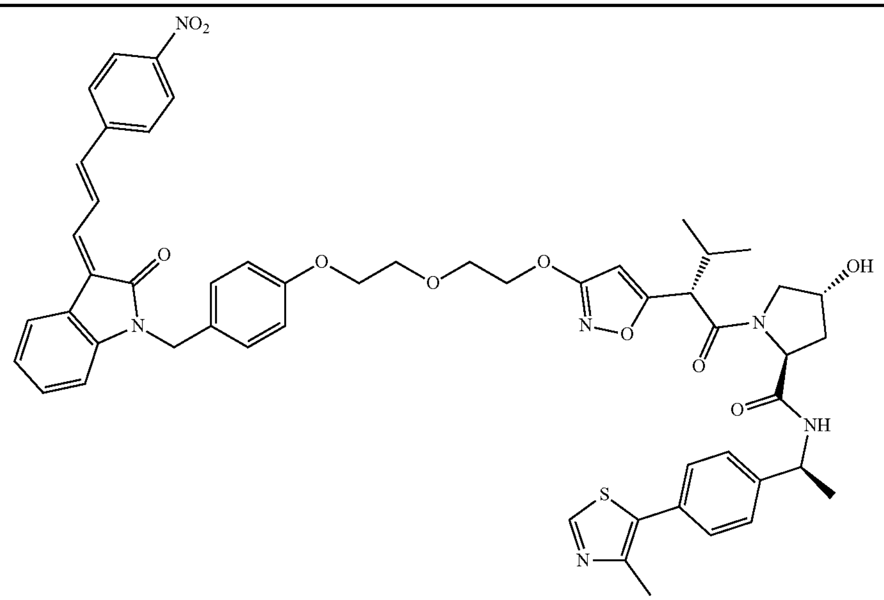 | (2S,4R)-4-hydroxy-1-((S)-3-methyl-2-(3-(2-(2-(4-(((Z)-3-((E)-3-(4-nitrophenyl)allylidene)-2-oxoindolin-1-yl)methyl)phenoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued

| Exemplary Compounds of the Present Disclosure | | |
|---|---|---|
| Ex. No. | Structure | Compound Name |
| 68 | 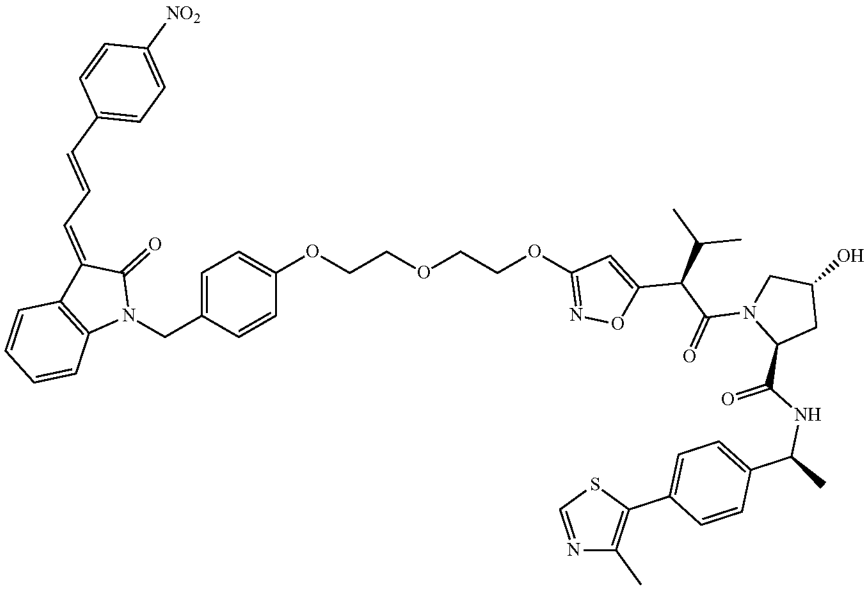 [SMILES: Cc1ncsc1-c1ccc([C@H](C)NC(=O)[C@@H]2C[C@@H](O)CN2C(=O)[C@@H](c2cc(OCCOCCOc3ccc(CN4C(=O)/C(=C\C=C\c5ccc([N+](=O)[O-])cc5)c5ccccc54)cc3)no2)C(C)C)cc1] | (2S,4R)-4-hydroxy-1-((R)-3-methyl-2-(3-(2-(2-(4-(((Z)-3-((E)-3-(4-nitrophenyl)allylidene)-2-oxoindolin-1-yl)methyl)phenoxy)ethoxy)ethoxy)isoxazol-5-yl)butanoyl)-N-((S)-1-(4-(4-methylthiazol-5-yl)phenyl)ethyl)pyrrolidine-2-carboxamide |
| 69 | 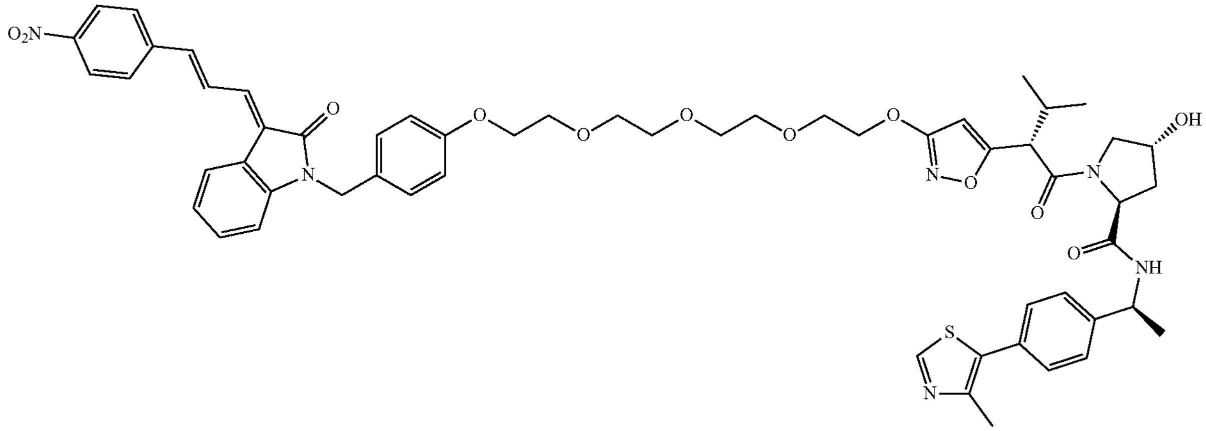 [SMILES: Cc1ncsc1-c1ccc([C@H](C)NC(=O)[C@@H]2C[C@@H](O)CN2C(=O)[C@H](c2cc(OCCOCCOCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-((S)-3-methyl-2-(3-(2-(2-(2-(2-(4-(((E)-3-((E)-3-(4-nitrophenyl)allylidene)-2-oxoindolin-1-yl)methyl)phenoxy)ethoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 70 | 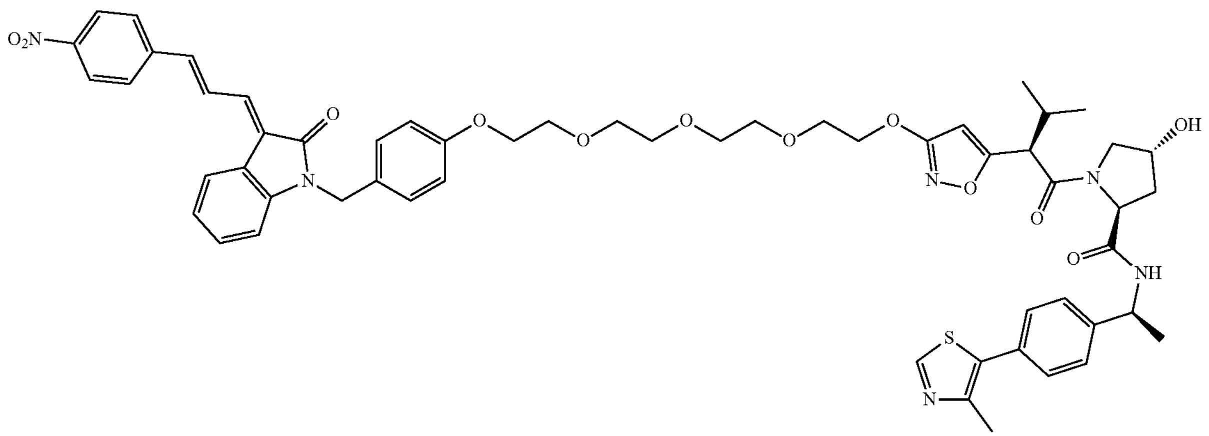 [SMILES: Cc1ncsc1-c1ccc([C@H](C)NC(=O)[C@@H]2C[C@@H](O)CN2C(=O)[C@@H](c2cc(OCCOCCOCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-((R)-3-methyl-2-(3-(2-(2-(2-(2-(4-(((E)-3-((E)-3-(4-nitrophenyl)allylidene)-2-oxoindolin-1-yl)methyl)phenoxy)ethoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 71 | 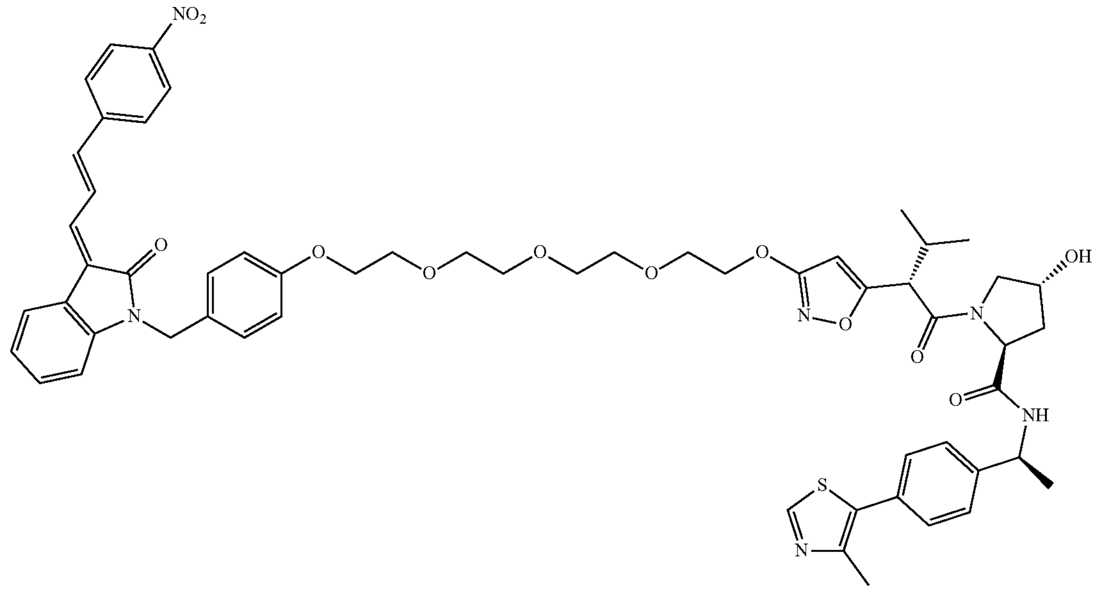 [SMILES: Cc1ncsc1-c1ccc([C@H](C)NC(=O)[C@@H]2C[C@@H](O)CN2C(=O)[C@H](c2cc(OCCOCCOCCOCCOc3ccc(CN4C(=O)/C(=C\C=C\c5ccc([N+](=O)[O-])cc5)c5ccccc54)cc3)no2)C(C)C)cc1] | (2S,4R)-4-hydroxy-1-((S)-3-methyl-2-(3-(2-(2-(2-(2-(4-(((Z)-3-((E)-3-(4-nitrophenyl)allylidene)-2-oxoindolin-1-yl)methyl)phenoxy)ethoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 72 | 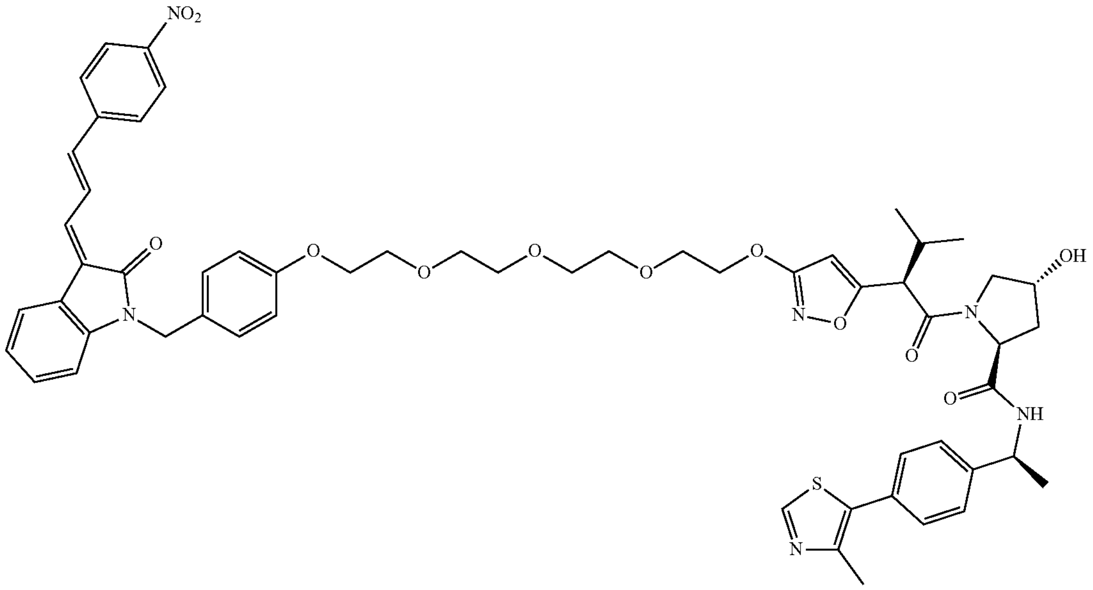 [SMILES: Cc1ncsc1-c1ccc([C@H](C)NC(=O)[C@@H]2C[C@@H](O)CN2C(=O)[C@@H](c2cc(OCCOCCOCCOCCOc3ccc(CN4C(=O)/C(=C\C=C\c5ccc([N+](=O)[O-])cc5)c5ccccc54)cc3)no2)C(C)C)cc1] | (2S,4R)-4-hydroxy-1-((R)-3-methyl-2-(3-(2-(2-(2-(2-(4-(((Z)-3-((E)-3-(4-nitrophenyl)allylidene)-2-oxoindolin-1-yl)methyl)phenoxy)ethoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 73 | 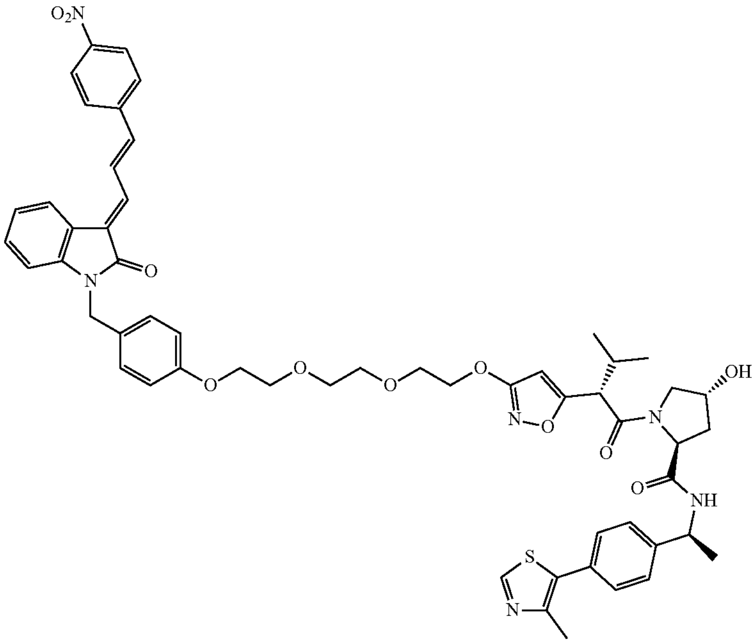 [SMILES: Cc1ncsc1-c1ccc([C@H](C)NC(=O)[C@@H]2C[C@@H](O)CN2C(=O)[C@H](c2cc(OCCOCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-(S)-3-methyl-2-(3-(2-(2-(2-(4-(((E)-3-((E)-3-(4-nitrophenyl)allylidene)-2-oxoindolin-1-yl)methyl)phenoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 74 | 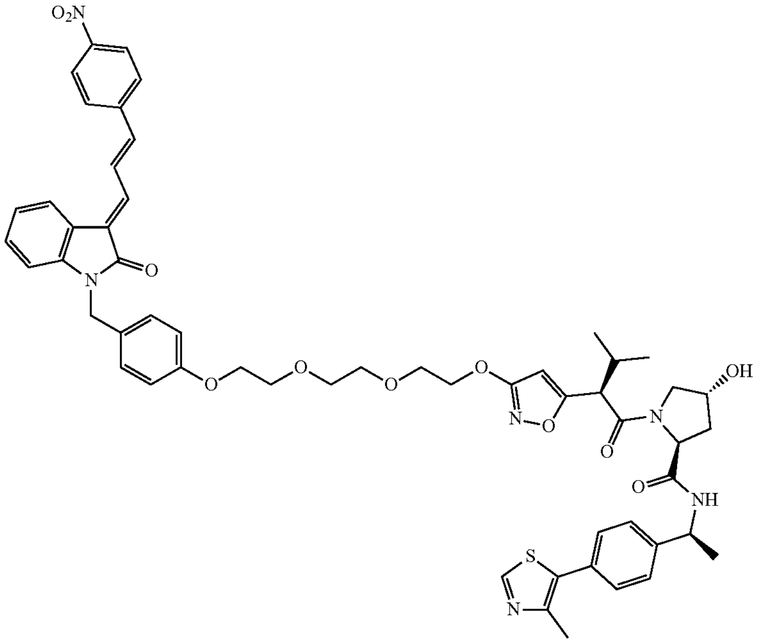 [SMILES: Cc1ncsc1-c1ccc([C@H](C)NC(=O)[C@@H]2C[C@@H](O)CN2C(=O)[C@@H](c2cc(OCCOCCOCCOc3ccc(CN4C(=O)/C(=C/C=C/c5ccc([N+](=O)[O-])cc5)c5ccccc54)cc3)no2)C(C)C)cc1] | (2S,4R)-4-hydroxy-1-((R)-3-methyl-2-(3-(2-(2-(2-(4-(((E)-3-((E)-3-(4-nitrophenyl)allylidene)-2-oxoindolin-1-yl)methyl)phenoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 75 | 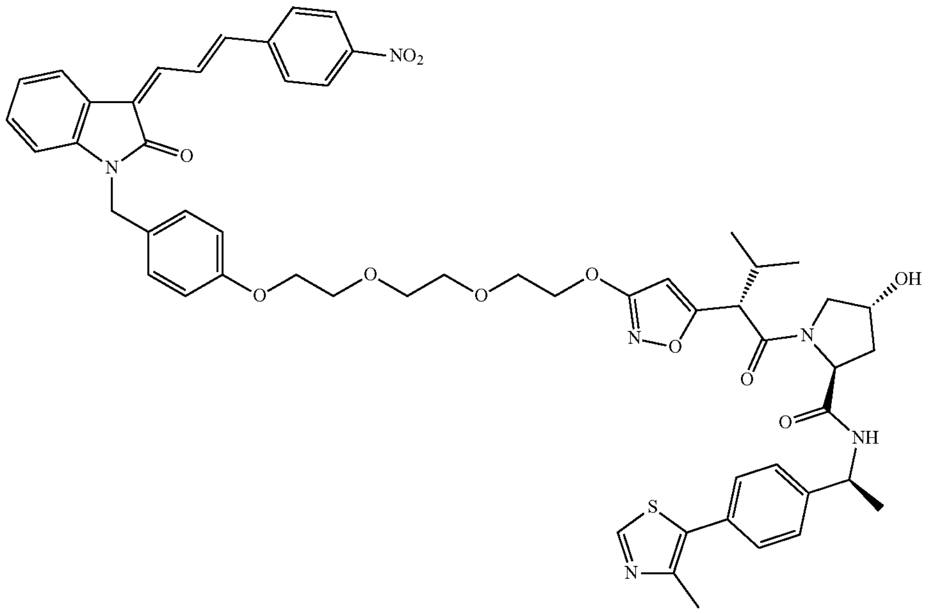 [SMILES: Cc1ncsc1-c1ccc([C@H](C)NC(=O)[C@@H]2C[C@@H](O)CN2C(=O)[C@H](c2cc(OCCOCCOCCOc3ccc(CN4C(=O)/C(=C\C=C\c5ccc([N+](=O)[O-])cc5)c5ccccc54)cc3)no2)C(C)C)cc1] | (2S,4R)-4-hydroxy-1-((S)-3-methyl-2-(3-(2-(2-(2-(4-(((Z)-3-((E)-3-(4-nitrophenyl)allylidene)-2-oxoindolin-1-yl)methyl)phenoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 76 | 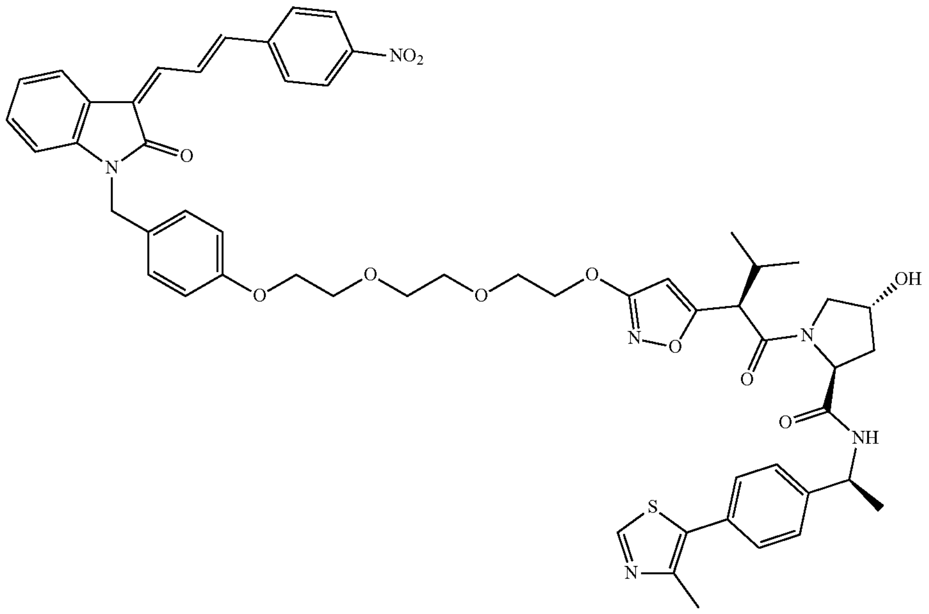 [SMILES: Cc1ncsc1-c1ccc([C@H](C)NC(=O)[C@@H]2C[C@@H](O)CN2C(=O)[C@@H](c2cc(OCCOCCOCCOc3ccc(CN4C(=O)/C(=C\C=C\c5ccc([N+](=O)[O-])cc5)c5ccccc54)cc3)no2)C(C)C)cc1] | (2S,4R)-4-hydroxy-1-((R)-3-methyl-2-(3-(2-(2-(2-(4-(((Z)-3-((E)-3-(4-nitrophenyl)allylidene)-2-oxoindolin-1-yl)methyl)phenoxy)ethoxy)ethoxy)ethoxy)isoxazol-5-yl)butanoyl)-N-((S)-1-(4-(4-methylthiazol-5-yl)phenyl)ethyl)pyrrolidine-2-carboxamide |

TABLE 1-continued
Exemplary Compounds of the Present Disclosure
| Ex. No. | Structure | Compound Name |
| --- | --- | --- |
| 77 | 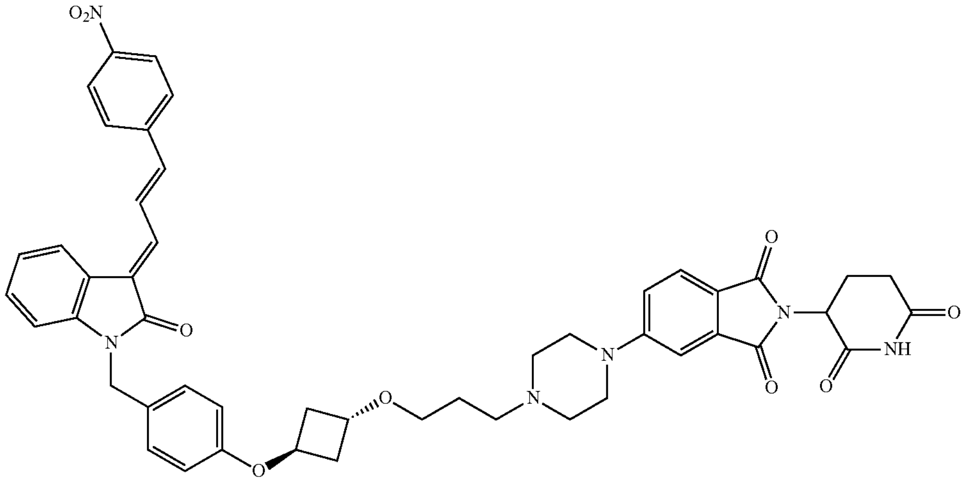 [SMILES: O=C1CCC(N2C(=O)c3ccc(N4CCN(CCCO[C@H]5C[C@H](Oc6ccc(CN7C(=O)/C(=C/C=C/c8ccc([N+](=O)[O-])cc8)c8ccccc87)cc6)C5)CC4)cc3C2=O)C(=O)N1] | 2-(2,6-dioxopiperidin-3-yl)-5-(4-(3-((1r,3r)-3-(4-(((E)-3-((E)-3-(4-nitrophenyl)allylidene)-2-oxoindolin-1-yl)methyl)phenoxy)cyclobutoxy)propyl)piperazin-1-yl)isoindoline-1,3-dione |
| 78 | 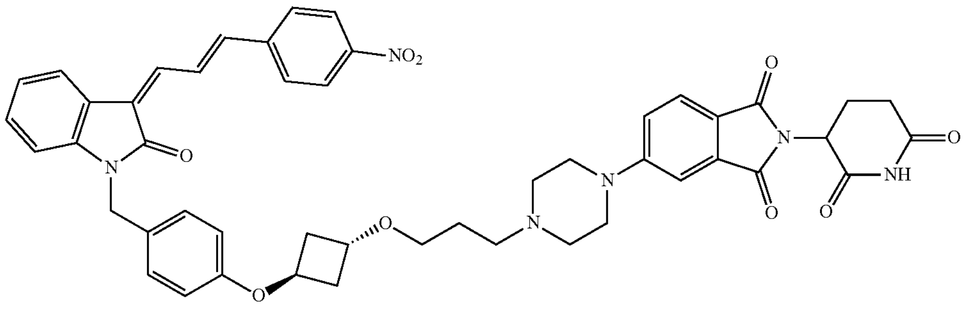 [SMILES: O=C1CCC(N2C(=O)c3ccc(N4CCN(CCCO[C@H]5C[C@H](Oc6ccc(CN7C(=O)/C(=C\C=C\c8ccc([N+](=O)[O-])cc8)c8ccccc87)cc6)C5)CC4)cc3C2=O)C(=O)N1] | 2-(2,6-dioxopiperidin-3-yl)-5-(4-(3-((1r,3r)-3-(4-(((Z)-3-((E)-3-(4-nitrophenyl)allylidene)-2-oxoindolin-1-yl)methyl)phenoxy)cyclobutoxy)propyl)piperazin-1-yl)isoindoline-1,3-dione |

TABLE 1-continued

| Exemplary Compounds of the Present Disclosure | | |
|---|---|---|
| Ex. No. | Structure | Compound Name |
| 79 | 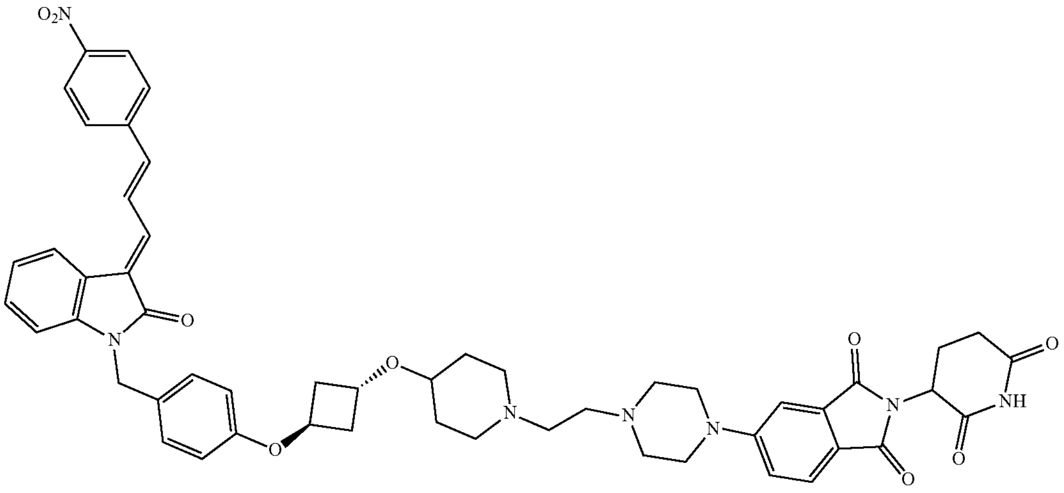 [SMILES: O=C1CCC(N2C(=O)c3ccc(N4CCN(CCN5CCC(O[C@H]6C[C@H](Oc7ccc(CN8C(=O)/C(=C/C=C/c9ccc([N+](=O)[O-])cc9)c9ccccc98)cc7)C6)CC5)CC4)cc3C2=O)C(=O)N1] | 2-(2,6-dioxopiperidin-3-yl)-5-(4-(2-(4-((1r,3r)-3-(4-(((E)-3-((E)-3-(4-nitrophenyl)allylidene)-2-oxoindolin-1-yl)methyl)phenoxy)cyclobutoxy)piperidin-1-yl)ethyl)piperazin-1-yl)isoindoline-1,3-dione |
| 80 | 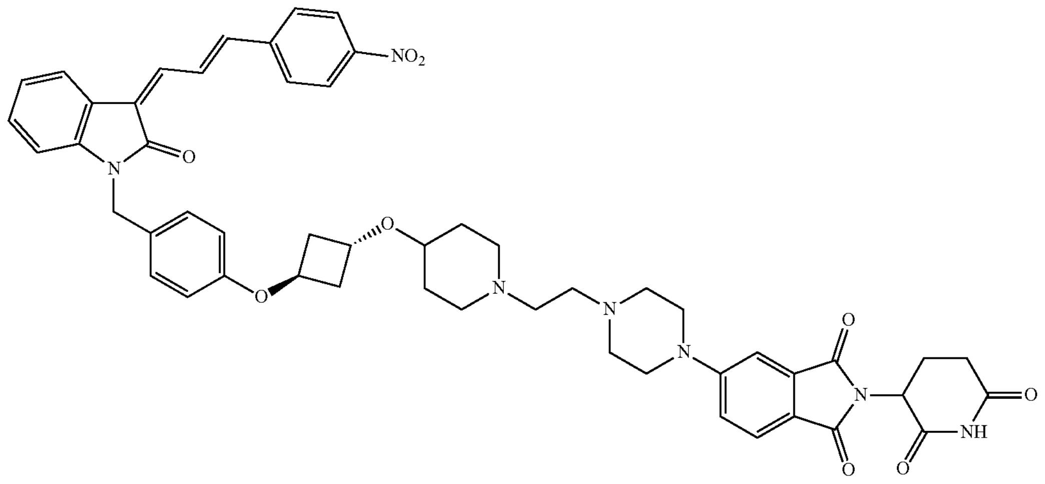 [SMILES: O=C1CCC(N2C(=O)c3ccc(N4CCN(CCN5CCC(O[C@H]6C[C@H](Oc7ccc(CN8C(=O)/C(=C\C=C\c9ccc([N+](=O)[O-])cc9)c9ccccc98)cc7)C6)CC5)CC4)cc3C2=O)C(=O)N1] | 2-(2,6-dioxopiperidin-3-yl)-5-(4-(2-(4-((1r,3r)-3-(4-(((Z)-3-((E)-3-(4-nitrophenyl)allylidene)-2-oxoindolin-1-yl)methyl)phenoxy)cyclobutoxy)piperidin-1-yl)ethyl)piperazin-1-yl)isoindoline-1,3-dione |

TABLE 1-continued
| Exemplary Compounds of the Present Disclosure | | |
|---|---|---|
| Ex. No. | Structure | Compound Name |
| 81 | 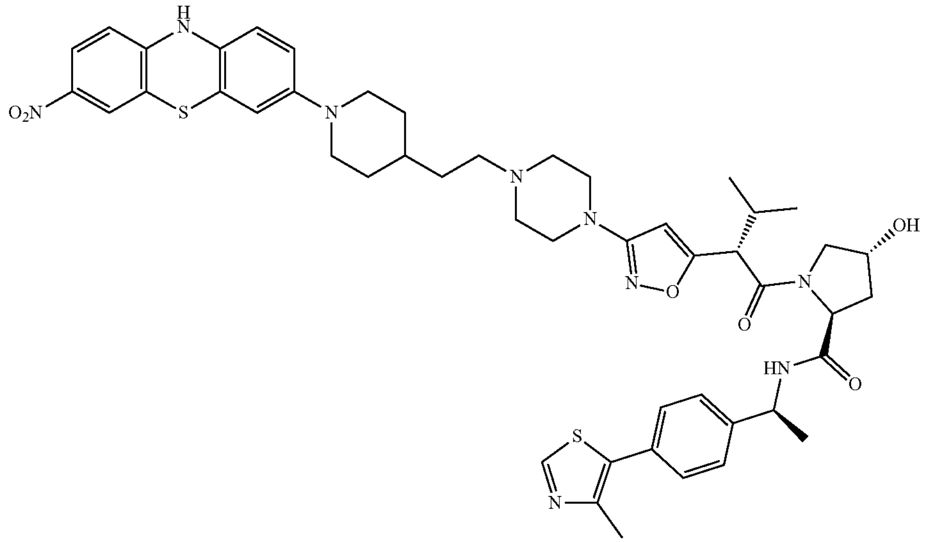 [SMILES: Cc1ncsc1-c1ccc([C@H](C)NC(=O)[C@@H]2C[C@@H](O)CN2C(=O)[C@H](c2cc(N3CCN(CCC4CCN(c5ccc6c(c5)Sc5cc([N+](=O)[O-])ccc5N6)CC4)CC3)no2)C(C)C)cc1] | (2S,4R)-4-hydroxy-1-((S)-3-methyl-2-(3-(4-(2-(1-(7-nitro-10H-phenothiazin-3-yl)piperidin-4-yl)ethyl)piperazin-1-yl)isoxazol-5-yl)butanoyl)-N-((S)-1-(4-(4-methylthiazol-5-yl)phenyl)ethyl)pyrrolidine-2-carboxamide |

TABLE 1-continued
Exemplary Compounds of the Present Disclosure
| Ex. No. | Structure | Compound Name |
|---|---|---|
| 82 | 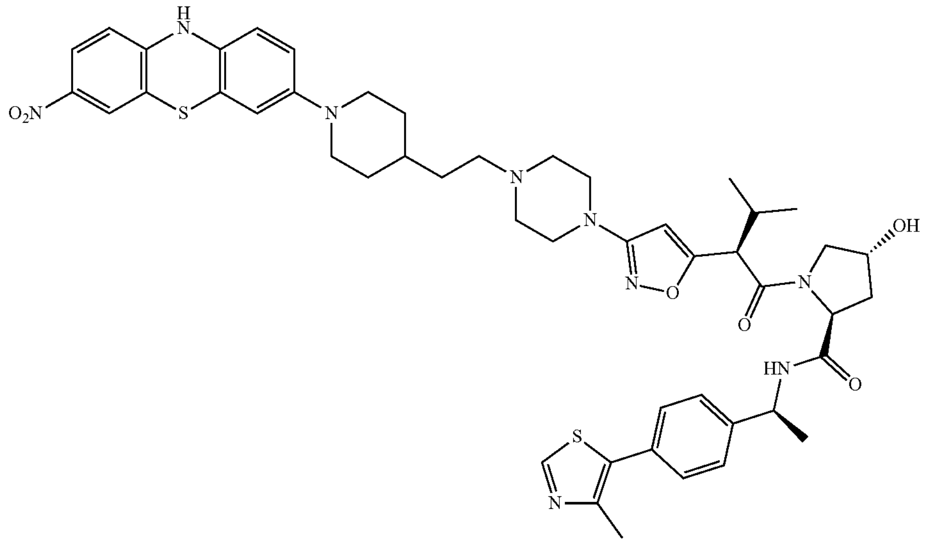 [SMILES: Cc1ncsc1-c1ccc([C@H](C)NC(=O)[C@@H]2C[C@@H](O)CN2C(=O)[C@@H](c2cc(N3CCN(CCC4CCN(c5ccc6c(c5)Sc5cc([N+](=O)[O-])ccc5N6)CC4)CC3)no2)C(C)C)cc1] | (2S,4R)-4-hydroxy-1-((R)-3-methyl-2-(3-(4-(2-(1-(7-nitro-10H-phenothiazin-3-yl)piperidin-4-yl)ethyl)piperazin-1-yl)isoxazol-5-yl)butanoyl)-N-((S)-1-(4-(4-methylthiazol-5-yl)phenyl)ethyl)pyrrolidine-2-carboxamide |
| 83 | 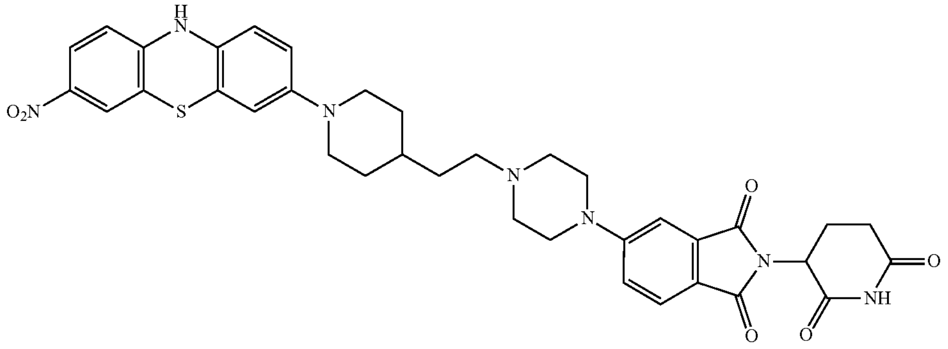 [SMILES: O=C1CCC(N2C(=O)c3ccc(N4CCN(CCC5CCN(c6ccc7c(c6)Sc6cc([N+](=O)[O-])ccc6N7)CC5)CC4)cc3C2=O)C(=O)N1] | 2-(2,6-dioxopiperidin-3-yl)-5-(4-(2-(1-(7-nitro-10H-phenothiazin-3-yl)piperidin-4-yl)ethyl)piperazin-1-yl)isoindoline-1,3-dione |

TABLE 1-continued

| Exemplary Compounds of the Present Disclosure | | |
|---|---|---|
| Ex. No. | Structure | Compound Name |
| 84 | 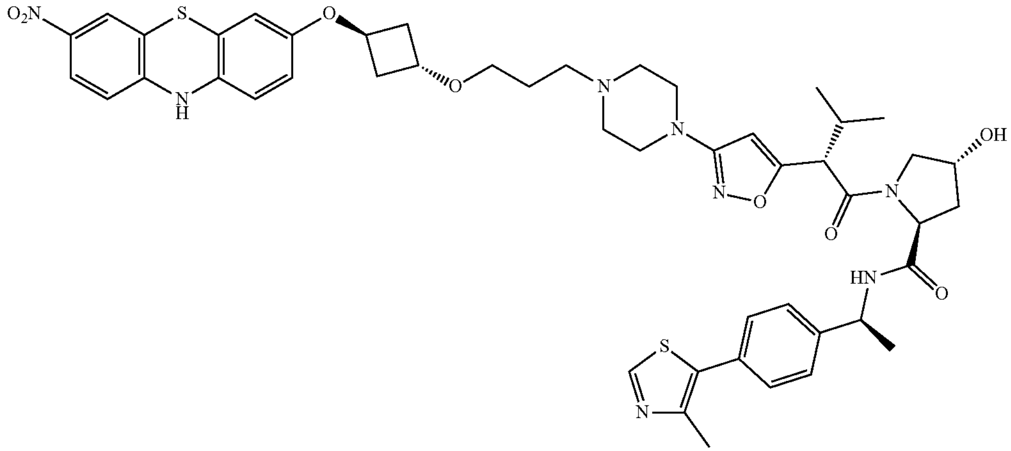 [SMILES: Cc1ncsc1-c1ccc([C@H](C)NC(=O)[C@@H]2C[C@@H](O)CN2C(=O)[C@H](c2cc(N3CCN(CCCO[C@H]4C[C@H](Oc5ccc6c(c5)Sc5cc([N+](=O)[O-])ccc5N6)C4)CC3)no2)C(C)C)cc1] | (2S,4R)-4-hydroxy-1-((S)-3-methyl-2-(3-(4-(3-((1r,3S)-3-((7-nitro-10H-phenothiazin-3-yl)oxy)cyclobutoxy)propyl)piperazin-1-yl)isoxazol-5-yl)butanoyl)-N-((S)-1-(4-(4-methylthiazol-5-yl)phenyl)ethyl)pyrrolidine-2-carboxamide |
| 85 | 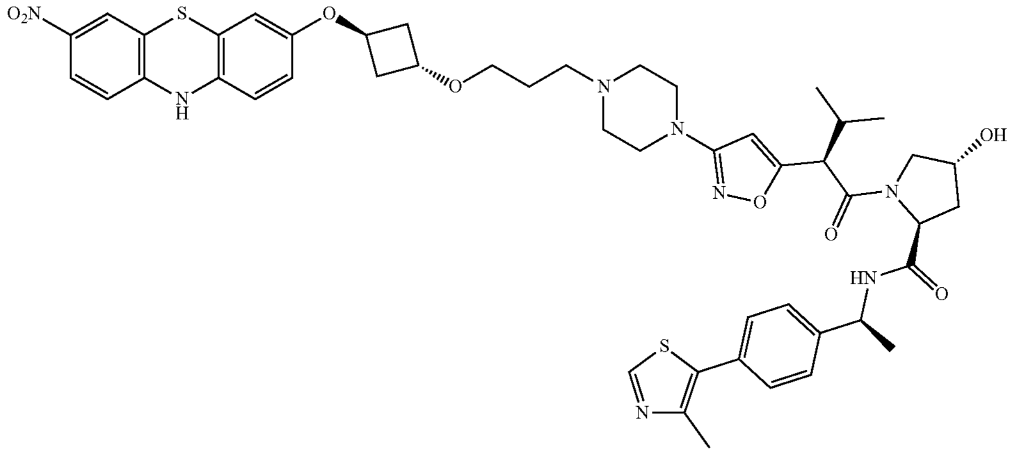 [SMILES: Cc1ncsc1-c1ccc([C@H](C)NC(=O)[C@@H]2C[C@@H](O)CN2C(=O)[C@@H](c2cc(N3CCN(CCCO[C@H]4C[C@H](Oc5ccc6c(c5)Sc5cc([N+](=O)[O-])ccc5N6)C4)CC3)no2)C(C)C)cc1] | (2S,4R)-4-hydroxy-1-((R)-3-methyl-2-(3-(4-(3-((1r,3R)-3-((7-nitro-10H-phenothiazin-3-yl)oxy)cyclobutoxy)propyl)piperazin-1-yl)isoxazol-5-yl)butanoyl)-N-((S)-1-(4-(4-methylthiazol-5-yl)phenyl)ethyl)pyrrolidine-2-carboxamide |

TABLE 1-continued
| Exemplary Compounds of the Present Disclosure | | |
|---|---|---|
| Ex. No. | Structure | Compound Name |
| 86 | 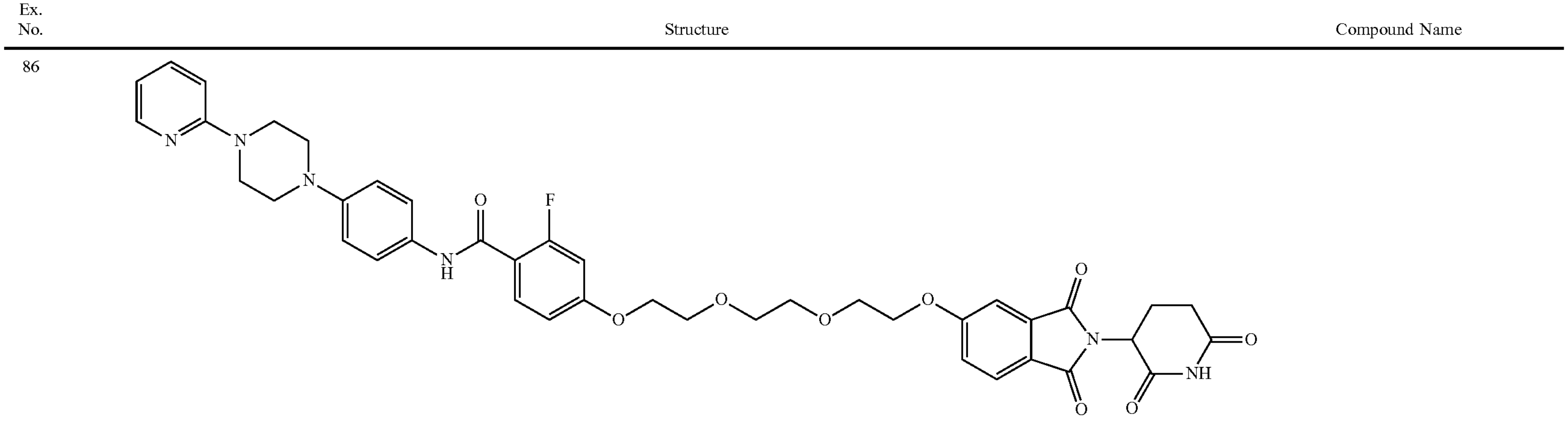 | |
| 87 | 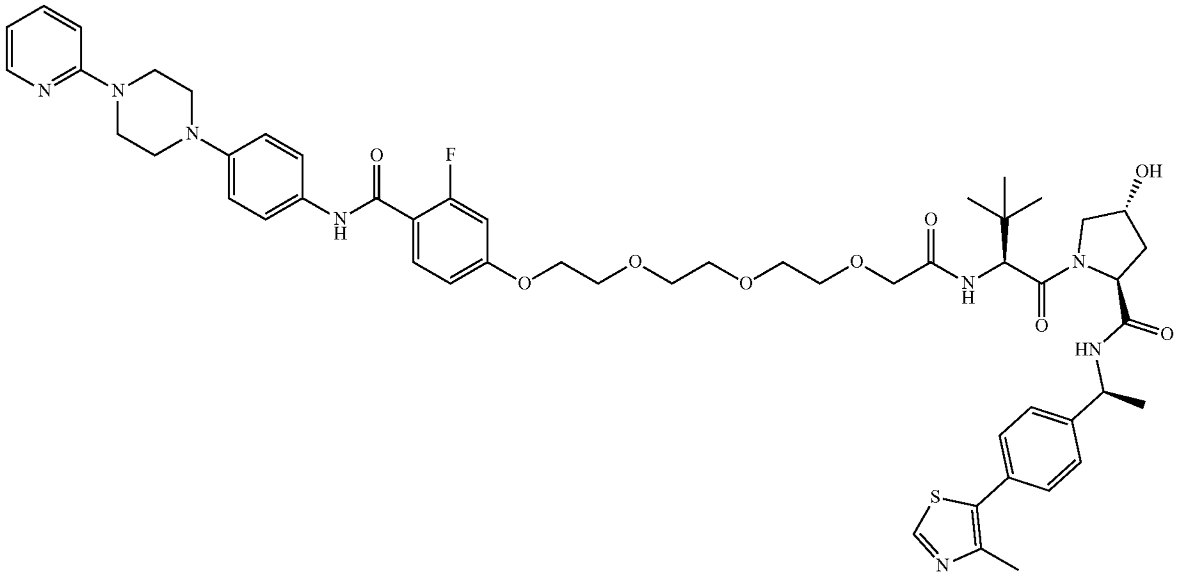 [SMILES: Cc1ncsc1-c1ccc([C@H](C)NC(=O)[C@@H]2C[C@@H](O)CN2C(=O)[C@@H](NC(=O)COCCOCCOCCOc2ccc(C(=O)Nc3ccc(N4CCN(c5ccccn5)CC4)cc3)c(F)c2)C(C)(C)C)cc1] | |

TABLE 1-continued
| Exemplary Compounds of the Present Disclosure | | |
| --- | --- | --- |
| Ex. No. | Structure | Compound Name |
| 88 | 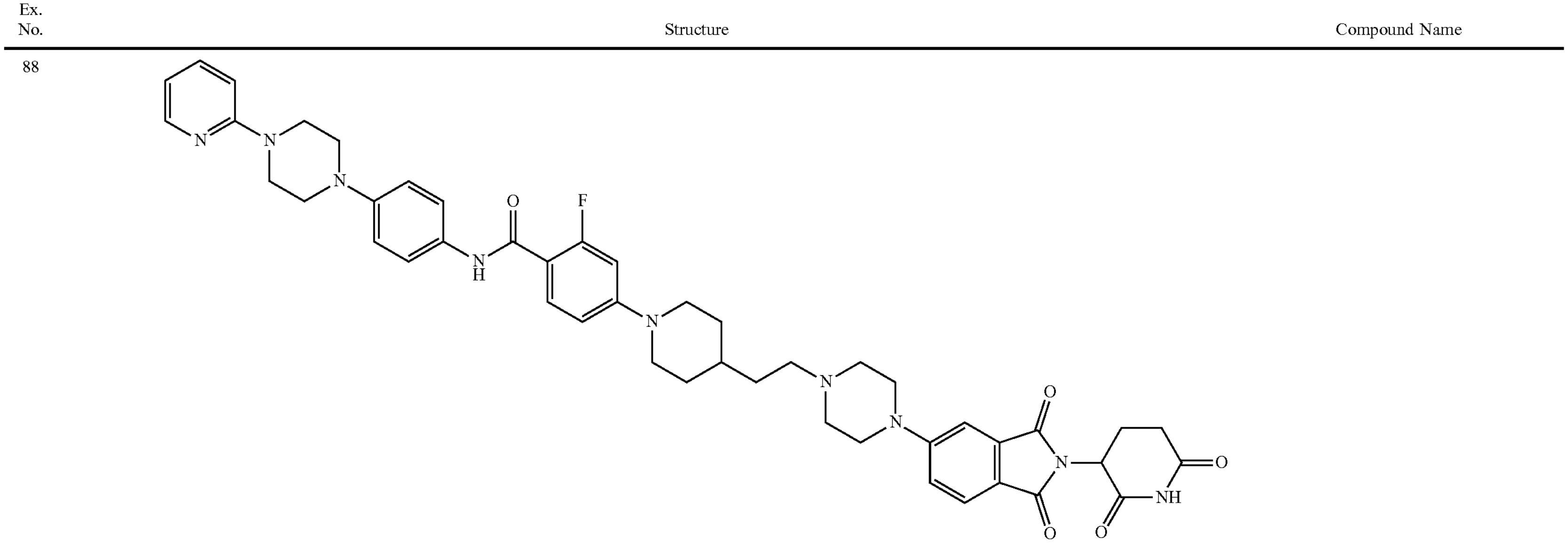 | |

TABLE 1-continued
| Exemplary Compounds of the Present Disclosure | | |
| --- | --- | --- |
| Ex. No. | Structure | Compound Name |
| 89 | 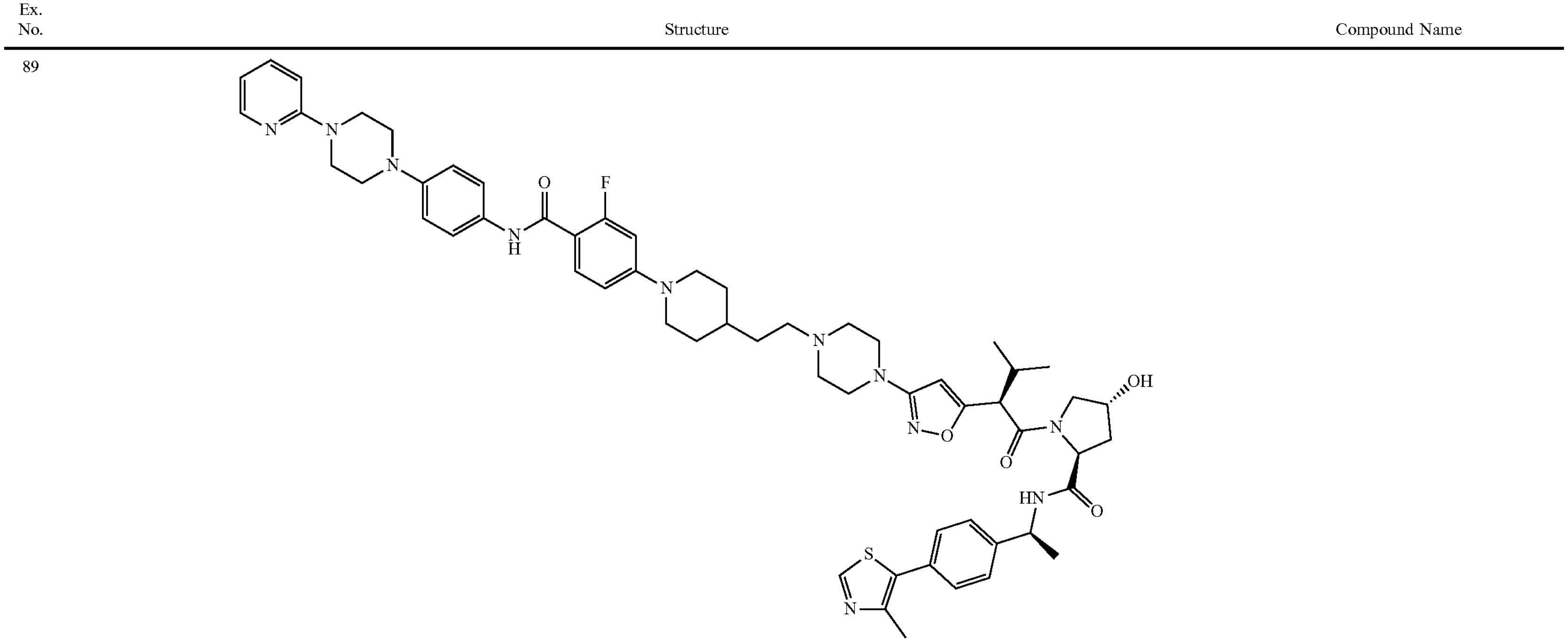 | |

TABLE 1-continued
| Exemplary Compounds of the Present Disclosure | | |
|---|---|---|
| Ex. No. | Structure | Compound Name |
| 90 | 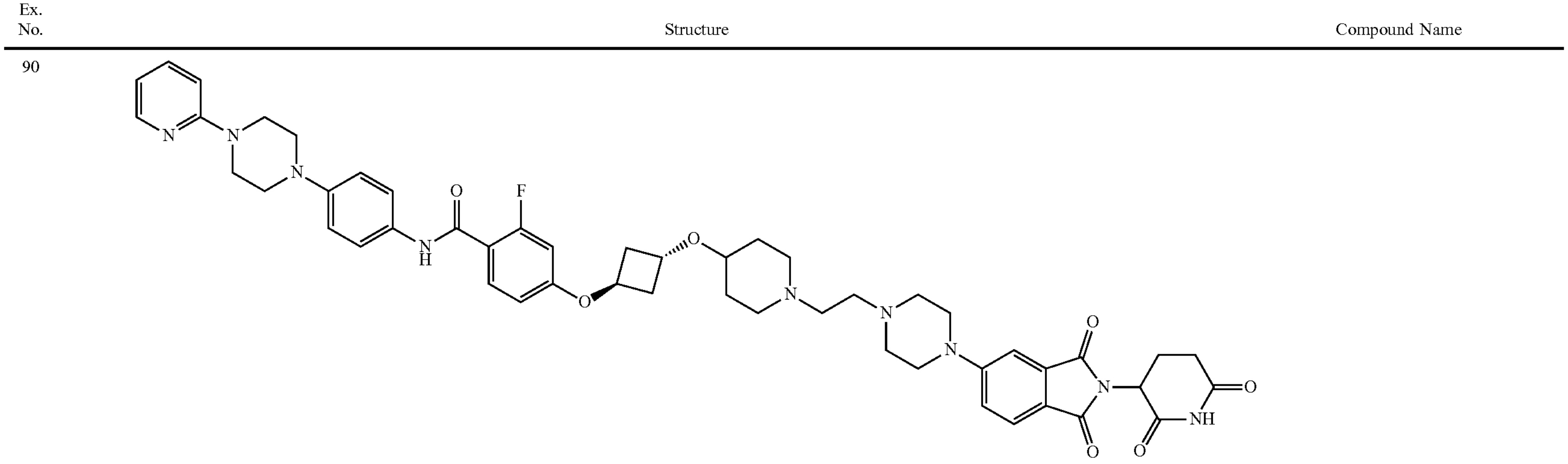 | |
| 91 | 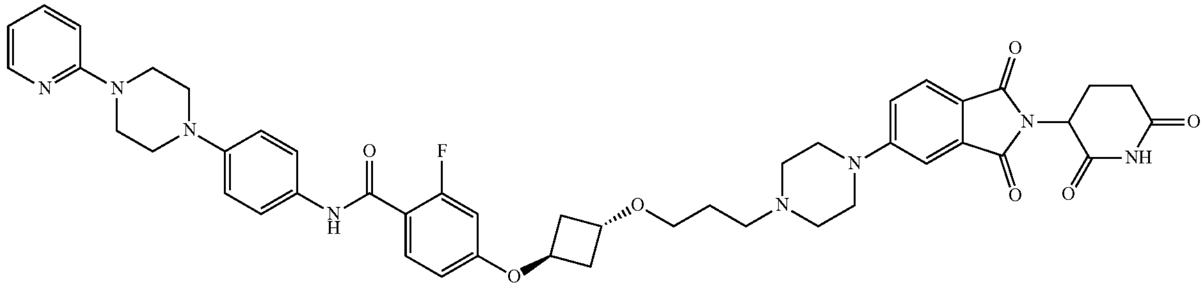 [SMILES: O=C1CCC(N2C(=O)c3ccc(N4CCN(CCCO[C@H]5C[C@H](Oc6ccc(C(=O)Nc7ccc(N8CCN(c9ccccn9)CC8)cc7)c(F)c6)C5)CC4)cc3C2=O)C(=O)N1] | |

TABLE 1-continued
| Exemplary Compounds of the Present Disclosure | | |
|---|---|---|
| Ex. No. | Structure | Compound Name |
| 92 | 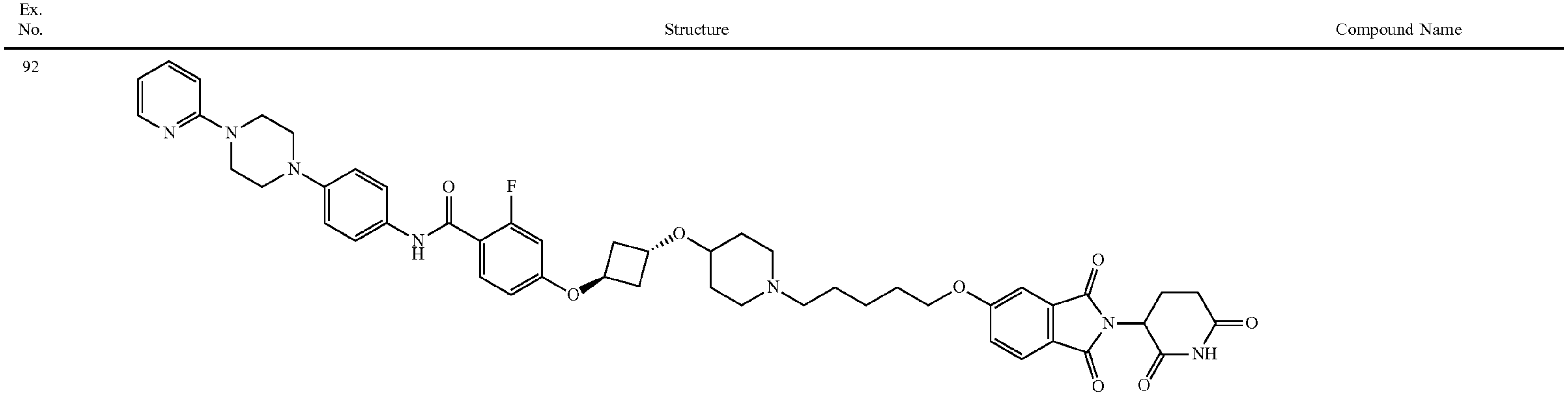 | |
| 93 | 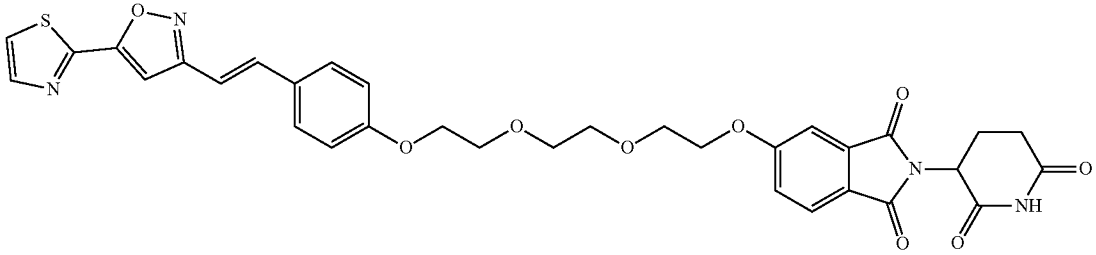 [SMILES: O=C1CCC(N2C(=O)c3ccc(OCCOCCOCCOc4ccc(/C=C/c5cc(-c6nccs6)on5)cc4)cc3C2=O)C(=O)N1] | |

TABLE 1-continued
| Exemplary Compounds of the Present Disclosure | | |
|---|---|---|
| Ex. No. | Structure | Compound Name |
| 94 | 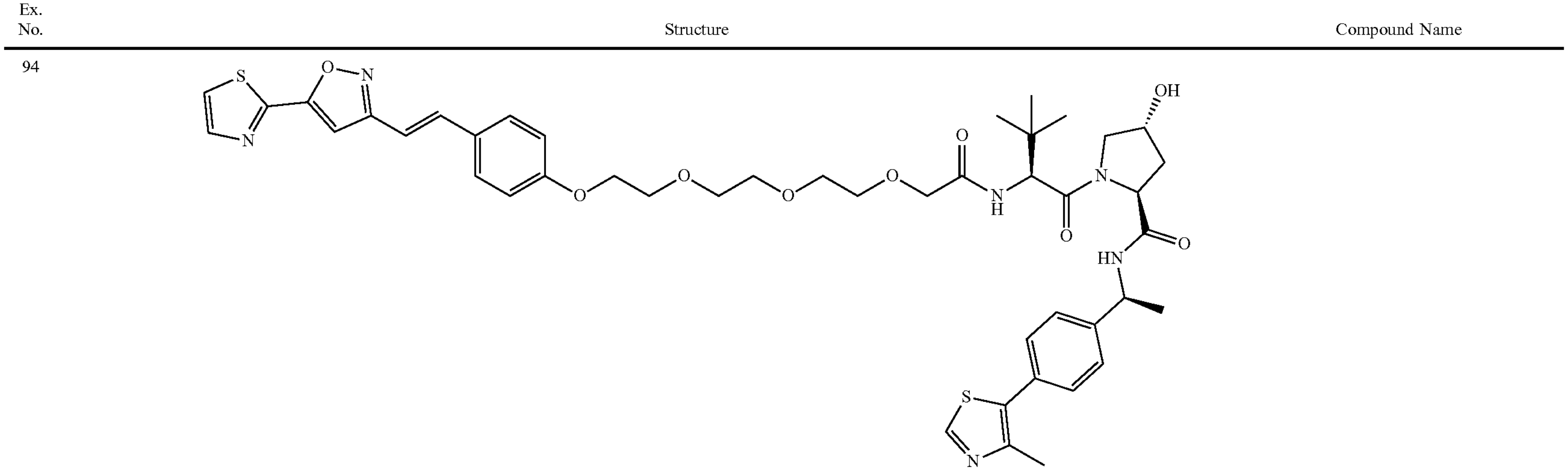 | |
| 95 | 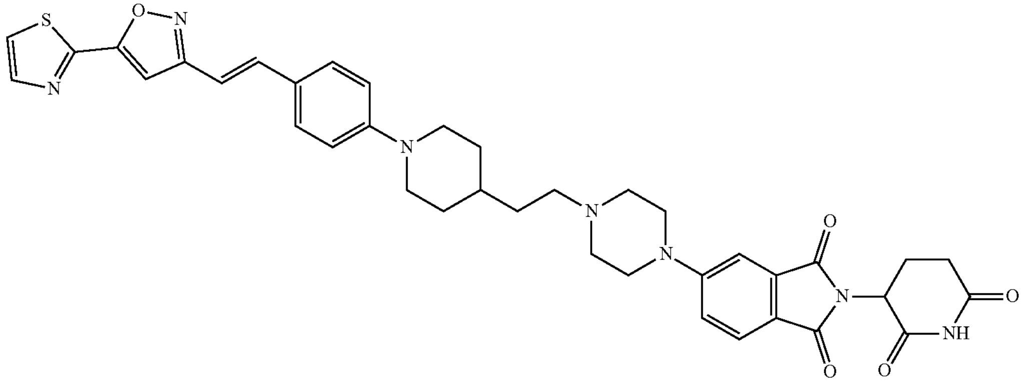 [SMILES: O=C1CCC(N2C(=O)c3ccc(N4CCN(CCC5CCN(c6ccc(/C=C/c7cc(-c8nccs8)on7)cc6)CC5)CC4)cc3C2=O)C(=O)N1] | |

TABLE 1-continued
| Exemplary Compounds of the Present Disclosure | | |
|---|---|---|
| Ex. No. | Structure | Compound Name |
| 96 | 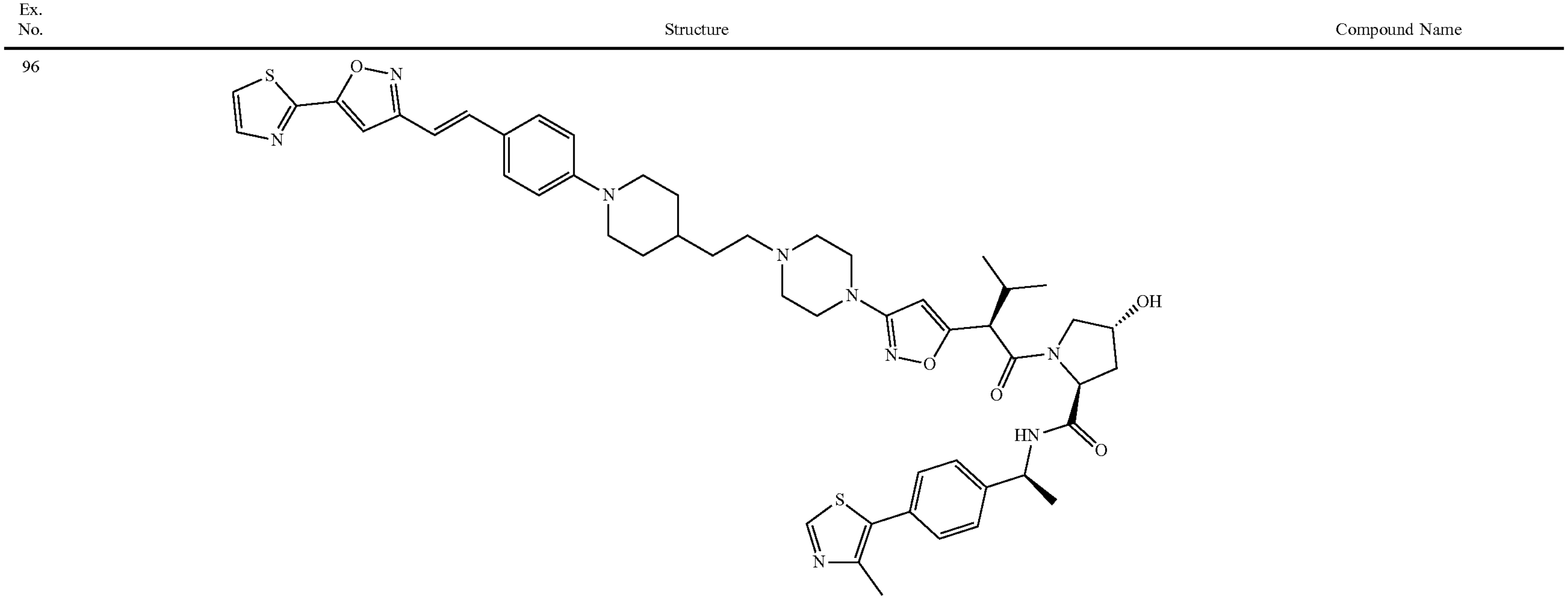 | |
| 97 | 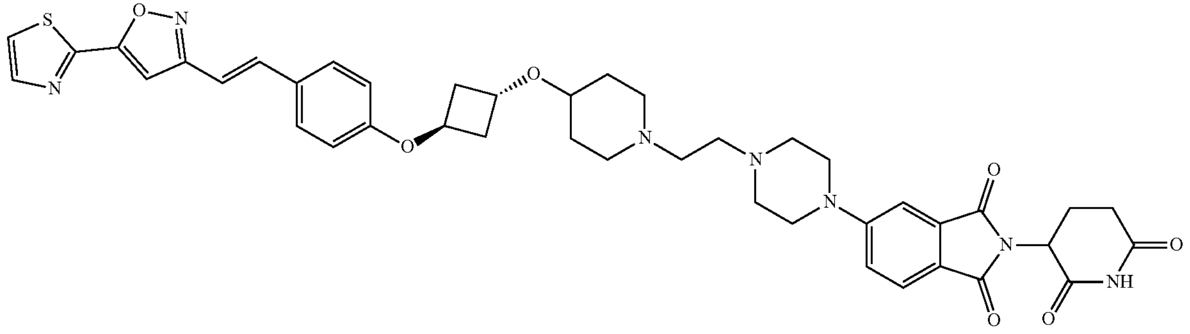 [SMILES: O=C1CCC(N2C(=O)c3ccc(N4CCN(CCN5CCC(O[C@H]6C[C@H](Oc7ccc(/C=C/c8cc(-c9nccs9)on8)cc7)C6)CC5)CC4)cc3C2=O)C(=O)N1] | |

TABLE 1-continued
| Ex. No. | Structure | Compound Name |
| --- | --- | --- |
| | Exemplary Compounds of the Present Disclosure | |
| 98 | 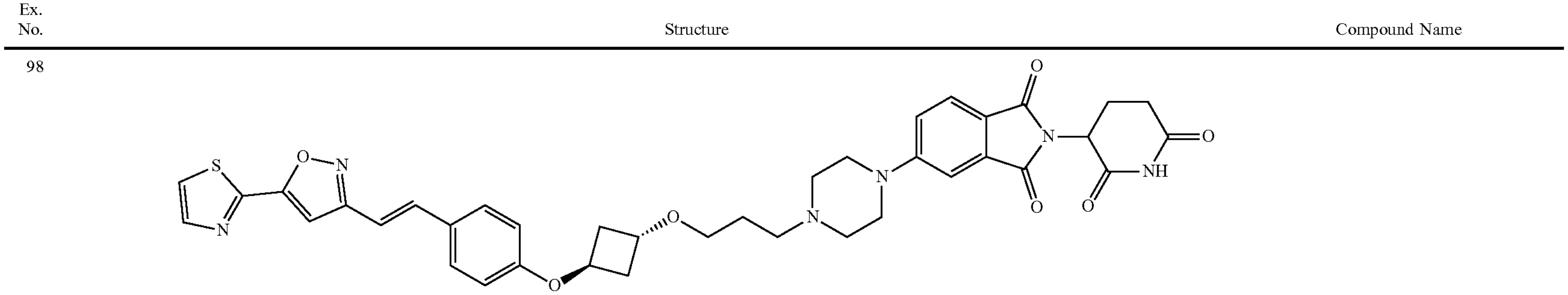 | |
| 99 | 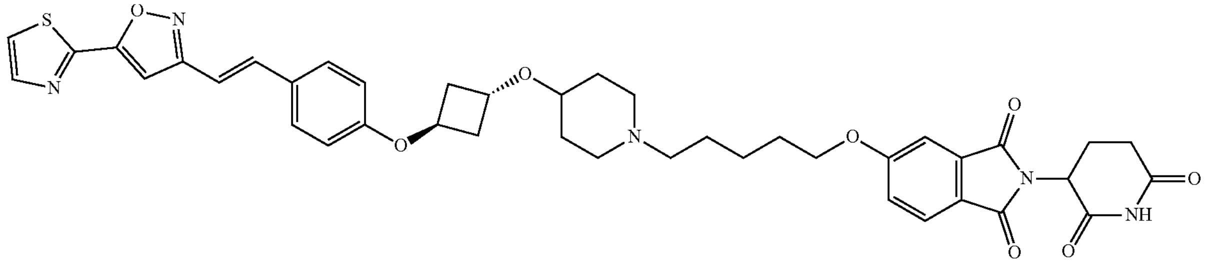 [SMILES: O=C1CCC(N2C(=O)c3ccc(OCCCCCN4CCC(O[C@H]5C[C@H](Oc6ccc(/C=C/c7cc(-c8nccs8)on7)cc6)C5)CC4)cc3C2=O)C(=O)N1] | |
| 100 | 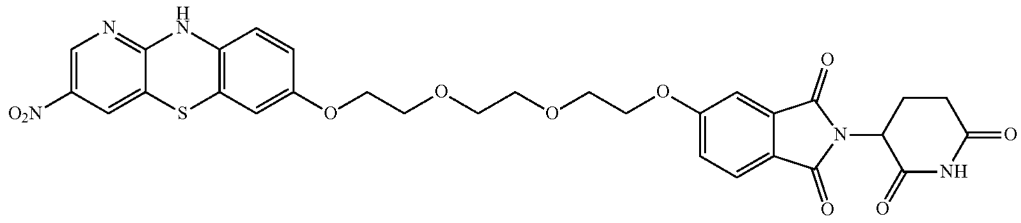 [SMILES: O=C1CCC(N2C(=O)c3ccc(OCCOCCOCCOc4ccc5c(c4)Sc4cc([N+](=O)[O-])cnc4N5)cc3C2=O)C(=O)N1] | |

TABLE 1-continued
| Exemplary Compounds of the Present Disclosure | | |
|---|---|---|
| Ex. No. | Structure | Compound Name |
| 101 | 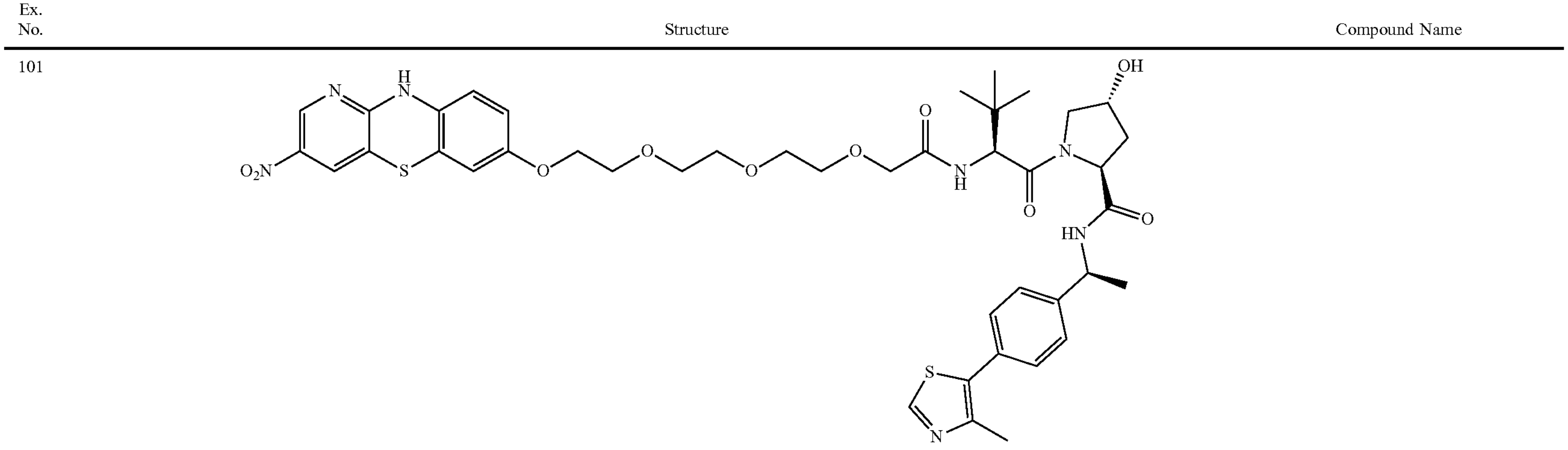 | |
| 102 | 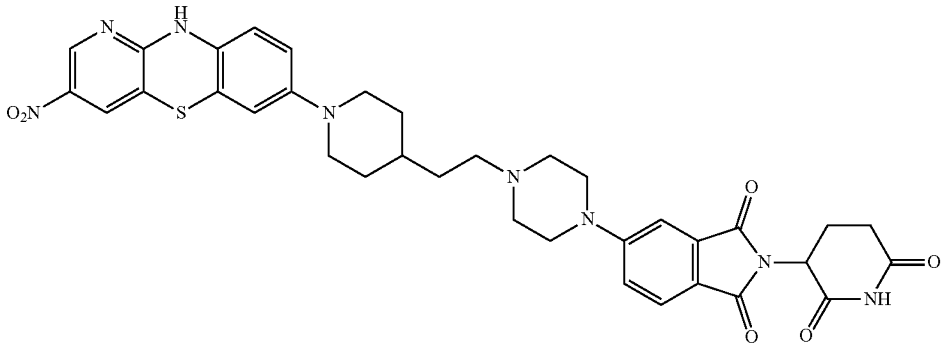 [SMILES: O=C1CCC(N2C(=O)c3ccc(N4CCN(CCC5CCN(c6ccc7c(c6)Sc6cc([N+](=O)[O-])cnc6N7)CC5)CC4)cc3C2=O)C(=O)N1] | |

TABLE 1-continued
| Ex. No. | Structure | Compound Name |
| --- | --- | --- |
| | Exemplary Compounds of the Present Disclosure | |
| 103 | 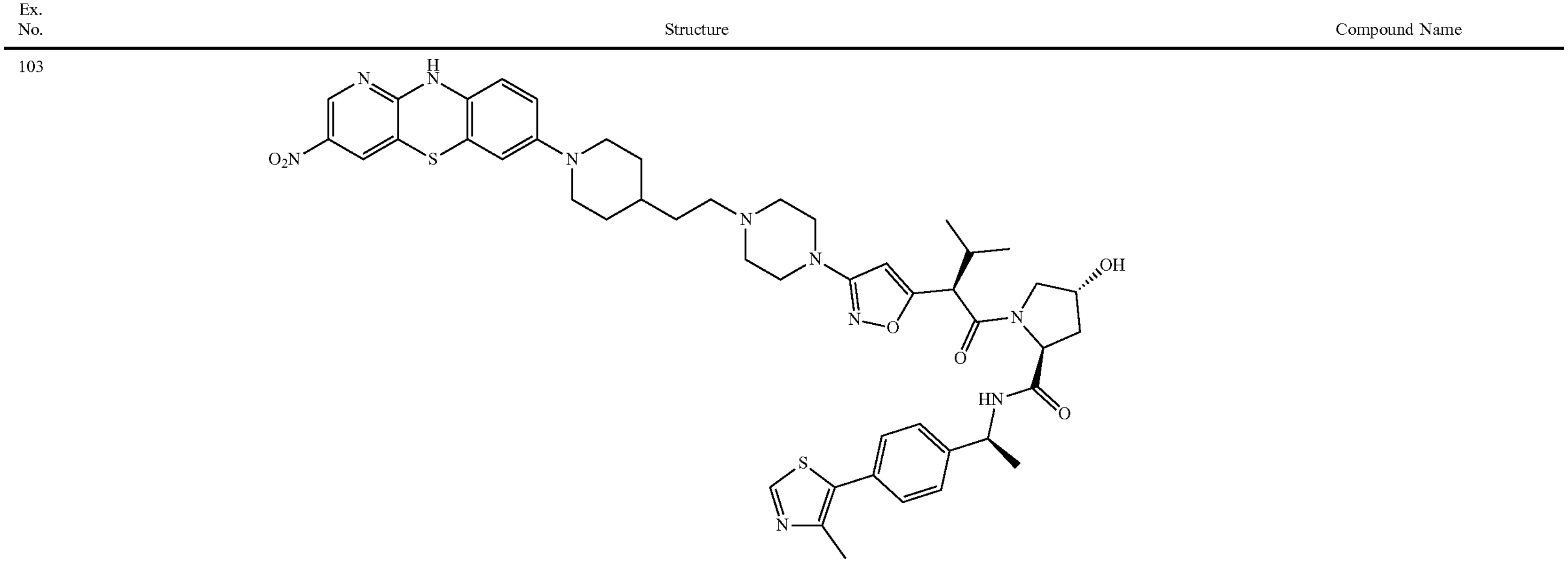 | |
| 104 | 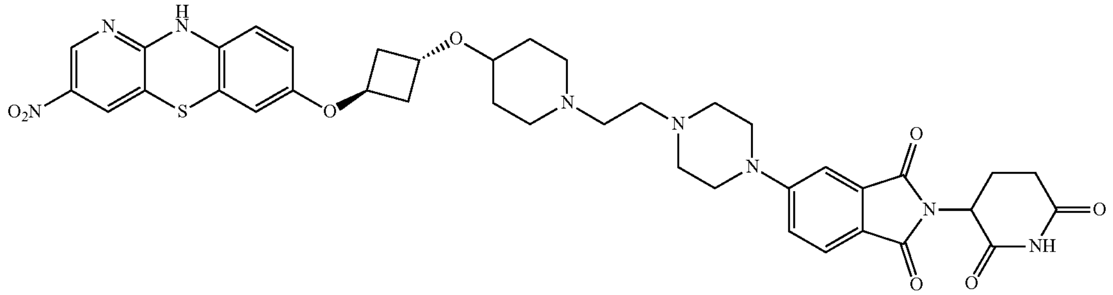 [SMILES: O=C1CCC(N2C(=O)c3ccc(N4CCN(CCN5CCC(O[C@H]6C[C@H](Oc7ccc8c(c7)Sc7cc([N+](=O)[O-])cnc7N8)C6)CC5)CC4)cc3C2=O)C(=O)N1] | |

TABLE 1-continued
Exemplary Compounds of the Present Disclosure
| Ex. No. | Structure | Compound Name |
| --- | --- | --- |
| 105 | 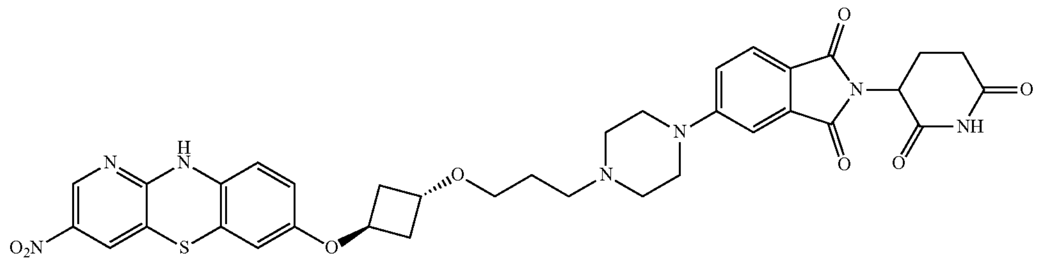 [SMILES: O=C1CCC(N2C(=O)c3ccc(N4CCN(CCCO[C@H]5C[C@H](Oc6ccc7c(c6)Sc6cc([N+](=O)[O-])cnc6N7)C5)CC4)cc3C2=O)C(=O)N1] | |
| 106 | 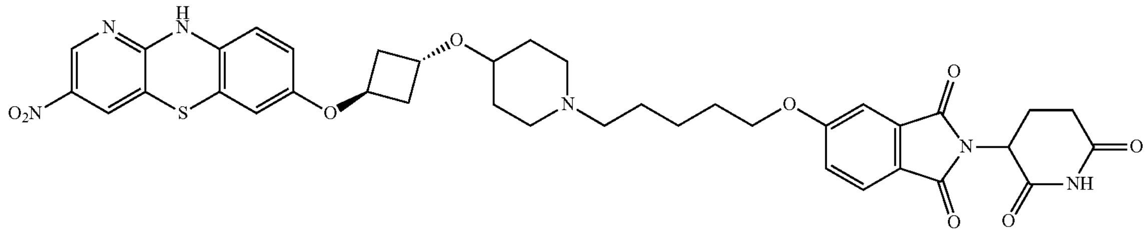 [SMILES: O=C1CCC(N2C(=O)c3ccc(OCCCCCN4CCC(O[C@H]5C[C@H](Oc6ccc7c(c6)Sc6cc([N+](=O)[O-])cnc6N7)C5)CC4)cc3C2=O)C(=O)N1] | |
| 107 | 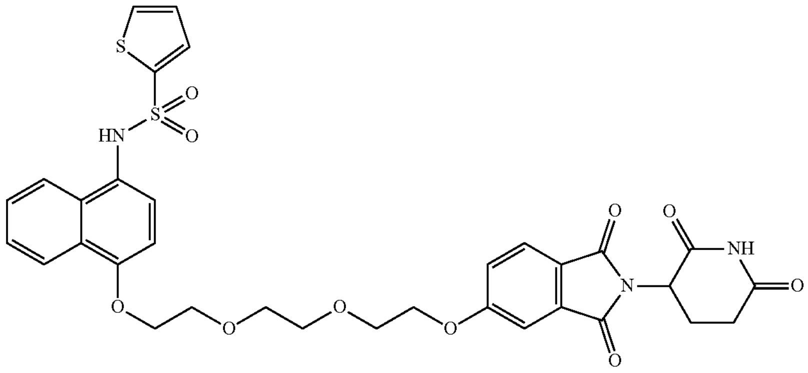 [SMILES: O=C1CCC(N2C(=O)c3ccc(OCCOCCOCCOc4ccc(NS(=O)(=O)c5cccs5)c5ccccc45)cc3C2=O)C(=O)N1] | |

TABLE 1-continued
| Exemplary Compounds of the Present Disclosure | | |
|---|---|---|
| Ex. No. | Structure | Compound Name |
| 108 | 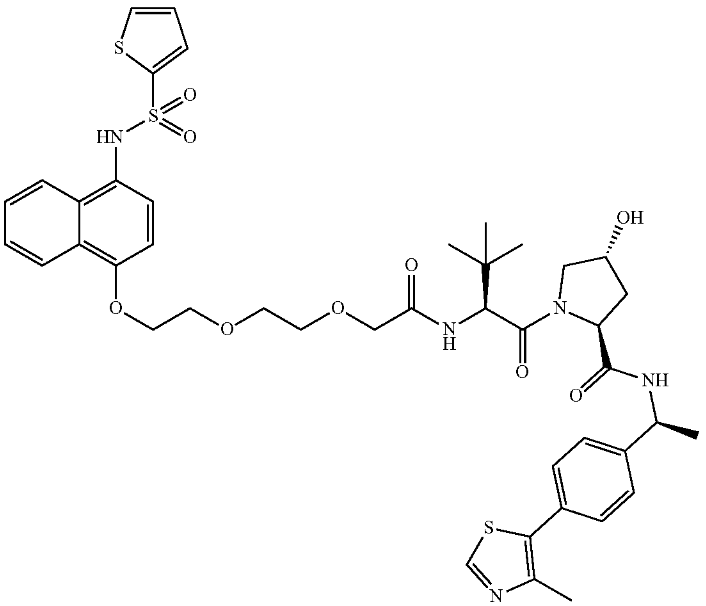 [SMILES: Cc1ncsc1-c1ccc([C@H](C)NC(=O)[C@@H]2C[C@@H](O)CN2C(=O)[C@@H](NC(=O)COCCOCCOc2ccc(NS(=O)(=O)c3cccs3)c3ccccc23)C(C)(C)C)cc1] | |
| 109 | 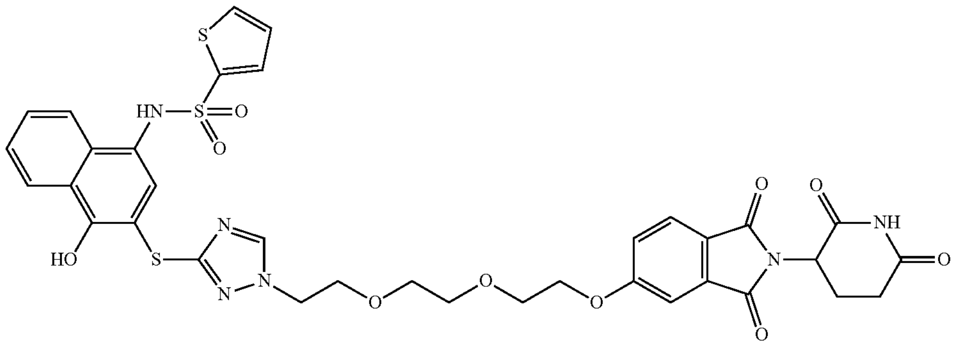 [SMILES: O=C1CCC(N2C(=O)c3ccc(OCCOCCOCCn4cnc(Sc5cc(NS(=O)(=O)c6cccs6)c6ccccc6c5O)n4)cc3C2=O)C(=O)N1] | |

TABLE 1-continued
Exemplary Compounds of the Present Disclosure
| Ex. No. | Structure | Compound Name |
| --- | --- | --- |
| 110 | 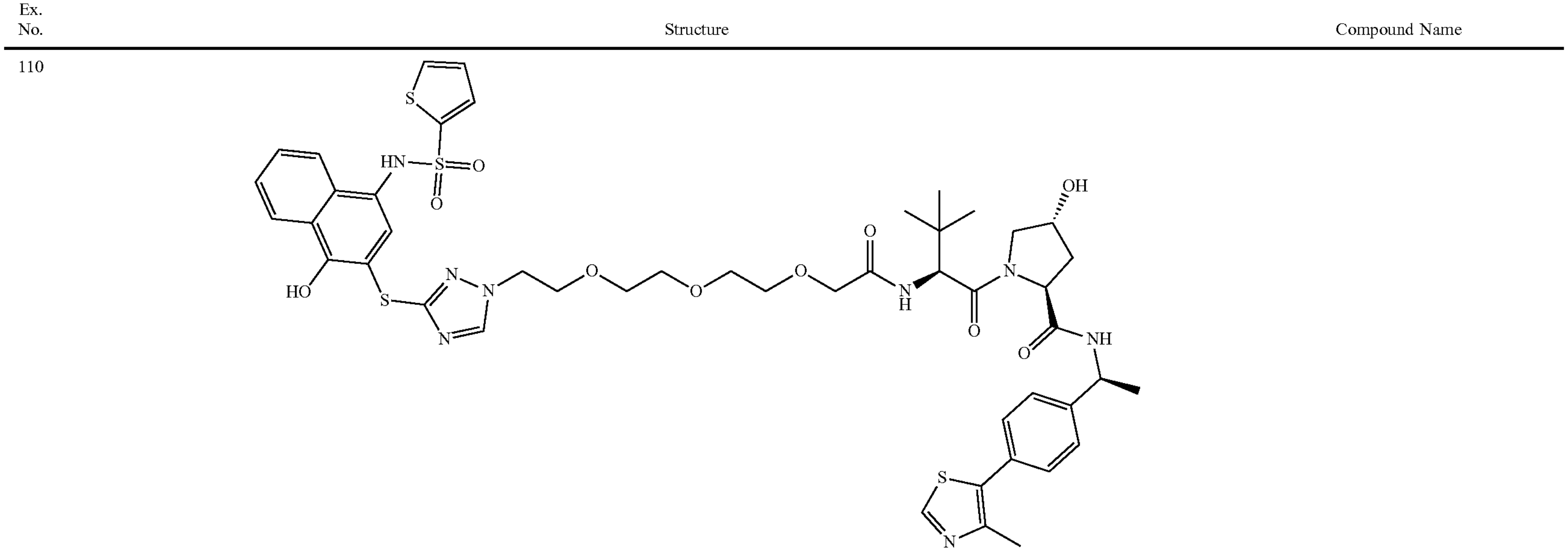 | |
| 111 | 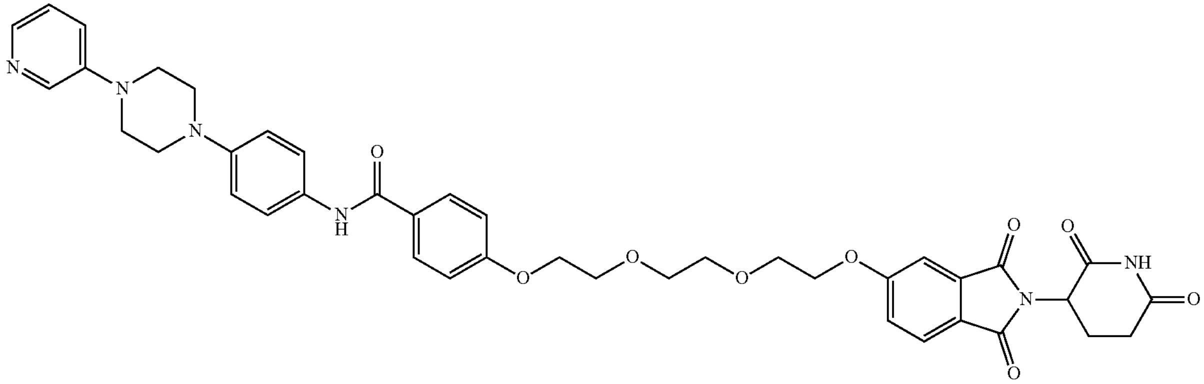 [SMILES: O=C1CCC(N2C(=O)c3ccc(OCCOCCOCCOc4ccc(C(=O)Nc5ccc(N6CCN(c7cccnc7)CC6)cc5)cc4)cc3C2=O)C(=O)N1] | |

TABLE 1-continued
| Exemplary Compounds of the Present Disclosure | | |
|---|---|---|
| Ex. No. | Structure | Compound Name |
| 112 | 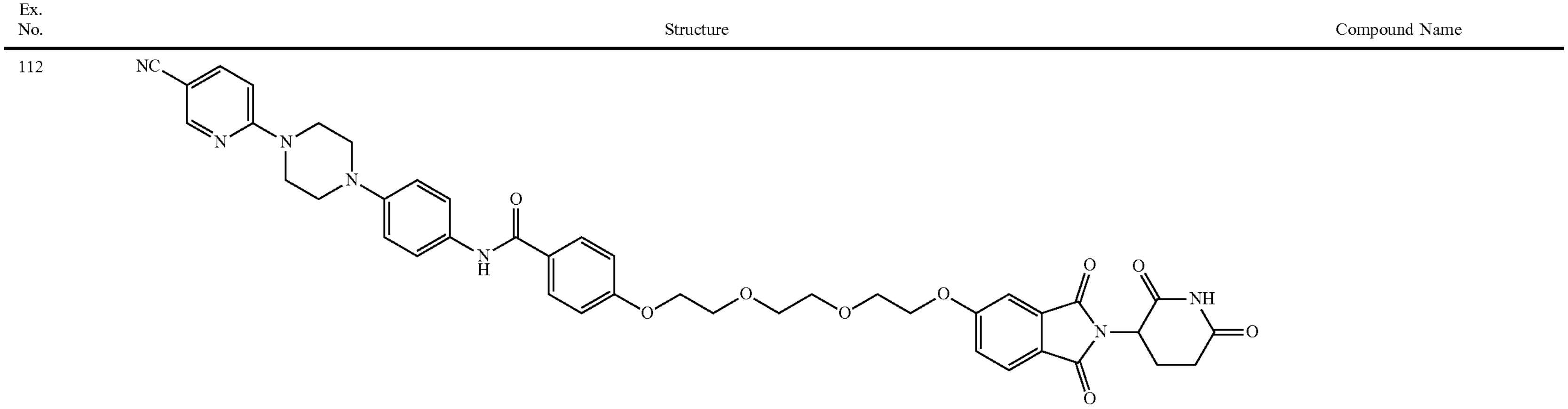 | |
| 113 | 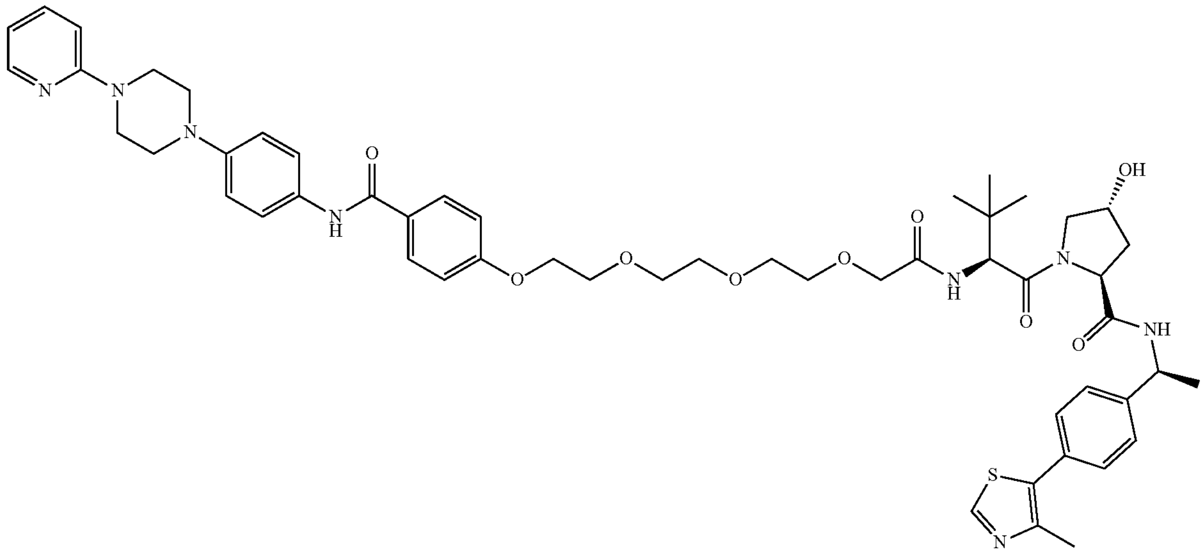 [SMILES: Cc1ncsc1-c1ccc([C@H](C)NC(=O)[C@@H]2C[C@@H](O)CN2C(=O)[C@@H](NC(=O)COCCOCCOCCOc2ccc(C(=O)Nc3ccc(N4CCN(c5ccccn5)CC4)cc3)cc2)C(C)(C)C)cc1] | |

TABLE 1-continued
| Exemplary Compounds of the Present Disclosure | | |
|---|---|---|
| Ex. No. | Structure | Compound Name |
| 114 | 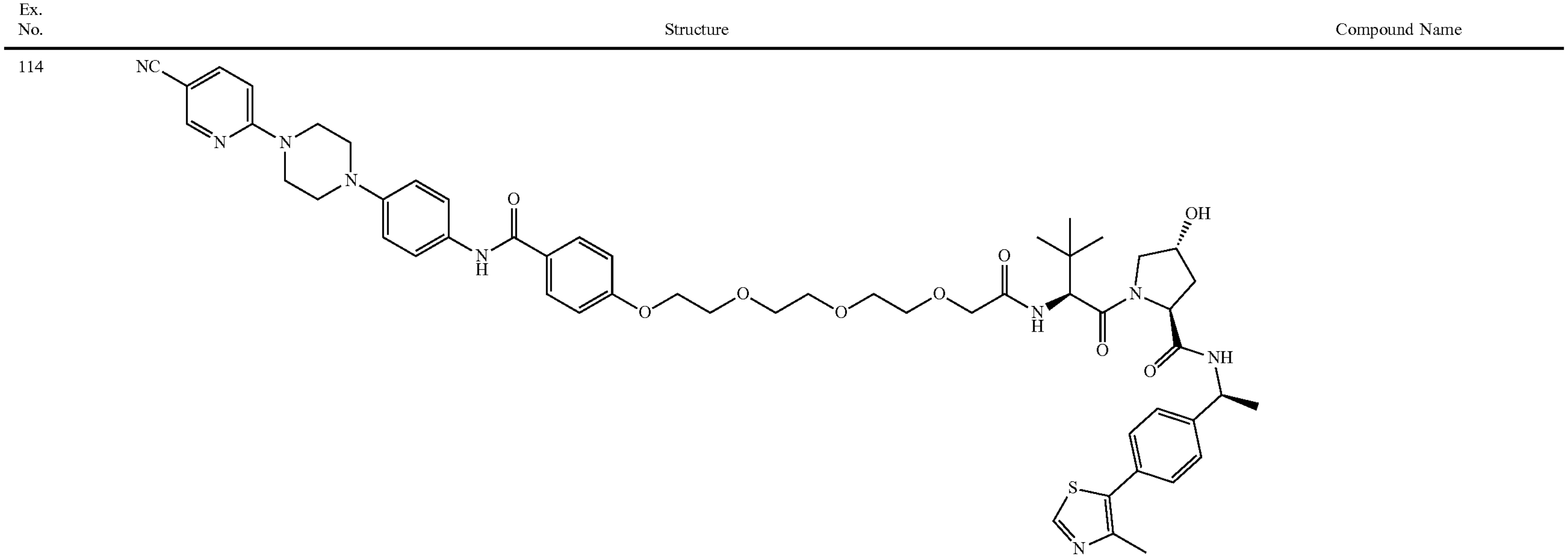 | |

TABLE 1-continued
| Exemplary Compounds of the Present Disclosure | | |
|---|---|---|
| Ex. No. | Structure | Compound Name |
| 115 | 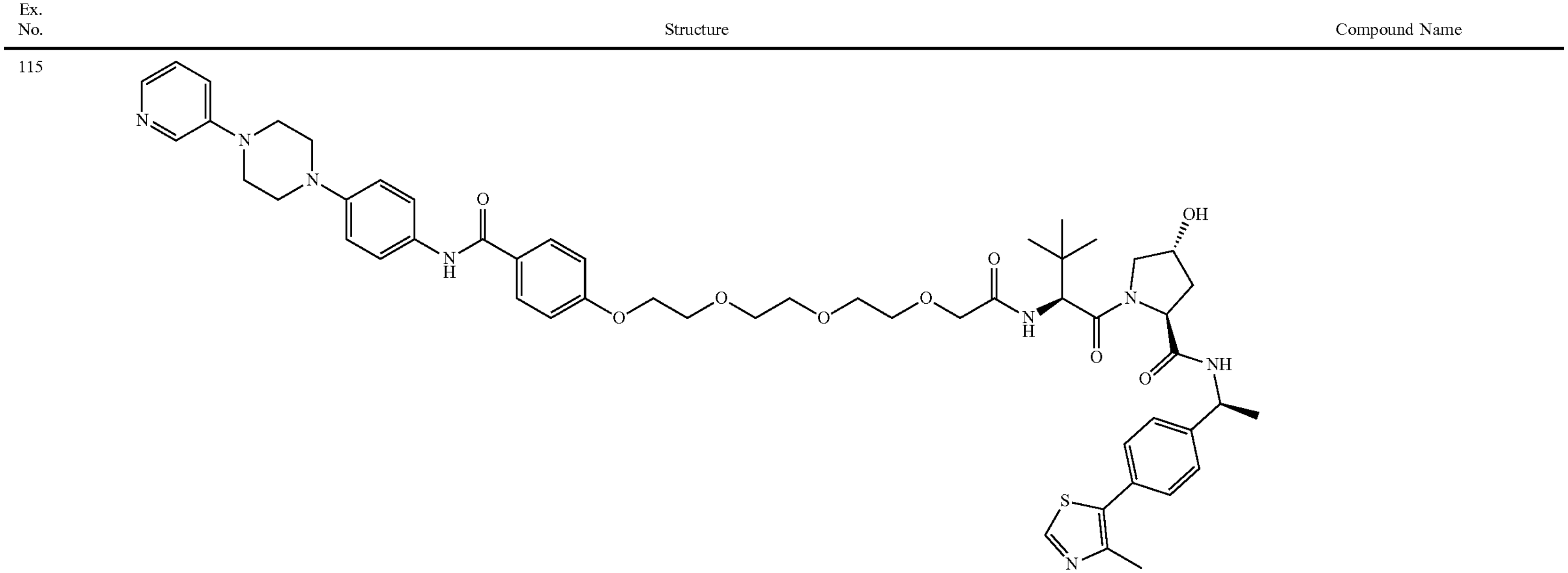 | |
| 116 | 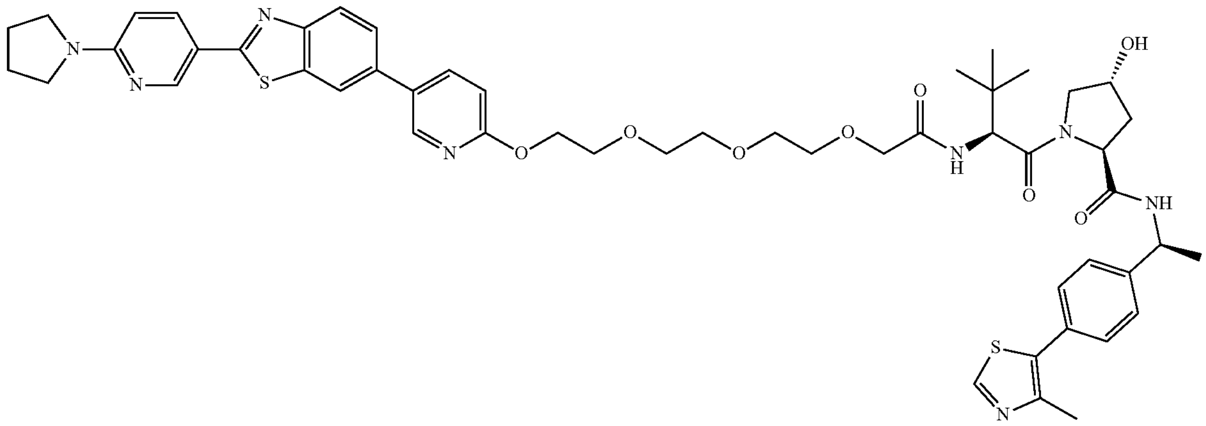 [SMILES: Cc1ncsc1-c1ccc([C@H](C)NC(=O)[C@@H]2C[C@@H](O)CN2C(=O)[C@@H](NC(=O)COCCOCCOCCOc2ccc(-c3ccc4nc(-c5ccc(N6CCCC6)nc5)sc4c3)cn2)C(C)(C)C)cc1] | |

TABLE 1-continued
| Exemplary Compounds of the Present Disclosure | | |
|---|---|---|
| Ex. No. | Structure | Compound Name |
| 117 | 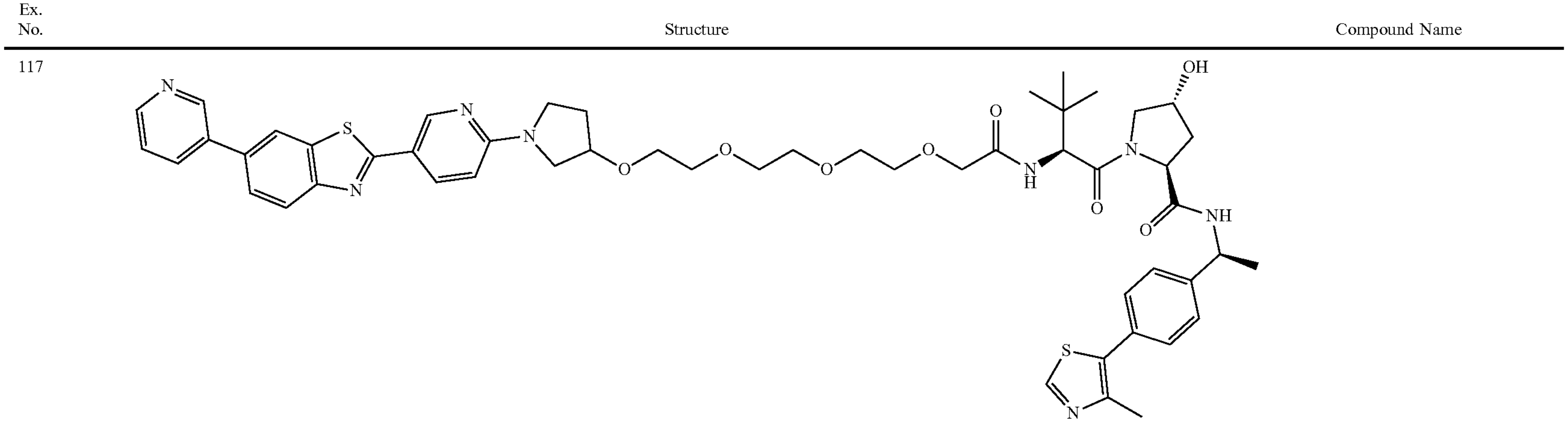 | |
| 118 | 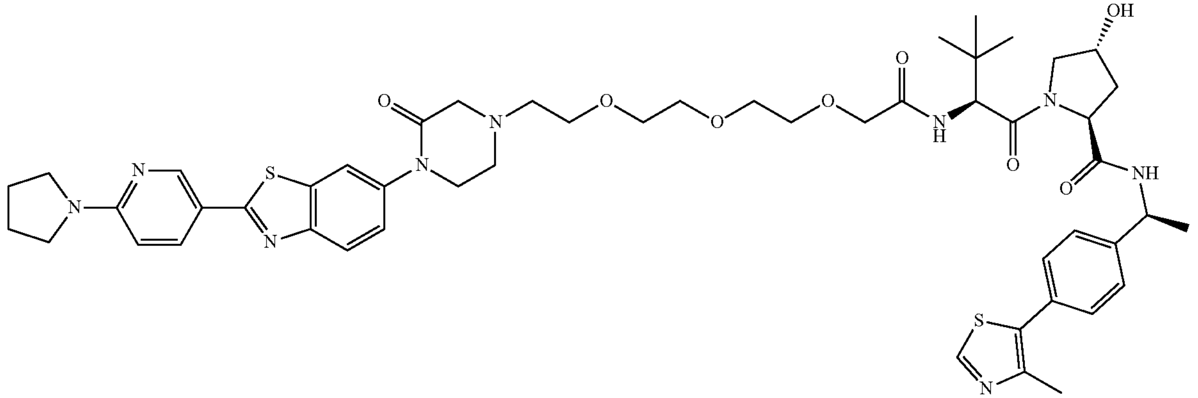 [SMILES: Cc1ncsc1-c1ccc([C@H](C)NC(=O)[C@@H]2C[C@@H](O)CN2C(=O)[C@@H](NC(=O)COCCOCCOCCN2CCN(c3ccc4nc(-c5ccc(N6CCCC6)nc5)sc4c3)C(=O)C2)C(C)(C)C)cc1] | |

TABLE 1-continued
| Exemplary Compounds of the Present Disclosure | | |
|---|---|---|
| Ex. No. | Structure | Compound Name |
| 119 | 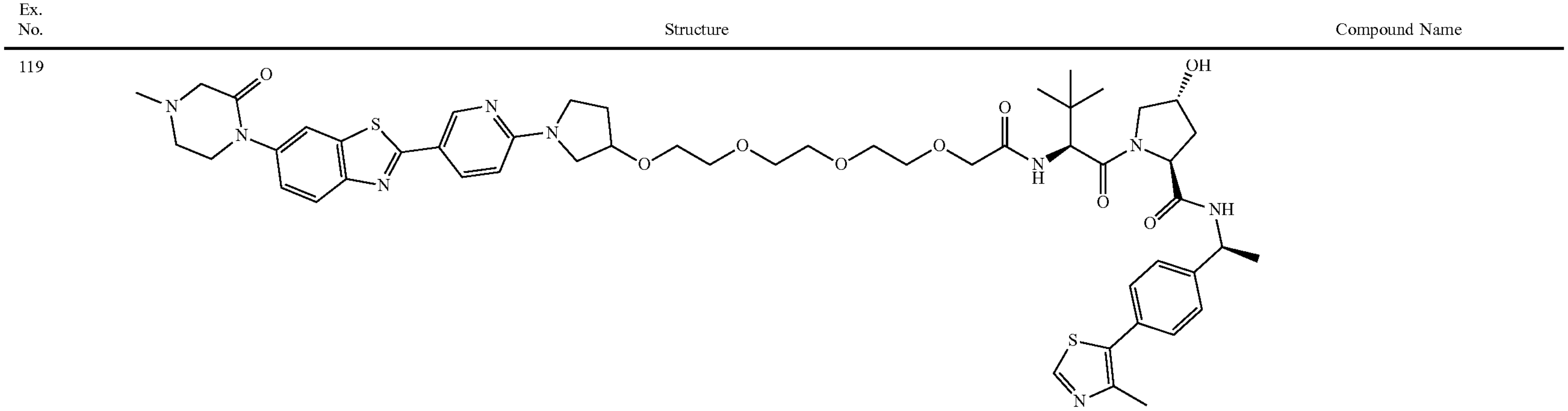 | |
| 120 | 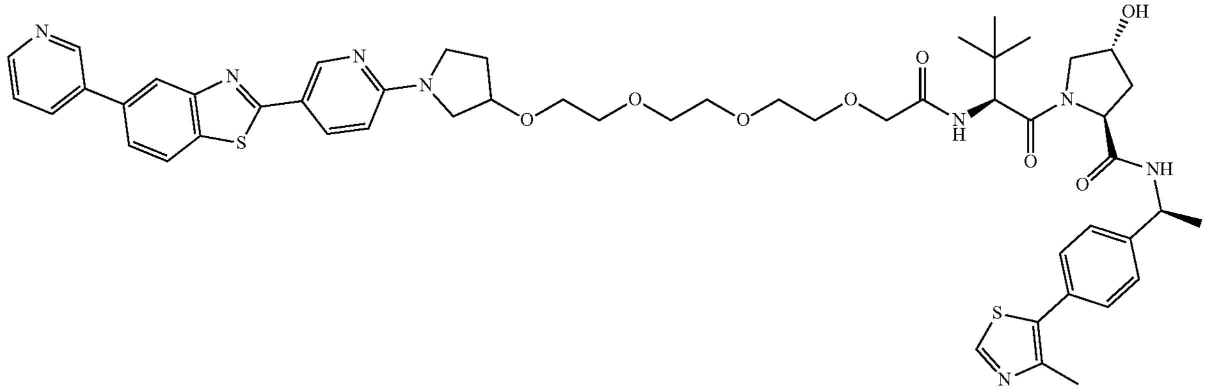 [SMILES: Cc1ncsc1-c1ccc([C@H](C)NC(=O)[C@@H]2C[C@@H](O)CN2C(=O)[C@@H](NC(=O)COCCOCCOCCOC2CCN(c3ccc(-c4nc5cc(-c6cccnc6)ccc5s4)cn3)C2)C(C)(C)C)cc1] | |

TABLE 1-continued
| Exemplary Compounds of the Present Disclosure | | |
|---|---|---|
| Ex. No. | Structure | Compound Name |
| 121 | 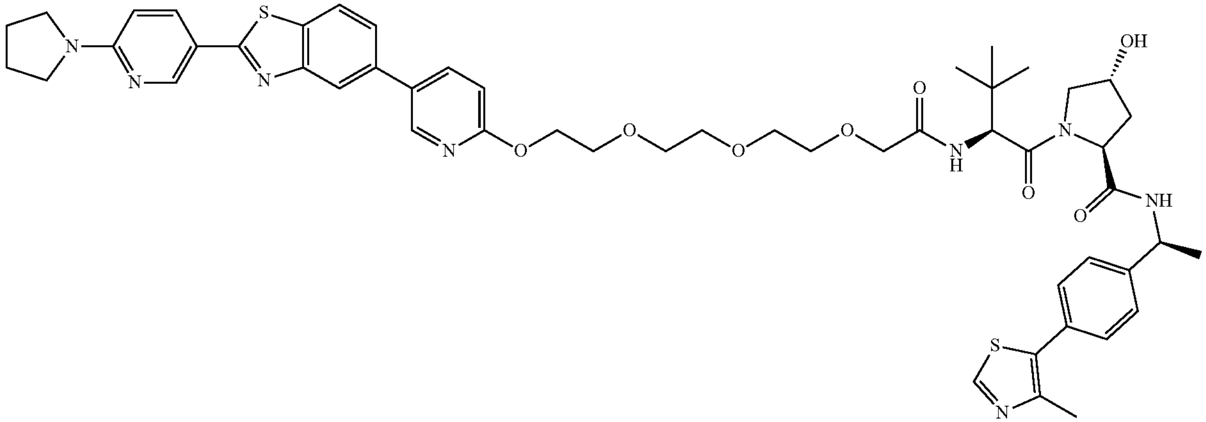 [SMILES: Cc1ncsc1-c1ccc([C@H](C)NC(=O)[C@@H]2C[C@@H](O)CN2C(=O)[C@@H](NC(=O)COCCOCCOCCOc2ccc(-c3ccc4sc(-c5ccc(N6CCCC6)nc5)nc4c3)cn2)C(C)(C)C)cc1] | |
| 122 | 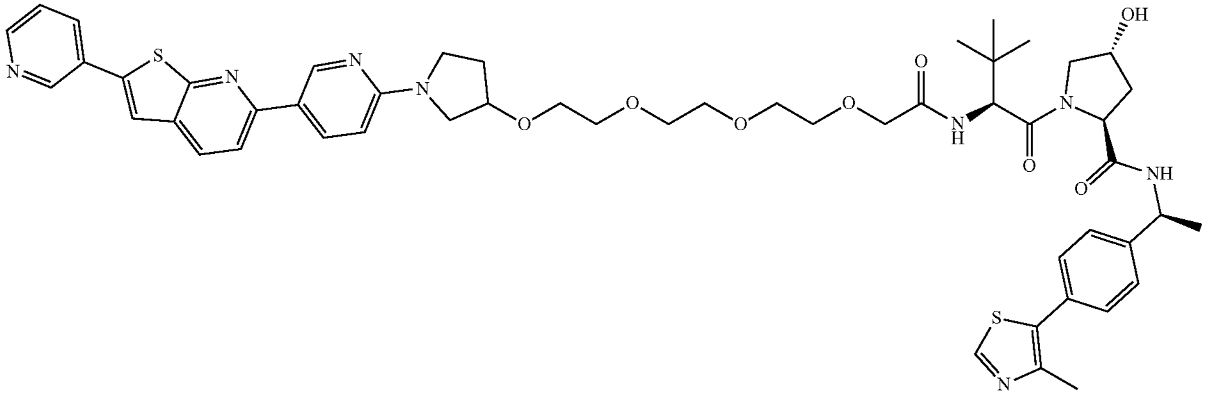 [SMILES: Cc1ncsc1-c1ccc([C@H](C)NC(=O)[C@@H]2C[C@@H](O)CN2C(=O)[C@@H](NC(=O)COCCOCCOCCOC2CCN(c3ccc(-c4ccc5cc(-c6cccnc6)sc5n4)cn3)C2)C(C)(C)C)cc1] | |

TABLE 1-continued
| Exemplary Compounds of the Present Disclosure | | |
|---|---|---|
| Ex. No. | Structure | Compound Name |
| 123 | 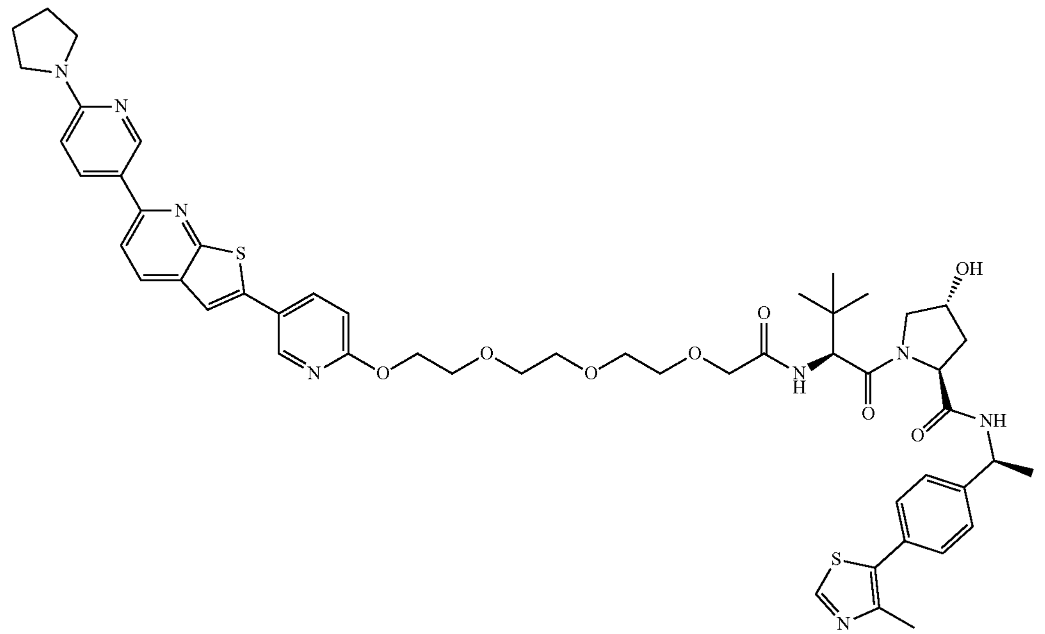 [SMILES: Cc1ncsc1-c1ccc([C@H](C)NC(=O)[C@@H]2C[C@@H](O)CN2C(=O)[C@@H](NC(=O)COCCOCCOCCOc2ccc(-c3cc4ccc(-c5ccc(N6CCCC6)nc5)nc4s3)cn2)C(C)(C)C)cc1] | |
| 124 | 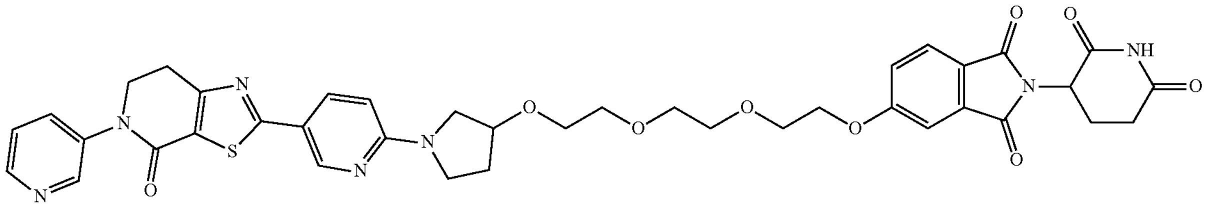 [SMILES: O=C1CCC(N2C(=O)c3ccc(OCCOCCOCCOC4CCN(c5ccc(-c6nc7c(s6)C(=O)N(c6cccnc6)CC7)cn5)C4)cc3C2=O)C(=O)N1] | |

TABLE 1-continued
| Exemplary Compounds of the Present Disclosure | | |
|---|---|---|
| Ex. No. | Structure | Compound Name |
| 125 | 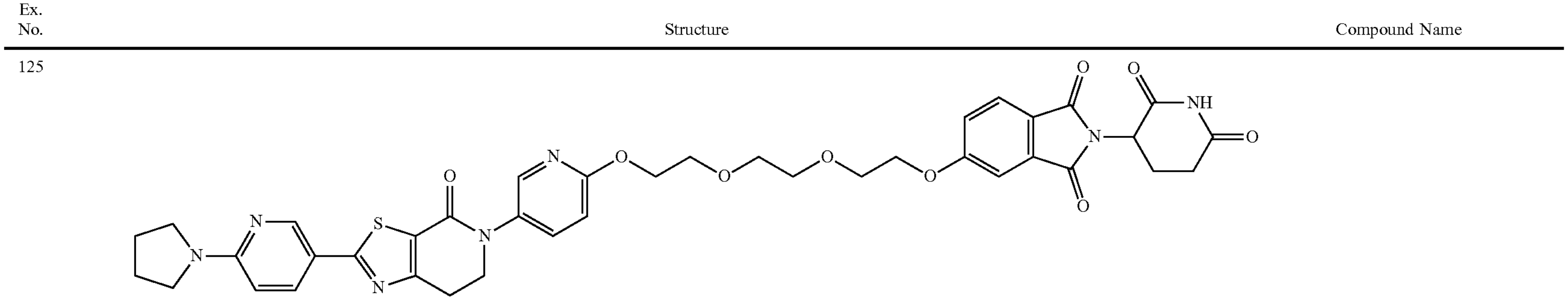 | |
| 126 | 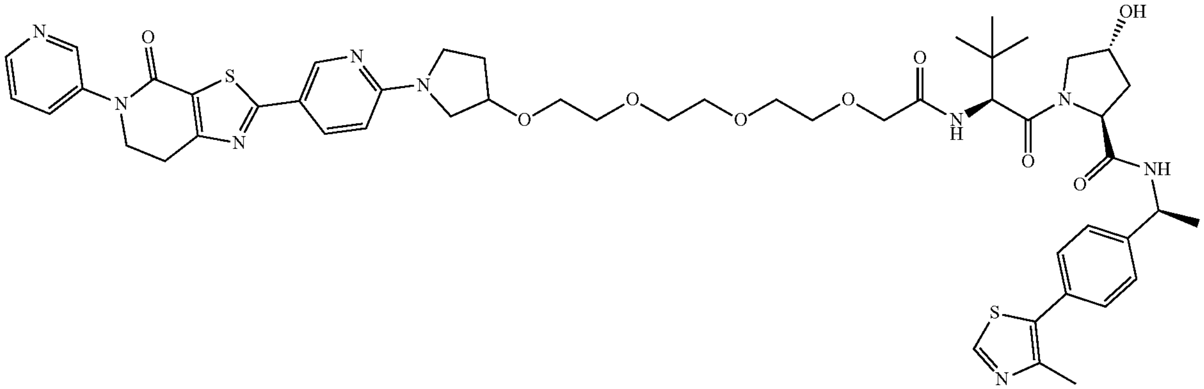 [SMILES: Cc1ncsc1-c1ccc([C@H](C)NC(=O)[C@@H]2C[C@@H](O)CN2C(=O)[C@@H](NC(=O)COCCOCCOCCOC2CCN(c3ccc(-c4nc5c(s4)C(=O)N(c4cccnc4)CC5)cn3)C2)C(C)(C)C)cc1] | |

TABLE 1-continued
| Exemplary Compounds of the Present Disclosure | | |
|---|---|---|
| Ex. No. | Structure | Compound Name |
| 127 | 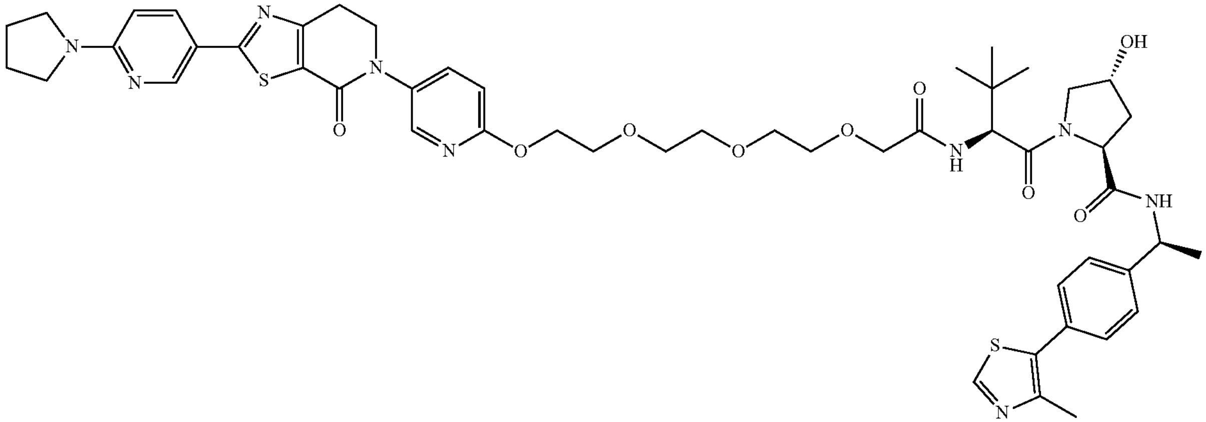 [SMILES: Cc1ncsc1-c1ccc([C@H](C)NC(=O)[C@@H]2C[C@@H](O)CN2C(=O)[C@@H](NC(=O)COCCOCCOCCOc2ccc(N3CCc4nc(-c5ccc(N6CCCC6)nc5)sc4C3=O)cn2)C(C)(C)C)cc1] | |
| 128 | 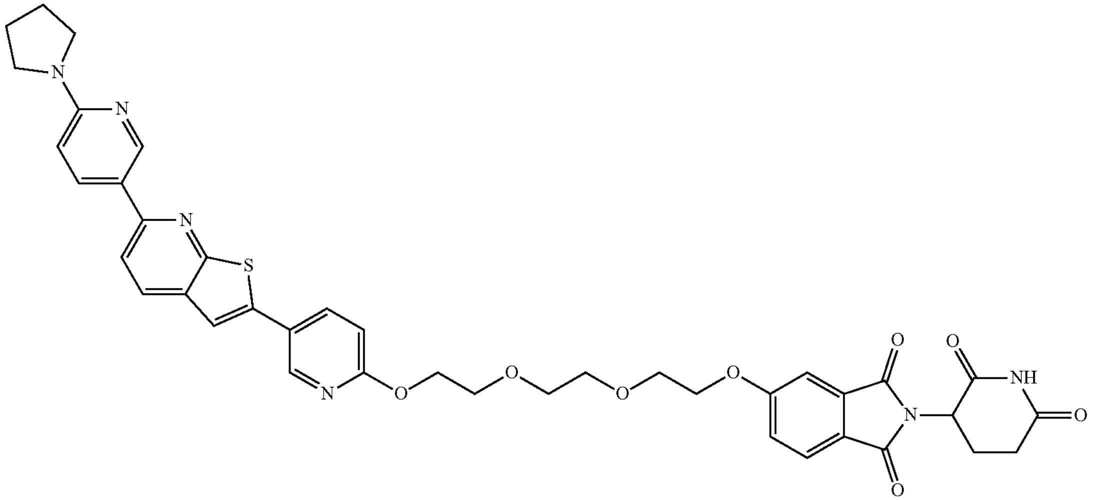 [SMILES: O=C1CCC(N2C(=O)c3ccc(OCCOCCOCCOc4ccc(-c5cc6ccc(-c7ccc(N8CCCC8)nc7)nc6s5)cn4)cc3C2=O)C(=O)N1] | |

TABLE 1-continued
| Exemplary Compounds of the Present Disclosure | | |
|---|---|---|
| Ex. No. | Structure | Compound Name |
| 129 | 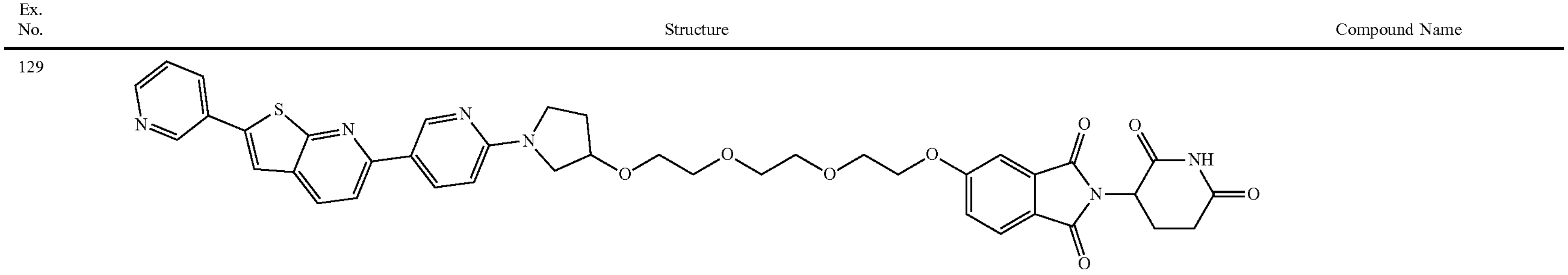 | |
| 130 | 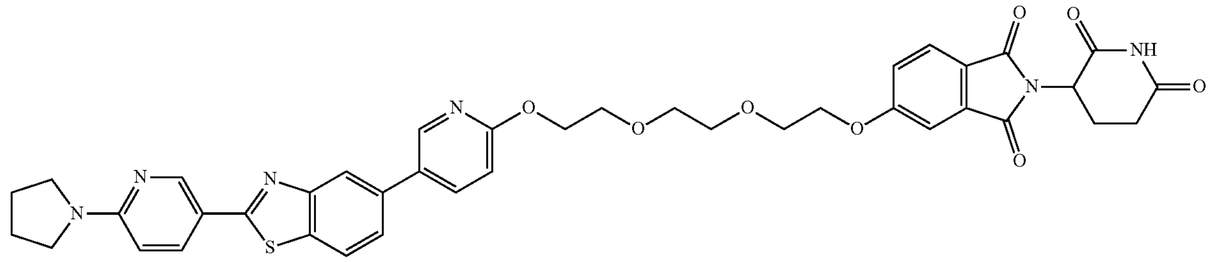 [SMILES: O=C1CCC(N2C(=O)c3ccc(OCCOCCOCCOc4ccc(-c5ccc6sc(-c7ccc(N8CCCC8)nc7)nc6c5)cn4)cc3C2=O)C(=O)N1] | |
| 131 | 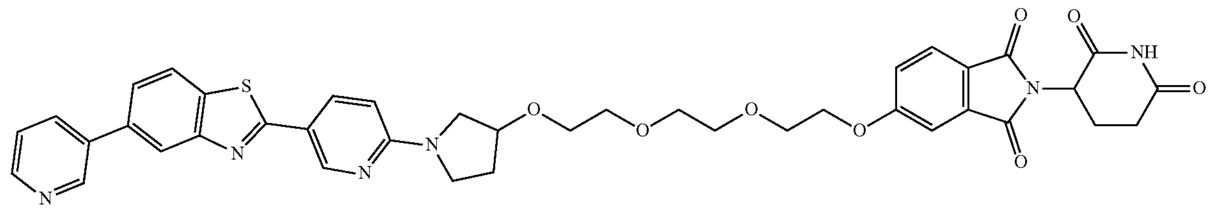 [SMILES: O=C1CCC(N2C(=O)c3ccc(OCCOCCOCCOC4CCN(c5ccc(-c6nc7cc(-c8cccnc8)ccc7s6)cn5)C4)cc3C2=O)C(=O)N1] | |
| 132 | 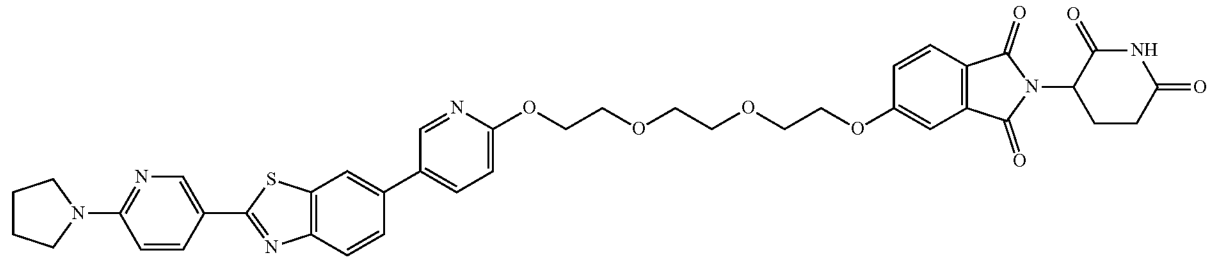 | |

TABLE 1-continued
| Exemplary Compounds of the Present Disclosure | | |
|---|---|---|
| Ex. No. | Structure | Compound Name |
| 133 | 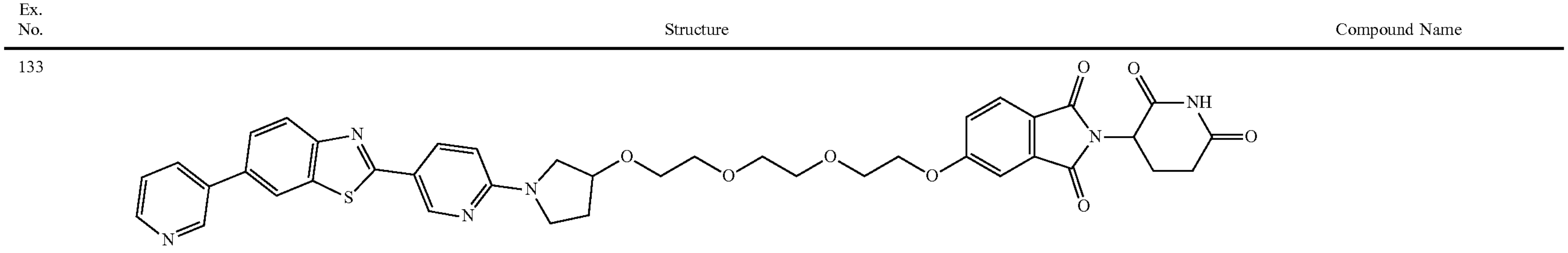 | |
| 134 | 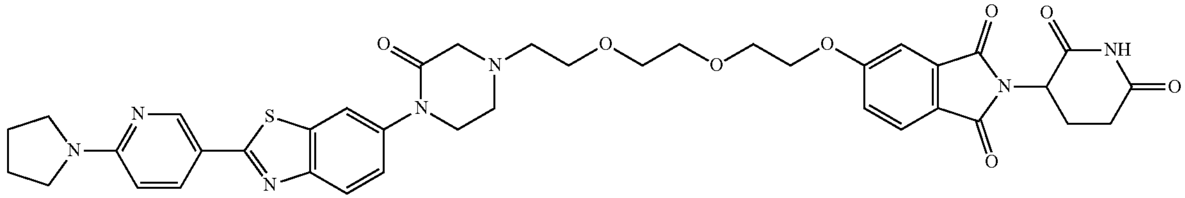 [SMILES: O=C1CCC(N2C(=O)c3ccc(OCCOCCOCCN4CCN(c5ccc6nc(-c7ccc(N8CCCC8)nc7)sc6c5)C(=O)C4)cc3C2=O)C(=O)N1] | |
| 135 | 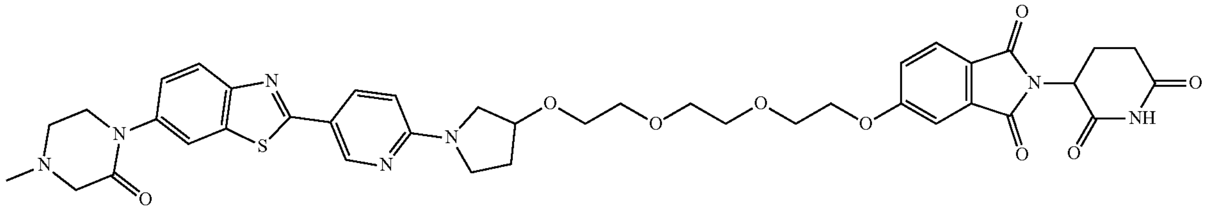 [SMILES: CN1CCN(c2ccc3nc(-c4ccc(N5CCC(OCCOCCOCCOc6ccc7c(c6)C(=O)N(C6CCC(=O)NC6=O)C7=O)C5)nc4)sc3c2)C(=O)C1] | |

TABLE 2

Target Protein Degradation via Exemplary Compounds of the Present Disclosure

| Ex. No. | Protein Degradation at 1 | MH + (1) μM † | NMR transcript |
|---|---|---|---|
| 1 | A | 829.3 | $^1$H NMR (400 MHz, DMSO-$d_6$): δ = 8.98 (s, 1H), 8.52-8.39 (m, 1H), 7.83-7.71 (m, 3H), 7.64-7.58 (m, 1H), 7.46-7.31 (m, 5H), 7.07 (dd, J = 2.4, 8.8 Hz, 1H), 6.67-6.59 (m, 2H), 6.41 (m, 1H), 5.17 (s, 1H), 4.89 (m, , 1H), 4.55 (d, J = 9.4 Hz, 1H), 4.45 (t, J = 8.4 Hz, 1H), 4.31-4.16 (m, 3H), 4.00-3.93 (m, 2H), 3.86-3.78 (m, 2H), 3.70-3.54 (m, 6H), 2.75 (d, J = 4.8 Hz, 3H), 2.44 (s, 3H), 2.05 (m, 1H), 1.82-1.72 (m, 1H), 1.50-1.27 (m, 3H), 0.93 (s, 9H) |
| 2 | B | 873.3 | $^1$H NMR (400 MHz, DMSO-$d_6$): δ = 8.99 (s, 1H), 8.45 (d, J = 7.6 Hz, 1H), 7.85-7.73 (m, 3H), 7.62 (d, J = 2.4 Hz, 1H), 7.47-7.33 (m, 5H), 7.07 (dd, J = 2.4, 8.8 Hz, 1H), 6.64 (d, J = 8.8 Hz, 2H), 6.41 (m, 1H), 5.15 (s, 1H), 4.90 (m, 1H), 4.56 (d, J = 9.6 Hz, 1H), 4.45 (t, J = 8.4 Hz, 1H), 4.33-4.14 (m, 3H), 4.00-3.91 (m, 2H), 3.83-3.75 (m, 2H), 3.67-3.55 (m, 10H), 2.75 (d, J = 4.8 Hz, 3H), 2.45 (s, 3H), 2.06 (m, 1H), 1.78 (m, 1H), 1.49-1.31 (m, 3H), 0.94 (s, 9H) |
| 3 | B | 917.4 | $^1$H NMR (400 MHz, DMSO-$d_6$): δ = 8.98 (s, 1H), 8.53-8.38 (m, 1H), 7.81-7.71 (m, 3H), 7.62 (d, J = 2.4 Hz, 1H), 7.47-7.31 (m, 5H), 7.06 (m, 1H), 6.41 (d, J = 4.8 Hz, 1H), 5.15 (s, 1H), 4.89 (t, J = 7.2 Hz, 1H), 4.54 (d, J = 9.6 Hz, 1H), 4.44 (t, J = 8.0 Hz, 1H), 4.28 (s, 1H), 4.21-4.12 (m, 2H), 3.95 (s, 2H), 3.81-3.74 (m, 2H), 3.63-3.54 (m, 14H), 2.74 (d, J = 5.2 Hz, 3H), 2.44 (s, 3H), 2.04 (m, 1H), 1.82-1.70 (m, 1H), 1.50-1.31 (m, 3H), 0.93 (s, 9H) |
| 4 | A | 961.4 | $^1$H NMR (400 MHz, DMSO-$d_6$): δ = 8.97 (s, 1H), 8.50-8.40 (m, 1H), 7.82-7.72 (m, 3H), 7.61 (d, J = 2.4 Hz, 1H), 7.47-7.30 (m, 5H), 7.05 (m, 1H), 6.62 (d, J = 8.8 Hz, 2H), 6.45-6.37 (m, 1H), 5.14 (s, 1H), 4.89 (t, J = 7.2 Hz, 1H), 4.53 (d, J = 9.6 Hz, 1H), 4.43 (t, J = 8.0 Hz, 1H), 4.27 (s, 1H), 4.19-4.11 (m, 2H), 3.95 (s, 2H), 3.83-3.73 (m, 2H), 3.62-3.50 (m, 18H), 2.74 (d, J = 5.0 Hz, 3H), 2.44 (s, 3H), 2.10-2.00 (m, 1H), 1.81-1.70 (m, 1H), 1.48-1.32 (m, 3H), 0.93 (s, 9H) |
| 5 | A | 1005.4 | $^1$H NMR (400 MHz, DMSO-$d_6$): δ = 8.97 (s, 1H), 8.44 (d, J = 7.6 Hz, 1H), 7.83-7.70 (m, 3H), 7.61 (d, J = 2.4 Hz, 1H), 7.46-7.32 (m, 5H), 7.05 (m, 1H), 6.63 (d, J = 8.8 Hz, 2H), 6.40 (q, J = 4.8 Hz, 1H), 5.15 (s, 1H), 4.90 (t, J = 7.2 Hz, 1H), 4.54 (d, J = 9.5 Hz, 1H), 4.44 (t, J = 8.4 Hz, 1H), 4.27 (s, 1H), 4.19-4.11 (m, 2H), 3.95 (s, 2H), 3.80-3.72 (m, 2H), 3.61-3.49 (m, 22H), 2.74 (d, J = 4.8 Hz, 3H), 2.44 (s, 3H), 2.04 (m, 1H), 1.76 (m, 1H), 1.48-1.33 (m, 3H), 0.93 (s, 9H) |
| 6 | B | 971.4 | $^1$H NMR: (400 MHz, DMSO-$d_6$) δ: 9.00-8.96 (m, 1H), 8.79-8.66 (m, 1H), 8.55-8.43 (m, 5H), 8.32-8.23 (m, 2H), 8.15-8.06 (m, 2H), 8.02-7.84 (m, 1H), 7.76-7.66 (m, 1H), 7.56 (d, J = 15.2 Hz, 1H), 7.49-7.22 (m, 9H), 7.11-7.02 (m, 1H), 7.01-6.96 (m, 1H), 6.94-6.88 (m, 2H), 5.19 (s, 1H), 4.93-4.85 (m, 3H), 4.53 (d, J = 9.8 Hz, 1H), 4.44 (t, J = 8.0 Hz, 1H), 4.28 (s, 1H), 4.13-4.05 (m, 2H), 3.98-3.91 (m, 2H), 3.79-3.73 (m, 2H), 3.61-3.49 (m, 4H), 2.46-2.42 (m, 3H), 2.11-1.97 (m, 1H), 1.81-1.73 (m, 1H), 1.41-1.23 (m, 3H), 0.91 (s, 9H) |
| 7 | B | 971.4 | $^1$H NMR: (400 MHz, DMSO-$d_6$) δ: 8.98 (s, 1H), 8.71 (dd, J = 11.2, 15.6 Hz, 1H), 8.52-8.41 (m, 2H), 8.33-8.22 (m, 2H), 7.90-7.82 (m, 2H), 7.77-7.64 (m, 2H), 7.48-7.19 (m, 9H), 7.06-6.95 (m, 2H), 6.94-6.87 (m, 2H), 5.16 (s, 1H), 4.98-4.80 (m, 3H), 4.53 (d, J = 9.6 Hz, 1H), 4.44 (t, J = 8.0 Hz, 1H), 4.28 (s, 1H), 4.12-4.04 (m, 2H), 3.99-3.88 (m, 2H), 3.80-3.71 (m, 2H), 3.62-3.50 (m, 3H), 2.45 (s, 3H), 2.12-1.96 (m, 1H), 1.76 (ddd, J = 4.4, 8.4, 12.8 Hz, 1H), 1.47-1.27 (m, 3H), 0.91 (s, 9H) |
| 8 | C | 833.2 | $^1$H NMR (400 MHz, DMSO-$d_6$): δ = 9.43 (s, 1H), 8.98 (s, 1H), 8.51-8.36 (m, 1H), 7.83 (dd, J = 2.4, 8.8 Hz, 1H), 7.71 (d, J = 2.4 Hz, 1H), 7.49-7.30 (m, 5H), 6.70-6.55 (m, 4H), 5.15 (s, 1H), 4.96-4.83 (m, 1H), 4.59-4.50 (m, 1H), 4.44 (t, J = 8.0 Hz, 1H), 4.32-4.22 (m, 1H), 4.07-3.89 (m, 4H), 3.77-3.67 (m, 2H), 3.66-3.53 (m, 6H), 2.45 (s, 3H), 2.11-1.99 (m, 1H), 1.82-1.71 (m, 1H), 1.49-1.32 (m, 3H), 0.97-0.88 (m, 9H). |
| 9 | D | 877.3 | $^1$H NMR (400 MHz, DMSO-$d_6$): δ = 9.41 (s, 1H), 8.97 (s, 1H), 8.55-8.33 (m, 1H), 7.82 (dd, J = 2.4, 9.2 Hz, 1H), 7.70 (d, J = 2.4 Hz, 1H), 7.46-7.31 (m, 5H), 6.71-6.52 (m, 4H), 5.16-5.10 (m, 1H), 4.89 (t, J = 7.2 Hz, 1H), 4.54 (d, J = 9.6 Hz, 1H), 4.43 (t, J = 8.4 Hz, 1H), 4.28 (d, J = 1.2 Hz, 1H), 4.06-3.89 (m, 4H), 3.72-3.65 (m, 2H), 3.63-3.52 (m, 10H), 2.44 (s, 3H), 2.09-1.99 (m, 1H), 1.76 (d, J = 4.0 Hz, 1H), 1.48-1.31 (m, 3H), 0.93 (s, 9H). |
| 10 | | 921.3 | $^1$H NMR (400 MHz, DMSO-$d_6$): δ = 9.43 (s, 1H), 8.97 (s, 1H), 8.50-8.41 (m, 1H), 7.82 (m, 1H), 7.70 (d, J = 2.4 Hz, 1H), |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| | | | 7.46-7.32 (m, 5H), 6.68-6.55 (m, 4H), 5.14 (s, 1H), 4.89 (m, 1H), 4.54 (d, J = 9.6 Hz, 1H), 4.43 (t, J = 8.4 Hz, 1H), 4.28 (s, 1H), 4.02-3.88 (m, 4H), 3.71-3.64 (m, 2H), 3.62-3.51 (m, 14H), 2.44 (s, 3H), 2.08-1.99 (m, 1H), 1.75 (d, J = 4.4 Hz, 1H), 1.36 (d, J = 7.2 Hz, 3H), 0.93 (s, 9H). |
| 11 | D | 965.3 | $^1$H NMR (400 MHz, DMSO-$d_6$): δ = 9.43 (s, 1H), 8.98 (s, 1H), 8.56-8.34 (m, 1H), 7.82 (dd, J = 2.4, 8.8 Hz, 1H), 7.70 (d, J = 2.4 Hz, 1H), 7.47-7.30 (m, 5H), 6.69-6.55 (m, 4H), 5.14 (s, 1H), 4.90 (t, J = 7.2 Hz, 1H), 4.54 (d, J = 9.2 Hz, 1H), 4.44 (t, J = 8.0 Hz, 1H), 4.28 (s, 1H), 4.04-3.89 (m, 4H), 3.70-3.65 (m, 2H), 3,63-3.48 (m, 18H), 2.45 (s, 3H), 2.10-2.00 (m, 1H), 1.83-1.71 (m, 1H), 1.50-1.31 (m, 3H), 0.93 (s, 9H). |
| 12 | D | 1009.4 | $^1$H NMR (400 MHz, DMSO-$d_6$): δ = 9.43 (s, 1H), 8.98 (s, 1H), 8.55-8.32 (m, 1H), 7.82 (dd, J = 2.4, 8.8 Hz, 1H), 7.71 (d, J = 2.4 Hz, 1H), 7.47-7.32 (m, 5H), 6.68-6.56 (m, 4H), 5.19-5.11 (m, 1H), 4.90 (t, J = 7.2 Hz, 1H), 4.54 (d, J = 9.6 Hz, 1H), 4.48-4.39 (m, 1H), 4.28 (s, 1H), 4.02-3.89 (m, 4H), 3.71-3.65 (m, 2H), 3.63-3.48 (m, 22H), 2.45 (s, 3H), 2.09-2.00 (m, 1H), 1.82-1.71 (m, 1H), 1.37 (d, J = 7.0 Hz, 3H), 0.93 (s, 9H). |
| 13 | | 693.3 | $^1$H NMR (400 MHz, $CDCl_3$): δ: 7.80 (dd, J = 2.8, 8.8 Hz, 1H), 7.52 (d, J = 8.4 Hz, 1H), 7.67 (J = 2.8 Hz, 1H), 7.37 (d, J = 2.4 Hz, 1H), 7.29 (dd, J = 2.4, 8.4 Hz, 1H), 6.60-6.57 (m, 1H), 6.55-6.52 (m, 2H), 6.50 (d, J = 2.4 Hz, 1H), 5.12 (dd, J = 5.2, 12.4 Hz, 1H), 4.27-4.25 (m, 2H), 4.04-4.02 (m, 2H), 3.91-3.88 (m, 2H), 3.81-3.78 (m, 2H), 3.73-3.65 (m, 8H), 2.89-2.88 (m, 1H), 2.79-2.70 (m, 2H), 2.15-2.11 (m, 1H). |
| 14 | B | 737.3 | $^1$H NMR (400 MHz, DMSO): δ: 11.11 (br s, 1H), 9.49 (br s, 1H), 8.49 (br s, 1H), 7.82 (br d, J = 8.6 Hz, 2H), 7.69 (br s, 1H), 7.44 (s, 1H), 7.36 (br d, J = 7.8 Hz, 1H), 6.66-6.61 (m, 4H), 5.12 (br dd, J = 4.6, 13.0 Hz, 1H), 4.31 (br s, 2H), 3.99 (br s, 2H), 3.79 (br s, 2H), 3.68 (br s, 2H), 3.62-3.47 (m, 1.2H), 2.95-2.84 (m, 1H), 2.64-2.54 (m, 2H), 2.06 (br d, J = 16.5 Hz, 1H). |
| 15 | B | 659.4 | $^1$H NMR (400 MHz, DMSO-$d_6$): δ: 11.10 (s, 1H), 8.18 (s, 1H), 7.80 (d, J = 8.3 Hz, 1H), 7.42 (d, J = 2.2 Hz, 1H), 7.32 (dd, J = 2.3, 8.3 Hz, 1H), 7.22-7.15 (m, 2H), 7.12 (dd, J = 1.5, 7.6 Hz, 2H), 7.01 (d, J = 7.7 Hz, 2H), 6.92 (dt, J = 0.9, 7.5 Hz, 2H), 5.12 (dd, J = 5.4, 12.9 Hz, 1H), 4.34-4.19 (m, 2H), 3.89 (t, J = 6.7 Hz, 2H), 3.80-3.69 (m, 2H), 3.59-3.51 (m, 2H), 3.48-3.37 (m, 4H), 2.97-2.79 (m, 1H), 2.64-2.51 (m, 2H), 2.49-2.45 (m, 4H), 2.18 (s, 3H), 2.10-1.98 (m, 1H), 1.78 (quin, J = 6.7 Hz, 2H). |
| 16 | C | 703.4 | $^1$H NMR (400 MHz, DMSO-$d_6$): δ: 11.10 (s, 1H), 7.82 (d, J = 8.3 Hz, 1H), 7.43 (d, J = 1.8 Hz, 1H), 7.34 (dd, J = 2.2, 8.4 Hz, 1H), 7.24-7.10 (m, 4H), 7.02 (d, J = 8.3 Hz, 2H), 6.99-6.88 (m, 2H), 5.12 (dd, J = 5.3, 12.9 Hz, 1H), 4.35-4.20 (m, 2H), 3.90 (br t, J = 6.4 Hz, 2H), 3.81-3.70 (m, 2H), 3.61-3.37 (m, 10H), 2.98-2.82 (m, 1H), 2.59 (br d, J = 16.8 Hz, 3H), 2.41 (br s, 3H), 2.30-1.99 (m, 4H), 1.81 (br s, 2H). |
| 17 | | 695.5 | $^1$H NMR (400 MHz, DMSO-d6): δ 11.04 (s, 1H), 7.83-7.80 (m, 3H), 7.68-7.68 (m, 2H), 7.33-7.23 (m, 2H), 7.08-7.05 (m, 1H), 6.54-6.52 (m, 2H), 5.06 (d, J = 12.7, 5.4 Hz, 1H), 4.46-4.44 (m, 1H), 4.18-4.14 (m, 2H), 3.83 (s, 3H), 3.75-3.71 (m, 2H), 3.43-3.48 (m, 6H) 2.89-2.83 (m, 1H), 2.60-2.56 (m, 6H), 2.54-2.50 (m, 2H), 2.07-1.99 (m, 1H), 1.75-1.73 (m, 2H) |
| 18 | C | 782.5 | $^1$H NMR (400 MHz, DMSO-d6): δ: 11.06 (s, 1H), 9.45-9.32 (m, 1H), 8.23 (s, 1H), 7.83 (dd, J = 2.6, 8.9 Hz, 2H), 7.73-7.59 (m, 2H), 7.33 (s, 1H), 7.25 (br d, J = 8.7 Hz, 1H), 6.62 (dd, J = 2.4, 8.8 Hz, 2H), 6.55-6.46 (m, 1H), 6.44 (d, J = 2.7 Hz, 1H), 5.06 (dd, J = 5.4, 12.7 Hz, 1H), 4.70 (br s, 1H), 4.27 (br t, J = 6.5 Hz, 1H), 3.42 (br s, 8H), 2.94-2.82 (m, 1H), 2.72 (br s, 2H), 2.60 (br s, 3H), 2.44 (br s, 4H), 2.30 (br d, J = 6.0 Hz, 3H), 2.10-1.97 (m, 3H), 1.75 (br s, 2H), 1.39 (br d, d, J = 8.7 Hz, 2H) |
| 19 | B | 756.6 | $^1$H NMR (400 MHz, DMSO-d6): δ: 11.11 (br s, 1H), 9.41 (s, 1H), 8.21 (s, 1H), 7.83 (dd, J = 1.6, 9.8 Hz, 2H), 7.71 (d, J = 2.6 Hz, 1H), 7.42 (d, J = 2.2 Hz, 1H), 7.34 (dd, J = 2.3, 8.4 Hz, 1H), 6.62 (dd, J = 2.2, 8.8 Hz, 2H), 6.53-6.48 (m, 1H), 6.43 (d, J = 2.7 Hz, 1H), 5.12 (dd, J = 5.4, 12.8 Hz, 1H), 4.80-4.57 (m, 1H), 4.31-4.22 (m, 1H), 4.17 (t, J = 6.4 Hz, 2H), 3.27 (br d, J = 9.0 Hz, 1H), 2.97-2.81 (m, 2H), 2.71 (br d, J = 10.5 Hz, 2H), 2.64-2.54 (m, 2H), 2.30-2.21 (m, 5H), 2.09-1.95 (m, 3H), 1.77 (br d, J = 6.4 Hz, 4H), 1.53-1.35 (m, 6H) |
| 20 | | 691.5 | $^1$H NMR (400 MHz, DMSO): 11.12 (s, 1H), 8.35 (s, 1H), 7.96 |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| | | | (br s, 1H), 7.82 (br d, J = 8.2 Hz, 1H), 7.45 (s, 1H), 7.36 (br d, J = 8.4 Hz, 1H), 6.61-6.52 (m, 3H), 6.46 (br d, J = 7.3 Hz, 1H), 6.36 (br s, 1H), 5.12 (br dd, J = 5.1, 12.8 Hz, 1H) 4.30 (br s, 2H), 3.96 (br s, 2H), 3.78 (br s, 2H), 3.67 (br s, 2H), 3.61-3.54 (m, 8H), 2.93-2.84 (m, 1H), 2.74 (s, 6H), 2.64-2.56 (m, 2H), 2.11-1.99 (m, 1H). |
| 21 | B | 735.6 | $^1$H NMR (400 MHz, DMSO): δ = 11.10 (s, 1H), 7.95 (br s, 1H), 7.82 (d, J = 8.3 Hz, 1H), 7.44 (s, 1H), 7.36 (br d, J = 8.2 Hz, 1H), 6.58-6.47 (m, 4H), 6.36 (br s, 1H), 5.12 (dd, J = 5.2, 12.9 Hz, 1H), 4.30 (br s, 2H), 3.96 (br s, 2H), 3.78 (br s, 2H), 3.67 (br s, 2H), 3.61-3.52 (m, 8H), 3.32 (br s, 6H), 2.94-2.80 (m, 1H), 2.75 (br s, 4H), 2.63-2.52 (m, 2H), 2.06-2.03 (m, 1H). |
| 22 | B | 738.6 | $^1$H NMR (400 MHz, DMSO-$d_6$): δ: 11.13 (s, 1H), 10.18 (br s, 1H), 9.65 (br s, 1H), 7.85 (br d, J = 8.2 Hz, 1H), 7.42 (s, 1H), 7.34 (br d, J = 8.4 Hz, 1H), 7.26-7.17 (m, 4H), 7.07 (br d, J = 7.9 Hz, 2H), 6.99 (t, J = 7.4 Hz, 2H), 5.12 (br dd, J = 4.9, 12.7 Hz, 1H), 4.39 (br s, 2H), 4.19 (br s, 3H), 4.05 (br s, 1H), 3.94 (br s, 2H), 3.86 (br s, 1H), 3.74 (br s, 1H), 3.50 (br d, J = 11.9 Hz, 2H), 3.36-3.18 (m, 3H), 3.06 (br s, 2H), 3.00 (br s, 1H), 2.96-2.83 (m, 2H), 2.63-2.53 (m, 1H), 2.45-2.20 (m, 1H), 2.04 (br d, J = 7.1 Hz, 2H), 1.87 (br d, J = 13.9 Hz, 3H), 1.79 (br s, 2H), 1.70 (br s, 2H), 1.65-1.51 (m, 1H), 1.45 (br d, J = 6.2 Hz, 2H). |
| 23 | B | 764.7 | $^1$H NMR (400 MHz, methanol-$d_4$): δ: 8.40 (s, 2H), 7.70 (d, J = 8.6 Hz, 1H), 7.37 (d, J = 2.2 Hz, 1H), 7.26-7.16 (m, 5H), 7.04-6.95 (m, 4H), 5.07 (dd, J = 5.4, 12.4 Hz, 1H), 4,36 (quin, J = 5.8 Hz, 1H), 4,03 (br t, J = 6.4 Hz, 4H), 3.63-3.45 (m, 7H), 3.29-3.20 (m, 2H), 3.14-2.96 (m, 6H), 2.91-2.66 (m, 9H), 2.14-2.07 (m, 1H), 2.03-1.93 (m, 4H), 1.80 (td, J = 3.4, 7.0 Hz, 2H). |
| 24 | D | 723.6 | $^1$H NMR (300 MHz, DMSO-d6): δ 11.08 (s, 1H), 7.83-7.80 (m, 3H), 7.78-7.66 (m, 1H), 7.46 (s, 1H), 7.34-7.27 (m, 1H), 7.24 (m, 1H), 7.00-6.96 (m, 1H), 6.82-6.79 (m, 2H), 5.10-5.04 (m, 2H), 4.90-4.88 (m, 1H), 4.18 (s, 1H), 3.44-3.39 (m, 4H), 3.37-3.32 (m, 2H), 3.01 (m, 6H), 2.88-2.84 (m, 1H), 2.60-2.58 (m, 2H), 2.50-2.40 (m, 9H), 2.34-2.32 (m, 1H), 2.03-1.99 (m, 2H) |
| 25 | D | 738.6 | $^1$H NMR (300 MHz, DMSO-d6): δ 11.17 (s, 1H), 7.85-7.81 (m, 4H), 7.64 (s, 1H), 7.43 (s, 1H), 7.37-7.34 (m, 1H), 7.09-7.06 (m, 1H), 6.53 (d, J = 6 Hz, 2.H), 5.14-5.10 (m, 1.H), 4.59-4.57 (m, 1H), 4.21-4.16 (m, 4H), 3.85 (s, 3H), 3.60-3.71 (m, 2H), 2.94-2.91 (m, 1H), 2.89-2.79 (m, 3H), 2.28-2.25 (m, 2H), 2.07-1.98 (m, 3H), 1.79-1.76 (m, 4H), 1.35-1.49 (m, 6H), 1.21-1.29 (m, 2H) |
| 26 | B | 764.6 | $^1$H NMR (300 MHz, DMSO-d6): δ 11.08 (s, 1H), 7.85-7.81 (m, 3H), 7.69-7.64 (m, 2H), 7.34 (s, 1H), 7.25 (d, J = 6 Hz, 1H), 7.09-7.07 (m, 1H), 6.53 (d, J = 6 Hz, 2H), 5.10-5.05 (m, 1H), 4.59-4.57 (m, 1H), 4.22-4.18 (m, 2H), 3.85 (s, 3H), 3.71-3.68 (m, 2H), 3.43-3.32 (m, 4H), 2.94-2.92 (m, 1H), 2.89-2.84 (m, 2H), 2.77-2.75 (m, 7H), 2.68-2.34 (m, 4H), 2.11-2.04 (m, 3H), 1.79-1.89 (m, 2H), 1.40-1.55 (m, 2H). |
| 27 | D | 766.6 | H NMR (300 MHz, $CDCl_3$ ): δ 7.90-7.74 (m, 4H), 7.31-7.25 (m, 1H), 7.17-7.14 (m, 2H), 6.94-6.92 (m, 1H), 6.74-6.71 (m, 2H), 4.95-4.85 (m, 2H), 4.38-4.37 (m, 1H), 4.06 (s, 2H), 3.33-3.23 (m, 1H), 3.09-3.03 (m, 6H), 2.96-2.60 (m, 5H), 2.47-2.36 (m, 6H), 2.11-2.01 (m, 3H), 1.99-1.97 (m, 4H), 1.84-1.49 (m, 6H). |
| 28 | | 695.6 | |
| 29 | | 792.7 | H NMR (400 MHz, $CD_3OD$): δ 8.11 (d, J = 9.6 Hz, 3H), 7.91(d, J = 8.8 Hz, 1H), 7.76 (d, J = 8.4 Hz, 1H), 7.54-7.48 (m, 3H), 7.38 (d, J = 8 Hz, 1H), 7.31 (d, J = 8.8 Hz, 2H), 7.21 (d, J = 9.2 Hz, 1H), 5.12-5.07 (m, 1H), 4.99 (s, 1H), 4.44-4.41 (m, 1H), 3.84-3.70 (m, 9H), 3.65-3.62 (m, 2H), 3.49-342 (m, 4H), 3.25 (s, 6H), 2.88-2.69 (m, 3H), 2.60-2.51 (m, 4H), 2.27-2.26 (m, 1H), 2.14-2.12 (m, 3H), 1.93-1.91 (m, 1H). |
| 30 | B | 713.5 | 1H NMR (400 MHz, DMSO-d6): δ: 11.08 (br s, 1H), 9.41 (s, 1H), 8.23 (s, 1H), 7.82 (dd, J = 2.6, 8.9 Hz, 1H), 7.73-7.61 (m, 2H), 7.34 (d, J = 2.0 Hz, 1H), 7.26 (br d, J = 8.7 Hz, 1H), 6.63 (d, J = 9.2 Hz, 2H), 6.56-6.49 (m, 1H), 6.44 (d, J = 2.6 Hz, 1H), 5.07 (dd, J = 5.4, 13.0 Hz, 1H), 4.76-4.66 (m, 1H), 4.17-4.06 (m, 1H), 3.37-3.32 (m, 8H), 2.98-2.78 (m, 2H), 2.58 (br d, J = 16.8 Hz, 2H), 2.43-2.29 (m, 5H), 2.28-2.19 (m, 2H), 2.08-1.96 (m, 1H), 1.69 (quin, J = 6.6 Hz, 2H) |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| 31 | C | 894.7 | 1H NMR (400 MHz, CDCl3) δ: 12.25 (br s, 1H), 8.30 (d, J = 8.7 Hz, 2H), 8.10 (br s, 1H), 7.84-7.70 (m, 5H), 7.55 (d, J = 12.1 Hz, 1H), 7.32 (s, 1H), 7.27-7.13 (m, 4H), 7.10 (br t, J = 7.5 Hz, 1H), 6.84-6.67 (m, 3H), 5.01-4.87 (m, 3H), 4.86-4.74 (m, 1H), 4.38-4.24 (m, 1H), 4.09 (br t, J = 5.8 Hz, 2H), 3.71 (br s, 1H), 3.45 (br d, J = 9.4 Hz, 2H), 3.08-2.63 (m, 8H), 2.50-2.30 (m, 3H), 2.25-2.11 (m, 3H), 2.05 (br d, J = 14.4 Hz, 2H), 1.92-1.88 (m, 4H), 1.57 (br s, 2H). |
| 32 | | 894.7 | 1H NMR(400 MHz, CDCl3) δ: 8.84 (dd, J = 11.6, 15.7 Hz, 1H), 8.25 (d, J = 8.7 Hz, 2H), 8.13 (br s, 1H), 7.85-7.70 (m, 3H), 7.49 (d, J = 7.5 Hz, 1H), 7.37-7.32 (m, 2H), 7.26-7.15 (m, 3H), 7.11-7.01 (m, 2H), 6.81-6.70 (m, 3H), 5.00-4.89 (m, 3H), 4.81-4.74 (m, 1H), 4.38-4.23 (m, 1H), 4.10 (t, J = 6.3 Hz, 2H), 3.42 (br s, 2H), 2.96-2.71 (m, 5H), 2.55-2.35 (m, 5H), 2.21-2.09 (m, 2H), 2.03-1.82 (m, 5H), 1.55-1.43 (m, 2H), 1.40-1.23 (m, 3H), 0.98-0.74 (m, 1H). |
| 33 | | 984.8 | |
| 34 | A | 1010.8 | $^1$H NMR (400 MHz, DMSO-d6) δ: 9.40 (s, 1H), 8.98 (s, 1H), 8.44 (d, J = 7.6 Hz, 1H), 8.23 (s, 2H), 7.82 (dd, J = 2.8, 8.8 Hz, 1H), 7.72-7.69 (m, 1H), 7.46-7.41 (m, 2H), 7.39-7.34 (m, 2H), 6.62 (dd, J = 2.4, 8.8 Hz, 2H), 6.53-6.48 (m, 1H), 6.43 (d, J = 2.8 Hz, 1H), 4.89 (br t, J = 7.2 Hz, 1H), 4.69 (br d, J = 3.6 Hz, 1H), 4.52-4.38 (m, 2H), 4.31-4.21 (m, 2H), 3.56 (br s, 1H), 3.02 (br d, J = 16.8 Hz, 1H), 2.92-2.85 (m, 1H), 2.71 (br s, 1H), 2.46-2.35 (m, 16H), 2.29 (br d, J = 6.8 Hz, 5H), 2.13-1.95 (m, 4H), 1.75 (br s, 3H), 1.38 (br d, J = 7.2 Hz, 5H), 0.93 (s, 9H). |
| 35 | B | 895.4 | $^1$H NMR (400 MHz, DMSO-$d_6$) δ: 8.98 (s, 1 H), 8.42 (dd, J = 8.00, 3.60 Hz, 2 H), 8.21 (d, J = 5.20 Hz, 1 H), 7.97 (dd, J = 8.80, 6.40 Hz, 2 H), 7.81-7.67 (m, 2 H), 7.51 (dd, J = 9.20, 2.80 Hz, 1 H), 7.47 (d, J = 2.40 Hz, 1 H), 7.43-7.39 (m, 2 H), 7.39-7.30 (m, 4 H), 7.09 (s, 1 H), 4.89 (t, J = 7.20 Hz, 1 H), 4.55 (d, J = 9.60 Hz, 2 H), 4.29-4.26 (m, 4 H), 3.96 (s, 2 H), 3.89 (s, 3 H), 3.86-3.82 (m, 2 H), 3.68-3.64 (m, 2 H), 3.63-3.57 (m, 8 H), 2.44 (s, 3 H), 2.09-2.00 (m, 1 H), 1.81-1.72 (m, 1 H), 1.34 (d, J = 7.20 Hz, 3 H), 0.93 (s, 9H). |
| 36 | D | 667.2 | 1H NMR: (400 MHz, DMSO-d6) δ: 11.12 (s, 1H), 8.39-8.32 (m, 1H), 8.21 (d, J = 5.4 Hz, 1H), 7.99-7.88 (m, 2H), 7.82-7.63 (m, 3H), 7.50-7.40 (m, 3H), 7.37-7.30 (m, 2H), 7.08 (s, 1H), 5.14-5.07 (m, 1H), 4.28-4.25 (m, 4H), 3.89 (s, 3H), 3.84-3.80 (m, 2H), 3.79-3.74 (m, 2H), 3.65-3.53 (m, 8H), 2.95-2.79 (m, 1H), 2.64-2.51 (m, 2H), 2.10-1.95 (m, 1H) |
| 47 | C | 667.2 | $^1$H NMR: (400 MHz, DMSO-$d_6$) δ: 11.11 (s, 1H), 8.30 (d, J = 8.8 Hz, 1H), 8.20 (d, J = 5.6 Hz, 1H), 7.92 (d, J = 9.2 Hz, 1H), 7.87 (d, J = 8.8 Hz, 1H), 7.80 (d, J = 8.4 Hz, 1H), 7.74-7.64 (m, 2H), 7.46-7.42 (m, 2H), 7.40 (d, J = 2.8 Hz, 1H), 7.36-7.32 (m, 2H), 7.08 (s, 1H), 5.11 (dd, J = 5.2, 13.2 Hz, 1H), 4.32-4.28 (m, 2H), 4.26-4.23 (m, 2H), 3.89 (s, 3H), 3.85-3.82 (m, 2H), 3.82-3.78 (m, 2H), 3.65 (s, 4H), 2.92-2.83 (m, 1H), 2.62-2.53 (m, 2H), 2.07-1.99 (m, 1H) |
| 48 | | 939.4 | $^1$H NMR: (400 MHz, DMSO-$d_6$) δ: 8.98 (s, 1H), 8.48-8.39 (m, 2H), 8.22 (d, J = 5.6 Hz, 1H), 7.99 (d, J = 9.2 Hz, 2H), 7.84-7.76 (m, 1H), 7.74-7.66 (m, 1H), 7.53 (dd, J = 2.4, 9.2 Hz, 1H), 7.49 (d, J = 2.4 Hz, 1H), 7.45-7.37 (m, 3H), 7.37-7.30 (m, 4H), 7.09 (s, 1H), 4.94-4.85 (m, 6H), 4.54 (d, J = 9.6 Hz, 1H), 4.44 (t, J = 8.4 Hz, 1H), 4.30-4.25 (m, 3H), 3.95 (s, 2H), 3.89 (s, 3H), 3.86-3.81 (m, 2H), 3.65-3.59 (m, 4H), 3.57 (d, J = 2.4 Hz, 6H), 2.44 (s, 3H), 2.09-2.00 (m, 1H), 1.77 (ddd, J = 4.6, 8.4, 13.2 Hz, 1H), 1.35 (d, J = 7.2 Hz, 3H), 0.93 (s, 9H) |
| 49 | | 1028.5 | $^1$H NMR (400 MHz, methanol-$d_4$) δ 8.85 (s, 1H), 7.68 (s, 1H), 7.58 (d, J = 7.9 Hz, 1H), 7.46-7.33 (m, 4H), 7.30 (d, J = 8.1 Hz, 1H), 7.05 (q, J = 5.5, 3.7 Hz, 2H), 6.97 (t, J = 7.4 Hz, 1H), 5.00 (q, J = 7.0 Hz, 1H), 4.69 (s, 1.H), 4.62-4.54 (m, 1H), 4.43 (s, 1H), 4.27 (dd, J = 9.5, 5.0 Hz, 1H), 4.12-4.03 (m, 2H), 3.84 (d, J = 11.1 Hz, 1H), 3.78-3.57 (m, 11H), 3.57-3.50 (m, 4H), 2.96 (d, J = 6.6 Hz, 2H), 2.71-2.64 (m, 6H), 2.46 (s, 3H), 2.25-2.15 (m, 1H), 2.05-1.90 (m, 1H), 1.69-1.60 (m, 1H), 1.60-1.50 (m, 4H), 1.41-1.25 (m, 5H), 1.07-1.01 (m, 9H), 0.85 (t, J = 6.7 Hz, 3H). |
| 50 | | 1072.5 | $^1$H NMR (400 MHz, methanol-$d_4$) δ 8.86 (d, J = 1.8 Hz, 1H), 7.69 (s, 1H), 7.59 (d, J = 7.9 Hz, 1H), 7.48-7.35 (m, 4H), |

TABLE 2-continued

| Target Protein Degradation via Exemplary Compounds of the Present Disclosure | | | |
|---|---|---|---|
| Ex. No. | Protein Degradation at 1 μM † | MH + (1) | NMR transcript |
| | | | 7.31 (d, J = 8.1 Hz, 1H), 7.11-7.02 (m, 2H), 7.02-6.94 (m, 1H), 5.02 (q, J = 7.0 Hz, 1H), 4.70 (s, 1H), 4.63-4.54 (m, 1H), 4.44 (s, 1H), 4.28 (dd, J = 9.4, 5.0 Hz, 1H), 4.06 (d, J = 4.0 Hz, 2H), 3.85 (d, J = 11.0 Hz, 1H), 3.80-3.61 (m, 12H), 3.55 (t, J = 5.2 Hz, 5H), 2.98 (d, J = 6.7 Hz, 2H), 2.72-2.64 (m, 2H), 2.68 (s, 5H), 2.48 (s, 3H), 2.21 (t, J = 10.0 Hz, 1H), 1.98 (ddd, J = 13.3, 9.1, 4.4 Hz, 1H), 1.55 (dd, J = 21.7, 7.0 Hz, 3H), 1.37-1.28 (m, 1H), 1.05 (d, J = 7.3 Hz, 9H), 0.87 (t, J = 6.9 Hz, 3H). |
| 51 | | 1116.5 | $^1$H NMR (400 MHz, chloroform-d) δ 8.69 (s, 1H), 8.46 (d, J = 14.8 Hz, 1H), 7.64 (d, J = 7.8 Hz, 1H), 7.51 (d, J = 7.9 Hz, 1H), 7.39 (qd, J = 12.1, 10.1, 6.7 Hz, 7H), 7.20 (t, J = 7.5 Hz, 1H), 7.13 (t, J = 7.4 Hz, 1H), 7.06 (t, J = 2.2 Hz, 1H), 5.10 (p, J = 7.0 Hz, 1H), 4.76 (t, J = 7.8 Hz, 1H), 4.61-4.55 (m, 1H), 4.50 (s, 1H), 4.45-4.37 (m, 1H), 4.10-3.94 (m, 3H), 3.71-3.57 (m, 20H), 3.56 (s, 2H), 3.13-2.96 (m, 2H), 2.69 (d, J = 10.3 Hz, 4H), 2.55 (s, 4H), 2.06 (td, J = 12.0, 11.1, 5.9 Hz, 2H), 1.68-1.60 (m, 2H), 1.49 (d, J = 6.9 Hz, 4H), 1.45-1.25 (m, 9H), 1.08 (s, 8H), 0.89 (q, J = 6.4 Hz, 5H), 0.09 (s, 15H). |
| 52 | | 800.3 | $^1$H NMR (400 MHz, DMSO-d$_6$) δ 11.12 (s, 1H), 10.76 (s, 1H), 7.94 (d, J = 8.5 Hz, 1H), 7.87-7.78 (m, 2H), 7.58 (d, J = 7.8 Hz, 1H), 7.47 (d, J = 2.2 Hz, 1H), 7.38 (dd, J = 8.3, 2.3 Hz, 1H), 7.31 (d, J = 8.1 Hz, 1H), 7.12-7.01 (m, 2H), 6.96 (t, J = 7.0 Hz, 1H), 5.12 (dd, J = 13.0, 5,4 Hz, 1H), 4.36-4.29 (m, 2H), 4.18-4.09 (m, 1H), 3.83-3.77 (m, 2H), 3.61 (dd, J = 5.7, 3.2 Hz, 2H), 3.54 (t, J = 4.5 Hz, 4H), 3.46-3.38 (m, 4H), 3.30-3.29 (m, 2H), 2.94-2.86 (m, 3H), 2.70-2.52 (m, 4H), 2.48-2.49 (m, 2H), 2.08-2.01 (m, 1H), 1.60-1.40 (m, 2H), 1.40-1.15 (m, 4H), 0.81 (t, J = 6.9 Hz, 3H). |
| 53 | | 844.4 | $^1$H NMR (400 MHz, DMSO-d$_6$) δ 11.11 (s, 1H), 10.75 (s, 1H), 7.94 (d, J = 8.6 Hz, 1.H), 7.87-7.78 (m, 2H), 7.58 (d, J = 7.8 Hz, 1H), 7.46 (d, J = 2.1 Hz, 1H), 7.37 (dd, J = 8.3, 2.2 Hz, 1H), 7.31 (d, J = 8.0 Hz, 1H), 7.10 (d, J = 2.1 Hz, 1H), 7.05 (t, J = 7.0 Hz, 1H), 6.96 (t, J = 7.4 Hz, 1H), 5.12 (dd, J = 12.9, 5.4 Hz, 1H), 4.35-4.29 (m, 2H), 3.83-3.76 (m, 3H), 3.64-3.49 (m, 11H), 3.41 (d, J = 4.9 Hz, 4H), 2.86 (ddd, J = 32.1, 14.5, 7.2 Hz, 5H), 2.58 (s, 1H), 2.09-2.01 (m, 1H), |

TABLE 2-continued

| Target Protein Degradation via Exemplary Compounds of the Present Disclosure | | | |
|---|---|---|---|
| Ex. No. | Protein Degradation at 1 μM † | MH + (1) | NMR transcript |
| | | | 1.24 (dd, J = 14.6, 8.5 Hz, 3H), 0.81 (t, J = 6.9 Hz, 2H). |
| 54 | | 884.4 | $^1$H NMR (400 MHz, DMSO-d$_6$) δ 11.12 (s, 1H), 10.76 (d, J = 2.4 Hz, 1H), 7.95 (d, J = 8.5 Hz, 1H), 7.87-7.76 (m, 2H), 7.58 (d, J = 7.9 Hz, 1H), 7.46 (d, J = 2.3 Hz, 1H), 7.37 (dd, J = 8.3, 2.3 Hz, 1H), 7.31 (d, J = 8.1 Hz, 1H), 7.10 (d, J = 2.3 Hz, 1H), 7.08-7.00 (m, 1H), 6.96 (t, J = 7.4 Hz, 1H), 5.12 (dd, J = 12.9, 5.4 Hz, 1H), 4.35-4.28 (m, 2H), 3.82-3.76 (m, 2H), 3.64-3.51 (m, 6H), 3.42 (d, J = 10.3 Hz, 1H), 2.86 (tdd, J = 21.2, 12.9, 6.9 Hz, 3H), 2.65-2.57 (m, 1H), 2.54 (d, J = 8.5 Hz, 2H), 2.10-1.97 (m, 1H), 1.56-1.42 (m, 1H), 1.23 (tq, J = 11.6, 5.7, 4.3 Hz, 3H), 0.87-0.77 (m, 3H). |
| 55 | | 1076.5 | $^1$H NMR (300 MHz, DMSO-d$_6$) δ 8.70 (s, 1H), 8.25 (s, 1H), 7.70-7.62 (m, 1H), 7.52-7.32 (m, 8H), 7.25-7.05 (m, 5H), 6.99-6.89 (m, 2H), 5.80-5.65 (m, 1H), 5.15-5.05 (m, 1H), 4.80-4.73 (m, 1H), 4.60-4.35 (m, 3H), 4.20-4.10 (m, 3H), 4.05-3.99 (m, 2H), 3.90-3.68 (m, 10H), 3.65-3.58 (m, 1H), 3.25 (s, 4H), 3.11-3.00 (m, 2H), 2.65 (s, 4H), 2.15-2.05 (m, 2H), 1.70-1.60 (m, 2H),1.55-1.25 (m, 6H), 1.05 (s, 9H), 0.95-0.80 (m, 5H). |
| 56 | | 1120.5 | $^1$H NMR (300 MHz, DMSO-d$_6$) δ (ppm): 10.75 (s, 1H), 8.98 (s, 1H), 8.45-8.42 (m, 1H), 7.99-7.97 (m, 1H), 7.82 (s, 1H), 7.60-7.57 (m, 1H), 7.46-7.28 (m, 6H), 7.10 (s, 1H), 7.06-7.04 (m, 1H), 6.98-6.90 (m, 3H), 6.88-6.80 (m, 2H), 5.15-5.11(m, 1H), 4.93-4.89(m, 1H), 4.57-4.53 (m, 1H), 4.47-4.43 (m, 1H), 4.28 (s, 1H), 4.19-4.06 (m, 1H), 4.05-3.95(m, 4H), 3.74-3.68 (m, 2H), 3.60(s, 14H), 3.12 (s, 4H), 2.95-2.80 (m, 2H), 2.45 (s, 3H), 2.10-1.97 (m, 1H), 1.83-1.72 (m, 1H), 1.60-1.46 (m, 3H), 1.40-1.34 (m, 3H), 1.31-1.15 (m, 6H), 0.95 (s, 9H). |
| 57 | | 848.3 | $^1$H NMR (400 MHz, DMSO-d$_6$) δ (ppm): 11.13 (s, 1H), 10.77 (s, 1H), 7.99 (s, 1H), 7.90-7.84 (m, 2H), 7.59 (s, 1H), 7.47 (s, 1H), 7.38 (s, 1H), 7.33 (s, 1H), 7.11 (s, 1H), 7.06 (s, 1H), 6.96-6.80 (m, 3H), 6.86-6.83 (m, 2H), 5.13 (s, 1H), 4.40-4.35 (m, 2H), 4.10-4.06 (m, 3H), 3.90-3.84 (m, 2H), 3.81-3.79 (m, 2H), 3.64-3.51 (m, 4H), 3.17-3.05 (m, 4H), 2.92-2.85 (m, 2H), 2.85 (s, 1H), 2.65 (s, 1H), 2.07 (s, 1H), 1.53-1.49 (m, 2H), 1.45-1.22 (m, 5H), 0.88-0.82 (m, 3H). |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| 58 | | 892.4 | $^1$H NMR (300 MHz, DMSO-d$_6$) δ 11.13 (s, 1H), 10.78 (s, 1H), 8.04-8.00 (m, 1H), 7.90-7.80 (m, 2H), 7.62-7.59 (m, 1H), 7.48 (s, 1H), 7.41-7.30 (m, 2H), 7.16-7.02 (m, 2H), 7.00-6.82 (m, 5H), 5.20-5.10 (m, 1H), 4.33 (s, 2H), 4.20-4.10 (m, 1H), 4.02 (s, 2H), 3.85-3.55 (m, 12H), 3.22-3.05 (m, 4H), 3.00-2.80 (m, 3H), 2.75-2.65 (m, 2H), 2.10-2.00 (m, 1H), 1.60-1.45 (m, 2H), 1.40-1.15 (m, 4H), 0.83 (s, 3H). |
| 59 | | 743.2 | $^1$H NMR (400 MHz, DMSO-d$_6$) δ 11.09 (s, 1H), 8.26 (d, 2H), 8.15-8.05 (m, 3H), 7.96 (t, 1H), 7.80 (d, 1H), 7.56 (d, 1H), 7.45 (d, 2H), 7.37-7.15 (m, 4H), 7.07 (t, 1H), 6.97 (d, 1H), 6.88 (d, 2H), 5.15-5.06 (m, 1H), 4.88 (s, 2H), 4.31 (s, 2H), 4.10-4.03 (m, 2H), 3.80 (dd, 4H), 2.88 (t, 1H), 2.59 (d, 1H), 2.03 (d, 1H), 1.23 (s, 1H). |
| 60 | | 743.2 | $^1$H NMR (300 MHz, DMSO-d$_6$) δ 11.10 (s, 1H), 8.75-8.60 (m, 1H), 8.26 (d, 2H), 7.88-7.74 (m, 3H), 7.73-7.60 (m, 2H) 7.46-7.12 (m, 6H), 7.06-6.83 (m, 4H), 5.16-5.04 (m, 1H), 4.86 (s, 2H), 4.29 (s, 2H), 4.04 (d, 2H), 3.85-3.74 (m, 4H), 2.90-2.80 (m, 1H), 2.65-2.51 (m, 2H), 2.11-1.91 (m, 1H). |
| 61 | | 787.7 | $^1$H NMR (300 MHz, DMSO-d$_6$) δ 11.13 (s, 1H), 8.30-8.26 (m, 2H), 8.16-8.04 (m, 3H), 8.00-7.92 (m, 1H), 7.84-7.80 (m, 1H), 7.60-7.53 (m, 1H), 7.50-7.40 (m, 2H), 7.38-7.30 (m, 1H), 7.30-7.20 (m, 4H), 7.13-7.04 (m, 1H), 7.02-6.97 (m, 1H), 6.95-6.88 (m, 2H), 5.15-5.06 (m, 1H), 4.90 (s, 2H), 4.32-4.25 (m, 2H) 4.08-4.00 (m, 2H), 3.83-3.70 (m, 4H), 3.60 (s, 4H), 3.30 (s, 2H), 2.93-2.80 (m, 1H), 2.10-1.99 (m, 1H). |
| 62 | | 787.1 | $^1$H NMR (300 MHz, DMSO-d$_6$) δ 11.13 (s, 1H), 8.78-8.65 (m, 1H), 8.30-8.26 (m, 2H), 7.91-7.80 (m, 3H), 7.79-7.65 (m, 2H), 7.45 (s, 1H), 7.38-7.20 (m, 5H), 7.05-6.95 (m, 2H), 6.90-6.85 (m, 2H), 5.15-5.06 (m, 1H), 4.90(s, 2H) 4.32-4.25 (m, 2H), 4.08-4.00 (m, 2H), 3.80-3.68 (m, 4H), 3.60 (s, 4H),2.93-2.80 (m, 1H), 2.65-2.65(m, 1H), 2.10-2.00 (m, 2H). |
| 63 | | 831.2 | $^1$H NMR (400 MHz, DMSO-d$_6$) δ 11.10 (s, 1H), 8.28-8.24 (m, 2H), 8.16-8.09 (m, 3H), 7.99 (s, 1H), 7.68 (s, 1H), 7.58 (s, 1H), 7.50-7.41 (m, 2H), 7.34 (s, 1H), 7.30-7.26 (m, 3H), 7.09 (s, 1H), 7.01 (s, 1H), 6.88-6.92 (m, 2H) 5.08(s, 1H), 4.92-4.82 (m, 2H), 4.32-4.24 (m, 2H), 4.05-3.98 (m, 2H), 3.80-3.73 (m, 2H), 3.72-3.66(m, 2H), |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| | | | 3.60-3.48 (m, 8H), 2.95-2.83 (s, 1H), 2.63-2.54 (m, 2H), 2.02 (s, 1H). |
| 64 | | 831.2 | $^1$H NMR (400 MHz, DMSO-d$_6$) δ 11.11 (s, 1H), 8.71 (s, 1H), 8.37-8.30 (m, 2H), 7.94-7.85 (m, 2H), 7.81 (s, 1H), 7.72-7.60 (m, 2H), 7.44 (s, 1H), 7.37-7.29 (m, 2H) 7.28-7.20 (m, 3H), 7.05 (s, 1H), 6.98 (s, 1H), 6.91-6.82 (m, 2H), 5.13 (m, 1H), 4.89 (s, 2H), 4.28 (t, 2H), 4.04 (t, 2H), 3.80-3.76 (m, 4H), 3.58-3.49 (m, 8H), 2.85 (s, 1H), 2.60 (s, 1H), 2.09-2.00 (m, 3H). |
| 65 | | 967.2 | $^1$H NMR (400 MHz, DMSO-d$_6$) δ (ppm): 8.99 (d, 1H), 8.36-8.25 (m, 3H), 8.17-8.07 (m, 3H), 8.04-7.93 (m, 1H), 7.58 (d, 1H), 7.51-7.38 (m, 3H), 7.35-7.22 (m, 5H), 7.08 (t, 1H), 7.02-6.95 (m, 1H), 6.94-6.86 (m, 2H), 6.09 (s, 1H), 5.12 (d, 1H), 4.89 (s, 3H), 4.43 (t, 1H), 4.25 (s, 3H), 4.04 (t, 2H), 3.81-3.72 (m, 5H), 3.59-3.52 (m, 1H), 3.50-3.43 (m, 4H), 2.46 (d, 3H), 2.29-2.20 (m, 1H), 2.05 (s, 1H), 1.82-1.73 (m, 1H), 1.49-1.31 (m, 3H), 0.96 (d, 2H), 0.82 (d, 4H). |
| 66 | | 967.2 | $^1$H NMR (400 MHz, DMSO-d$_6$) δ (ppm): 9.00 (s, 1H), 8.43 (d, 1H), 8.28 (d, 2H), 8.12 (dd, 3H), 8.04-7.93 (m, 1H), 7.63-7.42 (m, 4H), 7.41-7.18 (m, 5H), 7.09 (t, 1H), 7.00 (d, 1H), 6.91 (d, 2H), 6.02 (d, 1.H), 5.11 (d, 1H), 4.92 (d, 3H), 4.38 (t, 1H), 4.28 (s, 3H), 4.06 (d, 2H), 3.87-3.61 (m, 6H), 3.48-3.41 (m, 2H), 2.47 (s, 3H), 2.24 (s, 1H), 2.05-1.98 (m, 1H), 1.96-1.71 (m, 1H), 1.50-1.19 (m, 4H), 1.04-0.67 (m, 6H). |
| 67 | | 967.2 | $^1$H NMR (400 MHz, DMSO-d$_6$) δ 9.00 (d, 1H), 8,77-8.66 (m, 1H), 8.37-8.27 (m, 3H), 7.88 (d, 2H), 7.71 (dd, 2H), 7,45-7.36 (m, 3H), 7.36-7.26 (m, 5H), 7.08-6.95 (m, 2H), 6.90 (d, 2H), 6.12 (d, 1H), 5.12 (d, 1H), 4.89 (s, 3H), 4.43 (t, 1H), 4.25 (s, 3H), 4.05 (s, 2H), 3.75 (s, 5H), 3.58-3.39 (m, 3H), 2.46 (d, 4H), 2.39-2.20 (m, 2H), 2.05 (s, 1H), 1.92-1.71 (m, 1H),1.50-1.29 (m, 3H), 0.88-0.71 (m, 4H). |
| 68 | | 967.2 | $^1$H NMR (400 MHz, DMSO-d$_6$) δ 9.00 (s, 1H), 8.77-8.66 (m, 1H), 8.43 (d, 1H), 8.30 (d, 2H), 7.88 (d, 2H), 7.77-7.65 (m, 2H), 7.51-7.33 (m, 5H), 7.32-7.21 (m, 3H), 7.08-6.96 (m, 2H), 6.92 (d, 2H), 6.10 (s, 1H), 5.10 (d, 1H), 4.93 (d, 1H), 5.04-4.86 (m, 3H), 4.38 (t, 1H), 4.31-4.24 (m, 3H), 4.10-4.04 (m, 2.H), 3.82-3.75 (m, 4H), 3.74-3.62 (m, 2H), 3.50-3.41 (m, 1H), 2.47 (s, 3H), 2.24 (s, 1H), |

TABLE 2-continued

Target Protein Degradation via Exemplary Compounds of the Present Disclosure

| Ex. No. | Protein Degradation at 1 | MH + (1) µM † | NMR transcript |
|---|---|---|---|
| | | | 2.03 (s, 1H), 1.8-1.76 (m, 1H), 1.39 (d, 3H), 0.96 (d, 3H), 0.81 (dd, 3H). |
| 69 | | 1055.2 | $^1H$ NMR (400 MHz, DMSO-$d_6$) δ 8.99 (d, 1H), 8.38-8.21 (m, 3H), 8.19-8.04 (m, 3H), 7.94-8.05 (m, 1H), 7.58 (d, J = 15.2 Hz, 1H), 7.50-7.36 (m, 4H), 7.32-7.21 (m, 5H), 7.08 (t, J = 7.6 Hz, 1H), 6.99 (d, J = 7.9 Hz, 1H), 6.92-6.81 (m, 2H), 6.10 (s, 1H), 5.12 (d, J = 3.6 Hz, 1H), 4.90 (s, 3H), 4.43 (t, J = 7.8 Hz, 1H), 4.35-4.12 (m, 3H), 4.21 (d, J = 2.9 Hz, 2H), 3.82-3.62 (m, 5H), 3.59-3.44 (m, 11H), 2.46-2.40 (m, 3H), 2.32-2.18 (m, 1H), 1.46 (d, J = 6.9 Hz, 1H), 1.35 (d, J = 7.0 Hz, 3H), 0.97 (d, J = 6.6 Hz, 2H), 0.83 (d, J = 6.7 Hz, 3H), 0.76 (d, J = 6.7 Hz, 1H). |
| 70 | | 1055.2 | $^1H$ NMR (400 MHz, DMSO-$d_6$) δ 9.00 (s, 1H), 8.43 (d, J = 7.6 Hz, 1H), 8.31-8.24 (m, 2H), 8.12 (dd, J = 14.3, 8.2 Hz, 3H), 7.99 (dd, J = 15.3, 12.2 Hz, 1H), 7.58 (d, J = 15.2 Hz, 1H), 7.51-7.41 (m, 3H), 7.41-7.34 (m, 2H), 7.33-7.23 (m, 3H), 7.09 (t, J = 7.6 Hz, 1H), 7.00 (d, J = 7.9 Hz, 1H), 6.91 (dd, J = 8.9, 2.6 Hz, 2H), 6.11 (s, 1H), 5.11 (d, J = 3.7 Hz, 1H), 5.00-4.81(m, 3H), 4.39 (t, J = 7.8 Hz, 1H), 4.34-4.21 (m, 3H), 4.05 (t, J = 4.7 Hz, 2H), 3.75-3.62 (m, 6H), 3.63-3.50 (m, 8H), 3.42 (d, J = 9.9 Hz, 1H), 2.47 (s, 3H), 2.30-2.12 (m, 1H), 2.04 (t, J = 10.3 Hz, 1H), 1.82-1.75 (m , 1H), 1.38 (d, J = 7.0 Hz, 3H), 0.97 (t, J = 6.7 Hz, 3H), 0.81 (dd, J = 15.6, 6.7 Hz, 3H). |
| 71 | | 1055.2 | $^1H$ NMR (400 MHz, DMSO-$d_6$) δ 8.99 (d, J = 9.2 Hz, 1H), 8.72 (dd, J = 15.8, 11.5 Hz, 1H), 8.32 (dd, J = 15.7, 8.3 Hz, 3H), 7.88 (d, J = 8.8 Hz, 2H), 7.78-7.62 (m, 2H), 7.52-7.35(m, 1H),7.34-7.19 (m, 5H), 7.04-6.98 (m, 2H), 6.91 (dd, J = 9.0, 2.9 Hz, 2H), 6.10 (s, 1H), 5.12 (d, J = 3.6 Hz, 1H), 4.89 (s, 3H), 4.43 (t, J = 7.8 Hz, 1H), 4.32-4.12 (m, 3H), 4.04 (t, J = 4.8 Hz, 2H), 3.79-3.64 (m, 5H), 3.59-3.42 (m, 10H), 2.46 (d, J = 7.7 Hz, 3H), 2.31-2.23 (m, 1H), 2.05 (s, 1H), 1.82-1.74 (m, 1H), 1.49-1.31 (m, 3H), 1.03-0.97 (d, J = 7.0 Hz, 2H), 0.83 (d, J = 6.7 Hz, 3H), 0.76 (d, J = 6.7 Hz, 1H). |
| 72 | | 1055.2 | $^1H$ NMR (400 MHz, DMSO-$d_6$) δ 9.00 (s, 1H), 8.72 (dd, J = 15.7, 11.5 Hz, 1H), 8.43 (d, J = 7.6 Hz, 1H), 8.30 (d, J = 8.6 Hz, 2H), 7.88 (d, J = 8.6 Hz, 2H), 7.73-7.69 (m, 2H), 7.45 (d, J = 8.0 Hz, 2H), 7.40-7.23 (m, 6H), 7.04-6.99 (m, 2H), 6.91 (d, J = 8.6 Hz, 2H), 6.10 (s, 1H), 5.11 (d, J = 3.8 Hz, 1H), 4.95-4.85 (m, 3H), 4.38 (t, J = 7.9 Hz, 1H), 4.29-4.17 (m, 3H), 4.05 (t, J = 4.7 Hz, 2H), 3.80-3.66 (m, 5H), 3.6-3.50 (m, 8H), 3.48-3.36 (m, 2H), 2.47 (s, 3H), 2.30-2.17(m, 1H), 2.09-1.98 (m, 1H), 1.97-1.74(m, 1H), 1.38 (d, J = 7.0 Hz, 3H), 0.97 (t, J = 6.9 Hz, 3H), 0.81 (dd, J = 15.7, 6.7 Hz, 3H) |
| 73 | | 1011.2 | $^1H$ NMR (400 MHz, DMSO-$d_6$) δ 8.98 (d, 1H), 8.35-8.23 (m, 3H), 8.10 (m, 3H), 8.03-7.91 (m, 1H), 7.60-7.37 (m, 4H), 7.34-7.21 (m, 5H), 7.10-6.94 (m, 2H), 6.93-6.84 (m, 2H), 6.08 (s, 1.H), 5.10 (d, 1H), 4.92-4.82 (m, 3H), 4.54-4.38 (m, 1H), 4.27-4.17 (m, 3H), 4.07-3.99 (m, 2H), 3.37-3.64 (m, 5H), 3.60-3.39 (m, 6H), 2.45 (d, J = 8.4 Hz, 3H), 2.31-2.18 (m, 1H), 2.10-1.99 (m, 1H), 1.81-1.71 (m, 1H), 1.47-1.30 (m, 3H), 0.95 (d, 2H), 0.85-0.69 (m, 4H). |
| 74 | | 1011.2 | $^1H$ NMR (400 MHz, DMSO-$d_6$) δ 8.98 (s, 1H), 8.50-8.20 (m, 3H), 8.16-8.06 (m, 3H), 8.03-7.92 (m, 1H), 7.62-7.32 (m, 6H), 7.31-7.20 (m, 3H), 7.13-6.95 (m, 2H), 6.93-6.86 (m, 2H), 6.09 (s, 1H), 5.09 (d, 1H), 4.96-4.86 (m, 3H), 4.37 (t, 1H), 4.29-4.19 (m, 3H), 4.04 (dd, 2H), 3.79-3.61 (m, 6H), 3.57 (s, 4H), 3.48-3.39 (m, 1H), 2.45 (s, 3H), 2.37-2.11 (m, 1H), 2.07-1.97 (m, 1H), 1.83-1.72 (m, 1H), 1.50-1.29 (m, 3H), 0.95 (t, 3H), 0.85-0.75 (m, 3H). |
| 75 | | 1011.2 | $^1H$ NMR (400 MHz, DMSO-$d_6$) δ 8.98 (d, 1H), 8.76-8.64 (m, 1H), 8.35-8.23 (m, 3H), 7.90-7.83 (m, 2H), 7.75-7.64 (m, 2H), 7.50-7.18 (m, 8H), 7.05-6.93 (m, 2H), 6.93-6.85 (m, 2H), 6.11 (d, 1H), 5.10 (d, 1H), 5.04-4.93 (m, 1H), 4.96-4.78 (m, 3H), 4.54-438 (m, 1H), 4.28-4.16 (m, 3H), 4.02 (dd, 2H), 3.77-3.64 (m, 5H), 3.59-3.51 (m, 6H), 2.45 (d, 3H), 2.31-2.18 (m, 1H), 2.09-1.99 (m, 1H), 1.81-1.71 (m, 1H), 1.49-1.28 (m, 3H), 0.95 (d, 2H), 0.86-0.67 (m, 4H). |
| 76 | | 1011.2 | $^1H$ NMR (400 MHz, DMSO-$d_6$) δ 8.98 (s, 1H), 8.76-8.65 (m, 1H), 8.44-8.24 (m, 3H), 7.91-7.84 (m, 2H), 7.76-7.64 (m, 2H), 7.48-7.19 (m, 8H), 7.07-6.94 (m, 2H), 6.94-6.86 (m, 2H), 6.10-5.91 (m, 1H), 5.12-5.06 (m, 1H), 4.95-4.85 (m, 3H), 4.41-4.32 (m, 1H), 4.31-4.18 (m, 3H), 4.07-4.00 (m, 2H), 3.74-3.60 (m, 5H), 3.57 (s, 4H), 3.49-3.39 (m, 1H), 2.48-2.43 (m, 4H), 2.35-2.15 (m, 1H), 2.09-1.97 (m, 1H), 1.83-1.72 (m, 1H), 1.47-1.31 (m, 3H), 0.99-0.91 |

TABLE 2-continued

Target Protein Degradation via Exemplary Compounds of the Present Disclosure

| Ex. No. | Protein Degradation at 1 | MH + (1) μM † | NMR transcript |
|---|---|---|---|
| | | | (m, 3H), 0.85-0.75 (m, 3H). |
| 77 | | | $^1$H NMR (400 MHz, DMSO-d$_6$) δ 11.08 (s, 1H), 8.30-8.23 (m, 2H), 8.17-8.05 (m, 3H), 8.03-7.91 (m, 1H), 7.70-7.64 (m, 1H), 7.61-7.52 (m, 1H), 7.49-7.42 (m, 1H), 7.36-7.19 (m, 5H), 7.12-7.04 (m, 1H), 7.04-6.97 (m, 1H), 6.80-6.74 (m, 2H), 5.11-5.02 (m, 1H), 4.88 (s, 2H), 4.81-4.73 (m, 1H), 4.16-4.06 (m, 1H), 3.45-3.38 (m, 4H), 3.32-3.26 (m, 7H), 2.95-2.81 (m, 1H), 2.63-2.52 (m, 1H), 2.42-2.32 (m, 4H), 2.30-2.19 (m, 2H), 2.05-1.97 (m, 1H), 1.72-1.64 (m, 2H). |
| 78 | | | $^1$H NMR (400 MHz, DMSO-d$_6$) δ 11.08 (s, 1H), 8.75-8.64 (m, 1H), 8.32-8.23 (m, 2H), 7.90-7.83 (m, 2H), 7.75-7.63 (m, 3H), 7.39-7.15 (m, 6H), 7.07-6.95 (m, 2H), 6.81-6.74 (m, 2H), 5.11-5.02 (m, 1H), 4.87 (s, 2H), 4.82-4.72 (m, 1H), 4.17-4.06 (m, 1H), 3.42 (s, 4H), 3.31 (s, 5H), 2.95-2.81 (m, 1H), 2.63-2.51 (m, 2H), 2.42-2.31 (m, 4H), 2.10-1.97 (m, 2H), 2.07 (s, 1H), 2.05-1.96 (m, 1H), 1.74-1.64 (m, 2H). |
| 79 | | | $^1$H NMR (400 MHz, DMSO-d$_6$) δ 11.10 (s, 1H), 8.28 (d, J = 8.7 Hz, 2H), 8.12 (dd, J = 14.5, 8.1 Hz, 3H), 7.99 (dd, J = 15.3, 12.2 Hz, 1H), 7.68 (d, J = 8.5 Hz, 1H), 7.42-7.21 (m, 5H), 7.09 (t, J = 7.6 Hz, 1H), 7.01 (d, J = 7.9 Hz, 1H), 6.77 (d, J = 8.5 Hz, 2H), 5.08 (dd, J = 13.0, 5.4 Hz, 1H), 4.89 (s, 2H), 4.81-4.67(m, 1H), 4.32-4.24 (m, 1H), 3.58-3.40(m, 4H), 3.32-3.22(m, 4H), 2.99-2.83 (m, 1H), 2.73 (s, 2H), 2,64-2.52 (m, 2H), 2.43 (s, 4H), 2.41-2.26 (m, 4H), 2.11-1.91(m, 3H), 1.77 (d, J = 12.0 Hz, 2H), 1.39 (d, J = 10.7 Hz, 2H), 1.25 (s, 1H). |
| 80 | | | $^1$H NMR (400 MHz, DMSO-d$_6$) δ 11.10 (s, 1H), 8.77-8.65 (m, 1H), 8.33-8.25 (m, 2H), 7.91-7.85 (m, 2H), 7.78-7.61 (m, 3H), 7.40-7.22 (m, 6H), 7.09-6.97 (m, 2H), 6.81-6.75 (m, 2H), 5.13-5.04 (m, 1H), 4.89 (s, 2H), 4.82-4.69 (m, 1H), 4.32-4.24 (m, 1H), 3.41 (s, 5H), 3.35 (s, 2H), 2.97-2.56 (m, 4H), 2.44 (s, 4H), 2.39-2.26 (m, 4H), 2.04 (s, 3H), 1.81-1.74 (m, 2H), 1.43-1.36 (m, 3H). |

† A = less than 35% protein remaining relative to DMSO control;
B = between 35 and 70% protein remaining relative to DMSO control;
C = between 70 and 120% protein present relative to DMSO control;
D = more than 120% protein present relative to DMSO control.

A novel bifunctional molecule, which contains a α-synuclein recruiting moiety and an E3 Ligase Cereblon recruiting moiety, through PROTAC technology is described. The bifunctional molecules of the present disclosure actively inhibits and/or degrades α-synuclein, leading to significant and persistent α-synuclein suppression and anti-neurodegenerative effect. PROTAC mediated protein degradation provides a promising strategy in targeting the "undruggable" pathological proteins by traditional approaches.

In certain embodiments, the description provides a compound as exemplified by the PTM, L, and ULMs illustrated in Tables 1 and 2. That is, the description encompasses compounds formed as a result of interchanging the PTM, L, and ULM moieties exemplified in Table 1 in order to provide additional embodiments of compounds as described herein.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

REFERENCES

The following references are incorporated herein by reference in their entirety for all purposes.

1. Crew A P, Raina K, Dong H, Qian Y, Wang J, Vigil D, Serebrenik Y V, Hamman B D, Morgan A, Ferraro C, Siu K, Neklesa T K, Winkler J D, Coleman K G. Crews C M. Identification and Characterization of Von Hippel-Lindau-Recruiting Proteolysis Targeting Chimeras (PROTACs) of TANK-Binding Kinase 1. *J Med Chem.* 2018 Jan. 25; 61(2):583-598.
2. Lu J, Qian Y. Altieri M, Dong H, Wang J, Raina K, Hines J. Winkler J D, Crew A P, Coleman K, Crews C M. Hijacking the E3 Ubiquitin Ligase Cereblon to Efficiently Target BRD4. *Chem Biol.* 2015 Jun. 18; 22(6):755-63.
3. Bondeson D P. Mares A. Smith I E, Ko E, Campos S, Miah A H. Mulholland K E, Routly N, Buckley D L, Gustafson J L, Zinn N, Grandi P. Shimamura S. Bergamini G, Faelth-Savitski M, Bantscheff M, Cox C. Gordon D A, Willard R R. Flanagan J J. Casillas L N, Votta B J. den Besten W. Famm K, Kruidenier L, Carter P S, Harling J D, Churcher I, Crews C M. Catalytic in vivo protein knockdown by small-molecule PROTACs. *Nat Chem Biol.* 2015 August; 11(8):611-7.

4. Tomoshige S, Nomura S, Ohgane K. Hashimoto Y. Ishikawa M. Degradation of huntingtin mediated by a hybrid molecule composed of IAP antagonist linked to phenyldiazenyl benzothiazole derivative. *Bioorg Med Chem Lett.* 2018 Feb. 15; 28(4):707-710.

5. Lu M, Liu T, Jiao Q, Ji J, Tao M, Liu Y, You Q, Jiang Z. Discovery of a Keap1-dependent peptide PROTAC to knockdown Tau by ubiquitination-proteasome degradation pathway. *Eur J Med Chem.* 2018 Feb. 25; 146:251-259.

6. Bondeson D P, Smith B E. Burslem G M, Buhimschi A D. Hines J. Jaime-Figueroa S, Wang J. Hamman B D, Ishchenko A, Crews C M. Lessons in PROTAC Design from Selective Degradation with a Promiscuous Warhead. *Cell Chem Biol.* 2018 Jan. 18; 25(1):78-87.e5.

7. Falkenburger B H. Saridaki T, Dinter E. Cellular models for Parkinson's disease. *J Neurochem.* 2016 October; 139 Suppl 1:121-130.

8. McLean P J, Kawamata H. Hyman B T. Alpha-synuclein-enhanced green fluorescent protein fusion proteins form proteasome sensitive inclusions in primary neurons. *Neuroscience.* 2001; 104(3):901-12.

9. Luk K C, Song C, O'Brien P. Stieber A, Branch J R, Brunden K R, Trojanowski J Q, Lee V M. Exogenous alpha-synuclein fibrils seed the formation of Lewy body-like intracellular inclusions in cultured cells. *Proc Natl Acad Sci USA.* 2009 Nov. 24; 106(47):20051-6.

10. Waxman E A, Giasson B I. A novel, high-efficiency cellular model of fibrillar alpha-synuclein inclusions and the examination of mutations that inhibit amyloid formation. *J Neurochem.* 2010 April; 113(2):374-88.

11. Nonaka T. Watanabe S T. Iwatsubo T, Hasegawa M. Seeded aggregation and toxicity of alpha-synuclein and tau: cellular models of neurodegenerative diseases. *J Biol Chem.* 2010 Nov. 5; 285(45):34885-98.

12. Schmid A W, Fauvet B, Moniatte M, Lashuel H A. Alpha-synuclein post-translational modifications as potential biomarkers for Parkinson disease and other synucleinopathies. *Mol Cell Proteomics.* 2013 December; 12(12):3543-58.

13. Peng C. Gathagan R J, Covell D J, Medellin C, Stieber A. Robinson J L. Zhang B, Pitkin R M, Olufemi M F, Luk K C. Trojanowski J Q, Lee V M. Cellular milieu imparts distinct pathological α-synuclein strains in α-synucleinopathies. *Nature.* 2018 May 9.

14. Kovalevich J. Langford D. Considerations for the use of SH-SY5Y neuroblastoma cells in neurobiology. *Methods Mol Biol.* 2013:1078:9-21.

15. Lassen L B, Gregersen E. Isager A K. Betzer C, Kofoed R H. Jensen P H. ELISA method to detect α-synuclein oligomers in cell and animal models. *PLoS One.* 2018 Apr. 26; 13(4):e0196056.

16. Nielsen S B, Macchi F, Raccosta S, Langkilde A E, Giehm L, Kyrsting A, Svane A S, Manno M, Christiansen G, Nielsen N C, Oddershede L, Vestergaard B, Otzen D E. Wildtype and A30P mutant alpha-synuclein form different fibril structures. *PLoS One.* 2013 Jul. 4; 8(7): e67713.

17. Polinski N K, Volpicelli-Daley L A, Sortwell C E, Luk K C, Cremades N, Gottler L M, Froula J, Duffy M F, Lee V M Y, Martinez T N, Dave K D. Best Practices for Generating and Using Alpha-Synuclein Pre-Formed Fibrils to Model Parkinson's Disease in Rodents. *J Parkinsons Dis.* 2018; 8(2):303-322.

18. Poster from the Michael J Fox Foundation (2017). The Michael J. Fox Foundation's Efforts to Generate, Characterize, and Promote the Use of a Variety of Preclinical Models of Parkinson's Disease.

19. Fares M B, Maco B, Oueslati A, Rockenstein E, Ninkina N, Buchman V L, Masliah E, Lashuel H A. Induction of de novo α-synuclein fibrillization in a neuronal model for Parkinson's disease. *Proc Natl Acad Sci USA.* 2016 Feb. 16; 113(7): E912-21.

20. Luk K C, Covell D J, Kehm V M, Zhang B, Song I Y, Byrne M D, Pitkin R M, Decker S C, Trojanowski J Q, Lee V M. Molecular and Biological Compatibility with Host Alpha-Synuclein Influences Fibril Pathogenicity. *Cell Rep.* 2016 Sep. 20; 16(12):3373-3387.

21. Luk K C, Kehm V, Carroll J, Zhang B, O'Brien P, Trojanowski J Q, Lee V M. Pathological alpha-synuclein transmission initiates Parkinson-like neurodegeneration in nontransgenic mice. *Science.* 2012 Nov. 16; 338(6109): 949-53.

22. Luk K C, Kehm V M, Zhang B. O'Brien P, Trojanowski J Q, Lee V M. Intracerebral inoculation of pathological α-synuclein initiates a rapidly progressive neurodegenerative alpha-synucleinopathy in mice. *J Exp Med.* 2012 May 7; 209(5):975-86.

23. Jones D R, Delenclos M, Baine A T, DeTure M, Murray, M E, Dickson, D W, and McLean P J, 2015 *Neuropathol Exp Neurol.* Transmission of Soluble and Insoluble α-Synuclein to Mice.

24. Wolff M, Mittag J J, Herling T W, De Genst E, Dobson C M, Knowles T P, Braun D. Buell 25. A K. 2016. *Sci Reports.* Quantitative thermophoretic study of disease-related protein aggregates 25. Graef J D, Hoque N, Polson P. Yang L, Iben L, Cao Y, Devidze N. Ahlijanian M, Meredith J. 2018 Characterization of pathology-inducing α-synuclein species from human diseased brain tissue. www.biorxiv.org/content/biorxiv/early/2019/03/25/588335.full.pdf

What is claimed is:

1. A bifunctional compound having the chemical structure:

ULM-L-PTM, or a pharmaceutically acceptable salt thereof, wherein:

(a) ULM is;

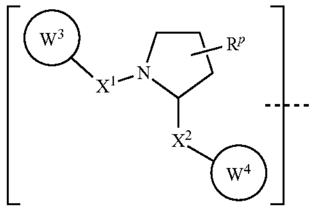

, wherein:

$X^1$, $X^2$ are each independently selected from a bond, O, $NR^{Y3}$, $CR^{Y3}R^{Y4}$, C═O, C═S, SO, and $SO_2$;

$R^{Y3}$, $R^{Y4}$ are each independently selected from H, linear or branched $C_1$-$C_6$ alkyl optionally substituted by 1 or more halo, and $C_1$-$C_6$ alkoxyl optionally substituted by 0-3 $R^P$ groups;

$R^P$ is independently selected from H, halo, —OH, $C_1$-$C_3$ alkyl, and C═O;

$W^3$ is selected from an optionally substituted T, an optionally substituted -T-N($R^{1a}R^{1b}$)$X^3$, an optionally substituted -T-N($R^{1a}R^{1b}$), an optionally substituted -T-aryl, an optionally substituted -T-heteroaryl, an optionally substituted T-biheteroaryl, an optionally substituted -T-heterocycle, an optionally substituted -T-biheterocycle, an optionally substituted —$NR^1$-T-aryl, an optionally substituted —$NR^1$-T-heteroaryl and an optionally substituted —$NR^1$-T-Heterocycle;

$X^3$ is selected from C═O, $R^1$, $R^{1a}$, and $R^{1b}$;

each of $R^1$, $R^{1a}$, $R^{1b}$ is independently selected from H, linear or branched $C_1$-$C_6$ alkyl group optionally substituted by 1 or more halo or —OH groups, $R^{Y3}$C═O, $R^{Y3}$C═S, $R^{Y3}$SO, $R^{Y3}SO_2$, N($R^{Y3}R^{Y4}$) C═O, N($R^{Y3}R^{Y4}$) C═S, N($R^{Y3}R^{Y4}$) SO, and N($R^{Y3}R^{Y4}$) $SO_2$;

T is selected from an optionally substituted alkyl, —$(CH_2)_n$— group, wherein each one of the methylene groups is optionally substituted with one or two substituents selected from halogen, methyl, optionally substituted alkoxy, and a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocyclyl, or —OH groups or an amino acid side chain optionally substituted; and n is 0, 1, 2, 3, 4, 5, or 6, $W^4$ is

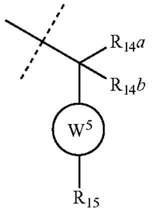 or 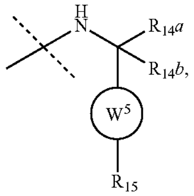

$R_{14a}$ and $R_{14b}$, are each independently selected from H, haloalkyl, and optionally substituted alkyl;

$W^5$ is an optionally substituted phenyl or an optionally substituted 5-10-membered heteroaryl, $R^{15}$ is selected from H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, and optionally substituted cyclo-heteroalkyl; and ⋰ is the attachment of a chemical linker moiety (L);

(b) PTM is selected from:

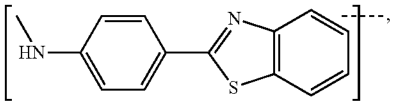

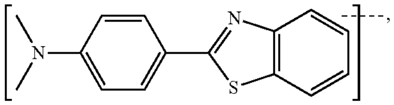

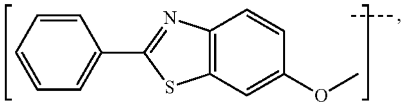

-continued

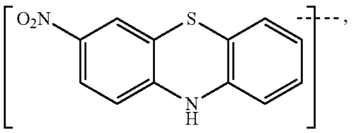

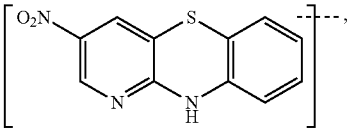

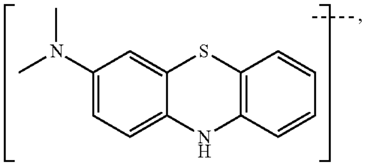

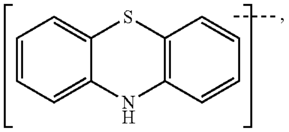

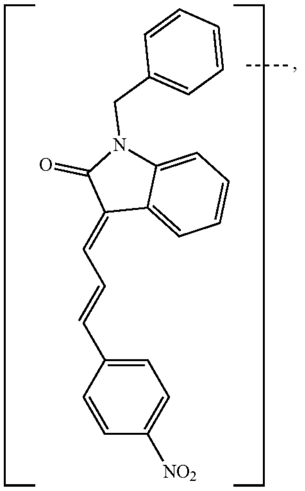

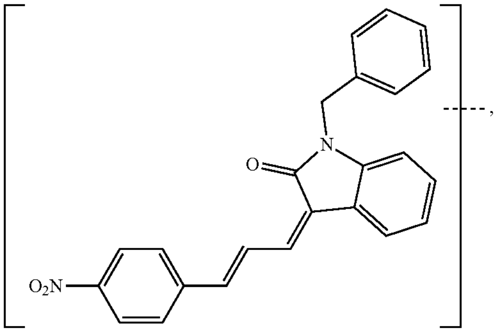

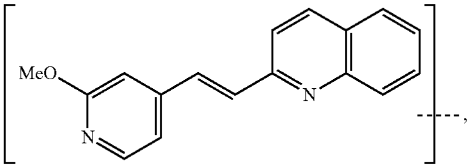

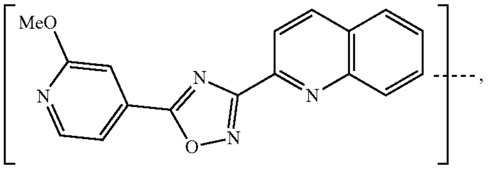

-continued
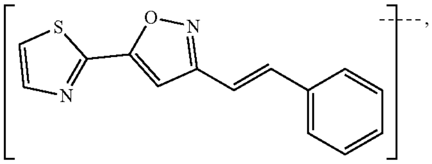
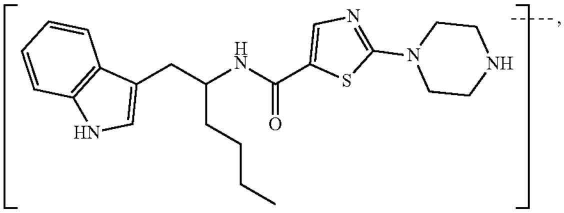
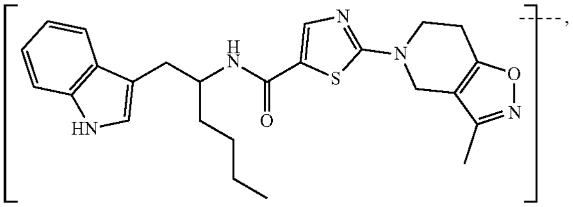
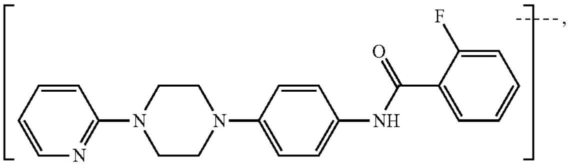
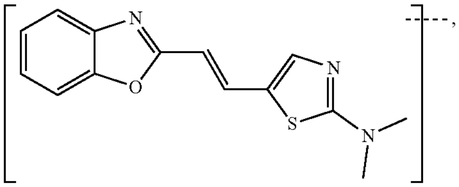
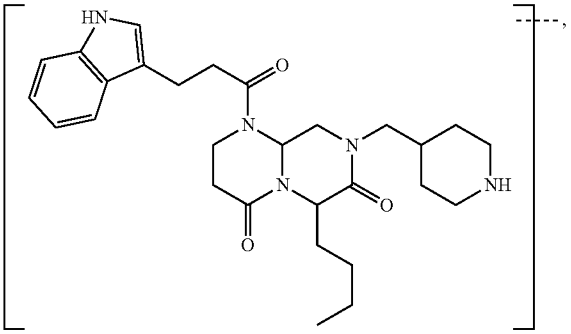
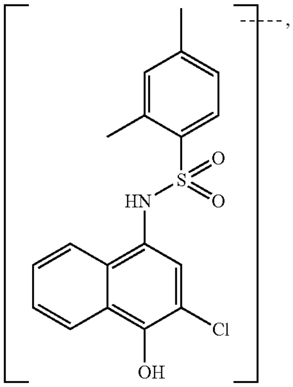
-continued
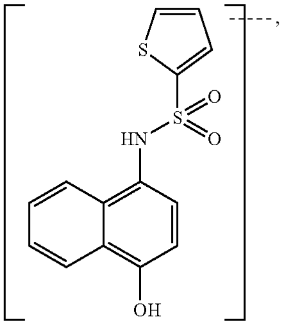
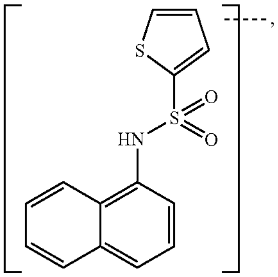
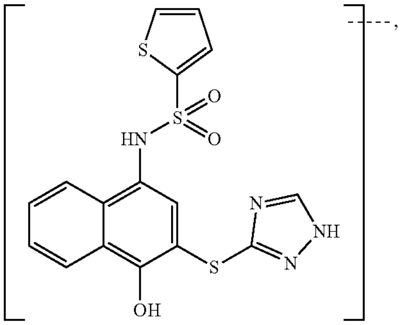
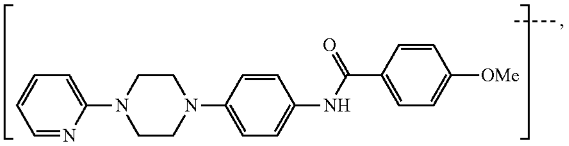
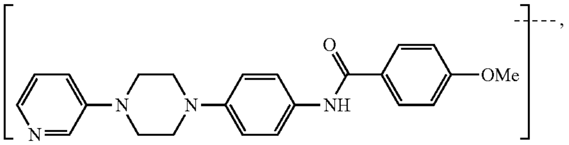
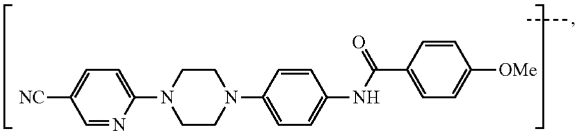
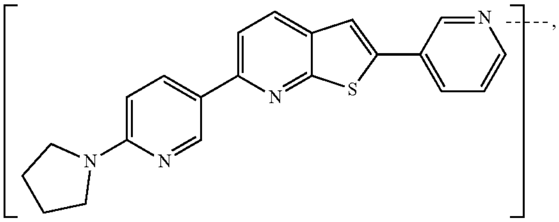

-continued

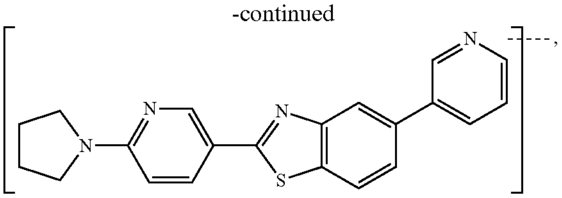

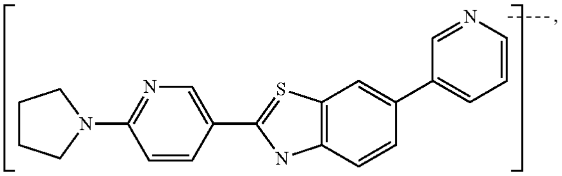

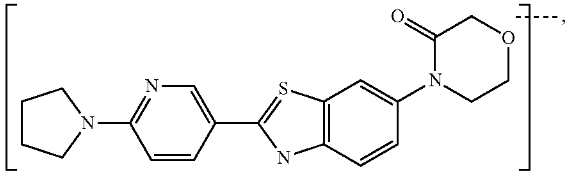

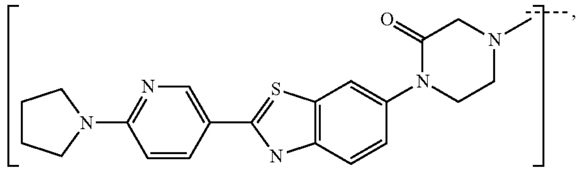

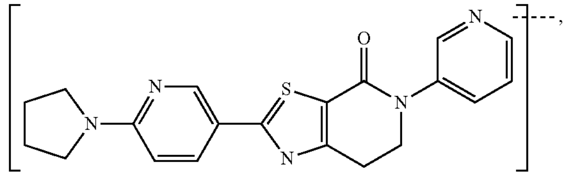

wherein:

A, B, C, D, and E are independently selected from an optionally substituted 5- or 6-membered aryl or an optionally substituted 5- or 6-membered heteroaryl, and the optional substitutions are 1, 2, 3, or 4 substituents independently selected from H, $C_1$-$C_6$ alkyl, O, N, halogen, $C_1$-$C_6$ haloalkyl, $C_1$-$C_6$ alkoxy, hydroxy, carbonyl, amino, alkylamino, dialkylamino, cyano, nitro, and —$SO_2$— or an optionally substituted 4- to 7-membered cycloalkyl or heterocycloalkyl, and the optional substitutions are 1, 2, 3, or 4 substituents independently selected from H, alkyl, O, N, halogen, $C_1$-$C_6$ haloalkyl, alkoxy, hydroxy, carbonyl, amino, alkylamino, dialkylamino, cyano, nitro, and —$SO_2$—, wherein contact between circles indicates ring fusion;

$M_1$, $M_2$, and $M_3$ are independently selected from a single bond; O—; —S—; —$NR^{100}$—; —$SO_2$—; —S(O)—; —$SO_2$NH—; —C(O)—; —C(O) NH—; and an optionally substituted $C_1$-$C_6$ alkyl or $C_1$-$C_6$ haloalkyl, wherein a carbon of the alkyl group may be replaced with a group independently selected from —O—, —S—, —$NR^{100}$—, —$SO_2$—, —S(O)—, —$SO_2$NH—, —C(O)— or —C(O)NH—, and the optional substitutions are selected from halogen, amino, alkyl or a haloalkyl, and a two to four carbon conjugated alkenyl fragment; an alkynyl fragment; and a two to four carbon conjugated alkenyl or alkynyl fragment, wherein at least one of the carbon of the alkenyl or alkynyl group may be part of A, B, C, or D;

each $R^{100}$ is independently selected from H, $C_1$-$C_6$ alkyl, and an optionally substituted $C_1$-$C_6$ haloalkyl;

- - - indicates the attachment of a chemical linker moiety (L); and (c) L is a chemical linker moiety comprising an optionally substituted $C_1$-$C_{50}$ alkyl, wherein:

each carbon is optionally substituted with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}$C(=NCN) $NR^{L4}$, $NR^{L3}$C(=NCN), $NR^{L3}C(=CNO_2)NR^{L4}$, $C_{3-11}$ cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heteocyclyl optionally substituted with 0-6 $R^{L1}$ and/or $R^{L2}$ groups, $C_{5-13}$ spiroheterocyclyl optionally substituted with 0-8 $R^{L1}$ and/or $R^{L2}$ groups, aryl optionally substituted with 0-6 $R^{L1}$ and/or $R^{L2}$ groups, and heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently selected from H, halo, $C_1$-$C_8$ alkyl, O $C_1$-$C_8$ alkyl, S $C_1$-$C_8$ alkyl, NH $C_1$-$C_8$ alkyl, N($C_1$-$C_8$ alkyl)$_2$, $C_3$-$C_{11}$ cycloalkyl, aryl, heteroaryl, $C_3$-$C_{11}$ heterocyclyl, O$C_3$-$C_8$ cycloalkyl, S$C_3$-$C_8$ cycloalkyl, NH$C_3$-$C_8$ cycloalkyl, N($C_3$-$C_8$ cycloalkyl)$_2$, N($C_3$-$C_8$ cycloalkyl) ($C_1$-$C_8$ alkyl), OH, $NH_2$, SH, $SO_2C_1$-$C_8$alkyl, P(O)(O$C_1$-$C_8$ alkyl) ($C_1$-$C_8$ alkyl), P(O)(O$C_1$-$C_8$ alkyl)$_2$, CC≡$C_1$-$C_8$ alkyl, CCH, CH=CH($C_1$-$C_8$ alkyl), C($C_1$-$C_8$ alkyl)=CH($C_1$-$C_8$ alkyl), C($C_1$-$C_8$ alkyl)=C($C_1$-$C_8$ alkyl)$_2$, $Si(OH)_3$, Si($C_1$-$C_8$ alkyl)$_3$, Si(OH)($C_1$-$C_8$ alkyl)$_2$, CO$C_1$-$C_8$ alkyl, $CO_2H$, halogen, CN, $CF_3$, $CHF_2$, $CH_2F$, $NO_2$, $SF_5$, $SO_2NHC_1$-$C_8$alkyl, $SO_2N$($C_1$-$C_8$ alkyl)$_2$, SONH$C_1$-$C_8$ alkyl, SON($C_1$-$C_8$ alkyl)$_2$, CONH$C_1$-$C_8$ alkyl, CON($C_1$-$C_8$ alkyl)$_2$, N($C_1$-$C_8$ alkyl)CONH($C_1$-$C_8$ alkyl), N($C_1$-$C_8$ alkyl)CON($C_1$-$C_8$ alkyl)$_2$, NHCONH($C_1$-$C_8$ alkyl), NHCON($C_1$-$C_8$ alkyl)$_2$, $NHCONH_2$, N($C_1$-$C_8$ alkyl)$SO_2$NH($C_1$-$C_8$ alkyl), N($C_1$-$C_8$alkyl) $SO_2$N($C_1$-$C_8$ alkyl)$_2$, $NHSO_2NH$ ($C_1$-$C_8$ alkyl), $NHSO_2N$($C_1$-$C_8$ alkyl)$_2$, and $NHSO_2NH_2$.

2. The compound according to claim 1, wherein the ULM is:

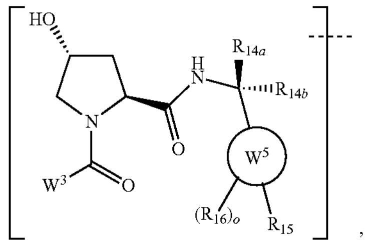

wherein:

$W^3$ is selected from an optionally substituted aryl, optionally substituted heteroaryl, and

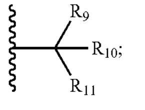

$R_9$ and $R_{10}$ are independently selected from hydrogen, optionally substituted alkyl, optionally substituted cycloalkyl, optionally substituted hydroxyalkyl, optionally substituted heteroaryl, and haloalkyl; or $R_9$, $R_{10}$, and the carbon atom to which they are attached form an optionally substituted cycloalkyl;

$R_{11}$ is selected from an optionally substituted heterocyclic, optionally substituted alkoxy, optionally substituted heteroaryl, optionally substituted aryl,

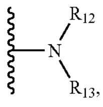
,
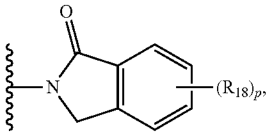

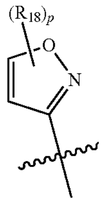
, and
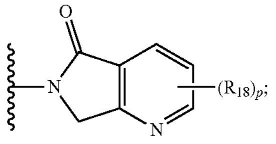

$R_{12}$ is H or optionally substituted alkyl;

$R_{13}$ is selected from H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl) carbonyl, and optionally substituted aralkyl;

$R_{14a}$ $R^{14b}$ are each independently selected from H, haloalkyl, and optionally substituted alkyl;

$W^5$ is selected from an optionally substituted phenyl or an optionally substituted 5-10 membered heteroaryl;

$R_{15}$ is selected from H, halogen, CN, OH, $NO_2$, N $R^{14a}R_{14b}$, $OR_{14a}$, $CONR_{14a}R^{14b}$, $NR^{14a}COR_{14b}$, $SO_2NR^{14a}R_{14b}$, $NR^{14a}$ $SO_2R^{14b}$, optionally substituted alkyl, optionally substituted haloalkyl, optionally substituted haloalkoxy, optionally substituted aryl, optionally substituted heteroaryl, optionally substituted cycloalkyl, and optionally substituted cyclo-heteroalkyl;

each $R_{16}$ is independently selected from H, CN, halo, optionally substituted alkyl, optionally substituted haloalkyl, hydroxy, and optionally substituted haloalkoxy;

o is 0, 1, 2, 3, or 4;

$R_{18}$ is independently selected from H, halo, optionally substituted alkoxy, cyano, optionally substituted alkyl, haloalkyl, and haloalkoxy; and p is 0, 1, 2, 3, or 4; and

 is the site of attachment of the chemical linker moiety (L).

3. The compound of claim 1, wherein the ULM is selected from:

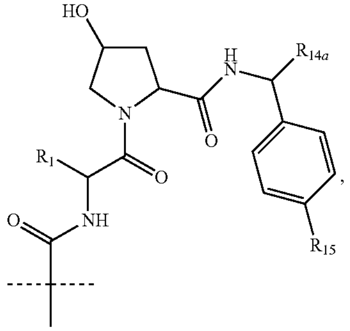
,
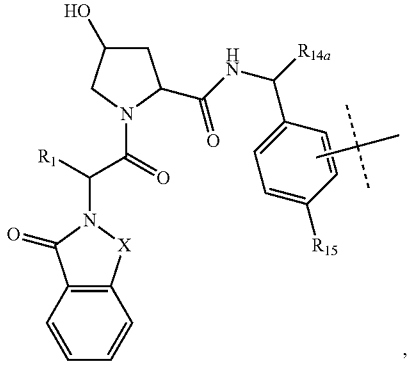
, and
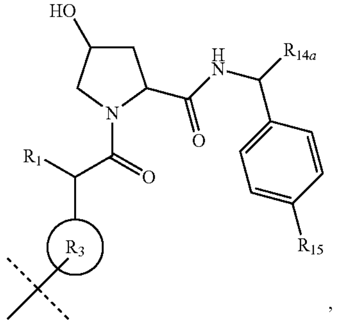
, wherein:

$R_1$ is selected from H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, and haloalkyl;

$R^{14a}$ is selected from H, haloalkyl, optionally substituted alkyl, methyl, fluoromethyl, hydroxymethyl, ethyl, isopropyl, and cyclopropyl;

$R^{15}$ is selected from H, halogen, CN, OH, $NO_2$, optionally substituted heteroaryl, optionally substituted aryl, optionally substituted alkyl, optionally substituted haloalkyl, optionally substituted haloalkoxy, optionally substituted cycloalkyl, and optionally substituted cycloheteroalkyl;

X is C, $CH_2$, or C═O $R_3$ is absent or an optionally substituted 5 or 6 membered heteroaryl; and wherein  indicates the site of attachment of a chemical linker moiety (L).

4. The compound according to claim 1, wherein the ULM is:

ULM-f

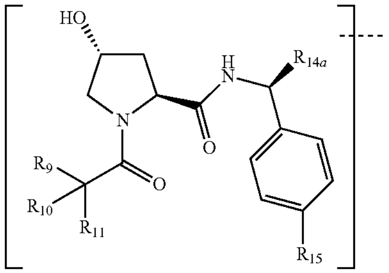

, wherein:

$R_{14a}$ is H, haloalkyl, optionally substituted alkyl, methyl, fluoromethyl, hydroxymethyl, ethyl, isopropyl, and cyclopropyl;

$R_9$ is H;

$R_{10}$ is H, ethyl, isopropyl, tert-butyl, sec-butyl, cyclopropyl, cyclobutyl, cyclopentyl, and cyclohexyl;

$R^{11}$ is

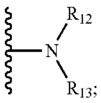 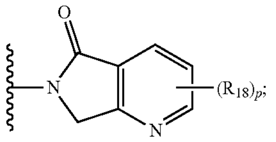

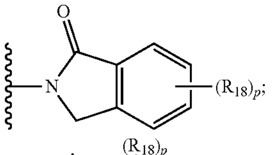 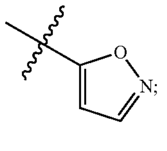

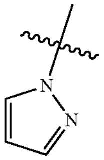 ; 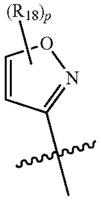 ;

and optionally substituted heteroaryl;

p is 0, 1, 2, 3, or 4;

each $R_{18}$ is independently selected from halo, optionally substituted alkoxy, cyano, optionally substituted alkyl, haloalkyl, and haloalkoxy;

$R_{12}$ is H or C═O;

$R_{13}$ is H, optionally substituted alkyl, optionally substituted alkylcarbonyl, optionally substituted (cycloalkyl) alkylcarbonyl, optionally substituted aralkylcarbonyl, optionally substituted arylcarbonyl, optionally substituted (heterocyclyl) carbonyl, and optionally substituted aralkyl;

$R_{15}$ is selected from H, halogen, Cl, CN, OH, $NO_2$, optionally substituted heteroaryl, an optionally substituted aryl;

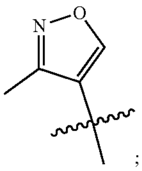 ; 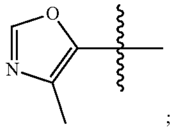 ; 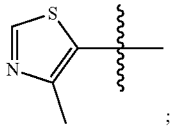 ;

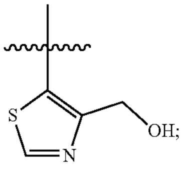 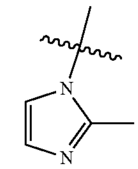 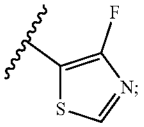

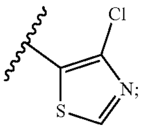 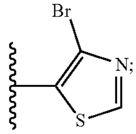 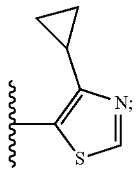

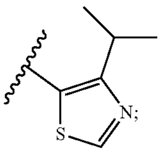 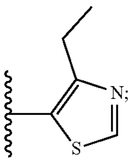 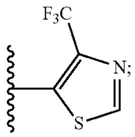

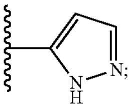 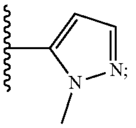 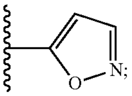

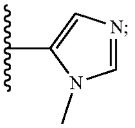 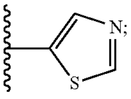 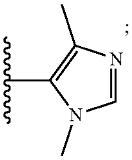

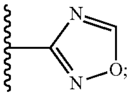

and wherein - - - indicates the site of attachment of the chemical linker moiety (L).

5. The compound according to claim 1, wherein the unit $A^L$ of linker (L) is selected from:

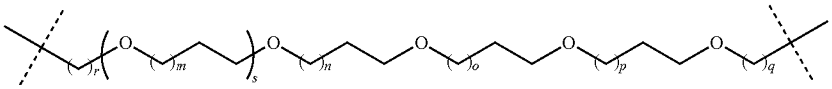

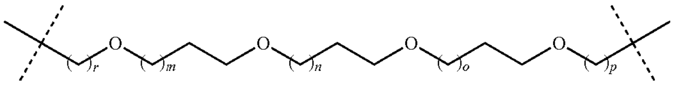

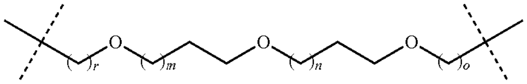 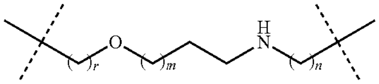

-continued
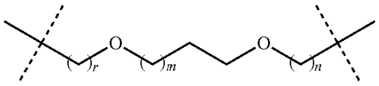
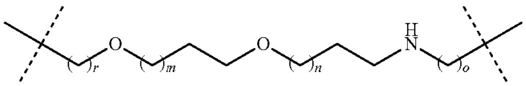
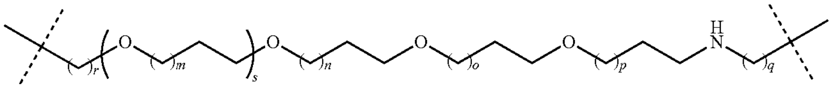
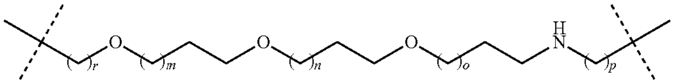
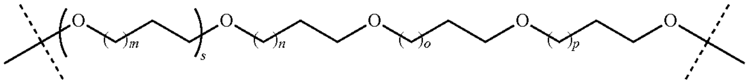
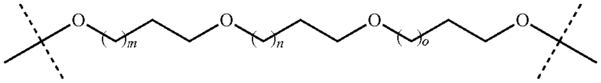
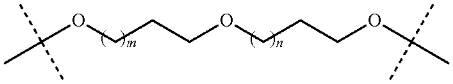
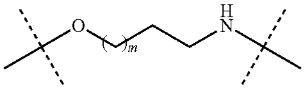
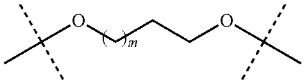
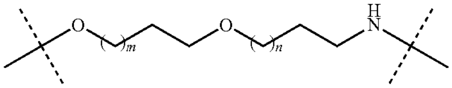
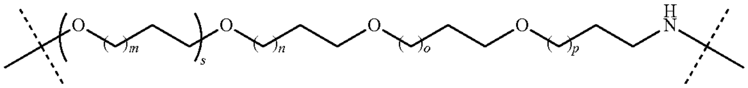
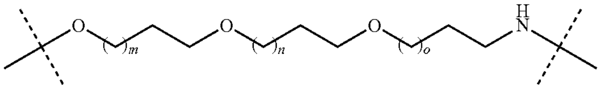
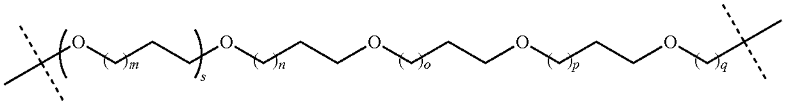
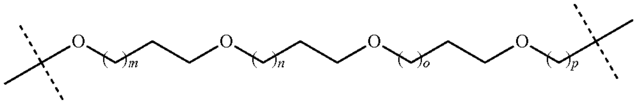
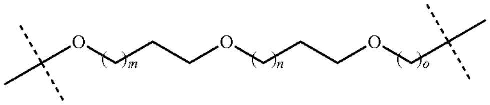
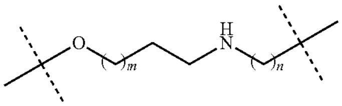
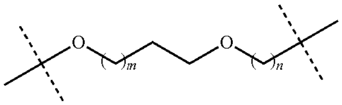
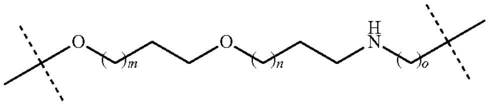
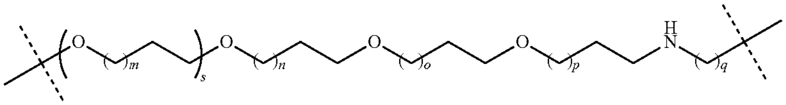
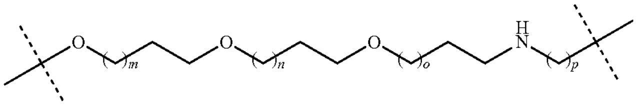
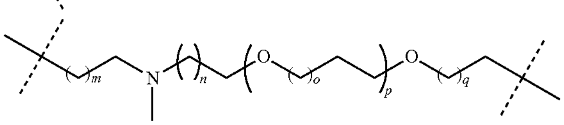
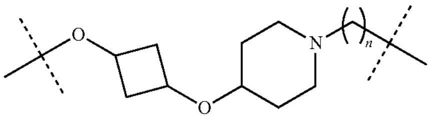
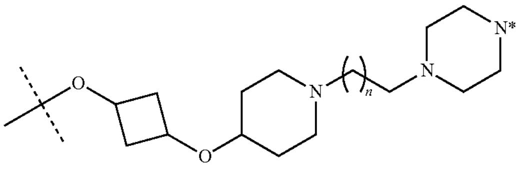

-continued

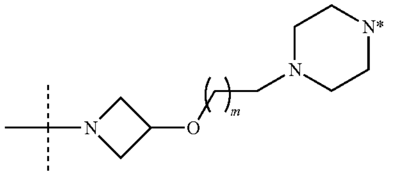
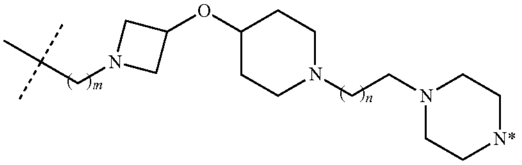
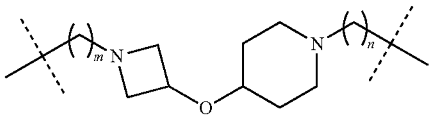
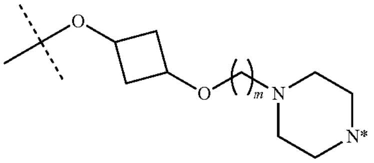
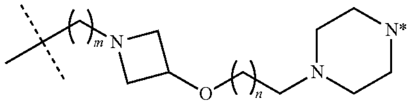
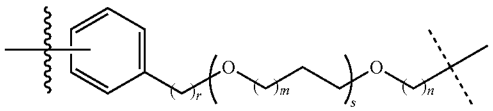
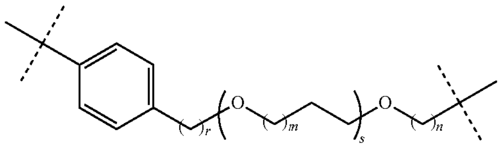
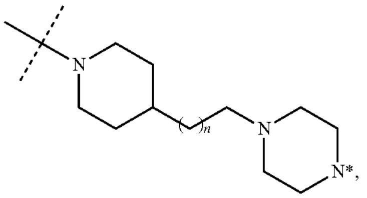

wherein:

each m, n, o, p, q, r, and s are independently selected from 0, 1, 2, 3, 4, 5, 6, 7, 8, 9, 10, 11, 12, 13, 14, 15, 16, 17, 18, 19, and 20; and N* of the heterocycloalkyl is shared with the PTM or the ULM or is linked to the PTM or the ULM via a bond.

6. The compound according to claim 1, wherein the unit $A^L$ of linker (L) is:

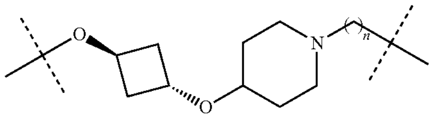
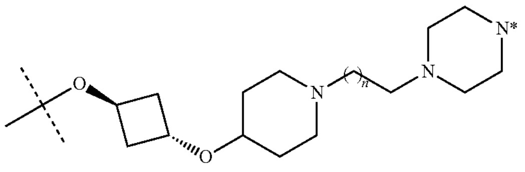

-continued

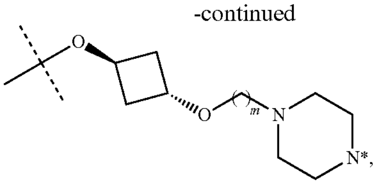

wherein:

each m, n, o, p, q, r, and s are independently selected from 0, 1, 2, 3, 4, 5, 6, 7, 8, 9, 10, 11, 12, 13, 14, 15, 16, 17, 18, 19, and 20; and N* of the heterocycloalkyl is shared with the PTM or the ULM or is linked to the PTM or the ULM via a bond.

7. The compound according to claim 1, wherein the unit $A^L$ of linker (L) is selected from:

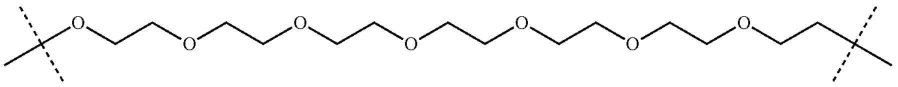
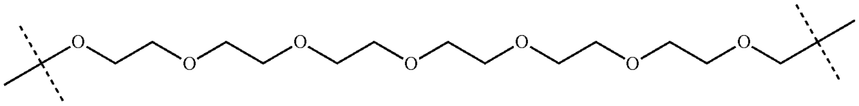
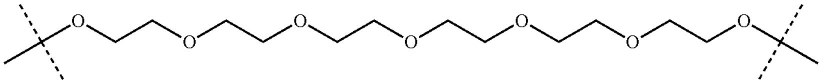
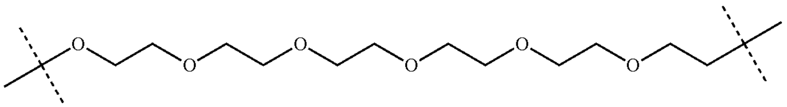

-continued
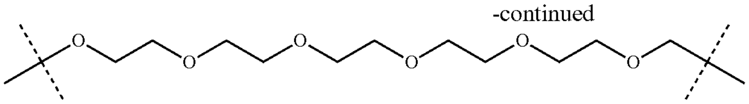
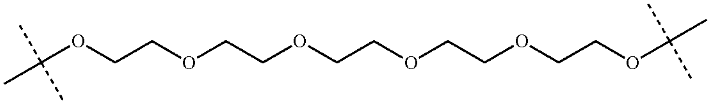
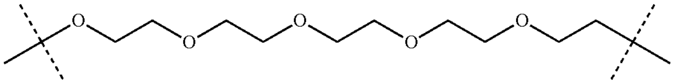
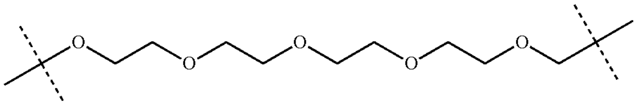
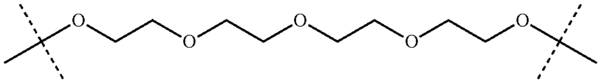
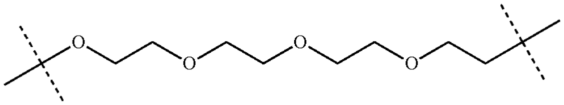
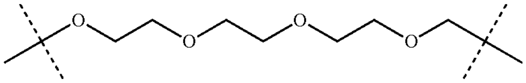
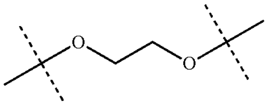
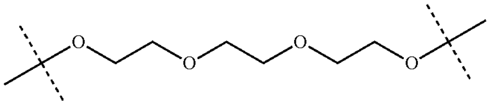
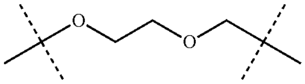
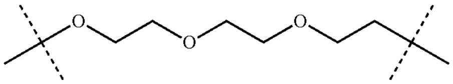
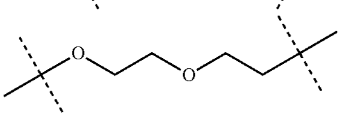
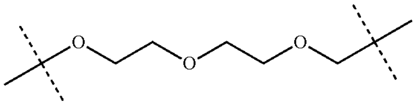
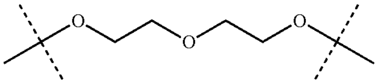
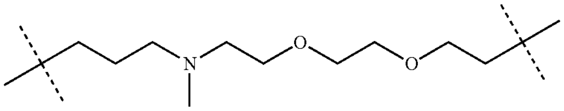
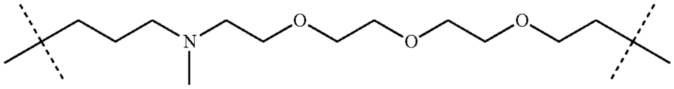
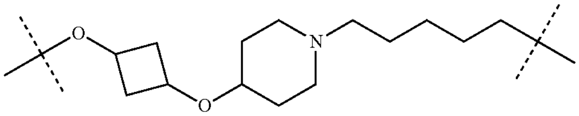
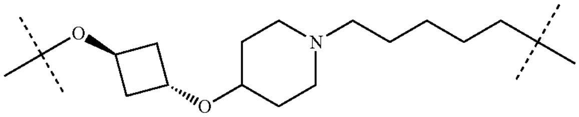
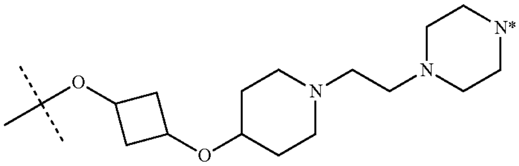
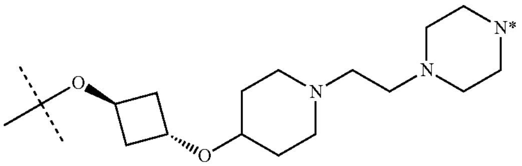
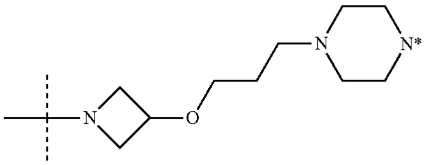
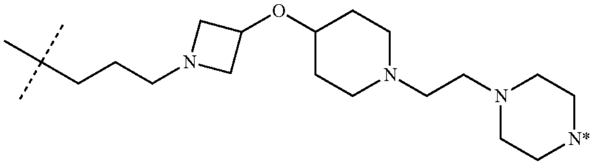

-continued
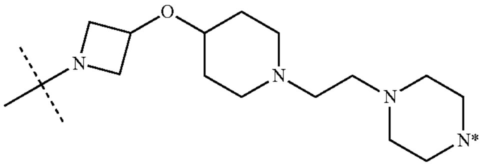
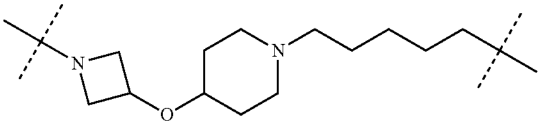
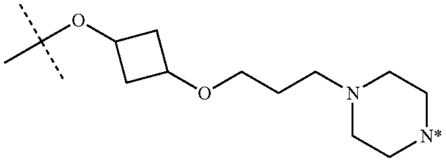
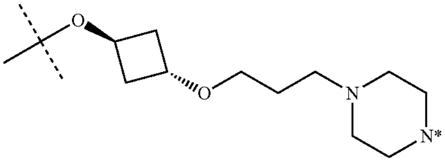
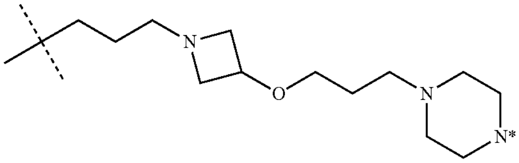
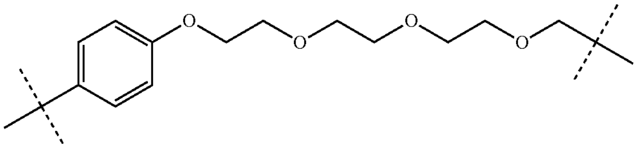
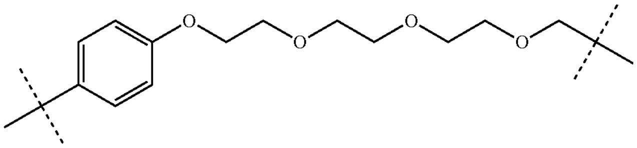
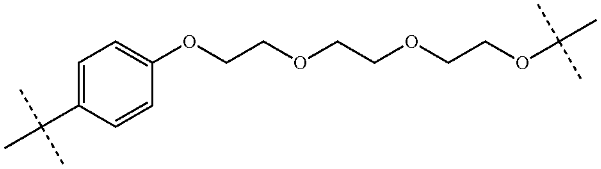
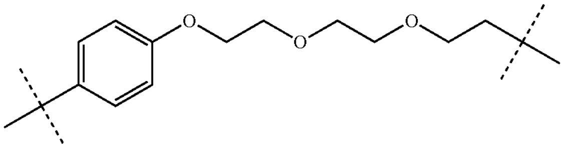
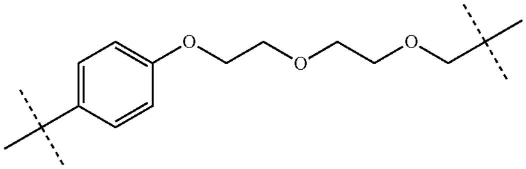
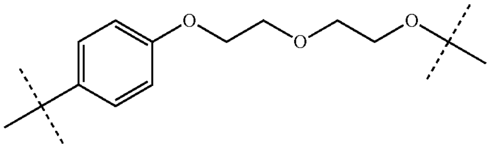
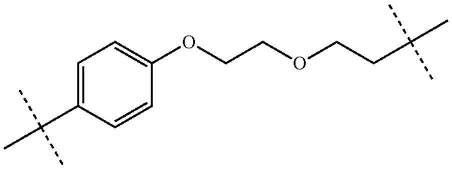
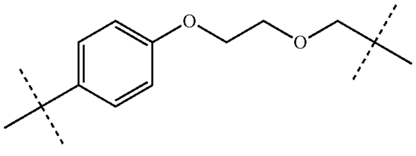
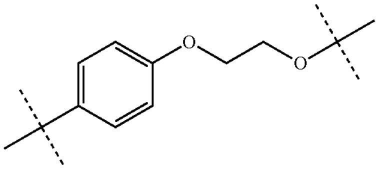
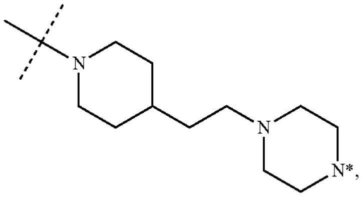
, wherein N* of the hetero-cycloalkyl is shared with the PTM or the ULM or is linked to the PTM or the ULM via a bond.

8. The compound of claim 1, wherein the linker (L) is:

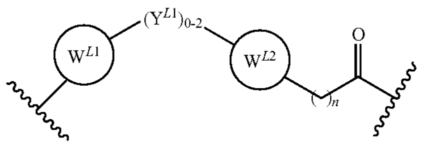

or

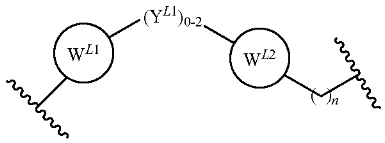

, wherein:

$W^{L1}$ and $W^{L2}$ are each independently absent, a 4-8 membered ring with 0-4 heteroatoms, optionally substituted with RQ, each RQ is independently a H, halo, OH, CN, $CF_3$, optionally substituted linear or branched $C_1$-$C_6$ alkyl, optionally substituted linear or branched $C_1$-$C_6$ alkoxy, or 2 RQ groups taken together with the atom they are attached to, form a 4-8 membered ring system containing 0-4 heteroatoms;

$Y^{L1}$ is each independently a bond, optionally substituted linear or branched $C_1$-$C_6$ alkyl and optionally one or more C atoms are replaced with O; or optionally substituted linear or branched $C_1$-$C_6$ alkoxy;

n is 0, 2, 3, 4, 5, 6, 7, 8, 9, or 10; and

⌄ indicates the attachment point to the PTM or ULM moieties.

9. The compound according to claim 1, wherein the linker (L) is:

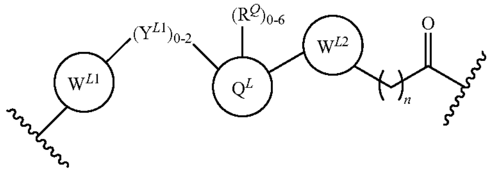

,

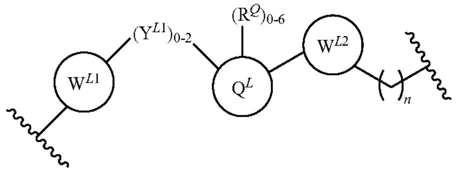

,

-continued

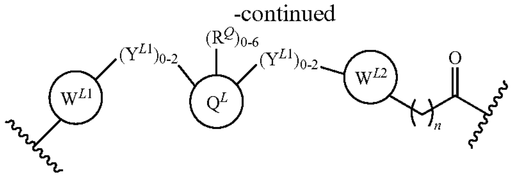

, or

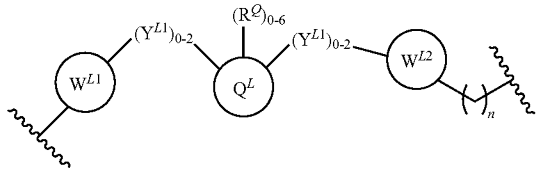

, wherein:

$W^{L1}$ and $W^{L2}$ are each independently selected from absent, aryl, heteroaryl, cyclic, heterocyclic, $C_1$-$C_6$ alkyl and optionally one or more C atoms are replaced with O, $C_1$-$C_6$ alkene and optionally one or more C atoms are replaced with O, $C_1$-$C_6$ alkyne and optionally one or more C atoms are replaced with O, bicyclic, bi-aryl, bi-heteroaryl, or bi-heterocyclic, each optionally substituted with $R^Q$, each $R^Q$ is independently a H, halo, OH, CN, $CF_3$, hydroxyl, nitro, C≡CH, $C_{2-6}$alkenyl, $C_{2-6}$alkynyl, optionally substituted linear or branched $C_1$-$C_6$ alkyl, $C_1$-$C_6$ alkoxy (linear, branched, optionally substituted), optionally substituted linear or branched $OC_{1-3}$alkyl, OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently selected from a bond, $NR^{YL1}$, O, S, $NR^{YL2}$, $CR^{YL1}R^{YL2}$, C═O, C═S, SO, $SO_2$, optionally substituted linear or branched $C_1$-$C_6$ alkyl and optionally one or more C atoms are replaced with O; and optionally substituted linear or branched $C_1$-$C_6$ alkoxy;

$Q^L$ is selected from a 3-6 membered alicyclic or aromatic ring with 0-4 heteroatoms, optionally bridged, optionally substituted with 0-6 $R^Q$, each $R^Q$ is independently H, optionally substituted linear or branched $C_1$-$C_6$ alkyl, or 2 $R^Q$ groups taken together with the atom they are attached to, form a 3-8 membered ring system containing 0-2 heteroatoms;

$R^{YL1}$ and $R^{YL2}$ are each independently selected from H, OH, and optionally substituted linear or branched $C_1$-$C_6$ alkyl, or $R^1$, $R^2$ together with the atom they are attached to, form a 3-8 membered ring system containing 0-2 heteroatoms;

n is 0, 1, 2, 3, 4, 5, 6, 7, 8, 9, or 10; and

⌄ indicates the attachment point to the PTM or the ULM moieties.

10. A compound selected from
(1)
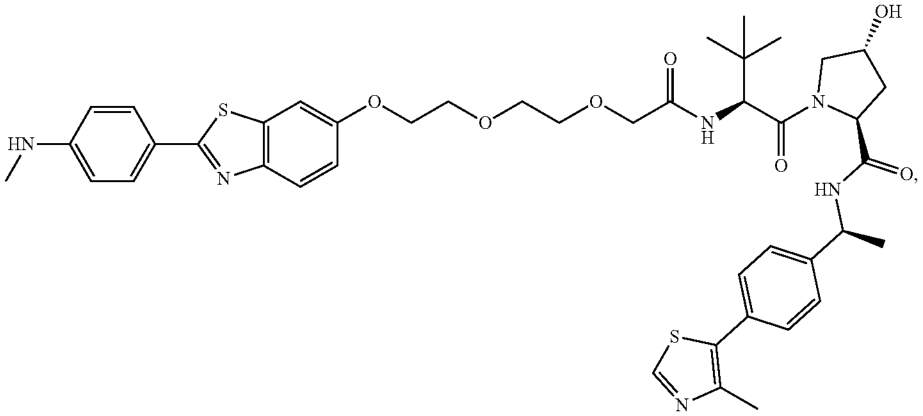
(2)
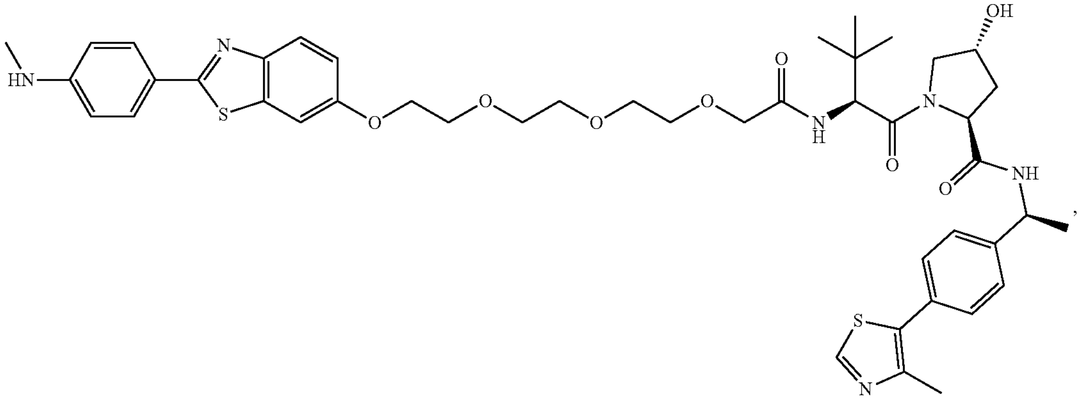
(3)
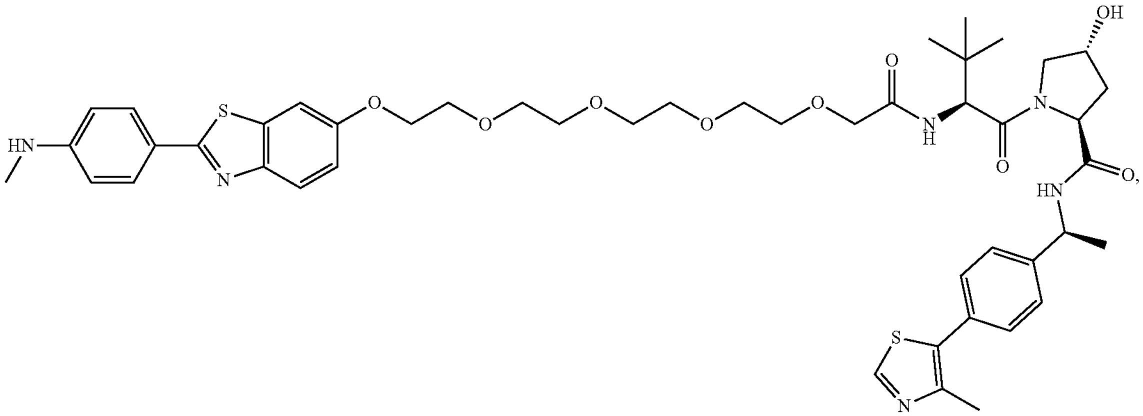

-continued
(4)
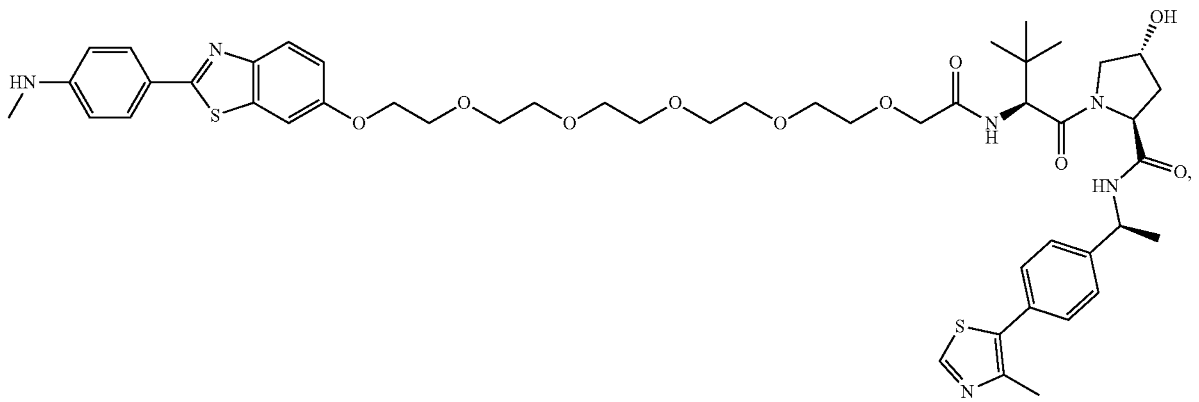
(5)
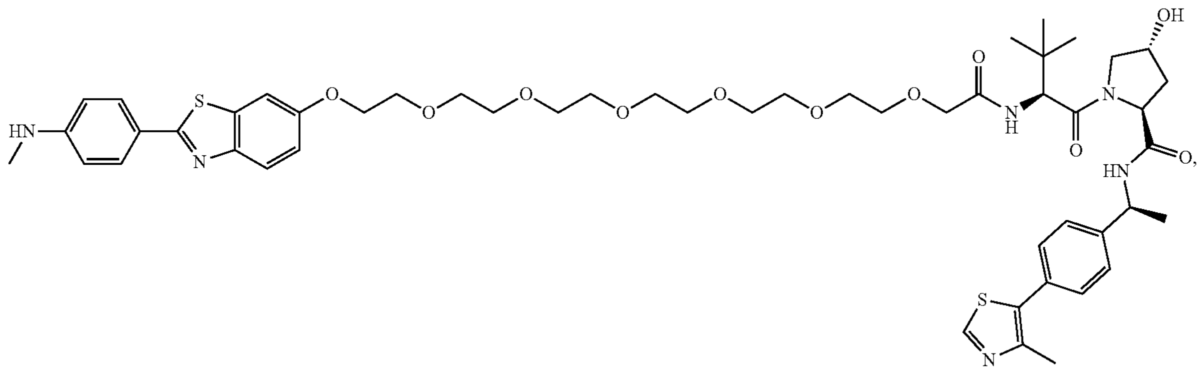
(6)
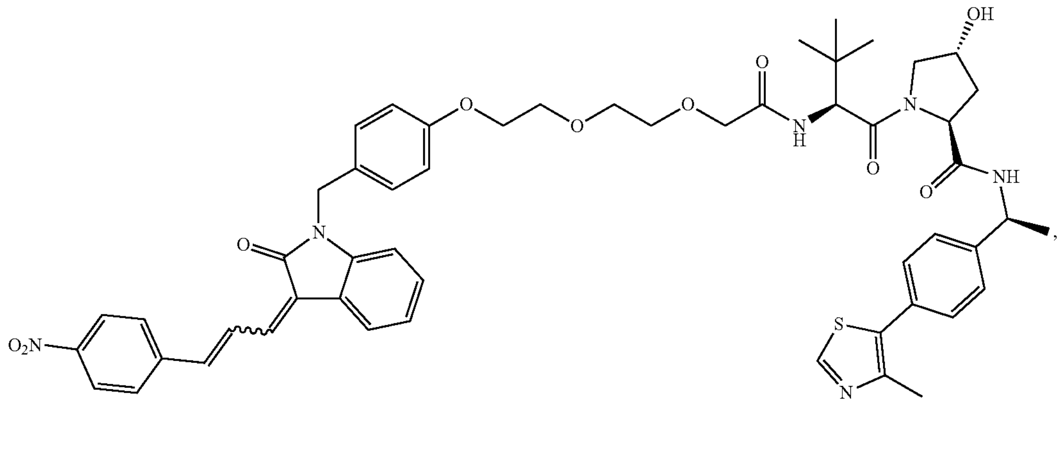

-continued
(7)
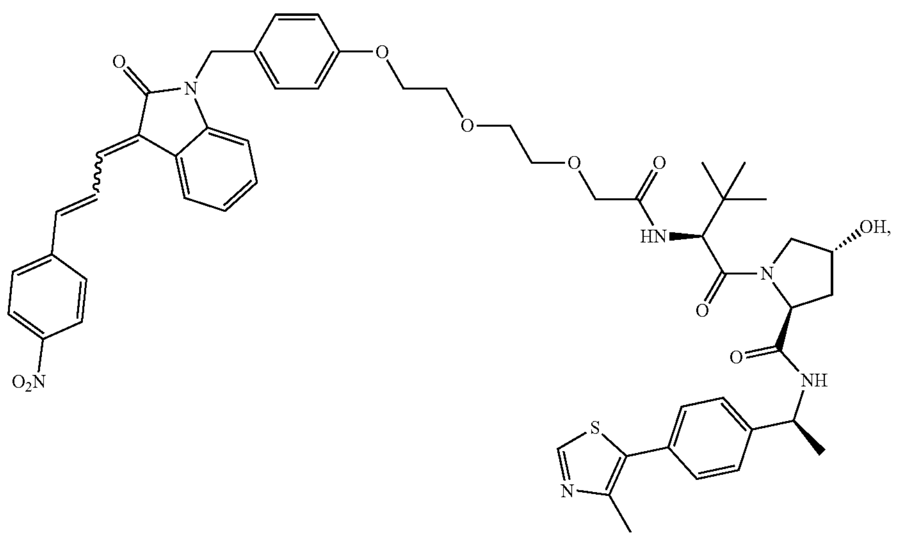
(8)
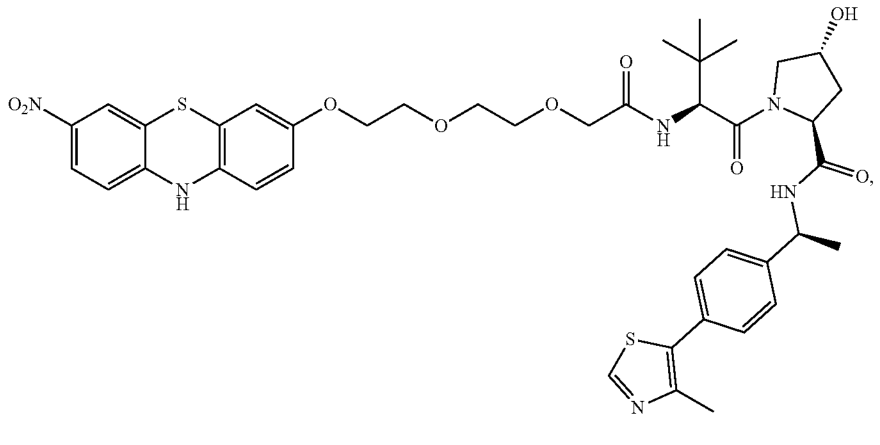
(9)
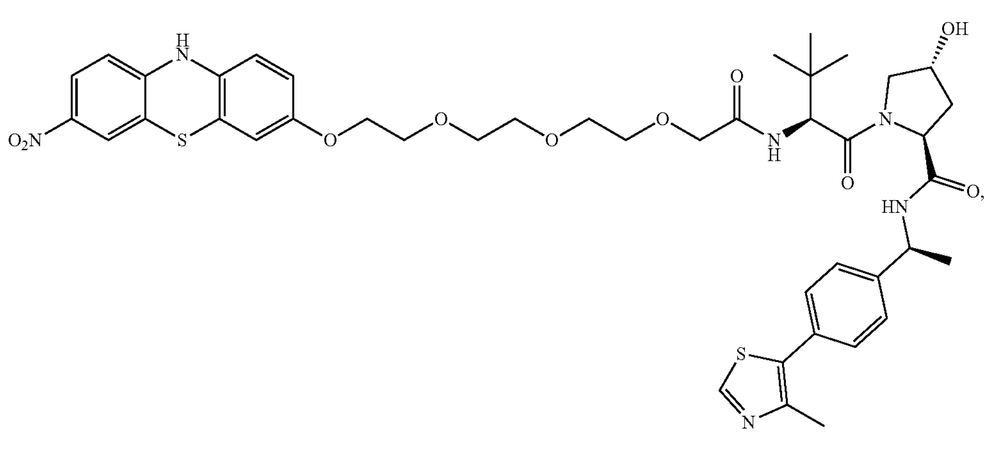

-continued
(10)
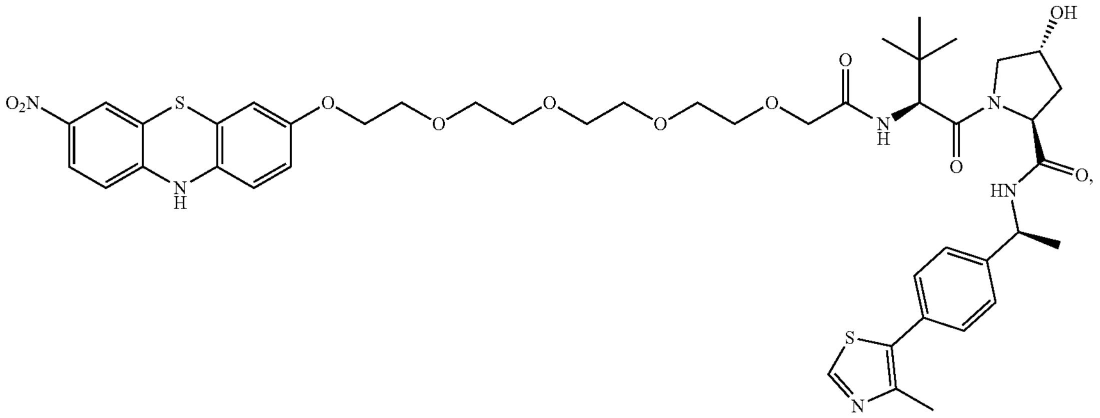
(11)
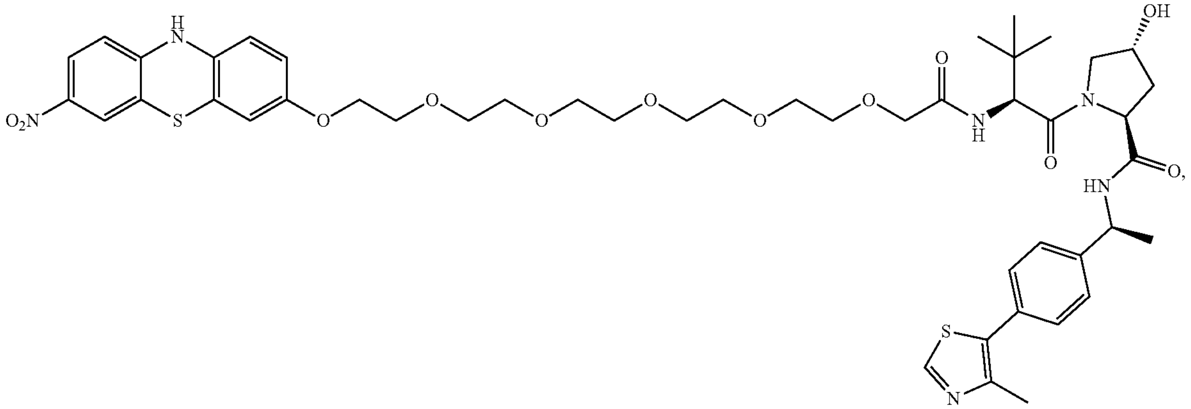
(12)
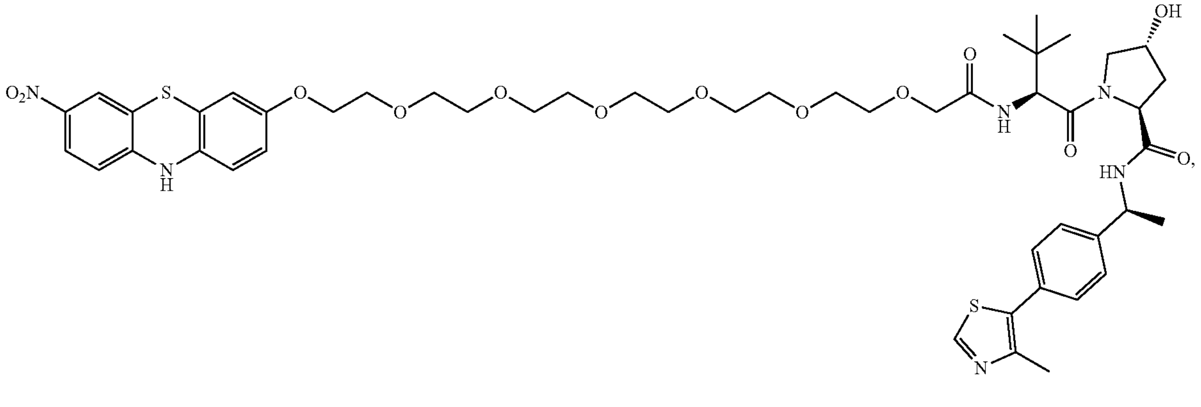

-continued
(33)
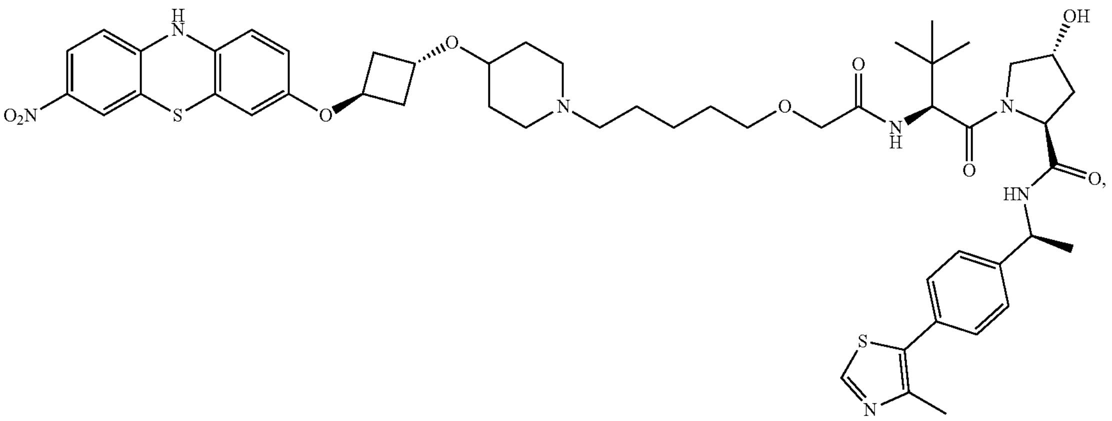
(34)
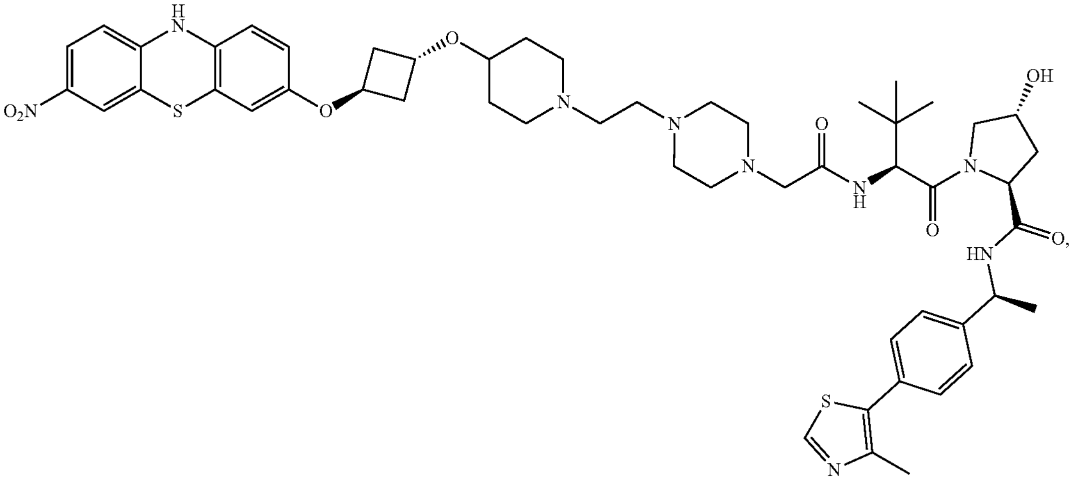
(35)
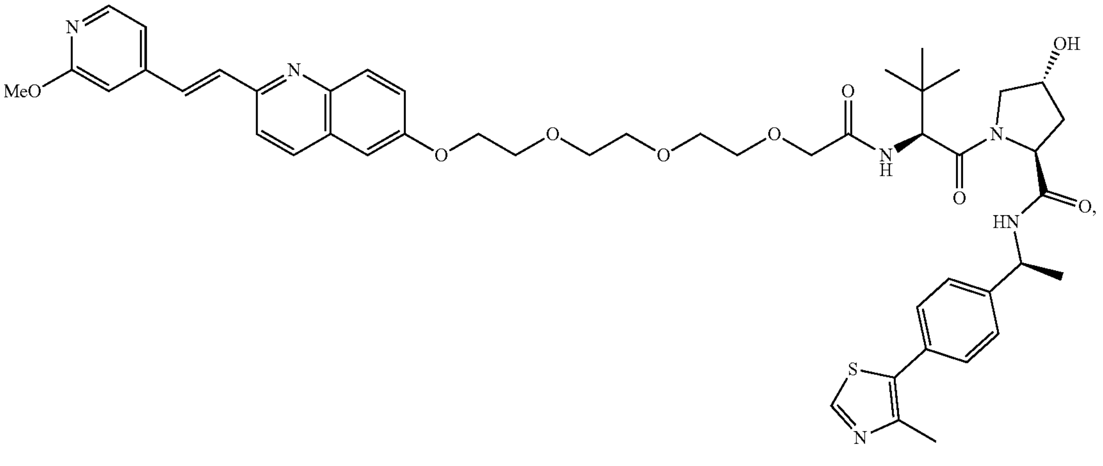

-continued
(41)
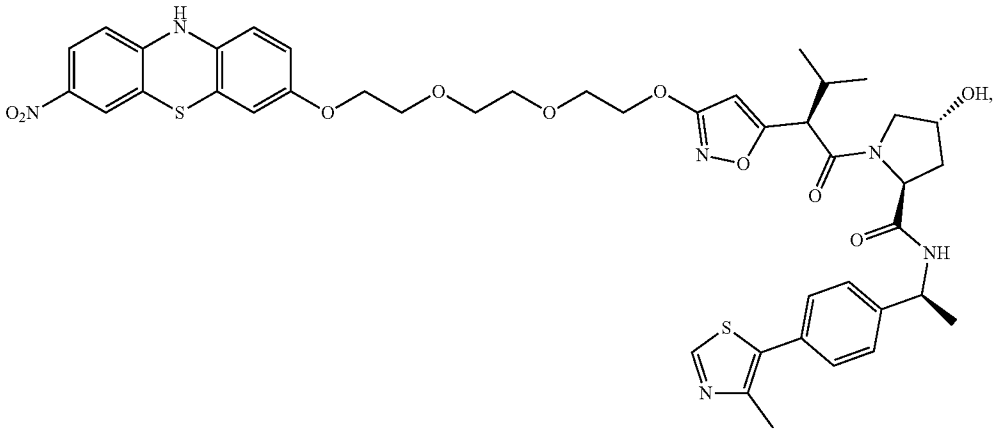
(42)
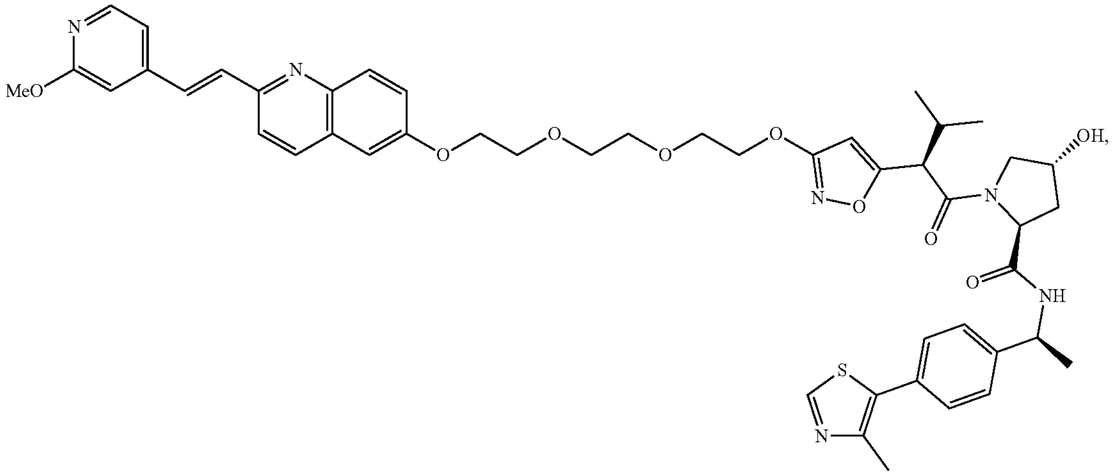
(43)
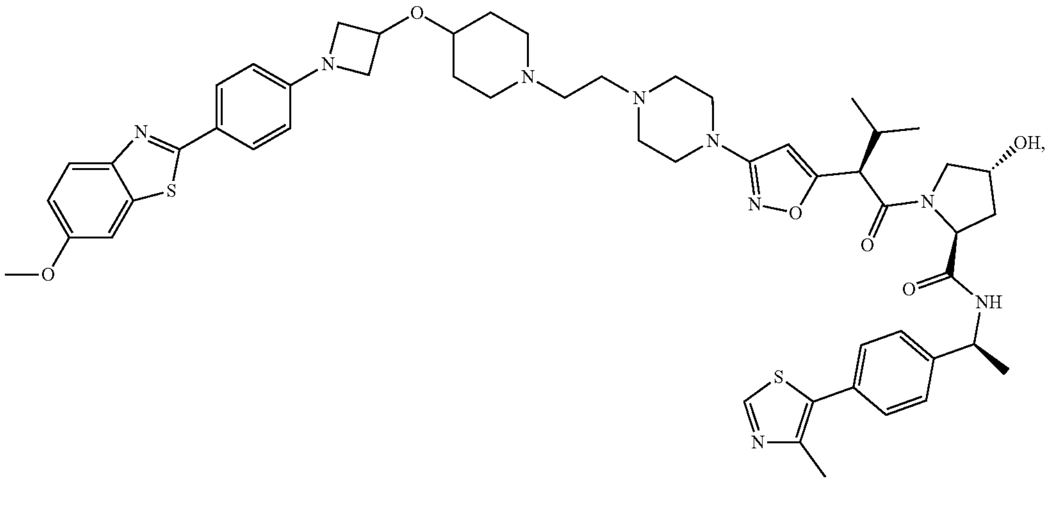

-continued
(44)
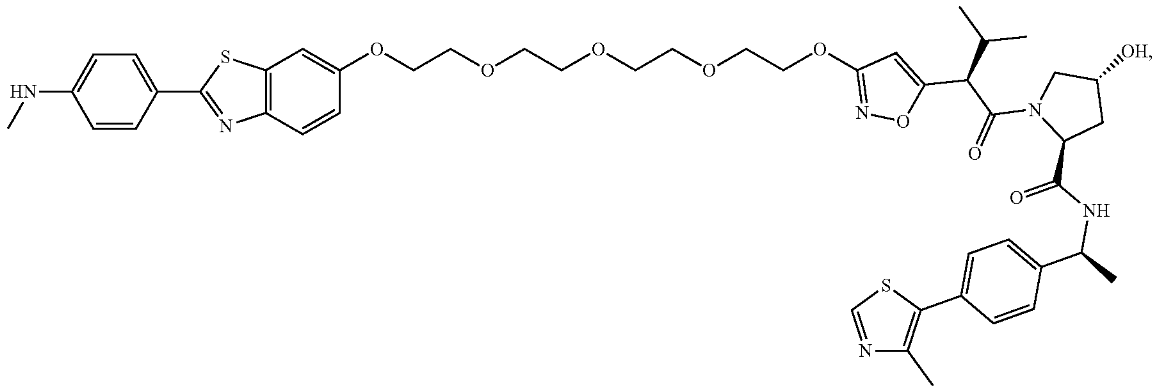
(45)
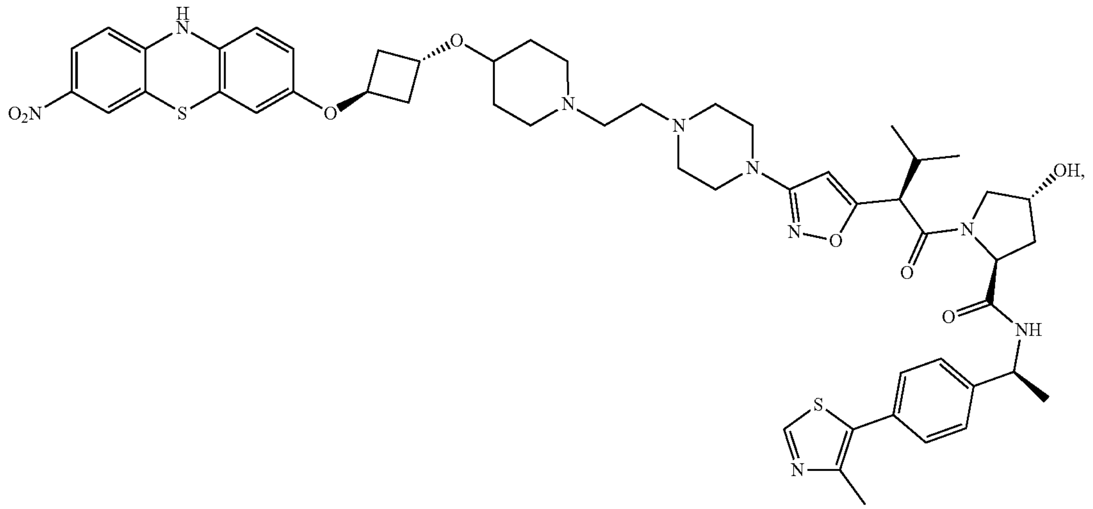
(46)
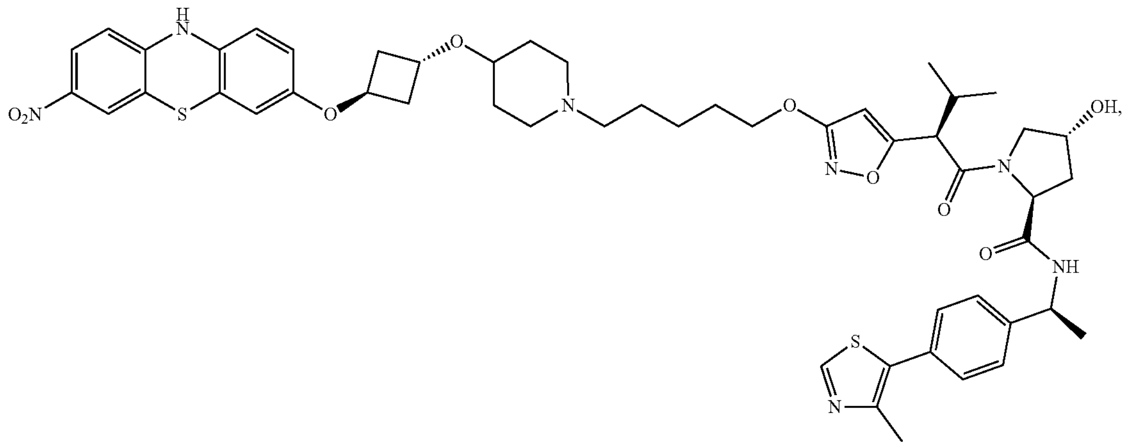

-continued
(48)
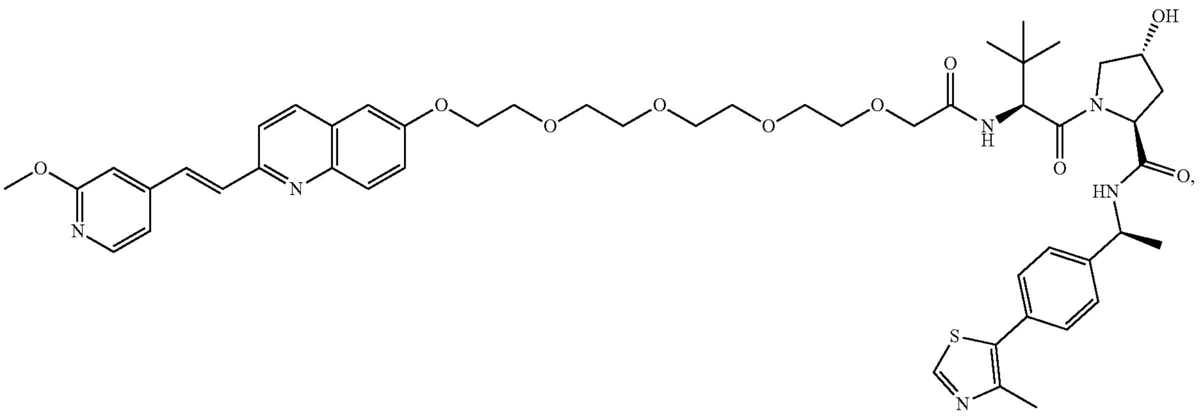
(49)
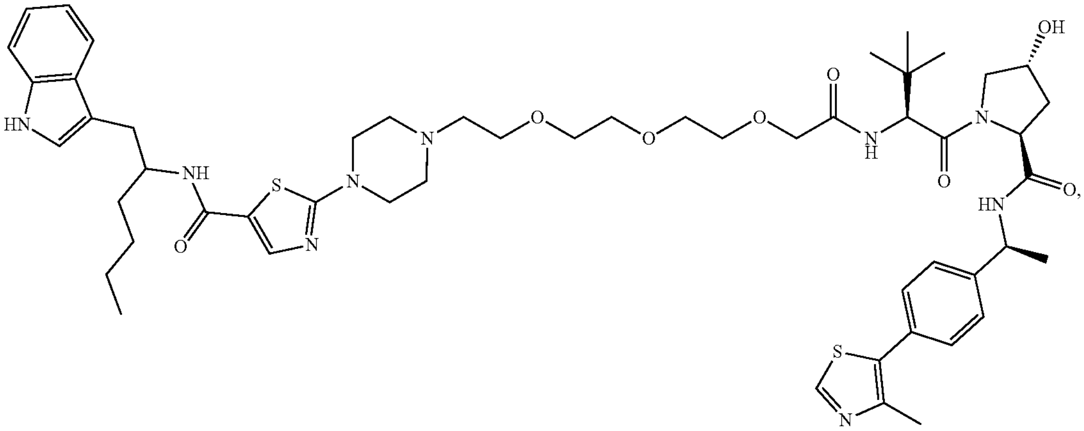
(50)
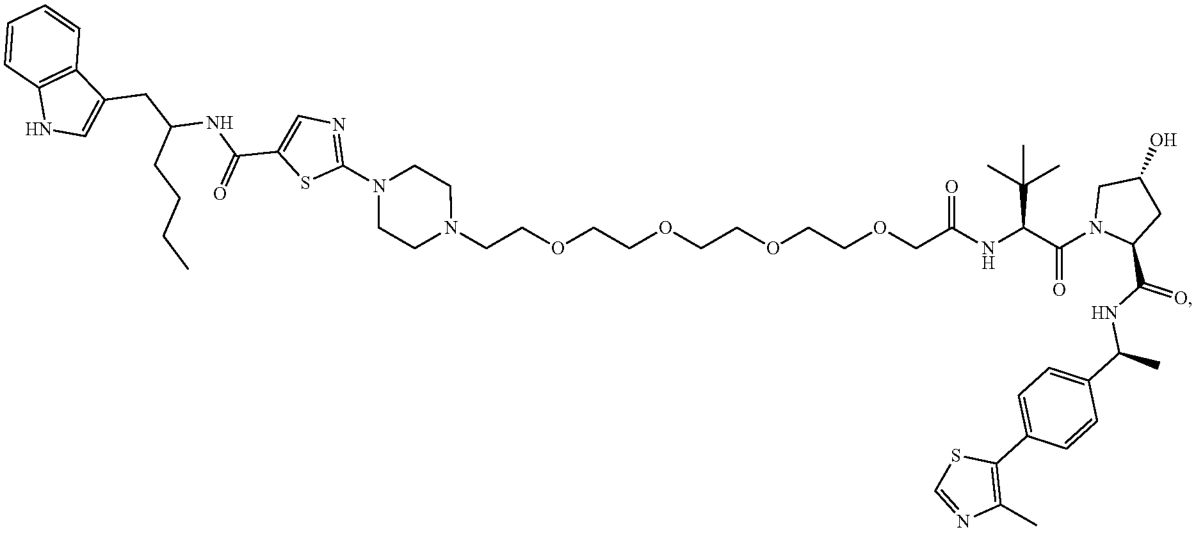

-continued
(51)
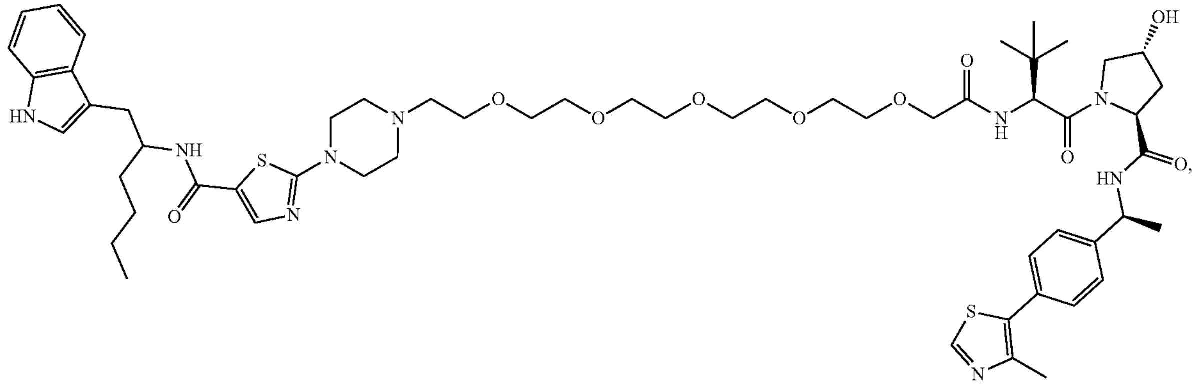
(55)
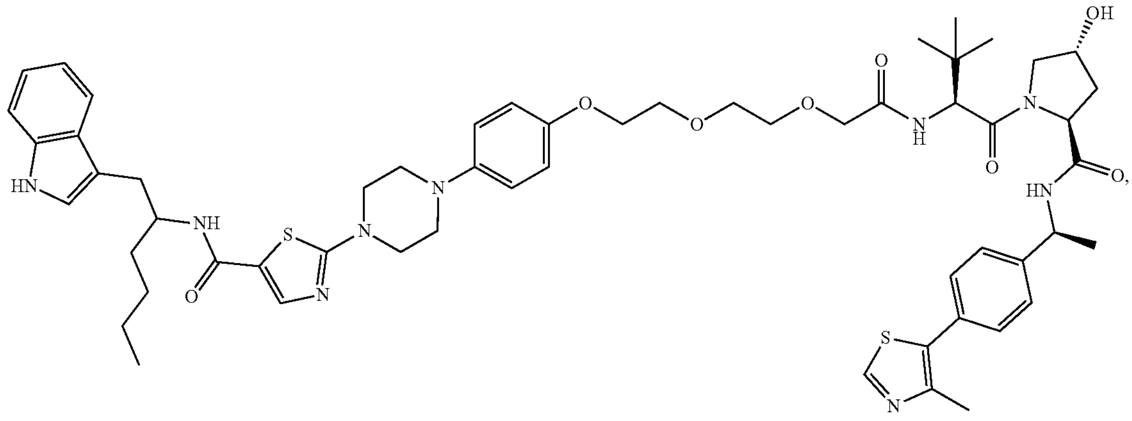
(56)
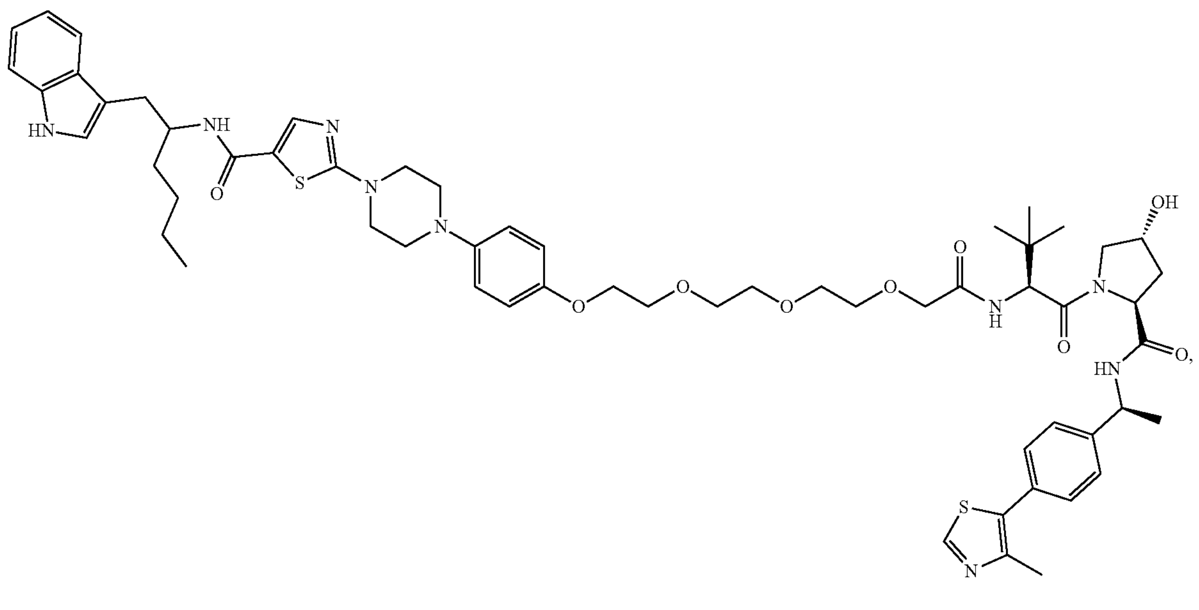

-continued
(65)
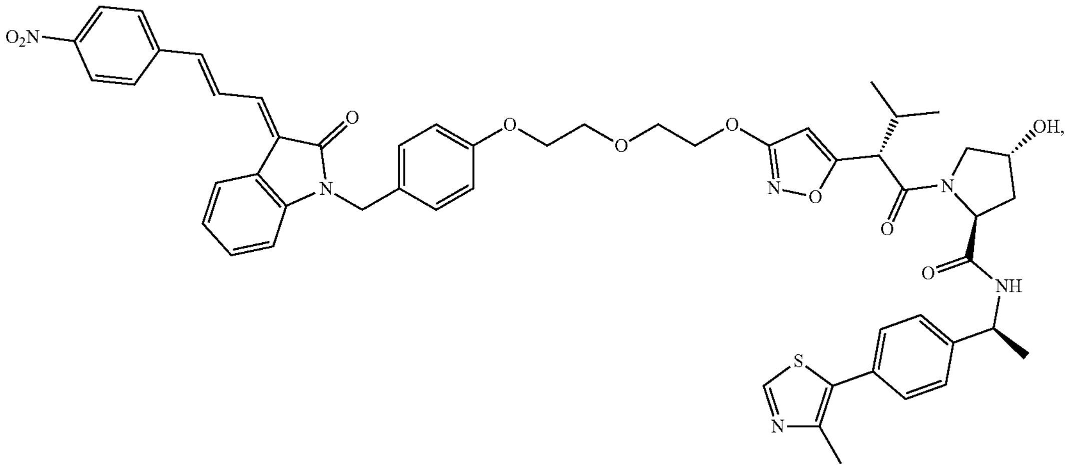
(66)
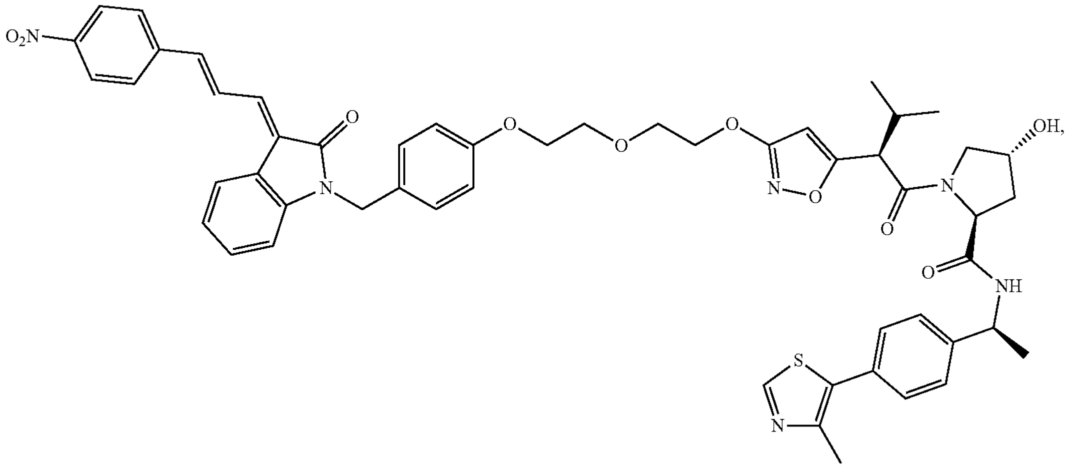
(67)
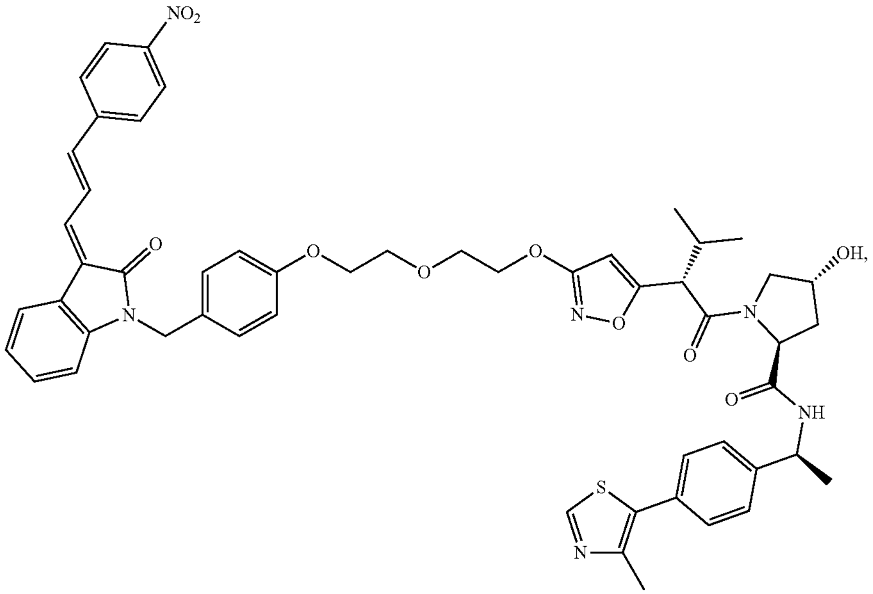

-continued
(68)
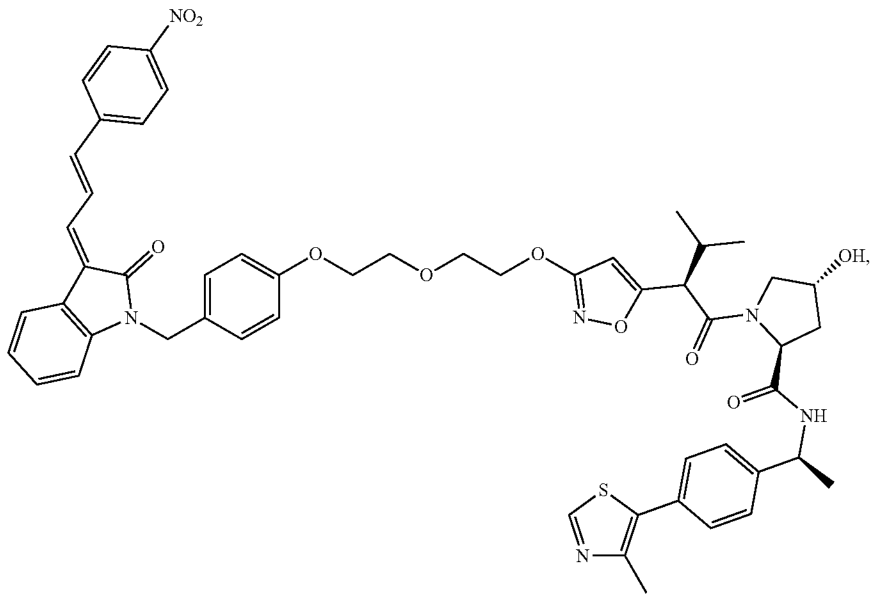
(69)
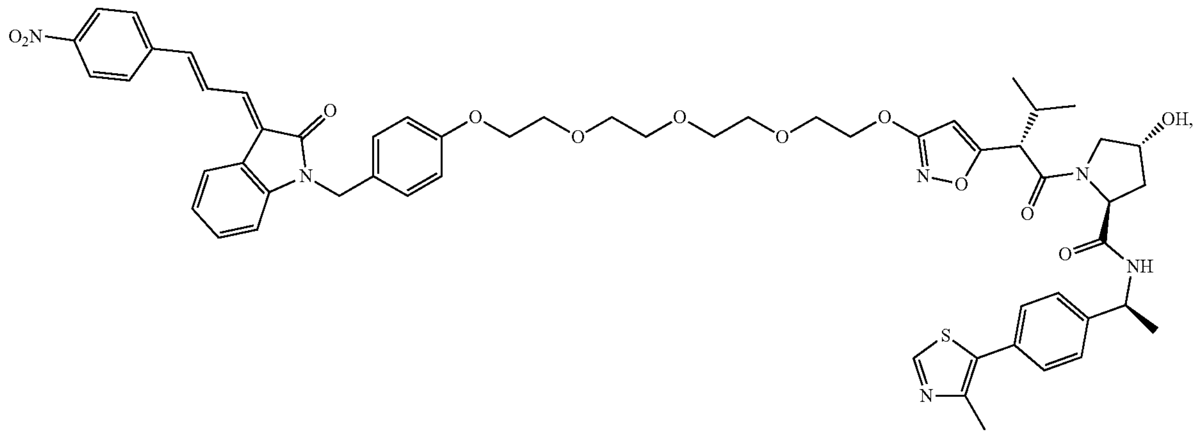
(70)
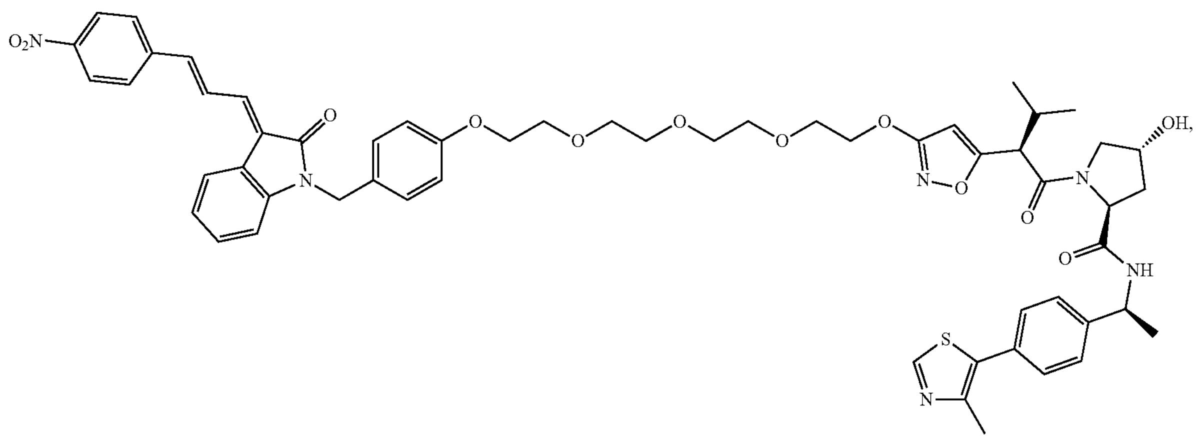

-continued
(71)
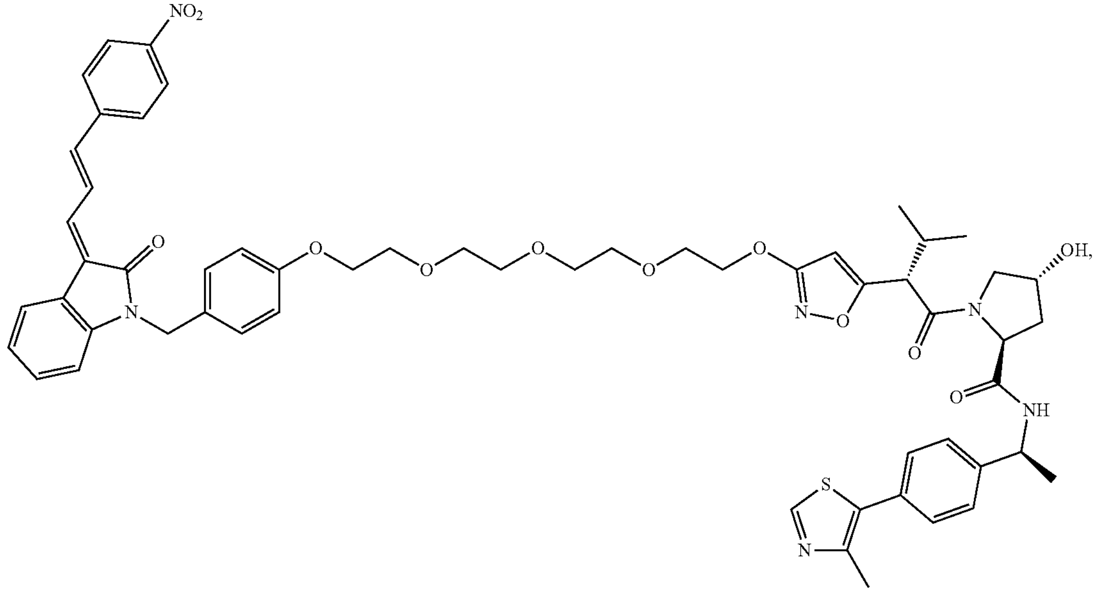
(72)
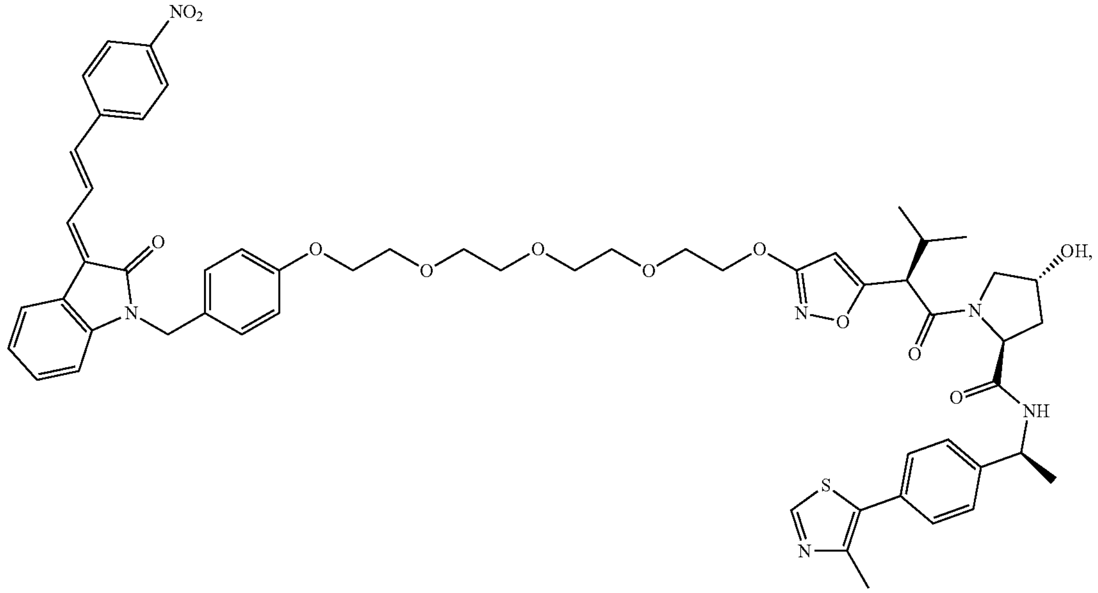

-continued
(73)
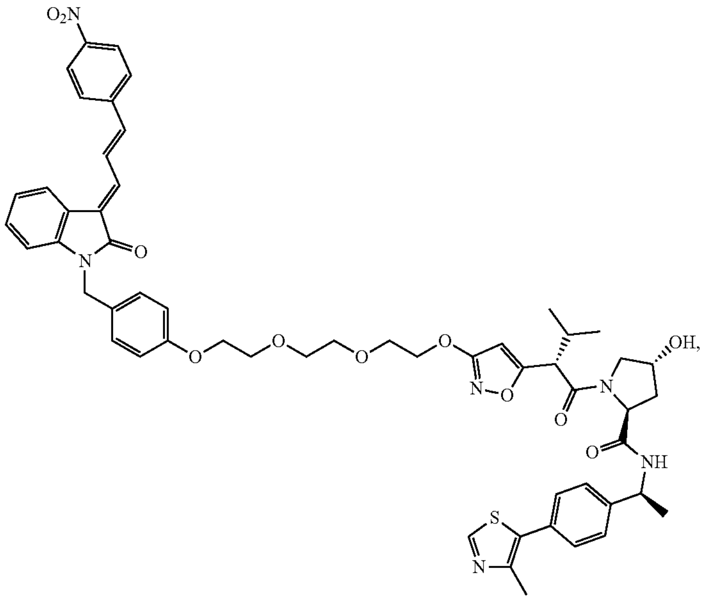
(74)
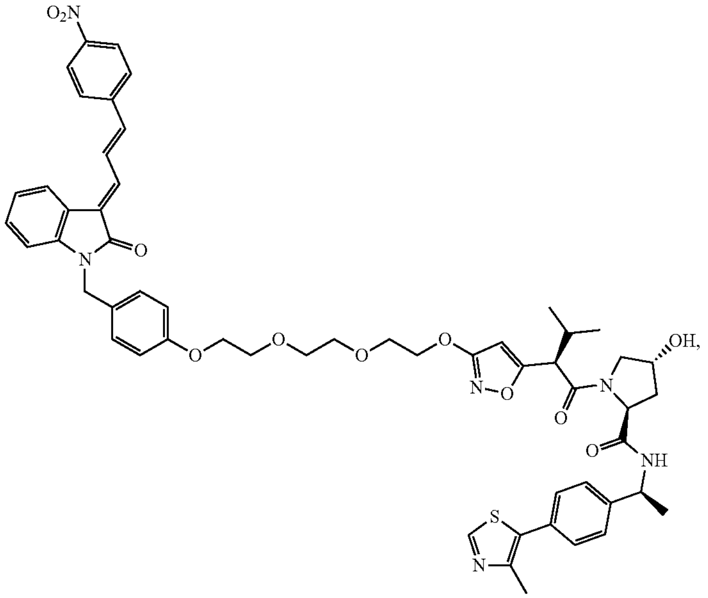

-continued
(75)
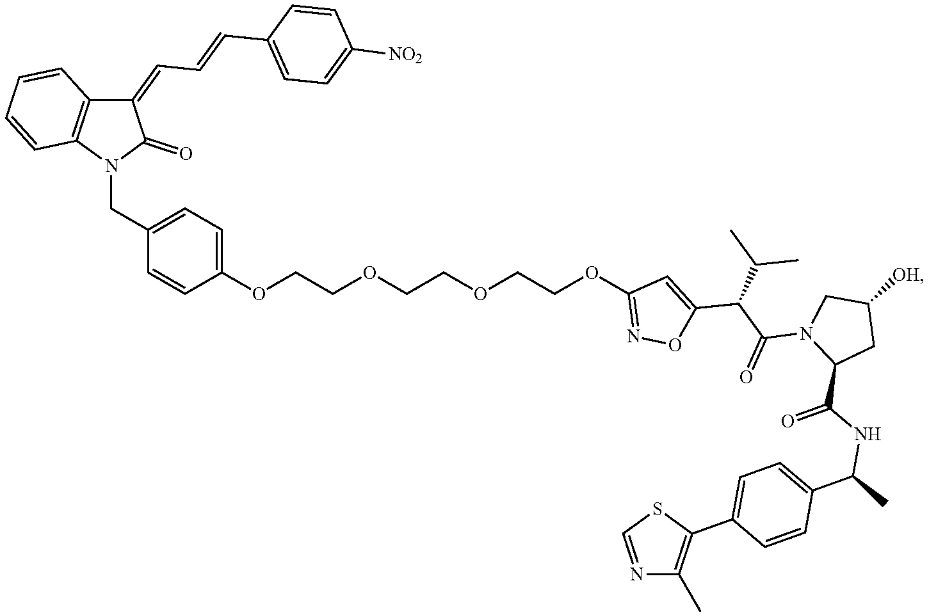
(76)
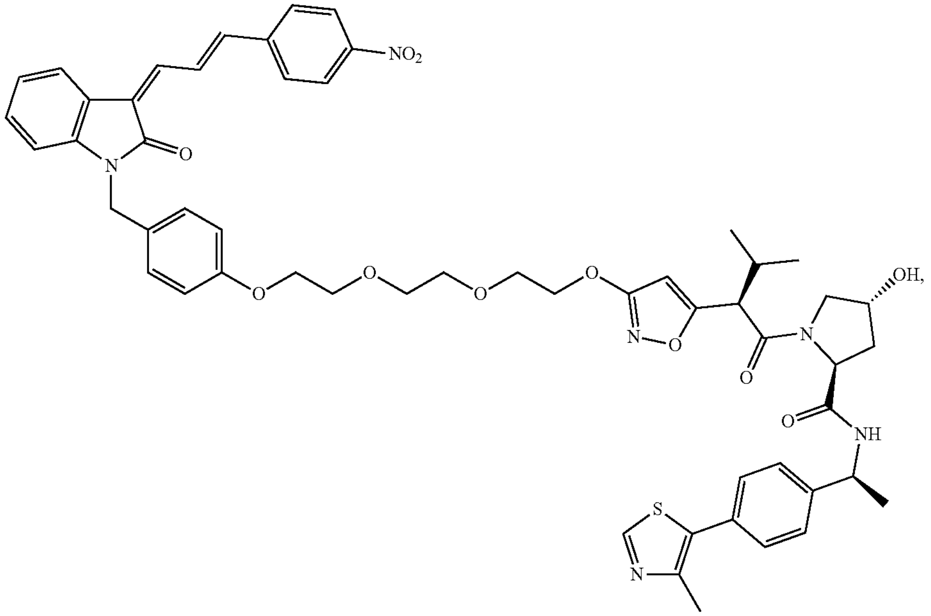

-continued
(81)
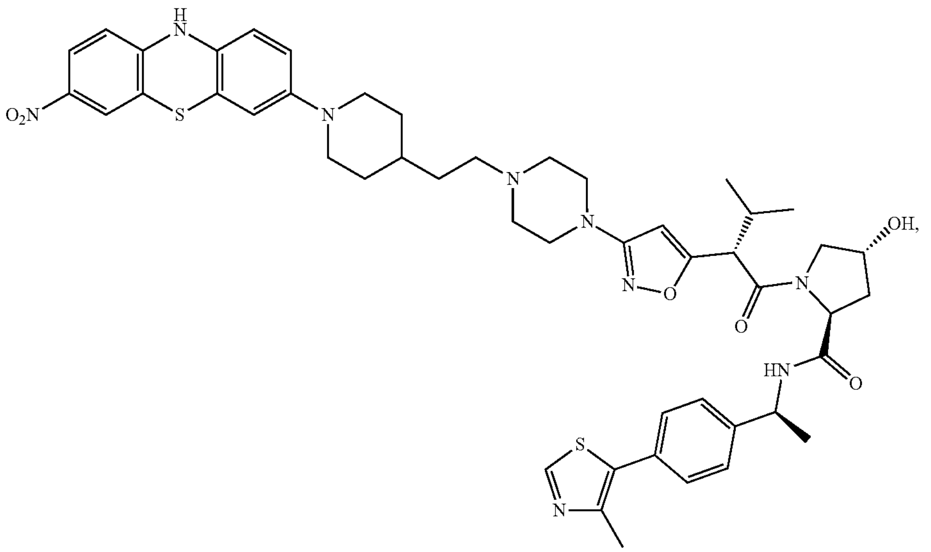
(82)
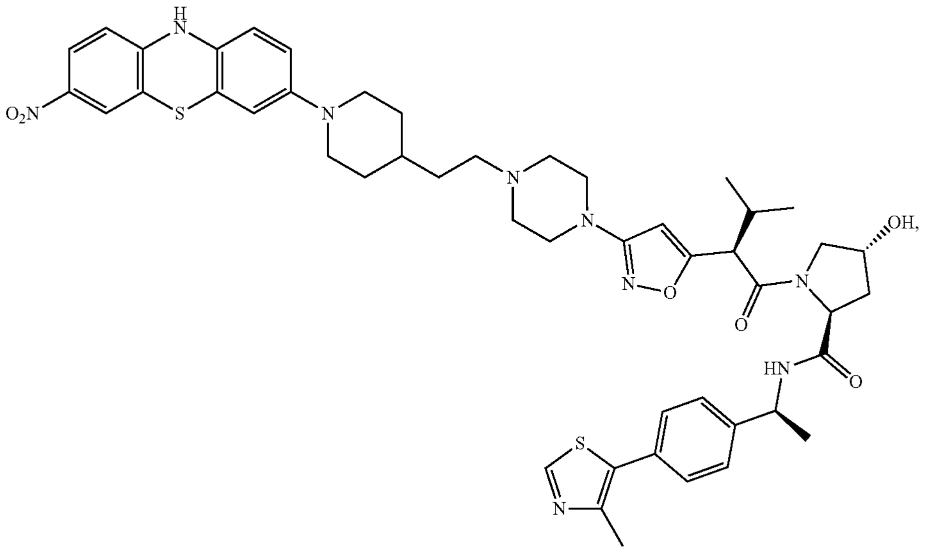
(84)
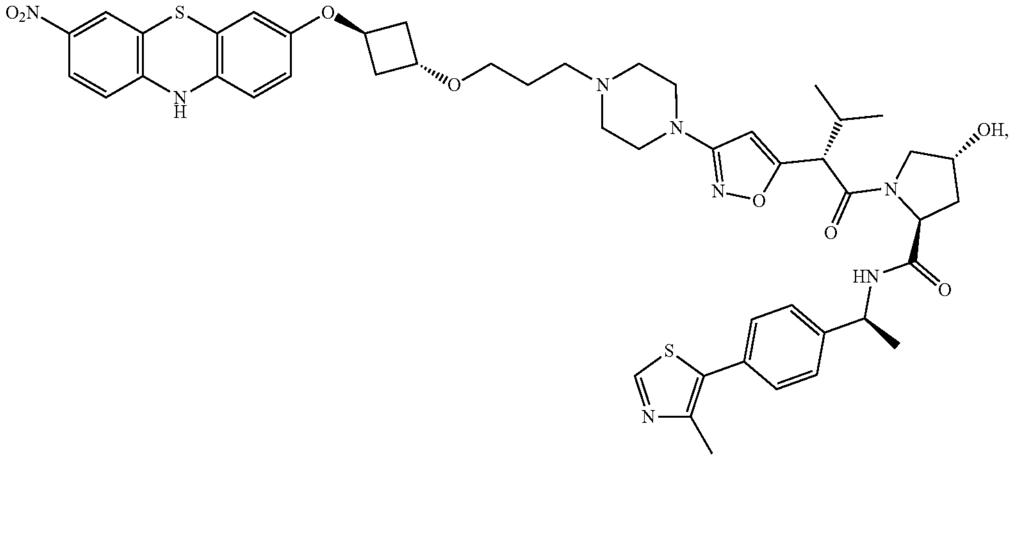

-continued
(85)
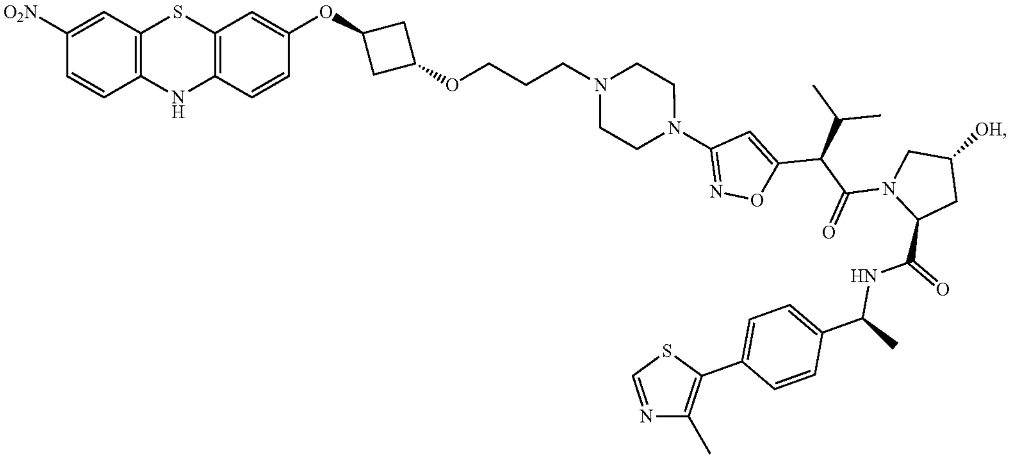
(87)
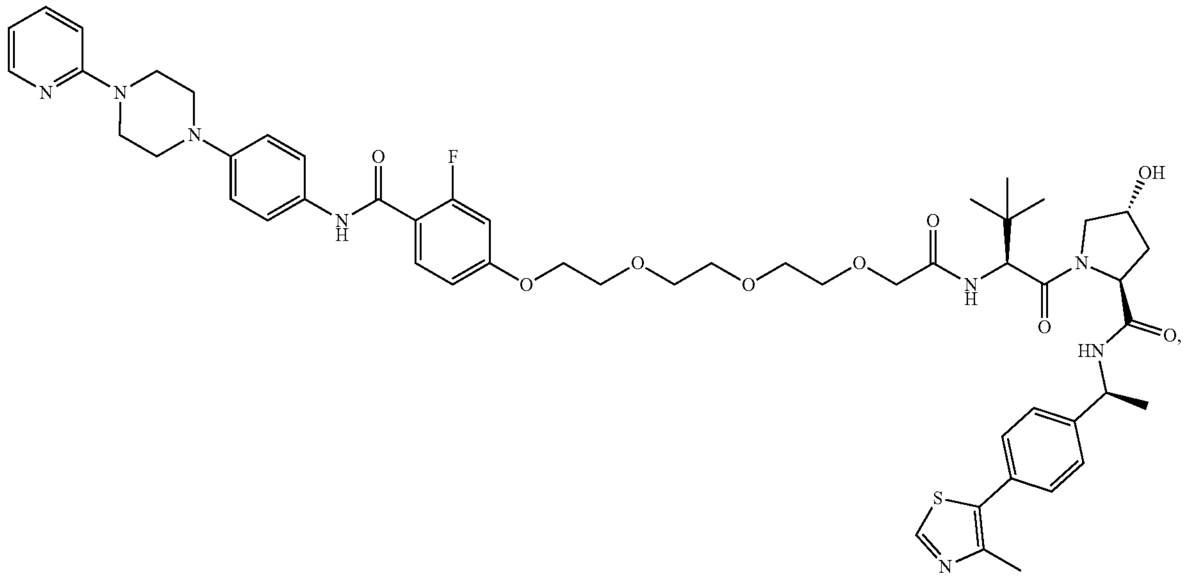
(89)
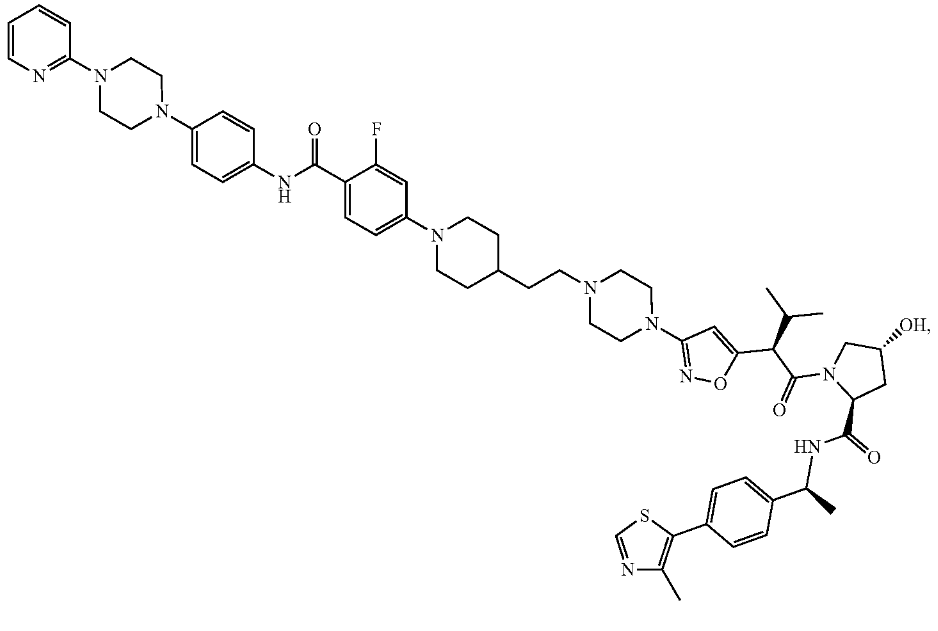

-continued
(94)
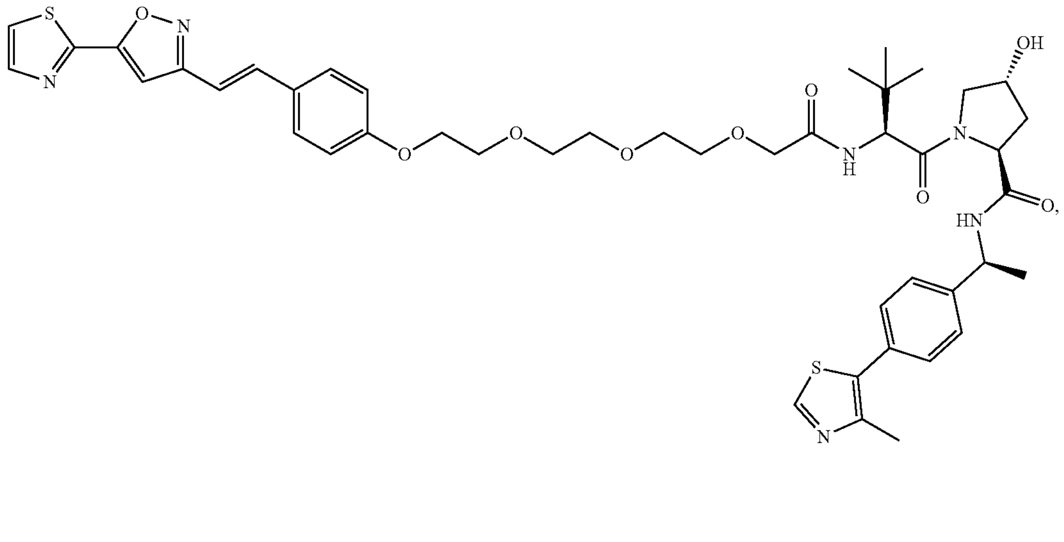
(96)
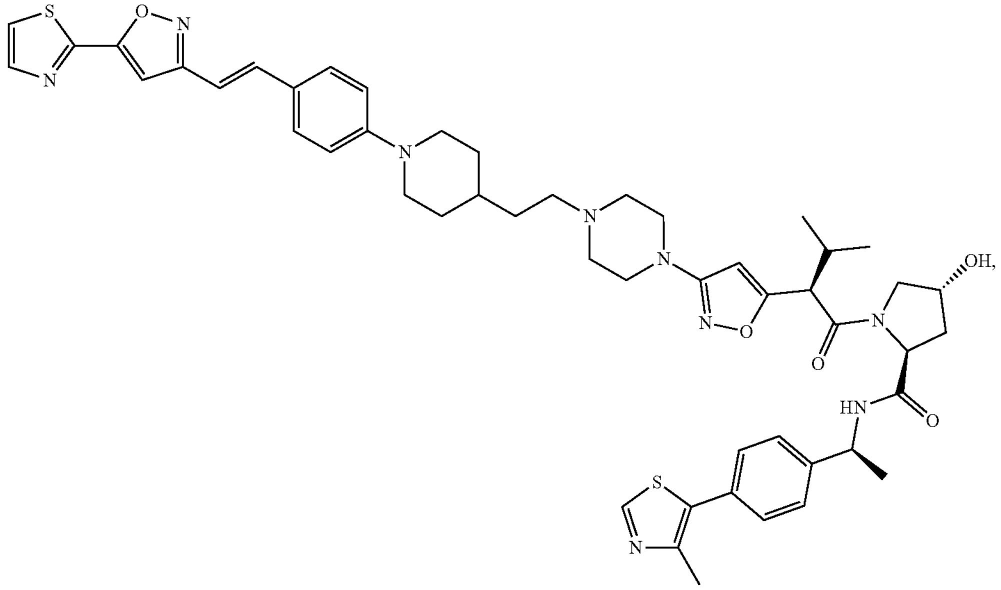
(101)
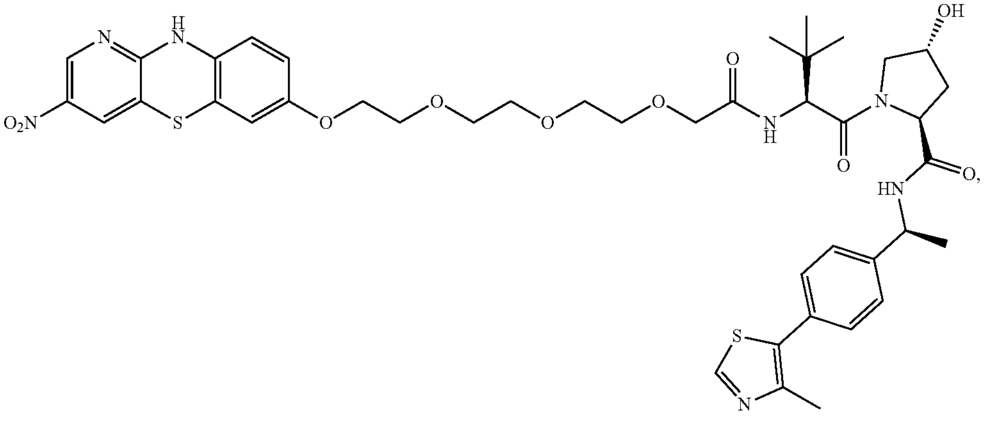

-continued
(103)
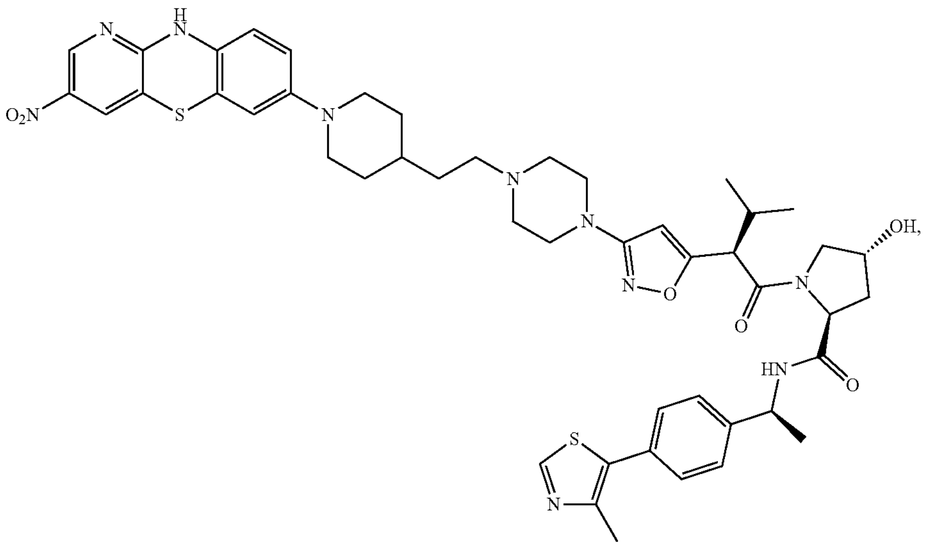
(108)
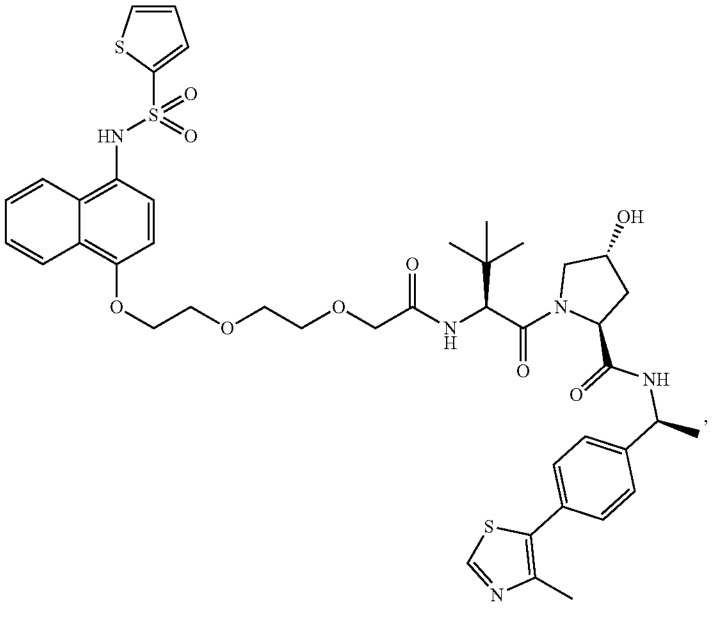

-continued
(110)
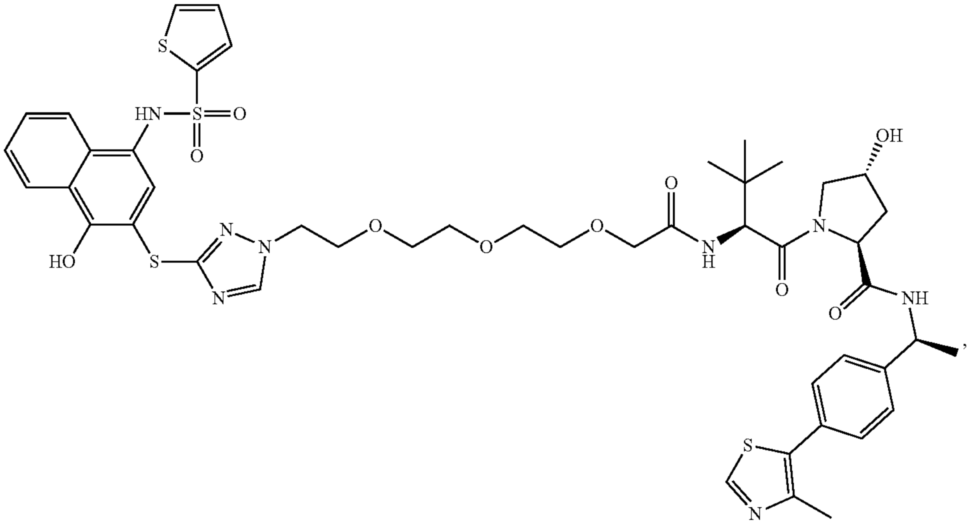
(113)
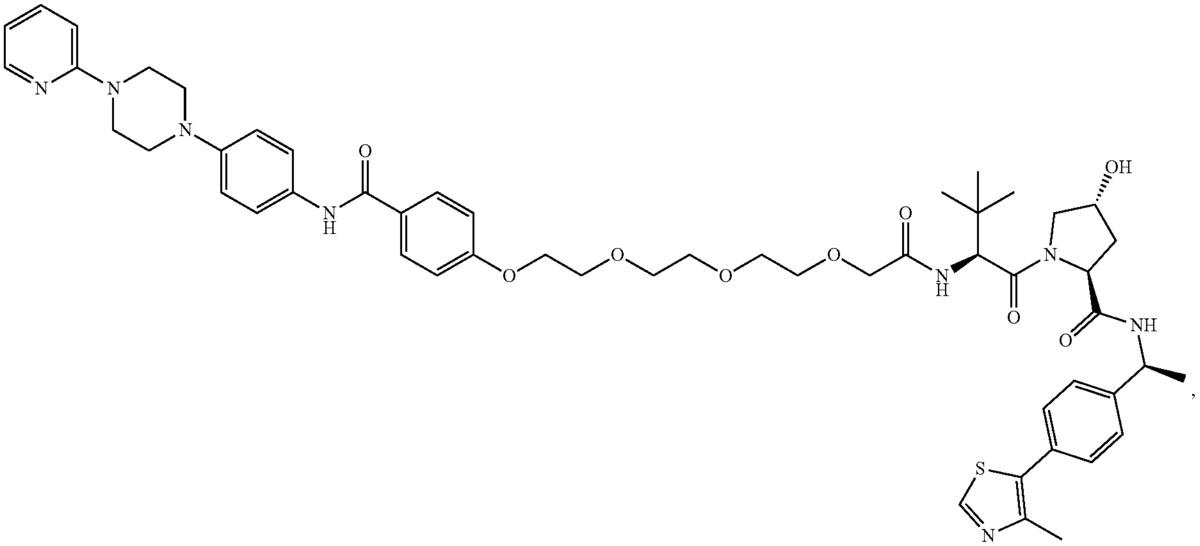
(114)
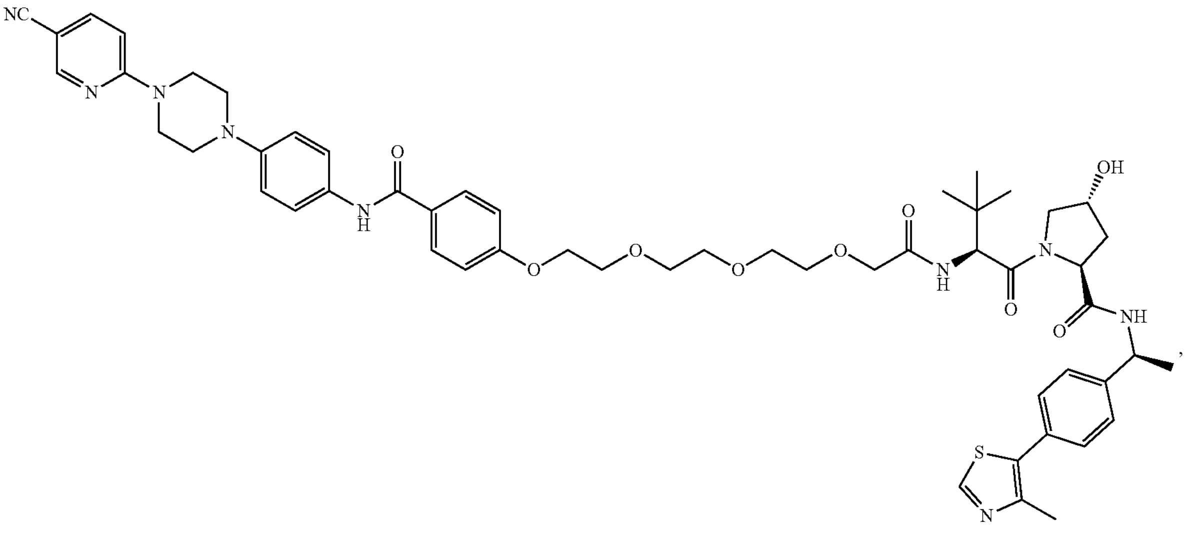

-continued
(115)
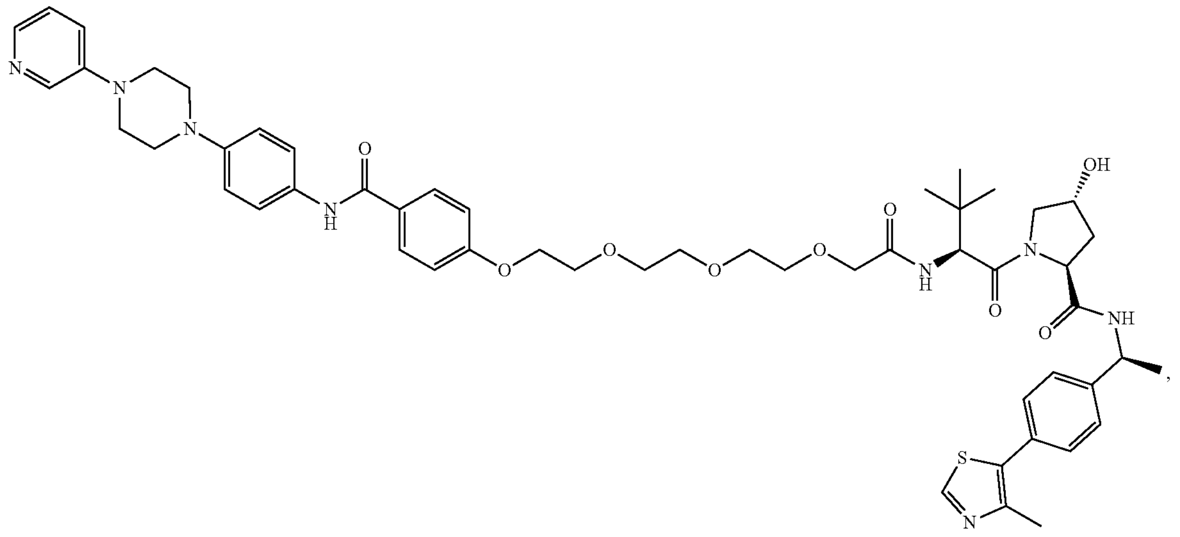
(116)
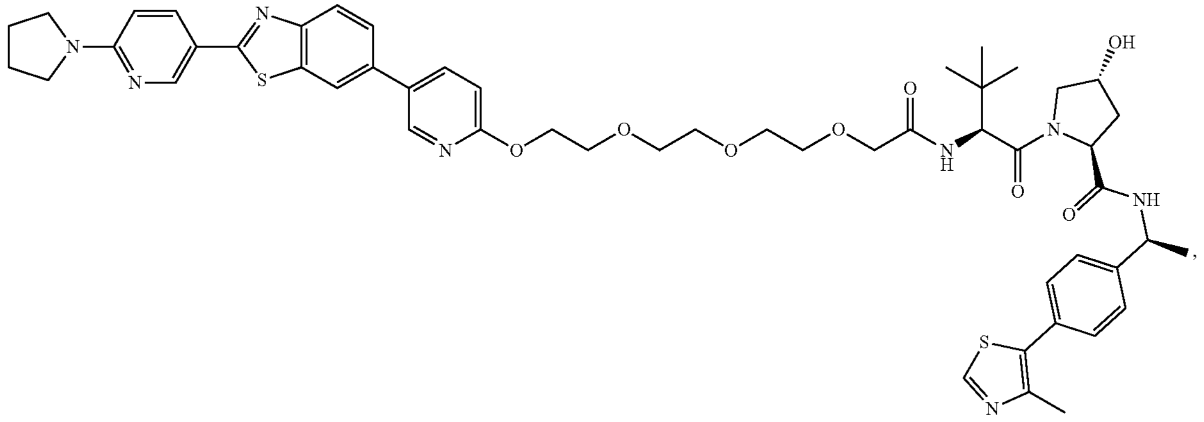
(117)
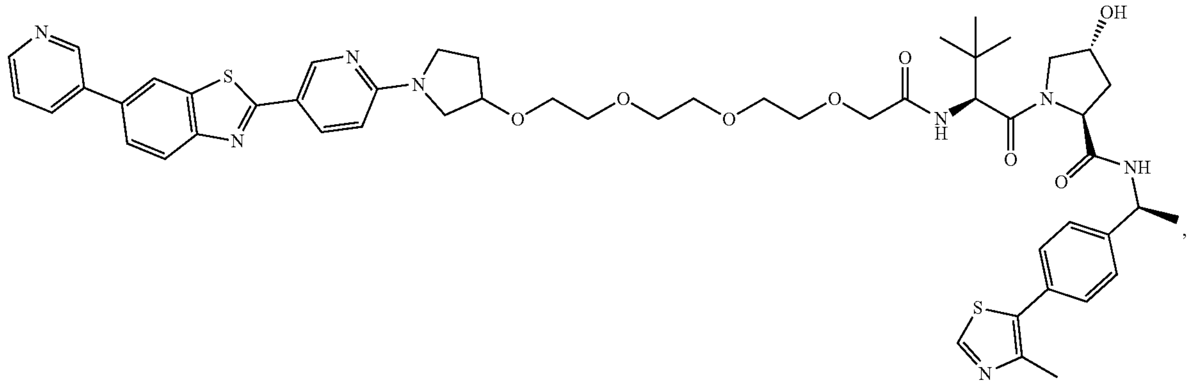

-continued
(118)
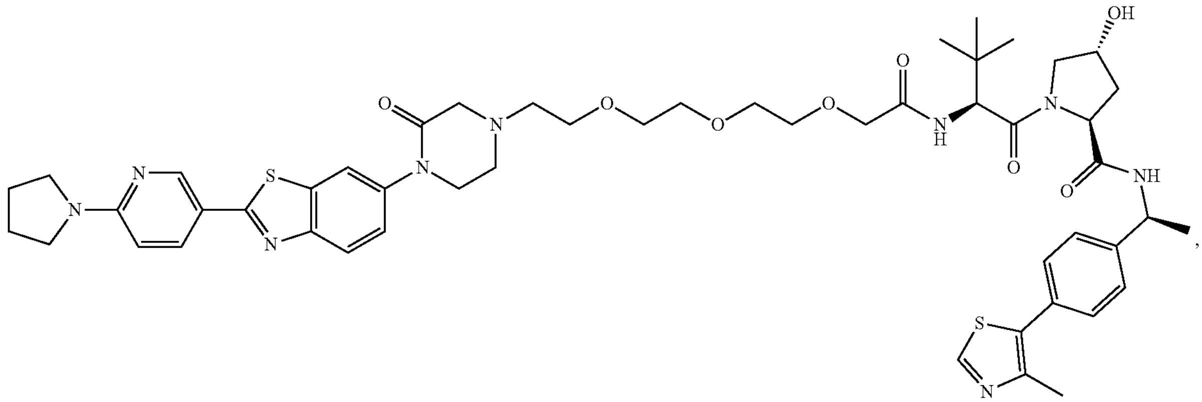
,
(119)
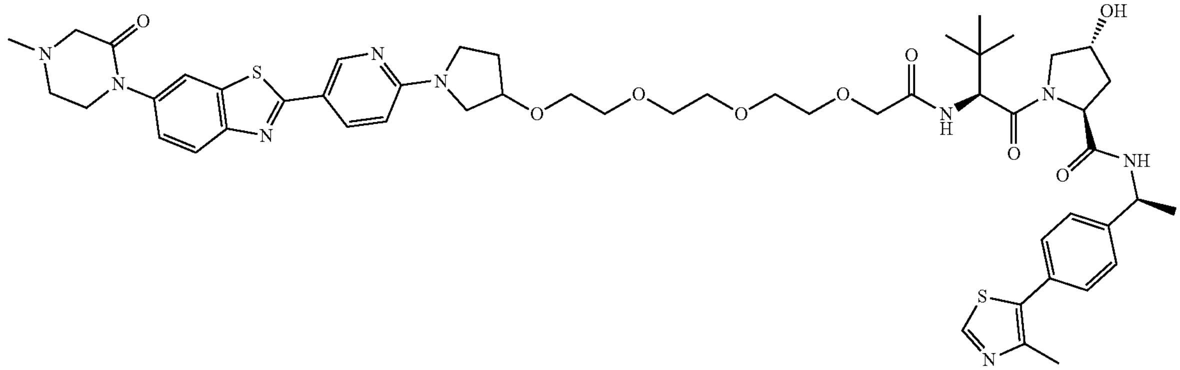
,
(120)
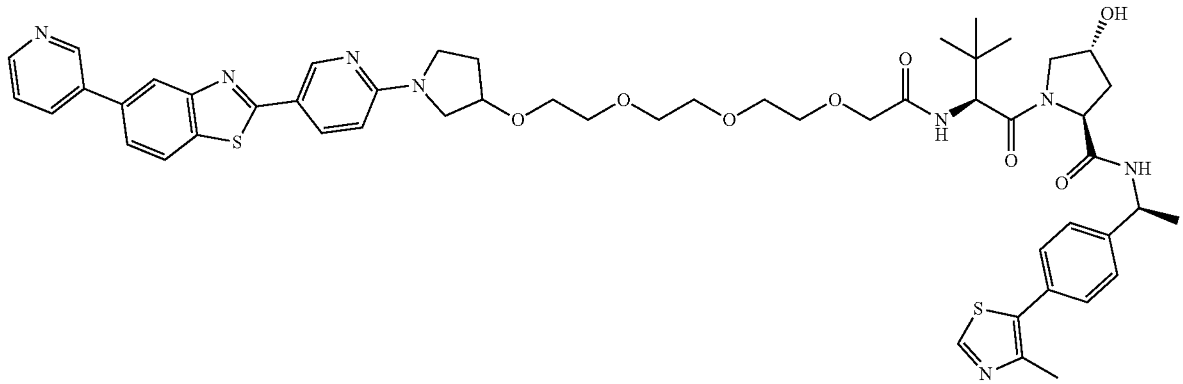
,

-continued
(121)
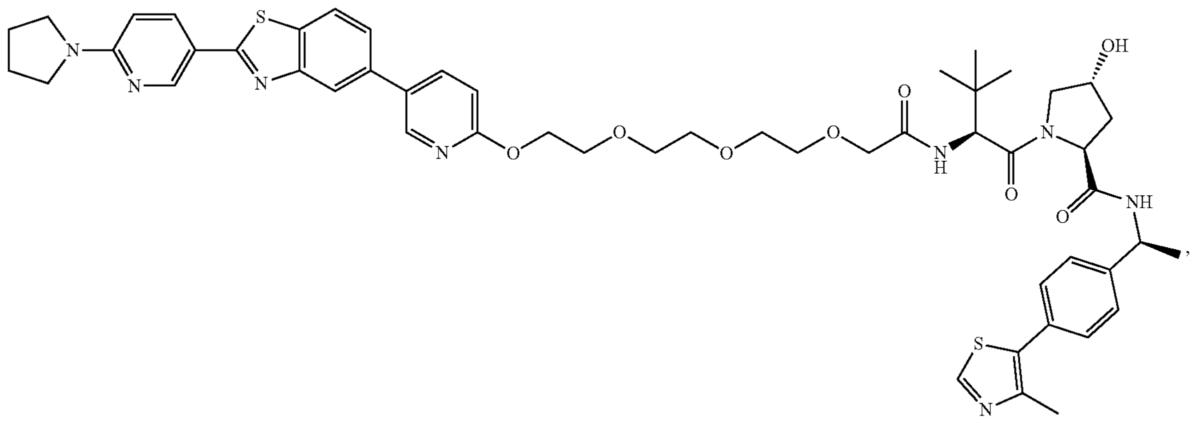
(122)
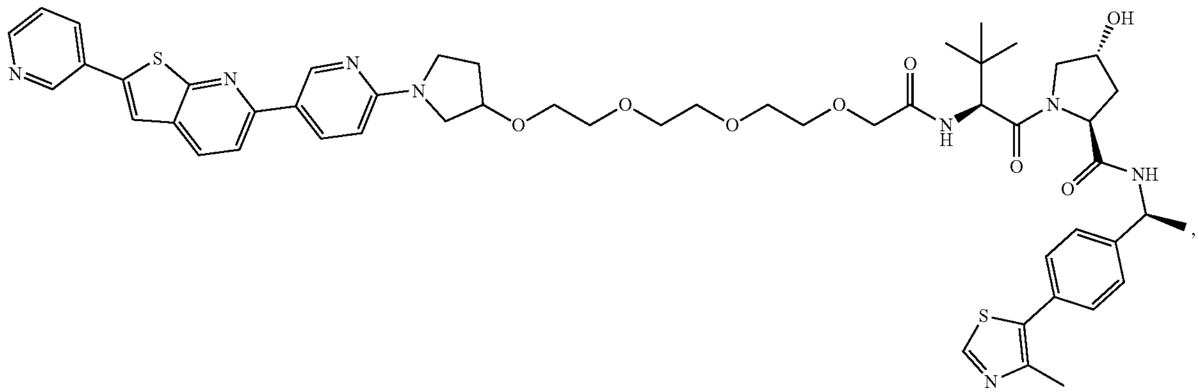
(123)
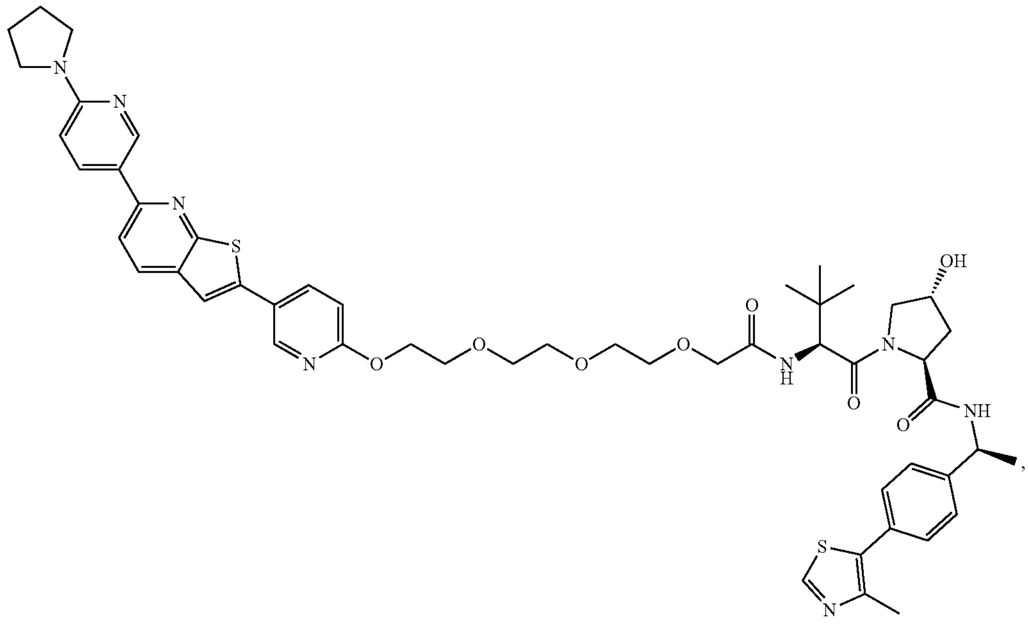

-continued (126)

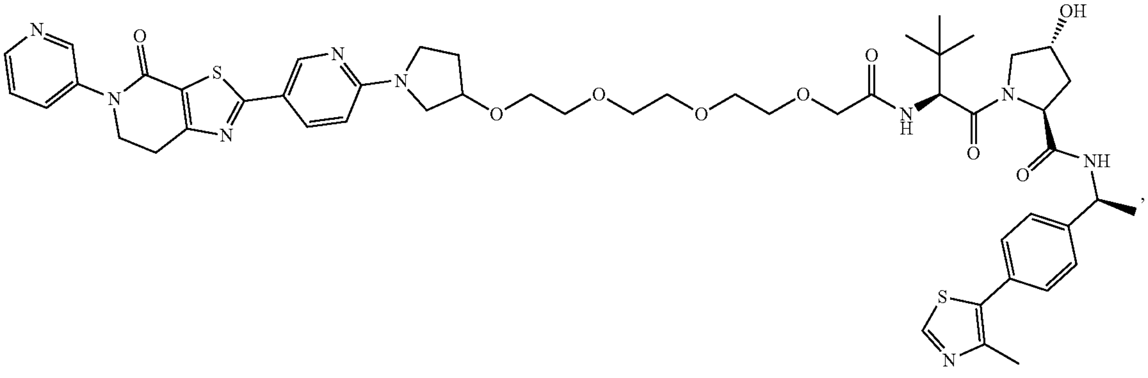

, and (127)

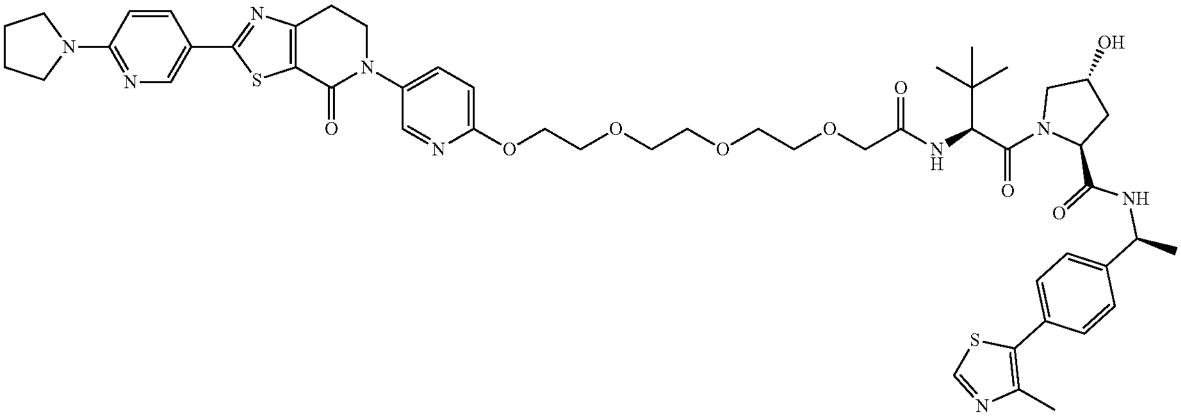

,

11. A pharmaceutical composition comprising a compound of claim 1, and a pharmaceutically acceptable carrier.

12. The pharmaceutical composition of claim 11, wherein the composition further comprises at least one additional bioactive agent.

13. The pharmaceutical composition of claim 12, wherein the additional bioactive agent is anti-neurodegenerative agent.

14. A method of treating a disease or disorder, comprising administering an effective amount of a compound of claim 1 to a subject;

wherein the disease or disorder is associated with α-synuclein accumulation and aggregation.

15. The method of claim 14, wherein the disease or disorder is a α-synucleinopathies or a neurodegenerative disease associated with α-synuclein accumulation and aggregation.

16. The method of claim 14, wherein the disease or disorder is Parkinson Disease, Alzheimer's Disease, dementia, dementia with Lewy bodies, or multiple system atrophy.

17. The method of claim 14, wherein the disease or disorder is Parkinson's Disease.

18. A pharmaceutical composition comprising the compound of claim 10, and a pharmaceutically acceptable carrier.

* * * * *